(12) United States Patent
Hiebert et al.

(10) Patent No.: US 9,527,885 B2
(45) Date of Patent: *Dec. 27, 2016

(54) HEPATITIS C VIRUS INHIBITORS

(71) Applicant: BRISTOL-MYERS SQUIBB COMPANY, Princeton, NJ (US)

(72) Inventors: Sheldon Hiebert, Steinbach (CA); Ramkumar Rajamani, Woodbridge, CT (US); Li-Qiang Sun, Glastonbury, CT (US); Eric Mull, Guilford, CT (US); Eric P. Gillis, Cheshire, CT (US); Michael S. Bowsher, Prospect, CT (US); Qian Zhao, Wallingford, CT (US); Nicholas A. Meanwell, East Hampton, CT (US); Kishore V. Renduchintala, Bangalore (IN); Kandhasamy Sarkunam, Hosur (IN); Pulicharla Nagalakshmi, Bangalore (IN); P. V. K. Suresh Babu, Bangalore (IN); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/592,313

(22) Filed: Jan. 8, 2015

(65) Prior Publication Data

US 2015/0125422 A1 May 7, 2015

Related U.S. Application Data

(63) Continuation of application No. 13/459,403, filed on Apr. 30, 2012, now Pat. No. 8,957,203.

(60) Provisional application No. 61/611,171, filed on Mar. 15, 2012, provisional application No. 61/482,658, filed on May 5, 2011.

(51) Int. Cl.

| | | |
|---|---|---|
| C07D 225/02 | (2006.01) |
| C07K 5/097 | (2006.01) |
| C07D 487/04 | (2006.01) |
| C07K 5/083 | (2006.01) |
| C07K 5/08 | (2006.01) |
| A61K 38/20 | (2006.01) |
| A61K 38/21 | (2006.01) |
| A61K 45/06 | (2006.01) |
| A61K 31/13 | (2006.01) |
| A61K 31/4745 | (2006.01) |
| A61K 31/7056 | (2006.01) |
| A61K 38/06 | (2006.01) |
| A61K 38/00 | (2006.01) |

(52) U.S. Cl.
CPC ............ *C07K 5/0823* (2013.01); *A61K 31/13* (2013.01); *A61K 31/4745* (2013.01); *A61K 31/7056* (2013.01); *A61K 38/06* (2013.01); *A61K 38/204* (2013.01); *A61K 38/2013* (2013.01); *A61K 38/2053* (2013.01); *A61K 38/21* (2013.01); *A61K 38/212* (2013.01); *A61K 45/06* (2013.01); *C07D 487/04* (2013.01); *C07K 5/0804* (2013.01); *C07K 5/0827* (2013.01); *A61K 38/00* (2013.01)

(58) Field of Classification Search
None
See application file for complete search history.

(56) References Cited

U.S. PATENT DOCUMENTS

| | | |
|---|---|---|
| 5,223,432 A | 6/1993 | Wirz et al. |
| 7,449,479 B2 | 11/2008 | Wang et al. |
| 7,582,605 B2 | 9/2009 | Moore et al. |
| 7,601,709 B2 | 10/2009 | Miao et al. |
| 7,605,126 B2 | 10/2009 | Niu et al. |
| 7,635,683 B2 | 12/2009 | Gai et al. |
| 7,741,281 B2 | 6/2010 | D'Andrea et al. |
| 7,915,291 B2 | 3/2011 | Wang et al. |
| 8,232,246 B2 | 7/2012 | McDaniel et al. |
| 8,268,776 B2 | 9/2012 | Sun et al. |

(Continued)

FOREIGN PATENT DOCUMENTS

| | | |
|---|---|---|
| WO | WO 98/17679 | 4/1998 |
| WO | WO 99/07733 | 2/1999 |

(Continued)

OTHER PUBLICATIONS

Lauer, G.M. et al., "Hepatitis C Virus Infection", The New England Journal of Medicine, vol. 345, No. 1, pp. 41-52 (2001).

(Continued)

*Primary Examiner* — Jeffrey S Lundgren
*Assistant Examiner* — Stephanie Springer
(74) *Attorney, Agent, or Firm* — Pamela A. Mingo

(57) ABSTRACT

Hepatitis C virus inhibitors having the general formula (I)

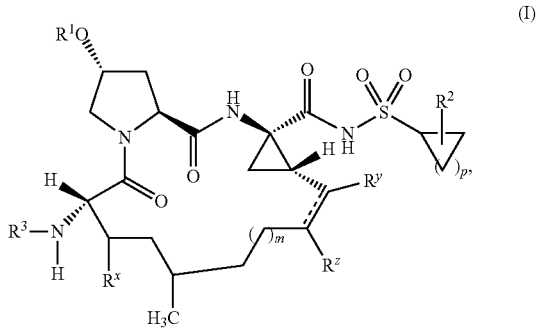

are disclosed. Compositions comprising the compounds and methods for using the compounds to inhibit HCV are also disclosed.

8 Claims, No Drawings

(56) References Cited

U.S. PATENT DOCUMENTS

| | | | |
|---|---|---|---|
| 8,299,094 | B2 | 10/2012 | Wang et al. |
| 8,309,685 | B2 | 11/2012 | Petter et al. |
| 8,338,606 | B2 | 12/2012 | Perrone et al. |
| 8,507,722 | B2 | 8/2013 | Wang et al. |
| 2005/0209135 | A1 | 9/2005 | Busacca et al. |
| 2006/0199773 | A1 | 9/2006 | Sausker et al. |
| 2006/0257980 | A1 | 11/2006 | Li |
| 2007/0078081 | A1 | 4/2007 | Casarez et al. |
| 2008/0279821 | A1 | 11/2008 | Niu et al. |
| 2013/0115190 | A1 | 5/2013 | Hiebert et al. |

FOREIGN PATENT DOCUMENTS

| | | |
|---|---|---|
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 02/08244 | 1/2002 |
| WO | WO 02/060926 | 8/2002 |
| WO | WO 03/053349 | 7/2003 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/099274 | 12/2003 |
| WO | WO 03/099316 | 12/2003 |
| WO | WO 2004/009121 | 1/2004 |
| WO | WO 2004/032827 | 4/2004 |
| WO | WO 2004/037855 | 5/2004 |
| WO | WO 2004/043339 | 5/2004 |
| WO | WO 2004/072243 | 8/2004 |
| WO | WO 2004/093798 | 11/2004 |
| WO | WO 2004/093915 | 11/2004 |
| WO | WO 2004/094452 | 11/2004 |
| WO | WO 2004/101602 | 11/2004 |
| WO | WO 2004/101605 | 11/2004 |
| WO | WO 2004/103996 | 12/2004 |
| WO | WO 2004/113365 | 12/2004 |
| WO | WO 2005/010029 | 2/2005 |
| WO | WO 2005/028501 | 3/2005 |
| WO | WO 2005/037214 | 4/2005 |
| WO | WO 2005/037860 | 4/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/070955 | 8/2005 |
| WO | WO 2005/073216 | 8/2005 |
| WO | WO 2005/095403 | 10/2005 |
| WO | WO 2005/116054 | 12/2005 |
| WO | WO 2006/000085 | 1/2006 |
| WO | WO 2006/007700 | 1/2006 |
| WO | WO 2006/007708 | 1/2006 |
| WO | WO 2006/016930 | 2/2006 |
| WO | WO 2006/020276 | 2/2006 |
| WO | WO 2006/026352 | 3/2006 |
| WO | WO 2006/033878 | 3/2006 |
| WO | WO 2006/043145 | 4/2006 |
| WO | WO 2006/086381 | 8/2006 |
| WO | WO 2006/096652 | 9/2006 |
| WO | WO 2006/119061 | 11/2006 |
| WO | WO 2006/122188 | 11/2006 |
| WO | WO 2006/130552 | 12/2006 |
| WO | WO 2006/130553 | 12/2006 |
| WO | WO 2006/130554 | 12/2006 |
| WO | WO 2006/130607 | 12/2006 |
| WO | WO 2006/130626 | 12/2006 |
| WO | WO 2006/130627 | 12/2006 |
| WO | WO 2006/130628 | 12/2006 |
| WO | WO 2006/130666 | 12/2006 |
| WO | WO 2006/130686 | 12/2006 |
| WO | WO 2006/130687 | 12/2006 |
| WO | WO 2006/130688 | 12/2006 |
| WO | WO 2007/001406 | 1/2007 |
| WO | WO 2007/008657 | 1/2007 |
| WO | WO 2007/009109 | 1/2007 |
| WO | WO 2007/009227 | 1/2007 |
| WO | WO 2007/011658 | 1/2007 |
| WO | WO 2007/014918 | 2/2007 |
| WO | WO 2007/014919 | 2/2007 |
| WO | WO 2007/014920 | 2/2007 |
| WO | WO 2007/014921 | 2/2007 |
| WO | WO 2007/014922 | 2/2007 |
| WO | WO 2007/014923 | 2/2007 |
| WO | WO 2007/014924 | 2/2007 |
| WO | WO 2007/014925 | 2/2007 |
| WO | WO 2007/014926 | 2/2007 |
| WO | WO 2007/014927 | 2/2007 |
| WO | WO 2007/015787 | 2/2007 |
| WO | WO 2007/015824 | 2/2007 |
| WO | WO 2007/015855 | 2/2007 |
| WO | WO 2007/016441 | 2/2007 |
| WO | WO 2007/016476 | 2/2007 |
| WO | WO 2007/017144 | 2/2007 |
| WO | WO 2007/025307 | 3/2007 |
| WO | WO 2007/030656 | 3/2007 |
| WO | WO 2007/044893 | 4/2007 |
| WO | WO 2007/044933 | 4/2007 |
| WO | WO 2007/056120 | 5/2007 |
| WO | WO 2007/082131 | 7/2007 |
| WO | WO 2007/106317 | 9/2007 |
| WO | WO 2007/120595 | 10/2007 |
| WO | WO 2007/131966 | 11/2007 |
| WO | WO 2007/143694 | 12/2007 |
| WO | WO 2007/148135 | 12/2007 |
| WO | WO 2008/002924 | 1/2008 |
| WO | WO 2008/005511 | 1/2008 |
| WO | WO 2008/005565 | 1/2008 |
| WO | WO 2008/008502 | 1/2008 |
| WO | WO 2008/008776 | 1/2008 |
| WO | WO 2008/019266 | 2/2008 |
| WO | WO 2008/019289 | 2/2008 |
| WO | WO 2008/019303 | 2/2008 |
| WO | WO 2008/021733 | 2/2008 |
| WO | WO 2008/021871 | 2/2008 |
| WO | WO 2008/021956 | 2/2008 |
| WO | WO 2008/021960 | 2/2008 |
| WO | WO 2008/022006 | 2/2008 |
| WO | WO 2008/051475 | 5/2008 |
| WO | WO 2008/051477 | 5/2008 |
| WO | WO 2008/051514 | 5/2008 |
| WO | WO 2008/057208 | 5/2008 |
| WO | WO 2008/057209 | 5/2008 |
| WO | WO 2008/057871 | 5/2008 |
| WO | WO 2008/057873 | 5/2008 |
| WO | WO 2008/057875 | 5/2008 |
| WO | WO 2008/057995 | 5/2008 |
| WO | WO 2008/059046 | 5/2008 |
| WO | WO 2008/060927 | 5/2008 |
| WO | WO 2008/064057 | 5/2008 |
| WO | WO 2008/064061 | 5/2008 |
| WO | WO 2008/064066 | 5/2008 |
| WO | WO 2008/070358 | 6/2008 |
| WO | WO 2008/086161 | 7/2008 |
| WO | WO 2008/092954 | 8/2008 |
| WO | WO 2008/092955 | 8/2008 |
| WO | WO 2008/095058 | 8/2008 |
| WO | WO 2008/095999 | 8/2008 |
| WO | WO 2008/096001 | 8/2008 |
| WO | WO 2008/096002 | 8/2008 |
| WO | WO 2008/098368 | 8/2008 |
| WO | WO 2008/101665 | 8/2008 |
| WO | WO 2008/106130 | 9/2008 |
| WO | WO 2008/128921 | 10/2008 |
| WO | WO 2008/134395 | 11/2008 |
| WO | WO 2008/134397 | 11/2008 |
| WO | WO 2008/134398 | 11/2008 |
| WO | WO 2008/137779 | 11/2008 |
| WO | WO 2008/141227 | 11/2008 |
| WO | WO 2009/005676 | 1/2009 |
| WO | WO 2009/005677 | 1/2009 |
| WO | WO 2009/005690 | 1/2009 |
| WO | WO 2009/010804 | 1/2009 |

(56) References Cited

FOREIGN PATENT DOCUMENTS

| | | |
|---|---|---|
| WO | WO 2009/014730 | 1/2009 |
| WO | WO 2009/047264 | 4/2009 |
| WO | WO 2009/053828 | 4/2009 |
| WO | WO 2009/055335 | 4/2009 |
| WO | WO 2009/064955 | 5/2009 |
| WO | WO 2009/064975 | 5/2009 |
| WO | WO 2009/070689 | 6/2009 |
| WO | WO 2009/070692 | 6/2009 |
| WO | WO 2009/073713 | 6/2009 |
| WO | WO 2009/073719 | 6/2009 |
| WO | WO 2009/073780 | 6/2009 |
| WO | WO 2009/076166 | 6/2009 |
| WO | WO 2009/076173 | 6/2009 |
| WO | WO 2009/079352 | 6/2009 |
| WO | WO 2009/079353 | 6/2009 |
| WO | WO 2009/080542 | 7/2009 |
| WO | WO 2009/082697 | 7/2009 |
| WO | WO 2009/082701 | 7/2009 |
| WO | WO 2009/085659 | 7/2009 |
| WO | WO 2009/094438 | 7/2009 |
| WO | WO 2009/094443 | 7/2009 |
| WO | WO 2009/108507 | 9/2009 |
| WO | WO 2009/117594 | 9/2009 |
| WO | WO 2009/129109 | 10/2009 |
| WO | WO 2009/134624 | 11/2009 |
| WO | WO 2009/134987 | 11/2009 |
| WO | WO 2009/139792 | 11/2009 |
| WO | WO 2009/140475 | 11/2009 |
| WO | WO 2009/140500 | 11/2009 |
| WO | WO 2009/142842 | 11/2009 |
| WO | WO 2009/146347 | 12/2009 |
| WO | WO 2009/148923 | 12/2009 |
| WO | WO 2010/011566 | 1/2010 |
| WO | WO 2010/015545 | 2/2010 |
| WO | WO 2010/030359 | 3/2010 |
| WO | WO 2010/031829 | 3/2010 |
| WO | WO 2010/031832 | 3/2010 |
| WO | WO 2010/033466 | 3/2010 |
| WO | WO 2010/034105 | 4/2010 |
| WO | WO 2010/036551 | 4/2010 |
| WO | WO 2010/036871 | 4/2010 |
| WO | WO 2010/036896 | 4/2010 |
| WO | WO 2010/059937 | 5/2010 |
| WO | WO 2010/065577 | 6/2010 |
| WO | WO 2010/068760 | 6/2010 |
| WO | WO 2010/068761 | 6/2010 |
| WO | WO 2010/075127 | 7/2010 |
| WO | WO 2010/077783 | 7/2010 |
| WO | WO 2010/080389 | 7/2010 |
| WO | WO 2010/088394 | 8/2010 |
| WO | WO 2010/115981 | 10/2010 |
| WO | WO 2010/116248 | 10/2010 |
| WO | WO 2010/132163 | 11/2010 |
| WO | WO 2010/145523 | 12/2010 |
| WO | WO 2011/002807 | 1/2011 |
| WO | WO 2011/002808 | 1/2011 |
| WO | WO 2011/005646 | 1/2011 |
| WO | WO 2011/014487 | 2/2011 |
| WO | WO 2011/025849 | 3/2011 |
| WO | WO 2011/034518 | 3/2011 |
| WO | WO 2011/038283 | 3/2011 |
| WO | WO 2011/038293 | 3/2011 |
| WO | WO 2011/041551 | 4/2011 |
| WO | WO 2011/046811 | 4/2011 |
| WO | WO 2011/049908 | 4/2011 |
| WO | WO 2011/063501 | 6/2011 |
| WO | WO 2011/063502 | 6/2011 |
| WO | WO 2011/072370 | 6/2011 |
| WO | WO 2011/091757 | 8/2011 |
| WO | WO 2011/150190 | 12/2011 |
| WO | WO 2011/156337 | 12/2011 |
| WO | WO 2012/018829 | 2/2012 |
| WO | WO 2012/019299 | 2/2012 |
| WO | WO 2012/037259 | 3/2012 |
| WO | WO 2012/040040 | 3/2012 |
| WO | WO 2012/040167 | 3/2012 |
| WO | WO 2012/040242 | 3/2012 |
| WO | WO 2012/047764 | 4/2012 |
| WO | WO 2012/054874 | 4/2012 |
| WO | WO 2012/082672 | 6/2012 |
| WO | WO 2012/092409 | 7/2012 |
| WO | WO 2012/092411 | 7/2012 |
| WO | WO 2012/166459 | 12/2012 |
| WO | WO 2012/173983 | 12/2012 |
| WO | WO 2013/028465 | 2/2013 |
| WO | WO 2013/028470 | 2/2013 |
| WO | WO 2013/028471 | 2/2013 |
| WO | WO 2013/074386 | 5/2013 |
| WO | WO 2013/106689 | 7/2013 |
| WO | WO 2013/120371 | 8/2013 |

OTHER PUBLICATIONS

Llinás-Brunet, M. et al., "A Systematic Approach to the Optimization of Substrate-Based Inhibitors of the Hepatitis C Virus NS3 Protease: Discovery of Potent and Specific Tripeptide Inhibitors", Journal of Medicinal Chemistry, vol. 47, No. 26, pp. 6584-6594 (2004).

Poupart, M.-A. et al., "Solid-Phase Synthesis of Peptidomimetic Inhibitors for the Hepatitis C Virus NS3 Protease", The Journal of Organic Chemistry, vol. 66, No. 14, pp. 4743-4751 (2001).

Ribeiro, C.M.R. et al., "Ultrasound in enzymatic resolution of ethyl 3-hydroxy-3-phenylpropanoate", Tetrahedron Letters, vol. 42, pp. 6477-6479 (2001).

Tsantrizos, Y.S. et al., "Olefin ring-closing metathesis as a powerful tool in drug discovery and development—potent macrocyclic inhibitors of the hepatitis C virus NS3 protease", Journal of Organometallic Chemistry, vol. 691, pp. 5163-5174 (2006).

Wirz, B. et al., "Enzymatic preparation of homochiral 2-isobutyl succinic acid derivatives", Tetrahedron: Asymmetry, vol. 8, No. 2, pp. 187-189 (1997).

Yang, S., "Chemoenzymatic Synthesis of (R)-(—)-Citramalic Acid", Synthesis, pp. 365-366 (1992).

HEPATITIS C VIRUS INHIBITORS

CROSS-REFERENCE TO RELATED APPLICATIONS

This Continuation application claims the benefit of U.S. Ser. No. 13/459,403 filed Apr. 30, 2012, now allowed, which in turn is a Non-Provisional application which claims the benefit of Provisional applications U.S. Ser. No. 61/611,171 filed Mar. 15, 2012 and U.S. Ser. No. 61/482,658 filed May 5, 2011, hereby incorporated by reference in their entireties.

The present disclosure is generally directed to antiviral compounds, and more specifically directed to compounds which inhibit the function of the NS3 protease (also referred to herein as "serine protease") encoded by Hepatitis C virus (HCV), compositions comprising such compounds, and methods for inhibiting the function of the NS3 protease.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. Six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a co-factor for the NS3 protease and possibly assisting in the membrane localization of NS3 and other viral replicase components. The complex formation of the NS3 protein with NS4A is essential for efficient polyprotein processing, enhancing the proteolytic cleavage at all of the sites. The NS3 protein also exhibits nucleoside triphosphatase and RNA helicase activities. NS5B is a RNA-dependent RNA polymerase that is involved in the replication of HCV.

The present disclosure provides peptide compounds that can inhibit the functioning of the NS3 protease, e.g., in combination with the NS4A protease. Further, the present disclosure describes the administration of combination therapy to a patient whereby a compound in accordance with the present disclosure, which is effective to inhibit the HCV NS3 protease, can be administered with additional compounds having anti-HCV activity.

In its first aspect the present disclosure provides a compound of formula (I)

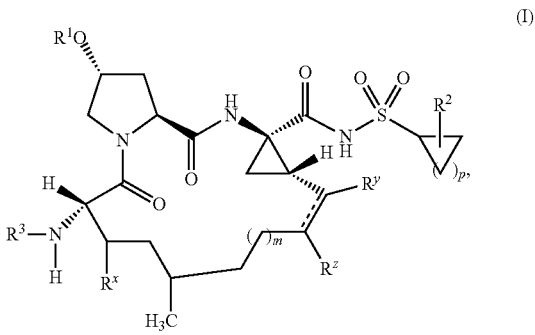

(I)

or a pharmaceutically acceptable salt thereof, wherein
p is 1 or 2;
----- is a single or double bond;
$R^1$ is selected from

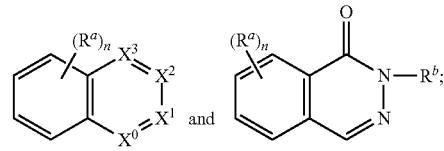

wherein $R^1$ is attached to the parent molecular moiety through any substitutable carbon atom in the group;
m is 0, 1, or 2;
n is 0, 1, 2, 3, 4, 5, or 6;
$X^0$ is selected from CH and N;
$X^1$ is selected from CH and N;
$X^2$ and $X^3$ are independently selected from CH, C($R^a$) and N; provided that at least one of $X^1$, $X^2$, and $X^3$ is other than N;
each $R^a$ is independently selected from alkenyloxy, alkoxy, alkoxyalkoxy, alkyl, benzodioxanyl, carboxamido, carboxy, carboxyalkoxy, cyano, cycloalkylalkoxy, cycloalkyloxy, deuteroalkoxy, dialkylamino, halo, haloalkyl, haloalkoxy, haloalkoxycarbonyl, hydroxy, morpholinyl, phenyl, piperazinyl, pyrazolyl, and pyridinyl, pyrrolidinyl, wherein the morpholinyl, the phenyl, the piperazinyl, the pyridinyl, and the pyrrolidinyl are optionally substituted with one or two groups independently selected from alkoxy, alkyl, alkylsulfonyl, halo, haloalkoxy, haloalkyl, and morpholinyl; and wherein two adjacent $R^a$ groups, together with the carbon atoms to which they are attached, can optionally form a ring selected from dioxanyl, dioxolanyl, morpholinyl, pyranyl, and phenyl, wherein the ring is optionally substituted with one or two groups independently selected from alkyl and halo;

$R^b$ is alkyl;

$R^x$ is selected from methyl and ethyl;

$R^y$ and $R^z$ are independently selected from hydrogen and hydroxy; provided that when ----- is a double bond, $R^y$ and $R^z$ are each hydrogen;

$R^2$ is selected from hydrogen, alkyl, halo, haloalkoxy, haloalkyl, and hydroxyalkyl; and $R^3$ is selected from hydrogen, alkoxyalkoxycarbonyl, alkoxycarbonyl, alkylaminocarbonyl, alkylcarbonyl, cycloalkylalkoxycarbonyl, cycloalkylcarbonyl, cycloalkyloxycarbonyl, deuteroalkoxycarbonyl, deuterohaloalkoxycarbonyl, dialkylaminocarbonyl, dialkylaminocarbonylcarbonyl, haloalkoxycarbonyl, haloalkylaminocarbonyl, haloalkylcarbonyl, heterocyclylcarbonyl, heterocyclyloxycarbonyl, phenylcarbonyl, and phenyloxycarbonyl, wherein the cycloalkyl part of the cycloalkylalkoxycarbonyl, the cycloalkylcarbonyl, and the cycloalkyloxycarbonyl, the heterocyclyl part of the heterocyclylcarbonyl and the heterocyclyloxycarbonyl, and the phenyl part of the phenylcarbonyl and the phenyloxycarbonyl, is optionally substituted with one, two, or three groups independently selected from alkyl, alkylamino, alkylcarbonyl, cycloalkyl, dialkylamino, halo, haloalkoxy, and haloalkyl.

In a first embodiment of the first aspect the present disclosure provides a compound of formula (I), or a pharmaceutically acceptable salt thereof, wherein m is 1.

In a second embodiment of the first aspect the present disclosure provides a compound of formula (I), or a pharmaceutically acceptable salt thereof, wherein ----- is a double bond.

In a third embodiment of the first aspect the present disclosure provides a compound of formula (I), or a pharmaceutically acceptable salt thereof, wherein ----- is a double bond. In a fourth embodiment Rx is ethyl.

In a fifth embodiment of the first aspect the present disclosure provides a compound of formula (I), or a pharmaceutically acceptable salt thereof, wherein ----- is a double bond and $R^x$ is methyl.

In a sixth embodiment of the first aspect the present disclosure provides a compound of formula (I), or a pharmaceutically acceptable salt thereof, wherein $R^1$ is

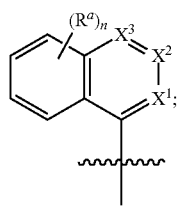

In a seventh embodiment of the first aspect the present disclosure provides a compound of formula (I), or a pharmaceutically acceptable salt thereof, wherein $R^1$ is

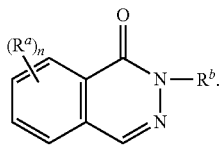

wherein $X^1$ and $X^2$ are N;
$X^3$ is $C(R^a)$;
n and $R^a$ are as defined in claim 1; and
"⁓" denotes the point of attachment to the parent molecular moiety.

In an eighth embodiment of the first aspect the present disclosure provides a compound of formula (I), or a pharmaceutically acceptable salt thereof, wherein $R^1$ is

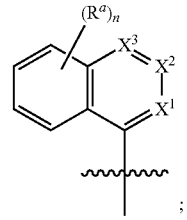

wherein $X^1$ is N;
$X^2$ and $X^3$ are independently selected from CH and $C(R^a)$;
n and $R^a$ are as defined in claim 1; and
"⁓" denotes the point of attachment to the parent molecular moiety.

In a ninth embodiment of the first aspect the present disclosure provides a compound of formula (I), or a pharmaceutically acceptable salt thereof, wherein $R^1$ is

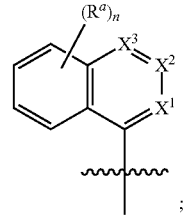

wherein $X^1$ and $X^3$ are N;
$X^2$ is $C(R^a)$;
n and $R^a$ are as defined in claim 1; and
"⁓" denotes the point of attachment to the parent molecular moiety.

In a tenth embodiment of the first aspect the present disclosure provides a compound of formula (I), or a pharmaceutically acceptable salt thereof, wherein $R^1$ is

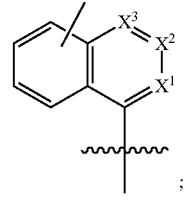

wherein $X^1$ and $X^3$ are N;
$X^2$ and $X^3$ are independently selected from CH and $C(R^a)$;
n and $R^a$ are as defined in claim 1; and
"⁓" denotes the point of attachment to the parent molecular moiety.

In an eleventh embodiment of the first aspect the present disclosure provides a compound of formula (I), or a pharmaceutically acceptable salt thereof, wherein $R^1$ is

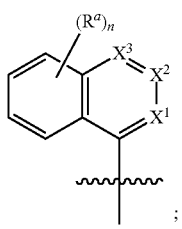

wherein $X^1$ and $X^2$ are independently selected from CH and $C(R^a)$;
$X^3$ is N;
n and $R^a$ are as defined in claim 1; and
"⌇" denotes the point of attachment to the parent molecular moiety.

In a twelfth embodiment of the first aspect the present disclosure provides a compound of formula (I), or a pharmaceutically acceptable salt thereof, wherein $R^1$ is

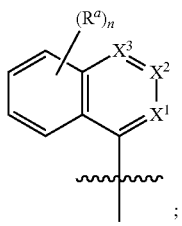

wherein $X^1$ and $X^3$ are N;
$X^2$ is CH;
n and $R^a$ are as defined in claim 1; and
"⌇" denotes the point of attachment to the parent molecular moiety.

In a thirteenth embodiment of the first aspect the present disclosure provides a compound of formula (I), or a pharmaceutically acceptable salt thereof, wherein $R^1$ is

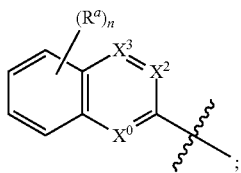

wherein $X^0$ and $X^3$ are N;
$X^2$ is selected from CH and $C(R^a)$;
n and $R^a$ are as defined in claim 1; and
"⌇" denotes the point of attachment to the parent molecular moiety.

In a second aspect the present disclosure provides a compound of formula (II)

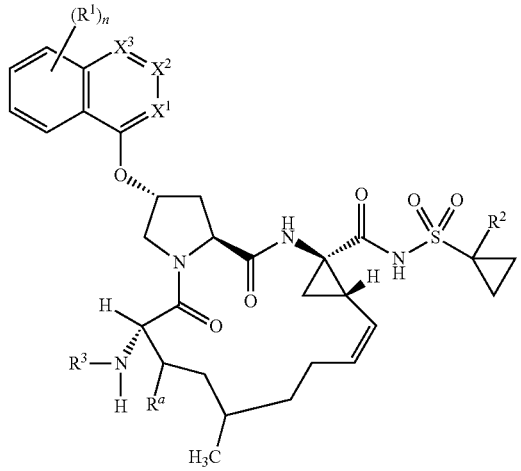

or a pharmaceutically acceptable salt thereof, wherein
n is 0, 1, 2, 3, 4, 5, or 6;
$X^1$ is selected from CH and N;
$X^2$ and $X^3$ are independently selected from CH, $C(R^1)$ and N;
$R^a$ is selected from methyl and ethyl;
each $R^1$ is independently selected from alkoxy, alkyl, carboxamido, carboxy, cyano, cycloalkyloxy, dialkylamino, halo, haloalkyl, haloalkoxy, phenyl, and pyridinyl, wherein the phenyl and the pyridinyl are optionally substituted with one or two groups independently selected from alkoxy, alkyl, halo, haloalkoxy, and haloalkyl;
$R^2$ is selected from hydrogen, alkyl, halo, and haloalkyl; and
$R^3$ is selected from alkoxycarbonyl, alkylcarbonyl, haloalkoxycarbonyl, haloalkylcarbonyl, and phenylcarbonyl, wherein the phenyl is optionally substituted with one or two groups independently selected from alkyl and halo.

In a third aspect the present disclosure provides a compound of formula (III)

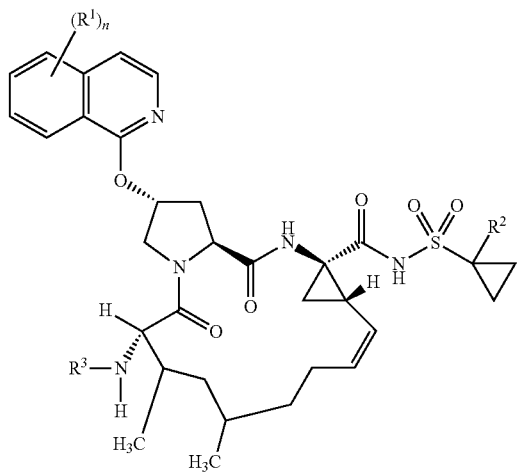

or a pharmaceutically acceptable salt thereof, wherein
n is 0, 1, 2, 3, 4, 5, or 6;
each $R^1$ is independently selected from alkoxy, alkyl, carboxamido, carboxy, cyano, cycloalkyloxy, dialkylamino, halo, haloalkyl, haloalkoxy, and phenyl, wherein the phenyl is optionally substituted with one or two groups independently selected from alkoxy, alkyl, halo, haloalkoxy, and haloalkyl;
$R^2$ is selected from hydrogen, alkyl, halo, and haloalkyl; and
$R^3$ is selected from alkoxycarbonyl, alkylcarbonyl, haloalkoxycarbonyl, haloalkylcarbonyl, and phenylcarbonyl, wherein the phenyl is optionally substituted with one or two groups independently selected from alkyl and halo;
or a pharmaceutically acceptable salt thereof.

In a fourth aspect the present disclosure provides a composition comprising a compound of formula (I), or a pharmaceutically acceptable salt thereof, and a pharmaceutically acceptable carrier. In a first embodiment of the fourth aspect the present disclosure provides a composition comprising a compound of formula (I), or a pharmaceutically acceptable salt thereof, at least one additional compound having anti-HCV activity, and a pharmaceutical carrier. In a second embodiment at least one of the additional compounds is an interferon or a ribavirin. In a third embodiment the interferon is selected from interferon alpha 2B, pegylated interferon alpha, consensus interferon, interferon alpha 2A, and lymphoblastiod interferon tau. In a fourth embodiment of the fourth aspect the present disclosure provides a composition comprising a compound of formula (I), or a pharmaceutically acceptable salt thereof, at least one additional compound having anti-HCV activity, and a pharmaceutical carrier, wherein at least one of the additional compounds is selected from interleukin 2, interleukin 6, interleukin 12, Imiquimod, ribavirin, an inosine 5'-monophospate dehydrogenase inhibitor, amantadine, and rimantadine. In a fifth embodiment of the fourth aspect the present disclosure provides a composition comprising a compound of formula (I), or a pharmaceutically acceptable salt thereof, at least one additional compound having anti-HCV activity, and a pharmaceutical carrier, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a fifth aspect the present disclosure provides a method of treating an HCV infection in a patient, comprising administering to the patient a therapeutically effective amount of a compound of formula (I), or a pharmaceutically acceptable salt thereof. In a first embodiment of the fifth aspect the method further comprises administering at least one additional compound having anti-HCV activity prior to, after, or simultaneously with the compound of formula (I), or a pharmaceutically acceptable salt thereof. In a second embodiment of the fifth aspect at least one of the additional compounds is an interferon or a ribavirin. In a third embodiment the interferon is selected from interferon alpha 2B, pegylated interferon alpha, consensus interferon, interferon alpha 2A, and lymphoblastiod interferon tau. In a fourth embodiment of the third aspect the present disclosure provides a method of treating an HCV infection in a patient, comprising administering to the patient a therapeutically effective amount of a compound of formula (I), or a pharmaceutically acceptable salt thereof, and at least one additional compound having anti-HCV activity prior to, after, or simultaneously with the compound of formula (I), or a pharmaceutically acceptable salt thereof, wherein at least one of the additional compounds is selected from interleukin 2, interleukin 6, interleukin 12, Imiquimod, ribavirin, an inosine 5'-monophosphate dehydrogenase inhibitor, amantadine, and rimantadine. In a fifth embodiment of the fifth aspect the present disclosure provides a method of treating an HCV infection in a patient, comprising administering to the patient a therapeutically effective amount of a compound of formula (I), or a pharmaceutically acceptable salt thereof, and at least one additional compound having anti-HCV activity prior to, after, or simultaneously with the compound of formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substitutent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when n is 2, each of the two $R^1$ groups may be the same or different.

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

The term "alkoxy," as used herein, refers to an alkyl group attached to the parent molecular moiety through an oxygen atom.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to ten carbon atoms.

The term "alkylcarbonyl," as used herein, refers to an alkyl group attached to the parent molecular moiety through a carbonyl group.

The term "alkylsulfonyl," as used herein, refers to an alkyl group attached to the parent molecular moiety through a sulfonyl group.

The term "carbonyl," as used herein, refers to —C(O)—.

The term "carboxamido," as used herein, refers to —C(O)NR$^x$R$^y$, wherein R$^x$ and R$^y$ are independently selected from hydrogen and alkyl.

The term "carboxy," as used herein, refers to —CO$_2$H.

The term "cyano," as used herein, refers to —CN.

The term "cycloalkyl," as used herein, refers to a saturated monocyclic or bicyclic hydrocarbon ring system having three to seven carbon atoms and zero heteroatoms.

Representative examples of cycloalkyl groups include, but are not limited to, cyclopropyl, cyclobutyl, and cyclopentyl.

The term "cycloalkyloxy," as used herein, refers to a cycloalkyl group attached to the parent molecular moiety through an oxygen atom.

The term "dialkylamino," as used herein, refers to —NR$^p$R$^q$, wherein R$^p$ and R$^q$ are alkyl groups. The alkyl groups may be the same or different.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkoxycarbonyl," as used herein, refers to a haloalkoxy group attached to the parent molecular moiety through a carbonyl group.

The term "haloalkyl," as used herein, refers to an alkyl group substituted with one, two, three, or four halogen atoms.

The term "haloalkylcarbonyl," as used herein, refers to a haloalkyl group attached to the parent molecular moiety through a carbonyl group.

The term "phenylcarbonyl," as used herein, refers to a phenyl group attached to the parent molecular moiety through a carbonyl group.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable basic functionality with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting an acidic group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

As used herein, the term "anti-HCV activity" means the compound is effective to treat the HCV virus.

The term "compounds of the disclosure", and equivalent expressions, are meant to embrace compounds of formula (I), and pharmaceutically acceptable enantiomers, diastereomers, and salts thereof. Similarly, references to intermediates, are meant to embrace their salts where the context so permits.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "sulfonyl," as used herein, refers to —SO$_2$—.

The term "sulfoxyl," as used herein, refers to —S(O)—.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "treat" and "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

Where used in naming compounds of the present disclosure, the designations P1', P1, P2, P2*, P3, and P4, as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend toward the C-terminus. For example, P1' refers to the first position away from the right hand end of the C-terminus of the cleavage site (i.e. N-terminus first position); whereas P1 starts the numbering from the left hand side of the C-terminus cleavage site, P2: second position from the C-terminus, etc.). (see Berger A. & Schechter I., Transactions of the Royal Society London series (1970), B257, 249-264].

Asymmetric centers exist in the compounds of the present disclosure. For example, the compounds may include P1 cyclopropyl element of formula

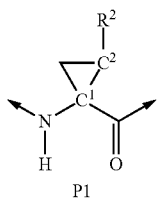

P1 wherein $C_1$ and $C_2$ each represent an asymmetric carbon atom at positions 1 and 2 of the cyclopropyl ring.

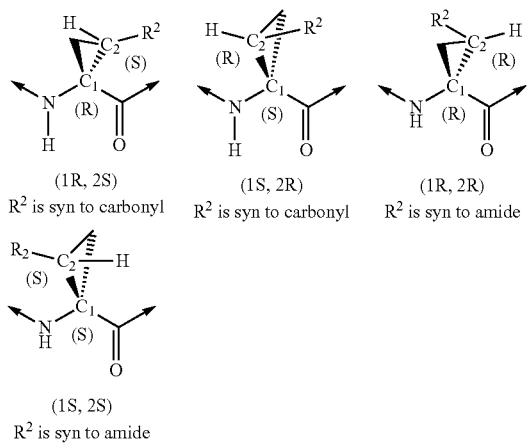

It should be understood that the disclosure encompasses all stereochemical forms, or mixtures thereof, which possess the ability to inhibit HCV protease.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 150 milligram per kilogram ("mg/kg") body weight per day, preferably between about 0.05 and about 100 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic and/or prophylactic agent, both the compound and the additional agent can be present in a dose that is less than or equal to the dosage normally administered in a monotherapy regimen. The compositions of this disclosure may be co-formulated with one or more additional therapeutic or prophylactic agents, for example, in the form of a monolithic and/or bi/multi-layer tablet or may be administered separately from the therapeutic or prophylactic agent(s).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/ Novartis |
| GL-60667 | Antiviral | NS5B Replicase Inhibitor | Gene Labs/ Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |

TABLE 1-continued

| Brand Name | Physiological Class | Type of Inhibitor or Target | Source Company |
|---|---|---|---|
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon - α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/ Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |

TABLE 1-continued

| Brand Name | Physiological Class | Type of Inhibitor or Target | Source Company |
|---|---|---|---|
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |
| INX-189 | Antiviral | Nucleotide NS5B Polymerase Inhibitor | Inhibitex |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/Bristol-Myers Squibb |

The compounds of the disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The abbreviations used in the present application, including particularly in the illustrative schemes and examples which follow, are well-known to those skilled in the art. Some of the abbreviations used are as follows: LAH for lithium aluminum hydride; THF for tetrahydrofuran; min for minutes; h or hr or hrs for hours; r.t. or RT or Rt for room temperature or retention time (context will dictate); MS for methanesulfonyl; DCM for dichloromethane; TBME for tert-butyl methyl ether; pet ether or pet-ether for petroleum ether; DMAP for N,N-dimethylaminpyridine; Ph for phenyl;

LiHMDS for lithium hexamethyldisilazide; DIPEA or DIEA for diisopropylethylamine; (BOC)$_2$O for di-tert-butyl dicarbonate; t-BuOK or tert-BuOK for potassium tert-butoxide; DMSO for N,N-dimethylsulfoxide; HATU for O-(7-azabenzotriazol-1-yl)-N,N,N',N'-tetramethyluronium phosphate; TFA for trifluoroacetic acid; EtOAC or EtOAc for ethyl acetate; DBU for 1,8-diazabicyclo(5.4.0)undec-7-ene; DMF for N,N-dimethylformamide; CDI for 1, 1'-carbonyldiimidazole; NH$_4$OAc for ammonium acetate; EtOH for ethanol; DDQ for 2,3-dichloro-5,6-dicyano-1,4-benzoquinone; DAST for (diethylamino) sulfur trifluoride; PPh$_3$ for triphenylphoshphine; TMS for trimethylsilane; and DPPA for diphenylphosphoryl azide.

The starting materials useful to synthesize the compounds of the present disclosure are known to those skilled in the art and can be readily manufactured or are commercially available.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art The preparation of intermediates and Compounds for Formula 1 is described in following three sections: Section 1, Section 2 and Section 3. Compounds were named using ChemDraw.

Preparation of Intermediates and Compounds of Formula 1

Section 1

Preparation of 1-(fluoromethyl)cyclopropane-1-sulfonamide

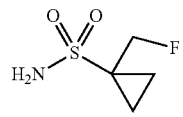

Scheme:

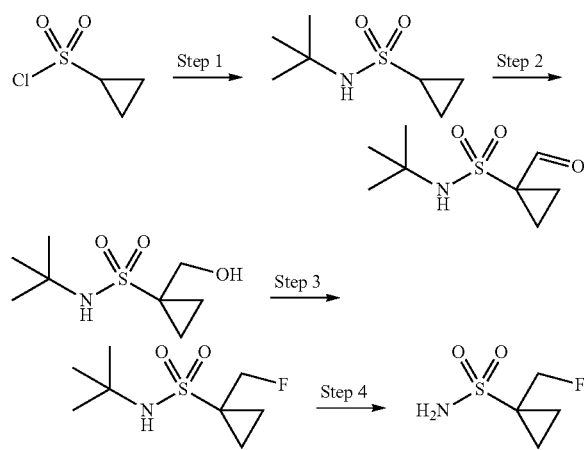

Step 1:

To a round-bottom flask equipped with a stir bar was added tert-butylamine (32.9 mL, 313 mmol) and dry THF (330 mL). The solution was cooled to −20° C. and to the stirred solution was added dropwise cyclopropanesulfonyl chloride (14.5 mL, 142 mmol). The solution was allowed to warm to room temperature with stirring for 18 h. The mixture was filtered and the filtrate was concentrated in vacuo. The residue was dissolved in DCM, washed with 1N HCl; water; and then brine. The organic solution was dried over MgSO$_4$, filtered, and then concentrated in vacuo. The resulting solid was recrystallized from hexanes:EtOAc (5:1) to afford N-(tert-butyl)cyclopropanesulfonamide as a colorless crystalline solid (20.95 g, 83%). $^1$H NMR (400 MHz, CDCl$_3$) δ 4.22 (br. s., 1H), 2.47 (tt, J=8.0, 4.9 Hz, 1H), 1.40 (s, 9H), 1.22-1.16 (m, 2H), 1.04-0.97 (m, 2H).

Step 2:

To a round-bottom flask equipped with a stir bar was added N-(tert-butyl)cyclopropanesulfonamide (10.0 g, 56.4 mmol) and THF (220 mL). The flask was placed under a nitrogen atmosphere and the solution was then cooled to −78° C. To the stirred solution was added dropwise over 10 minutes n-butyllithium (46.3 mL, 2.5M in hexanes). The resulting solution was stirred at −78° C. for 30 mins and then the cold bath was removed and the solution was allowed to warm to room temperature temperature with stirring for 30 mins. The solution was cooled to −78° C. To the solution was added N,N-dimethylformamide (13.1 mL, 169 mmol). The solution was allowed to slowly warm to room temperature with stirring for 17 h. The mixture was concentrated and the resulting yellow residue was dissolved in EtOAc (100 mL). The solution was transferred to a separatory funnel and was washed with aq. 1N HCl (150 mL). The aqueous phase was extracted with EtOAc (2×100 mL) and the combined organics were washed with sat. aq. NaCl (50 mL); dried over Na$_2$SO$_4$; and filtered. The filtrate concentrated in vacuo to afford a yellow viscous oil which solidified upon standing at room temperature. This material was dissolved in EtOAc (10 mL); diluted with hexanes (50 mL); and the resulting solution was then stored at −78° C. for 2 h upon which crystals formed. The crystals were collected via filtration; were washed with cold hexanes; and residual solvent was removed in vacuo to afford N-(tert-butyl)-1-formylcyclopropane-1-sulfonamide as a colorless, crystalline solid (8.89 g, 77%). $^1$H NMR (500 MHz, CDCl$_3$) δ 9.52 (s, 1H), 4.72 (br. s., 1H), 1.90-1.85 (m, 2H), 1.66-1.62 (m, 2H), 1.36 (s, 9H).

Step 3:

A round-bottom flask equipped with a stir bar was charged with a solution of N-(tert-butyl)-1-formylcyclopropane-1-sulfonamide (8.89 g, 43.3 mmol) in MeOH (110 mL). The solution was cooled to 0° C. and to the solution was added portionwise sodium borohydride (1.64 g, 43.3 mmol). The solution was stirred for 1 h. To the solution was added brine and the mixture was stirred for 15 min. The mixture was concentrated in vacuo to remove MeOH and the aqueous solution was then transferred to separatory funnel and was twice extracted with EtOAc. The combined organics were washed with sat. aq. NaCl; dried over MgSO$_4$; filtered; and then concentrated in vacuo to afford N-(tert-butyl)-1-(hydroxymethyl)cyclopropane-1-sulfonamide as a colorless, crystalline solid (8.66 g, 96%). $^1$H NMR (400 MHz, CDCl$_3$) δ 4.35 (br. s., 1H), 3.86 (d, J=6.0 Hz, 2H), 2.77 (t, J=6.0 Hz, 1H), 1.50-1.45 (m, 2H), 1.39 (s, 9H), 1.06-1.01 (m, 2H).

Step 4:

To a round-bottom flask equipped with a stir bar was added N-(tert-butyl)-1-(hydroxymethyl)cyclopropane-1-sulfonamide (8.66 g, 41.8 mmol) and CH$_2$Cl$_2$ (110 mL). The stirred solution was cooled to 0° C. and to the solution was added (diethylamino)sulfur trifluoride (11 mL, 84 mmol). The solution was allowed to warm to room temperature with stirring for 4 h. The solution was then slowly added to a stirred sat. aq. sodium bicarbonate (100 mL) and following the addition stirring was maintained for 18 h. The pH of the aqueous phase was adjusted to pH=4 using aq. HCl. The mixture was transferred to a separatory funnel and was twice extracted with $CH_2Cl_2$. The combined organics were washed with brine; dried over $MgSO_4$; filtered; and then concentrated in vacuo to afford a brown solid residue. This material was subjected to $SiO_2$ chromatography (hexanes:EtOAc, 90:10 to 40:60) to afford N-(tert-butyl)-1-(fluoromethyl)cyclopropane-1-sulfonamide as a colorless, crystalline solid (5.66 g, 65%). $^1$H NMR (400 MHz, $CDCl_3$) δ 4.73 (s, 1H), 4.60 (s, 1H), 4.22 (br. s., 1H), 1.59-1.53 (m, 2H), 1.37 (s, 9H), 1.12-1.07 (m, 2H).

Step 5:

To a round-bottom flask equipped with a stir bar was added N-(tert-butyl)-1-(fluoromethyl)cyclopropane-1-sulfonamide (5.66 g, 27.0 mmol) and trifluoroacetic acid (20 mL). The solution was stirred at room temperature for 18 h. The solution was concentrated in vacuo to afford a dark orange oil. The oil was treated with hexanes:EtOAc (4:1) upon which a solid crystallized. The crystals were collected via filtrated and residual solvent was removed in vacuo to afford 1-(fluoromethyl)cyclopropane-1-sulfonamide as a colorless, crystalline solid (3.5 g, 84%). $^1$H NMR (400 MHz, $CDCl_3$) δ 4.79 (s, 1H), 4.67 (s, 1H), 3.28 (br. s., 2H), 1.63-1.56 (m, 2H), 1.16-1.10 (m, 2H).

Preparation of (1R,2S)-1-amino-N-(cyclopropylsulfonyl)-2-vinylcyclopropanecarboxamide, HCl salt

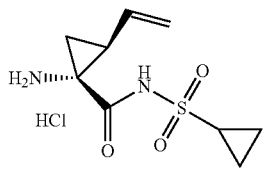

Scheme

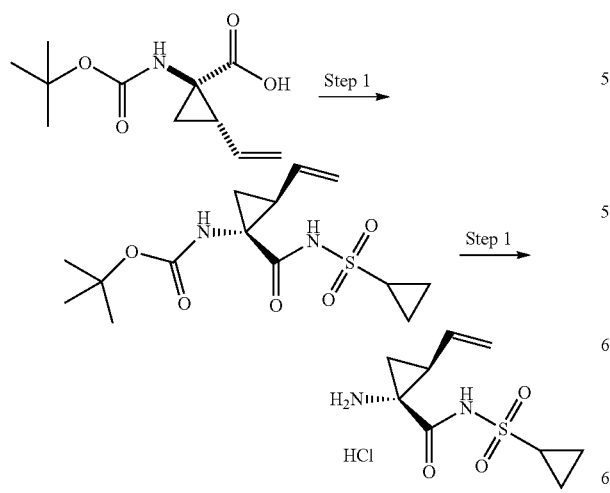

Step 1: tert-butyl ((1R,2S)-1-((cyclopropylsulfonyl)carbamoyl)-2-vinylcyclopropyl)carbamate A solution of (1R,2S)-1-((tert-butoxycarbonyl)amino)-2-vinylcyclopropanecarboxylic acid (2.62 g, 11.5 mmol) and CDI (2.43 g, 15.0 mmol) in THF (40 mL) was heated at reflux for 50 min under nitrogen. The solution was cooled to room temperature and transferred by cannula to a solution of cyclopropylsulfonamide (1.82 g, 15.0 mmol) in THF (10 mL). To the resulting solution was added DBU (2.40 mL, 16.1 mmol) and stirring was continued for 20 h. The mixture was quenched with 1N HCl to pH 1 and THF was evaporated in vacuo. The suspension was extracted with EtOAc (2×50 mL) and the combined organic extracts dried (Na2SO4). Purification by recrystallization from hexanes-EtOAc (1:1) afforded the title compound (2.4 g) as a white solid. The mother liquor was purified by a Biotage 40S column (eluted 9% acetone in DCM) to give a second batch of the compound tert-butyl ((1R,2S)-1-((cyclopropylsulfonyl)carbamoyl)-2-vinylcyclopropyl)carbamate (1.1 g). Both batches were combined (total yield 92%).

$^1$H NMR: (DMSO-d6) δ ppm 0.96-1.10 (m, 4H), 1.22 (dd, J=5.5, 9.5 Hz, 1H), 1.39 (s, 9H), 1.70 (t, J=5.5 Hz, 1H), 2.19-2.24 (m, 1H), 2.90 (m, 1H), 5.08 (d, J=10 Hz, 1H), 5.23 (d, J=17 Hz, 1H), 5.45 (m, 1H), 6.85, 7.22 (s, NH (rotamers); LC-MS MS m/z 331 (M$^+$+H).

Step 2: (1R,2S)-1-amino-N-(cyclopropylsulfonyl)-2-vinylcyclopropanecarboxamide, HCl A solution of tert-butyl ((1R,2S)-1-((cyclopropylsulfonyl)carbamoyl)-2-vinylcyclopropyl)carbamate (3.5 g, 10.6 mmol) in DCM (35 mL) and TFA (32 mL) was stirred at room temperature for 1.5 h. The volatiles were removed in vacuo and the residue suspended in 1N HCl in diethyl ether (20 mL) and concentrated in vacuo. This procedure was repeated once. The resulting mixture was triturated from pentane and filtered to give the compound (1R,2S)-1-amino-N-(cyclopropylsulfonyl)-2-vinylcyclopropanecarboxamide, HCl (2.60 g, 92%). $^1$H NMR: (DMSO-d6) δ ppm 1.01-1.15 (m, 4H), 1.69-1.73 (m, 1H), 1.99-2.02 (m, 1H), 2.38 (q, J=9 Hz, 1H), 2.92-2.97 (m, 1H), 5.20 (d, J=11 Hz, 1H), 5.33 (d, J=17 Hz, 1H), 5.52-5.59 (m, 1H), 9.17 (br s, 3H); LC-MS MS m/z 231 (M$^+$+H).

General Synthetic Scheme

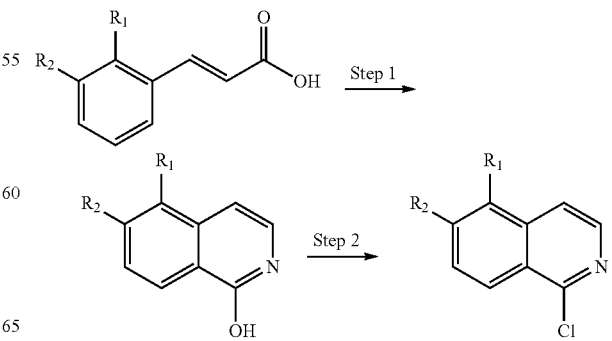

Preparation of P2 Intermediates

Preparation of intermediate 7-chloro-2,3-dihydro-[1,4]dioxino[2,3-f]isoquinoline

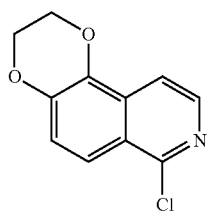 [SMILES: Clc1nccc2c3c(ccc12)OCCO3]

Step 1:

(E)-3-(2,3-dihydrobenzo[b][1,4]dioxin-5-yl)acrylic acid (5 g, 24.25 mmol), diphenylphosphoryl azide (4.96 mL, 23.04 mmol), and Et$_3$N (6.76 mL, 48.5 mmol) were dissolved in benzene and stirred for 16 h. The solution was concentrated under vacuum and the residue was purified by silica gel chromatography using 20% EtOAc/Hexanes to give 4.5 g of (E)-3-(2,3-dihydrobenzo[b][1,4]dioxin-5-yl) acryloyl azide as a yellow solid, which was taken into PhCH$_2$Ph (50 mL). The resulting solution was slowly heated to 80° C. for 1 h and then to reflux for 3 h. After cooling to rt, the solid was collected washing with benzene to give 3.5 g of the desired product 2,3-dihydro-[1,4]dioxino[2,3-f]isoquinolin-7-ol as a solid. $^1$H NMR (400 MHz, CD$_3$OD) δ ppm 4.37 (m, 4H), 6.83 (d, J=7.09 Hz, 1H), 7.02 (d, J=8.80 Hz, 1H), 7.12 (d, J=7.34 Hz, 1H), 7.79 (d, J=8.80 Hz, 1H); MS: (M+H)$^+$ 204.

Step 2:

A solution of 2,3-dihydro-[1,4]dioxino[2,3-f]isoquinolin-7-ol (5 g, 24.61 mmol) in POCl$_3$ (50 mL) was refluxed for 14 h. After Concentration, the residue was taken into the mixture of DCM and 4N NaOH solution. The organic phase was collected and dried over sodium sulfate, filtered, then concentrated under vacuum. The crude material was purified by silica gel chromatography using 20% EtOAc/Hexanes as eluent to give 4 g of the desired product 7-chloro-2,3-dihydro-[1,4]dioxino[2,3-f]isoquinoline as a solid. $^1$H NMR (400 Hz, CDCl$_3$) δ ppm 4.42 (m, 4H), 7.24 (d, J=9.05 Hz, 1H), 7.77 (d, J=5.87 Hz, 1H), 7.84 (d, J=9.05 Hz, 1H), 8.18 (d, J=5.87 Hz, 1H); MS: (M+H)$^+$ 222.

Preparation of intermediate 6-chloro-2,2-difluoro[1,3]dioxolo[4,5-f]isoquinoline

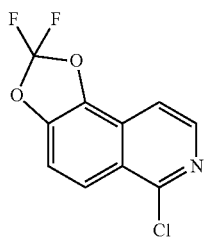 [SMILES: FC1(F)Oc2ccc3c(Cl)nccc3c2O1]

The intermediate 6-chloro-2,2-difluoro-[1,3]dioxolo[4,5-f]isoquinoline was prepared by following above General Scheme except that 3-(2,2-difluoro-benzo[1,3]dioxol-4-yl)-acrylic acid was used instead in step 1.

Step 1:

Modifications: 4.56 g 3-(2,2-difluoro-benzo[1,3]dioxol-4-yl)-acrylic acid used, 2.2 g product 2,2-difluoro-[1,3]dioxolo[4,5-f]isoquinolin-6(7H)-one was obtained (55% yield). $^1$H NMR (400 MHz, CD$_3$OD) δ ppm 6.63 (d, J=7.09 Hz, 1H), 7.29 (d, J=7.34 Hz, 1H), 7.40 (d, J=8.80 Hz, 1H), 8.19 (d, J=8.80 Hz, 1H); MS: (M+H)$^+$ 226.

Step 2:

Modifications: 2.2 g 2,2-difluoro-7H-1,3-dioxa-7-aza-cyclopenta[a]naphthalen-6-one used, 2.1 g product 6-chloro-2,2-difluoro-[1,3]dioxolo[4,5-f]isoquinoline obtained (87% yield). $^1$H NMR (500 Hz, CDCl$_3$) δ ppm 7.51 (d, J=9.29 Hz, 1H), 7.65 (d, J=5.87 Hz, 1H), 8.22 (d, J=9.05 Hz, 1H), 8.32 (d, J=5.87 Hz, 1H); MS: (M+H)$^+$ 244.

Preparation of intermediate 7-chloro-4-methyl-3,4-dihydro-2H[1,4]oxazino[2,3-f]isoquinoline

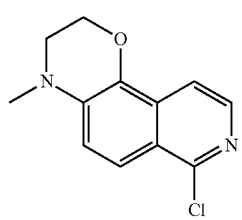 [SMILES: CN1CCOc2c1ccc1c(Cl)nccc21]

The intermediate 7-chloro-4-methyl-3,4-dihydro-2H-[1,4]oxazino[2,3-f]isoquinoline was prepared by following above General Scheme except that (E)-3-(4-methyl-3,4-dihydro-2H-benzo[b][1,4]oxazin-8-yl)acrylic acid was used instead in step 1.

Step 1:

Modifications: 0.876 g (E)-3-(4-methyl-3,4-dihydro-2H-benzo[b][1,4]oxazin-8-yl)acrylic acid used, 0.6 g product 4-methyl-3,4-dihydro-2H[1,4]oxazino[2,3-f]isoquinolin-7-ol was obtained.

Step 2:

Modifications: 0.6 g 4-methyl-3,4-dihydro-2H-[1,4]oxazino[2,3-f]isoquinolin-7-ol used, 0.49 g product 7-chloro-4-methyl-3,4-dihydro-2H-[1,4]oxazino[2,3-f]isoquinoline obtained. $^1$H NMR (400 MHz, CHLOROFORM-d) δ ppm 8.05 (d, J=6.0 Hz, 1H), 7.82 (dd, J=9.3, 0.8 Hz, 1H), 7.67 (dd, J=5.8, 0.8 Hz, 1H), 7.16 (d, J=9.3 Hz, 1H), 4.47-4.36 (m, 2H), 3.48-3.41 (m, 2H), 3.06 (s, 3H); MS: (M+H)$^+$ 235.03.

Preparation of intermediate 4-(1-chloroisoquinolin-5-yl)morpholine

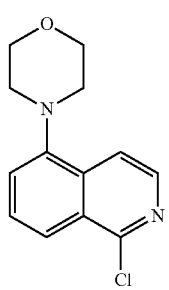 [SMILES: Clc1nccc2c(N3CCOCC3)cccc12]

The intermediate 4-(1-chloroisoquinolin-5-yl)morpholine was prepared by following above General Synthetic Scheme except that (E)-3-(2-morpholinophenyl)acrylic acid was used instead in step 1.

Step 1:

Modifications: 7 g (E)-3-(2-morpholinophenyl)acrylic acid used, 5 g 5-morpholinoisoquinolin-1-ol obtained (71% yield). $^1$H NMR (400 MHz, CD$_3$OD) δ ppm 3.02 (m, 4H), 3.91 (m, 4H), 6.97 (d, J=7.34 Hz, 1H), 7.18 (d, J=7.34 Hz, 1H), 7.44 (m, 2H), 8.02 (d, J=7.83 Hz, 1H); MS (M+H)$^+$ 231.

Step 2:

Modifications: 2.2 g 5-morpholin-4-yl-2H-isoquinolin-1-one used, 2.1 g 4-(1-chloroisoquinolin-5-yl)morpholine obtained (87% yield). $^1$H NMR (400 MHz, CCl$_3$D) δ ppm 3.09 (m, 4H), 3.97 (m, 4H), 7.32 (d, J=7.58 Hz, 1H), 7.60 (m, 1H), 7.91 (d, J=5.87 Hz, 1H), 8.06 (d, J=8.56 Hz, 1H), 8.26 (d, J=5.87 Hz, 1H).

Preparation of intermediate 1-fluoro-3-(4-isopropoxyphenyl)-4,6-dimethoxyisoquinoline

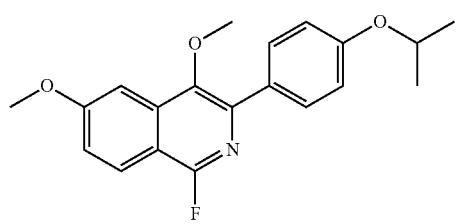 [SMILES: COc1ccc2c(F)nc(-c3ccc(OC(C)C)cc3)c(OC)c2c1]

Scheme

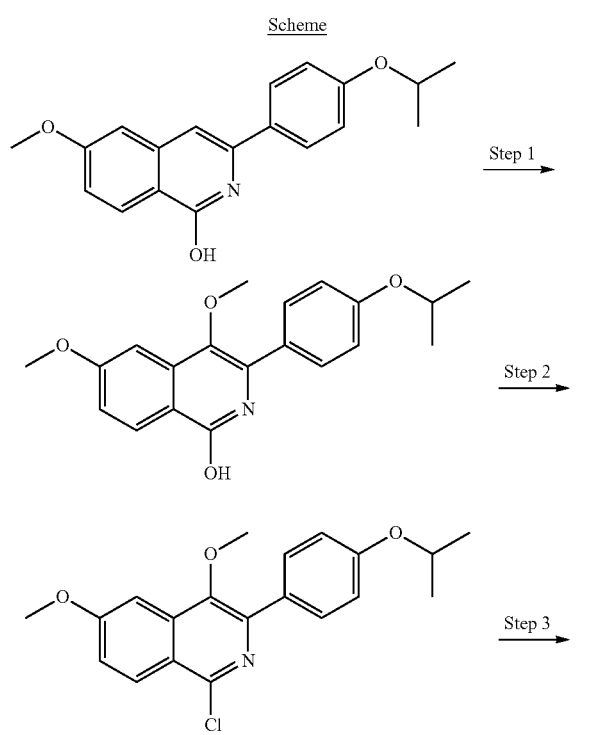

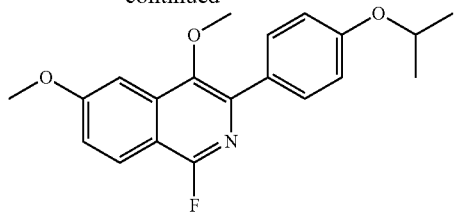

Step 1:

In a 70 mL Chemglass pressure vessel were combined 3-(4-isopropoxyphenyl)-6-methoxyisoquinolin-1-ol (1 g, 3.23 mmol), iodobenzene diacetate (1.145 g, 3.56 mmol) and MeOH (15 mL). To the mixture was added methanesulfonic acid (0.252 mL, 3.88 mmol), a mild exotherm resulted. The threaded stopper was affixed to the vessel and the mixture was heated first to 70° C. for 4 h and then to 130° C. for 3 h. Let the mixture stand at rt for 16 h. After filtration washing thoroughly with 1:1 methanol, the filtrate was extracted with ethyl acetate washing with water, dried over MgSO$_4$, concentrated to give an impure material that will be used in the next step as it is (1 g). MS: MS m/z 340.1 (M$^+$+1).

Step 2:

A solution of impure 3-(4-isopropoxyphenyl)-4,6-dimethoxyisoquinolin-1-ol (1 g, 2.95 mmol) in POCl$_3$ (10 mL) was refluxed for 1.5 hs. After concentration, the residue was taken into the mixture of DCM and 4N NaOH solution. The organic phase was collected and dried over sodium sulfate, filtered, then concentrated under vacuum. The crude material was purified by silica gel chromatography using 20% EtOAc/Hexanes as eluent to give 150 mg of the desired product. $^1$H NMR (400 MHz, CHLOROFORM-d) δ ppm 8.14 (d, J=9.3 Hz, 1H), 8.08 (d, J=9.0 Hz, 2H), 7.39 (d, J=2.5 Hz, 1H), 7.22 (dd, J=9.3, 2.5 Hz, 1H), 7.01 (d, J=9.0 Hz, 2H), 4.65 (quin, J=6.1 Hz, 1H), 3.98 (s, 3H), 3.68 (s, 3H), 1.39 (d, J=6.0 Hz, 6H).

Step 3:

To a solution of 1-chloro-3-(4-isobutylphenyl)-4,6-dimethoxyisoquinoline (142 mg, 0.4 mmol) in DMSO (2 mL), was added CsF (122 mg, 0.800 mmol) and the mixture was heated to 140° C. for 4 hrs. The reaction was diluted with ethylactetate and washed with water, and brine. The organic phase was collected, dried over sodium sulfate, and concentrated under vacuum to give the crude product which was purified by silica gel chromatography using a gradient of 5-25% EtOAc/Hexanes. The product fractions were collected and the solvent removed under vacuum to give 120 mg of the desired product as a white solid containing starting material. MS: MS m/z 342.1 (M$^+$+1).

Preparation of intermediate 1-chloro-3-(5-isopropoxypyridin-2-yl)-6-methoxyisoquinoline

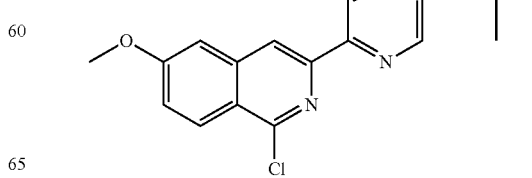

Scheme

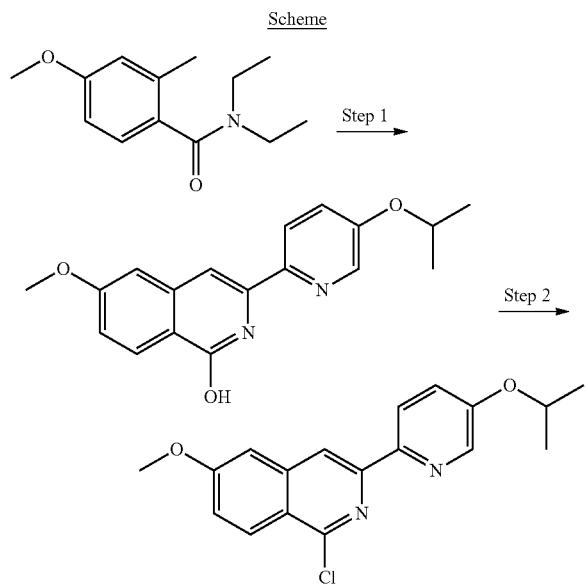

Step 1:
To a solution of N,N-diethyl-4-methoxy-2-methylbenzamide (4.43 g, 20 mmol) in THF (100 ml) at −78° C., tert-butyllithium 1.7 M in pentane (17.65 ml, 30.0 mmol) solution was added dropwise. The reaction mixture was stirred for 0.5 h before addition of 5-isopropoxypicolinonitrile (3.41 g, 21.00 mmol) in THF (2 mL). The resulting solution was warmed to rt and stirred for 16 h. The reaction mixture was quenched with water, neutralized with 1 N HCl. The precipitated solid (5 g) was collected and washed with water to give the product 3-(5-isopropoxypyridin-2-yl)-6-methoxyisoquinolin-1-ol 4 g as a white solid. MS: MS m/z 311.11 (M$^+$+1).

Step 2:
A solution of 3-(5-isopropoxypyridin-2-yl)-6-methoxyisoquinolin-1-ol (4 g, 12.89 mmol) in POCl$_3$ (20 mL) was refluxed for 2 hs. After concentration, the residue was taken into the mixture of DCM and 4N NaOH solution. The organic phase was collected and dried over sodium sulfate, filtered, then concentrated under vacuum. The crude material was purified by silica gel chromatography using CH$_2$Cl$_2$ as eluent to give 3.4 g of the desired product 1-chloro-3-(5-isopropoxypyridin-2-yl)-6-methoxyisoquinoline as a solid. $^1$H NMR (400 MHz, CHLOROFORM-d) δ ppm 8.49 (s, 1H), 8.39 (d, J=8.8 Hz, 1H), 8.33 (d, J=2.5 Hz, 1H), 8.19 (d, J=9.1 Hz, 1H), 7.29 (dd, J=8.8, 3.0 Hz, 1H), 7.23 (dd, J=6.8, 2.5 Hz, 1H), 7.16 (d, J=2.3 Hz, 1H), 4.65 (spt, J=6.0 Hz, 1H), 3.94 (s, 3H), 1.38 (d, J=6.3 Hz, 6H).

Preparation of intermediate 1-chloro-3-(6-isopropoxypyridin-3-yl)-6-methoxyisoquinoline

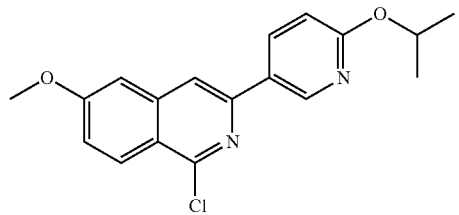 [SMILES: COc1ccc2c(Cl)nc(-c3ccc(OC(C)C)nc3)cc2c1]

Scheme

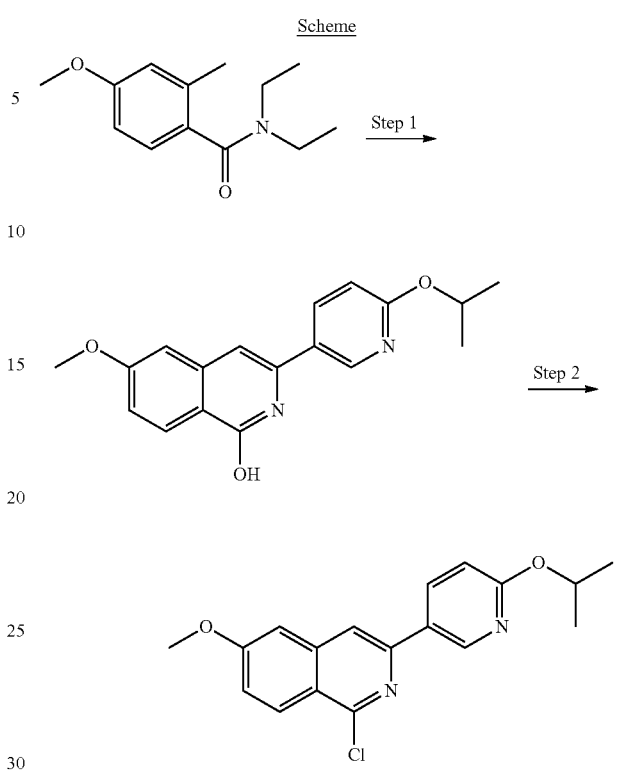

Step 1:
To a solution of N,N-diethyl-4-methoxy-2-methylbenzamide (1 g, 4.52 mmol) in THF (10 ml) at −78° C., tert-butyllithium 1.7 M, in pentane (3.19 ml, 5.42 mmol) was added dropwise. The reaction was stirred for 0.5 h before addition of 6-isopropoxynicotinonitrile (0.733 g, 4.52 mmol) in THF (2 mL). The resulting solution was warmed to rt and stirred for 16 h. The reaction mixture was quenched with water, neutralized with 1 N HCl. The precipitated solid (1.1 g) was collected and washed with water to give 500 mg of the product 3-(6-isopropoxypyridin-3-yl)-6-methoxyisoquinolin-1-ol as a white solid. MS: MS m/z 311.11 (M$^+$+1).

Step 2:
A solution of 3-(6-isopropoxypyridin-3-yl)-6-methoxyisoquinolin-1-ol (400 mg, 1.289 mmol) in POCl$_3$ (5 mL, 53.6 mmol) was refluxed for 14 h. Concentrated the solvent. The residue was taken into a mixture of DCM and 4N NaOH solution. The solution was adjusted PH to 7. The organic phase was collected and dried over sodium sulfate, filtered, then concentrated under vacuum. The crude material was purified by silica gel chromatography using 10% EtOAc/ Hexanes as eluent to give 289 mg of the desired product 1-chloro-3-(6-isopropoxypyridin-3-yl)-6-methoxyisoquinoline as a solid. $^1$H NMR (400 MHz, CHLOROFORM-d) δ ppm 8.83 (dd, J=2.6, 0.6 Hz, 1H), 8.32 (dd, J=8.5, 2.5 Hz, 1H), 8.22 (d, J=9.3 Hz, 1H), 7.82 (s, 1H), 7.253 (dd, J=6.8, 2.5 Hz, 1H), 7.13 (d, J=2.5 Hz, 1H), 6.81 (dd, J=8.7, 0.6 Hz, 1H), 5.40 (quin, J=6.1 Hz, 1H), 4.00 (s, 3H), 1.41 (d, J=6.0 Hz, 6H). MS: MS m/z 329.02 (M$^+$+1).

Preparation of intermediate 1-chloro-3-(2,3-dihydrobenzo[b][1,4]dioxin-6-yl)-6-methoxyisoquinoline

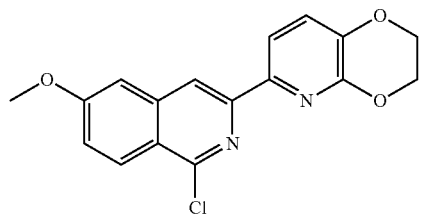 [SMILES: COc1ccc2c(Cl)nc(-c3ccc4c(n3)OCCO4)cc2c1]

Scheme

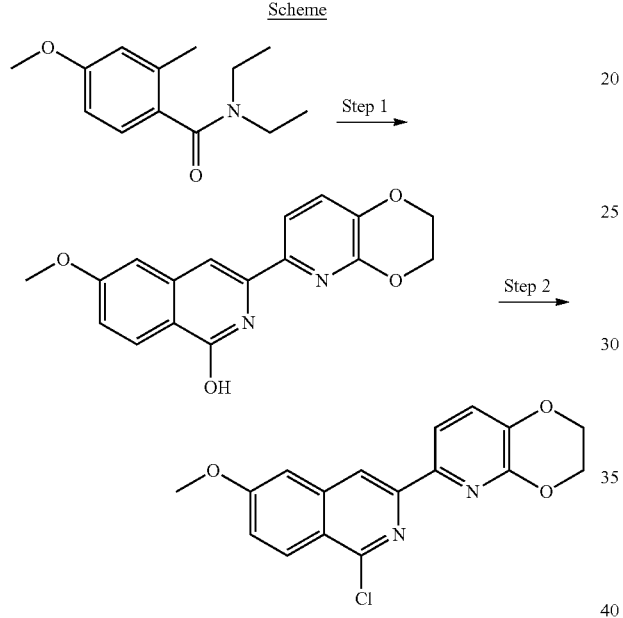

Step 1:
To a solution of N,N-diethyl-4-methoxy-2-methylbenzamide (100 mg, 0.452 mmol) in THF (10 ml) at −78° C., tert-butyllithium 1.7 M in pentane (0.319 ml, 0.542 mmol) was added dropwise. The solution was stirred for 0.5 h before addition of 2,3-dihydrobenzo[b][1,4]dioxine-6-carbonitrile (72.8 mg, 0.452 mmol) in THF (2 mL). The resulting solution was warmed to rt and stirred for 16 h. The reaction mixture was quenched with water, neutralized with 1 N HCl. The precipitated solid was collected and washed with water to give the product 3-(2,3-dihydro-[1,4]dioxino[2,3-b]pyridin-6-yl)-6-methoxyisoquinolin-1-ol 120 mg as a solid after drying. $^1$H NMR (400 MHz, DMSO-$d_6$) δ ppm 8.07 (d, J=8.8 Hz, 1H), 7.31 (d, J=2.3 Hz, 1H), 7.27 (dd, J=8.3, 2.3 Hz, 1H), 7.14 (d, J=2.5 Hz, 1H), 7.02 (dd, J=8.8, 2.5 Hz, 1H), 6.96 (d, J=8.6 Hz, 1H), 6.77 (s, 1H), 4.29 (s, 4H), 3.87 (s, 3H).

Step 2:
A solution of 3-(2,3-dihydrobenzo[b][1,4]dioxin-6-yl)-6-methoxyisoquinolin-1-ol (250 mg, 0.808 mmol) in POCl$_3$ (5 mL, 53.6 mmol) was refluxed for 14 h. Concentrated the solvent. The residue was taken into a mixture of DCM and 4N NaOH solution. Adjust pH to 7. The organic phase was collected and dried over sodium sulfate, filtered, then concentrated under vacuum. The crude material was purified by silica gel chromatography using 10% EtOAc/Hexanes as eluent to give 200 mg of the desired product 1-chloro-3-(2,3-dihydrobenzo[b][1,4]dioxin-6-yl)-6-methoxyisoquinoline as a solid. $^1$H NMR (400 MHz, CHLOROFORM-d) δ ppm 8.18 (d, J=9.3 Hz, 1H), 7.77 (s, 1H), 7.65-7.55 (m, 2H), 7.21 (dd, J=9.2, 2.4 Hz, 1H), 7.08 (d, J=2.3 Hz, 1H), 6.95 (d, J=8.3 Hz, 1H), 4.30 (s, 4H), 3.95 (s, 3H).

Preparation of intermediate 1-fluoro-(4-D3-methoxy)isoquinoline

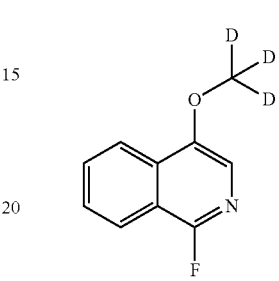

Scheme

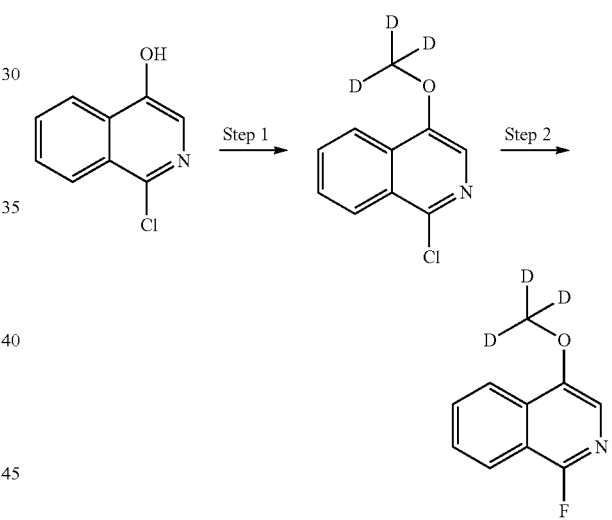

Step 1:
A mixture of 1-chloroisoquinolin-4-ol (898 mg, 5 mmol), CD$_3$I (1450 mg, 10.00 mmol), and K$_2$CO$_3$ (2073 mg, 15.00 mmol) in Acetone (20 mL) was refluxed for 16 h. After filtration, the solid was washed with acetone. The filtrate was concentrated and purified by silica gel chromatography eluting with 10-20% ethyl acetate in hexane to give 300 mg of 1-chloro-(4-D3-methoxy)isoquinoline. MS: MS m/z 197.1 (M$^+$+1).

Step 2:
To a solution of 1-chloro-(4-D3-methoxy)isoquinoline (197 mg, 1 mmol) in DMSO (2 mL), added CsF (304 mg, 2.000 mmol) and the mixture was heated to 140° C. for 4 hrs. The reaction was diluted with ethylactetate and washed with water, and brine. The organic phase was collected, dried over sodium sulfate, and concentrated under vacuum to give the crude product which was purified by silica gel chromatography using a gradient of 5-25% EtOAc/Hexanes. The product fractions were collected and the solvent removed under vacuum to give 180 mg of 1-fluoro-(4-D3-methoxy) isoquinoline as a white solid.

Preparation of intermediate
1-fluoro-4-propoxyisoquinoline

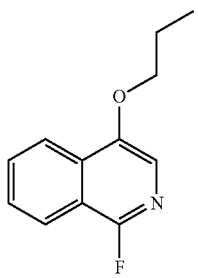

Scheme

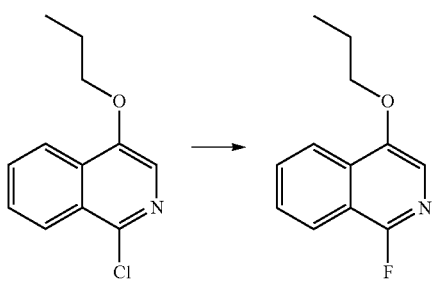

To a solution of 1-chloro-4-propoxyisoquinoline (1.1 g, 4.96 mmol) in DMSO (6 mL), added CsF (1.508 g, 9.92 mmol) and heated to 140° C. for 6 h. The reaction was diluted with ethylactetate and washed with water, and brine. The organic phase was collected, dried over sodium sulfate, and concentrated under vacuum to give the crude product which was purified by silica gel chromatography using a gradient of 5-25% EtOAc/Hexanes. The product fractions were collected and the solvent removed under vacuum to give 700 mg of the desired product 1-fluoro-4-propoxyisoquinoline as a white solid. MS: MS m/z 206.17 (M$^+$+1).

Preparation of intermediate
1-chloro-4-ethoxyphthalazine

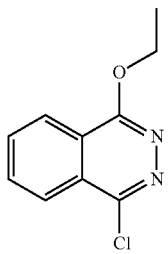

Scheme

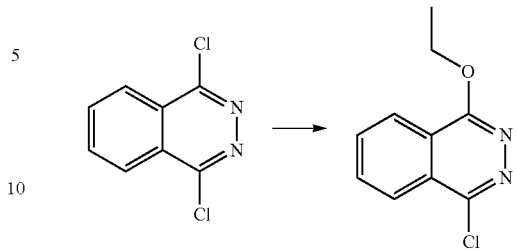

Sodium (33.8 mg, 1.470 mmol) was allowed to react with EtOH (10 mL), then 1,4-dichlorophthalazine (279 mg, 1.4 mmol) was added and the reaction mixture was refluxing for 30 min. The hot solution was filtered and evaporated. The crude product was purified by silica gel chromatography eluting with 20% ethyl acetate in hexane to give 200 mg of the crude product 1-chloro-4-ethoxyphthalazine. $^1$H NMR (400 MHz, CHLOROFORM-d) δ ppm 8.29-8.18 (m, 2H), 7.99-7.90 (m, 2H), 4.73 (q, J=7.1 Hz, 2H), 1.57 (t, J=7.2 Hz, 3H); MS: MS m/z 209.06 (M$^+$+1).

Preparation of intermediate
4-chloro-2-ethylphthalazin-1(2H)-one

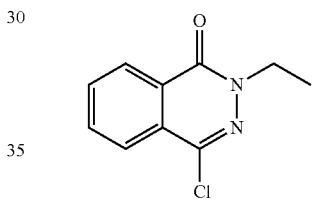

Scheme

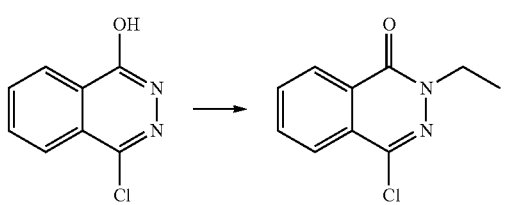

To a suspension of sodium hydride, 60% in mineral oil, (0.480 g, 12.00 mmol) in DMF (50 mL) was added 4-chlorophthalazin-1-ol (1.806 g, 10 mmol) at 0° C. After stirring 30 min, the solution was transferred to a solution of iodoethane (2.339 g, 15.00 mmol) in DMF (50 mL) through a cannula. The formed slurry was stirred at 0° C. for 30 min. The slurry was warmed to rt and stirred for 2 h. The formed light yellow solid was filtered off and washed the cake with THF. The filtrate was diluted with EtOAc, washed with brine, dried over MgSO$_4$, filtered, concentrated to give a residue that was purified by silica gel chromatography eluting with 20% EtOAc in hexanes to afford 1.8 g of the desired product 4-chloro-2-ethylphthalazin-1(2H)-one as an oil. MS: MS m/z 209.06 (M$^+$+1). $^1$H NMR (400 MHz, CHLOROFORM-d) δ ppm 8.52-8.42 (m, 1H), 8.04-7.98 (m, 1H), 7.88 (dtd, J=18.5, 7.5, 1.5 Hz, 2H), 4.29 (q, J=7.1 Hz, 2H), 1.44 (t, J=7.2 Hz, 3H).

Preparation of intermediate
1-chloro-6-propoxyisoquinoline

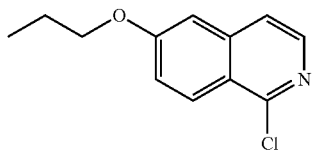

Scheme

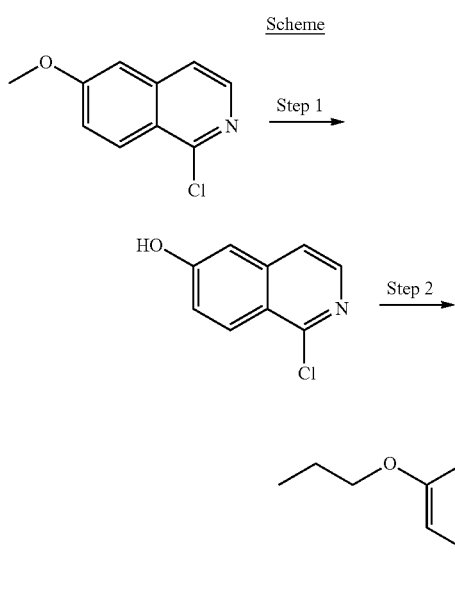

Step 1:

To a solution of 1-chloro-6-methoxyisoquinoline (1.93 g) in CH$_2$Cl$_2$ (30 mL) at −78° C. was added BBr$_3$ (30 mL, 30 mmol) via syringe. After warming to rt, the reaction mixture was stirred for 16 h. The reaction mixture was cooled to −78° C. then quenched with 1 ml of MeOH. After concentration of the solvent, the residue was twice triturated with water to give 1.4 g of the desired product 1-chloroisoquinolin-6-ol as a solid. $^1$H NMR (400 MHz, CDCl$_3$) δ ppm 8.26 (d, J=9.0 Hz, 1H), 8.16 (d, J=5.6 Hz, 1H), 7.43 (d, J=5.9 Hz, 1H), 7.27 (d, J=2.4 Hz, 1H), 7.12 (d, J=2.2 Hz, 1H).

Step 2:

A mixture of 1-chloroisoquinolin-6-ol (0.898 g, 5 mmol), 1-bromopropane (1.230 g, 10.00 mmol), and K$_2$CO$_3$ (2.073 g, 15.00 mmol) in acetone (20 mL) was refluxed for 16 h. The reaction mixture was filtrated and washed with acetone. the filtrate was concentrated and purified by silica gel chromatography eluting with 10-20% ethyl acetate in hexane to give 700 mg of the product 1-chloro-6-propoxy-isoquinoline as a solid. $^1$H NMR (400 MHz, CHLOROFORM-d) δ ppm 8.27-8.16 (m, 2H), 7.48 (d, J=5.8 Hz, 1H), 7.31 (dd, J=9.3, 2.5 Hz, 1H), 7.09 (d, J=2.5 Hz, 1H), 4.09 (t, J=6.5 Hz, 2H), 2.02-1.84 (m, 2H), 1.11 (d, J=14.8 Hz, 1H); MS: MS m/z 222.16 (M$^+$+1).

Preparation of intermediate
1-chloro-6-isopropoxyisoquinoline

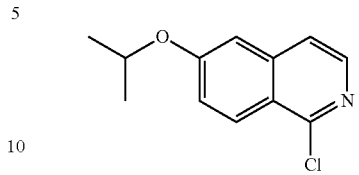

A mixture of 1-chloroisoquinolin-6-ol (898 mg, 5 mmol), 2-iodopropane (1700 mg, 10.00 mmol), and K$_2$CO$_3$ (2073 mg, 15.00 mmol) in acetone (20 mL) was refluxed for 16 h. The reaction mixture was filtrated and washed with acetone. the filtrate was concentrated and purified by silica gel chromatography eluting with 10-20% ethyl acetate in hexane to give 650 mg of the product 1-chloro-6-isopropoxyisoquinoline as a solid. $^1$H NMR (400 MHz, CHLOROFORM-d) δ ppm 8.30-8.13 (m, 2H), 7.47 (d, J=5.3 Hz, 1H), 7.27 (d, J=2.5 Hz, 1H), 7.09 (d, J=2.5 Hz, 1H), 4.77 (dt, J=12.2, 6.1 Hz, 1H), 1.45 (d, J=6.0 Hz, 6H); MS: MS m/z 222.16 (M$^+$+1).

Preparation of 1-chloro-3-methoxyisoquinoline

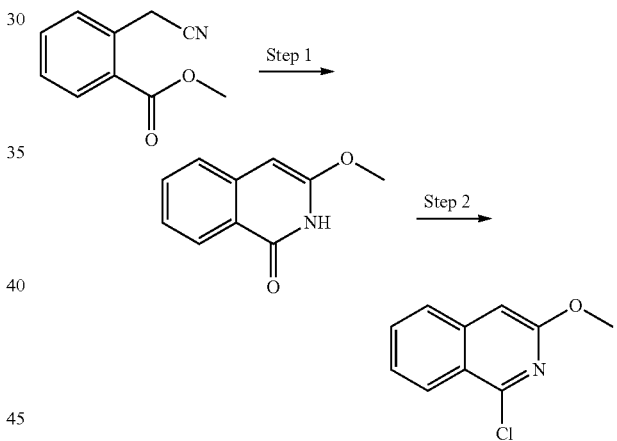

Step 1:

A mixture of methyl 2-(cyanomethyl)benzoate (3.50 g, 20 mmol) and sodium methoxide (10 mL, 25% wt in methanol) in 35 mL MeOH was heated to reflux under nitrogen for 3 h. While still hot, the solution was acidified with 1N HCl solution until the green solution turned to yellow color and a lot of white solid precipitated out. After cooling, the precipitated product was collected by filtration, washed with water and dried to yield the desired product 3-methoxyisoquinolin-1(2H)-one as a white solid (2.8 g, 80%). MS: MS m/z 176.1 (M$^+$+1).

Step 2:

3-Methoxyisoquinolin-1(2H)-one (2.8 g, 16.0 mmol) in POCl$_3$ (10 mL) was heated to reflux for 3 h then evaporated in vacuo. The residue was poured into iced NaHCO$_3$ solution (50 mL). The product was extracted with EtOAc (2×). The organic layer was washed with brine, dried over MgSO$_4$, filtered, evaporated. The residue was purified by flash chromatography with 20% then 40% of EtOAc/hexane to afford 1.36 g (44%) of the desired product 1-chloro-3- methoxyisoquinoline as a white solid. ¹H NMR (400 MHz, CHLOROFORM-d) δ ppm 8.29-8.16 (d, J=8.3 Hz, 1H), 7.72 (d, J=8.3 Hz, 1H), 7.63 (ddd, J=8.3, 6.8, 1.1 Hz, 1H), 7.47 (ddd, J=8.5, 7.0, 1.1 Hz, 1H), 6.98 (s, 1H), 4.05 (s, 3H). MS: MS m/z 194.0 (M⁺+1).

Preparation of
6-chloro-3,4-dihydro-2H-pyrano[3,2-c]isoquinoline

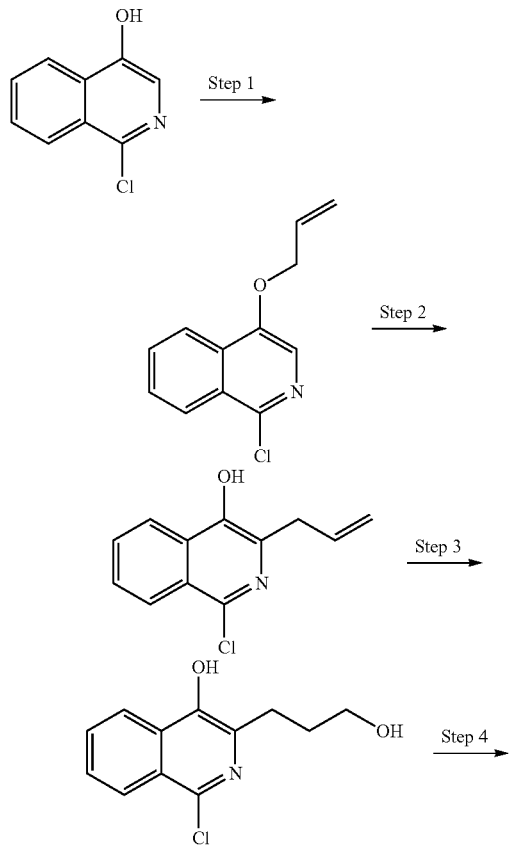

Step 1:
To a stirring solution of NaH (0.334 g, 8.35 mmol) in DMF (10 mL) at 0° C. was added 1-chloroisoquinolin-4-ol (1 g, 5.57 mmol). The mixture was stirred at 0° C. for 10 min. before the addition of allyl bromide (0.808 g, 6.68 mmol) dropwise. The reaction mixture was stirred at rt for 1 h. The reaction mixture was diluted with ethyl acetate and then quenched with 1N HCl solution. The organic layer was washed with brine, dried over MgSO₄, filtered and evaporated to get the crude material. The material was purified by flash chromatography with 20% of EtOAc/hexane to afford 4-(allyloxy)-1-chloroisoquinoline (1.0 g, 4.55 mmol, 83% yield) as a white solid. MS: MS m/z 220.1 (M⁺+1).
Step 2:
4-(allyloxy)-1-chloroisoquinoline (1.0 g, 4.55 mmol) was dissolved in diglyme (5 mL) and heated to 180° C. for 1 h. The reaction was cooled down to rt before adding EtOAc and water. Washed EtOAc layer with water then brine solution. The organic layer was then dried and concentrated. The residue was purified by flash chromatography with 20% of EtOAc/hexane to afford 3-allyl-1-chloroisoquinolin-4-ol (670 mg, 67%) as product. MS: MS m/z 220.1 (M⁺+1).
Step 3:
To a stirred solution of 3-allyl-1-chloroisoquinolin-4-ol (670 mg, 3.05 mmol) in dry tetrahydrofuran (5 mL) at room temperature was added 0.5 M in THF solution of 9-BBN (18.30 mL, 9.15 mmol) and the mixture was stirred for overnight. 3N NaOH (9.15 mL, 27.5 mmol) and H₂O₂ (2.83 mL, 30.5 mmol) were then added to the mixture. The mixture was stirred for 45 min before quenching with sat. NaCl solution. 1 N HCl was then added to the solution to adjust PH<7. The reaction was extracted with EtOAc. The organic layer was washed with brine, dried and concentrated to afford a yellow oil that was purified by silica gel chromatography using 20-40% EtOAc/hexane to obtain 1-chloro-3-(3-hydroxypropyl)isoquinolin-4-ol (520 mg, 70%) as product. MS: MS m/z 238.0 (M⁺+1).
Step 4:
To a solution of triphenylphosphine (1.03 g, 3.94 mmol) and 1-chloro-3-(3-hydroxypropyl)isoquinolin-4-ol (520 mg, 2.18 mmol) in THF (2 mL) at 0° C. was added diisopropyl azodicarboxylate (0.85 mL, 4.38 mmol) dropwise. The resulting solution was stirred for 4 h at rt. After concentration of solvent, the residue was purified by silica gel chromatography eluting with 0%-20% ethyl acetate in hexane to give the desired product 6-chloro-3,4-dihydro-2H-pyrano[3,2-c]isoquinoline (350 mg, 73%) as a white solid. ¹H NMR (400 MHz, CHLOROFORM-d) δ ppm 8.27-8.20 (m, 1H), 8.13 (d, J=8.3 Hz, 1H), 7.73 (ddd, J=8.2, 6.8, 1.3 Hz, 1H), 7.67-7.60 (m, 1H), 4.45-4.31 (m, 2H), 3.07 (t, J=6.5 Hz, 2H), 2.29-2.15 (m, 2H); MS: MS m/z 220.0 (M⁺+1).

Preparation of
4-chloro-7-methoxy-N,N-dimethylquinazolin-2-amine

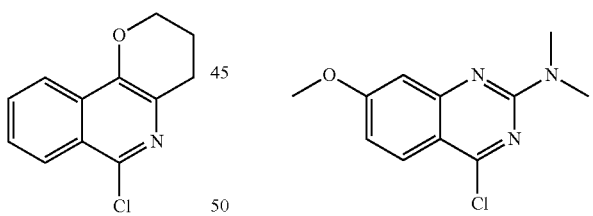

Scheme

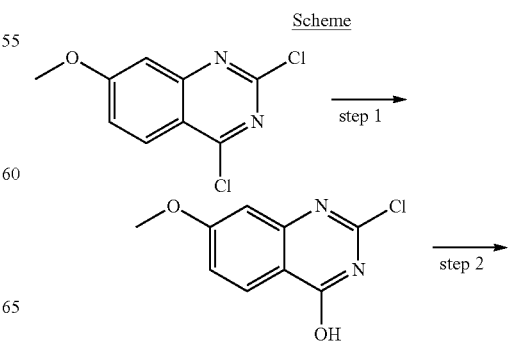

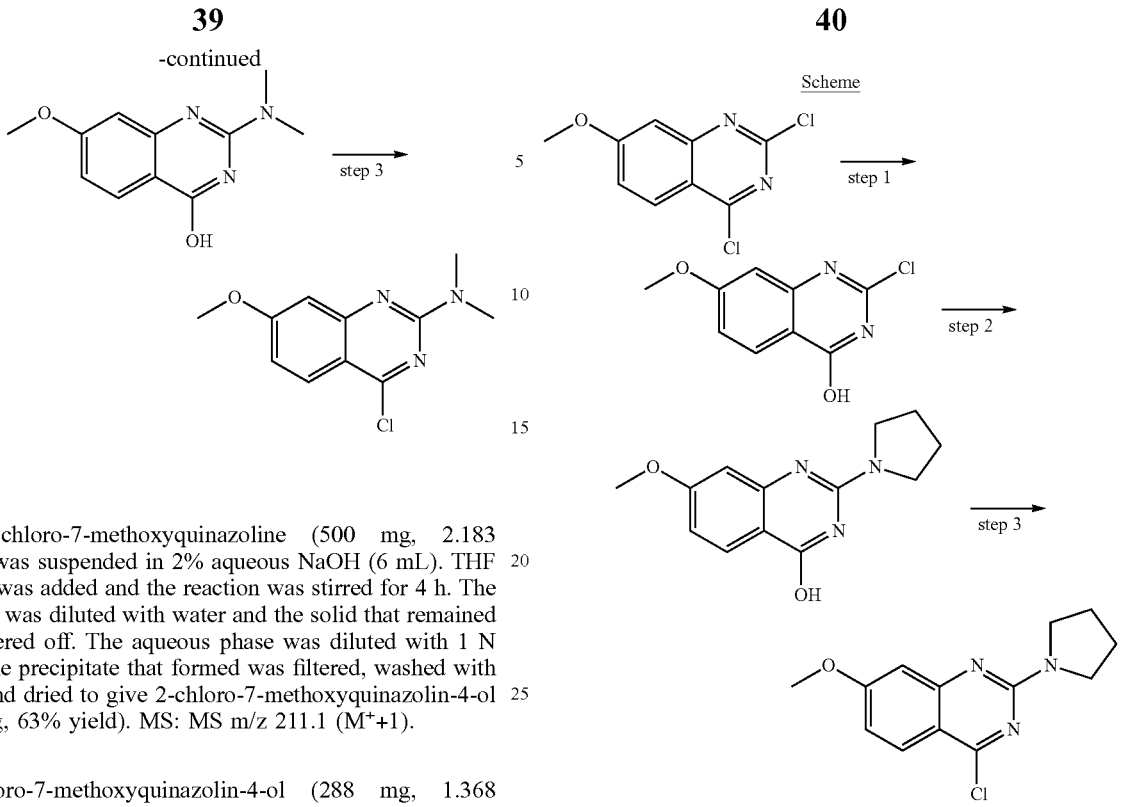

Step 1:

2,4-dichloro-7-methoxyquinazoline (500 mg, 2.183 mmol) was suspended in 2% aqueous NaOH (6 mL). THF (1 mL) was added and the reaction was stirred for 4 h. The reaction was diluted with water and the solid that remained was filtered off. The aqueous phase was diluted with 1 N HCl. The precipitate that formed was filtered, washed with water and dried to give 2-chloro-7-methoxyquinazolin-4-ol (288 mg, 63% yield). MS: MS m/z 211.1 ($M^+$+1).

Step 2:

2-chloro-7-methoxyquinazolin-4-ol (288 mg, 1.368 mmol) was dissolved in Dimethylamine 2 M in THF (2 ml, 4.00 mmol) and heated to 100° C. for 1 h in a sealed tube. The reaction was cooled and the volatiles were removed under vacuum. The crude solid was collected and washed with water, filtered and dried to give 2-(dimethylamino)-7-methoxyquinazolin-4-ol which was carried to the next step without further purification. MS: MS m/z 220.1 ($M^+$+1).

Step 3:

A solution of 2-(dimethylamino)-7-methoxyquinazolin-4-ol (300 mg, 1.368 mmol) in $POCl_3$ (2 ml, 21.46 mmol) was refluxed at 90° C. for 4 h. The reaction mixture was concentrated. The residue was dissolved in DCM and the pH was adjusted to 7 with 4N NaOH. The organic phase was collected and dried over sodium sulfate, filtered, then concentrated under vacuum. The crude material was purified by silica gel chromatography using DCM as eluent. The product fractions were collected and the solvent removed under vacuum to give 4-chloro-7-methoxy-2-(pyrrolidin-1-yl)quinazoline (325 mg, 100% yield). $^1$H NMR (400 MHz, CHLOROFORM-d) δ ppm 8.29 (d, J=2.1 Hz, 1H), 7.97 (d, J=9.3 Hz, 1H), 7.07 (dd, J=9.2, 2.1 Hz, 1H), 4.08 (s, 3H), 3.71 (s, 3H), 3.49 (s, 3H); MS: MS m/z 238.0 ($M^+$+1).

Preparation of
4-chloro-7-methoxy-2-(pyrrolidin-1-yl)quinazoline

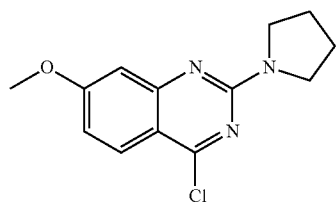 [SMILES: COc1ccc2c(Cl)nc(N3CCCC3)nc2c1]

Step 1:

2,4-dichloro-7-methoxyquinazoline (500 mg, 2.183 mmol) was suspended in 2% aqueous NaOH (6 mL). THF (1 mL) was added and the reaction was stirred for 4 h. The reaction was diluted with water and the solid that remained was filtered off. The aqueous phase was diluted with 1 N HCl. The precipitate that formed was filtered, washed with water and dried to give 2-chloro-7-methoxyquinazolin-4-ol (288 mg, 63% yield). MS: MS m/z 211.1 ($M^+$+1).

Step 2:

2-chloro-7-methoxyquinazolin-4-ol (165 mg, 0.783 mmol) and pyrolidine (0.130 mL, 1.567 mmol) were dissolved in THF (2 mL) and heated to 100° C. for 2 h in a sealed tube. The reaction was cooled and the volatiles were removed under vacuum. The crude solid was collected and washed with water, filtered and dried to give 7-methoxy-2-(pyrrolidin-1-yl)quinazolin-4-ol which was carried to the next step without further purification. MS: MS m/z 246.2 ($M^+$+1).

Step 3:

A solution of 7-methoxy-2-(pyrrolidin-1-yl)quinazolin-4-ol (155 mg, 0.632 mmol) in $POCl_3$ (2 ml, 21.46 mmol) was refluxed at 90° C. for 4 h. The reaction mixture was concentrated. The residue was dissolved in DCM and the pH was adjusted to 7 with 4N NaOH. The organic phase was collected and dried over sodium sulfate, filtered, then concentrated under vacuum. The crude material was purified by silica gel chromatography using 50% DCM in hexanes. The product fractions were collected and the solvent was removed under vacuum to give 4-chloro-7-methoxy-2-(pyrrolidin-1-yl)quinazoline (140 mg, 84% yield). $^1$H NMR (400 MHz, CHLOROFORM-d) δ ppm 7.86 (d, J=9.0 Hz, 1H), 6.91 (d, J=2.3 Hz, 1H), 6.82 (dd, J=9.0, 2.5 Hz, 1H), 3.92 (s, 3H), 3.69 (br. s., 4H), 2.03 (t, J=6.8 Hz, 4H); MS: MS m/z 264.1 ($M^+$+1).

Preparation of 4-chloro-2,7-dimethoxyquinazoline

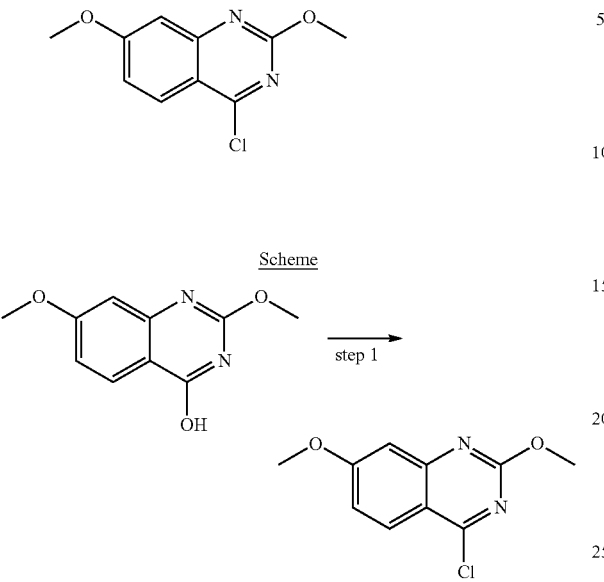

Step 1:

A solution of 2,7-dimethoxyquinazolin-4-ol (155 mg, 0.752 mmol) in POCl$_3$ (2 ml, 21.46 mmol) was refluxed for 4 h. The reaction mixture was concentrated. The residue was dissolved in DCM and the pH was adjusted to 7 with 4N NaOH. The organic phase was collected and dried over sodium sulfate, filtered, then concentrated under vacuum. The crude material was purified by silica gel chromatography using 50% DCM in hexanes. The product fractions were collected and the solvent removed under vacuum to give 4-chloro-2,7-dimethoxyquinazoline (61 mg, 36% yield). MS: MS m/z 225.1 (M$^+$+1).

Preparation of 4-chloro-2-(4-isopropoxyphenyl)-7-methoxyquinazoline

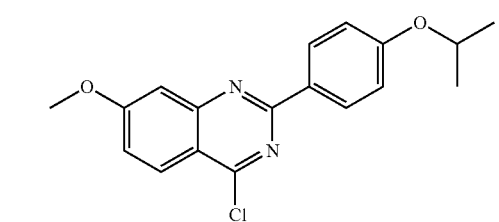 [SMILES: COc1ccc2c(Cl)nc(-c3ccc(OC(C)C)cc3)nc2c1]

Scheme

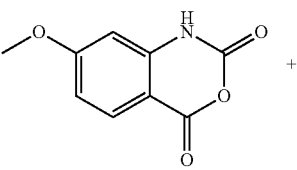

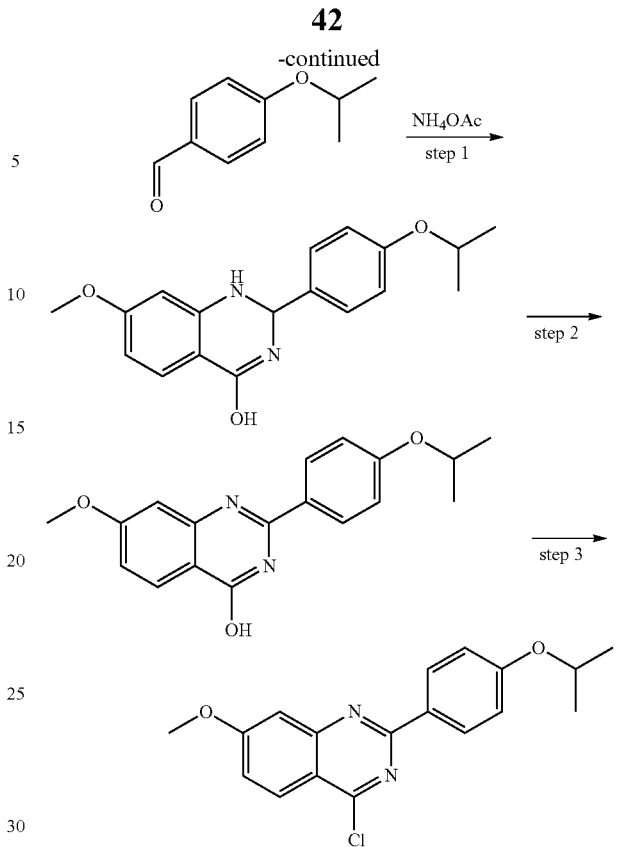

Step 1:

7-methoxy-1H-benzo[d][1,3]oxazine-2,4-dione (0.5 g, 2.59 mmol), 4-isopropoxybenzaldehyde (0.425 g, 2.59 mmol), and ammonium acetate (0.239 g, 3.11 mmol) were dissolved in EtOH (1 mL) and heated at 80° C. for 0.5 h. The solvent was removed under vacuum and the crude material was purified by silica gel chromatography using a gradient of 40-100% EtOAc in Hexanes. The product fractions were collected and concentrated under vacuum to give 2-(4-isopropoxyphenyl)-7-methoxy-1,2-dihydroquinazolin-4-ol (685 mg, 85% yield). MS: MS m/z 313.2 (M$^+$+1).

Step 2:

2-(4-isopropoxyphenyl)-7-methoxy-1,2-dihydroquinazolin-4-ol (685 mg, 2.193 mmol) was dissolved in DCM (10 mL) followed by the addition of DDQ (597 mg, 2.63 mmol). The reaction was stirred for 1 h. The reaction was diluted with DCM and filtered through celite. The filtrate was collected and concentrated under vacuum. The crude material was purified by silica gel chromatography using 40% EtOAc in hexanes. The product fractions were collected and the solvent removed under vacuum to give 2-(4-isopropoxyphenyl)-7-methoxyquinazolin-4-ol (495, 73% yield). MS: MS m/z 311.1 (M$^+$+1).

Step 3:

A solution of 2-(4-isopropoxyphenyl)-7-methoxyquinazolin-4-ol (495 mg, 1.595 mmol) in POCl$_3$ (2 ml, 21.46 mmol) was refluxed for 4 h. The reaction mixture was concentrated. The residue was dissolved in DCM and the pH was adjusted to 7 with 4N NaOH. The organic phase was collected and dried over sodium sulfate, filtered, then concentrated under vacuum. The crude material was purified by silica gel chromatography using 50% DCM in hexanes. The product fractions were collected and the solvent was removed under vacuum to give 4-chloro-2-(4-isopropoxyphenyl)-7-methoxyquinazoline (420 mg, 80% yield). $^1$H NMR (400 MHz, CHLOROFORM-d) δ ppm 8.59-8.53 (m, 2H), 8.11 (d, J=9.3 Hz, 1H), 7.24 (dd, J=9.2, 2.4 Hz, 1H), 7.04-7.00 (m, 3H), 4.70 (quin, J=6.0 Hz, 1H), 4.03 (s, 3H), 1.40 (d, J=6.0 Hz, 6H); MS: MS m/z 329.1 (M$^+$+1).

Preparation of 1,7-difluoro-3-(4-isopropoxyphenyl)-6-methoxyisoquinoline

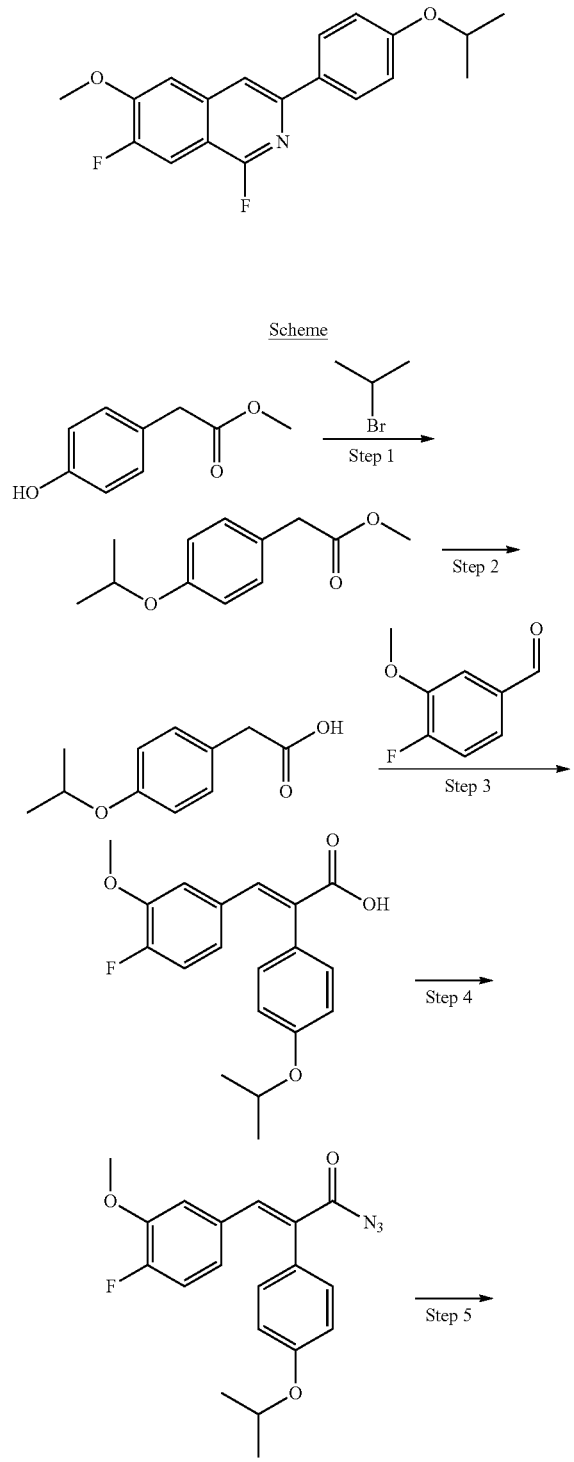

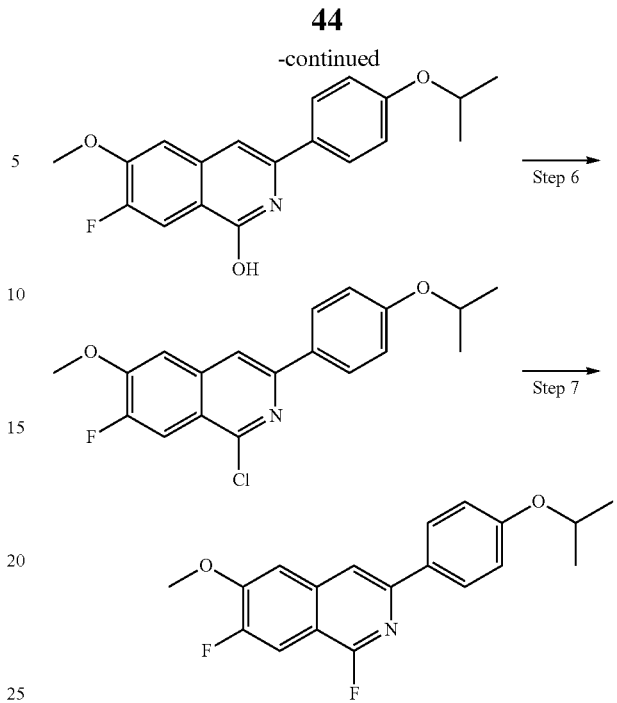

Step 1:

Methyl 2-(4-hydroxyphenyl)acetate (10 g, 60.2 mmol), 2-bromopropane (6.49 mL, 69.2 mmol), and potassium carbonate (8.32 g, 60.2 mmol) were heated to 50° C. in DMF (100 mL) for overnight. The reaction was filtered and the organic layer was concentrated under vacuum. The crude material was purified by silica gel chromatography using a gradient of 0-20% EtOAc/hexanes. The product fractions were collected and the solvent removed under vacuum to give methyl 2-(4-isopropoxyphenyl)acetate (10 g, 80% yield). $^1$H NMR (400 MHz, CHLOROFORM-d) δ ppm 7.22-7.14 (m, 2H), 6.88-6.82 (m, 2H), 4.53 (spt, J=6.1 Hz, 1H), 3.70 (s, 3H), 3.57 (s, 2H), 1.34 (d, J=6.0 Hz, 6H).

Step 2:

Methyl 2-(4-isopropoxyphenyl)acetate (10 g, 48.0 mmol), and NaOH (5.76 g, 144 mmol) were heated in methanol (50 mL)/Water (50 mL) solution at reflux for 2 h. Most of the MeOH was removed under vacuum and the remaining aqueous solution was acidified with 1 N HCl. The solid that precipitated from the solution was extracted into EtOAc solution. The organic layer was collected, dried over sodium sulfate, and concentrated under vacuum to give 2-(4-isopropoxyphenyl)acetic acid (8.9 g, 95% yield). $^1$H NMR (400 MHz, CHLOROFORM-d) δ ppm 7.22-7.16 (m, 2H), 6.88-6.83 (m, 2H), 4.53 (spt, J=6.1 Hz, 1H), 3.59 (s, 2H), 1.34 (d, J=6.0 Hz, 6H).

Step 3:

2-(4-isopropoxyphenyl)acetic acid (3.97 g, 20.44 mmol), 4-fluoro-3-methoxybenzaldehyde (3.15 g, 20.44 mmol), Ac2O (3.47 ml, 36.8 mmol), and Et3N (1.994 ml, 14.31 mmol) were heated to 110° C. for 16 h. The reaction was cooled down to rt and diluted with water and EtOAc. The organic layer was collected, dried over sodium sulfate, and concentrated under vacuum. The crude material was purified by silica gel chromatography using 10-20% EtOAc/Hexanes. The product fractions were collected and the solvent removed under vacuum to give (E)-3-(4-fluoro-3-methoxyphenyl)-2-(4-isopropoxyphenyl)acrylic acid (4.4 g, 65% yield). $^1$H NMR (400 MHz, CHLOROFORM-d) δ ppm 7.85 (s, 1H), 7.22-7.16 (m, 2H), 6.98-6.91 (m, 3H), 6.82

(ddd, J=8.3, 4.6, 2.1 Hz, 1H), 6.63 (dd, J=8.5, 2.0 Hz, 1H), 4.64-4.54 (m, 1H), 3.51 (s, 3H), 1.39-1.35 (m, 6H).

Step 4:

(E)-3-(4-fluoro-3-methoxyphenyl)-2-(4-isopropoxyphenyl)acrylic acid (4.38 g, 13.26 mmol), (PhO)$_2$PON$_3$ (2.71 mL, 12.60 mmol), and Et3N (3.70 mL, 26.5 mmol) were dissolved in benzene and stirred for 16 h. The solution was concentrated under vacuum and the residue was purified by silica gel chromatography using 20% EtOAc/Hexanes to give (E)-3-(4-fluoro-3-methoxyphenyl)-2-(4-isopropoxyphenyl)acryloyl azide (2.3 g, 49% yield). $^1$H NMR (400 MHz, CHLOROFORM-d) δ ppm 7.80 (s, 1H), 7.16-7.11 (m, 2H), 6.97-6.92 (m, 2H), 6.84-6.78 (m, 1H), 6.63-6.53 (m, 2H), 4.63-4.54 (m, 1H), 3.49 (s, 3H), 1.38-1.35 (m, 6H).

Step 5:

A mixture of (E)-3-(4-fluoro-3-methoxyphenyl)-2-(4-isopropoxyphenyl)acryloyl azide (2.3 g, 6.47 mmol) in PhCH$_2$Ph (30 ml) was slowly heated to 80° C. for 1 h and then to reflux for 3 h. After cooling to rt, the solid was collected, washed with benzene and dried under vacuum to give 7-fluoro-3-(4-isopropoxyphenyl)-6-methoxyisoquinolin-1-ol (383 mg, 20% yield). $^1$H NMR (400 MHz, DMSO-d$_6$) δ ppm 7.83 (d, J=11.8 Hz, 1H), 7.70 (d, J=8.8 Hz, 2H), 7.40 (d, J=8.3 Hz, 1H), 7.03 (d, J=8.8 Hz, 2H), 6.82 (s, 1H), 4.72 (quin, J=6.0 Hz, 1H), 3.98 (s, 3H), 1.31 (d, J=6.0 Hz, 6H).

Step 6:

A solution of 7-fluoro-3-(4-isopropoxyphenyl)-6-methoxyisoquinolin-1-ol (1.8 g, 5.50 mmol) in POCl$_3$ (7.69 ml, 82 mmol) was refluxed for 4 h. The reaction mixture was concentrated. The residue was dissolved in DCM and the pH was adjusted to 7 with 4N NaOH. The organic phase was collected and dried over sodium sulfate, filtered, then concentrated under vacuum. The crude material was purified by silica gel chromatography using 50% DCM in hexanes. The product fractions were collected and the solvent removed under vacuum to give 1-chloro-7-fluoro-3-(4-isopropoxyphenyl)-6-methoxyisoquinoline (1.8 g, 95% yield). MS: MS m/z 346.1 (M$^+$+1).

Step 7:

To a solution of 1-chloro-7-fluoro-3-(4-isopropoxyphenyl)-6-methoxyisoquinoline (1 g, 2.89 mmol) in DMSO (6 mL), was added CsF (0.879 g, 5.78 mmol) and the mixture was heated to 140° C. for 4 hrs. The reaction was diluted with Ethylactetate and washed with water, and brine. The organic phase was collected, dried over sodium sulfate, and concentrated under vacuum to give the crude product which was purified by silica gel chromatography using 50% DCM/Hexanes. The product fractions were collected and the solvent removed under vacuum to give 1,7-difluoro-3-(4-isopropoxyphenyl)-6-methoxyisoquinoline (750 mg, 79% yield). MS: MS m/z 330.1 (M$^+$+1).

Preparation of 1-chloro-3-(3-chloro-4-methoxyphenyl)-6-methoxyisoquinoline

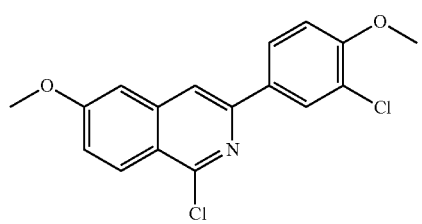

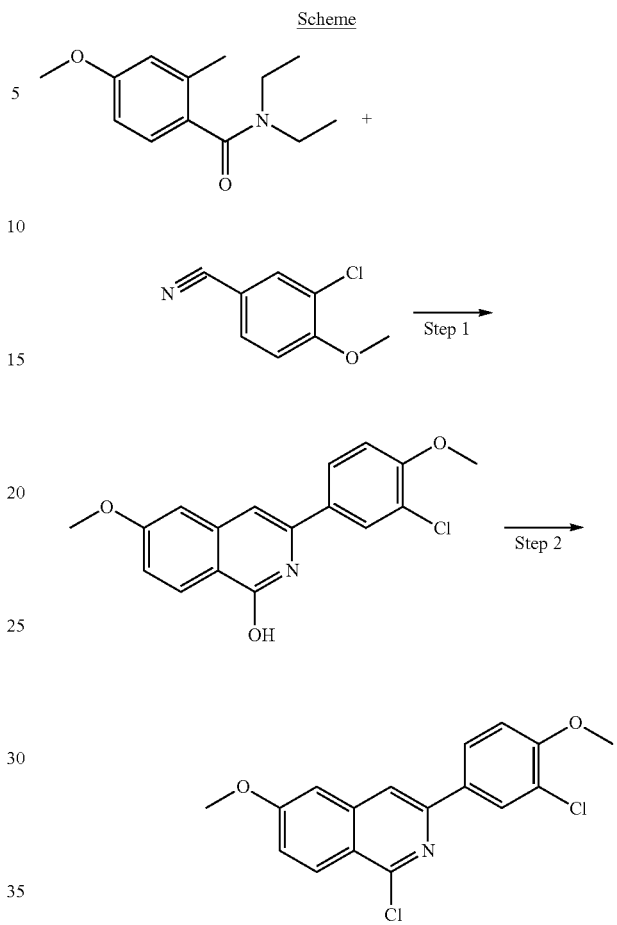

Step 1:

To a solution of N,N-diethyl-4-methoxy-2-methylbenzamide (1 g, 4.52 mmol) in THF (9 ml) at −78° C. was added dropwise tert-butyllithium 1.7 M in pentane (3.19 ml, 5.42 mmol) and the solution was stirred for 0.5 h before addition of 3-chloro-4-methoxybenzonitrile (0.757 g, 4.52 mmol) in THF (9 ml). The resulting solution was warmed to rt and stirred for 16 h. The reaction mixture was quenched with water, neutralized with 1 N HCl. The precipitated solid was collected and washed with water to give 3-(3-chloro-4-methoxyphenyl)-6-methoxyisoquinolin-1-ol (1.2 g, 84% yield) as a solid after drying. MS: MS m/z 316.1 (M$^+$+1).

Step 2:

A solution of 3-(3-chloro-4-methoxyphenyl)-6-methoxyisoquinolin-1-ol (1.2 g, 3.80 mmol) in POCl$_3$ (5.31 ml, 57.0 mmol) was refluxed for 4 h. The reaction mixture was concentrated. The residue was dissolved in DCM and the pH was adjusted to 7 with 4N NaOH. The organic phase was collected and dried over sodium sulfate, filtered, then concentrated under vacuum to give 1-chloro-3-(3-chloro-4-methoxyphenyl)-6-methoxyisoquinoline (1.2 g, 95% yield). δ ppm $^1$H NMR (400 MHz, CHLOROFORM-d) δ 8.22 (d, J=9.3 Hz, 1H), 8.15 (d, J=2.3 Hz, 1H), 8.02 (dd, J=8.7, 2.4 Hz, 1H), 7.27-7.24 (m, 1H), 7.13 (d, J=2.5 Hz, 1H), 7.05 (d, J=8.5 Hz, 1H), 3.99 (s, 6H); MS: MS m/z 334.1 (M$^+$+1).

Preparation of 1-chloro-3-(3-fluoro-4-methoxyphenyl)-6-methoxyisoquinoline

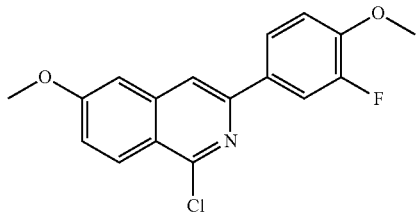

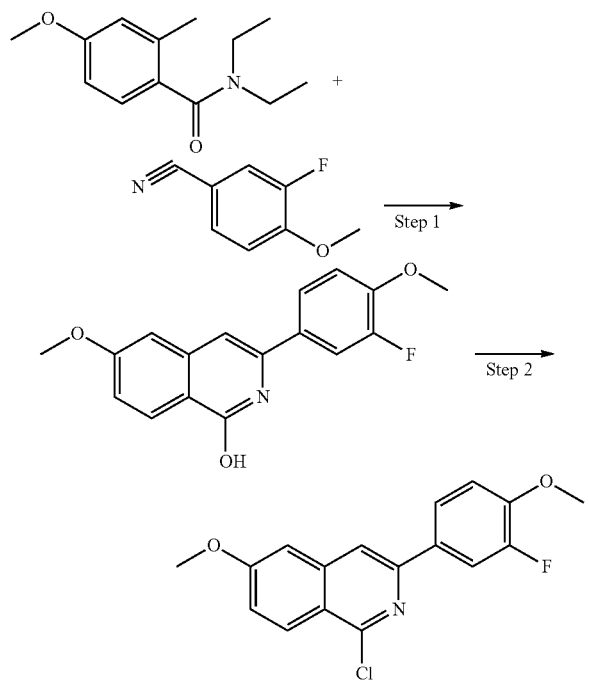

Step 1:
To a solution of N,N-diethyl-4-methoxy-2-methylbenzamide (1.00 g, 4.52 mmol) in THF (9 ml) at −78° C. was added dropwise tert-butyllithium 1.7 M in pentane (3.19 ml, 5.42 mmol) and the solution was stirred for 0.5 h before addition of 3-fluoro-4-methoxybenzonitrile (0.683 g, 4.52 mmol) in THF (9 ml). The resulting solution was warmed to rt and stirred for 16 h. The reaction mixture was quenched with water, neutralized with 1 N HCl. The precipitated solid was collected and washed with water to give 3-(3-fluoro-4-methoxyphenyl)-6-methoxyisoquinolin-1-ol (926 mg, 69% yield) as a solid after drying. MS: MS m/z 300.1 (M$^+$+1).
Step 2:
A solution of 3-(3-fluoro-4-methoxyphenyl)-6-methoxyisoquinolin-1-ol (1.2 g, 4.01 mmol) in POCl$_3$ (5.61 ml, 60.1 mmol) was refluxed for 4 h. The reaction mixture was concentrated. The residue was dissolved in DCM and the pH was adjusted to 7 with 4N NaOH. The organic phase was collected and dried over sodium sulfate, filtered, then concentrated under vacuum to give 1-chloro-3-(3-fluoro-4-methoxyphenyl)-6-methoxyisoquinoline (933 mg, 95% yield). δ ppm $^1$H NMR (400 MHz, CHLOROFORM-d) δ 8.21 (d, J=9.3 Hz, 1H), 7.90-7.87 (m, 1H), 7.86 (s, 1H), 7.81 (s, 1H), 7.27-7.23 (m, 1H), 7.12 (d, J=2.3 Hz, 1H), 7.10-7.04 (m, 1H), 3.98 (d, J=6.0 Hz, 6H); MS: MS m/z 318.1 (M$^+$+1).

Preparation of 1-chloro-3-(3-fluoro-4-isopropoxyphenyl)-6-methoxyisoquinoline

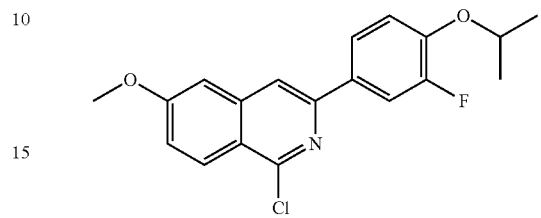

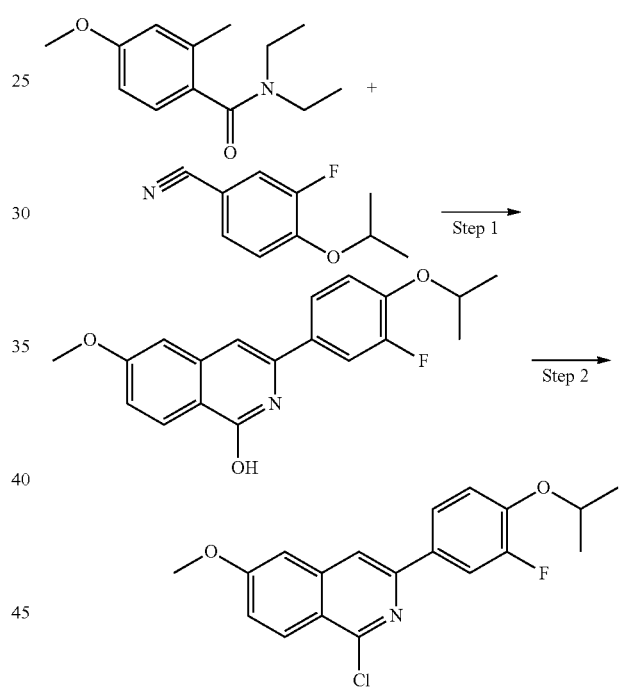

Step 1:
To a solution of N,N-diethyl-4-methoxy-2-methylbenzamide (500 mg, 2.259 mmol) in THF (5 ml) at −78° C. was added dropwise tert-butyllithium 1.7 M in pentane (1595 μl, 2.71 mmol) and the solution was stirred for 0.5 h before addition of 3-fluoro-4-isopropoxybenzonitrile (405 mg, 2.259 mmol) in THF (5 ml). The resulting solution was warmed to rt and stirred for 16 h. The reaction mixture was quenched with water, neutralized with 1 N HCl. The precipitated solid was collected washing with water to give 3-(3-fluoro-4-isopropoxyphenyl)-6-methoxyisoquinolin-1-ol (520 mg, 70% yield) as a solid after drying. MS: MS m/z 328.1 (M$^+$+1).
Step 2:
A solution of 3-(3-fluoro-4-isopropoxyphenyl)-6-methoxyisoquinolin-1-ol (700 mg, 2.138 mmol) in POCl$_3$ (2990 μl, 32.1 mmol) was refluxed for 4 h. The reaction mixture was concentrated. The residue was dissolved in DCM and the pH was adjusted to 7 with 4N NaOH. The organic phase was collected and dried over sodium sulfate, filtered, then concentrated under vacuum. The crude material was purified by silica gel chromatography using 50% DCM in hexanes as eluent. The product fractions were collected and the solvent removed under vacuum to give 1-chloro-3-(4-fluorophenyl)-6-methoxyisoquinoline (665 mg, 90% yield). MS: MS m/z 346.1 (M⁺+1).

Preparation of
1-chloro-3-(4-fluorophenyl)-6-methoxyisoquinoline

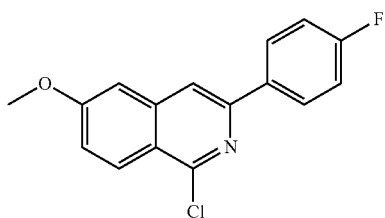 [SMILES: COc1ccc2c(Cl)nc(-c3ccc(F)cc3)cc2c1]

Scheme

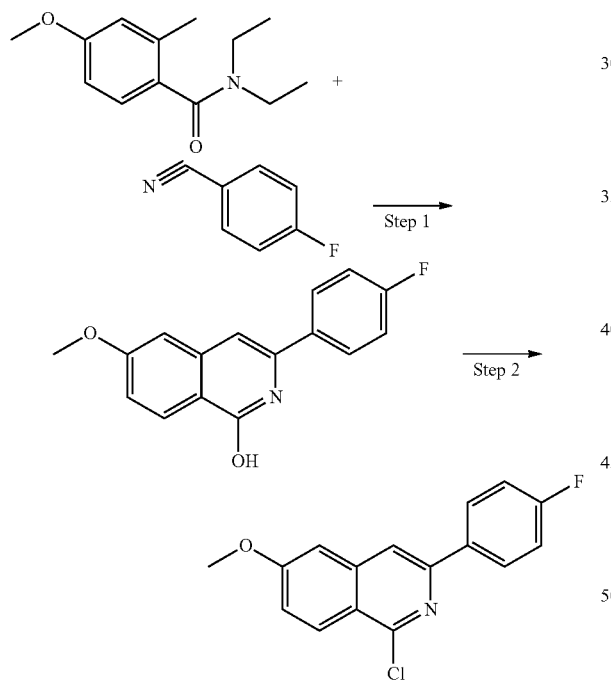

Step 1:

To a solution of N,N-diethyl-4-methoxy-2-methylbenzamide (500 mg, 2.259 mmol) in THF (4.52 ml) at −78° C. was added dropwise tert-butyllithium 1.7 M in pentane (1.59 ml, 2.71 mmol) and the solution was stirred for 0.5 h before addition of 4-fluorobenzonitrile (274 mg, 2.259 mmol) in THF (4.52 ml). The resulting solution was warmed to RT and stirred for 16 h. The reaction mixture was quenched with water, neutralized with 1 N HCl. The precipitated solid was collected and washed with water to give 3-(4-fluorophenyl)-6-methoxyisoquinolin-1-ol (350 mg, 58% yield) as a solid after drying.

Step 2:

A solution of 3-(4-fluorophenyl)-6-methoxyisoquinolin-1-ol (350 mg, 1.300 mmol) in POCl₃ (1.82 ml, 19.50 mmol) was refluxed (90° C.) for 4 h. The reaction mixture was concentrated. The residue was dissolved in DCM and the pH was adjusted to 7 with 4N NaOH. The organic phase was collected and dried over sodium sulfate, filtered, then concentrated under vacuum. The crude material was purified by silica gel chromatography using 50% DCM in Hexanes as eluent. The product fractions were collected and the solvent removed under vacuum to give 1-chloro-3-(4-fluorophenyl)-6-methoxyisoquinoline (340 mg, 91% yield). MS: MS m/z 288.1 (M⁺+1).

Preparation of
4-(1-chloro-6-methoxyisoquinolin-3-yl)morpholine

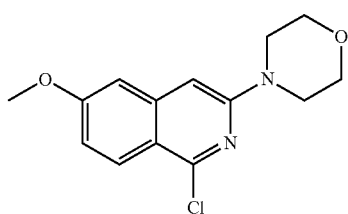 [SMILES: COc1ccc2c(Cl)nc(N3CCOCC3)cc2c1]

Scheme

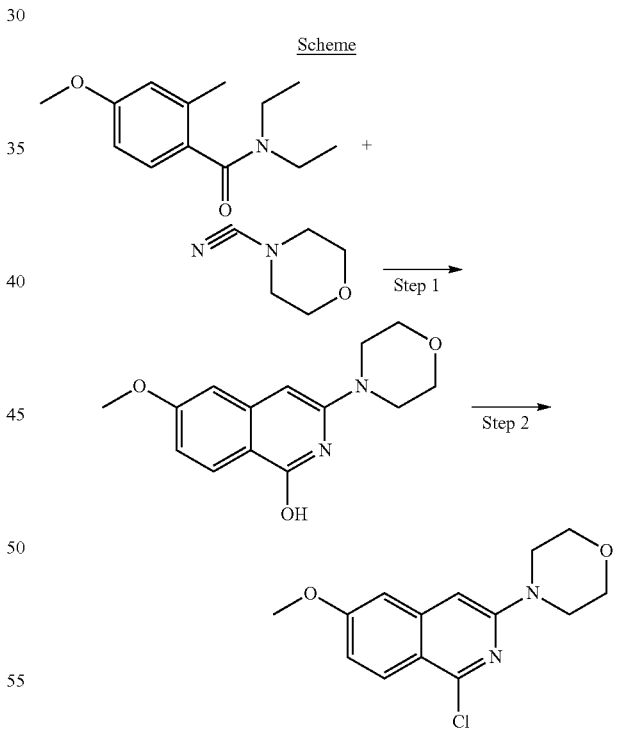

Step 1:

To a solution of N,N-diethyl-4-methoxy-2-methylbenzamide (500 mg, 2.259 mmol) in THF (5 ml) at −78° C. was added dropwise tert-butyllithium 1.7 M in pentane (2658 μl, 4.52 mmol) and the solution was stirred for 0.5 h before addition of morpholine-4-carbonitrile (253 mg, 2.259 mmol) in THF (5 ml). The resulting solution was warmed to rt and stirred for 16 h. The reaction mixture was quenched with water, neutralized with 1 N HCl. The precipitated solid was collected and washed with water to give 6-methoxy-3-morpholinoisoquinolin-1-ol (350 mg, 60% yield) as a solid after drying.

Step 2:

A solution of 6-methoxy-3-morpholinoisoquinolin-1-ol (315 mg, 1.210 mmol) in POCl$_3$ (1692 μl, 18.15 mmol) was refluxed for 4 h. The reaction mixture was concentrated. The residue was dissolved in DCM and the pH was adjusted to 7 with 4N NaOH. The organic phase was collected and dried over sodium sulfate, filtered, then concentrated under vacuum. The crude material was purified by silica gel chromatography using 50% DCM in Hexanes as eluent. The product fractions were collected and the solvent removed under vacuum to give 4-(1-chloro-6-methoxyisoquinolin-3-yl)morpholine (323 mg, 95% yield). $^1$H NMR (400 MHz, CHLOROFORM-d) δ ppm 8.01 (d, J=9.3 Hz, 1H), 6.97 (dd, J=9.3, 2.5 Hz, 1H), 6.86 (d, J=2.5 Hz, 1H), 6.59 (s, 1H), 3.92 (s, 3H), 3.90-3.85 (m, 4H), 3.56-3.50 (m, 4H); MS: MS m/z 279.1 (M$^+$+1).

Preparation of
1-chloro-6-methoxy-N,N-dimethylisoquinolin-3-amine

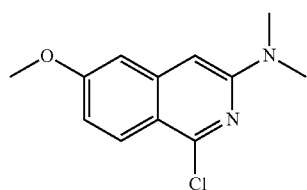

Scheme

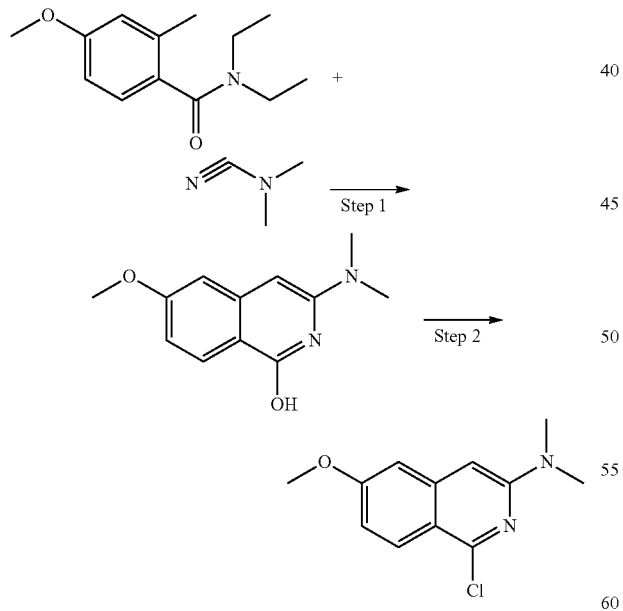

Step 1:

To a solution of N,N-diethyl-4-methoxy-2-methylbenzamide (1000 mg, 4.52 mmol) in THF (10 ml) at −78° C. was added dropwise tert-butyllithium 1.7 M in pentane (5316 μl, 9.04 mmol) and the solution was stirred for 0.5 h before addition of N,N-dimethylcyanamide (317 mg, 4.52 mmol) in THF (10 ml). The resulting solution was warmed to rt and stirred for 16 h. The reaction mixture was quenched with water, neutralized with 1 N HCl, and extracted with EtOAc. The organic layer was collected, dried over sodium sulfate, filtered, followed by removal of solvent under vacuum to give 3-(dimethylamino)-6-methoxyisoquinolin-1-ol (700 mg, 71% yield) which was carried to the next step without further purification. MS: MS m/z 219.1 (M$^+$+1).

Step 2:

A solution of 3-(dimethylamino)-6-methoxyisoquinolin-1-ol (700 mg, 3.21 mmol) in POCl$_3$ (2 ml, 21.46 mmol) was refluxed for 4 h. The reaction mixture was concentrated. The residue was dissolved in DCM and the pH was adjusted to 7 with 4N NaOH. The organic phase was collected and dried over sodium sulfate, filtered, then concentrated under vacuum. The crude material was purified by silica gel chromatography using 50% DCM in hexanes as eluent. The product fractions were collected and the solvent was removed under vacuum to give 1-chloro-6-methoxy-N,N-dimethylisoquinolin-3-amine (400 mg, 53% yield). $^1$H NMR (400 MHz, CHLOROFORM-d) δ ppm 7.96 (d, J=9.3 Hz, 1H), 6.87 (dd, J=9.2, 2.4 Hz, 1H), 6.80 (d, J=2.3 Hz, 1H), 6.43 (s, 1H), 3.91 (s, 3H), 3.14 (s, 6H); MS m/z 237.0 (M$^+$+1).

Preparation of
1-chloro-6-methoxy-3-(pyrrolidin-1-yl)isoquinoline

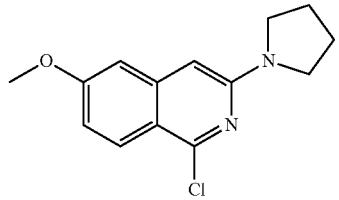 [SMILES: COc1ccc2c(Cl)nc(N3CCCC3)cc2c1]

Scheme

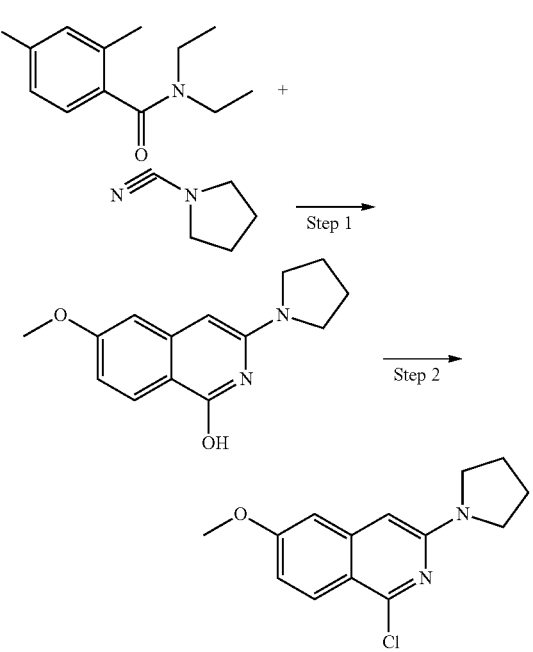

Step 1:
To a solution of N,N-diethyl-4-methoxy-2-methylbenzamide (0.270 g, 1.220 mmol) in THF (10 mL) was added tert-butyllithium (1.077 mL, 1.830 mmol) dropwise at −78° C. After stirring for 0.5 h, pyrrolidine-1-carbonitrile (0.135 mL, 1.342 mmol) was added, then the solution was warmed to rt, and stirred for 16 h. The reaction mixture was quenched with MeOH, neutralized with 1.5 mL of 4.0M HCl in dioxane. Extracted product with 20 mL of DCM. The solution was evaporated on rotovap and then placed under high vacuum for 1 h to give 6-methoxy-3-(pyrrolidin-1-yl)isoquinolin-1-ol (298 mg, 100% yield) which was used in the next step without further purification. MS m/z 245.1 ($M^+$+1).

Step 2:
A solution of 6-methoxy-3-(pyrrolidin-1-yl)isoquinolin-1-ol (300 mg, 1.228 mmol) in POCl$_3$ (8 mL) was refluxed for 4 h. After concentration, the residue was taken into a mixture of 100 mL of DCM and 50 mL of water, cooled to 0° C., neutralized with 3 N NaOH, dried over MgSO4, concentrated and purified via silica gel chromatography (5-20% EtOAc:Hex) to give 1-chloro-6-methoxy-3-(pyrrolidin-1-yl)isoquinoline (156 mg, 48.3% yield) as a yellow solid. $^1$H NMR (500 MHz, CHLOROFORM-d) δ ppm 7.95 (d, J=9.5 Hz, 1H), 6.85 (d, J=9.2 Hz, 1H), 6.80 (s, 1H), 6.43 (br. s., 1H), 3.89 (s, 3H), 3.56-3.49 (m, 4H), 2.08-2.03 (m, 4H); MS m/z 263.1 ($M^+$+1).

Preparation of 1-chloro-6-fluoro-4-methoxyisoquinoline

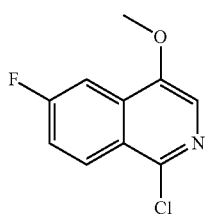

Scheme

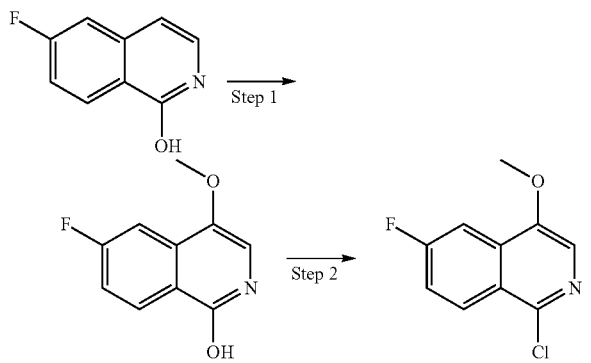

Step 1:
6-fluoroisoquinolin-1-ol (1 g, 6.13 mmol), iodobenzene diacetate (2.172 g, 6.74 mmol) and MeOH (15 ml) were added to a sealed tube. To the mixture was added methanesulfonic acid (0.477 ml, 7.36 mmol). The threaded stopper was affixed to the vessel and the mixture was heated first to 70° C. for 4 h and then to 130° C. for 3 h. The mixture was concentrated in vacuo to remove half of methanol, then 5 mL of water was added and the solid was collected by filtration and washed thoroughly with 1:1 methanol/water then dried in vacuo to give 6-fluoro-4-methoxyisoquinolin-1-ol (800 mg, 68% yield). $^1$H NMR (400 MHz, DMSO-d$_6$) δ ppm 8.27 (dd, J=9.0, 5.8 Hz, 1H), 7.49 (dd, J=10.0, 2.5 Hz, 1H), 7.46-7.42 (m, 1H), 6.83 (d, J=6.3 Hz, 1H), 3.81 (s, 3H); MS m/z 194.1 ($M^+$+1).

Step 2:
A solution of 6-fluoro-4-methoxyisoquinolin-1-ol (2.9 g, 15.01 mmol) in POCl$_3$ (10 ml, 107 mmol) was refluxed for 4 h. The reaction mixture was concentrated. The residue was dissolved in DCM and the pH was adjusted to 7 with 4N NaOH. The organic phase was collected and dried over sodium sulfate, filtered, then concentrated under vacuum. The crude material was purified by silica gel chromatography using 50% DCM in Hexanes as eluent. The product fractions were collected and the solvent removed under vacuum to give 1-chloro-6-fluoro-4-methoxyisoquinoline (2.2 g, 67% yield). $^1$H NMR (400 MHz, CHLOROFORM-d) δ ppm 8.29 (dd, J=9.2, 5.4 Hz, 1H), 7.84-7.79 (m, 2H), 7.45 (ddd, J=9.3, 8.2, 2.6 Hz, 1H), 4.06 (s, 3H); MS m/z 212.0 ($M^+$+1).

Preparation of 1,6-difluoro-4-methoxyisoquinoline

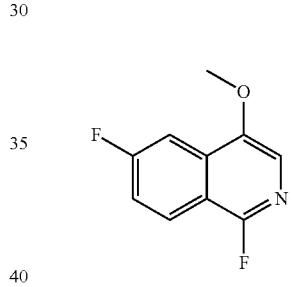

Scheme

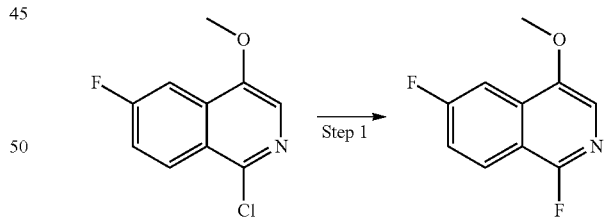

Step 1:
To a solution of 1-chloro-6-fluoro-4-methoxyisoquinoline (115 mg, 0.543 mmol) in DMSO (5 mL), was added CsF (165 mg, 1.087 mmol) and the reaction was heated to 140° C. for 2 h. The reaction was diluted with EtOAc and washed with water, and brine. The organic phase was collected, dried over sodium sulfate, and concentrated under vacuum to give the crude product which was purified by silica gel chromatography using 20-40% DCM in hexanes. The product fractions were collected and the solvent was removed under vacuum to give 1,6-difluoro-4-methoxyisoquinoline (71 mg, 67% yield). MS m/z 196.1 ($M^+$+1).

Preparation of 1-fluoro-4-methoxy-N,N-dimethylisoquinolin-6-amine

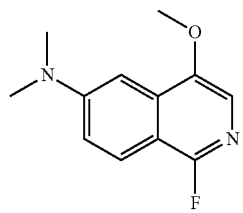 [SMILES: COc1cnc(F)c2ccc(N(C)C)cc12]

Scheme

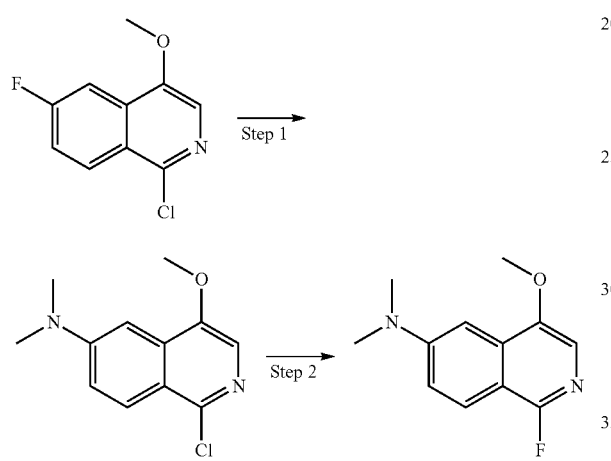

Step 1:

To 1-chloro-6-fluoro-4-methoxyisoquinoline (200 mg, 0.945 mmol) was added dimethylamine 2 M in THF (2 ml, 4.00 mmol) and the solution was heated to 100° C. in a sealed tube for 16 h. The reaction was cooled and the volatiles were removed under vacuum. The crude residue was purified by silica gel chromatography using DCM as eluent. The product factions were collected and the solvent removed under vacuum to give 1-chloro-4-methoxy-N,N-dimethylisoquinolin-6-amine (150 mg, 70% yield). MS m/z 237.1 ($M^+$+1).

Step 2:

To a solution of 1-chloro-4-methoxy-N,N-dimethylisoquinolin-6-amine (250 mg, 1.056 mmol) in DMSO (5 mL) was added tetramethylammonium fluoride (295 mg, 3.17 mmol) and the solution was heated to 110° C. for 1 h. The reaction was diluted with Ethylactetate and washed with water, and brine. The organic phase was collected, dried over sodium sulfate, and concentrated under vacuum to give the crude product which was purified by silica gel chromatography using 80% DCM/hexanes. The product fractions were collected and the solvent removed under vacuum to give 1-fluoro-4-methoxy-N,N-dimethylisoquinolin-6-amine (130 mg, 56% yield). $^1$H NMR (400 MHz, CHLOROFORM-d) δ ppm 8.00 (d, J=9.3 Hz, 1H), 7.37 (d, J=1.3 Hz, 1H), 7.28-7.24 (m, 1H), 7.17 (s, 1H), 4.04 (s, 3H), 3.20 (s, 6H); MS m/z 221.0 ($M^+$+1).

Preparation of 1-chloro-6-ethoxy-4-methoxyisoquinoline

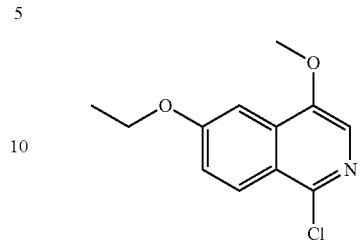

Scheme

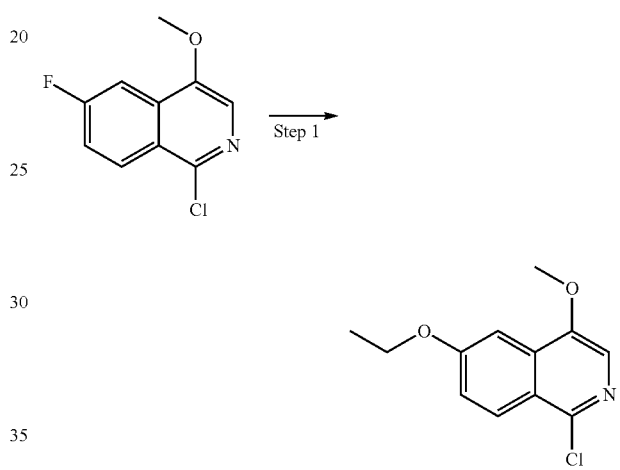

Step 1:

1-chloro-6-fluoro-4-methoxyisoquinoline (533 mg, 2.52 mmol) was dissolved in DMSO (5 mL) then NaOEt (171 mg, 2.52 mmol) was added to the solution. The reaction was stirred for 16 h. The reaction was diluted with EtOAc and washed with 1N HCl, then brine. The organic layer was collected, dried over sodium sulfate and concentrated under vacuum. The crude material was purified by silica gel chromatography using DCM as eluent. The product fractions were collected and solvent was removed under vacuum to give 1-chloro-6-ethoxy-4-methoxyisoquinoline (320 mg, 54% yield). MS m/z 238.0 ($M^+$+1).

Preparation of 1,7-difluoro-5-methoxyisoquinoline

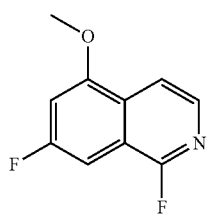

Scheme

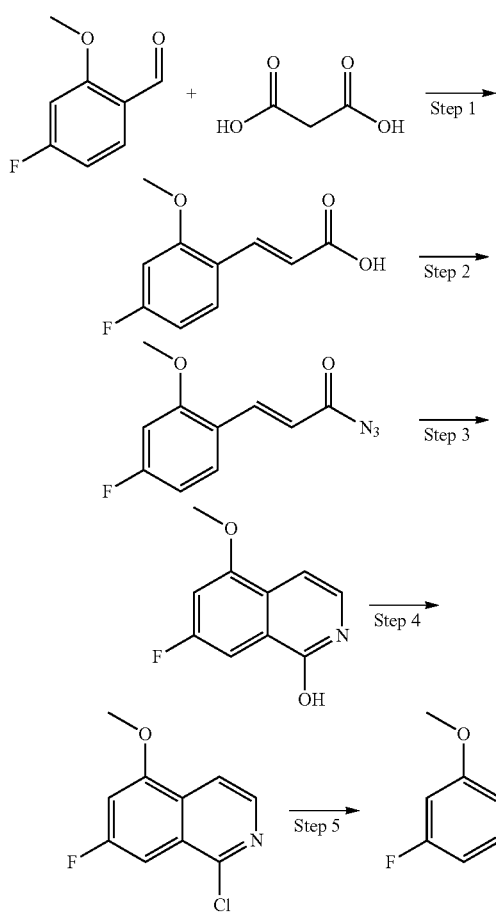

Step 1:

A solution of 4-fluoro-2-methoxybenzaldehyde (1.0 g, 6.49 mmol) and malonic acid (1.350 g, 12.98 mmol) in pyridine (10 mL) was refluxed for 16 h. After concentration the residue was taken into water. The solid was filtered, washed with water, then dried to give (E)-3-(4-fluoro-2-methoxyphenyl)acrylic acid (1.22 g, 96% yield). $^1$H NMR (400 MHz, CHLOROFORM-d) δ ppm 8.03 (d, J=16.1 Hz, 1H), 7.53 (dd, J=8.5, 6.8 Hz, 1H), 6.75-6.65 (m, 2H), 6.52 (d, J=16.1 Hz, 1H), 3.92 (s, 3H).

Step 2:

(E)-3-(4-fluoro-2-methoxyphenyl)acrylic acid (1.22 g, 6.22 mmol), diphenylphosphinyl azide (1.273 mL, 5.91 mmol), and Et3N (1.734 mL, 12.44 mmol) were dissolved in benzene and stirred for 16 h. The solution was concentrated under vacuum and the residue was purified by silica gel chromatography using 20% EtOAc/Hexanes to give (E)-3-(4-fluoro-2-methoxyphenyl)acryloyl azide (1.0 g, 73% yield).

Step 3:

A mixture of (E)-3-(4-fluoro-2-methoxyphenyl)acryloyl azide (1 g, 4.52 mmol) in PhCH$_2$Ph (5 mL) was slowly heated to 80° C. for 1 h and then to reflux for 3 h. After cooling to RT, the solid was collected and washed with benzene to give 7-fluoro-5-methoxyisoquinolin-1-ol (383 mg, 46% yield). MS m/z 194.2 (M$^+$+1).

Step 4:

A solution of 7-fluoro-5-methoxyisoquinolin-1-ol (383 mg, 1.983 mmol) in POCl$_3$ (2772 μl, 29.7 mmol) was refluxed (90° C.) for 4 h. The reaction mixture was concentrated. The residue was dissolved in DCM and the pH was adjusted to 7 with 4N NaOH. The organic phase was collected and dried over sodium sulfate, filtered, then concentrated under vacuum to give 1-chloro-7-fluoro-5-methoxyisoquinoline (399 mg, 95% yield).

Step 5:

To a solution of 1-chloro-7-fluoro-5-methoxyisoquinoline (350 mg, 1.654 mmol) in DMSO (3 mL), was added CsF (502 mg, 3.31 mmol) and the mixture was heated to 140° C. for 4 h. The reaction was diluted with EtOAc and washed with water, and brine. The organic phase was collected, dried over sodium sulfate, and concentrated under vacuum to give 1,7-difluoro-5-methoxyisoquinoline (340 mg, 105% yield) which was not purified further. MS m/z 196.1 (M$^+$+1).

Preparation of 1-chloro-5-methoxyisoquinoline

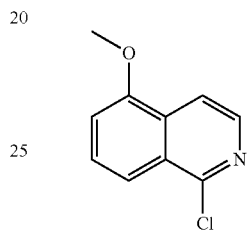

Scheme

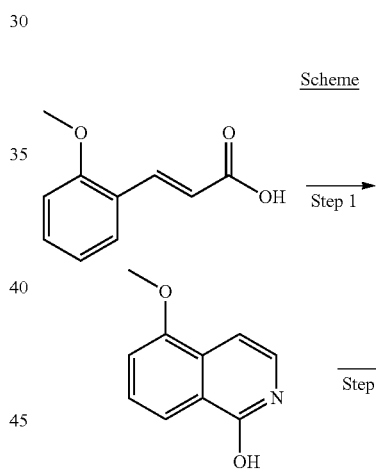

1-chloro-5-methoxyisoquinoline was prepared by a similar method for the preparation of 1,7-difluoro-5-methoxyisoquinoline with the following modifications:

Step 1:

Modification: 10 g of (E)-3-(2-methoxyphenyl)acrylic acid was used instead of (E)-3-(4-fluoro-2-methoxyphenyl) acrylic acid which gave 5-methoxyisoquinolin-1-ol (5.3 g, 53% yield). $^1$H NMR (400 MHz, CD$_3$OD) δ ppm 10.92 (s, 1H), 7.43 (t, J=8.1 Hz, 1H), 7.14 (d, J=7.3 Hz, 1H), 7.08 (d, J=8.1 Hz, 1H), 6.94 (d, J=7.3 Hz, 1H), 3.95 (s, 3H); MS m/z 176.1 (M$^+$+1).

Step 2:

Modifications: 5.3 g 5-methoxyisoquinolin-1-ol used instead of 7-fluoro-5-methoxyisoquinolin-1-ol, 5.38 g 1-chloro-5-methoxyisoquinoline obtained (92% yield). $^1$H NMR (400 MHz, CDCl$_3$) δ ppm 8.25 (d, J=5.9 Hz, 1H), 7.97 (d, J=5.9 Hz, 1H), 7.88 (d, J=8.6 Hz, 1H), 7.57 (t, J=8.1 Hz, 1H), 7.04 (d, J=7.8 Hz, 1H), 4.01 (s, 3H); MS m/z 194.1 (M$^+$+1).

Preparation of 1,5-difluoro-6-methoxyisoquinoline

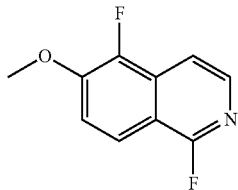

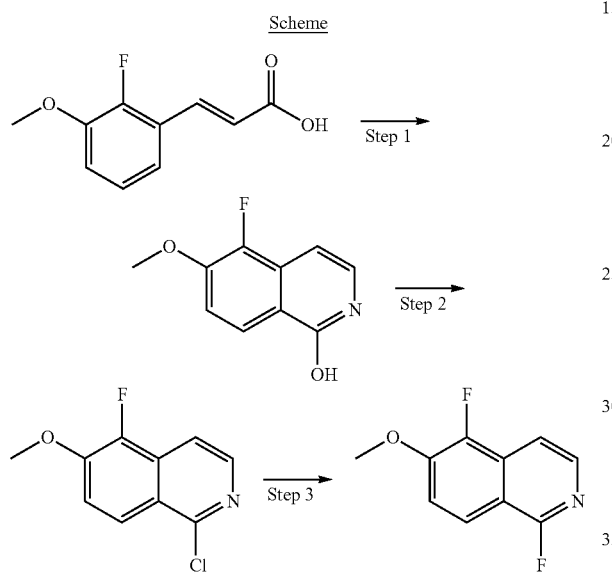

1,5-difluoro-6-methoxyisoquinoline was prepared by a similar method for the preparation of 1,7-difluoro-5-methoxyisoquinoline with the following modifications:

Step 1:

Modifications: 3.92 g (E)-3-(2-fluoro-3-methoxyphenyl)acrylic acid was used instead of (E)-3-(4-fluoro-2-methoxyphenyl)acrylic acid which gave 5-fluoro-6-methoxyisoquinolin-1-ol (2.4 g, 61% yield). $^1$H NMR (400 MHz, CD$_3$OD) δ ppm 8.09 (d, J=8.80 Hz, 1H), 7.35 (t, J=8.44 Hz, 1H), 7.16 (d, J=7.34 Hz, 1H), 6.72 (m, 1H), 4.00 (s, 3H).

Step 2:

Modifications: 1.93 g 5-fluoro-6-methoxyisoquinolin-1-ol was used instead of 7-fluoro-5-methoxyisoquinolin-1-ol, 1.7 g 1-chloro-5-fluoro-6-methoxyisoquinoline obtained (80% yield). $^1$H NMR (CDCl$_3$) δ ppm 8.22 (d, J=5.87 Hz, 1H), 8.12 (d, J=9.29 Hz, 1H), 7.75 (d, J=5.87 Hz, 1H), 7.44 (dd, J=9.29, 7.83 Hz, 1H), 4.08 (s, 3H); MS m/z 212.1 (M$^+$+1).

Step 3:

To a solution of 1-chloro-5-fluoro-6-methoxyisoquinoline (0.5 g, 2.363 mmol) in DMSO (5 mL), was added CsF (0.718 g, 4.73 mmol). The mixture was heated to 140° C. for 2 h. The reaction was diluted with ethylactetate and washed with water, and brine. The organic phase was collected, dried over sodium sulfate, and concentrated under vacuum to give the crude product which was purified by silica gel chromatography using a gradient of 30-50% DCM in hexanes. The product fractions were collected and the solvent was removed under vacuum to give 1,5-difluoro-6-methoxyisoquinoline (340 mg, 74% yield). MS m/z 196.2 (M$^+$+1).

Preparation of Tripeptide Intermediates

The tripeptide intermediates described in this section can be used to prepare compounds of Formula I by the methods described herein.

Tripeptide Elements

Preparation of (2S,4R)-methyl 1-((2S,3R)-2-((tert-butoxycarbonyl)amino)-3,5-dimethylnon-8-enoyl)-4-hydroxypyrrolidine-2-carboxylate

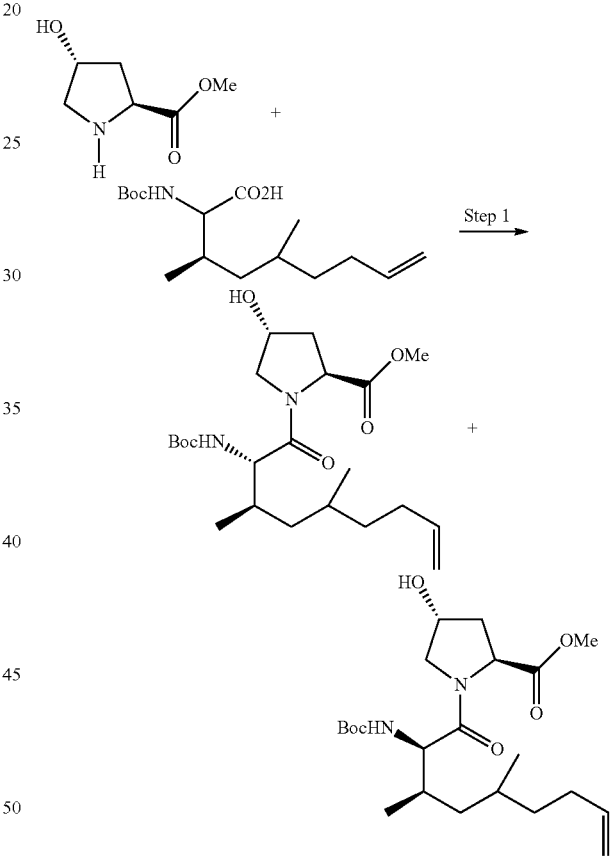

Step 1:

O-(7-Azabenzotriazol-1-yl)-N,N,N',N'-tetramethyluronium hexafluorophosphate (HATU, 31.7 g, 83 mmol) was added to a solution of (2S,4R)-methyl 4-hydroxypyrrolidine-2-carboxylate HCl (16.68 g, 92 mmol), (3R)-2-((tert-butoxycarbonyl)amino)-3,5-dimethylnon-8-enoic acid (25 g, 83 mmol) and NEt$_3$ (34.9 mL, 250 mmol) in DCM (250 mL) and stirred at RT for 16 h. The reaction was washed with 1N HCl (3×) and then brine. The organics were dried with magnesium sulfate, filtered and concentrated under vacuum. The crude material was purified via silica gel chromatography using 20-60% Acetone in hexanes to give the desired product (2S,4R)-methyl 1-((2S,3R)-2-((tert-butoxycarbonyl)amino)-3,5-dimethylnon-8-enoyl)-4-hydroxypyrrolidine-2-carboxylate (10.8 g, 30% yield), MS: MS m/z 427.2 (M⁺+1) and the undesired product (2S,4R)-methyl 1-((2R,3R)-2-((tert-butoxycarbonyl)amino)-3,5-dimethyl-non-8-enoyl)-4-hydroxypyrrolidine-2-carboxylate (12 g, 34% yield), MS: MS m/z 427.2 (M⁺+1).

General Method for the Preparation of Tripeptide

Preparation of tert-butyl ((2R,6S,7R,13aS,14aR,16aS,Z)-2-hydroxy-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate

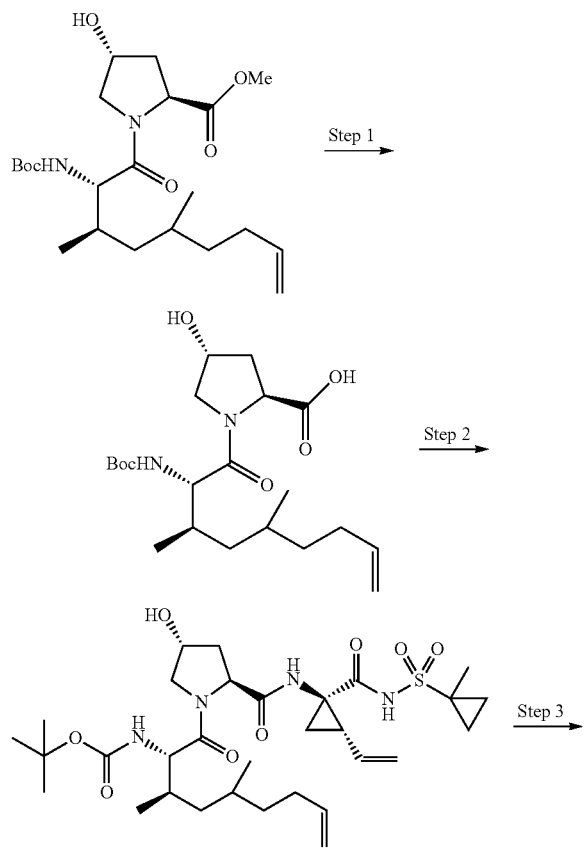

Scheme

-continued

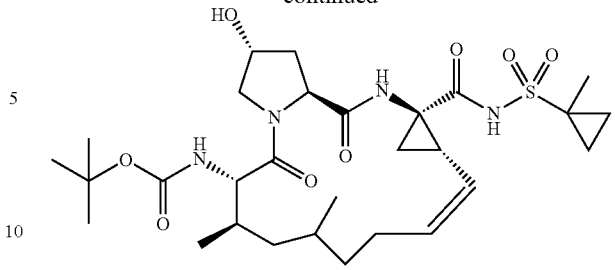

Step 1:
(2S,4R)-methyl 1-((2S,3R)-2-((tert-butoxycarbonyl)amino)-3,5-dimethylnon-8-enoyl)-4-hydroxypyrrolidine-2-carboxylate (10.8 g, 25.3 mmol) was dissolved in THF (50 mL), MeOH (50 mL) and to this solution was added LiOH (2.425 g, 101 mmol) in Water (50.0 mL). The reaction mixture was stirred at rt for 16 h. The solvent was removed under vacuum and the resulting aqueous residue was diluted with water, and EtOAc. The mixture was neutralised with 1 N HCl and adjusted the pH~2.5 and the mixture was extracted with EtOAc. The organic layer was collected, washed with brine, dried over Na₂SO₄, and concentrated to give (2S,4R)-1-((2S,3R)-2-((tert-butoxycarbonyl)amino)-3,5-dimethylnon-8-enoyl)-4-hydroxypyrrolidine-2-carboxylic acid (12 g, 29.1 mmol, 115% yield) as yellow viscous oil. MS: MS m/z 413.2 (M⁺+1).

Step 2:
HATU (7.60 g, 20.00 mmol) was added to a solution of (2S,4R)-1-((2S,3R)-2-((tert-butoxycarbonyl)amino)-3,5-dimethylnon-8-enoyl)-4-hydroxypyrrolidine-2-carboxylic acid (7.86 g, 19.05 mmol), (1R,2S)-1-amino-N-((1-methylcyclopropyl)sulfonyl)-2-vinylcyclopropanecarboxamide HCl (5.62 g, 20 mmol), and Hunig's Base (13.31 mL, 76 mmol) in DCM (110 mL). The reaction mixture was stirred at rt for 16 h. The reaction was washed with 1N HCl (3×), and then brine. The organic layer was collected, dried over sodium sulfate, and concentrated under vacuum. The crude material was purified by silica gel chromatography using a gradient of 20-60% Acetone in hexanes. The product fractions were collected and the solvent removed under vacuum to give tert-butyl ((2S,3R)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-3,5-dimethyl-1-oxonon-8-en-2-yl)carbamate (9 g, 74.0% yield) as a light orange foam. MS: MS m/z 639.3 (M⁺+1).

Step 3:
A solution of tert-butyl ((2S,3R)-1-((2S,4R)-4-hydroxy-2-(((1R,2S)-1-(((1-methylcyclopropyl)sulfonyl)carbamoyl)-2-vinylcyclopropyl)carbamoyl)pyrrolidin-1-yl)-3,5-dimethyl-1-oxonon-8-en-2-yl)carbamate (8.4 g, 13.15 mmol) in DCE (1500 ml) was sparged with nitrogen for 30 min. and then (1,3-Bis-(2,4,6-trimethylphenyl)-2-imidazolidinylidene)dichloro(o-isopropoxyphenylmethylene)ruthenium) Hoveyda-Grubbs Catalyst 2nd Generation, 0.413 g, 0.657 mmol) was added. The reaction solution was heated to 80° C. for 2 h. The reaction was concentrated and purified by silica gel chromatography using a gradient of 20-60% Acetone in hexanes to give tert-butyl ((2R,6S,7R,13aS,14aR,16aS,Z)-2-hydroxy-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (5.6 g, 70% yield) as a brown solid.
MS: MS m/z 611.3 (M⁺+1).

Preparation of tert-butyl ((2R,6S,7R,13aS,14aR,16aS,Z)-14a-(((1-(fluoromethyl)cyclopropyl)sulfonyl)carbamoyl)-2-hydroxy-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate

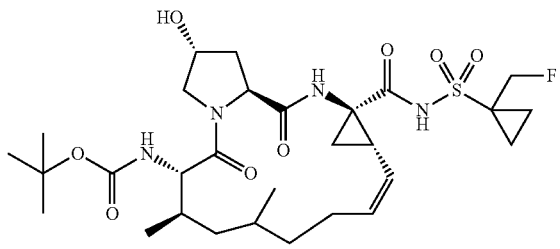 [SMILES: CC1CC/C=C\[C@@H]2C[C@@]2(C(=O)NS(=O)(=O)C2(CF)CC2)NC(=O)[C@@H]2C[C@@H](O)CN2C(=O)[C@@H](NC(=O)OC(C)(C)C)[C@H](C)C1]

Scheme

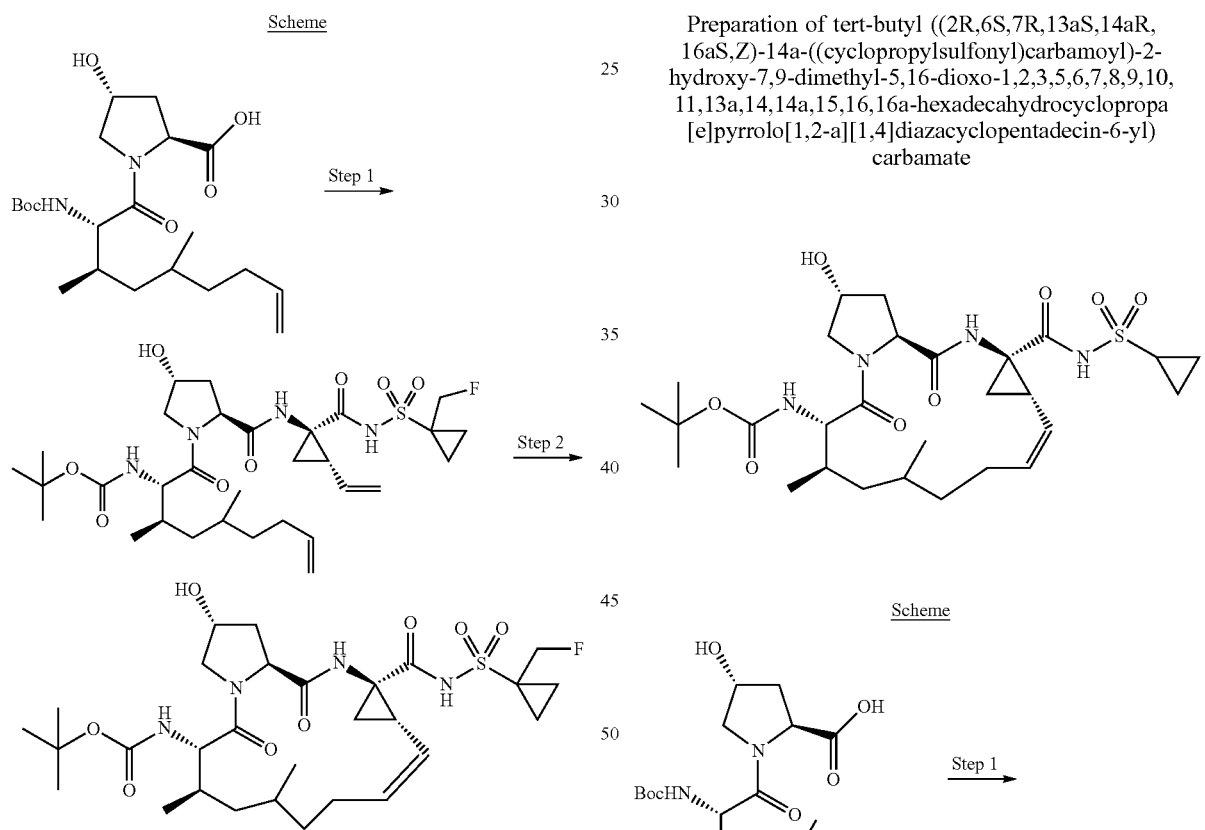

Step 1:

HATU (11.61 g, 30.5 mmol) was added to a solution of (2S,4R)-1-((2S,3R)-2-((tert-butoxycarbonyl)amino)-3,5-dimethylnon-8-enoyl)-4-hydroxypyrrolidine-2-carboxylic acid (10.50 g, 25.5 mmol), (1R,2S)-1-amino-N-((1-(fluoromethyl)cyclopropyl)sulfonyl)-2-vinylcyclopropanecarboxamide HCl (8.37 g, 28 mmol), and triethylamine (14.19 mL, 102 mmol) in DCM (220 mL) and was stirred at RT for overnight. The reaction was washed with 1N HCl (3×) and then brine and evaporated on rotovap. The crude material was purified by silica gel chromatography using 20-40% Acetone in hexanes. The product fractions were collected and the solvent removed under vacuum to give the desired product tert-butyl ((2S,3R)-1-((2S,4R)-2-(((1R,2S)-1-(((1-(fluoromethyl)cyclopropyl)sulfonyl)carbamoyl)-2-vinylcyclopropyl)carbamoyl)-4-hydroxypyrrolidin-1-yl)-3,5-dimethyl-1-oxonon-8-en-2-yl)carbamate (15 g, 90% yield). MS: MS m/z 657.3 (M$^+$+1).

Step 2:

A solution of tert-butyl ((2S,3R)-1-((2S,4R)-2-(((1R,2S)-1-(((1-(fluoromethyl)cyclopropyl)sulfonyl)carbamoyl)-2-vinylcyclopropyl)carbamoyl)-4-hydroxypyrrolidin-1-yl)-3,5-dimethyl-1-oxonon-8-en-2-yl)carbamate (7.5 g, 22.84 mmol) in DCE (2855 ml) was sparged with nitrogen for 30 min. and then Hoveyda-Grubbs Catalyst 2nd Generation (0.718 g, 1.142 mmol) was added and the reaction heated to 80° C. for 2 hrs. The reaction was concentrated and purified by flash chromatography on silica gel (20-60% Acetone in hexanes) to give tert-butyl ((2R,6S,7R,13aS,14aR,16aS,Z)-14a-(((1-(fluoromethyl)cyclopropyl)sulfonyl)carbamoyl)-2-hydroxy-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (4 g, 6.36 mmol, 27.9% yield). MS: MS m/z 629.3 (M$^+$+1).

Preparation of tert-butyl ((2R,6S,7R,13aS,14aR,16aS,Z)-14a-((cyclopropylsulfonyl)carbamoyl)-2-hydroxy-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate

Scheme

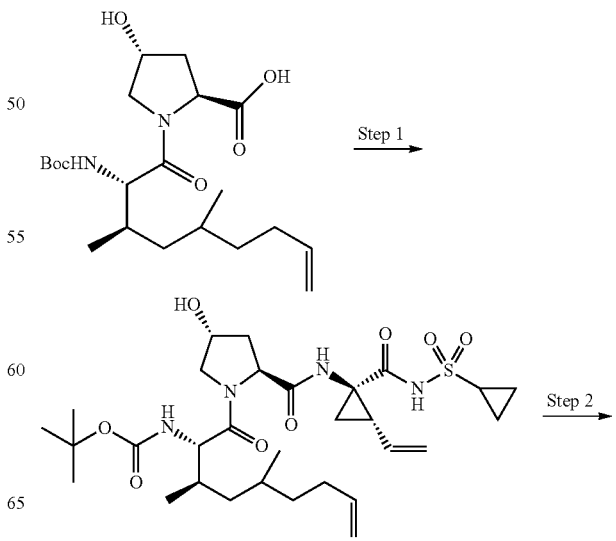

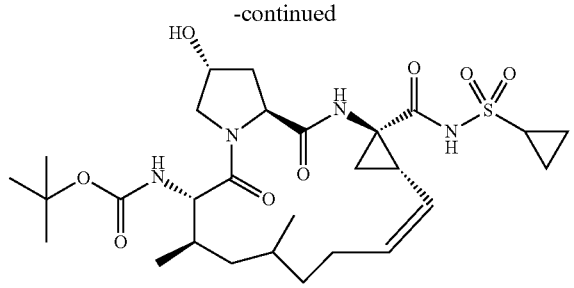

Step 1:

HATU (11.54 g, 30.4 mmol) was added to a solution of (2S,4R)-1-((2S,3R)-2-((tert-butoxycarbonyl)amino)-3,5-dimethylnon-8-enoyl)-4-hydroxypyrrolidine-2-carboxylic acid (10.44 g, 25.3 mmol), (1R,2S)-1-amino-N-(cyclopropylsulfonyl)-2-vinylcyclopropanecarboxamide, p-toluenesulfonate salt (11.17 g, 27.8 mmol), and Hunig's Base (17.67 ml, 101 mmol) in DCM (200 ml) and was stirred at RT for overnight. The reaction was washed with 1N HCl (3×) and then brine and evaporated on rotovap, and purified to get the final product tert-butyl ((2S,3R)-1-((2S,4R)-2-(((1R,2S)-1-((cyclopropylsulfonyl)carbamoyl)-2-vinylcyclopropyl)carbamoyl)-4-hydroxypyrrolidin-1-yl)-3,5-dimethyl-1-oxonon-8-en-2-yl)carbamate (14.8 g, 23.69 mmol, 94% yield) as a light orange foam.

Step 2:

A solution of tert-butyl ((2S,3R)-1-((2S,4R)-2-(((1R,2S)-1-((cyclopropylsulfonyl)carbamoyl)-2-vinylcyclopropyl)carbamoyl)-4-hydroxypyrrolidin-1-yl)-3,5-dimethyl-1-oxonon-8-en-2-yl)carbamate (9.5 g, 15.21 mmol) in DCE (2500 ml) was sparged with nitrogen for 30 min. and then Hoveyda-Grubbs Catalyst 2nd Generation (0.574 g, 0.912 mmol) was added and the reaction heated to 80° C. for 2 hrs then cooled down to 45° C. and stirred for 2 days. The reaction was concentrated and purified by flash chromatography on silica gel (20-60% Acetone in hexanes) to give the product tert-Butyl ((2R,6S,7R,13 aS,14aR,16aS,Z)-14a-((cyclopropylsulfonyl)carbamoyl)-2-hydroxy-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (7 g). MS: MS m/z 597.35 (M$^+$+1).

Preparation of (2R,6S,7R,13aS,14aR,16aS,Z)-methyl 6-((tert-butoxycarbonyl)amino)-2-hydroxy-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate

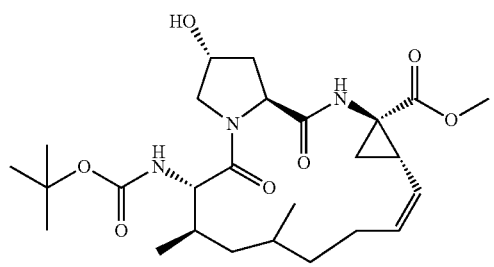 [SMILES: COC(=O)[C@@]12C[C@H]1/C=C\CCC(C)C[C@@H](C)[C@H](NC(=O)OC(C)(C)C)C(=O)N1C[C@H](O)C[C@H]1C(=O)N2]

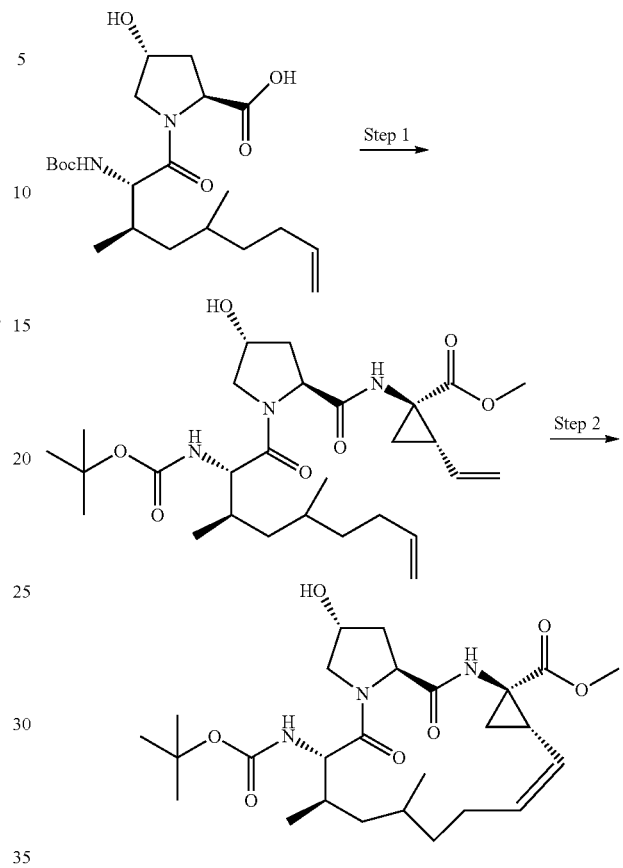

Step 1:

HATU (2.510 g, 6.60 mmol) was added to a solution of (2S,4R)-1-((2S,3R)-2-((tert-butoxycarbonyl)amino)-3,5-dimethylnon-8-enoyl)-4-hydroxypyrrolidine-2-carboxylic acid (2.269 g, 5.5 mmol), (1R,2S)-methyl 1-amino-2-vinylcyclopropanecarboxylate HCl (1.172 g, 6.60 mmol), and Hunig's Base (3.84 ml, 22.00 mmol) in DCM (20 ml) and was stirred at RT for overnight. The reaction was washed with 1N HCl (3×) and then brine and evaporated on rotovap, then purified via silica gel chromatography to get the product (1R,2S)-methyl 1-((2S,4R)-1-((2S,3R)-2-((tert-butoxycarbonyl)amino)-3,5-dimethylnon-8-enoyl)-4-hydroxypyrrolidine-2-carboxamido)-2-vinylcyclopropanecarboxylate (2.68 g, 5.00 mmol, 91% yield) as a light orange foam. MS: MS m/z 558.16 (M$^+$+23).

Step 2:

A solution of (1R,2S)-methyl 1-((2S,4R)-1-((2S,3R)-2-((tert-butoxycarbonyl)amino)-3,5-dimethylnon-8-enoyl)-4-hydroxypyrrolidine-2-carboxamido)-2-vinylcyclopropanecarboxylate (2.68 g, 5 mmol) in DCE (600 mL) was sparged with nitrogen for 30 min. and then Hoveyda-Grubbs Catalyst 2nd Generation (0.189 g, 0.300 mmol) was added and the reaction heated to 80° C. for 2 hrs. The reaction was concentrated and purified by flash chromatography on silica gel (20-60% Acetone in hexanes) to give 2.1 g of the product (2R,6S,7R,13aS,14aR,16aS,Z)-methyl 6-((tert-butoxycarbonyl)amino)-2-hydroxy-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate. MS: MS m/z 530.18 (M$^+$+23).

Preparation of Compound 3116 and Compound 3117

Scheme

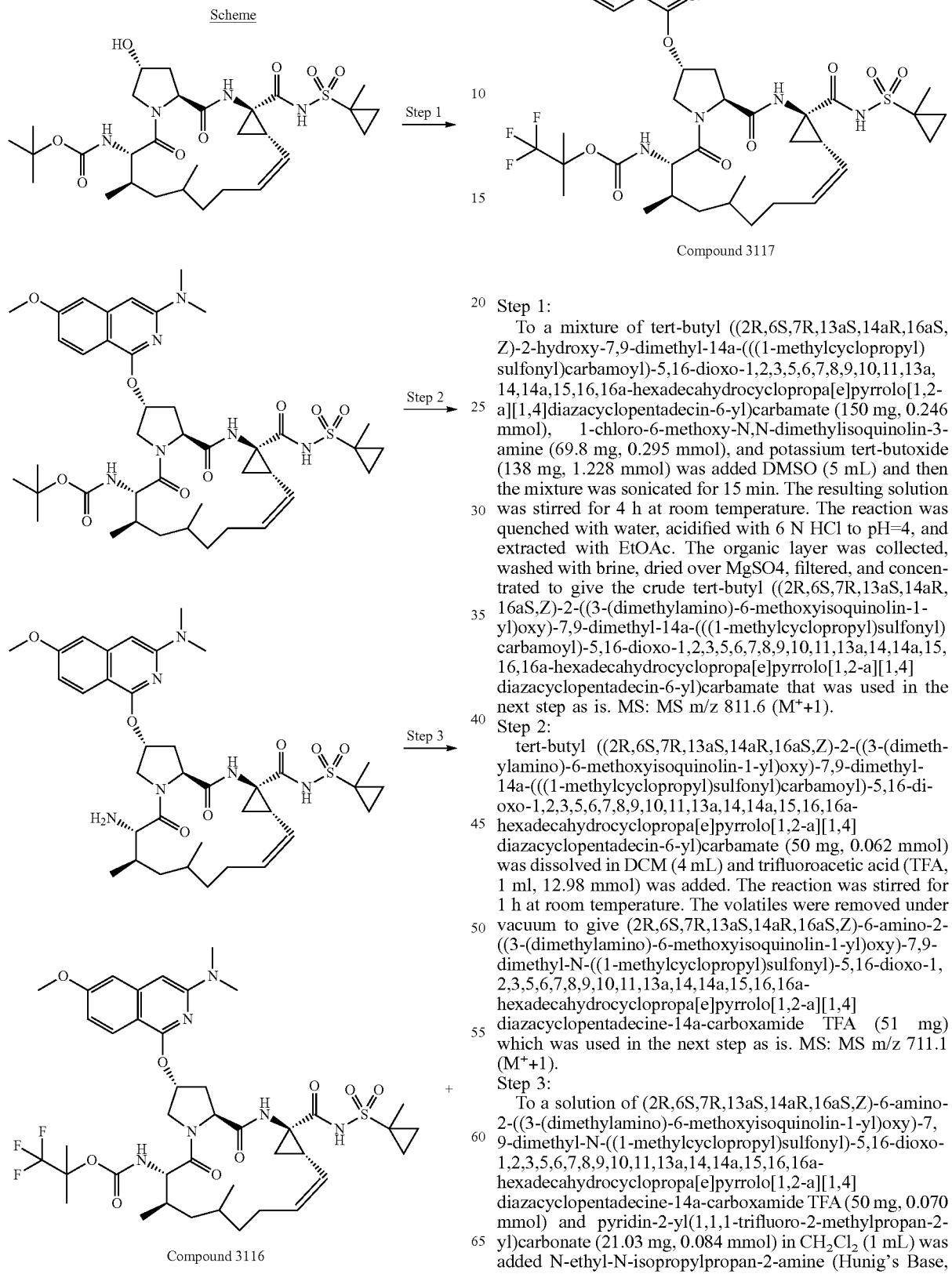

Compound 3117

Compound 3116

Step 1:

To a mixture of tert-butyl ((2R,6S,7R,13aS,14aR,16aS,Z)-2-hydroxy-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (150 mg, 0.246 mmol), 1-chloro-6-methoxy-N,N-dimethylisoquinolin-3-amine (69.8 mg, 0.295 mmol), and potassium tert-butoxide (138 mg, 1.228 mmol) was added DMSO (5 mL) and then the mixture was sonicated for 15 min. The resulting solution was stirred for 4 h at room temperature. The reaction was quenched with water, acidified with 6 N HCl to pH=4, and extracted with EtOAc. The organic layer was collected, washed with brine, dried over MgSO4, filtered, and concentrated to give the crude tert-butyl ((2R,6S,7R,13aS,14aR,16aS,Z)-2-((3-(dimethylamino)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate that was used in the next step as is. MS: MS m/z 811.6 (M$^+$+1).

Step 2:

tert-butyl ((2R,6S,7R,13aS,14aR,16aS,Z)-2-((3-(dimethylamino)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (50 mg, 0.062 mmol) was dissolved in DCM (4 mL) and trifluoroacetic acid (TFA, 1 ml, 12.98 mmol) was added. The reaction was stirred for 1 h at room temperature. The volatiles were removed under vacuum to give (2R,6S,7R,13aS,14aR,16aS,Z)-6-amino-2-((3-(dimethylamino)-6-methoxyisoquinolin-1-yl)oxy)-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide TFA (51 mg) which was used in the next step as is. MS: MS m/z 711.1 (M$^+$+1).

Step 3:

To a solution of (2R,6S,7R,13aS,14aR,16aS,Z)-6-amino-2-((3-(dimethylamino)-6-methoxyisoquinolin-1-yl)oxy)-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide TFA (50 mg, 0.070 mmol) and pyridin-2-yl(1,1,1-trifluoro-2-methylpropan-2-yl)carbonate (21.03 mg, 0.084 mmol) in CH$_2$Cl$_2$ (1 mL) was added N-ethyl-N-isopropylpropan-2-amine (Hunig's Base, 0.061 mL, 0.352 mmol). The reaction was stirred for 16 h.

After concentration the crude material was purified via preparative HPLC as follows: Column: Waters XBridge C18, 19×200 mm, 5-μm particles; Guard Column: Waters XBridge C18, 19×10 mm, 5-μm particles; Mobile Phase A: water; Mobile Phase B: acetonitrile; Buffer: 20-mM ammonium acetate; Gradient: 20-95% B over 20.5 minutes, then a 7.0 minute hold at 95% B; Flow: 25 mL/min. Compound 3116 eluted first under the described conditions, followed by Compound 3117. Fractions containing pure Compound 3116 were pooled and concentrated via centrifugal evaporation to give to 5.0 mg of Compound 3116 as a solid; fractions containing pure Compound 3117 were pooled and concentrated via centrifugal evaporation to give 8.6 mg of Compound 3117 as a solid.

Compound 3116: 1,1,1-trifluoro-2-methylpropan-2-yl ((2R,6S,7R,9S,13aS,14aR,16aS,Z)-2-((3-(dimethylamino)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 865.5 ($M^+$+1). Compound 3117: 1,1,1-trifluoro-2-methylpropan-2-yl ((2R,6S,7R,9R,13aS,14aR,16aS,Z)-2-((3-(dimethylamino)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-$d_6$) 11.05 (br. s., 1H), 9.11 (br. s., 1H), 7.86 (d, J=7.9 Hz, 1H), 7.76 (d, J=9.2 Hz, 1H), 6.95 (d, J=2.4 Hz, 1H), 6.65 (dd, J=9.2, 2.4 Hz, 1H), 6.23 (s, 1H), 5.77 (br. s., 1H), 5.60-5.46 (m, 1H), 5.03-4.92 (m, 1H), 4.53-4.40 (m, 2H), 3.95 (dd, J=11.4, 3.5 Hz, 1H), 3.83 (s, 3H), 3.76 (dd, J=10.7, 8.2 Hz, 1H), 3.07 (s, 6H), 2.73-2.58 (m, 2H), 2.39-2.25 (m, 2H), 1.97-1.81 (m, 2H), 1.75-1.08 (m, 17H), 0.99-0.85 (m, 8H), 0.76 (t, J=11.7 Hz, 1H); MS: MS m/z 865.5 ($M^+$+1).

Crystal Structure Data of Compound 3117

Crystallization Conditions for Compound 3117

10 mg of Compound 3117 was dissolved in 1.5 ml methanol. The resultant solution was slow evaporated at 2-5° C. to afford the solid crystalline form.

Cell Dimensions:
a=14.7856(2)Å
b=24.3272(2)Å
c=25.8319(2)Å
α=90.0°
β=90.0°
γ=90.0°
Space group: $P2_12_12_1$
Molecules of Compound/asymmetric unit: 2
Volume=9292(2) Å$^3$
Density (calculated)=1.294 g/cm$^3$ Measurement of said crystalline form is at a temperature of about −123° C.

Single Crystal X-Ray Measurements:

A Bruker SMART APEX II diffractometer equipped with graphite-monochromated Mo Kα radiation, (λ=0.71073 Å) was used to collect diffraction data at −123° C. A full data set was collected using the ω scan mode over the 2θ range with a crystal-to-detector distance of 4.0 cm. An empirical absorption correction utilized the SADABS routine associated with the diffractometer (Bruker AXS. 1998, SMART and SAINTPLUS. Area Detector Control and Integration Software, Bruker AXS, Madison, Wis., USA). The final unit cell parameters were determined using the entire data set.

All structures were solved by direct methods and refined by the full-matrix least-squares techniques, using the SHELXTL software package (Sheldrick, G. M., 2008, SHELXTL. Structure Determination Programs. Version 6.10, Bruker AXS, Madison, Wis., USA.). The function minimized in the refinements was $\Sigma_w(|F_O|-|F_C|)^2$. R is defined as $\Sigma\|F_O|-|F_C\|/\Sigma|F_O|$, while $R_W=[\Sigma_w(|F_O|-|F_C|)^2/\Sigma_w|F_O|^2]^{1/2}$, Where w is an appropriate weighting function based on errors in the observed intensities.

Difference FOURIER® maps were examined at all stages of refinement. All non-hydrogen atoms were refined with anisotropic thermal displacement parameters. The hydrogen atoms associated with hydrogen bonding were located in the final difference FOURIER® maps while the positions of the other hydrogen atoms were calculated from an idealized geometry with standard bond lengths and angles. They were assigned isotropic temperature factors and included in structure factor calculations with fixed parameters.

TABLE 1

Fractional Atomic Coordinates for Compound 3117 at T = −123° C.

| Atom | x | y | z | Atom | x | y | z |
| --- | --- | --- | --- | --- | --- | --- | --- |
| S(1A) | 0.0898(2) | 0.2239(1) | 0.0621(1) | S(1B) | 0.3016(2) | 0.1467(1) | 0.4300(1) |
| F(1A) | 0.2852(4) | 0.6576(2) | 0.3427(2) | F(1B) | 0.3698(4) | 0.5653(3) | 0.1181(2) |
| F(2A) | 0.2178(4) | 0.7290(2) | 0.3719(2) | F(2B) | 0.3228(4) | 0.6371(2) | 0.1560(2) |
| F(3A) | 0.2678(4) | 0.7276(2) | 0.2935(2) | F(3B) | 0.4524(4) | 0.6380(3) | 0.1207(2) |
| O(1A) | −0.0071(5) | 0.2396(3) | 0.0678(2) | O(1B) | 0.3293(4) | 0.0911(2) | 0.4185(2) |
| O(2A) | 0.1222(6) | 0.1744(2) | 0.0831(2) | O(2B) | 0.3596(4) | 0.1813(2) | 0.4606(2) |
| O(3A) | 0.2893(5) | 0.2421(2) | 0.0952(2) | O(3B) | 0.1978(4) | 0.1244(2) | 0.3297(2) |
| O(4A) | 0.1992(4) | 0.4762(2) | 0.1854(2) | O(4B) | 0.2902(4) | 0.3672(2) | 0.2663(2) |
| O(5A) | 0.0818(4) | 0.3723(2) | 0.1219(2) | O(5B) | 0.3271(3) | 0.2855(2) | 0.3539(2) |
| O(6A) | −0.0636(4) | 0.4491(2) | 0.2816(2) | O(6B) | 0.6104(3) | 0.3665(2) | 0.2810(2) |
| O(7A) | 0.0227(5) | 0.6145(2) | 0.2482(2) | O(7B) | 0.4462(4) | 0.5345(2) | 0.2943(2) |
| O(8A) | 0.1646(4) | 0.6437(2) | 0.2677(2) | O(8B) | 0.3675(3) | 0.5559(2) | 0.2211(2) |
| O(9A) | −0.0259(4) | 0.5403(2) | 0.5073(2) | O(9B) | 0.7840(5) | 0.4716(2) | 0.0805(2) |
| N(1A) | 0.1456(6) | 0.2754(3) | 0.0901(2) | N(1B) | 0.2903(4) | 0.1811(2) | 0.3753(2) |
| N(2A) | 0.0519(4) | 0.4568(2) | 0.1952(2) | N(2B) | 0.4219(4) | 0.3686(2) | 0.3084(2) |
| N(3A) | 0.1988(5) | 0.3474(2) | 0.1729(2) | N(3B) | 0.3335(4) | 0.2353(2) | 0.2809(2) |
| N(4A) | −0.1351(4) | 0.3777(3) | 0.3226(2) | N(4B) | 0.6583(4) | 0.4504(3) | 0.3138(3) |
| N(5A) | −0.2061(5) | 0.3052(3) | 0.3643(2) | N(5B) | 0.7005(5) | 0.5342(3) | 0.3476(3) |
| N(6A) | 0.1453(4) | 0.5867(2) | 0.2031(2) | N(6B) | 0.3221(4) | 0.4865(2) | 0.2694(2) |
| C(1A) | 0.1035(11) | 0.1759(5) | −0.0317(4) | C(1B) | 0.1950(5) | 0.1462(3) | 0.4586(3) |
| C(2A) | 0.2056(11) | 0.2025(5) | −0.0184(5) | C(2B) | 0.1837(6) | 0.1027(3) | 0.5000(3) |
| C(3A) | 0.1146(8) | 0.2297(4) | −0.0029(3) | C(3B) | 0.1379(6) | 0.0977(3) | 0.4491(3) |
| C(4A) | 0.814(10) | 0.2806(5) | −0.0283(4) | C(4B) | 0.1529(7) | 0.2016(3) | 0.4636(3) |
| C(5A) | 0.2336(8) | 0.2767(3) | 0.1039(3) | C(5B) | 0.2440(6) | 0.1651(3) | 0.3315(3) |

TABLE 1-continued

Fractional Atomic Coordinates for Compound 3117 at T = −123° C.

| Atom | x | y | z | Atom | x | y | z |
|---|---|---|---|---|---|---|---|
| C(6A) | 0.2573(6) | 0.3297(3) | 0.1316(3) | C(6B) | 0.2492(5) | 0.2067(3) | 0.2887(3) |
| C(7A) | 0.3551(7) | 0.3455(4) | 0.1378(4) | C(7B) | 0.1910(5) | 0.1966(3) | 0.2426(3) |
| C(8A) | 0.2980(7) | 0.3758(3) | 0.0980(3) | C(8B) | 0.1646(5) | 0.2413(3) | 0.2795(3) |
| C(9A) | 0.3114(7) | 0.3684(4) | 0.0411(4) | C(9B) | 0.0845(5) | 0.2373(3) | 0.3126(3) |
| C(10A) | 0.2687(9) | 0.3925(5) | 0.0056(4) | C(10B) | 0.0523(5) | 0.2766(3) | 0.3435(3) |
| C(11A) | 0.1703(8) | 0.4224(4) | 0.0105(4) | C(11B) | 0.0938(5) | 0.3313(3) | 0.3501(2) |
| C(12A) | 0.1880(8) | 0.4797(4) | 0.0113(3) | C(12B) | 0.1195(6) | 0.3422(3) | 0.4073(3) |
| C(13A) | 0.1069(7) | 0.5171(3) | 0.0185(3) | C(13B) | 0.1535(6) | 0.3988(3) | 0.4203(3) |
| C(14A) | 0.0285(8) | 0.5055(5) | −0.0183(4) | C(14B) | 0.1656(7) | 0.4014(4) | 0.4796(3) |
| C(15A) | 0.0747(6) | 0.5187(3) | 0.0753(3) | C(15B) | 0.2438(5) | 0.4135(3) | 0.3931(3) |
| C(16A) | 0.1260(6) | 0.5592(3) | 0.1111(3) | C(16B) | 0.2344(5) | 0.4492(3) | 0.3445(3) |
| C(17A) | 0.1104(6) | 0.6193(3) | 0.0960(3) | C(17B) | 0.2084(6) | 0.5076(3) | 0.3576(3) |
| C(18A) | 0.0970(5) | 0.5502(3) | 0.1673(3) | C(18B) | 0.3218(5) | 0.4491(3) | 0.3134(3) |
| C(19A) | 0.1186(6) | 0.4917(3) | 0.1835(3) | C(19B) | 0.3429(6) | 0.3914(3) | 0.2939(3) |
| C(20A) | 0.0759(5) | 0.4002(3) | 0.2106(2) | C(20B) | 0.4405(5) | 0.3109(3) | 0.2929(3) |
| C(21A) | 0.1181(6) | 0.3719(3) | 0.1642(3) | C(21B) | 0.3621(5) | 0.2766(3) | 0.3109(3) |
| C(22A) | −0.0164(5) | 0.3740(3) | 0.2235(3) | C(22B) | 0.5286(5) | 0.2977(3) | 0.3228(3) |
| C(23A) | −0.0799(6) | 0.4231(3) | 0.2324(3) | C(23B) | 0.5715(6) | 0.3544(3) | 0.3303(3) |
| C(24A) | −0.0459(5) | 0.4651(3) | 0.1937(3) | C(24B) | 0.4931(5) | 0.3910(3) | 0.3416(3) |
| C(25A) | −0.0946(5) | 0.4256(3) | 0.3254(3) | C(25B) | 0.6502(5) | 0.4174(3) | 0.2744(3) |
| C(26A) | −0.1578(5) | 0.3532(3) | 0.3686(3) | C(26B) | 0.6960(6) | 0.5010(3) | 0.3049(3) |
| C(27A) | −0.1358(5) | 0.3769(3) | 0.4164(3) | C(27B) | 0.7248(5) | 0.5162(3) | 0.2575(3) |
| C(28A) | −0.0966(5) | 0.4295(3) | 0.4175(3) | C(28B) | 0.7177(5) | 0.4812(3) | 0.2153(3) |
| C(29A) | −0.0785(5) | 0.4563(3) | 0.4652(3) | C(29B) | 0.7467(6) | 0.4941(3) | 0.1645(3) |
| C(30A) | −0.0461(6) | 0.5090(3) | 0.4644(3) | C(30B) | 0.7449(6) | 0.4559(4) | 0.1269(3) |
| C(31A) | −0.0308(5) | 0.5365(3) | 0.4173(3) | C(31B) | 0.7103(7) | 0.4039(4) | 0.1349(3) |
| C(32A) | −0.0447(5) | 0.5105(3) | 0.3718(3) | C(32B) | 0.6767(6) | 0.3900(3) | 0.1834(3) |
| C(33A) | −0.0779(5) | 0.4561(3) | 0.3710(3) | C(33B) | 0.6772(5) | 0.4280(3) | 0.2232(3) |
| C(34A) | −0.0323(7) | 0.5132(3) | 0.5565(3) | C(34B) | 0.7814(11) | 0.4346(5) | 0.0391(4) |
| C(35A) | −0.2071(6) | 0.2750(3) | 0.3159(3) | C(35B) | 0.7480(7) | 0.5860(3) | 0.3432(3) |
| C(36A) | −0.2215(7) | 0.2722(3) | 0.4097(3) | C(36B) | 0.6922(7) | 0.5117(3) | 0.3994(3) |
| C(37A) | 0.1024(7) | 0.6141(3) | 0.2403(3) | C(37B) | 0.3851(7) | 0.5253(3) | 0.2654(3) |
| C(38A) | 0.1363(7) | 0.6754(3) | 0.3129(3) | C(38B) | 0.4409(6) | 0.5870(3) | 0.1979(3) |
| C(39A) | 0.0971(6) | 0.6402(3) | 0.3541(3) | C(39B) | 0.5194(6) | 0.5509(5) | 0.1869(4) |
| C(40A) | 0.0757(6) | 0.7230(3) | 0.2987(3) | C(40B) | 0.4628(8) | 0.6372(4) | 0.2310(4) |
| C(41A) | 0.2262(8) | 0.6972(4) | 0.3292(4) | C(41B) | 0.3965(7) | 0.6065(4) | 0.1477(4) |
| O(1W) | 0.4115(4) | 0.2148(2) | 0.1796(2) | O(4W) | 0.4776(5) | 0.1146(3) | 0.1411(2) |
| O(2W) | −0.0760(20) | 0.3406(11) | 0.0561(8) | O(5W) | 0.4208(12) | 0.3006(6) | 0.4566(5) |
| O(3W) | 0.3819(15) | 0.1445(8) | 0.0508(6) | H(1B) | 0.3170 | 0.2135 | 0.3739 |
| H(1A) | 0.1140 | 0.3052 | 0.0967 | H(2BA) | 0.2356 | 0.0781 | 0.5071 |
| H(1AA) | 0.0835 | 0.1433 | −0.0118 | H(2BB) | 0.1461 | 0.1118 | 0.5305 |
| H(1AB) | 0.0820 | 0.1773 | −0.0680 | H(3B) | 0.3680 | 0.2251 | 0.2548 |
| H(2AA) | 0.2422 | 0.1849 | 0.0092 | H(3BA) | 0.1610 | 0.0695 | 0.4247 |
| H(2AB) | 0.2406 | 0.2190 | −0.0471 | H(3BB) | 0.0716 | 0.1032 | 0.4481 |
| H(3A) | 0.2163 | 0.3421 | 0.2051 | H(4BA) | 0.1382 | 0.2158 | 0.4292 |
| H(4AA) | 0.0152 | 0.2818 | −0.0265 | H(4BB) | 0.0975 | 0.1988 | 0.4843 |
| H(4AB) | 0.1006 | 0.2809 | −0.0646 | H(4BC) | 0.1953 | 0.2266 | 0.4808 |
| H(4AC) | 0.1066 | 0.3128 | −0.0105 | H(6B) | 0.2803 | 0.4834 | 0.2453 |
| H(6A) | 0.2042 | 0.5906 | 0.1998 | H(7BA) | 0.1538 | 0.1627 | 0.2423 |
| H(7AA) | 0.4013 | 0.3196 | 0.1248 | H(7BB) | 0.2148 | 0.2077 | 0.2083 |
| H(7AB) | 0.3724 | 0.3657 | 0.1696 | H(8B) | 0.1773 | 0.2792 | 0.2666 |
| H(8A) | 0.2797 | 0.4138 | 0.1085 | H(9B) | 0.0524 | 0.2035 | 0.3120 |
| H(9A) | 0.3566 | 0.3429 | 0.0307 | H(10) | 0.2967 | 0.3934 | −0.0275 |
| H(10A) | −0.0011 | 0.2688 | 0.3626 | H(11A) | 0.1315 | 0.4128 | −0.0194 |
| H(11C) | 0.1487 | 0.3338 | 0.3283 | H(11B) | 0.1393 | 0.4109 | 0.0427 |
| H(11D) | 0.0508 | 0.3599 | 0.3383 | H(12A) | 0.2180 | 0.4897 | −0.0216 |
| H(12C) | 0.1667 | 0.3153 | 0.4174 | H(12B) | 0.2314 | 0.4872 | 0.0396 |
| H(12D) | 0.0657 | 0.3347 | 0.4290 | H(13) | 0.1283 | 0.5551 | 0.0102 |
| H(13A) | 0.1066 | 0.4262 | 0.4099 | H(14A) | −0.065 | 0.4742 | −0.0053 |
| H(14D) | 0.2127 | 0.3755 | 0.4903 | H(14B) | 0.0522 | 0.4969 | −0.0527 |
| H(14E) | 0.1084 | 0.3918 | 0.4966 | H(14C) | −0.0106 | 0.5379 | −0.0203 |
| H(14F) | 0.1832 | 0.4388 | 0.4897 | H(15A) | 0.0803 | 0.4812 | 0.0899 |
| H(15C) | 0.2749 | 0.3790 | 0.3835 | H(15B) | 0.0097 | 0.5285 | 0.0756 |
| H(15D) | 0.2830 | 0.4331 | 0.4182 | H(16) | 0.1922 | 0.5512 | 0.1083 |
| H(16A) | 0.1855 | 0.4332 | 0.3224 | H(17A) | 0.1196 | 0.6237 | 0.0586 |
| H(17D) | 0.2012 | 0.5289 | 0.3257 | H(17B) | 0.0485 | 0.6300 | 0.1050 |
| H(17E) | 0.1513 | 0.5077 | 0.3769 | H(17C) | 0.1533 | 0.6428 | 0.1147 |
| H(17F) | 0.2559 | 0.5243 | 0.3789 | H(18) | 0.0304 | 0.5566 | 0.1706 |
| H(18A) | 0.3719 | 0.4605 | 0.3372 | H(20) | 0.1174 | 0.3998 | 0.2412 |
| H(20A) | 0.4495 | 0.3076 | 0.2546 | H(22A) | −0.0381 | 0.3510 | 0.1944 |
| H(22C) | 0.5686 | 0.2732 | 0.3024 | H(22B) | −0.0123 | 0.3509 | 0.2550 |
| H(22D) | 0.5152 | 0.2801 | 0.3565 | H(23) | −0.1450 | 0.4135 | 0.2270 |
| H(23A) | 0.6174 | 0.3547 | 0.3587 | H(24A) | −0.0704 | 0.4580 | 0.1587 |
| H(24C) | 0.4758 | 0.3890 | 0.3786 | H(24B) | −0.0623 | 0.5029 | 0.2044 |

TABLE 1-continued

Fractional Atomic Coordinates for Compound 3117 at T = −123° C.

| Atom | x | y | z | Atom | x | y | z |
|---|---|---|---|---|---|---|---|
| H(24D) | 0.5068 | 0.4296 | 0.3325 | H(27) | −0.1472 | 0.3576 | 0.4477 |
| H(27A) | 0.7505 | 0.5516 | 0.2528 | H(29) | −0.0887 | 0.4379 | 0.4971 |
| H(29A) | 0.7678 | 0.5301 | 0.1569 | H(31) | −0.0106 | 0.5735 | 0.4176 |
| H(31A) | 0.7094 | 0.3779 | 0.1075 | H(32) | −0.0322 | 0.5290 | 0.3402 |
| H(32A) | 0.6532 | 0.3542 | 0.1892 | H(34A) | 0.0115 | 0.4830 | 0.5579 |
| H(34D) | 0.7334 | 0.4076 | 0.0450 | H(34B) | −0.0935 | 0.4986 | 0.5611 |
| H(34E) | 0.7694 | 0.4547 | 0.0070 | H(34C) | −0.0191 | 0.5396 | 0.5842 |
| H(34F) | 0.8398 | 0.4157 | 0.0365 | H(35A) | −0.1510 | 0.2538 | 0.3125 |
| H(35D) | 0.7141 | 0.6107 | 0.3203 | H(35B) | −0.2589 | 0.2499 | 0.3154 |
| H(35E) | 0.8084 | 0.5796 | 0.3287 | H(35C) | −0.2119 | 0.3008 | 0.2869 |
| H(35F) | 0.7537 | 0.6028 | 0.3775 | H(36A) | −0.2703 | 0.2460 | 0.4028 |
| H(36D) | 0.6553 | 0.4782 | 0.3983 | H(36B) | −0.1660 | 0.2521 | 0.4184 |
| H(36E) | 0.6633 | 0.5388 | 0.4220 | H(36C) | −0.2385 | 0.2960 | 0.4387 |
| H(36F) | 0.7525 | 0.5028 | 0.4128 | H(39A) | 0.0391 | 0.6252 | 0.3424 |
| H(39D) | 0.4979 | 0.5156 | 0.1733 | H(39B) | 0.1388 | 0.6099 | 0.3618 |
| H(39E) | 0.5535 | 0.5446 | 0.2189 | H(39C) | 0.0876 | 0.6621 | 0.3855 |
| H(39F) | 0.5587 | 0.5685 | 0.1613 | H(40A) | 0.0179 | 0.7089 | 0.2857 |
| H(40D) | 0.4064 | 0.6540 | 0.2433 | H(40B) | 0.1048 | 0.7452 | 0.2719 |
| H(40E) | 0.4994 | 0.6260 | 0.2608 | H(40C) | 0.0649 | 0.7457 | 0.3294 |
| H(40F) | 0.4966 | 0.6640 | 0.2103 | | | | |

Preparation of Compound 3108 and Compound 3109

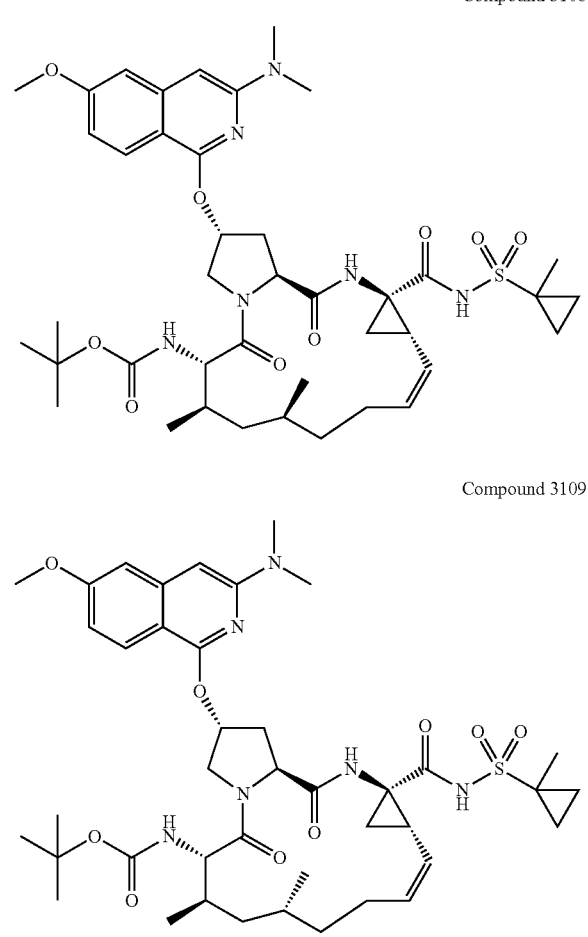

Compound 3108

Compound 3109

Step 1:

A diastereomeric mixture of tert-butyl ((2R,6S,7R,13aS,14aR,16aS,Z)-2-((3-(dimethylamino)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (50 mg) was purified via preparative HPLC with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 60-100% B over 12 minutes, then a 5-minute hold at 100% B; Flow: 20 mL/min. The diastereomers were separated and concentrated under centrifugal evaporation to give Compound 3108 (6.9 mg) and Compound 3109 (8.0 mg) respectively.

Compound 3108: tert-butyl ((2R,6S,7R,9S,13aS,14aR,16aS,Z)-2-((3-(dimethylamino)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 811.7 ($M^+$+1). Compound 3109: tert-butyl ((2R,6S,7R,9R,13aS,14aR,16aS,Z)-2-((3-(dimethylamino)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-$d_6$) δ 11.06 (br. s., 1H), 9.07 (br. s., 1H), 7.79 (d, J=8.9 Hz, 1H), 7.21 (d, J=6.1 Hz, 1H), 6.94 (d, J=2.4 Hz, 1H), 6.62 (dd, J=9.2, 2.4 Hz, 1H), 6.23 (s, 1H), 5.75 (br. s., 1H), 5.59-5.46 (m, 1H), 5.08-4.94 (m, 1H), 4.58-4.36 (m, 2H), 3.95 (dd, J=11.3, 3.7 Hz, 1H), 3.83 (s, 3H), 3.77 (dd, J=10.4, 8.9 Hz, 1H), 3.07 (s, 6H), 2.73-2.56 (m, 2H), 2.41-2.23 (m, 2H), 1.96-0.81 (m, 30H), 0.73 (br. t, J=12.4 Hz, 1H); MS: MS m/z 811.6 ($M^+$+1).

Preparation of Compound 5353 and Compound 5354
Scheme
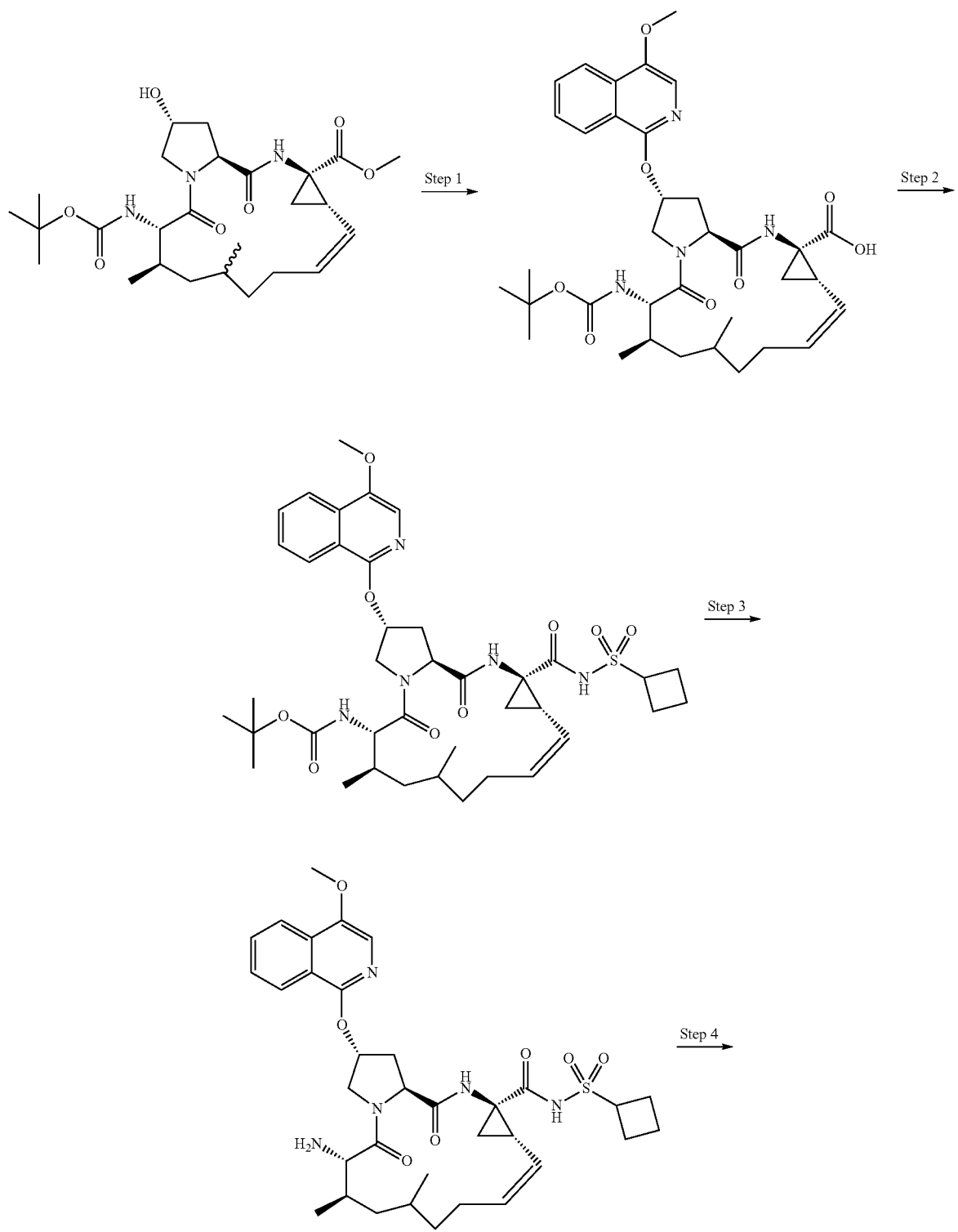

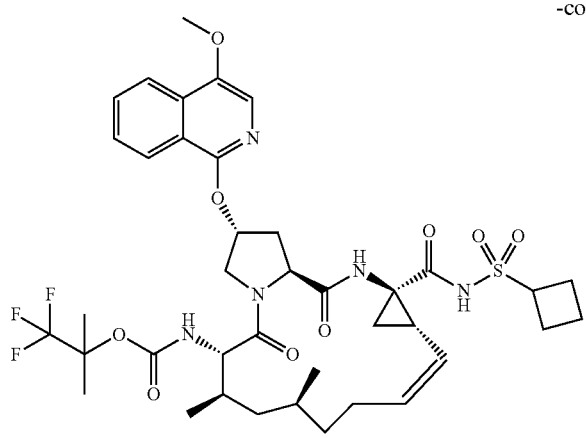

Compound 5353

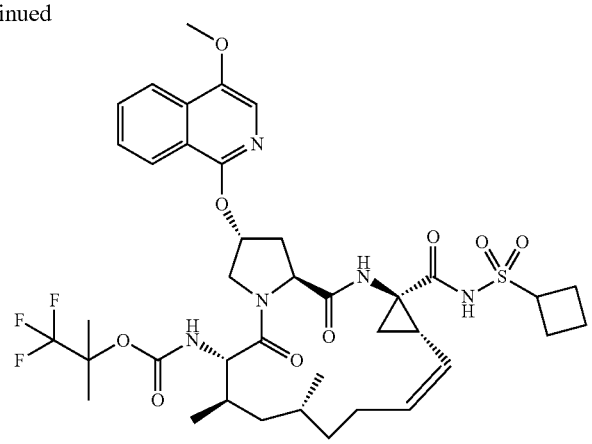

Compound 5354

Step 1

To a mixture of (2R,6S,7R,13aS,14aR,16aS,Z)-methyl 6-((tert-butoxycarbonyl)amino)-2-hydroxy-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (152 mg, 0.3 mmol), 1-fluoro-4-methoxyisoquinoline (128 mg, 0.720 mmol), and t-BuOK (168 mg, 1.500 mmol) was added DMSO (5 mL) and then sonicated for 15 min. The resulting solution was stirred for 4 h. The reaction was quenched with water, acidified with 6 N HCl, extracted with EtOAc, washed with brine, dried over MgSO4. After concentration, the residue (2R,6S,7R,13aS,14aR,16aS,Z)-6-((tert-butoxycarbonyl)amino)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid was obtained as a solid (150 mg) that will be used as it is. LC/MS: MS m/z (M+H)$^+$ 651.23.

Step 2

A mixture of (2R,6S,7R,13aS,14aR,16aS,Z)-6-((tert-butoxycarbonyl)amino)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid (70 mg, 0.108 mmol), CDI (34.9 mg, 0.215 mmol) in tetrahydrofuran (3 mL) was refluxed for 2 h. It was then cooled to rt and cyclobutanesulfonamide (32.0 mg, 0.237 mmol) was added and followed by DBU (0.036 mL, 0.237 mmol). The mixture was stirred at rt for 16 h. It was then concentrated and purified by silica gel chromatography, eluting with 40% acetone/hexane to isolate 70 mg of the diastereomers tert-butyl ((2R,6S,7R,13aS,14aR,16aS,Z)-14a-((cyclobutylsulfonyl)carbamoyl)-2((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate that was used as it was.

Step 3

To a solution of tert-butyl ((2R,6S,7R,13aS,14aR,16aS,Z)-14a-((cyclobutylsulfonyl)carbamoyl)-2((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (50 mg, 0.065 mmol) in CH$_2$Cl$_2$ (1 mL) was added TFA (0.050 mL, 0.651 mmol).

The resulting solution was stirred for 1 h and concentrated to give 51 mg of a crude product (2R,6S,7R,13aS,14aR,16aS,Z)-6-amino-N-(cyclobutylsulfonyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide TFA that was used in the next step as it is. LC/MS: MS m/z (M+H)$^+$ 668.32.

Step 4

A solution of (2R,6S,7R,13aS,14aR,16aS,Z)-6-amino-N-(cyclobutylsulfonyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide, TFA (46.9 mg, 0.06 mmol), pyridin-2-yl (1,1,1-trifluoro-2-methylpropan-2-yl)carbonate (17.94 mg, 0.072 mmol), and N-ethyl-N-isopropylpropan-2-amine (0.052 mL, 0.300 mmol) in CH$_2$Cl$_2$ (1 mL) was stirred for 16 h. After concentration, the residue was purified by prep HPLC to give 12.2 mg of Compound 5353 as a solid and 17.2 mg of Compound 5354 as a solid, respectively.

Compound 5353: 1,1,1-trifluoro-2-methylpropan-2-yl ((2R,6S,7R,9S,13aS,14aR,16aS,Z)-14a-((cyclobutylsulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. LC/MS: MS m/z (M+H)$^+$ 822.5.

Compound 5354: 1,1,1-trifluoro-2-methylpropan-2-yl ((2R,6S,7R,9R,13aS,14aR,16aS,Z)-14a-((cyclobutylsulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.05 (s, 1H), 9.05 (br. s., 1H), 8.08 (dd, J=11.7, 8.4 Hz, 2H), 7.86-7.76 (m, 2H), 7.69-7.55 (m, 2H), 5.77 (br. s., 1H), 5.53 (d, J=6.1 Hz, 1H), 5.00 (t, J=9.9 Hz, 1H), 4.61-4.45 (m, 2H), 4.28-4.16 (m, 1H), 3.98 (s, 3H), 3.90 (dd, J=11.7, 3.8 Hz, 1H), 3.70 (dd, J=10.8, 8.1 Hz, 1H), 2.71-2.59 (m, 2H), 2.43-2.14 (m, 7H), 2.02-1.79 (m, 5H), 1.75-1.01 (m, 10H), 0.93 (d, J=6.7 Hz, 3H), 0.88 (d, J=6.4 Hz, 3H), 0.74 (t, J=12.4 Hz, 1H); LC/MS: MS m/z (M+H)$^+$ 822.5.

Preparation of Compound 5351 and Compound 5352

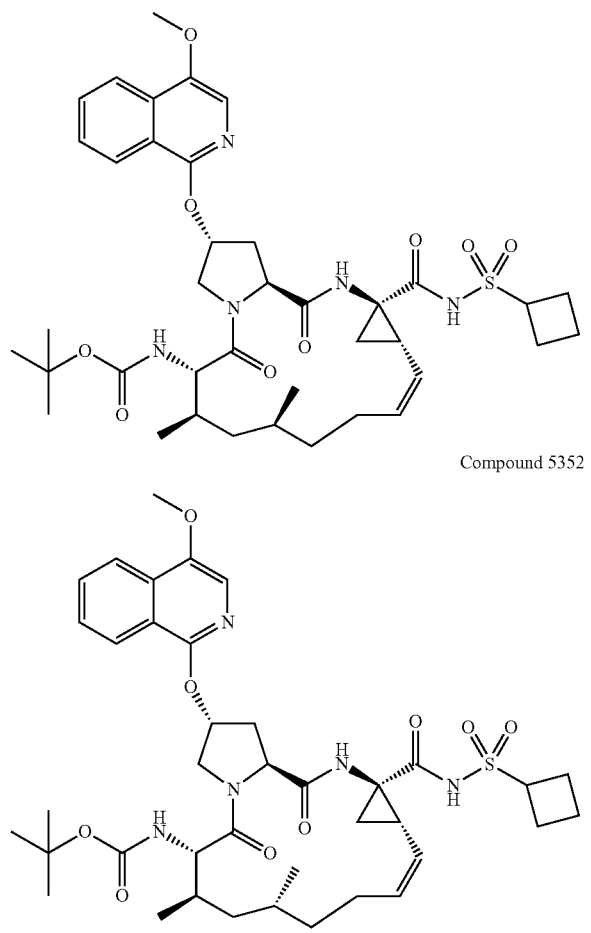

Compound 5351

Compound 5352

Step 1

A diastereomer mixture tert-butyl ((2R,6S,7R,13aS,14aR,16aS,Z)-14a-((cyclobutylsulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (23.6 mg) was purified by prep HLC to give 1.6 mg of Compound 5351 as a solid and 6.1 mg of the Compound 5352 as a solid, respectively.

Compound 5351: tert-butyl ((2R,6S,7R,9S,13aS,14aR,16aS,Z)-14a-((cyclobutylsulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. LC/MS: MS m/z (M+H)+ 768.5.

Compound 5352: tert-butyl ((2R,6S,7R,9R,13aS,14aR,16aS,Z)-14a-((cyclobutylsulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-$d_6$) δ 11.06 (s, 1H), 9.01 (s, 1H), 8.11 (d, J=8.2 Hz, 1H), 8.06 (d, J=8.5 Hz, 1H), 7.79 (t, J=7.6 Hz, 1H), 7.65 (s, 1H), 7.59 (t, J=7.8 Hz, 1H), 7.18 (d, J=7.3 Hz, 1H), 5.76 (br. s., 1H), 5.52 (br. s., 1H), 5.00 (t, J=9.3 Hz, 1H), 4.60 (d, J=11.0 Hz, 1H), 4.49-4.41 (m, 1H), 4.22 (t, J=7.9 Hz, 1H), 3.98 (s, 3H), 3.93-3.88 (m, 1H), 3.75-3.67 (m, 1H), 3.18 (d, J=5.2 Hz, 1H), 2.73-2.58 (m, 2H), 2.41-2.14 (m, 7H), 2.01-1.00 (m, 17H), 0.93 (d, J=7.0 Hz, 3H), 0.88 (d, J=6.4 Hz, 3H), 0.72 (t, J=12.1 Hz, 1H); LC/MS: MS m/z (M+H)+ 768.5.

Preparation of Compound 5116 and Compound 5117

Scheme

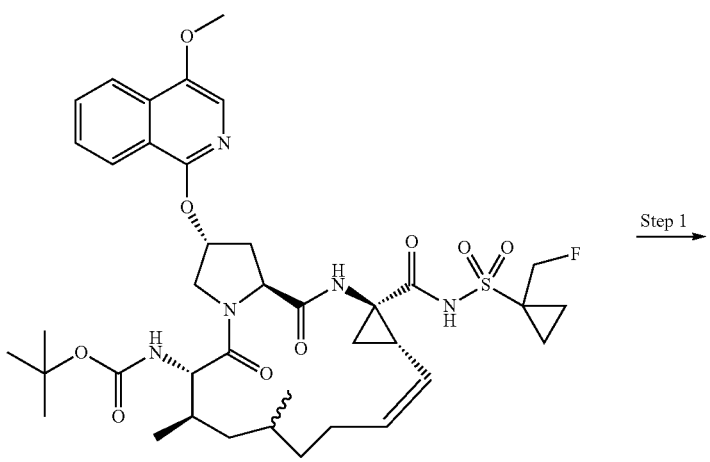

Step 1

-continued

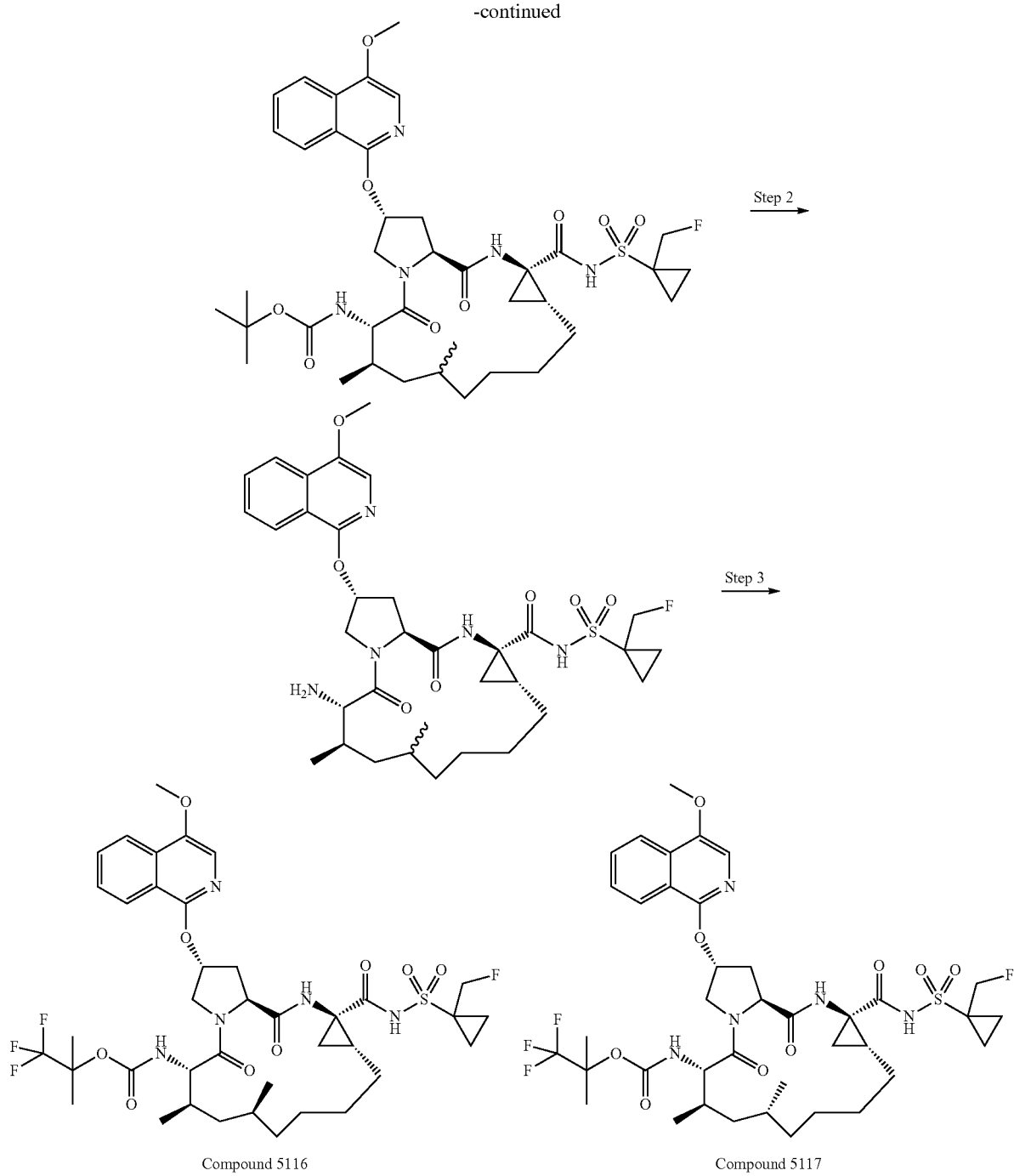

Compound 5116

Compound 5117

Step 1

A suspension of tert-butyl ((2R,6S,7R,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (220 mg, 0.280 mmol) and 5% Pt(S)/C (27.3 mg, 7.00 μmol) in AcOEt (5 mL)) was hydrogenated under a 50 PSI atmosphere of H2 for 1 h. After filtration through a celite-containing plug washing with AcOEt, the filtrate was concentrated to give 220 mg of a crude product that will be used in the next step as it is. LC/MS: MS m/z (M+H)$^+$ 788.40.

Step 2

To a solution of tert-butyl ((2R,6S,7R,13aR,14aR,16aS)-14a-(((1-(fluoromethyl)cyclopropyl)sulfonyl)carbamoyl)-2-((4-methoxyisoquinolin-1-yl)oxy)-7,9-dimethyl-5,16-dioxooctadecahydrocyclopropa[e]pyrrolo[1,2-a][1,4]diazacyclopentadecin-6-yl)carbamate (240 mg, 0.305 mmol) in CH2Cl2 (1 mL) was added TFA (0.235 mL, 3.05 mmol). The resulting solution was stirred for 1 h and concentrated to give 244 mg of a crude product as TFA salt that was used in the next step as it is. LC/MS: MS m/z (M+H)$^+$ 688.24.

Step 3

A solution of (2R,6S,7R,13aR,14aR,16aS)-6-amino-N-((1-(fluoromethyl)cyclopropyl)sulfonyl)-2-((4-methoxyisoquinolin-1-yl)oxy)-7,9-dimethyl-5,16-dioxooctadecahydrocyclopropa[e]pyrrolo[1,2-a][1,4]diazacyclopentadecine-14a-carboxamide (34.4 mg, 0.05 mmol), pyridin-2-yl (1,1,1-trifluoro-2-methylpropan-2-yl)carbonate (14.95 mg, 0.060 mmol), and N-ethyl-N-isopropylpropan-2-amine (0.044 mL, 0.250 mmol) in CH2C12 (1 mL) was stirred for 16 h. After concentration, the residue was purified by prep HPLC to 9.3 mg of Compound 5116 1,1,1-trifluoro-2-methylpropan-2-yl ((2R,6S,7R,9S,13aR,14aR,16aS)-14a-(((1-(fluoromethyl)cyclopropyl)sulfonyl)carbamoyl)-2-((4-methoxyisoquinolin-1-yl)oxy)-7,9-dimethyl-5,16-dioxooctadecahydrocyclopropa[e]pyrrolo[1,2-a][1,4]diazacyclopentadecin-6-yl)carbamate as a solid and 11.3 mg of Compound 5117 1,1,1-trifluoro-2-methylpropan-2-yl ((2R,6S,7R,9R,13aR,14aR,16aS)-14a-(((1-(fluoromethyl)cyclopropyl)sulfonyl)carbamoyl)-2-((4-methoxyisoquinolin-1-yl)oxy)-7,9-dimethyl-5,16-dioxooctadecahydrocyclopropa[e]pyrrolo[1,2-a][1,4]diazacyclopentadecin-6-yl)carbamate as a solid.

Compound 5116: 1,1,1-trifluoro-2-methylpropan-2-yl ((2R,6S,7R,9S,13aR,14aR,16aS)-14a-(((1-(fluoromethyl)cyclopropyl)sulfonyl)carbamoyl)-2-((4-methoxyisoquinolin-1-yl)oxy)-7,9-dimethyl-5,16-dioxooctadecahydrocyclopropa[e]pyrrolo[1,2-a][1,4]diazacyclopentadecin-6-yl)carbamate. MS: MS m/z 842.3 (M$^+$+1).

Compound 5117: 1,1,1-trifluoro-2-methylpropan-2-yl ((2R,6S,7R,9R,13aR,14aR,16aS)-14a-(((1-(fluoromethyl)cyclopropyl)sulfonyl)carbamoyl)-2-((4-methoxyisoquinolin-1-yl)oxy)-7,9-dimethyl-5,16-dioxooctadecahydrocyclopropa[e]pyrrolo[1,2-a][1,4]diazacyclopentadecin-6-yl)carbamate. $^1$H NMR (500 MHz, DMSO-d$_6$) δ ppm 11.38 (s, 1H), 8.99 (br. s., 1H), 8.07 (d, J=8.5 Hz, 1H), 8.10 (d, J=8.2 Hz, 1H), 7.83-7.76 (m, 2H), 7.67 (s, 1H), 7.62 (t, J=7.6 Hz, 1H), 5.76 (br. s., 1H), 4.84-4.74 (d, J=11.3 Hz, 1H), 4.69-4.59 (d, J=11.3 Hz, 1H), 4.57-4.43 (m, 2H), 3.98 (s, 3H), 3.94-3.87 (m, 1H), 3.70 (dd, J=10.8, 8.1 Hz, 1H), 2.60 (d, J=7.0 Hz, 1H), 2.34-2.22 (m, 1H), 1.96-1.86 (m, 1H), 1.78 (d, J=6.4 Hz, 1H), 1.69 (d, J=12.2 Hz, 1H), 1.56 (br. s., 4H), 1.35 (s, 6H), 1.26 (s, 3H), 1.28 (s, 3H), 1.09 (s, 3H), 1.02 (d, J=11.6 Hz, 1H), 0.95 (d, J=6.7 Hz, 4H), 0.88 (d, J=6.1 Hz, 3H), 0.71 (t, J=12.2 Hz, 1H);

Compound 5114

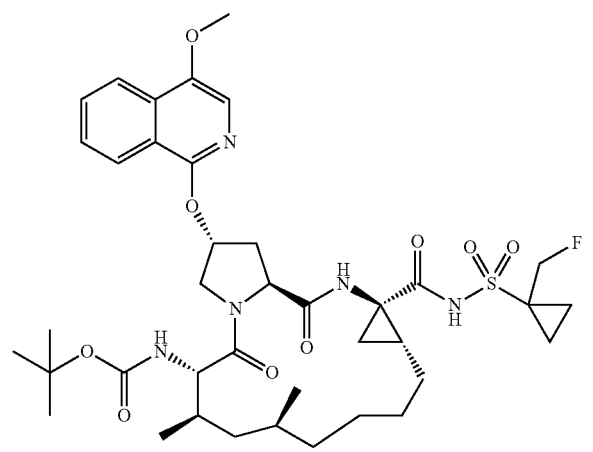

Compound 5115

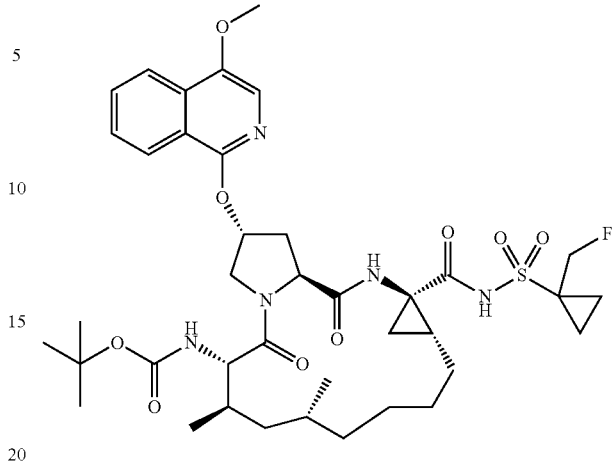

MS: MS m/z 842.3 (M$^+$+1).

Preparation of Compound 5114 and Compound 5115

A suspension of tert-butyl ((2R,6S,7R,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (15 mg, 0.019 mmol) and 5% Pt(S)/C (1.862 mg, 0.477 µmol) in AcOEt (5 mL)) was hydrogenated under a 50 PSI atmosphere of H2 for 1 h. After filtration through a celite-containing plug washing with AcOEt, the filtrate was concentrated, the residue was purified by prep HPLC to 0.4 mg of Compound 5114 tert-butyl ((2R,6S,7R,9S,13aR,14aR,16aS)-14a-(((1-(fluoromethyl)cyclopropyl)sulfonyl)carbamoyl)-2-((4-methoxyisoquinolin-1-yl)oxy)-7,9-dimethyl-5,16-dioxooctadecahydrocyclopropa[e]pyrrolo[1,2-a][1,4]diazacyclopentadecin-6-yl)carbamate as a solid and 9.9 mg of Compound 5115 tert-butyl ((2R,6S,7R,9R,13aR,14aR,16aS)-14a-(((1-(fluoromethyl)cyclopropyl)sulfonyl)carbamoyl)-2-((4-methoxyisoquinolin-1-yl)oxy)-7,9-dimethyl-5,16-dioxooctadecahydrocyclopropa[e]pyrrolo[1,2-a][1,4]diazacyclopentadecin-6-yl)carbamate as a solid, respectively.

Compound 5114: tert-butyl ((2R,6S,7R,9S,13aR,14aR,16aS)-14a-(((1-(fluoromethyl)cyclopropyl)sulfonyl)carbamoyl)-2-((4-methoxyisoquinolin-1-yl)oxy)-7,9-dimethyl-5,16-dioxooctadecahydrocyclopropa[e]pyrrolo[1,2-a][1,4]diazacyclopentadecin-6-yl)carbamate. MS: MS m/z 788.4 (M$^+$+1).

Compound 5115: tert-butyl ((2R,6S,7R,9R,13aR,14aR,16aS)-14a-(((1-(fluoromethyl)cyclopropyl)sulfonyl)carbamoyl)-2-((4-methoxyisoquinolin-1-yl)oxy)-7,9-dimethyl-5,16-dioxooctadecahydrocyclopropa[e]pyrrolo[1,2-a][1,4]diazacyclopentadecin-6-yl)carbamate. $^1$H NMR (500 MHz, DMSO-d$_6$) δ ppm 11.38 (br. s., 1H), 8.96 (br. s., 1H), 8.12 (d, J=8.2 Hz, 1H), 8.06 (d, J=8.5 Hz, 1H), 7.79 (t, J=7.2 Hz, 1H), 7.68-7.63 (m, 1H), 7.59 (t, J=7.3 Hz, 1H), 7.14 (d, J=8.5 Hz, 1H), 5.76 (br. s., 1H), 4.79-4.65 (m, 1H), 4.59 (d, J=11.0 Hz, 1H), 4.47-4.36 (m, 1H), 3.98 (s, 3H), 3.94-3.86 (m, 1H), 3.76-3.65 (m, 1H), 2.64-2.56 (m, 1H), 2.27 (t, J=10.4 Hz, 1H), 1.92 (s, 1H), 1.76 (d, J=6.7 Hz, 1H), 1.69 (d, J=10.7 Hz, 1H), 1.62 (br. s., 1H), 1.56 (br. s., 2H), 1.38 (br. s., 1H), 1.31 (br. s., 3H), 1.29-1.20 (m, 6H), 1.15 (s, 8H), 1.07-0.98 (m, 2H), 0.95 (d, J=6.7 Hz, 4H), 0.88 (d, J=6.4 Hz, 3H), 0.79 (d, J=6.4 Hz, 1H), 0.73-0.64 (m, 1H); MS: MS m/z 788.5 (M⁺+1).

Preparation of Compound 3001 and Compound 3002

Preparation of Compound 3003 and Compound 3004

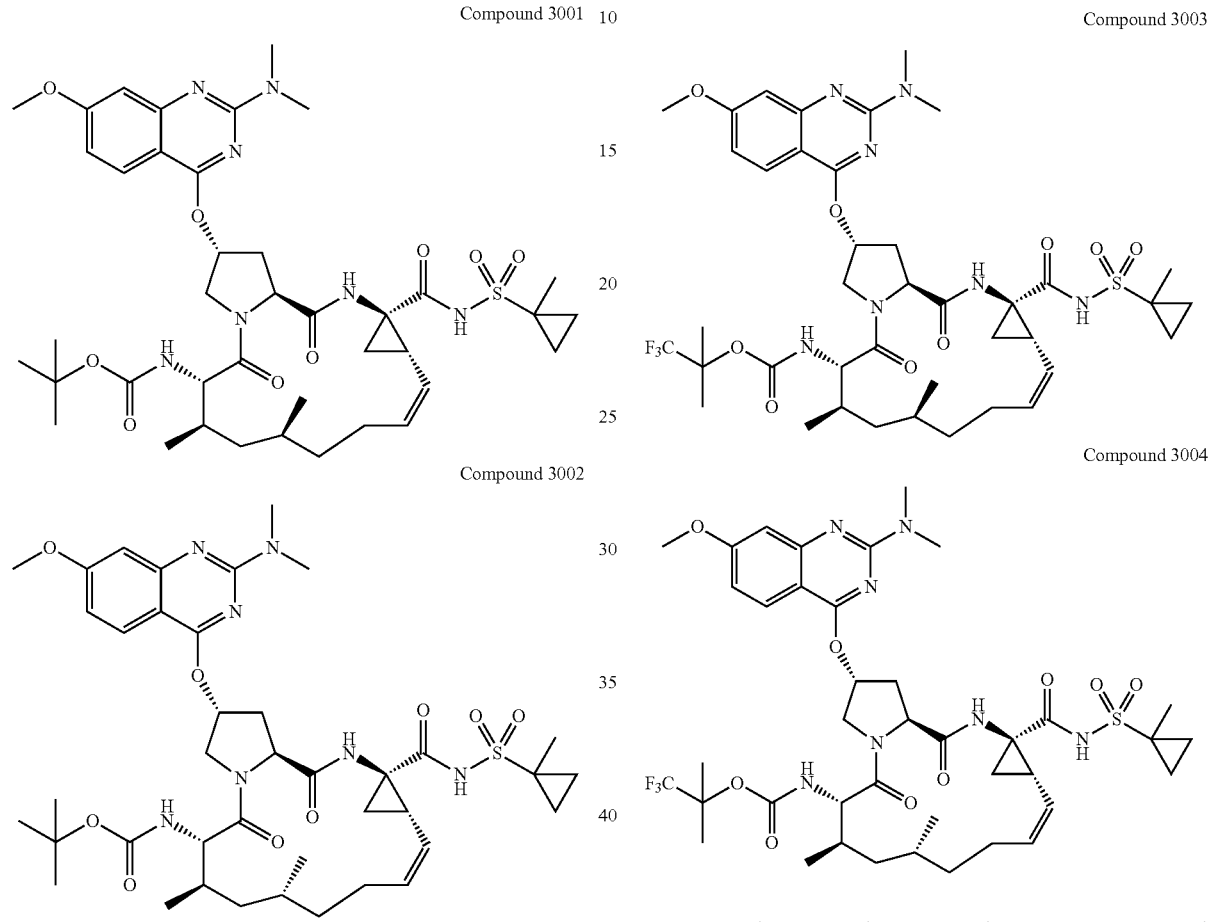

Compound 3001 and Compound 3002 were prepared using the intermediates described herein and by following the general procedure described for the synthesis of Compound 3117:

Compound 3001: tert-butyl ((2R,6S,7R,9S,13aS,14aR,16aS,Z)-2-((2-(dimethylamino)-7-methoxyquinazolin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 812.5 (M⁺+1).

Compound 3002: tert-butyl ((2R,6S,7R,9R,13aS,14aR,16aS,Z)-2-((2-(dimethylamino)-7-methoxyquinazolin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; ¹H NMR (500 MHz, DMSO-d₆) δ 11.05 (br. s., 1H), 9.10 (br. s., 1H), 7.72 (d, J=8.9 Hz, 1H), 7.22 (d, J=7.9 Hz, 1H), 6.82 (d, J=2.1 Hz, 1H), 6.65 (dd, J=8.9, 2.4 Hz, 1H), 5.81 (br. s., 1H), 5.59-5.47 (m, 1H), 5.04-4.93 (m, 1H), 4.57 (d, J=10.7 Hz, 1H), 4.45 (t, J=8.5 Hz, 1H), 3.97-3.90 (m, 1H), 3.85 (s, 3H), 3.73 (dd, J=10.5, 8.4 Hz, 1H), 3.24-3.16 (m, 6H), 2.75-2.58 (m, 2H), 2.41-2.24 (m, 2H), 1.98-0.67 (m, 31H); MS: MS m/z 812.5 (M⁺+1).

Compound 3003 and Compound 3004 were prepared using the intermediates described herein and by following the general procedure described for the synthesis of Compound 3117:

Compound 3003: 1,1,1-trifluoro-2-methylpropan-2-yl ((2R,6S,7R,9S,13aS,14aR,16aS,Z)-2-((2-(dimethylamino)-7-methoxyquinazolin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 866.5 (M⁺+1).

Compound 3004: 1,1,1-trifluoro-2-methylpropan-2-yl ((2R,6S,7R,9R,13aS,14aR,16aS,Z)-2-((2-(dimethylamino)-7-methoxyquinazolin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; ¹H NMR (500 MHz, DMSO-d₆) δ 11.04 (br. s., 1H), 9.13 (br. s., 1H), 7.87 (d, J=7.9 Hz, 1H), 7.69 (d, J=9.2 Hz, 1H), 6.83 (d, J=2.4 Hz, 1H), 6.69 (dd, J=8.9, 2.4 Hz, 1H), 5.81 (br. s., 1H), 5.58-5.47 (m, 1H), 5.03-4.92 (m, 1H), 4.60-4.42 (m, 2H), 3.98-3.89

(m, 1H), 3.85 (s, 3H), 3.72 (dd, J=10.7, 7.9 Hz, 1H), 3.25-3.14 (m, 6H), 2.72-2.58 (m, 2H), 2.39-2.24 (m, 2H), 1.96-1.78 (m, 2H), 1.74-0.70 (m, 26H); MS: MS m/z 866.5 (M$^+$+1).

Preparation of Compound 3005 and Compound 3006

Compound 3005

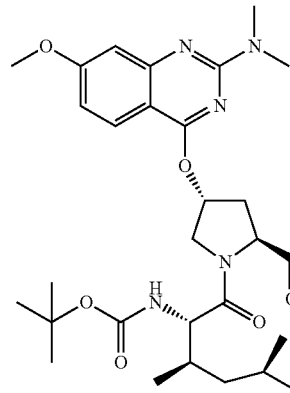

Compound 3006

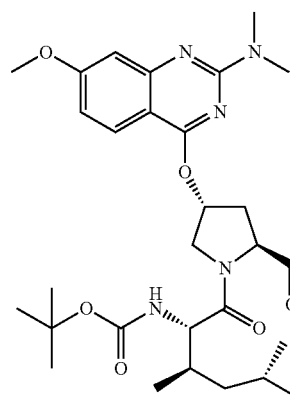

Compound 3005 and Compound 3006 were prepared using the intermediates described herein and by following the general procedure described for the synthesis of Compound 3117:

Compound 3005: tert-butyl ((2R,6S,7R,9S,13aS,14aR,16aS,Z)-2-((2-(dimethylamino)-7-methoxyquinazolin-4-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 830.5 (M$^+$+1).

Compound 3006: tert-butyl ((2R,6S,7R,9R,13aS,14aR,16aS,Z)-2-((2-(dimethylamino)-7-methoxyquinazolin-4-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.27 (s, 1H), 9.01 (br. s., 1H), 7.72 (d, J=8.9 Hz, 1H), 7.22 (d, J=7.9 Hz, 1H), 6.83 (d, J=2.4 Hz, 1H), 6.65 (dd, J=8.9, 2.4 Hz, 1H), 5.80 (br. s., 1H), 5.58-5.44 (m, 1H), 5.00 (t, J=9.6 Hz, 1H), 4.88-4.72 (m, 1H), 4.65-4.46 (m, 2H), 4.42 (t, J=8.1 Hz, 1H), 3.98-3.89 (m, 1H), 3.85 (s, 3H), 3.73 (dd, J=10.4, 8.5 Hz, 1H), 3.21 (s, 6H), 2.72-2.58 (m, 2H), 2.36-2.22 (m, 2H), 1.97-1.76 (m, 2H), 1.73-0.66 (m, 26H); MS: MS m/z 830.5 (M$^+$+1).

Preparation of Compound 3007 and Compound 3008

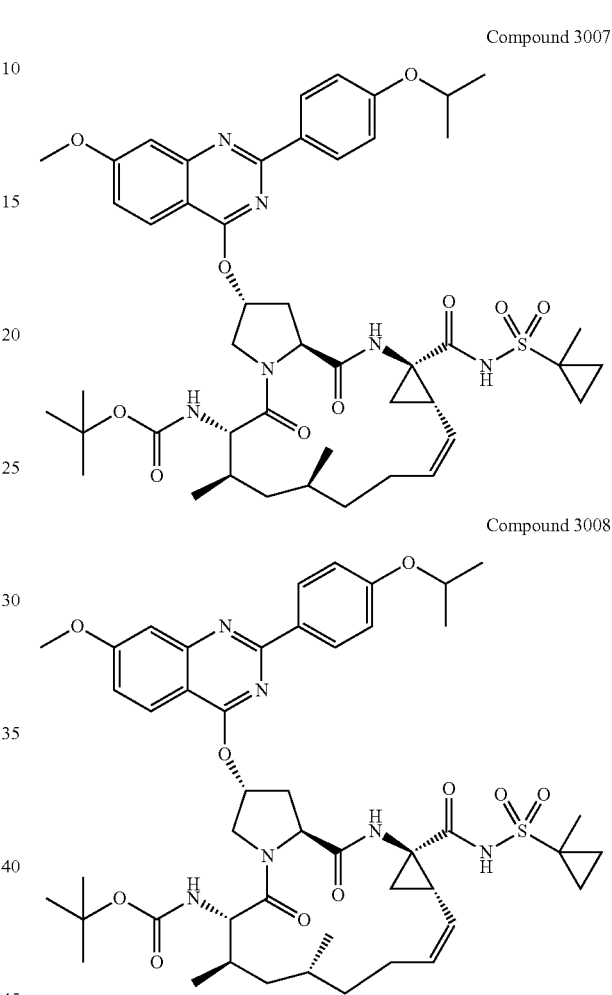

Compound 3007 and Compound 3008 were prepared using the intermediates described herein and by following the general procedure described for the synthesis of Compound 3117:

Compound 3007: tert-butyl ((2R,6S,7R,9S,13aS,14aR,16aS,Z)-2-((2-(4-isopropoxyphenyl)-7-methoxyquinazolin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 903.5 (M$^+$+1).

Compound 3008: tert-butyl ((2R,6S,7R,9R,13aS,14aR,16aS,Z)-2-((2-(4-isopropoxyphenyl)-7-methoxyquinazolin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.07 (s, 1H), 9.11 (s, 1H), 8.51-8.41 (m, 2H), 7.98 (d, J=9.2 Hz, 1H), 7.32 (d, J=2.4 Hz, 1H), 7.22 (d, J=7.9 Hz, 1H), 7.14-7.04 (m, 3H), 6.06 (br. s., 1H), 5.60-5.48 (m, 1H), 4.99 (t, J=9.8 Hz, 1H), 4.83-4.72 (m, 1H), 4.69

(d, J=12.2 Hz, 1H), 4.53 (dd, J=9.3, 7.5 Hz, 1H), 4.02-3.93 (m, 4H), 3.70 (dd, J=10.7, 8.2 Hz, 1H), 2.78-2.61 (m, 2H), 2.46-2.24 (m, 2H), 1.97-1.76 (m, 2H), 1.74-1.65 (m, 1H), 1.65-1.58 (m, 1H), 1.57-1.50 (m, 1H), 1.49-0.69 (m, 32H); MS: MS m/z 903.5 (M$^+$+1).

Preparation of Compound 3009 and Compound 3010

Compound 3009

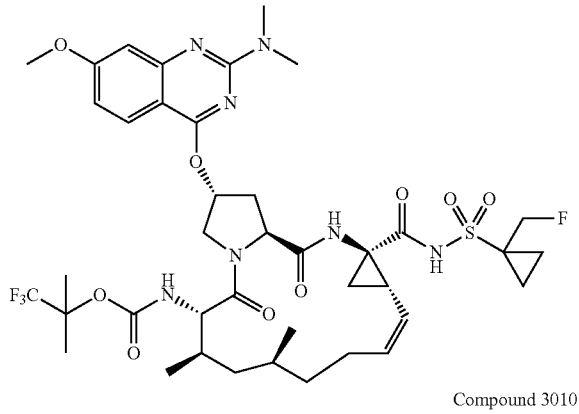

Compound 3010

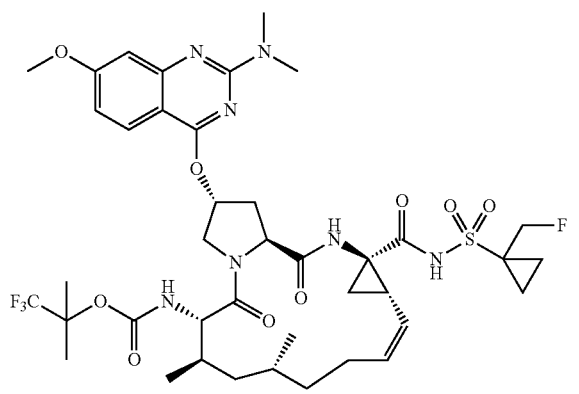

Compound 3009 and Compound 3010 were prepared using the intermediates described herein and by following the general procedure described for the synthesis of Compound 3117:

Compound 3009: 1,1,1-trifluoro-2-methylpropan-2-yl ((2R,6S,7R,9S,13aS,14aR,16aS,Z)-2-((2-(dimethylamino)-7-methoxyquinazolin-4-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 884.4 (M$^+$+1).

Compound 3010: 1,1,1-trifluoro-2-methylpropan-2-yl ((2R,6S,7R,9R,13aS,14aR,16aS,Z)-2-((2-(dimethylamino)-7-methoxyquinazolin-4-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.27 (br. s, 1H), 9.04 (br. s., 1H), 7.86 (d, J=7.9 Hz, 1H), 7.69 (d, J=8.9 Hz, 1H), 6.84 (d, J=2.4 Hz, 1H), 6.69 (dd, J=8.9, 2.4 Hz, 1H), 5.81 (br. s., 1H), 5.56-5.47 (m, 1H), 5.01 (t, J=9.8 Hz, 1H), 4.88-4.72 (m, 1H), 4.63-4.42 (m, 3H), 3.97-3.90 (m, 1H), 3.72 (dd, J=10.8, 8.1 Hz, 1H), 3.21 (s, 6H), 2.70-2.59 (m, 2H), 2.41-2.23 (m, 2H), 1.96-1.80 (m, 2H), 1.73-1.64 (m, 1H), 1.61-1.08 (m, 18H), 0.93 (d, J=7.0 Hz, 3H), 0.90 (d, J=6.1 Hz, 3H), 0.75 (t, J=12.4 Hz, 1H); MS: MS m/z 884.4 (M$^+$+1).

Preparation of Compound 3011 and Compound 3012

Compound 3011

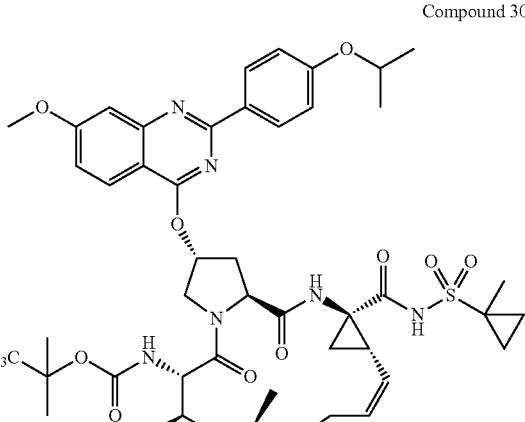

Compound 3012

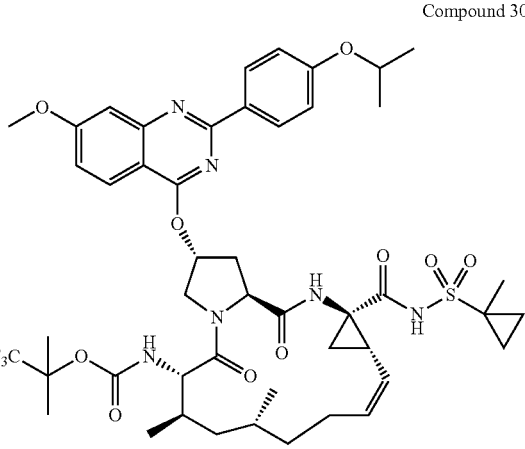

Compounds 3011 and 3012 were prepared using the intermediates described herein and by following the general procedure described for the synthesis of Compound 3117:

Compound 3011: 1,1,1-trifluoro-2-methylpropan-2-yl ((2R,6S,7R,9S,13aS,14aR,16aS,Z)-2-((2-(4-isopropoxyphenyl)-7-methoxyquinazolin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 957.5 (M$^+$+1).

Compound 3012: 1,1,1-trifluoro-2-methylpropan-2-yl ((2R,6S,7R,9R,13aS,14aR,16aS,Z)-2-((2-(4-isopropoxyphenyl)-7-methoxyquinazolin-4-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.06 (br. s., 1H), 9.14 (br. s., 1H), 8.47 (d, J=8.9 Hz, 2H), 7.95 (d, J=9.2 Hz, 1H), 7.33 (d, J=2.4 Hz, 1H), 7.14 (dd, J=8.9, 2.4 Hz, 1H), 7.09 (d, J=8.9 Hz, 2H), 6.06 (br. s., 1H), 5.60-5.47 (m, 1H), 5.06-4.94 (m, 1H), 4.82-4.71 (m, 1H), 4.68-4.48 (m, 2H), 4.03-3.98 (m, 1H), 3.96 (s, 3H), 3.69 (dd, J=10.5, 8.1 Hz, 1H), 2.79-2.63 (m, 2H), 2.46-2.26 (m, 2H), 1.97-1.79 (m, 2H), 1.76-0.69 (m, 33H); MS: MS m/z 957.5 (M⁺+1).

Preparation of Compound 3013 and Compound 3014

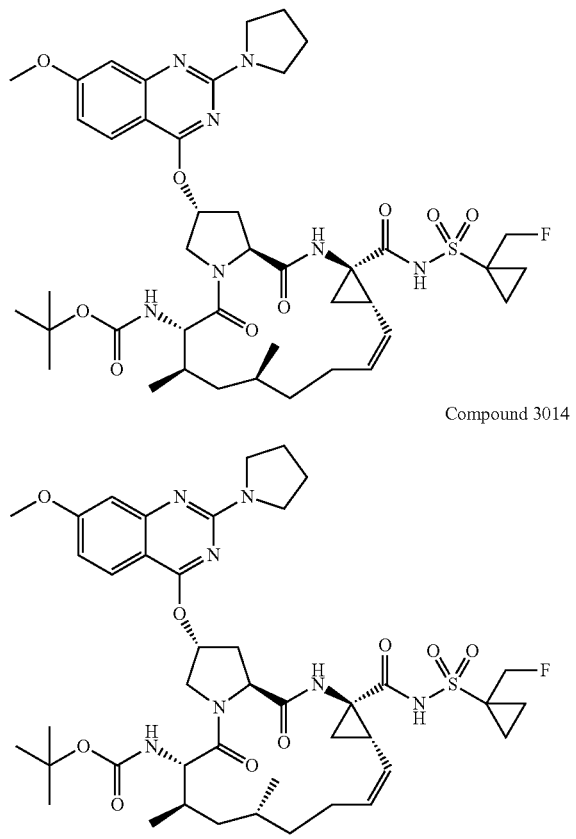

Compound 3013

Compound 3014

Compounds 3013 and 3014 were prepared using the intermediates described herein and by following the general procedure described for the synthesis of Compound 3117:

Compound 3013: tert-butyl ((2R,6S,7R,9S,13aS,14aR,16aS,Z)-14a-(((1-(fluoromethyl)cyclopropyl)sulfonyl)carbamoyl)-2-((7-methoxy-2-(pyrrolidin-1-yl)quinazolin-4-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 856.4 (M⁺+1).

Compound 3014: tert-butyl ((2R,6S,7R,9R,13aS,14aR,16aS,Z)-14a-(((1-(fluoromethyl)cyclopropyl)sulfonyl)carbamoyl)-2-((7-methoxy-2-(pyrrolidin-1-yl)quinazolin-4-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; ¹H NMR (500 MHz, DMSO-d₆) δ 11.27 (br. s., 1H), 9.02 (br. s., 1H), 7.72 (d, J=8.9 Hz, 1H), 7.21 (d, J=7.3 Hz, 1H), 6.82 (d, J=2.1 Hz, 1H), 6.64 (dd, J=9.0, 2.3 Hz, 1H), 5.78 (br. s., 1H), 5.57-5.45 (m, 1H), 5.08-4.93 (m, 1H), 4.90-4.69 (m, 1H), 4.65-4.38 (m, 3H), 3.95 (dd, J=11.4, 3.5 Hz, 1H), 3.85 (s, 3H), 3.74 (dd, J=10.7, 8.5 Hz, 1H), 3.58 (br. s., 4H), 2.72-2.59 (m, 2H), 2.35-2.24 (m, 2H), 2.02-1.07 (m, 25H), 0.93 (d, J=7.0 Hz, 3H), 0.89 (d, J=6.1 Hz, 3H), 0.73 (t, J=12.1 Hz, 1H); MS: MS m/z 856.4 (M⁺+1).

Preparation of Compound 3015

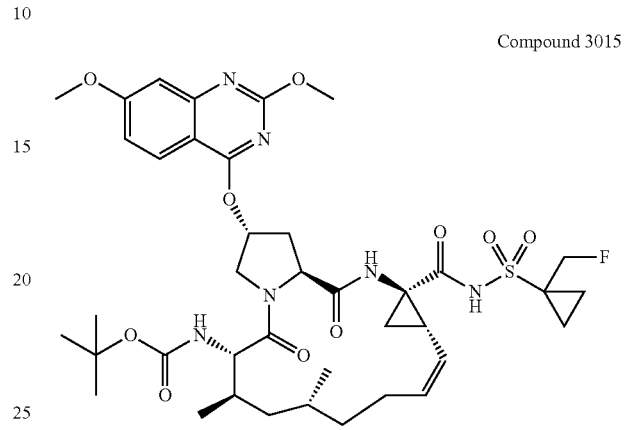

Compound 3015

Compound 3015 was prepared using the intermediates described herein and by following the general procedure described for the synthesis of Compound 3117:

Compound 3015: tert-butyl ((2R,6S,7R,9R,13aS,14aR,16aS,Z)-2-((2,7-dimethoxyquinazolin-4-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; ¹H NMR (500 MHz, DMSO-d₆) δ 11.27 (br. s., 1H), 9.04 (br. s., 1H), 7.88 (d, J=9.2 Hz, 1H), 7.19 (br. s., 1H), 7.11 (d, J=2.1 Hz, 1H), 6.96 (dd, J=9.0, 2.3 Hz, 1H), 5.79 (br. s., 1H), 5.58-5.45 (m, 1H), 5.09-4.95 (m, 1H), 4.89-4.72 (m, 1H), 4.70-4.40 (m, 3H), 3.98 (s, 3H), 3.94-3.87 (m, 4H), 3.67 (dd, J=10.7, 8.2 Hz, 1H), 2.72-2.59 (m, 2H), 2.41-2.22 (m, 2H), 1.95-0.66 (m, 28H); MS: MS m/z 817.4 (M⁺+1).

Preparation of Compound 3016 and Compound 3017

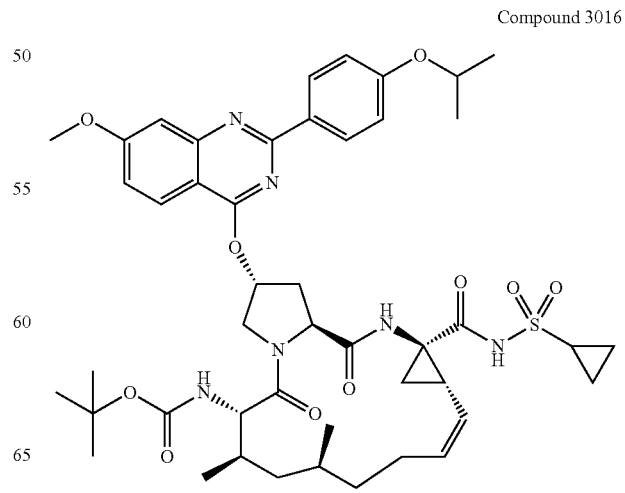

Compound 3016

-continued

Compound 3017

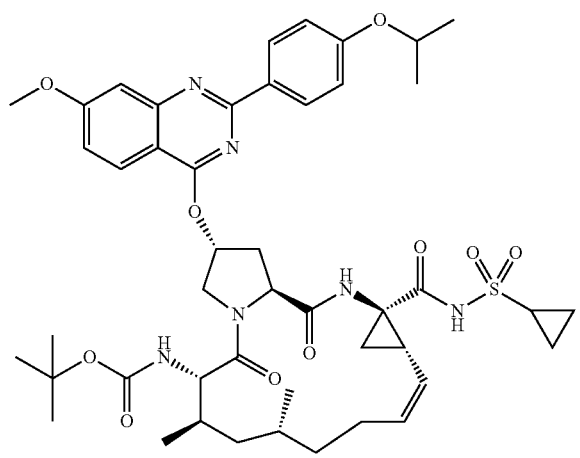

Compounds 3016 and 3017 were prepared using the intermediates described herein and by following the general procedure described for the synthesis of Compound 3117:

Compound 3016: tert-butyl ((2R,6S,7R,9S,13aS,14aR, 16aS,Z)-14a-((cyclopropylsulfonyl)carbamoyl)-2-((2-(4-isopropoxyphenyl)-7-methoxyquinazolin-4-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 889.5 $(M^++1)$.

Compound 3017: tert-butyl ((2R,6S,7R,9R,13aS,14aR, 16aS,Z)-14a-((cyclopropylsulfonyl)carbamoyl)-2-((2-(4-isopropoxyphenyl)-7-methoxyquinazolin-4-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.22 (br. s., 1H), 8.97 (br. s., 1H), 8.47 (d, J=8.9 Hz, 2H), 7.98 (d, J=8.9 Hz, 1H), 7.32 (d, J=2.1 Hz, 1H), 7.21 (d, J=7.6 Hz, 1H), 7.13-7.04 (m, 3H), 6.03 (br. s., 1H), 5.59-5.46 (m, 1H), 5.14-5.02 (m, 1H), 4.76 (spt, J=6.0 Hz, 1H), 4.67 (d, J=11.6 Hz, 1H), 4.48 (t, J=8.5 Hz, 1H), 4.02-3.93 (m, 4H), 3.70 (dd, J=10.7, 8.2 Hz, 1H), 2.99-2.87 (m, 1H), 2.79-2.62 (m, 2H), 2.45-2.36 (m, 1H), 2.34-2.21 (m, 1H), 1.98-0.65 (m, 34H); MS: MS m/z 889.5 $(M^++1)$.

Preparation of Compound 3018 and Compound 3019

Compound 3018

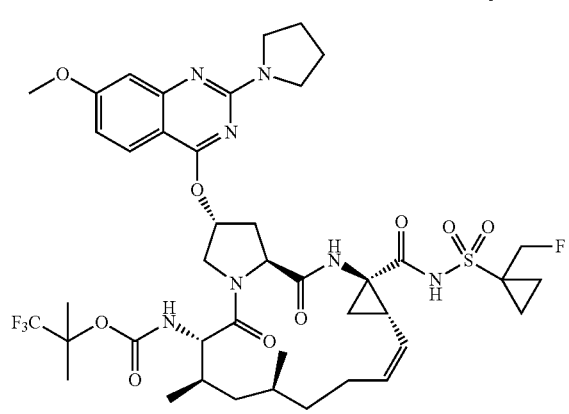

-continued

Compound 3019

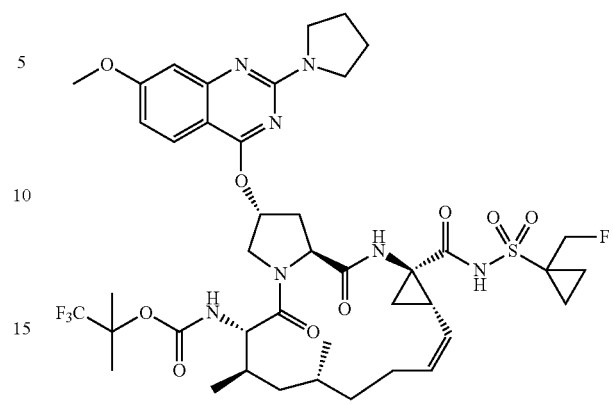

Compounds 3018 and 3019 were prepared using the intermediates described herein and by following the general procedure described for the synthesis of Compound 3117:

Compound 3018: 1,1,1-trifluoro-2-methylpropan-2-yl ((2R,6S,7R,9S,13aS,14aR,16aS,Z)-14a-(((1-(fluoromethyl)cyclopropyl)sulfonyl)carbamoyl)-2-((7-methoxy-2-(pyrrolidin-1-yl)quinazolin-4-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 910.4 $(M^++1)$.

Compound 3019: 1,1,1-trifluoro-2-methylpropan-2-yl ((2R,6S,7R,9R,13aS,14aR,16aS,Z)-14a-(((1-(fluoromethyl)cyclopropyl)sulfonyl)carbamoyl)-2-((7-methoxy-2-(pyrrolidin-1-yl)quinazolin-4-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.26 (br. s., 1H), 9.03 (br. s., 1H), 7.86 (d, J=7.9 Hz, 1H), 7.69 (d, J=8.9 Hz, 1H), 6.83 (d, J=2.4 Hz, 1H), 6.67 (dd, J=8.9, 2.4 Hz, 1H), 5.79 (br. s., 1H), 5.58-5.45 (m, 1H), 5.03 (br. s., 1H), 4.89-4.70 (m, 1H), 4.65-4.42 (m, 3H), 3.94 (dd, J=11.6, 3.4 Hz, 1H), 3.85 (s, 3H), 3.73 (dd, J=10.7, 8.2 Hz, 1H), 3.59 (br. s., 4H), 2.68-2.57 (m, 2H), 2.37-2.22 (m, 2H), 2.02-1.09 (m, 22H), 0.94 (d, J=6.7 Hz, 3H), 0.90 (d, J=6.4 Hz, 3H), 0.75 (t, J=12.1 Hz, 1H); MS: MS m/z 910.4 $(M^++1)$.

Preparation of Compound 3020

Compound 3020

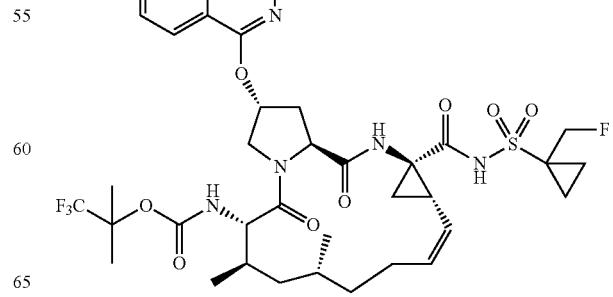

Compound 3020 was prepared using the intermediates described herein and by following the general procedure described for the synthesis of Compound 3117:

Compound 3020: 1,1,1-trifluoro-2-methylpropan-2-yl ((2R,6S,7R,9R,13aS,14aR,16aS,Z)-2-((2,7-dimethoxyquinazolin-4-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 8.41 (br. s., 1H), 7.86 (d, J=8.9 Hz, 1H), 7.78 (d, J=7.9 Hz, 1H), 7.11 (d, J=2.4 Hz, 1H), 6.99 (dd, J=9.2, 2.4 Hz, 1H), 5.77 (br. s., 1H), 5.51 (t, J=9.6 Hz, 1H), 5.35 (td, J=10.1, 5.8 Hz, 1H), 4.70 (s, 1H), 4.60 (s, 1H), 4.53 (d, J=11.3 Hz, 1H), 4.44 (dd, J=9.5, 7.3 Hz, 1H), 3.98 (s, 3H), 3.91 (s, 3H), 3.87 (dd, J=11.4, 3.2 Hz, 1H), 3.66 (dd, J=10.5, 8.1 Hz, 1H), 2.51-2.46 (m, 1H), 2.40-2.18 (m, 3H), 1.89-1.75 (m, 3H), 1.43 (dd, J=8.1, 3.8 Hz, 1H), 1.38-1.17 (m, 12H), 1.05 (s, 3H), 0.92 (d, J=7.0 Hz, 3H), 0.90-0.82 (m, 5H), 0.66 (t, J=11.3 Hz, 1H); MS: MS m/z 871.4 (M$^+$+1).

Preparation of Compound 3021 and Compound 3022

Compound 3021

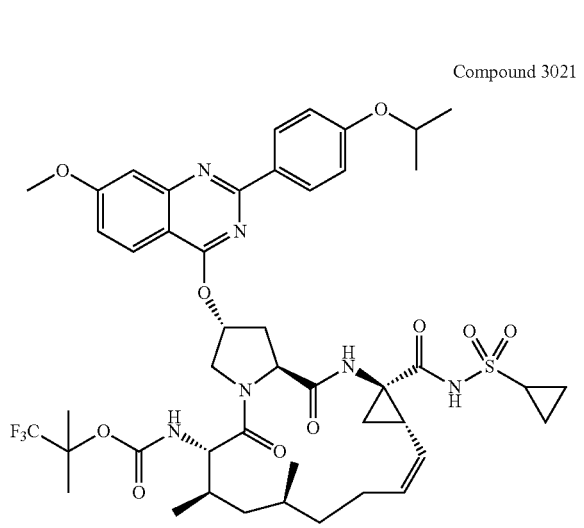

Compound 3022

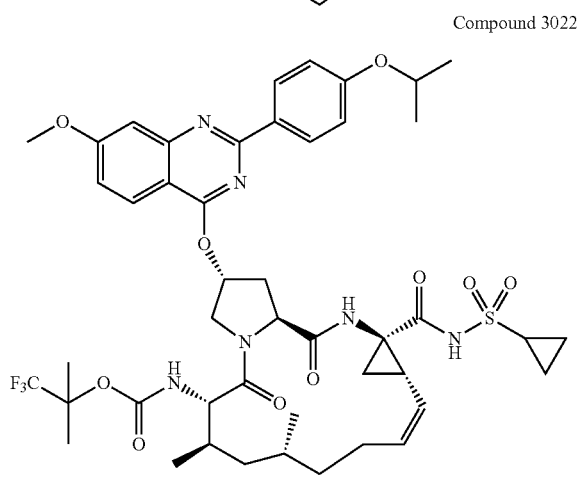

Compounds 3021 and 3022 were prepared using the intermediates described herein and by following the general procedure described for the synthesis of Compound 3117:

Compound 3021: 1,1,1-trifluoro-2-methylpropan-2-yl ((2R,6S,7R,9S,13aS,14aR,16aS,Z)-14a-(((cyclopropylsulfonyl)carbamoyl)-2-((2-(4-isopropoxyphenyl)-7-methoxyquinazolin-4-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 943.5 (M$^+$+1). Compound 3022: 1,1,1-trifluoro-2-methylpropan-2-yl ((2R,6S,7R,9R,13aS,14aR,16aS,Z)-14a-((cyclopropylsulfonyl)carbamoyl)-2-((2-(4-isopropoxyphenyl)-7-methoxyquinazolin-4-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.21 (br. s., 1H), 9.00 (br. s., 1H), 8.47 (d, J=8.9 Hz, 2H), 7.95 (d, J=8.9 Hz, 1H), 7.85 (d, J=7.3 Hz, 1H), 7.33 (d, J=2.4 Hz, 1H), 7.14 (dd, J=8.9, 2.4 Hz, 1H), 7.09 (d, J=9.2 Hz, 2H), 6.04 (br. s., 1H), 5.61-5.46 (m, 1H), 5.18-5.01 (m, 1H), 4.76 (spt, J=6.1 Hz, 1H), 4.61 (d, J=11.3 Hz, 1H), 4.52 (t, J=8.5 Hz, 1H), 4.01-3.93 (m, 4H), 3.69 (dd, J=10.7, 7.6 Hz, 1H), 3.00-2.86 (m, 1H), 2.80-2.60 (m, 2H), 2.47-2.36 (m, 1H), 2.29 (d, J=12.8 Hz, 1H), 1.99-0.67 (m, 31H); MS: MS m/z 943.5 (M$^+$+1).

Preparation of Compound 3023 and Compound 3024

Compound 3023

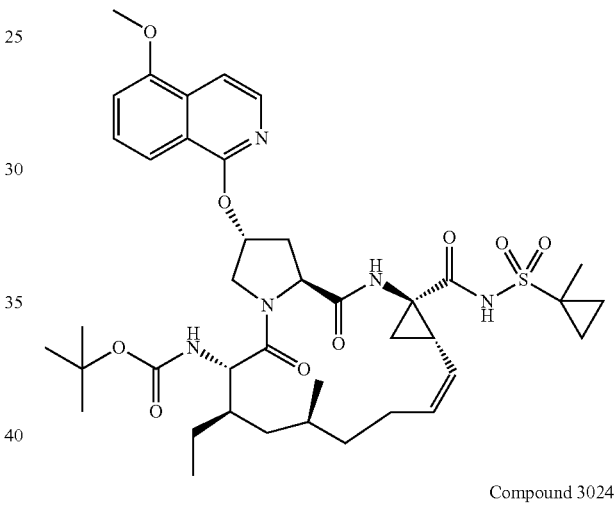

Compound 3024

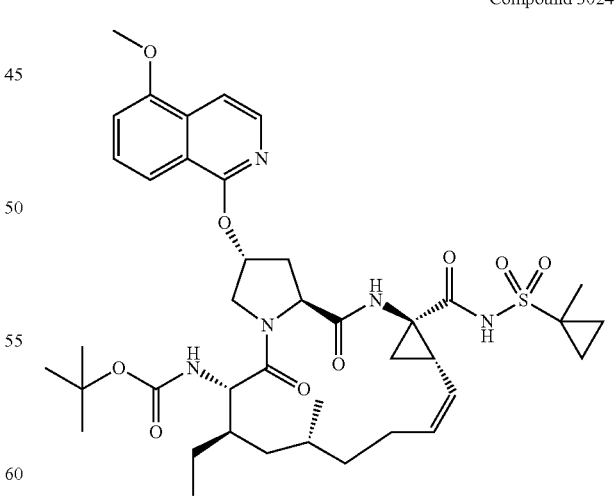

Compounds 3023 and 3024 were prepared using the intermediates described herein and by following the general procedure described for the synthesis of Compound 3117:

Compound 3023: tert-butyl ((2R,6S,7R,9S,13aS,14aR,16aS,Z)-7-ethyl-2-((5-methoxyisoquinolin-1-yl)oxy)-9- methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 782.4 ($M^+$+1).

Compound 3024: tert-butyl ((2R,6S,7R,9R,13aS,14aR,16aS,Z)-7-ethyl-2-((5-methoxyisoquinolin-1-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-$d_6$) θ 11.04 (br. s., 1H), 9.10 (br. s., 1H), 8.03 (d, J=6.1 Hz, 1H), 7.69 (d, J=8.2 Hz, 1H), 7.54 (d, J=5.8 Hz, 1H), 7.46 (t, J=8.1 Hz, 1H), 7.25-7.17 (m, 2H), 5.84 (br. s., 1H), 5.59-5.46 (m, J=4.6 Hz, 1H), 4.98 (t, J=9.6 Hz, 1H), 4.63 (d, J=11.0 Hz, 1H), 4.53-4.43 (m, 1H), 4.01-3.89 (m, 5H), 2.77-2.58 (m, 2H), 2.41-2.24 (m, 2H), 2.01-0.67 (m, 33H); MS: MS m/z 782.5 ($M^+$+1).

Preparation of Compound 3025 and Compound 3026

Compound 3025: tert-butyl ((2R,6S,7R,9S,13aS,14aR,16aS,Z)-14a-((cyclopropylsulfonyl)carbamoyl)-7-ethyl-2-((5-methoxyisoquinolin-1-yl)oxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 768.4 ($M^+$+1).

Compound 3026: tert-butyl ((2R,6S,7R,9R,13aS,14aR,16aS,Z)-14a-((cyclopropylsulfonyl)carbamoyl)-7-ethyl-2-((5-methoxyisoquinolin-1-yl)oxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-$d_6$) δ 11.18 (s, 1H), 8.97 (s, 1H), 8.03 (d, J=6.1 Hz, 1H), 7.69 (d, J=8.2 Hz, 1H), 7.54 (d, J=6.1 Hz, 1H), 7.46 (t, J=8.1 Hz, 1H), 7.25-7.17 (m, 2H), 5.83 (br. s., 1H), 5.58-5.48 (m, 1H), 5.05 (t, J=9.9 Hz, 1H), 4.63 (d, J=11.6 Hz, 1H), 4.50-4.41 (m, 1H), 4.02-3.87 (m, 5H), 2.97-2.87 (m, 1H), 2.77-2.59 (m, 2H), 2.40-2.24 (m, 2H), 2.01-1.85 (m, 2H), 1.67-0.67 (m, 28H); MS: MS m/z 768.4 ($M^+$+1).

Preparation of Compound 3027 and Compound 3028

Compound 3025

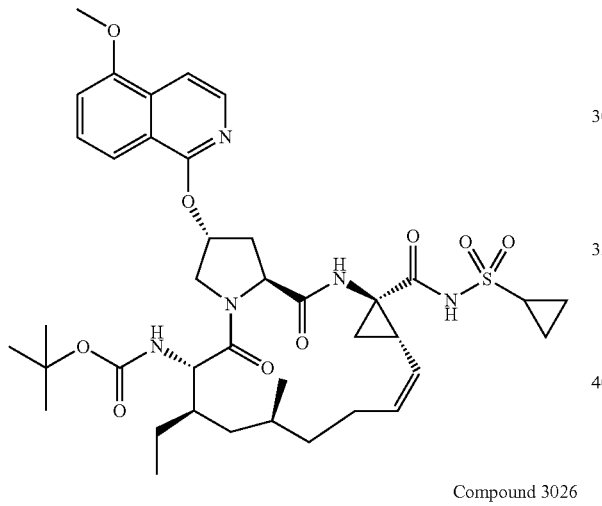

Compound 3026

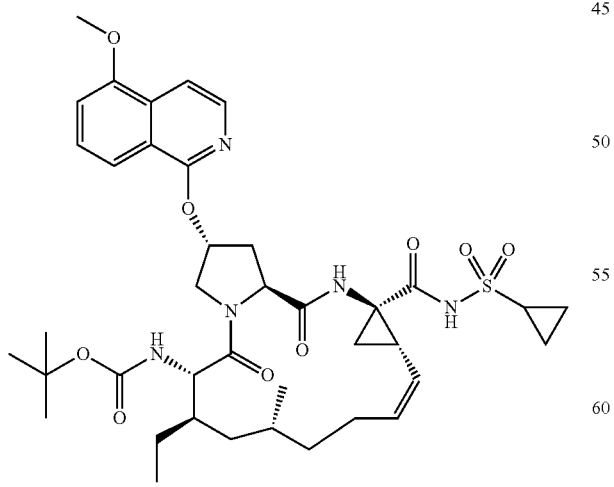

Compound 3027

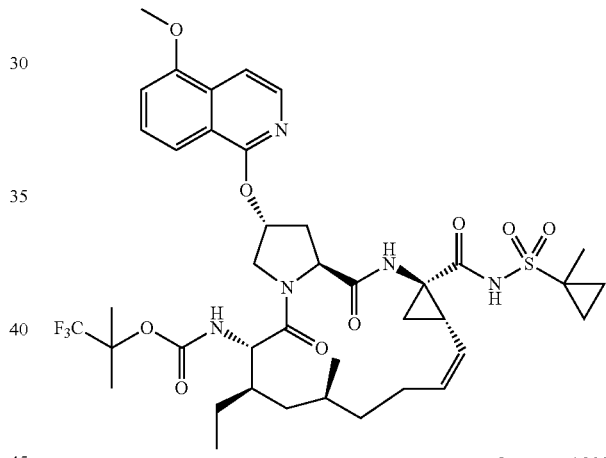

Compound 3028

Compounds 3025 and 3026 were prepared using the intermediates described herein and by following the general procedure described for the synthesis of Compound 3117:

Compounds 3027 and 3028 were prepared using the intermediates described herein and by following the general procedure described for the synthesis of Compound 3117:

Compound 3027: 1,1,1-trifluoro-2-methylpropan-2-yl ((2R,6S,7R,9S,13aS,14aR,16aS,Z)-7-ethyl-2-((5-methoxy-isoquinolin-1-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 836.4 (M⁺+1).

Compound 3028: 1,1,1-trifluoro-2-methylpropan-2-yl ((2R,6S,7R,9R,13aS,14aR,16aS,Z)-7-ethyl-2-((5-methoxy-isoquinolin-1-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; ¹H NMR (500 MHz, DMSO-d₆) δ 11.04 (br. s., 1H), 9.13 (br. s., 1H), 8.04 (d, J=6.1 Hz, 1H), 7.86 (d, J=8.5 Hz, 1H), 7.67 (d, J=8.2 Hz, 1H), 7.55 (d, J=5.8 Hz, 1H), 7.49 (t, J=8.1 Hz, 1H), 7.24 (d, J=7.6 Hz, 1H), 5.85 (br. s., 1H), 5.59-5.47 (m, 1H), 5.05-4.91 (m, 1H), 4.62-4.47 (m, 2H), 4.01-3.86 (m, 5H), 2.76-2.59 (m, 2H), 2.42-2.26 (m, 2H), 2.02-1.85 (m, 2H), 1.68-0.68 (m, 28H); MS: MS m/z 836.4 (M⁺+1).

Preparation of Compound 3029 and Compound 3030

Compounds 3029 and 3030 were prepared using the intermediates described herein and by following the general procedure described for the synthesis of Compound 3117:

Compound 3029: (2R,6S,7R,9S,13aS,14aR,16aS,Z)-6-(3-(tert-butyl)ureido)-N-(cyclopropylsulfonyl)-7-ethyl-2-((5-methoxyisoquinolin-1-yl)oxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide; MS: MS m/z 767.4 (M⁺+1).

Compound 3030: (2R,6S,7R,9R,13aS,14aR,16aS,Z)-6-(3-(tert-butyl)ureido)-N-(cyclopropylsulfonyl)-7-ethyl-2-((5-methoxyisoquinolin-1-yl)oxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide; ¹H NMR (500 MHz, DMSO-d₆) δ 11.18 (br. s., 1H), 8.93 (br. s., 1H), 8.03 (d, J=6.1 Hz, 1H), 7.70 (d, J=8.5 Hz, 1H), 7.54 (d, J=6.1 Hz, 1H), 7.44 (t, J=8.1 Hz, 1H), 7.23 (d, J=7.9 Hz, 1H), 5.96 (d, J=9.2 Hz, 1H), 5.88-5.79 (m, 1H), 5.56-5.46 (m, 1H), 5.12-5.00 (m, 1H), 4.63 (d, J=10.4 Hz, 1H), 4.40 (dd, J=9.9, 7.2 Hz, 1H), 4.07 (t, J=10.2 Hz, 1H), 3.98 (s, 3H), 3.95-3.87 (m, 1H), 2.91 (s, 1H), 2.79-2.57 (m, 2H), 2.41-2.24 (m, 2H), 2.00-0.69 (m, 31H); MS: MS m/z 767.4 (M⁺+1).

Preparation of Compound 3031 and Compound 3032

Compound 3029

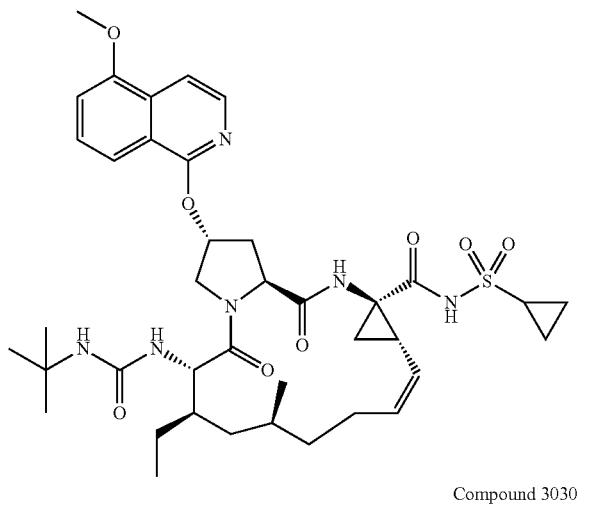

Compound 3031

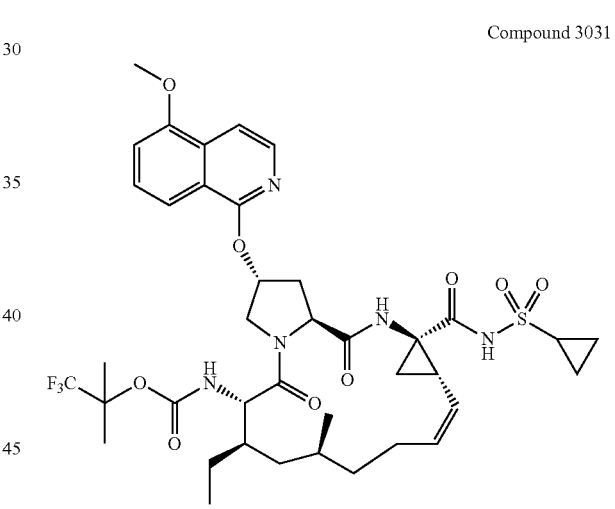

Compound 3030

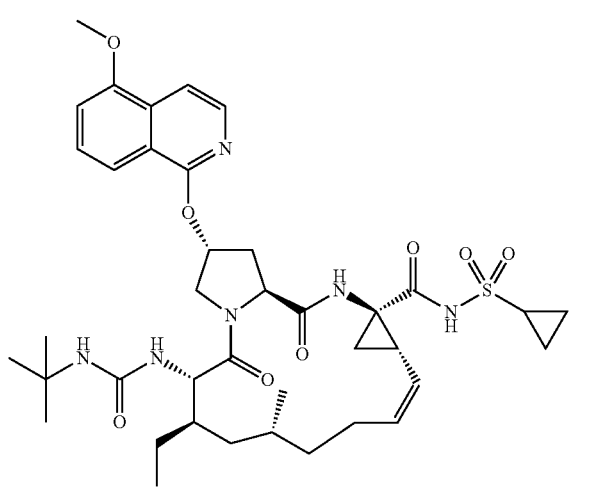

Compound 3032

Compounds 3031 and 3032 were prepared using the intermediates described herein and by following the general procedure described for the synthesis of Compound 3117:

Compound 3031: 1,1,1-trifluoro-2-methylpropan-2-yl ((2R,6S,7R,9S,13 aS,14aR,16aS,Z)-14a-((cyclopropylsulfonyl)carbamoyl)-7-ethyl-2-((5-methoxyisoquinolin-1-yl)oxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 822.4 (M$^+$+1).

Compound 3032: 1,1,1-trifluoro-2-methylpropan-2-yl ((2R,6S,7R,9R,13aS,14aR,16aS,Z)-14a-((cyclopropylsulfonyl)carbamoyl)-7-ethyl-2-((5-methoxyisoquinolin-1-yl)oxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.19 (s, 1H), 9.01 (s, 1H), 8.04 (d, J=6.1 Hz, 1H), 7.86 (d, J=8.2 Hz, 1H), 7.67 (d, J=8.5 Hz, 1H), 7.55 (d, J=5.8 Hz, 1H), 7.49 (t, J=8.1 Hz, 1H), 7.24 (d, J=7.9 Hz, 1H), 5.84 (br. s., 1H), 5.60-5.47 (m, 1H), 5.06 (t, J=9.8 Hz, 1H), 4.56 (d, J=11.6 Hz, 1H), 4.52-4.45 (m, 1H), 3.98 (s, 3H), 3.95-3.86 (m, 2H), 2.97-2.88 (m, 1H), 2.72-2.61 (m, 2H), 2.40-2.25 (m, 2H), 2.01-1.86 (m, 2H), 1.67-0.67 (m, 25H); MS: MS m/z 822.4 (M$^+$+1).

Preparation of Compound 3033 and Compound 3034

Compounds 3033 and 3034 were prepared using the intermediates described herein and by following the general procedure described for the synthesis of Compound 3117:

Compound 3033: (2R,6S,7R,9S,13aS,14aR,16aS,Z)-6-(3-(tert-butyl)ureido)-7-ethyl-2-((5-methoxyisoquinolin-1-yl)oxy)-9-methyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide; MS: MS m/z 781.5 (M$^+$+1).

Compound 3034: (2R,6S,7R,9R,13aS,14aR,16aS,Z)-6-(3-(tert-butyl)ureido)-7-ethyl-2-((5-methoxyisoquinolin-1-yl)oxy)-9-methyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide; $^1$H NMR (500 MHz, DMSO-d$_6$) δ 11.04 (s, 1H), 9.06 (br. s., 1H), 8.02 (d, J=5.8 Hz, 1H), 7.70 (d, J=8.5 Hz, 1H), 7.54 (d, J=6.1 Hz, 1H), 7.45 (t, J=8.1 Hz, 1H), 7.23 (d, J=7.6 Hz, 1H), 5.96 (d, J=9.2 Hz, 1H), 5.84 (br. s., 1H), 5.56-5.47 (m, 1H), 4.98 (t, J=10.1 Hz, 1H), 4.64 (d, J=10.7 Hz, 1H), 4.48-4.39 (m, 1H), 4.07 (t, J=10.1 Hz, 1H), 4.01-3.89 (m, 4H), 2.80-2.69 (m, 1H), 2.68-2.57 (m, 1H), 2.42-2.24 (m, 2H), 1.98-1.85 (m, 1H), 1.76 (br. s., 1H), 1.66-0.73 (m, 32H); MS: MS m/z 781.4 (M$^+$+1).

Preparation of Compound 3035 and Compound 3036

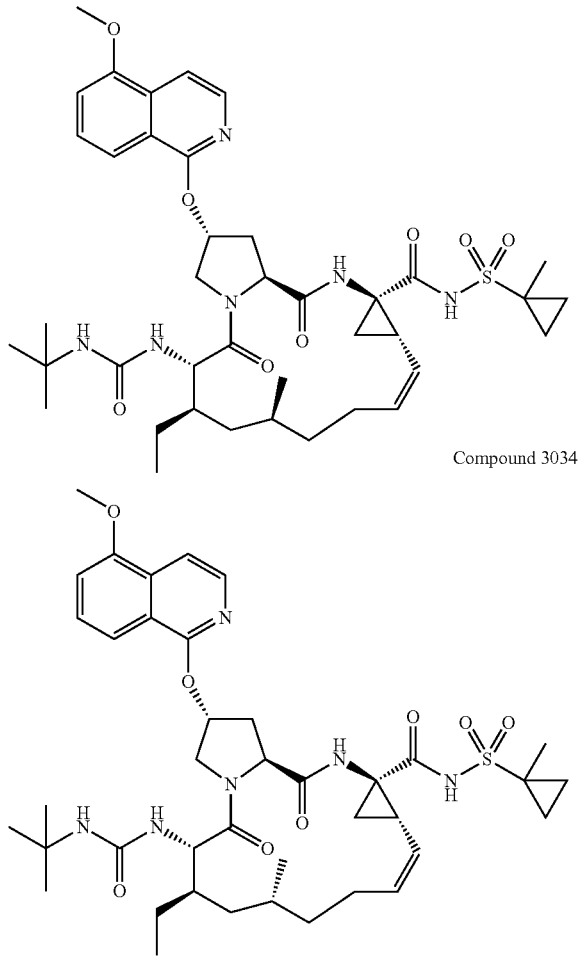

Compound 3033

Compound 3034

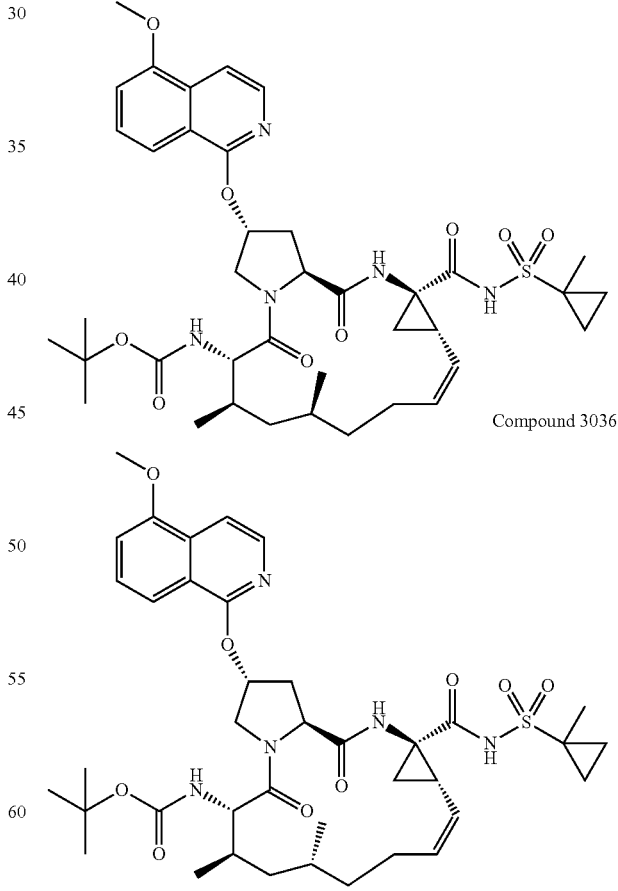

Compound 3035

Compound 3036

Compounds 3035 and 3036 were prepared using the intermediates described herein and by following the general procedure described for the synthesis of Compound 3117:

Compound 3035: tert-butyl ((2R,6S,7R,9S,13aS,14aR,16aS,Z)-2-((5-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 768.4 (M⁺+1).

Compound 3036: tert-butyl ((2R,6S,7R,9R,13aS,14aR,16aS,Z)-2-((5-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-$d_6$) δ 11.04 (br. s., 1H), 9.10 (br. s., 1H), 8.02 (d, J=6.1 Hz, 1H), 7.71 (d, J=7.9 Hz, 1H), 7.53 (d, J=5.8 Hz, 1H), 7.46 (t, J=8.1 Hz, 1H), 7.23 (d, J=7.9 Hz, 1H), 7.18 (d, J=7.9 Hz, 1H), 5.83 (br. s., 1H), 5.58-5.47 (m, 1H), 5.09-4.90 (m, 1H), 4.61 (d, J=11.9 Hz, 1H), 4.52-4.45 (m, 1H), 4.04-3.88 (m, 4H), 3.72 (t, J=9.5 Hz, 1H), 2.79-2.56 (m, 2H), 2.40-2.24 (m, 2H), 1.99-0.63 (m, 31H); MS: MS m/z 768.4 (M⁺+1).

Preparation of Compound 3037 and Compound 3038

Compound 3037: 1,1,1-trifluoro-2-methylpropan-2-yl ((2R,6S,7R,9S,13aS,14aR,16aS,Z)-2-((5-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 822.4 (M⁺+1).

Compound 3038: 1,1,1-trifluoro-2-methylpropan-2-yl ((2R,6S,7R,9R,13aS,14aR,16aS,Z)-2-((5-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-$d_6$) δ 11.04 (br. s., 1H), 9.14 (s, 1H), 8.03 (d, J=5.8 Hz, 1H), 7.83 (d, J=7.9 Hz, 1H), 7.69 (d, J=8.2 Hz, 1H), 7.54 (d, J=5.8 Hz, 1H), 7.49 (t, J=8.1 Hz, 1H), 7.24 (d, J=7.9 Hz, 1H), 5.84 (br. s., 1H), 5.54 (td, J=10.1, 6.1 Hz, 1H), 4.98 (t, J=9.9 Hz, 1H), 4.61-4.49 (m, 2H), 3.98 (s, 3H), 3.96-3.90 (m, 1H), 3.71 (dd, J=10.7, 7.9 Hz, 1H), 2.73-2.60 (m, 2H), 2.40-2.26 (m, 2H), 1.96-1.79 (m, 2H), 1.70 (dd, J=12.8, 7.3 Hz, 1H), 1.62 (dd, J=8.2, 5.2 Hz, 1H), 1.52 (dd, J=9.3, 5.3 Hz, 1H), 1.48-0.84 (m, 22H), 0.76 (t, J=12.2 Hz, 1H); MS: MS m/z 822.4 (M⁺+1).

Preparation of Compound 3039

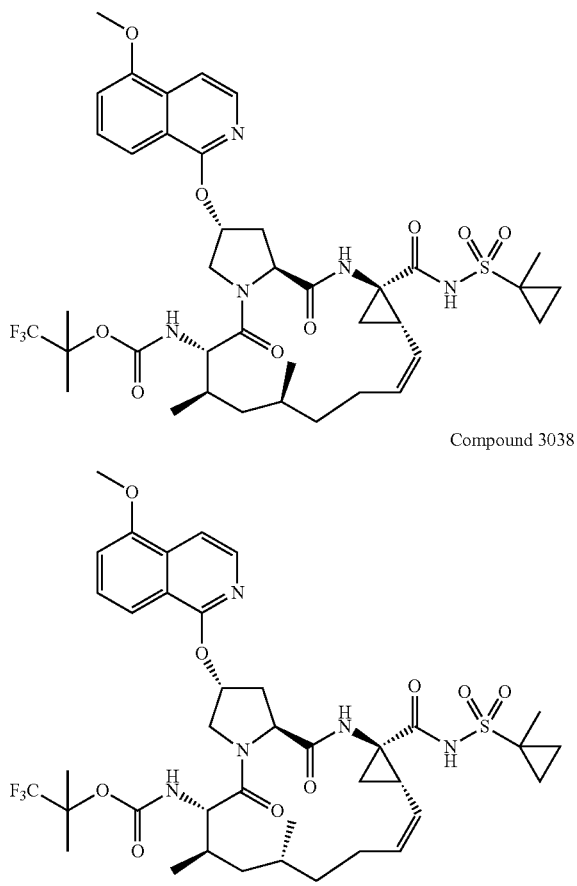

Compound 3037

Compound 3038

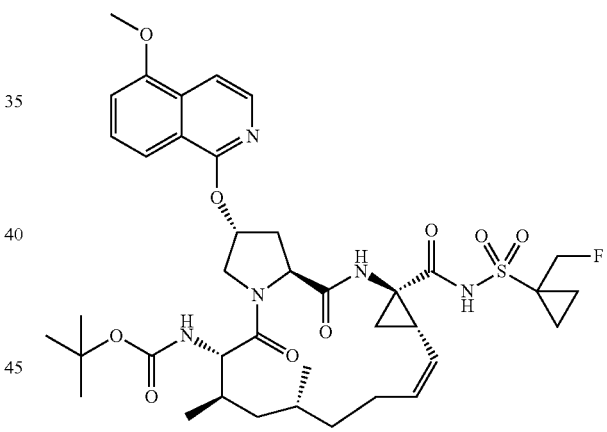

Compound 3039

Compound 3039 was prepared using the intermediates described herein and by following the general procedure described for the synthesis of Compound 3117:

Compound 3039: tert-butyl ((2R,6S,7R,9R,13aS,14aR,16aS,Z)-14a-(((1-(fluoromethyl)cyclopropyl)sulfonyl)carbamoyl)-2-((5-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-$d_6$) δ 11.27 (s, 1H), 9.02 (br. s., 1H), 8.03 (d, J=6.1 Hz, 1H), 7.72 (d, J=8.2 Hz, 1H), 7.54 (d, J=5.8 Hz, 1H), 7.46 (t, J=8.1 Hz, 1H), 7.23 (d, J=7.9 Hz, 1H), 7.19 (d, J=7.9 Hz, 1H), 5.82 (br. s., 1H), 5.58-5.47 (m, 1H), 5.07-4.95 (m, 1H), 4.91-4.73 (m, 1H), 4.67-4.40 (m, 3H), 3.98 (s, 3H), 3.95-3.89 (m, 1H), 3.73 (dd, J=10.5, 8.4 Hz, 1H), 2.73-2.57 (m, 2H), 2.36-2.24 (m, 2H), 1.96-1.75 (m, 2H), 1.69 (br. s., 1H), 1.60-0.83 (m, 24H), 0.73 (t, J=12.2 Hz, 1H); MS: MS m/z 786.4 (M⁺+1).

Compounds 3037 and 3038 were prepared using the intermediates described herein and by following the general procedure described for the synthesis of Compound 3117:

Preparation of Compound 3040

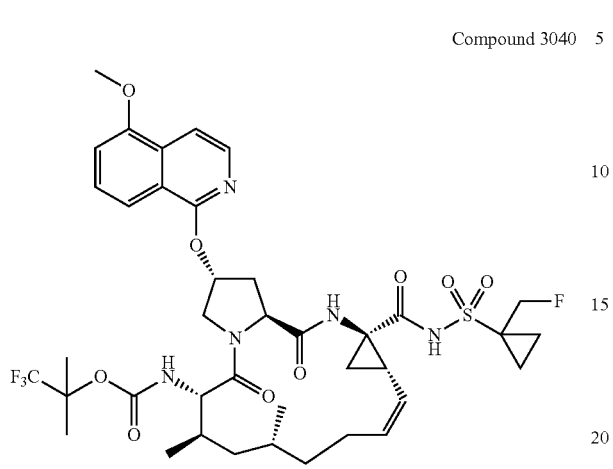

Compound 3040

Compound 3040 was prepared using the intermediates described herein and by following the general procedure described for the synthesis of Compound 3117:

Compound 3040: 1,1,1-trifluoro-2-methylpropan-2-yl ((2R,6S,7R,9R,13aS,14aR,16aS,Z)-14a-(((1-(fluoromethyl)cyclopropyl)sulfonyl)carbamoyl)-2-((5-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-$d_6$) δ 11.28 (s, 1H), 9.06 (s, 1H), 8.04 (d, J=5.8 Hz, 1H), 7.84 (d, J=7.9 Hz, 1H), 7.69 (d, J=8.2 Hz, 1H), 7.54 (d, J=6.1 Hz, 1H), 7.49 (t, J=7.9 Hz, 1H), 7.24 (d, J=7.9 Hz, 1H), 5.83 (br. s., 1H), 5.57-5.46 (m, 1H), 5.00 (t, J=10.1 Hz, 1H), 4.92-4.71 (m, 1H), 4.65-4.44 (m, 3H), 3.98 (s, 3H), 3.95-3.89 (m, 1H), 3.71 (dd, J=10.8, 8.1 Hz, 1H), 2.71-2.59 (m, 2H), 2.42-2.25 (m, 2H), 1.96-1.79 (m, 2H), 1.75-1.03 (m, 16H), 0.99-0.85 (m, 6H), 0.75 (t, J=12.2 Hz, 1H); MS: MS m/z 840.4 (M$^+$+1).

Preparation of Compound 3041 and Compound 3042

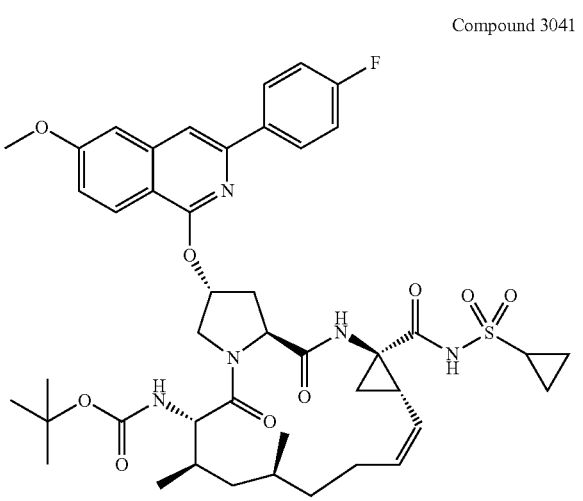

Compound 3041

Compound 3042

Compounds 3041 and 3042 were prepared using the intermediates described herein and by following the general procedure described for the synthesis of Compound 3117:

Compound 3041: tert-butyl ((2R,6S,7R,9S,13aS,14aR,16aS,Z)-14a-((cyclopropylsulfonyl)carbamoyl)-2-((3-(4-fluorophenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 848.5 (M$^+$+1).

Compound 3042: tert-butyl ((2R,6S,7R,9R,13aS,14aR,16aS,Z)-14a-((cyclopropylsulfonyl)carbamoyl)-2-((3-(4-fluorophenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-$d_6$) δ 11.22 (br. s., 1H), 8.94 (br. s., 1H), 8.29-8.21 (m, 2H), 8.06 (d, J=9.2 Hz, 1H), 7.92 (s, 1H), 7.41-7.31 (m, 3H), 7.22 (br. s., 1H), 7.10 (dd, J=9.2, 2.4 Hz, 1H), 5.97 (br. s., 1H), 5.60-5.46 (m, 1H), 5.15-5.00 (m, 1H), 4.71-4.57 (m, 1H), 4.51-4.39 (m, 1H), 4.00-3.89 (m, 4H), 3.80-3.71 (m, 1H), 2.91 (s, 1H), 2.79-2.64 (m, 2H), 2.44-2.23 (m, 2H), 2.00-0.67 (m, 28H); MS: MS m/z 848.5 (M$^+$+1).

Preparation of Compound 3043 and Compound 3044

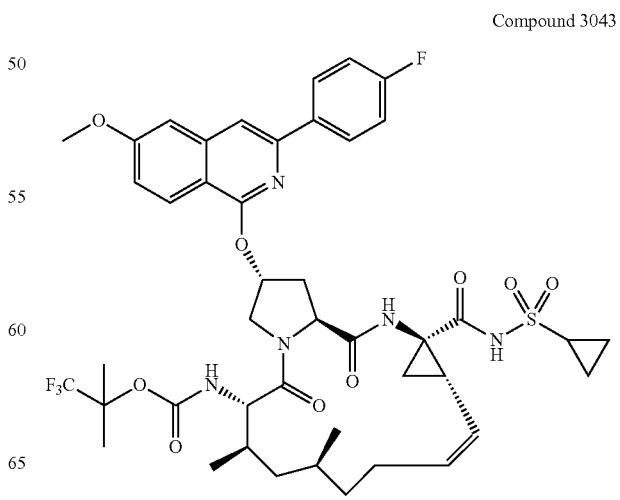

Compound 3043

-continued

Compound 3044

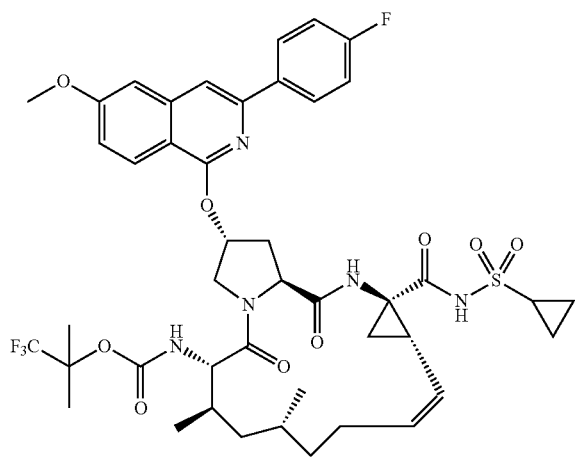

Compounds 3043 and 3044 were prepared using the intermediates described herein and by following the general procedure described for the synthesis of Compound 3117:

Compound 3043: 1,1,1-trifluoro-2-methylpropan-2-yl ((2R,6S,7R,9S,13aS,14aR,16aS,Z)-14a-((cyclopropylsulfonyl)carbamoyl)-2-((3-(4-fluorophenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 902.4 (M$^+$+1).

Compound 3044: 1,1,1-trifluoro-2-methylpropan-2-yl ((2R,6S,7R,9R,13aS,14aR,16aS,Z)-14a-((cyclopropylsulfonyl)carbamoyl)-2-((3-(4-fluorophenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.21 (s, 1H), 8.98 (s, 1H), 8.28-8.21 (m, 2H), 8.03 (d, J=9.2 Hz, 1H), 7.93 (s, 1H), 7.86 (d, J=7.6 Hz, 1H), 7.41-7.34 (m, 3H), 7.13 (dd, J=8.9, 2.4 Hz, 1H), 5.99 (br. s., 1H), 5.59-5.48 (m, 1H), 5.07 (t, J=9.8 Hz, 1H), 4.57 (d, J=11.3 Hz, 1H), 4.50 (dd, J=10.1, 7.0 Hz, 1H), 4.01-3.89 (m, 4H), 3.74 (dd, J=10.7, 7.9 Hz, 1H), 2.99-2.88 (m, 1H), 2.77-2.64 (m, 2H), 2.43-2.25 (m, 2H), 1.98-1.80 (m, 2H), 1.73 (dd, J=12.7, 6.6 Hz, 1H), 1.65-1.52 (m, 2H), 1.50-0.84 (m, 19H), 0.76 (t, J=12.2 Hz, 1H); MS: MS m/z 902.4 (M$^+$+1).

Preparation of Compound 3045 and Compound 3046

Compound 3045

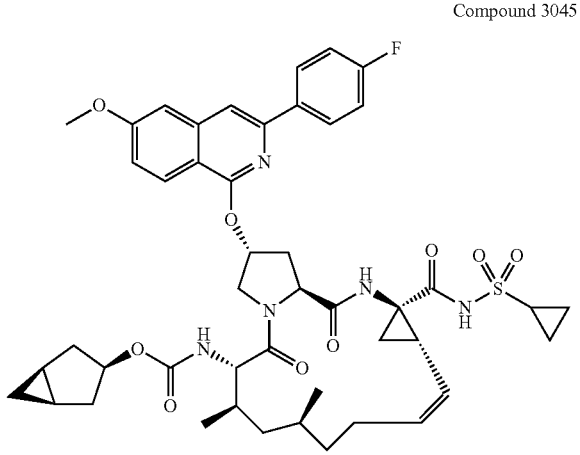

-continued

Compound 3046

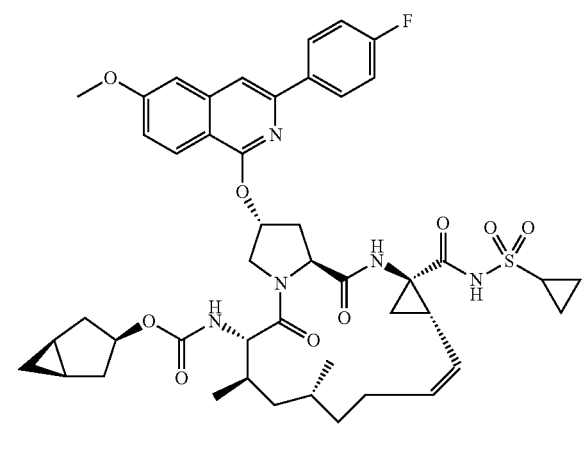

Compounds 3045 and 3046 were prepared using the intermediates described herein and by following the general procedure described for the synthesis of Compound 3117:

Compound 3045: (1R,3r,5S)-bicyclo[3.1.0]hexan-3-yl ((2R,6S,7R,9S,13aS,14aR,16aS,Z)-14a-((cyclopropylsulfonyl)carbamoyl)-2-((3-(4-fluorophenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 872.5 (M$^+$+1).

Compound 3046: (1R,3r,5S)-bicyclo[3.1.0]hexan-3-yl ((2R,6S,7R,9R,13aS,14aR,16aS,Z)-14a-((cyclopropylsulfonyl)carbamoyl)-2-((3-(4-fluorophenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.21 (br. s., 1H), 8.91 (br. s., 1H), 8.29-8.20 (m, 2H), 8.04 (d, J=8.9 Hz, 1H), 7.93 (s, 1H), 7.46-7.33 (m, 4H), 7.16 (dd, J=9.0, 2.6 Hz, 1H), 5.97 (br. s., 1H), 5.59-5.41 (m, 1H), 5.19-4.99 (m, 1H), 4.70 (t, J=6.7 Hz, 1H), 4.60-4.38 (m, 2H), 3.99 (d, J=7.9 Hz, 1H), 3.93 (s, 3H), 3.79 (t, J=9.6 Hz, 1H), 2.98-2.83 (m, 1H), 2.79-2.60 (m, 2H), 2.45-2.20 (m, 2H), 2.05-0.29 (m, 27H); MS: MS m/z 872.5 (M$^+$+1).

Preparation of Compound 3047 and Compound 3048

Compound 3047

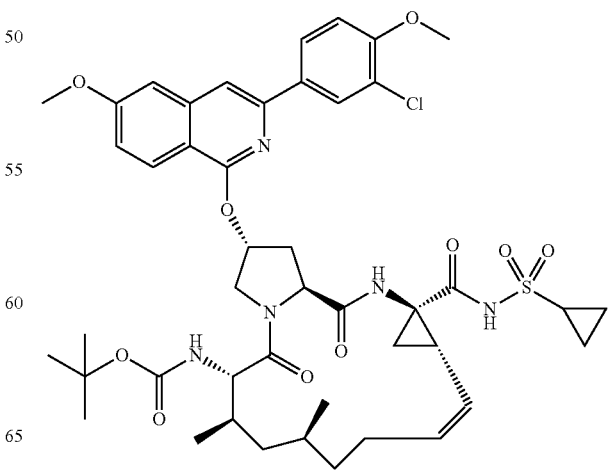

Compound 3048

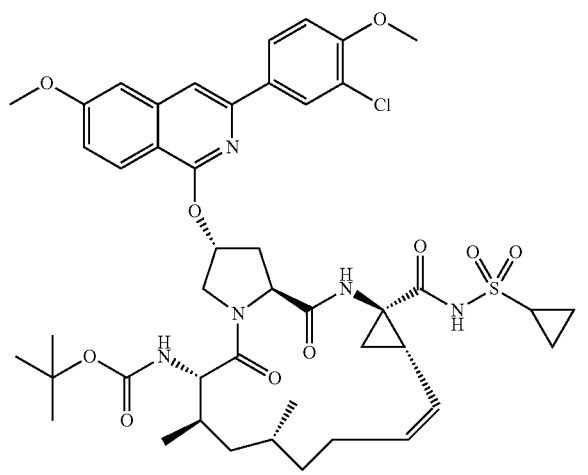

Compound 3050

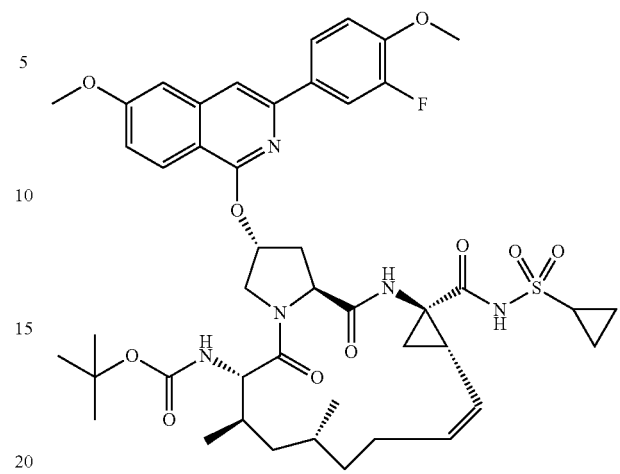

Compounds 3047 and 3048 were prepared using the intermediates described herein and by following the general procedure described for the synthesis of Compound 3117:

Compound 3047: tert-butyl ((2R,6S,7R,9S,13aS,14aR,16aS,Z)-2-((3-(3-chloro-4-methoxyphenyl)-6-methoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 894.6 (M$^+$+1).

Compound 3048: tert-butyl ((2R,6S,7R,9R,13aS,14aR,16aS,Z)-2-((3-(3-chloro-4-methoxyphenyl)-6-methoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.24 (br. s., 1H), 8.78 (br. s., 1H), 8.22 (d, J=2.1 Hz, 1H), 8.16 (dd, J=8.5, 1.8 Hz, 1H), 8.05 (d, J=9.2 Hz, 1H), 7.93 (s, 1H), 7.37-7.30 (m, 2H), 7.19 (d, J=8.2 Hz, 1H), 7.07 (dd, J=9.0, 2.3 Hz, 1H), 5.96 (br. s., 1H), 5.55-5.40 (m, 1H), 5.34-5.06 (m, 1H), 4.58 (d, J=10.4 Hz, 1H), 4.43 (t, J=8.2 Hz, 1H), 4.01-3.89 (m, 7H), 3.81-3.72 (m, 1H), 2.89-2.80 (m, 1H), 2.72-2.57 (m, 2H), 2.43-2.23 (m, 2H), 1.99-0.63 (m, 28H); MS: MS m/z 894.5 (M$^+$+1).

Preparation of Compound 3049 and Compound 3050

Compound 3049

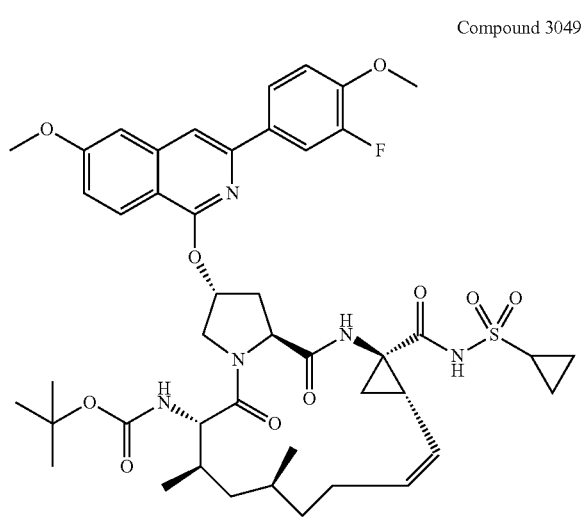

Compounds 3049 and 3050 were prepared using the intermediates described herein and by following the general procedure described for the synthesis of Compound 3117:

Compound 3049: tert-butyl ((2R,6S,7R,9S,13aS,14aR,16aS,Z)-14a-((cyclopropylsulfonyl)carbamoyl)-2-((3-(3-fluoro-4-methoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 878.5 (M$^+$+1).

Compound 3050: tert-butyl ((2R,6S,7R,9R,13aS,14aR,16aS,Z)-14a-((cyclopropylsulfonyl)carbamoyl)-2-((3-(3-fluoro-4-methoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.23 (br. s., 1H), 8.89 (br. s., 1H), 8.08-7.98 (m, 3H), 7.90 (s, 1H), 7.38-7.29 (m, 2H), 7.18 (d, J=8.2 Hz, 1H), 7.08 (dd, J=8.9, 2.4 Hz, 1H), 5.96 (br. s., 1H), 5.56-5.40 (m, 1H), 5.30-5.05 (m, 1H), 4.63-4.53 (m, 1H), 4.43 (t, J=8.5 Hz, 1H), 4.02-3.89 (m, 7H), 3.76 (dd, J=10.5, 8.7 Hz, 1H), 2.88-2.80 (m, 1H), 2.72-2.60 (m, 2H), 2.44-2.23 (m, 2H), 2.00-0.62 (m, 28H); MS: MS m/z 878.6 (M$^+$+1).

Preparation of Compound 3051 and Compound 3052

Compound 3051

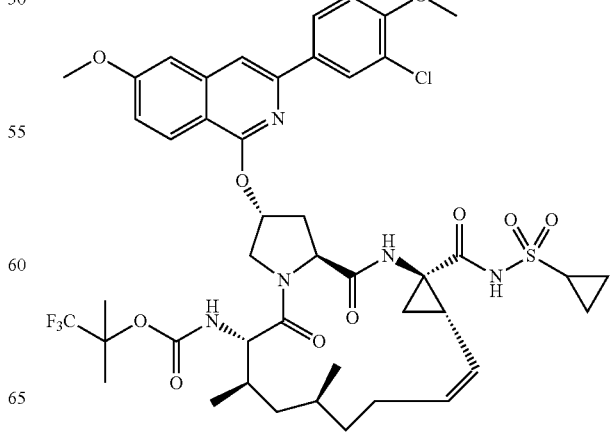

Compound 3052

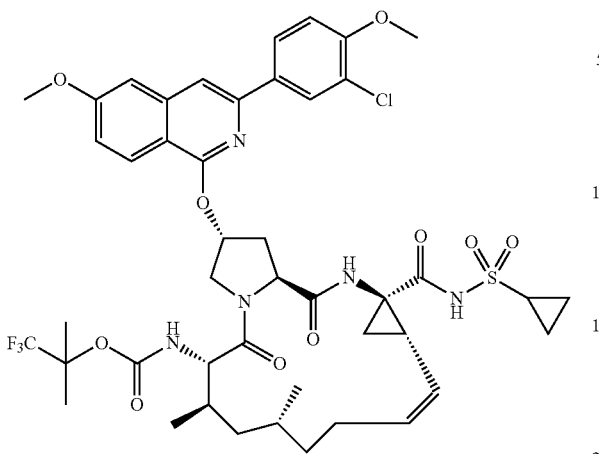

Compounds 3051 and 3052 were prepared using the intermediates described herein and by following the general procedure described for the synthesis of Compound 3117:

Compound 3051: 1,1,1-trifluoro-2-methylpropan-2-yl ((2R,6S,7R,9S,13aS,14aR,16aS,Z)-2-((3-(3-chloro-4-methoxyphenyl)-6-methoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 948.6 (M$^+$+1).

Compound 3052: 1,1,1-trifluoro-2-methylpropan-2-yl ((2R,6S,7R,9R,13aS,14aR,16aS,Z)-2-((3-(3-chloro-4-methoxyphenyl)-6-methoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, METHANOL-d$_4$) δ 8.16 (d, J=2.1 Hz, 1H), 8.09 (dd, J=8.5, 2.1 Hz, 1H), 8.05 (d, J=9.2 Hz, 1H), 7.68 (s, 1H), 7.23 (d, J=2.4 Hz, 1H), 7.18 (d, J=8.9 Hz, 1H), 7.04 (dd, J=8.9, 2.4 Hz, 1H), 5.99 (br. s., 1H), 5.61-5.52 (m, 1H), 4.74 (d, J=11.6 Hz, 1H), 4.66-4.58 (m, 2H), 4.08 (dd, J=11.6, 3.4 Hz, 1H), 3.95 (d, J=8.9 Hz, 6H), 3.87 (d, J=10.7 Hz, 1H), 2.94-2.88 (m, 1H), 2.79 (dd, J=13.9, 7.2 Hz, 1H), 2.68-2.59 (m, 1H), 2.54-2.45 (m, 1H), 2.43-2.32 (m, 1H), 2.02-1.92 (m, 1H), 1.91-1.84 (m, 1H), 1.80 (dd, J=13.1, 5.2 Hz, 1H), 1.74 (dd, J=8.1, 5.3 Hz, 1H), 1.57 (dd, J=9.5, 5.2 Hz, 1H), 1.54-0.77 (m, 20H); MS: MS m/z 948.6 (M$^+$+1).

Preparation of Compound 3053 and Compound 3054

Compound 3054

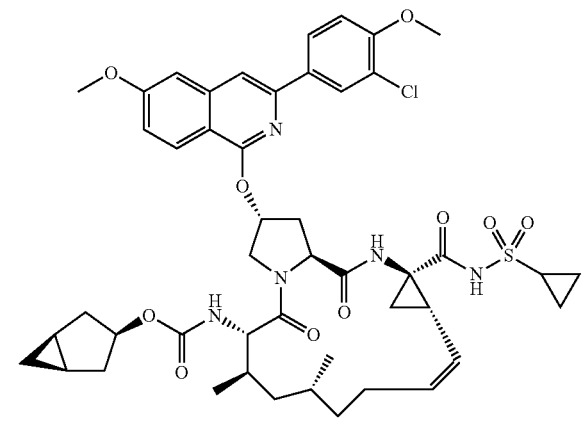

Compounds 3053 and 3054 were prepared using the intermediates described herein and by following the general procedure described for the synthesis of Compound 3117:

Compound 3053: (1R,3r,5S)-bicyclo[3.1.0]hexan-3-yl ((2R,6S,7R,9S,13aS,14aR,16aS,Z)-2-((3-(3-chloro-4-methoxyphenyl)-6-methoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 918.5 (M$^+$+1).

Compound 3054: (1R,3r,5S)-bicyclo[3.1.0]hexan-3-yl ((2R,6S,7R,9R,13aS,14aR,16aS,Z)-2-((3-(3-chloro-4-methoxyphenyl)-6-methoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, METHANOL-d$_4$) δ 8.16 (s, 1H), 8.08 (dd, J=8.9, 2.1 Hz, 1H), 8.04 (d, J=8.9 Hz, 1H), 7.68 (s, 1H), 7.23 (d, J=2.1 Hz, 1H), 7.17 (d, J=8.5 Hz, 1H), 7.06 (dd, J=9.2, 2.4 Hz, 1H), 6.02 (br. s., 1H), 5.58-5.47 (m, 1H), 4.67 (t, J=6.7 Hz, 1H), 4.65-4.55 (m, 2H), 4.10 (dd, J=11.6, 3.4 Hz, 1H), 3.99-3.91 (m, 7H), 2.92-2.85 (m, 1H), 2.80 (dd, J=13.7, 7.0 Hz, 1H), 2.61 (br. s., 1H), 2.54-2.45 (m, 1H), 2.41-2.28 (m, 1H), 2.07-0.76 (m, 26H), 0.41-0.29 (m, 2H); MS: MS m/z 918.5 (M$^+$+1).

Preparation of Compound 3055 and Compound 3056

Compound 3053

Compound 3055

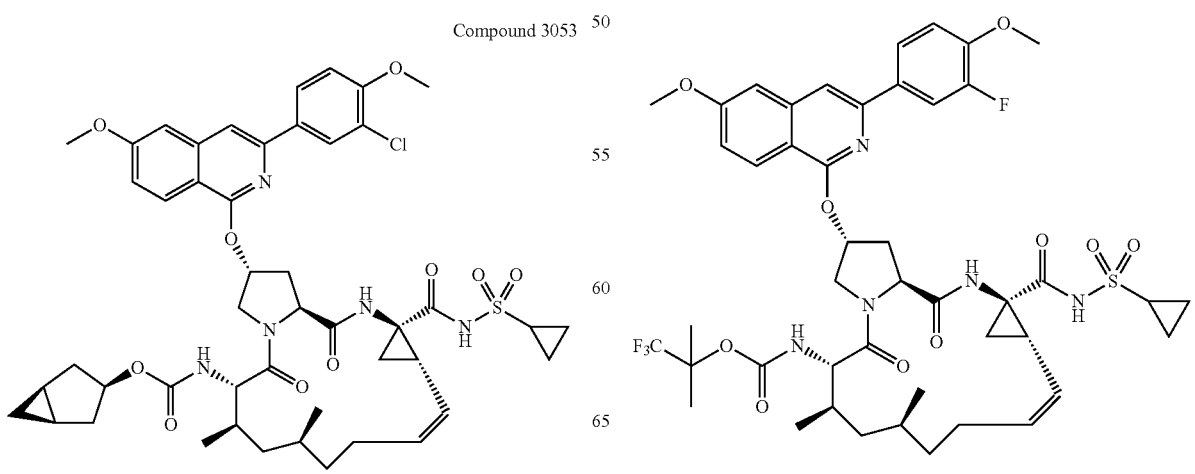

-continued

Compound 3056

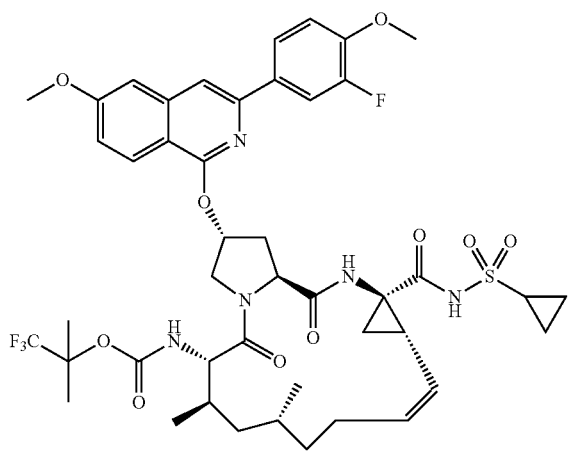

Compounds 3055 and 3056 were prepared using the intermediates described herein and by following the general procedure described for the synthesis of Compound 3117:

Compound 3055: 1,1,1-trifluoro-2-methylpropan-2-yl ((2R,6S,7R,9S,13aS,14aR,16aS,Z)-14a-((cyclopropylsulfonyl)carbamoyl)-2-((3-(3-fluoro-4-methoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 932.5 (M$^+$+1).

Compound 3056: 1,1,1-trifluoro-2-methylpropan-2-yl ((2R,6S,7R,9R,13aS,14aR,16aS,Z)-14a-((cyclopropylsulfonyl)carbamoyl)-2-((3-(3-fluoro-4-methoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, METHANOL-d$_4$) δ 8.05 (d, J=9.2 Hz, 1H), 8.01-7.89 (m, 2H), 7.69 (s, 1H), 7.23 (d, J=2.4 Hz, 1H), 7.20 (t, J=8.7 Hz, 1H), 7.04 (dd, J=9.2, 2.4 Hz, 1H), 6.00 (br. s., 1H), 5.57 (td, J=9.9, 6.1 Hz, 1H), 4.74 (d, J=11.3 Hz, 1H), 4.67-4.58 (m, 2H), 4.09 (dd, J=11.6, 3.7 Hz, 1H), 3.95 (d, J=2.7 Hz, 6H), 3.87 (d, J=10.7 Hz, 1H), 2.95-2.88 (m, 1H), 2.79 (dd, J=13.7, 7.3 Hz, 1H), 2.70-2.60 (m, 1H), 2.49 (ddd, J=13.9, 10.1, 4.1 Hz, 1H), 2.44-2.32 (m, 1H), 2.01-1.92 (m, 1H), 1.91-1.84 (m, 1H), 1.80 (dd, J=13.1, 5.5 Hz, 1H), 1.74 (dd, J=8.4, 5.3 Hz, 1H), 1.60-0.92 (m, 20H), 0.83 (t, J=11.4 Hz, 1H); MS: MS m/z 932.5 (M$^+$+1).

Preparation of Compound 3057 and Compound 3058

Compound 3057

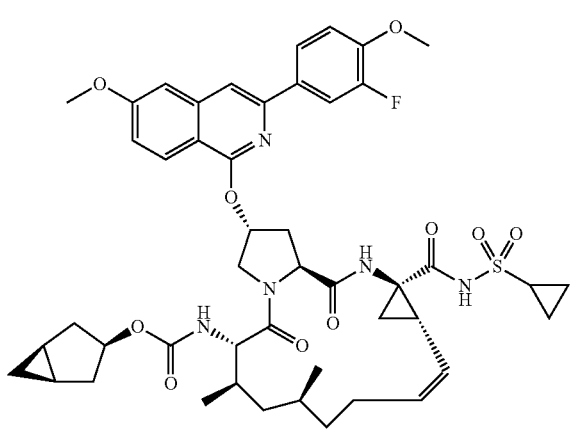

-continued

Compound 3058

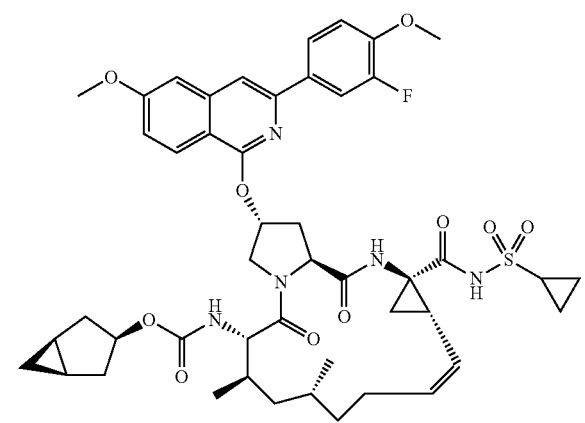

Compounds 3057 and 3058 were prepared using the intermediates described herein and by following the general procedure described for the synthesis of Compound 3117:

Compound 3057: (1R,3r,5S)-bicyclo[3.1.0]hexan-3-yl ((2R,6S,7R,9S,13aS,14aR,16aS,Z)-14a-((cyclopropylsulfonyl)carbamoyl)-2-((3-(3-fluoro-4-methoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 902.6 (M$^+$+1).

Compound 3058: (1R,3r,5S)-bicyclo[3.1.0]hexan-3-yl ((2R,6S,7R,9R,13aS,14aR,16aS,Z)-14a-((cyclopropylsulfonyl)carbamoyl)-2-((3-(3-fluoro-4-methoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, METHANOL-d$_4$) δ 8.04 (d, J=8.9 Hz, 1H), 8.00-7.88 (m, 2H), 7.69 (s, 1H), 7.23 (d, J=2.1 Hz, 1H), 7.19 (t, J=8.7 Hz, 1H), 7.06 (dd, J=9.2, 2.4 Hz, 1H), 6.01 (br. s., 1H), 5.54-5.45 (m, 1H), 4.67 (t, J=6.9 Hz, 1H), 4.64-4.55 (m, 2H), 4.12 (dd, J=11.4, 3.5 Hz, 1H), 4.00-3.92 (m, 7H), 2.91-2.76 (m, 2H), 2.60-2.47 (m, 2H), 2.40-2.27 (m, 1H), 2.06-0.74 (m, 26H), 0.41-0.29 (m, 2H); MS: MS m/z 902.6 (M$^+$+1).

Preparation of Compound 3059 and Compound 3060

Compound 3059

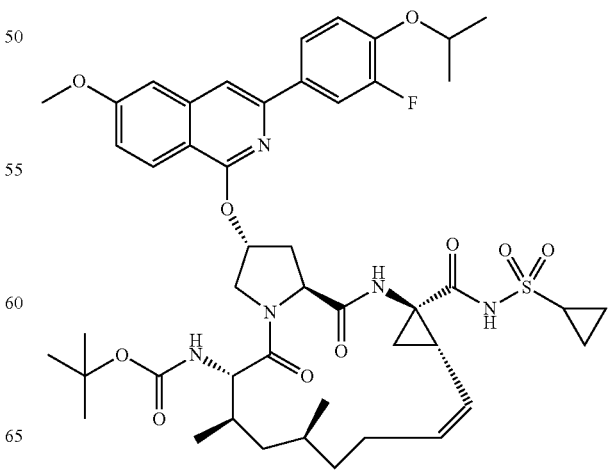

-continued

Compound 3060

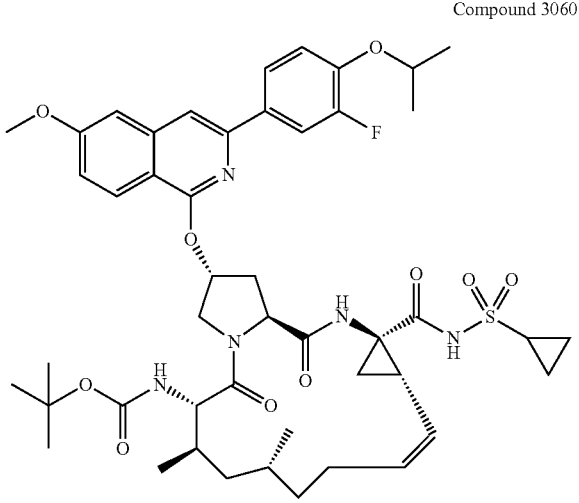

Compounds 3059 and 3060 were prepared using the intermediates described herein and by following the general procedure described for the synthesis of Compound 3117:

Compound 3059: tert-butyl ((2R,6S,7R,9S,13aS,14aR,16aS,Z)-14a-((cyclopropylsulfonyl)carbamoyl)-2-((3-(3-fluoro-4-isopropoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 906.8 (M$^+$+1).

Compound 3060: tert-butyl ((2R,6S,7R,9R,13aS,14aR,16aS,Z)-14a-((cyclopropylsulfonyl)carbamoyl)-2-((3-(3-fluoro-4-isopropoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.22 (br. s., 1H), 8.94 (br. s., 1H), 8.08-7.95 (m, 3H), 7.90 (s, 1H), 7.38-7.29 (m, 2H), 7.21 (d, J=7.0 Hz, 1H), 7.08 (dd, J=9.0, 2.3 Hz, 1H), 5.98 (br. s., 1H), 5.61-5.46 (m, 1H), 5.13-5.00 (m, 1H), 4.75 (spt, J=6.0 Hz, 1H), 4.65-4.54 (m, 1H), 4.45 (t, J=8.5 Hz, 1H), 4.01-3.88 (m, 4H), 3.80-3.71 (m, 1H), 2.91 (s, 1H), 2.79-2.62 (m, 2H), 2.43-2.24 (m, 2H), 2.02-0.63 (m, 34H); MS: MS m/z 906.8 (M$^+$+1).

Preparation of Compound 3061 and Compound 3062

Compound 3061

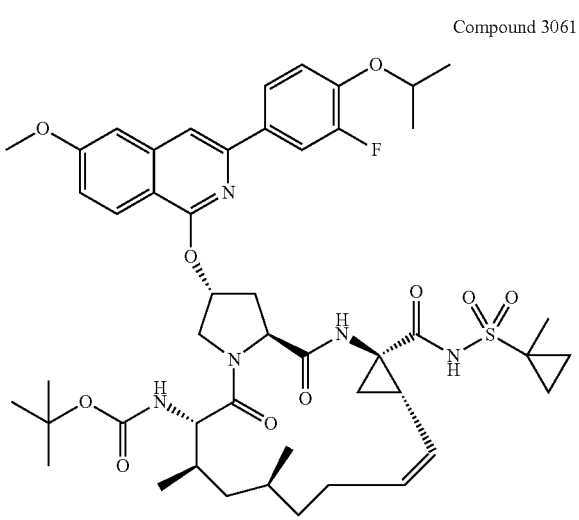

-continued

Compound 3062

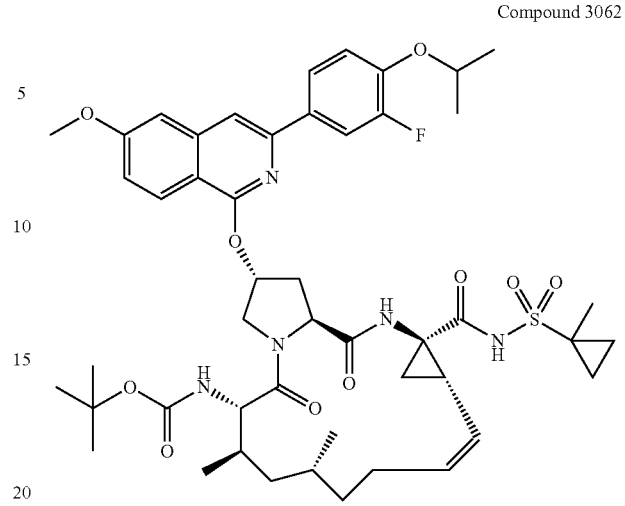

Compounds 3061 and 3062 were prepared using the intermediates described herein and by following the general procedure described for the synthesis of Compound 3117:

Compound 3061: tert-butyl ((2R,6S,7R,9S,13aS,14aR,16aS,Z)-2-((3-(3-fluoro-4-isopropoxyphenyl)-6-methoxy-isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 920.7 (M$^+$+1).

Compound 3062: tert-butyl ((2R,6S,7R,9R,13aS,14aR,16aS,Z)-2-((3-(3-fluoro-4-isopropoxyphenyl)-6-methoxy-isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.07 (br. s., 1H), 9.08 (br. s., 1H), 8.08-7.94 (m, 4H), 7.90 (s, 1H), 7.37-7.30 (m, 2H), 7.21 (d, J=7.9 Hz, 1H), 7.08 (dd, J=9.0, 2.3 Hz, 1H), 6.00 (br. s., 1H), 5.59-5.48 (m, 1H), 4.99 (t, J=9.3 Hz, 1H), 4.75 (spt, J=6.1 Hz, 1H), 4.61 (d, J=11.0 Hz, 1H), 4.49 (t, J=8.1 Hz, 1H), 4.03-3.95 (m, 1H), 3.92 (s, 3H), 3.80-3.71 (m, 1H), 2.78-2.62 (m, 2H), 2.42-2.28 (m, 2H), 1.99-0.84 (m, 35H), 0.76 (t, J=12.7 Hz, 1H); MS: MS m/z 920.8 (M$^+$+1).

Preparation of Compound 3063 and Compound 3064

Compound 3063

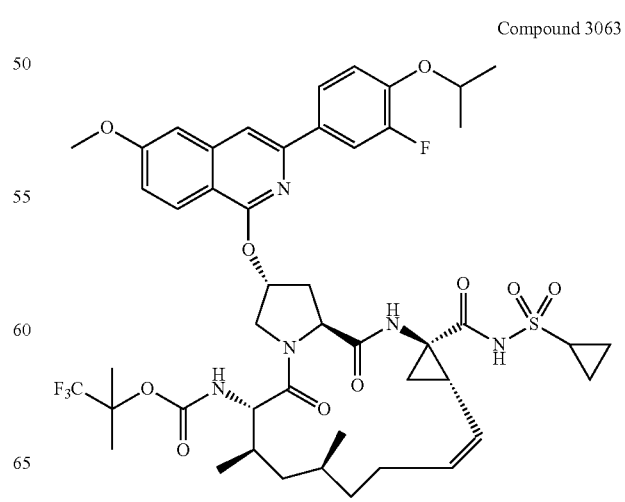

117

-continued

Compound 3064

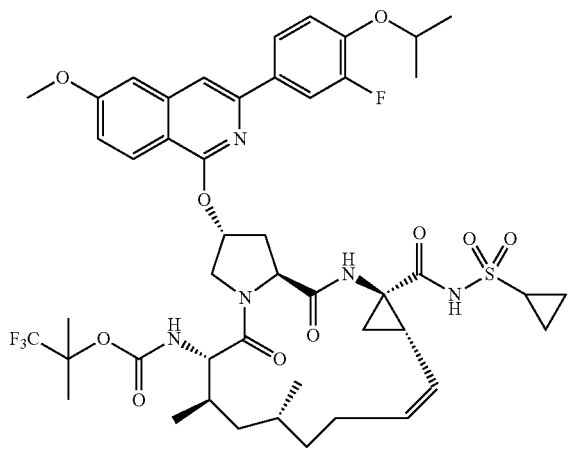

Compounds 3063 and 3064 were prepared using the intermediates described herein and by following the general procedure described for the synthesis of Compound 3117:

Compound 3063: 1,1,1-trifluoro-2-methylpropan-2-yl ((2R,6S,7R,9S,13aS,14aR,16aS,Z)-14a-((cyclopropylsulfonyl)carbamoyl)-2-((3-(3-fluoro-4-isopropoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 960.8 (M$^+$+1).

Compound 3064: 1,1,1-trifluoro-2-methylpropan-2-yl ((2R,6S,7R,9R,13aS,14aR,16aS,Z)-14a-((cyclopropylsulfonyl)carbamoyl)-2-((3-(3-fluoro-4-isopropoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.22 (s, 1H), 8.98 (br. s., 1H), 8.06-7.95 (m, 3H), 7.91 (s, 1H), 7.85 (d, J=7.6 Hz, 1H), 7.38-7.29 (m, 2H), 7.12 (dd, J=9.2, 2.4 Hz, 1H), 6.00 (br. s., 1H), 5.59-5.48 (m, 1H), 5.07 (t, J=9.3 Hz, 1H), 4.75 (spt, J=6.0 Hz, 1H), 4.62-4.45 (m, 2H), 4.01-3.89 (m, 4H), 3.74 (dd, J=10.7, 7.9 Hz, 1H), 2.98-2.88 (m, 1H), 2.74-2.62 (m, 2H), 2.42-2.24 (m, 2H), 1.99-0.70 (m, 31H); MS: MS m/z 960.8 (M$^+$+1).

Preparation of Compound 3065 and Compound 3066

Compound 3065

118

-continued

Compound 3066

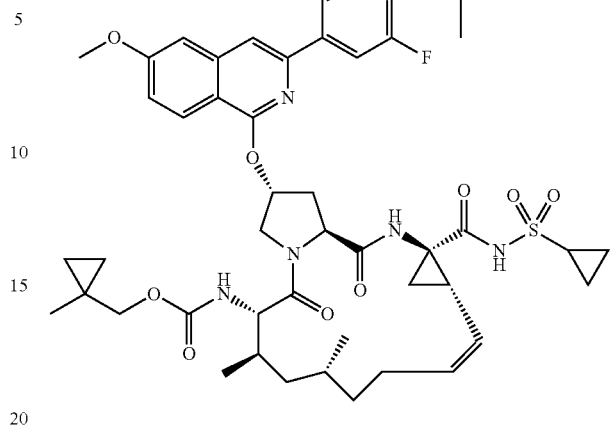

Compounds 3065 and 3066 were prepared using the intermediates described herein and by following the general procedure described for the synthesis of Compound 3117:

Compound 3065: (1-methylcyclopropyl)methyl ((2R,6S,7R,9S,13aS,14aR,16aS,Z)-14a-((cyclopropylsulfonyl)carbamoyl)-2-((3-(3-fluoro-4-isopropoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 918.8 (M$^+$+1).

Compound 3066: (1-methylcyclopropyl)methyl ((2R,6S,7R,9R,13aS,14aR,16aS,Z)-14a-((cyclopropylsulfonyl)carbamoyl)-2-((3-(3-fluoro-4-isopropoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.22 (br. s., 1H), 8.93 (br. s., 1H), 8.06-7.95 (m, 3H), 7.90 (s, 1H), 7.52 (br. s., 1H), 7.38-7.29 (m, 2H), 7.11 (dd, J=9.2, 2.4 Hz, 1H), 5.99 (br. s., 1H), 5.63-5.42 (m, 1H), 5.19-5.00 (m, 1H), 4.75 (spt, J=6.1 Hz, 2H), 4.61-4.38 (m, 2H), 4.03-3.96 (m, 1H), 3.93 (s, 3H), 3.78 (t, J=9.6 Hz, 1H), 3.52-3.41 (m, 2H), 2.91 (s, 1H), 2.77-2.61 (m, 2H), 2.45-2.22 (m, 2H), 2.01-0.65 (m, 27H), 0.35-0.18 (m, 4H); MS: MS m/z 918.9 (M$^+$+1).

Preparation of Compound 3067 and Compound 3068

Compound 3067

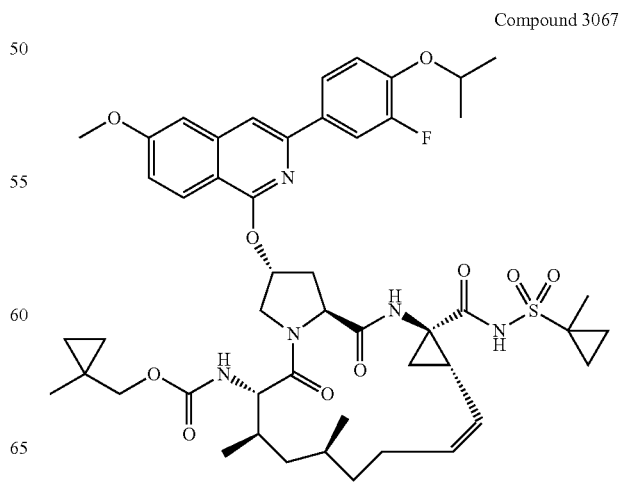

-continued

Compound 3068

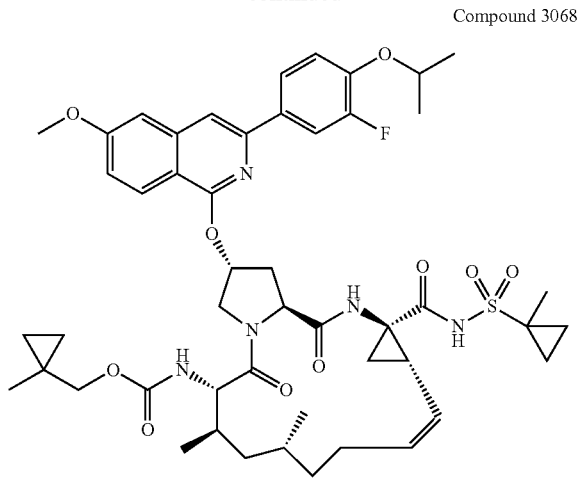

Compounds 3067 and 3068 were prepared using the intermediates described herein and by following the general procedure described for the synthesis of Compound 3117:

Compound 3067: (1-methylcyclopropyl)methyl ((2R,6S,7R,9S,13aS,14aR,16aS,Z)-2-((3-(3-fluoro-4-isopropoxyphenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 932.8 (M$^+$+1).

Compound 3068: (1-methylcyclopropyl)methyl ((2R,6S,7R,9R,13aS,14aR,16aS,Z)-2-((3-(3-fluoro-4-isopropoxyphenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.07 (br. s., 1H), 9.06 (br. s., 1H), 8.05-7.93 (m, 3H), 7.90 (s, 1H), 7.53 (d, J=7.9 Hz, 1H), 7.37-7.30 (m, 2H), 7.11 (dd, J=9.2, 2.4 Hz, 1H), 6.02 (br. s., 1H), 5.61-5.48 (m, 1H), 5.07-4.95 (m, 1H), 4.75 (spt, J=6.1 Hz, 1H), 4.61-4.45 (m, 2H), 4.01 (dd, J=11.1, 3.2 Hz, 1H), 3.96-3.90 (m, 3H), 3.78 (dd, J=10.5, 8.7 Hz, 1H), 3.50-3.39 (m, 2H), 2.78-2.63 (m, 2H), 2.43-2.27 (m, 2H), 2.00-0.67 (m, 31H), 0.34-0.17 (m, 4H); MS: MS m/z 932.9 (M$^+$+1).

Preparation of Compound 3069 and Compound 3070

Compound 3069

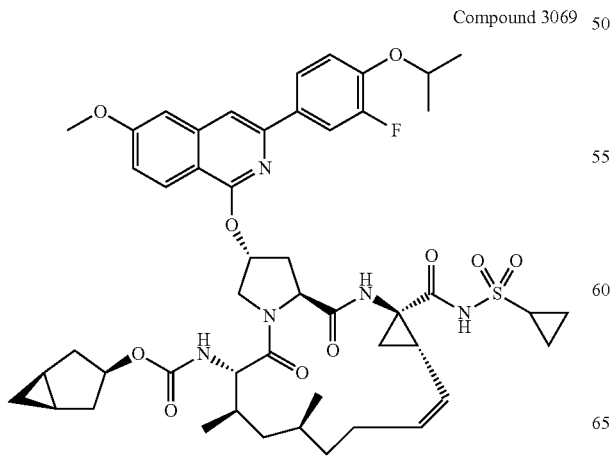

-continued

Compound 3070

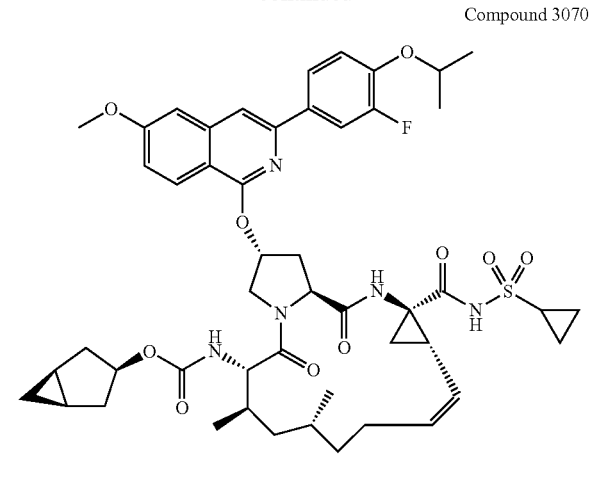

Compounds 3069 and 3070 were prepared using the intermediates described herein and by following the general procedure described for the synthesis of Compound 3117:

Compound 3069: (1R,3r,5S)-bicyclo[3.1.0]hexan-3-yl ((2R,6S,7R,9S,13aS,14aR,16aS,Z)-14a-((cyclopropylsulfonyl)carbamoyl)-2-((3-(3-fluoro-4-isopropoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 930.8 (M$^+$+1).

Compound 3070: (1R,3r,5S)-bicyclo[3.1.0]hexan-3-yl ((2R,6S,7R,9R,13aS,14aR,16aS,Z)-14a-((cyclopropylsulfonyl)carbamoyl)-2-((3-(3-fluoro-4-isopropoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.22 (br. s., 1H), 8.90 (br. s., 1H), 8.06-7.95 (m, 3H), 7.91 (s, 1H), 7.42 (d, J=7.6 Hz, 1H), 7.38-7.29 (m, 2H), 7.14 (dd, J=9.0, 2.3 Hz, 1H), 5.99 (br. s., 1H), 5.60-5.44 (m, 1H), 5.17-5.02 (m, 1H), 4.82-4.66 (m, 2H), 4.57-4.40 (m, 2H), 4.04-3.96 (m, 1H), 3.93 (s, 3H), 3.83-3.73 (m, 1H), 2.97-2.87 (m, 1H), 2.79-2.60 (m, 2H), 2.44-2.20 (m, 2H), 2.04-0.66 (m, 31H), 0.45-0.32 (m, 2H); MS: MS m/z 930.7 (M$^+$+1).

Preparation of Compound 3071 and Compound 3072

Compound 3071

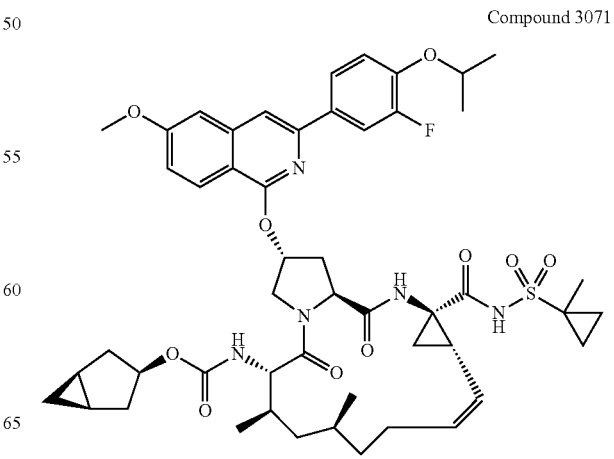

-continued

Compound 3072

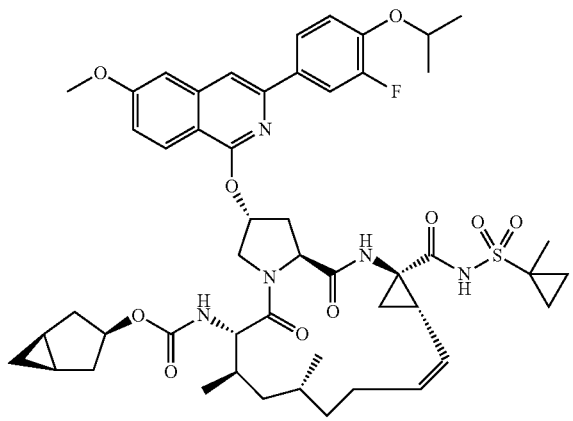

Compounds 3071 and 3072 were prepared using the intermediates described herein and by following the general procedure described for the synthesis of Compound 3117:

Compound 3071: (1R,3r,5S)-bicyclo[3.1.0]hexan-3-yl ((2R,6S,7R,9S,13aS,14aR,16aS,Z)-2-((3-(3-fluoro-4-isopropoxyphenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 944.8 (M$^+$+1).

Compound 3072: (1R,3r,5S)-bicyclo[3.1.0]hexan-3-yl ((2R,6S,7R,9R,13aS,14aR,16aS,Z)-2-((3-(3-fluoro-4-isopropoxyphenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.07 (br. s., 1H), 9.04 (br. s., 1H), 8.04-7.94 (m, 3H), 7.91 (s, 1H), 7.43 (d, J=8.2 Hz, 1H), 7.37-7.28 (m, 2H), 7.14 (dd, J=8.9, 2.4 Hz, 1H), 6.02 (br. s., 1H), 5.59-5.49 (m, 1H), 5.06-4.94 (m, 1H), 4.75 (spt, J=6.0 Hz, 1H), 4.68 (t, J=6.6 Hz, 1H), 4.55-4.46 (m, 2H), 4.01 (dd, J=11.1, 3.5 Hz, 1H), 3.93 (s, 3H), 3.83-3.75 (m, 1H), 2.79-2.63 (m, 2H), 2.42-2.25 (m, 2H), 2.02-1.76 (m, 4H), 1.72-0.71 (m, 30H), 0.44-0.32 (m, 2H); MS: MS m/z 944.7 (M$^+$+1).

Preparation of Compound 3073 and Compound 3074

Compound 3073

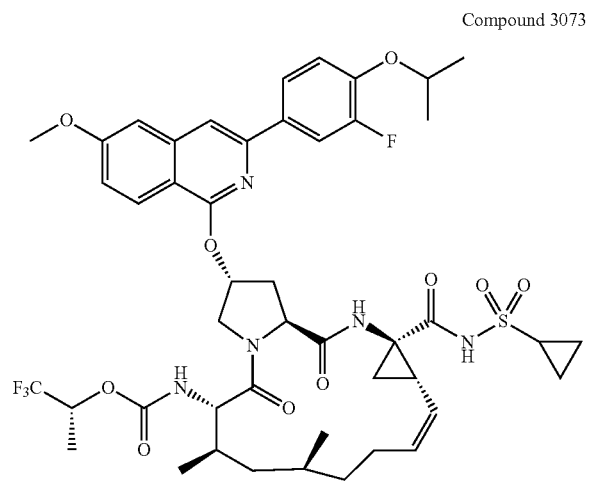

-continued

Compound 3074

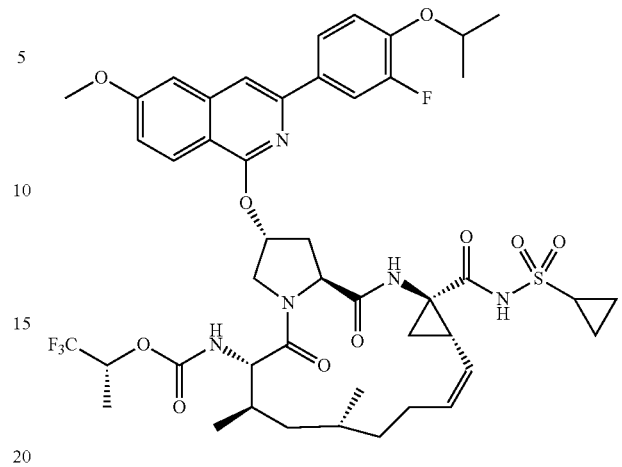

Compounds 3073 and 3074 were prepared using the intermediates described herein and by following the general procedure described for the synthesis of Compound 3117:

Compound 3073: (R)-1,1,1-trifluoropropan-2-yl ((2R,6S,7R,9S,13aS,14aR,16aS,Z)-14a-((cyclopropylsulfonyl)carbamoyl)-2-((3-(3-fluoro-4-isopropoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 946.7 (M$^+$+1).

Compound 3074: (R)-1,1,1-trifluoropropan-2-yl ((2R,6S,7R,9R,13aS,14aR,16aS,Z)-14a-((cyclopropylsulfonyl)carbamoyl)-2-((3-(3-fluoro-4-isopropoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.21 (br. s., 1H), 8.93 (br. s., 1H), 8.10 (d, J=7.3 Hz, 1H), 8.05-7.95 (m, 3H), 7.91 (s, 1H), 7.37-7.30 (m, 2H), 7.06 (dd, J=8.9, 2.4 Hz, 1H), 5.99 (br. s., 1H), 5.60-5.45 (m, 1H), 5.18-5.01 (m, 1H), 4.82 (quin, J=6.9 Hz, 1H), 4.75 (spt, J=6.0 Hz, 1H), 4.60-4.50 (m, 1H), 4.46 (t, J=8.2 Hz, 1H), 3.99 (d, J=7.9 Hz, 1H), 3.92 (s, 3H), 3.81 (dd, J=10.7, 8.2 Hz, 1H), 2.91 (s, 1H), 2.78-2.59 (m, 2H), 2.44-2.23 (m, 2H), 2.01-0.66 (m, 28H); MS: MS m/z 946.7 (M$^+$+1).

Preparation of Compound 3075 and Compound 3076

Compound 3075

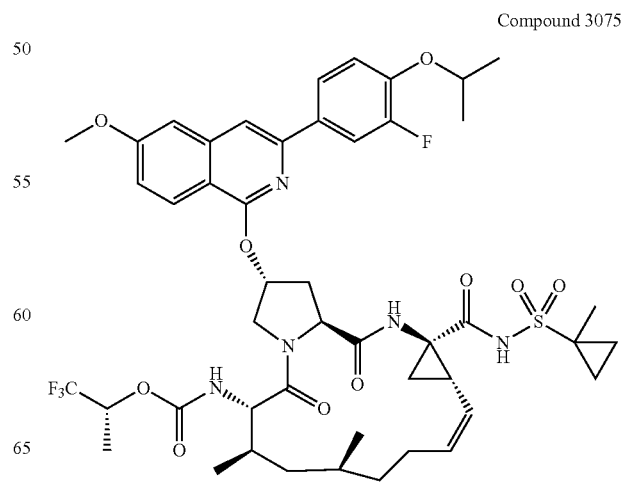

Compound 3076

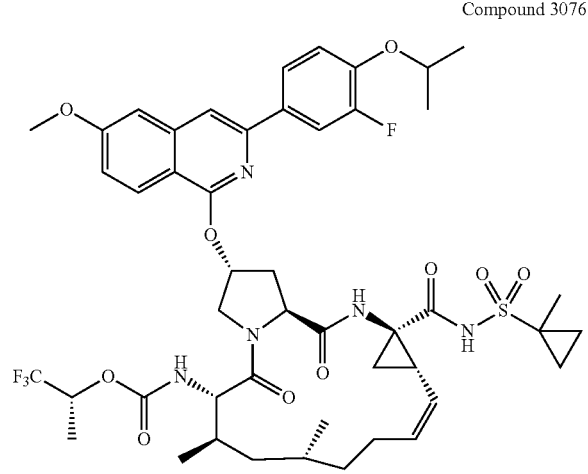 [SMILES: COc1ccc2c(O[C@@H]3C[C@H]4C(=O)N[C@]5(C(=O)NS(=O)(=O)C6(C)CC6)C[C@H]5/C=C\CC[C@@H](C)C[C@@H](C)[C@H](NC(=O)O[C@H](C)C(F)(F)F)C(=O)N4C3)nc(-c3ccc(F)cc3)cc2c1]

Compound 3078

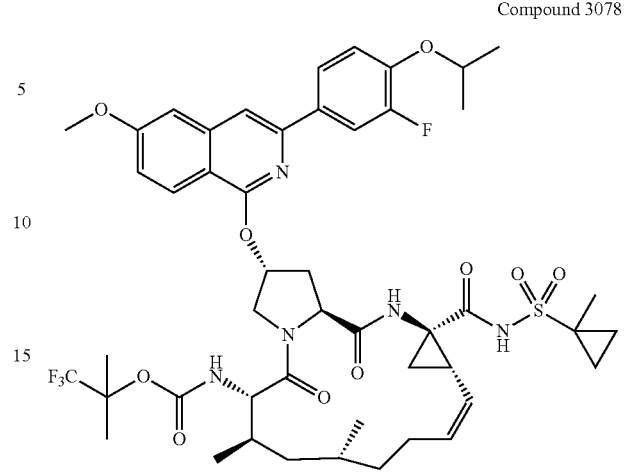

Compounds 3075 and 3076 were prepared using the intermediates described herein and by following the general procedure described for the synthesis of Compound 3117:

Compound 3075: (R)-1,1,1-trifluoropropan-2-yl ((2R,6S,7R,9S,13aS,14aR,16aS,Z)-2-((3-(3-fluoro-4-isopropoxyphenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 960.7 (M$^+$+1).

Compound 3076: (R)-1,1,1-trifluoropropan-2-yl ((2R,6S,7R,9R,13aS,14aR,16aS,Z)-2-((3-(3-fluoro-4-isopropoxyphenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.05 (br. s., 1H), 9.07 (br. s., 1H), 8.10 (d, J=7.3 Hz, 1H), 8.04-7.94 (m, 3H), 7.91 (s, 1H), 7.39-7.29 (m, 2H), 7.06 (dd, J=9.0, 2.3 Hz, 1H), 6.01 (br. s., 1H), 5.60-5.47 (m, 1H), 5.06-4.96 (m, 1H), 4.86-4.69 (m, 2H), 4.64-4.44 (m, 2H), 4.01 (dd, J=11.0, 3.4 Hz, 1H), 3.92 (s, 3H), 3.80 (dd, J=10.7, 8.2 Hz, 1H), 2.77-2.62 (m, 2H), 2.44-2.27 (m, 2H), 1.98-1.83 (m, 2H), 1.80-0.67 (m, 29H); MS: MS m/z 960.7 (M$^+$+1).

Compounds 3077 and 3078 were prepared using the intermediates described herein and by following the general procedure described for the synthesis of Compound 3117:

Compound 3077: 1,1,1-trifluoro-2-methylpropan-2-yl ((2R,6S,7R,9S,13aS,14aR,16aS,Z)-2-((3-(3-fluoro-4-isopropoxyphenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 974.8 (M$^+$+1).

Compound 3078: 1,1,1-trifluoro-2-methylpropan-2-yl ((2R,6S,7R,9R,13aS,14aR,16aS,Z)-2-((3-(3-fluoro-4-isopropoxyphenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.05 (br. s., 1H), 9.07 (br. s., 1H), 8.10 (d, J=7.3 Hz, 1H), 8.04-7.94 (m, 3H), 7.91 (s, 1H), 7.39-7.29 (m, 2H), 7.06 (dd, J=9.0, 2.3 Hz, 1H), 6.01 (br. s., 1H), 5.60-5.47 (m, 1H), 5.06-4.96 (m, 1H), 4.86-4.69 (m, 2H), 4.64-4.44 (m, 2H), 4.01 (dd, J=11.0, 3.4 Hz, 1H), 3.92 (s, 3H), 3.80 (dd, J=10.7, 8.2 Hz, 1H), 2.77-2.62 (m, 2H), 2.44-2.27 (m, 2H), 1.98-1.83 (m, 2H), 1.80-0.67 (m, 29H); MS: MS m/z 974.8 (M$^+$+1).

Preparation of Compound 3077 and Compound 3078

Compound 3077

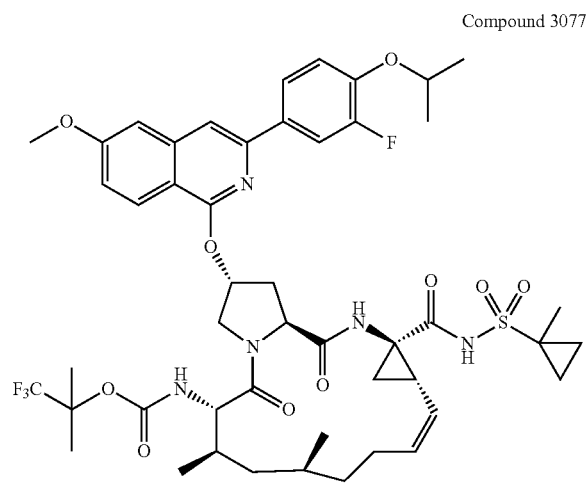

Preparation of Compound 3079 and Compound 3080

Compound 3079

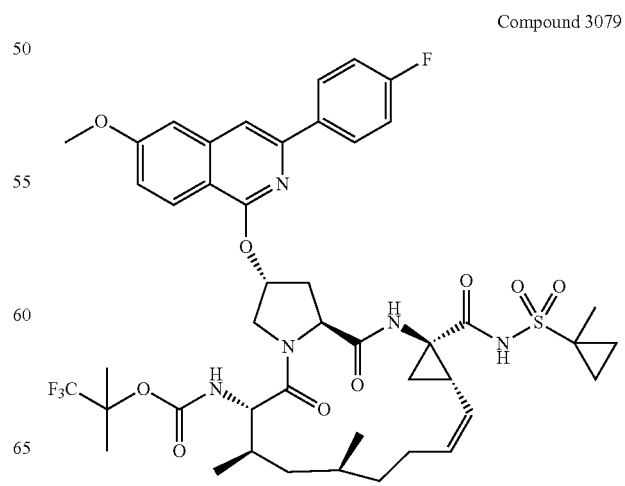

-continued

Compound 3080

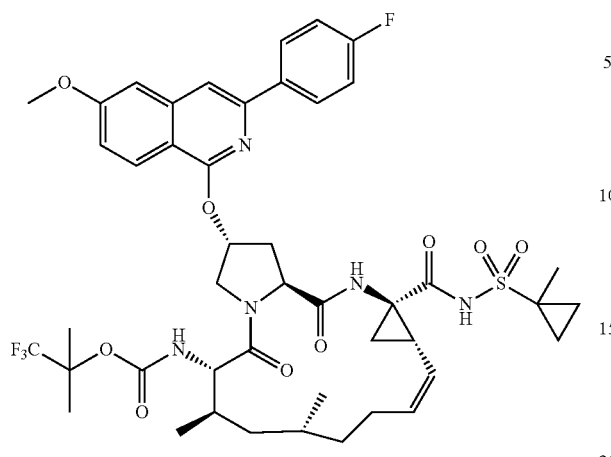

Compounds 3079 and 3080 were prepared using the intermediates described herein and by following the general procedure described for the synthesis of Compound 3117:

Compound 3079: 1,1,1-trifluoro-2-methylpropan-2-yl ((2R,6S,7R,9S,13aS,14aR,16aS,Z)-2-((3-(4-fluorophenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 916.7 (M$^+$+1).

Compound 3080: 1,1,1-trifluoro-2-methylpropan-2-yl ((2R,6S,7R,9R,13aS,14aR,16aS,Z)-2-((3-(4-fluorophenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.06 (br. s., 1H), 9.11 (br. s., 1H), 8.24 (dd, J=8.9, 5.5 Hz, 2H), 8.03 (d, J=9.2 Hz, 1H), 7.93 (s, 1H), 7.85 (d, J=7.6 Hz, 1H), 7.41-7.31 (m, 3H), 7.14 (dd, J=9.2, 2.4 Hz, 1H), 6.00 (br. s., 1H), 5.61-5.47 (m, 1H), 5.08-4.94 (m, 1H), 4.64-4.47 (m, 2H), 3.98 (dd, J=11.4, 3.2 Hz, 1H), 3.93 (s, 3H), 3.74 (dd, J=10.7, 8.2 Hz, 1H), 2.79-2.62 (m, 2H), 2.43-2.26 (m, 2H), 1.96-0.70 (m, 28H); MS: MS m/z 916.7 (M$^+$+1).

Preparation of Compound 3081 and Compound 3082

Compound 3081

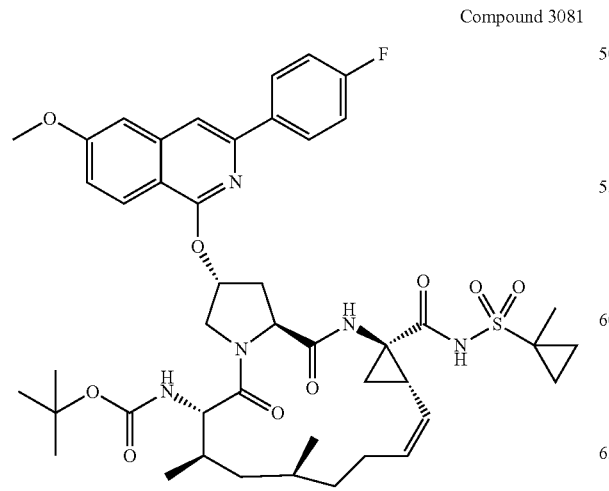

-continued

Compound 3082

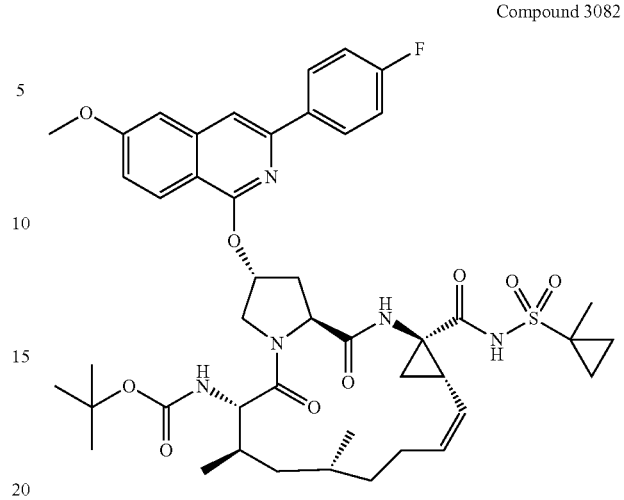

Compounds 3081 and 3082 were prepared using the intermediates described herein and by following the general procedure described for the synthesis of Compound 3117:

Compound 3081: tert-butyl ((2R,6S,7R,9S,13aS,14aR,16aS,Z)-2-((3-(4-fluorophenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 862.7.7 (M$^+$+1).

Compound 3082: tert-butyl ((2R,6S,7R,9R,13aS,14aR,16aS,Z)-2-((3-(4-fluorophenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.07 (br. s., 1H), 9.08 (br. s., 1H), 8.23 (dd, J=8.9, 5.8 Hz, 2H), 8.06 (d, J=9.2 Hz, 1H), 7.92 (s, 1H), 7.40-7.33 (m, 3H), 7.21 (d, J=7.9 Hz, 1H), 7.10 (dd, J=9.2, 2.4 Hz, 1H), 5.99 (br. s., 1H), 5.60-5.48 (m, 1H), 5.05-4.93 (m, 1H), 4.68-4.60 (m, 1H), 4.53-4.46 (m, 1H), 3.98 (dd, J=11.0, 3.1 Hz, 1H), 3.93 (s, 3H), 3.75 (dd, J=10.8, 8.4 Hz, 1H), 2.79-2.64 (m, 2H), 2.43-2.26 (m, 2H), 1.99-0.69 (m, 31H); MS: MS m/z 862.7 (M$^+$+1).

Preparation of Compound 3083

Compound 3083

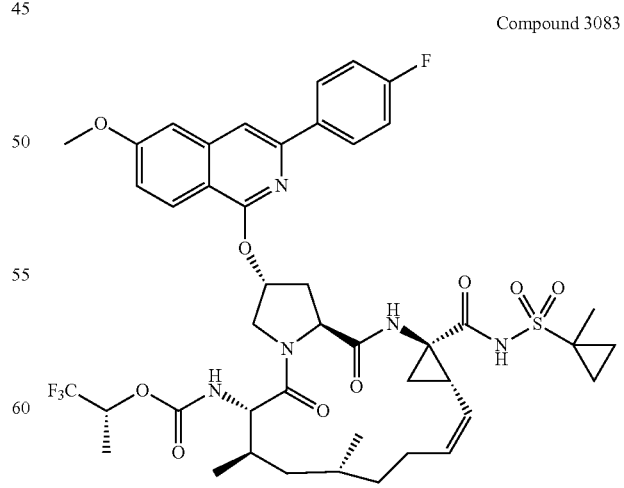

Compound 3083 was prepared using the intermediates described herein and by following the general procedure described for the synthesis of Compound 3117:

Compound 3083: (R)-1,1,1-trifluoropropan-2-yl ((2R,6S,7R,9R,13aS,14aR,16aS,Z)-2-((3-(4-fluorophenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-$d_6$) δ 11.05 (br. s., 1H), 9.08 (br. s., 1H), 8.27-8.21 (m, 2H), 8.11 (d, J=7.9 Hz, 1H), 8.00 (d, J=9.2 Hz, 1H), 7.93 (s, 1H), 7.41-7.33 (m, 3H), 7.07 (dd, J=9.2, 2.4 Hz, 1H), 6.01 (br. s., 1H), 5.59-5.48 (m, 1H), 5.00 (t, J=9.2 Hz, 1H), 4.80 (dt, J=13.4, 6.7 Hz, 1H), 4.57 (d, J=11.3 Hz, 1H), 4.54-4.46 (m, 1H), 4.00 (dd, J=11.3, 3.4 Hz, 1H), 3.92 (s, 3H), 3.81 (dd, J=10.7, 8.2 Hz, 1H), 2.79-2.63 (m, 2H), 2.43-2.27 (m, 2H), 2.00-1.84 (m, 2H), 1.76-0.72 (m, 23H); MS: MS m/z 902.7 (M$^+$+1).

Preparation of Compound 3084 and Compound 3085

Compound 3085: (1-methylcyclopropyl)methyl ((2R,6S,7R,9R,13aS,14aR,16aS,Z)-2-((3-(4-fluorophenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-$d_6$) δ 11.07 (br. s., 1H), 9.06 (br. s., 1H), 8.23 (dd, J=8.5, 5.5 Hz, 2H), 8.04 (d, J=8.9 Hz, 1H), 7.93 (s, 1H), 7.54 (d, J=8.2 Hz, 1H), 7.41-7.32 (m, J=17.7 Hz, 3H), 7.13 (dd, J=9.0, 2.3 Hz, 1H), 6.01 (br. s., 1H), 5.58-5.48 (m, 1H), 5.06-4.94 (m, 1H), 4.58 (d, J=11.3 Hz, 1H), 4.51 (t, J=8.1 Hz, 1H), 4.00 (dd, J=11.4, 3.2 Hz, 1H), 3.93 (s, 3H), 3.78 (dd, J=10.2, 8.7 Hz, 1H), 3.50-3.40 (m, 2H), 2.79-2.63 (m, 2H), 2.43-2.27 (m, 2H), 2.00-1.81 (m, 2H), 1.77-0.66 (m, 23H), 0.37-0.16 (m, 4H); MS: MS m/z 874.8 (M$^+$+1).

Preparation of Compound 3086 and Compound 3087

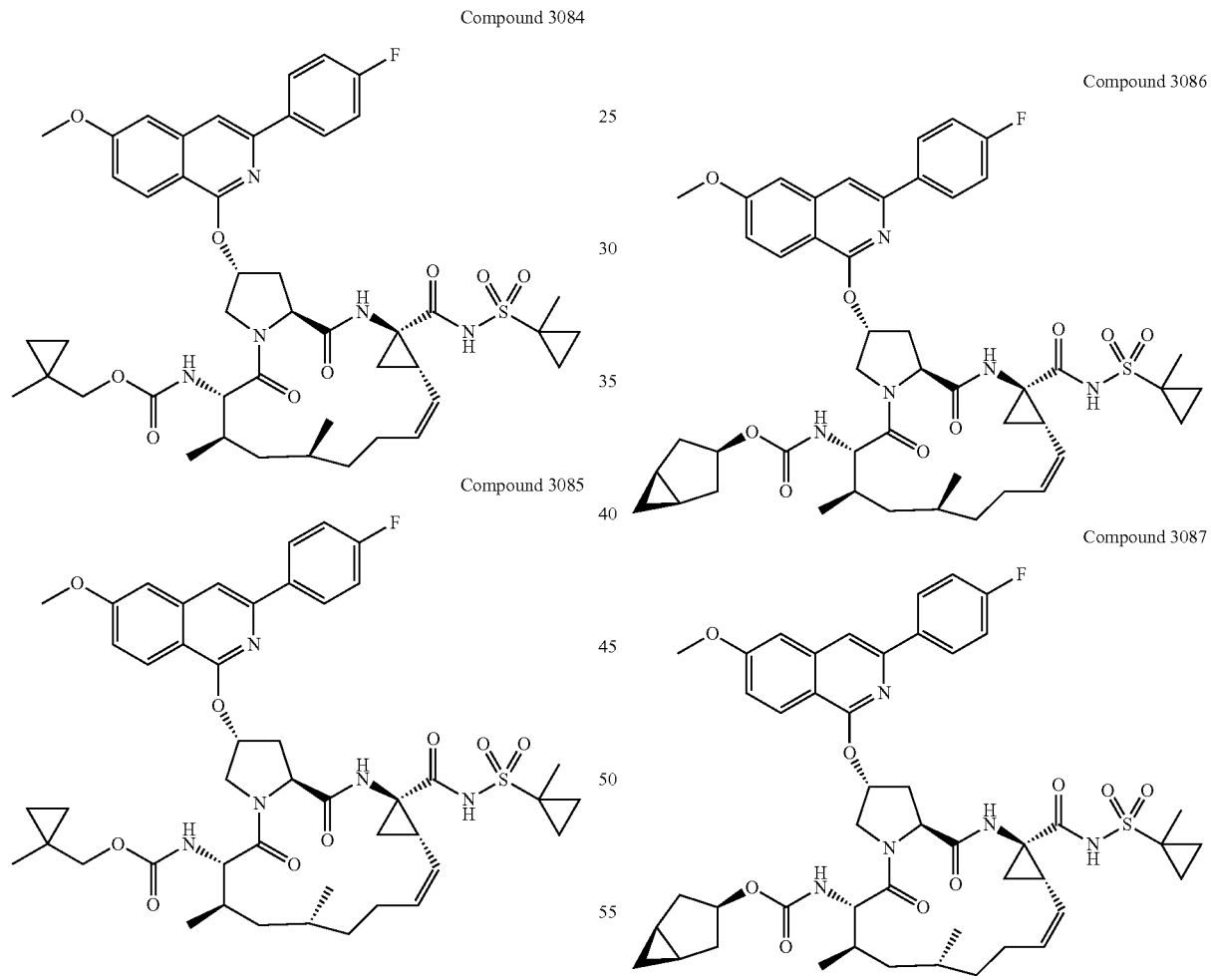

Compound 3084

Compound 3085

Compound 3086

Compound 3087

Compounds 3084 and 3085 were prepared using the intermediates described herein and by following the general procedure described for the synthesis of Compound 3117:

Compound 3084: (1-methylcyclopropyl)methyl ((2R,6S,7R,9S,13aS,14aR,16aS,Z)-2-((3-(4-fluorophenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 874.8 (M$^+$+1).

Compounds 3086 and 3087 were prepared using the intermediates described herein and by following the general procedure described for the synthesis of Compound 3117:

Compound 3086: (1R,3r,5S)-bicyclo[3.1.0]hexan-3-yl ((2R,6S,7R,9S,13aS,14aR,16aS,Z)-2-((3-(4-fluorophenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a- hexadecahydrocyclopropa[e]pyrrolo[1,2-a][1,4]diazacyclopentadecin-6-yl)carbamate; MS: MS m/z 886.7 (M⁺+1).

Compound 3087: (1R,3r,5S)-bicyclo[3.1.0]hexan-3-yl ((2R,6S,7R,9R,13aS,14aR,16aS,Z)-2-((3-(4-fluorophenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; ¹H NMR (500 MHz, DMSO-d₆) δ 11.07 (br. s., 1H), 9.04 (br. s., 1H), 8.29-8.19 (m, 2H), 8.03 (d, J=9.2 Hz, 1H), 7.93 (s, 1H), 7.43 (d, J=8.2 Hz, 1H), 7.40-7.33 (m, 3H), 7.16 (dd, J=9.0, 2.3 Hz, 1H), 6.00 (br. s., 1H), 5.59-5.46 (m, 1H), 5.08-4.94 (m, 1H), 4.69 (t, J=6.6 Hz, 1H), 4.58-4.44 (m, 2H), 4.00 (dd, J=11.4, 3.5 Hz, 1H), 3.96-3.91 (m, 3H), 3.79 (t, J=9.8 Hz, 1H), 2.79-2.64 (m, 2H), 2.42-2.25 (m, 2H), 2.03-1.77 (m, 4H), 1.75-0.69 (m, 24H), 0.43-0.32 (m, 2H); MS: MS m/z 886.8 (M⁺+1).

Preparation of Compound 3088 and Compound 3089 oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 853.8 (M⁺+1).

Compound 3089: tert-butyl ((2R,6S,7R,9R,13aS,14aR,16aS,Z)-2-((6-methoxy-3-morpholinoisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; ¹H NMR (500 MHz, DMSO-d₆) δ 11.07 (br. s., 1H), 9.06 (br. s., 1H), 7.84 (d, J=9.2 Hz, 1H), 7.22 (d, J=8.2 Hz, 1H), 7.00 (d, J=2.1 Hz, 1H), 6.72 (dd, J=9.0, 2.3 Hz, 1H), 6.45 (s, 1H), 5.76 (br. s., 1H), 5.61-5.47 (m, 1H), 5.04-4.91 (m, 1H), 4.52 (d, J=11.6 Hz, 1H), 4.43 (t, J=8.4 Hz, 1H), 3.95-3.89 (m, 1H), 3.84 (s, 3H), 3.80-3.72 (m, 5H), 3.51-3.39 (m, 4H), 2.71 (br. s., 1H), 2.63-2.54 (m, 1H), 2.40-2.22 (m, 2H), 1.97-1.79 (m, 2H), 1.76-0.83 (m, 28H), 0.74 (t, J=12.4 Hz, 1H); MS: MS m/z 853.8 (M⁺+1).

Preparation of Compound 3090 and Compound 3091

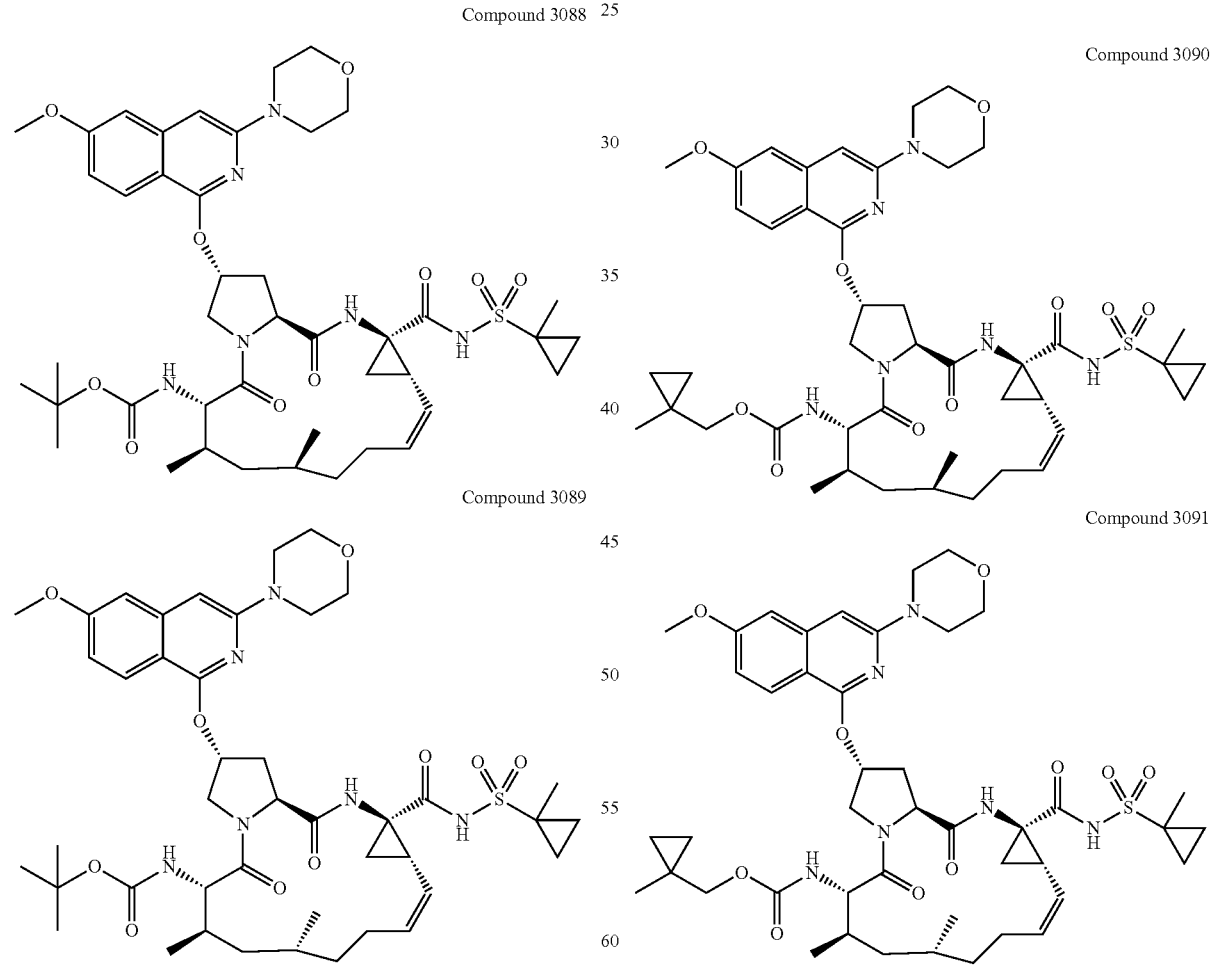

Compounds 3088 and 3089 were prepared using the intermediates described herein and by following the general procedure described for the synthesis of Compound 3117:

Compound 3088: tert-butyl ((2R,6S,7R,9S,13aS,14aR,16aS,Z)-2-((6-methoxy-3-morpholinoisoquinolin-1-yl)

Compounds 3090 and 3091 were prepared using the intermediates described herein and by following the general procedure described for the synthesis of Compound 3117:

Compound 3090: (1-methylcyclopropyl)methyl ((2R,6S,7R,9S,13aS,14aR,16aS,Z)-2-((6-methoxy-3-morpholinoisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 865.8 (M$^+$+1).

Compound 3091: (1-methylcyclopropyl)methyl ((2R,6S,7R,9R,13aS,14aR,16aS,Z)-2-((6-methoxy-3-morpholinoisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.05 (br. s., 1H), 9.04 (br. s., 1H), 7.81 (d, J=8.9 Hz, 1H), 7.54 (d, J=7.0 Hz, 1H), 7.01 (s, 1H), 6.79-6.73 (m, 1H), 6.46 (s, 1H), 5.76 (br. s., 1H), 5.57-5.45 (m, 1H), 5.12-4.94 (m, 1H), 4.42 (br. s., 1H), 3.95 (dd, J=11.4, 3.5 Hz, 1H), 3.85 (s, 3H), 3.77 (t, J=4.7 Hz, 5H), 3.50-3.40 (m, 4H), 2.61-2.54 (m, 2H), 2.36-2.25 (m, 2H), 1.98-0.65 (m, 31H), 0.40-0.19 (m, 4H); MS: MS m/z 865.8 (M$^+$+1).

Preparation of Compound 3092 and Compound 3093 noisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 893.6 (M$^+$+1).

Compound 3093: (R)-1,1,1-trifluoropropan-2-yl ((2R,6S,7R,9R,13aS,14aR,16aS,Z)-2-((6-methoxy-3-morpholinoisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.04 (br. s., 1H), 9.06 (br. s., 1H), 8.12 (d, J=8.2 Hz, 1H), 7.78 (d, J=9.2 Hz, 1H), 7.01 (d, J=2.4 Hz, 1H), 6.70 (dd, J=9.0, 2.3 Hz, 1H), 6.46 (s, 1H), 5.77 (br. s., 1H), 5.59-5.47 (m, 1H), 5.03-4.92 (m, 2H), 4.51-4.39 (m, 2H), 3.95 (dd, J=11.4, 3.5 Hz, 1H), 3.87-3.80 (m, 4H), 3.79-3.75 (m, 4H), 3.50-3.39 (m, 4H), 2.72-2.56 (m, 2H), 2.41-2.22 (m, 2H), 1.98-1.82 (m, 2H), 1.75-1.66 (m, 1H), 1.63-1.56 (m, 1H), 1.55-0.70 (m, 21H); MS: MS m/z 893.7 (M$^+$+1).

Preparation of Compound 3094 and Compound 3095

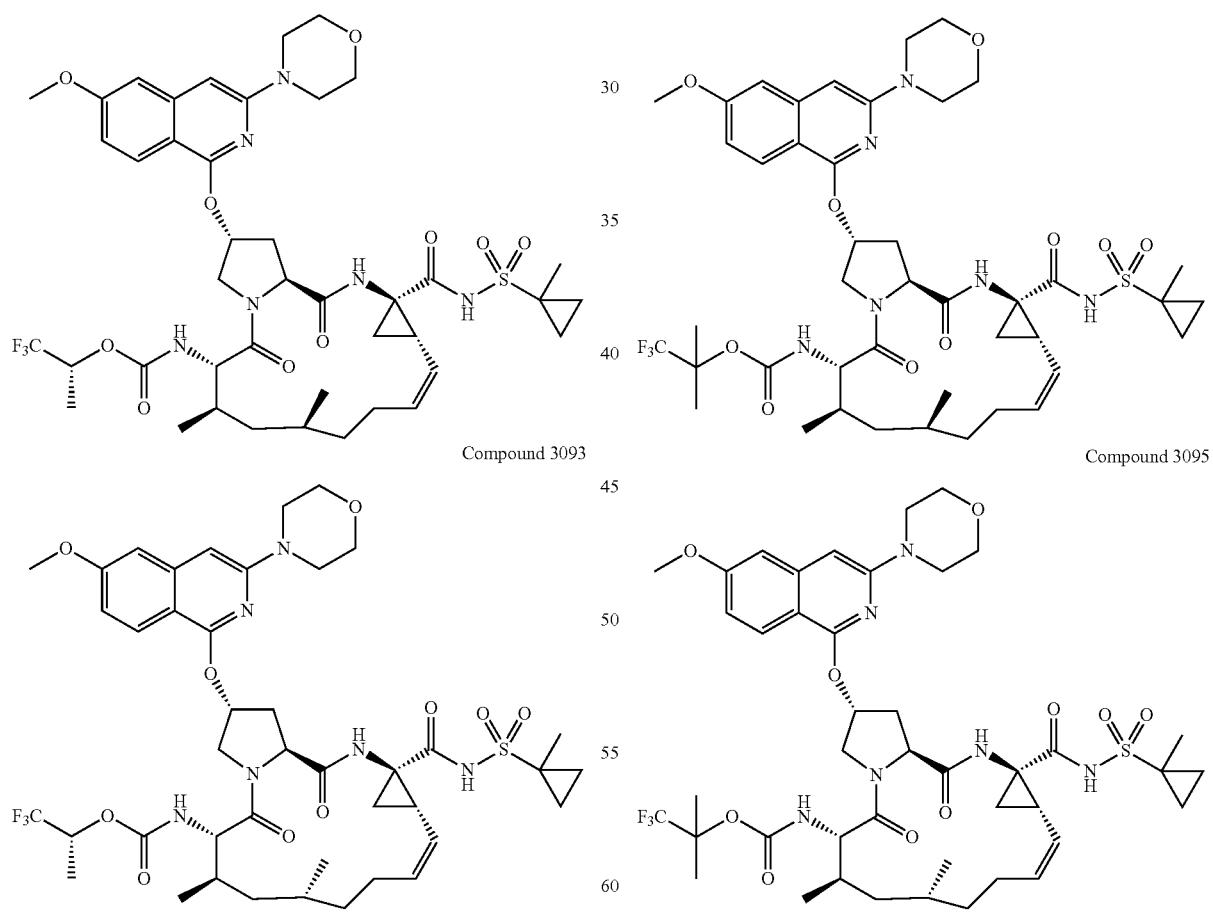

Compounds 3092 and 3093 were prepared using the intermediates described herein and by following the general procedure described for the synthesis of Compound 3117:

Compound 3092: (R)-1,1,1-trifluoropropan-2-yl ((2R,6S,7R,9S,13aS,14aR,16aS,Z)-2-((6-methoxy-3-morpholi- Compounds 3094 and 3095 were prepared using the intermediates described herein and by following the general procedure described for the synthesis of Compound 3117:

Compound 3094: 1,1,1-trifluoro-2-methylpropan-2-yl ((2R,6S,7R,9S,13aS,14aR,16aS,Z)-2-((6-methoxy-3-morpholinoisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 907.7 (M$^+$+1).

Compound 3095: 1,1,1-trifluoro-2-methylpropan-2-yl ((2R,6S,7R,9R,13aS,14aR,16aS,Z)-2-((6-methoxy-3-morpholinoisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.05 (br. s., 1H), 9.08 (br. s., 1H), 7.86 (d, J=8.2 Hz, 1H), 7.81 (d, J=9.2 Hz, 1H), 7.01 (d, J=2.4 Hz, 1H), 6.76 (dd, J=9.2, 2.4 Hz, 1H), 6.46 (s, 1H), 5.76 (br. s., 1H), 5.57-5.45 (m, 1H), 5.15-4.90 (m, 1H), 4.53-4.39 (m, 2H), 3.97-3.89 (m, 1H), 3.84 (s, 3H), 3.80-3.74 (m, 5H), 3.51-3.39 (m, 4H), 2.69-2.55 (m, 2H), 2.42-2.23 (m, 2H), 1.97-1.81 (m, 2H), 1.77-0.68 (m, 26H); MS: MS m/z 907.7 (M$^+$+1).

Preparation of Compound 3096 and Compound 3097

Compound 3096

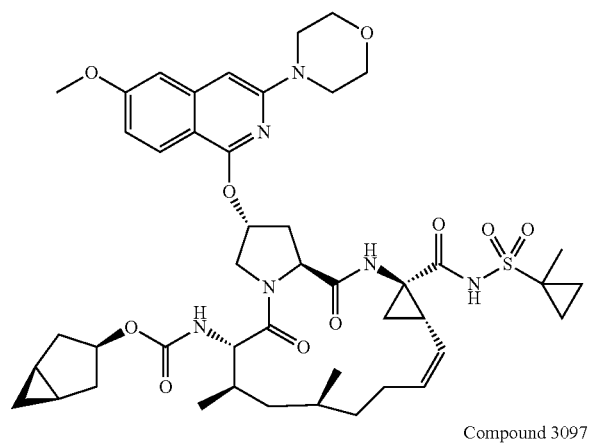

Compound 3097

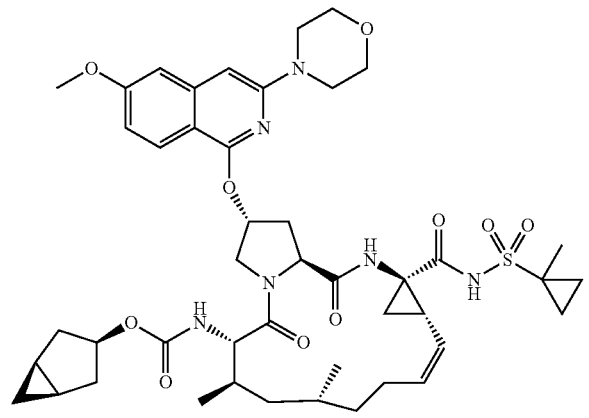

Compounds 3096 and 3097 were prepared using the intermediates described herein and by following the general procedure described for the synthesis of Compound 3117:

Compound 3096: (1R,3r,5S)-bicyclo[3.1.0]hexan-3-yl ((2R,6S,7R,9S,13aS,14aR,16aS,Z)-2-((6-methoxy-3-morpholinoisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 877.8 (M$^+$+1).

Compound 3097: (1R,3r,5S)-bicyclo[3.1.0]hexan-3-yl ((2R,6S,7R,9R,13aS,14aR,16aS,Z)-2-((6-methoxy-3-morpholinoisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.03 (br. s., 1H), 9.00 (br. s., 1H), 7.81 (d, J=8.9 Hz, 1H), 7.43 (d, J=8.5 Hz, 1H), 7.02 (d, J=2.1 Hz, 1H), 6.78 (dd, J=9.0, 2.3 Hz, 1H), 6.47 (s, 1H), 5.76 (br. s., 1H), 5.58-5.45 (m, 1H), 5.13-4.96 (m, 1H), 4.81 (t, J=6.7 Hz, 1H), 4.48-4.36 (m, 2H), 3.95 (dd, J=11.0, 3.4 Hz, 1H), 3.85 (s, 3H), 3.83-3.75 (m, 5H), 3.50-3.41 (m, 4H), 2.63-2.53 (m, 2H), 2.36-2.22 (m, 2H), 2.08-1.79 (m, 4H), 1.72-1.09 (m, 15H), 0.99-0.67 (m, 9H), 0.46-0.33 (m, 2H); MS: MS m/z 877.7 (M$^+$+1).

Preparation of Compound 3098 and Compound 3099

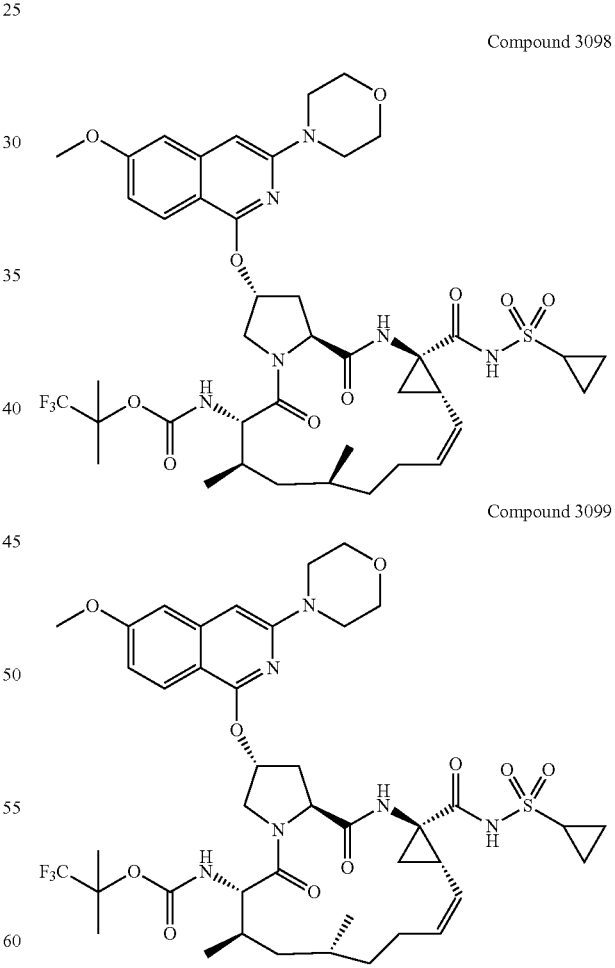

Compounds 3098 and 3099 were prepared using the intermediates described herein and by following the general procedure described for the synthesis of Compound 3117:

Compound 3098: 1,1,1-trifluoro-2-methylpropan-2-yl ((2R,6S,7R,9S,13aS,14aR,16aS,Z)-14a-((cyclopropylsulfonyl)carbamoyl)-2-((6-methoxy-3-morpholinoisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 893.8 (M$^+$+1).

Compound 3099: 1,1,1-trifluoro-2-methylpropan-2-yl ((2R,6S,7R,9R,13aS,14aR,16aS,Z)-14a-((cyclopropylsulfonyl)carbamoyl)-2-((6-methoxy-3-morpholinoisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.20 (br. s., 1H), 8.96 (br. s., 1H), 7.86 (d, J=7.9 Hz, 1H), 7.81 (d, J=9.2 Hz, 1H), 7.01 (d, J=2.1 Hz, 1H), 6.75 (dd, J=9.0, 2.3 Hz, 1H), 6.46 (s, 1H), 5.75 (br. s., 1H), 5.58-5.46 (m, 1H), 5.13-4.99 (m, 1H), 4.50-4.40 (m, 2H), 3.93-3.88 (m, 1H), 3.84 (s, 3H), 3.80-3.73 (m, 5H), 3.50-3.41 (m, 4H), 2.91 (s, 1H), 2.71-2.55 (m, 2H), 2.36-2.24 (m, 2H), 1.98-1.82 (m, 2H), 1.71 (br. s., 1H), 1.63-0.84 (m, 21H), 0.74 (t, J=12.5 Hz, 1H); MS: MS m/z 893.7 (M$^+$+1).

Preparation of Compound 3100 and Compound 3101

((cyclopropylsulfonyl)carbamoyl)-2-((6-methoxy-3-morpholinoisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 899.8 (M$^+$+1).

Compound 3101: 1,1,1,3,3,3-hexadeutero-2-(trifluoromethyl)propan-2-yl ((2R,6S,7R,9R,13aS,14aR,16aS,Z)-14a-((cyclopropylsulfonyl)carbamoyl)-2-((6-methoxy-3-morpholinoisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.20 (br. s., 1H), 8.95 (br. s., 1H), 7.85 (d, J=7.9 Hz, 1H), 7.81 (d, J=9.2 Hz, 1H), 7.01 (d, J=2.1 Hz, 1H), 6.75 (dd, J=8.9, 2.4 Hz, 1H), 6.46 (s, 1H), 5.75 (br. s., 1H), 5.58-5.45 (m, 1H), 5.18-5.04 (m, 1H), 4.53-4.38 (m, 2H), 3.93-3.88 (m, 1H), 3.84 (s, 3H), 3.80-3.73 (m, 5H), 3.51-3.40 (m, 4H), 2.91 (s, 1H), 2.69-2.55 (m, 2H), 2.36-2.22 (m, 2H), 1.97-1.80 (m, 2H), 1.77-1.67 (m, 1H), 1.65-0.85 (m, 15H), 0.73 (t, J=12.2 Hz, 1H); MS: MS m/z 899.8 (M$^+$+1).

Preparation of Compound 3102 and Compound 3103

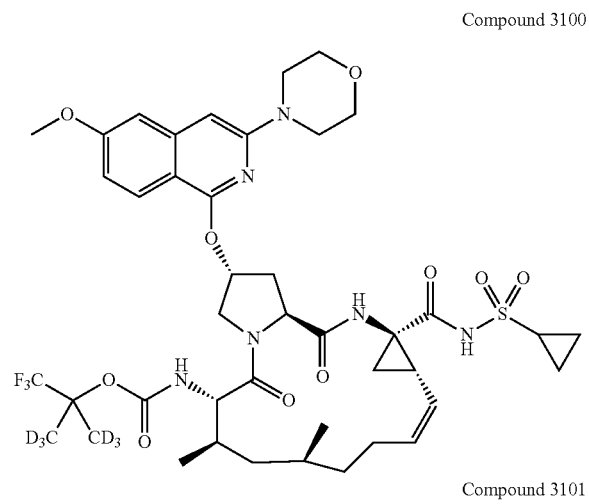

Compound 3100

Compound 3101

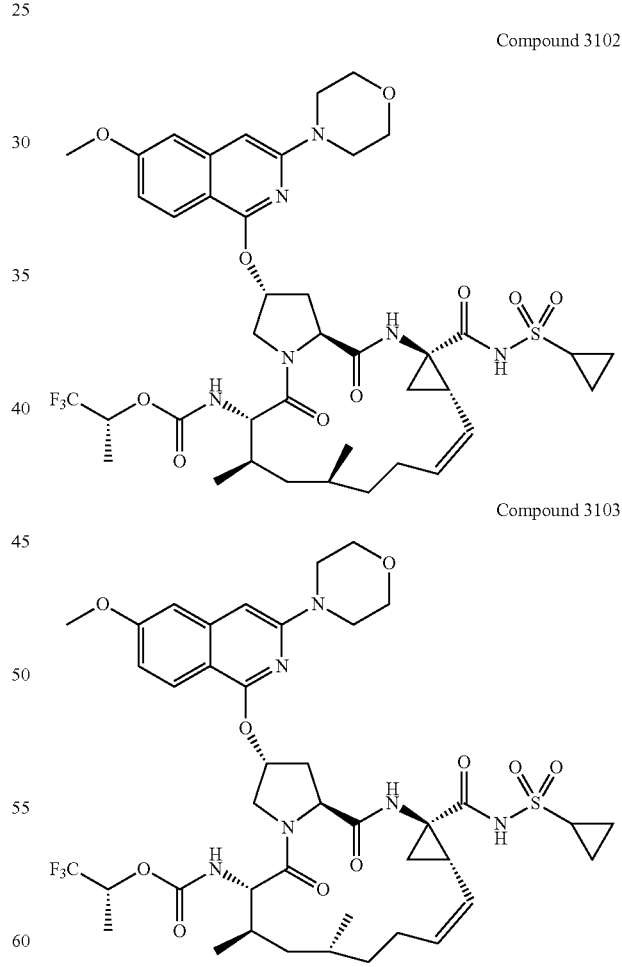

Compound 3102

Compound 3103

Compounds 3100 and 3101 were prepared using the intermediates described herein and by following the general procedure described for the synthesis of Compound 3117:

Compound 3100: 1,1,1,3,3,3-hexadeutero-2-(trifluoromethyl)propan-2-yl ((2R,6S,7R,9S,13aS,14aR,16aS,Z)-14a-

Compounds 3102 and 3103 were prepared using the intermediates described herein and by following the general procedure described for the synthesis of Compound 3117:

Compound 3102: (R)-1,1,1-trifluoropropan-2-yl ((2R,6S,7R,9S,13aS,14aR,16aS,Z)-14a-((cyclopropylsulfonyl)carbamoyl)-2-((6-methoxy-3-morpholinoisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 879.7 (M$^+$+1).

Compound 3103: (R)-1,1,1-trifluoropropan-2-yl ((2R,6S,7R,9R,13aS,14aR,16aS,Z)-14a-((cyclopropylsulfonyl)carbamoyl)-2-((6-methoxy-3-morpholinoisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.20 (br. s., 1H), 8.91 (br. s., 1H), 8.11 (d, J=8.2 Hz, 1H), 7.78 (d, J=8.9 Hz, 1H), 7.01 (d, J=2.1 Hz, 1H), 6.70 (dd, J=9.0, 2.3 Hz, 1H), 6.46 (s, 1H), 5.75 (br. s., 1H), 5.57-5.47 (m, 1H), 5.14-5.04 (m, 1H), 5.04-4.93 (m, 1H), 4.49-4.34 (m, 2H), 3.97-3.90 (m, 1H), 3.86-3.80 (m, 4H), 3.79-3.75 (m, 4H), 3.53-3.39 (m, 4H), 2.91 (s, 1H), 2.70-2.55 (m, 2H), 2.35-2.24 (m, 2H), 2.01-1.84 (m, 2H), 1.77-1.66 (m, 1H), 1.63-0.81 (m, 18H), 0.75 (t, J=12.4 Hz, 1H); MS: MS m/z 879.7 (M$^+$+1).

Preparation of Compound 3104 and Compound 3105 nyl)carbamoyl)-2-((6-methoxy-3-morpholinoisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 863.8 (M$^+$+1).

Compound 3105: (1R,3r,5S)-bicyclo[3.1.0]hexan-3-yl ((2R,6S,7R,9R,13aS,14aR,16aS,Z)-14a-((cyclopropylsulfonyl)carbamoyl)-2-((6-methoxy-3-morpholinoisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.20 (br. s., 1H), 8.89 (br. s., 1H), 7.81 (d, J=9.2 Hz, 1H), 7.43 (d, J=8.5 Hz, 1H), 7.02 (d, J=2.4 Hz, 1H), 6.78 (dd, J=9.0, 2.3 Hz, 1H), 6.47 (s, 1H), 5.75 (br. s., 1H), 5.61-5.44 (m, 1H), 5.23-4.98 (m, 1H), 4.82 (t, J=6.7 Hz, 1H), 4.44-4.34 (m, 2H), 3.96-3.90 (m, J=3.4 Hz, 1H), 3.85 (s, 3H), 3.83-3.73 (m, 5H), 3.52-3.40 (m, 4H), 2.94-2.86 (m, 1H), 2.63-2.54 (m, 2H), 2.34-2.22 (m, 2H), 2.08-1.80 (m, 4H), 1.74-0.84 (m, 20H), 0.72 (t, J=12.4 Hz, 1H), 0.47-0.34 (m, 2H); MS: MS m/z 863.8 (M$^+$+1).

Preparation of Compound 3106 and Compound 3107

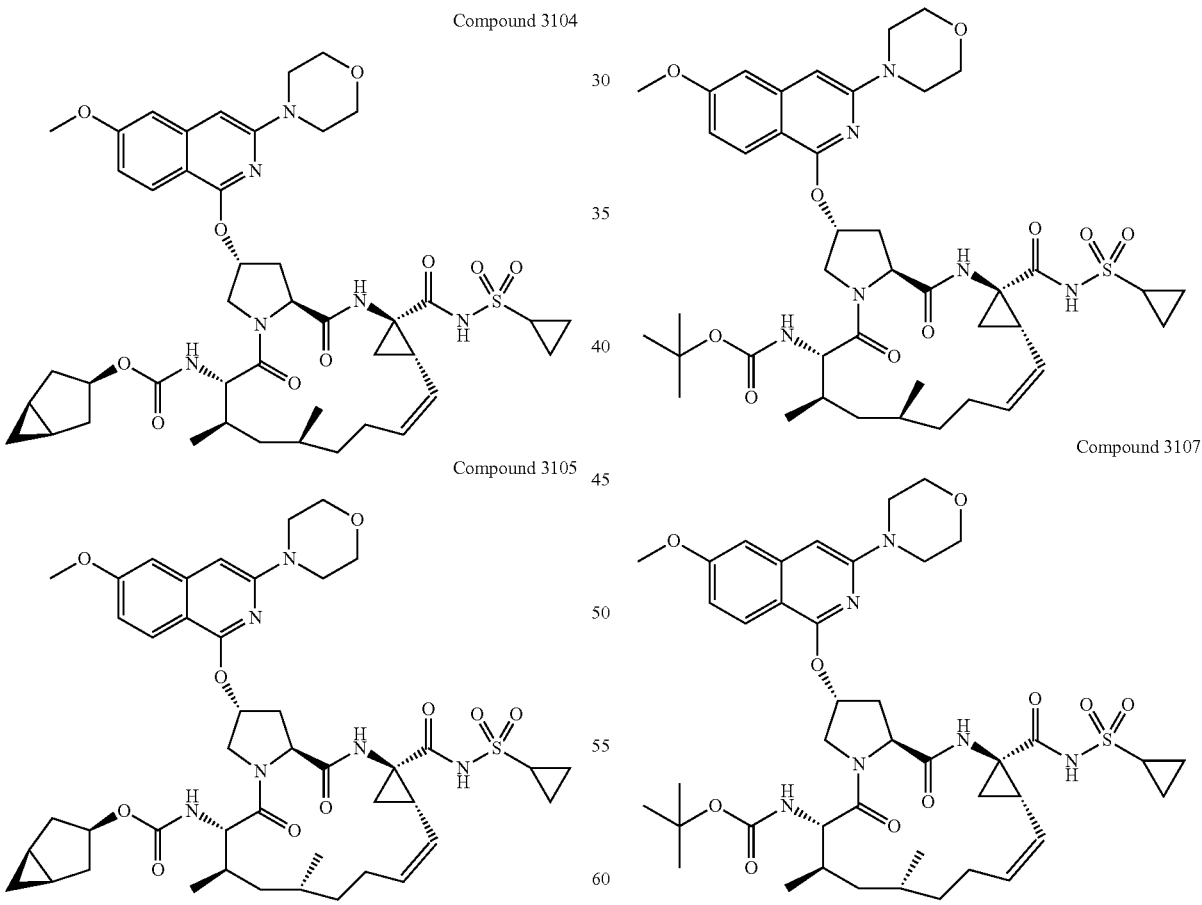

Compound 3104

Compound 3105

Compound 3106

Compound 3107

Compounds 3104 and 3105 were prepared using the intermediates described herein and by following the general procedure described for the synthesis of Compound 3117:

Compound 3104: (1R,3r,5S)-bicyclo[3.1.0]hexan-3-yl ((2R,6S,7R,9S,13aS,14aR,16aS,Z)-14a-((cyclopropylsulfo- Compounds 3106 and 3107 were prepared using the intermediates described herein and by following the general procedure described for the synthesis of Compound 3117:

Compound 3106: tert-butyl ((2R,6S,7R,9S,13aS,14aR,16aS,Z)-14a-((cyclopropylsulfonyl)carbamoyl)-2-((6- methoxy-3-morpholinoisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 839.7 (M⁺+1).

Compound 3107: tert-butyl ((2R,6S,7R,9R,13aS,14aR,16aS,Z)-14a-((cyclopropylsulfonyl)carbamoyl)-2-((6-methoxy-3-morpholinoisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; ¹H NMR (500 MHz, DMSO-d₆) δ 11.23 (br. s., 1H), 8.93 (br. s., 1H), 7.84 (d, J=8.9 Hz, 1H), 7.20 (d, J=5.8 Hz, 1H), 7.00 (d, J=2.1 Hz, 1H), 6.72 (dd, J=9.2, 2.4 Hz, 1H), 6.45 (s, 1H), 5.73 (br. s., 1H), 5.63-5.44 (m, 1H), 5.20-5.00 (m, 1H), 4.58-4.45 (m, 1H), 4.42-4.32 (m, 1H), 3.94-3.87 (m, 1H), 3.84 (s, 3H), 3.81-3.73 (m, 5H), 3.52-3.39 (m, 4H), 2.95-2.84 (m, 1H), 2.67-2.55 (m, 2H), 2.34-2.19 (m, 2H), 2.01-0.84 (m, 31H), 0.71 (t, J=12.4 Hz, 1H); MS: MS m/z 839.6 (M⁺+1).

Preparation of Compound 3110 and Compound 3111 hexadecahydrocyclopropa[e]pyrrolo[1,2-a][1,4]diazacyclopentadecin-6-yl)carbamate; MS: MS m/z 835.6 (M⁺+1).

Compound 3111: (1R,3r,5S)-bicyclo[3.1.0]hexan-3-yl ((2R,6S,7R,9R,13aS,14aR,16aS,Z)-2-((3-(dimethylamino)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; ¹H NMR (500 MHz, DMSO-d₆) δ 11.05 (br. s., 1H), 9.04 (br. s., 1H), 7.76 (d, J=9.2 Hz, 1H), 7.45 (d, J=8.9 Hz, 1H), 6.96 (d, J=2.4 Hz, 1H), 6.68 (dd, J=9.0, 2.3 Hz, 1H), 6.24 (s, 1H), 5.78 (br. s., 1H), 5.60-5.48 (m, 1H), 5.04-4.94 (m, 1H), 4.81 (t, J=6.7 Hz, 1H), 4.47-4.37 (m, 2H), 3.99 (dd, J=11.3, 3.7 Hz, 1H), 3.87-3.77 (m, 4H), 3.11-3.05 (m, 6H), 2.74-2.58 (m, 2H), 2.37-2.24 (m, 2H), 2.08-1.80 (m, 4H), 1.72-1.09 (m, 16H), 0.97-0.85 (m, 8H), 0.75 (t, J=12.1 Hz, 1H), 0.47-0.32 (m, 2H); MS: MS m/z 835.5 (M⁺+1).

Preparation of Compound 3112 and Compound 3113

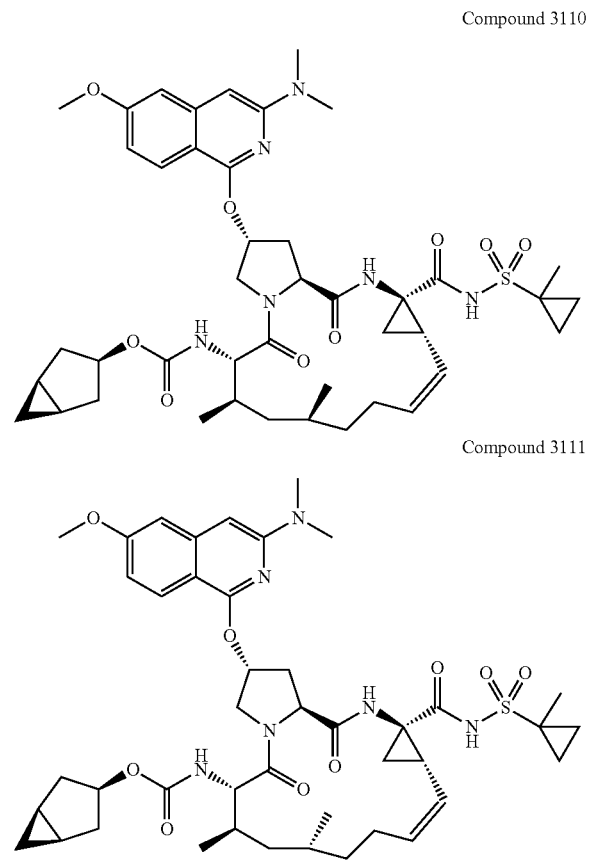

Compound 3110

Compound 3111

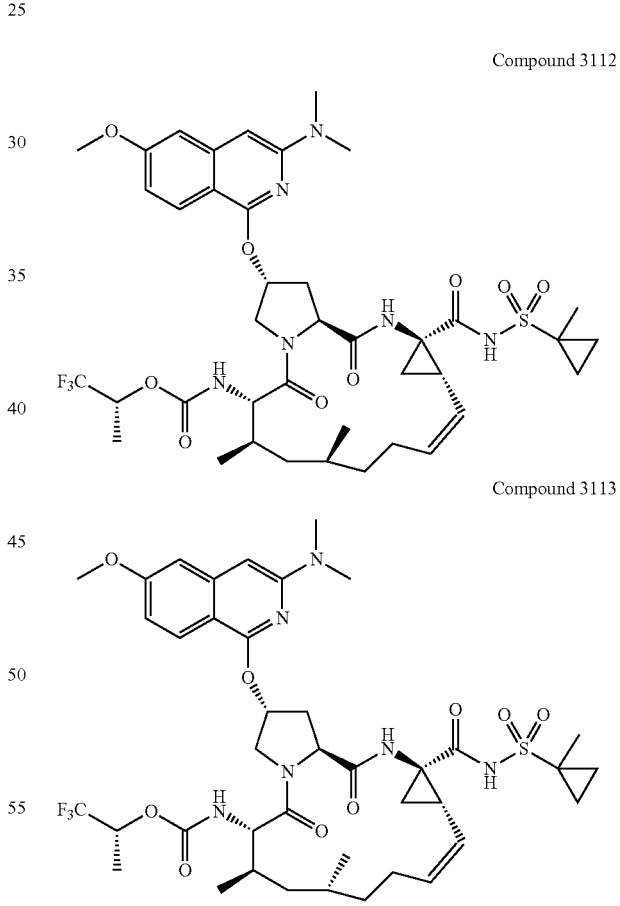

Compound 3112

Compound 3113

Compounds 3110 and 3111 were prepared using the intermediates described herein and by following the general procedure described for the synthesis of Compound 3117:

Compound 3110: (1R,3r,5S)-bicyclo[3.1.0]hexan-3-yl ((2R,6S,7R,9S,13aS,14aR,16aS,Z)-2-((3-(dimethylamino)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-

Compounds 3112 and 3113 were prepared using the intermediates described herein and by following the general procedure described for the synthesis of Compound 3117:

Compound 3112: (R)-1,1,1-trifluoropropan-2-yl ((2R,6S,7R,9S,13aS,14aR,16aS,Z)-2-((3-(dimethylamino)-6-methoxyisoquinolin-1-yl)oxy)-7,9-dimethyl-14a-(((1-methylcyclopropyl)sulfonyl)carbamoyl)-5,16-dioxo-1,2,3,5,6,7, 8,9,10,11,13a,14,14a,15,16,16a-hexadecahydrocyclopropa[e]pyrrolo[1,2-a][1,4]diazacyclopentadecin-6-yl)carbamate; MS: MS m/z 851.5 (M$^+$+1).

Compound 3113: (R)-1,1,1-trifluoropropan-2-yl ((2R,6S,7R,9R,13aS,14aR,16aS,Z)-2-((3-(dimethylamino)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.03 (s, 1H), 9.07 (br. s., 1H), 8.12 (d, J=8.2 Hz, 1H), 7.73 (d, J=8.9 Hz, 1H), 6.95 (d, J=2.4 Hz, 1H), 6.61 (dd, J=9.2, 2.4 Hz, 1H), 6.24 (s, 1H), 5.78 (br. s., 1H), 5.58-5.48 (m, 1H), 5.05-4.92 (m, 2H), 4.49-4.40 (m, 2H), 3.99 (dd, J=11.0, 3.7 Hz, 1H), 3.87-3.78 (m, 4H), 3.07 (s, 6H), 2.72-2.58 (m, 2H), 2.39-2.24 (m, 2H), 1.99-1.84 (m, 2H), 1.76-1.66 (m, 1H), 1.60 (d, J=5.5 Hz, 1H), 1.55-1.09 (m, 12H), 0.97-0.73 (m, 9H); MS: MS m/z 851.5 (M$^+$+1).

Preparation of Compound 3114 and Compound 3115 hexadecahydrocyclopropa[e]pyrrolo[1,2-a][1,4]diazacyclopentadecin-6-yl)carbamate; MS: MS m/z 871.6 (M$^+$+1).

Compound 3115: 1,1,1,3,3,3-hexadeutero-2-(trifluoromethyl)propan-2-yl ((2R,6S,7R,9R,13 aS,14aR,16aS,Z)-2-((3-(dimethylamino)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.05 (br. s., 1H), 9.11 (br. s., 1H), 7.86 (d, J=7.9 Hz, 1H), 7.76 (d, J=9.2 Hz, 1H), 6.95 (d, J=2.4 Hz, 1H), 6.65 (dd, J=9.0, 2.3 Hz, 1H), 6.23 (s, 1H), 5.77 (br. s., 1H), 5.53 (br. s., 1H), 5.05-4.90 (m, 1H), 4.53-4.39 (m, 2H), 3.95 (dd, J=11.3, 3.7 Hz, 1H), 3.83 (s, 3H), 3.76 (dd, J=10.7, 8.2 Hz, 1H), 3.07 (s, 6H), 2.73-2.58 (m, 2H), 2.40-2.25 (m, 2H), 1.97-1.81 (m, 2H), 1.76-1.10 (m, 11H), 0.97-0.84 (m, 8H), 0.76 (t, J=12.4 Hz, 1H); MS: MS m/z 871.6 (M$^+$+1).

Preparation of Compound 3118 and Compound 3119

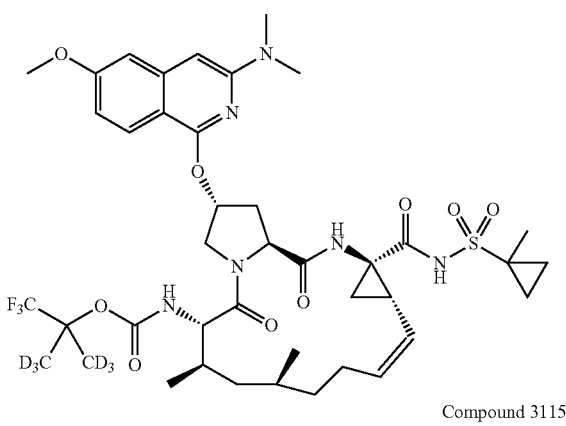

Compound 3114

Compound 3115

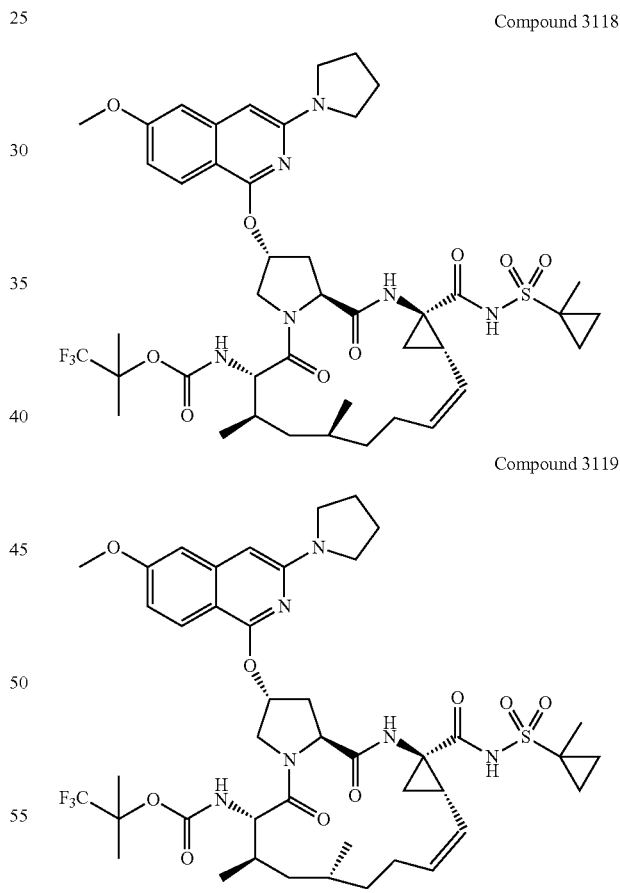

Compound 3118

Compound 3119

Compounds 3114 and 3115 were prepared using the intermediates described herein and by following the general procedure described for the synthesis of Compound 3117:

Compound 3114: 1,1,1,3,3,3-hexadeutero-2-(trifluoromethyl)propan-2-yl ((2R,6S,7R,9S,13aS,14aR,16aS,Z)-2-((3-(dimethylamino)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-

Compounds 3118 and 3119 were prepared using the intermediates described herein and by following the general procedure described for the synthesis of Compound 3117:

Compound 3118: 1,1,1-trifluoro-2-methylpropan-2-yl ((2R,6S,7R,9S,13aS,14aR,16aS,Z)-2-((6-methoxy-3-(pyrrolidin-1-yl)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a- hexadecahydrocyclopropa[e]pyrrolo[1,2-a][1,4]diazacyclopentadecin-6-yl)carbamate; MS: MS m/z 891.5 (M$^+$+1).

Compound 3119: 1,1,1-trifluoro-2-methylpropan-2-yl ((2R,6S,7R,9R,13aS,14aR,16aS,Z)-2-((6-methoxy-3-(pyrrolidin-1-yl)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.05 (s, 1H), 9.11 (br. s., 1H), 7.87 (d, J=8.2 Hz, 1H), 7.75 (d, J=9.2 Hz, 1H), 6.91 (d, J=2.1 Hz, 1H), 6.61 (dd, J=9.0, 2.3 Hz, 1H), 6.05 (s, 1H), 5.76 (br. s., 1H), 5.59-5.49 (m, 1H), 4.97 (t, J=9.9 Hz, 1H), 4.51-4.40 (m, 2H), 3.97 (dd, J=11.3, 3.7 Hz, 1H), 3.83 (s, 3H), 3.77 (dd, J=10.7, 8.2 Hz, 1H), 3.52-3.39 (m, 4H), 2.75-2.59 (m, 2H), 2.40-2.24 (m, 2H), 2.04-1.82 (m, 6H), 1.74-1.66 (m, 1H), 1.65-1.59 (m, 1H), 1.56-1.23 (m, 14H), 1.20-1.09 (m, 1H), 0.98-0.86 (m, 8H), 0.76 (t, J=12.2 Hz, 1H); MS: MS m/z 891.5 (M$^+$+1).

Preparation of Compound 3120 and Compound 3121

Compound 3121: tert-butyl ((2R,6S,7R,9R,13aS,14aR,16aS,Z)-14a-((cyclopropylsulfonyl)carbamoyl)-2-((3-(dimethylamino)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.21 (s, 1H), 8.94 (s, 1H), 7.79 (d, J=8.9 Hz, 1H), 7.22 (d, J=8.5 Hz, 1H), 6.94 (d, J=2.1 Hz, 1H), 6.62 (dd, J=8.9, 2.4 Hz, 1H), 6.23 (s, 1H), 5.75 (br. s., 1H), 5.58-5.48 (m, 1H), 5.05 (t, J=9.9 Hz, 1H), 4.49 (d, J=10.7 Hz, 1H), 4.43-4.36 (m, 1H), 3.94 (dd, J=11.3, 3.5 Hz, 1H), 3.83 (s, 3H), 3.77 (dd, J=10.5, 8.7 Hz, 1H), 3.07 (s, 6H), 2.96-2.88 (m, 1H), 2.73-2.58 (m, 2H), 2.36-2.23 (m, 2H), 1.98-1.79 (m, 2H), 1.71 (dd, J=12.5, 7.3 Hz, 1H), 1.64-1.50 (m, 2H), 1.49-0.85 (m, 22H), 0.73 (t, J=12.7 Hz, 1H); MS: MS m/z 797.5 (M$^+$+1).

Preparation of Compound 3122 and Compound 3123

Compound 3120

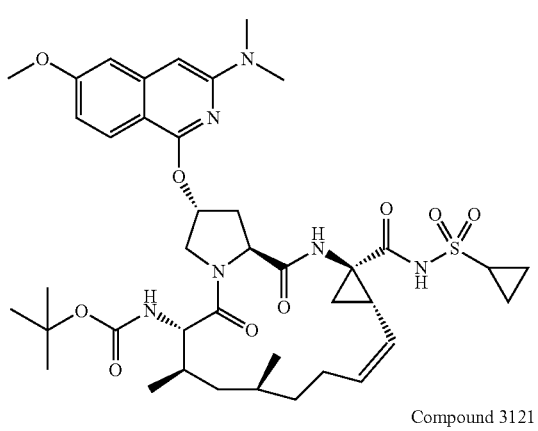

Compound 3122

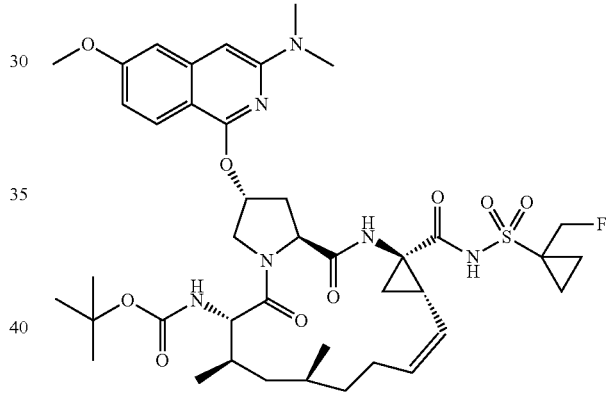

Compound 3121

Compound 3123

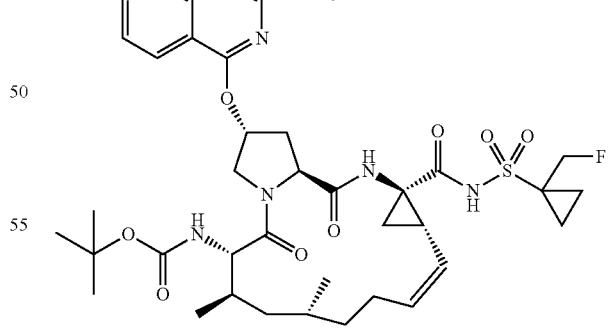

Compounds 3120 and 3121 were prepared using the intermediates described herein and by following the general procedure described for the synthesis of Compound 3117:

Compound 3120: tert-butyl ((2R,6S,7R,9S,13aS,14aR,16aS,Z)-14a-((cyclopropylsulfonyl)carbamoyl)-2-((3-(dimethylamino)-6-methoxyisoquinolin-1-yl)oxy)-7,9-dimethyl-5,16-dioxo-1,2,3,5,6,7,8,9,10,11,13a,14,14a,15,16,16a-

Compounds 3122 and 3123 were prepared using the intermediates described herein and by following the general procedure described for the synthesis of Compound 3117:

Compound 3122: tert-butyl ((2R,6S,7R,9S,13aS,14aR,16aS,Z)-2-((3-(dimethylamino)-6-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a, 14,14a,15,16,16a-hexadecahydrocyclopropa[e]pyrrolo[1,2-a][1,4]diazacyclopentadecin-6-yl)carbamate; MS: MS m/z 829.5 (M⁺+1).

Compound 3123: tert-butyl ((2R,6S,7R,9R,13aS,14aR,16aS,Z)-2-((3-(dimethylamino)-6-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; ¹H NMR (500 MHz, METHANOL-d₄) δ 7.81 (d, J=9.2 Hz, 1H), 6.85 (d, J=2.1 Hz, 1H), 6.68 (d, J=8.9 Hz, 1H), 6.61 (dd, J=9.0, 2.3 Hz, 1H), 6.19 (s, 1H), 5.82 (br. s., 1H), 5.52 (td, J=10.0, 6.0 Hz, 1H), 5.07 (br. s., 1H), 4.86-4.72 (m, 1H), 4.64-4.49 (m, 3H), 4.06 (dd, J=11.4, 3.8 Hz, 1H), 3.96-3.90 (m, 1H), 3.85 (s, 3H), 3.10 (s, 6H), 2.72 (dd, J=13.7, 7.3 Hz, 1H), 2.63 (q, J=9.3 Hz, 1H), 2.45-2.31 (m, 2H), 1.97-1.08 (m, 21H), 1.02-0.95 (m, 6H), 0.85-0.76 (m, 1H); MS: MS m/z 829.5 (M⁺+1).

Preparation of Compound 3124 and Compound 3125

Compound 3126: 3,3-difluoro-2-methylbutan-2-yl ((2R,6S,7R,9R,13aS,14aR,16aS,Z)-2-((3-(dimethylamino)-6-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; ¹H NMR (500 MHz, DMSO-d₆) δ 11.28 (s, 1H), 9.00 (s, 1H), 7.76 (d, J=8.9 Hz, 1H), 7.66 (d, J=8.2 Hz, 1H), 6.95 (d, J=2.4 Hz, 1H), 6.64 (dd, J=9.0, 2.3 Hz, 1H), 6.24 (s, 1H), 5.77 (br. s., 1H), 5.57-5.45 (m, 1H), 5.01 (t, J=9.9 Hz, 1H), 4.88-4.72 (m, 1H), 4.62-4.47 (m, 1H), 4.46-4.40 (m, 2H), 3.96 (dd, J=11.1, 3.5 Hz, 1H), 3.83 (s, 3H), 3.77 (dd, J=10.4, 8.5 Hz, 1H), 3.07 (s, 6H), 2.73-2.58 (m, 2H), 2.36-2.26 (m, 2H), 1.98-1.79 (m, 2H), 1.75-1.08 (m, 19H), 0.94 (d, J=6.7 Hz, 3H), 0.91 (d, J=6.4 Hz, 3H), 0.76 (t, J=12.1 Hz, 1H); MS: MS m/z 879.5 (M⁺+1).

Preparation of Compound 3126 and Compound 3127

Compound 3124

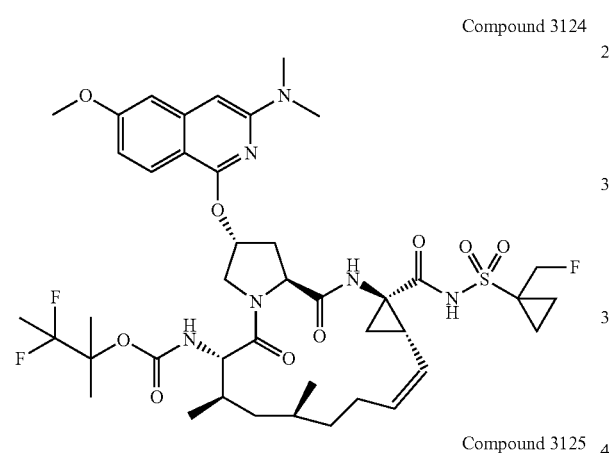

Compound 3125

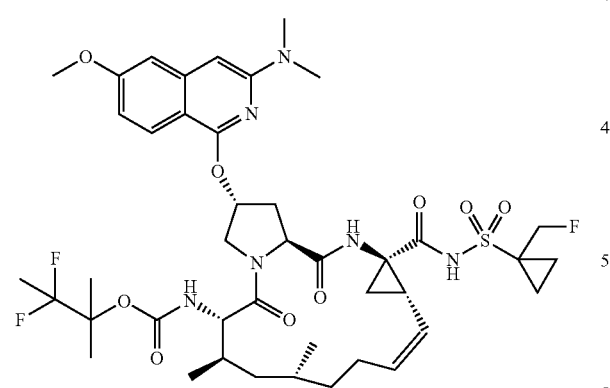

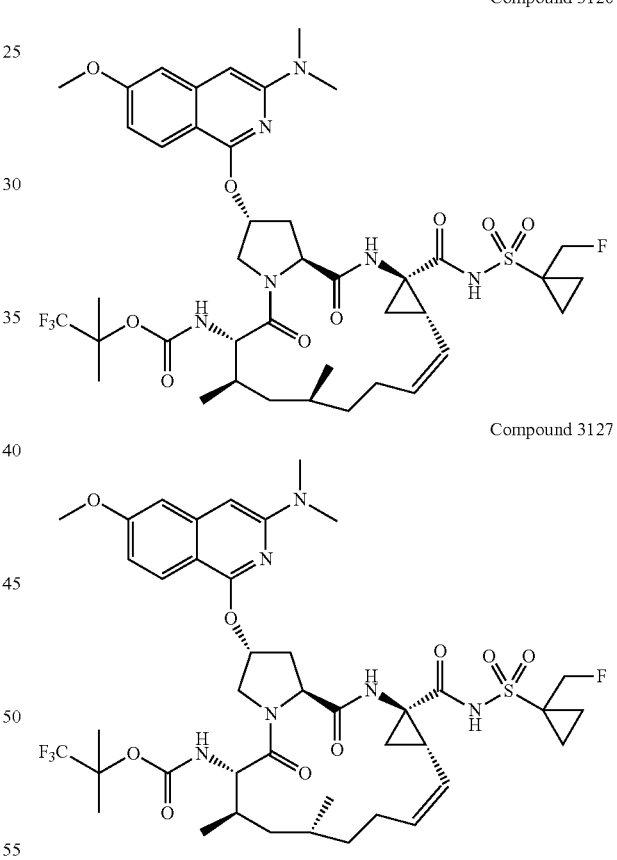

Compound 3126

Compound 3127

Compounds 3125 and 3126 were prepared using the intermediates described herein and by following the general procedure described for the synthesis of Compound 3117:

Compound 3125: 3,3-difluoro-2-methylbutan-2-yl ((2R,6S,7R,9S,13aS,14aR,16aS,Z)-2-((3-(dimethylamino)-6-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 879.5 (M⁺+1).

Compounds 3126 and 3127 were prepared using the intermediates described herein and by following the general procedure described for the synthesis of Compound 3117:

Compound 3126: 1,1,1-trifluoro-2-methylpropan-2-yl ((2R,6S,7R,9S,13aS,14aR,16aS,Z)-2-((3-(dimethylamino)-6-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 883.4 (M⁺+1).

Compound 3127: 1,1,1-trifluoro-2-methylpropan-2-yl ((2R,6S,7R,9R,13 aS,14aR,16aS,Z)-2-((3-(dimethylamino)-6-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, METHANOL-d$_4$) δ 7.81 (d, J=8.9 Hz, 1H), 6.87 (d, J=2.1 Hz, 1H), 6.64 (dd, J=9.0, 2.3 Hz, 1H), 6.21 (s, 1H), 5.83 (br. s., 1H), 5.57 (td, J=10.1, 5.8 Hz, 1H), 5.07 (t, J=9.5 Hz, 1H), 4.87-4.73 (m, 1H), 4.67 (d, J=11.6 Hz, 1H), 4.64-4.51 (m, 2H), 4.04 (dd, J=11.3, 3.4 Hz, 1H), 3.90-3.84 (m, 4H), 3.11 (s, 6H), 2.72 (dd, J=13.7, 7.0 Hz, 1H), 2.65 (q, J=9.1 Hz, 1H), 2.47-2.32 (m, 2H), 2.02-1.38 (m, 12H), 1.32-1.11 (m, 6H), 1.00 (d, J=7.0 Hz, 3H), 0.98 (d, J=6.4 Hz, 3H), 0.86-0.76 (m, 1H); MS: MS m/z 883.7 (M$^+$+1).

Preparation of Compound 3128

Compound 3128

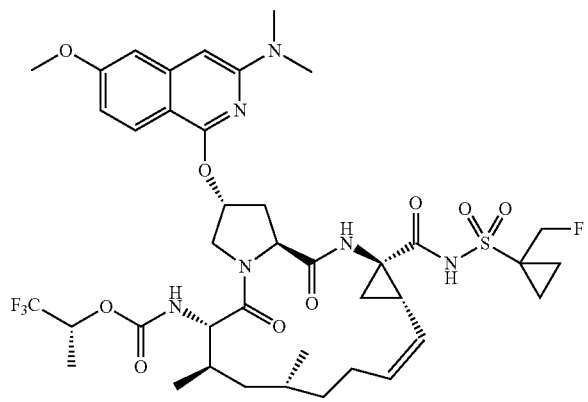

Compound 3128 was prepared using the intermediates described herein and by following the general procedure described for the synthesis of Compound 3117:

Compound 3128: (R)-1,1,1-trifluoropropan-2-yl ((2R,6S,7R,9R,13aS,14aR,16aS,Z)-2-((3-(dimethylamino)-6-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, METHANOL-d$_4$) δ 7.79 (d, J=8.9 Hz, 1H), 6.87 (d, J=2.4 Hz, 1H), 6.61 (dd, J=9.2, 2.4 Hz, 1H), 6.21 (s, 1H), 5.85 (br. s., 1H), 5.57 (td, J=10.1, 5.6 Hz, 1H), 5.03 (t, J=9.9 Hz, 1H), 4.86-4.74 (m, 2H), 4.70-4.48 (m, 3H), 4.04 (dd, J=11.3, 3.7 Hz, 1H), 3.93 (d, J=11.0 Hz, 1H), 3.85 (s, 3H), 3.10 (s, 6H), 2.73 (dd, J=13.9, 7.2 Hz, 1H), 2.65 (q, J=9.2 Hz, 1H), 2.47-2.32 (m, 2H), 2.01-1.85 (m, 2H), 1.79 (dd, J=13.3, 5.6 Hz, 1H), 1.73-1.37 (m, 6H), 1.30-1.12 (m, 6H), 1.06-0.94 (m, 6H), 0.91-0.75 (m, 1H); MS: MS m/z 869.5 (M$^+$+1).

Preparation of Compound 3129 and Compound 3130

Compound 3129

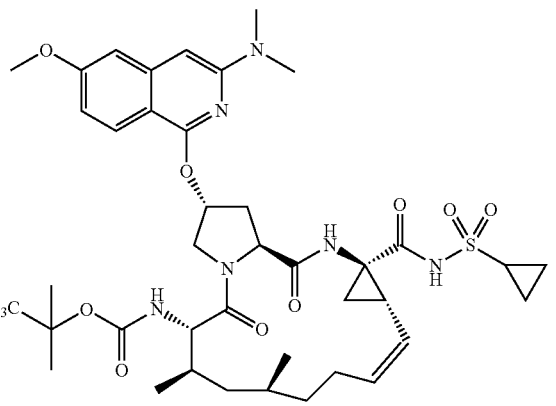

Compound 3130

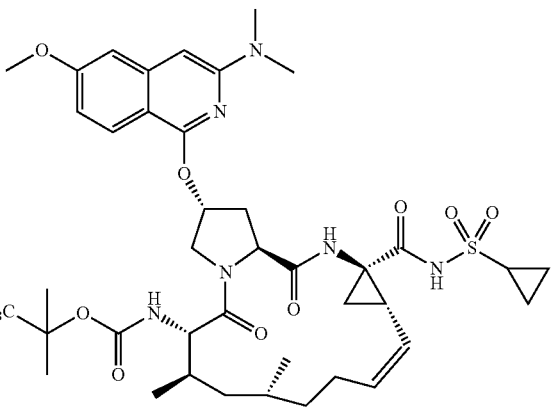

Compounds 3129 and 3130 were prepared using the intermediates described herein and by following the general procedure described for the synthesis of Compound 3117:

Compound 3129: 1,1,1-trifluoro-2-methylpropan-2-yl ((2R,6S,7R,9S,13aS,14aR,16aS,Z)-14a-((cyclopropylsulfonyl)carbamoyl)-2-((3-(dimethylamino)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 851.1 (M$^+$+1).

Compound 3130: 1,1,1-trifluoro-2-methylpropan-2-yl ((2R,6S,7R,9R,13aS,14aR,16aS,Z)-14a-((cyclopropylsulfonyl)carbamoyl)-2-((3-(dimethylamino)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.19 (br. s., 1H), 8.96 (br. s., 1H), 7.85 (d, J=8.2 Hz, 1H), 7.76 (d, J=8.9 Hz, 1H), 6.95 (d, J=2.4 Hz, 1H), 6.65 (dd, J=9.0, 2.3 Hz, 1H), 6.23 (s, 1H), 5.75 (br. s., 1H), 5.62-5.44 (m, 1H), 5.21-4.98 (m, 1H), 4.43 (d, J=8.2 Hz, 2H), 3.94 (dd, J=11.1, 3.5 Hz, 1H), 3.83 (s, 3H), 3.76 (dd, J=10.7, 8.2 Hz, 1H), 3.07 (s, 6H), 2.92-2.82 (m, 1H), 2.70-2.56 (m, 2H), 2.36-2.23 (m, 2H), 1.97-1.80 (m, 2H), 1.73 (br. s., 1H), 1.63-0.84 (m, 21H), 0.73 (t, J=11.7 Hz, 1H); MS: MS m/z 851.1 (M$^+$+1).

Preparation of Compound 3131 and Compound 3132

Preparation of Compound 3133 and Compound 3134

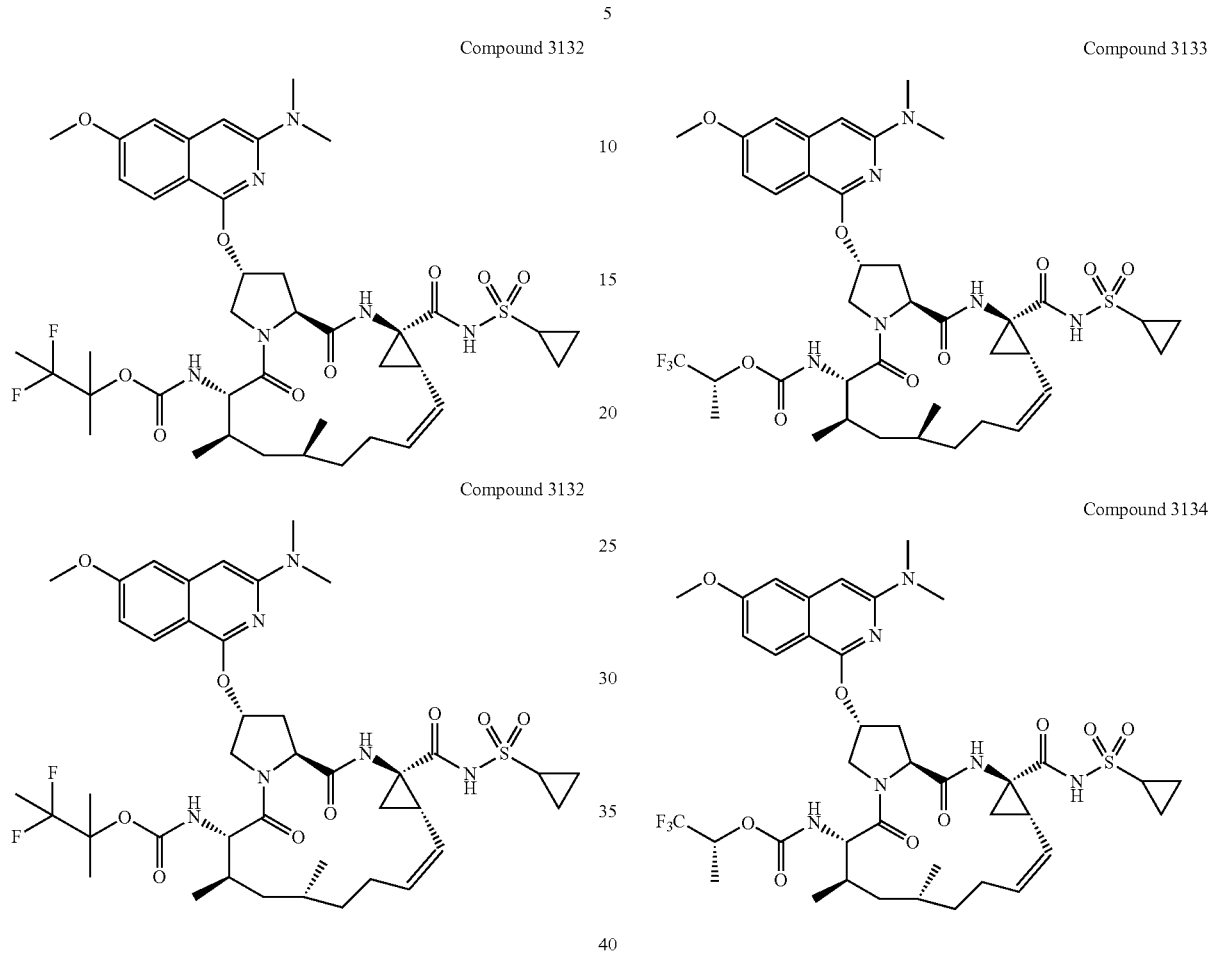

Compound 3132

Compound 3133

Compound 3132

Compound 3134

Compounds 3131 and 3132 were prepared using the intermediates described herein and by following the general procedure described for the synthesis of Compound 3117:

Compound 3131: 3,3-difluoro-2-methylbutan-2-yl ((2R,6S,7R,9S,13aS,14aR,16aS,Z)-14a-((cyclopropylsulfonyl)carbamoyl)-2-((3-(dimethylamino)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 847.1 (M$^+$+1).

Compound 3132: 3,3-difluoro-2-methylbutan-2-yl ((2R,6S,7R,9R,13aS,14aR,16aS,Z)-14a-((cyclopropylsulfonyl)carbamoyl)-2-((3-(dimethylamino)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.21 (br. s., 1H), 8.95 (br. s., 1H), 7.76 (d, J=9.2 Hz, 1H), 7.64 (d, J=7.9 Hz, 1H), 6.95 (d, J=2.4 Hz, 1H), 6.64 (dd, J=9.2, 2.4 Hz, 1H), 6.23 (s, 1H), 5.75 (br. s., 1H), 5.61-5.46 (m, 1H), 5.19-4.99 (m, 1H), 4.52-4.34 (m, 2H), 3.95 (dd, J=11.0, 3.4 Hz, 1H), 3.83 (s, 3H), 3.77 (dd, J=10.5, 8.7 Hz, 1H), 3.07 (s, 6H), 2.96-2.84 (m, 1H), 2.75-2.57 (m, 2H), 2.31 (ddd, J=13.4, 9.8, 4.0 Hz, 2H), 1.99-0.85 (m, 27H), 0.75 (t, J=12.4 Hz, 1H); MS: MS m/z 847.1 (M$^+$+1).

Compounds 3133 and 3134 were prepared using the intermediates described herein and by following the general procedure described for the synthesis of Compound 3117:

Compound 3133: (R)-1,1,1-trifluoropropan-2-yl ((2R,6S,7R,9S,13aS,14aR,16aS,Z)-14a-((cyclopropylsulfonyl)carbamoyl)-2-((3-(dimethylamino)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 837.4 (M$^+$+1).

Compound 3134: (R)-1,1,1-trifluoropropan-2-yl ((2R,6S,7R,9R,13aS,14aR,16aS,Z)-14a-((cyclopropylsulfonyl)carbamoyl)-2-((3-(dimethylamino)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.19 (s, 1H), 8.94 (br. s., 1H), 8.12 (d, J=7.9 Hz, 1H), 7.73 (d, J=9.2 Hz, 1H), 6.95 (d, J=2.4 Hz, 1H), 6.61 (dd, J=9.0, 2.3 Hz, 1H), 6.24 (s, 1H), 5.77 (br. s., 1H), 5.59-5.48 (m, 1H), 5.06 (t, J=9.6 Hz, 1H), 5.00 (dt, J=13.6, 6.9 Hz, 1H), 4.47-4.37 (m, 2H), 3.97 (dd, J=11.0, 3.4 Hz, 1H), 3.87-3.79 (m, 4H), 3.07 (s, 6H), 2.92 (d, J=8.2 Hz, 1H), 2.71-2.59 (m, 2H), 2.35-2.25 (m, 2H), 1.99-1.83 (m, 2H), 1.78-1.67 (m, 1H), 1.64-1.51 (m, 2H), 1.50-0.81 (m, 16H), 0.77 (t, J=11.9 Hz, 1H); MS: MS m/z 837.7 (M$^+$+1).

Preparation of Compound 3135 and Compound 3136

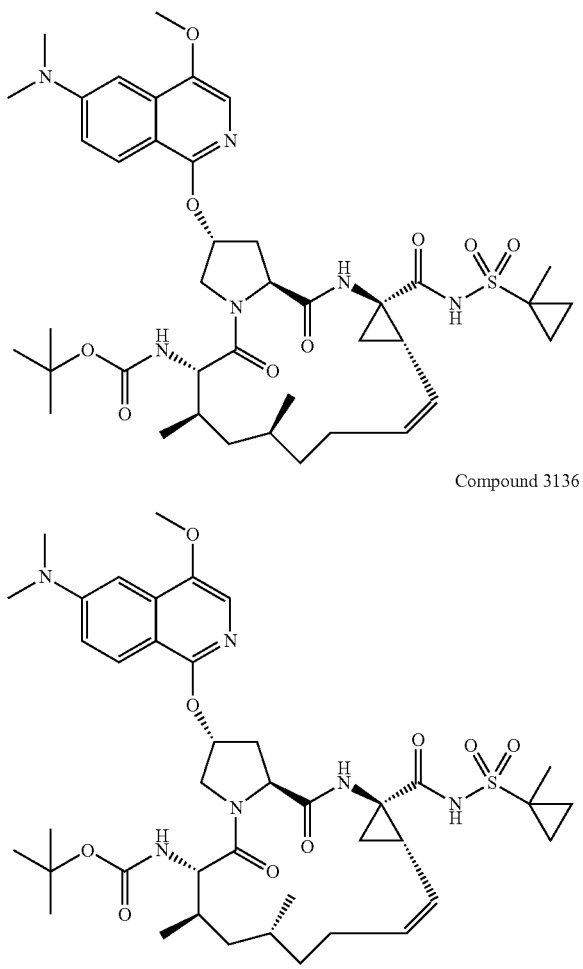

Compound 3135

Compound 3136

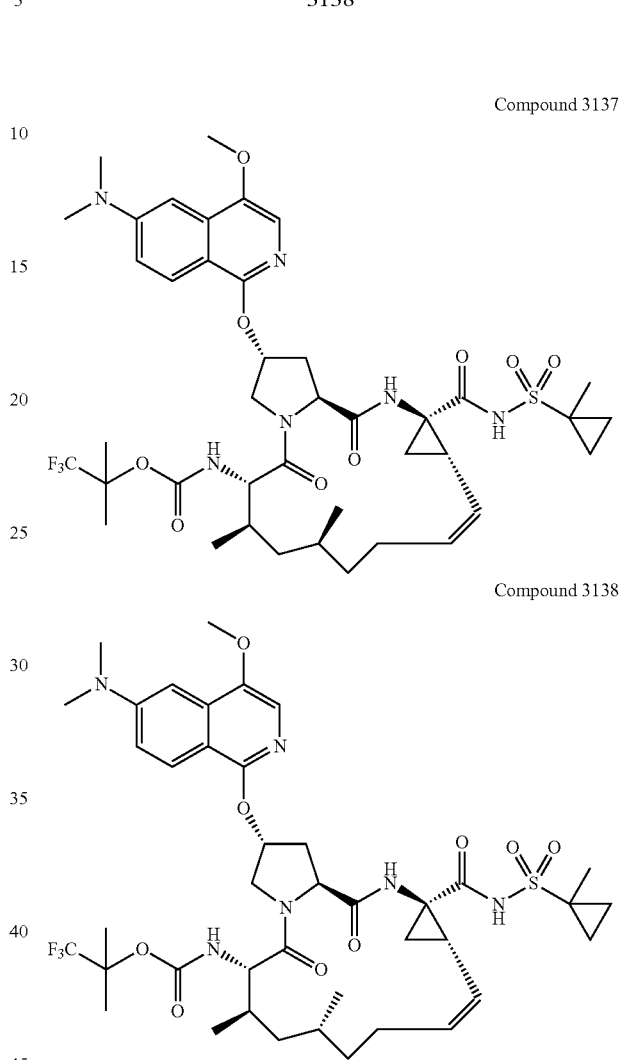

Compound 3137

Compound 3138

Compounds 3135 and 3136 were prepared using the intermediates described herein and by following the general procedure described for the synthesis of Compound 3117:

Compound 3135: tert-butyl ((2R,6S,7R,9S,13aS,14aR,16aS,Z)-2-((6-(dimethylamino)-4-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 811.6 (M$^+$+1).

Compound 3136: tert-butyl ((2R,6S,7R,9R,13aS,14aR,16aS,Z)-2-((6-(dimethylamino)-4-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.05 (br. s., 1H), 9.09 (br. s., 1H), 7.91 (d, J=9.2 Hz, 1H), 7.44 (s, 1H), 7.18 (d, J=8.2 Hz, 1H), 7.08 (dd, J=9.2, 2.4 Hz, 1H), 6.92 (d, J=2.4 Hz, 1H), 5.73 (br. s., 1H), 5.59-5.48 (m, 1H), 5.05-4.92 (m, 1H), 4.56-4.38 (m, 2H), 3.97-3.87 (m, 4H), 3.79-3.70 (m, 1H), 3.06 (s, 6H), 2.70 (br. s., 2H), 2.43-2.19 (m, 2H), 1.97-1.78 (m, 2H), 1.70 (br. s., 1H), 1.60 (br. s., 1H), 1.54-1.06 (m, 18H), 0.98-0.84 (m, 8H), 0.73 (t, J=11.7 Hz, 1H); MS: MS m/z 811.6 (M$^+$+1).

Preparation of Compound 3137 and Compound 3138

Compounds 3137 and 3138 were prepared using the intermediates described herein and by following the general procedure described for the synthesis of Compound 3117:

Compound 3137: 1,1,1-trifluoro-2-methylpropan-2-yl ((2R,6S,7R,9S,13aS,14aR,16aS,Z)-2-((6-(dimethylamino)-4-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 865.6 (M$^+$+1).

Compound 3138: 1,1,1-trifluoro-2-methylpropan-2-yl ((2R,6S,7R,9R,13aS,14aR,16aS,Z)-2-((6-(dimethylamino)-4-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.05 (br. s., 1H), 9.14 (br. s., 1H), 7.88 (d, J=9.2 Hz, 1H), 7.83 (d, J=7.9 Hz, 1H), 7.45 (s, 1H), 7.11 (dd, J=9.3, 2.6 Hz, 1H), 6.92 (d, J=2.4 Hz, 1H), 5.74 (br. s., 1H), 5.58-5.47 (m, 1H), 5.03-4.93 (m, 1H), 4.54-4.40 (m, 2H), 3.98-3.86 (m, 4H), 3.72 (dd, J=10.7, 8.2 Hz, 1H), 3.05 (s, 6H), 2.73-2.54 (m, 2H), 2.42-2.21 (m, 2H), 1.95-1.81 (m, 2H), 1.76-1.65 (m, 1H), 1.64-1.57 (m, 1H), 1.55-1.09 (m, 15H), 0.98-0.84 (m, 8H), 0.75 (t, J=12.2 Hz, 1H); MS: MS m/z 865.6 (M$^+$+1).

Preparation of Compound 3139 and Compound 3140

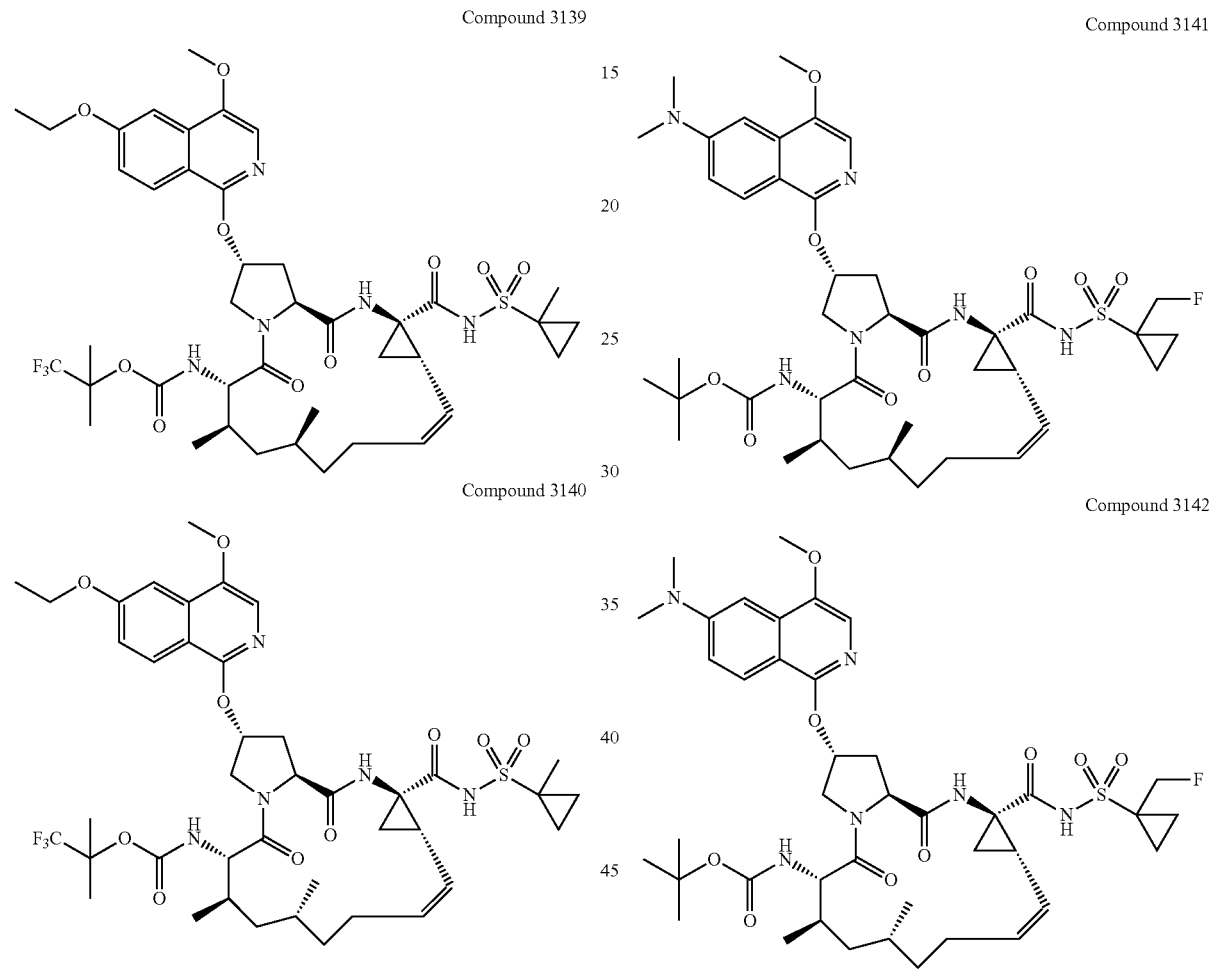

Compound 3139

Compound 3140

Compound 3141

Compound 3142

Compounds 3139 and 3140 were prepared using the intermediates described herein and by following the general procedure described for the synthesis of Compound 3117:

Compound 3139: MS: 1,1,1-trifluoro-2-methylpropan-2-yl ((2R,6S,7R,9S,13aS,14aR,16aS,Z)-2-((6-ethoxy-4-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS m/z 866.5 (M$^+$+1).

Compound 3140: 1,1,1-trifluoro-2-methylpropan-2-yl ((2R,6S,7R,9R,13aS,14aR,16aS,Z)-2-((6-ethoxy-4-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.04 (br. s., 1H), 9.12 (br. s., 1H), 7.98 (d, J=8.9 Hz, 1H), 7.82 (d, J=7.6 Hz, 1H), 7.60 (s, 1H), 7.32 (d, J=2.4 Hz, 1H), 7.18 (dd, J=9.2, 2.4 Hz, 1H), 5.74 (br. s., 1H), 5.57-5.45 (m, 1H), 5.10-4.93 (m, 1H), 4.55-4.40 (m, 2H), 4.19 (q, J=7.0 Hz, 2H), 3.96 (s, 3H), 3.93-3.87 (m, 1H), 3.71 (dd, J=10.5, 8.1 Hz, 1H), 2.70-2.54 (m, 2H), 2.37-2.23 (m, 2H), 1.94-1.08 (m, 22H), 0.98-0.84 (m, 8H), 0.73 (br. s., 1H); MS: MS m/z 866.5 (M$^+$+1).

Preparation of Compound 3141 and Compound 3142

Compounds 3141 and 3142 were prepared using the intermediates described herein and by following the general procedure described for the synthesis of Compound 3117:

Compound 3141: tert-butyl ((2R,6S,7R,9S,13aS,14aR,16aS,Z)-2-((6-(dimethylamino)-4-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 829.6 (M$^+$+1).

Compound 3142: tert-butyl ((2R,6S,7R,9R,13aS,14aR,16aS,Z)-2-((6-(dimethylamino)-4-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.28 (s, 1H), 9.01 (br. s., 1H), 7.91 (d, J=9.2 Hz, 1H), 7.45 (s, 1H), 7.19 (d, J=7.9 Hz, 1H), 7.08 (dd, J=9.0, 2.3 Hz, 1H), 6.92 (d, J=2.4 Hz, 1H), 5.71 (br. s., 1H), 5.59-5.45 (m, 1H), 4.99 (t, J=9.8 Hz, 1H), 4.90-4.72 (m, 1H), 4.64-4.36 (m, 3H), 3.96-3.86 (m, 4H), 3.80-3.71 (m, 1H), 3.06 (s, 6H), 2.73-2.54 (m, 2H), 2.37-2.20 (m, 2H), 1.97-1.77 (m, 2H), 1.74-1.65 (m, 1H), 1.61-1.04 (m, 18H), 0.94 (d, J=7.0 Hz, 3H), 0.89 (d, J=6.4 Hz, 3H), 0.73 (t, J=12.4 Hz, 1H); MS: MS m/z 829.6 (M$^+$+1).

Preparation of Compound 3143 and Compound 3144

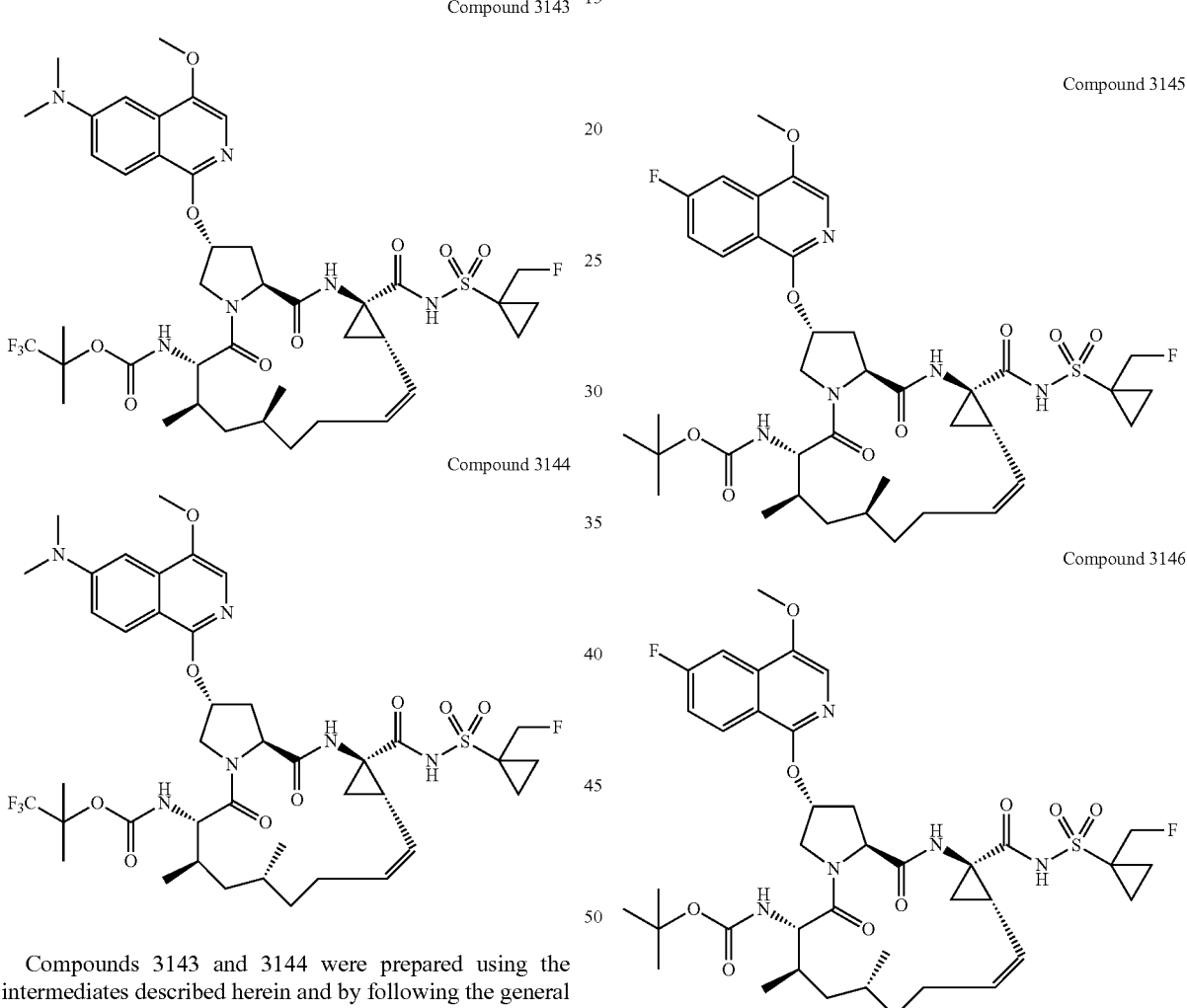

Compounds 3143 and 3144 were prepared using the intermediates described herein and by following the general procedure described for the synthesis of Compound 3117:

Compound 3143: 1,1,1-trifluoro-2-methylpropan-2-yl ((2R,6S,7R,9S,13aS,14aR,16aS,Z)-2-((6-(dimethylamino)-4-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 883.6 (M$^+$+1).

Compound 3144: 1,1,1-trifluoro-2-methylpropan-2-yl ((2R,6S,7R,9R,13aS,14aR,16aS,Z)-2-((6-(dimethylamino)-4-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.28 (s, 1H), 9.05 (s, 1H), 7.88 (d, J=9.2 Hz, 1H), 7.83 (d, J=7.9 Hz, 1H), 7.46 (s, 1H), 7.11 (dd, J=9.2, 2.4 Hz, 1H), 6.92 (d, J=2.4 Hz, 1H), 5.73 (br. s., 1H), 5.58-5.46 (m, 1H), 4.99 (t, J=9.9 Hz, 1H), 4.90-4.73 (m, 1H), 4.63-4.41 (m, 3H), 3.96-3.86 (m, 4H), 3.73 (dd, J=10.5, 8.4 Hz, 1H), 3.06 (s, 6H), 2.66 (q, J=9.1 Hz, 1H), 2.59 (dd, J=13.6, 6.6 Hz, 1H), 2.40-2.21 (m, 2H), 1.94-1.79 (m, 2H), 1.70 (dd, J=12.8, 6.4 Hz, 1H), 1.60-1.08 (m, 15H), 0.94 (d, J=7.0 Hz, 3H), 0.89 (d, J=6.4 Hz, 3H), 0.74 (t, J=12.4 Hz, 1H); MS: MS m/z 883.6 (M$^+$+1).

Preparation of Compound 3145 and Compound 3146

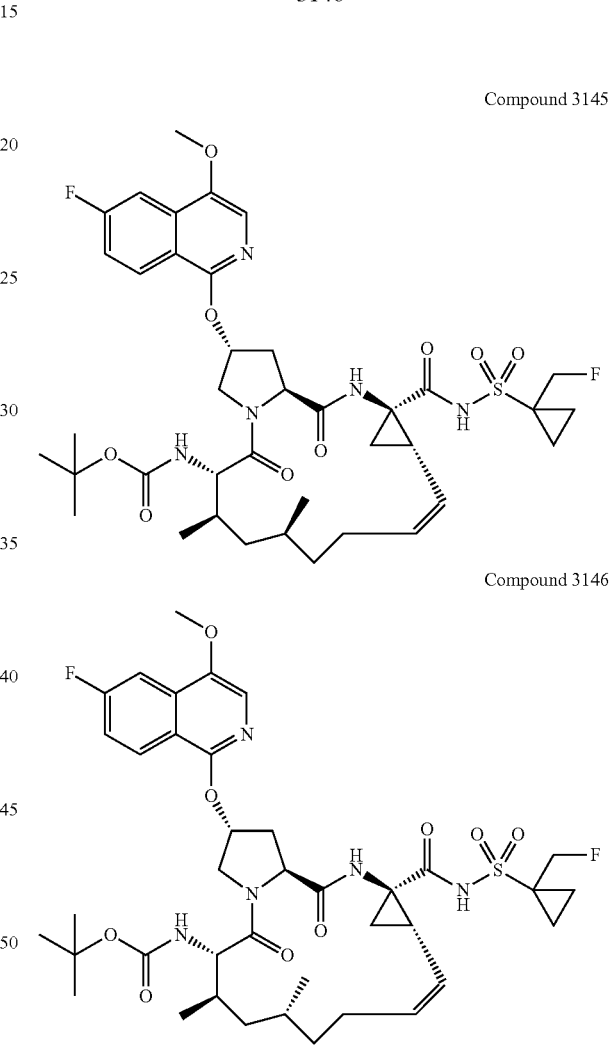

Compounds 3145 and 3146 were prepared using the intermediates described herein and by following the general procedure described for the synthesis of Compound 3117:

Compound 3145: tert-butyl ((2R,6S,7R,9S,13aS,14aR,16aS,Z)-2-((6-fluoro-4-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 804.4 (M$^+$+1).

Compound 3146: tert-butyl ((2R,6S,7R,9R,13aS,14aR,16aS,Z)-2-((6-fluoro-4-methoxyisoquinolin-1-yl)oxy)-14a-

(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-$d_6$) δ 11.30 (br. s., 1H), 9.05 (br. s., 1H), 8.17 (dd, J=9.2, 5.8 Hz, 1H), 7.74-7.66 (m, 2H), 7.48 (td, J=8.9, 2.4 Hz, 1H), 7.16 (br. s., 1H), 5.76 (br. s., 1H), 5.59-5.46 (m, 1H), 5.07-4.92 (m, 1H), 4.91-4.71 (m, 1H), 4.68-4.40 (m, 3H), 3.97 (s, 3H), 3.89 (dd, J=11.7, 3.2 Hz, 1H), 3.68 (dd, J=10.5, 8.7 Hz, 1H), 2.73-2.56 (m, 2H), 2.36-2.22 (m, 2H), 1.95-1.64 (m, 3H), 1.62-1.01 (m, 18H), 0.93 (d, J=6.7 Hz, 3H), 0.87 (d, J=6.4 Hz, 3H), 0.77-0.65 (m, 1H); MS: MS m/z 804.4 (M$^+$+1).

Preparation of Compound 3147 and Compound 3148

Compound 3148: tert-butyl ((2R,6S,7R,9R,13aS,14aR,16aS,Z)-14a-((cyclopropylsulfonyl)carbamoyl)-2-((5-fluoro-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-$d_6$) δ 11.21 (br. s., 1H), 9.01 (br. s., 1H), 8.03 (d, J=6.1 Hz, 1H), 7.99-7.92 (m, 1H), 7.49 (t, J=8.7 Hz, 1H), 7.38 (d, J=5.8 Hz, 1H), 7.15 (d, J=7.9 Hz, 1H), 5.83 (br. s., 1H), 5.59-5.45 (m, 1H), 5.16-5.00 (m, 1H), 4.61 (d, J=11.0 Hz, 1H), 4.48 (dd, J=9.8, 7.3 Hz, 1H), 4.01 (s, 3H), 3.89 (dd, J=11.3, 3.4 Hz, 1H), 3.68 (dd, J=10.5, 8.4 Hz, 1H), 2.96-2.86 (m, 1H), 2.73-2.57 (m, 2H), 2.37-2.23 (m, 2H), 1.91 (d, J=9.8 Hz, 1H), 1.85-1.75 (m, 1H), 1.69 (br. s., 1H), 1.64-1.50 (m, 2H), 1.47-0.80 (m, 22H), 0.71 (t, J=12.4 Hz, 1H); MS: MS m/z 772.5 (M$^+$+1).

Preparation of Compound 3149 and Compound 3150

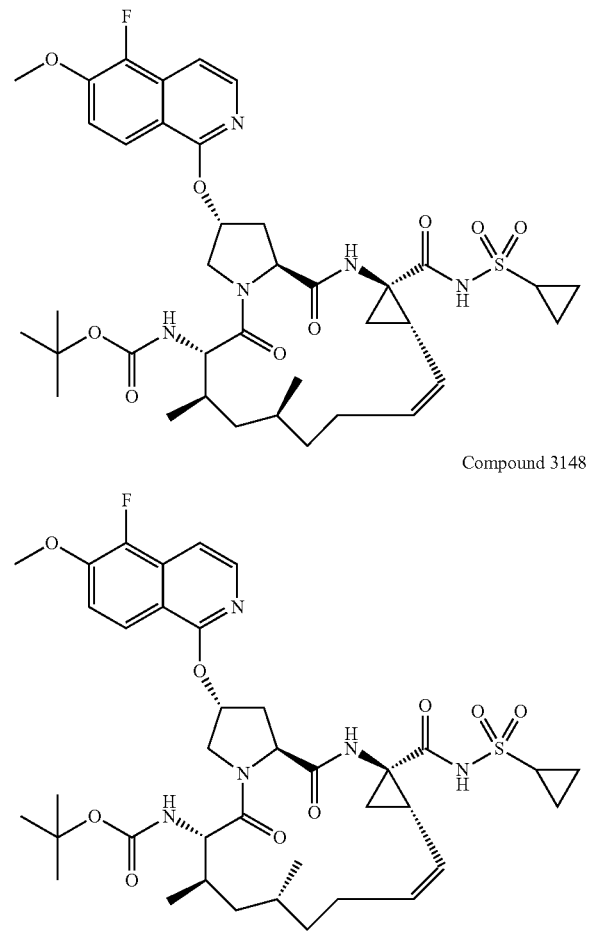

Compound 3147

Compound 3148

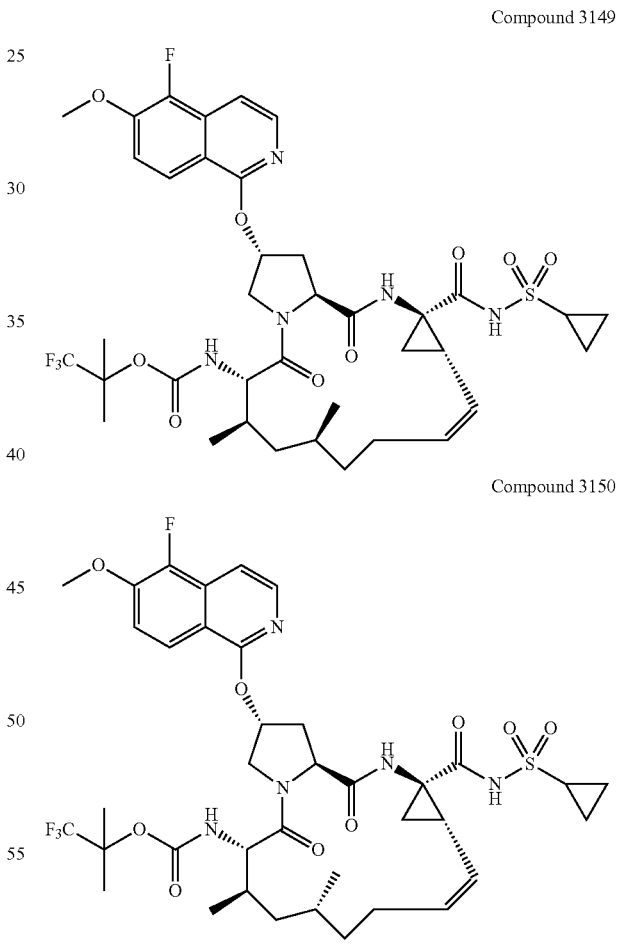

Compound 3149

Compound 3150

Compounds 3147 and 3148 were prepared using the intermediates described herein and by following the general procedure described for the synthesis of Compound 3117:

Compound 3147: tert-butyl ((2R,6S,7R,9S,13aS,14aR,16aS,Z)-14a-((cyclopropylsulfonyl)carbamoyl)-2-((5-fluoro-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 772.5 (M$^+$+1).

Compounds 3149 and 3150 were prepared using the intermediates described herein and by following the general procedure described for the synthesis of Compound 3117:

Compound 3149: MS: 1,1,1-trifluoro-2-methylpropan-2-yl ((2R,6S,7R,9S,13aS,14aR,16aS,Z)-14a-((cyclopropylsulfonyl)carbamoyl)-2-((5-fluoro-6-methoxyisoquinolin-1-yl)oxy)-7,9-dimethyl-5,16-dioxo-1,2,3,5,6,7,8,9,10,11,13a,14, 14a,15,16,16a-hexadecahydrocyclopropa[e]pyrrolo[1,2-a][1,4]diazacyclopentadecin-6-yl)carbamate; MS m/z 826.5 (M⁺+1).

Compound 3150: 1,1,1-trifluoro-2-methylpropan-2-yl ((2R,6S,7R,9R,13aS,14aR,16aS,Z)-14a-((cyclopropylsulfonyl)carbamoyl)-2-((5-fluoro-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; ¹H NMR (500 MHz, METHANOL-d₄) δ 8.05-7.96 (m, 2H), 7.45-7.36 (m, 2H), 5.88 (t, J=3.4 Hz, 1H), 5.59 (td, J=10.2, 5.8 Hz, 1H), 5.14 (br. s., 1H), 4.74 (d, J=11.0 Hz, 1H), 4.68-4.58 (m, 2H), 4.03 (s, 3H), 4.01 (dd, J=11.7, 3.2 Hz, 1H), 3.79 (d, J=10.7 Hz, 1H), 2.96-2.89 (m, 1H), 2.74 (dd, J=14.0, 7.0 Hz, 1H), 2.70-2.60 (m, 1H), 2.50-2.33 (m, 2H), 2.01-1.91 (m, 1H), 1.90-1.73 (m, 3H), 1.58 (dd, J=9.6, 5.3 Hz, 1H), 1.53-1.41 (m, 2H), 1.37-1.17 (m, 5H), 1.13-1.04 (m, 2H), 1.04-0.91 (m, 9H), 0.85-0.77 (m, 1H); MS: MS m/z 826.5 (M⁺+1).

Preparation of Compound 3151 and Compound 3152

Compound 3152: (1R,3r,5S)-bicyclo[3.1.0]hexan-3-yl ((2R,6S,7R,9R,13aS,14aR,16aS,Z)-14a-((cyclopropylsulfonyl)carbamoyl)-2-((5-fluoro-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; ¹H NMR (500 MHz, METHANOL-d₄) δ 8.04-7.95 (m, 2H), 7.48-7.37 (m, 2H), 5.90 (br. s., 1H), 5.56 (td, J=10.1, 6.1 Hz, 1H), 5.18 (br. s., 1H), 4.66-4.58 (m, 3H), 4.51 (t, J=6.9 Hz, 1H), 4.06-3.99 (m, 4H), 3.88 (d, J=11.0 Hz, 1H), 2.94-2.88 (m, 1H), 2.73 (dd, J=13.7, 7.0 Hz, 1H), 2.68-2.58 (m, 1H), 2.44 (ddd, J=13.7, 10.1, 4.3 Hz, 1H), 2.40-2.31 (m, 1H), 2.01-1.92 (m, 2H), 1.86 (d, J=6.1 Hz, 1H), 1.78-1.69 (m, 3H), 1.64 (d, J=14.6 Hz, 1H), 1.58 (dd, J=9.5, 5.2 Hz, 1H), 1.52-0.90 (m, 15H), 0.84-0.75 (m, 1H), 0.38-0.29 (m, 1H), 0.26 (q, J=4.2 Hz, 1H); MS: MS m/z 796.5 (M⁺+1).

Preparation of Compound 3153 and Compound 3154

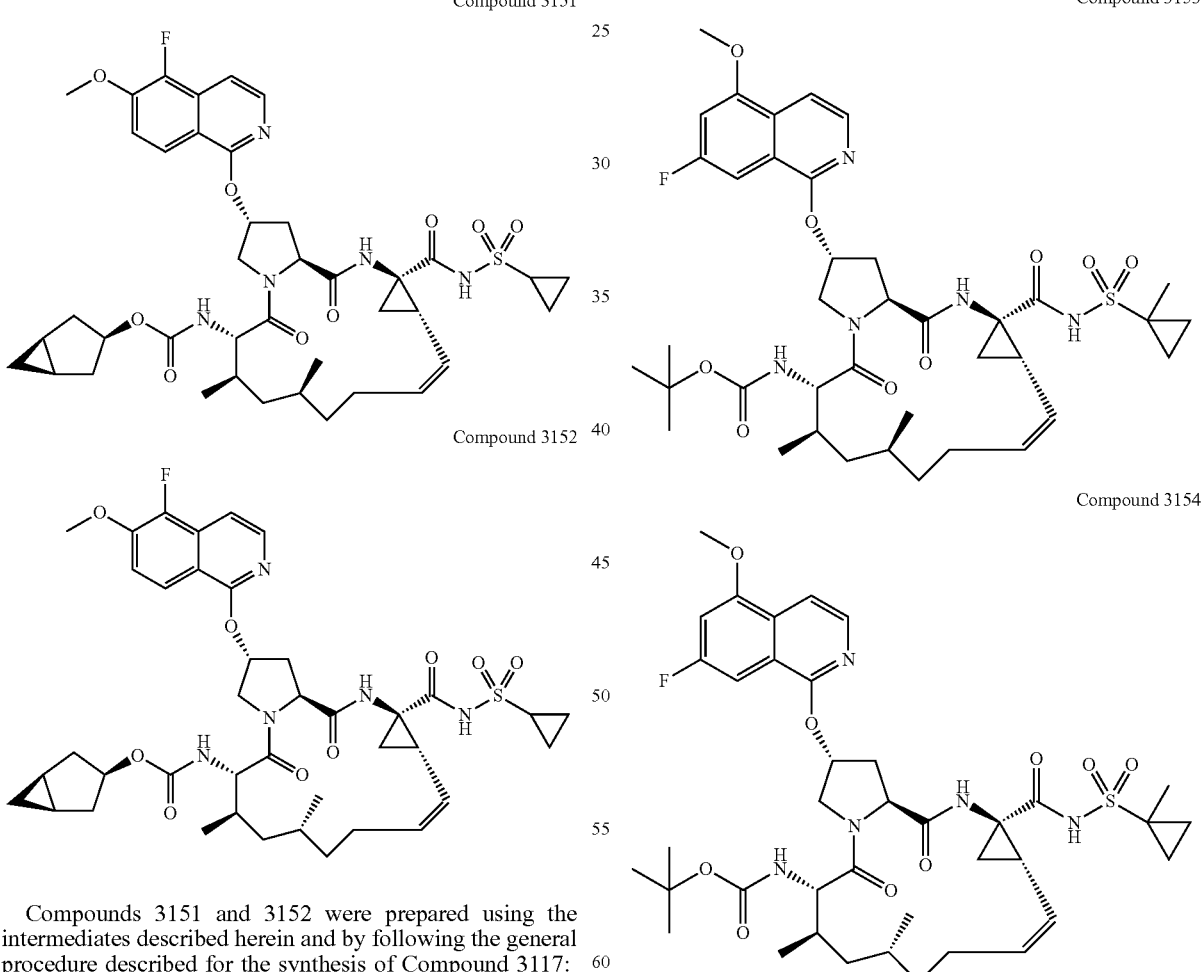

Compound 3151

Compound 3152

Compound 3153

Compound 3154

Compounds 3151 and 3152 were prepared using the intermediates described herein and by following the general procedure described for the synthesis of Compound 3117:

Compound 3151: (1R,3r,5S)-bicyclo[3.1.0]hexan-3-yl ((2R,6S,7R,9S,13aS,14aR,16aS,Z)-14a-((cyclopropylsulfonyl)carbamoyl)-2-((5-fluoro-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 796.5 (M⁺+1).

Compounds 3153 and 3154 were prepared using the intermediates described herein and by following the general procedure described for the synthesis of Compound 3117:

Compound 3153: tert-butyl ((2R,6S,7R,9S,13aS,14aR,16aS,Z)-2-((7-fluoro-5-methoxyisoquinolin-1-yl)oxy)-7,9- dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 786.6 (M$^+$+1).

Compound 3154: tert-butyl ((2R,6S,7R,9R,13aS,14aR,16aS,Z)-2-((7-fluoro-5-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.04 (br. s., 1H), 9.09 (br. s., 1H), 8.01 (d, J=6.1 Hz, 1H), 7.51 (d, J=6.1 Hz, 1H), 7.28 (dd, J=9.2, 1.8 Hz, 1H), 7.21 (dd, J=11.3, 2.1 Hz, 1H), 7.17 (d, J=7.6 Hz, 1H), 5.82 (br. s., 1H), 5.58-5.45 (m, 1H), 5.11-4.90 (m, 1H), 4.61 (d, J=10.7 Hz, 1H), 4.49 (t, J=6.9 Hz, 1H), 4.01 (s, 3H), 3.94-3.87 (m, 1H), 3.68 (dd, J=10.7, 8.2 Hz, 1H), 2.74-2.55 (m, 2H), 2.40-2.25 (m, 2H), 1.97-1.04 (m, 24H), 0.93 (d, J=7.0 Hz, 3H), 0.88 (d, J=6.4 Hz, 3H), 0.73 (t, J=12.7 Hz, 1H); MS: MS m/z 786.6 (M$^+$+1).

Compound 3155: 1,1,1-trifluoro-2-methylpropan-2-yl ((2R,6S,7R,9S,13aS,14aR,16aS,Z)-2-((7-fluoro-5-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 840.7 (M$^+$+1).

Compound 3156: 1,1,1-trifluoro-2-methylpropan-2-yl ((2R,6S,7R,9R,13aS,14aR,16aS,Z)-2-((7-fluoro-5-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.02 (br. s., 1H), 9.11 (br. s., 1H), 8.02 (d, J=6.1 Hz, 1H), 7.83 (d, J=6.4 Hz, 1H), 7.52 (d, J=5.8 Hz, 1H), 7.31-7.26 (m, 1H), 7.23 (dd, J=11.1, 2.3 Hz, 1H), 5.82 (br. s., 1H), 5.61-5.45 (m, 1H), 5.10-4.87 (m, 1H), 4.63-4.45 (m, 2H), 4.01 (s, 3H), 3.94-3.88 (m, 1H), 3.69 (dd, J=10.7, 8.2 Hz, 1H), 2.73-2.56 (m, 2H), 2.37-2.23 (m, 2H), 1.95-0.83 (m, 27H), 0.80-0.69 (m, 1H); MS: MS m/z 840.7 (M$^+$+1).

Preparation of Compound 3155 and Compound 3156

Preparation of Compound 3157 and Compound 3158

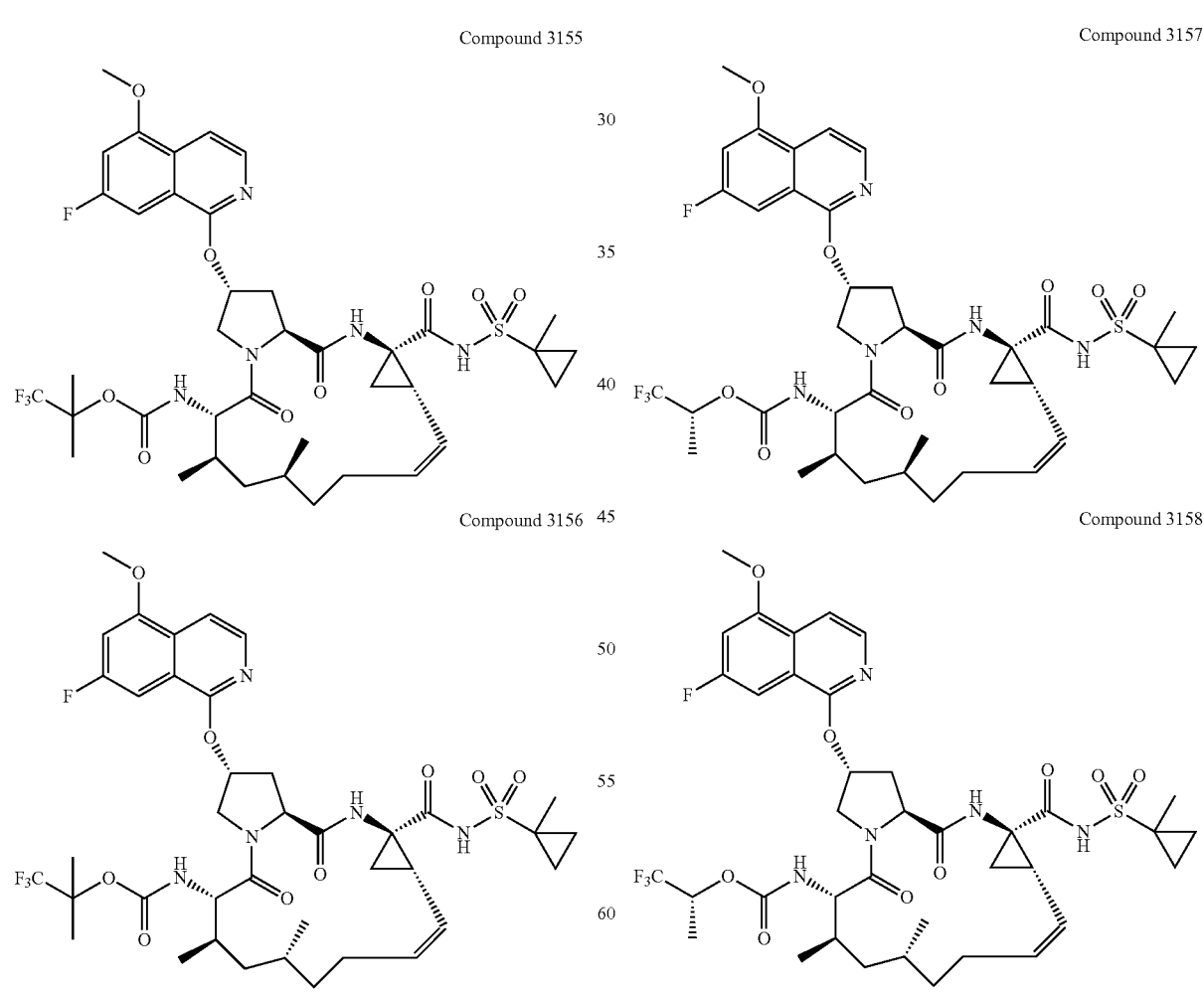

Compounds 3155 and 3156 were prepared using the intermediates described herein and by following the general procedure described for the synthesis of Compound 3117:

Compounds 3157 and 3158 were prepared using the intermediates described herein and by following the general procedure described for the synthesis of Compound 3117:

Compound 3157: (R)-1,1,1-trifluoropropan-2-yl ((2R,6S,7R,9S,13aS,14aR,16aS,Z)-2-((7-fluoro-5-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 826.6 (M⁺+1).

Compound 3158: (R)-1,1,1-trifluoropropan-2-yl ((2R,6S,7R,9R,13aS,14aR,16aS,Z)-2-((7-fluoro-5-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; ¹H NMR (500 MHz, DMSO-d₆) δ 11.01 (br. s., 1H), 9.07 (br. s., 1H), 8.12 (d, J=7.6 Hz, 1H), 8.01 (d, J=6.1 Hz, 1H), 7.52 (d, J=6.1 Hz, 1H), 7.36 (dd, J=9.5, 2.1 Hz, 1H), 7.22 (dd, J=11.3, 2.1 Hz, 1H), 5.81 (br. s., 1H), 5.59-5.47 (m, 1H), 5.07-4.94 (m, 1H), 4.78 (quin, J=6.9 Hz, 1H), 4.56 (d, J=11.0 Hz, 1H), 4.52-4.43 (m, 1H), 4.01 (s, 3H), 3.95-3.88 (m, 1H), 3.78 (dd, J=10.7, 7.9 Hz, 1H), 2.66 (br. s., 2H), 2.35-2.24 (m, 2H), 1.98-1.81 (m, 2H), 1.74-1.66 (m, 1H), 1.64-1.57 (m, 1H), 1.56-1.49 (m, 1H), 1.49-1.07 (m, 11H), 0.98-0.85 (m, 8H), 0.78 (t, J=11.3 Hz, 1H); MS: MS m/z 826.6 (M⁺+1).

Preparation of Compound 3159 and Compound 3160

Compound 3159: (1R,3r,5S)-bicyclo[3.1.0]hexan-3-yl ((2R,6S,7R,9S,13aS,14aR,16aS,Z)-2-((7-fluoro-5-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 810.7 (M⁺+1).

Compound 3160: (1R,3r,5S)-bicyclo[3.1.0]hexan-3-yl ((2R,6S,7R,9R,13aS,14aR,16aS,Z)-2-((7-fluoro-5-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; ¹H NMR (500 MHz, DMSO-d₆) δ 11.03 (br. s., 1H), 9.03 (br. s., 1H), 8.01 (d, J=6.1 Hz, 1H), 7.52 (d, J=6.1 Hz, 1H), 7.41 (br. s., 1H), 7.35 (dd, J=9.3, 2.0 Hz, 1H), 7.24 (dd, J=11.3, 2.1 Hz, 1H), 5.82 (br. s., 1H), 5.60-5.43 (m, 1H), 5.06-4.93 (m, 1H), 4.70 (t, J=6.9 Hz, 1H), 4.59-4.40 (m, 2H), 4.02 (s, 3H), 3.96-3.89 (m, 1H), 3.74 (dd, J=10.7, 8.5 Hz, 1H), 2.74-2.56 (m, 2H), 2.36-2.23 (m, 2H), 2.01-1.07 (m, 19H), 0.97-0.82 (m, 8H), 0.74 (br. s., 1H), 0.42-0.30 (m, 2H); MS: MS m/z 810.7 (M⁺+1).

Preparation of Compound 3161 and Compound 3162

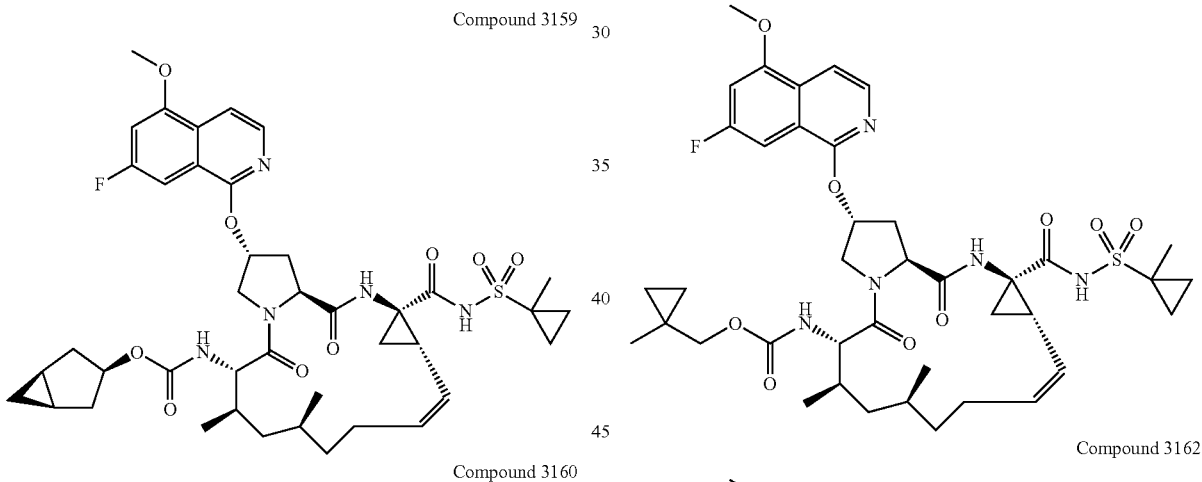

Compound 3159

Compound 3160

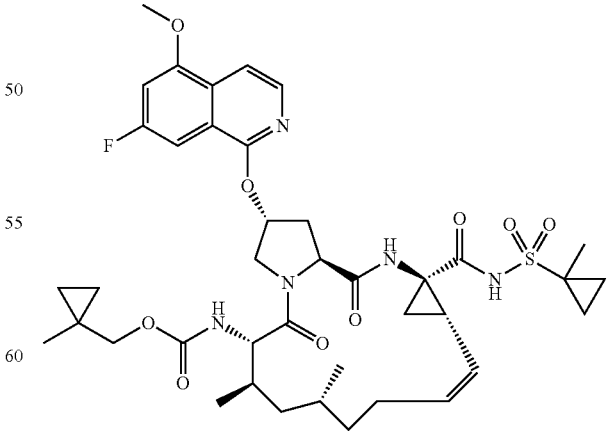

Compound 3161

Compound 3162

Compounds 3159 and 3160 were prepared using the intermediates described herein and by following the general procedure described for the synthesis of Compound 3117:

Compounds 3161 and 3162 were prepared using the intermediates described herein and by following the general procedure described for the synthesis of Compound 3117:

Compound 3161: (1-methylcyclopropyl)methyl ((2R,6S,7R,9S,13aS,14aR,16aS,Z)-2-((7-fluoro-5-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 798.7 (M$^+$+1).

Compound 3162: (1-methylcyclopropyl)methyl ((2R,6S,7R,9R,13aS,14aR,16aS,Z)-2-((7-fluoro-5-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.03 (br. s., 1H), 9.04 (br. s., 1H), 8.00 (d, J=6.1 Hz, 1H), 7.54 (d, J=6.4 Hz, 1H), 7.51 (d, J=6.1 Hz, 1H), 7.38 (dd, J=9.5, 2.1 Hz, 1H), 7.23 (dd, J=11.3, 2.1 Hz, 1H), 5.80 (br. s., 1H), 5.62-5.46 (m, 1H), 5.10-4.91 (m, 1H), 4.58 (d, J=9.8 Hz, 1H), 4.51-4.39 (m, 1H), 4.01 (s, 3H), 3.95-3.88 (m, 1H), 3.75 (dd, J=10.7, 8.2 Hz, 1H), 3.55-3.43 (m, 2H), 2.64 (d, J=15.9 Hz, 2H), 2.36-2.21 (m, 2H), 1.99-0.84 (m, 24H), 0.75 (t, J=11.9 Hz, 1H), 0.35-0.15 (m, 4H); MS: MS m/z 798.7 (M$^+$+1).

Preparation of Compound 3163 and Compound 3164

Compounds 3163 and 3164 were prepared using the intermediates described herein and by following the general procedure described for the synthesis of Compound 3117:

Compound 3163: tert-butyl ((2R,6S,7R,9S,13aS,14aR,16aS,Z)-14a-((cyclopropylsulfonyl)carbamoyl)-2-((7-fluoro-5-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 772.7 (M$^+$+1).

Compound 3164: tert-butyl ((2R,6S,7R,9R,13aS,14aR,16aS,Z)-14a-((cyclopropylsulfonyl)carbamoyl)-2-((7-fluoro-5-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.18 (br. s., 1H), 8.96 (br. s., 1H), 8.01 (d, J=5.8 Hz, 1H), 7.51 (d, J=5.8 Hz, 1H), 7.31-7.25 (m, 1H), 7.23-7.14 (m, 2H), 5.80 (br. s., 1H), 5.56-5.45 (m, 1H), 5.12-5.00 (m, 1H), 4.60 (d, J=7.9 Hz, 1H), 4.51-4.39 (m, 1H), 4.01 (s, 3H), 3.88 (dd, J=11.1, 2.9 Hz, 1H), 3.68 (dd, J=10.4, 8.5 Hz, 1H), 2.96-2.83 (m, 1H), 2.74-2.56 (m, 2H), 2.38-2.24 (m, 2H), 1.96-0.81 (m, 27H), 0.72 (t, J=12.1 Hz, 1H); MS: MS m/z 772.7 (M$^+$+1).

Preparation of Compound 3165 and Compound 3166

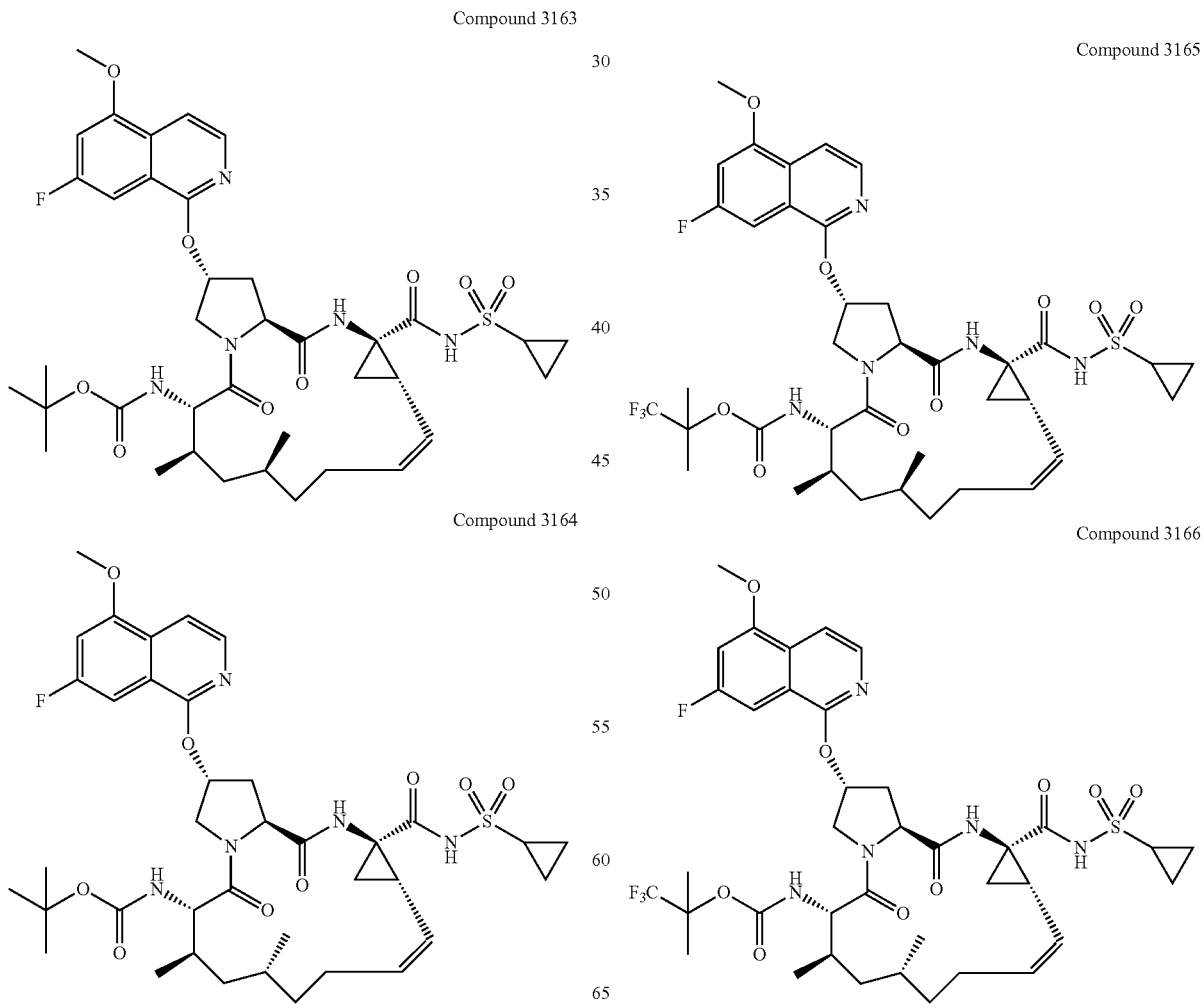

Compound 3163

Compound 3164

Compound 3165

Compound 3166

Compounds 3165 and 3166 were prepared using the intermediates described herein and by following the general procedure described for the synthesis of Compound 3117:

Compound 3165: 1,1,1-trifluoro-2-methylpropan-2-yl ((2R,6S,7R,9S,13aS,14aR,16aS,Z)-14a-((cyclopropylsulfonyl)carbamoyl)-2-((7-fluoro-5-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 826.6 (M$^+$+1).

Compound 3166: 1,1,1-trifluoro-2-methylpropan-2-yl ((2R,6S,7R,9R,13aS,14aR,16aS,Z)-14a-((cyclopropylsulfonyl)carbamoyl)-2-((7-fluoro-5-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.18 (s, 1H), 8.99 (br. s., 1H), 8.02 (d, J=6.1 Hz, 1H), 7.85 (d, J=7.6 Hz, 1H), 7.52 (d, J=6.1 Hz, 1H), 7.28 (dd, J=9.3, 2.0 Hz, 1H), 7.23 (dd, J=11.3, 2.1 Hz, 1H), 5.81 (br. s., 1H), 5.58-5.48 (m, 1H), 5.06 (t, J=9.8 Hz, 1H), 4.61-4.44 (m, 2H), 4.01 (s, 3H), 3.89 (dd, J=11.4, 3.2 Hz, 1H), 3.69 (dd, J=10.7, 7.9 Hz, 1H), 2.96-2.87 (m, 1H), 2.72-2.59 (m, 2H), 2.37-2.27 (m, 2H), 1.96-1.79 (m, 2H), 1.77-1.68 (m, 1H), 1.65-1.53 (m, 2H), 1.51-0.96 (m, 13H), 0.94 (d, J=7.0 Hz, 3H), 0.90 (d, J=6.4 Hz, 3H), 0.75 (t, J=12.7 Hz, 1H); MS: MS m/z 826.6 (M$^+$+1).

Preparation of Compound 3167 and Compound 3168

Compounds 3167 and 3168 were prepared using the intermediates described herein and by following the general procedure described for the synthesis of Compound 3117:

Compound 3167: (1R,3r,5S)-bicyclo[3.1.0]hexan-3-yl ((2R,6S,7R,9S,13aS,14aR,16aS,Z)-14a-((cyclopropylsulfonyl)carbamoyl)-2-((7-fluoro-5-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 796.5 (M$^+$+1).

Compound 3168: (1R,3r,5S)-bicyclo[3.1.0]hexan-3-yl ((2R,6S,7R,9R,13aS,14aR,16aS,Z)-14a-((cyclopropylsulfonyl)carbamoyl)-2-((7-fluoro-5-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.18 (s, 1H), 8.91 (br. s., 1H), 8.01 (d, J=5.8 Hz, 1H), 7.52 (d, J=5.8 Hz, 1H), 7.43 (d, J=7.9 Hz, 1H), 7.38-7.32 (m, 1H), 7.24 (dd, J=11.3, 2.1 Hz, 1H), 5.81 (br. s., 1H), 5.59-5.47 (m, 1H), 5.07 (t, J=9.8 Hz, 1H), 4.72 (t, J=6.9 Hz, 1H), 4.53 (d, J=11.3 Hz, 1H), 4.48-4.40 (m, 1H), 4.02 (s, 3H), 3.90 (dd, J=11.1, 2.9 Hz, 1H), 3.74 (dd, J=10.5, 8.7 Hz, 1H), 2.96-2.88 (m, 1H), 2.74-2.58 (m, 2H), 2.35-2.24 (m, 2H), 2.00-1.89 (m, 2H), 1.88-1.75 (m, 2H), 1.73-0.96 (m, 14H), 0.93 (d, J=7.0 Hz, 3H), 0.88 (d, J=6.4 Hz, 3H), 0.74 (t, J=12.4 Hz, 1H), 0.41-0.32 (m, 2H); MS: MS m/z 796.5 (M$^+$+1).

Preparation of Compound 3169 and Compound 3170

Compound 3167

Compound 3168

Compound 3169

Compound 3170

Compounds 3169 and 3170 were prepared using the intermediates described herein and by following the general procedure described for the synthesis of Compound 3117:

Compound 3169: (R)-1,1,1-trifluoropropan-2-yl ((2R,6S,7R,9S,13aS,14aR,16aS,Z)-14a-((cyclopropylsulfonyl)carbamoyl)-2-((7-fluoro-5-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 812.5 (M$^+$+1).

Compound 3170: (R)-1,1,1-trifluoropropan-2-yl ((2R,6S,7R,9R,13aS,14aR,16aS,Z)-14a-((cyclopropylsulfonyl)carbamoyl)-2-((7-fluoro-5-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.16 (s, 1H), 8.94 (s, 1H), 8.12 (d, J=7.6 Hz, 1H), 8.01 (d, J=5.8 Hz, 1H), 7.52 (d, J=5.8 Hz, 1H), 7.37 (dd, J=9.5, 2.1 Hz, 1H), 7.22 (dd, J=11.1, 2.3 Hz, 1H), 5.79 (br. s., 1H), 5.57-5.47 (m, 1H), 5.07 (t, J=9.6 Hz, 1H), 4.81 (dt, J=13.5, 6.8 Hz, 1H), 4.55 (d, J=11.0 Hz, 1H), 4.44 (dd, J=10.2, 7.2 Hz, 1H), 4.01 (s, 3H), 3.90 (dd, J=11.1, 2.9 Hz, 1H), 3.78 (dd, J=10.5, 7.8 Hz, 1H), 2.96-2.87 (m, 1H), 2.70-2.59 (m, 2H), 2.36-2.24 (m, 2H), 2.02-1.81 (m, 2H), 1.77-1.66 (m, 1H), 1.64-1.52 (m, 2H), 1.50-1.31 (m, 2H), 1.23 (d, J=6.7 Hz, 3H), 1.20-0.86 (m, 11H), 0.77 (t, J=12.4 Hz, 1H); MS: MS m/z 812.4 (M$^+$+1).

Compounds 3171 and 3172 were prepared using the intermediates described herein and by following the general procedure described for the synthesis of Compound 3117:

Compound 3171: (1-methylcyclopropyl)methyl ((2R,6S,7R,9S,13aS,14aR,16aS,Z)-14a-((cyclopropylsulfonyl)carbamoyl)-2-((7-fluoro-5-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 784.5 (M$^+$+1).

Compound 3172: (1-methylcyclopropyl)methyl ((2R,6S,7R,9R,13aS,14aR,16aS,Z)-14a-((cyclopropylsulfonyl)carbamoyl)-2-((7-fluoro-5-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.17 (br. s., 1H), 8.91 (br. s., 1H), 8.00 (d, J=6.1 Hz, 1H), 7.55 (d, J=7.6 Hz, 1H), 7.51 (d, J=6.1 Hz, 1H), 7.39 (dd, J=9.6, 2.0 Hz, 1H), 7.23 (dd, J=11.3, 2.1 Hz, 1H), 5.79 (br. s., 1H), 5.57-5.47 (m, 1H), 5.13-5.01 (m, 1H), 4.59 (d, J=11.0 Hz, 1H), 4.49-4.37 (m, 1H), 4.01 (s, 3H), 3.89 (dd, J=11.3, 3.1 Hz, 1H), 3.75 (dd, J=10.4, 8.2 Hz, 1H), 3.55-3.44 (m, 2H), 2.91 (s, 1H), 2.64 (d, J=12.8 Hz, 2H), 2.35-2.23 (m, 2H), 1.99-1.79 (m, 2H), 1.71 (br. s., 1H), 1.64-1.51 (m, 2H), 1.49-1.32 (m, 2H), 1.25-0.88 (m, 14H), 0.75 (t, J=12.1 Hz, 1H), 0.36-0.18 (m, 4H); MS: MS m/z 784.5 (M$^+$+1).

Preparation of Compound 3171 and Compound 3172

Preparation of Compound 3173 and Compound 3174

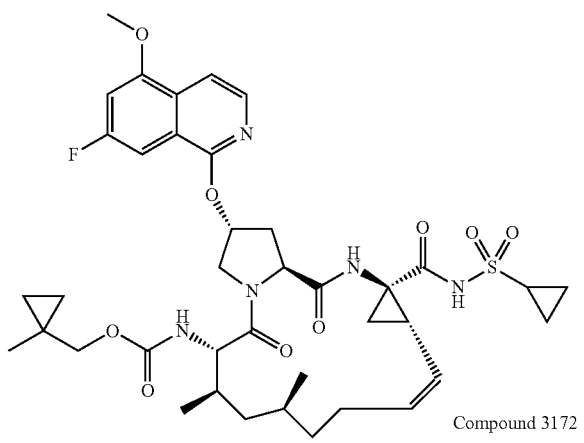

Compound 3171

Compound 3172

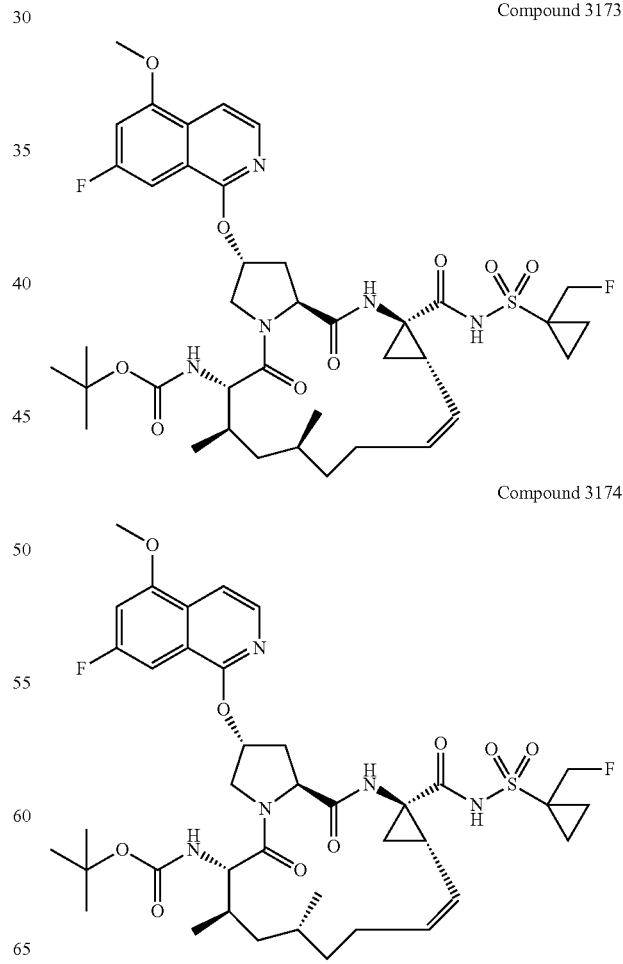

Compound 3173

Compound 3174

Compounds 3173 and 3174 were prepared using the intermediates described herein and by following the general procedure described for the synthesis of Compound 3117:

Compound 3173: tert-butyl ((2R,6S,7R,9S,13aS,14aR,16aS,Z)-2-((7-fluoro-5-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 804.4 (M$^+$+1).

Compound 3174: tert-butyl ((2R,6S,7R,9R,13aS,14aR,16aS,Z)-2-((7-fluoro-5-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.27 (br. s., 1H), 9.01 (br. s., 1H), 8.02 (d, J=6.1 Hz, 1H), 7.51 (d, J=5.8 Hz, 1H), 7.32-7.26 (m, 1H), 7.24-7.14 (m, 2H), 5.81 (br. s., 1H), 5.59-5.46 (m, 1H), 5.07-4.95 (m, 1H), 4.91-4.71 (m, 1H), 4.67-4.40 (m, 3H), 4.01 (s, 3H), 3.91-3.88 (m, J=8.5 Hz, 1H), 3.68 (dd, J=10.4, 8.2 Hz, 1H), 2.73-2.56 (m, 2H), 2.36-2.23 (m, 2H), 1.92-1.64 (m, 3H), 1.61-1.04 (m, 18H), 0.93 (d, J=6.7 Hz, 3H), 0.89 (d, J=6.4 Hz, 3H), 0.73 (t, J=12.5 Hz, 1H); MS: MS m/z 804.4 (M$^+$+1).

Preparation of Compound 3175 and Compound 3176

Compounds 3175 and 3176 were prepared using the intermediates described herein and by following the general procedure described for the synthesis of Compound 3117:

Compound 3175: 1,1,1-trifluoro-2-methylpropan-2-yl ((2R,6S,7R,9S,13aS,14aR,16aS,Z)-2-((7-fluoro-5-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 858.4 (M$^+$+1).

Compound 3176: 1,1,1-trifluoro-2-methylpropan-2-yl ((2R,6S,7R,9R,13aS,14aR,16aS,Z)-2-((7-fluoro-5-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.27 (s, 1H), 9.03 (br. s., 1H), 8.03 (d, J=5.8 Hz, 1H), 7.85 (d, J=7.0 Hz, 1H), 7.52 (d, J=5.8 Hz, 1H), 7.29 (dd, J=9.2, 1.8 Hz, 1H), 7.23 (dd, J=11.3, 2.1 Hz, 1H), 5.81 (br. s., 1H), 5.57-5.44 (m, 1H), 5.01 (t, J=9.6 Hz, 1H), 4.93-4.72 (m, 1H), 4.64-4.45 (m, 3H), 4.01 (s, 3H), 3.95-3.87 (m, 1H), 3.69 (dd, J=10.5, 8.1 Hz, 1H), 2.71-2.59 (m, 2H), 2.40-2.25 (m, 2H), 1.92-1.78 (m, 2H), 1.75-1.66 (m, 1H), 1.60-1.08 (m, 15H), 0.94 (d, J=6.7 Hz, 3H), 0.90 (d, J=6.4 Hz, 3H), 0.75 (t, J=12.5 Hz, 1H); MS: MS m/z 858.4 (M$^+$+1).

Preparation of Compound 3177 and Compound 3178

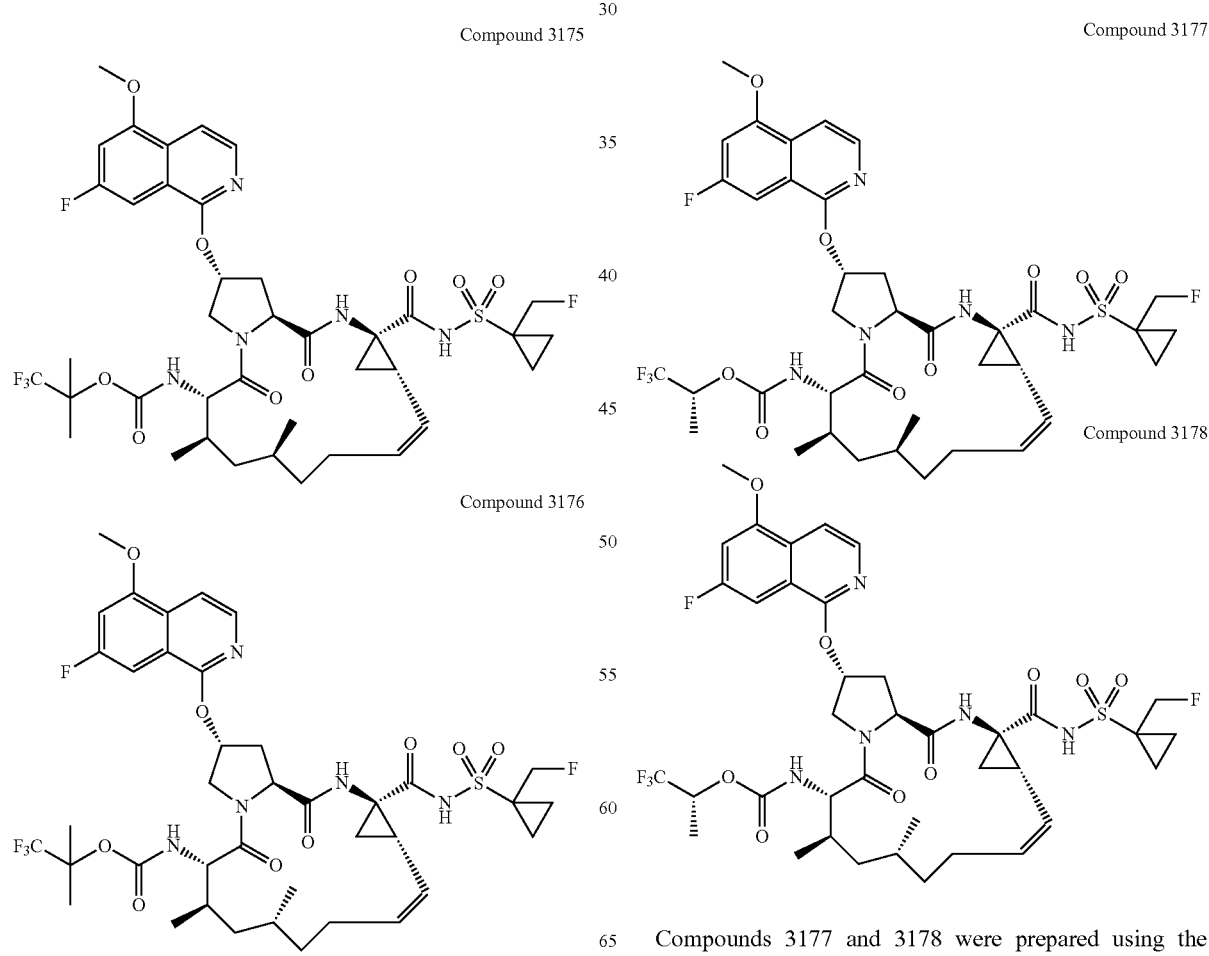

Compound 3175

Compound 3176

Compound 3177

Compound 3178

Compounds 3177 and 3178 were prepared using the intermediates described herein and by following the general procedure described for the synthesis of Compound 3117:

Compound 3177: (R)-1,1,1-trifluoropropan-2-yl ((2R,6S,7R,9S,13aS,14aR,16aS,Z)-2-((7-fluoro-5-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 858.4 (M$^+$+1).

Compound 3178: (R)-1,1,1-trifluoropropan-2-yl ((2R,6S,7R,9R,13aS,14aR,16aS,Z)-2-((7-fluoro-5-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;
$^1$H NMR (500 MHz, DMSO-d$_6$) δ 11.25 (br. s., 1H), 8.99 (br. s., 1H), 8.13 (d, J=7.6 Hz, 1H), 8.01 (d, J=6.1 Hz, 1H), 7.52 (d, J=6.1 Hz, 1H), 7.37 (dd, J=9.6, 2.0 Hz, 1H), 7.22 (dd, J=11.1, 2.3 Hz, 1H), 5.80 (br. s., 1H), 5.57-5.47 (m, 1H), 5.07-4.97 (m, 1H), 4.91-4.72 (m, 2H), 4.64-4.40 (m, 3H), 4.01 (s, 3H), 3.95-3.88 (m, 1H), 3.79 (dd, J=10.7, 7.9 Hz, 1H), 2.63 (d, J=8.9 Hz, 2H), 2.34-2.24 (m, 2H), 1.95-1.79 (m, 2H), 1.75-1.65 (m, 1H), 1.59-1.10 (m, 12H), 0.93 (t, J=7.5 Hz, 6H), 0.77 (t, J=11.6 Hz, 1H); MS: MS m/z 858.4 (M$^+$+1).

Preparation of Compound 3179 and Compound 3180

Compounds 3179 and 3180 were prepared using the intermediates described herein and by following the general procedure described for the synthesis of Compound 3117:

Compound 3179: 3,3-difluoro-2-methylbutan-2-yl ((2R,6S,7R,9S,13 aS,14aR,16aS,Z)-2-((7-fluoro-5-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 854.4 (M$^+$+1).

Compound 3180: 3,3-difluoro-2-methylbutan-2-yl ((2R,6S,7R,9R,13aS,14aR,16aS,Z)-2-((7-fluoro-5-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate;
$^1$H NMR (500 MHz, METHANOL-d$_4$) δ 7.96 (d, J=6.1 Hz, 1H), 7.57 (d, J=6.1 Hz, 1H), 7.34 (dd, J=9.2, 2.1 Hz, 1H), 7.02 (dd, J=11.0, 2.1 Hz, 1H), 5.88 (t, J=3.4 Hz, 1H), 5.56 (td, J=10.2, 5.8 Hz, 1H), 5.14 (t, J=9.8 Hz, 1H), 4.88-4.74 (m, 1H), 4.71 (d, J=11.9 Hz, 1H), 4.66-4.51 (m, 2H), 4.04-3.99 (m, 4H), 3.82 (d, J=10.7 Hz, 1H), 2.72 (dd, J=14.0, 7.3 Hz, 1H), 2.63 (q, J=9.2 Hz, 1H), 2.45 (ddd, J=14.0, 10.1, 4.0 Hz, 1H), 2.41-2.34 (m, 1H), 1.98-1.77 (m, 4H), 1.72-1.40 (m, 9H), 1.33-1.10 (m, 6H), 1.03-0.96 (m, 8H), 0.81 (t, J=12.3 Hz, 1H); MS: MS m/z 854.4 (M$^+$+1).

Preparation of Compound 3181 and Compound 3181

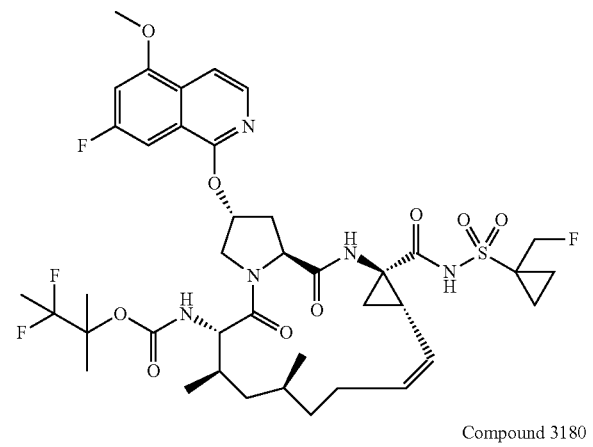

Compound 3179

Compound 3180

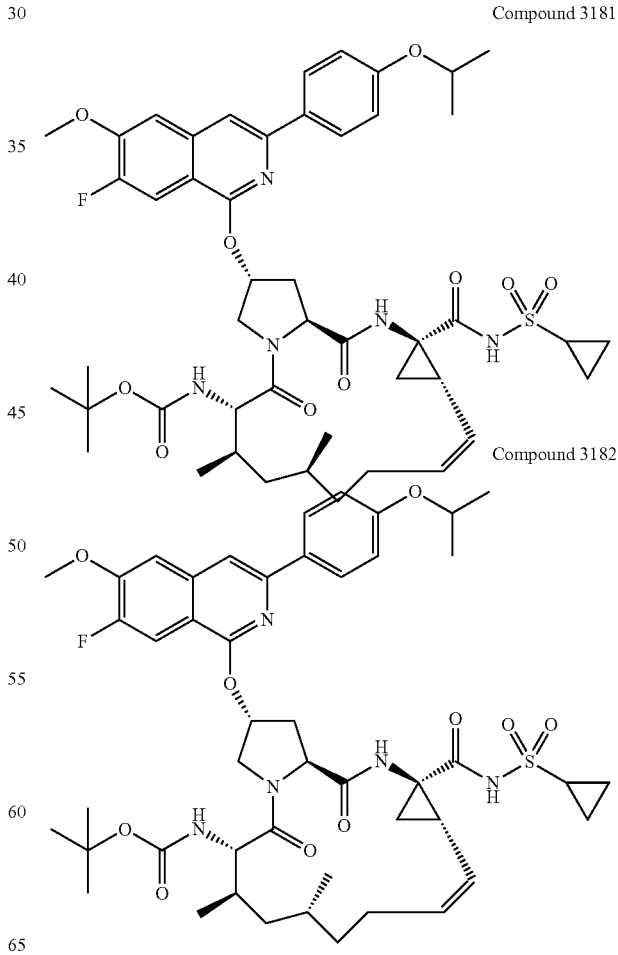

Compound 3181

Compound 3182

Compounds 3181 and 3182 were prepared using the intermediates described herein and by following the general procedure described for the synthesis of Compound 3117:

Compound 3181: tert-butyl ((2R,6S,7R,9S,13aS,14aR,16aS,Z)-14a-((cyclopropylsulfonyl)carbamoyl)-2-((7-fluoro-3-(4-isopropoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 906.8 ($M^{+}+1$).

Compound 3182: tert-butyl ((2R,6S,7R,9R,13aS,14aR,16aS,Z)-14a-((cyclopropylsulfonyl)carbamoyl)-2-((7-fluoro-3-(4-isopropoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^{1}$H NMR (500 MHz, DMSO-$d_{6}$) δ 11.23 (br. s., 1H), 8.93 (br. s., 1H), 8.10 (d, J=8.5 Hz, 2H), 7.85 (s, 1H), 7.71 (d, J=11.3 Hz, 1H), 7.55 (d, J=8.2 Hz, 1H), 7.22 (d, J=7.6 Hz, 1H), 7.06 (d, J=8.9 Hz, 2H), 5.96 (br. s., 1H), 5.59-5.47 (m, 1H), 5.07 (t, J=8.5 Hz, 1H), 4.72 (spt, J=6.1 Hz, 1H), 4.60 (d, J=11.3 Hz, 1H), 4.51-4.43 (m, 1H), 4.00 (s, 3H), 3.94 (dd, J=11.0, 3.1 Hz, 1H), 3.72 (dd, J=10.4, 8.5 Hz, 1H), 2.97-2.87 (m, 1H), 2.77-2.64 (m, 2H), 2.42-2.25 (m, 2H), 1.98-1.68 (m, 3H), 1.66-1.51 (m, 2H), 1.49-0.84 (m, 28H), 0.75 (t, J=12.5 Hz, 1H); MS: MS m/z 906.8 ($M^{+}+1$).

Compounds 3183 and 3184 were prepared using the intermediates described herein and by following the general procedure described for the synthesis of Compound 3117:

Compound 3183: tert-butyl ((2R,6S,7R,9S,13aS,14aR,16aS,Z)-2-((7-fluoro-3-(4-isopropoxyphenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 920.8 ($M^{+}+1$).

Compound 3184: tert-butyl ((2R,6S,7R,9R,13aS,14aR,16aS,Z)-2-((7-fluoro-3-(4-isopropoxyphenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^{1}$H NMR (500 MHz, DMSO-$d_{6}$) δ 11.07 (br. s., 1H), 9.06 (br. s., 1H), 8.09 (d, J=8.9 Hz, 2H), 7.85 (s, 1H), 7.71 (d, J=11.3 Hz, 1H), 7.55 (d, J=8.2 Hz, 1H), 7.22 (d, J=7.6 Hz, 1H), 7.06 (d, J=8.9 Hz, 2H), 5.97 (br. s., 1H), 5.57-5.47 (m, 1H), 5.06-4.94 (m, 1H), 4.72 (spt, J=6.0 Hz, 1H), 4.60 (d, J=13.4 Hz, 1H), 4.55-4.46 (m, 1H), 4.00 (s, 3H), 3.96 (dd, J=11.3, 3.1 Hz, 1H), 3.72 (dd, J=10.5, 8.4 Hz, 1H), 2.79-2.62 (m, 2H), 2.43-2.27 (m, 2H), 1.97-0.84 (m, 36H), 0.75 (t, J=12.2 Hz, 1H); MS: MS m/z 920.8 ($M^{+}+1$).

Preparation of Compound 3185 and Compound 3186

Preparation of Compound 3183 and Compound 3184

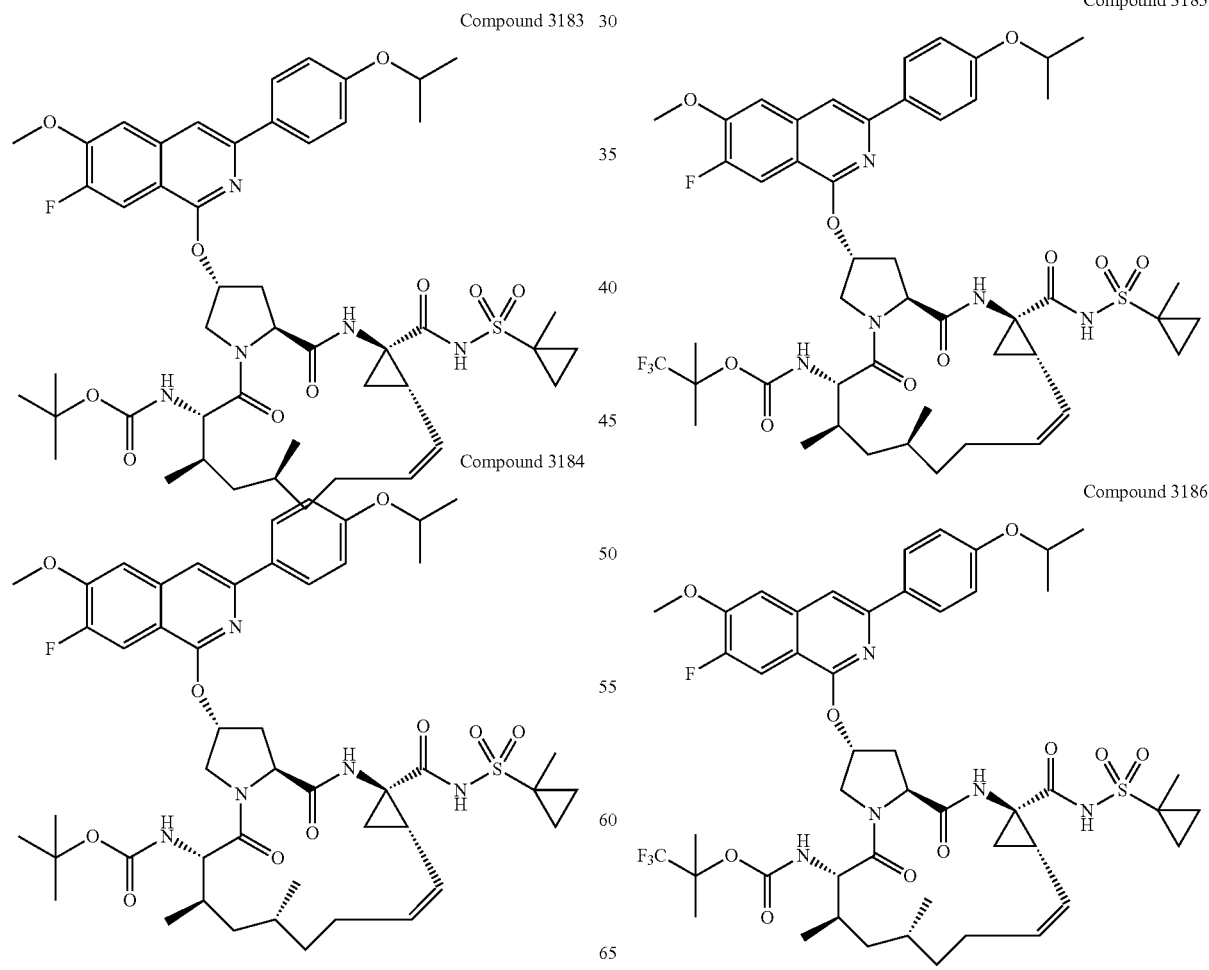

Compound 3183

Compound 3184

Compound 3185

Compound 3186

Compounds 3185 and 3186 were prepared using the intermediates described herein and by following the general procedure described for the synthesis of Compound 3117:

Compound 3185: MS: 1,1,1-trifluoro-2-methylpropan-2-yl ((2R,6S,7R,9S,13aS,14aR,16aS,Z)-2-((7-fluoro-3-(4-isopropoxyphenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS m/z 974.7 (M$^+$+1).

Compound 3186: 1,1,1-trifluoro-2-methylpropan-2-yl ((2R,6S,7R,9R,13aS,14aR,16aS,Z)-2-((7-fluoro-3-(4-isopropoxyphenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.06 (s, 1H), 9.09 (br. s., 1H), 8.09 (d, J=8.9 Hz, 2H), 7.86 (s, 1H), 7.71 (d, J=11.6 Hz, 1H), 7.56 (d, J=8.5 Hz, 1H), 7.07 (d, J=8.9 Hz, 2H), 5.98 (br. s., 1H), 5.54 (d, J=5.5 Hz, 1H), 5.00 (t, J=9.6 Hz, 1H), 4.73 (spt, J=6.1 Hz, 1H), 4.59-4.48 (m, 2H), 4.01 (s, 3H), 3.97 (dd, J=11.4, 3.2 Hz, 1H), 3.74 (dd, J=10.7, 7.9 Hz, 1H), 2.74-2.63 (m, 2H), 2.41-2.27 (m, 2H), 1.96-1.79 (m, 2H), 1.78-1.68 (m, 1H), 1.65-1.58 (m, 1H), 1.57-1.51 (m, 1H), 1.50-1.09 (m, 28H), 0.99-0.85 (m, 8H), 0.78 (t, J=12.7 Hz, 1H); MS: MS m/z 974.7 (M$^+$+1).

Compounds 3187 and 3188 were prepared using the intermediates described herein and by following the general procedure described for the synthesis of Compound 3117:

Compound 3187: (1R,3r,5S)-bicyclo[3.1.0]hexan-3-yl ((2R,6S,7R,9S,13aS,14aR,16aS,Z)-14a-((cyclopropylsulfonyl)carbamoyl)-2-((7-fluoro-3-(4-isopropoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 930.7 (M$^+$+1).

Compound 3188: (1R,3r,5S)-bicyclo[3.1.0]hexan-3-yl ((2R,6S,7R,9R,13aS,14aR,16aS,Z)-14a-((cyclopropylsulfonyl)carbamoyl)-2-((7-fluoro-3-(4-isopropoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.21 (s, 1H), 8.87 (s, 1H), 8.10 (d, J=8.5 Hz, 2H), 7.86 (s, 1H), 7.81 (d, J=11.6 Hz, 1H), 7.56 (d, J=8.5 Hz, 1H), 7.47 (d, J=8.2 Hz, 1H), 7.07 (d, J=8.9 Hz, 2H), 5.94 (br. s., 1H), 5.58-5.48 (m, 1H), 5.08 (t, J=10.1 Hz, 1H), 4.84 (t, J=6.7 Hz, 1H), 4.72 (spt, J=6.0 Hz, 1H), 4.55 (d, J=11.3 Hz, 1H), 4.45 (dd, J=10.1, 7.0 Hz, 1H), 4.01 (s, 3H), 3.94 (dd, J=11.1, 3.2 Hz, 1H), 3.77 (dd, J=10.7, 8.2 Hz, 1H), 2.97-2.88 (m, 1H), 2.80-2.64 (m, 2H), 2.42-2.22 (m, 2H), 2.06-1.79 (m, 4H), 1.75-0.86 (m, 26H), 0.76 (t, J=12.4 Hz, 1H), 0.47-0.34 (m, 2H); MS: MS m/z 930.7 (M$^+$+1).

Preparation of Compound 3187 and Compound 3188

Compound 3187

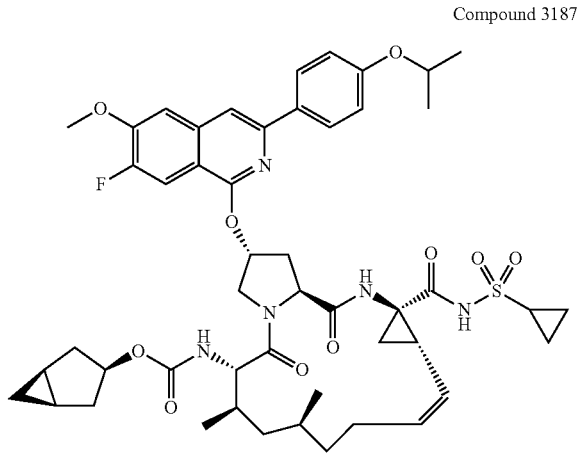

Compound 3188

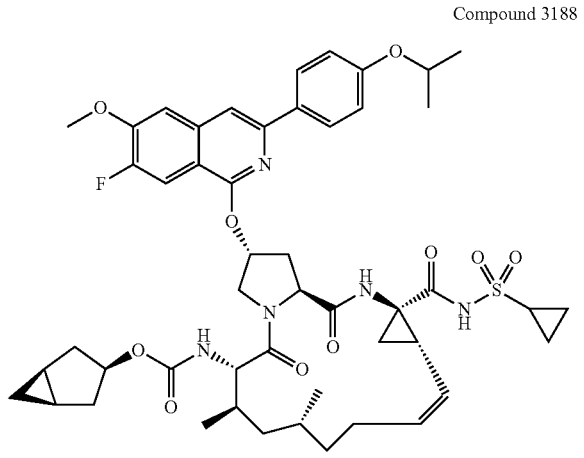

Preparation of Compound 3189 and Compound 3190

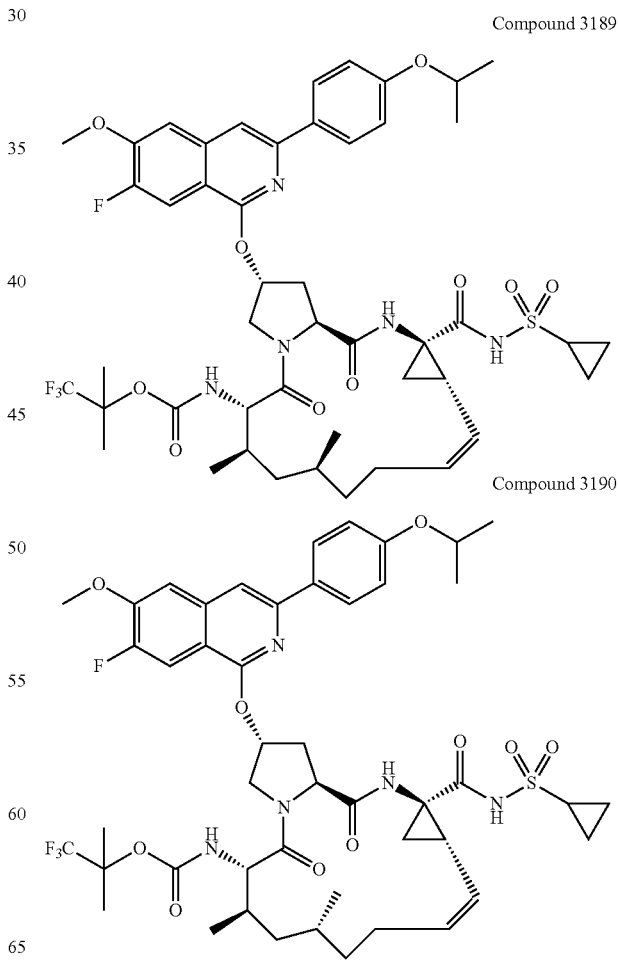

Compound 3189

Compound 3190

Compounds 3189 and 3190 were prepared using the intermediates described herein and by following the general procedure described for the synthesis of Compound 3117:

Compound 3189: 1,1,1-trifluoro-2-methylpropan-2-yl ((2R,6S,7R,9S,13aS,14aR,16aS,Z)-14a-((cyclopropylsulfonyl)carbamoyl)-2-((7-fluoro-3-(4-isopropoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 960.8 ($M^+$+1).

Compound 3190: 1,1,1-trifluoro-2-methylpropan-2-yl ((2R,6S,7R,9R,13aS,14aR,16aS,Z)-14a-((cyclopropylsulfonyl)carbamoyl)-2-((7-fluoro-3-(4-isopropoxyphenyl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-$d_6$) δ 11.21 (s, 1H), 8.95 (s, 1H), 8.10 (d, J=8.9 Hz, 2H), 7.87 (s, 2H), 7.71 (d, J=11.6 Hz, 1H), 7.57 (d, J=8.2 Hz, 1H), 7.07 (d, J=8.9 Hz, 2H), 5.96 (br. s., 1H), 5.59-5.48 (m, 1H), 5.08 (t, J=9.9 Hz, 1H), 4.73 (spt, J=6.0 Hz, 1H), 4.59-4.44 (m, 2H), 4.01 (s, 3H), 3.95 (dd, J=11.4, 3.2 Hz, 1H), 3.74 (dd, J=10.7, 7.6 Hz, 1H), 2.98-2.88 (m, 1H), 2.80-2.63 (m, 2H), 2.44-2.24 (m, 2H), 1.99-1.81 (m, 2H), 1.79-1.71 (m, 1H), 1.65-1.53 (m, 2H), 1.51-0.97 (m, 19H), 0.95 (d, J=7.0 Hz, 3H), 0.91 (d, J=6.1 Hz, 3H), 0.77 (t, J=12.2 Hz, 1H); MS: MS m/z 960.8 ($M^+$+1).

Preparation of Compound 3191 and Compound 3192

Compound 3191: (1R,3r,5S)-bicyclo[3.1.0]hexan-3-yl ((2R,6S,7R,9S,13aS,14aR,16aS,Z)-2-((7-fluoro-3-(4-isopropoxyphenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 944.8 ($M^+$+1).

Compound 3192: (1R,3r,5S)-bicyclo[3.1.0]hexan-3-yl ((2R,6S,7R,9R,13aS,14aR,16aS,Z)-2-((7-fluoro-3-(4-isopropoxyphenyl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-$d_6$) δ 11.06 (s, 1H), 9.00 (s, 1H), 8.09 (d, J=8.9 Hz, 2H), 7.86 (s, 1H), 7.80 (d, J=11.6 Hz, 1H), 7.56 (d, J=8.2 Hz, 1H), 7.47 (d, J=7.9 Hz, 1H), 7.07 (d, J=8.9 Hz, 2H), 5.96 (br. s., 1H), 5.58-5.48 (m, 1H), 5.00 (t, J=9.8 Hz, 1H), 4.82 (t, J=6.7 Hz, 1H), 4.72 (spt, J=6.1 Hz, 1H), 4.60-4.44 (m, 2H), 4.01 (s, 3H), 3.96 (dd, J=11.3, 3.4 Hz, 1H), 3.77 (dd, J=10.5, 8.4 Hz, 1H), 2.78-2.67 (m, 1H), 2.42-2.25 (m, 2H), 2.04-1.80 (m, 4H), 1.75-1.11 (m, 22H), 1.01-0.85 (m, 8H), 0.77 (t, J=12.1 Hz, 1H), 0.46-0.33 (m, 2H); MS: MS m/z 944.7 ($M^+$+1).

Preparation of Compound 5001 and Compound 5002

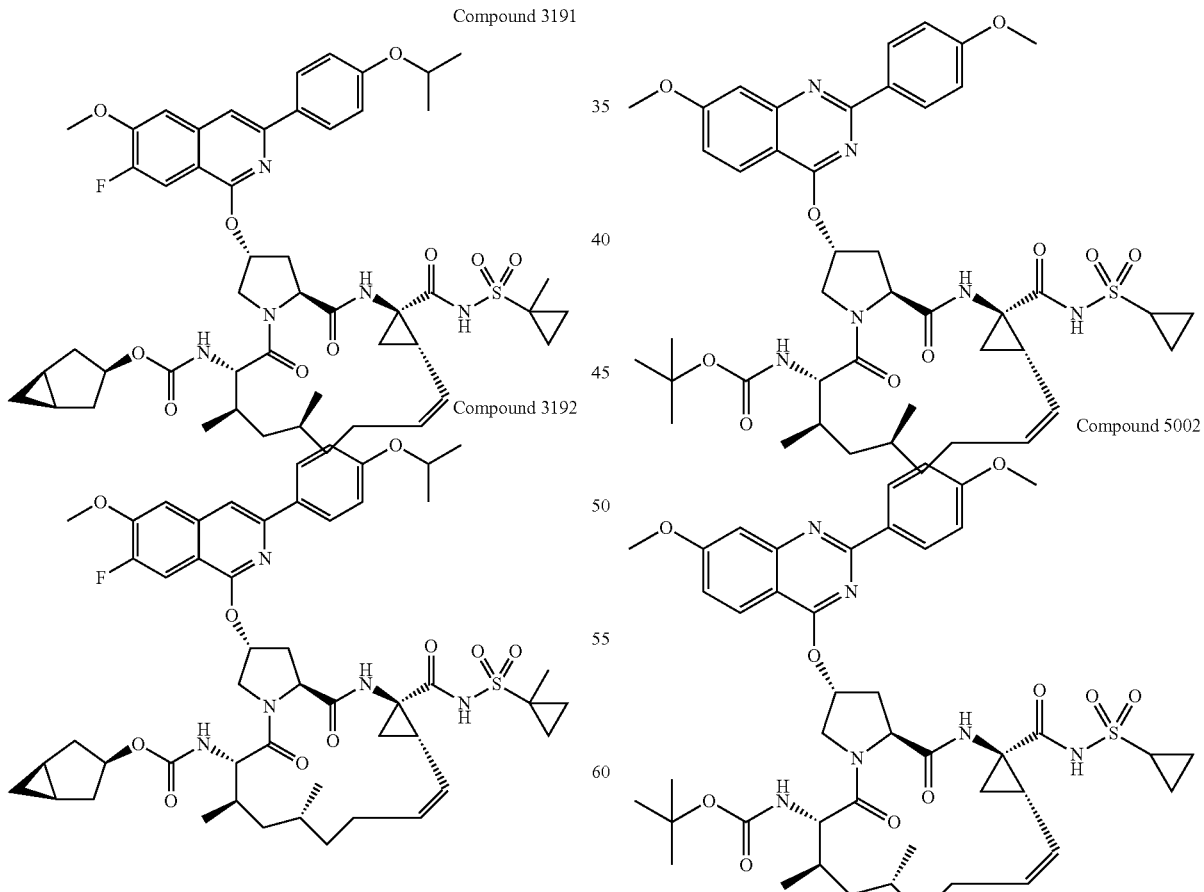

Compound 3191

Compound 3192

Compound 5001

Compound 5002

Compounds 3191 and 3192 were prepared using the intermediates described herein and by following the general procedure described for the synthesis of Compound 3117:

Compound 5001 and Compound 5002 were prepared using the intermediates described herein and by following the general procedure described for the synthesis of Compound 3117:

Compound 5001: tert-butyl ((2R,6S,7R,9S,13aS,14aR,16aS,Z)-14a-((cyclopropylsulfonyl)carbamoyl)-2-((7-methoxy-2-(4-methoxyphenyl)quinazolin-4-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 861.4 (M$^+$+1).

Compound 5002: tert-butyl ((2R,6S,7R,9R,13aR,14aR,16aS,Z)-14a-((cyclopropylsulfonyl)carbamoyl)-2-((7-methoxy-2-(4-methoxyphenyl)quinazolin-4-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-$d_6$) δ ppm 11.22 (br. s., 1H), 8.95 (br. s., 1H), 8.50 (d, J=8.9 Hz, 2H), 7.98 (d, J=9.2 Hz, 1H), 7.32 (d, J=2.4 Hz, 1H), 7.20 (d, J=7.6 Hz, 1H), 7.15-7.05 (m, 3H), 6.04 (br. s., 1H), 5.51 (br. s., 1H), 5.09 (br. s., 1H), 4.67 (d, J=10.4 Hz, 1H), 4.52-4.43 (m, 1H), 4.01-3.93 (m, 4H), 3.87 (s, 3H), 3.74-3.66 (m, 1H), 2.90 (s, 1H), 2.70-2.65 (br. s., 1H), 2.46-2.36 (m, 1H), 2.29 (d, J=12.5 Hz, 1H), 1.92 (s, 1H), 1.82 (d, J=5.5 Hz, 1H), 1.72 (br. s., 1H), 1.59 (br. s., 2H), 1.42-1.32 (m, 4H), 1.14-0.73 (m, 20H); MS: MS m/z 861.4 (M$^+$+1).

Compound 5003 and Compound 5004 were prepared using the intermediates described herein and by following the general procedure described for the synthesis of Compound 3117:

Compound 5003: tert-butyl ((2R,6S,7R,9S,13aS,14aR,16aS,Z)-14a-((cyclopropylsulfonyl)carbamoyl)-2-((4-methoxyphthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 755.34 (M$^+$+1).

Compound 5004: tert-butyl ((2R,6S,7R,9R,13aS,14aR,16aS,Z)-14a-((cyclopropylsulfonyl)carbamoyl)-2-((4-methoxyphthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-$d_6$) δ ppm 11.21 (br. s., 1H), 9.02 (br. s., 1H), 8.12 (d, J=7.9 Hz, 1H), 8.06 (d, J=7.9 Hz, 1H), 8.02-7.87 (m, 2H), 7.16 (d, J=7.6 Hz, 1H), 5.83 (br. s., 1H), 5.53 (br. s., 1H), 5.04 (br. s., 1H), 4.69 (d, J=11.0 Hz, 1H), 4.57-4.43 (m, 1H), 4.12 (s, 3H), 3.89 (dd, J=11.6, 3.1 Hz, 1H), 3.67 (dd, J=10.7, 8.2 Hz, 1H), 2.91 (d, J=7.9 Hz, 1H), 2.68 (d, J=6.4 Hz, 2H), 2.39-2.25 (m, 2H), 1.96-1.86 (m, 1H), 1.85-1.76 (m, 1H), 1.71 (br. s., 1H), 1.62 (br. s., 1H), 1.55 (br. s., 1H), 1.42 (br. s., 1H), 1.37 (br. s., 1H), 1.13-0.73 (m, 21H); MS: MS m/z 755.34 (M$^+$+1).

Preparation of Compound 5003 and Compound 5004

Compound 5003

Preparation of Compound 5005 and Compound 5006

Compound 5005

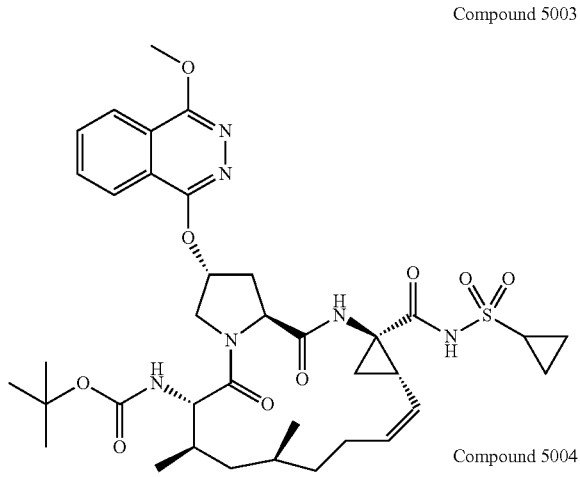

Compound 5004

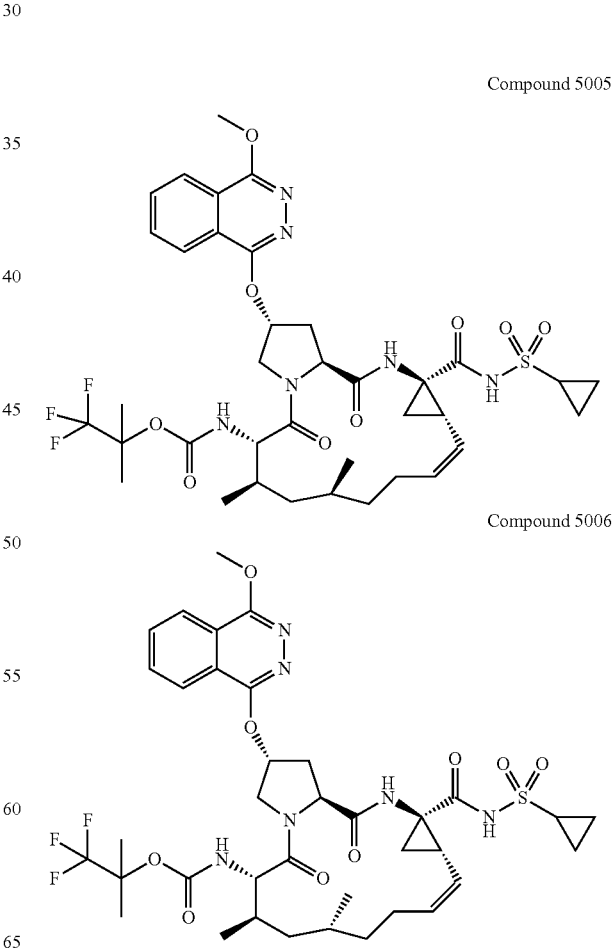

Compound 5006

Compound 5005 and Compound 5006 were prepared using the intermediates described herein and by following the general procedure described for the synthesis of Compound 3117:

Compound 5005: 1,1,1-trifluoro-2-methylpropan-2-yl ((2R,6S,7R,9S,13aS,14aR,16aS,Z)-14a-((cyclopropylsulfonyl)carbamoyl)-2-((4-methoxyphthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 809.3 ($M^+$+1).

Compound 5006: 1,1,1-trifluoro-2-methylpropan-2-yl ((2R,6S,7R,9R,13aS,14aR,16aS,Z)-14a-((cyclopropylsulfonyl)carbamoyl)-2-((4-methoxyphthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-$d_6$) δ ppm 11.21 (br. s., 1H), 9.05 (br. s., 1H), 8.13 (d, J=7.6 Hz, 1H), 8.07-7.93 (m, 3H), 7.81 (d, J=7.6 Hz, 1H), 5.84 (br. s., 1H), 5.54 (br. s., 1H), 5.05 (br. s., 1H), 4.62 (d, J=11.0 Hz, 1H), 4.56-4.47 (m, 1H), 4.12 (s, 3H), 3.95-3.86 (m, 1H), 3.67 (dd, J=10.7, 7.9 Hz, 1H), 2.99-2.88 (m, 1H), 2.66 (d, J=10.4 Hz, 2H), 2.40-2.23 (m, 2H), 1.95-1.78 (m, 2H), 1.71 (br. s., 1H), 1.62 (br. s., 1H), 1.57 (br. s., 1H), 1.48-1.32 (m, 2H), 1.27 (s, 3H), 1.14 (br. s., 3H), 1.05-0.85 (m, 11H), 0.75 (t, J=12.5 Hz, 1H); MS: MS m/z 809.3 ($M^+$+1).

Preparation of Compound 5007 and Compound 5008

Compound 5007 and Compound 5008 were prepared using the intermediates described herein and by following the general procedure described for the synthesis of Compound 3117:

Compound 5007: 1,1,1-trifluoro-2-methylpropan-2-yl ((2R,6S,7R,9S,13aS,14aR,16aS,Z)-2-((4-methoxyphthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 823.3 ($M^+$+1).

Compound 5008: 1,1,1-trifluoro-2-methylpropan-2-yl ((2R,6S,7R,9R,13aS,14aR,16aS,Z)-2-((4-methoxyphthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-$d_6$) δ ppm 11.06 (br. s., 1H), 9.17 (br. s., 1H), 8.14 (d, J=7.6 Hz, 1H), 8.04 (d, J=8.2 Hz, 1H), 8.02-7.94 (m, 2H), 7.82 (d, J=7.6 Hz, 1H), 5.85 (br. s., 1H), 5.52 (br. s., 1H), 4.99 (br. s., 1H), 4.63 (d, J=11.0 Hz, 1H), 4.55 (t, J=8.1 Hz, 1H), 4.12 (s, 3H), 3.96-3.89 (m, 1H), 3.67 (dd, J=10.5, 7.8 Hz, 1H), 2.67 (br. s., 2H), 2.35 (ddd, J=14.0, 10.4, 4.0 Hz, 2H), 1.92-1.79 (m, 2H), 1.70 (br. s., 1H), 1.61 (br. s., 1H), 1.50 (d, J=14.3 Hz, 1H), 1.41-1.17 (m, 11H), 0.98-0.76 (m, 12H); MS: MS m/z 823.3 ($M^+$+1).

Preparation of Compound 5009 and Compound 5010

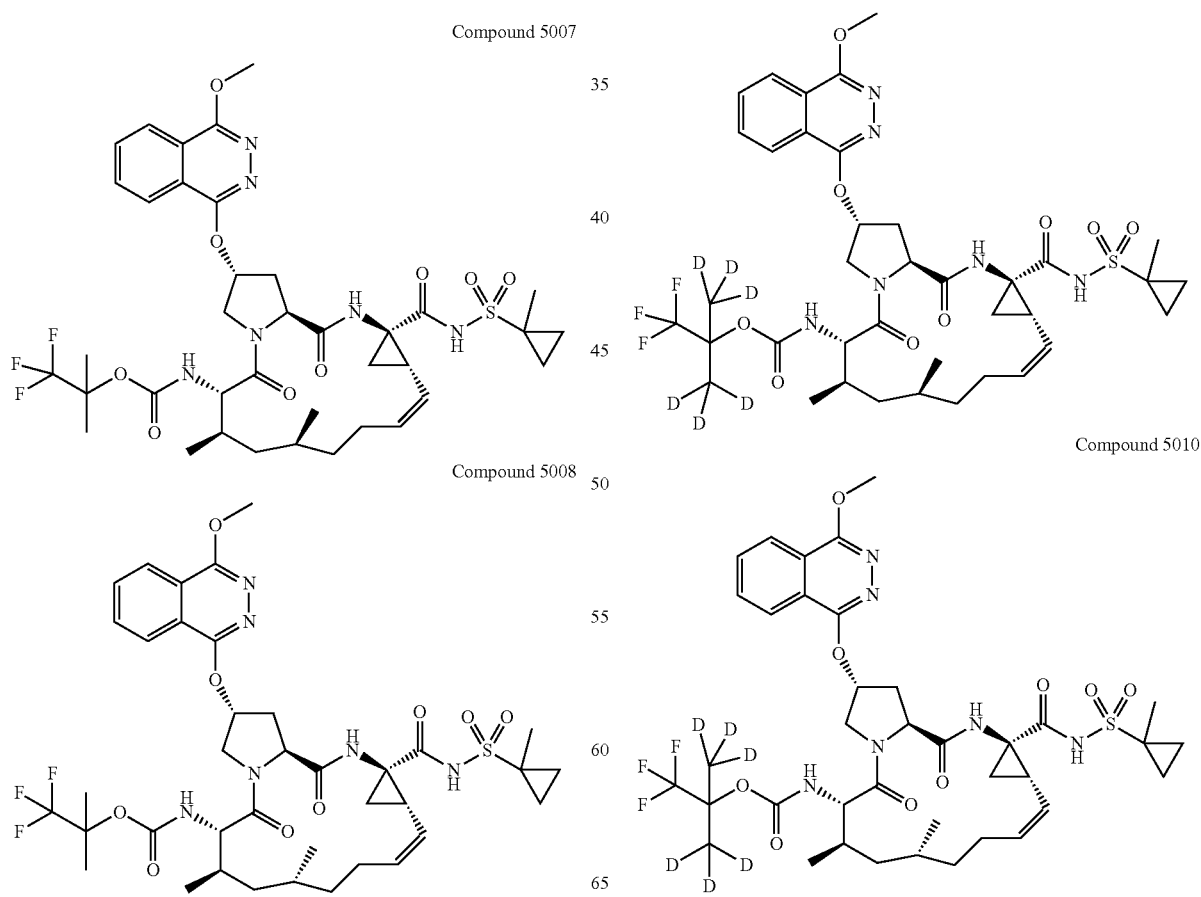

Compound 5007

Compound 5008

Compound 5009

Compound 5010

Compound 5009 and Compound 5010 were prepared using the intermediates described herein and by following the general procedure described for the synthesis of Compound 3117:

Compound 5009: MS: MS m/z 829.6 (M⁺+1).

Compound 5010: ¹H NMR (500 MHz, DMSO-d₆) δ ppm 11.06 (br. s., 1H), 9.18 (br. s., 1H), 8.14 (d, J=7.3 Hz, 1H), 8.04 (d, J=8.5 Hz, 1H), 8.02-7.94 (m, 2H), 7.82 (d, J=7.3 Hz, 1H), 5.85 (br. s., 1H), 5.52 (br. s., 1H), 4.99 (br. s., 1H), 4.63 (d, J=11.6 Hz, 1H), 4.55 (t, J=8.2 Hz, 1H), 3.95-3.88 (m, 1H), 3.67 (dd, J=10.7, 7.6 Hz, 1H), 2.67 (br. s., 2H), 2.35 (ddd, J=14.0, 10.2, 4.1 Hz, 2H), 1.96-1.79 (m, 2H), 1.70 (br. s., 1H), 1.62 (br. s., 1H), 1.52 (br. s., 1H), 1.41 (s, 5H), 1.34 (d, J=12.2 Hz, 2H), 1.31-1.21 (m, 1H), 1.16 (br. s., 2H), 0.98-0.83 (m, 8H), 0.76 (t, J=12.2 Hz, 2H); MS: MS m/z 829.6 (M⁺+1).

Preparation of Compound 5011 and Compound 5012 hexadecahydrocyclopropa[e]pyrrolo[1,2-a][1,4]diazacyclopentadecine-14a-carboxamide. MS: MS m/z 768.4 (M⁺+1).

Compound 5012: (2R,6S,7R,9R,13aS,14aR,16aS,Z)-6-(3-(tert-butyl)ureido)-2-((4-methoxyphthalazin-1-yl)oxy)-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. 1H NMR (500 MHz, DMSO-d₆) δ ppm 11.08 (br. s., 1H), 9.11 (br. s., 1H), 8.15-8.04 (m, 2H), 7.98 (t, J=7.2 Hz, 1H), 7.94-7.88 (m, 1H), 5.92 (d, J=8.5 Hz, 1H), 5.84 (br. s., 1H), 5.52 (s, 2H), 4.99 (br. s., 1H), 4.67 (br. s., 1H), 4.46 (br. s., 1H), 4.12 (s, 3H), 3.97-3.88 (m, 1H), 3.80 (t, J=9.5 Hz, 1H), 2.65 (br. s., 1H), 2.41-2.26 (m, 2H), 1.94-1.82 (m, 2H), 1.72 (br. s., 1H), 1.69-1.50 (m, 3H), 1.40 (br. s., 5H), 1.35 (br. s., 1H), 1.27 (br. s., 1H), 1.24-1.08 (m, 1H), 0.98-0.85 (m, 16H), 0.81 (br. s., 1H), 0.74 (t, J=11.7 Hz, 1H); MS: MS m/z 768.4 (M⁺+1).

Preparation of Compound 5013 and Compound 5014

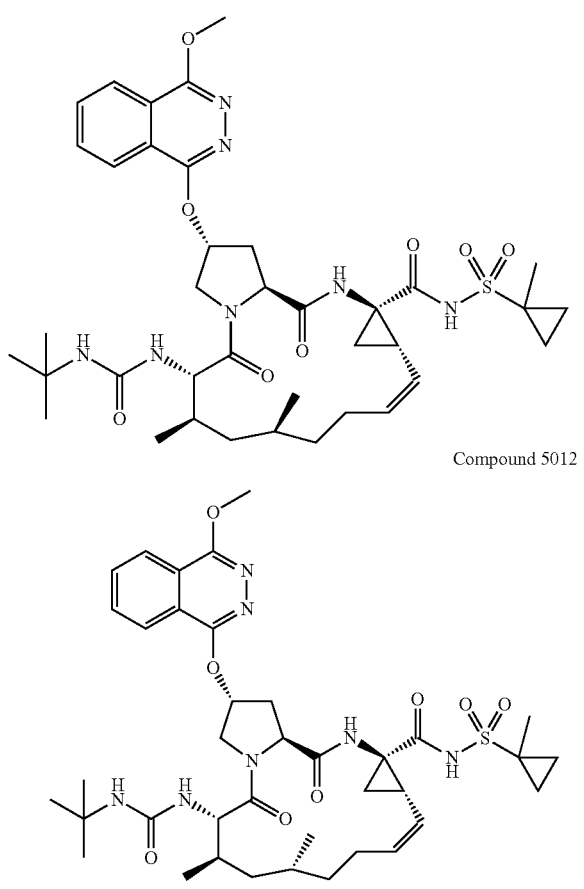

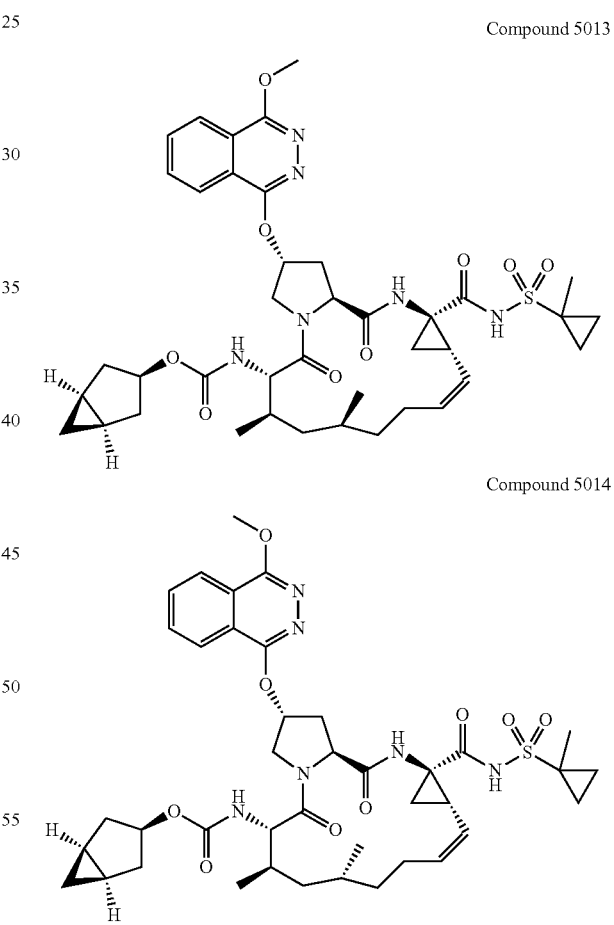

Compound 5011 and Compound 5012 were prepared using the intermediates described herein and by following the general procedure described for the synthesis of Compound 3117:

Compound 5011: (2R,6S,7R,9S,13aS,14aR,16aS,Z)-6-(3-(tert-butyl)ureido)-2-((4-methoxyphthalazin-1-yl)oxy)-7,9-dimethyl-N-((1-methylcyclopropyl)sulfonyl)-5,16-dioxo-1,2,3,5,6,7,8,9,10,11,13a,14,14a,15,16,16a-

Compound 5013 and Compound 5014 were prepared using the intermediates described herein and by following the general procedure described for the synthesis of Compound 3117:

Compound 5013: (1R,3r,5S)-bicyclo[3.1.0]hexan-3-yl ((2R,6S,7R,9S,13aS,14aR,16aS,Z)-2-((4-methoxyphthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 793.6 (M⁺+1).

Compound 5014: (1R,3r,5S)-bicyclo[3.1.0]hexan-3-yl ((2R,6S,7R,9R,13aS,14aR,16aS,Z)-2-((4-methoxyphthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (500 MHz, DMSO-d₆) δ ppm 11.06 (br. s., 1H), 9.10 (br. s., 1H), 8.14 (d, J=7.3 Hz, 1H), 8.08-7.92 (m, 3H), 7.38 (br. s., 1H), 5.86 (br. s., 1H), 5.52 (br. s., 1H), 4.99 (br. s., 1H), 4.51 (br. s., 2H), 4.43 (t, J=6.4 Hz, 1H), 4.13 (s, 3H), 3.97-3.92 (m, 1H), 3.77-3.67 (m, 1H), 2.67 (d, J=15.0 Hz, 2H), 2.40-2.24 (m, 2H), 1.99-1.77 (m, 4H), 1.74-1.59 (m, 3H), 1.52 (d, J=14.3 Hz, 2H), 1.41 (br. s., 5H), 1.30-1.23 (m, 2H), 1.21-1.12 (m, 2H), 1.12-1.05 (m, 1H), 0.93 (d, J=7.0 Hz, 4H), 0.87 (d, J=6.4 Hz, 4H), 0.74 (br. s., 1H), 0.36-0.24 (m, 2H); MS: MS m/z 793.6 (M⁺+1).

Preparation of Compound 5015 and Compound 5016

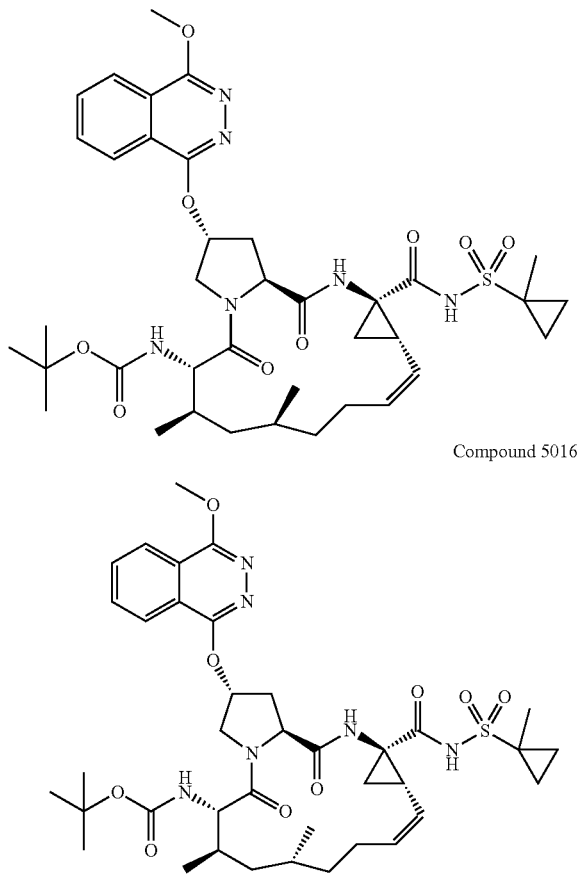

Compound 5015

Compound 5016

Compound 5015 and Compound 5016 were prepared using the intermediates described herein and by following the general procedure described for the synthesis of Compound 3117:

Compound 5015: tert-butyl ((2R,6S,7R,9S,13aS,14aR,16aS,Z)-2-((4-methoxyphthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 769.4 (M⁺+1).

Compound 5016: tert-butyl ((2R,6S,7R,9R,13aS,14aR,16aS,Z)-2-((4-methoxyphthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (500 MHz, DMSO-d₆) δ ppm 11.07 (br. s., 1H), 9.12 (br. s., 1H), 8.12 (d, J=7.9 Hz, 1H), 8.06 (d, J=7.9 Hz, 1H), 8.01-7.96 (m, 1H), 7.95-7.90 (m, 1H), 7.17 (d, J=7.3 Hz, 1H), 5.83 (br. s., 1H), 5.51 (br. s., 1H), 5.00 (br. s., 1H), 4.68 (d, J=11.0 Hz, 1H), 4.51 (br. s., 1H), 4.12 (s, 3H), 3.93-3.88 (m, 1H), 3.67 (dd, J=10.4, 8.2 Hz, 1H), 2.65 (br. s., 2H), 2.40-2.27 (m, 2H), 1.94-1.85 (m, 1H), 1.80 (d, J=6.4 Hz, 1H), 1.70 (br. s., 1H), 1.60 (br. s., 1H), 1.50 (br. s., 1H), 1.41 (br. s., 5H), 1.35-1.15 (m, 3H), 1.03 (s, 9H), 0.97-0.81 (m, 8H), 0.73 (t, J=12.4 Hz, 1H); MS: MS m/z 769.4 (M⁺+1).

Preparation of Compound 5017 and Compound 5018

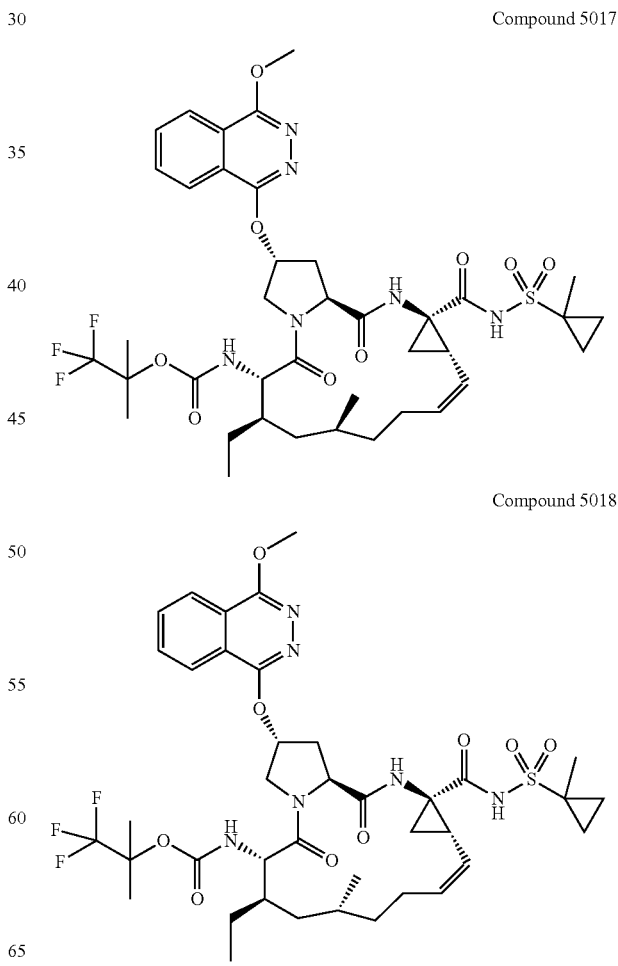

Compound 5017

Compound 5018

Compound 5017 and Compound 5018 were prepared using the intermediates described herein and by following the general procedure described for the synthesis of Compound 3117:

Compound 5017: 1,1,1-trifluoro-2-methylpropan-2-yl ((2R,6S,7R,9S,13aS,14aR,16aS,Z)-7-ethyl-2-((4-methoxyphthalazin-1-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 837.3 (M$^+$+1).

Compound 5018: 1,1,1-trifluoro-2-methylpropan-2-yl ((2R,6S,7R,9R,13aS,14aR,16aS,Z)-7-ethyl-2-((4-methoxyphthalazin-1-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
$^1$H NMR (500 MHz, DMSO-d$_6$) δ ppm 11.06 (br. s., 1H), 9.17 (br. s., 1H), 8.14 (d, J=7.3 Hz, 1H), 8.06-7.94 (m, 3H), 7.87 (d, J=7.9 Hz, 1H), 5.87 (br. s., 1H), 5.53 (br. s., 1H), 4.98 (br. s., 1H), 4.63 (d, J=11.6 Hz, 1H), 4.60-4.48 (m, 1H), 4.13 (s, 3H), 3.99-3.90 (m, 1H), 3.86 (dd, J=10.7, 8.5 Hz, 1H), 2.72-2.61 (m, 2H), 2.41-2.25 (m, 2H), 2.01-1.83 (m, 2H), 1.63 (br. s., 1H), 1.58-1.40 (m, 8H), 1.36 (d, J=13.1 Hz, 2H), 1.29 (s, 4H), 1.18 (br. s., 1H), 1.02 (t, J=11.9 Hz, 1H), 0.96-0.86 (m, 8H), 0.73 (t, J=7.5 Hz, 3H); MS: MS m/z 837.3 (M$^+$+1).

Compound 5019 and Compound 5020 were prepared using the intermediates described herein and by following the general procedure described for the synthesis of Compound 3117:

Compound 5019: MS: MS m/z 843.5 (M$^+$+1).

Compound 5020: $^1$H NMR (500 MHz, DMSO-d$_6$) δ ppm 11.06 (br. s., 1H), 9.17 (br. s., 1H), 8.14 (d, J=7.6 Hz, 1H), 8.06-7.93 (m, 3H), 7.86 (d, J=8.2 Hz, 1H), 5.87 (br. s., 1H), 5.53 (br. s., 1H), 4.98 (br. s., 1H), 4.63 (d, J=11.9 Hz, 1H), 4.55 (d, J=7.3 Hz, 1H), 4.17-4.07 (m, 3H), 3.98-3.91 (m, 1H), 3.90-3.81 (m, 1H), 2.67 (d, J=18.3 Hz, 2H), 2.41-2.24 (m, 2H), 2.00-1.85 (m, 2H), 1.62 (br. s., 1H), 1.51 (br. s., 2H), 1.46 (br. s., 2H), 1.42 (br. s., 5H), 1.35 (br. s., 1H), 1.32-1.22 (m, 1H), 1.18 (br. s., 1H), 1.08-0.98 (m, 1H), 0.93 (d, J=6.4 Hz, 5H), 0.73 (t, J=7.5 Hz, 3H); MS: MS m/z 843.5 (M$^+$+1).

Preparation of Compound 5021 and Compound 5022

Compound 5019

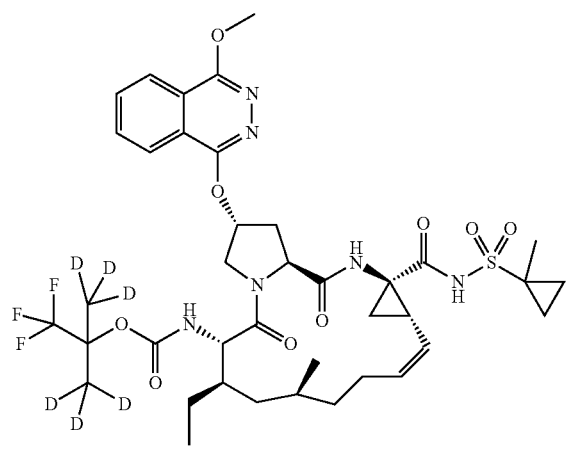

Compound 5020

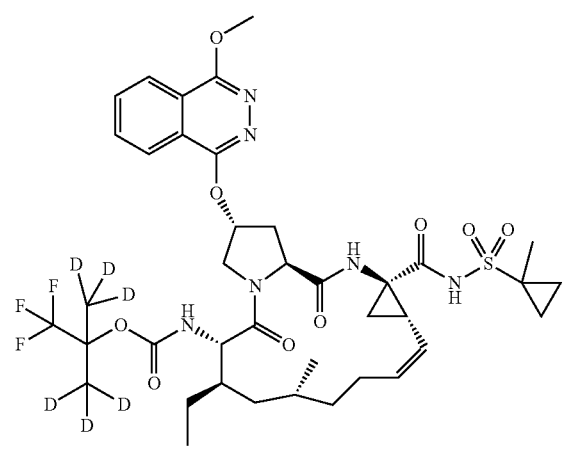

Compound 5021

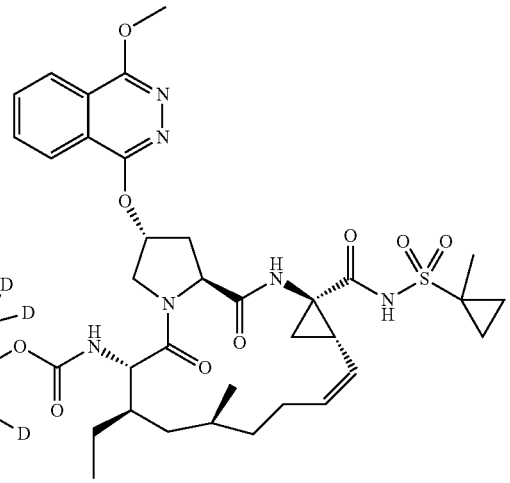

Compound 5022

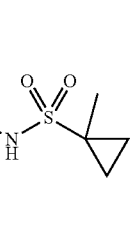

Compound 5021 and Compound 5022 were prepared using the intermediates described herein and by following the general procedure described for the synthesis of Compound 3117:

Compound 5021: MS: MS m/z 789.5 (M$^+$+1).

Compound 5022: $^1$H NMR (500 MHz, DMSO-d$_6$) δ ppm 11.07 (br. s., 1H), 9.14 (br. s., 1H), 8.12 (d, J=7.9 Hz, 1H), 8.04 (d, J=7.6 Hz, 1H), 8.01-7.90 (m, 2H), 7.18 (d, J=7.6 Hz, 1H), 5.85 (br. s., 1H), 5.52 (br. s., 1H), 4.99 (br. s., 1H), 4.70 (d, J=10.7 Hz, 1H), 4.51 (d, J=6.7 Hz, 1H), 4.12 (s, 4H), 4.01-3.82 (m, 2H), 2.75 (s, 1H), 2.66 (br. s., 2H), 2.41-2.25 (m, 2H), 1.92 (s, 2H), 1.61-1.10 (m, 11H), 1.01-0.73 (m, 12H); MS: MS m/z 789.5 (M$^+$+1).

Preparation of Compound 5023 and Compound 5024

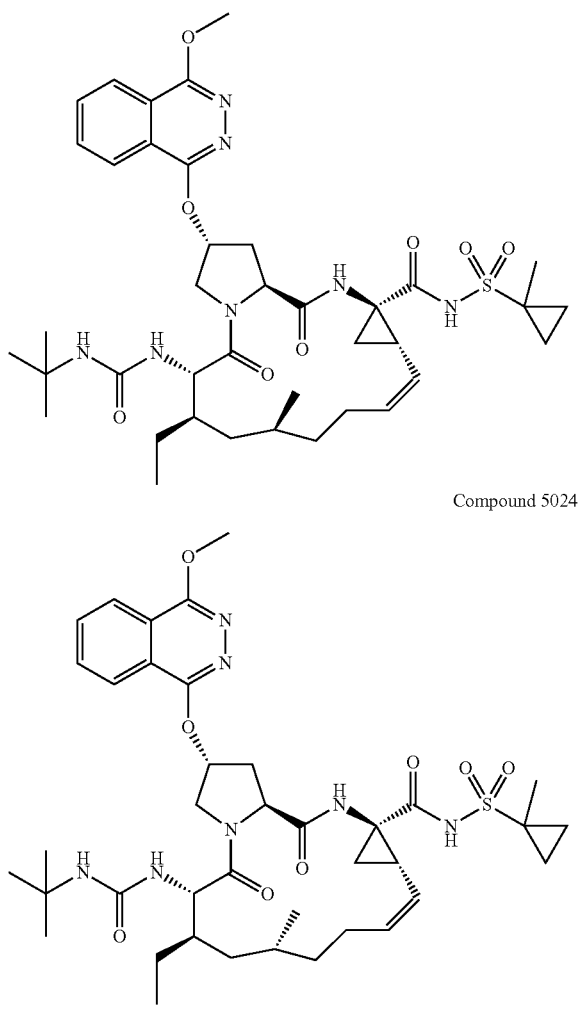

Compound 5023

Compound 5024

Compound 5023 and Compound 5024 were prepared using the intermediates described herein and by following the general procedure described for the synthesis of Compound 3117:

Compound 5023: (2R,6S,7R,9S,13aS,14aR,16aS,Z)-6-(3-(tert-butyl)ureido)-7-ethyl-2-((4-methoxyphthalazin-1-yl)oxy)-9-methyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. MS: MS m/z 782.5 (M$^+$+1).

Compound 5024: (2R,6S,7R,9R,13aS,14aR,16aS,Z)-6-(3-(tert-butyl)ureido)-7-ethyl-2-((4-methoxyphthalazin-1-yl)oxy)-9-methyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (500 MHz, DMSO-d$_6$) δ ppm 11.07 (br. s., 1H), 9.10 (br. s., 1H), 8.12 (d, J=8.2 Hz, 1H), 8.05 (d, J=7.9 Hz, 1H), 8.01-7.96 (m, 1H), 7.94-7.87 (m, 1H), 5.93 (d, J=8.9 Hz, 1H), 5.85 (br. s., 1H), 5.52 (s, 2H), 4.99 (br. s., 1H), 4.70 (d, J=11.3 Hz, 1H), 4.48 (t, J=8.1 Hz, 1H), 4.12 (s, 3H), 4.01 (t, J=9.9 Hz, 1H), 3.96-3.90 (m, 1H), 2.68 (m, 2H), 2.40-2.28 (m, 2H), 1.96-1.86 (m, 1H), 1.74 (br. s., 1H), 1.60 (br. s., 1H), 1.55-1.18 (m, 13H), 1.06-0.86 (m, 14H), 0.78 (t, J=7.5 Hz, 3H); MS: MS m/z 782.5 (M$^+$+1).

Preparation of Compound 5025 and Compound 5026

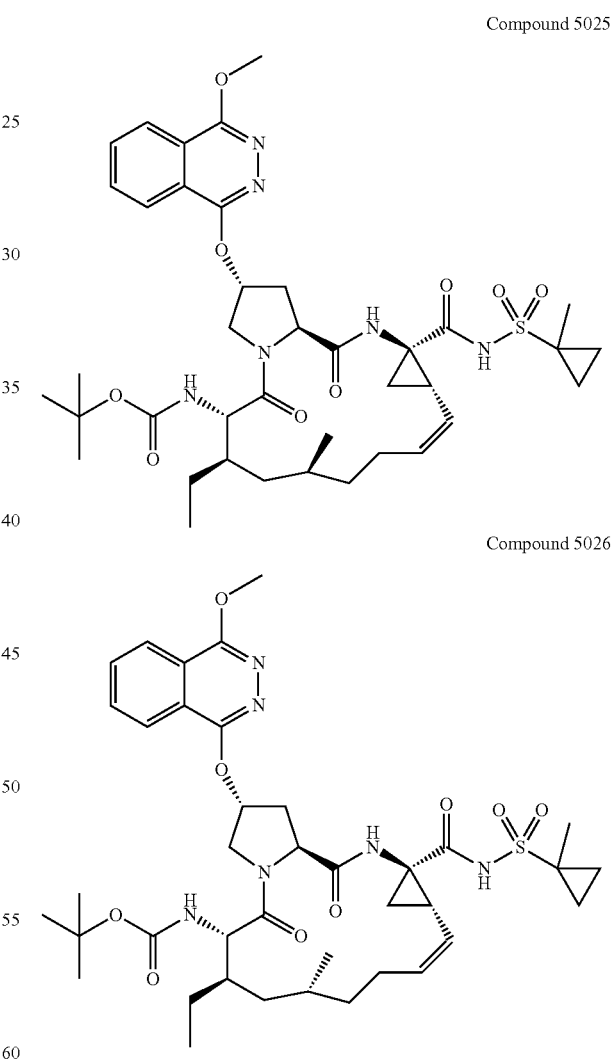

Compound 5025

Compound 5026

Compound 5025 and Compound 5026 were prepared using the intermediates described herein and by following the general procedure described for the synthesis of Compound 3117:

Compound 5025: tert-butyl ((2R,6S,7R,9S,13aS,14aR,16aS,Z)-7-ethyl-2-((4-methoxyphthalazin-1-yl)oxy)-9- methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 783.5 (M$^+$+1).

Compound 5026: tert-butyl ((2R,6S,7R,9R,13aS,14aR,16aS,Z)-7-ethyl-2-((4-methoxyphthalazin-1-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.07 (br. s., 1H), 9.14 (br. s., 1H), 8.12 (d, J=7.9 Hz, 1H), 8.04 (d, J=7.6 Hz, 1H), 8.01-7.89 (m, 2H), 7.19 (d, J=7.9 Hz, 1H), 5.86 (br. s., 1H), 5.54 (br. s., 1H), 4.97 (br. s., 1H), 4.71 (d, J=11.9 Hz, 1H), 4.52 (d, J=7.3 Hz, 1H), 3.98-3.84 (m, 2H), 2.69 (br. s., 2H), 2.41-2.26 (m, 2H), 1.92 (s, 2H), 1.62-1.15 (m, 14H), 1.02-0.86 (m, 17H), 0.73 (t, J=7.5 Hz, 3H); MS: MS m/z 783.5 (M$^+$+1).

Preparation of Compound 5027

Compound 5027

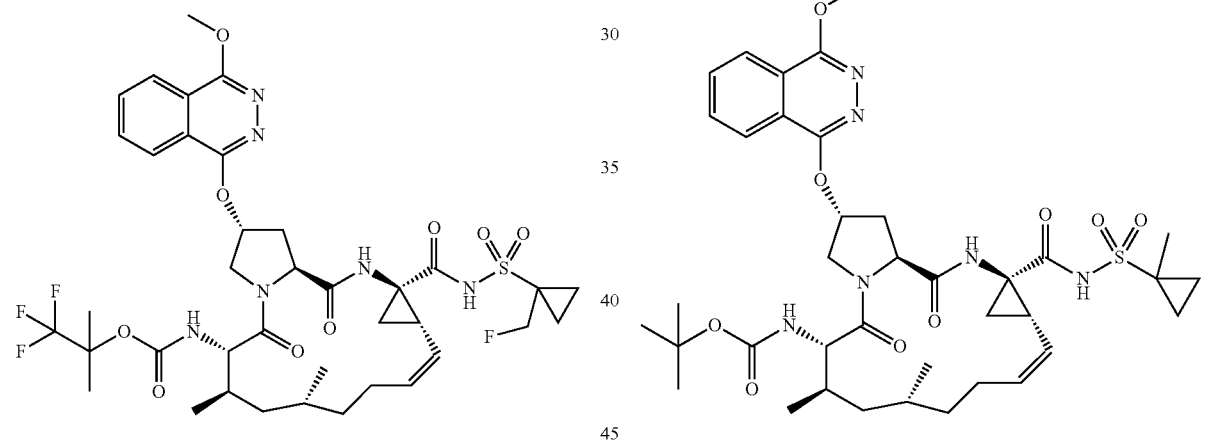

Compound 5027 was prepared using the intermediates described herein and by following the general procedure described for the synthesis of Compound 3117:

Compound 5027: 1,1,1-trifluoro-2-methylpropan-2-yl ((2R,6S,7R,9R,13aS,14aR,16aS,Z)-14a-(((1-(fluoromethyl)cyclopropyl)sulfonyl)carbamoyl)-2-((4-methoxyphthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.30 (br. s., 1H), 9.10 (br. s., 1H), 8.14 (d, J=7.6 Hz, 1H), 8.06-7.93 (m, 3H), 7.83 (d, J=7.0 Hz, 1H), 5.84 (br. s., 1H), 5.52 (br. s., 1H), 4.99 (br. s., 1H), 4.88-4.76 (m, 1H), 4.67-4.52 (m, 3H), 4.16-4.09 (m, 3H), 3.94-3.88 (m, 1H), 3.68 (dd, J=10.7, 7.9 Hz, 1H), 3.18 (d, J=5.2 Hz, 1H), 2.65 (m, 2H), 2.40-2.27 (m, 2H), 1.90-1.77 (m, 2H), 1.70 (br. s., 1H), 1.54 (br. s., 3H), 1.41 (br. s., 1H), 1.37 (br. s., 1H), 1.31-1.21 (m, 5H), 1.16 (br. s., 1H), 0.99 (s, 3H), 0.94 (d, J=6.7 Hz, 3H), 0.89 (d, J=6.1 Hz, 3H), 0.80-0.72 (m, 1H); MS: MS m/z 841.6 (M$^+$+1).

Preparation of Compound 5028 and Compound 5029

Compound 5028

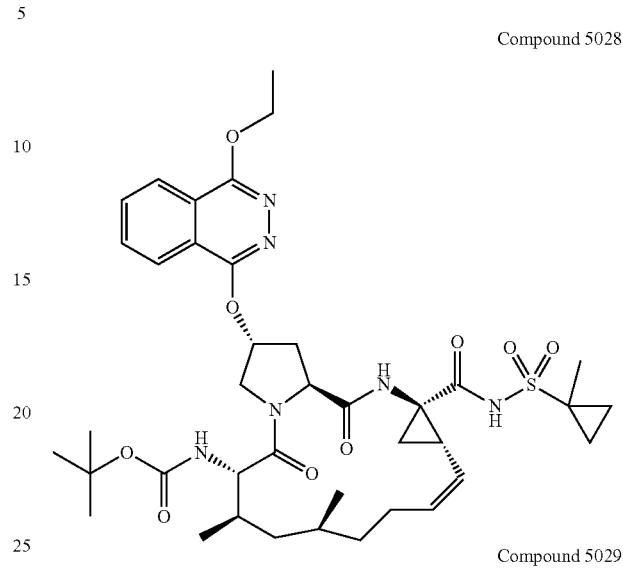

Compound 5029

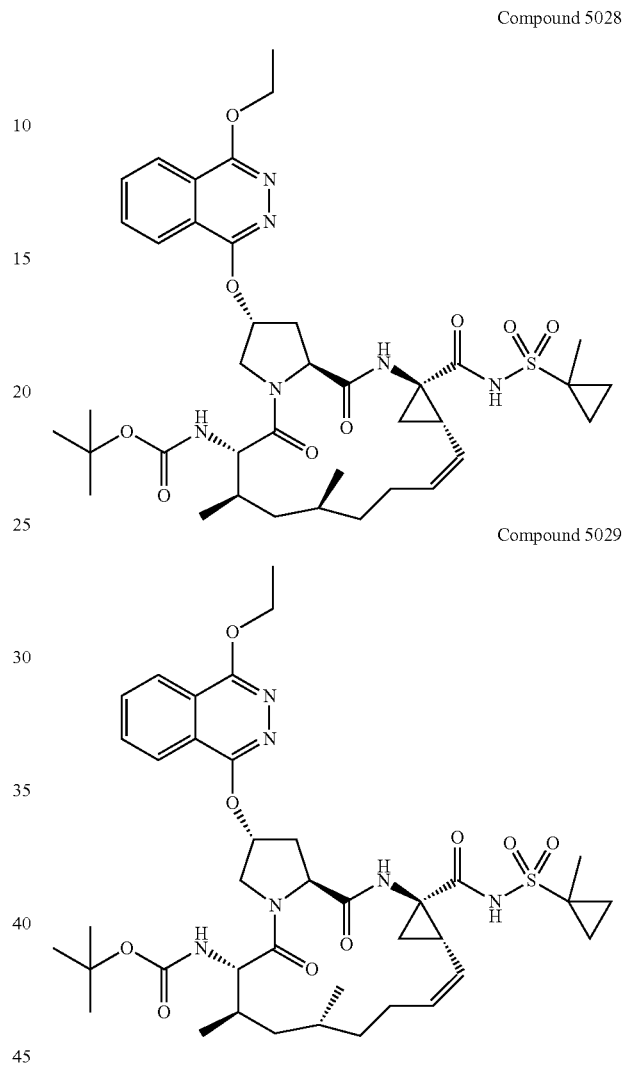

Compound 5028 and Compound 5029 were prepared using the intermediates described herein and by following the general procedure described for the synthesis of Compound 3117:

Compound 5028: tert-butyl ((2R,6S,7R,9S,13aS,14aR,16aS,Z)-2-((4-ethoxyphthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 783.4 (M$^+$+1).

Compound 5029: tert-butyl ((2R,6S,7R,9R,13aS,14aR,16aS,Z)-2-((4-ethoxyphthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.07 (br. s., 1H), 9.14 (br. s., 1H), 8.12 (d, J=7.9 Hz, 1H), 8.05 (d, J=7.9 Hz, 1H), 8.00-7.95 (m, 1H), 7.95-7.89 (m, 1H), 7.17 (d, J=7.3 Hz, 1H), 5.83 (br. s., 1H), 5.52 (br. s., 1H), 4.97 (br. s., 1H), 4.74-4.65 (m, 1H), 4.61-4.47 (m, 3H), 3.94-3.87 (m, 1H), 3.68 (dd, J=10.7, 8.2 Hz, 1H), 2.67 (br. s., 2H), 2.40-2.21 (m, 2H), 1.94-1.86 (m, 1H), 1.81 (d, J=6.1 Hz, 1H), 1.69 (br. s., 1H), 1.62 (br. s., 1H), 1.52-1.09 (m, 12H), 1.03 (s, 9H), 0.93-0.88 (m, 8H), 0.74 (t, J=12.2 Hz, 1H); MS: MS m/z 783.4 (M$^+$+1).

Preparation of Compound 5030 and Compound 5031

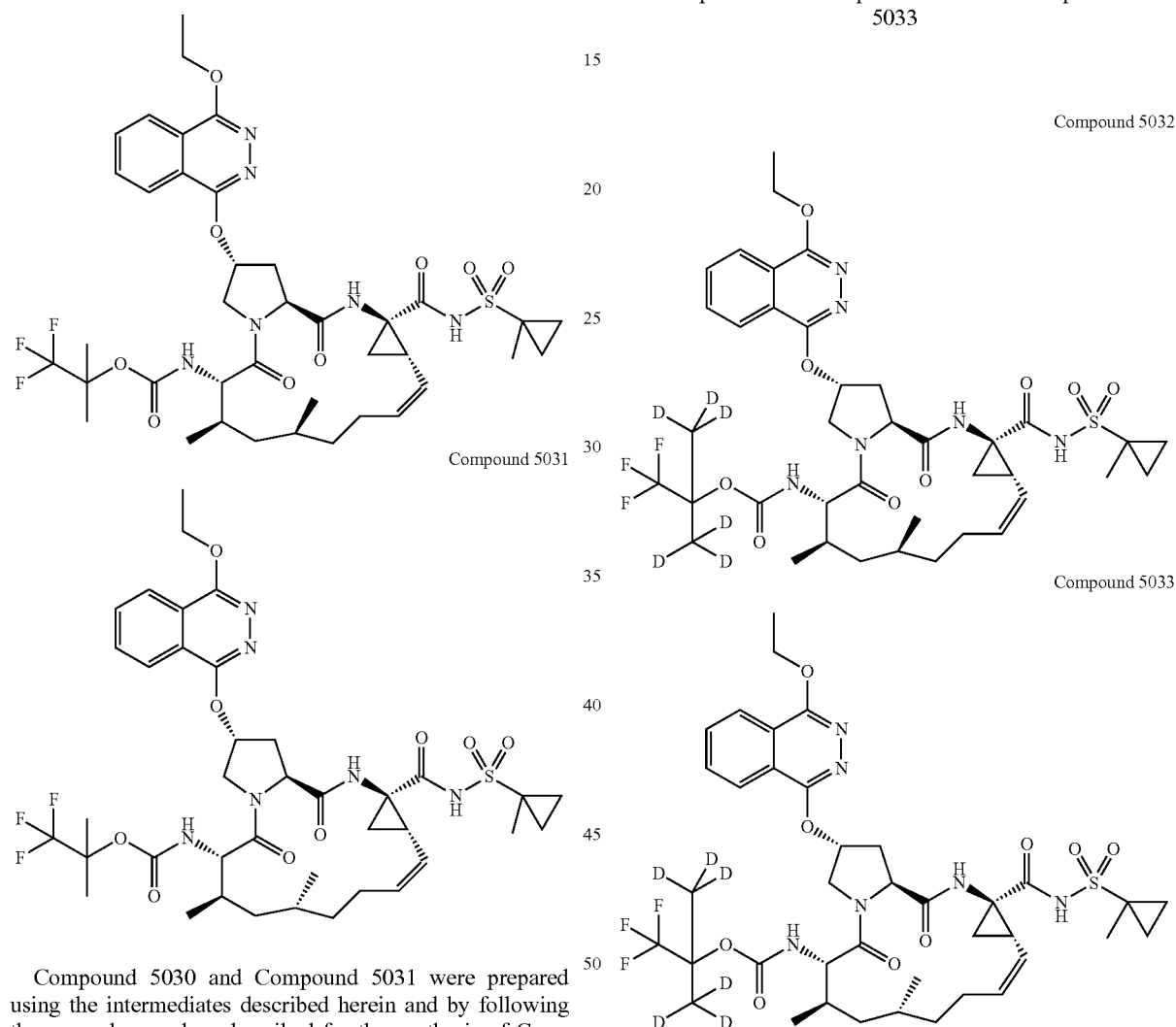

Compound 5030 and Compound 5031 were prepared using the intermediates described herein and by following the general procedure described for the synthesis of Compound 3117:

Compound 5030: 1,1,1-trifluoro-2-methylpropan-2-yl ((2R,6S,7R,9S,13aS,14aR,16aS,Z)-2-((4-ethoxyphthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 837.3 (M$^+$+1).

Compound 5031: 1,1,1-trifluoro-2-methylpropan-2-yl ((2R,6S,7R,9R,13aS,14aR,16aS,Z)-2-((4-ethoxyphthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.05 (br. s., 1H), 9.17 (br. s., 1H), 8.13 (d, J=7.3 Hz, 1H), 8.06-7.92 (m, 3H), 7.82 (d, J=7.3 Hz, 1H), 5.84 (br. s., 1H), 5.53 (br. s., 1H), 4.99 (br. s., 1H), 4.67-4.60 (m, 1H), 4.60-4.50 (m, 3H), 3.96-3.86 (m, 1H), 3.68 (dd, J=10.8, 7.8 Hz, 1H), 2.67 (br. s., 2H), 2.35 (ddd, J=13.9, 10.4, 4.1 Hz, 2H), 1.93-1.79 (m, 2H), 1.70 (br. s., 1H), 1.61 (br. s., 1H), 1.52 (br. s., 1H), 1.47 (t, J=7.0 Hz, 4H), 1.41 (br. s., 4H), 1.35-1.15 (m, 7H), 0.96 (s, 3H), 0.93 (d, J=7.0 Hz, 3H), 0.89 (d, J=6.4 Hz, 4H), 0.76 (t, J=12.1 Hz, 1H); MS: MS m/z 837.3 (M$^+$+1).

Preparation of Compound 5032 and Compound 5033

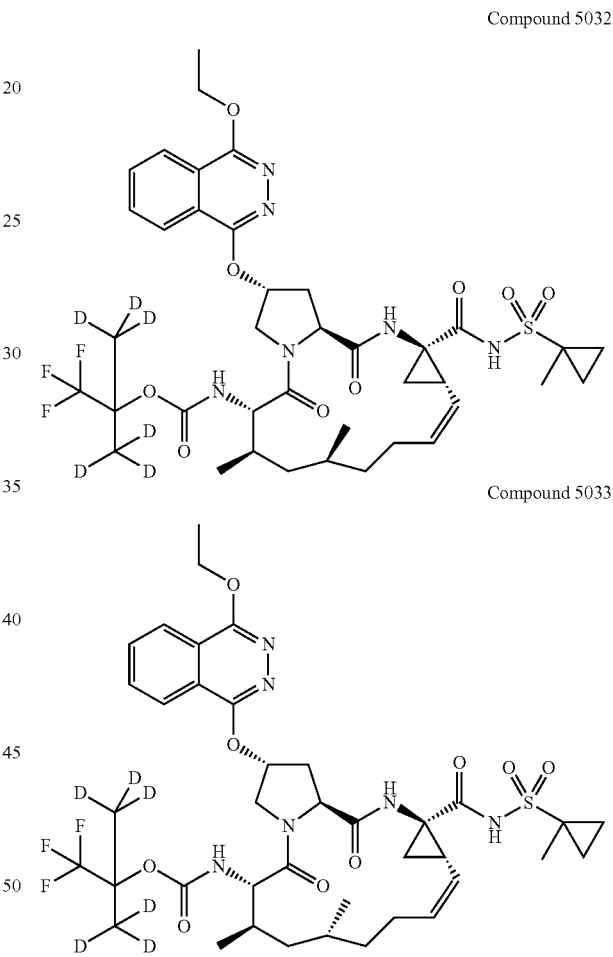

Compound 5032 and Compound 5033 were prepared using the intermediates described herein and by following the general procedure described for the synthesis of Compound 3117:

Compound 5032: MS: MS m/z 843.5 (M$^+$+1).

Compound 5033: $^1$H NMR (500 MHz, DMSO-d$_6$) δ ppm 11.06 (br. s., 1H), 9.17 (br. s., 1H), 8.13 (d, J=7.3 Hz, 1H), 8.06-7.92 (m, 3H), 7.82 (d, J=7.6 Hz, 1H), 5.84 (br. s., 1H), 5.54 (d, J=4.9 Hz, 1H), 4.98 (br. s., 1H), 4.64 (d, J=11.6 Hz, 1H), 4.59-4.47 (m, 3H), 3.97-3.89 (m, 1H), 3.68 (dd, J=10.7, 7.9 Hz, 1H), 2.68 (br. s., 2H), 2.41-2.28 (m, 2H), 1.94-1.79 (m, 2H), 1.74-1.67 (m, 1H), 1.63 (br. s., 1H), 1.53 (br. s., 1H), 1.47 (t, J=7.0 Hz, 4H), 1.42 (s, 4H), 1.37-11.14 (m, 4H), 0.93 (d, J=7.0 Hz, 3H), 0.89 (d, J=6.1 Hz, 4H), 0.76 (t, J=12.5 Hz, 1H); MS: MS m/z 843.5 (M⁺+1).

Preparation of Compound 5034 and Compound 5035

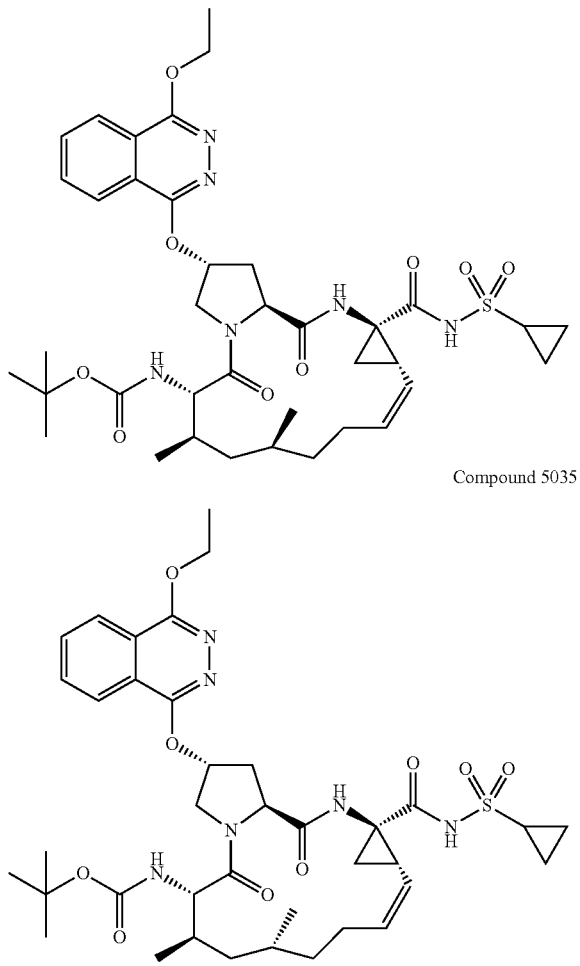

Compound 5034

Compound 5035

Compound 5034 and Compound 5035 were prepared using the intermediates described herein and by following the general procedure described for the synthesis of Compound 3117:

Compound 5034: tert-butyl ((2R,6S,7R,9S,13aS,14aR, 16aS,Z)-14a-((cyclopropylsulfonyl)carbamoyl)-2-((4-ethoxyphthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 769.4 (M⁺+1).

Compound 5035: tert-butyl ((2R,6S,7R,9R,13aS,14aR, 16aS,Z)-14a-((cyclopropylsulfonyl)carbamoyl)-2-((4-ethoxyphthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (500 MHz, DMSO-d₆) δ ppm 11.21 (br. s., 1H), 9.02 (br. s., 1H), 8.12 (d, J=8.2 Hz, 1H), 8.05 (d, J=7.9 Hz, 1H), 7.98 (t, J=7.0 Hz, 1H), 7.95-7.89 (m, 1H), 7.16 (d, J=7.0 Hz, 1H), 5.82 (br. s., 1H), 5.53 (br. s., 1H), 5.05 (br. s., 1H), 4.69 (d, J=10.7 Hz, 1H), 4.61-4.52 (m, 2H), 4.51-4.42 (m, 1H), 3.95-3.86 (m, 1H), 3.68 (dd, J=10.4, 8.5 Hz, 1H), 2.91 (d, J=6.4 Hz, 1H), 2.68 (br. s., 2H), 2.42-2.23 (m, 2H), 1.96-1.86 (m, 1H), 1.85-1.76 (m, 1H), 1.72 (br. s., 1H), 1.61 (br. s., 1H), 1.55 (br. s., 1H), 1.49-1.39 (m, 4H), 1.36 (br. s., 1H), 1.13 (br. s., 2H), 1.05 (s, 10H), 1.00 (br. s., 1H), 0.94 (d, J=7.0 Hz, 4H), 0.88 (d, J=6.1 Hz, 3H), 0.73 (t, J=12.1 Hz, 1H); MS: MS m/z 769.4 (M⁺+1).

Preparation of Compound 5036 and Compound 5037

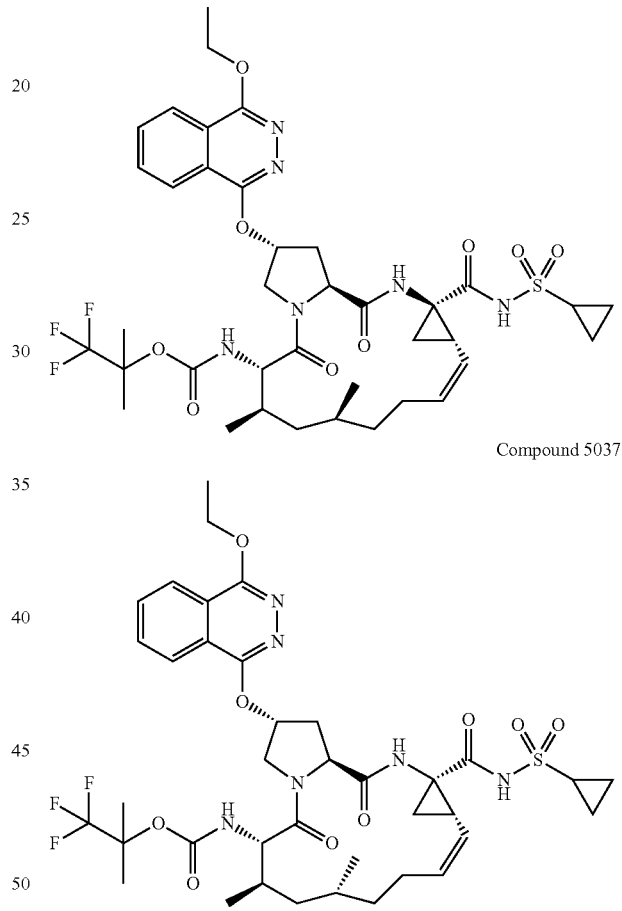

Compound 5036

Compound 5037

Compound 5036 and Compound 5037 were prepared using the intermediates described herein and by following the general procedure described for the synthesis of Compound 3117:

Compound 5036: 1,1,1-trifluoro-2-methylpropan-2-yl ((2R,6S,7R,9S,13aS,14aR,16aS,Z)-14a-((cyclopropylsulfonyl)carbamoyl)-2-((4-ethoxyphthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 823.3 (M⁺+1).

Compound 5037: 1,1,1-trifluoro-2-methylpropan-2-yl ((2R,6S,7R,9R,13aS,14aR,16aS,Z)-14a-((cyclopropylsulfonyl)carbamoyl)-2-((4-ethoxyphthalazin-1-yl)oxy)-7,9-dimethyl-5,16-dioxo-1,2,3,5,6,7,8,9,10,11,13a,14,14a,15,16, 16a-hexadecahydrocyclopropa[e]pyrrolo[1,2-a][1,4]diazacyclopentadecin-6-yl)carbamate. ¹H NMR (500 MHz, DMSO-d₆) δ ppm 11.20 (br. s., 1H), 9.04 (br. s., 1H), 8.17-8.10 (m, 1H), 8.06-7.90 (m, 3H), 7.81 (br. s., 1H), 5.82 (br. s., 1H), 5.52 (br. s., 1H), 5.06 (br. s., 1H), 4.66-4.45 (m, 4H), 3.93-3.81 (m, 1H), 3.74-3.60 (m, 1H), 2.91 (br. s., 1H), 2.67 (br. s., 2H), 2.34 (dd, J=14.5, 10.5 Hz, 2H), 1.95-1.82 (m, 2H), 1.71 (br. s., 1H), 1.59 (d, J=19.2 Hz, 2H), 1.46-1.36 (m, 4H), 1.28 (d, J=6.4 Hz, 3H), 1.20-1.13 (br. s., 3H), 1.03-0.85 (m, 12H), 0.74 (br. s., 1H); MS: MS m/z 823.3 (M⁺+1).

Preparation of Compound 5038 and Compound 5039

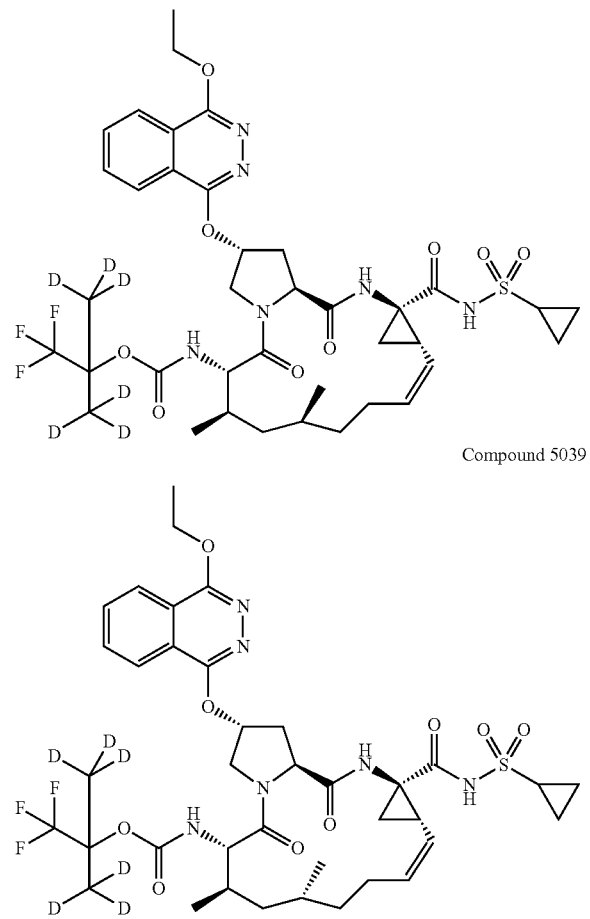

Compound 5038

Compound 5039

Compound 5038 and Compound 5037 were prepared using the intermediates described herein and by following the general procedure described for the synthesis of Compound 3117:

Compound 5038: MS: MS m/z 829.5 (M⁺+1).
Compound 5039: ¹H NMR (500 MHz, DMSO-d₆) δ ppm 11.20 (br. s., 1H), 9.04 (br. s., 1H), 8.13 (d, J=7.6 Hz, 1H), 8.07-7.92 (m, 3H), 7.81 (d, J=7.9 Hz, 1H), 5.83 (br. s., 1H), 5.53 (br. s., 1H), 5.06 (br. s., 1H), 4.67-4.44 (m, 4H), 3.96-3.84 (m, 1H), 3.68 (dd, J=10.8, 7.8 Hz, 1H), 2.91 (d, J=5.8 Hz, 1H), 2.67 (br. s., 2H), 2.40-2.23 (m, 2H), 1.94-1.78 (m, 2H), 1.71 (br. s., 1H), 1.61 (br. s., 1H), 1.56 (br. s., 1H), 1.47 (t, J=7.2 Hz, 3H), 1.42 (br. s., 1H), 1.35 (d, J=13.1 Hz, 1H), 1.18-0.99 (m, 5H), 0.94 (d, J=7.0 Hz, 3H), 0.89 (d, J=6.4 Hz, 3H), 0.75 (t, J=12.2 Hz, 1H); MS: MS m/z 829.5 (M⁺+1).

Preparation of Compound 5040 and Compound 5041

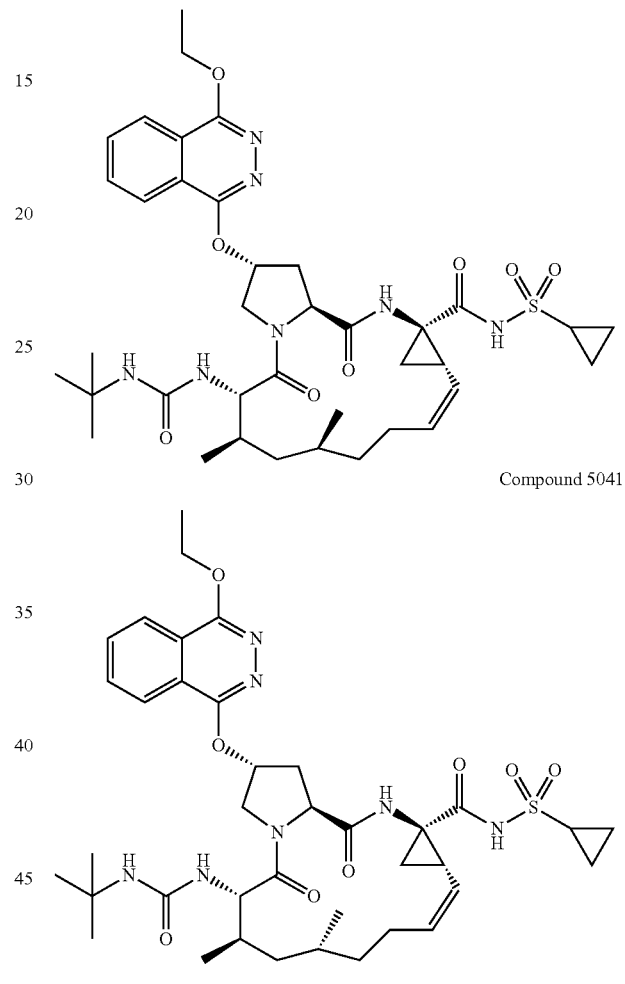

Compound 5040

Compound 5041

Compound 5040 and Compound 5041 were prepared using the intermediates described herein and by following the general procedure described for the synthesis of Compound 3117:

Compound 5040: (2R,6S,7R,9S,13aS,14aR,16aS,Z)-6-(3-(tert-butyl)ureido)-N-(cyclopropylsulfonyl)-2-((4-ethoxyphthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. MS: MS m/z 768.4 (M⁺+1).

Compound 5041: (2R,6S,7R,9R,13aS,14aR,16aS,Z)-6-(3-(tert-butyl)ureido)-N-(cyclopropylsulfonyl)-2-((4-ethoxyphthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. ¹H NMR (500

MHz, DMSO-$d_6$) δ ppm 11.21 (br. s., 1H), 8.98 (br. s., 1H), 8.11 (d, J=7.9 Hz, 1H), 8.06 (d, J=7.9 Hz, 1H), 8.00-7.93 (m, 1H), 7.92-7.85 (m, 1H), 5.92 (d, J=8.9 Hz, 1H), 5.83 (br. s., 1H), 5.52 (s, 2H), 5.05 (br. s., 1H), 4.68 (d, J=11.0 Hz, 1H), 4.56 (dtt, J=10.5, 7.0, 3.5 Hz, 2H), 4.49-4.39 (m, 1H), 3.94-3.87 (m, 1H), 3.83-3.75 (m, 1H), 2.91 (d, J=6.4 Hz, 1H), 2.69 (d, J=10.4 Hz, 2H), 2.39-2.23 (m, 2H), 1.96-1.85 (m, 1H), 1.71 (d, J=6.1 Hz, 1H), 1.63 (dd, J=18.6, 6.4 Hz, 2H), 1.54 (br. s., 1H), 1.47 (t, J=7.0 Hz, 4H), 1.44-1.32 (m, 2H), 1.14 (br. s., 2H), 1.08 (br. s., 2H), 0.98-0.93 (m, 12H), 0.90 (d, J=6.4 Hz, 3H), 0.74 (t, J=12.5 Hz, 1H); MS: MS m/z 768.4 (M$^+$+1).

Preparation of Compound 5042 and Compound 5043

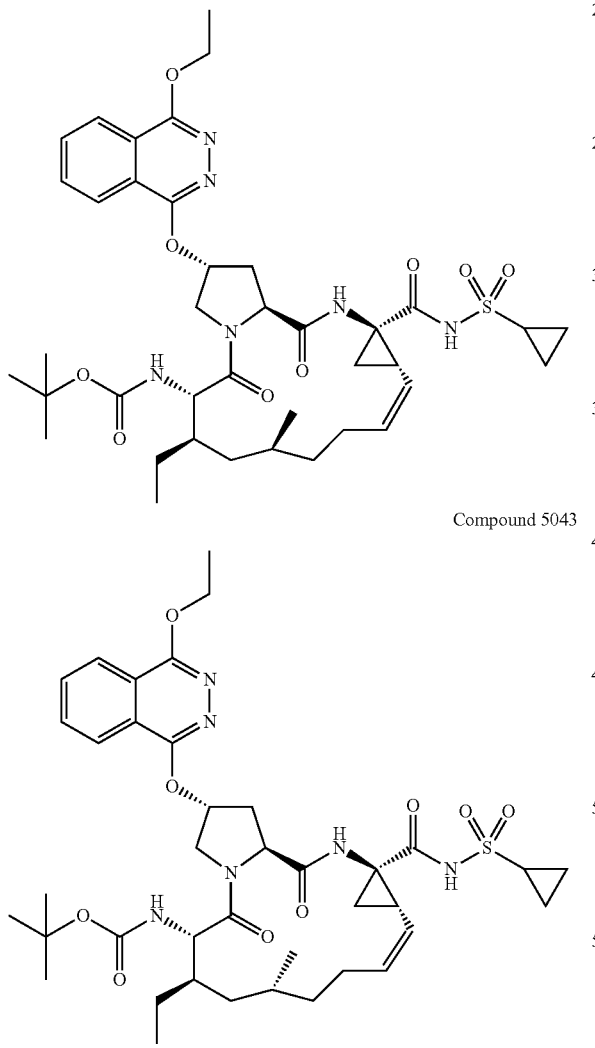

Compound 5042

Compound 5043

Compound 5042 and Compound 5043 were prepared using the intermediates described herein and by following the general procedure described for the synthesis of Compound 3117:

Compound 5042: tert-butyl ((2R,6S,7R,9S,13aS,14aR, 16aS,Z)-14a-((cyclopropylsulfonyl)carbamoyl)-2-((4-ethoxyphthalazin-1-yl)oxy)-7-ethyl-9-methyl-5,16-dioxo-1, 2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 783.4 (M$^+$+1).

Compound 5043: tert-butyl ((2R,6S,7R,9R,13aS,14aR, 16aS,Z)-14a-((cyclopropylsulfonyl)carbamoyl)-2-((4-ethoxyphthalazin-1-yl)oxy)-7-ethyl-9-methyl-5,16-dioxo-1, 2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-$d_6$) δ ppm 11.21 (br. s., 1H), 9.01 (br. s., 1H), 8.12 (d, J=7.9 Hz, 1H), 8.03 (d, J=7.6 Hz, 1H), 8.00-7.96 (m, 1H), 7.93 (t, J=7.6 Hz, 1H), 7.18 (d, J=7.0 Hz, 1H), 5.83 (br. s., 1H), 5.52 (br. s., 1H), 5.05 (br. s., 1H), 4.69 (d, J=10.7 Hz, 1H), 4.61-4.44 (m, 3H), 3.94-3.81 (m, 2H), 2.91 (m, 1H), 2.71-2.60 (m, 2H), 2.40-2.22 (m, 2H), 1.92 (s, 2H), 1.61-1.30 (m, 11H), 1.25-0.87 (m, 17H), 0.77-0.73 (t, J=7.5 Hz, 3H); MS: MS m/z 783.4 (M$^+$+1).

Preparation of Compound 5044 and Compound 5045

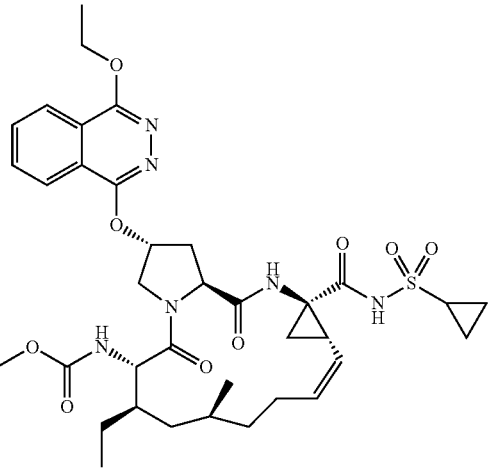

Compound 5044

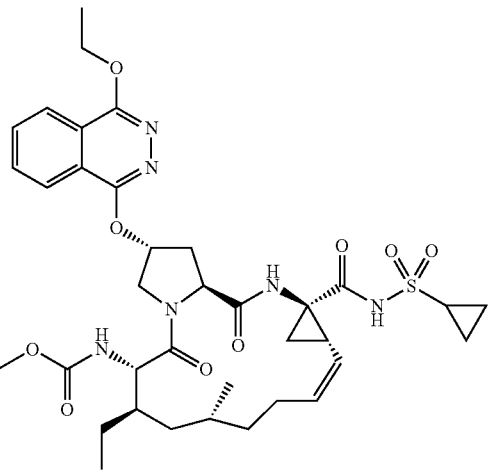

Compound 5045

Compound 5044 and Compound 5045 were prepared using the intermediates described herein and by following the general procedure described for the synthesis of Compound 3117:

Compound 5044: 1,1,1-trifluoro-2-methylpropan-2-yl ((2R,6S,7R,9S,13aS,14aR,16aS,Z)-14a-((cyclopropylsulfonyl)carbamoyl)-2-((4-ethoxyphthalazin-1-yl)oxy)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 837.3 (M$^+$+1).

Compound 5045: 1,1,1-trifluoro-2-methylpropan-2-yl ((2R,6S,7R,9R,13aS,14aR,16aS,Z)-14a-((cyclopropylsulfonyl)carbamoyl)-2-((4-ethoxyphthalazin-1-yl)oxy)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.20 (s, 1H), 9.04 (br. s., 1H), 8.13 (d, J=7.6 Hz, 1H), 8.04-7.93 (m, 3H), 7.86 (d, J=7.9 Hz, 1H), 5.85 (br. s., 1H), 5.54 (d, J=6.1 Hz, 1H), 5.06 (t, J=9.8 Hz, 1H), 4.66-4.46 (m, 4H), 3.99-3.81 (m, 2H), 2.99-2.87 (m, 1H), 2.72-2.63 (m, 2H), 2.40-2.22 (m, 2H), 2.01-1.87 (m, 2H), 1.62-1.31 (m, 13H), 1.18-1.12 (m, 3H), 1.05-0.91 (m, 9H), 0.73 (t, J=7.5 Hz, 3H); MS: MS m/z 837.3 (M$^+$+1).

Compound 5046 and Compound 5047 were prepared using the intermediates described herein and by following the general procedure described for the synthesis of Compound 3117:

Compound 5046: tert-butyl ((2R,6S,7R,9S,13aS,14aR,16aS,Z)-2-((4-ethoxyphthalazin-1-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 797.4 (M$^+$+1).

Compound 5047: tert-butyl ((2R,6S,7R,9R,13aS,14aR,16aS,Z)-2-((4-ethoxyphthalazin-1-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.06 (br. s., 1H), 9.13 (br. s., 1H), 8.11 (d, J=7.9 Hz, 1H), 8.07-7.88 (m, 3H), 7.18 (d, J=7.9 Hz, 1H), 5.85 (br. s., 1H), 5.52 (br. s., 1H), 4.99 (br. s., 1H), 4.70 (d, J=11.9 Hz, 1H), 4.62-4.48 (m, 3H), 3.99-3.83 (m, 2H), 2.68 (br. s., 2H), 2.38-2.27 (m, 2H), 1.97-1.86 (m, 2H), 1.61 (br. s., 1H), 1.56-1.39 (m, 10H), 1.39-1.30 (m, 2H), 1.26 (d, J=6.7 Hz, 2H), 1.16 (d, J=6.7 Hz, 1H), 1.07-0.96 (m, 10H), 0.95-0.85 (m, 5H), 0.73 (t, J=7.5 Hz, 3H); MS: MS m/z 797.4 (M$^+$+1).

Preparation of Compound 5046 and Compound 5047

Compound 5046

Preparation of Compound 5048 and Compound 5049

Compound 5048

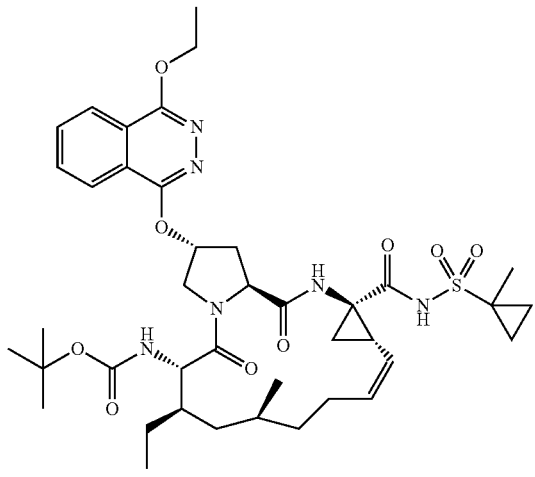

Compound 5047

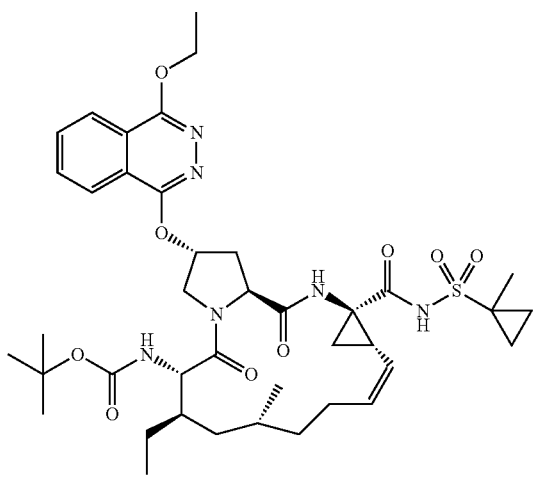

Compound 5049

Compound 5048 and Compound 5049 were prepared using the intermediates described herein and by following the general procedure described for the synthesis of Compound 3117:

Compound 5048: 1,1,1-trifluoro-2-methylpropan-2-yl ((2R,6S,7R,9S,13aS,14aR,16aS,Z)-2-((4-ethoxyphthalazin-1-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 851.4 (M$^+$+1).

Compound 5049: 1,1,1-trifluoro-2-methylpropan-2-yl ((2R,6S,7R,9R,13aS,14aR,16aS,Z)-2-((4-ethoxyphthalazin-1-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.05 (br. s., 1H), 9.17 (br. s., 1H), 8.13 (d, J=7.3 Hz, 1H), 8.04-7.93 (m, 3H), 7.86 (d, J=8.2 Hz, 1H), 5.86 (br. s., 1H), 5.53 (br. s., 1H), 4.98 (br. s., 1H), 4.68-4.50 (m, 4H), 4.01-3.79 (m, 2H), 2.69 (br. s., 2H), 2.41-2.24 (m, 2H), 1.99-1.85 (m, 2H), 1.63 (br. s., 1H), 1.57-1.40 (m, 11H), 1.36 (d, J=15.6 Hz, 2H), 1.30 (s, 4H), 1.17 (br. s., 1H), 1.02 (t, J=13.1 Hz, 1H), 0.96-0.84 (m, 8H), 0.73 (t, J=7.3 Hz, 3H); MS: MS m/z 851.4 (M$^+$+1).

Preparation of Compound 5050 and Compound 5051

Compound 5050 and Compound 5051 were prepared using the intermediates described herein and by following the general procedure described for the synthesis of Compound 3117:

Compound 5050: 3,3-difluoro-2-methylbutan-2-yl ((2R,6S,7R,9S,13aS,14aR,16aS,Z)-2-((4-ethoxyphthalazin-1-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 847.4 (M$^+$+1).

Compound 5051: 3,3-difluoro-2-methylbutan-2-yl ((2R,6S,7R,9R,13aS,14aR,16aS,Z)-2-((4-ethoxyphthalazin-1-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.06 (br. s., 1H), 9.14 (br. s., 1H), 8.13 (d, J=7.9 Hz, 1H), 8.06-7.92 (m, 3H), 7.64 (d, J=8.2 Hz, 1H), 5.86 (br. s., 1H), 5.60-5.48 (m, 1H), 4.98 (t, J=9.9 Hz, 1H), 4.68-4.49 (m, 4H), 3.99-3.81 (m, 2H), 2.77-2.64 (m, 2H), 2.41-2.26 (m, 2H), 1.92 (s, 2H), 1.62 (d, J=7.0 Hz, 1H), 1.60-1.39 (m, 15H), 1.39-1.28 (m, 2H), 1.20 (s, 4H), 1.03 (t, J=12.1 Hz, 1H), 0.96-0.87 (m, 5H), 0.84 (s, 3H), 0.74 (t, J=7.5 Hz, 3H); MS: MS m/z 847.4 (M$^+$+1).

Preparation of Compound 5052 and Compound 5053

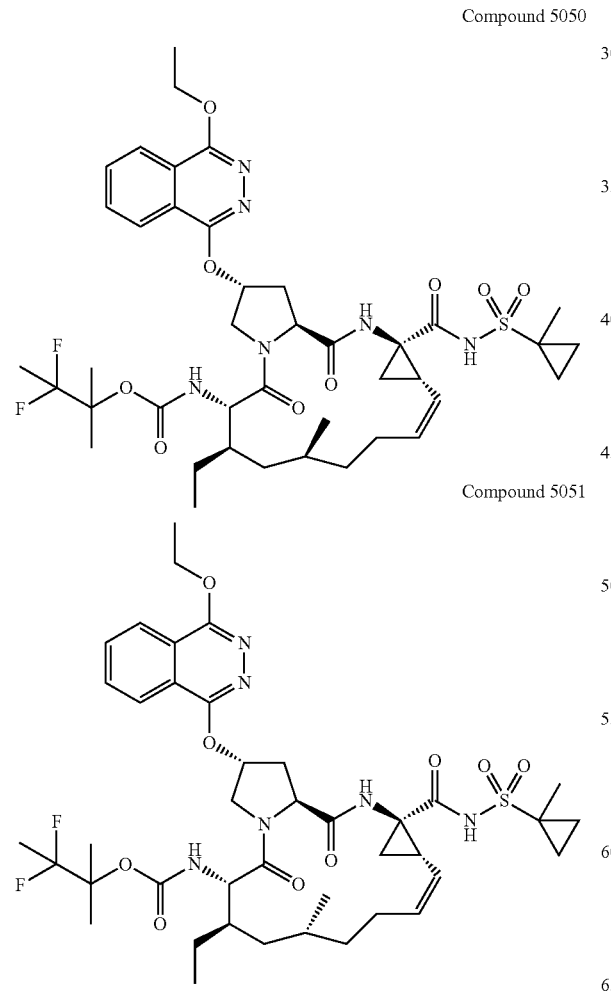

Compound 5050

Compound 5051

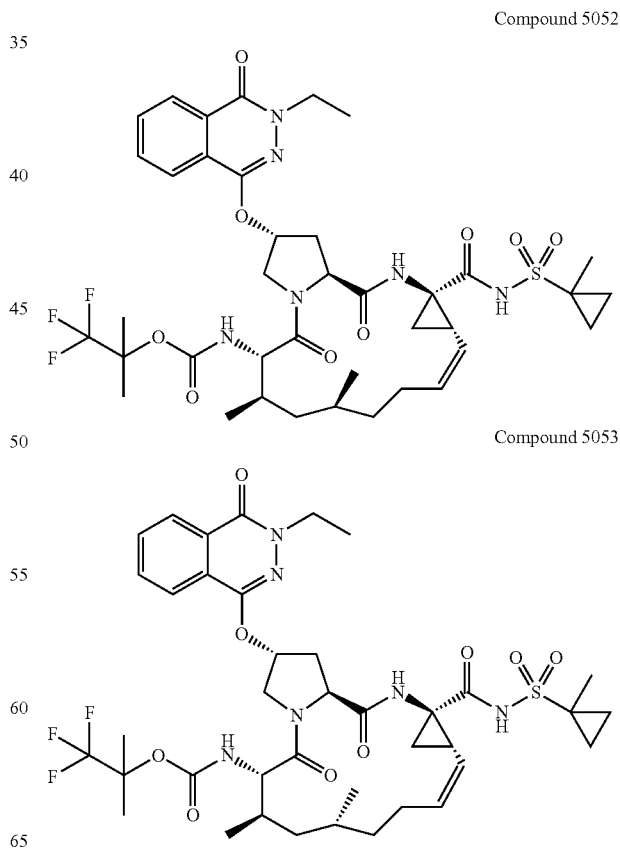

Compound 5052

Compound 5053

Compound 5052 and Compound 5053 were prepared using the intermediates described herein and by following the general procedure described for the synthesis of Compound 3117:

Compound 5052: 1,1,1-trifluoro-2-methylpropan-2-yl ((2R,6S,7R,9S,13aS,14aR,16aS,Z)-2-((3-ethyl-4-oxo-3,4-dihydrophthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 837.3 (M$^+$+1).

Compound 5053: 1,1,1-trifluoro-2-methylpropan-2-yl ((2R,6S,7R,9R,13aS,14aR,16aS,Z)-2-((3-ethyl-4-oxo-3,4-dihydrophthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.06 (br. s., 1H), 9.02 (br. s., 1H), 8.29-8.23 (m, 1H), 7.96-7.87 (m, 3H), 7.79 (d, J=7.9 Hz, 1H), 5.53 (br. s., 1H), 5.49 (br. s., 1H), 5.06 (br. s., 1H), 4.67 (d, J=12.5 Hz, 1H), 4.56-4.43 (m, 1H), 4.22-4.10 (m, 1H), 4.01 (dq, J=13.3, 6.9 Hz, 1H), 3.93-3.83 (m, 1H), 3.68 (dd, J=10.7, 8.2 Hz, 1H), 2.62 (dd, J=13.6, 6.3 Hz, 2H), 2.35-2.23 (m, 2H), 1.94-1.77 (m, 2H), 1.72-1.64 (m, 1H), 1.59 (br. s., 1H), 1.47 (br. s., 1H), 1.39 (s, 5H), 1.36-1.29 (m, 7H), 1.27-1.17 (m, 1H), 1.15 (br. s., 1H), 0.95-0.82 (m, 11H), 0.73 (t, J=11.9 Hz, 1H); MS: MS m/z 837.3 (M$^+$+1).

Preparation of Compound 5054 and Compound 5055

Compound 5054

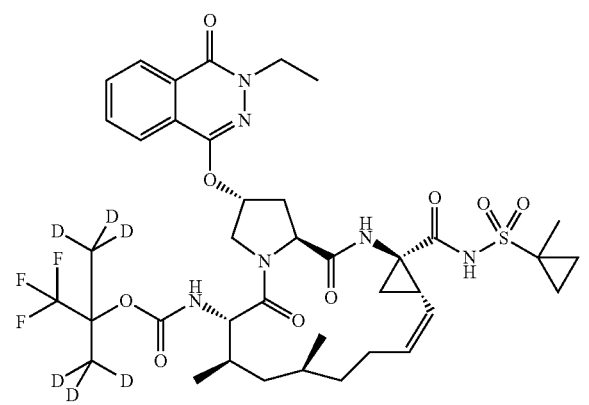

Compound 5055

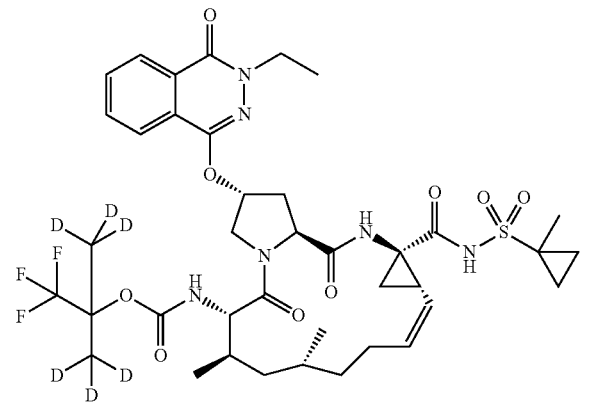

Compound 5054 and Compound 5055 were prepared using the intermediates described herein and by following the general procedure described for the synthesis of Compound 3117:

Compound 5054: MS: MS m/z 843.5 (M$^+$+1).

Compound 5055: $^1$H NMR (500 MHz, DMSO-d$_6$) δ ppm 11.04 (br. s., 1H), 9.17 (br. s., 1H), 8.31-8.24 (m, 1H), 7.95-7.86 (m, 3H), 7.83 (d, J=6.7 Hz, 1H), 5.54 (br. s., 2H), 4.99 (br. s., 1H), 4.67 (br. s., 1H), 4.51 (br. s., 1H), 4.16 (dd, J=13.4, 6.7 Hz, 1H), 4.03 (dd, J=13.0, 6.9 Hz, 1H), 3.95-3.82 (m, 1H), 3.70 (dd, J=10.7, 8.2 Hz, 1H), 2.65 (br. s., 2H), 2.36-2.23 (m, 2H), 1.92-1.84 (d, J=7.0 Hz, 2H), 1.70 (br. s., 1H), 1.61-1.53 (m, 1H), 1.40-1.17 (m, 13H), 1.00-0.83 (m, 7H), 0.75 (br. s., 1H); MS: MS m/z 843.5 (M$^+$+1).

Preparation of Compound 5056 and Compound 5057

Compound 5056

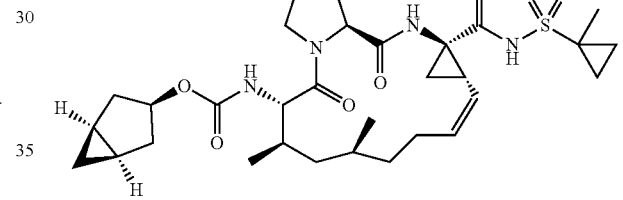

Compound 5057

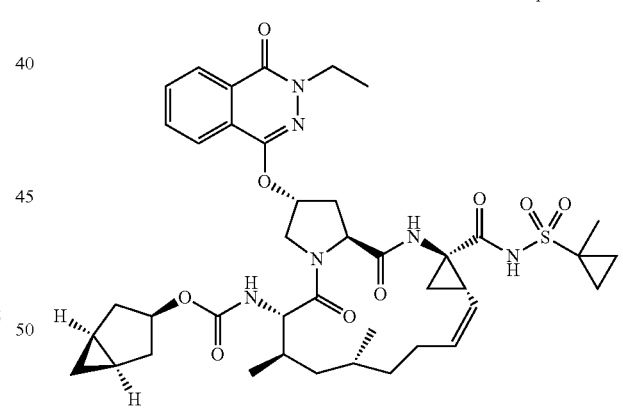

Compound 5056 and Compound 5057 were prepared using the intermediates described herein and by following the general procedure described for the synthesis of Compound 3117:

Compound 5056: (1R,3r,5S)-bicyclo[3.1.0]hexan-3-yl ((2R,6S,7R,9S,13aS,14aR,16aS,Z)-2-((3-ethyl-4-oxo-3,4-dihydrophthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 807.4 (M$^+$+1).

Compound 5057: (1R,3r,5S)-bicyclo[3.1.0]hexan-3-yl ((2R,6S,7R,9R,13aS,14aR,16aS,Z)-2-((3-ethyl-4-oxo-3,4- dihydrophthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-$d_6$) δ ppm 11.04 (br. s., 1H), 8.84 (br. s., 1H), 8.33-8.21 (m, 1H), 7.97-7.85 (m, 3H), 7.34 (d, J=8.9 Hz, 1H), 5.53 (br. s., 1H), 5.47 (br. s., 1H), 5.12 (br. s., 1H), 4.60 (d, J=11.9 Hz, 1H), 4.51-4.38 (m, 2H), 4.13-3.99 (m, 2H), 3.92-3.84 (m, 1H), 3.79-3.66 (m, 1H), 2.65-2.54 (m, 2H), 2.32-2.19 (m, 2H), 1.97-1.86 (m, 3H), 1.80 (d, J=4.9 Hz, 1H), 1.64 (dd, J=8.5, 5.8 Hz, 2H), 1.53 (d, J=14.6 Hz, 2H), 1.38 (s, 6H), 1.35-1.28 (m, 5H), 1.23 (br. s., 1H), 1.21-1.10 (m, 3H), 1.05-0.98 (m, 1H), 0.91 (d, J=6.7 Hz, 3H), 0.85 (d, J=6.4 Hz, 3H), 0.77-0.66 (m, 2H), 0.32-0.21 (m, 2H); MS: MS m/z 807.4 (M$^+$+1).

Preparation of Compound 5058 and Compound 5059

Compound 5058

Compound 5059

Compound 5058 and Compound 5059 were prepared using the intermediates described herein and by following the general procedure described for the synthesis of Compound 3117:

Compound 5058: (2R,6S,7R,9S,13aS,14aR,16aS,Z)-6-(3-(tert-butyl)ureido)-2-((3-ethyl-4-oxo-3,4-dihydrophthalazin-1-yl)oxy)-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. MS: MS m/z 782.4 (M$^+$+1).

Compound 5059: (2R,6S,7R,9R,13aS,14aR,16aS,Z)-6-(3-(tert-butyl)ureido)-2-((3-ethyl-4-oxo-3,4-dihydrophthalazin-1-yl)oxy)-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (500 MHz, DMSO-$d_6$) δ ppm 11.04 (br. s., 1H), 8.84 (br. s., 1H), 8.23 (d, J=7.9 Hz, 1H), 7.95-7.81 (m, 3H), 5.88 (d, J=8.9 Hz, 1H), 5.52 (s, 2H), 5.46 (br. s., 1H), 4.70 (d, J=11.6 Hz, 1H), 4.42 (br. s., 1H), 4.18-4.00 (m, 2H), 3.95-3.77 (m, 2H), 2.60-2.54 (m, 1H), 2.32-2.23 (m, 2H), 1.95-1.83 (m, 1H), 1.65 (d, J=14.0 Hz, 2H), 1.55 (br. s., 1H), 1.45-1.15 (m, 13H), 0.97-0.71 (m, 19H); MS: MS m/z 782.4 (M$^+$+1).

Preparation of Compound 5060 and Compound 5061

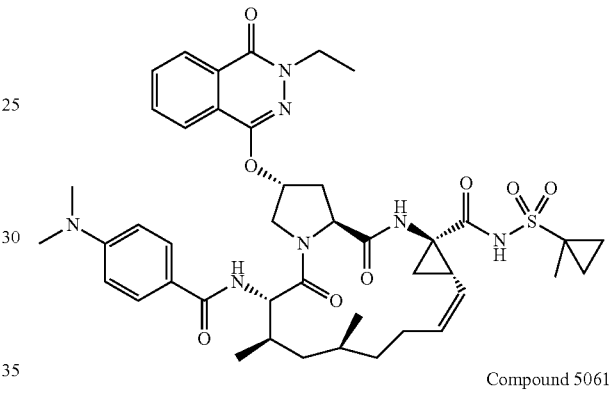

Compound 5060

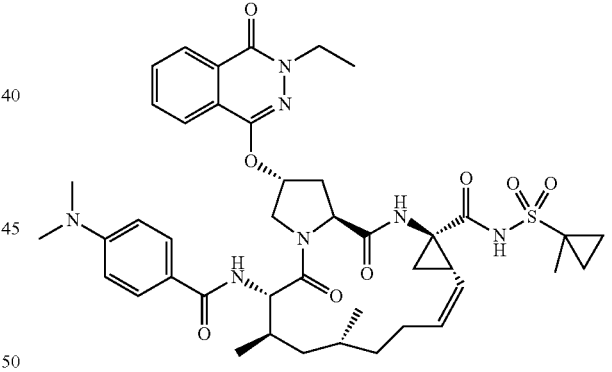

Compound 5061

Compound 5060 and Compound 5061 were prepared using the intermediates described herein and by following the general procedure described for the synthesis of Compound 3117:

Compound 5060: (2R,6S,7R,9S,13aS,14aR,16aS,Z)-6-(4-(dimethylamino)benzamido)-2-((3-ethyl-4-oxo-3,4-dihydrophthalazin-1-yl)oxy)-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. MS: MS m/z 830.4 (M$^+$+1).

Compound 5061: (2R,6S,7R,9R,13aS,14aR,16aS,Z)-6-(4-(dimethylamino)benzamido)-2-((3-ethyl-4-oxo-3,4-dihydrophthalazin-1-yl)oxy)-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a]

[1,4]diazacyclopentadecine-14a-carboxamide. $^1$H NMR (500 MHz, DMSO-d$_6$) δ ppm 11.07 (br. s., 1H), 9.06 (br. s., 1H), 8.27 (d, J=7.6 Hz, 2H), 7.95-7.86 (m, 2H), 7.83-7.76 (m, 1H), 7.51 (d, J=8.9 Hz, 2H), 6.58 (d, J=9.2 Hz, 2H), 5.58 (br. s., 2H), 5.00 (br. s., 1H), 4.91 (d, J=9.5 Hz, 1H), 4.45 (br. s., 1H), 4.24-4.02 (m, 3H), 3.98-3.88 (m, 1H), 2.96 (s, 6H), 2.75 (br. s., 1H), 2.65 (br. s., 1H), 2.39-2.28 (m, 2H), 2.12 (d, J=5.8 Hz, 1H), 2.00 (br. s., 1H), 1.73 (br. s., 1H), 1.61 (br. s., 1H), 1.48 (br. s., 3H), 1.42 (br. s., 4H), 1.34 (t, J=7.2 Hz, 3H), 1.28 (br. s., 1H), 1.19 (br. s., 1H), 1.00-0.86 (m, 8H), 0.83 (d, J=11.0 Hz, 1H); MS: MS m/z 830.4 (M$^+$+1).

hexadecahydrocyclopropa[e]pyrrolo[1,2-a][1,4]diazacyclopentadecin-6-yl)-N2,N2-dimethyloxalamide. $^1$H NMR (500 MHz, DMSO-d$_6$) δ ppm 11.07 (br. s., 1H), 8.95 (d, J=7.9 Hz, 1H), 8.82 (s, 1H), 8.26 (dd, J=6.1, 3.1 Hz, 1H), 7.97-7.83 (m, 3H), 5.57 (br. s., 1H), 5.46 (br. s., 1H), 5.17 (br. s., 1H), 4.57-4.49 (m, 1H), 4.42 (t, J=8.5 Hz, 1H), 4.15-4.03 (m, 4H), 4.00 (d, J=8.5 Hz, 2H), 2.78-2.71 (m, 3H), 2.66-2.58 (m, 4H), 2.35-2.21 (m, 2H), 1.91 (s, 2H), 1.79-1.67 (m, 1H), 1.54 (br. s., 1H), 1.42-1.31 (m, 9H), 1.23 (br. s., 2H), 0.91 (d, J=7.6 Hz, 3H), 0.98-0.86 (m, 3H), 0.75 (d, J=10.7 Hz, 3H); MS: MS m/z 782.3 (M$^+$+1).

Preparation of Compound 5062 and Compound 5063

Preparation of Compound 5064 and Compound 5065

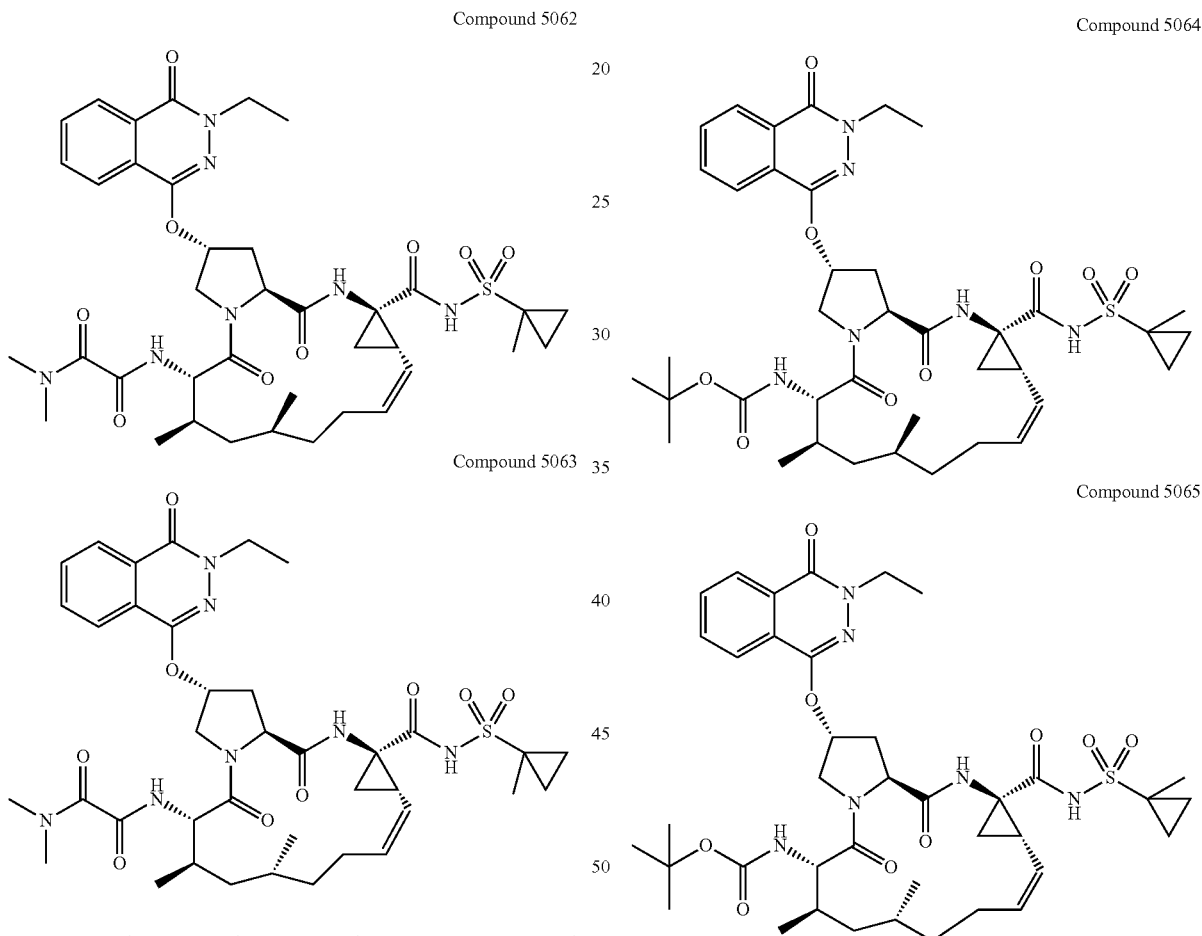

Compound 5062 and Compound 5063 were prepared using the intermediates described herein and by following the general procedure described for the synthesis of Compound 3117:

Compound 5062: N1-((2R,6S,7R,9S,13aS,14aR,16aS,Z)-2-((3-ethyl-4-oxo-3,4-dihydrophthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-N2,N2-dimethyloxalamide. MS: MS m/z 782.3 (M$^+$+1).

Compound 5063: N1-((2R,6S,7R,9R,13aS,14aR,16aS,Z)-2-((3-ethyl-4-oxo-3,4-dihydrophthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-

Compound 5064 and Compound 5065 were prepared using the intermediates described herein and by following the general procedure described for the synthesis of Compound 3117:

Compound 5064: tert-butyl ((2R,6S,7R,9S,13aS,14aR,16aS,Z)-2-((3-ethyl-4-oxo-3,4-dihydrophthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 783.4 (M$^+$+1).

Compound 5065: tert-butyl ((2R,6S,7R,9R,13aS,14aR,16aS,Z)-2-((3-ethyl-4-oxo-3,4-dihydrophthalazin-1-yl)

oxy)-7,9-dimethyl-14a-(((1-methylcyclopropyl)sulfonyl) carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-$d_6$) δ ppm 11.06 (br. s., 1H), 9.14 (br. s., 1H), 8.31-8.23 (m, 1H), 7.94-7.82 (m, 3H), 7.19 (d, J=7.9 Hz, 1H), 5.60-5.48 (m, 2H), 4.97 (t, J=9.5 Hz, 1H), 4.76 (d, J=11.6 Hz, 1H), 4.51 (dd, J=10.4, 6.7 Hz, 1H), 4.22-4.10 (m, 1H), 4.09-3.96 (m, 1H), 3.94-3.86 (m, 1H), 3.70 (dd, J=10.7, 8.5 Hz, 1H), 2.75-2.59 (m, 2H), 2.40-2.21 (m, 2H), 1.97-1.77 (m, 2H), 1.72-1.58 (m, 2H), 1.55-1.38 (m, 6H), 1.38-1.24 (m, 5H), 1.18-1.06 (m, 2H), 1.04 (s, 8H), 0.96-0.85 (m, 8H), 0.74 (t, J=12.1 Hz, 1H); MS: MS m/z 783.4 (M$^+$+1).

Preparation of Compound 5066 and Compound 5067

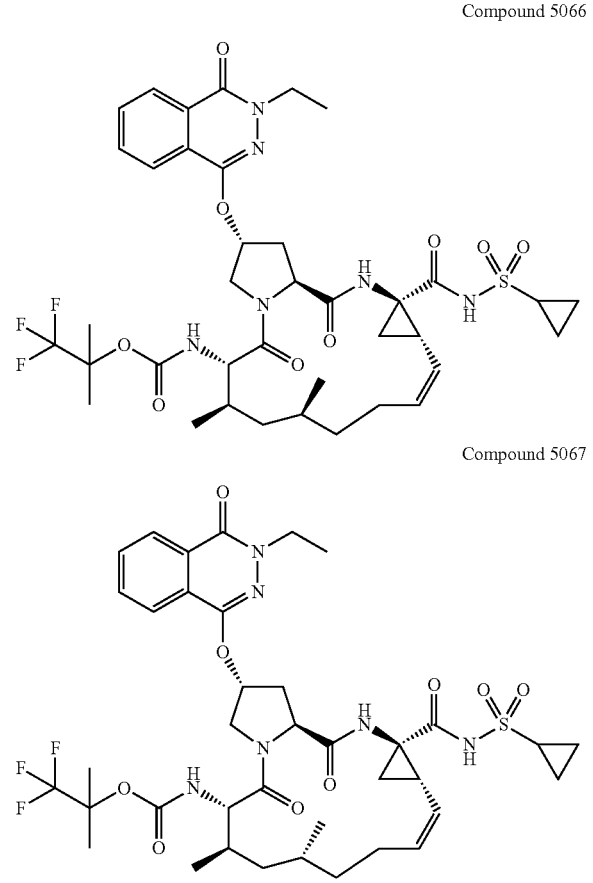

Compound 5066

Compound 5067

Compound 5066 and Compound 5067 were prepared using the intermediates described herein and by following the general procedure described for the synthesis of Compound 3117:

Compound 5066: 1,1,1-trifluoro-2-methylpropan-2-yl ((2R,6S,7R,9S,13aS,14aR,16aS,Z)-14a-((cyclopropylsulfonyl)carbamoyl)-2-((3-ethyl-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 823.3 (M$^+$+1).

Compound 5067: 1,1,1-trifluoro-2-methylpropan-2-yl ((2R,6S,7R,9R,13aS,14aR,16aS,Z)-14a-((cyclopropylsulfonyl)carbamoyl)-2-((3-ethyl-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-$d_6$) δ ppm 11.19 (br. s., 1H), 9.04 (br. s., 1H), 8.31-8.24 (m, 1H), 7.94-7.78 (m, 4H), 5.54 (br. s., 2H), 5.05 (br. s., 1H), 4.68 (d, J=11.6 Hz, 1H), 4.50 (dd, J=9.9, 7.2 Hz, 1H), 4.23-4.11 (m, 1H), 4.08-3.97 (m, 1H), 3.87 (dd, J=11.4, 2.9 Hz, 1H), 3.69 (dd, J=10.7, 7.9 Hz, 1H), 2.91 (d, J=7.6 Hz, 1H), 2.65 (dd, J=13.0, 6.6 Hz, 2H), 2.38-2.17 (m, 2H), 1.96-1.77 (m, 2H), 1.69 (dd, J=12.5, 6.7 Hz, 1H), 1.65-1.60 (m, 1H), 1.56 (br. s., 1H), 1.48-1.28 (m, 8H), 1.21-1.13 (m, 3H), 1.04-0.85 (m, 11H), 0.75 (t, J=12.2 Hz, 1H); MS: MS m/z 823.3 (M$^+$+1).

Preparation of Compound 5068 and Compound 5069

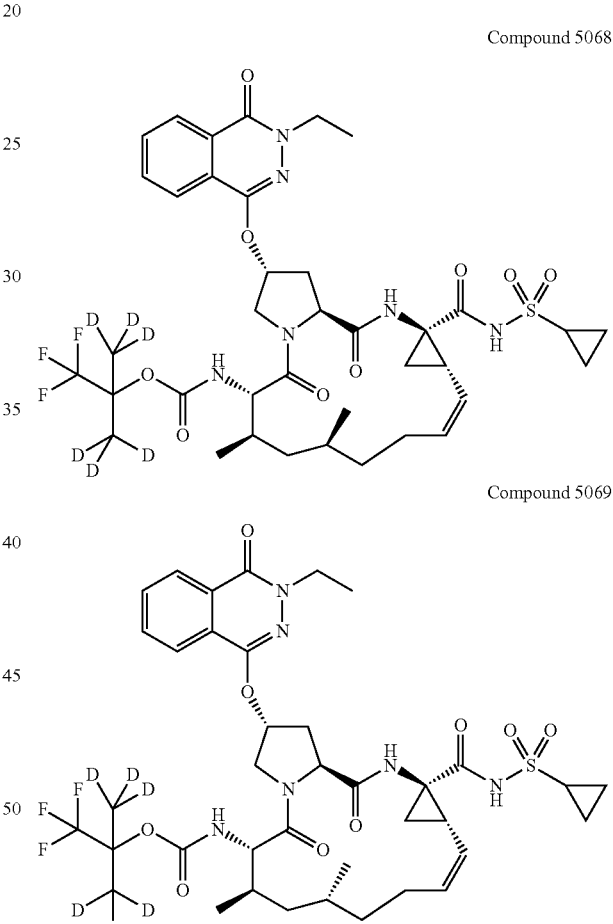

Compound 5068

Compound 5069

Compound 5068 and Compound 5069 were prepared using the intermediates described herein and by following the general procedure described for the synthesis of Compound 3117:

Compound 5068: MS: MS m/z 829.5 (M$^+$+1).

Compound 5069: $^1$H NMR (500 MHz, DMSO-$d_6$) δ ppm 11.19 (br. s., 1H), 9.04 (br. s., 1H), 8.31-8.23 (m, 1H), 7.94-7.87 (m, 3H), 7.84 (d, J=7.6 Hz, 1H), 5.54 (br. s., 2H), 5.06 (br. s., 1H), 4.68 (d, J=11.6 Hz, 1H), 4.50 (dd, J=9.9, 7.2 Hz, 1H), 4.22-4.09 (m, 1H), 4.09-3.98 (m, 1H), 3.87 (dd, J=11.4, 2.9 Hz, 1H), 3.69 (dd, J=10.7, 7.9 Hz, 1H), 2.91 (d, J=4.9 Hz, 1H), 2.64 (dd, J=13.0, 6.3 Hz, 2H), 2.38-2.23 (m, 2H), 1.96-1.78 (m, 2H), 1.74-1.66 (m, 1H), 1.62 (br. s., 1H), 1.55 (br. s., 1H), 1.47-1.29 (m, 5H), 1.13 (br. s., 3H), 1.04-0.86 (m, 8H), 0.75 (t, J=12.4 Hz, 1H); MS: MS m/z 829.5 (M$^+$+1).

Preparation of Compound 5070

Compound 5070

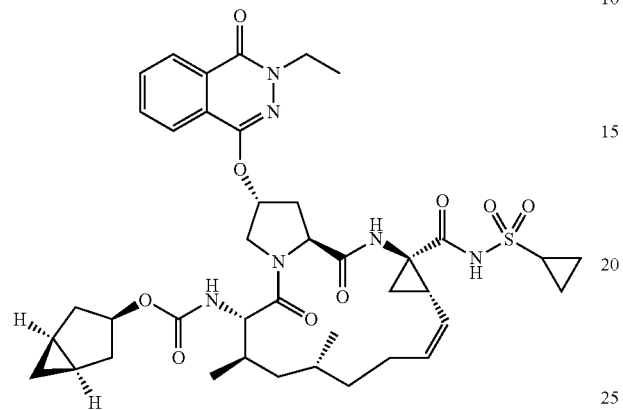

Compound 5070 was prepared using the intermediates described herein and by following the general procedure described for the synthesis of Compound 3117:

Compound 5070: (1R,3r,5S)-bicyclo[3.1.0]hexan-3-yl ((2R,6S,7R,9R,13aS,14aR,16aS,Z)-14a-((cyclopropylsulfonyl)carbamoyl)-2-((3-ethyl-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 8.34-8.21 (m, 1H), 7.99-7.81 (m, 3H), 7.35 (d, J=8.5 Hz, 1H), 5.53 (br. s., 1H), 5.43 (br. s., 1H), 4.58 (d, J=11.6 Hz, 1H), 4.51-4.39 (m, 2H), 4.15-4.04 (m, 2H), 3.87 (dd, J=11.4, 3.2 Hz, 1H), 3.78-3.67 (m, 1H), 2.79 (br. s., 1H), 2.57 (d, J=9.5 Hz, 1H), 2.35-2.14 (m, 2H), 1.98-1.87 (m, 3H), 1.86-1.76 (m, 1H), 1.67 (dt, J=14.1, 5.8 Hz, 2H), 1.54-1.41 (m, 4H), 1.33 (t, J=7.2 Hz, 5H), 1.24-1.13 (m, 3H), 1.07-0.68 (m, 12H), 0.33-0.22 (m, 2H); MS: MS m/z 793.4 (M$^+$+1).

Preparation of Compound 5071 and Compound 5072

Compound 5071

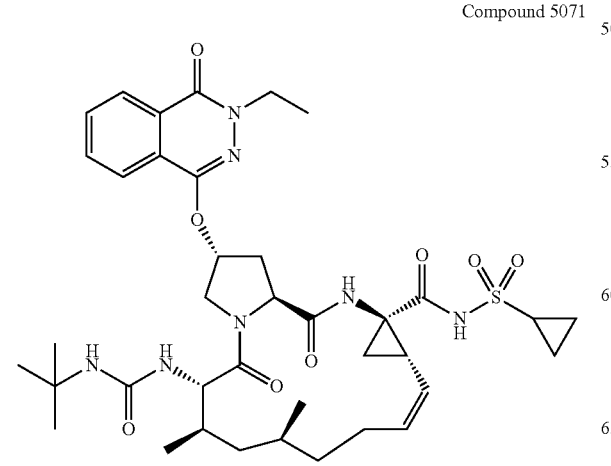

Compound 5072

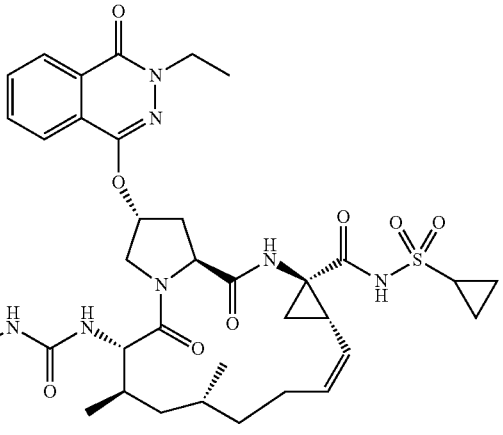

Compound 5071 and Compound 5072 were prepared using the intermediates described herein and by following the general procedure described for the synthesis of Compound 3117:

Compound 5071: (2R,6S,7R,9S,13aS,14aR,16aS,Z)-6-(3-(tert-butyl)ureido)-N-(cyclopropylsulfonyl)-2-((3-ethyl-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. MS: MS m/z 768.4 (M$^+$+1).

Compound 5072: (2R,6S,7R,9R,13aS,14aR,16aS,Z)-6-(3-(tert-butyl)ureido)-N-(cyclopropylsulfonyl)-2-((3-ethyl-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (500 MHz, DMSO-d$_6$) δ ppm 8.70 (br. s., 1H), 8.24 (d, J=7.3 Hz, 1H), 7.98-7.75 (m, 3H), 5.90 (d, J=9.2 Hz, 1H), 5.57-5.51 (m, 2H), 5.48-5.37 (m, 1H), 5.26 (br. s., 1H), 4.69 (d, J=11.6 Hz, 1H), 4.40 (dd, J=9.8, 7.0 Hz, 1H), 4.18-3.99 (m, 2H), 3.93-3.77 (m, 2H), 2.82 (br. s., 1H), 2.64-2.54 (m, 1H), 2.34-2.15 (m, 2H), 1.96-1.85 (m, 2H), 1.76-1.60 (m, 2H), 1.54 (dd, J=8.1, 4.4 Hz, 1H), 1.48-1.37 (m, 2H), 1.37-1.26 (m, 4H), 1.25-1.13 (m, 1H), 1.01-0.85 (m, 18H), 0.70 (t, J=11.3 Hz, 1H); MS: MS m/z 768.4 (M$^+$+1).

Preparation of Compound 5073 and Compound 5074

Compound 5073

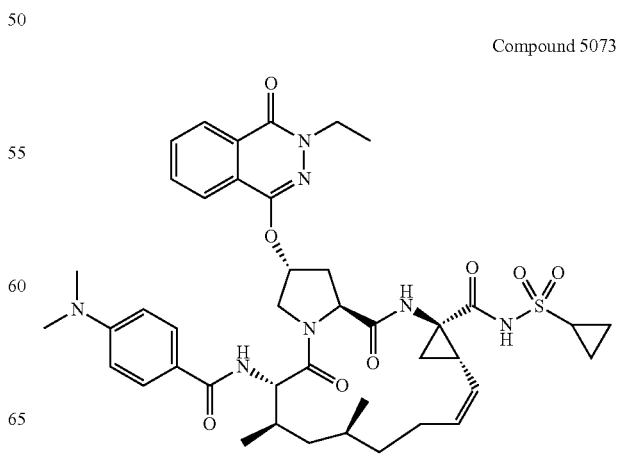

Compound 5074

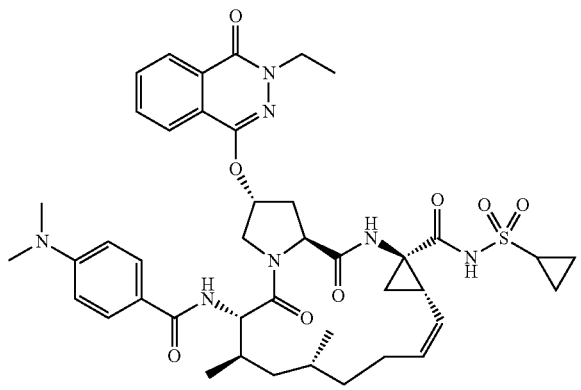

Compound 5076

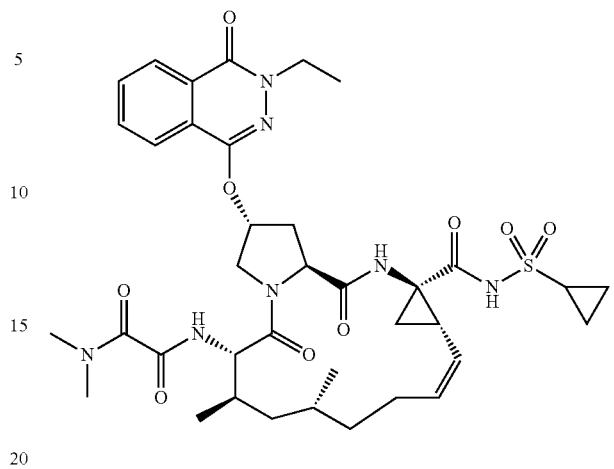

Compound 5073 and Compound 5074 were prepared using the intermediates described herein and by following the general procedure described for the synthesis of Compound 3117:

Compound 5073: (2R,6S,7R,9S,13aS,14aR,16aS,Z)-N-(cyclopropylsulfonyl)-6-(4-(dimethylamino)benzamido)-2-((3-ethyl-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. MS: MS m/z 816.4 (M$^+$+1).

Compound 5074: (2R,6S,7R,9R,13aS,14aR,16aS,Z)-N-(cyclopropylsulfonyl)-6-(4-(dimethylamino)benzamido)-2-((3-ethyl-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (500 MHz, DMSO-d$_6$) δ ppm 11.21 (br. s., 1H), 8.92 (br. s., 1H), 8.34-8.19 (m, 2H), 7.96-7.87 (m, 2H), 7.84-7.78 (m, 1H), 7.52 (d, J=8.9 Hz, 2H), 6.58 (d, J=9.2 Hz, 2H), 5.65-5.46 (m, 2H), 5.08 (br. s., 1H), 4.88 (d, J=10.7 Hz, 1H), 4.42 (t, J=8.2 Hz, 1H), 4.24-4.02 (m, 3H), 3.96-3.86 (m, 1H), 2.96 (s, 6H), 2.90 (s, 1H), 2.65 (br. s., 2H), 2.37-2.25 (m, 2H), 2.11 (d, J=6.4 Hz, 1H), 2.01 (br. s., 1H), 1.76 (d, J=9.8 Hz, 1H), 1.59 (br. s., 1H), 1.51 (br. s., 2H), 1.41 (br. s., 1H), 1.34 (t, J=7.2 Hz, 3H), 1.20 (br. s., 1H), 1.08 (d, J=7.3 Hz, 2H), 0.95 (t, J=7.3 Hz, 8H), 0.80 (t, J=12.2 Hz, 1H); MS: MS m/z 816.4 (M$^+$+1).

Preparation of Compound 5075 and Compound 5076

Compound 5075

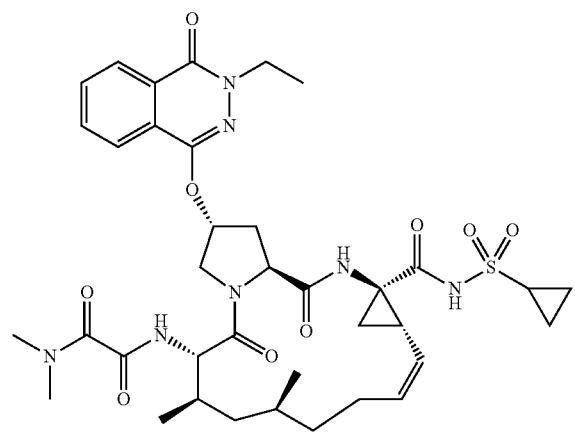

Compound 5075 and Compound 5076 were prepared using the intermediates described herein and by following the general procedure described for the synthesis of Compound 3117:

Compound 5075: N1-((2R,6S,7R,9S,13aS,14aR,16aS,Z)-14a-((cyclopropylsulfonyl)carbamoyl)-2-((3-ethyl-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-N2,N2-dimethyloxalamide. MS: MS m/z 768.3 (M$^+$+1).

Compound 5076: N1-((2R,6S,7R,9R,13aS,14aR,16aS,Z)-14a-((cyclopropylsulfonyl)carbamoyl)-2-((3-ethyl-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-N2,N2-dimethyloxalamide. MS: MS m/z 768.3 (M$^+$+1).

Preparation of Compound 5077

Compound 5077

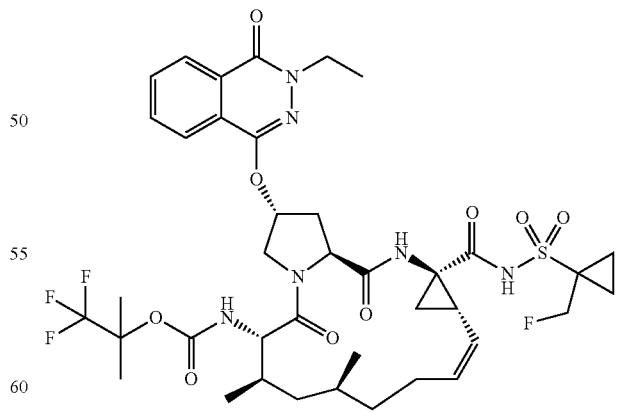

Compound 5077 was prepared using the intermediates described herein and by following the general procedure described for the synthesis of Compound 3117:

Compound 5077: 1,1,1-trifluoro-2-methylpropan-2-yl ((2R,6S,7R,9S,13aS,14aR,16aS,Z)-2-((3-ethyl-4-oxo-3,4- dihydrophthalazin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.28 (s, 1H), 9.09 (br. s., 1H), 8.27 (dd, J=6.1, 2.7 Hz, 1H), 7.94-7.87 (m, 3H), 7.84 (d, J=7.9 Hz, 1H), 5.64-5.46 (m, 2H), 4.99 (t, J=9.8 Hz, 1H), 4.69 (d, J=11.9 Hz, 1H), 4.61 (d, J=11.6 Hz, 1H), 4.51 (d, J=11.0 Hz, 1H), 4.23-4.13 (m, 1H), 4.08-3.96 (m, 1H), 3.93-3.83 (m, 1H), 3.70 (dd, J=10.7, 7.9 Hz, 1H), 2.72-2.57 (m, 2H), 2.37-2.23 (m, 2H), 1.96-1.79 (m, 2H), 1.66 (d, J=14.0 Hz, 1H), 1.55 (d, J=11.0 Hz, 4H), 1.42 (br. s., 1H), 1.39-1.30 (m, 7H), 1.30-1.14 (m, 4H), 0.99-0.85 (m, 9H), 0.82-0.71 (m, 1H); MS: MS m/z 855.33 (M$^+$+1).

Preparation of Compound 5078 and Compound 5079

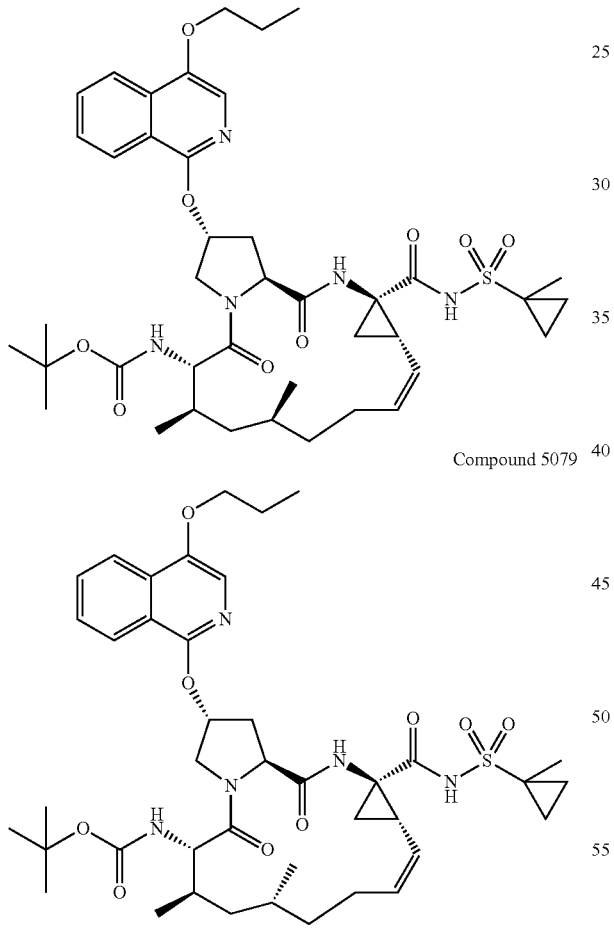

Compound 5078

Compound 5079

Compound 5078 and Compound 5079 were prepared using the intermediates described herein and by following the general procedure described for the synthesis of Compound 3117:

Compound 5078: tert-butyl ((2R,6S,7R,9S,13aS,14aR,16aS,Z)-7,9-dimethyl-14a-(((1-methylcyclopropyl)sulfonyl)carbamoyl)-5,16-dioxo-2-((4-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 796.4 (M$^+$+1).

Compound 5079: tert-butyl ((2R,6S,7R,9R,13aS,14aR,16aS,Z)-7,9-dimethyl-14a-(((1-methylcyclopropyl)sulfonyl)carbamoyl)-5,16-dioxo-2-((4-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.06 (s, 1H), 9.11 (s, 1H), 8.08 (d, J=8.2 Hz, 1H), 8.11 (d, J=8.2 Hz, 1H), 7.79 (t, J=7.6 Hz, 1H), 7.64 (s, 1H), 7.59 (t, J=7.8 Hz, 1H), 7.18 (d, J=8.2 Hz, 1H), 5.76 (br. s., 1H), 5.58-5.47 (m, 1H), 4.97 (t, J=9.9 Hz, 1H), 4.61 (d, J=11.3 Hz, 1H), 4.49 (dd, J=10.1, 7.0 Hz, 1H), 4.17-4.05 (m, 2H), 3.95-3.86 (m, 1H), 3.72 (dd, J=10.5, 8.4 Hz, 1H), 2.76-2.66 (m, 1H), 2.61 (dd, J=13.9, 6.3 Hz, 1H), 2.40-2.25 (m, 2H), 1.96-1.78 (m, 4H), 1.69 (dd, J=12.7, 6.9 Hz, 1H), 1.64-1.58 (m, 1H), 1.51 (dd, J=9.0, 5.0 Hz, 1H), 1.48-1.21 (m, 7H), 1.18-1.02 (m, 13H), 0.95-0.85 (m, 8H), 0.74 (t, J=12.2 Hz, 1H); MS: MS m/z 796.4 (M$^+$+1).

Preparation of Compound 5080 and Compound 5081

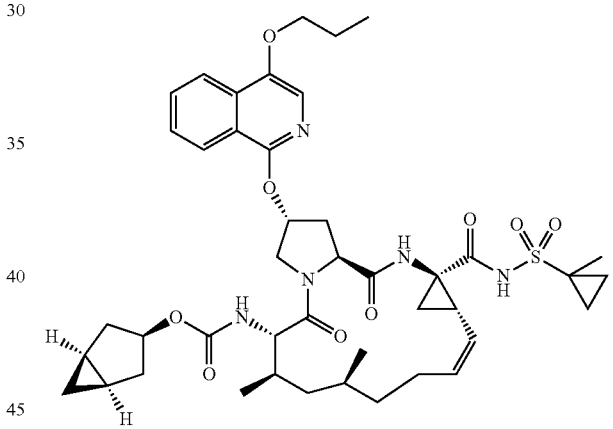

Compound 5080

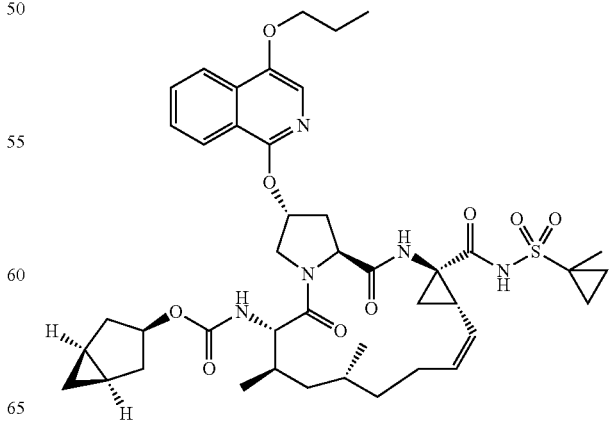

Compound 5081

Compound 5080 and Compound 5081 were prepared using the intermediates described herein and by following the general procedure described for the synthesis of Compound 3117:

Compound 5080: (1R,3r,5S)-bicyclo[3.1.0]hexan-3-yl ((2R,6S,7R,9S,13aS,14aR,16aS,Z)-7,9-dimethyl-14a-(((1-methylcyclopropyl)sulfonyl)carbamoyl)-5,16-dioxo-2-((4-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 820.4 (M$^+$+1).

Compound 5081: (1R,3r,5S)-bicyclo[3.1.0]hexan-3-yl ((2R,6S,7R,9R,13aS,14aR,16aS,Z)-7,9-dimethyl-14a-(((1-methylcyclopropyl)sulfonyl)carbamoyl)-5,16-dioxo-2-((4-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.05 (br. s., 1H), 9.07 (br. s., 1H), 8.09 (d, J=8.9 Hz, 2H), 7.85-7.75 (m, 1H), 7.68-7.61 (m, 2H), 7.40 (d, J=8.5 Hz, 1H), 5.78 (br. s., 1H), 5.52 (br. s., 1H), 4.98 (br. s., 1H), 4.59 (t, J=6.7 Hz, 1H), 4.48 (d, J=5.2 Hz, 2H), 4.12 (t, J=6.4 Hz, 2H), 3.94 (dd, J=12.1, 4.1 Hz, 1H), 3.81-3.61 (m, 1H), 2.77-2.68 (m, 1H), 2.61 (br. s., 1H), 2.35-2.19 (m, 2H), 1.98-1.80 (m, 5H), 1.79-1.71 (m, 1H), 1.69-1.54 (m, 3H), 1.51 (br. s., 2H), 1.41 (s, 5H), 1.37-1.16 (m, 3H), 1.15-1.06 (m, 5H), 0.96-0.85 (m, 8H), 0.74 (t, J=12.4 Hz, 1H), 0.37-0.29 (m, 2H); MS: MS m/z 820.4 (M$^+$+1).

Preparation of Compound 5082 and Compound 5083

Compound 5082 and Compound 5083 were prepared using the intermediates described herein and by following the general procedure described for the synthesis of Compound 3117:

Compound 5082: (1-methylcyclopropyl)methyl ((2R,6S,7R,9S,13aS,14aR,16aS,Z)-7,9-dimethyl-14a-(((1-methylcyclopropyl)sulfonyl)carbamoyl)-5,16-dioxo-2-((4-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 808.8 (M$^+$+1).

Compound 5083: (1-methylcyclopropyl)methyl ((2R,6S,7R,9R,13aS,14aR,16aS,Z)-7,9-dimethyl-14a-(((1-methylcyclopropyl)sulfonyl)carbamoyl)-5,16-dioxo-2-((4-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.05 (s, 1H), 9.09 (br. s., 1H), 8.09 (d, J=8.2 Hz, 2H), 7.80 (t, J=7.6 Hz, 1H), 7.66-7.58 (m, 2H), 7.50 (d, J=8.2 Hz, 1H), 5.79 (br. s., 1H), 5.61-5.44 (m, 1H), 4.98 (t, J=9.6 Hz, 1H), 4.60-4.41 (m, 2H), 4.12 (t, J=6.4 Hz, 2H), 3.97-3.90 (m, 1H), 3.76 (dd, J=10.5, 8.7 Hz, 1H), 2.76-2.68 (m, 1H), 2.61 (dd, J=13.1, 6.7 Hz, 1H), 2.40-2.22 (m, 2H), 1.97-1.81 (m, 4H), 1.68 (dd, J=13.0, 6.3 Hz, 1H), 1.61 (d, J=6.7 Hz, 1H), 1.51 (br. s., 1H), 1.48-1.39 (m, 6H), 1.39-1.32 (m, 1H), 1.32-1.24 (m, 1H), 1.18-1.05 (m, 4H), 0.97-0.86 (m, 12H), 0.80-0.70 (m, 1H), 0.29-0.12 (m, 4H); MS: MS m/z 808.7 (M$^+$+1).

Preparation of Compound 5084 and Compound 5085

Compound 5082

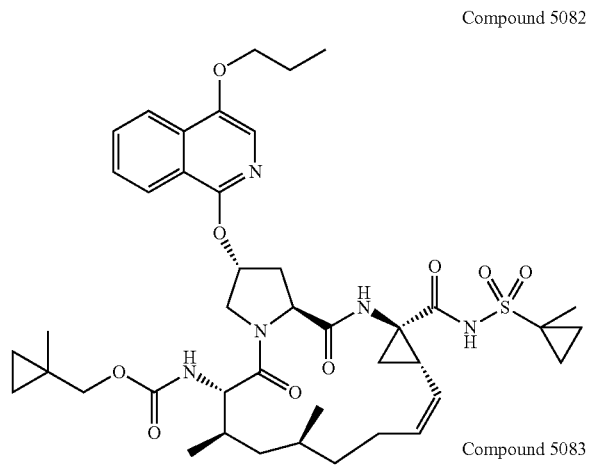

Compound 5083

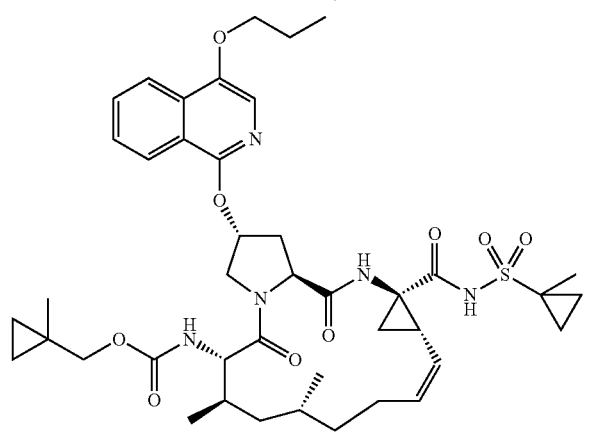

Compound 5084

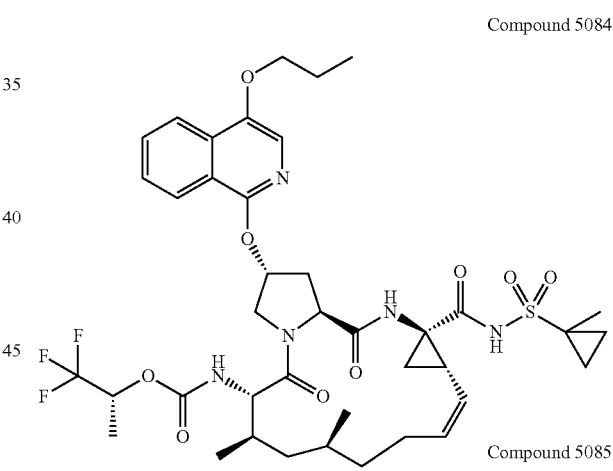

Compound 5085

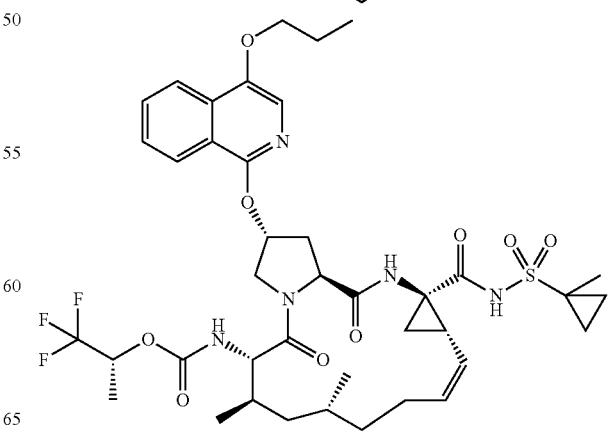

Compound 5084 and Compound 5085 were prepared using the intermediates described herein and by following the general procedure described for the synthesis of Compound 3117:

Compound 5084: (R)-1,1,1-trifluoropropan-2-yl ((2R,6S,7R,9S,13aS,14aR,16aS,Z)-7,9-dimethyl-14a-(((1-methylcyclopropyl)sulfonyl)carbamoyl)-5,16-dioxo-2-((4-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 836.7 (M$^+$+1).

Compound 5085: (R)-1,1,1-trifluoropropan-2-yl ((2R,6S,7R,9R,13aS,14aR,16aS,Z)-7,9-dimethyl-14a-(((1-methylcyclopropyl)sulfonyl)carbamoyl)-5,16-dioxo-2-((4-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.03 (br. s., 1H), 9.10 (br. s., 1H), 8.06 (d, J=8.5 Hz, 1H), 8.09 (d, J=8.2 Hz, 2H), 7.83-7.76 (m, 1H), 7.66-7.61 (m, 1H), 7.59-7.51 (m, 1H), 5.53 (br. s., 1H), 4.98 (br. s., 1H), 4.68 (dt, J=13.5, 6.8 Hz, 1H), 4.56-4.43 (m, 2H), 4.16-4.07 (m, 2H), 3.99-3.87 (m, 1H), 3.78 (dd, J=10.7, 8.2 Hz, 1H), 2.73-2.57 (m, 2H), 2.37-2.22 (m, 2H), 1.96-1.81 (m, 4H), 1.68 (d, J=6.7 Hz, 1H), 1.61 (br. s., 1H), 1.52 (br. s., 1H), 1.41-1.23 (m, 8H), 1.21-1.12 (m, 4H), 1.08 (t, J=7.3 Hz, 3H), 0.96-0.87 (m, 8H), 0.82-0.70 (m, 1H); MS: MS m/z 836.7 (M$^+$+1).

Compound 5086 and Compound 5087 were prepared using the intermediates described herein and by following the general procedure described for the synthesis of Compound 3117:

Compound 5086: (2R,6S,7R,9S,13aS,14aR,16aS,Z)-7,9-dimethyl-N-((1-methylcyclopropyl)sulfonyl)-5,16-dioxo-2-((4-propoxyisoquinolin-1-yl)oxy)-6-(3-(1,1,1-trifluoro-2-methylpropan-2-yl)ureido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide. MS: MS m/z 849.7 (M$^+$+1).

Compound 5087: (2R,6S,7R,9R,13aS,14aR,16aS,Z)-7,9-dimethyl-N-((1-methylcyclopropyl)sulfonyl)-5,16-dioxo-2-((4-propoxyisoquinolin-1-yl)oxy)-6-(3-(1,1,1-trifluoro-2-methylpropan-2-yl)ureido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (500 MHz, DMSO-d$_6$) δ ppm 11.04 (br. s., 1H), 9.09 (br. s., 1H), 8.09 (t, J=7.2 Hz, 2H), 7.80 (t, J=7.6 Hz, 1H), 7.64 (s, 1H), 7.59 (t, J=7.5 Hz, 1H), 6.24 (d, J=8.5 Hz, 1H), 6.07 (s, 1H), 5.77 (br. s., 1H), 5.53 (d, J=5.2 Hz, 1H), 4.98 (t, J=10.1 Hz, 1H), 4.56-4.40 (m, 2H), 4.18-4.05 (m, 2H), 3.97-3.89 (m, 1H), 3.85 (t, J=9.6 Hz, 1H), 2.75-2.66 (m, 1H), 2.66-2.56 (m, 1H), 2.42-2.18 (m, 2H), 1.96-1.82 (m, 3H), 1.75-1.64 (m, 2H), 1.61 (br. s., 1H), 1.51 (br. s., 1H), 1.47-1.39 (m, 5H), 1.39-1.33 (m, 1H), 1.33-1.23 (m, 1H), 1.18 (s, 4H), 1.21 (s, 3H), 1.10-1.04 (m, 3H), 0.92 (dd, J=15.0, 6.7 Hz, 8H), 0.76 (t, J=12.2 Hz, 1H); MS: MS m/z 849.7 (M$^+$+1).

Preparation of Compound 5086 and Compound 5087

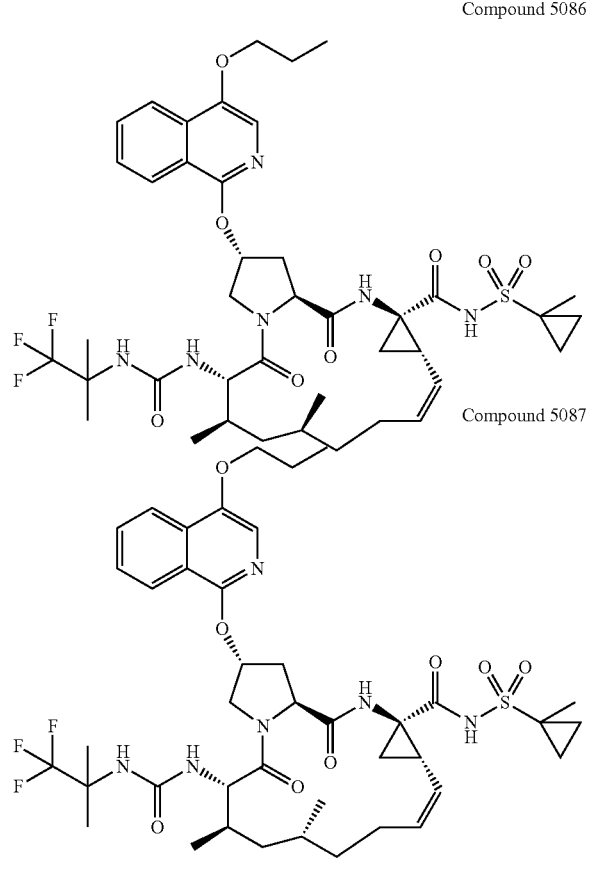

Compound 5086

Compound 5087

Preparation of Compound 5088 and Compound 5089

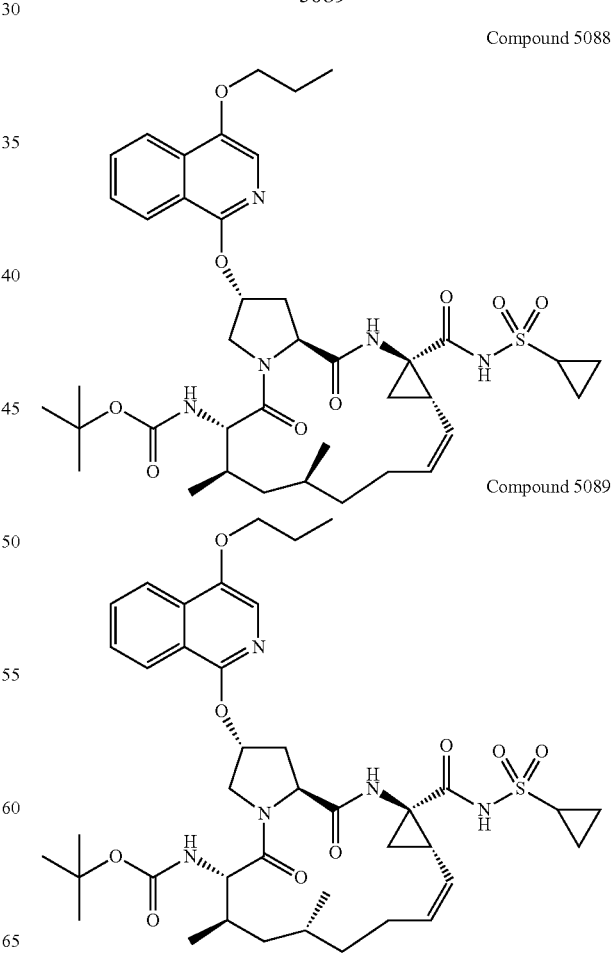

Compound 5088

Compound 5089

Compound 5088 and Compound 5089 were prepared using the intermediates described herein and by following the general procedure described for the synthesis of Compound 3117:

Compound 5088: tert-butyl ((2R,6S,7R,9S,13aS,14aR,16aS,Z)-14a-((cyclopropylsulfonyl)carbamoyl)-7,9-dimethyl-5,16-dioxo-2-((4-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 782.7 (M$^+$+1).

Compound 5089: tert-butyl ((2R,6S,7R,9R,13aS,14aR,16aS,Z)-14a-((cyclopropylsulfonyl)carbamoyl)-7,9-dimethyl-5,16-dioxo-2-((4-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.20 (br. s., 1H), 8.98 (br. s., 1H), 8.08 (d, J=8.5 Hz, 1H), 8.11 (d, J=8.2 Hz, 1H), 7.79 (t, J=7.6 Hz, 1H), 7.64 (s, 1H), 7.59 (t, J=7.5 Hz, 1H), 7.16 (d, J=7.6 Hz, 1H), 5.75 (br. s., 1H), 5.52 (br. s., 1H), 5.04 (br. s., 1H), 4.60 (d, J=10.7 Hz, 1H), 4.45 (br. s., 1H), 4.17-4.06 (m, 2H), 3.93-3.85 (m, 1H), 3.77-3.66 (m, 1H), 2.91 (s, 1H), 2.75-2.58 (m, 2H), 2.35-2.24 (m, 2H), 1.96-1.77 (m, 4H), 1.70 (br. s., 1H), 1.60 (br. s., 1H), 1.54 (br. s., 1H), 1.48-1.31 (m, 2H), 1.18-1.04 (m, 15H), 1.00 (br. s., 1H), 0.94 (d, J=7.0 Hz, 4H), 0.88 (d, J=6.4 Hz, 3H), 0.77-0.68 (m, 1H); MS: MS m/z 782.7 (M$^+$+1).

Compound 5090 and Compound 5091 were prepared using the intermediates described herein and by following the general procedure described for the synthesis of Compound 3117:

Compound 5090: 1,1,1-trifluoro-2-methylpropan-2-yl ((2R,6S,7R,9S,13aS,14aR,16aS,Z)-14a-((cyclopropylsulfonyl)carbamoyl)-7,9-dimethyl-5,16-dioxo-2-((4-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 836.7 (M$^+$+1).

Compound 5091: 1,1,1-trifluoro-2-methylpropan-2-yl ((2R,6S,7R,9R,13aS,14aR,16aS,Z)-14a-((cyclopropylsulfonyl)carbamoyl)-7,9-dimethyl-5,16-dioxo-2-((4-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.20 (br. s., 1H), 9.01 (br. s., 1H), 8.09 (d, J=8.9 Hz, 2H), 7.84-7.77 (m, 2H), 7.67-7.60 (m, 2H), 5.75 (br. s., 1H), 5.52 (br. s., 1H), 5.06 (br. s., 1H), 4.62-4.45 (m, 2H), 4.18-4.07 (m, 2H), 3.93-3.85 (m, 1H), 3.70 (dd, J=10.7, 7.9 Hz, 1H), 2.91 (br. s., 1H), 2.62 (br. s., 2H), 2.31 (ddd, J=13.7, 10.2, 3.8 Hz, 2H), 1.86 (dq, J=13.8, 7.0 Hz, 4H), 1.72 (br. s., 1H), 1.60 (br. s., 1H), 1.55 (br. s., 1H), 1.47-1.29 (m, 5H), 1.28-1.03 (m, 10H), 0.94 (d, J=6.7 Hz, 4H), 0.89 (d, J=6.4 Hz, 3H), 0.73 (t, J=12.4 Hz, 1H); MS: MS m/z 836.8 (M$^+$+1).

Preparation of Compound 5092 and Compound 5093

Preparation of Compound 5090 and Compound 5091

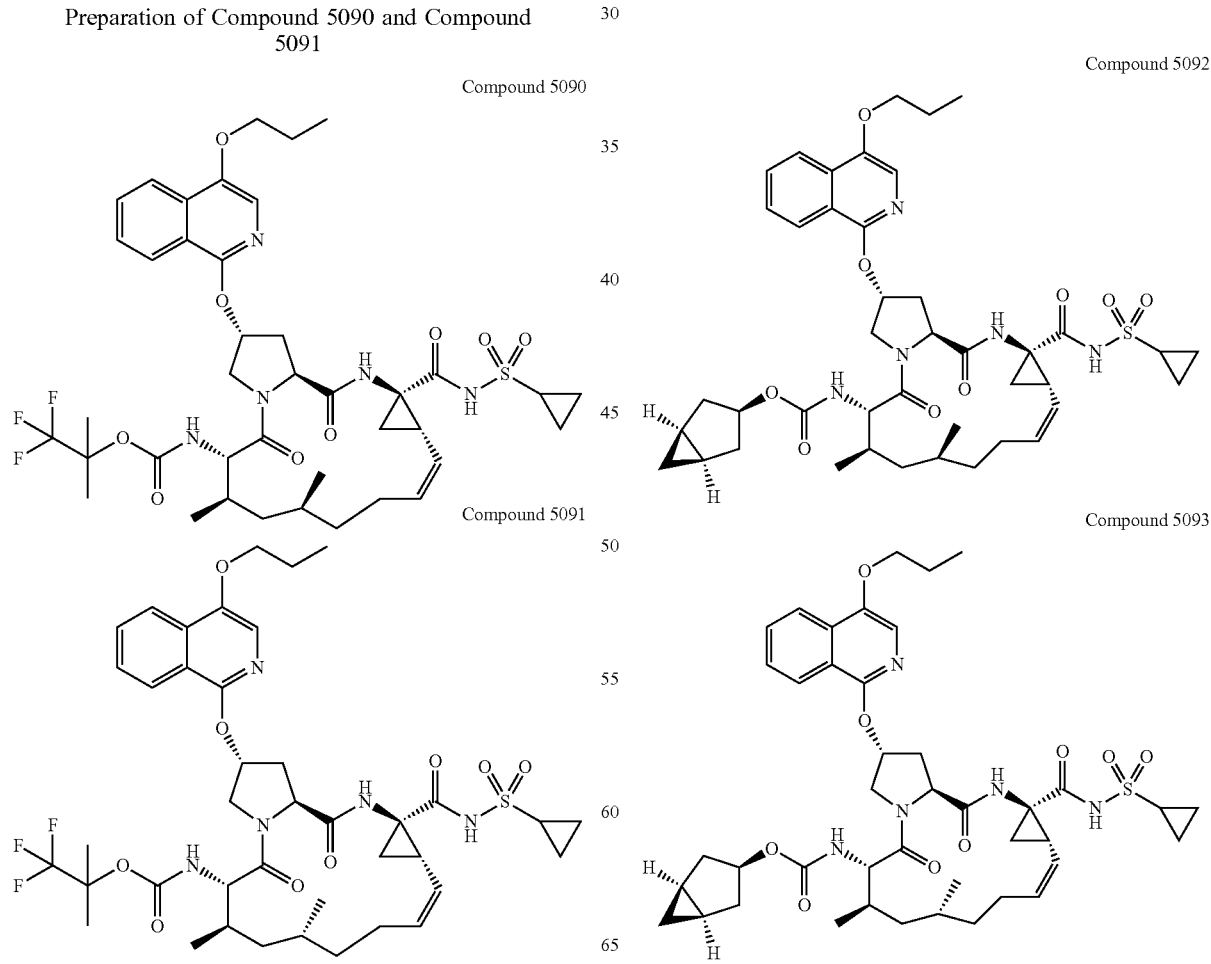

Compound 5090

Compound 5091

Compound 5092

Compound 5093

Compound 5092 and Compound 5093 were prepared using the intermediates described herein and by following the general procedure described for the synthesis of Compound 3117:

Compound 5092: (1R,3r,5S)-bicyclo[3.1.0]hexan-3-yl ((2R,6S,7R,9S,13aS,14aR,16aS,Z)-14a-((cyclopropylsulfonyl)carbamoyl)-7,9-dimethyl-5,16-dioxo-2-((4-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 806.7 (M$^+$+1).

Compound 5093: (1R,3r,5S)-bicyclo[3.1.0]hexan-3-yl ((2R,6S,7R,9R,13aS,14aR,16aS,Z)-14a-((cyclopropylsulfonyl)carbamoyl)-7,9-dimethyl-5,16-dioxo-2-((4-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.19 (br. s., 1H), 8.95 (br. s., 1H), 8.10 (d, J=9.2 Hz, 2H), 7.81 (t, J=8.1 Hz, 1H), 7.68-7.60 (m, 2H), 7.38 (d, J=8.5 Hz, 1H), 5.77 (br. s., 1H), 5.52 (br. s., 1H), 5.06 (br. s., 1H), 4.61 (t, J=6.6 Hz, 1H), 4.52-4.39 (m, 2H), 4.12 (t, J=6.4 Hz, 2H), 3.96-3.86 (m, 1H), 3.81-3.68 (m, 1H), 2.91 (br. s., 1H), 2.73 (d, J=18.3 Hz, 1H), 2.61 (br. s., 1H), 2.35-2.24 (m, 2H), 1.98-1.74 (m, 6H), 1.66 (br. s., 1H), 1.57 (d, J=14.3 Hz, 3H), 1.44 (br. s., 1H), 1.41-1.30 (m, 2H), 1.26-1.06 (m, 8H), 0.93 (d, J=7.0 Hz, 5H), 0.87 (d, J=6.4 Hz, 3H), 0.72 (t, J=12.4 Hz, 1H), 0.38-0.30 (m, 2H); MS: MS m/z 806.7 (M$^+$+1).

Preparation of Compound 5094 and Compound 5095

Compound 5094 and Compound 5095 were prepared using the intermediates described herein and by following the general procedure described for the synthesis of Compound 3117:

Compound 5094: (R)-1,1,1-trifluoropropan-2-yl ((2R,6S,7R,9S,13aS,14aR,16aS,Z)-14a-((cyclopropylsulfonyl)carbamoyl)-7,9-dimethyl-5,16-dioxo-2-((4-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 822.7 (M$^+$+1).

Compound 5095: (R)-1,1,1-trifluoropropan-2-yl ((2R,6S,7R,9R,13aS,14aR,16aS,Z)-14a-((cyclopropylsulfonyl)carbamoyl)-7,9-dimethyl-5,16-dioxo-2-((4-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.18 (br. s., 1H), 8.97 (br. s., 1H), 8.12-8.03 (m, 3H), 7.80 (t, J=7.6 Hz, 1H), 7.64 (s, 1H), 7.57 (t, J=7.6 Hz, 1H), 5.77 (br. s., 1H), 5.52 (br. s., 1H), 5.06 (br. s., 1H), 4.71 (dt, J=13.6, 6.9 Hz, 1H), 4.54-4.39 (m, 2H), 4.12 (t, J=6.4 Hz, 2H), 3.96-3.89 (m, 1H), 3.83-3.72 (m, 1H), 2.91 (br. s., 1H), 2.65 (br. s., 2H), 2.35-2.24 (m, 2H), 1.98-1.82 (m, 4H), 1.71 (br. s., 1H), 1.59 (br. s., 1H), 1.55 (br. s., 1H), 1.44 (br. s., 1H), 1.38 (d, J=14.3 Hz, 1H), 1.20 (d, J=6.7 Hz, 3H), 1.08 (t, J=7.3 Hz, 6H), 1.00 (d, J=6.4 Hz, 2H), 0.94 (d, J=6.7 Hz, 3H), 0.92-0.87 (m, 3H), 0.76 (t, J=11.9 Hz, 1H); MS: MS m/z 822.7 (M$^+$+1).

Preparation of Compound 5096 and Compound 5097

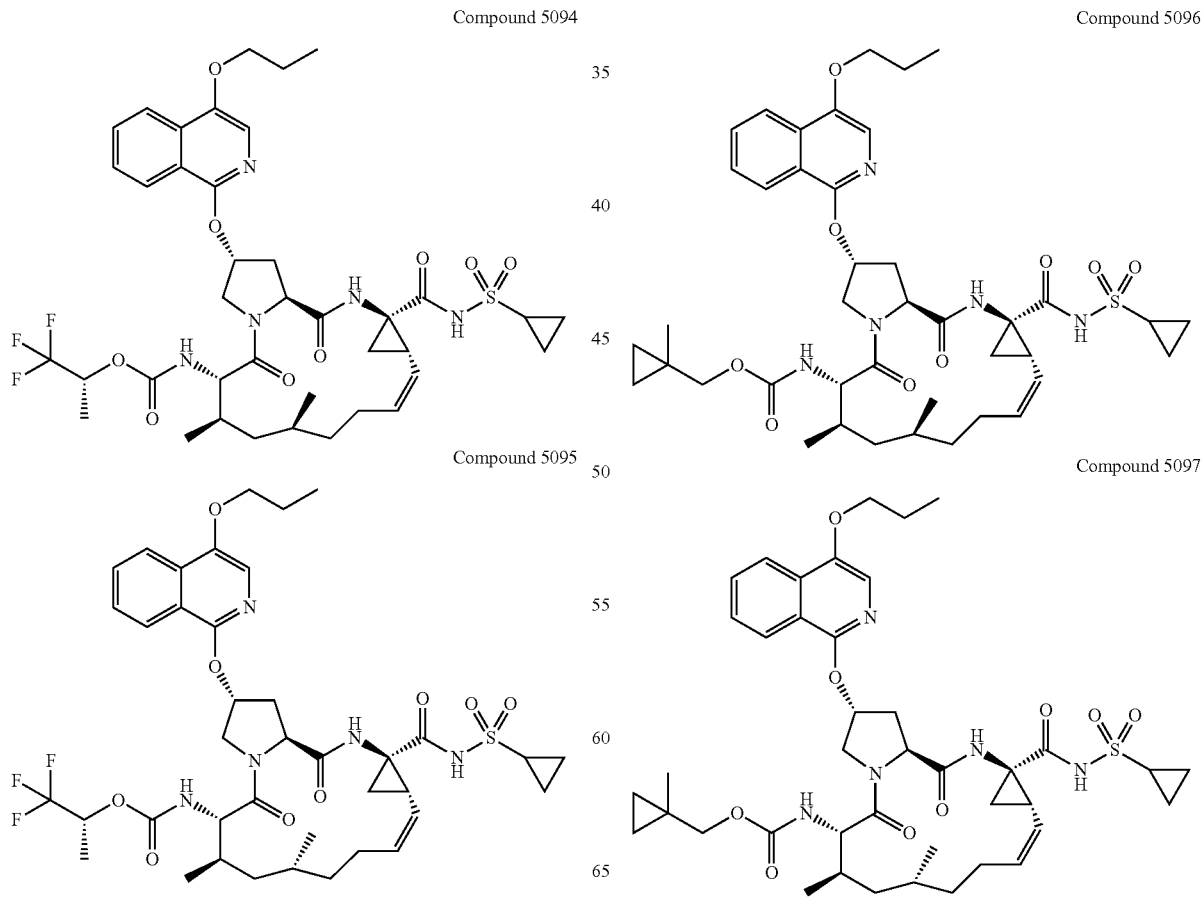

Compound 5094

Compound 5095

Compound 5096

Compound 5097

Compound 5096 and Compound 5097 were prepared using the intermediates described herein and by following the general procedure described for the synthesis of Compound 3117:

Compound 5096: (1-methylcyclopropyl)methyl ((2R,6S,7R,9S,13aS,14aR,16aS,Z)-14a-((cyclopropylsulfonyl)carbamoyl)-7,9-dimethyl-5,16-dioxo-2-((4-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 794.7 (M⁺+1).

Compound 5097: (1-methylcyclopropyl)methyl ((2R,6S,7R,9R,13aS,14aR,16aS,Z)-14a-((cyclopropylsulfonyl)carbamoyl)-7,9-dimethyl-5,16-dioxo-2-((4-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-$d_6$) δ ppm 11.19 (br. s., 1H), 8.96 (br. s., 1H), 8.09 (dd, J=8.2, 3.7 Hz, 2H), 7.80 (t, J=7.8 Hz, 1H), 7.67-7.58 (m, 2H), 7.49 (d, J=8.2 Hz, 1H), 5.77 (br. s., 1H), 5.52 (br. s., 1H), 5.06 (br. s., 1H), 4.57-4.41 (m, 2H), 4.12 (t, J=6.4 Hz, 2H), 3.96-3.88 (m, 1H), 3.83-3.73 (m, 1H), 2.91 (br. s., 1H), 2.69 (br. s., 1H), 2.60 (br. s., 1H), 2.30 (t, J=9.8 Hz, 2H), 1.99-1.80 (m, 5H), 1.70 (br. s., 1H), 1.60 (br. s., 1H), 1.54 (br. s., 1H), 1.48-1.28 (m, 2H), 1.08 (t, J=7.3 Hz, 7H), 1.01-0.87 (m, 11H), 0.80-0.70 (m, 1H), 0.31-0.14 (m, 4H); MS: MS m/z 794.7 (M⁺+1).

Compound 5098 and Compound 5099 were prepared using the intermediates described herein and by following the general procedure described for the synthesis of Compound 3117:

Compound 5098: (2R,6S,7R,9S,13aS,14aR,16aS,Z)—N-(cyclopropylsulfonyl)-7,9-dimethyl-5,16-dioxo-2-((4-propoxyisoquinolin-1-yl)oxy)-6-(3-(1,1,1-trifluoro-2-methylpropan-2-yl)ureido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide. MS: MS m/z 835.7 (M⁺+1).

Compound 5099: (2R,6S,7R,9R,13aS,14aR,16aS,Z)—N-(cyclopropylsulfonyl)-7,9-dimethyl-5,16-dioxo-2-((4-propoxyisoquinolin-1-yl)oxy)-6-(3-(1,1,1-trifluoro-2-methylpropan-2-yl)ureido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (500 MHz, DMSO-$d_6$) δ ppm 11.18 (br. s., 1H), 8.96 (br. s., 1H), 8.14-8.05 (m, 2H), 7.80 (t, J=7.6 Hz, 1H), 7.64 (s, 1H), 7.59 (t, J=7.8 Hz, 1H), 6.23 (d, J=8.2 Hz, 1H), 6.08 (s, 1H), 5.75 (br. s., 1H), 5.51 (br. s., 1H), 5.07 (br. s., 1H), 4.49 (br. s., 1H), 4.46-4.35 (m, 1H), 4.17-4.05 (m, 2H), 3.97-3.77 (m, 2H), 2.91 (s, 1H), 2.67 (d, J=16.2 Hz, 1H), 2.60 (br. s., 1H), 2.35-2.25 (m, 2H), 1.96-1.82 (m, 3H), 1.73-1.37 (m, 7H), 1.25-1.17 (m, 6H), 1.14-1.05 (m, 5H), 0.92 (dd, J=18.3, 6.7 Hz, 8H), 0.78-0.70 (m, 1H); MS: MS m/z 835.7 (M⁺+1).

Preparation of Compound 5100 and Compound 5101

Preparation of Compound 5098 and Compound 5099

Compound 5098

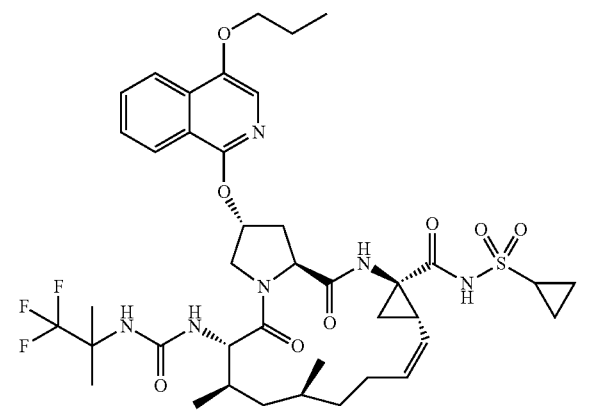

Compound 5099

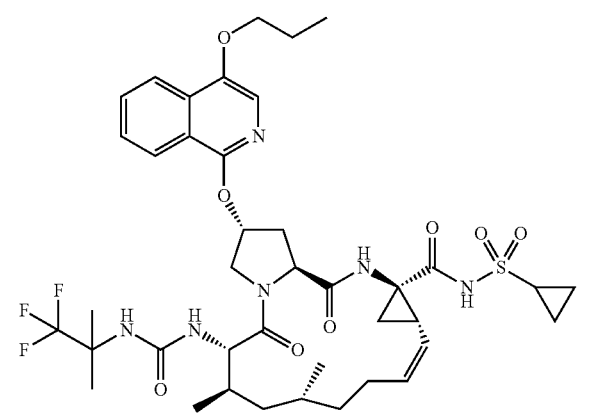

Compound 5100

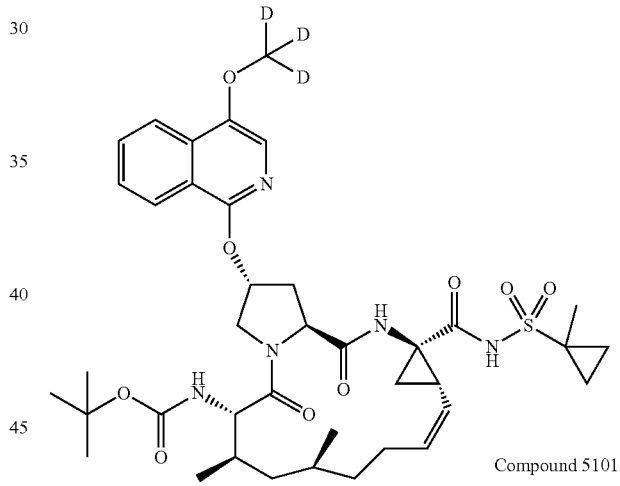

Compound 5101

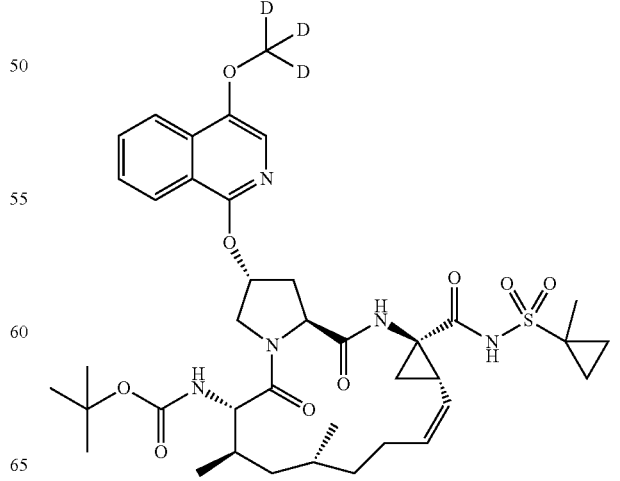

Compound 5100 and Compound 5101 were prepared using the intermediates described herein and by following the general procedure described for the synthesis of Compound 3117:

Compound 5100: tert-butyl ((2R,6S,7R,9S,13aS,14aR,16aS,Z)-7,9-dimethyl-14a-(((1-methylcyclopropyl)sulfonyl)carbamoyl)-5,16-dioxo-2-((4-(trideuteromethoxy)isoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 771.6 (M$^+$+1).

Compound 5101: tert-butyl ((2R,6S,7R,9S,13aS,14aR,16aS,Z)-7,9-dimethyl-14a-(((1-methylcyclopropyl)sulfonyl)carbamoyl)-5,16-dioxo-2-((4-(trideuteromethoxy)isoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.06 (br. s., 1H), 9.10 (br. s., 1H), 8.12 (d, J=8.2 Hz, 1H), 8.06 (d, J=8.5 Hz, 1H), 7.79 (t, J=7.8 Hz, 1H), 7.65 (s, 1H), 7.60 (t, J=7.5 Hz, 1H), 7.17 (br. s., 1H), 5.77 (br. s., 1H), 5.52 (br. s., 1H), 4.96 (br. s., 1H), 4.59 (br. s., 1H), 4.48 (br. s., 1H), 3.96-3.87 (m, 1H), 3.77-3.66 (m, 1H), 2.76-2.66 (m, 1H), 2.60 (br. s., 1H), 2.41-2.24 (m, 2H), 1.91 (d, J=13.7 Hz, 1H), 1.83 (br. s., 1H), 1.70 (br. s., 1H), 1.60 (br. s., 1H), 1.50 (br. s., 1H), 1.40 (br. s., 5H), 1.28 (br. s., 2H), 1.12 (s, 10H), 0.98-0.84 (m, 8H), 0.74 (d, J=10.1 Hz, 1H); MS: MS m/z 771.6 (M$^+$+1).

Compound 5102 and Compound 5103 were prepared using the intermediates described herein and by following the general procedure described for the synthesis of Compound 3117:

Compound 5102: 1,1,1-trifluoro-2-methylpropan-2-yl ((2R,6S,7R,9S,13aS,14aR,16aS,Z)-7,9-dimethyl-14a-(((1-methylcyclopropyl)sulfonyl)carbamoyl)-5,16-dioxo-2-((4-(trideuteromethoxy)isoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 825.7 (M$^+$+1).

Compound 5103: 1,1,1-trifluoro-2-methylpropan-2-yl ((2R,6S,7R,9R,13aS,14aR,16aS,Z)-7,9-dimethyl-14a-(((1-methylcyclopropyl)sulfonyl)carbamoyl)-5,16-dioxo-2-((4-(trideuteromethoxy)isoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
$^1$H NMR (500 MHz, DMSO-d$_6$) δ ppm 11.05 (br. s., 1H), 9.14 (br. s., 1H), 8.07 (d, J=8.2 Hz, 1H), 8.10 (d, J=8.2 Hz, 1H), 7.87-7.75 (m, 2H), 7.67-7.57 (m, 2H), 5.78 (br. s., 1H), 5.53 (br. s., 1H), 4.97 (br. s., 1H), 4.62-4.43 (m, 2H), 3.97-3.86 (m, 1H), 3.70 (dd, J=10.7, 7.9 Hz, 1H), 2.74-2.57 (m, 2H), 2.36-2.25 (m, 2H), 1.96-1.79 (m, 2H), 1.70 (d, J=6.7 Hz, 1H), 1.62 (br. s., 1H), 1.51 (d, J=7.6 Hz, 1H), 1.41 (s, 5H), 1.39-1.25 (m, 5H), 1.16 (br. s., 1H), 1.03 (s, 3H), 0.96-0.85 (m, 8H), 0.75 (t, J=12.5 Hz, 1H); MS: MS m/z 825.7 (M$^+$+1).

Preparation of Compound 5102 and Compound 5103

Preparation of Compound 5104 and Compound 5105

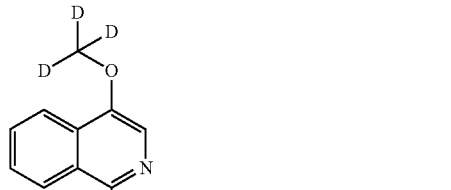

Compound 5102

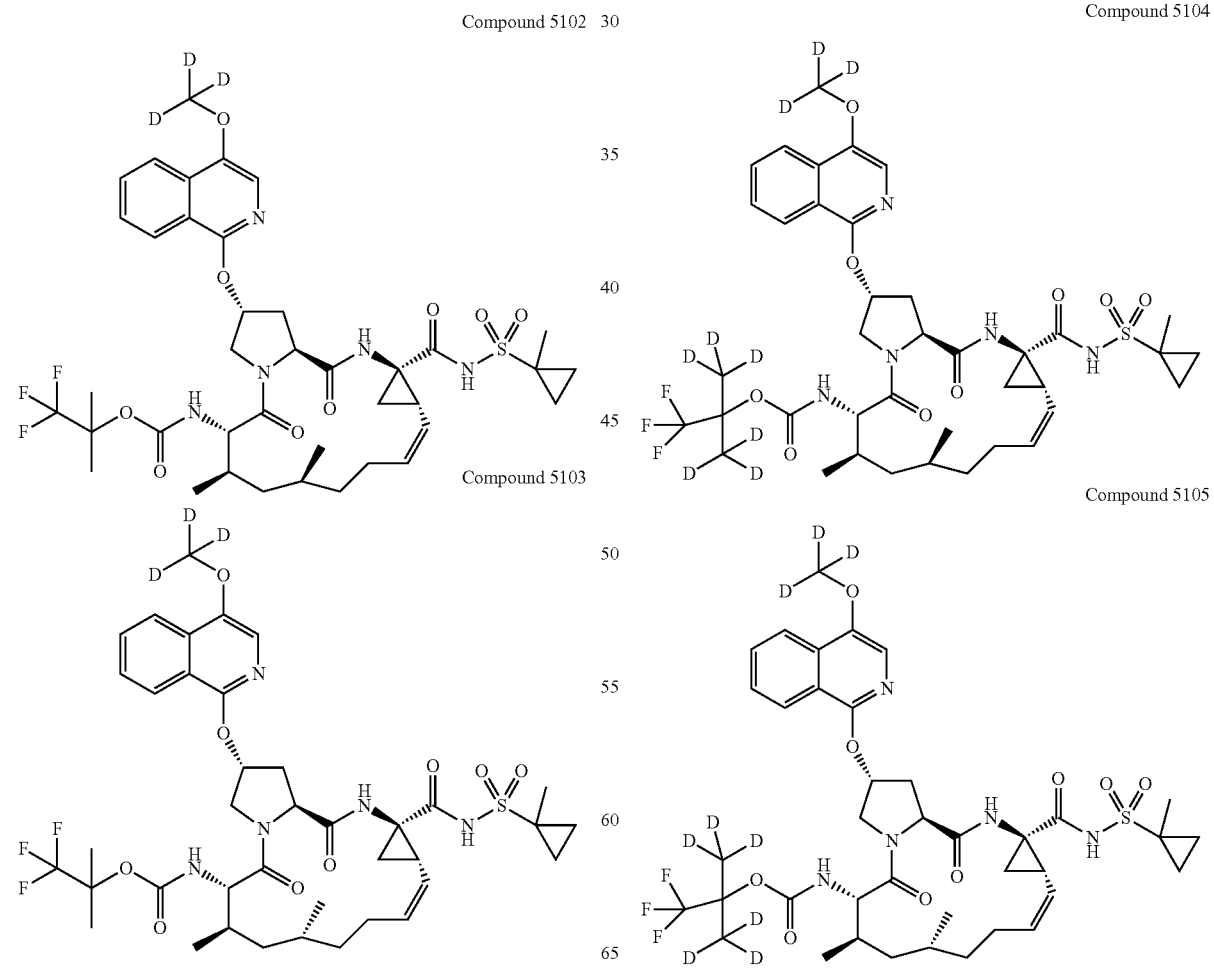

Compound 5103

Compound 5104

Compound 5105

Compound 5104 and Compound 5105 were prepared using the intermediates described herein and by following the general procedure described for the synthesis of Compound 3117:

Compound 5104: 1,1,1,3,3,3-hexadeutero-2-(trifluoromethyl)propan-2-yl ((2R,6S,7R,9S,13aS,14aR,16aS,Z)-7,9-dimethyl-14a-(((1-methylcyclopropyl)sulfonyl)carbamoyl)-5,16-dioxo-2-((4-(trideuteromethoxy)isoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 831.8 (M$^+$+1).

Compound 5105: 1,1,1,3,3,3-hexadeutero-2-(trifluoromethyl)propan-2-yl ((2R,6S,7R,9R,13aS,14aR,16aS,Z)-7,9-dimethyl-14a-(((1-methylcyclopropyl)sulfonyl)carbamoyl)-5,16-dioxo-2-((4-(trideuteromethoxy)isoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.05 (br. s., 1H), 9.14 (br. s., 1H), 8.07 (d, J=8.2 Hz, 1H), 8.10 (d, J=8.2 Hz, 1H), 7.87-7.75 (m, 2H), 7.68-7.58 (m, 2H), 5.78 (br. s., 1H), 5.53 (br. s., 1H), 4.97 (br. s., 1H), 4.64-4.41 (m, 2H), 3.96-3.88 (m, 1H), 3.70 (dd, J=10.7, 7.9 Hz, 1H), 2.69 (d, J=8.9 Hz, 1H), 2.62 (br. s., 1H), 2.39-2.25 (m, 2H), 1.95-1.80 (m, 2H), 1.70 (br. s., 1H), 1.62 (br. s., 1H), 1.52 (br. s., 1H), 1.41 (br. s., 5H), 1.35 (d, J=11.0 Hz, 1H), 1.29 (br. s., 1H), 1.15 (br. s., 1H), 0.97-0.86 (m, 8H), 0.75 (t, J=12.2 Hz, 1H); MS: MS m/z 831.8 (M$^+$+1).

Preparation of Compound 5106 and Compound 5107

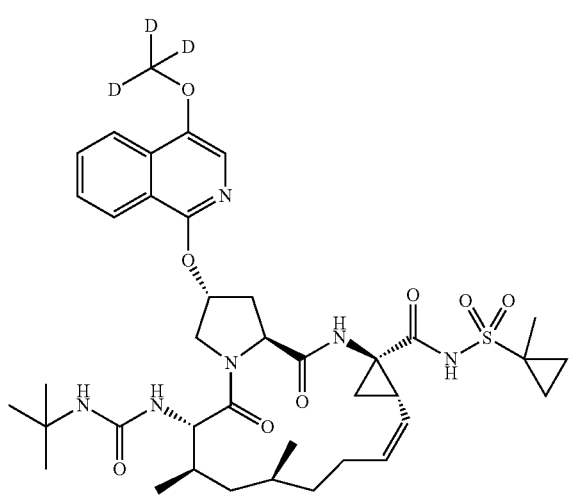

Compound 5106

Compound 5106 and Compound 5107 were prepared using the intermediates described herein and by following the general procedure described for the synthesis of Compound 3117:

Compound 5106: (2R,6S,7R,9S,13aS,14aR,16aS,Z)-6-(3-(tert-butyl)ureido)-7,9-dimethyl-N-((1-methylcyclopropyl)sulfonyl)-5,16-dioxo-2-((4-(trideuteromethoxy)isoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide. MS: MS m/z 770.7 (M$^+$+1).

Compound 5107: (2R,6S,7R,9R,13aS,14aR,16aS,Z)-6-(3-(tert-butyl)ureido)-7,9-dimethyl-N-((1-methylcyclopropyl)sulfonyl)-5,16-dioxo-2-((4-(trideuteromethoxy)isoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (500 MHz, DMSO-d$_6$) δ ppm 11.05 (br. s., 1H), 9.07 (br. s., 1H), 8.12 (d, J=8.2 Hz, 1H), 8.06 (d, J=8.5 Hz, 1H), 7.79 (t, J=7.8 Hz, 1H), 7.64 (s, 1H), 7.58 (t, J=7.6 Hz, 1H), 5.94 (d, J=8.9 Hz, 1H), 5.78 (br. s., 1H), 5.56 (s, 1H), 5.52 (br. s., 1H), 4.97 (br. s., 1H), 4.58 (d, J=10.4 Hz, 1H), 4.49-4.37 (m, 1H), 3.98-3.82 (m, 2H), 2.75 (s, 1H), 2.59 (br. s., 1H), 2.38-2.23 (m, 2H), 1.94-1.85 (m, 1H), 1.69 (dd, J=17.2, 6.3 Hz, 2H), 1.60 (br. s., 1H), 1.41 (br. s., 6H), 1.36 (br. s., 1H), 1.28 (d, J=6.7 Hz, 1H), 1.15 (br. s., 1H), 1.02 (s, 9H), 0.92 (dd, J=16.6, 6.6 Hz, 8H), 0.74 (t, J=12.4 Hz, 1H); MS: MS m/z 770.7 (M$^+$+1).

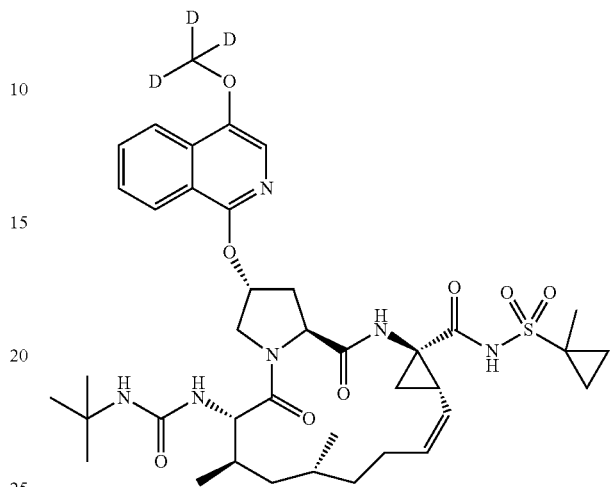

Compound 5107

Preparation of Compound 5108 and Compound 5109

Compound 5108

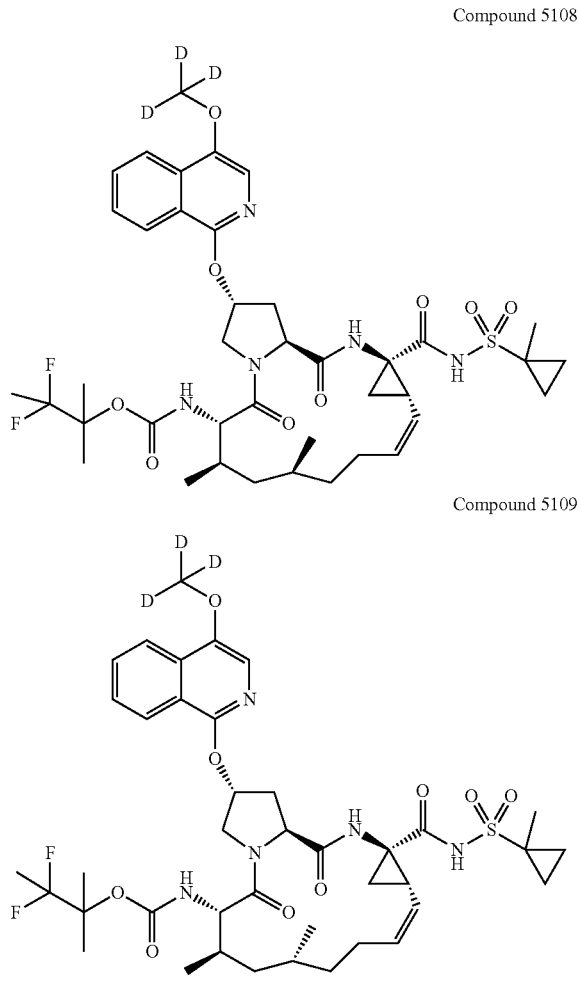 [SMILES: [2H]C([2H])([2H])Oc1cnc(O[C@@H]2C[C@H]3C(=O)N[C@]4(C(=O)NS(=O)(=O)C5(C)CC5)C[C@H]4/C=C\CC[C@H](C)C[C@@H](C)[C@H](NC(=O)OC(C)(C)C(F)(F)F)C(=O)N3C2)c2ccccc12 ; [2H]C([2H])([2H])Oc1cnc(O[C@@H]2C[C@H]3C(=O)N[C@]4(C(=O)NS(=O)(=O)C5(C)CC5)C[C@H]4/C=C\CC[C@@H](C)C[C@@H](C)[C@H](NC(=O)OC(C)(C)C(F)(F)F)C(=O)N3C2)c2ccccc12]

Compound 5109

Compound 5108 and Compound 5109 were prepared using the intermediates described herein and by following the general procedure described for the synthesis of Compound 3117:

Compound 5108: 3,3-difluoro-2-methylbutan-2-yl ((2R,6S,7R,9S,13aS,14aR,16aS,Z)-7,9-dimethyl-14a-(((1-methylcyclopropyl)sulfonyl)carbamoyl)-5,16-dioxo-2-((4-(trideuteromethoxy)isoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 821.7 (M$^+$+1).

Compound 5109: 3,3-difluoro-2-methylbutan-2-yl ((2R,6S,7R,9R,13aS,14aR,16aS,Z)-7,9-dimethyl-14a-(((1-methylcyclopropyl)sulfonyl)carbamoyl)-5,16-dioxo-2-((4-(trideuteromethoxy)isoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.06 (br. s., 1H), 9.12 (br. s., 1H), 8.08 (m, 2H), 7.79 (t, J=7.6 Hz, 1H), 7.69-7.52 (m, 3H), 5.77 (br. s., 1H), 5.53 (m, 1H), 4.98 (m, 1H), 4.51 (m, 2H), 4.00-3.88 (m, 1H), 3.72 (dd, J=10.7, 8.5 Hz, 1H), 2.77-2.58 (m, 2H), 2.40-2.25 (m, 2H), 1.95-1.65 (m, 5H), 1.56 (t, J=19.7 Hz, 4H), 1.41 (m, 6H), 1.25 (s, 3H), 1.03-0.85 (m, 12H), 0.75 (m, 1H); MS: MS m/z 821.7 (M$^+$+1).

Preparation of Compound 5110 and Compound 5111

Compound 5110

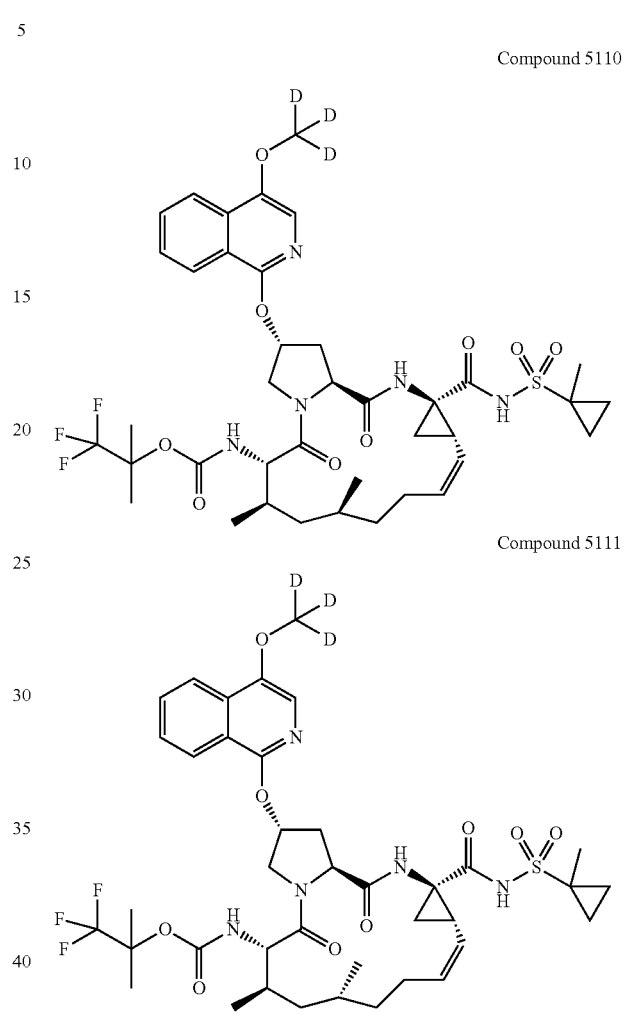

Compound 5111

Compound 5110 and Compound 5111 were prepared using the intermediates described herein and by following the general procedure described for the synthesis of Compound 5117:

Compound 5110: 1,1,1-trifluoro-2-methylpropan-2-yl ((2R,6S,7R,9S,13aR,14aR,16aS)-7,9-dimethyl-14a-(((1-methylcyclopropyl)sulfonyl)carbamoyl)-5,16-dioxo-2-((4-(trideuteromethoxy)isoquinolin-1-yl)oxy)octadecahydrocyclopropa[e]pyrrolo[1,2-a][1,4]diazacyclopentadecin-6-yl)carbamate. MS: MS m/z 827.5 (M$^+$+1).

Compound 5111: 1,1,1-trifluoro-2-methylpropan-2-yl ((2R,6S,7R,9R,13aR,14aR,16aS)-7,9-dimethyl-14a-(((1-methylcyclopropyl)sulfonyl)carbamoyl)-5,16-dioxo-2-((4-(trideuteromethoxy)isoquinolin-1-yl)oxy)octadecahydrocyclopropa[e]pyrrolo[1,2-a][1,4]diazacyclopentadecin-6-yl)carbamate. $^1$H NMR (500 MHz, DMSO-d$_6$) δ ppm 11.08 (br. s., 1H), 9.04 (br. s., 1H), 8.07 (d, J=8.5 Hz, 1H), 8.10 (d, J=8.2 Hz, 1H), 7.83-7.73 (m, 2H), 7.67-7.57 (m, 2H), 5.77 (br. s., 1H), 4.59-4.45 (m, 2H), 3.93-3.86 (m, 1H), 3.70 (dd, J=10.7, 8.2 Hz, 1H), 2.61 (br. s., 1H), 2.32-2.23 (m, 1H), 1.92 (s, 1H), 1.83-1.74 (m, 1H), 1.69 (d, J=13.1 Hz, 1H), 1.59 (d, J=10.4 Hz, 2H), 1.52-1.43 (m, 4H), 1.40 (d, J=6.1

Hz, 2H), 1.34 (s, 6H), 1.25 (br. s., 3H), 1.08-0.91 (m, 10H), 0.88 (d, J=6.4 Hz, 3H), 0.71 (t, J=11.4 Hz, 1H); MS: MS m/z 827.5 (M⁺+1).

Preparation of Compound 5112 and Compound 5113

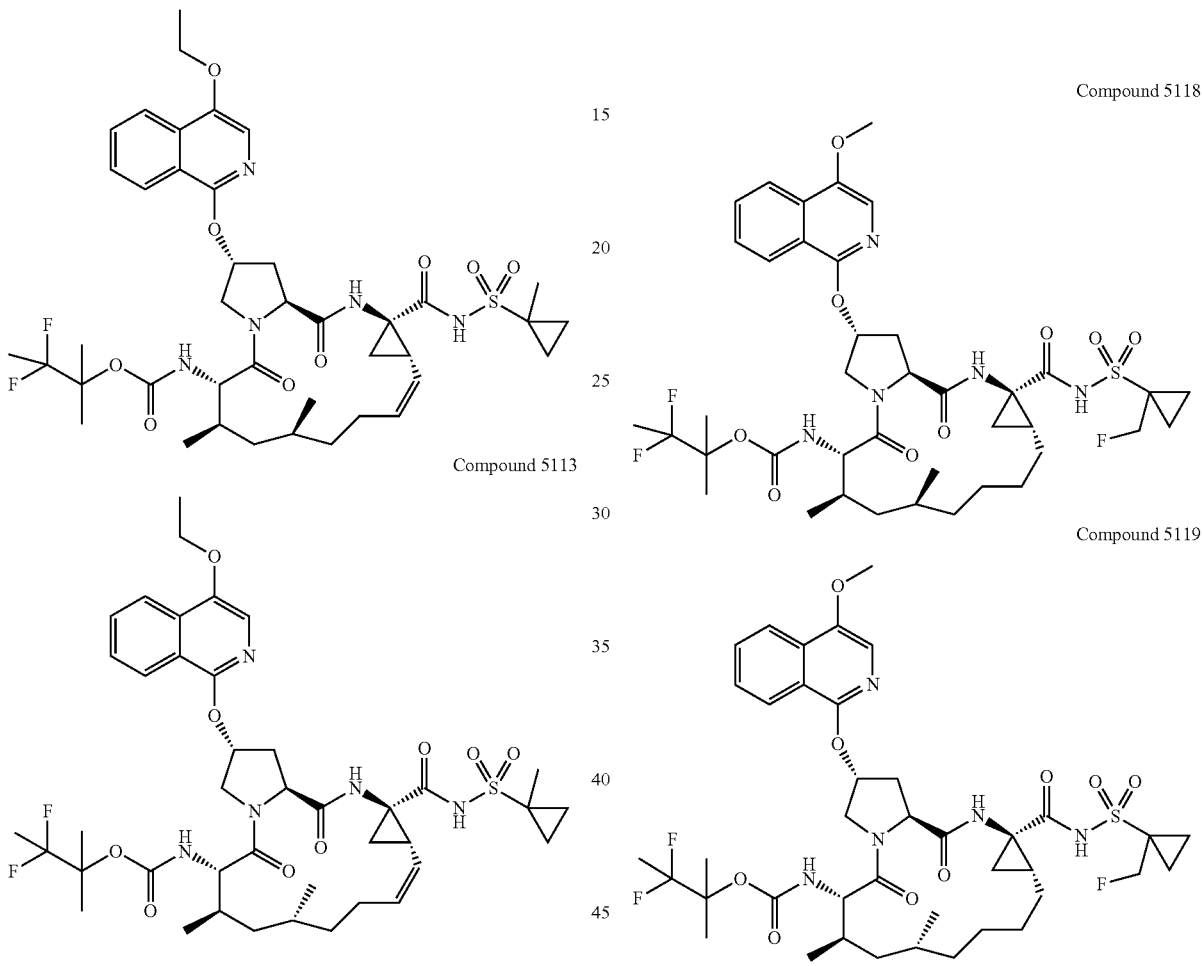

Compound 5112 and Compound 5113 were prepared using the intermediates described herein and by following the general procedure described for the synthesis of Compound 3117:

Compound 5112: 3,3-difluoro-2-methylbutan-2-yl ((2R,6S,7R,9S,13aS,14aR,16aS,Z)-2-((4-ethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 832.4 (M⁺+1).

Compound 5113: 3,3-difluoro-2-methylbutan-2-yl ((2R,6S,7R,9R,13 aS,14aR,16aS,Z)-2-((4-ethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (500 MHz, DMSO-d₆) δ ppm 11.05 (br. s., 1H), 9.11 (br. s., 1H), 8.08 (t, J=7.3 Hz, 2H), 7.79 (t, J=8.1 Hz, 1H), 7.67-7.58 (m, 3H), 5.78 (br. s., 1H), 5.53 (d, J=5.5 Hz, 1H), 4.98 (br. s., 1H), 4.62-4.44 (m, 2H), 4.21 (q, J=7.0 Hz, 2H), 3.98-3.84 (m, 1H), 3.72 (dd, J=10.7, 8.5 Hz, 1H), 2.77-2.68 (m, 1H), 2.68-2.58 (m, 1H), 2.40-2.23 (m, 2H), 1.98-1.79 (m, 2H), 1.69 (br. s., 1H), 1.56 (t, J=19.5 Hz, 5H), 1.49-1.39 (m, 8H), 1.36 (d, J=11.3 Hz, 1H), 1.32-1.23 (m, 4H), 1.15 (d, J=11.9 Hz, 1H), 1.01-0.84 (m, 11H), 0.76 (t, J=12.4 Hz, 1H); MS: MS m/z 832.5 (M⁺+1).

Preparation of Compound 5118 and Compound 5119

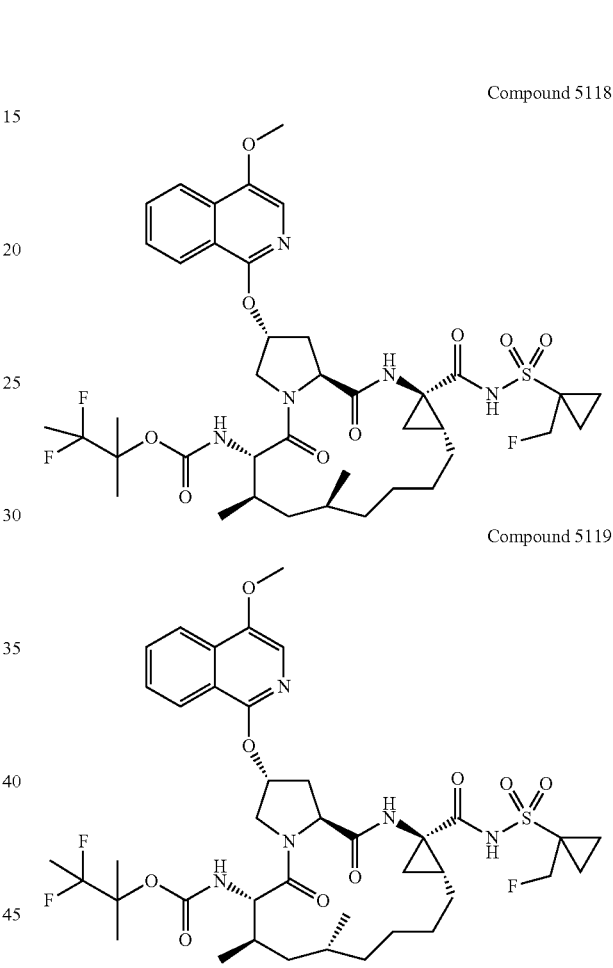

Compound 5118 and Compound 5119 were prepared using the intermediates described herein and by following the general procedure described for the synthesis of Compound 5117:

Compound 5118: 3,3-difluoro-2-methylbutan-2-yl((2R,6S,7R,9S,13aR,14aR,16aS)-14a-(((1-(fluoromethyl)cyclopropyl)sulfonyl)carbamoyl)-2-((4-methoxyisoquinolin-1-yl)oxy)-7,9-dimethyl-5,16-dioxooctadecahydrocyclopropa[e]pyrrolo[1,2-a][1,4]diazacyclopentadecin-6-yl)carbamate. MS: MS m/z 838.4 (M⁺+1).

Compound 5119: 3,3-difluoro-2-methylbutan-2-yl ((2R,6S,7R,9R,13aR,14aR,16aS)-14a-(((1-(fluoromethyl)cyclopropyl)sulfonyl)carbamoyl)-2-((4-methoxyisoquinolin-1-yl)oxy)-7,9-dimethyl-5,16-dioxooctadecahydrocyclopropa[e]pyrrolo[1,2-a][1,4]diazacyclopentadecin-6-yl)carbamate. ¹H NMR (500 MHz, DMSO-d₆) δ ppm 11.39 (s, 1H), 8.97 (s, 1H), 8.07 (d, J=8.2 Hz, 1H), 8.10 (d, J=8.2 Hz, 1H), 7.79 (t, J=7.8 Hz, 1H), 7.66 (s, 1H), 7.64-7.53 (m, 2H), 5.77 (br. s., 1H), 4.86-4.69 (m, 1H), 4.68-4.45 (m, 3H), 3.98 (s, 3H), 3.95-3.86 (m, 1H), 3.71 (dd, J=10.5, 8.4 Hz, 1H), 2.60 (dd, J=13.4, 6.4 Hz, 1H), 2.34-2.21 (m, 1H), 1.92 (d, J=6.1 Hz, 1H), 1.83-1.73 (m, 1H), 1.69 (d, J=12.5 Hz, 1H), 1.57 (t, J=19.5 Hz, 7H), 1.40-1.21 (m, 12H), 1.06-0.92 (m, 8H), 0.89 (d, J=6.4 Hz, 3H), 0.72 (t, J=11.4 Hz, 1H); MS: MS m/z 838.4 (M$^+$+1).

Preparation of Compound 5120

Compound 5120

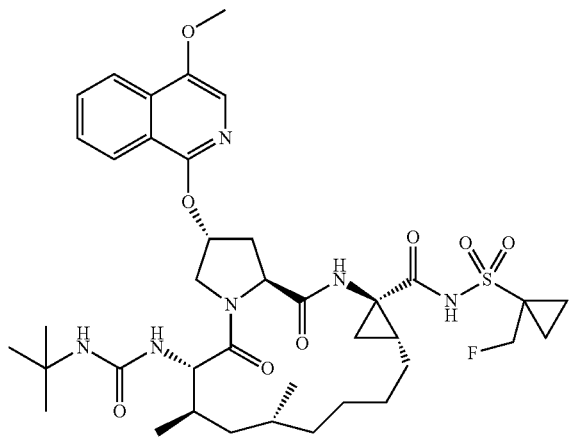

Compound 5120 was prepared using the intermediates described herein and by following the general procedure described for the synthesis of Compound 5117:

Compound 5120: (2R,6S,7R,9R,13aR,14aR,16aS)-6-(3-(tert-butyl)ureido)-N-((1-(fluoromethyl)cyclopropyl)sulfonyl)-2-((4-methoxyisoquinolin-1-yl)oxy)-7,9-dimethyl-5,16-dioxooctadecahydrocyclopropa[e]pyrrolo[1,2-a][1,4]diazacyclopentadecine-14a-carboxamide. $^1$H NMR (500 MHz, METHANOL-d$_4$) δ ppm 8.17 (d, J=8.2 Hz, 1H), 8.09 (d, J=8.2 Hz, 1H), 7.74-7.67 (m, 1H), 7.55 (s, 1H), 7.54-7.49 (m, 1H), 5.85-5.74 (m, 1H), 4.81-4.64 (m, 2H), 4.64-4.50 (m, 2H), 4.08-4.03 (m, 2H), 4.01 (s, 3H), 2.73 (dd, J=13.9, 7.2 Hz, 1H), 2.41 (ddd, J=13.9, 9.9, 4.3 Hz, 1H), 1.86 (d, J=8.5 Hz, 1H), 1.77-1.55 (m, 6H), 1.49-1.37 (m, 2H), 1.36-1.15 (m, 6H), 1.15-1.06 (m, 10H), 1.04-0.90 (m, 7H), 0.81-0.68 (m, 2H); MS: MS m/z 787.4 (M$^+$+1).

Preparation of Compound 5121 and Compound 5122

Compound 5121

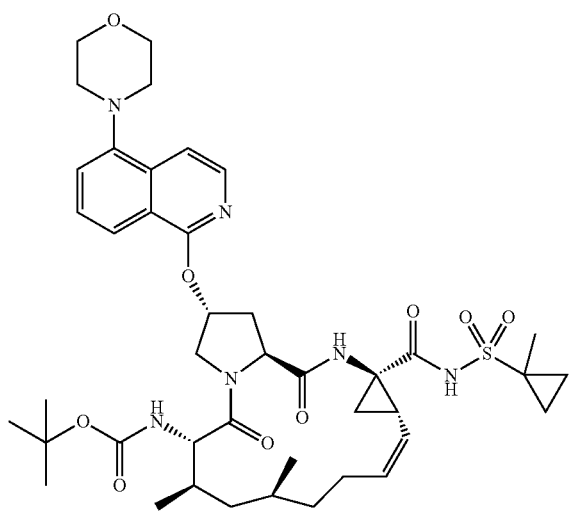

Compound 5122

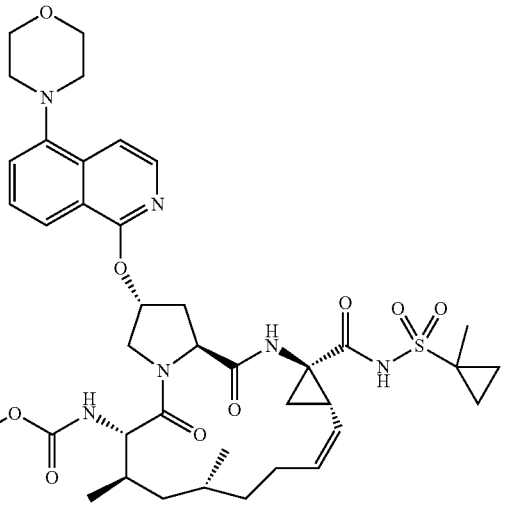

Compound 5121 and Compound 5122 were prepared using the intermediates described herein and by following the general procedure described for the synthesis of Compound 3117:

Compound 5121: tert-butyl ((2R,6S,7R,9S,13aS,14aR,16aS,Z)-7,9-dimethyl-14a-(((1-methylcyclopropyl)sulfonyl)carbamoyl)-2-((5-morpholinoisoquinolin-1-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 823.4 (M$^+$+1).

Compound 5122: tert-butyl ((2R,6S,7R,9R,13aS,14aR,16aS,Z)-7,9-dimethyl-14a-(((1-methylcyclopropyl)sulfonyl)carbamoyl)-2-((5-morpholinoisoquinolin-1-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.05 (br. s., 1H), 9.10 (br. s., 1H), 8.03 (d, J=6.1 Hz, 1H), 7.86 (d, J=8.2 Hz, 1H), 7.59-7.50 (m, 1H), 7.46 (t, J=7.9 Hz, 1H), 7.35 (d, J=7.6 Hz, 1H), 7.17 (br. s., 1H), 5.83 (br. s., 1H), 5.51 (br. s., 1H), 4.98 (br. s., 1H), 4.61 (br. s., 1H), 4.47 (br. s., 1H), 3.97-3.82 (m, 5H), 3.76-3.65 (m, 1H), 3.09-2.92 (m, 4H), 2.60 (m, 2H), 2.35-2.23 (m, 2H), 1.94-1.85 (m, 1H), 1.81 (br. s., 1H), 1.71 (br. s., 1H), 1.59 (br. s., 1H), 1.40 (br. s., 6H), 1.24 (d, J=6.4 Hz, 2H), 1.11 (s, 10H), 1.04 (br. s., 1H), 0.96-0.84 (m, 7H), 0.72 (br. s., 1H); MS: MS m/z 823.4 (M$^+$+1).

Preparation of Compound 5123 and Compound 5124

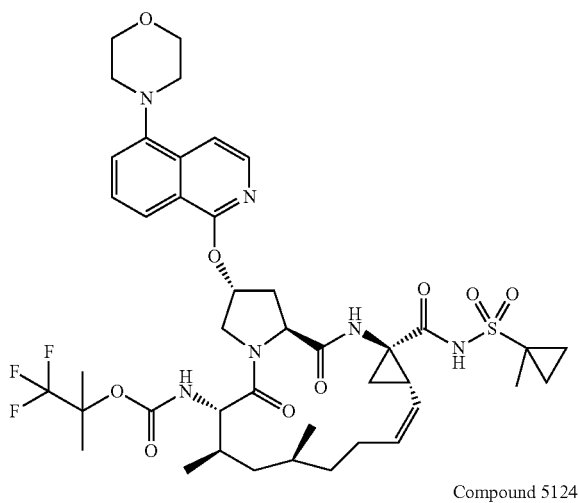

Compound 5123

Compound 5124

Compound 5123 and Compound 5124 were prepared using the intermediates described herein and by following the general procedure described for the synthesis of Compound 3117:

Compound 5123: 1,1,1-trifluoro-2-methylpropan-2-yl ((2R,6S,7R,9S,13aS,14aR,16aS,Z)-7,9-dimethyl-14a-(((1-methylcyclopropyl)sulfonyl)carbamoyl)-2-((5-morpholinoisoquinolin-1-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 877.4 (M$^+$+1).

Compound 5124: 1,1,1-trifluoro-2-methylpropan-2-yl ((2R,6S,7R,9R,13aS,14aR,16aS,Z)-7,9-dimethyl-14a-(((1-methylcyclopropyl)sulfonyl)carbamoyl)-2-((5-morpholinoisoquinolin-1-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.05 (br. s., 1H), 9.14 (br. s., 1H), 8.04 (d, J=6.1 Hz, 1H), 7.84 (d, J=8.2 Hz, 2H), 7.59-7.46 (m, 2H), 7.36 (d, J=7.0 Hz, 1H), 5.84 (br. s., 1H), 5.52 (br. s., 1H), 4.98 (br. s., 1H), 4.63-4.43 (m, 2H), 3.98-3.83 (m, 5H), 3.70 (dd, J=10.7, 7.9 Hz, 1H), 3.08-2.95 (m, 4H), 2.72-2.58 (m, 2H), 2.39-2.24 (m, 2H), 1.94-1.79 (m, 2H), 1.70 (br. s., 1H), 1.61 (br. s., 1H), 1.50 (br. s., 2H), 1.41 (br. s., 4H), 1.38-1.24 (m, 5H), 1.17 (d, J=13.1 Hz, 1H), 1.04 (s, 3H), 0.98-0.84 (m, 8H), 0.75 (br. s., 1H); MS: MS m/z 877.4 (M$^+$+1).

Preparation of Compound 5125 and Compound 5126

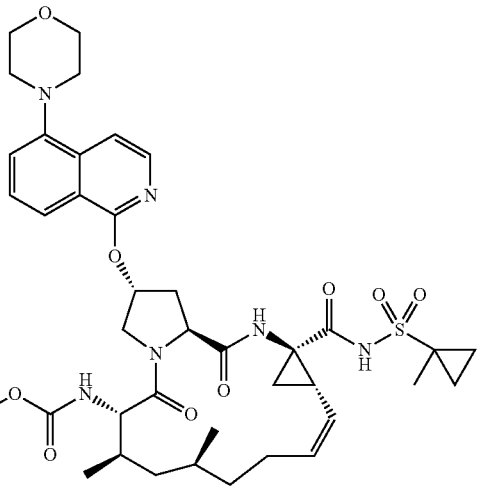

Compound 5125

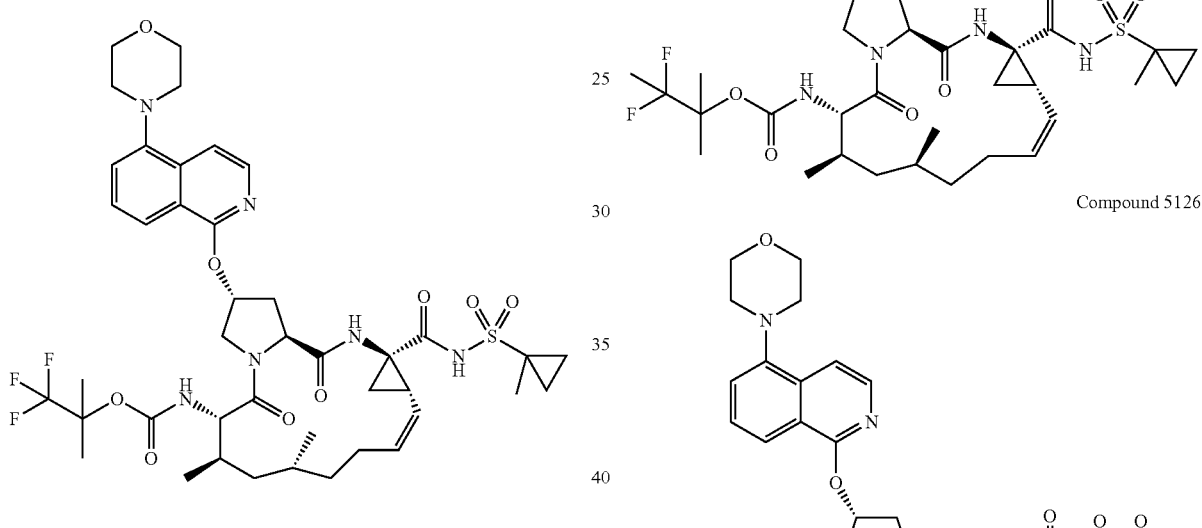

Compound 5126

Compound 5125 and Compound 5126 were prepared using the intermediates described herein and by following the general procedure described for the synthesis of Compound 3117:

Compound 5125: 3,3-difluoro-2-methylbutan-2-yl ((2R,6S,7R,9S,13aS,14aR,16aS,Z)-7,9-dimethyl-14a-(((1-methylcyclopropyl)sulfonyl)carbamoyl)-2-((5-morpholinoisoquinolin-1-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 873.4 (M$^+$+1).

Compound 5126: 3,3-difluoro-2-methylbutan-2-yl ((2R,6S,7R,9R,13aS,14aR,16aS,Z)-7,9-dimethyl-14a-(((1-methylcyclopropyl)sulfonyl)carbamoyl)-2-((5-morpholinoisoquinolin-1-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500

MHz, DMSO-d$_6$) δ ppm 11.05 (br. s., 1H), 9.11 (br. s., 1H), 8.04 (d, J=6.1 Hz, 1H), 7.84 (d, J=8.2 Hz, 1H), 7.62 (d, J=8.5 Hz, 1H), 7.54 (d, J=6.1 Hz, 1H), 7.48 (t, J=7.9 Hz, 1H), 7.36 (d, J=7.3 Hz, 1H), 5.84 (br. s., 1H), 5.53 (br. s., 1H), 4.98 (br. s., 1H), 4.58 (d, J=11.3 Hz, 1H), 4.52 (br. s., 1H), 3.97-3.82 (m, 5H), 3.72 (dd, J=10.7, 8.2 Hz, 1H), 3.08-2.94 (m, 4H), 2.78-2.68 (m, 1H), 2.65 (br. s., 1H), 2.42-2.26 (m, 2H), 1.94-1.87 (m, 1H), 1.83 (d, J=7.3 Hz, 1H), 1.69 (br. s., 1H), 1.57 (t, J=19.7 Hz, 5H), 1.41 (br. s., 5H), 1.37 (br. s., 1H), 1.29 (br. s., 1H), 1.24 (s, 3H), 1.14 (br. s., 1H), 1.00-0.85 (m, 11H), 0.81-0.70 (m, 1H); MS: MS m/z 873.4 (M$^+$+1).

Preparation of Compound 5127 and Compound 5128

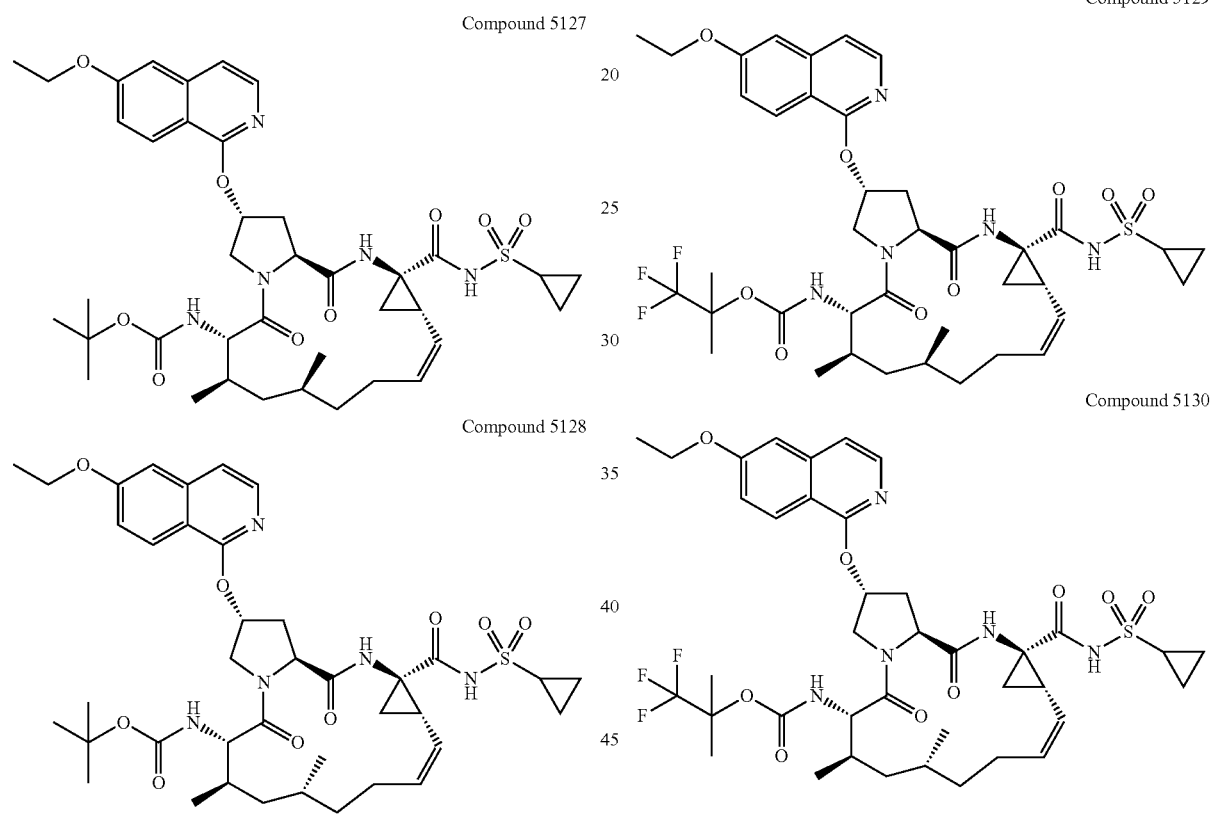

Compound 5127 and Compound 5128 were prepared using the intermediates described herein and by following the general procedure described for the synthesis of Compound 3117:

Compound 5127: tert-butyl ((2R,6S,7R,9S,13aS,14aR,16aS,Z)-14a-((cyclopropylsulfonyl)carbamoyl)-2-((6-ethoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 768.4 (M$^+$+1).

Compound 5128: tert-butyl ((2R,6S,7R,9R,13aS,14aR,16aS,Z)-14a-((cyclopropylsulfonyl)carbamoyl)-2-((6-ethoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.18 (br. s., 1H), 8.97 (br. s., 1H), 8.04 (d, J=8.9 Hz, 1H), 7.98-7.90 (m, 1H), 7.35-7.27 (m, 2H), 7.19 (d, J=6.4 Hz, 1H), 7.09 (dd, J=9.2, 2.4 Hz, 1H), 5.80 (br. s., 1H), 5.52 (br. s., 1H), 5.05 (br. s., 1H), 4.57 (br. s., 1H), 4.43 (br. s., 1H), 4.18 (q, J=6.9 Hz, 2H), 3.95-3.82 (m, 1H), 3.77-3.67 (m, 1H), 2.67 (d, J=18.9 Hz, 1H), 2.61 (br. s., 1H), 2.36-2.23 (m, 2H), 1.91 (d, J=10.1 Hz, 1H), 1.82 (d, J=6.7 Hz, 1H), 1.72 (br. s., 1H), 1.59 (br. s., 1H), 1.53 (br. s., 1H), 1.47-1.34 (m, 6H), 1.18-1.06 (m, 12H), 1.03-0.84 (m, 8H), 0.72 (t, J=11.4 Hz, 1H); MS: MS m/z 768.4 (M$^+$+1).

Preparation of Compound 5129 and Compound 5130

Compound 5129 and Compound 5130 were prepared using the intermediates described herein and by following the general procedure described for the synthesis of Compound 3117:

Compound 5129: 1,1,1-trifluoro-2-methylpropan-2-yl ((2R,6S,7R,9S,13aS,14aR,16aS,Z)-14a-((cyclopropylsulfonyl)carbamoyl)-2-((6-ethoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 822.3 (M$^+$+1).

Compound 5130: 1,1,1-trifluoro-2-methylpropan-2-yl ((2R,6S,7R,9R,13aS,14aR,16aS,Z)-14a-((cyclopropylsulfonyl)carbamoyl)-2-((6-ethoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.19 (br. s., 1H), 9.01 (br. s., 1H), 8.01 (d, J=9.2 Hz, 1H), 7.96 (d, J=5.8 Hz, 1H), 7.83 (d, J=8.2 Hz, 1H), 7.37-7.27 (m, 2H), 7.14 (dd, J=9.2, 2.4 Hz, 1H), 5.81 (br. s., 1H), 5.52 (br. s., 1H), 5.05 (br. s., 1H), 4.59-4.43 (m, 2H), 4.18 (q, J=6.9 Hz, 2H), 3.95-3.83 (m, 1H), 3.71 (dd, J=10.8, 8.1 Hz, 1H), 2.71-2.57 (m, 2H), 2.36-2.23 (m, 2H), 1.94-1.76 (m, 2H), 1.71 (br. s., 1H), 1.61-1.13 (m, 16H), 1.04-0.84 (m, 9H), 0.74 (t, J=13.0 Hz, 1H); MS: MS m/z 822.3 (M$^+$+1).

Preparation of Compound 5131 and Compound 5132

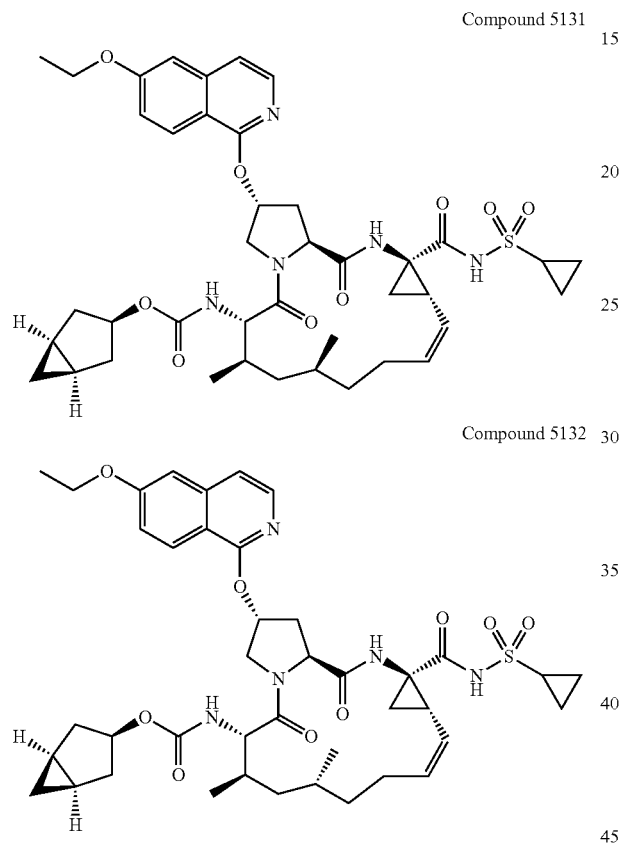

Compound 5131 and Compound 5132 were prepared using the intermediates described herein and by following the general procedure described for the synthesis of Compound 3117:

Compound 5131: (1R,3r,5S)-bicyclo[3.1.0]hexan-3-yl ((2R,6S,7R,9S,13aS,14aR,16aS,Z)-14a-((cyclopropylsulfonyl)carbamoyl)-2-((6-ethoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 792.4 (M$^+$+1).

Compound 5132: (1R,3r,5S)-bicyclo[3.1.0]hexan-3-yl ((2R,6S,7R,9R,13aS,14aR,16aS,Z)-14a-((cyclopropylsulfonyl)carbamoyl)-2-((6-ethoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.19 (br. s., 1H), 8.94 (br. s., 1H), 8.02 (d, J=8.9 Hz, 1H), 7.98-7.91 (m, 1H), 7.40 (d, J=8.2 Hz, 1H), 7.35-7.27 (m, 2H), 7.16 (dd, J=9.2, 2.4 Hz, 1H), 5.82 (br. s., 1H), 5.52 (br. s., 1H), 5.07 (br. s., 1H), 4.67 (t, J=6.7 Hz, 1H), 4.55-4.37 (m, 2H), 4.18 (q, J=7.0 Hz, 2H), 3.96-3.86 (m, 1H), 3.81-3.70 (m, 1H), 2.61 (m, 2H), 2.35-2.22 (m, 2H), 2.02-1.90 (m, 2H), 1.88-1.76 (m, 2H), 1.67 (br. s., 1H), 1.62-1.51 (m, 3H), 1.48-1.31 (m, 7H), 1.26-1.06 (m, 5H), 0.93 (d, J=7.0 Hz, 5H), 0.87 (d, J=6.4 Hz, 3H), 0.72 (t, J=13.0 Hz, 1H), 0.40-0.32 (m, 2H); MS: MS m/z 792.4 (M$^+$+1).

Preparation of Compound 5133 and Compound 5134

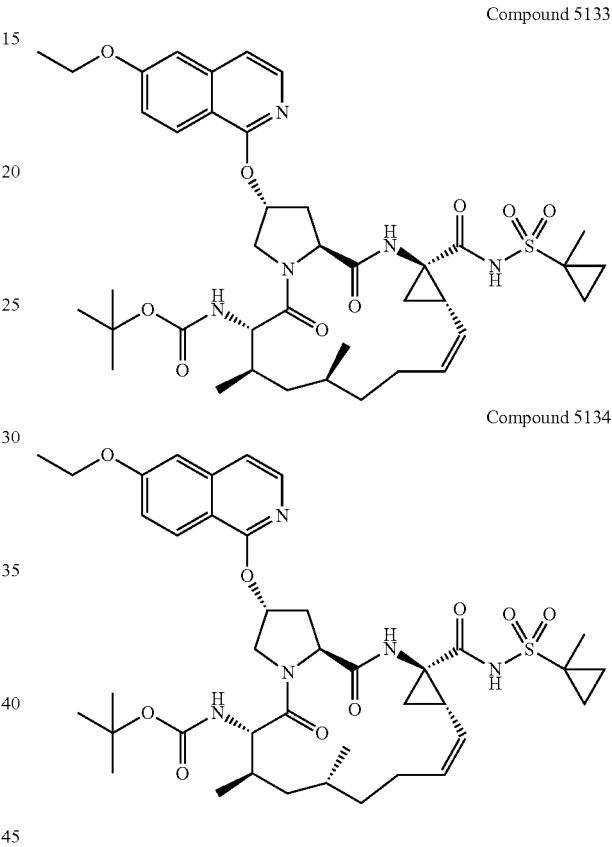

Compound 5133 and Compound 5134 were were prepared using the intermediates described herein and by following the general procedure described for the synthesis of Compound 3117:

Compound 5133: tert-butyl ((2R,6S,7R,9S,13aS,14aR,16aS,Z)-2-((6-ethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 782.4 (M$^+$+1).

Compound 5134: tert-butyl ((2R,6S,7R,9R,13aS,14aR,16aS,Z)-2-((6-ethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.04 (br. s., 1H), 9.09 (br. s., 1H), 8.04 (d, J=9.2 Hz, 1H), 7.97-7.91 (m, 1H), 7.34-7.25 (m, 2H), 7.19 (d, J=7.3 Hz, 1H), 7.10 (dd, J=9.2, 2.4 Hz, 1H), 5.82 (br. s., 1H), 5.52 (br. s., 1H), 4.97 (br. s., 1H), 4.59 (d, J=9.2 Hz, 1H), 4.47 (br. s., 1H), 4.18 (q, J=6.9 Hz, 2H), 3.95-3.88

(m, 1H), 3.73 (dd, J=10.4, 8.5 Hz, 1H), 2.71 (s, 1H), 2.59 (br. s., 1H), 2.39-2.25 (m, 2H), 1.94-1.77 (m, 2H), 1.70-1.23 (m, 13H), 1.17-1.06 (m, 10H), 0.98-0.82 (m, 8H), 0.73 (t, J=11.7 Hz, 1H); MS: MS m/z 782.4 (M$^+$+1).

Preparation of Compound 5135 and Compound 5136

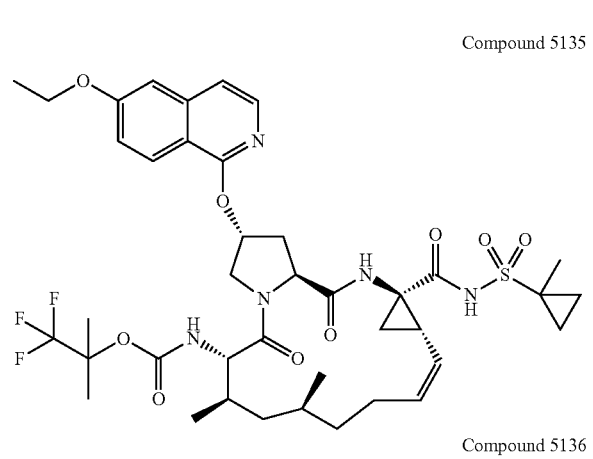

Compound 5135

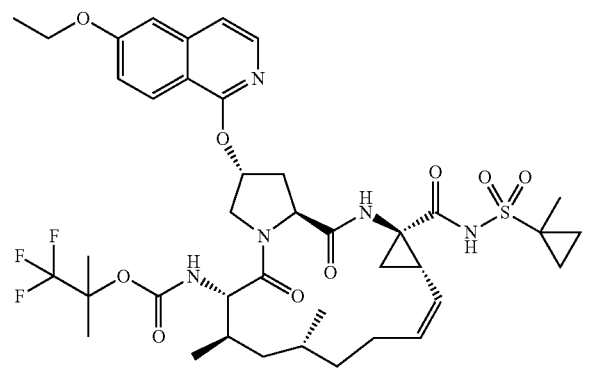

Compound 5136

Compound 5135 and Compound 5136 were prepared using the intermediates described herein and by following the general procedure described for the synthesis of Compound 3117:

Compound 5135: 1,1,1-trifluoro-2-methylpropan-2-yl ((2R,6S,7R,9S,13aS,14aR,16aS,Z)-2-((6-ethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 836.3 (M$^+$+1).

Compound 5136: 1,1,1-trifluoro-2-methylpropan-2-yl ((2R,6S,7R,9R,13aS,14aR,16aS,Z)-2-((6-ethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.04 (br. s., 1H), 9.13 (br. s., 1H), 8.01 (d, J=9.2 Hz, 1H), 7.96 (d, J=6.1 Hz, 1H), 7.84 (d, J=7.9 Hz, 1H), 7.34-7.28 (m, 2H), 7.14 (dd, J=9.0, 2.3 Hz, 1H), 5.82 (br. s., 1H), 5.53 (br. s., 1H), 4.98 (br. s., 1H), 4.53 (br. s., 2H), 4.18 (q, J=6.8 Hz, 2H), 3.96-3.86 (m, 1H), 3.71 (dd, J=10.7, 7.9 Hz, 1H), 2.73 (d, J=18.0 Hz, 1H), 2.61 (br. s., 1H), 2.41-2.22 (m, 2H), 1.94-1.81 (m, 2H), 1.70 (br. s., 1H), 1.61 (br. s., 1H), 1.51 (br. s., 1H), 1.48-1.32 (m, 12H), 1.27 (d, J=17.7 Hz, 1H), 1.15 (br. s., 1H), 1.11 (s, 3H), 0.98-0.82 (m, 8H), 0.75 (t, J=12.4 Hz, 1H); MS: MS m/z 836.3 (M$^+$+1).

Preparation of Compound 5137 and Compound 5138

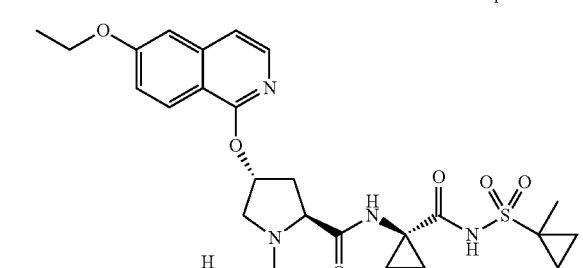

Compound 5137

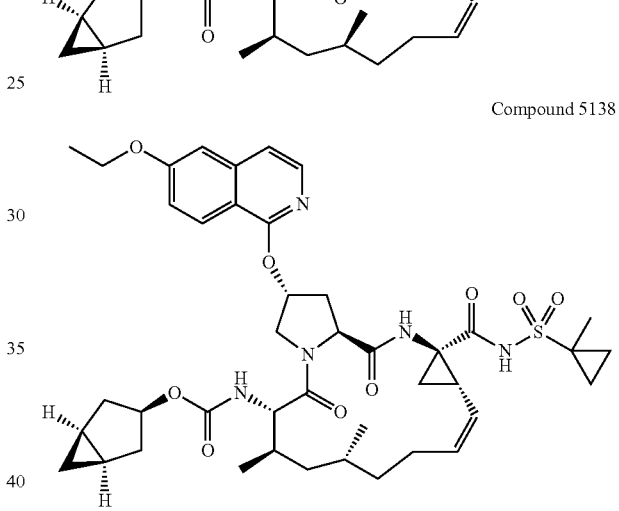

Compound 5138

Compound 5137 and Compound 5138 were prepared using the intermediates described herein and by following the general procedure described for the synthesis of Compound 3117:

Compound 5137: (1R,3r,5S)-bicyclo[3.1.0]hexan-3-yl ((2R,6S,7R,9S,13aS,14aR,16aS,Z)-2-((6-ethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 806.4 (M$^+$+1).

Compound 5138: (1R,3r,5S)-bicyclo[3.1.0]hexan-3-yl ((2R,6S,7R,9R,13 aS,14aR,16aS,Z)-2-((6-ethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.04 (br. s., 1H), 9.06 (br. s., 1H), 8.02 (d, J=9.2 Hz, 1H), 7.98-7.89 (m, 1H), 7.40 (d, J=7.9 Hz, 1H), 7.35-7.27 (m, 2H), 7.16 (dd, J=9.0, 2.3 Hz, 1H), 5.83 (br. s., 1H), 5.51 (br. s., 1H), 4.99 (br. s., 1H), 4.65 (t, J=6.7 Hz, 1H), 4.47 (br. s., 2H), 4.18 (q, J=7.0 Hz, 2H), 3.99-3.88 (m, 1H), 3.76 (dd, J=10.5, 9.0 Hz, 1H), 2.76-2.68 (m, 1H), 2.59 (br. s., 1H), 2.37-2.24 (m, 2H), 2.02-1.89 (m, 2H), 1.87-1.74 (m, 2H), 1.67-1.07 (m, 18H), 0.93-0.73 (m, 9H), 0.40-0.29 (m, 2H); MS: MS m/z 806.4 (M⁺+1).

Preparation of Compound 5139 and Compound 5140

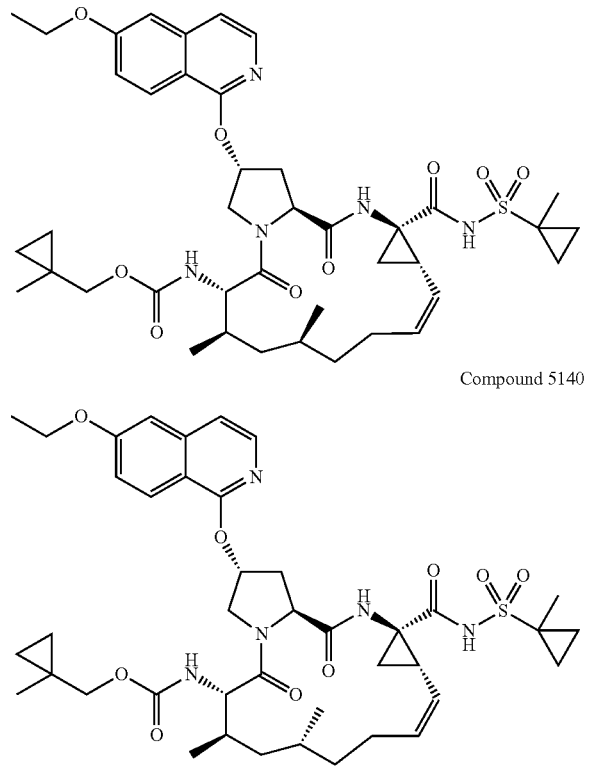

Compound 5139

Compound 5140

Compound 5139 and Compound 5140 were prepared using the intermediates described herein and by following the general procedure described for the synthesis of Compound 3117:

Compound 5139: (1-methylcyclopropyl)methyl ((2R,6S,7R,9S,13aS,14aR,16aS,Z)-2-((6-ethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 794.4 (M⁺+1).

Compound 5140: (1-methylcyclopropyl)methyl ((2R,6S,7R,9R,13aS,14aR,16aS,Z)-2-((6-ethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (500 MHz, DMSO-d₆) δ ppm 8.01 (d, J=9.2 Hz, 1H), 7.98-7.87 (m, 1H), 7.47 (d, J=6.7 Hz, 1H), 7.36-7.26 (m, 2H), 7.13 (dd, J=8.9, 2.4 Hz, 1H), 5.82 (br. s., 1H), 5.43 (br. s., 1H), 4.44 (br. s., 2H), 4.24-4.07 (m, 2H), 3.99-3.86 (m, 1H), 3.82-3.65 (m, 1H), 3.48-3.38 (m, 2H), 2.36-2.25 (m, 2H), 1.95-1.86 (m, 1H), 1.83 (d, J=5.2 Hz, 1H), 1.75 (br. s., 1H), 1.49 (br. s., 1H), 1.46-1.31 (m, 10H), 1.25 (br. s., 2H), 1.20 (br. s., 2H), 0.97-0.84 (m, 10H), 0.80 (br. s., 1H), 0.70 (br. s., 2H), 0.32-0.09 (m, 4H); MS: MS m/z 794.4 (M⁺+1).

Preparation of Compound 5141 and Compound 5142

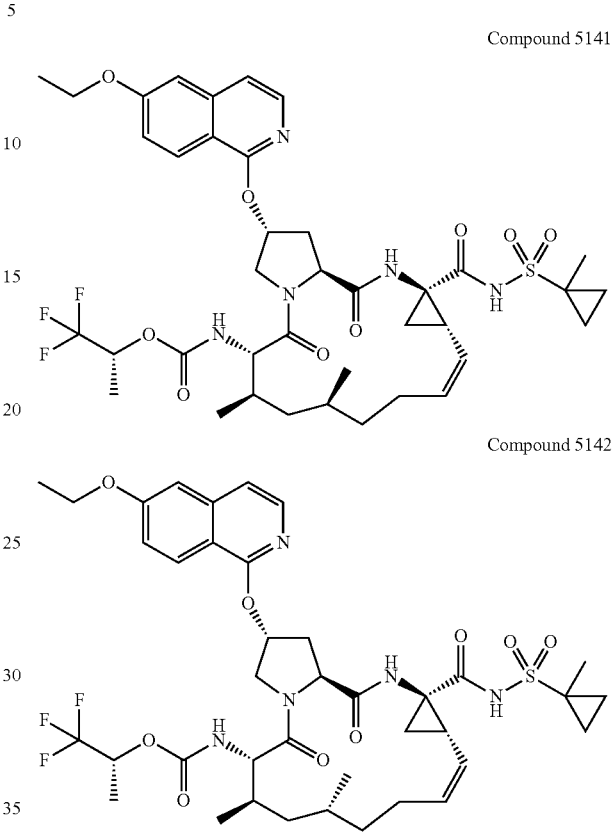

Compound 5141

Compound 5142

Compound 5141 and Compound 5142 were prepared using the intermediates described herein and by following the general procedure described for the synthesis of Compound 3117:

Compound 5141: (R)-1,1,1-trifluoropropan-2-yl ((2R,6S,7R,9S,13aS,14aR,16aS,Z)-2-((6-ethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 822.3 (M⁺+1).

Compound 5142: (R)-1,1,1-trifluoropropan-2-yl ((2R,6S,7R,9R,13aS,14aR,16aS,Z)-2-((6-ethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (500 MHz, DMSO-d₆) δ ppm 11.03 (br. s., 1H), 9.10 (br. s., 1H), 8.08 (d, J=8.2 Hz, 1H), 8.00-7.91 (m, 2H), 7.33-7.28 (m, 2H), 7.08 (dd, J=9.2, 2.4 Hz, 1H), 5.83 (br. s., 1H), 5.52 (br. s., 1H), 4.98 (br. s., 1H), 4.73 (dt, J=13.6, 6.6 Hz, 1H), 4.59-4.39 (m, 2H), 4.22-4.10 (m, 2H), 3.99-3.89 (m, 1H), 3.78 (dd, J=10.7, 8.2 Hz, 1H), 2.75-2.63 (m, 1H), 2.61 (br. s., 1H), 2.35-2.19 (m, 2H), 1.98-1.80 (m, 2H), 1.70 (br. s., 1H), 1.60 (br. s., 1H), 1.52 (br. s., 1H), 1.47-1.31 (m, 9H), 1.31-1.24 (m, 1H), 1.23-1.08 (m, 4H), 1.00-0.82 (m, 8H), 0.81-0.66 (m, 1H); MS: MS m/z 822.3 (M⁺+1).

Preparation of Compound 5143 and Compound 5144

Preparation of Compound 5145 and Compound 5146

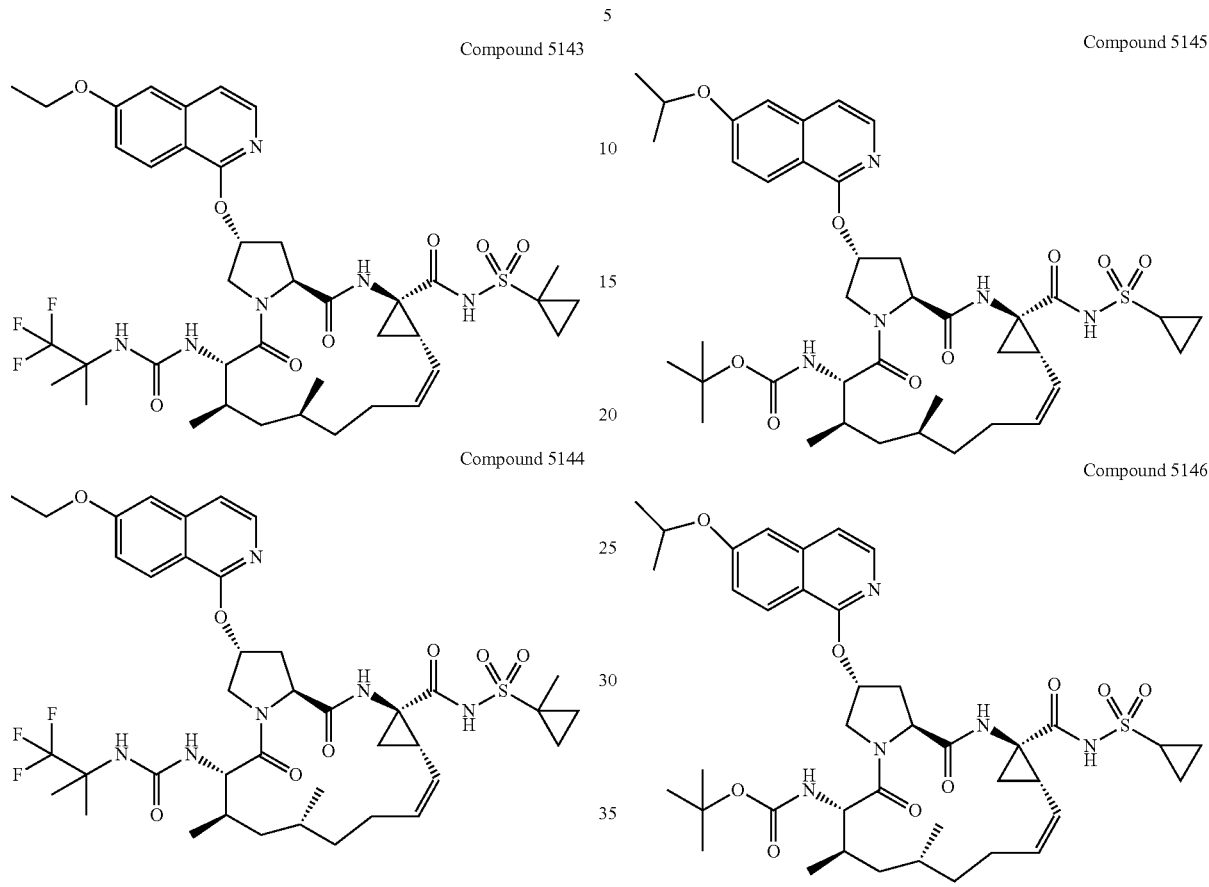

Compound 5143

Compound 5144

Compound 5145

Compound 5146

Compound 5143 and Compound 5144 were prepared using the intermediates described herein and by following the general procedure described for the synthesis of Compound 3117:

Compound 5143: (2R,6S,7R,9S,13aS,14aR,16aS,Z)-2-((6-ethoxyisoquinolin-1-yl)oxy)-7,9-dimethyl-N-((1-methylcyclopropyl)sulfonyl)-5,16-dioxo-6-(3-(1,1,1-trifluoro-2-methylpropan-2-yl)ureido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide. MS: MS m/z 835.4 (M$^+$+1).

Compound 5144: (2R,6S,7R,9R,13aS,14aR,16aS,Z)-2-((6-ethoxyisoquinolin-1-yl)oxy)-7,9-dimethyl-N-((1-methylcyclopropyl)sulfonyl)-5,16-dioxo-6-(3-(1,1,1-trifluoro-2-methylpropan-2-yl)ureido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (500 MHz, DMSO-d$_6$) δ ppm 8.13 (s, 1H), 8.02 (d, J=9.2 Hz, 1H), 7.95 (d, J=6.1 Hz, 1H), 7.32-7.26 (m, 2H), 7.10 (dd, J=8.9, 2.4 Hz, 1H), 6.20 (d, J=8.9 Hz, 1H), 6.15 (s, 1H), 5.78 (br. s., 1H), 5.66 (t, J=10.2 Hz, 1H), 5.31 (td, J=10.1, 6.0 Hz, 1H), 4.39-4.27 (m, 2H), 4.18 (q, J=6.9 Hz, 2H), 4.00-3.80 (m, 3H), 2.46-2.10 (m, 2H), 1.84 (d, J=13.7 Hz, 3H), 1.63 (d, J=6.7 Hz, 1H), 1.46-1.16 (m, 17H), 1.07 (s, 2H), 0.97-0.84 (m, 6H), 0.65 (t, J=10.2 Hz, 1H), 0.46-0.30 (m, 2H); MS: MS m/z 835.4 (M$^+$+1).

Compound 5145 and Compound 5146 were prepared using the intermediates described herein and by following the general procedure described for the synthesis of Compound 3117:

Compound 5145: tert-butyl ((2R,6S,7R,9S,13aS,14aR,16aS,Z)-14a-((cyclopropylsulfonyl)carbamoyl)-2-((6-isopropoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 782.4 (M$^+$+1).

Compound 5146: tert-butyl ((2R,6S,7R,9R,13aS,14aR,16aS,Z)-14a-((cyclopropylsulfonyl)carbamoyl)-2-((6-isopropoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.19 (br. s., 1H), 8.98 (br. s., 1H), 8.03 (d, J=8.9 Hz, 1H), 7.94 (d, J=5.8 Hz, 1H), 7.37-7.25 (m, 2H), 7.18 (d, J=5.8 Hz, 1H), 7.06 (dd, J=9.2, 2.4 Hz, 1H), 5.80 (br. s., 1H), 5.52 (br. s., 1H), 5.05 (br. s., 1H), 4.81 (dt, J=12.1, 6.0 Hz, 1H), 4.58 (d, J=8.9 Hz, 1H), 4.44 (br. s., 1H), 3.94-3.82 (m, 1H), 3.79-3.64 (m, 1H), 2.91 (s, 1H), 2.70 (br. s., 1H), 2.61 (br. s., 1H), 2.36-2.17 (m, 2H), 1.96-1.71 (m, 3H), 1.60 (br. s., 1H), 1.54 (br. s., 1H), 1.42 (br. s., 1H), 1.35 (dd, J=6.0, 2.9 Hz, 7H), 1.16-0.85 (m, 20H), 0.76-0.67 (m, 1H); MS: MS m/z 782.4 (M$^+$+1).

Preparation of Compound 5147 and Compound 5148

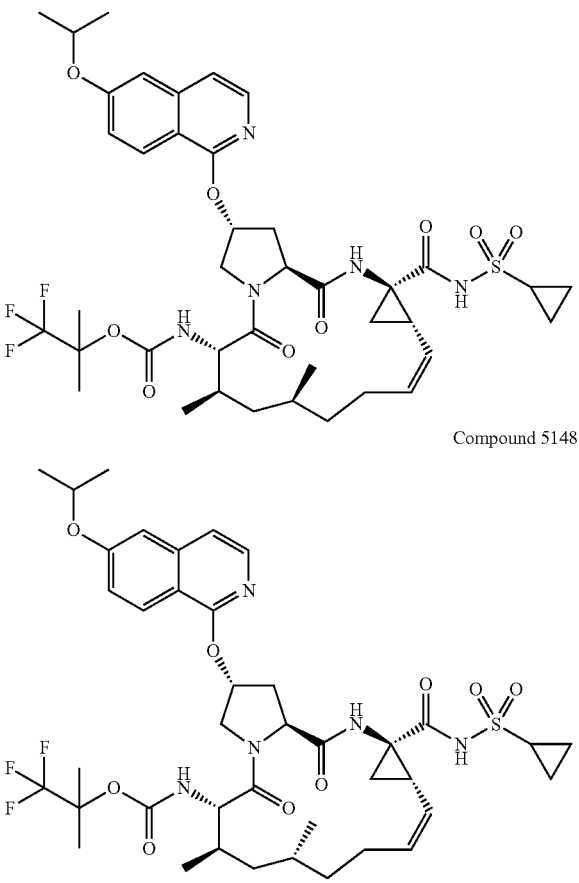

Compound 5147

Compound 5148

Compound 5147 and Compound 5148 were prepared using the intermediates described herein and by following the general procedure described for the synthesis of Compound 3117:

Compound 5147: 1,1,1-trifluoro-2-methylpropan-2-yl ((2R,6S,7R,9S,13aS,14aR,16aS,Z)-14a-((cyclopropylsulfonyl)carbamoyl)-2-((6-isopropoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 836.3 (M$^+$+1).

Compound 5148: 1,1,1-trifluoro-2-methylpropan-2-yl ((2R,6S,7R,9R,13aS,14aR,16aS,Z)-14a-((cyclopropylsulfonyl)carbamoyl)-2-((6-isopropoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.20 (br. s., 1H), 9.03 (br. s., 1H), 8.03-7.91 (m, 2H), 7.81 (d, J=6.7 Hz, 1H), 7.35-7.26 (m, 2H), 7.11 (dd, J=9.2, 2.4 Hz, 1H), 5.81 (br. s., 1H), 5.52 (br. s., 1H), 5.05 (br. s., 1H), 4.82 (dt, J=12.0, 6.1 Hz, 1H), 4.50 (d, J=8.9 Hz, 2H), 3.94-3.78 (m, 1H), 3.69 (dd, J=10.5, 8.1 Hz, 1H), 2.90 (br. s., 1H), 2.66 (d, J=10.1 Hz, 1H), 2.61 (br. s., 1H), 2.36-2.28 (m, 2H), 1.95-1.78 (m, 2H), 1.70 (br. s., 1H), 1.60 (br. s., 1H), 1.56 (br. s., 1H), 1.42 (br. s., 1H), 1.39-1.27 (m, 11H), 1.13 (br. s., 2H), 1.04 (s, 4H), 0.93 (d, J=6.7 Hz, 4H), 0.88 (d, J=6.1 Hz, 3H), 0.73 (br. s., 1H); MS: MS m/z 836.3 (M$^+$+1).

Preparation of Compound 5149 and Compound 5150

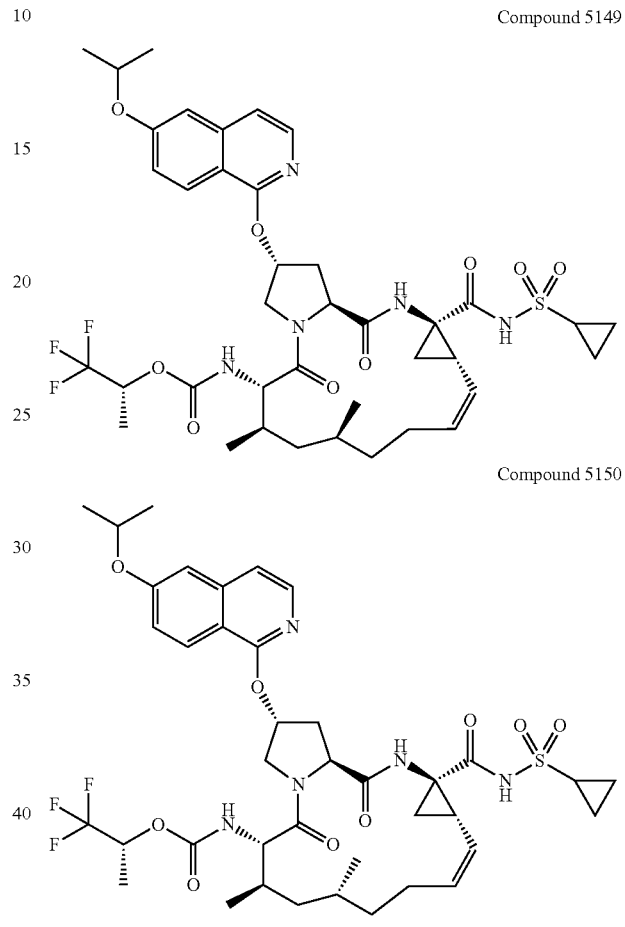

Compound 5149

Compound 5150

Compound 5149 and Compound 5150 were prepared using the intermediates described herein and by following the general procedure described for the synthesis of Compound 3117:

Compound 5149: (R)-1,1,1-trifluoropropan-2-yl ((2R,6S,7R,9S,13aS,14aR,16aS,Z)-14a-((cyclopropylsulfonyl)carbamoyl)-2-((6-isopropoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 822.3 (M$^+$+1).

Compound 5150: (R)-1,1,1-trifluoropropan-2-yl ((2R,6S,7R,9R,13aS,14aR,16aS,Z)-14a-((cyclopropylsulfonyl)carbamoyl)-2-((6-isopropoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.17 (s, 1H), 8.97 (br. s., 1H), 8.08 (d, J=7.9 Hz, 1H), 8.00-7.91 (m, 2H), 7.35-7.26 (m, 2H), 7.05 (dd, J=9.2, 2.1 Hz, 1H), 5.82 (br. s., 1H), 5.52 (br. s., 1H), 5.06 (t, J=8.9 Hz, 1H), 4.86-4.72 (m, 2H), 4.55-4.40 (m, 2H), 3.96-3.88 (m, 1H), 3.78 (dd, J=10.4, 8.2 Hz, 1H), 2.98-2.87 (m, 1H), 2.73-2.55 (m, 2H), 2.35-2.21 (m, 2H), 1.97-1.82 (m, 2H), 1.70-1.55 (m, 3H), 1.44-1.35 (m, 8H), 1.20 (d, J=6.7 Hz, 4H), 1.11 (d, J=6.1 Hz, 2H), 1.01-0.86 (m, 8H), 0.82-0.70 (m, 1H); MS: MS m/z 822.3 (M$^+$+1).

Preparation of Compound 5151

Compound 5151

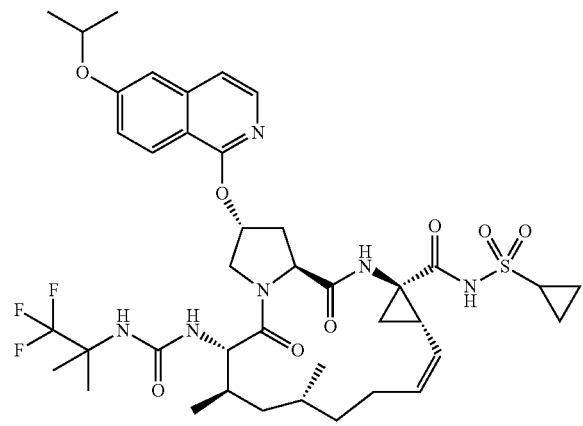

Compound 5151 was prepared using the intermediates described herein and by following the general procedure described for the synthesis of Compound 3117:

Compound 5151: (R)-1,1,1-trifluoropropan-2-yl((2R,6S,7R,9R,13aS,14aR,16aS,Z)-14a-((cyclopropylsulfonyl)carbamoyl)-2-((6-isopropoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.17 (br. s., 1H), 8.96 (br. s., 1H), 8.05-7.90 (m, 2H), 7.33-7.25 (m, 2H), 7.06 (dd, J=9.2, 2.4 Hz, 1H), 6.23 (d, J=6.4 Hz, 1H), 6.08 (s, 1H), 5.81 (br. s., 1H), 5.51 (br. s., 1H), 5.06 (br. s., 1H), 4.88-4.69 (m, 1H), 4.48 (br. s., 1H), 4.41 (br. s., 1H), 3.97-3.78 (m, 2H), 2.91 (s, 1H), 2.61 (m, 2H), 2.35-2.25 (m, 2H), 1.91-1.35 (m, 13H), 1.23-1.10 (m, 9H), 0.92 (dd, J=17.2, 6.6 Hz, 8H), 0.74 (br. s., 1H); MS: MS m/z 835.4 (M$^+$+1).

Preparation of Compound 5152 and Compound 5153

Compound 5152

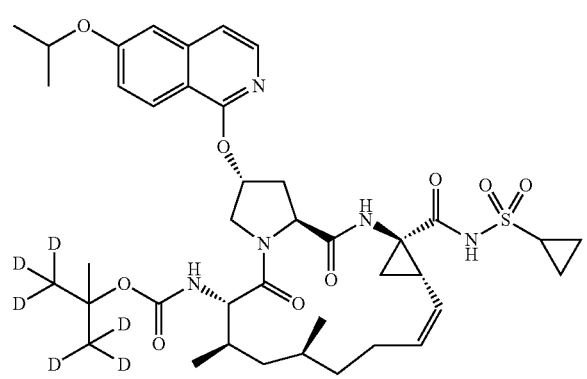

Compound 5153

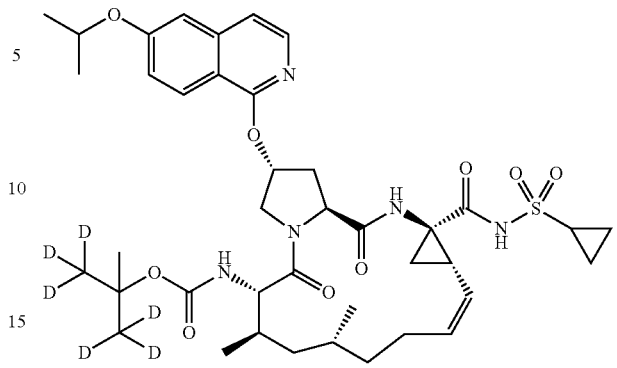

Compound 5152 and Compound 5153 were prepared using the intermediates described herein and by following the general procedure described for the synthesis of Compound 3117:

Compound 5152: 1,1,1,3,3,3-hexadeutero-2-methylpropan-2-yl ((2R,6S,7R,9S,13aS,14aR,16aS,Z)-14a-((cyclopropylsulfonyl)carbamoyl)-2-((6-isopropoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 788.8 (M$^+$+1).

Compound 5153: 1,1,1,3,3,3-hexadeutero-2-methylpropan-2-yl ((2R,6S,7R,9R,13aS,14aR,16aS,Z)-14a-((cyclopropylsulfonyl)carbamoyl)-2-((6-isopropoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.18 (br. s., 1H), 8.97 (br. s., 1H), 8.03 (d, J=9.2 Hz, 1H), 7.93 (d, J=5.8 Hz, 1H), 7.36-7.24 (m, 2H), 7.16 (br. s., 1H), 7.06 (dd, J=9.0, 2.3 Hz, 1H), 5.80 (br. s., 1H), 5.51 (br. s., 1H), 5.05 (br. s., 1H), 4.81 (dt, J=12.0, 6.1 Hz, 1H), 4.56 (br. s., 1H), 4.43 (br. s., 1H), 3.94-3.82 (m, 1H), 3.79-3.60 (m, 1H), 2.91 (s, 1H), 2.67 (d, J=16.5 Hz, 1H), 2.59 (br. s., 1H), 2.35-2.21 (m, 2H), 1.97-1.86 (m, 1H), 1.82 (d, J=6.1 Hz, 1H), 1.72 (br. s., 1H), 1.59-1.35 (m, 10H), 1.21-1.08 (m, 5H), 1.05 (br. s., 1H), 1.01-0.85 (m, 8H), 0.71 (br. s., 1H); MS: MS m/z 788.7 (M$^+$+1).

Preparation of Compound 5154 and Compound 5155

Compound 5154

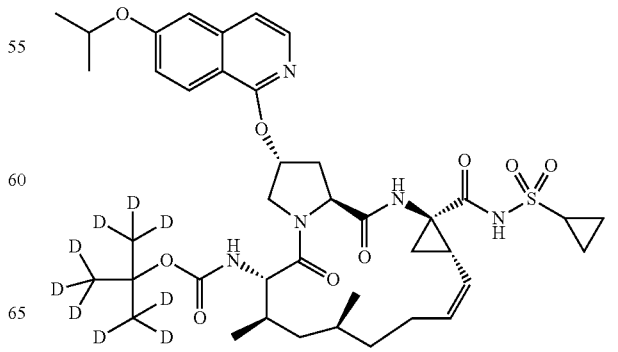

-continued

Compound 5155

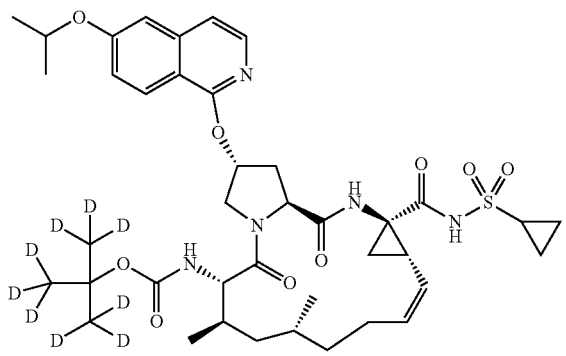

Compounds 5154 and 5155 were prepared using the intermediates described herein and by following the general procedure described for the synthesis of Compound 3117:

Compound 5154: 1,1,1,3,3,3-hexadeutero-2-(trideuteromethyl)propan-2-yl ((2R,6S,7R,9S,13aS,14aR,16aS,Z)-14a-((cyclopropylsulfonyl)carbamoyl)-2-((6-isopropoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 791.8 (M$^+$+1).

Compound 5155: 1,1,1,3,3,3-hexadeutero-2-(trideuteromethyl)propan-2-yl ((2R,6S,7R,9R,13aS,14aR,16aS,Z)-14a-((cyclopropylsulfonyl)carbamoyl)-2-((6-isopropoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.18 (br. s., 1H), 8.97 (br. s., 1H), 8.03 (d, J=9.2 Hz, 1H), 7.94 (d, J=6.1 Hz, 1H), 7.35-7.26 (m, 2H), 7.15 (br. s., 1H), 7.06 (dd, J=9.2, 2.4 Hz, 1H), 5.80 (br. s., 1H), 5.52 (br. s., 1H), 5.06 (br. s., 1H), 4.81 (dt, J=12.1, 6.0 Hz, 1H), 4.56 (br. s., 1H), 4.43 (br. s., 1H), 3.96-3.83 (m, 1H), 3.76-3.60 (m, 1H), 2.91 (s, 1H), 2.67 (d, J=19.8 Hz, 1H), 2.59 (br. s., 1H), 2.34-2.25 (m, 2H), 1.96-1.86 (m, 1H), 1.82 (d, J=6.1 Hz, 1H), 1.72 (br. s., 1H), 1.59 (br. s., 2H), 1.42 (br. s., 1H), 1.35 (dd, J=6.0, 2.9 Hz, 8H), 1.11 (br. s., 2H), 1.02-0.85 (m, 8H), 0.71 (br. s., 1H); MS: MS m/z 791.8 (M$^+$+1).

Preparation of Compound 5156 and Compound 5157

Compound 5156

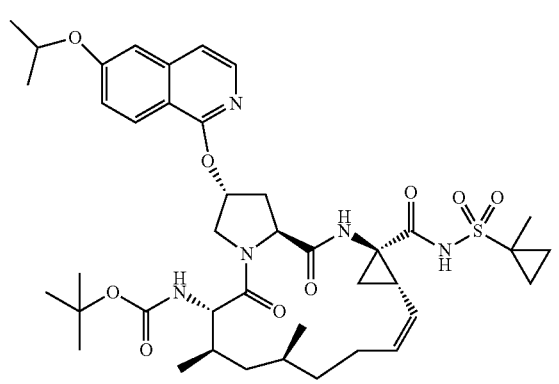

-continued

Compound 5157

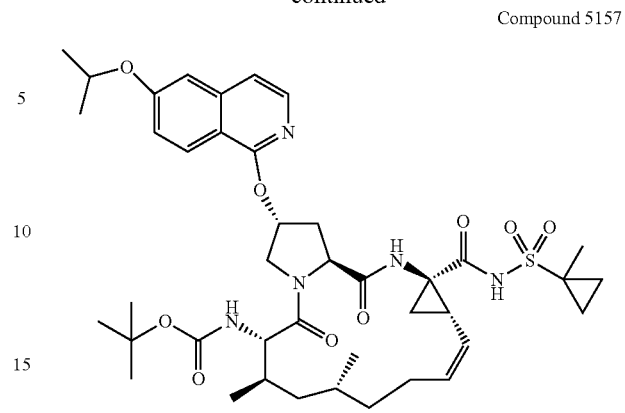

Compounds 5156 and 5157 were prepared using the intermediates described herein and by following the general procedure described for the synthesis of Compound 3117:

Compound 5156: tert-butyl ((2R,6S,7R,9S,13aS,14aR,16aS,Z)-2-((6-isopropoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 796.7 (M$^+$+1).

Compound 5157: tert-butyl ((2R,6S,7R,9R,13aS,14aR,16aS,Z)-2-((6-isopropoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.05 (br. s., 1H), 9.10 (br. s., 1H), 8.03 (d, J=9.2 Hz, 1H), 7.93 (d, J=5.8 Hz, 1H), 7.32-7.26 (m, 2H), 7.17 (d, J=7.9 Hz, 1H), 7.07 (dd, J=9.0, 2.3 Hz, 1H), 5.82 (br. s., 1H), 5.58-5.47 (m, 1H), 4.93-5.01 (m, 1H), 4.81 (quin, J=6.0 Hz, 1H), 4.58 (d, J=10.7 Hz, 1H), 4.48 (br. s., 1H), 3.95-3.88 (m, 1H), 3.77-3.67 (m, 1H), 2.76-2.55 (m, 2H), 2.40-2.24 (m, 2H), 1.95-0.66 (m, 37H); MS: MS m/z 796.7 (M$^+$+1).

Preparation of Compound 5158 and Compound 5159

Compound 5158

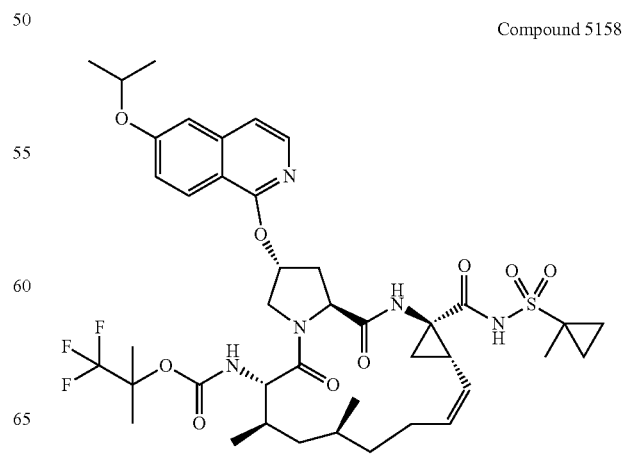

Compound 5159

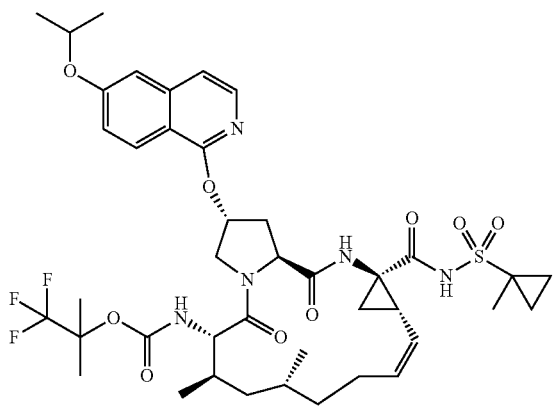

Compound 5161

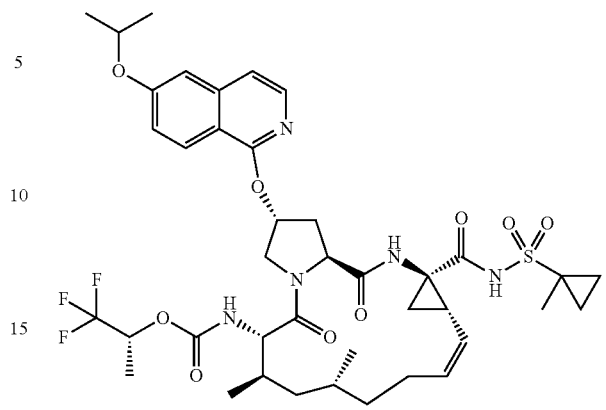

Compounds 5158 and 5159 were prepared using the intermediates described herein and by following the general procedure described for the synthesis of Compound 3117:

Compound 5158: 1,1,1-trifluoro-2-methylpropan-2-yl ((2R,6S,7R,9S,13aS,14aR,16aS,Z)-2-((6-isopropoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 850.4 (M$^+$+1).

Compound 5159: 1,1,1-trifluoro-2-methylpropan-2-yl ((2R,6S,7R,9R,13aS,14aR,16aS,Z)-2-((6-isopropoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.05 (br. s., 1H), 9.15 (br. s., 1H), 8.06-7.90 (m, 2H), 7.81 (d, J=7.9 Hz, 1H), 7.36-7.23 (m, 2H), 7.11 (dd, J=9.2, 2.1 Hz, 1H), 5.82 (br. s., 1H), 5.53 (br. s., 1H), 4.97 (br. s., 1H), 4.82 (dt, J=12.0, 6.1 Hz, 1H), 4.53 (br. s., 2H), 3.96-3.85 (m, 1H), 3.69 (dd, J=10.7, 8.2 Hz, 1H), 2.72-2.63 (m, 1H), 2.61 (br. s., 1H), 2.41-2.19 (m, 2H), 1.91 (d, J=15.9 Hz, 1H), 1.84 (d, J=6.1 Hz, 1H), 1.69 (br. s., 1H), 1.62 (br. s., 1H), 1.51 (br. s., 1H), 1.41-1.15 (m, 17H), 1.01 (s, 3H), 0.96-0.84 (m, 8H), 0.75 (t, J=12.2 Hz, 1H); MS: MS m/z 850.4 (M$^+$+1).

Preparation of Compound 5160 and Compound 5161

Compounds 5160 and 5161 were prepared using the intermediates described herein and by following the general procedure described for the synthesis of Compound 3117:

Compound 5160: (R)-1,1,1-trifluoropropan-2-yl ((2R,6S,7R,9S,13aS,14aR,16aS,Z)-2-((6-isopropoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 836.3 (M$^+$+1).

Compound 5161: (R)-1,1,1-trifluoropropan-2-yl ((2R,6S,7R,9R,13aS,14aR,16aS,Z)-2-((6-isopropoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.03 (s, 1H), 9.10 (br. s., 1H), 8.07 (d, J=7.6 Hz, 1H), 8.01-7.84 (m, 2H), 7.35-7.22 (m, 2H), 7.05 (dd, J=9.2, 2.4 Hz, 1H), 5.84 (br. s., 1H), 5.53 (d, J=5.2 Hz, 1H), 4.98 (t, J=9.3 Hz, 1H), 4.86-4.68 (m, 2H), 4.57-4.39 (m, 2H), 4.00-3.83 (m, 1H), 3.78 (dd, J=10.7, 8.2 Hz, 1H), 2.72-2.63 (m, 1H), 2.60 (br. s., 1H), 2.35-2.22 (m, 2H), 2.00-1.81 (m, 2H), 1.69-1.25 (m, 16H), 1.21-1.12 (m, 4H), 0.92 (dd, J=15.3, 6.7 Hz, 8H), 0.80-0.69 (m, 1H); MS: MS m/z 836.3 (M$^+$+1).

Preparation of Compound 5162 and Compound 5163

Compound 5160

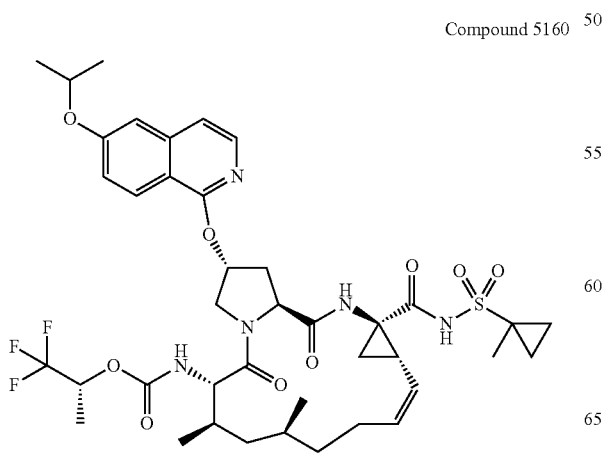

Compound 5162

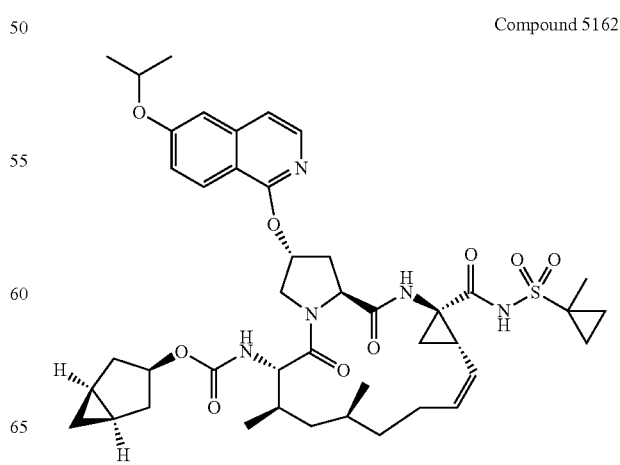

-continued

Compound 5163

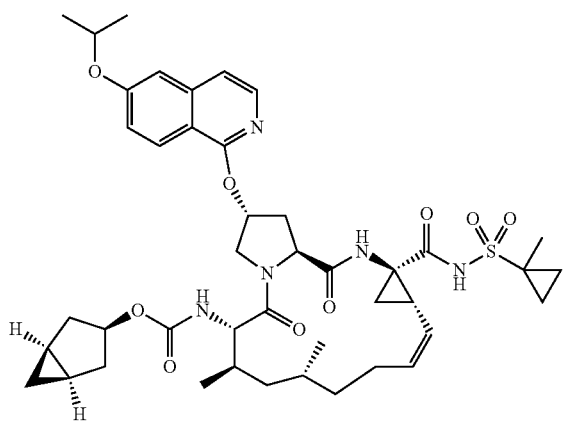

Compounds 5162 and 5163 were prepared using the intermediates described herein and by following the general procedure described for the synthesis of Compound 3117:

Compound 5162: (1R,3r,5S)-bicyclo[3.1.0]hexan-3-yl ((2R,6S,7R,9S,13aS,14aR,16aS,Z)-2-((6-isopropoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 820.4 (M⁺+1).

Compound 5163: (1R,3r,5S)-bicyclo[3.1.0]hexan-3-yl ((2R,6S,7R,9R,13aS,14aR,16aS,Z)-2-((6-isopropoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-$d_6$) δ ppm 11.05 (br. s., 1H), 9.08 (br. s., 1H), 8.00 (d, J=8.9 Hz, 1H), 7.93 (d, J=6.1 Hz, 1H), 7.38 (d, J=8.5 Hz, 1H), 7.35-7.26 (m, 2H), 7.13 (dd, J=9.0, 2.3 Hz, 1H), 5.84 (br. s., 1H), 5.53 (br. s., 1H), 4.98 (br. s., 1H), 4.82 (dt, J=12.1, 5.9 Hz, 1H), 4.59 (t, J=6.7 Hz, 1H), 4.48 (d, J=9.8 Hz, 2H), 3.96-3.86 (m, 1H), 3.78-3.67 (m, 1H), 2.73 (d, J=16.8 Hz, 1H), 2.60 (br. s., 1H), 2.41-2.22 (m, 2H), 1.97-1.87 (m, 2H), 1.83 (d, J=6.4 Hz, 1H), 1.80-1.28 (m, 19H), 1.22-1.15 (m, 1H), 1.15-1.06 (m, 2H), 0.99-0.82 (m, 8H), 0.73 (t, J=12.4 Hz, 1H), 0.38-0.27 (m, 2H); MS: MS m/z 820.4 (M⁺+1).

Preparation of Compound 5164 and Compound 5165

Compound 5164

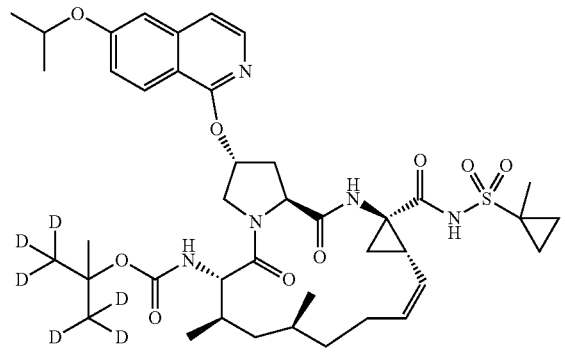

-continued

Compound 5165

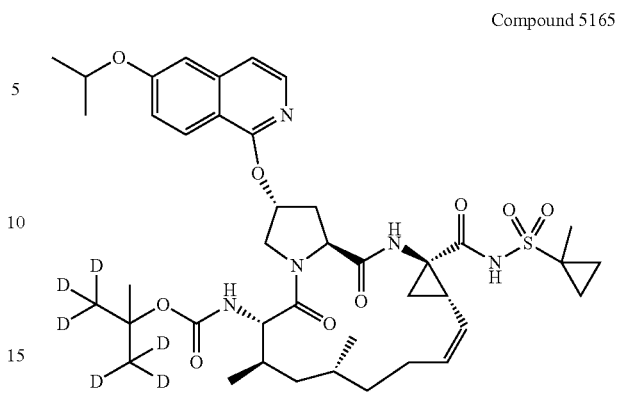

Compounds 5164 and 5165 were prepared using the intermediates described herein and by following the general procedure described for the synthesis of Compound 3117:

Compound 5164: 1,1,1,3,3,3-hexachloro-2-methylpropan-2-yl ((2R,6S,7R,9S,13aS,14aR,16aS,Z)-2-((6-isopropoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 802.7 (M⁺+1).

Compound 5165: 1,1,1,3,3,3-hexachloro-2-methylpropan-2-yl ((2R,6S,7R,9R,13aS,14aR,16aS,Z)-2-((6-isopropoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-$d_6$) δ ppm 11.05 (br. s., 1H), 9.10 (br. s., 1H), 8.03 (d, J=9.2 Hz, 1H), 7.93 (d, J=6.1 Hz, 1H), 7.35-7.24 (m, 2H), 7.17 (d, J=7.6 Hz, 1H), 7.07 (dd, J=9.0, 2.3 Hz, 1H), 5.82 (br. s., 1H), 5.53 (br. s., 1H), 4.97 (br. s., 1H), 4.81 (dt, J=11.9, 6.0 Hz, 1H), 4.59 (d, J=11.3 Hz, 1H), 4.48 (br. s., 1H), 3.99-3.87 (m, 1H), 3.78-3.64 (m, 1H), 2.77-2.68 (m, 1H), 2.60 (br. s., 1H), 2.40-2.24 (m, 2H), 1.91-1.28 (m, 19H), 1.13 (s, 3H), 0.97-0.83 (m, 8H), 0.74 (t, J=12.4 Hz, 1H); MS: MS m/z 802.7 (M⁺+1).

Preparation of Compound 5166 and Compound 5167

Compound 5166

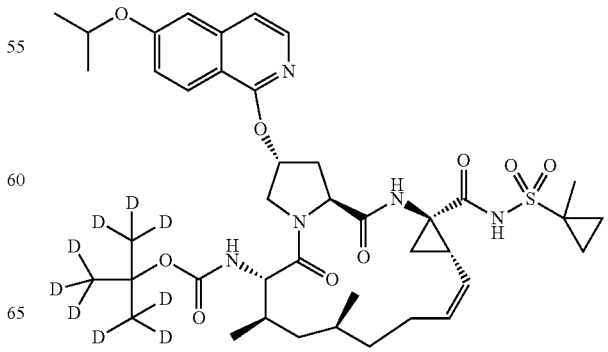

-continued

Compound 5167

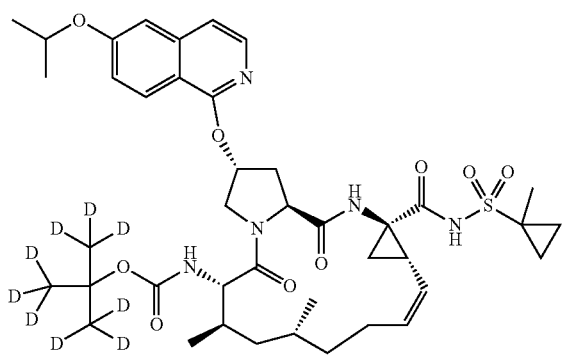

Compounds 5166 and 5167 were prepared using the intermediates described herein and by following the general procedure described for the synthesis of Compound 3117:

Compound 5166: 1,1,1,3,3,3-hexadeutero-2-(trideuteromethyl)propan-2-yl ((2R,6S,7R,9S,13aS,14aR,16aS,Z)-2-((6-isopropoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 805.8 (M$^+$+1).

Compound 5167: 1,1,1,3,3,3-hexadeutero-2-(trideuteromethyl)propan-2-yl ((2R,6S,7R,9R,13aS,14aR,16aS,Z)-2-((6-isopropoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.05 (br. s., 1H), 9.10 (br. s., 1H), 8.03 (d, J=9.2 Hz, 1H), 7.93 (d, J=6.1 Hz, 1H), 7.37-7.23 (m, 2H), 7.17 (d, J=7.9 Hz, 1H), 7.07 (dd, J=9.0, 2.3 Hz, 1H), 5.82 (br. s., 1H), 5.53 (br. s., 1H), 4.97 (br. s., 1H), 4.81 (quin, J=6.0 Hz, 1H), 4.58 (d, J=10.7 Hz, 1H), 4.48 (br. s., 1H), 3.99-3.84 (m, 1H), 3.82-3.68 (m, 1H), 2.73 (d, J=18.0 Hz, 1H), 2.59 (br. s., 1H), 2.45-2.22 (m, 2H), 1.91 (d, J=12.8 Hz, 1H), 1.82 (d, J=6.7 Hz, 1H), 1.70 (br. s., 1H), 1.61-1.15 (m, 16H), 0.98-0.84 (m, 8H), 0.73 (t, J=12.4 Hz, 1H); MS: MS m/z 805.8 (M$^+$+1).

Preparation of Compound 5168 and Compound 5169

Compound 5169

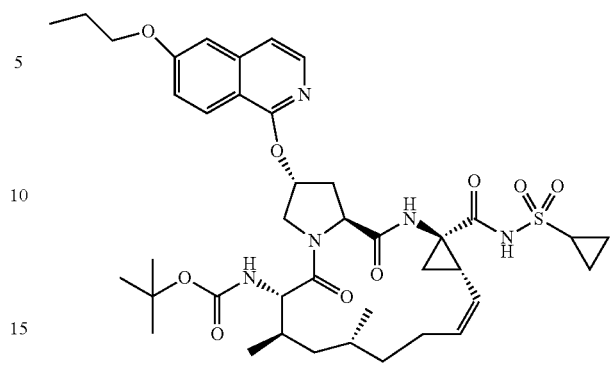

Compounds 5168 and 5169 were prepared using the intermediates described herein and by following the general procedure described for the synthesis of Compound 3117:

Compound 5168: tert-butyl ((2R,6S,7R,9S,13aS,14aR,16aS,Z)-14a-((cyclopropylsulfonyl)carbamoyl)-7,9-dimethyl-5,16-dioxo-2-((6-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 782.4 (M$^+$+1).

Compound 5169: tert-butyl ((2R,6S,7R,9R,13aS,14aR,16aS,Z)-14a-((cyclopropylsulfonyl)carbamoyl)-7,9-dimethyl-5,16-dioxo-2-((6-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.18 (br. s., 1H), 9.10 (br. s., 1H), 8.04 (d, J=9.2 Hz, 1H), 7.97-7.92 (m, 1H), 7.36-7.25 (m, 2H), 7.16 (d, J=7.6 Hz, 1H), 7.10 (dd, J=9.0, 2.3 Hz, 1H), 5.80 (br. s., 1H), 5.47 (br. s., 1H), 5.09 (br. s., 1H), 4.55 (d, J=9.5 Hz, 1H), 4.41 (t, J=8.5 Hz, 1H), 4.08 (t, J=6.6 Hz, 2H), 3.93-3.83 (m, 1H), 3.79-3.63 (m, 1H), 2.85 (br. s., 1H), 2.56 (br. s., 1H), 2.37-2.21 (m, 2H), 1.94-1.17 (m, 19H), 1.11-0.83 (m, 14H), 0.70 (t, J=11.6 Hz, 1H); MS: MS m/z 782.4 (M$^+$+1).

Preparation of Compound 5170 and Compound 5171

Compound 5168

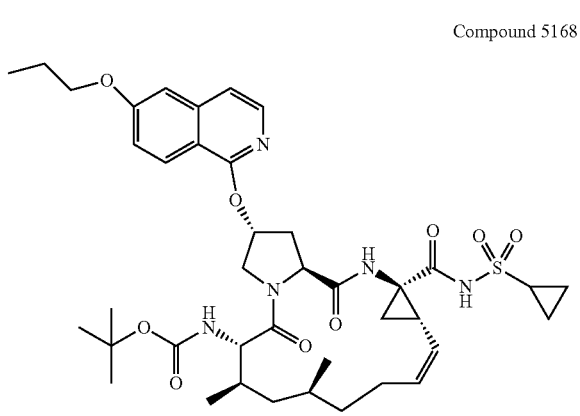

Compound 5170

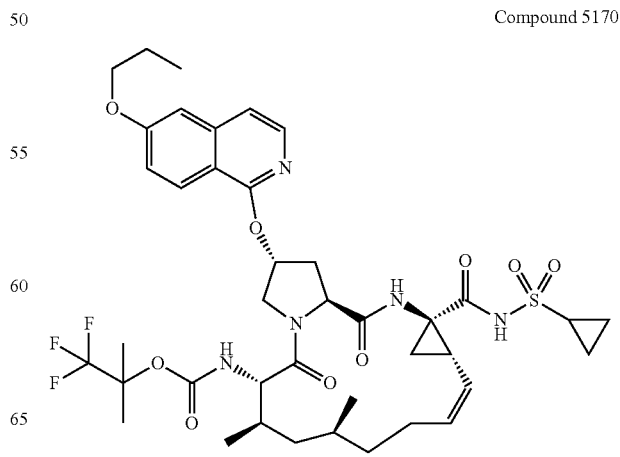

Compound 5171

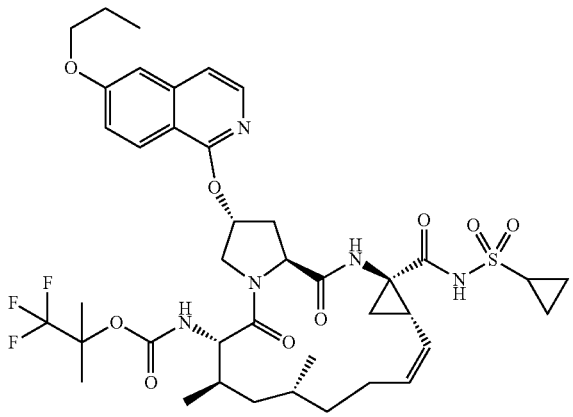

Compound 5173

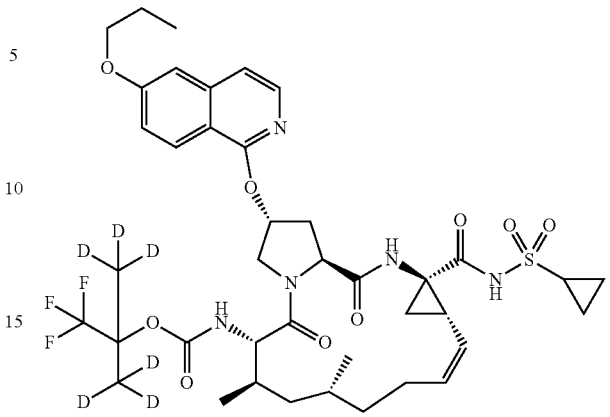

Compounds 5170 and 5171 were prepared using the intermediates described herein and by following the general procedure described for the synthesis of Compound 3117:

Compound 5170: 1,1,1-trifluoro-2-methylpropan-2-yl ((2R,6S,7R,9S,13aS,14aR,16aS,Z)-14a-((cyclopropylsulfonyl)carbamoyl)-7,9-dimethyl-5,16-dioxo-2-(((6-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 836.3 (M$^+$+1).

Compound 5171: 1,1,1-trifluoro-2-methylpropan-2-yl ((2R,6S,7R,9R,13aS,14aR,16aS,Z)-14a-((cyclopropylsulfonyl)carbamoyl)-7,9-dimethyl-5,16-dioxo-2-(((6-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.20 (br. s., 1H), 9.00 (br. s., 1H), 8.06-7.92 (m, 2H), 7.82 (d, J=7.6 Hz, 1H), 7.36-7.26 (m, 2H), 7.15 (dd, J=9.2, 2.1 Hz, 1H), 5.81 (br. s., 1H), 5.51 (br. s., 1H), 5.07 (br. s., 1H), 4.60-4.42 (m, 2H), 4.08 (t, J=6.4 Hz, 2H), 3.97-3.86 (m, 1H), 3.70 (dd, J=10.7, 8.2 Hz, 1H), 2.90 (s, 1H), 2.65 (br. s., 1H), 2.61 (br. s., 1H), 2.36-2.22 (m, 2H), 1.95-1.74 (m, 4H), 1.72 (br. s., 1H), 1.59 (br. s., 1H), 1.52 (d, J=12.5 Hz, 1H), 1.41 (br. s., 1H), 1.37 (s, 4H), 1.21-1.07 (m, 5H), 1.02 (t, J=7.5 Hz, 5H), 0.97-0.85 (m, 7H), 0.73 (t, J=12.1 Hz, 1H); MS: MS m/z 836.3 (M$^+$+1).

Preparation of Compound 5172 and Compound 5173

Compounds 5172 and 5173 were prepared using the intermediates described herein and by following the general procedure described for the synthesis of Compound 3117:

Compound 5172: 1,1,1,3,3,3-hexachloro-2-(trifluoromethyl)propan-2-yl ((2R,6S,7R,9S,13aS,14aR,16aS,Z)-14a-((cyclopropylsulfonyl)carbamoyl)-7,9-dimethyl-5,16-dioxo-2-((6-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 842.8 (M$^+$+1).

Compound 5172: 1,1,1,3,3,3-hexachloro-2-(trifluoromethyl)propan-2-yl ((2R,6S,7R,9R,13aS,14aR,16aS,Z)-14a-((cyclopropylsulfonyl)carbamoyl)-7,9-dimethyl-5,16-dioxo-2-((6-propoxyisoquinolin-1-yl)oxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
$^1$H NMR (500 MHz, DMSO-d$_6$) δ ppm 11.20 (br. s., 1H), 9.01 (br. s., 1H), 8.11-7.91 (m, 2H), 7.82 (d, J=7.6 Hz, 1H), 7.38-7.25 (m, 2H), 7.15 (dd, J=9.2, 2.4 Hz, 1H), 5.81 (br. s., 1H), 5.52 (br. s., 1H), 5.06 (br. s., 1H), 4.61-4.40 (m, 2H), 4.08 (t, J=6.6 Hz, 2H), 3.98-3.84 (m, 1H), 3.70 (dd, J=10.7, 8.2 Hz, 1H), 2.91 (s, 1H), 2.61 (br. s., 2H), 2.31 (ddd, J=13.7, 10.1, 4.0 Hz, 2H), 1.96-1.74 (m, 5H), 1.71-1.36 (m, 4H), 1.14-0.84 (m, 14H), 0.73 (t, J=12.7 Hz, 1H); MS: MS m/z 842.8 (M$^+$+1).

Preparation of Compound 5174 and Compound 5175

Compound 5172

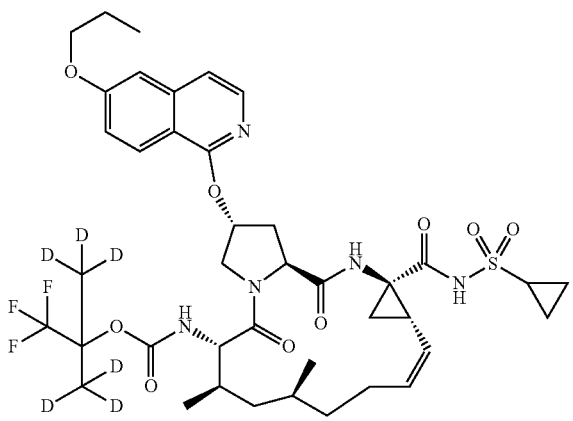

Compound 5174

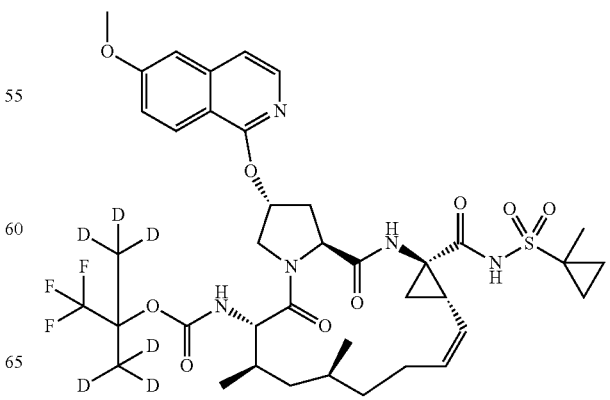

-continued

Compound 5175

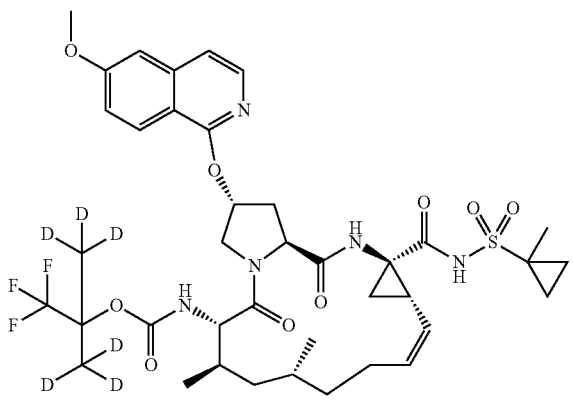

Compounds 5174 and 5175 were prepared using the intermediates described herein and by following the general procedure described for the synthesis of Compound 3117:

Compound 5174: 1,1,1,3,3,3-hexadeutero-2-(trifluoromethyl)propan-2-yl ((2R,6S,7R,9S,13aS,14aR,16aS,Z)-2-((6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 828.6 (M$^+$+1).

Compound 5175: 1,1,1,3,3,3-hexadeutero-2-(trifluoromethyl)propan-2-yl ((2R,6S,7R,9R,13aS,14aR,16aS,Z)-2-((6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.04 (br. s., 1H), 9.14 (br. s., 1H), 8.09-7.92 (m, 2H), 7.83 (d, J=7.9 Hz, 1H), 7.37-7.29 (m, 2H), 7.15 (dd, J=9.2, 2.4 Hz, 1H), 5.83 (br. s., 1H), 5.53 (br. s., 1H), 4.98 (br. s., 1H), 4.52 (br. s., 2H), 3.98-3.85 (m, 4H), 3.71 (dd, J=10.8, 8.1 Hz, 1H), 2.69 (br. s., 1H), 2.61 (br. s., 1H), 2.41-2.21 (m, 2H), 1.97-1.77 (m, 2H), 1.71 (br. s., 1H), 1.61 (br. s., 1H), 1.52 (br. s., 1H), 1.41 (br. s., 5H), 1.36 (br. s., 1H), 1.28 (br. s., 1H), 1.15 (br. s., 1H), 0.99-0.84 (m, 8H), 0.75 (t, J=12.1 Hz, 1H); MS: MS m/z 828.6 (M$^+$+1).

Preparation of Compound 5176 and Compound 5177

Compound 5176

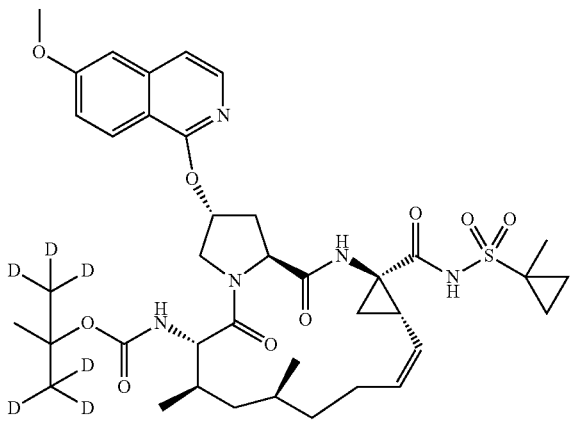

-continued

Compound 5177

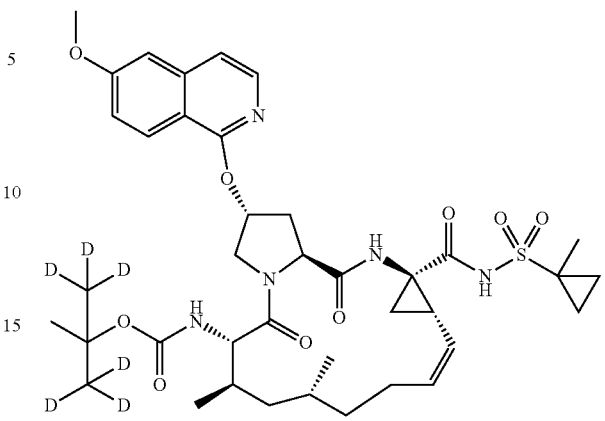

Compounds 5176 and 5177 were prepared using the intermediates described herein and by following the general procedure described for the synthesis of Compound 3117:

Compound 5176: 1,1,1,3,3,3-hexadeutero-2-methylpropan-2-yl ((2R,6S,7R,9S,13aS,14aR,16aS,Z)-2-((6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 774.6 (M$^+$+1).

Compound 5177: 1,1,1,3,3,3-hexadeutero-2-methylpropan-2-yl ((2R,6S,7R,9R,13aS,14aR,16aS,Z)-2-((6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.05 (br. s., 1H), 9.10 (br. s., 1H), 8.05 (d, J=9.2 Hz, 1H), 7.96 (d, J=5.8 Hz, 1H), 7.39-7.26 (m, 2H), 7.18 (d, J=7.6 Hz, 1H), 7.11 (dd, J=9.2, 2.4 Hz, 1H), 5.82 (br. s., 1H), 5.52 (br. s., 1H), 4.97 (br. s., 1H), 4.59 (d, J=11.0 Hz, 1H), 4.47 (br. s., 1H), 3.98-3.83 (m, 4H), 3.73 (dd, J=10.4, 8.5 Hz, 1H), 2.78-2.66 (m, 1H), 2.60 (br. s., 1H), 2.41-2.22 (m, 2H), 1.96-1.78 (m, 2H), 1.70-1.26 (m, 10H), 1.15 (s, 4H), 0.95-0.83 (m, 8H), 0.74 (t, J=12.2 Hz, 1H); MS: MS m/z 774.7 (M$^+$+1).

Preparation of Compound 5178 and Compound 5179

Compound 5178

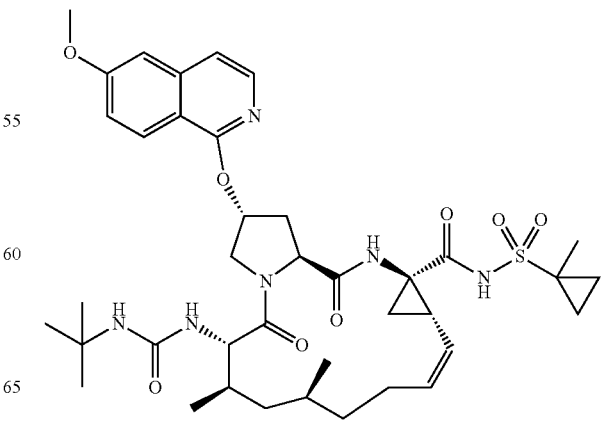

Compound 5179

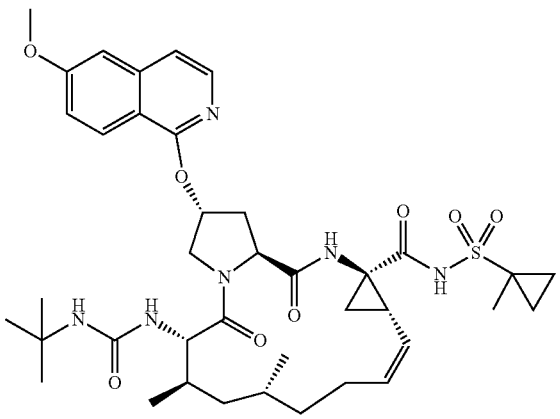

Compounds 5178 and 5179 were prepared using the intermediates described herein and by following the general procedure described for the synthesis of Compound 3117:

Compound 5178: (2R,6S,7R,9S,13aS,14aR,16aS,Z)-6-(3-(tert-butyl)ureido)-2-((6-methoxyisoquinolin-1-yl)oxy)-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. MS: MS m/z 767.4 (M$^+$+1).

Compound 5179: (2R,6S,7R,9R,13aS,14aR,16aS,Z)-6-(3-(tert-butyl)ureido)-2-((6-methoxyisoquinolin-1-yl)oxy)-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (500 MHz, DMSO-d$_6$) δ ppm 11.05 (br. s., 1H), 9.06 (br. s., 1H), 8.06 (d, J=9.2 Hz, 1H), 7.96 (d, J=6.1 Hz, 1H), 7.38-7.23 (m, 2H), 7.09 (dd, J=9.2, 2.4 Hz, 1H), 5.96 (d, J=8.9 Hz, 1H), 5.83 (br. s., 1H), 5.58 (s, 1H), 5.52 (br. s., 1H), 4.98 (br. s., 1H), 4.56 (br. s., 1H), 4.42 (br. s., 1H), 3.98-3.78 (m, 5H), 2.75 (s, 1H), 2.57 (d, J=13.1 Hz, 1H), 2.41-2.20 (m, 2H), 1.96-1.81 (m, 1H), 1.78-1.63 (m, 2H), 1.59 (br. s., 1H), 1.40 (br. s., 7H), 1.28 (br. s., 1H), 1.22-1.10 (m, 1H), 1.06 (s, 9H), 0.92 (dd, J=13.0, 6.6 Hz, 8H), 0.80-0.70 (m, 1H); MS: MS m/z 767.4 (M$^+$+1).

Preparation of Compound 5180 and Compound 5181

Compound 5180

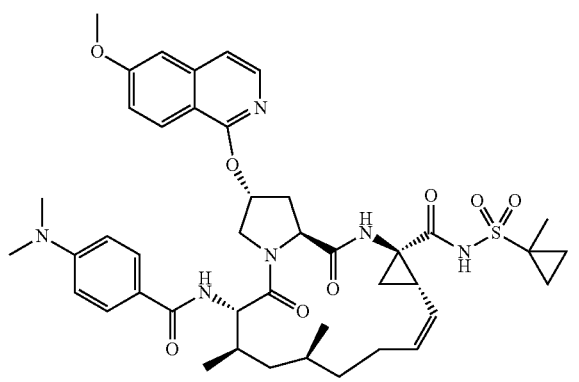

Compound 5181

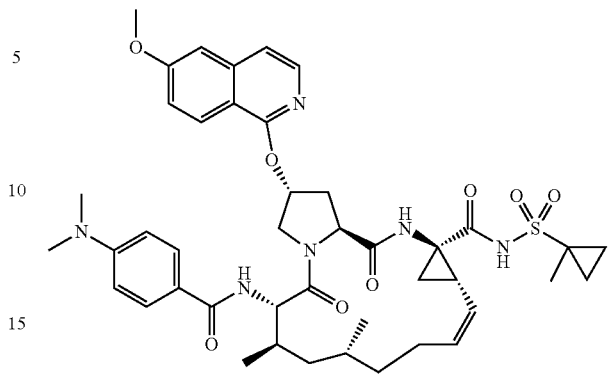

Compounds 5180 and 5181 were prepared using the intermediates described herein and by following the general procedure described for the synthesis of Compound 3117:

Compound 5180: (2R,6S,7R,9S,13aS,14aR,16aS,Z)-6-(4-(dimethylamino)benzamido)-2-((6-methoxyisoquinolin-1-yl)oxy)-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. MS: MS m/z 815.4 (M$^+$+1).

Compound 5181: (2R,6S,7R,9R,13aS,14aR,16aS,Z)-6-(4-(dimethylamino)benzamido)-2-((6-methoxyisoquinolin-1-yl)oxy)-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (500 MHz, DMSO-d$_6$) δ ppm 11.06 (br. s., 1H), 9.03 (br. s., 1H), 8.28 (d, J=8.2 Hz, 1H), 8.08-7.86 (m, 2H), 7.64-7.55 (m, J=8.9 Hz, 2H), 7.39-7.25 (m, 2H), 7.04 (dd, J=8.9, 2.4 Hz, 1H), 6.66-6.54 (m, J=9.2 Hz, 2H), 5.85 (br. s., 1H), 5.55 (br. s., 1H), 5.09-4.91 (m, 1H), 4.80 (d, J=11.0 Hz, 1H), 4.56-4.34 (m, 1H), 4.23 (dd, J=10.5, 8.4 Hz, 1H), 3.98 (dd, J=11.3, 3.4 Hz, 1H), 3.92 (s, 4H), 2.97 (s, 6H), 2.82-2.70 (m, 1H), 2.70-2.60 (m, 1H), 2.42-2.23 (m, 2H), 2.20-2.04 (m, 1H), 2.04-1.94 (m, 1H), 1.81-1.20 (m, 10H), 0.96 (t, J=7.3 Hz, 6H), 0.90 (br. s., 2H), 0.82 (t, J=11.9 Hz, 1H); MS: MS m/z 815.4 (M$^+$+1).

Preparation of Compound 5182 and Compound 5183

Compound 5182

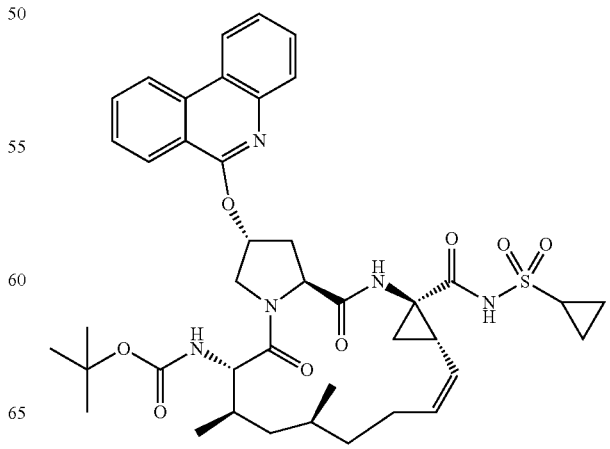

-continued

Compound 5183

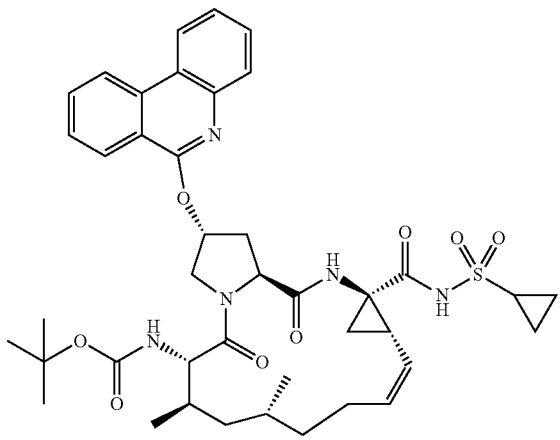

Compounds 5182 and 5183 were prepared using the intermediates described herein and by following the general procedure described for the synthesis of Compound 3117:

Compound 5182: tert-butyl ((2R,6S,7R,9S,13aS,14aR,16aS,Z)-14a-((cyclopropylsulfonyl)carbamoyl)-7,9-dimethyl-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 774.3 (M$^+$+1).

Compound 5183: tert-butyl ((2R,6S,7R,9R,13aS,14aR,16aS,Z)-14a-((cyclopropylsulfonyl)carbamoyl)-7,9-dimethyl-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, METHANOL-d$_4$) δ ppm 8.63 (d, J=8.2 Hz, 1H), 8.53 (d, J=7.9 Hz, 1H), 8.33 (d, J=7.9 Hz, 1H), 7.93-7.80 (m, 2H), 7.73-7.57 (m, 2H), 7.57-7.47 (m, 1H), 6.09 (br. s., 1H), 5.55 (td, J=10.1, 6.0 Hz, 1H), 5.06 (t, J=9.6 Hz, 1H), 4.81 (d, J=11.6 Hz, 1H), 4.64 (dd, J=10.1, 7.0 Hz, 1H), 4.10 (dd, J=11.6, 3.7 Hz, 1H), 3.96-3.76 (m, 1H), 2.98-2.88 (m, 1H), 2.88-2.78 (m, 1H), 2.76-2.60 (m, 1H), 2.54-2.30 (m, 2H), 2.02-1.90 (m, 1H), 1.88-1.70 (m, 3H), 1.57-1.16 (m, 4H), 1.14-0.91 (m, 18H), 0.91-0.78 (m, 2H); MS: MS m/z 774.3 (M$^+$+1).

Preparation of Compound 5184 and Compound 5185

-continued

Compound 5185

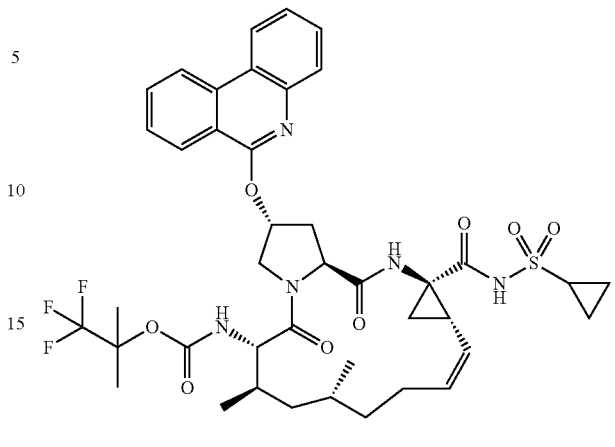

Compounds 5184 and 5185 were prepared using the intermediates described herein and by following the general procedure described for the synthesis of Compound 3117:

Compound 5184: 1,1,1-trifluoro-2-methylpropan-2-yl ((2R,6S,7R,9S,13aS,14aR,16aS,Z)-14a-((cyclopropylsulfonyl)carbamoyl)-7,9-dimethyl-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 828.4 (M$^+$+1).

Compound 5185: 1,1,1-trifluoro-2-methylpropan-2-yl ((2R,6S,7R,9R,13aS,14aR,16aS,Z)-14a-((cyclopropylsulfonyl)carbamoyl)-7,9-dimethyl-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, METHANOL-d$_4$) δ ppm 8.65 (d, J=8.2 Hz, 1H), 8.55 (d, J=7.9 Hz, 1H), 8.32 (d, J=7.6 Hz, 1H), 7.94-7.83 (m, 2H), 7.72-7.60 (m, 2H), 7.57-7.48 (m, 1H), 6.06 (t, J=3.2 Hz, 1H), 5.56 (td, J=10.1, 5.6 Hz, 1H), 5.17 (t, J=9.8 Hz, 1H), 4.86 (d, J=12.2 Hz, 1H), 4.67 (dd, J=10.4, 7.0 Hz, 1H), 4.08 (dd, J=11.7, 3.2 Hz, 1H), 3.88-3.75 (m, 1H), 2.97-2.76 (m, 2H), 2.65 (q, J=9.2 Hz, 1H), 2.50 (ddd, J=14.0, 10.1, 4.3 Hz, 1H), 2.44-2.30 (m, 1H), 2.01-1.89 (m, 2H), 1.89-1.70 (m, 3H), 1.58 (dd, J=9.5, 5.2 Hz, 1H), 1.52-1.39 (m, 2H), 1.34-1.15 (m, 5H), 1.12-0.93 (m, 8H), 0.90 (s, 3H), 0.82 (t, J=11.7 Hz, 1H); MS: MS m/z 828.3 (M$^+$+1).

Preparation of Compound 5186 and Compound 5187

Compound 5184

Compound 5186

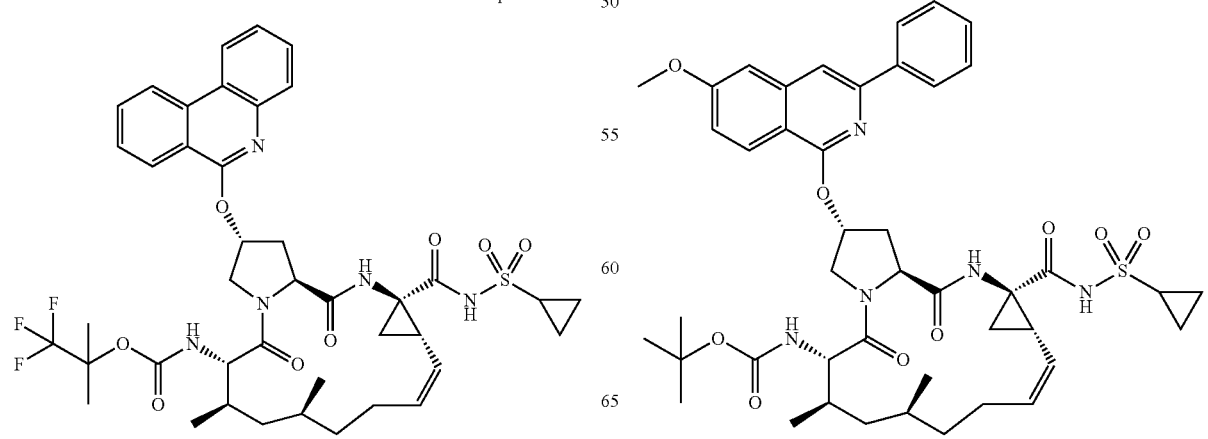

Compound 5187

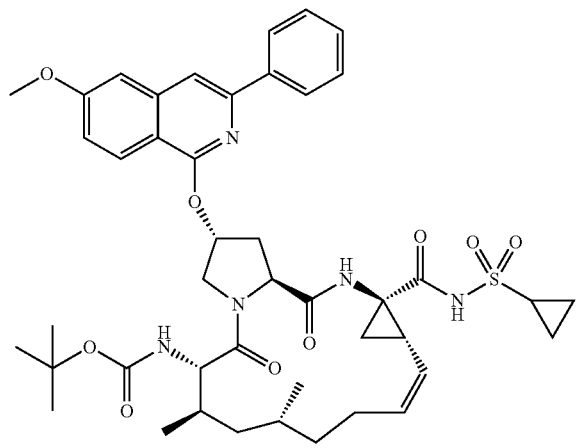

Compounds 5186 and 5187 were prepared using the intermediates described herein and by following the general procedure described for the synthesis of Compound 3117:

Compound 5186: tert-butyl ((2R,6S,7R,9S,13aS,14aR,16aS,Z)-14a-((cyclopropylsulfonyl)carbamoyl)-2-((6-methoxy-3-phenylisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 830.4 (M$^+$+1).

Compound 5187: tert-butyl ((2R,6S,7R,9R,13aS,14aR,16aS,Z)-14a-((cyclopropylsulfonyl)carbamoyl)-2-((6-methoxy-3-phenylisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.22 (br. s., 1H), 8.94 (br. s., 1H), 8.26-8.17 (m, 2H), 8.07 (d, J=8.9 Hz, 1H), 8.00-7.92 (m, 1H), 7.58-7.50 (m, 2H), 7.47-7.35 (m, 2H), 7.21 (d, J=9.2 Hz, 1H), 7.10 (dd, J=8.9, 2.4 Hz, 1H), 5.98 (br. s., 1H), 5.52 (br. s., 1H), 5.07 (br. s., 1H), 4.62 (d, J=8.9 Hz, 1H), 4.46 (t, J=8.1 Hz, 1H), 4.02-3.88 (m, 4H), 3.76 (dd, J=10.7, 8.2 Hz, 1H), 2.91 (s, 1H), 2.79-2.66 (m, 2H), 2.41-2.22 (m, 2H), 1.92 (br. s., 1H), 1.84 (d, J=7.0 Hz, 1H), 1.73 (br. s., 1H), 1.59 (br. s., 1H), 1.55 (br. s., 1H), 1.43 (br. s., 1H), 1.40-1.33 (m, 1H), 1.21 (s, 9H), 1.10 (d, J=19.2 Hz, 2H), 0.95-0.85 (m, 9H), 0.75 (t, J=11.7 Hz, 1H); MS: MS m/z 830.4 (M$^+$+1).

Preparation of Compound 5188 and Compound 5189

Compound 5188

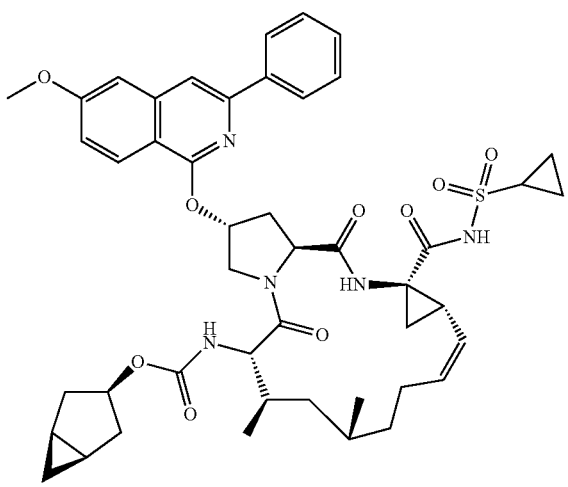

Compound 5189

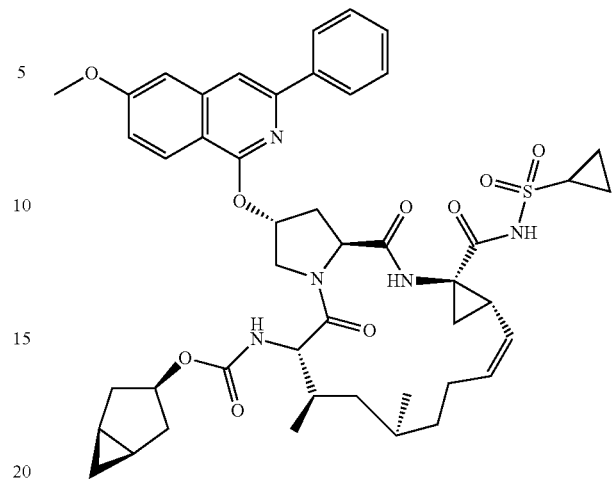

Compounds 5188 and 5189 were prepared using the intermediates described herein and by following the general procedure described for the synthesis of Compound 3117:

Compound 5188: (1R,3r,5S)-bicyclo[3.1.0]hexan-3-yl ((2R,6S,7R,9R,13aS,14aR,16aS,Z)-14a-((cyclopropylsulfonyl)carbamoyl)-2-((6-methoxy-3-phenylisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 854.4 (M$^+$+1).

Compound 5189: (1R,3r,5S)-bicyclo[3.1.0]hexan-3-yl ((2R,6S,7R,9S,13aS,14aR,16aS,Z)-14a-((cyclopropylsulfonyl)carbamoyl)-2-((6-methoxy-3-phenylisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.18 (br. s., 1H), 8.90 (br. s., 1H), 8.20 (d, J=7.3 Hz, 2H), 8.05 (d, J=9.0 Hz, 1H), 8.00-7.92 (m, 1H), 7.59-7.50 (m, 2H), 7.48-7.35 (m, 3H), 7.16 (dd, J=9.0, 2.5 Hz, 1H), 6.00 (br. s., 1H), 5.52 (br. s., 1H), 5.07 (br. s., 1H), 4.72 (t, J=7.0 Hz, 1H), 4.62-4.37 (m, 2H), 4.01 (dd, J=11.2, 3.4 Hz, 1H), 3.94 (s, 3H), 3.84-3.74 (m, 1H), 2.91 (s, 1H), 2.76-2.65 (m, 2H), 2.44-2.21 (m, 2H), 2.04-1.90 (m, 2H), 1.90-1.80 (m, 2H), 1.69 (d, J=5.3 Hz, 1H), 1.65-1.50 (m, 3H), 1.50-1.33 (m, 3H), 1.29-1.05 (m, 5H), 0.95 (d, J=6.8 Hz, 5H), 0.88 (d, J=6.3 Hz, 3H), 0.76 (t, J=12.3 Hz, 1H), 0.44-0.31 (m, 2H); MS: MS m/z 854.4 (M$^+$+1).

Preparation of Compound 5190 and Compound 5191

Compound 5190

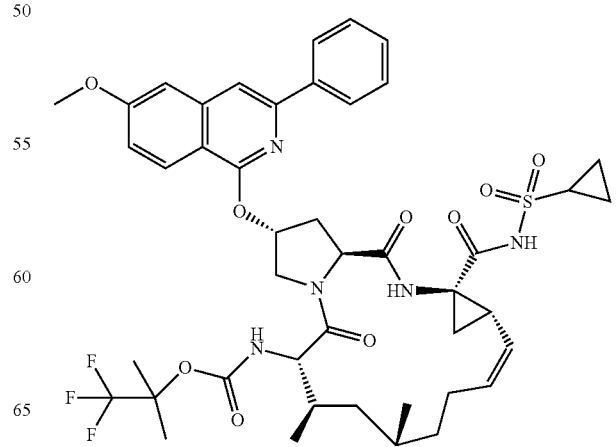

Compound 5191

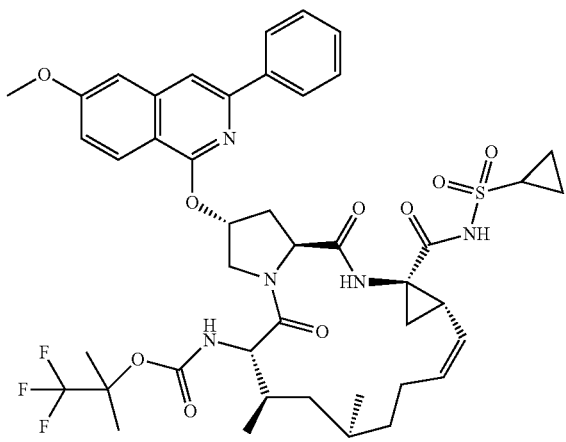

Compounds 5190 and 5191 were prepared using the intermediates described herein and by following the general procedure described for the synthesis of Compound 3117:

Compound 5190: 1,1,1-trifluoro-2-methylpropan-2-yl ((2R,6S,7R,9R,13aS,14aR,16aS,Z)-14a-((cyclopropylsulfonyl)carbamoyl)-2-((6-methoxy-3-phenylisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 884.3 (M$^+$+1).

Compound 5191: 1,1,1-trifluoro-2-methylpropan-2-yl ((2R,6S,7R,9S,13aS,14aR,16aS,Z)-14a-((cyclopropylsulfonyl)carbamoyl)-2-((6-methoxy-3-phenylisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.21 (s, 1H), 8.98 (br. s., 1H), 8.24-8.16 (m, 2H), 8.03 (d, J=8.9 Hz, 1H), 7.98-7.94 (m, 1H), 7.86 (d, J=7.9 Hz, 1H), 7.58-7.52 (m, 2H), 7.47-7.38 (m, 2H), 7.14 (dd, J=9.2, 2.4 Hz, 1H), 6.00 (br. s., 1H), 5.62-5.44 (m, 1H), 5.07 (t, J=9.5 Hz, 1H), 4.63-4.44 (m, 2H), 4.03-3.88 (m, 4H), 3.74 (dd, J=10.7, 7.9 Hz, 1H), 2.97-2.90 (m, 1H), 2.78-2.64 (m, 2H), 2.45-2.25 (m, 2H), 1.89 (td, J=12.7, 6.4 Hz, 2H), 1.79-1.66 (m, 1H), 1.66-1.54 (m, 2H), 1.45 (d, J=13.4 Hz, 1H), 1.40 (s, 4H), 1.36-1.06 (m, 6H), 1.05-0.92 (m, 5H), 0.89 (d, J=6.4 Hz, 3H), 0.77 (t, J=12.4 Hz, 1H); MS: MS m/z 884.3 (M$^+$+1).

Preparation of Compound 5192 and Compound 5193

Compound 5192

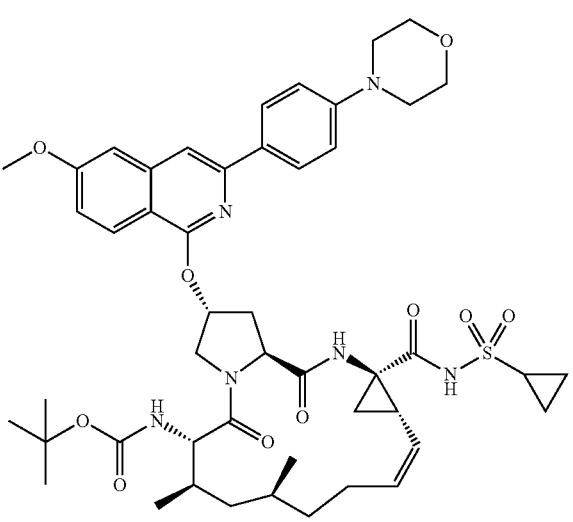

Compound 5193

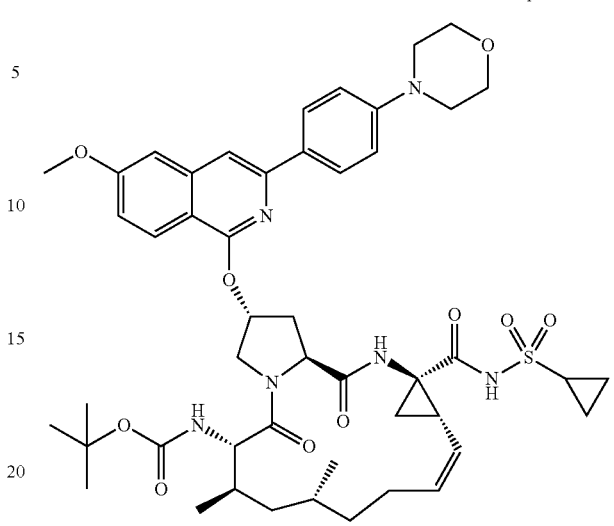

Compounds 5192 and 5193 were prepared using the intermediates described herein and by following the general procedure described for the synthesis of Compound 3117:

Compound 5192: tert-butyl ((2R,6S,7R,9S,13aS,14aR,16aS,Z)-14a-((cyclopropylsulfonyl)carbamoyl)-2-((6-methoxy-3-(4-morpholinophenyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 915.7 (M$^+$+1).

Compound 5193: tert-butyl ((2R,6S,7R,9R,13aS,14aR,16aS,Z)-14a-((cyclopropylsulfonyl)carbamoyl)-2-((6-methoxy-3-(4-morpholinophenyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 915.7 (M$^+$+1).

Preparation of Compound 5194 and Compound 5195

Compound 5194

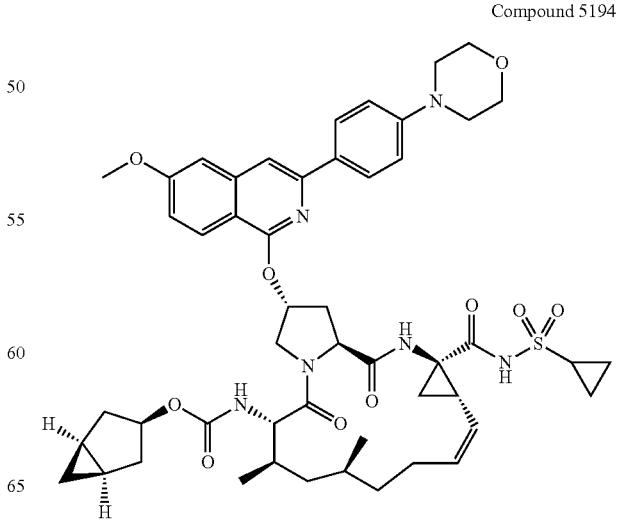

Compound 5195

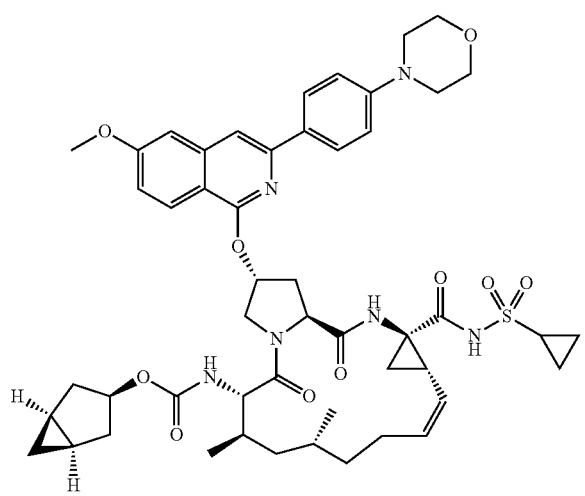

Compound 5197

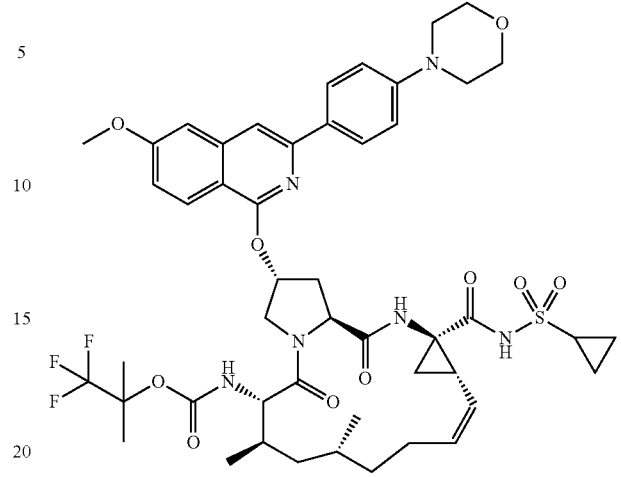

Compounds 5194 and 5195 were prepared using the intermediates described herein and by following the general procedure described for the synthesis of Compound 3117:

Compound 5194: (1R,3r,5S)-bicyclo[3.1.0]hexan-3-yl ((2R,6S,7R,9S,13aS,14aR,16aS,Z)-14a-((cyclopropylsulfonyl)carbamoyl)-2-((6-methoxy-3-(4-morpholinophenyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 939.7 (M$^+$+1).

Compound 5195: (1R,3r,5S)-bicyclo[3.1.0]hexan-3-yl ((2R,6S,7R,9R,13aS,14aR,16aS,Z)-14a-((cyclopropylsulfonyl)carbamoyl)-2-((6-methoxy-3-(4-morpholinophenyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 939.7 (M$^+$+1).

Compounds 5196 and 5197 were prepared using the intermediates described herein and by following the general procedure described for the synthesis of Compound 3117:

Compound 5196: 1,1,1-trifluoro-2-methylpropan-2-yl ((2R,6S,7R,9S,13aS,14aR,16aS,Z)-14a-((cyclopropylsulfonyl)carbamoyl)-2-((6-methoxy-3-(4-morpholinophenyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 969.4 (M$^+$+1).

Compound 5197: 1,1,1-trifluoro-2-methylpropan-2-yl ((2R,6S,7R,9R,13aS,14aR,16aS,Z)-14a-((cyclopropylsulfonyl)carbamoyl)-2-((6-methoxy-3-(4-morpholinophenyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 969.4 (M$^+$+1).

Preparation of Compound 5196 and Compound 5197

Preparation of Compound 5198 and Compound 5199

Compound 5196

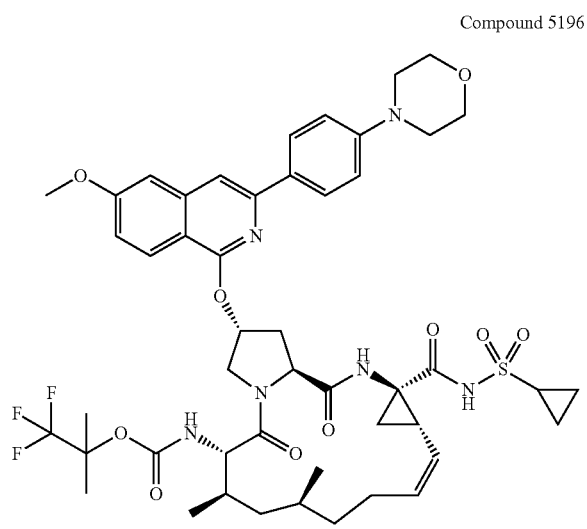

Compound 5198

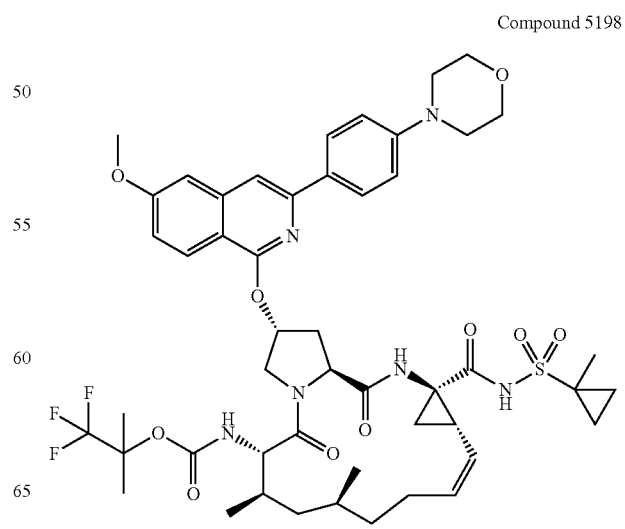

-continued

Compound 5199

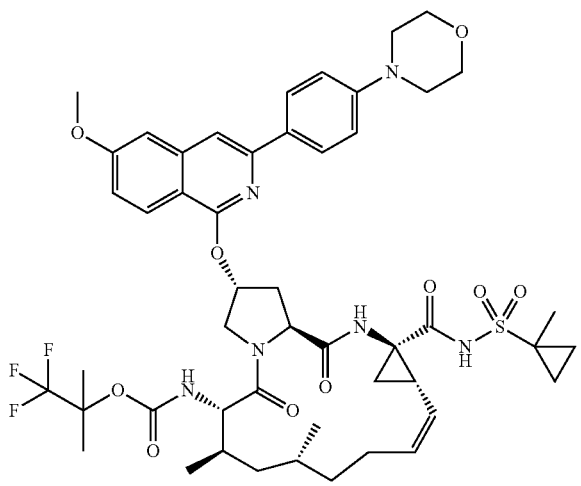

Compounds 5198 and 5199 were prepared using the intermediates described herein and by following the general procedure described for the synthesis of Compound 3117:

Compound 5198: 1,1,1-trifluoro-2-methylpropan-2-yl ((2R,6S,7R,9S,13aS,14aR,16aS,Z)-2-((6-methoxy-3-(4-morpholinophenyl)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 983.4 (M$^+$+1).

Compound 5199: 1,1,1-trifluoro-2-methylpropan-2-yl ((2R,6S,7R,9R,13aS,14aR,16aS,Z)-2-((6-methoxy-3-(4-morpholinophenyl)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ ppm 11.06 (s, 1H), 9.10 (s, 1H), 8.07 (d, J=8.9 Hz, 2H), 8.02-7.94 (m, 1H), 7.86 (d, J=7.9 Hz, 1H), 7.80 (s, 1H), 7.32 (d, J=2.4 Hz, 1H), 7.13-7.03 (m, 3H), 5.99 (br. s., 1H), 5.54 (d, J=6.1 Hz, 1H), 4.99 (t, J=9.6 Hz, 1H), 4.62-4.48 (m, 2H), 3.99 (dd, J=11.3, 3.1 Hz, 1H), 3.91 (s, 3H), 3.83-3.68 (m, 5H), 3.26-3.17 (m, 4H), 2.75-2.64 (m, 2H), 2.43-2.26 (m, 2H), 1.99-1.82 (m, 2H), 1.71 (d, J=6.1 Hz, 1H), 1.62 (br. s., 1H), 1.53 (br. s., 1H), 1.50-1.33 (m, 9H), 1.33-1.16 (m, 5H), 0.97-0.86 (m, 8H), 0.78 (t, J=11.9 Hz, 1H); MS: MS m/z 983.4 (M$^+$+1).

Preparation of Compound 5200 and Compound 5201

Compound 5200

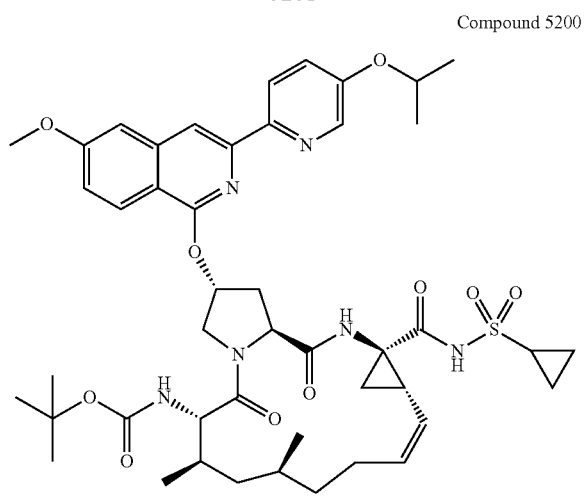

-continued

Compound 5201

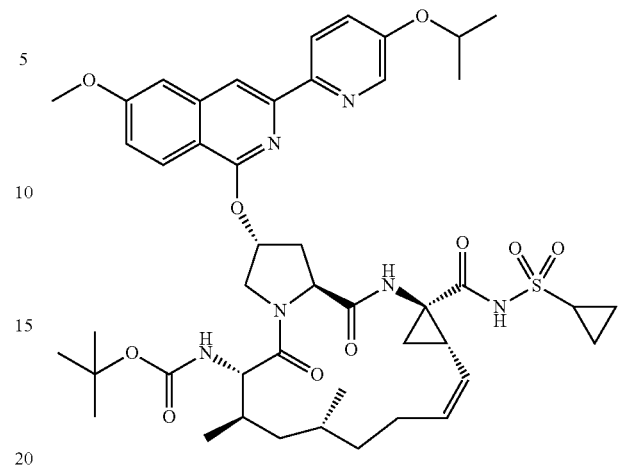

Compounds 5200 and 5201 were prepared using the intermediates described herein and by following the general procedure described for the synthesis of Compound 3117:

Compound 5200: tert-butyl ((2R,6S,7R,9S,13aS,14aR,16aS,Z)-14a-((cyclopropylsulfonyl)carbamoyl)-2-((3-(5-isopropoxypyridin-2-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 889.8 (M$^+$+1).

Compound 5201: tert-butyl ((2R,6S,7R,9R,13aS,14aR,16aS,Z)-14a-((cyclopropylsulfonyl)carbamoyl)-2-((3-(5-isopropoxypyridin-2-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.23 (s, 1H), 8.95 (br. s., 1H), 8.42-8.34 (m, 2H), 8.26 (s, 1H), 8.06 (d, J=8.9 Hz, 1H), 7.58 (dd, J=8.9, 2.7 Hz, 1H), 7.45 (d, J=2.1 Hz, 1H), 7.22 (d, J=7.9 Hz, 1H), 7.09 (dd, J=9.0, 2.3 Hz, 1H), 5.98 (br. s., 1H), 5.59-5.48 (m, 1H), 5.07 (t, J=9.6 Hz, 1H), 4.81 (spt, J=6.0 Hz, 1H), 4.63 (d, J=11.6 Hz, 1H), 4.49-4.42 (m, 1H), 4.00-3.94 (m, 1H), 3.94-3.89 (m, 3H), 3.75 (dd, J=10.4, 8.5 Hz, 1H), 2.98-2.89 (m, 1H), 2.80-2.63 (m, 2H), 2.43-2.24 (m, 2H), 2.00-1.68 (m, 3H), 1.65-1.50 (m, 2H), 1.49-0.97 (m, 22H), 0.95 (d, J=6.7 Hz, 3H), 0.90 (d, J=6.4 Hz, 3H), 0.75 (t, J=12.5 Hz, 1H); MS: MS m/z 889.8 (M$^+$+1).

Preparation of Compound 5202 and Compound 5203

Compound 5202

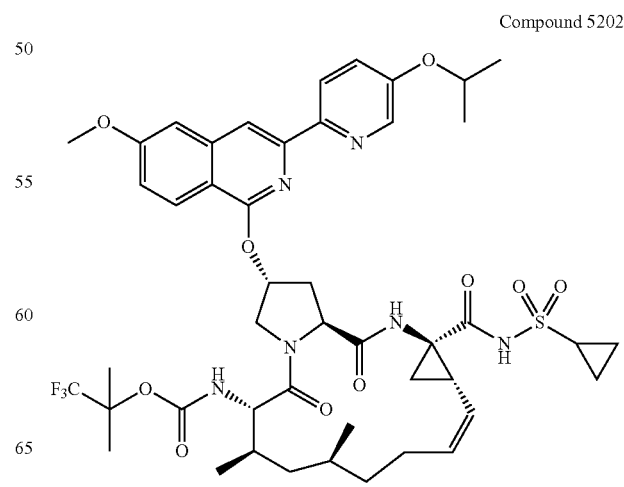

Compound 5203

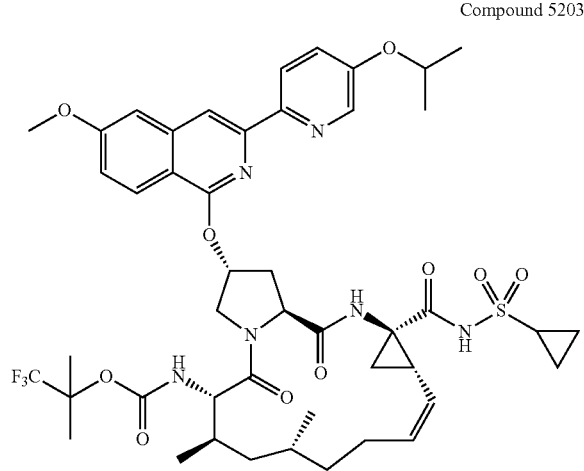

Compound 5205

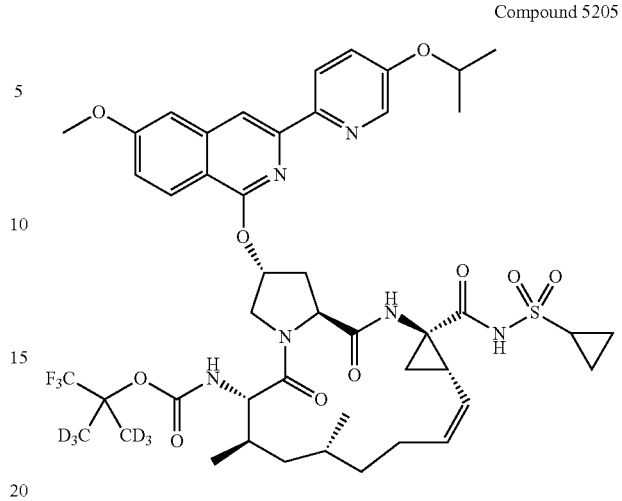

Compounds 5202 and 5203 were prepared using the intermediates described herein and by following the general procedure described for the synthesis of Compound 3117:

Compound 5202: 1,1,1-trifluoro-2-methylpropan-2-yl ((2R,6S,7R,9S,13aS,14aR,16aS,Z)-14a-((cyclopropylsulfonyl)carbamoyl)-2-((3-(5-isopropoxypyridin-2-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 943.6 (M$^+$+1).

Compound 5203: 1,1,1-trifluoro-2-methylpropan-2-yl ((2R,6S,7R,9R,13aS,14aR,16aS,Z)-14a-((cyclopropylsulfonyl)carbamoyl)-2-((3-(5-isopropoxypyridin-2-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.23 (br. s., 1H), 8.99 (br. s., 1H), 8.41-8.35 (m, 2H), 8.27 (s, 1H), 8.03 (d, J=8.9 Hz, 1H), 7.86 (d, J=7.6 Hz, 1H), 7.58 (dd, J=8.7, 2.6 Hz, 1H), 7.47 (d, J=2.4 Hz, 1H), 7.13 (dd, J=9.2, 2.4 Hz, 1H), 6.00 (br. s., 1H), 5.60-5.48 (m, 1H), 5.12-5.01 (m, 1H), 4.81 (spt, J=6.0 Hz, 1H), 4.57 (d, J=10.7 Hz, 1H), 4.53-4.44 (m, 1H), 4.01-3.94 (m, 1H), 3.92 (s, 3H), 3.74 (dd, J=10.5, 8.1 Hz, 1H), 2.99-2.88 (m, 1H), 2.79-2.63 (m, 2H), 2.45-2.26 (m, 2H), 1.98-1.81 (m, 2H), 1.78-1.69 (m, 1H), 1.64-1.52 (m, 2H), 1.50-0.85 (m, 25H), 0.76 (t, J=11.7 Hz, 1H); MS: MS m/z 943.7 (M$^+$+1).

Compounds 5204 and 5205 were prepared using the intermediates described herein and by following the general procedure described for the synthesis of Compound 3117:

Compound 5204: 1,1,1,3,3,3-hexadeutero-2-(trifluoromethyl)propan-2-yl ((2R,6S,7R,9S,13aS,14aR,16aS,Z)-14a-((cyclopropylsulfonyl)carbamoyl)-2-((3-(5-isopropoxypyridin-2-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 949.8 (M$^+$+1).

Compound 5205: 1,1,1,3,3,3-hexadeutero-2-(trifluoromethyl)propan-2-yl ((2R,6S,7R,9R,13aS,14aR,16aS,Z)-14a-((cyclopropylsulfonyl)carbamoyl)-2-((3-(5-isopropoxypyridin-2-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.23 (br. s., 1H), 8.99 (br. s., 1H), 8.41-8.34 (m, 2H), 8.27 (s, 1H), 8.03 (d, J=9.2 Hz, 1H), 7.85 (d, J=6.4 Hz, 1H), 7.58 (dd, J=8.5, 2.4 Hz, 1H), 7.46 (d, J=2.4 Hz, 1H), 7.13 (dd, J=9.2, 2.4 Hz, 1H), 6.00 (br. s., 1H), 5.60-5.46 (m, 1H), 5.13-5.01 (m, 1H), 4.81 (spt, J=6.1 Hz, 1H), 4.57 (d, J=9.8 Hz, 1H), 4.53-4.45 (m, 1H), 4.02-3.95 (m, 1H), 3.92 (s, 3H), 3.74 (dd, J=10.5, 8.1 Hz, 1H), 2.98-2.88 (m, 1H), 2.79-2.63 (m, 2H), 2.45-2.23 (m, 2H), 1.99-1.81 (m, 2H), 1.78-1.67 (m, 1H), 1.65-1.51 (m, 2H), 1.50-0.85 (m, 19H), 0.76 (t, J=11.6 Hz, 1H); MS: MS m/z 949.8 (M$^+$+1).

Preparation of Compound 5204 and Compound 5205

Compound 5204

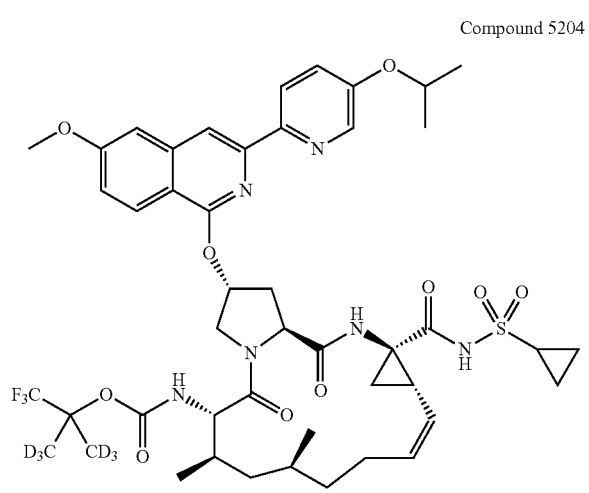

Preparation of Compound 5206 and Compound 5207

Compound 5206

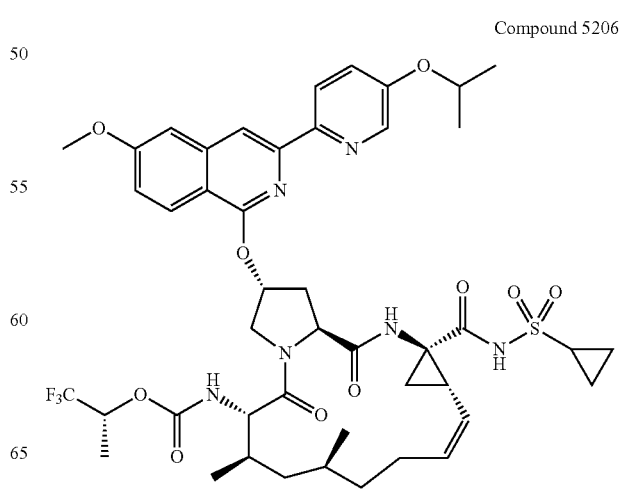

Compound 5207

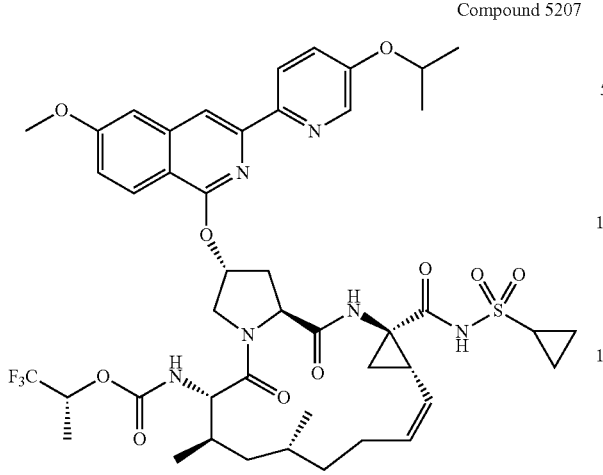

Compound 5209

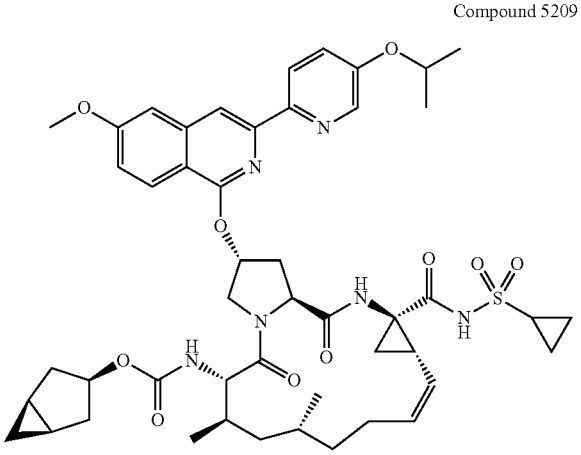

Compounds 5206 and 5207 were prepared using the intermediates described herein and by following the general procedure described for the synthesis of Compound 3117:

Compound 5206: (R)-1,1,1-trifluoropropan-2-yl ((2R,6S,7R,9S,13aS,14aR,16aS,Z)-14a-((cyclopropylsulfonyl)carbamoyl)-2-((3-(5-isopropoxypyridin-2-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 929.7 (M⁺+1).

Compound 5207: (R)-1,1,1-trifluoropropan-2-yl ((2R,6S,7R,9R,13aS,14aR,16aS,Z)-14a-((cyclopropylsulfonyl)carbamoyl)-2-((3-(5-isopropoxypyridin-2-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; ¹H NMR (500 MHz, DMSO-d₆) δ 11.22 (br. s., 1H), 8.95 (br. s., 1H), 8.42-8.34 (m, 2H), 8.27 (s, 1H), 8.11 (d, J=7.6 Hz, 1H), 8.00 (d, J=9.2 Hz, 1H), 7.58 (dd, J=8.7, 2.6 Hz, 1H), 7.46 (d, J=2.4 Hz, 1H), 7.07 (dd, J=9.0, 2.3 Hz, 1H), 5.99 (br. s., 1H), 5.58-5.49 (m, 1H), 5.15-5.03 (m, 1H), 4.89-4.75 (m, 2H), 4.57 (d, J=11.6 Hz, 1H), 4.52-4.42 (m, 1H), 4.03-3.97 (m, 1H), 3.91 (s, 3H), 3.81 (dd, J=10.8, 8.1 Hz, 1H), 2.97-2.87 (m, 1H), 2.79-2.62 (m, 2H), 2.45-2.24 (m, 2H), 1.99-1.83 (m, 2H), 1.77-1.67 (m, 1H), 1.58 (br. s., 2H), 1.50-0.86 (m, 22H), 0.78 (t, J=12.2 Hz, 1H); MS: MS m/z 929.7 (M⁺+1).

Preparation of Compound 5208 and Compound 5209

Compounds 5208 and 5209 were prepared using the intermediates described herein and by following the general procedure described for the synthesis of Compound 3117:

Compound 5208: (1R,3r,5S)-bicyclo[3.1.0]hexan-3-yl ((2R,6S,7R,9S,13aS,14aR,16aS,Z)-14a-((cyclopropylsulfonyl)carbamoyl)-2-((3-(5-isopropoxypyridin-2-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 913.7 (M⁺+1).

Compound 5209: (1R,3r,5S)-bicyclo[3.1.0]hexan-3-yl ((2R,6S,7R,9R,13aS,14aR,16aS,Z)-14a-((cyclopropylsulfonyl)carbamoyl)-2-((3-(5-isopropoxypyridin-2-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; ¹H NMR (500 MHz, DMSO-d₆) δ 11.23 (s, 1H), 8.92 (s, 1H), 8.40-8.35 (m, 2H), 8.27 (s, 1H), 8.04 (d, J=9.2 Hz, 1H), 7.57 (dd, J=8.7, 2.9 Hz, 1H), 7.47 (d, J=2.4 Hz, 1H), 7.44 (d, J=8.5 Hz, 1H), 7.15 (dd, J=9.0, 2.3 Hz, 1H), 6.00 (br. s., 1H), 5.59-5.50 (m, 1H), 5.08 (t, J=9.8 Hz, 1H), 4.80 (spt, J=6.0 Hz, 1H), 4.70 (t, J=6.7 Hz, 1H), 4.54 (d, J=11.0 Hz, 1H), 4.47 (dd, J=9.5, 7.3 Hz, 1H), 4.00 (dd, J=11.1, 3.2 Hz, 1H), 3.93 (s, 3H), 3.79 (dd, J=10.5, 9.0 Hz, 1H), 2.98-2.89 (m, 1H), 2.77-2.66 (m, 2H), 2.44-2.22 (m, 2H), 2.03-1.90 (m, 2H), 1.89-1.78 (m, 2H), 1.73-1.64 (m, 1H), 1.63-0.96 (m, 19H), 0.95 (d, J=6.7 Hz, 3H), 0.88 (d, J=6.4 Hz, 3H), 0.75 (t, J=12.4 Hz, 1H), 0.44-0.34 (m, 2H); MS: MS m/z 913.7 (M⁺+1).

Preparation of Compound 5210 and Compound 5211

Compound 5208

Compound 5210

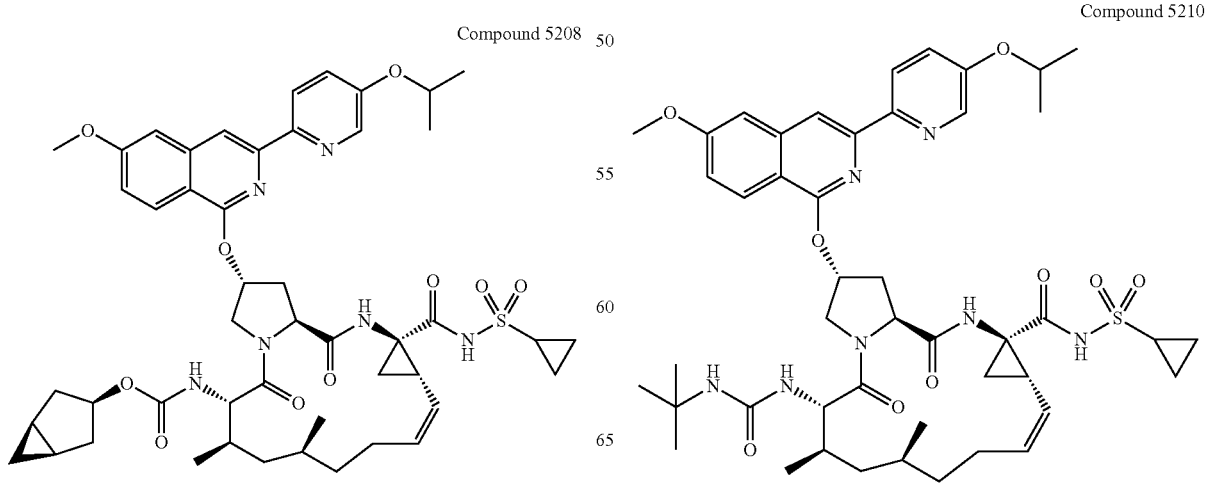

-continued

Compound 5211

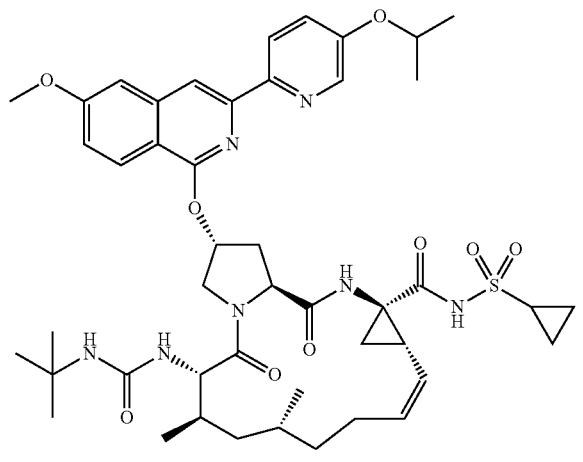

Compounds 5210 and 5211 were prepared using the intermediates described herein and by following the general procedure described for the synthesis of Compound 3117:

Compound 5210: (2R,6S,7R,9S,13aS,14aR,16aS,Z)-6-(3-(tert-butyl)ureido)-N-(cyclopropylsulfonyl)-2-((3-(5-isopropoxypyridin-2-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide; MS: MS m/z 888.8 (M⁺+1).

Compound 5211: (2R,6S,7R,9R,13aS,14aR,16aS,Z)-6-(3-(tert-butyl)ureido)-N-(cyclopropylsulfonyl)-2-((3-(5-isopropoxypyridin-2-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide; ¹H NMR (500 MHz, DMSO-d₆) δ 11.24 (br. s., 1H), 8.92 (br. s., 1H), 8.39 (d, J=8.9 Hz, 1H), 8.36 (d, J=2.7 Hz, 1H), 8.26 (s, 1H), 8.08 (d, J=9.2 Hz, 1H), 7.58 (d, J=6.7 Hz, 1H), 7.45 (d, J=2.1 Hz, 1H), 7.07 (dd, J=9.0, 2.3 Hz, 1H), 5.98 (br. s., 2H), 5.62 (s, 1H), 5.57-5.49 (m, 1H), 5.12-5.04 (m, 1H), 4.80 (spt, J=6.1 Hz, 1H), 4.62 (d, J=11.9 Hz, 1H), 4.49-4.36 (m, 1H), 4.03-3.96 (m, 1H), 3.94-3.84 (m, 4H), 2.98-2.88 (m, 1H), 2.79-2.68 (m, 2H), 2.44-2.28 (m, 2H), 1.99-1.87 (m, 1H), 1.81-1.63 (m, 2H), 1.62-0.85 (m, 30H), 0.76 (t, J=12.4 Hz, 1H); MS: MS m/z 888.8 (M⁺+1).

Preparation of Compound 5212 and Compound 5213

Compound 5212

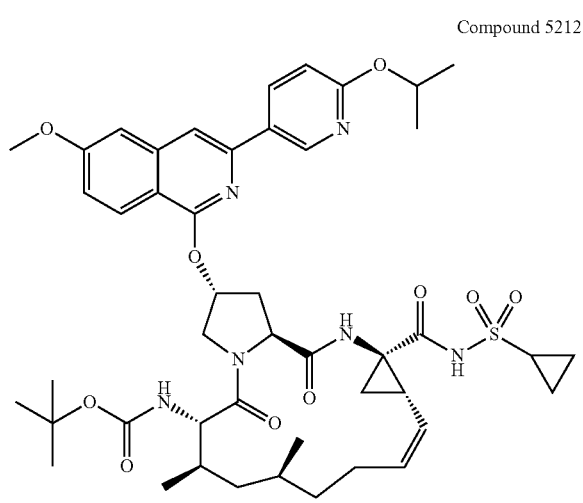

-continued

Compound 5213

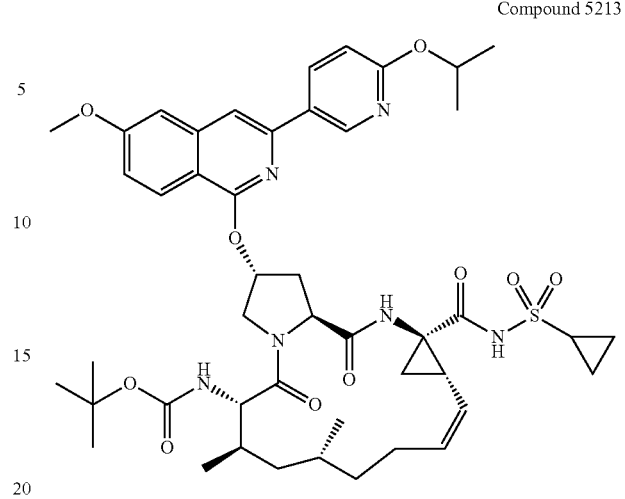

Compounds 5212 and 5213 were prepared using the intermediates described herein and by following the general procedure described for the synthesis of Compound 3117:

Compound 5212: tert-butyl ((2R,6S,7R,9S,13aS,14aR,16aS,Z)-14a-((cyclopropylsulfonyl)carbamoyl)-2-((3-(6-isopropoxypyridin-3-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 889.7 (M⁺+1).

Compound 5213: tert-butyl ((2R,6S,7R,9R,13aS,14aR,16aS,Z)-14a-((cyclopropylsulfonyl)carbamoyl)-2-((3-(6-isopropoxypyridin-3-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; ¹H NMR (500 MHz, DMSO-d₆) δ 11.21 (br. s., 1H), 8.99 (d, J=2.4 Hz, 1H), 8.95 (br. s., 1H), 8.42 (dd, J=8.9, 2.4 Hz, 1H), 8.05 (d, J=9.2 Hz, 1H), 7.87 (s, 1H), 7.32 (d, J=2.1 Hz, 1H), 7.20 (d, J=7.3 Hz, 1H), 7.08 (dd, J=9.0, 2.3 Hz, 1H), 6.90 (d, J=8.5 Hz, 1H), 5.96 (br. s., 1H), 5.57-5.49 (m, 1H), 5.36 (spt, J=6.1 Hz, 1H), 5.13-5.00 (m, 1H), 4.62 (d, J=11.0 Hz, 1H), 4.46 (t, J=8.5 Hz, 1H), 3.96 (dd, J=10.8, 2.9 Hz, 1H), 3.92 (s, 3H), 3.75 (dd, J=10.4, 8.5 Hz, 1H), 2.91 (d, J=4.9 Hz, 1H), 2.78-2.65 (m, 2H), 2.42-2.24 (m, 2H), 2.00-1.68 (m, 3H), 1.66-1.51 (m, 2H), 1.49-0.96 (m, 22H), 0.95 (d, J=6.7 Hz, 3H), 0.89 (d, J=6.1 Hz, 3H), 0.75 (t, J=11.9 Hz, 1H); MS: MS m/z 889.7 (M⁺+1).

Preparation of Compound 5214 and Compound 5215

Compound 5214

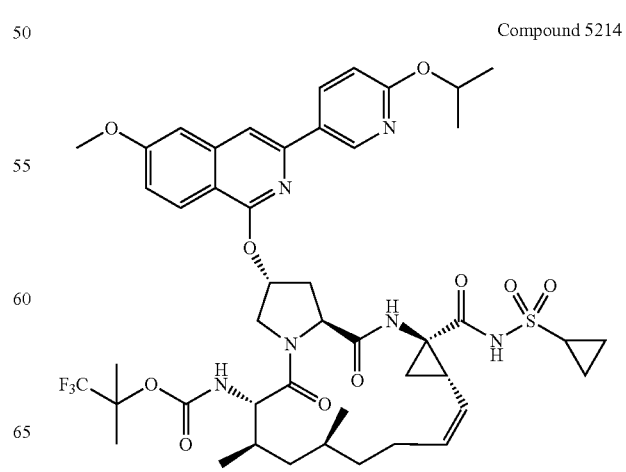

287

-continued

Compound 5215

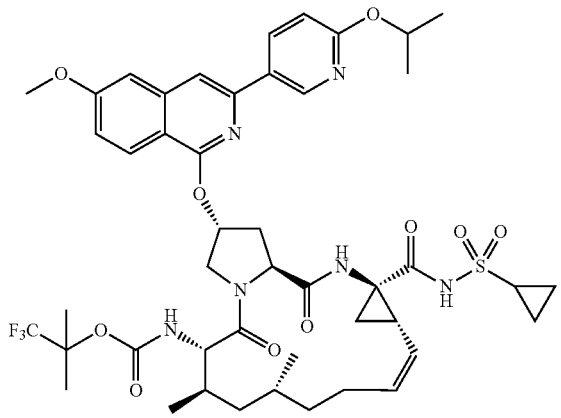

Compounds 5214 and 5215 were prepared using the intermediates described herein and by following the general procedure described for the synthesis of Compound 3117:

Compound 5214: 1,1,1-trifluoro-2-methylpropan-2-yl ((2R,6S,7R,9S,13aS,14aR,16aS,Z)-14a-((cyclopropylsulfonyl)carbamoyl)-2-((3-(6-isopropoxypyridin-3-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 943.7 ($M^+$+1).

Compound 5215: 1,1,1-trifluoro-2-methylpropan-2-yl ((2R,6S,7R,9R,13aS,14aR,16aS,Z)-14a-((cyclopropylsulfonyl)carbamoyl)-2-((3-(6-isopropoxypyridin-3-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-$d_6$) δ 11.21 (br. s., 1H), 9.03-8.95 (m, 2H), 8.42 (dd, J=8.5, 2.4 Hz, 1H), 8.02 (d, J=9.2 Hz, 1H), 7.88 (s, 1H), 7.84 (d, J=7.6 Hz, 1H), 7.33 (d, J=2.4 Hz, 1H), 7.12 (dd, J=9.0, 2.3 Hz, 1H), 6.90 (d, J=8.9 Hz, 1H), 5.98 (br. s., 1H), 5.59-5.50 (m, 1H), 5.36 (spt, J=6.2 Hz, 1H), 5.15-5.02 (m, 1H), 4.57 (d, J=11.6 Hz, 1H), 4.54-4.47 (m, 1H), 3.97 (dd, J=11.4, 3.2 Hz, 1H), 3.93 (s, 3H), 3.74 (dd, J=10.7, 7.9 Hz, 1H), 2.98-2.88 (m, 1H), 2.78-2.63 (m, 2H), 2.42-2.24 (m, 2H), 2.00-1.81 (m, 2H), 1.78-1.67 (m, 1H), 1.65-1.52 (m, 2H), 1.50-0.97 (m, 19H), 0.95 (d, J=6.7 Hz, 3H), 0.89 (d, J=6.4 Hz, 3H), 0.77 (t, J=12.5 Hz, 1H); MS: MS m/z 943.6 ($M^+$+1).

Preparation of Compound 5216 and Compound 5217

Compound 5216

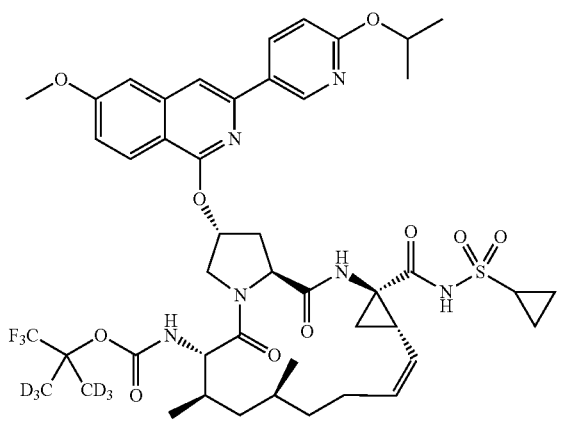

288

-continued

Compound 5217

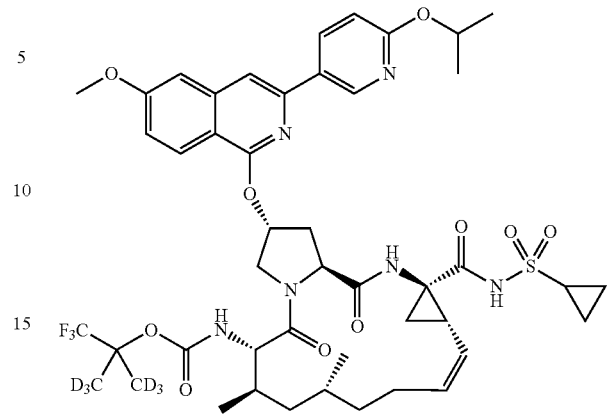

Compounds 5216 and 5217 were prepared using the intermediates described herein and by following the general procedure described for the synthesis of Compound 3117:

Compound 5216: 1,1,1,3,3,3-hexadeutero-2-(trifluoromethyl)propan-2-yl ((2R,6S,7R,9S,13aS,14aR,16aS,Z)-14a-((cyclopropylsulfonyl)carbamoyl)-2-((3-(6-isopropoxypyridin-3-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 949.7 ($M^+$+1).

Compound 5217: 1,1,1,3,3,3-hexadeutero-2-(trifluoromethyl)propan-2-yl ((2R,6S,7R,9R,13aS,14aR,16aS,Z)-14a-((cyclopropylsulfonyl)carbamoyl)-2-((3-(6-isopropoxypyridin-3-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-$d_6$) δ 11.21 (s, 1H), 9.04-8.96 (m, 2H), 8.42 (dd, J=8.7, 2.6 Hz, 1H), 8.02 (d, J=9.2 Hz, 1H), 7.89 (s, 1H), 7.84 (d, J=7.9 Hz, 1H), 7.33 (d, J=2.1 Hz, 1H), 7.12 (dd, J=8.9, 2.4 Hz, 1H), 6.90 (d, J=8.5 Hz, 1H), 5.98 (br. s., 1H), 5.60-5.49 (m, 1H), 5.36 (spt, J=6.2 Hz, 1H), 5.15-5.01 (m, 1H), 4.57 (d, J=11.3 Hz, 1H), 4.54-4.45 (m, 1H), 3.97 (dd, J=11.3, 3.1 Hz, 1H), 3.93 (s, 3H), 3.74 (dd, J=10.7, 8.2 Hz, 1H), 2.91 (d, J=8.2 Hz, 1H), 2.70 (d, J=7.9 Hz, 2H), 2.45-2.24 (m, 2H), 1.99-1.81 (m, 2H), 1.78-1.68 (m, 1H), 1.65-1.52 (m, 2H), 1.50-0.97 (m, 13H), 0.95 (d, J=7.0 Hz, 3H), 0.89 (d, J=6.4 Hz, 3H), 0.77 (t, J=11.7 Hz, 1H); MS: MS m/z 949.7 ($M^+$+1).

Preparation of Compound 5218 and Compound 5219

Compound 5218

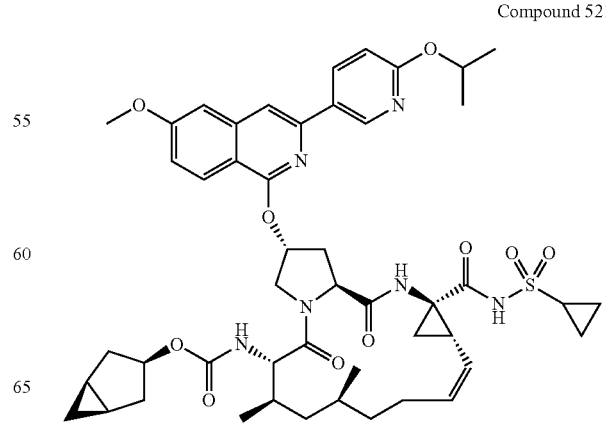

Compound 5219

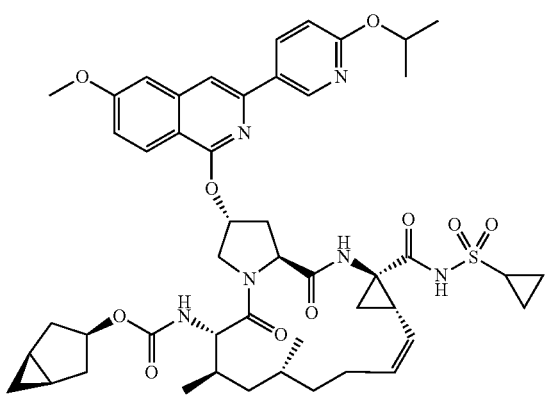

Compounds 5218 and 5219 were prepared using the intermediates described herein and by following the general procedure described for the synthesis of Compound 3117:

Compound 5218: (1R,3r,5S)-bicyclo[3.1.0]hexan-3-yl ((2R,6S,7R,9S,13aS,14aR,16aS,Z)-14a-((cyclopropylsulfonyl)carbamoyl)-2-((3-(6-isopropoxypyridin-3-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 913.7 (M$^+$+1).

Compound 5219: (1R,3r,5S)-bicyclo[3.1.0]hexan-3-yl ((2R,6S,7R,9R,13aS,14aR,16aS,Z)-14a-((cyclopropylsulfonyl)carbamoyl)-2-((3-(6-isopropoxypyridin-3-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.21 (br. s., 1H), 8.99 (d, J=2.4 Hz, 1H), 8.92 (br. s., 1H), 8.42 (dd, J=8.9, 2.4 Hz, 1H), 8.03 (d, J=9.2 Hz, 1H), 7.89 (s, 1H), 7.42 (d, J=8.2 Hz, 1H), 7.33 (d, J=2.4 Hz, 1H), 7.15 (dd, J=9.0, 2.3 Hz, 1H), 6.90 (d, J=8.9 Hz, 1H), 5.98 (br. s., 1H), 5.58-5.49 (m, 1H), 5.35 (spt, J=6.1 Hz, 1H), 5.07 (t, J=9.6 Hz, 1H), 4.69 (t, J=6.7 Hz, 1H), 4.52 (d, J=11.0 Hz, 1H), 4.49-4.43 (m, 1H), 3.99 (dd, J=11.1, 3.2 Hz, 1H), 3.93 (s, 3H), 3.81-3.76 (m, 1H), 2.98-2.89 (m, 1H), 2.80-2.63 (m, 2H), 2.43-2.24 (m, 2H), 2.02-1.91 (m, 2H), 1.88-1.76 (m, 2H), 1.72-1.64 (m, 1H), 1.63-0.97 (m, 19H), 0.95 (d, J=6.7 Hz, 3H), 0.87 (d, J=6.4 Hz, 3H), 0.76 (t, J=12.1 Hz, 1H), 0.42-0.31 (m, 2H); MS: MS m/z 913.7 (M$^+$+1).

Preparation of Compound 5220 and Compound 5221

Compound 5220

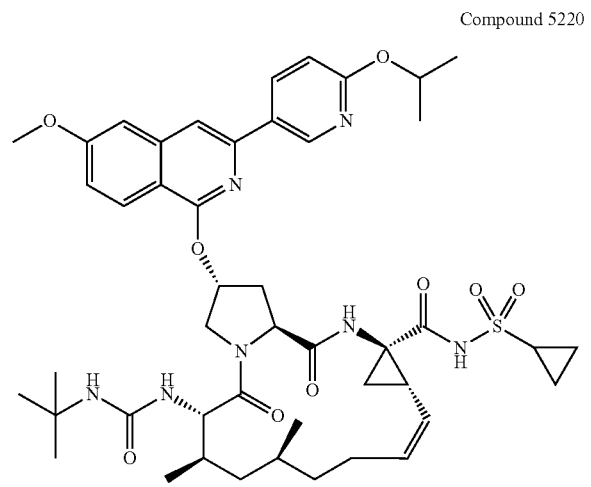

Compound 5221

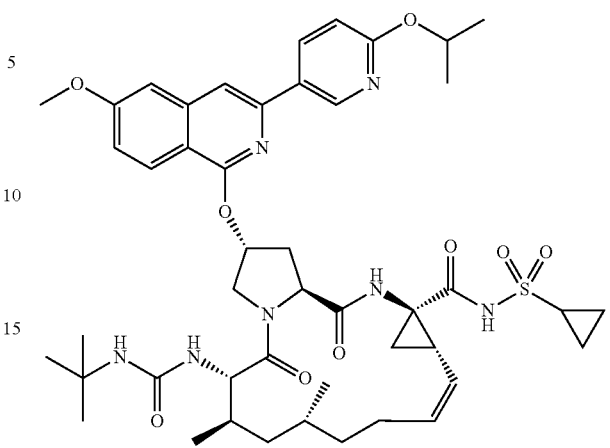

Compounds 5220 and 5221 were prepared using the intermediates described herein and by following the general procedure described for the synthesis of Compound 3117:

Compound 5220: (2R,6S,7R,9S,13aS,14aR,16aS,Z)-6-(3-(tert-butyl)ureido)-N-(cyclopropylsulfonyl)-2-((3-(6-isopropoxypyridin-3-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide; MS: MS m/z 888.7 (M$^+$+1).

Compound 5221: (2R,6S,7R,9R,13aS,14aR,16aS,Z)-6-(3-(tert-butyl)ureido)-N-(cyclopropylsulfonyl)-2-((3-(6-isopropoxypyridin-3-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide; $^1$H NMR (500 MHz, DMSO-d$_6$) δ 11.21 (s, 1H), 8.99 (d, J=2.4 Hz, 1H), 8.92 (br. s., 1H), 8.42 (dd, J=8.7, 2.6 Hz, 1H), 8.06 (d, J=9.2 Hz, 1H), 7.87 (s, 1H), 7.31 (d, J=2.4 Hz, 1H), 7.07 (dd, J=9.2, 2.4 Hz, 1H), 6.89 (d, J=8.5 Hz, 1H), 6.02-5.94 (m, 2H), 5.60 (s, 1H), 5.57-5.47 (m, 1H), 5.36 (spt, J=6.2 Hz, 1H), 5.06 (t, J=10.2 Hz, 1H), 4.61 (d, J=10.1 Hz, 1H), 4.49-4.37 (m, 1H), 3.98 (dd, J=11.1, 3.2 Hz, 1H), 3.92 (s, 3H), 3.88 (t, J=9.8 Hz, 1H), 2.96-2.88 (m, 1H), 2.79-2.65 (m, 2H), 2.43-2.27 (m, 2H), 2.00-1.88 (m, 1H), 1.79-1.64 (m, 2H), 1.63-0.97 (m, 24H), 0.96 (d, J=6.7 Hz, 3H), 0.91 (d, J=6.4 Hz, 3H), 0.77 (t, J=12.2 Hz, 1H); MS: MS m/z 888.7 (M$^+$+1).

Preparation of Compound 5222 and Compound 5223

Compound 5222

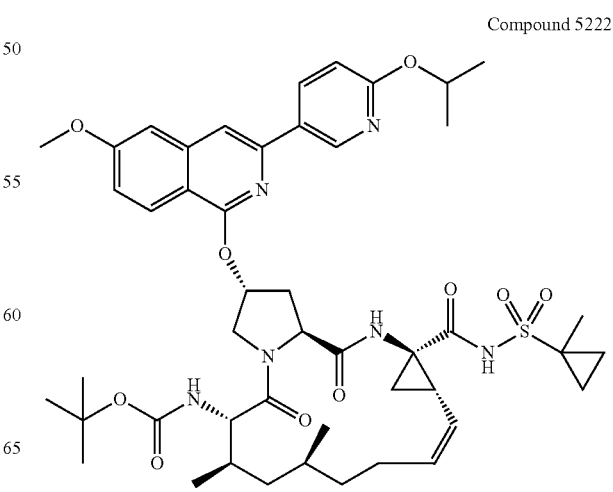

Compound 5223

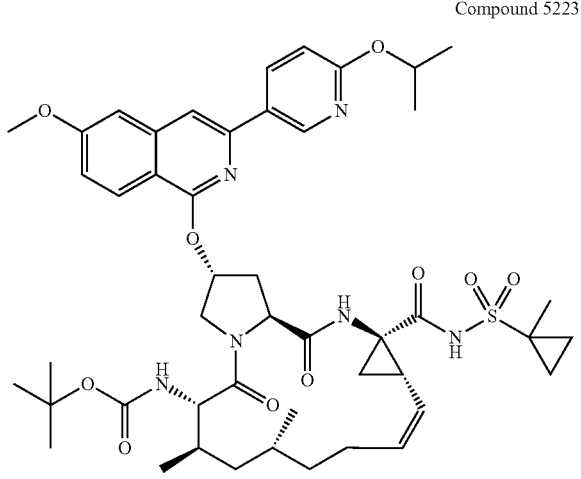

Compounds 5222 and 5223 were prepared using the intermediates described herein and by following the general procedure described for the synthesis of Compound 3117:

Compound 5222: tert-butyl ((2R,6S,7R,9S,13aS,14aR,16aS,Z)-2-((3-(6-isopropoxypyridin-3-yl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 903.7 (M⁺+1).

Compound 5223: tert-butyl ((2R,6S,7R,9R,13aS,14aR,16aS,Z)-2-((3-(6-isopropoxypyridin-3-yl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.06 (br. s., 1H), 9.08 (br. s., 1H), 8.98 (d, J=2.1 Hz, 1H), 8.41 (dd, J=8.9, 2.4 Hz, 1H), 8.05 (d, J=8.9 Hz, 1H), 7.87 (s, 1H), 7.32 (d, J=2.1 Hz, 1H), 7.19 (d, J=8.2 Hz, 1H), 7.09 (dd, J=9.0, 2.3 Hz, 1H), 6.89 (d, J=8.9 Hz, 1H), 5.98 (br. s., 1H), 5.58-5.49 (m, 1H), 5.36 (spt, J=6.2 Hz, 1H), 5.04-4.93 (m, 1H), 4.63 (d, J=10.7 Hz, 1H), 4.55-4.46 (m, 1H), 3.99 (dd, J=11.2, 3.2 Hz, 1H), 3.92 (s, 3H), 3.75 (dd, J=10.2, 8.7 Hz, 1H), 2.78-2.64 (m, 2H), 2.42-2.27 (m, 2H), 1.98-1.79 (m, 2H), 1.75-1.67 (m, 1H), 1.65-1.58 (m, 1H), 1.56-1.10 (m, 24H), 0.99-0.85 (m, 8H), 0.76 (t, J=12.4 Hz, 1H); MS: MS m/z 903.7 (M⁺+1).

Preparation of Compound 5224 and Compound 5225

Compound 5225

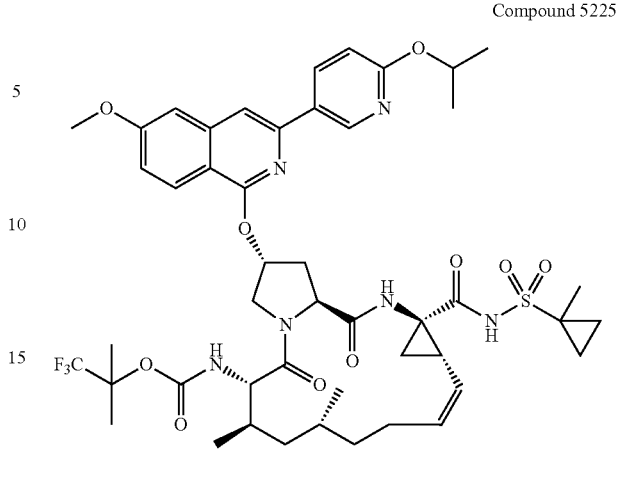

Compounds 5214 and 5215 were prepared using the intermediates described herein and by following the general procedure described for the synthesis of Compound 3117:

Compound 5224: 1,1,1-trifluoro-2-methylpropan-2-yl ((2R,6S,7R,9S,13aS,14aR,16aS,Z)-2-((3-(6-isopropoxypyridin-3-yl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 957.6 (M⁺+1).

Compound 5225: 1,1,1-trifluoro-2-methylpropan-2-yl ((2R,6S,7R,9R,13aS,14aR,16aS,Z)-2-((3-(6-isopropoxypyridin-3-yl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.05 (s, 1H), 9.12 (br. s., 1H), 8.99 (d, J=2.4 Hz, 1H), 8.41 (dd, J=8.9, 2.4 Hz, 1H), 8.02 (d, J=9.2 Hz, 1H), 7.88 (s, 1H), 7.83 (d, J=7.9 Hz, 1H), 7.33 (d, J=2.4 Hz, 1H), 7.13 (dd, J=9.0, 2.3 Hz, 1H), 6.90 (d, J=8.5 Hz, 1H), 6.00 (br. s., 1H), 5.57-5.50 (m, 1H), 5.36 (spt, J=6.1 Hz, 1H), 4.99 (t, J=9.8 Hz, 1H), 4.64-4.50 (m, 2H), 4.00 (dd, J=11.3, 3.1 Hz, 1H), 3.93 (s, 3H), 3.74 (dd, J=10.7, 8.2 Hz, 1H), 2.76-2.65 (m, 2H), 2.41-2.28 (m, 2H), 1.97-1.82 (m, 2H), 1.77-1.67 (m, 1H), 1.65-1.58 (m, 1H), 1.57-1.50 (m, 1H), 1.50-1.08 (m, 20H), 0.98-0.85 (m, 8H), 0.79 (t, J=12.5 Hz, 1H); MS: MS m/z 957.7 (M⁺+1).

Preparation of Compound 5226 and Compound 5227

Compound 5224

Compound 5226

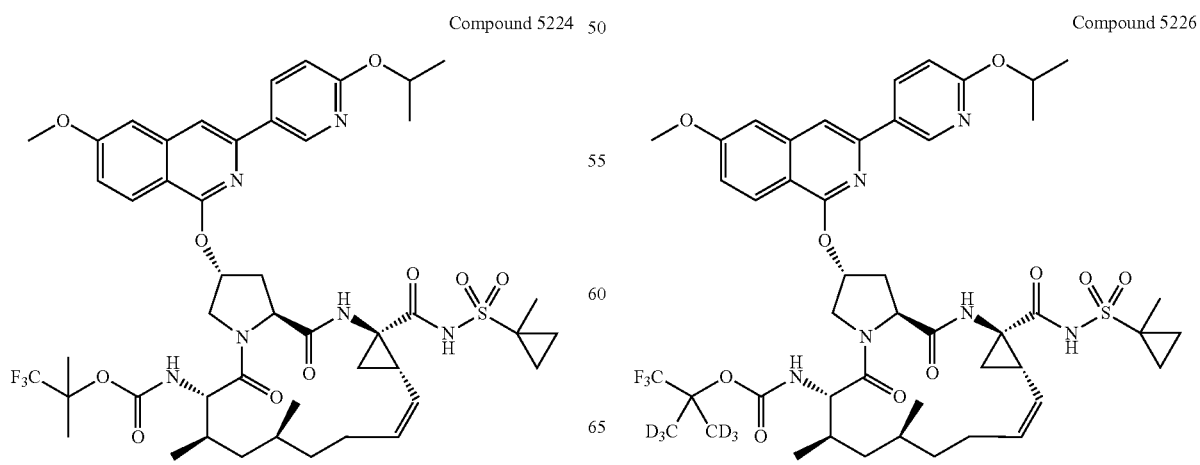

-continued

Compound 5227

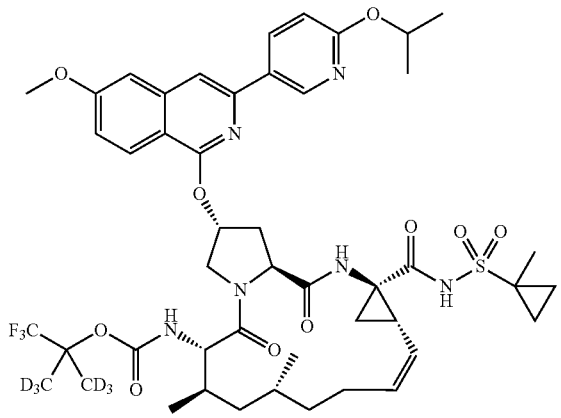

Compounds 5226 and 5227 were prepared using the intermediates described herein and by following the general procedure described for the synthesis of Compound 3117:

Compound 5226: 1,1,1,3,3,3-hexadeutero-2-(trifluoromethyl)propan-2-yl ((2R,6S,7R,9S,13aS,14aR,16aS,Z)-2-((3-(6-isopropoxypyridin-3-yl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 963.7 (M$^+$+1).

Compound 5227: 1,1,1,3,3,3-hexadeutero-2-(trifluoromethyl)propan-2-yl ((2R,6S,7R,9R,13aS,14aR,16aS,Z)-2-((3-(6-isopropoxypyridin-3-yl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.06 (s, 1H), 9.12 (br. s., 1H), 8.99 (d, J=2.4 Hz, 1H), 8.41 (dd, J=8.5, 2.4 Hz, 1H), 8.02 (d, J=9.2 Hz, 1H), 7.88 (s, 1H), 7.84 (d, J=7.9 Hz, 1H), 7.33 (d, J=2.1 Hz, 1H), 7.13 (dd, J=9.2, 2.4 Hz, 1H), 6.90 (d, J=8.5 Hz, 1H), 5.99 (br. s., 1H), 5.60-5.48 (m, 1H), 5.36 (spt, J=6.1 Hz, 1H), 4.99 (t, J=9.8 Hz, 1H), 4.65-4.47 (m, 2H), 3.99 (dd, J=11.3, 3.4 Hz, 1H), 3.93 (s, 3H), 3.74 (dd, J=10.8, 8.1 Hz, 1H), 2.77-2.66 (m, 2H), 2.42-2.30 (m, 2H), 1.97-1.80 (m, 2H), 1.76-1.67 (m, 1H), 1.66-1.59 (m, 1H), 1.57-1.50 (m, 1H), 1.50-1.10 (m, 14H), 1.00-0.85 (m, 8H), 0.78 (t, J=12.4 Hz, 1H); MS: MS m/z 963.7 (M$^+$+1).

Preparation of Compound 5218 and Compound 5219

Compound 5228

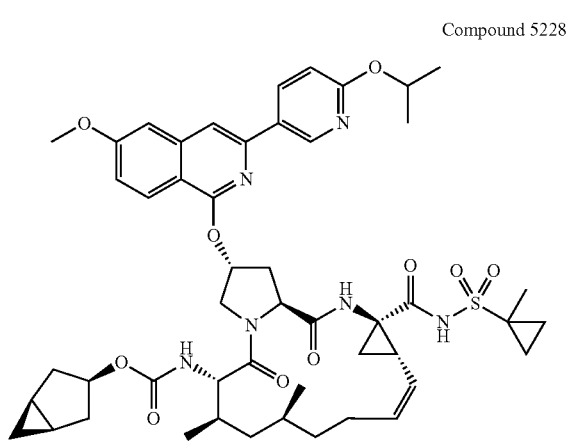

-continued

Compound 5229

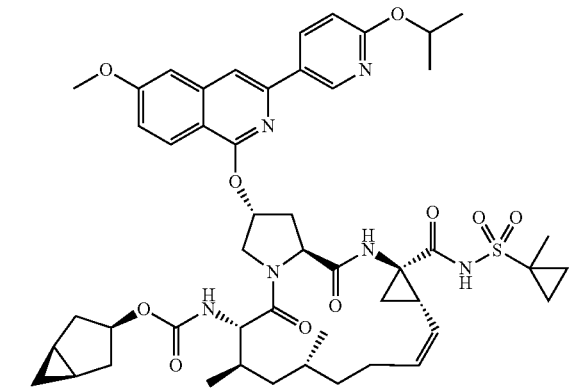

Compounds 5228 and 5229 were prepared using the intermediates described herein and by following the general procedure described for the synthesis of Compound 3117:

Compound 5228: (1R,3r,5S)-bicyclo[3.1.0]hexan-3-yl ((2R,6S,7R,9S,13aS,14aR,16aS,Z)-2-((3-(6-isopropoxypyridin-3-yl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 927.7 (M$^+$+1).

Compound 5229: (1R,3r,5S)-bicyclo[3.1.0]hexan-3-yl ((2R,6S,7R,9R,13aS,14aR,16aS,Z)-2-((3-(6-isopropoxypyridin-3-yl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.06 (br. s., 1H), 9.05 (br. s., 1H), 8.98 (d, J=2.4 Hz, 1H), 8.41 (dd, J=8.5, 2.4 Hz, 1H), 8.02 (d, J=9.2 Hz, 1H), 7.89 (s, 1H), 7.42 (d, J=8.2 Hz, 1H), 7.33 (d, J=2.1 Hz, 1H), 7.15 (dd, J=9.2, 2.4 Hz, 1H), 6.90 (d, J=8.5 Hz, 1H), 6.00 (br. s., 1H), 5.58-5.48 (m, 1H), 5.36 (spt, J=6.2 Hz, 1H), 5.09-4.93 (m, 1H), 4.66 (t, J=6.7 Hz, 1H), 4.58-4.45 (m, 2H), 4.01 (dd, J=11.3, 3.1 Hz, 1H), 3.93 (s, 3H), 3.78 (t, J=9.8 Hz, 1H), 2.79-2.62 (m, 2H), 2.42-2.24 (m, 2H), 2.01-1.73 (m, 4H), 1.72-1.08 (m, 21H), 1.00-0.83 (m, 8H), 0.77 (t, J=12.4 Hz, 1H), 0.41-0.31 (m, 2H); MS: MS m/z 927.7 (M$^+$+1).

Preparation of Compound 5230 and Compound 5231

Compound 5230

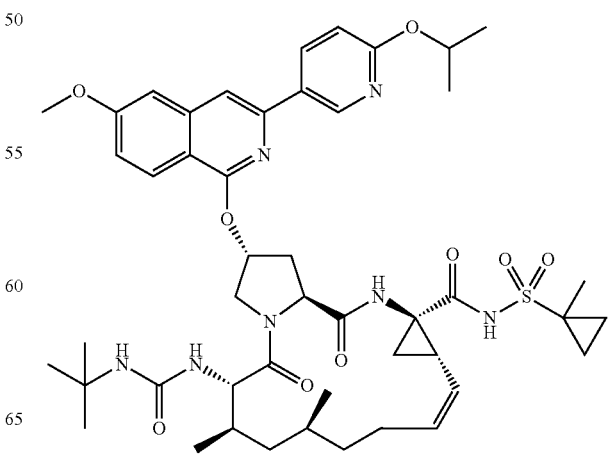

Compound 5231

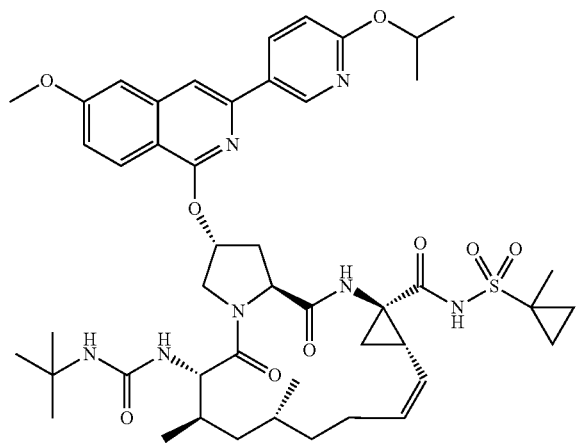

Compounds 5230 and 5231 were prepared using the intermediates described herein and by following the general procedure described for the synthesis of Compound 3117:

Compound 5230: (2R,6S,7R,9S,13aS,14aR,16aS,Z)-6-(3-(tert-butyl)ureido)-2-((3-(6-isopropoxypyridin-3-yl)-6-methoxyisoquinolin-1-yl)oxy)-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide; MS: MS m/z 902.7 (M⁺+1).

Compound 5231: (2R,6S,7R,9R,13aS,14aR,16aS,Z)-6-(3-(tert-butyl)ureido)-2-((3-(6-isopropoxypyridin-3-yl)-6-methoxyisoquinolin-1-yl)oxy)-7,9-dimethyl-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide; $^1$H NMR (500 MHz, DMSO-$d_6$) δ 11.07 (br. s., 1H), 9.05 (br. s., 1H), 8.98 (d, J=2.1 Hz, 1H), 8.41 (dd, J=8.9, 2.4 Hz, 1H), 8.06 (d, J=8.9 Hz, 1H), 7.87 (s, 1H), 7.32 (d, J=2.4 Hz, 1H), 7.07 (dd, J=8.9, 2.4 Hz, 1H), 6.89 (d, J=8.5 Hz, 1H), 5.98 (br. s., 2H), 5.59 (s, 1H), 5.57-5.46 (m, 1H), 5.36 (spt, J=6.2 Hz, 1H), 5.07-4.91 (m, 1H), 4.70-4.55 (m, 1H), 4.51-4.37 (m, 1H), 4.00 (dd, J=11.1, 3.5 Hz, 1H), 3.94-3.84 (m, 4H), 2.81-2.63 (m, 2H), 2.42-2.27 (m, 2H), 1.92 (s, 1H), 1.79-0.83 (m, 35H), 0.81-0.73 (m, 1H); MS: MS m/z 902.7 (M⁺+1).

Preparation of Compound 5232 and Compound 5233

Compound 5232

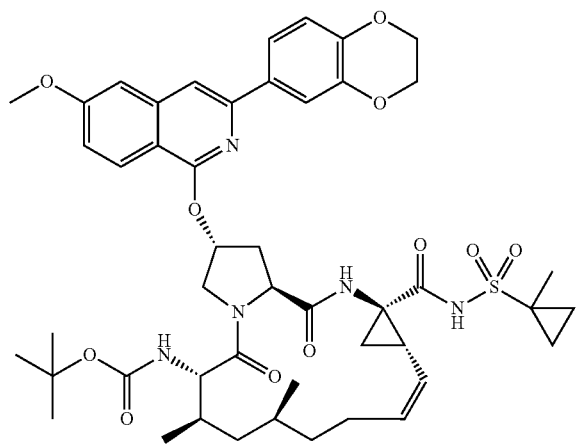

Compound 5233

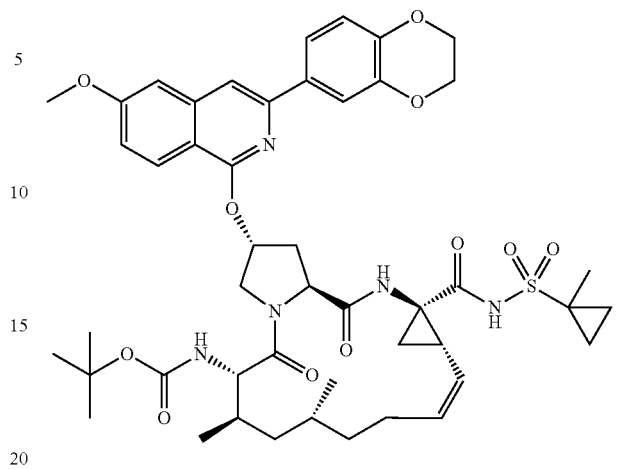

Compounds 5232 and 5233 were prepared using the intermediates described herein and by following the general procedure described for the synthesis of Compound 3117:

Compound 5232: tert-butyl ((2R,6S,7R,9S,13aS,14aR,16aS,Z)-2-((3-(2,3-dihydrobenzo[b][1,4]dioxin-6-yl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 902.1 (M⁺+1).

Compound 5233: tert-butyl ((2R,6S,7R,9R,13aS,14aR,16aS,Z)-2-((3-(2,3-dihydrobenzo[b][1,4]dioxin-6-yl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-$d_6$) δ 11.07 (br. s., 1H), 9.06 (br. s., 1H), 8.03 (d, J=9.2 Hz, 1H), 7.82 (s, 1H), 7.69 (s, 1H), 7.66 (dd, J=8.5, 1.8 Hz, 1H), 7.33 (d, J=2.1 Hz, 1H), 7.22 (d, J=7.9 Hz, 1H), 7.05 (dd, J=9.0, 2.3 Hz, 1H), 6.99 (d, J=8.5 Hz, 1H), 5.96 (br. s., 1H), 5.58-5.50 (m, 1H), 5.03-4.95 (m, 1H), 4.61 (d, J=11.9 Hz, 1H), 4.52-4.44 (m, 1H), 4.32 (s, 4H), 3.97 (dd, J=11.1, 2.9 Hz, 1H), 3.91 (s, 3H), 3.78-3.72 (m, 1H), 2.78-2.63 (m, 2H), 2.42-2.29 (m, 2H), 1.97-1.78 (m, 2H), 1.76-1.67 (m, 1H), 1.64-1.58 (m, 1H), 1.56-1.08 (m, 18H), 1.01-0.85 (m, 8H), 0.76 (t, J=12.5 Hz, 1H); MS: MS m/z 902.1 (M⁺+1).

Preparation of Compound 5234 and Compound 5235

Compound 5234

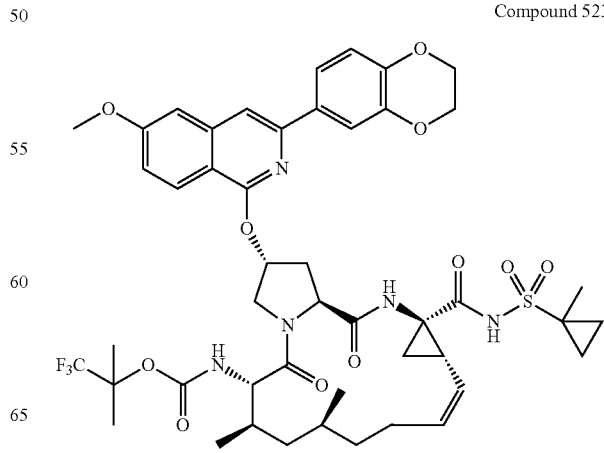

-continued

Compound 5235

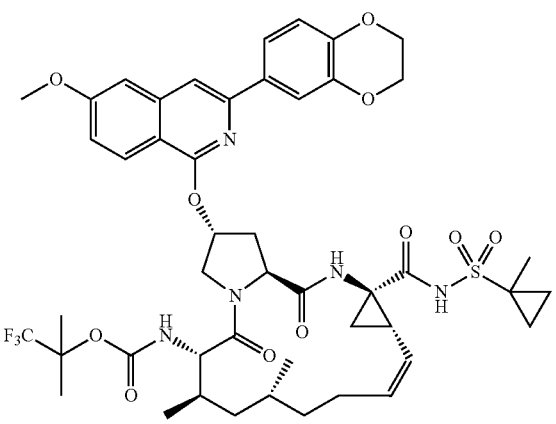

Compounds 5234 and 5235 were prepared using the intermediates described herein and by following the general procedure described for the synthesis of Compound 3117:

Compound 5234: 1,1,1-trifluoro-2-methylpropan-2-yl ((2R,6S,7R,9S,13aS,14aR,16aS,Z)-2-((3-(2,3-dihydrobenzo[b][1,4]dioxin-6-yl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 956.5 (M$^+$+1).

Compound 5235: 1,1,1-trifluoro-2-methylpropan-2-yl ((2R,6S,7R,9R,13aS,14aR,16aS,Z)-2-((3-(2,3-dihydrobenzo[b][1,4]dioxin-6-yl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.06 (s, 1H), 9.10 (s, 1H), 7.99 (d, J=9.2 Hz, 1H), 7.86 (d, J=7.9 Hz, 1H), 7.83 (s, 1H), 7.72-7.65 (m, 2H), 7.34 (d, J=2.4 Hz, 1H), 7.09 (dd, J=9.0, 2.3 Hz, 1H), 7.00 (d, J=8.2 Hz, 1H), 5.98 (br. s., 1H), 5.60-5.47 (m, 1H), 5.00 (t, J=9.8 Hz, 1H), 4.60-4.49 (m, 2H), 4.32 (s, 4H), 3.97 (dd, J=11.3, 3.4 Hz, 1H), 3.92 (s, 3H), 3.73 (dd, J=10.7, 8.2 Hz, 1H), 2.77-2.65 (m, 2H), 2.41-2.31 (m, 2H), 1.97-1.81 (m, 2H), 1.76-1.67 (m, 1H), 1.65-1.58 (m, 1H), 1.56-1.50 (m, 1H), 1.50-1.10 (m, 14H), 0.98-0.86 (m, 8H), 0.78 (t, J=12.4 Hz, 1H); MS: MS m/z 956.5 (M$^+$+1).

Preparation of Compound 5236 and Compound 5237

Compound 5236

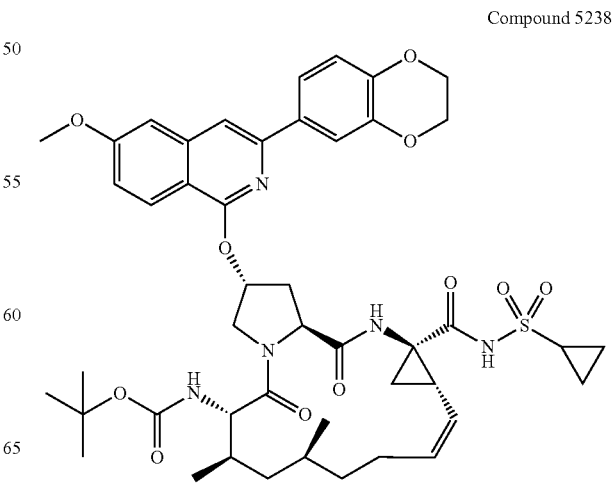

-continued

Compound 5237

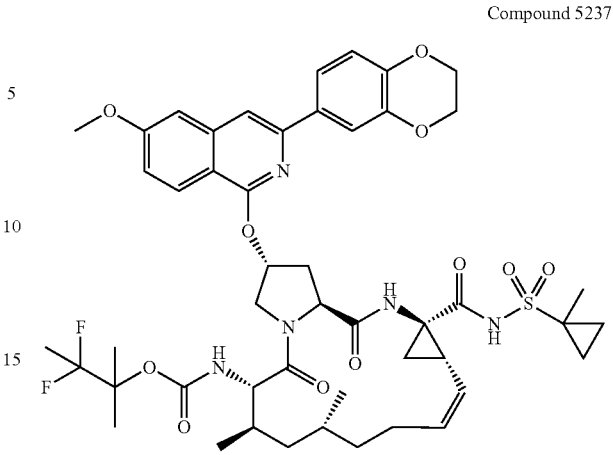

Compounds 5236 and 5237 were prepared using the intermediates described herein and by following the general procedure described for the synthesis of Compound 3117:

Compound 5236: 3,3-difluoro-2-methylbutan-2-yl ((2R,6S,7R,9S,13aS,14aR,16aS,Z)-2-((3-(2,3-dihydrobenzo[b][1,4]dioxin-6-yl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 952.5 (M$^+$+1).

Compound 5237: 3,3-difluoro-2-methylbutan-2-yl ((2R,6S,7R,9R,13aS,14aR,16aS,Z)-2-((3-(2,3-dihydrobenzo[b][1,4]dioxin-6-yl)-6-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.06 (br. s., 1H), 9.07 (br. s., 1H), 8.00 (d, J=9.2 Hz, 1H), 7.83 (s, 1H), 7.73-7.61 (m, 3H), 7.34 (d, J=2.1 Hz, 1H), 7.08 (dd, J=9.2, 2.4 Hz, 1H), 7.00 (d, J=8.5 Hz, 1H), 5.98 (br. s., 1H), 5.59-5.49 (m, 1H), 5.06-4.95 (m, 1H), 4.61-4.46 (m, 2H), 4.32 (s, 4H), 3.98 (dd, J=11.0, 3.1 Hz, 1H), 3.91 (s, 3H), 3.75 (dd, J=10.4, 8.5 Hz, 1H), 2.80-2.67 (m, 2H), 2.42-2.29 (m, 2H), 1.99-1.80 (m, 2H), 1.77-1.67 (m, 1H), 1.66-1.05 (m, 19H), 1.00-0.84 (m, 8H), 0.78 (t, J=12.4 Hz, 1H); MS: MS m/z 952.5 (M$^+$+1).

Preparation of Compound 5238 and Compound 5239

Compound 5238

-continued

Compound 5239

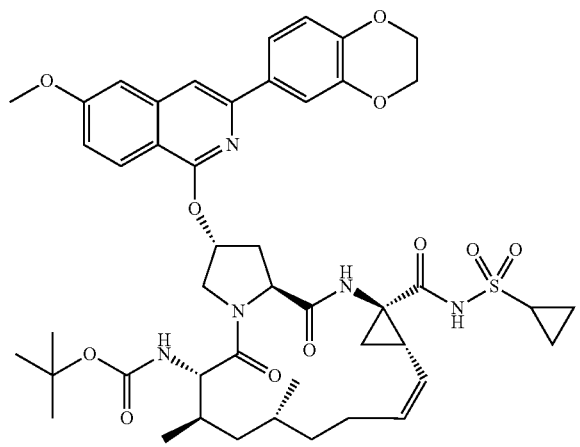

Compounds 5238 and 5239 were prepared using the intermediates described herein and by following the general procedure described for the synthesis of Compound 3117:

Compound 5238: tert-butyl ((2R,6S,7R,9S,13aS,14aR,16aS,Z)-14a-((cyclopropylsulfonyl)carbamoyl)-2-((3-(2,3-dihydrobenzo[b][1,4]dioxin-6-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 888.5 (M$^+$+1).

Compound 5239: tert-butyl ((2R,6S,7R,9R,13aS,14aR,16aS,Z)-14a-((cyclopropylsulfonyl)carbamoyl)-2-((3-(2,3-dihydrobenzo[b][1,4]dioxin-6-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.21 (s, 1H), 8.92 (br. s., 1H), 8.03 (d, J=9.2 Hz, 1H), 7.82 (s, 1H), 7.70 (d, J=1.5 Hz, 1H), 7.67 (dd, J=8.4, 2.0 Hz, 1H), 7.33 (d, J=2.1 Hz, 1H), 7.21 (d, J=7.9 Hz, 1H), 7.05 (dd, J=9.2, 2.1 Hz, 1H), 7.00 (d, J=8.2 Hz, 1H), 5.94 (br. s., 1H), 5.58-5.47 (m, 1H), 5.07 (t, J=9.6 Hz, 1H), 4.61 (d, J=11.6 Hz, 1H), 4.49-4.39 (m, 1H), 4.32 (s, 4H), 3.95 (dd, J=11.6, 3.1 Hz, 1H), 3.91 (s, 3H), 3.75 (dd, J=10.4, 8.5 Hz, 1H), 2.98-2.88 (m, 1H), 2.79-2.66 (m, 2H), 2.40-2.23 (m, 2H), 2.01-1.68 (m, 3H), 1.65-1.51 (m, 2H), 1.49-1.32 (m, 2H), 1.30-0.96 (m, 14H), 0.95 (d, J=7.0 Hz, 3H), 0.90 (d, J=6.4 Hz, 3H), 0.75 (t, J=12.2 Hz, 1H); MS: MS m/z 888.5 (M$^+$+1).

Preparation of Compound 5240 and Compound 5241

Compound 5240

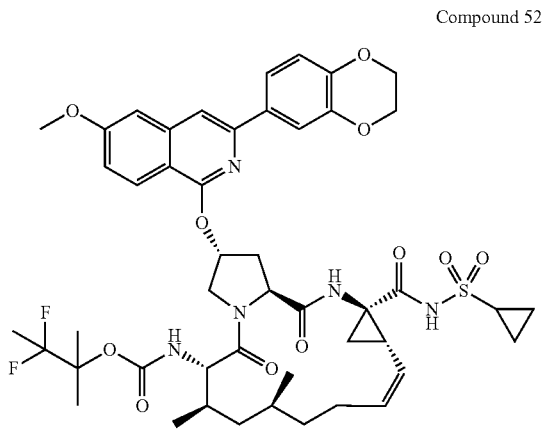

-continued

Compound 5241

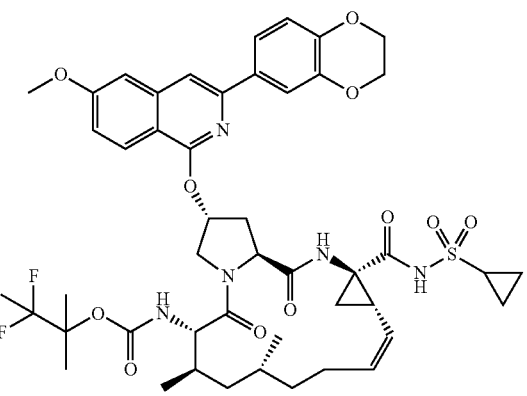

Compounds 5240 and 5241 were prepared using the intermediates described herein and by following the general procedure described for the synthesis of Compound 3117:

Compound 5240: 3,3-difluoro-2-methylbutan-2-yl ((2R,6S,7R,9S,13aS,14aR,16aS,Z)-14a-((cyclopropylsulfonyl)carbamoyl)-2-((3-(2,3-dihydrobenzo[b][1,4]dioxin-6-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 938.5 (M$^+$+1).

Compound 5241: 3,3-difluoro-2-methylbutan-2-yl ((2R,6S,7R,9R,13aS,14aR,16aS,Z)-14a-((cyclopropylsulfonyl)carbamoyl)-2-((3-(2,3-dihydrobenzo[b][1,4]dioxin-6-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.22 (br. s., 1H), 8.93 (br. s., 1H), 8.00 (d, J=8.9 Hz, 1H), 7.83 (s, 1H), 7.70 (d, J=1.5 Hz, 1H), 7.67 (dd, J=8.4, 2.0 Hz, 1H), 7.64 (d, J=6.4 Hz, 1H), 7.33 (d, J=2.1 Hz, 1H), 7.07 (dd, J=9.0, 2.3 Hz, 1H), 7.00 (d, J=8.2 Hz, 1H), 5.95 (br. s., 1H), 5.59-5.47 (m, 1H), 5.17-5.02 (m, 1H), 4.58-4.50 (m, 1H), 4.50-4.42 (m, 1H), 4.32 (s, 4H), 3.96 (dd, J=11.1, 2.9 Hz, 1H), 3.91 (s, 3H), 3.75 (dd, J=10.5, 8.4 Hz, 1H), 2.98-2.85 (m, 1H), 2.79-2.63 (m, 2H), 2.41-2.24 (m, 2H), 1.99-1.69 (m, 3H), 1.66-0.97 (m, 18H), 0.95 (d, J=7.0 Hz, 3H), 0.90 (d, J=6.1 Hz, 3H), 0.77 (t, J=12.4 Hz, 1H); MS: MS m/z 938.5 (M$^+$+1).

Preparation of Compound 5242 and Compound 5243

Compound 5242

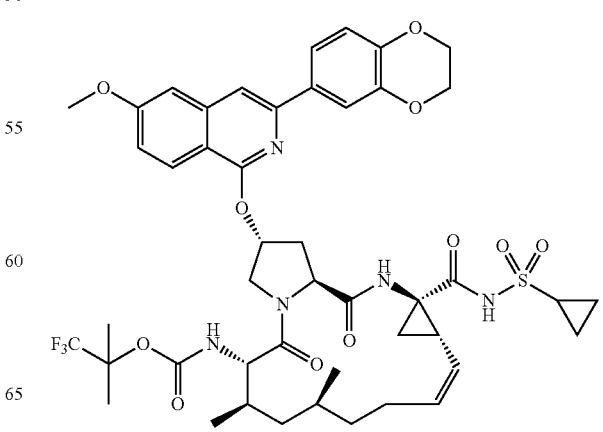

-continued

Compound 5243

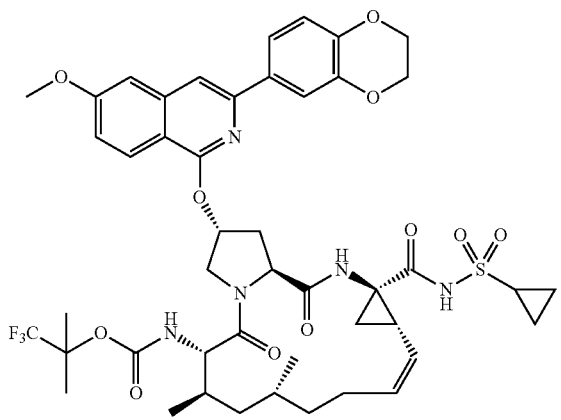

Compounds 5242 and 5243 were prepared using the intermediates described herein and by following the general procedure described for the synthesis of Compound 3117:

Compound 5242: 1,1,1-trifluoro-2-methylpropan-2-yl ((2R,6S,7R,9S,13aS,14aR,16aS,Z)-14a-((cyclopropylsulfonyl)carbamoyl)-2-((3-(2,3-dihydrobenzo[b][1,4]dioxin-6-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 942.1 (M$^+$+1).

Compound 5243: 1,1,1-trifluoro-2-methylpropan-2-yl ((2R,6S,7R,9R,13aS,14aR,16aS,Z)-14a-((cyclopropylsulfonyl)carbamoyl)-2-((3-(2,3-dihydrobenzo[b][1,4]dioxin-6-yl)-6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.21 (br. s., 1H), 8.96 (br. s., 1H), 8.00 (d, J=8.9 Hz, 1H), 7.90-7.79 (m, 2H), 7.70 (d, J=1.8 Hz, 1H), 7.67 (dd, J=8.5, 1.8 Hz, 1H), 7.34 (d, J=2.1 Hz, 1H), 7.09 (dd, J=9.0, 2.3 Hz, 1H), 7.00 (d, J=8.2 Hz, 1H), 5.96 (br. s., 1H), 5.59-5.49 (m, 1H), 5.18-5.02 (m, 1H), 4.61-4.44 (m, 2H), 4.32 (s, 4H), 3.95 (dd, J=11.1, 3.2 Hz, 1H), 3.92 (s, 3H), 3.74 (dd, J=10.4, 8.2 Hz, 1H), 2.98-2.87 (m, 1H), 2.77-2.63 (m, 2H), 2.42-2.25 (m, 2H), 1.97-1.81 (m, 2H), 1.78-1.68 (m, 1H), 1.64-0.85 (m, 21H), 0.76 (t, J=12.4 Hz, 1H); MS: MS m/z 942.0 (M$^+$+1).

Preparation of Compound 5244 and Compound 5245

Compound 5244

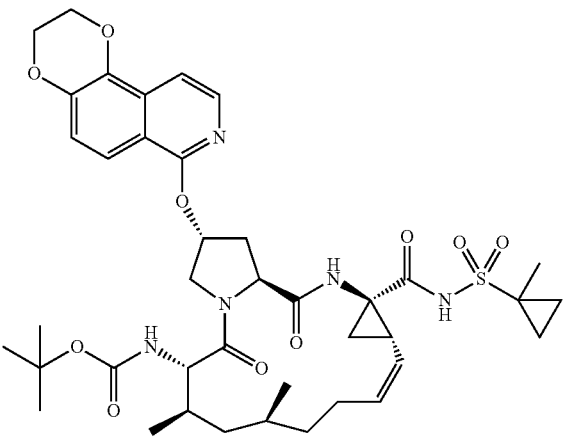

-continued

Compound 5245

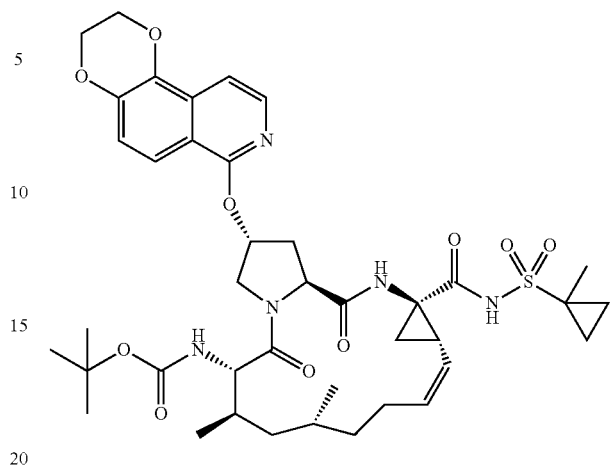

Compounds 5244 and 5245 were prepared using the intermediates described herein and by following the general procedure described for the synthesis of Compound 3117:

Compound 5244: tert-butyl ((2R,6S,7R,9S,13aS,14aR,16aS,Z)-2-((2,3-dihydro-[1,4]dioxino[2,3-f]isoquinolin-7-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 796.7 (M$^+$+1).

Compound 5245: tert-butyl ((2R,6S,7R,9R,13aS,14aR,16aS,Z)-2-((2,3-dihydro-[1,4]dioxino[2,3-f]isoquinolin-7-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.04 (br. s., 1H), 9.10 (br. s., 1H), 7.96 (d, J=6.1 Hz, 1H), 7.66 (d, J=8.9 Hz, 1H), 7.37 (d, J=6.1 Hz, 1H), 7.16 (d, J=7.6 Hz, 1H), 7.08 (d, J=8.9 Hz, 1H), 5.81 (br. s., 1H), 5.58-5.46 (m, 1H), 5.08-4.92 (m, 1H), 4.58 (d, J=10.4 Hz, 1H), 4.50-4.34 (m, 5H), 3.90 (dd, J=11.1, 3.2 Hz, 1H), 3.70 (dd, J=10.5, 8.7 Hz, 1H), 2.74-2.54 (m, 2H), 2.40-2.24 (m, 2H), 1.96-1.03 (m, 24H), 0.93 (d, J=7.0 Hz, 3H), 0.88 (d, J=6.4 Hz, 3H), 0.72 (t, J=11.7 Hz, 1H); MS: MS m/z 796.7 (M$^+$+1).

Preparation of Compound 5246 and Compound 5247

Compound 5246

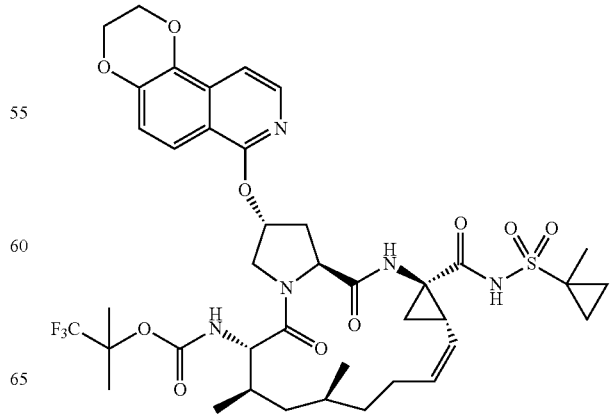

Compound 5247

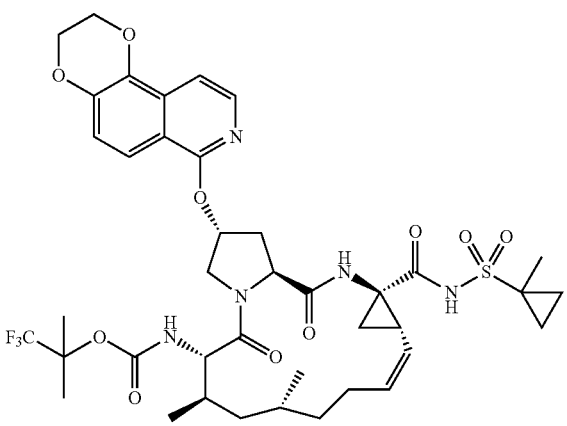

Compound 5249

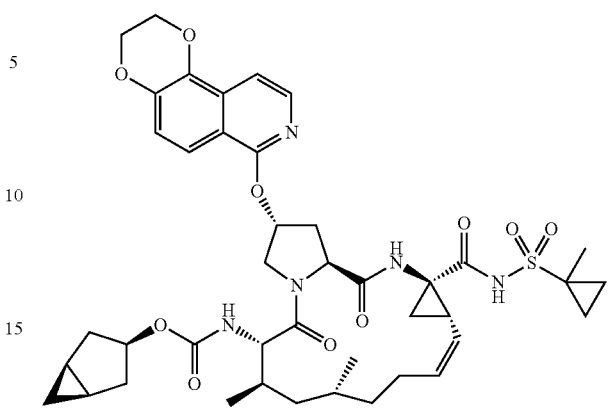

Compounds 5246 and 5247 were prepared by one of the general procedures described above:

Compound 5246: 1,1,1-trifluoro-2-methylpropan-2-yl ((2R,6S,7R,9S,13aS,14aR,16aS,Z)-2-((2,3-dihydro-[1,4]dioxino[2,3-f]isoquinolin-7-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 850.7 (M$^+$+1).

Compound 5247: 1,1,1-trifluoro-2-methylpropan-2-yl ((2R,6S,7R,9R,13aS,14aR,16aS,Z)-2-((2,3-dihydro-[1,4]dioxino[2,3-f]isoquinolin-7-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.04 (br. s., 1H), 9.15 (br. s., 1H), 7.97 (d, J=6.1 Hz, 1H), 7.82 (d, J=7.9 Hz, 1H), 7.63 (d, J=8.9 Hz, 1H), 7.38 (d, J=6.1 Hz, 1H), 7.13 (d, J=8.9 Hz, 1H), 5.82 (br. s., 1H), 5.59-5.48 (m, 1H), 5.04-4.93 (m, 1H), 4.59-4.48 (m, 2H), 4.48-4.32 (m, 4H), 3.91 (dd, J=11.1, 3.2 Hz, 1H), 3.69 (dd, J=10.5, 8.1 Hz, 1H), 2.72-2.57 (m, 2H), 2.40-2.25 (m, 2H), 1.95-1.78 (m, 2H), 1.76-1.04 (m, 17H), 0.98-0.84 (m, 8H), 0.75 (t, J=11.9 Hz, 1H); MS: MS m/z 850.7 (M$^+$+1).

Preparation of Compound 5248 and Compound 5249

Compounds 5248 and 5249 were prepared using the intermediates described herein and by following the general procedure described for the synthesis of Compound 3117:

Compound 5248: (1R,3r,5S)-bicyclo[3.1.0]hexan-3-yl ((2R,6S,7R,9S,13aS,14aR,16aS,Z)-2-((2,3-dihydro-[1,4]dioxino[2,3-f]isoquinolin-7-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 820.7 (M$^+$+1).

Compound 5249: (1R,3r,5S)-bicyclo[3.1.0]hexan-3-yl ((2R,6S,7R,9R,13aS,14aR,16aS,Z)-2-((2,3-dihydro-[1,4]dioxino[2,3-f]isoquinolin-7-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.04 (br. s., 1H), 9.07 (br. s., 1H), 7.97 (d, J=5.8 Hz, 1H), 7.64 (d, J=9.2 Hz, 1H), 7.42-7.35 (m, 2H), 7.15 (d, J=9.2 Hz, 1H), 5.83 (br. s., 1H), 5.60-5.44 (m, 1H), 5.12-4.92 (m, 1H), 4.62 (t, J=6.6 Hz, 1H), 4.52-4.32 (m, 5H), 3.93 (dd, J=11.1, 3.2 Hz, 1H), 3.75 (dd, J=10.5, 9.0 Hz, 1H), 2.76-2.54 (m, 2H), 2.35-2.22 (m, 2H), 2.03-1.07 (m, 20H), 0.99-0.82 (m, 8H), 0.72 (t, J=12.4 Hz, 1H), 0.36 (d, J=4.9 Hz, 2H); MS: MS m/z 820.7 (M$^+$+1).

Preparation of Compound 5250 and Compound 5251

Compound 5248

Compound 5250

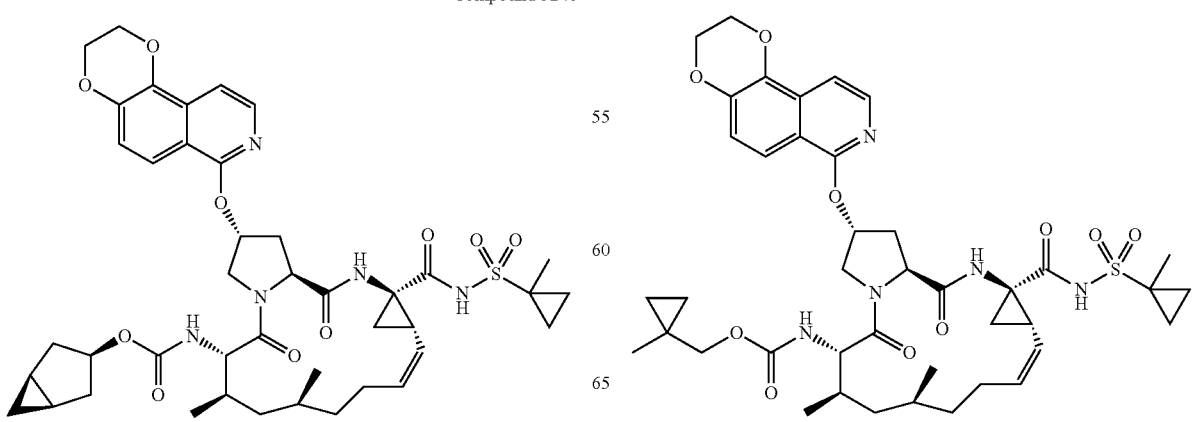

Compound 5251

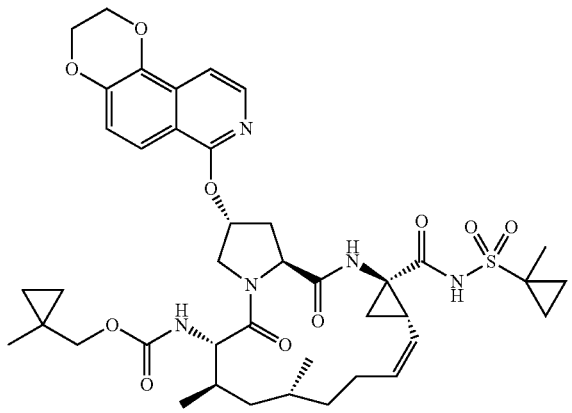

Compound 5253

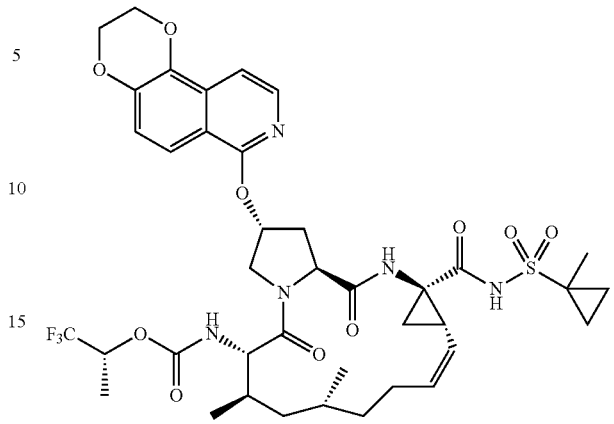

Compounds 5250 and 5251 were prepared using the intermediates described herein and by following the general procedure described for the synthesis of Compound 3117:

Compound 5250: (1-methylcyclopropyl)methyl ((2R,6S,7R,9S,13aS,14aR,16aS,Z)-2-((2,3-dihydro-[1,4]dioxino[2,3-f]isoquinolin-7-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 808.7 (M$^+$+1).

Compound 5251: (1-methylcyclopropyl)methyl ((2R,6S,7R,9R,13aS,14aR,16aS,Z)-2-((2,3-dihydro-[1,4]dioxino[2,3-f]isoquinolin-7-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.04 (br. s., 1H), 9.09 (br. s., 1H), 7.96 (d, J=6.1 Hz, 1H), 7.63 (d, J=9.2 Hz, 1H), 7.50 (d, J=7.3 Hz, 1H), 7.38 (d, J=5.8 Hz, 1H), 7.12 (d, J=8.9 Hz, 1H), 5.83 (br. s., 1H), 5.58-5.48 (m, 1H), 5.06-4.94 (m, 1H), 4.58-4.35 (m, 6H), 3.94 (dd, J=11.1, 3.2 Hz, 1H), 3.76 (dd, J=10.7, 8.5 Hz, 1H), 3.46-3.39 (m, 2H), 2.75-2.54 (m, 2H), 2.39-2.23 (m, 2H), 1.97-1.79 (m, 2H), 1.74-0.82 (m, 22H), 0.74 (t, J=12.3 Hz, 1H), 0.31-0.25 (m, 1H), 0.24-0.15 (m, 3H); MS: MS m/z 808.7 (M$^+$+1).

Preparation of Compound 5252 and Compound 5253

Compounds 5252 and 5253 were prepared using the intermediates described herein and by following the general procedure described for the synthesis of Compound 3117:

Compound 5252: (R)-1,1,1-trifluoropropan-2-yl ((2R,6S,7R,9S,13aS,14aR,16aS,Z)-2-((2,3-dihydro-[1,4]dioxino[2,3-f]isoquinolin-7-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 836.7 (M$^+$+1).

Compound 5253: (R)-1,1,1-trifluoropropan-2-yl ((2R,6S,7R,9R,13aS,14aR,16aS,Z)-2-((2,3-dihydro-[1,4]dioxino[2,3-f]isoquinolin-7-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.03 (br. s., 1H), 9.10 (br. s., 1H), 8.08 (d, J=7.9 Hz, 1H), 7.97 (d, J=5.8 Hz, 1H), 7.60 (d, J=9.2 Hz, 1H), 7.39 (d, J=6.1 Hz, 1H), 7.06 (d, J=8.9 Hz, 1H), 5.83 (br. s., 1H), 5.61-5.46 (m, 1H), 5.09-4.93 (m, 1H), 4.77-4.67 (m, 1H), 4.58-4.32 (m, 6H), 3.94 (dd, J=11.1, 3.2 Hz, 1H), 3.77 (dd, J=10.8, 8.1 Hz, 1H), 2.72-2.56 (m, 2H), 2.36-2.25 (m, 2H), 1.96-1.81 (m, 2H), 1.74-0.85 (m, 22H), 0.77 (t, J=12.4 Hz, 1H); MS: MS m/z 836.7 (M$^+$+1).

Preparation of Compound 5254 and Compound 5255

Compound 5252

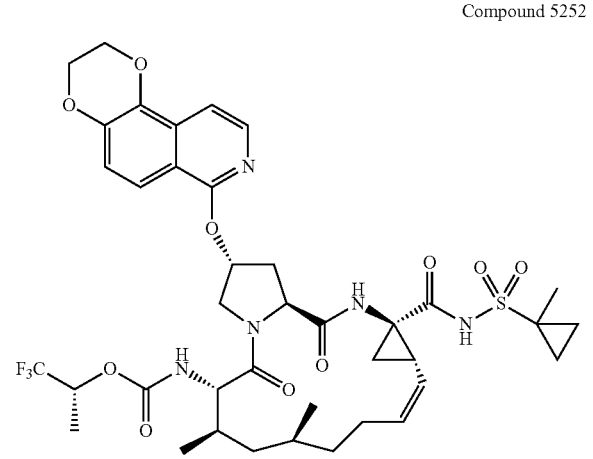 [SMILES: CCC(C)(OC(=O)N[C@@H]1C(=O)N2C[C@H](Oc3nccc4c5c(ccc34)OCCO5)C[C@H]2C(=O)N[C@]2(C(=O)NS(=O)(=O)C3CC3)C[C@H]2/C=C\CC[C@@H](C)C[C@H]1C)C(F)(F)F]

Compound 5254

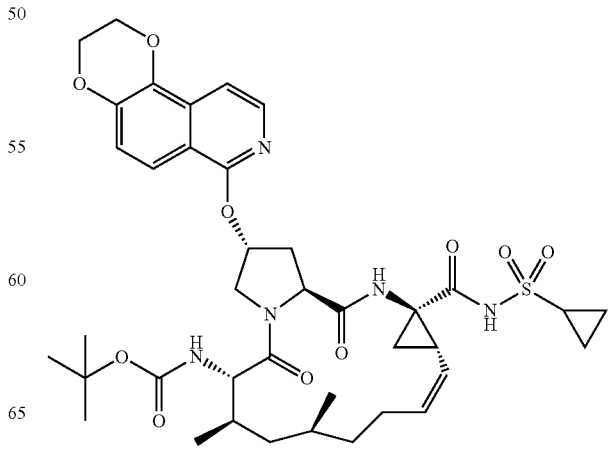

Compound 5255

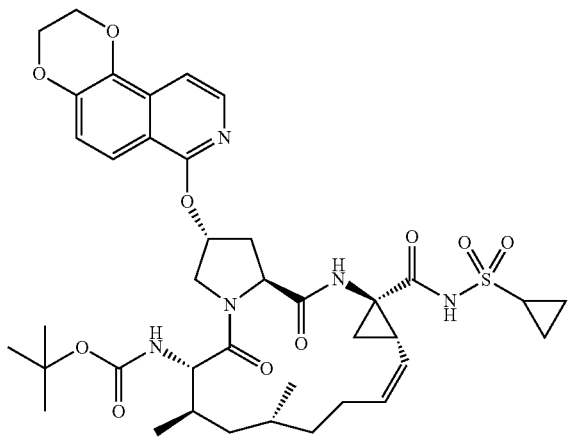

Compounds 5254 and 5255 were prepared using the intermediates described herein and by following the general procedure described for the synthesis of Compound 3117:

Compound 5254: tert-butyl ((2R,6S,7R,9S,13aS,14aR,16aS,Z)-14a-((cyclopropylsulfonyl)carbamoyl)-2-((2,3-dihydro-[1,4]dioxino[2,3-f]isoquinolin-7-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 796.7 (M$^+$+1).

Compound 5255: tert-butyl ((2R,6S,7R,9R,13aS,14aR,16aS,Z)-14a-((cyclopropylsulfonyl)carbamoyl)-2-((2,3-dihydro-[1,4]dioxino[2,3-f]isoquinolin-7-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.04 (br. s., 1H), 9.10 (br. s., 1H), 7.96 (d, J=6.1 Hz, 1H), 7.66 (d, J=8.9 Hz, 1H), 7.37 (d, J=6.1 Hz, 1H), 7.16 (d, J=7.6 Hz, 1H), 7.08 (d, J=8.9 Hz, 1H), 5.81 (br. s., 1H), 5.58-5.46 (m, 1H), 5.08-4.92 (m, 1H), 4.58 (d, J=10.4 Hz, 1H), 4.50-4.34 (m, 5H), 3.90 (dd, J=11.1, 3.2 Hz, 1H), 3.70 (dd, J=10.5, 8.7 Hz, 1H), 2.74-2.54 (m, 2H), 2.40-2.24 (m, 2H), 1.96-1.03 (m, 24H), 0.93 (d, J=7.0 Hz, 3H), 0.88 (d, J=6.4 Hz, 3H), 0.72 (t, J=11.7 Hz, 1H); MS: MS m/z 796.7 (M$^+$+1).

Preparation of Compound 5256 and Compound 5257

Compound 5256

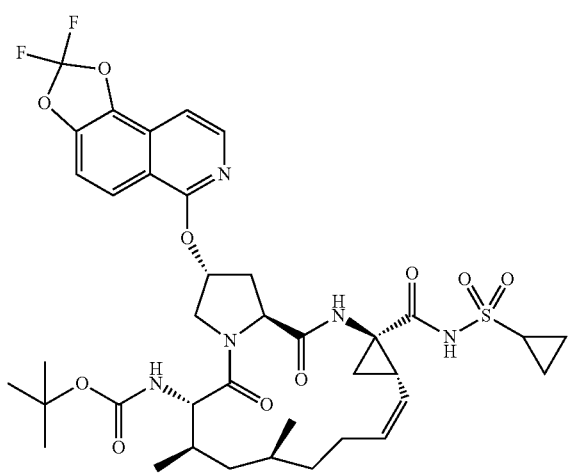

Compound 5257

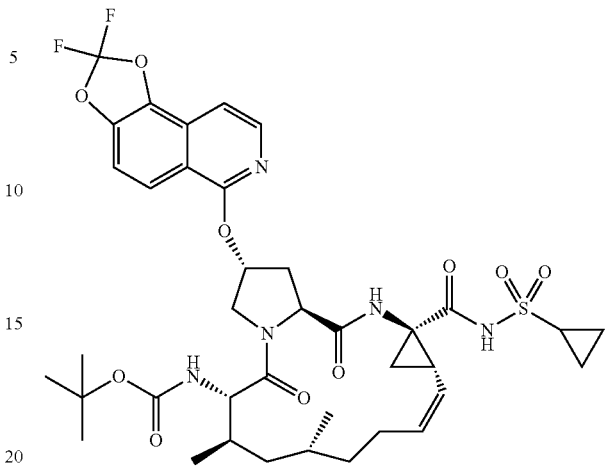

Compounds 5256 and 5257 were prepared using the intermediates described herein and by following the general procedure described for the synthesis of Compound 3117:

Compound 5256: tert-butyl ((2R,6S,7R,9S,13aS,14aR,16aS,Z)-14a-((cyclopropylsulfonyl)carbamoyl)-2-((2,2-difluoro-[1,3]dioxolo[4,5-f]isoquinolin-6-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 804.5 (M$^+$+1).

Compound 5257: tert-butyl ((2R,6S,7R,9R,13aS,14aR,16aS,Z)-14a-((cyclopropylsulfonyl)carbamoyl)-2-((2,2-difluoro-[1,3]dioxolo[4,5-f]isoquinolin-6-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.20 (br. s., 1H), 9.03 (br. s., 1H), 8.17 (d, J=5.8 Hz, 1H), 8.06 (d, J=8.9 Hz, 1H), 7.71 (d, J=9.2 Hz, 1H), 7.41 (d, J=5.8 Hz, 1H), 7.15 (d, J=7.3 Hz, 1H), 5.85 (br. s., 1H), 5.61-5.46 (m, 1H), 5.10-4.98 (m, 1H), 4.65 (d, J=11.6 Hz, 1H), 4.58-4.45 (m, 1H), 3.88 (dd, J=11.6, 3.1 Hz, 1H), 3.62 (dd, J=10.4, 8.2 Hz, 1H), 2.98-2.88 (m, 1H), 2.72-2.60 (m, 2H), 2.40-2.24 (m, 2H), 1.95-1.85 (m, 1H), 1.84-1.75 (m, 1H), 1.73-1.65 (m, 1H), 1.64-1.52 (m, 2H), 1.49-1.31 (m, 2H), 1.23-0.83 (m, 20H), 0.72 (t, J=12.7 Hz, 1H); MS: MS m/z 804.6 (M$^+$+1).

Preparation of Compound 5258 and Compound 5259

Compound 5258

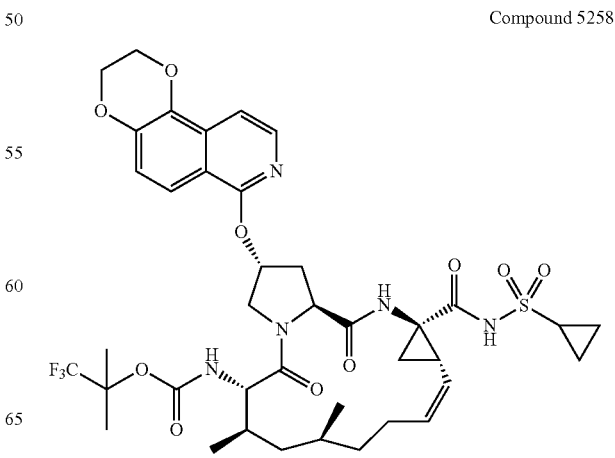

-continued

Compound 5259

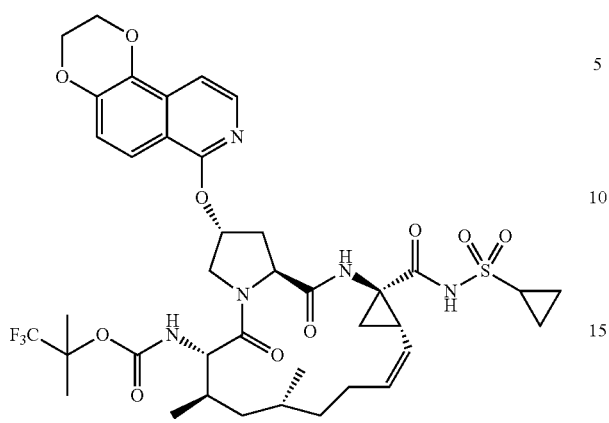

Compounds 5258 and 5259 were prepared using the intermediates described herein and by following the general procedure described for the synthesis of Compound 3117:

Compound 5258: 1,1,1-trifluoro-2-methylpropan-2-yl ((2R,6S,7R,9S,13aS,14aR,16aS,Z)-14a-((cyclopropylsulfonyl)carbamoyl)-2-((2,3-dihydro-[1,4]dioxino[2,3-f]isoquinolin-7-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 836.6 (M$^+$+1).

Compound 5259: 1,1,1-trifluoro-2-methylpropan-2-yl ((2R,6S,7R,9R,13aS,14aR,16aS,Z)-14a-((cyclopropylsulfonyl)carbamoyl)-2-((2,3-dihydro-[1,4]dioxino[2,3-f]isoquinolin-7-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.18 (br. s., 1H), 9.01 (br. s., 1H), 7.98 (d, J=6.1 Hz, 1H), 7.82 (d, J=7.6 Hz, 1H), 7.63 (d, J=8.9 Hz, 1H), 7.38 (d, J=5.8 Hz, 1H), 7.12 (d, J=8.9 Hz, 1H), 5.81 (br. s., 1H), 5.59-5.48 (m, 1H), 5.11-5.00 (m, 1H), 4.61-4.30 (m, 6H), 3.89 (dd, J=11.3, 3.1 Hz, 1H), 3.69 (dd, J=10.7, 8.2 Hz, 1H), 2.95-2.87 (m, 1H), 2.71-2.57 (m, 2H), 2.31 (ddd, J=13.7, 10.2, 3.8 Hz, 2H), 1.95-1.79 (m, 2H), 1.75-1.67 (m, 1H), 1.65-1.53 (m, 2H), 1.47-0.84 (m, 19H), 0.74 (t, J=12.4 Hz, 1H); MS: MS m/z 836.6 (M$^+$+1).

Preparation of Compound 5260

Compound 5260

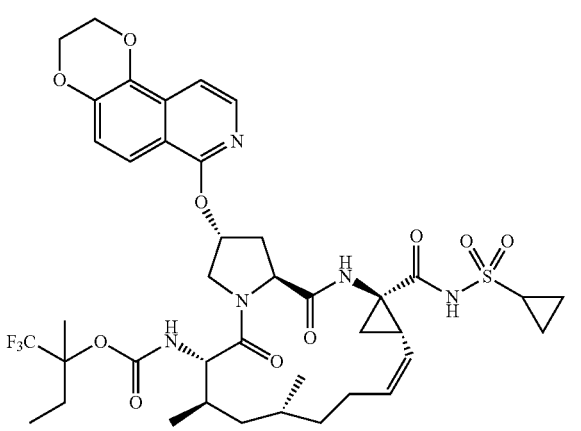

Compound 5260 was prepared using the intermediates described herein and by following the general procedure described for the synthesis of Compound 3117:

Compound 5260: 1,1,1-trifluoro-2-methylbutan-2-yl ((2R,6S,7R,9R,13aS,14aR,16aS,Z)-14a-((cyclopropylsulfonyl)carbamoyl)-2-((2,3-dihydro-[1,4]dioxino[2,3-f]isoquinolin-7-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 850.7 (M$^+$+1).

Preparation of Compound 5261 and Compound 5262

Compound 5261

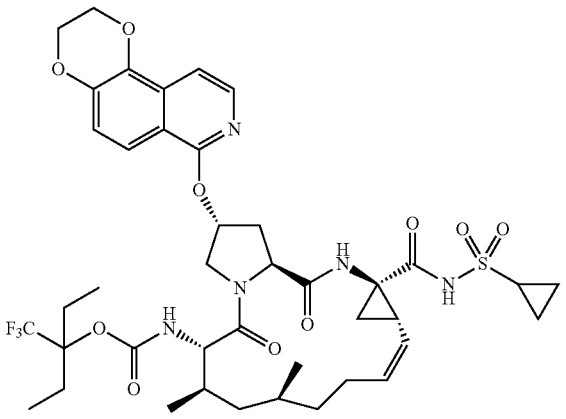

Compound 5262

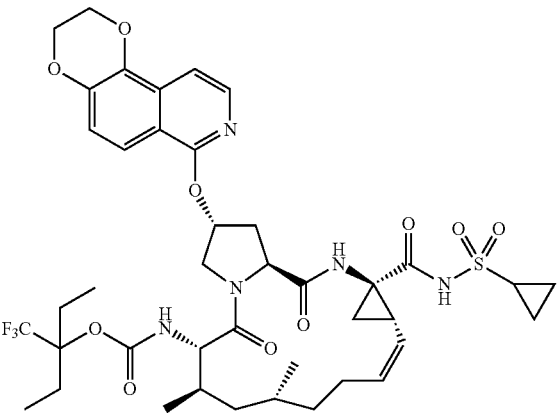

Compounds 5261 and 5262 were prepared using the intermediates described herein and by following the general procedure described for the synthesis of Compound 3117:

Compound 5261: 3-(trifluoromethyl)pentan-3-yl ((2R,6S,7R,9S,13aS,14aR,16aS,Z)-14a-((cyclopropylsulfonyl)carbamoyl)-2-((2,3-dihydro-[1,4]dioxino[2,3-f]isoquinolin-7-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 864.7 (M$^+$+1).

Compound 5262: 3-(trifluoromethyl)pentan-3-yl ((2R,6S,7R,9R,13aS,14aR,16aS,Z)-14a-((cyclopropylsulfonyl)carbamoyl)-2-((2,3-dihydro-[1,4]dioxino[2,3-f]isoquinolin-7-yl)oxy)-7,9-dimethyl-5,16-dioxo-1,2,3,5,6,7,8,9,10,11,13a,14,14a,15,16,16a-hexadecahydrocyclopropa[e]pyrrolo[1,2- a][1,4]diazacyclopentadecin-6-yl)carbamate; ¹H NMR (500 MHz, DMSO-d₆) δ 11.18 (br. s., 1H), 9.03 (br. s., 1H), 7.97 (d, J=6.1 Hz, 1H), 7.86 (d, J=7.9 Hz, 1H), 7.59 (d, J=9.2 Hz, 1H), 7.38 (d, J=6.1 Hz, 1H), 7.12 (d, J=8.9 Hz, 1H), 5.80 (br. s., 1H), 5.62-5.47 (m, 1H), 5.15-4.98 (m, 1H), 4.58-4.34 (m, 6H), 3.93 (dd, J=11.1, 3.4 Hz, 1H), 3.74 (dd, J=10.7, 8.5 Hz, 1H), 2.96-2.87 (m, 1H), 2.73-2.57 (m, 2H), 2.37-2.25 (m, 2H), 1.95-0.86 (m, 22H), 0.77 (t, J=7.5 Hz, 4H), 0.60 (t, J=7.5 Hz, 3H); MS: MS m/z 864.6 (M⁺+1).

Preparation of Compound 5263 and Compound 5264

(br. s., 1H), 7.97 (d, J=6.1 Hz, 1H), 7.64 (d, J=9.2 Hz, 1H), 7.43-7.35 (m, 2H), 7.14 (d, J=8.9 Hz, 1H), 5.82 (br. s., 1H), 5.59-5.45 (m, 1H), 5.18-4.99 (m, 1H), 4.64 (t, J=6.7 Hz, 1H), 4.52-4.33 (m, 6H), 3.91 (dd, J=11.3, 3.4 Hz, 1H), 3.75 (dd, J=10.5, 9.0 Hz, 1H), 2.96-2.85 (m, 1H), 2.72-2.54 (m, 2H), 2.37-2.21 (m, 2H), 2.01-1.89 (m, 2H), 1.87-1.76 (m, 2H), 1.75-0.82 (m, 20H), 0.71 (t, J=12.4 Hz, 1H), 0.40-0.31 (m, 2H); MS: MS m/z 806.7 (M⁺+1).

Preparation of Compound 5265 and Compound 5266

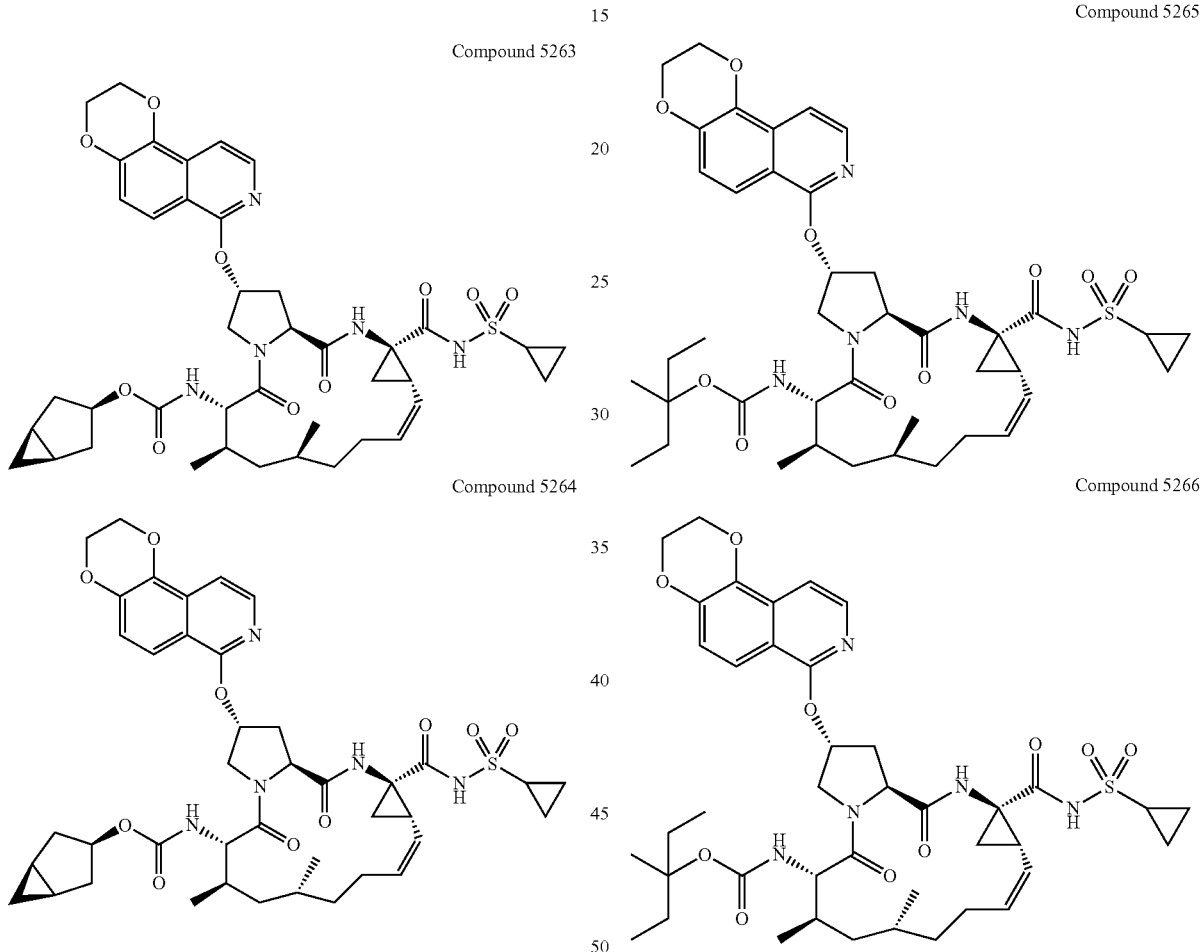

Compounds 5263 and 5264 were prepared using the intermediates described herein and by following the general procedure described for the synthesis of Compound 3117:

Compound 5263: (1R,3r,5S)-bicyclo[3.1.0]hexan-3-yl ((2R,6S,7R,9S,13aS,14aR,16aS,Z)-14a-((cyclopropylsulfonyl)carbamoyl)-2-((2,3-dihydro-[1,4]dioxino[2,3-f]isoquinolin-7-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 806.7 (M⁺+1).

Compound 5264: (1R,3r,5S)-bicyclo[3.1.0]hexan-3-yl ((2R,6S,7R,9R,13aS,14aR,16aS,Z)-14a-((cyclopropylsulfonyl)carbamoyl)-2-((2,3-dihydro-[1,4]dioxino[2,3-f]isoquinolin-7-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; ¹H NMR (500 MHz, DMSO-d₆) δ 11.18 (br. s., 1H), 8.95

Compounds 5265 and 5266 were prepared using the intermediates described herein and by following the general procedure described for the synthesis of Compound 3117:

Compound 5265: 3-methylpentan-3-yl((2R,6S,7R,9S,13aS,14aR,16aS,Z)-14a-((cyclopropylsulfonyl)carbamoyl)-2-((2,3-dihydro-[1,4]dioxino[2,3-f]isoquinolin-7-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 810.7 (M⁺+1).

Compound 5266: 3-methylpentan-3-yl ((2R,6S,7R,9R,13aS,14aR,16aS,Z)-14a-((cyclopropylsulfonyl)carbamoyl)-2-((2,3-dihydro-[1,4]dioxino[2,3-f]isoquinolin-7-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; ¹H NMR (500 MHz, DMSO-d$_6$) δ 11.19 (br. s., 1H), 8.99 (br. s., 1H), 7.96 (d, J=6.1 Hz, 1H), 7.63 (d, J=9.2 Hz, 1H), 7.38 (d, J=6.1 Hz, 1H), 7.17 (d, J=8.2 Hz, 1H), 7.09 (d, J=8.9 Hz, 1H), 5.80 (br. s., 1H), 5.59-5.47 (m, 1H), 5.13-4.97 (m, 1H), 4.54 (d, J=11.0 Hz, 1H), 4.48-4.33 (m, 5H), 3.90 (dd, J=11.3, 3.4 Hz, 1H), 3.72 (dd, J=10.4, 8.9 Hz, 1H), 2.94-2.85 (m, 1H), 2.73-2.55 (m, 2H), 2.37-2.23 (m, 2H), 1.97-1.78 (m, 2H), 1.76-1.65 (m, 1H), 1.65-0.83 (m, 22H), 0.78-0.59 (m, 7H); MS: MS m/z 810.7 (M$^+$+1).

Preparation of Compound 5267 and Compound 5268

11,13a,14,14a,15,16,16a-hexadecahydrocyclopropa[e]pyrrolo[1,2-a][1,4]diazacyclopentadecin-6-yl)carbamate;
$^1$H NMR (500 MHz, DMSO-d$_6$) δ 11.19 (br. s., 1H), 9.05 (br. s., 1H), 8.18 (d, J=5.8 Hz, 1H), 8.05 (d, J=9.2 Hz, 1H), 7.81 (d, J=7.3 Hz, 1H), 7.76 (d, J=9.2 Hz, 1H), 7.42 (d, J=5.8 Hz, 1H), 5.85 (br. s., 1H), 5.60-5.46 (m, 1H), 5.13-4.99 (m, 1H), 4.63-4.48 (m, 2H), 3.89 (dd, J=11.3, 3.1 Hz, 1H), 3.64 (dd, J=10.5, 7.8 Hz, 1H), 2.91 (s, 1H), 2.71-2.58 (m, 2H), 2.43-2.21 (m, 2H), 1.95-0.90 (m, 21H), 0.88 (d, J=6.1 Hz, 3H), 0.74 (t, J=12.1 Hz, 1H); MS: MS m/z 858.7 (M$^+$+1).

Preparation of Compound 5269 and Compound 5270

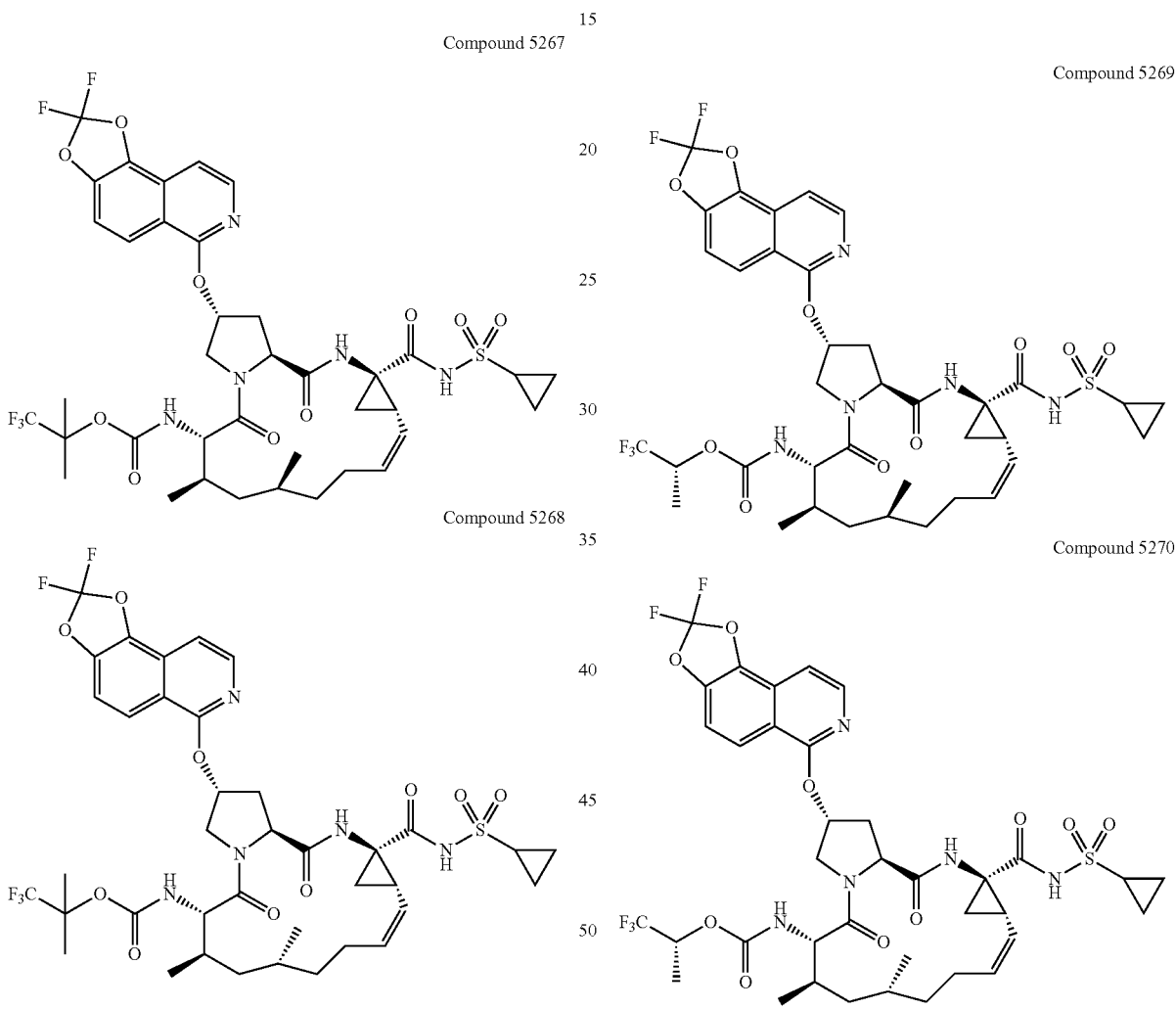

Compounds 5267 and 5268 were prepared using the intermediates described herein and by following the general procedure described for the synthesis of Compound 3117:

Compound 5267: 1,1,1-trifluoro-2-methylpropan-2-yl ((2R,6S,7R,9S,13aS,14aR,16aS,Z)-14a-((cyclopropylsulfonyl)carbamoyl)-2-((2,2-difluoro-[1,3]dioxolo[4,5-f]isoquinolin-6-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 858.7 (M$^+$+1).

Compound 5268: 1,1,1-trifluoro-2-methylpropan-2-yl ((2R,6S,7R,9R,13aS,14aR,16aS,Z)-14a-((cyclopropylsulfonyl)carbamoyl)-2-((2,2-difluoro-[1,3]dioxolo[4,5-f]isoquinolin-6-yl)oxy)-7,9-dimethyl-5,16-dioxo-1,2,3,5,6,7,8,9,10, Compounds 5269 and 5270 were prepared using the intermediates described herein and by following the general procedure described for the synthesis of Compound 3117:

Compound 5269: (R)-1,1,1-trifluoropropan-2-yl ((2R,6S,7R,9S,13aS,14aR,16aS,Z)-14a-((cyclopropylsulfonyl)carbamoyl)-2-((2,2-difluoro-[1,3]dioxolo[4,5-f]isoquinolin-6-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 844.6 (M$^+$+1).

Compound 5270: (R)-1,1,1-trifluoropropan-2-yl ((2R,6S,7R,9R,13aS,14aR,16aS,Z)-14a-((cyclopropylsulfonyl)carbamoyl)-2-((2,2-difluoro-[1,3]dioxolo[4,5-f]isoquinolin-6- yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-$d_6$) δ 11.20 (br. s., 1H), 9.04 (br. s., 1H), 8.16 (d, J=5.8 Hz, 1H), 8.06-7.98 (m, 2H), 7.70 (d, J=8.9 Hz, 1H), 7.42 (d, J=5.8 Hz, 1H), 5.85 (br. s., 1H), 5.59-5.47 (m, 1H), 5.12-5.00 (m, 1H), 4.65-4.49 (m, 2H), 4.31 (quin, J=6.8 Hz, 1H), 3.90 (dd, J=11.3, 3.1 Hz, 1H), 3.69 (dd, J=10.7, 8.2 Hz, 1H), 2.99-2.89 (m, 1H), 2.70-2.60 (m, 2H), 2.41-2.32 (m, 1H), 2.32-2.19 (m, 1H), 1.99-1.77 (m, 2H), 1.71-1.52 (m, 3H), 1.48-1.31 (m, 2H), 1.21-0.95 (m, 8H), 0.93 (d, J=7.0 Hz, 3H), 0.87 (d, J=6.4 Hz, 3H), 0.74 (t, J=11.9 Hz, 1H); MS: MS m/z 844.6 (M$^+$+1).

Preparation of Compound 5271 and Compound 5272

Compound 5272: (1-methylcyclopropyl)methyl ((2R,6S,7R,9R,13aS,14aR,16aS,Z)-14a-((cyclopropylsulfonyl)carbamoyl)-2-((2,2-difluoro-[1,3]dioxolo[4,5-f]isoquinolin-6-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-$d_6$) δ 11.20 (br. s., 1H), 9.00 (br. s., 1H), 8.16 (d, J=6.1 Hz, 1H), 8.04 (d, J=9.2 Hz, 1H), 7.75 (d, J=8.9 Hz, 1H), 7.46 (d, J=7.6 Hz, 1H), 7.42 (d, J=5.8 Hz, 1H), 5.86 (br. s., 1H), 5.59-5.45 (m, 1H), 5.14-4.95 (m, 1H), 4.59 (d, J=11.3 Hz, 1H), 4.52 (t, J=8.1 Hz, 1H), 3.90 (dd, J=11.3, 3.1 Hz, 1H), 3.68 (dd, J=10.5, 8.4 Hz, 1H), 3.30-3.12 (m, 2H), 2.98-2.87 (m, 1H), 2.72-2.57 (m, 2H), 2.40-2.31 (m, 1H), 2.31-2.20 (m, 1H), 1.97-1.87 (m, 1H), 1.87-1.76 (m, 1H), 1.73-1.51 (m, 3H), 1.48-1.30 (m, 2H), 1.22-0.77 (m, 14H), 0.73 (t, J=12.1 Hz, 1H), 0.23-0.04 (m, 4H); MS: MS m/z 816.7 (M$^+$+1).

Preparation of Compound 5273 and Compound 5274

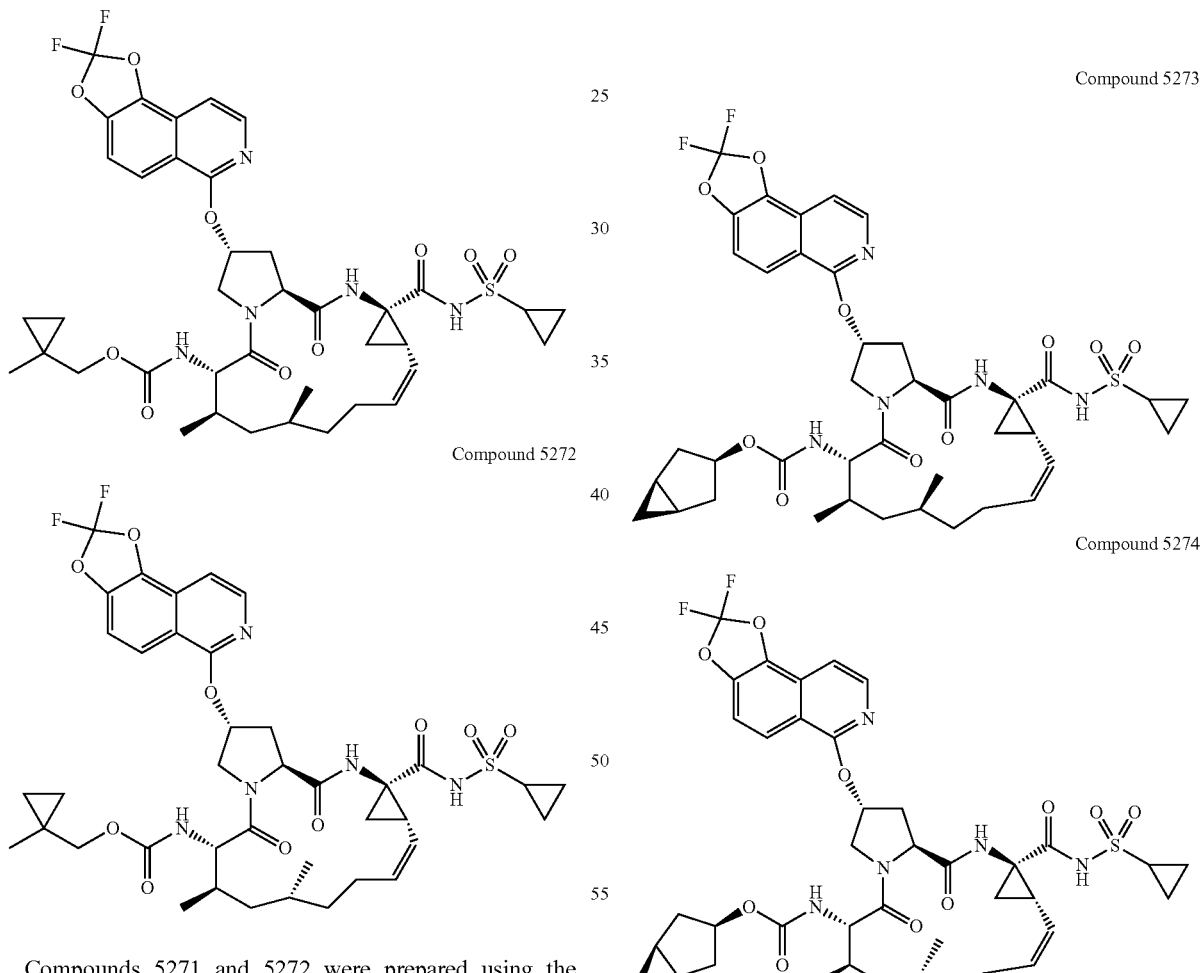

Compounds 5271 and 5272 were prepared using the intermediates described herein and by following the general procedure described for the synthesis of Compound 3117:

Compound 5271: (1-methylcyclopropyl)methyl ((2R,6S,7R,9S,13aS,14aR,16aS,Z)-14a-((cyclopropylsulfonyl)carbamoyl)-2-((2,2-difluoro-[1,3]dioxolo[4,5-f]isoquinolin-6-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 816.7 (M$^+$+1).

Compounds 5273 and 5274 were were prepared using the intermediates described herein and by following the general procedure described for the synthesis of Compound 3117:

Compound 5273: (1R,3r,5S)-bicyclo[3.1.0]hexan-3-yl ((2R,6S,7R,9S,13aS,14aR,16aS,Z)-14a-((cyclopropylsulfonyl)carbamoyl)-2-((2,2-difluoro-[1,3]dioxolo[4,5-f]isoquinolin-6-yl)oxy)-7,9-dimethyl-5,16-dioxo-1,2,3,5,6,7,8,9,10, 11,13a,14,14a,15,16,16a-hexadecahydrocyclopropa[e]pyrrolo[1,2-a][1,4]diazacyclopentadecin-6-yl)carbamate; MS: MS m/z 828.6 (M$^+$+1).

Compound 5274: (1R,3r,5S)-bicyclo[3.1.0]hexan-3-yl ((2R,6S,7R,9R,13aS,14aR,16aS,Z)-14a-((cyclopropylsulfonyl)carbamoyl)-2-((2,2-difluoro-[1,3]dioxolo[4,5-f]isoquinolin-6-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.19 (br. s., 1H), 8.98 (br. s., 1H), 8.16 (d, J=5.8 Hz, 1H), 8.06 (d, J=8.9 Hz, 1H), 7.78 (d, J=8.9 Hz, 1H), 7.43 (d, J=6.1 Hz, 1H), 7.36 (d, J=7.9 Hz, 1H), 5.87 (br. s., 1H), 5.57-5.47 (m, 1H), 5.12-4.99 (m, 1H), 4.58-4.42 (m, 3H), 3.91 (dd, J=11.3, 3.1 Hz, 1H), 3.69 (dd, J=10.7, 8.5 Hz, 1H), 2.91 (s, 1H), 2.72-2.59 (m, 2H), 2.41-2.21 (m, 2H), 2.00-1.75 (m, 3H), 1.72-0.87 (m, 18H), 0.85 (d, J=6.4 Hz, 3H), 0.72 (t, J=11.7 Hz, 1H), 0.38-0.24 (m, 2H); MS: MS m/z 828.5 (M$^+$+1).

Preparation of Compound 5275 and Compound 5276 quinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 795.6 (M$^+$+1).

Compound 5276: tert-butyl ((2R,6S,7R,9R,13aS,14aR,16aS,Z)-14a-((cyclopropylsulfonyl)carbamoyl)-7,9-dimethyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.19 (br. s., 1H), 8.97 (br. s., 1H), 7.81 (d, J=6.1 Hz, 1H), 7.62 (d, J=9.2 Hz, 1H), 7.24 (d, J=6.1 Hz, 1H), 7.17 (d, J=8.2 Hz, 1H), 7.05 (d, J=9.2 Hz, 1H), 5.78 (br. s., 1H), 5.59-5.45 (m, 1H), 5.13-4.99 (m, 1H), 4.53 (d, J=11.6 Hz, 1H), 4.45-4.33 (m, 3H), 3.88 (dd, J=11.3, 3.4 Hz, 1H), 3.73 (dd, J=9.9, 9.0 Hz, 1H), 3.43-3.38 (m, 2H), 2.98 (s, 3H), 2.95-2.88 (m, 1H), 2.73-2.64 (m, 1H), 2.62-2.54 (m, 1H), 2.36-2.22 (m, 2H), 1.98-0.95 (m, 21H), 0.93 (d, J=6.7 Hz, 3H), 0.88 (d, J=6.1 Hz, 3H), 0.72 (t, J=12.4 Hz, 1H); MS: MS m/z 795.6 (M$^+$+1).

Preparation of Compound 5277 and Compound 5278

Compound 5275

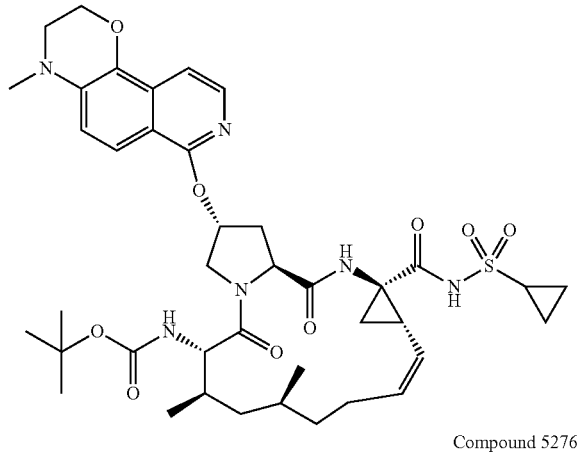

Compound 5276

Compound 5277

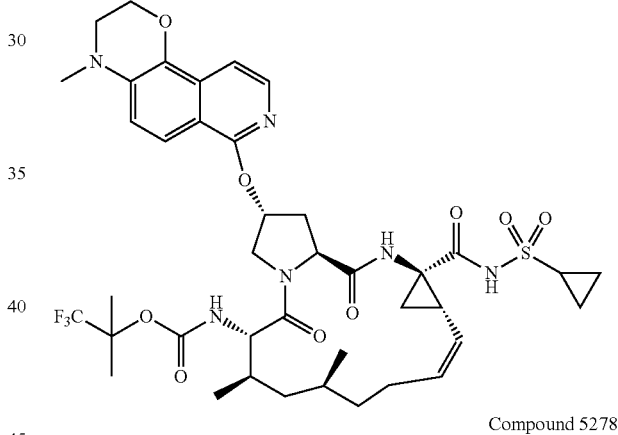

Compound 5278

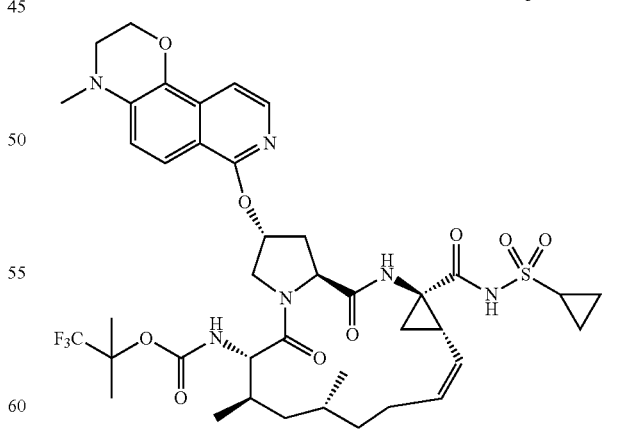

Compounds 5275 and 5276 were prepared using the intermediates described herein and by following the general procedure described for the synthesis of Compound 3117:

Compound 5275: tert-butyl ((2R,6S,7R,9S,13aS,14aR,16aS,Z)-14a-((cyclopropylsulfonyl)carbamoyl)-7,9-dimethyl-2-((4-methyl-3,4-dihydro-2H-[1,4]oxazino[2,3-f]iso- Compounds 5277 and 5278 were prepared using the intermediates described herein and by following the general procedure described for the synthesis of Compound 3117:

Compound 5277: 1,1,1-trifluoro-2-methylpropan-2-yl ((2R,6S,7R,9S,13aS,14aR,16aS,Z)-14a-((cyclopropylsulfonyl)carbamoyl)-7,9-dimethyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; MS: MS m/z 849.6 (M$^+$+1).

Compound 5278: 1,1,1-trifluoro-2-methylpropan-2-yl ((2R,6S,7R,9R,13aS,14aR,16aS,Z)-14a-((cyclopropylsulfonyl)carbamoyl)-7,9-dimethyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.19 (br. s., 1H), 9.00 (br. s., 1H), 7.85-7.77 (m, 2H), 7.59 (d, J=8.9 Hz, 1H), 7.25 (d, J=6.1 Hz, 1H), 7.08 (d, J=9.2 Hz, 1H), 5.79 (br. s., 1H), 5.58-5.44 (m, 1H), 5.17-5.02 (m, 1H), 4.51-4.43 (m, 2H), 4.42-4.30 (m, 2H), 3.88 (dd, J=11.4, 3.2 Hz, 1H), 3.71 (dd, J=10.7, 8.2 Hz, 1H), 3.46-3.37 (m, 2H), 2.98 (s, 3H), 2.94-2.86 (m, 1H), 2.72-2.54 (m, 2H), 2.36-2.23 (m, 2H), 1.95-1.80 (m, 2H), 1.77-1.67 (m, 1H), 1.63-0.96 (m, 15H), 0.93 (d, J=7.0 Hz, 3H), 0.88 (d, J=6.4 Hz, 3H), 0.72 (t, J=12.5 Hz, 1H); MS: m/z 849.5 (M$^+$+1).

Preparation of Compound 5279 and Compound 5280

Compound 5279: 1,1,1,3,3,3-hexadeutero-2-(trifluoromethyl)propan-2-yl ((2R,6S,7R,9S,13aS,14aR,16aS,Z)-14a-((cyclopropylsulfonyl)carbamoyl)-7,9-dimethyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate MS: MS m/z 855.6 (M$^+$+1).

Compound 5280: 1,1,1,3,3,3-hexadeutero-2-(trifluoromethyl)propan-2-yl ((2R,6S,7R,9R,13aS,14aR,16aS,Z)-14a-((cyclopropylsulfonyl)carbamoyl)-7,9-dimethyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate; $^1$H NMR (500 MHz, DMSO-d$_6$) δ 11.19 (br. s., 1H), 9.01 (br. s., 1H), 7.85-7.77 (m, 2H), 7.59 (d, J=9.2 Hz, 1H), 7.25 (d, J=6.1 Hz, 1H), 7.08 (d, J=9.2 Hz, 1H), 5.79 (br. s., 1H), 5.61-5.48 (m, 1H), 5.11-4.99 (m, 1H), 4.51-4.43 (m, 2H), 4.42-4.31 (m, 2H), 3.88 (dd, J=11.3, 3.4 Hz, 1H), 3.71 (dd, J=10.5, 8.4 Hz, 1H), 3.47-3.37 (m, 2H), 2.98 (s, 3H), 2.91 (s, 1H), 2.73-2.55 (m, 2H), 2.36-2.20 (m, 2H), 1.94-1.78 (m, 2H), 1.76-1.67 (m, 1H), 1.64-0.95 (m, 9H), 0.94 (d, J=6.7 Hz, 3H), 0.88 (d, J=6.4 Hz, 3H), 0.73 (t, J=12.2 Hz, 1H); MS: MS m/z 855.6 (M$^+$+1).

Preparation of Compound 5281 and Compound 5282

Compound 5279

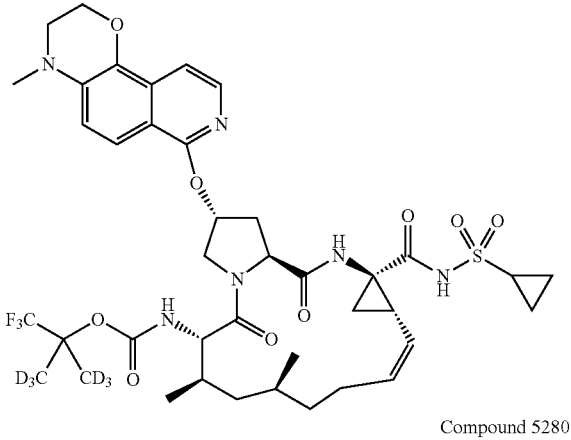
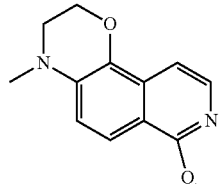

Compound 5281

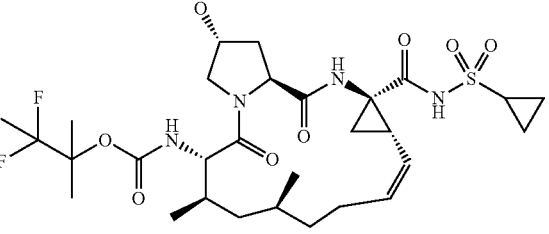

Compound 5280

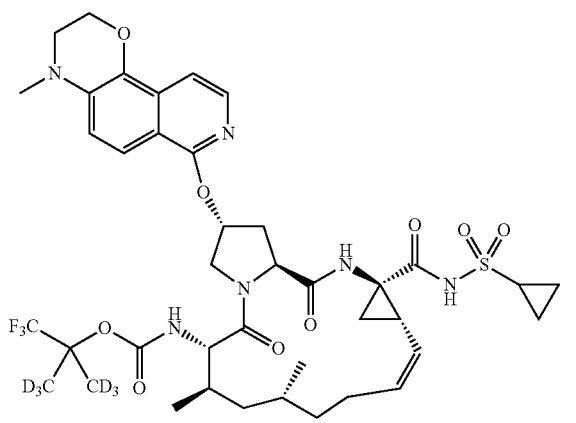
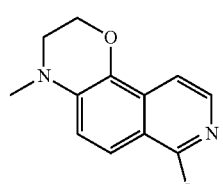

Compound 5282

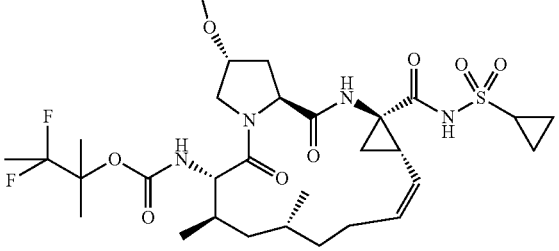

Compounds 5279 and 5280 were prepared using the intermediates described herein and by following the general procedure described for the synthesis of Compound 3117:

Compounds 5281 and 5282 were prepared using the intermediates described herein and by following the general procedure described for the synthesis of Compound 3117:

Compound 5281: 3,3-difluoro-2-methylbutan-2-yl ((2R,6S,7R,9S,13aS,14aR,16aS,Z)-14a-((cyclopropylsulfonyl)carbamoyl)-7,9-dimethyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 845.6 ($M^+$+1).

Compound 5282: 3,3-difluoro-2-methylbutan-2-yl ((2R,6S,7R,9R,13aS,14aR,16aS,Z)-14a-((cyclopropylsulfonyl)carbamoyl)-7,9-dimethyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-$d_6$) δ 11.19 (br. s., 1H), 8.98 (br. s., 1H), 7.82 (d, J=6.1 Hz, 1H), 7.60 (m, 2H), 7.25 (d, J=6.1 Hz, 1H), 7.07 (d, J=9.2 Hz, 1H), 5.79 (m 1H), 5.52 (m 1H), 5.06 (m, 1H), 4.46 (d, J=7.9 Hz, 2H), 4.42-4.23 (m, 2H), 3.99-3.81 (m, 1H), 3.72 (dd, J=10.5, 8.7 Hz, 1H), 3.40 (m, 2H), 2.90-2.35 (m, 3H), 2.32-2.24 (m, 2H), 1.97-1.07 (m, 24H), 0.97-0.80 (m, 6H), 0.73 (m, 1H); MS: MS m/z 845.6 ($M^+$+1).

Preparation of Compound 5283 and Compound 5284

Compounds 5283 and 5284 were were prepared using the intermediates described herein and by following the general procedure described for the synthesis of Compound 3117:

Compound 5283: (2R,6S,7R,9S,13aS,14aR,16aS,Z)-6-(3-(tert-butyl)ureido)-N-(cyclopropylsulfonyl)-7,9-dimethyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. MS: MS m/z 794.7 ($M^+$+1).

Compound 5284: (2R,6S,7R,9R,13aS,14aR,16aS,Z)-6-(3-(tert-butyl)ureido)-N-(cyclopropylsulfonyl)-7,9-dimethyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (500 MHz, METHANOL-$d_4$) δ 7.82-7.66 (m, 2H), 7.32 (d, J=6.1 Hz, 1H), 7.00 (d, J=9.2 Hz, 1H), 5.81 (br. s., 1H), 5.44 (td, J=10.1, 5.6 Hz, 1H), 5.06 (t, J=10.1 Hz, 1H), 4.71 (d, J=11.3 Hz, 1H), 4.55 (dd, J=9.8, 7.3 Hz, 1H), 4.45-4.33 (m, 2H), 4.09-3.95 (m, 2H), 3.41 (dd, J=5.0, 3.5 Hz, 2H), 2.94-2.84 (m, 3H), 2.74-2.54 (m, 2H), 2.47-2.25 (m, 2H), 1.96 (s, 3H), 1.83-1.65 (m, 4H), 1.48 (dd, J=9.5, 5.5 Hz, 1H), 1.35-1.21 (m, 3H), 1.17 (s, 9H), 1.14-1.01 (m, 3H), 0.96 (m, 6H), 0.80 (t, J=11.7 Hz, 1H); MS: MS m/z 794.7 ($M^+$+1).

Preparation of Compound 5285 and Compound 5286

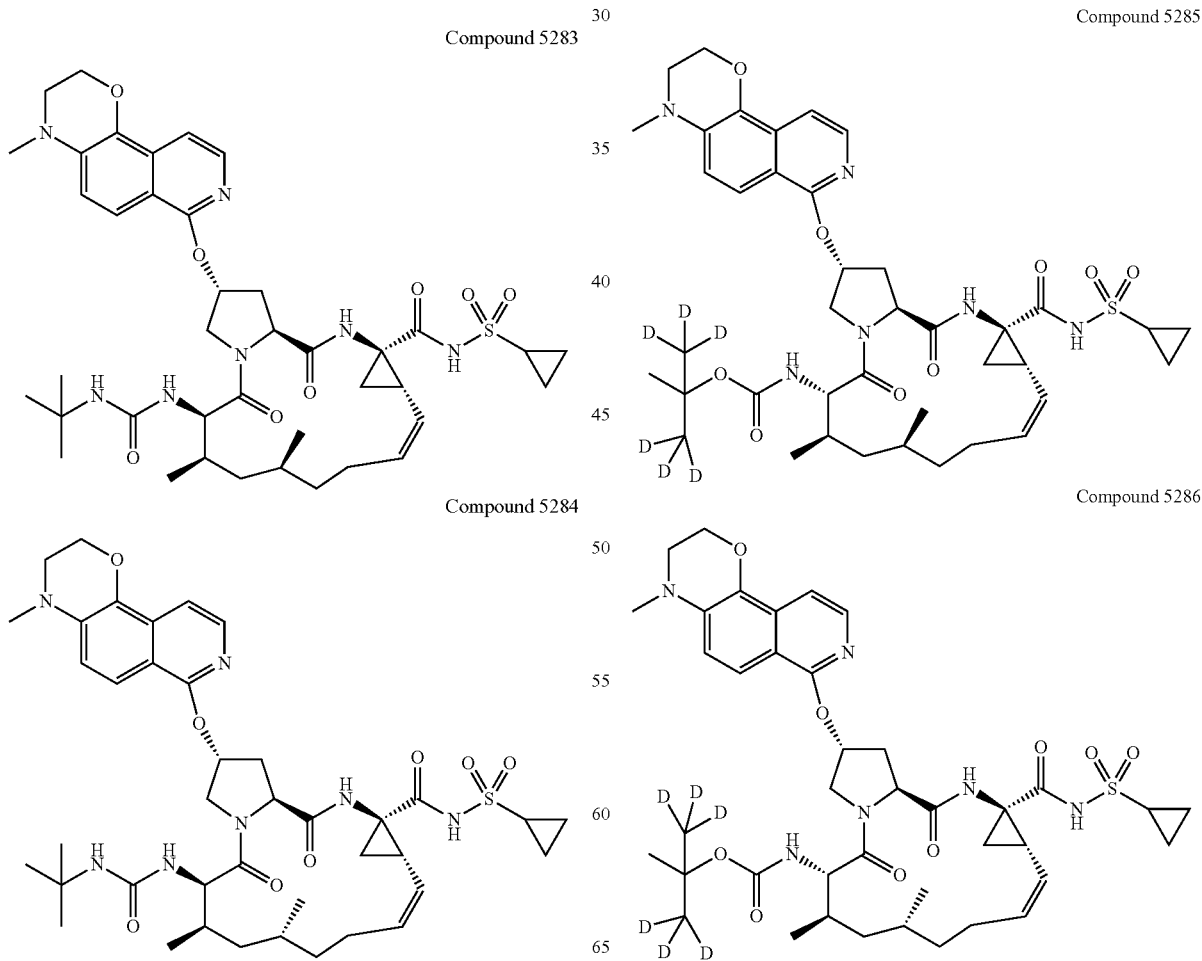

Compound 5283

Compound 5284

Compound 5285

Compound 5286

Compounds 5285 and 5286 were prepared using the intermediates described herein and by following the general procedure described for the synthesis of Compound 3117:

Compound 5285: 1,1,1,3,3,3-hexadeutero-2-methylpropan-2-yl ((2R,6S,7R,9S,13aS,14aR,16aS,Z)-14a-((cyclopropylsulfonyl)carbamoyl)-7,9-dimethyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate MS: MS m/z 801.7 (M$^+$+1).

Compound 5286: 1,1,1,3,3,3-hexadeutero-2-methylpropan-2-yl ((2R,6S,7R,9R,13aS,14aR,16aS,Z)-14a-((cyclopropylsulfonyl)carbamoyl)-7,9-dimethyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.19 (br. s., 1H), 8.96 (br. s., 1H), 7.81 (d, J=6.1 Hz, 1H), 7.62 (d, J=9.2 Hz, 1H), 7.24 (d, J=6.1 Hz, 1H), 7.13 (br. s., 1H), 7.05 (d, J=9.2 Hz, 1H), 5.78 (m, 1H), 5.49 (m, 1H), 5.06 (m, 1H), 4.49 (m, 1H), 4.42-4.34 (m, 3H), 3.98-3.82 (m, 1H), 3.79-3.63 (m, 1H), 2.98 9 s, 3H), 2.92-2.83 (m, 2H), 2.38-2.20 (m, 2H), 1.99-1.10 (m, 18H), 1.01-0.82 (m, 6H), 0.76-0.63 (m, 1H); MS: MS m/z 801.7 (M$^+$+1).

Preparation of Compound 5287 and Compound 5288

Compounds 5287 and 5288 were prepared using the intermediates described herein and by following the general procedure described for the synthesis of Compound 3117:

Compound 5287: 1,1,1,3,3,3-hexadeutero-2-(trideuteromethyl)propan-2-yl ((2R,6S,7R,9S,13aS,14aR,16aS,Z)-14a-((cyclopropylsulfonyl)carbamoyl)-7,9-dimethyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate MS: MS m/z 804.7 (M$^+$+1).

Compound 5288: 1,1,1,3,3,3-hexadeutero-2-(trideuteromethyl)propan-2-yl ((2R,6S,7R,9R,13aS,14aR,16aS,Z)-14a-((cyclopropylsulfonyl)carbamoyl)-7,9-dimethyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.18 (br. s., 1H), 8.96 (br. s., 1H), 7.81 (d, J=6.1 Hz, 1H), 7.62 (d, J=8.9 Hz, 1H), 7.24 (d, J=6.1 Hz, 1H), 7.13 (br. s., 1H), 7.05 (d, J=9.2 Hz, 1H), 5.78 (s 1H), 5.48 (m, 1H), 5.09 (m, 1H), 4.49 (m, 1H), 4.44-4.30 (m, 3H), 4.01-3.83 (m, 2H), 3.78-3.67 (m, 1H), 3.40 (d, J=2.7 Hz, 2H), 2.98 (s, 3H), 2.38-2.22 (m, 2H), 1.92-1.05 (m, 14H), 0.99-0.80 (m, 6H), 0.80-0.64 (m, 1H); MS: MS m/z 804.7 (M$^+$+1).

Preparation of Compound 5289 and Compound 5290

Compound 5287

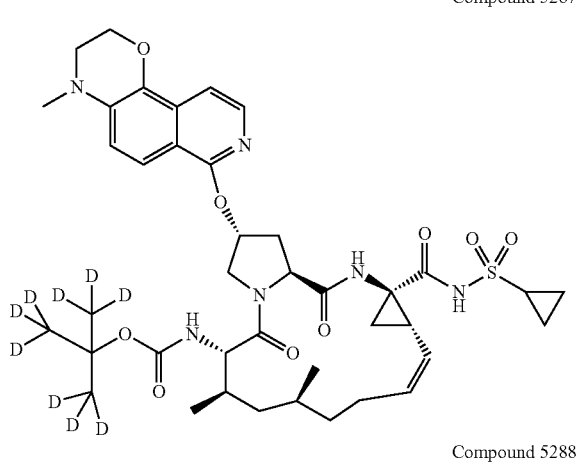

Compound 5288

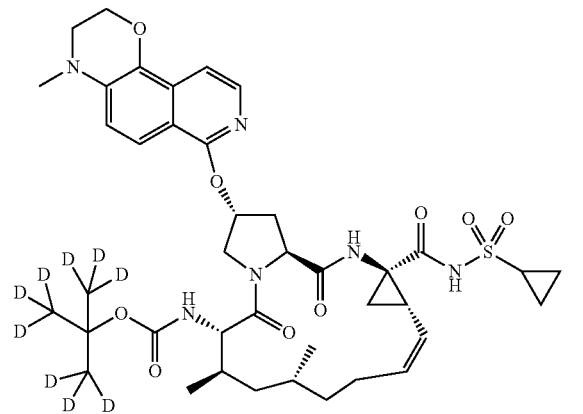

Compound 5289

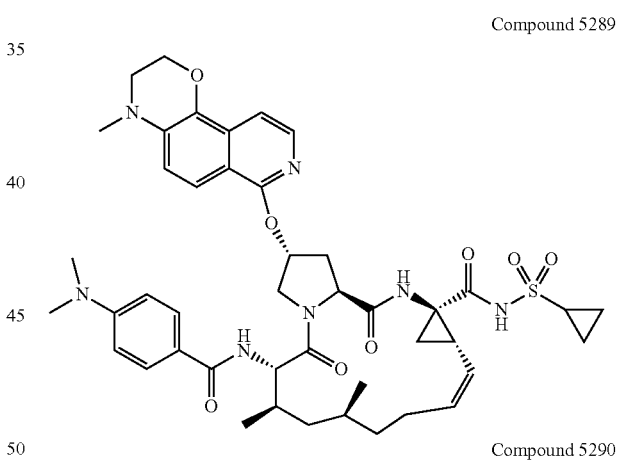

Compound 5290

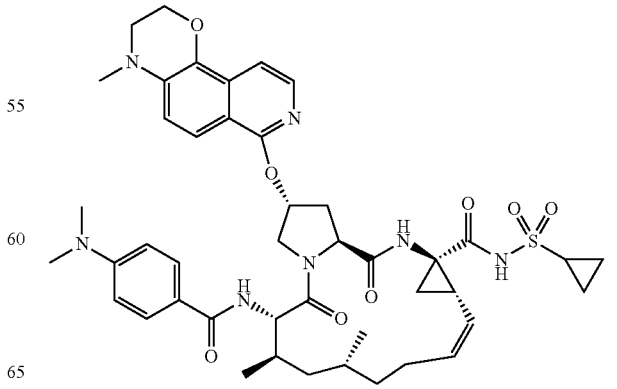

Compounds 5289 and 5290 were prepared using the intermediates described herein and by following the general procedure described for the synthesis of Compound 3117:

Compound 5289: (2R,6S,7R,9S,13aS,14aR,16aS,Z)—N-(cyclopropylsulfonyl)-6-(4-(dimethylamino)benzamido)-7,9-dimethyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. MS: MS m/z 842.7 (M$^+$+1).

Compound 5290: (2R,6S,7R,9R,13aS,14aR,16aS,Z)—N-(cyclopropylsulfonyl)-6-(4-(dimethylamino)benzamido)-7,9-dimethyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (500 MHz, DMSO-d$_6$) δ 11.18 (br. s., 1H), 8.96 (br. s., 1H), 8.27 (d, J=8.2 Hz, 1H), 7.82 (d, J=6.1 Hz, 1H), 7.72-7.65 (m, J=8.9 Hz, 2H), 7.52 (d, J=8.9 Hz, 1H), 7.25 (d, J=6.1 Hz, 1H), 6.91 (d, J=8.9 Hz, 1H), 6.69-6.60 (m, J=9.2 Hz, 2H), 5.79 (br. s., 1H), 5.49 (m, 1H), 4.68 (m, 1H), 4.45-4.25 (m, 4H), 3.97 (dd, J=11.0, 3.7 Hz, 1H), 3.41 (m, 2H), 3.03-2.89 (m, 10H), 2.37-2.23 (m, 1H), 2.17-2.08 (m, 1H), 1.99 (m, 1H), 1.80 (m, 1H), 1.49-1.25 (m, 9H), 0.95 (m, 9H), 0.87-0.74 (m, 1H) MS: MS m/z 842.7 (M$^+$+1).

Preparation of Compound 5291 and Compound 5292

Compounds 5291 and 5292 were prepared using the intermediates described herein and by following the general procedure described for the synthesis of Compound 3117:

Compound 5291: (1R,3r,5S)-bicyclo[3.1.0]hexan-3-yl ((2R,6S,7R,9S,13aS,14aR,16aS,Z)-14a-((cyclopropylsulfonyl)carbamoyl)-7,9-dimethyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 819.6 (M$^+$+1).

Compound 5292: (1R,3r,5S)-bicyclo[3.1.0]hexan-3-yl ((2R,6S,7R,9R,13aS,14aR,16aS,Z)-14a-((cyclopropylsulfonyl)carbamoyl)-7,9-dimethyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.18 (br. s., 1H), 8.96 (br. s., 1H), 7.81 (d, J=6.1 Hz, 1H), 7.59 (d, J=9.2 Hz, 1H), 7.37 (m, 1H), 7.26 (d, J=6.1 Hz, 1H), 7.12 (d, J=9.2 Hz, 1H), 5.79 (br. s., 1H), 5.50 (m, 1H), 5.08 (m, 1H), 4.68 (t, J=6.9 Hz, 1H), 4.48-4.32 (m, 4H), 3.97-3.86 (m, 2H), 3.77 (t, J=9.8 Hz, 1H), 3.41 (m, 2H), 2.99 (s, 3H), 2.95-2.28 (m, 3H), 2.34-2.22 (m, 2H), 2.03-1.89 (m, 2H), 1.89-1.77 (m, 2H), 1.59-1.14 (m, 13H), 0.94-0.85 (m, 6H), 0.72 (m, 1H), 0.42-0.28 (m, 2H); MS: MS m/z 819.6 (M$^+$+1).

Preparation of Compound 5293 and Compound 5294

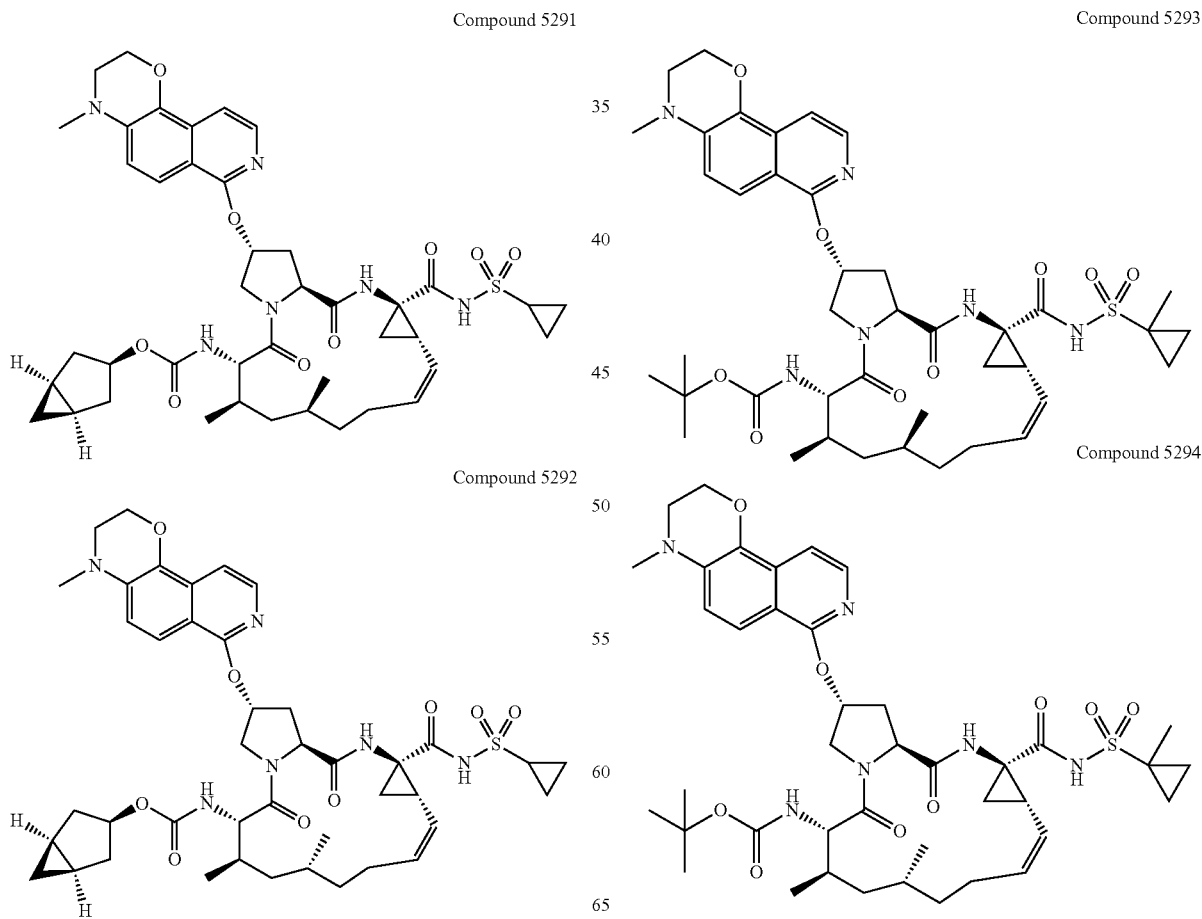

Compound 5291

Compound 5292

Compound 5293

Compound 5294

Compounds 5293 and 5294 were prepared using the intermediates described herein and by following the general procedure described for the synthesis of Compound 3117:

Compound 5293: tert-butyl ((2R,6S,7R,9S,13aS,14aR,16aS,Z)-7,9-dimethyl-2-((4-methyl-3,4-dihydro-2H-[1,4]oxazino[2,3-f]isoquinolin-7-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 809.5 (M$^+$+1).

Compound 5294: tert-butyl ((2R,6S,7R,9R,13aS,14aR,16aS,Z)-7,9-dimethyl-2-((4-methyl-3,4-dihydro-2H-[1,4]oxazino[2,3-f]isoquinolin-7-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
$^1$H NMR (500 MHz, DMSO-d$_6$) δ 11.05 (br. s., 1H), 9.09 (br. s., 1H), 7.81 (d, J=6.1 Hz, 1H), 7.62 (d, J=9.2 Hz, 1H), 7.24 (d, J=6.1 Hz, 1H), 7.17 (br. s., 1H), 7.06 (d, J=9.2 Hz, 1H), 5.79 (br. s., 1H), 5.52 (m, 1H), 4.97 (m, 1H), 4.52-4.37 (m, 4H), 3.97-3.85 (m, 1H), 3.73 (t, J=9.5 Hz, 1H), 3.40 (m, 2H), 2.98 (s, 3H), 2.95-2.28 (m, 3H), 2.41-2.24 (m, 2H), 1.92-1.09 (m, 23H), 0.97-0.85 (m, 6H), 0.73 (m, 1H); MS: MS m/z 809.5 (M$^+$+1).

Preparation of Compound 5295 and Compound 5296

Compounds 5295 and 5296 were prepared using the intermediates described herein and by following the general procedure described for the synthesis of Compound 3117:

Compound 5295: 1,1,1-trifluoro-2-methylpropan-2-yl ((2R,6S,7R,9S,13aS,14aR,16aS,Z)-7,9-dimethyl-2-((4-methyl-3,4-dihydro-2H-[1,4]oxazino[2,3-f]isoquinolin-7-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 863.5 (M$^+$+1).

Compound 5296: 1,1,1-trifluoro-2-methylpropan-2-yl ((2R,6S,7R,9R,13aS,14aR,16aS,Z)-7,9-dimethyl-2-((4-methyl-3,4-dihydro-2H-[1,4]oxazino[2,3-f]isoquinolin-7-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.05 (br. s., 1H), 9.14 (br. s., 1H), 7.82 (m, 2H), 7.59 (d, J=8.9 Hz, 1H), 7.25 (d, J=5.8 Hz, 1H), 7.09 (d, J=9.2 Hz, 1H), 5.81 (br. s., 1H), 5.53 (m, 1H), 4.98 (m, 1H), 4.50-4.34 (m, 4H), 3.92-3.84 (m, 1H), 3.70 (t, 1H), 3.52-3.38 (m, 2H), 2.98 (s, 3H), 2.95-2.28 (m, 3H), 2.38-2.23 (m, 2H), 1.94-1.24 (m, 17H), 1.10 (s, 3H), 0.95-0.86 (m, 6H), 0.74 (br. s., 1H); MS: MS m/z 863.5 (M$^+$+1).

Preparation of Compound 5297 and Compound 5298

Compound 5295

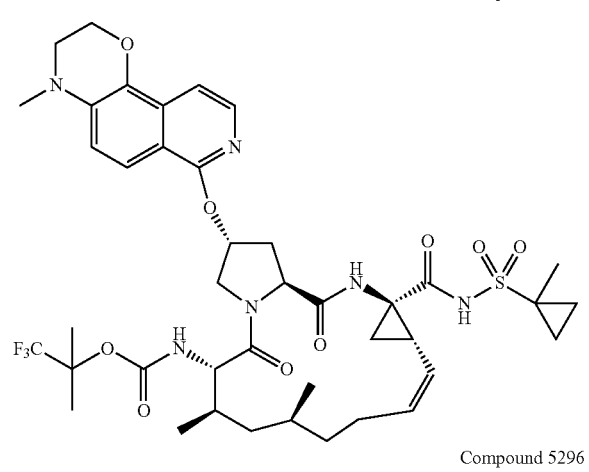

Compound 5296

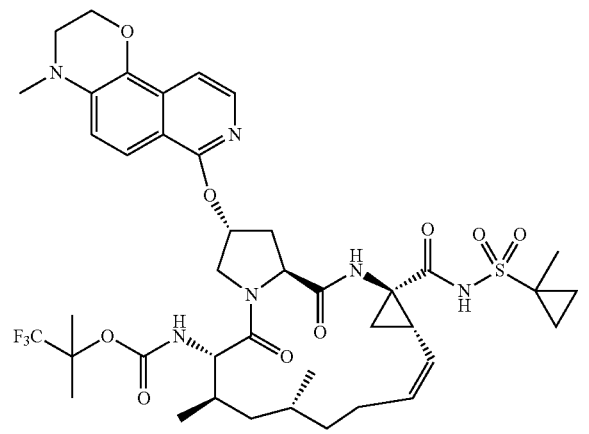

Compound 5297

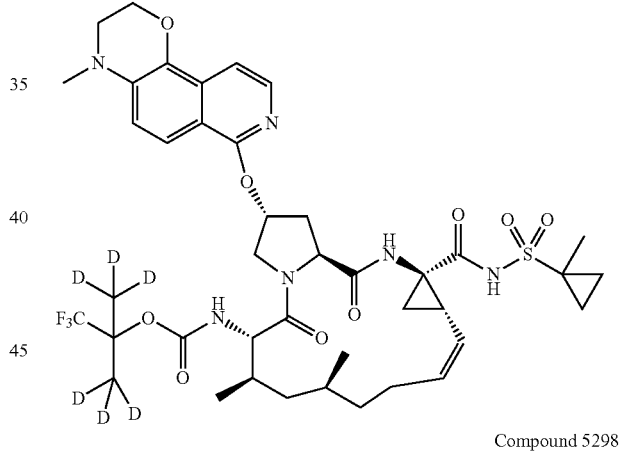

Compound 5298

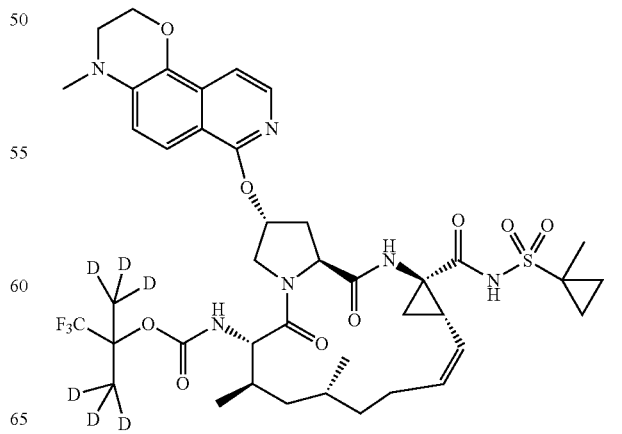

Compounds 5297 and 5298 were prepared using the intermediates described herein and by following the general procedure described for the synthesis of Compound 3117:

Compound 5297: 1,1,1,3,3,3-hexadeutero-2-(trifluoromethyl)propan-2-yl ((2R,6S,7R,9S,13aS,14aR,16aS,Z)-7,9-dimethyl-2-((4-methyl-3,4-dihydro-2H-[1,4]oxazino[2,3-f]isoquinolin-7-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 869.7 (M$^+$+1).

Compound 5298: MS: 1,1,1,3,3,3-hexadeutero-2-(trifluoromethyl)propan-2-yl ((2R,6S,7R,9R,13aS,14aR,16aS,Z)-7,9-dimethyl-2-((4-methyl-3,4-dihydro-2H-[1,4]oxazino[2,3-f]isoquinolin-7-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.05 (br. s., 1H), 9.15 (br. s., 1H), 7.82 (d, J=6.1 Hz, 2H), 7.68-7.53 (m, J=9.2 Hz, 1H), 7.25 (d, J=5.8 Hz, 1H), 7.13-7.04 (m, 1H), 5.80 (br. s., 1H), 5.53 (m, 1H), 4.98 (m, 1H), 4.50 (m, 2H), 4.44-4.30 (m, 2H), 3.99-3.85 (m, 1H), 3.70 (dd, J=10.5, 8.4 Hz, 1H), 3.43 (m, 1H), 2.98 (s, 3H), 2.95-2.28 (m, 3H), 2.35-2.18 (m, 2H), 2.01-1.25 (m, 15H), 0.99-0.81 (m, 6H), 0.74 (m, 1H); MS m/z 869.7 (M$^+$+1).

Preparation of Compound 5299 and Compound 5300

Compounds 5299 and 5300 were prepared using the intermediates described herein and by following the general procedure described for the synthesis of Compound 3117:

Compound 5299: (1R,3r,5S)-bicyclo[3.1.0]hexan-3-yl ((2R,6S,7R,9S,13aS,14aR,16aS,Z)-7,9-dimethyl-2-((4-methyl-3,4-dihydro-2H-[1,4]oxazino[2,3-f]isoquinolin-7-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 833.6 (M$^+$+1).

Compound 5300: (1R,3r,5S)-bicyclo[3.1.0]hexan-3-yl ((2R,6S,7R,9R,13aS,14aR,16aS,Z)-7,9-dimethyl-2-((4-methyl-3,4-dihydro-2H-[1,4]oxazino[2,3-f]isoquinolin-7-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.05 (br. s., 1H), 9.15 (br. s., 1H), 7.81 (d, J=6.1 Hz, 1H), 7.59 (d, J=8.9 Hz, 1H), 7.38 (d, J=8.5 Hz, 1H), 7.26 (d, J=6.1 Hz, 1H), 7.12 (d, J=9.2 Hz, 1H), 5.80 (br. s., 1H), 5.49 (m, 1H), 5.01 (m, 1H), 4.66 (t, J=6.9 Hz, 1H), 4.48-4.28 (m, 4H), 3.98-3.86 (m, 1H), 3.81-3.69 (m, 1H), 3.48-3.39 (m, 2H), 2.99 (s, 3H), 2.95-2.28 (m, 3H), 2.34-2.23 (m, 2H), 2.03-1.13 (m, 20H), 0.92 (d, J=7.0 Hz, 3H), 0.86 (d, J=6.4 Hz, 3H), 0.73 (m, 1H), 0.41-0.25 (m, 2H); MS: MS m/z 833.6 (M$^+$+1).

Preparation of Compound 5301 and Compound 5302

Compound 5299

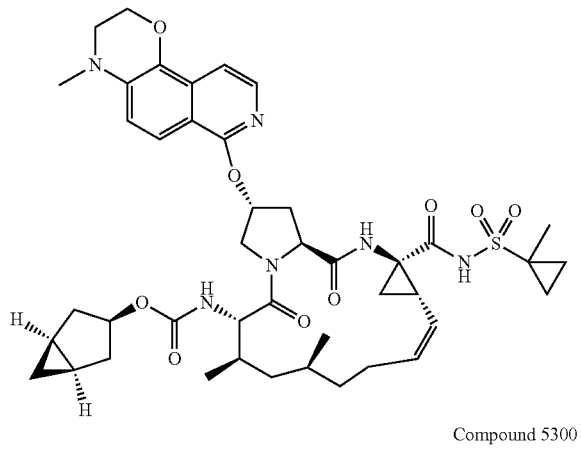

Compound 5301

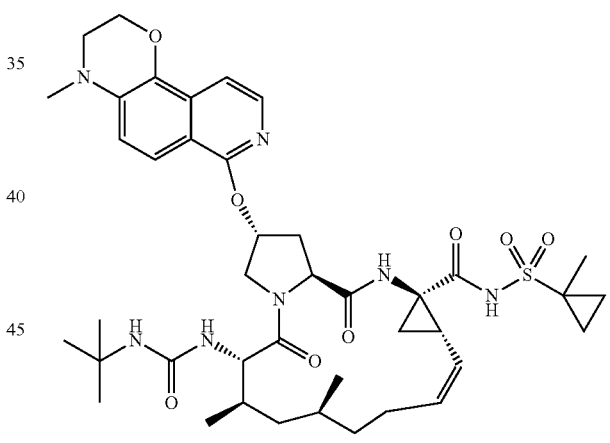

Compound 5300

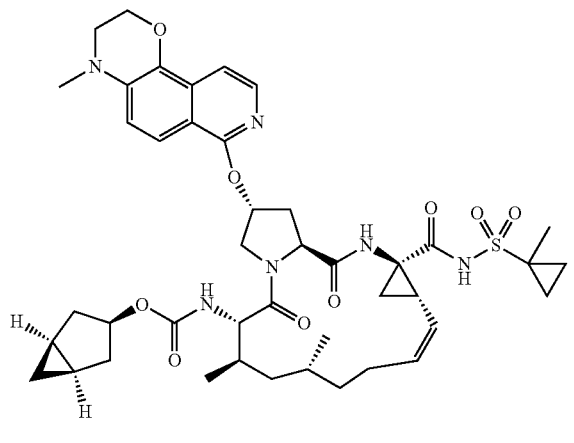

Compound 5302

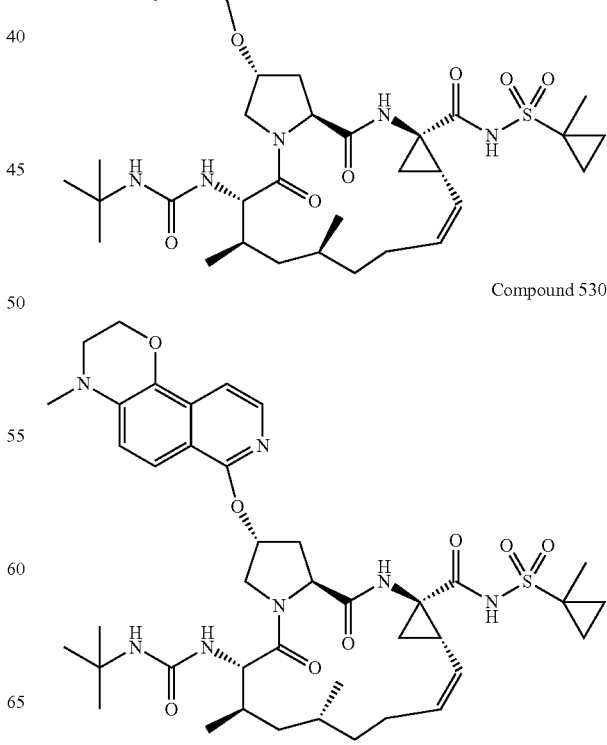

Compounds 5301 and 5302 were prepared using the intermediates described herein and by following the general procedure described for the synthesis of Compound 3117:

Compound 5301: (2R,6S,7R,9S,13aS,14aR,16aS,Z)-6-(3-(tert-butyl)ureido)-7,9-dimethyl-2-((4-methyl-3,4-dihydro-2H-[1,4]oxazino[2,3-f]isoquinolin-7-yl)oxy)-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide; MS: MS m/z 808.6 ($M^++1$).

Compound 5302: (2R,6S,7R,9R,13aS,14aR,16aS,Z)-6-(3-(tert-butyl)ureido)-7,9-dimethyl-2-((4-methyl-3,4-dihydro-2H-[1,4]oxazino[2,3-f]isoquinolin-7-yl)oxy)-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide; $^1$H NMR (500 MHz, DMSO-d$_6$) δ 11.04 (br. s., 1H), 9.07 (br. s., 1H), 7.81 (d, J=6.1 Hz, 1H), 7.63 (d, J=9.2 Hz, 1H), 7.25 (d, J=6.1 Hz, 1H), 7.04 (d, J=9.2 Hz, 1H), 5.97 (d, J=8.9 Hz, 1H), 5.80 (br. s., 1H), 5.59 (s, 1H), 5.52 (d, J=5.2 Hz, 1H), 4.98 (t, J=9.9 Hz, 1H), 4.51 (d, J=11.3 Hz, 1H), 4.46-4.28 (m, 3H), 3.99-3.75 (m, 2H), 3.41 (d, J=4.0 Hz, 2H), 2.98 (s, 3H), 2.77-2.66 (m, 1H), 2.56 (m, 2H), 2.36 (m, 1H), 2.32-2.20 (m, 1H), 2.00-1.85 (m, 1H), 1.79-1.07 (m, 12H), 1.08 (s, 9H), 0.92 (m, 7H), 0.74 (m, 1H); MS: MS m/z 808.6 ($M^++1$).

Preparation of Compound 5303 and Compound 5304

Compounds 5303 and 5304 were prepared using the intermediates described herein and by following the general procedure described for the synthesis of Compound 3117:

Compound 5303: (2R,6S,7R,9S,13aS,14aR,16aS,Z)-6-(4-(dimethylamino)benzamido)-7,9-dimethyl-2-((4-methyl-3,4-dihydro-2H-[1,4]oxazino[2,3-f]isoquinolin-7-yl)oxy)-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. MS: MS m/z 856.6 ($M^++1$).

Compound 5304: (2R,6S,7R,9R,13aS,14aR,16aS,Z)-6-(4-(dimethylamino)benzamido)-7,9-dimethyl-2-((4-methyl-3,4-dihydro-2H-[1,4]oxazino[2,3-f]isoquinolin-7-yl)oxy)-N-((1-methylcyclopropyl)sulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (500 MHz, METHANOL-d$_4$) δ 7.73 (d, J=6.4 Hz, 1H), 7.60-7.48 (m, 3H), 7.38 (d, J=6.4 Hz, 1H), 6.80 (d, J=9.2 Hz, 1H), 6.67 (d, J=8.9 Hz, 2H), 5.83 (br. s., 1H), 5.59 (m, 1H), 5.00 (t, J=9.9 Hz, 1H), 4.58 (dd, J=9.6, 7.5 Hz, 1H), 4.48 (d, J=11.0 Hz, 1H), 4.39 (m, 2H), 4.09 (dd, J=11.6, 3.4 Hz, 1H), 3.43 (t, J=4.1 Hz, 2H), 3.04-2.92 (m, 10H), 2.79-2.69 (m, 2H), 2.47-2.31 (m, 2H), 2.19-2.08 (m, 1H), 2.05-1.94 (m, 1H), 1.86-1.70 (m, 2H), 1.69-1.60 (m, 1H), 1.56-1.38 (m, 8H), 1.28-1.17 (m, 1H), 1.01 (d, J=6.7 Hz, 6H), 0.93-0.84 (m, 2H); MS: MS m/z 856.6 ($M^++1$).

Preparation of Compound 5305 and Compound 5306

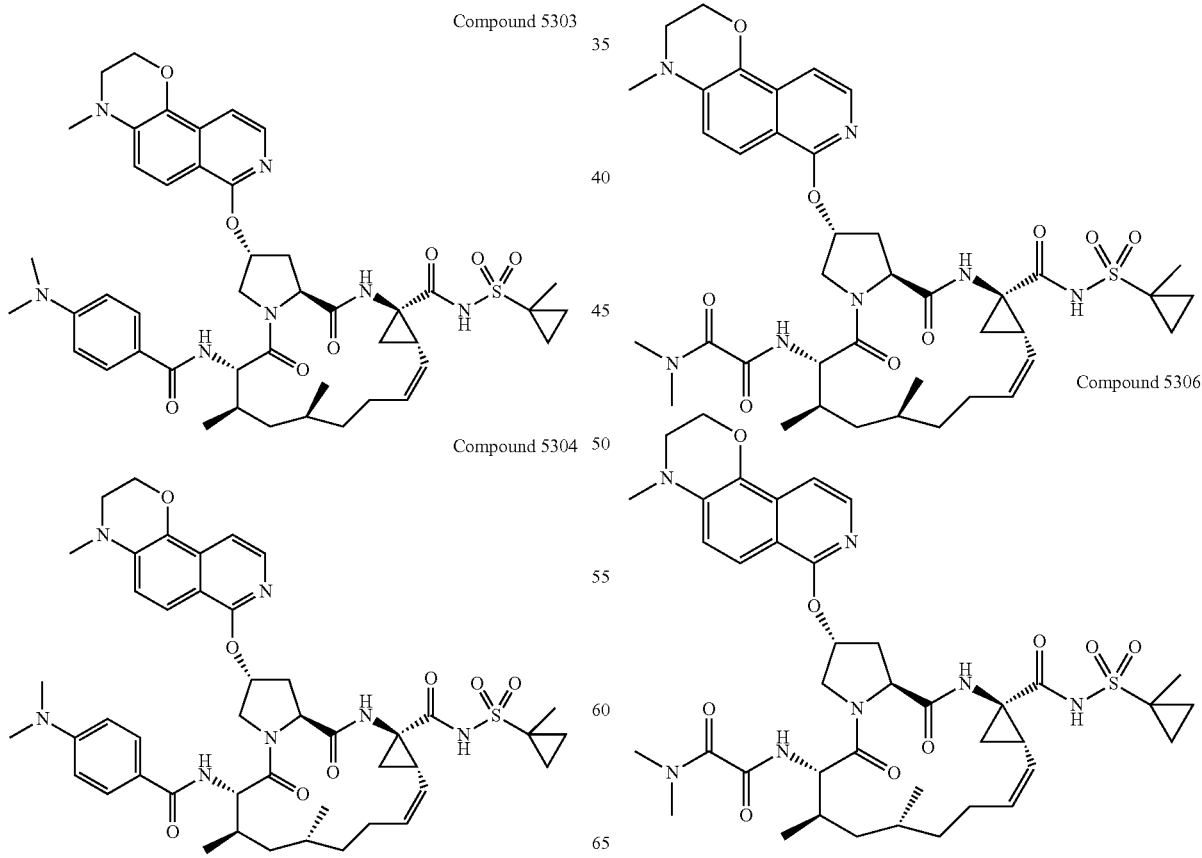

Compound 5303

Compound 5304

Compound 5305

Compound 5306

Compounds 5305 and 5306 were prepared using the intermediates described herein and by following the general procedure described for the synthesis of Compound 3117:

Compound 5305: N1-((2R,6S,7R,9S,13aS,14aR,16aS,Z)-7,9-dimethyl-2-((4-methyl-3,4-dihydro-2H-[1,4]oxazino[2,3-f]isoquinolin-7-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-N2,N2-dimethyloxalamide. MS: MS m/z 808.6 (M$^+$+1).

Compound 5306: N1-((2R,6S,7R,9R,13aS,14aR,16aS,Z)-7,9-dimethyl-2-((4-methyl-3,4-dihydro-2H-[1,4]oxazino[2,3-f]isoquinolin-7-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-N2,N2-dimethyloxalamide. $^1$H NMR (500 MHz, DMSO-d$_6$) δ 11.00 (br. s., 1H), 9.10 (br. s., 1H), 8.99 (d, J=8.2 Hz, 1H), 7.81 (d, J=6.1 Hz, 1H), 7.54 (d, J=8.9 Hz, 1H), 7.26 (d, J=6.1 Hz, 1H), 7.15 (d, J=9.2 Hz, 1H), 5.83 (br. s., 1H), 5.52 (m, 1H), 5.01 (m, 1H), 4.52-4.29 (m, 4H), 4.20-4.09 (m, 1H), 4.04 (dd, J=11.3, 3.4 Hz, 1H), 3.92 (s, 1H), 3.45-3.40 (m, 2H), 3.00 (s, 3H), 2.78 (s, 3H), 2.75-2.55 (m, 2H), 2.67 (s, 3H), 2.32 (m, 2H), 1.92 (m, 2H), 1.75-1.17 (m, 12H), 0.92 (dd, J=17.7, 6.7 Hz, 6H), 0.80 (m, 1H); MS: MS m/z 808.6 (M$^+$+1).

Compounds 5307 and 5308 were prepared using the intermediates described herein and by following the general procedure described for the synthesis of Compound 3117:

Compound 5307: tert-butyl ((2R,6S,7R,9S,13aS,14aR,16aS,Z)-14a-((cyclopropylsulfonyl)carbamoyl)-7-ethyl-9-methyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 809.5 (M$^+$+1).

Compound 5308: tert-butyl ((2R,6S,7R,9R,13aS,14aR,16aS,Z)-14a-((cyclopropylsulfonyl)carbamoyl)-7-ethyl-9-methyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.18 (s, 1H), 8.97 (br. s., 1H), 7.82 (d, J=6.1 Hz, 1H), 7.60 (d, J=9.2 Hz, 1H), 7.25 (d, J=6.4 Hz, 1H), 7.18 (d, J=8.5 Hz, 1H), 7.06 (d, J=9.2 Hz, 1H), 5.79 (br. s., 1H), 5.53 (d, J=4.9 Hz, 1H), 5.10-4.98 (m, 1H), 4.55 (d, J=11.6 Hz, 1H), 4.45-4.34 (m, 3H), 4.01-3.84 (m, 2H), 3.40 (d, J=2.4 Hz, 2H), 2.98 (s, 3H), 2.95-2.88 (m, 1H), 2.75-2.63 (m, 1H), 2.63-2.55 (m, 1H), 2.36-2.22 (m, 2H), 1.92 (m, 2H), 1.60-1.38 (m, 7H), 1.18 (s, 9H), 1.06-0.93 (m, 9H), 0.74 (m, 3H); MS m/z 809.5 (M$^+$+1).

Preparation of Compound 5307 and Compound 5308

Preparation of Compound 5309 and Compound 5310

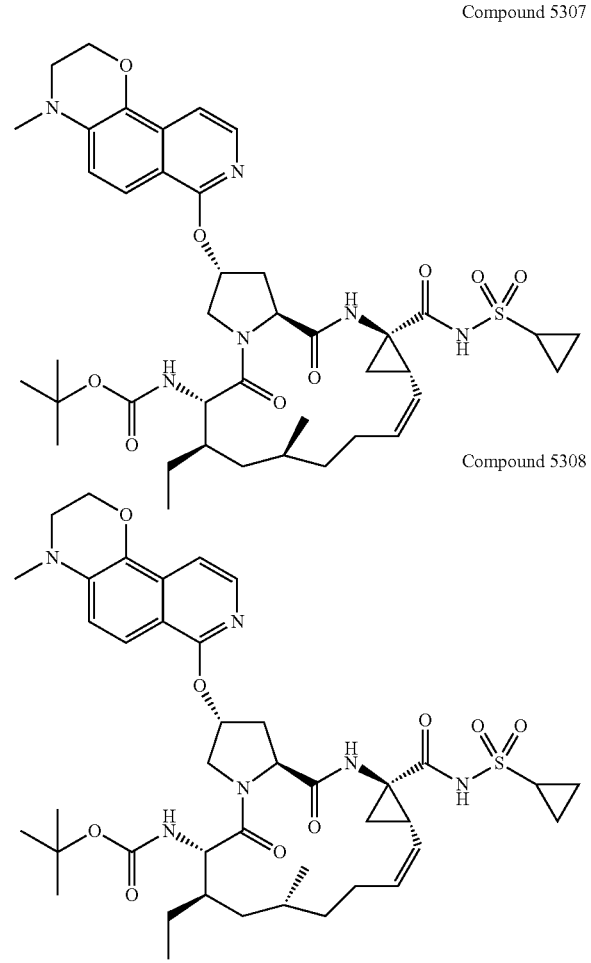

Compound 5307

Compound 5308

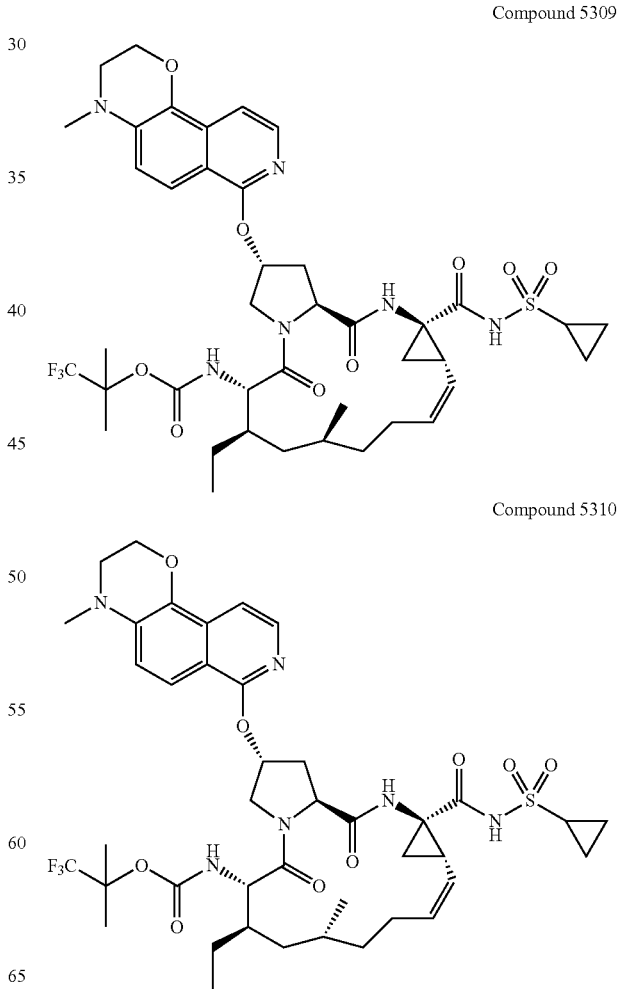

Compound 5309

Compound 5310

Compounds 5309 and 5310 were prepared using the intermediates described herein and by following the general procedure described for the synthesis of Compound 3117:

Compound 5309: 1,1,1-trifluoro-2-methylpropan-2-yl ((2R,6S,7R,9S,13aS,14aR,16aS,Z)-14a-((cyclopropylsulfonyl)carbamoyl)-7-ethyl-9-methyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 863.5 (M⁺+1).

Compound 5310: 1,1,1-trifluoro-2-methylpropan-2-yl ((2R,6S,7R,9R,13aS,14aR,16aS,Z)-14a-((cyclopropylsulfonyl)carbamoyl)-7-ethyl-9-methyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (500 MHz, DMSO-d₆) δ 11.18 (s, 1H), 8.97 (br. s., 1H), 7.83 (d, J=6.1 Hz, 2H), 7.58 (d, J=9.2 Hz, 1H), 7.25 (d, J=6.1 Hz, 1H), 7.09 (d, J=9.2 Hz, 1H), 5.81 (br. s., 1H), 5.52 (br. s., 1H), 5.07 (br. s., 1H), 4.48 (d, J=9.8 Hz, 2H), 4.43-4.30 (m, 2H), 3.98-3.83 (m, 2H), 3.46-3.38 (m, 1H), 2.98 (s, 3H), 2.90 (s, 1H), 2.65-2.59 (m, 2H), 2.36-2.20 (m, 2H), 2.03-1.88 (m, 2H), 1.69-0.92 (m, 23H), 0.73 (m, 3H); MS m/z 863.5 (M⁺+1).

Compounds 5311 and 5312 were prepared using the intermediates described herein and by following the general procedure described for the synthesis of Compound 3117:

Compound 5311: 1,1,1,3,3,3-hexadeutero-2-(trifluoromethyl)propan-2-yl ((2R,6S,7R,9S,13aS,14aR,16aS,Z)-14a-((cyclopropylsulfonyl)carbamoyl)-7-ethyl-9-methyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 869.6 (M⁺+1).

Compound 5312: 1,1,1,3,3,3-hexadeutero-2-(trifluoromethyl)propan-2-yl ((2R,6S,7R,9R,13aS,14aR,16aS,Z)-14a-((cyclopropylsulfonyl)carbamoyl)-7-ethyl-9-methyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (500 MHz, DMSO-d₆) δ 11.19 (s, 1H), 9.01 (br. s., 1H), 7.83 (d, J=5.8 Hz, 2H), 7.57 (d, J=8.9 Hz, 1H), 7.25 (d, J=6.1 Hz, 1H), 7.09 (d, J=8.9 Hz, 1H), 5.81 (br. s., 1H), 5.53 (d, J=6.4 Hz, 1H), 5.06 (t, J=9.8 Hz, 1H), 4.55-4.42 (m, 2H), 4.42-4.30 (m, 2H), 3.94-3.84 (m, 2H), 3.46-3.37 (m, 2H), 2.98 (s, 3H), 2.93-2.86 (m, 1H), 2.72-2.57 (m, 2H), 2.35-2.23 (m, 2H), 2.01-1.85 (m, 2H), 1.60 (d, J=6.7 Hz, 1H), 1.55 (m, 1H), 1.52-1.29 (m, 5H), 1.25-1.05 (m, 3H), 1.05-0.88 (m, 6H), 0.73 (t, J=7.5 Hz, 3H); MS: MS m/z 869.6 (M⁺+1).

Preparation of Compound 5311 and Compound 5312

Preparation of Compound 5313 and Compound 5314

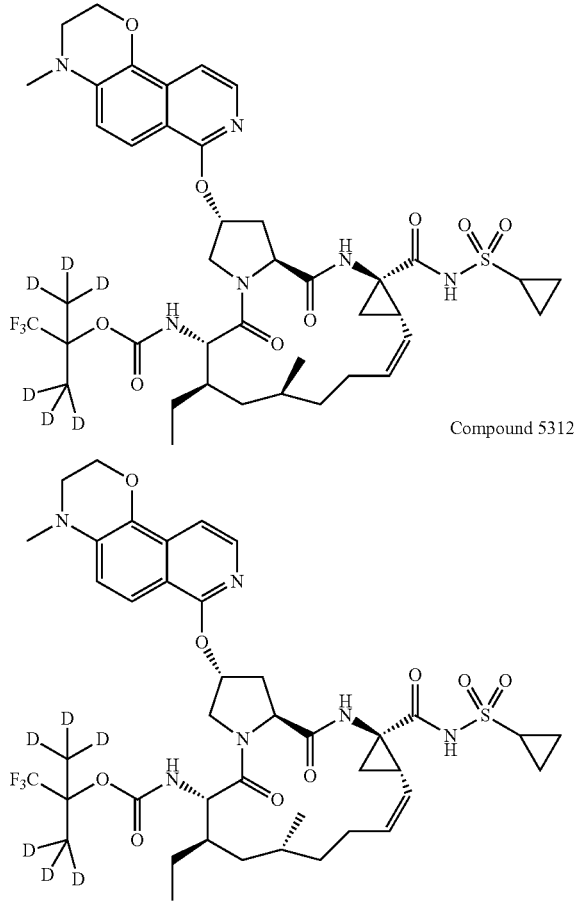

Compound 5311

Compound 5312

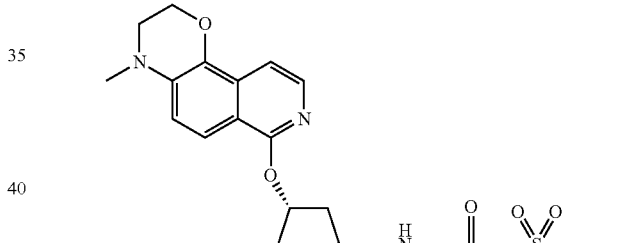

Compound 5313

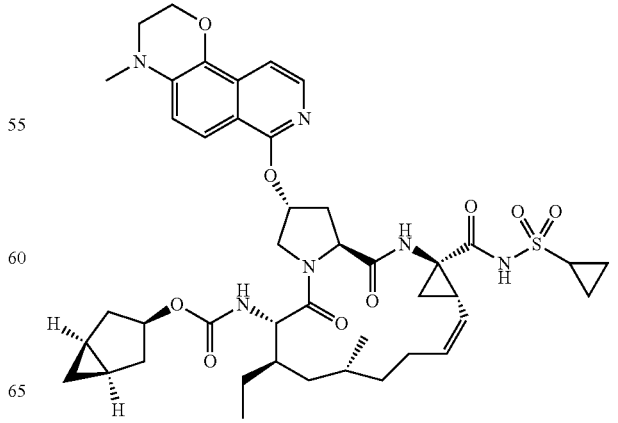

Compound 5314

Compounds 5313 and 5314 were prepared using the intermediates described herein and by following the general procedure described for the synthesis of Compound 3117:

Compound 5313: (1R,3r,5S)-bicyclo[3.1.0]hexan-3-yl ((2R,6S,7R,9S,13aS,14aR,16aS,Z)-14a-((cyclopropylsulfonyl)carbamoyl)-7-ethyl-9-methyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 833.5 (M$^+$+1).

Compound 5314: (1R,3r,5S)-bicyclo[3.1.0]hexan-3-yl ((2R,6S,7R,9R,13aS,14aR,16aS,Z)-14a-((cyclopropylsulfonyl)carbamoyl)-7-ethyl-9-methyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.18 (br. s., 1H), 8.95 (br. s., 1H), 7.82 (d, J=6.1 Hz, 1H), 7.58 (d, J=8.9 Hz, 1H), 7.39 (d, J=9.2 Hz, 1H), 7.26 (d, J=6.1 Hz, 1H), 7.12 (d, J=9.2 Hz, 1H), 5.80 (br. s., 1H), 5.51 (br. s., 1H), 5.08 (br. s., 1H), 4.66 (t, J=6.7 Hz, 1H), 4.51-4.31 (m, 4H), 4.06-3.83 (m, 2H), 3.46-3.38 (m, 2H), 2.99 (s, 3H), 2.90 (m, 1H), 2.75-2.57 (m, 2H), 2.29 (m, 2H), 2.03-1.87 (m, 3H), 1.82-1.74 (m, 1H), 1.58-0.92 (m, 20H), 0.73 (t, J=7.5 Hz, 3H), 0.42-0.31 (m, 2H); MS: MS m/z 833.5 (M$^+$+1).

Compounds 5315 and 5316 were prepared using the intermediates described herein and by following the general procedure described for the synthesis of Compound 3117:

Compound 5315: (2R,6S,7R,9S,13aS,14aR,16aS,Z)-6-(3-(tert-butyl)ureido)-N-(cyclopropylsulfonyl)-7-ethyl-9-methyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. MS: MS m/z 808.5 (M$^+$+1).

Compound 5316: (2R,6S,7R,9R,13aS,14aR,16aS,Z)-6-(3-(tert-butyl)ureido)-N-(cyclopropylsulfonyl)-7-ethyl-9-methyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (500 MHz, DMSO-d$_6$) δ 11.17 (br. s., 1H), 8.91 (br. s., 1H), 7.81 (d, J=6.1 Hz, 1H), 7.62 (d, J=9.2 Hz, 1H), 7.25 (d, J=6.4 Hz, 1H), 7.04 (d, J=9.2 Hz, 1H), 5.95 (d, J=9.5 Hz, 1H), 5.79 (br. s., 1H), 5.60 (s, 1H), 5.49 (br. s., 1H), 5.09 (br. s., 1H), 4.52 (d, J=9.5 Hz, 1H), 4.45-4.30 (m, 3H), 4.09 (t, J=10.2 Hz, 1H), 3.96-3.84 (m, 1H), 3.43-3.38 (m, 2H), 2.98 (s, 3H), 2.92-2.84 (m, 1H), 2.56 (m, 2H), 2.35-2.19 (m, 2H), 1.96-1.84 (m, 1H), 1.78-1.70 (m, 1H), 1.57-0.92 (m, 25H), 0.79 (t, J=7.3 Hz, 3H); MS: MS m/z 808.5 (M$^+$+1).

Preparation of Compound 5315 and Compound 5316

Compound 5315

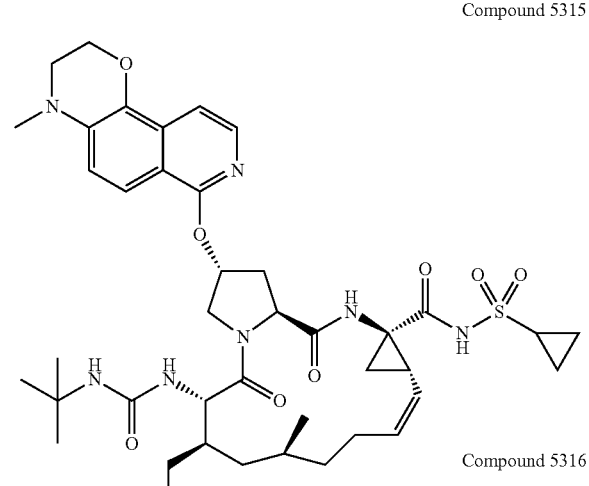

Compound 5316

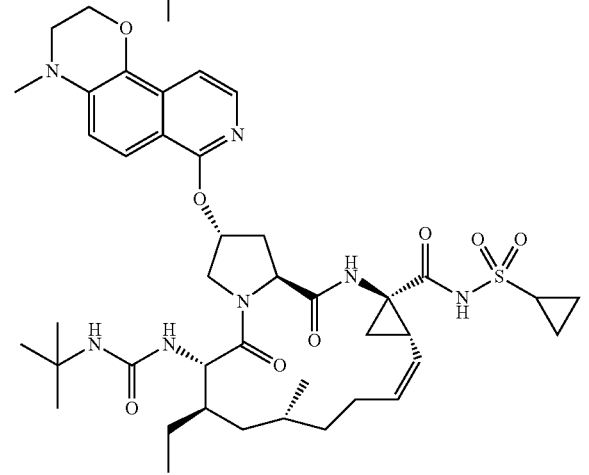

Preparation of Compound 5317 and Compound 5318

Compound 5317

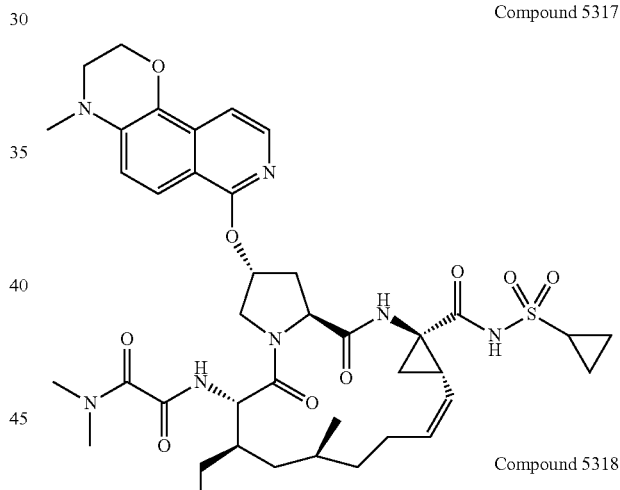

Compound 5318

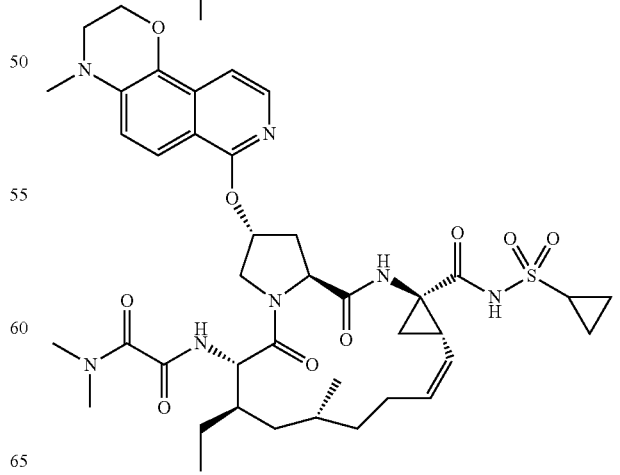

Compounds 5317 and 5318 were prepared using the intermediates described herein and by following the general procedure described for the synthesis of Compound 3117:

Compound 5317: N1-((2R,6S,7R,9S,13aS,14aR,16aS,Z)-14a-((cyclopropylsulfonyl)carbamoyl)-7-ethyl-9-methyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-N2,N2-dimethyloxalamide MS: MS m/z 808.5 (M$^+$+1).

Compound 5318: N1-((2R,6S,7R,9R,13aS,14aR,16aS,Z)-14a-((cyclopropylsulfonyl)carbamoyl)-7-ethyl-9-methyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-N2,N2-dimethyloxalamide $^1$H NMR (500 MHz, DMSO-d$_6$) δ 11.15 (br. s., 1H), 9.08-8.88 (m, 2H), 7.82 (d, J=6.1 Hz, 1H), 7.53 (d, J=8.9 Hz, 1H), 7.26 (d, J=6.1 Hz, 1H), 7.15 (d, J=9.2 Hz, 1H), 5.83 (br. s., 1H), 5.60-5.45 (m, 1H), 5.09 (t, J=9.8 Hz, 1H), 4.51-4.28 (m, 5H), 4.02 (dd, J=11.4, 3.8 Hz, 1H), 3.42 (dd, J=5.0, 3.2 Hz, 2H), 3.00 (s, 3H), 2.91 (d, J=4.9 Hz, 1H), 2.79 (s, 3H), 2.70 (s, 3H), 2.61 (dd, J=13.6, 6.9 Hz, 1H), 2.39-2.24 (m, 2H), 2.06 (t, J=10.5 Hz, 1H), 2.00-1.86 (m, 1H), 1.65-1.38 (m, 7H), 1.18-0.94 (m, 10H), 0.76 (t, J=7.5 Hz, 3H); MS: MS m/z 808.5 (M$^+$+1).

Preparation of Compound 5319 and Compound 5320

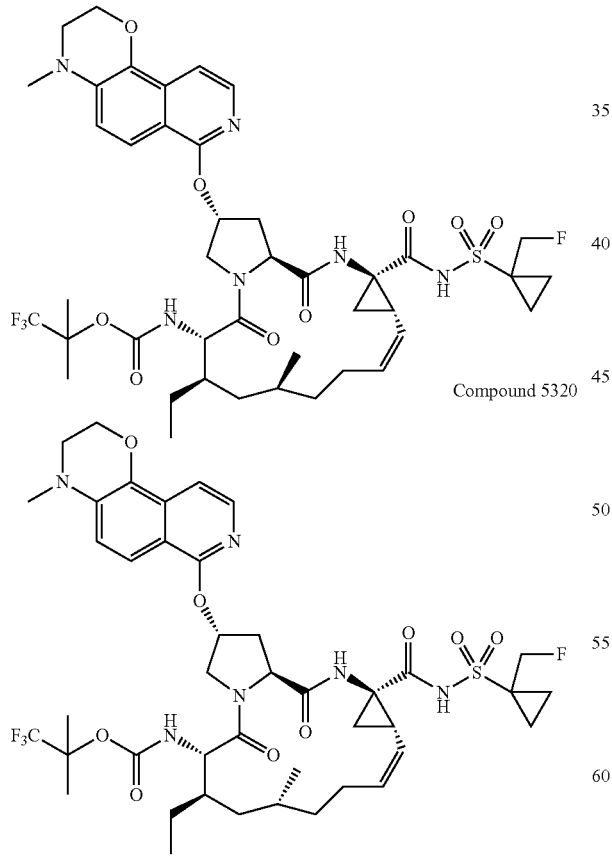

Compound 5319

Compound 5320

Compounds 5319 and 5320 were prepared using the intermediates described herein and by following the general procedure described for the synthesis of Compound 3117:

Compound 5319: 1,1,1-trifluoro-2-methylpropan-2-yl ((2R,6S,7R,9S,13aS,14aR,16aS,Z)-7-ethyl-14a-(((1-(fluoromethyl)cyclopropyl)sulfonyl)carbamoyl)-9-methyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 881.6 (M$^+$+1).

Compound 5320: 1,1,1-trifluoro-2-methylpropan-2-yl ((2R,6S,7R,9R,13aS,14aR,16aS,Z)-7-ethyl-14a-(((1-(fluoromethyl)cyclopropyl)sulfonyl)carbamoyl)-9-methyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.28 (s, 1H), 9.06 (br. s., 1H), 7.82 (d, J=6.1 Hz, 2H), 7.59 (d, J=8.9 Hz, 1H), 7.25 (d, J=6.1 Hz, 1H), 7.08 (d, J=9.2 Hz, 1H), 5.79 (br. s., 1H), 5.51 (m, 1H), 4.99 (t, J=10.1 Hz, 1H), 4.87-4.58 (m, 2H), 4.49 (d, J=11.6 Hz, 2H), 4.44-4.31 (m, 2H), 3.94-3.85 (m, 1H), 3.71 (dd, J=10.5, 8.4 Hz, 1H), 3.40 (m, 2H), 2.98 (s, 3H), 2.72-2.62 (m, 2H), 2.36-2.23 (m, 2H), 1.85 (m, 2H), 1.69 (m, 1H), 1.53 (m, 4H), 1.39 (m, 5H), 1.25 (m, 3H), 1.15 (s, 3H), 0.98-0.84 (m, 6H), 0.80-0.70 (m, 1H); MS: MS m/z 881.6 (M$^+$+1).

Preparation of Compound 5321

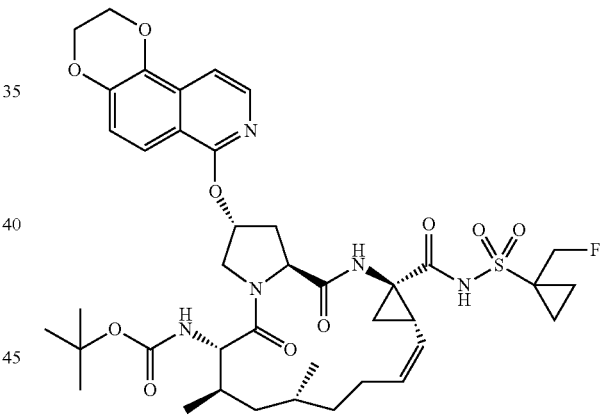

Compound 5321

Compound 5321 was prepared using the intermediates described herein and by following the general procedure described for the synthesis of Compound 3117:

Compound 5321: MS: tert-butyl ((2R,6S,7R,9R,13aS,14aR,16aS,Z)-2-((2,3-dihydro-[1,4]dioxino[2,3-f]isoquinolin-7-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.28 (s, 1H), 9.03 (s, 1H), 7.97 (d, J=6.1 Hz, 1H), 7.66 (d, J=8.9 Hz, 1H), 7.38 (d, J=6.1 Hz, 1H), 7.18 (d, J=8.2 Hz, 1H), 7.08 (d, J=8.9 Hz, 1H), 5.80 (br. s., 1H), 5.59-5.44 (m, 1H), 5.01-4.75 (m, 2H), 4.59 (d, J=8.2 Hz, 1H), 4.52-4.31 (m, 6H), 3.98-3.83 (m, 2H), 3.71 (dd, J=10.7, 8.2 Hz, 1H), 2.71-2.56 (m, 2H), 2.37-2.24 (m, 2H), 1.92-1.67 (m, 2H), 1.59-1.08 (m, 18H), 0.96-0.81 (m, 6H), 0.73 (t, J=12.5 Hz, 1H); MS m/z 814.4 (M$^+$+1).

Preparation of Compound 5322 and Compound 5323

Compound 5322

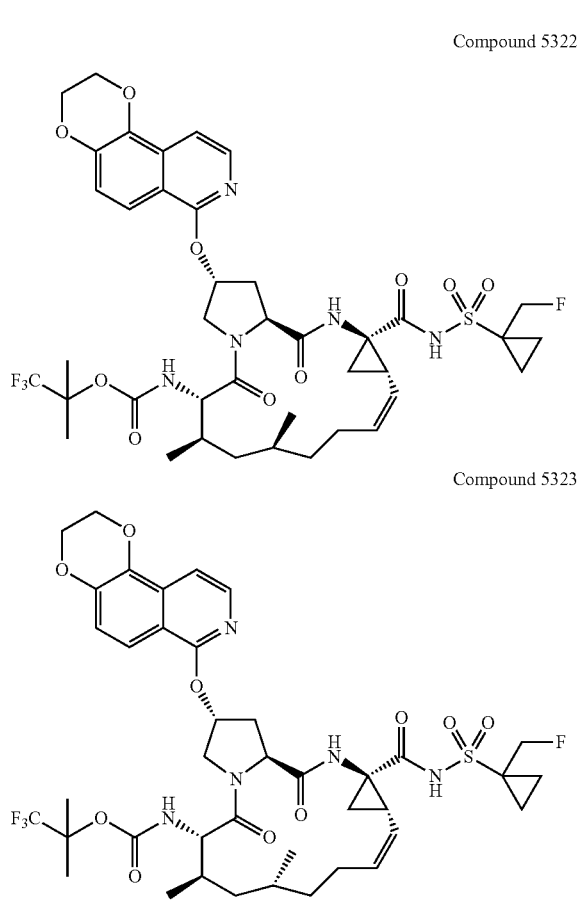 [SMILES: C[C@H]1CC/C=C\[C@@H]2C[C@@]2(C(=O)NS(=O)(=O)C2(CF)CC2)NC(=O)[C@@H]2C[C@@H](Oc3nccc4c5c(ccc34)OCCO5)CN2C(=O)[C@@H](NC(=O)OC(C)(C)C(F)(F)F)[C@H](C)C1 ; C[C@@H]1CC/C=C\[C@@H]2C[C@@]2(C(=O)NS(=O)(=O)C2(CF)CC2)NC(=O)[C@@H]2C[C@@H](Oc3nccc4c5c(ccc34)OCCO5)CN2C(=O)[C@@H](NC(=O)OC(C)(C)C(F)(F)F)[C@H](C)C1]

Compound 5323

Compounds 5322 and 5323 were prepared using the intermediates described herein and by following the general procedure described for the synthesis of Compound 3117:

Compound 5322: 1,1,1-trifluoro-2-methylpropan-2-yl ((2R,6S,7R,9S,13aS,14aR,16aS,Z)-2-((2,3-dihydro-[1,4]dioxino[2,3-f]isoquinolin-7-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 868.4 (M$^+$+1).

Compound 5323: 1,1,1-trifluoro-2-methylpropan-2-yl ((2R,6S,7R,9R,13aS,14aR,16aS,Z)-2-((2,3-dihydro-[1,4]dioxino[2,3-f]isoquinolin-7-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.28 (s, 1H), 9.06 (s, 1H), 7.98 (d, J=6.1 Hz, 2H), 7.63 (d, J=8.9 Hz, 1H), 7.38 (d, J=6.1 Hz, 1H), 7.13 (d, J=8.9 Hz, 1H), 5.81 (br. s., 1H), 5.59-5.40 (m, 1H), 4.99 (t, J=10.1 Hz, 1H), 4.86-4.76 (m, 1H), 4.64-4.30 (m, 7H), 3.94-3.87 (m, 1H), 3.70 (dd, J=10.7, 8.2 Hz, 1H), 2.69-2.56 (m, 2H), 2.38-2.25 (m, 2H), 1.96-1.77 (m, 2H), 1.74-1.64 (m, 1H), 1.53 (m, 4H), 1.46-1.31 (m, 6H), 1.30-1.19 (m, 2H), 1.12 (s, 3H), 0.98-0.87 (m, 6H), 0.75 (t, J=12.2 Hz, 1H); MS: MS m/z 868.4 (M$^+$+1).

Preparation of Compound 5324

Compound 5324

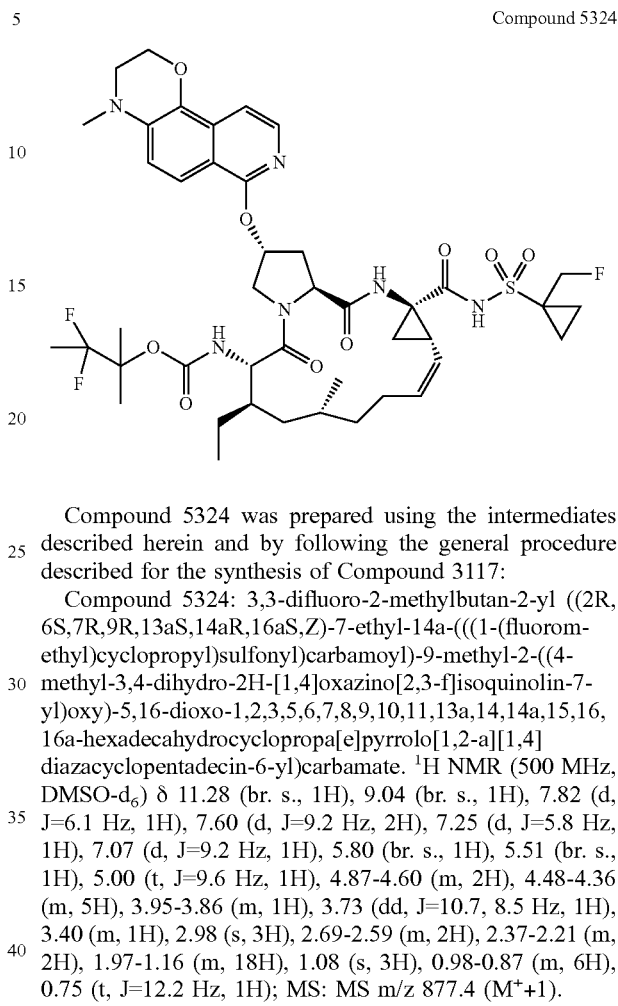

Compound 5324 was prepared using the intermediates described herein and by following the general procedure described for the synthesis of Compound 3117:

Compound 5324: 3,3-difluoro-2-methylbutan-2-yl ((2R,6S,7R,9R,13aS,14aR,16aS,Z)-7-ethyl-14a-(((1-(fluoromethyl)cyclopropyl)sulfonyl)carbamoyl)-9-methyl-2-((4-methyl-3,4-dihydro-2H-[1,4]oxazino[2,3-f]isoquinolin-7-yl)oxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.28 (br. s., 1H), 9.04 (br. s., 1H), 7.82 (d, J=6.1 Hz, 1H), 7.60 (d, J=9.2 Hz, 2H), 7.25 (d, J=5.8 Hz, 1H), 7.07 (d, J=9.2 Hz, 1H), 5.80 (br. s., 1H), 5.51 (br. s., 1H), 5.00 (t, J=9.6 Hz, 1H), 4.87-4.60 (m, 2H), 4.48-4.36 (m, 5H), 3.95-3.86 (m, 1H), 3.73 (dd, J=10.7, 8.5 Hz, 1H), 3.40 (m, 1H), 2.98 (s, 3H), 2.69-2.59 (m, 2H), 2.37-2.21 (m, 2H), 1.97-1.16 (m, 18H), 1.08 (s, 3H), 0.98-0.87 (m, 6H), 0.75 (t, J=12.2 Hz, 1H); MS: MS m/z 877.4 (M$^+$+1).

Preparation of Compound 5325 and Compound 5326

Compound 5325

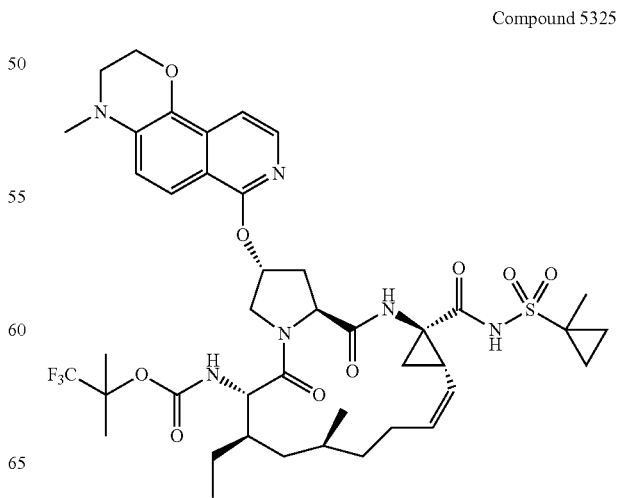

-continued

Compound 5326

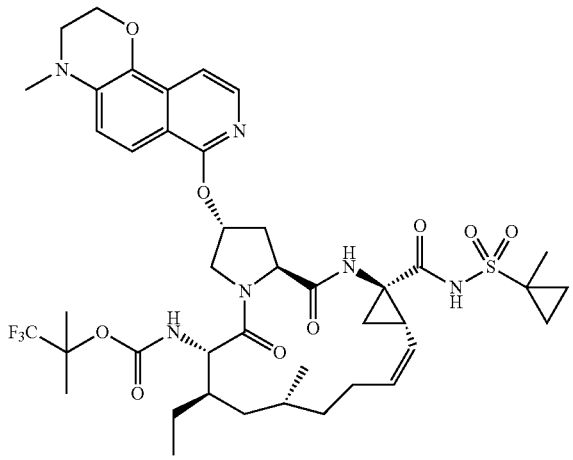

Compounds 5325 and 5326 were prepared using the intermediates described herein and by following the general procedure described for the synthesis of Compound 3117:

Compound 5325: 1,1,1-trifluoro-2-methylpropan-2-yl ((2R,6S,7R,9S,13aS,14aR,16aS,Z)-7-ethyl-9-methyl-2-((4-methyl-3,4-dihydro-2H-[1,4]oxazino[2,3-f]isoquinolin-7-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 877.5 (M$^+$+1).

Compound 5326: 1,1,1-trifluoro-2-methylpropan-2-yl ((2R,6S,7R,9R,13aS,14aR,16aS,Z)-7-ethyl-9-methyl-2-((4-methyl-3,4-dihydro-2H-[1,4]oxazino[2,3-f]isoquinolin-7-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.04 (br. s., 1H), 9.14 (br. s., 1H), 7.93-7.77 (m, 2H), 7.57 (d, J=9.2 Hz, 1H), 7.25 (d, J=6.1 Hz, 1H), 7.09 (d, J=8.9 Hz, 1H), 5.82 (br. s., 1H), 5.53 (d, J=4.9 Hz, 1H), 4.98 (m, 1H), 4.58-4.43 (m, 2H), 4.43-4.23 (m, 2H), 3.99-3.80 (m, 2H), 3.46-3.37 (m, 2H), 2.98 (s, 3H), 2.75-2.65 (m, 1H), 2.60 (d, J=7.0 Hz, 1H), 2.40-2.24 (m, 2H), 2.04-1.86 (m, 2H), 1.62 (m, 1H), 1.56-0.82 (m, 24H), 0.73 (t, J=7.5 Hz, 3H); MS: MS m/z 877.5 (M$^+$+1).

Preparation of Compound 5327 and Compound 5328

Compound 5327

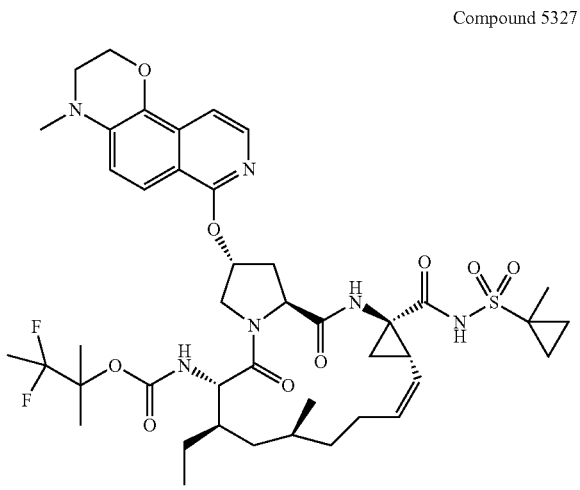

-continued

Compound 5328

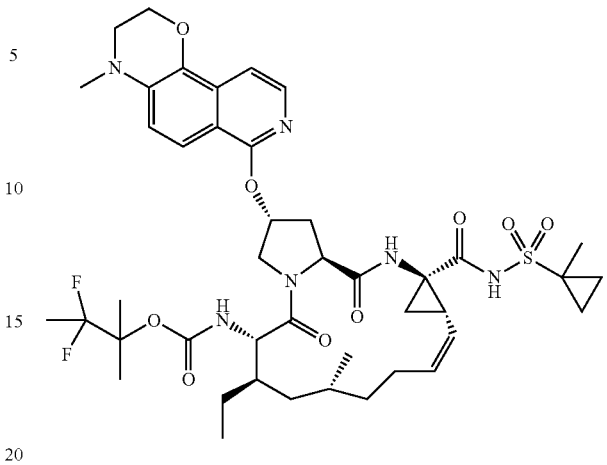

Compounds 5327 and 5328 were prepared using the intermediates described herein and by following the general procedure described for the synthesis of Compound 3117:

Compound 5327: 3,3-difluoro-2-methylbutan-2-yl ((2R,6S,7R,9S,13aS,14aR,16aS,Z)-7-ethyl-9-methyl-2-((4-methyl-3,4-dihydro-2H-[1,4]oxazino[2,3-f]isoquinolin-7-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 873.5 (M$^+$+1).

Compound 5328: 3,3-difluoro-2-methylbutan-2-yl ((2R,6S,7R,9R,13aS,14aR,16aS,Z)-7-ethyl-9-methyl-2-((4-methyl-3,4-dihydro-2H-[1,4]oxazino[2,3-f]isoquinolin-7-yl)oxy)-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.04 (br. s., 1H), 9.11 (br. s., 1H), 7.82 (d, J=6.1 Hz, 1H), 7.69-7.51 (m, 2H), 7.25 (d, J=6.1 Hz, 1H), 7.08 (d, J=9.2 Hz, 1H), 5.82 (br. s., 1H), 5.52 (m, 1H), 4.99 (m, 1H), 4.59-4.43 (m, 2H), 4.43-4.23 (m, 2H), 4.04-3.85 (m, 2H), 3.47-3.37 (m, 2H), 2.98 (s, 3H), 2.79-2.68 (m, 1H), 2.59 (m, 1H), 2.35-2.21 (m, 2H), 2.05-1.85 (m, 2H), 1.62-1.16 (m, 19H), 1.01-0.92 (m, 9H), 0.74 (s, 3H); MS: MS m/z 873.5 (M$^+$+1).

Preparation of Compound 5329 and Compound 5330

Compound 5329

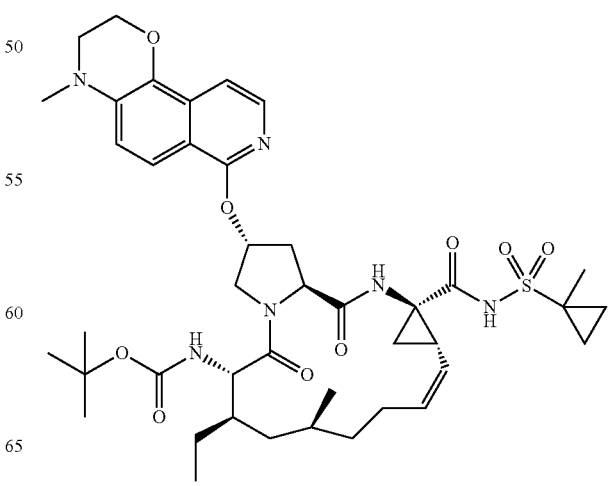

Compound 5330

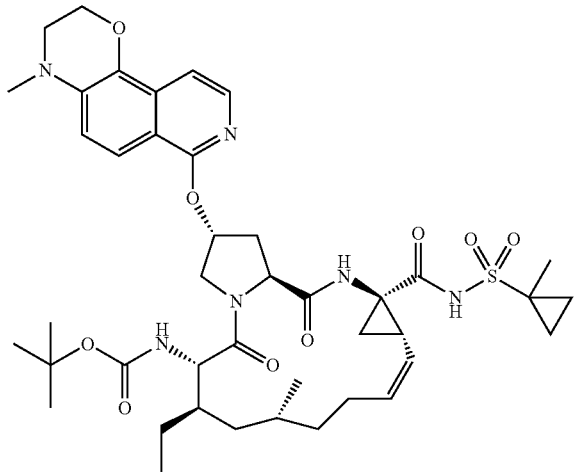

Compounds 5329 and 5330 were prepared using the intermediates described herein and by following the general procedure described for the synthesis of Compound 3117:

Compound 5329: tert-butyl ((2R,6S,7R,9S,13aS,14aR, 16aS,Z)-7-ethyl-9-methyl-2-((4-methyl-3,4-dihydro-2H-[1, 4]oxazino[2,3-f]isoquinolin-7-yl)oxy)-14a-(((1-methylcyclopropyl)sulfonyl)carbamoyl)-5,16-dioxo-1,2,3,5,6,7,8,9, 10,11,13a,14,14a,15,16,16a-hexadecahydrocyclopropa[e] pyrrolo[1,2-a][1,4]diazacyclopentadecin-6-yl)carbamate. MS: MS m/z 823.5 (M$^+$+1).

Compound 5330: tert-butyl ((2R,6S,7R,9R,13aS,14aR, 16aS,Z)-7-ethyl-9-methyl-2-((4-methyl-3,4-dihydro-2H-[1, 4]oxazino[2,3-f]isoquinolin-7-yl)oxy)-14a-(((1-methylcyclopropyl)sulfonyl)carbamoyl)-5,16-dioxo-1,2,3,5,6,7,8,9, 10,11,13a,14,14a,15,16,16a-hexadecahydrocyclopropa[e] pyrrolo[1,2-a][1,4]diazacyclopentadecin-6-yl)carbamate. $^1$H NMR (500 MHz, DMSO-d$_6$) δ 11.04 (br. s., 1H), 9.09 (br. s., 1H), 7.82 (d, J=6.1 Hz, 1H), 7.60 (d, J=9.2 Hz, 1H), 7.29-7.13 (m, 2H), 7.06 (d, J=8.9 Hz, 1H), 5.81 (br. s., 1H), 5.52 (m, 1H), 4.98 (m, 1H), 4.64-4.29 (m, 4H), 4.01-3.76 (m, 2H), 3.40 (d, J=2.7 Hz, 2H), 2.98 (s, 3H), 2.80-2.55 (m, 2H), 2.40-2.24 (m, 2H), 1.99-1.85 (m, 2H), 1.70-1.24 (m, 12H), 1.17 (s, 9H), 1.05 (m, 2H), 0.93 (m, 5H), 0.74 (s, 3H); MS: MS m/z 823.5 (M$^+$+1).

Preparation of Compound 5331 and Compound 5332

Compound 5331

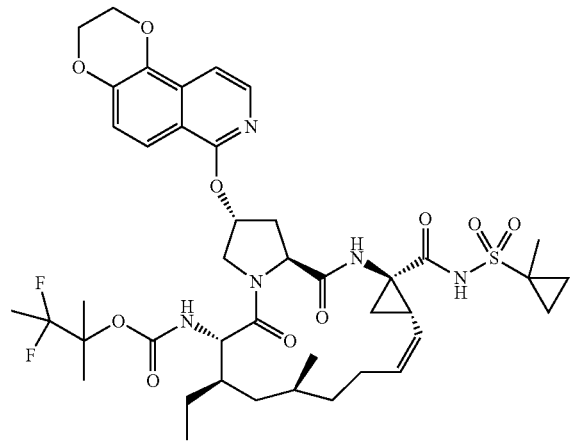

Compound 5332

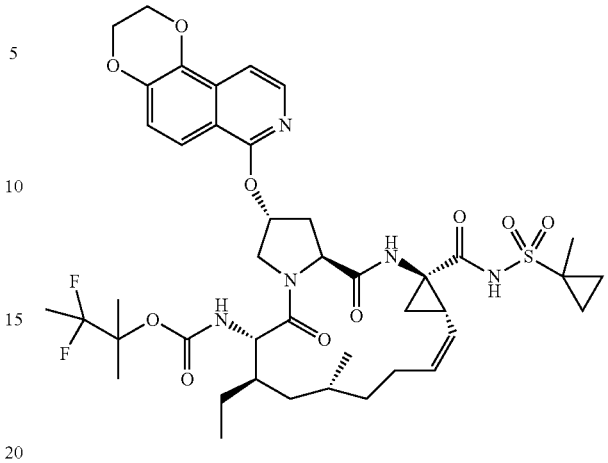

Compounds 5331 and 5332 were prepared using the intermediates described herein and by following the general procedure described for the synthesis of Compound 3117:

Compound 5331: 3,3-difluoro-2-methylbutan-2-yl ((2R, 6S,7R,9S,13aS,14aR,16aS,Z)-2-((2,3-dihydro-[1,4]dioxino [2,3-f]isoquinolin-7-yl)oxy)-7-ethyl-9-methyl-14a-(((1-methylcyclopropyl)sulfonyl)carbamoyl)-5,16-dioxo-1,2,3, 5,6,7,8,9,10,11,13a,14,14a,15,16,16a-hexadecahydrocyclopropa[e]pyrrolo[1,2-a][1,4] diazacyclopentadecin-6-yl)carbamate. MS: MS m/z 860.8 (M$^+$+1).

Compound 5332: 3,3-difluoro-2-methylbutan-2-yl ((2R, 6S,7R,9R,13aS,14aR,16aS,Z)-2-((2,3-dihydro-[1,4]dioxino [2,3-f]isoquinolin-7-yl)oxy)-7-ethyl-9-methyl-14a-(((1-methylcyclopropyl)sulfonyl)carbamoyl)-5,16-dioxo-1,2,3, 5,6,7,8,9,10,11,13a,14,14a,15,16,16a-hexadecahydrocyclopropa[e]pyrrolo[1,2-a][1,4] diazacyclopentadecin-6-yl)carbamate. $^1$H NMR (500 MHz, DMSO-d$_6$) δ 11.04 (s, 1H), 9.11 (s, 1H), 7.98 (d, J=5.8 Hz, 1H), 7.73-7.55 (m, 2H), 7.39 (d, J=6.1 Hz, 1H), 7.12 (d, J=8.9 Hz, 1H), 5.84 (br. s., 1H), 5.62-5.44 (m, 1H), 4.98 (t, J=9.9 Hz, 1H), 4.60-4.27 (m, 6H), 3.98-3.81 (m, 2H), 2.79-2.57 (m, 2H), 2.39-2.22 (m, 2H), 1.93 (d, J=9.8 Hz, 2H), 1.69-1.09 (m, 20H), 1.02-0.84 (m, 8H), 0.74 (t, J=7.5 Hz, 3H); MS: MS m/z 860.8 (M$^+$+1).

Preparation of Compound 5333 and Compound 5334

Compound 5333

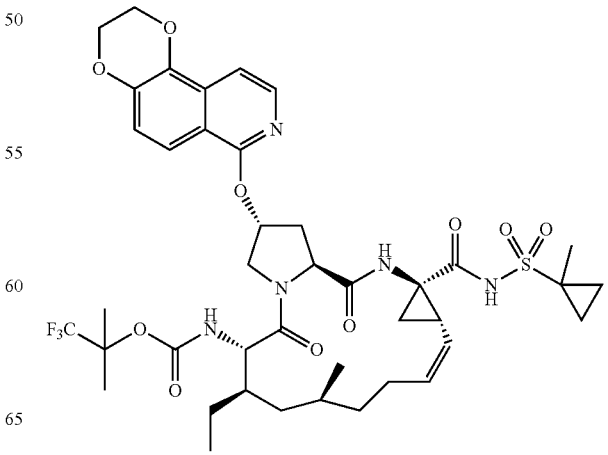

-continued

Compound 5334

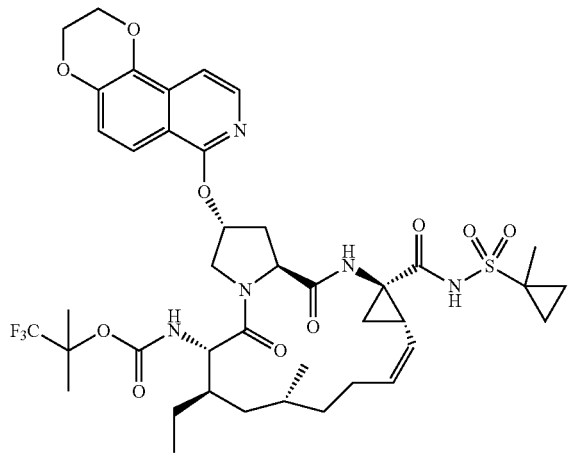

Compounds 5333 and 5334 were prepared using the intermediates described herein and by following the general procedure described for the synthesis of Compound 3117:

Compound 5333: 1,1,1-trifluoro-2-methylpropan-2-yl ((2R,6S,7R,9S,13aS,14aR,16aS,Z)-2-((2,3-dihydro-[1,4]dioxino[2,3-f]isoquinolin-7-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 864.4 (M$^+$+1).

Compound 5334: 1,1,1-trifluoro-2-methylpropan-2-yl ((2R,6S,7R,9R,13aS,14aR,16aS,Z)-2-((2,3-dihydro-[1,4]dioxino[2,3-f]isoquinolin-7-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.03 (s, 1H), 9.14 (s, 1H), 7.98 (d, J=5.8 Hz, 1H), 7.86 (d, J=8.2 Hz, 1H), 7.61 (d, J=8.9 Hz, 1H), 7.39 (d, J=5.8 Hz, 1H), 7.13 (d, J=8.9 Hz, 1H), 5.84 (br. s., 1H), 5.61-5.48 (m, 1H), 4.98 (t, J=10.1 Hz, 1H), 4.60-4.32 (m, 6H), 4.03-3.84 (m, 2H), 2.82-2.58 (m, 2H), 2.39-2.26 (m, 2H), 2.05-1.84 (m, 2H), 1.66-0.97 (m, 21H), 0.95-0.87 (m, 4H), 0.73 (t, J=7.5 Hz, 3H); MS: MS m/z 864.4 (M$^+$+1).

Preparation of Compound 5335 and Compound 5336

Compound 5335

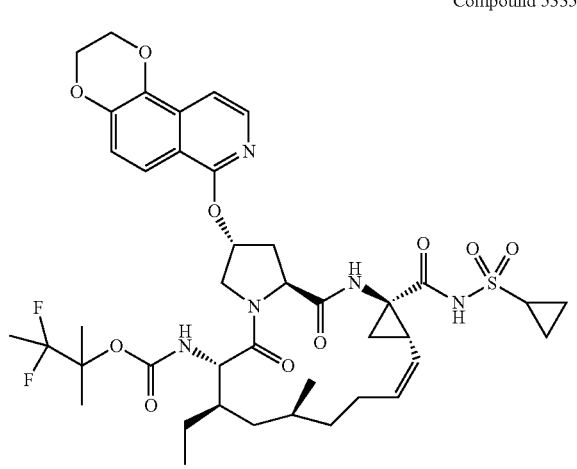

Compound 5336

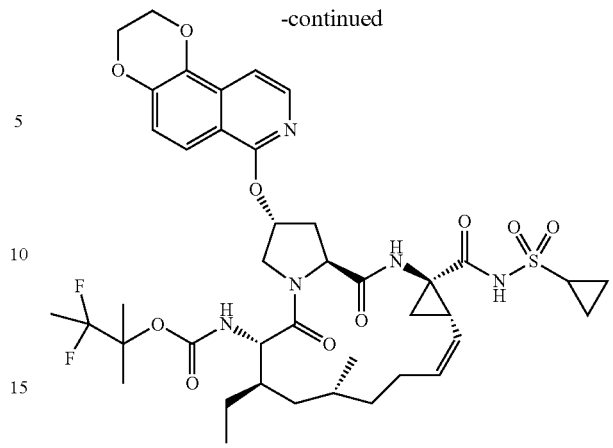

Compounds 5335 and 5336 were prepared using the intermediates described herein and by following the general procedure described for the synthesis of Compound 3117:

Compound 5335: 3,3-difluoro-2-methylbutan-2-yl ((2R,6S,7R,9S,13aS,14aR,16aS,Z)-14a-((cyclopropylsulfonyl)carbamoyl)-2-((2,3-dihydro-[1,4]dioxino[2,3-f]isoquinolin-7-yl)oxy)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 846.5 (M$^+$+1).

Compound 5336: 3,3-difluoro-2-methylbutan-2-yl ((2R,6S,7R,9R,13aS,14aR,16aS,Z)-14a-((cyclopropylsulfonyl)carbamoyl)-2-((2,3-dihydro-[1,4]dioxino[2,3-f]isoquinolin-7-yl)oxy)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.19 (s, 1H), 8.99 (s, 1H), 7.98 (d, J=5.8 Hz, 1H), 7.70-7.55 (m, 2H), 7.39 (d, J=6.1 Hz, 1H), 7.12 (d, J=9.2 Hz, 1H), 5.82 (br. s., 1H), 5.62-5.45 (m, 1H), 5.06 (t, J=9.6 Hz, 1H), 4.62-4.29 (m, 6H), 4.02-3.81 (m, 2H), 2.96-2.88 (m, 1H), 2.75-2.59 (m, 2H), 2.36-2.22 (m, 2H), 1.93 (d, J=6.4 Hz, 2H), 1.66-1.33 (m, 10H), 1.28 (s, 3H), 1.24-0.88 (m, 12H), 0.74 (t, J=7.3 Hz, 3H); MS: MS m/z 846.5 (M$^+$+1).

Preparation of Compound 5337 and Compound 5338

Compound 5337

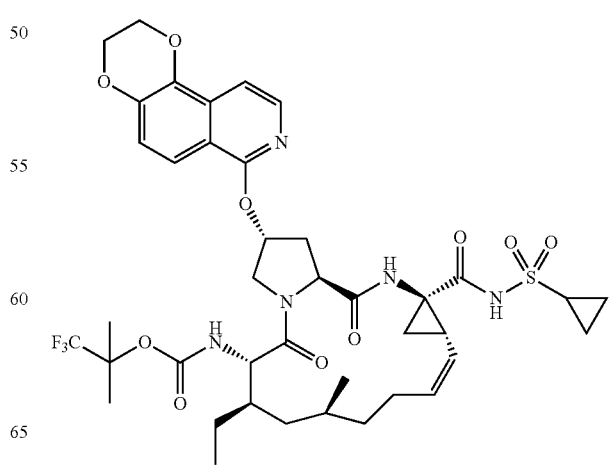

-continued

Compound 5338

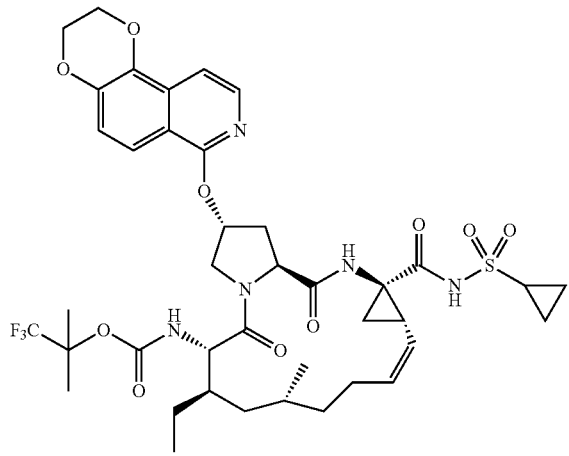

Compounds 5337 and 5338 were prepared using the intermediates described herein and by following the general procedure described for the synthesis of Compound 3117:

Compound 5337: 1,1,1-trifluoro-2-methylpropan-2-yl ((2R,6S,7R,9S,13aS,14aR,16aS,Z)-14a-((cyclopropylsulfonyl)carbamoyl)-2-((2,3-dihydro-[1,4]dioxino[2,3-f]isoquinolin-7-yl)oxy)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 850.7 (M$^+$+1).

Compound 5338: 1,1,1-trifluoro-2-methylpropan-2-yl ((2R,6S,7R,9R,13aS,14aR,16aS,Z)-14a-((cyclopropylsulfonyl)carbamoyl)-2-((2,3-dihydro-[1,4]dioxino[2,3-f]isoquinolin-7-yl)oxy)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.18 (s, 1H), 9.01 (s, 1H), 8.06-7.76 (m, 2H), 7.61 (d, J=8.9 Hz, 1H), 7.39 (d, J=5.8 Hz, 1H), 7.13 (d, J=8.9 Hz, 1H), 5.82 (br. s., 1H), 5.61-5.45 (m, 1H), 5.05 (t, J=9.9 Hz, 1H), 4.61-4.29 (m, 6H), 3.97-3.77 (m, 2H), 3.00-2.86 (m, 1H), 2.80-2.57 (m, 2H), 2.31 (ddd, J=13.9, 10.2, 4.0 Hz, 2H), 2.04-1.89 (m, 2H), 1.69-1.27 (m, 10H), 1.20-0.85 (m, 12H), 0.73 (t, J=7.5 Hz, 3H); MS: MS m/z 850.7 (M$^+$+1).

Preparation of Compound 5339 and Compound 5340

Compound 5339

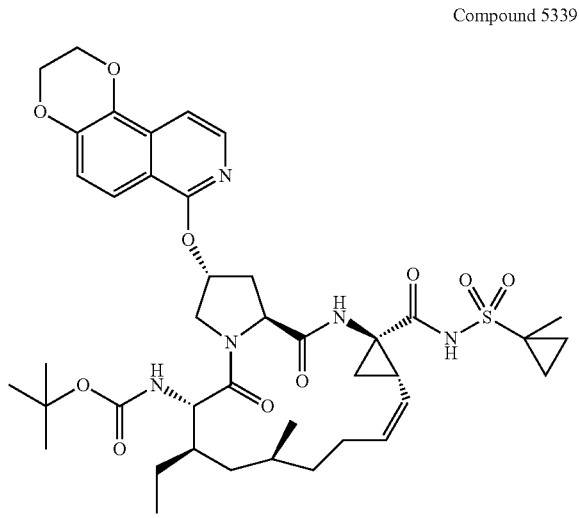 [SMILES: CC[C@@H]1C[C@H](C)CC/C=C\[C@@H]2C[C@@]2(C(=O)NS(=O)(=O)C2CC2)NC(=O)[C@@H]2C[C@@H](Oc3nccc4c5c(ccc34)OCCO5)CN2C(=O)[C@H]1NC(=O)OC(C)(C)C]

-continued

Compound 5340

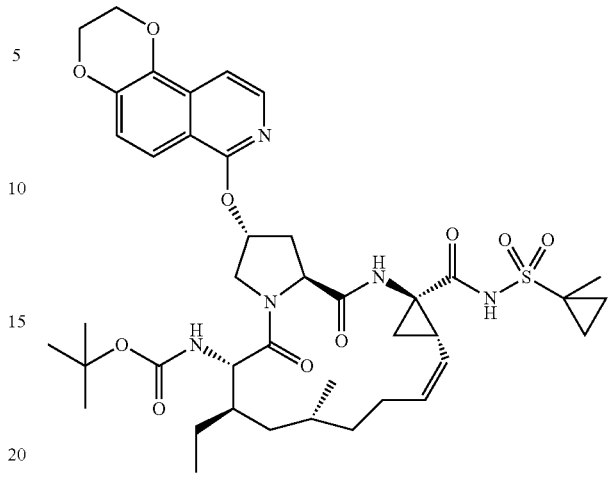

Compounds 5339 and 5340 were prepared using the intermediates described herein and by following the general procedure described for the synthesis of Compound 3117:

Compound 5339: tert-butyl ((2R,6S,7R,9S,13aS,14aR,16aS,Z)-2-((2,3-dihydro-[1,4]dioxino[2,3-f]isoquinolin-7-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 810.5 (M$^+$+1).

Compound 5340: tert-butyl ((2R,6S,7R,9R,13aS,14aR,16aS,Z)-2-((2,3-dihydro-[1,4]dioxino[2,3-f]isoquinolin-7-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.04 (s, 1H), 9.10 (s, 1H), 7.97 (d, J=5.8 Hz, 1H), 7.63 (d, J=8.9 Hz, 1H), 7.38 (d, J=6.1 Hz, 1H), 7.19 (d, J=8.9 Hz, 1H), 7.09 (d, J=9.2 Hz, 1H), 5.83 (br. s., 1H), 5.59-5.46 (m, 1H), 4.97 (t, J=9.9 Hz, 1H), 4.61 (d, J=11.3 Hz, 1H), 4.52-4.29 (m, 6H), 3.92 (t, J=5.2 Hz, 2H), 2.81-2.56 (m, 2H), 2.42-2.21 (m, 2H), 1.93 (t, J=5.8 Hz, 2H), 1.68-0.83 (m, 27H), 0.73 (s, 3H); MS: MS m/z 810.5 (M$^+$+1).

Preparation of Compound 5341

Compound 5341

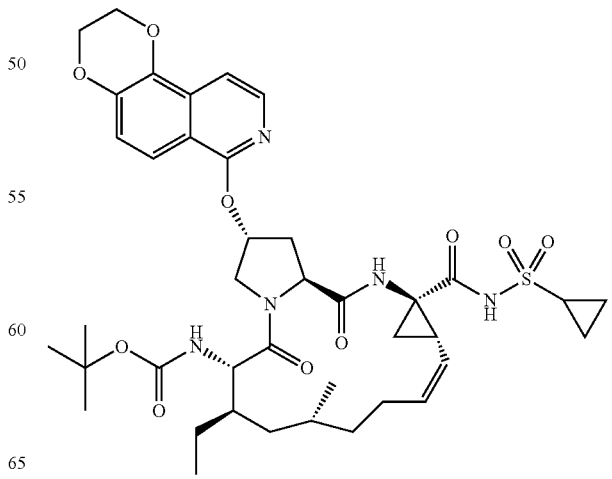

Compound 5341 was prepared using the intermediates described herein and by following the general procedure described for the synthesis of Compound 3117:

Compound 5341: tert-butyl ((2R,6S,7R,9R,13aS,14aR,16aS,Z)-14a-((cyclopropylsulfonyl)carbamoyl)-2-((2,3-dihydro-[1,4]dioxino[2,3-f]isoquinolin-7-yl)oxy)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-$d_6$) δ 11.18 (s, 1H), 8.97 (br. s., 1H), 7.97 (d, J=6.1 Hz, 1H), 7.63 (d, J=8.9 Hz, 1H), 7.38 (d, J=6.1 Hz, 1H), 7.19 (d, J=8.5 Hz, 1H), 7.09 (d, J=8.9 Hz, 1H), 5.81 (br. s., 1H), 5.53 (d, J=6.7 Hz, 1H), 5.05 (t, J=10.1 Hz, 1H), 4.60 (d, J=11.6 Hz, 1H), 4.42 (dd, J=20.0, 3.8 Hz, 6H), 3.98-3.79 (m, 2H), 2.96-2.86 (m, 1H), 2.74-2.58 (m, 2H), 2.35-2.23 (m, 2H), 1.92 (m, 2H), 1.66-1.31 (m, 7H), 1.14 (m, 10H), 1.07-0.90 (m, 7H), 0.73 (t, J=7.5 Hz, 3H); MS: MS m/z 796.5 (M$^+$+1).

Preparation of Compound 5342

Compound 5342

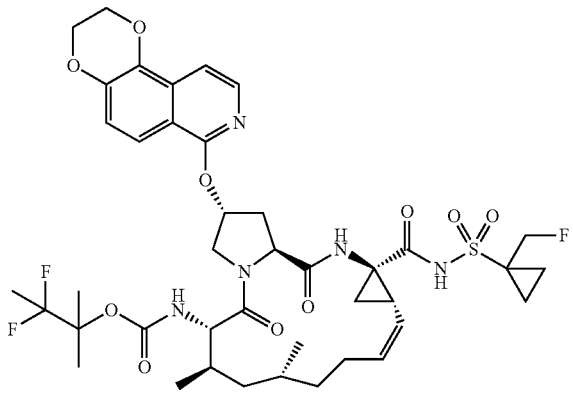

Compound 5342 was prepared using the intermediates described herein and by following the general procedure described for the synthesis of Compound 3117:

Compound 5342: 3,3-difluoro-2-methylbutan-2-yl ((2R,6S,7R,9R,13aS,14aR,16aS,Z)-2-((2,3-dihydro-[1,4]dioxino[2,3-f]isoquinolin-7-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-$d_6$) δ 11.28 (br. s., 1H), 9.04 (br. s., 1H), 7.98 (d, J=5.8 Hz, 1H), 7.68-7.54 (m, 2H), 7.38 (d, J=5.8 Hz, 1H), 7.11 (d, J=8.9 Hz, 1H), 5.81 (br. s., 1H), 5.51 (br. s., 1H), 5.00 (br. s., 1H), 4.90-4.57 (m, 2H), 4.55-4.27 (m, 6H), 3.96-3.84 (m, 1H), 3.71 (dd, J=10.4, 8.5 Hz, 1H), 2.73-2.56 (m, 2H), 2.39-2.26 (m, 2H), 1.98-1.11 (m, 18H), 1.04 (s, 3H), 0.96-0.86 (m, 6H), 0.75 (t, J=12.1 Hz, 3H); MS: MS m/z 864.4 (M$^+$+1).

Preparation of Compound 5343 and Compound 5344

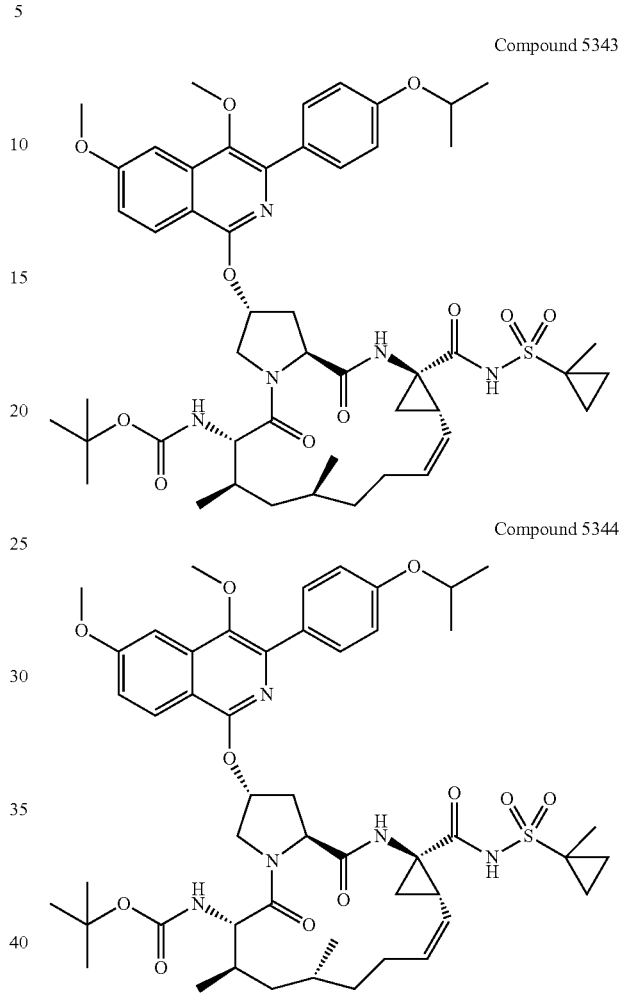

Compound 5343

Compound 5344

Compounds 5343 and 5344 were prepared using the intermediates described herein and by following the general procedure described for the synthesis of Compound 3117:

Compound 5343: tert-butyl ((2R,6S,7R,9S,13aS,14aR,16aS,Z)-2-((3-(4-isopropoxyphenyl)-4,6-dimethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 932.6 (M$^+$+1).

Compound 5344: tert-butyl ((2R,6S,7R,9R,13aS,14aR,16aS,Z)-2-((3-(4-isopropoxyphenyl)-4,6-dimethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-$d_6$) δ 11.08 (br. s., 1H), 9.08 (br. s., 1H), 8.11 (d, J=8.5 Hz, 2H), 8.04 (d, J=9.2 Hz, 1H), 7.34 (d, J=2.4 Hz, 1H), 7.20 (d, J=7.9 Hz, 1H), 7.13 (dd, J=9.0, 2.3 Hz, 1H), 7.06 (d, J=8.5 Hz, 1H), 5.86 (br. s., 1H), 5.53 (br. s., 1H), 4.98 (br. s., 1H), 4.73 (dt, J=12.1, 5.9 Hz, 1H), 4.66-4.45 (m, 2H), 4.00-3.87 (m, 4H), 3.81-3.70 (m, 1H), 3.62 (s, 3H), 2.77-2.61 (m, 2H), 2.41-2.25 (m, 2H), 2.00-1.08 (m, 28H), 1.00-0.83 (m, 8H), 0.74 (m, 1H); MS: MS m/z 932.6 (M⁺+1).

Preparation of Compound 5345 and Compound 5346

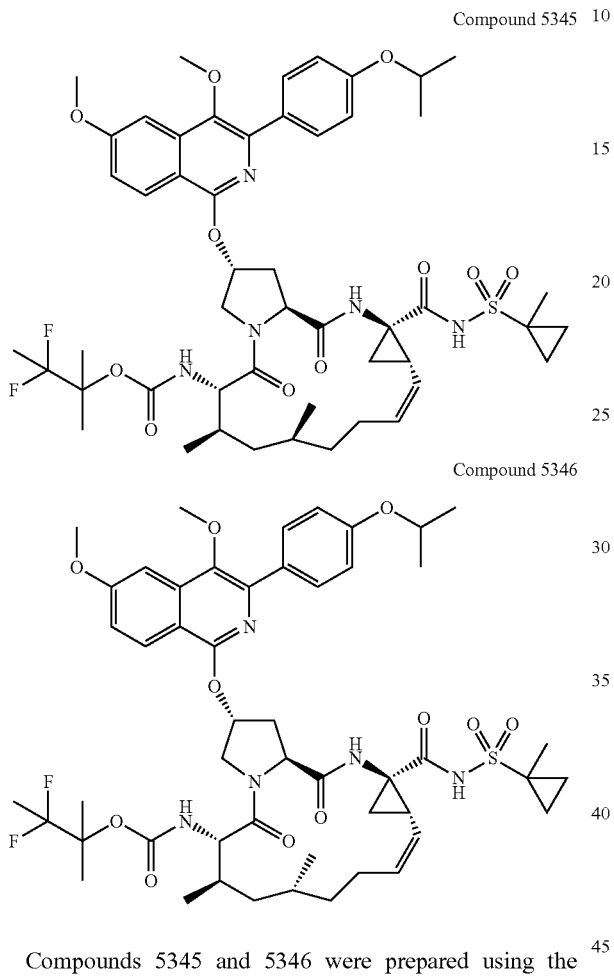

Compound 5345

Compound 5346

Compounds 5345 and 5346 were prepared using the intermediates described herein and by following the general procedure described for the synthesis of Compound 3117:

Compound 5345: 3,3-difluoro-2-methylbutan-2-yl ((2R,6S,7R,9S,13aS,14aR,16aS,Z)-2-((3-(4-isopropoxyphenyl)-4,6-dimethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 982.6 (M⁺+1).

Compound 5346: 3,3-difluoro-2-methylbutan-2-yl ((2R,6S,7R,9R,13aS,14aR,16aS,Z)-2-((3-(4-isopropoxyphenyl)-4,6-dimethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (500 MHz, DMSO-d₆) δ 11.07 (s, 1H), 9.09 (br. s., 1H), 8.23-7.92 (m, 3H), 7.64 (d, J=7.9 Hz, 1H), 7.35 (s, 1H), 7.15 (d, J=8.9 Hz, 1H), 7.07 (d, J=8.2 Hz, 2H), 5.88 (br. s., 1H), 5.54 (d, J=6.1 Hz, 1H), 4.99 (t, J=9.6 Hz, 1H), 4.83-4.69 (m, 1H), 4.64-

4.47 (m, 2H), 3.97 (m, 4H), 3.75 (t, J=9.6 Hz, 1H), 3.63 (s, 3H), 2.79-2.62 (m, 2H), 2.40-2.29 (m, 2H), 1.98-1.10 (m, 25H), 1.05 (m, 3H), 0.92 (m, 8H), 0.77 (t, J=12.2 Hz, 1H); MS: MS m/z 982.6 (M⁺+1).

Preparation of Compound 5347 and Compound 5348

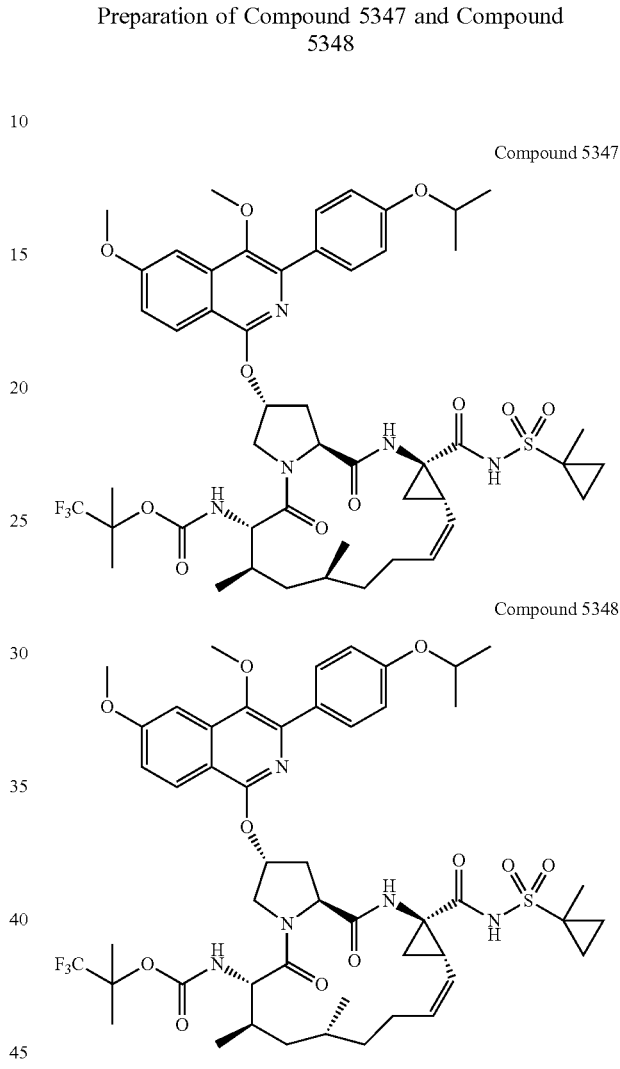

Compound 5347

Compound 5348

Compounds 5347 and 5348 were prepared using the intermediates described herein and by following the general procedure described for the synthesis of Compound 3117:

Compound 5347: 1,1,1-trifluoro-2-methylpropan-2-yl ((2R,6S,7R,9S,13aS,14aR,16aS,Z)-2-((3-(4-isopropoxyphenyl)-4,6-dimethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 986.5 (M⁺+1).

Compound 5348: 1,1,1-trifluoro-2-methylpropan-2-yl ((2R,6S,7R,9R,13aS,14aR,16aS,Z)-2-((3-(4-isopropoxyphenyl)-4,6-dimethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (500 MHz, DMSO-d₆) δ 11.06 (br. s., 1H), 9.11 (br. s., 1H), 8.12 (m, 2H), 8.01 (d, J=9.2 Hz, 1H), 7.83 (d, J=9.8 Hz, 1H), 7.35 (d, J=2.4 Hz, 1H), 7.16 (dd, J=9.2, 2.4 Hz, 1H), 7.06 (d, J=8.9

Hz, 2H), 5.88 (br. s., 1H), 5.53 (br. s., 1H), 4.99 (br. s., 1H), 4.82-4.69 (m, 1H), 4.55 (m, 2H), 4.03-3.88 (m, 4H), 3.73 (dd, J=10.7, 8.2 Hz, 1H), 3.63 (s, 3H), 2.69 (m, 2H), 2.40-2.29 (m, 2H), 1.98-1.09 (m, 25H), 0.97-0.83 (m, 8H), 0.76 (br. s., 1H); MS: MS m/z 986.5 (M$^+$+1).

Preparation of Compound 5349 and Compound 5350

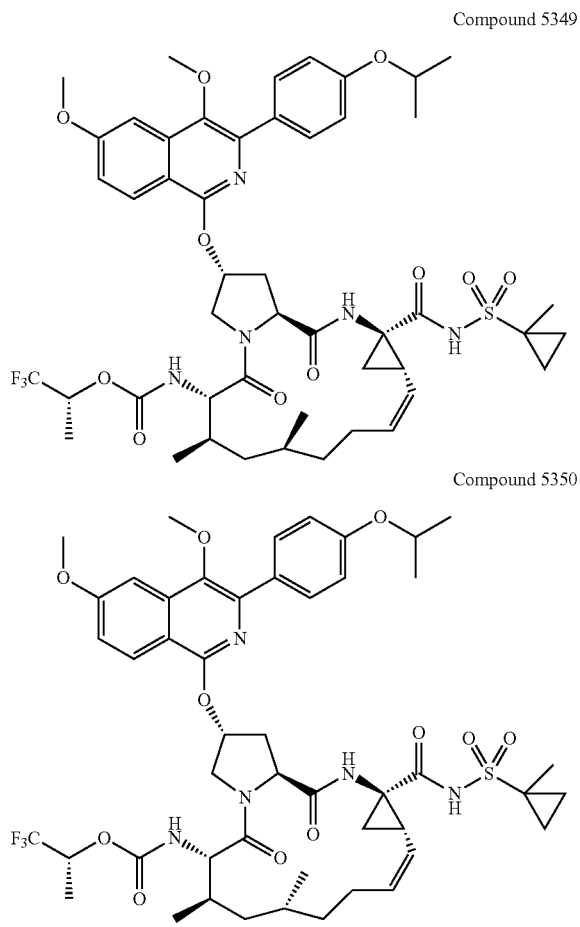 [SMILES: COc1ccc2c(O[C@@H]3C[C@H]4C(=O)N[C@]5(C(=O)NS(=O)(=O)C6(C)CC6)C[C@H]5/C=C\CC[C@H](C)C[C@@H](C)[C@H](NC(=O)O[C@H](C)C(F)(F)F)C(=O)N4C3)nc(-c3ccc(OC(C)C)cc3)c(OC)c2c1 ; COc1ccc2c(O[C@@H]3C[C@H]4C(=O)N[C@]5(C(=O)NS(=O)(=O)C6(C)CC6)C[C@H]5/C=C\CC[C@@H](C)C[C@@H](C)[C@H](NC(=O)O[C@H](C)C(F)(F)F)C(=O)N4C3)nc(-c3ccc(OC(C)C)cc3)c(OC)c2c1]

Compound 5349

Compound 5350

Compounds 5349 and 5350 were prepared using the intermediates described herein and by following the general procedure described for the synthesis of Compound 3117:

Compound 5349: (R)-1,1,1-trifluoropropan-2-yl ((2R,6S,7R,9S,13aS,14aR,16aS,Z)-2-((3-(4-isopropoxyphenyl)-4,6-dimethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 972.5 (M$^+$+1).

Compound 5350: (R)-1,1,1-trifluoropropan-2-yl ((2R,6S,7R,9R,13aS,14aR,16aS,Z)-2-((3-(4-isopropoxyphenyl)-4,6-dimethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.05 (s, 1H), 9.07 (s, 1H), 8.12 (m, 3H), 7.98 (d, J=8.9 Hz, 1H), 7.34 (d, J=2.4 Hz, 1H), 7.15-6.96 (m, 3H), 5.89 (br. s., 1H), 5.53 (d, J=5.8 Hz, 1H), 5.00 (t, J=9.9 Hz, 1H), 4.81-4.65 (m, 2H), 4.60-4.40 (m, 2H), 4.03-3.92 (m, 4H), 3.80 (dd, J=10.7, 8.5 Hz, 1H), 3.64 (s, 3H), 2.69 (d, J=9.5 Hz, 2H), 2.39-2.25 (m, 2H), 1.91 (d, J=13.7 Hz, 2H), 1.68 (d, J=11.9 Hz, 1H), 1.60 (d, J=4.9 Hz, 1H), 1.53 (br. s., 1H), 1.48-1.37 (m, 5H), 1.37-1.25 (m, 9H), 1.21 (d, J=6.4 Hz, 3H), 0.92 (m, 8H), 0.78 (t, J=12.1 Hz, 1H); MS: MS m/z 972.5 (M$^+$+1).

Preparation of Compound 6001

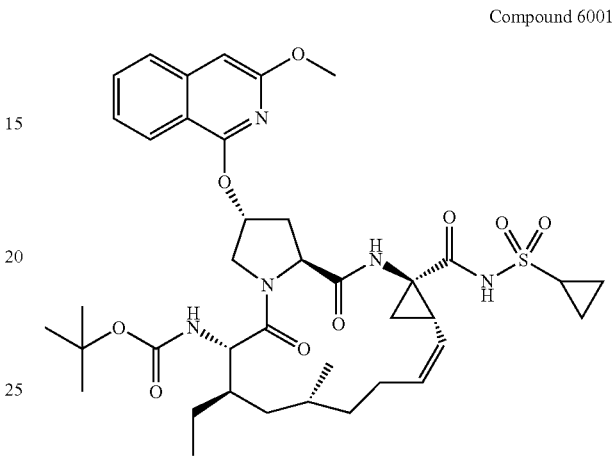

Compound 6001

Compound 6001 was prepared using the intermediates described herein and by following the general procedure described for the synthesis of Compound 3117:

Compound 6001: tert-butyl ((2R,6S,7R,9R,13aS,14aR,16aS,Z)-14a-((cyclopropylsulfonyl)carbamoyl)-7-ethyl-2-((3-methoxyisoquinolin-1-yl)oxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, METHANOL-d$_4$) δ 8.07 (d, J=8.5 Hz, 1H), 7.65 (d, J=8.2 Hz, 1H), 7.56 (d, J=7.9 Hz, 1H), 7.24 (t, J=7.5 Hz, 1H), 6.62 (s, 1H), 5.90 (br. s., 1H), 5.53 (td, J=10.0, 6.0 Hz, 1H), 5.07 (m, 1H), 4.79 (d, J=11.3 Hz, 1H), 4.60 (dd, J=9.8, 7.3 Hz, 1H), 4.20-4.02 (m, 2H), 4.00 (s, 3H), 2.92 (m, 1H), 2.76 (m, 1H), 2.68 (m, 1H), 2.52-2.32 (m, 2H), 1.99-1.88 (m, 2H), 1.75 (m, 1H), 1.65-1.51 (m, 5H), 1.38 (m, 1H), 1.34-1.27 (m, 1H), 1.18 (s, 9H), 1.15-1.03 (m, 4H), 1.00 (d, J=6.7 Hz, 4H), 0.84 (t, J=7.5 Hz, 3H); MS: MS m/z 768.3 (M$^+$+1).

Preparation of Compound 6002 and Compound 6003

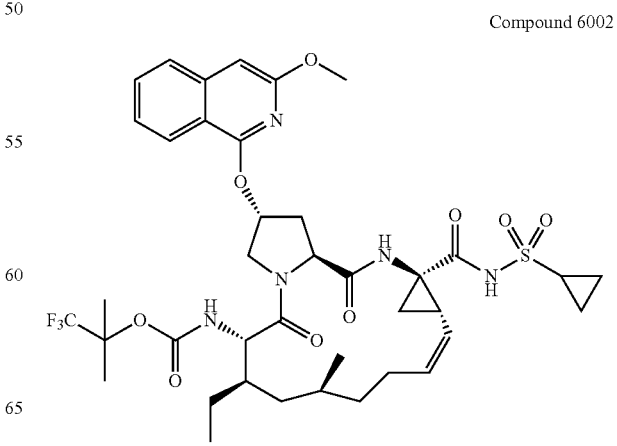

Compound 6002

Compound 6003

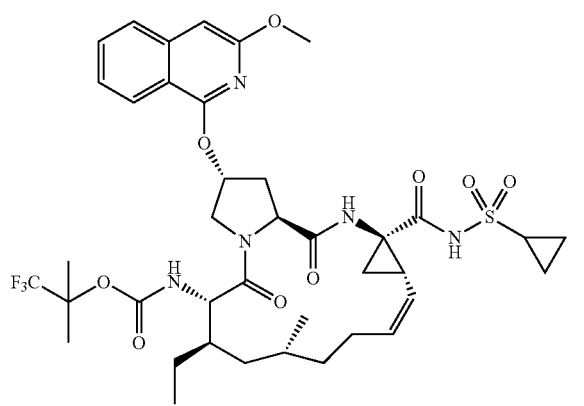

Compound 6005

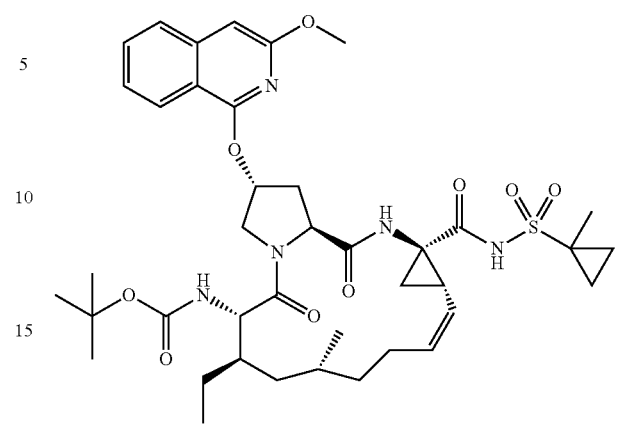

Compounds 6002 and 6003 were prepared using the intermediates described herein and by following the general procedure described for the synthesis of Compound 3117:

Compound 6002: 1,1,1-trifluoro-2-methylpropan-2-yl ((2R,6S,7R,9S,13aS,14aR,16aS,Z)-14a-((cyclopropylsulfonyl)carbamoyl)-7-ethyl-2-((3-methoxyisoquinolin-1-yl)oxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 822.3 (M$^+$+1).

Compound 6003: 1,1,1-trifluoro-2-methylpropan-2-yl ((2R,6S,7R,9R,13aS,14aR,16aS,Z)-14a-((cyclopropylsulfonyl)carbamoyl)-7-ethyl-2-((3-methoxyisoquinolin-1-yl)oxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.19 (br.s, 1H), 9.00 (br.s, 1H), 7.99 (d, J=8.5 Hz, 1H), 7.89 (d, J=8.5 Hz, 1H), 7.75 (d, J=8.2 Hz, 1H), 7.64 (t, J=7.6 Hz, 1H), 7.32 (t, J=7.6 Hz, 1H), 6.72 (br.s, 1H), 5.81 (br. s., 1H), 5.54 (m, 1H), 5.06 (t, J=9.8 Hz, 1H), 4.58 (d, J=11.0 Hz, 1H), 4.49 (dd, J=9.9, 7.2 Hz, 1H), 3.93 (s, 3H), 3.96-3.90 (m, 2H), 2.92 (m, 1H), 2.77-2.61 (m, 2H), 2.42-2.25 (m, 2H), 2.02-1.85 (m, 2H), 1.66-1.43 (m, 7H), 1.39 (s, 3H), 1.26-0.93 (m, 9H), 1.10 (s, 3H), 0.74 (t, J=7.5 Hz, 3H); MS: MS m/z 822.3 (M$^+$+1).

Preparation of Compound 6004 and Compound 6005

Compounds 6004 and 6005 were prepared using the intermediates described herein and by following the general procedure described for the synthesis of Compound 3117:

Compound 6004: tert-butyl ((2R,6S,7R,9S,13aS,14aR,16aS,Z)-7-ethyl-2-((3-methoxyisoquinolin-1-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 782.4 (M$^+$+1).

Compound 6005: tert-butyl ((2R,6S,7R,9R,13aS,14aR,16aS,Z)-7-ethyl-2-((3-methoxyisoquinolin-1-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, METHANOL-d$_4$) δ 8.07 (d, J=8.5 Hz, 1H), 7.65 (d, J=8.2 Hz, 1H), 7.56 (t, J=7.5 Hz, 1H), 7.25 (t, J=7.5 Hz, 1H), 6.62 (s, 1H), 5.91 (br. s., 1H), 5.62-5.45 (m, 1H), 5.09 (m, 1H), 4.79 (d, J=11.6 Hz, 1H), 4.61 (dd, J=9.8, 7.3 Hz, 1H), 4.21-4.03 (m, 2H), 3.99 (s, 3H), 2.77 (dd, J=13.6, 7.2 Hz, 1H), 2.66 (d, J=8.2 Hz, 1H), 2.54-2.31 (m, 2H), 2.03-1.83 (m, 2H), 1.73 (dd, J=8.2, 5.5 Hz, 1H), 1.65-1.44 (m, 9H), 1.43-1.30 (m, 2H), 1.17 (s, 9H), 1.28-1.04 (m, 2H), 0.99 (d, J=7.0 Hz, 3H), 0.84 (m, 5H); MS: MS m/z 782.4 (M$^+$+1).

Preparation of Compound 6006 and Compound 6007

Compound 6004

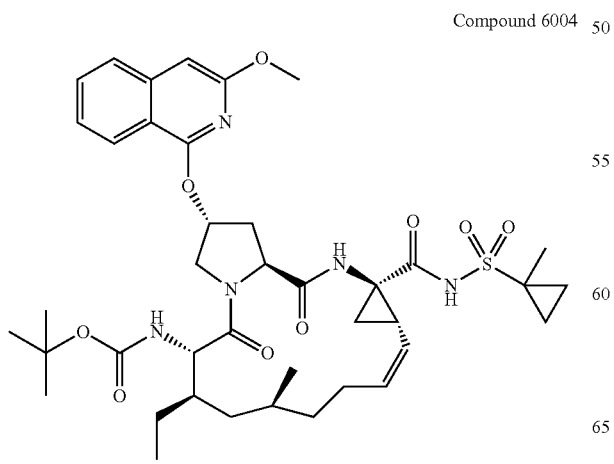

Compound 6006

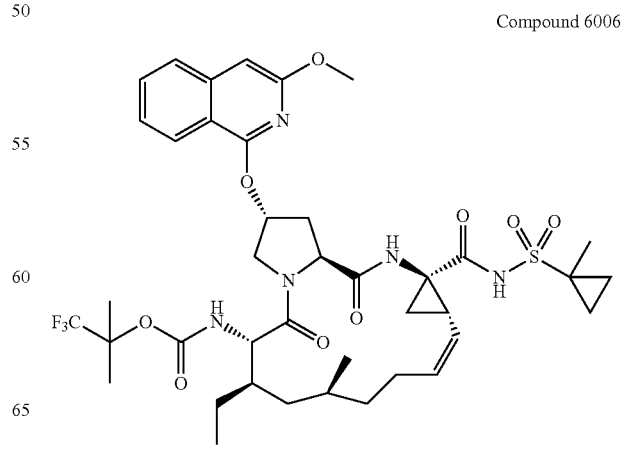

-continued

Compound 6007

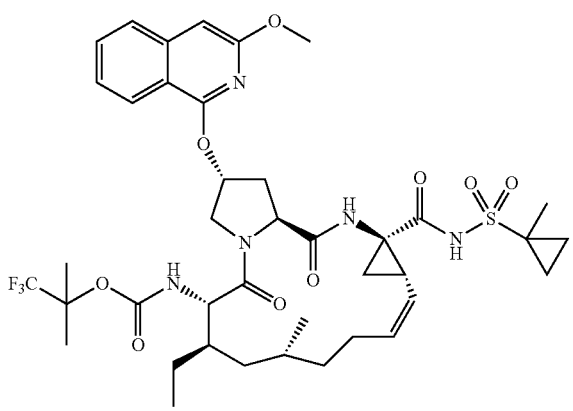

Compound 6009

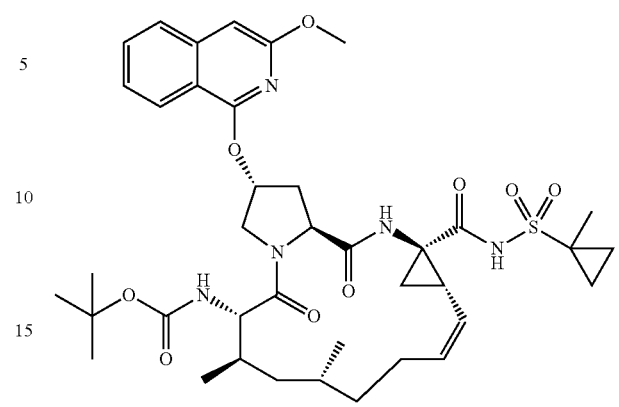

Compounds 6006 and 6007 were prepared using the intermediates described herein and by following the general procedure described for the synthesis of Compound 3117:

Compound 6006: 1,1,1-trifluoro-2-methylpropan-2-yl ((2R,6S,7R,9S,13aS,14aR,16aS,Z)-7-ethyl-2-((3-methoxy-isoquinolin-1-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 836.4 (M$^+$+1).

Compound 6007: 1,1,1-trifluoro-2-methylpropan-2-yl ((2R,6S,7R,9R,13aS,14aR,16aS,Z)-7-ethyl-2-((3-methoxy-isoquinolin-1-yl)oxy)-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, METHANOL-d$_4$) δ 8.06 (d, J=8.2 Hz, 1H), 7.66 (d, J=8.5 Hz, 1H), 7.56 (t, J=7.5 Hz, 1H), 7.27 (t, J=7.5 Hz, 1H), 6.63 (s, 1H), 5.89 (br. s., 1H), 5.56 (m, 1H), 5.17 (m, 1H), 4.81 (d, J=11.3 Hz, 1H), 4.64 (dd, J=10.1, 7.3 Hz, 1H), 4.13-4.03 (m, 2H), 4.00 (s, 3H), 2.77 (m, 1H), 2.64 (q, J=9.1 Hz, 1H), 2.52-2.33 (m, 2H), 2.03-1.87 (m, 2H), 1.74 (m, 1H), 1.64-1.26 (m, 15H), 1.10 (t, J=11.7 Hz, 1H), 1.02-0.93 (m, 6H), 0.83 (m, 5H); MS: MS m/z 836.4 (M$^+$+1).

Preparation of Compound 6008 and Compound 6009

Compounds 6008 and 6009 were prepared using the intermediates described herein and by following the general procedure described for the synthesis of Compound 3117:

Compound 6008: tert-butyl ((2R,6S,7R,9S,13aS,14aR,16aS,Z)-2-((3-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 768.3 (M$^+$+1).

Compound 6009: tert-butyl ((2R,6S,7R,9R,13aS,14aR,16aS,Z)-2-((3-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.05 (br.s, 1H), 9.10 (br. s., 1H), 8.04 (d, J=8.2 Hz, 1H), 7.75 (d, J=8.2 Hz, 1H), 7.64 (t, J=7.6 Hz, 1H), 7.29 (t, J=7.6 Hz, 1H), 7.21 (d, J=7.9 Hz, 1H), 6.71 (s, 1H), 5.81 (br. s., 1H), 5.53 (m, 1H), 4.98 (t, J=9.9 Hz, 1H), 4.64 (d, J=11.3 Hz, 1H), 4.54-4.38 (m, 1H), 4.02-3.85 (m, 1H), 3.92 (s, 3H), 3.80-3.67 (m, 1H), 2.80-2.59 (m, 2H), 2.41-2.22 (m, 2H), 1.92-1.27 (m, 11H), 1.29 (d, J=10.7 Hz, 1H), 1.15 (s, 9H), 1.05 (m, 1H), 0.96-0.85 (m, 8H), 0.75 (t, J=12.2 Hz, 1H); MS: MS m/z 768.3 (M$^+$+1).

Preparation of Compound 6010 and Compound 6011

Compound 6008

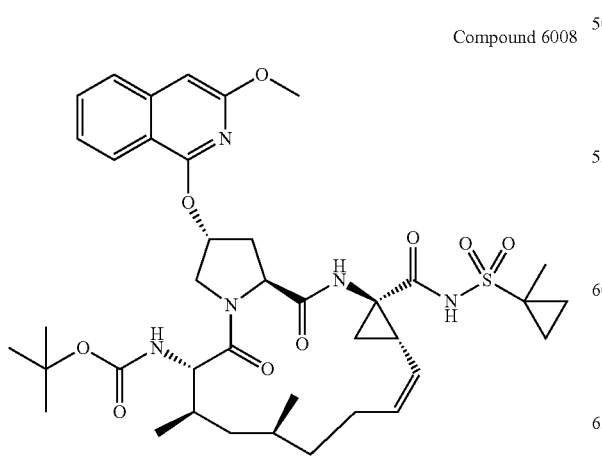

Compound 6010

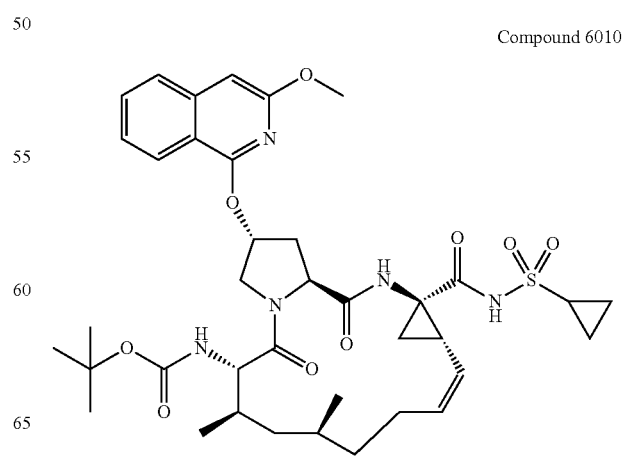

-continued

Compound 6011

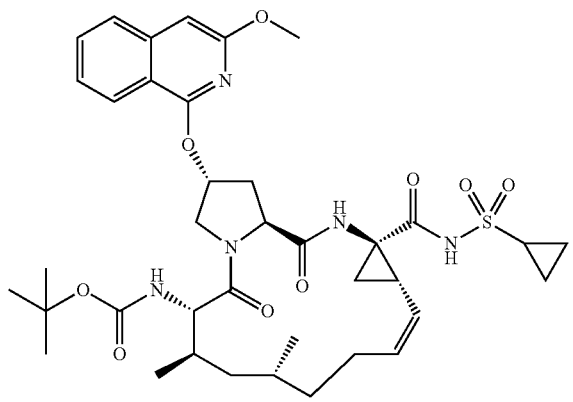

Compounds 6010 and 6011 were prepared using the intermediates described herein and by following the general procedure described for the synthesis of Compound 3117:

Compound 6010: tert-butyl ((2R,6S,7R,9S,13aS,14aR,16aS,Z)-14a-((cyclopropylsulfonyl)carbamoyl)-2-((3-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 754.3 (M$^+$+1).

Compound 6011: tert-butyl ((2R,6S,7R,9R,13aS,14aR,16aS,Z)-14a-((cyclopropylsulfonyl)carbamoyl)-2-((3-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.19 (br. s., 1H), 8.97 (br. s., 1H), 8.04 (d, J=8.2 Hz, 1H), 7.74 (d, J=8.2 Hz, 1H), 7.63 (t, J=7.6 Hz, 1H), 7.29 (t, J=7.5 Hz, 1H), 7.20 (d, J=7.6 Hz, 1H), 6.71 (s, 1H), 5.79 (br. s., 1H), 5.05 (m, 1H), 4.63 (m, 1H), 4.44 (m, 1H), 3.92 (m, 5H), 3.78-3.69 (m, 1H), 2.91 (m, 1H), 2.38-2.26 (m, 2H), 1.92-1.37 (m, 6H), 1.17 (s, 9H), 1.16-1.05 (m, 4H), 1.04 (m, 2H), 0.94 (d, J=7.0 Hz, 4H), 0.89 (d, J=6.4 Hz, 4H), 0.73 (t, J=11.9 Hz, 1H); MS: MS m/z 754.3 (M$^+$+1).

Preparation of Compound 6012 and Compound 6013

-continued

Compound 6013

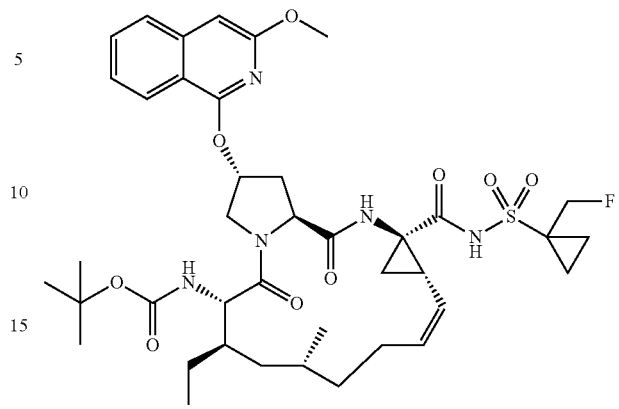

Compounds 6012 and 6013 were prepared using the intermediates described herein and by following the general procedure described for the synthesis of Compound 3117:

Compound 6012: tert-butyl ((2R,6S,7R,9S,13aS,14aR,16aS,Z)-7-ethyl-14a-(((1-(fluoromethyl)cyclopropyl)sulfonyl)carbamoyl)-2-((3-methoxyisoquinolin-1-yl)oxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 786.4 (M$^+$+1).

Compound 6013: tert-butyl ((2R,6S,7R,9R,13aS,14aR,16aS,Z)-7-ethyl-14a-(((1-(fluoromethyl)cyclopropyl)sulfonyl)carbamoyl)-2-((3-methoxyisoquinolin-1-yl)oxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.19 (br. s., 1H), 8.97 (br. s., 1H), 8.04 (d, J=8.2 Hz, 1H), 7.74 (d, J=8.2 Hz, 1H), 7.63 (t, J=7.6 Hz, 1H), 7.29 (t, J=7.5 Hz, 1H), 7.20 (d, J=7.6 Hz, 1H), 6.71 (s, 1H), 5.79 (br. s., 1H), 5.05 (m, 1H), 4.63 (m, 1H), 4.44 (m, 1H), 3.92 (m, 5H), 3.78-3.69 (m, 1H), 2.38-2.26 (m, 2H), 1.92-1.25 (m, 13H), 1.17 (s, 9H), 1.04 (m, 1H), 0.94 (d, J=7.0 Hz, 4H), 0.89 (d, J=6.4 Hz, 4H), 0.73 (t, J=11.9 Hz, 1H); MS: MS m/z 786.4 (M$^+$+1).

Preparation of Compound 6014 and Compound 6015

Compound 6012

Compound 6014

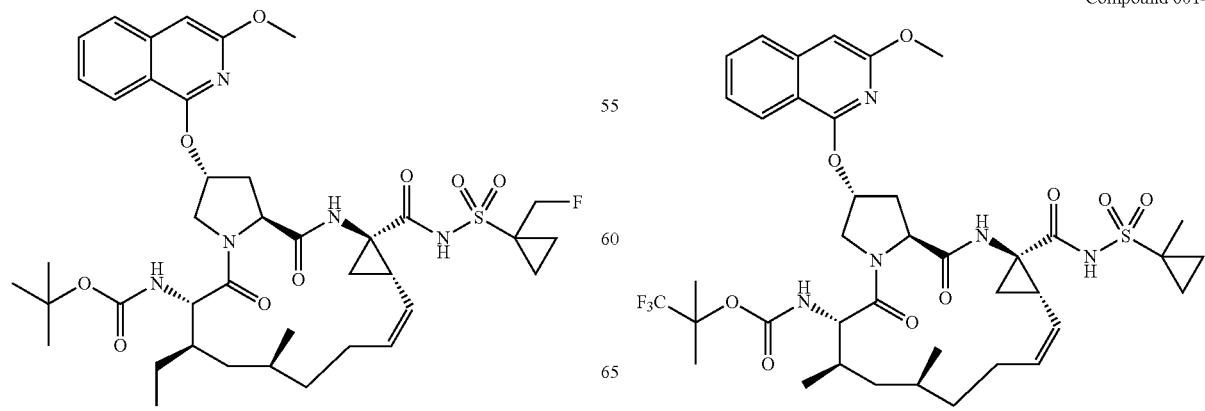

-continued

Compound 6015

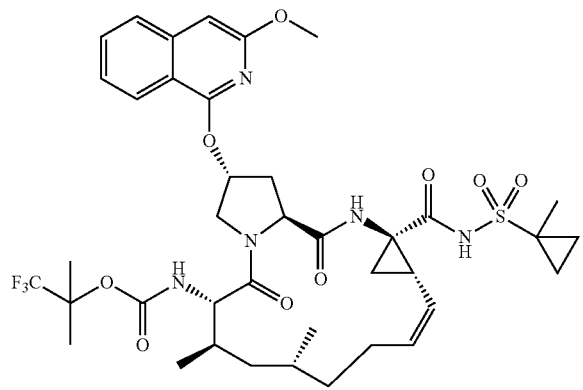

Compounds 6014 and 6015 were prepared using the intermediates described herein and by following the general procedure described for the synthesis of Compound 3117:

Compound 6014: 1,1,1-trifluoro-2-methylpropan-2-yl ((2R,6S,7R,9S,13aS,14aR,16aS,Z)-2-((3-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 822.3 (M$^+$+1).

Compound 6015: 1,1,1-trifluoro-2-methylpropan-2-yl ((2R,6S,7R,9R,13aS,14aR,16aS,Z)-2-((3-methoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.05 (br.s, 1H), 9.14 (br.s, 1H), 8.01 (d, J=8.2 Hz, 1H), 7.85 (d, J=7.9 Hz, 1H), 7.75 (d, J=8.2 Hz, 1H), 7.64 (t, J=7.6 Hz, 1H), 7.32 (t, J=7.6 Hz, 1H), 6.72 (s, 1H), 5.81 (br. s., 1H), 5.59-5.49 (m, 1H), 4.98 (t, J=9.8 Hz, 1H), 4.65-4.48 (m, 2H), 3.98-3.89 (m, 4H), 3.72 (m, 1H), 2.73-2.64 (m, 2H), 2.39-2.29 (m, 2H), 1.96-1.80 (m, 2H), 1.75-1.59 (m, 2H), 1.53 (m, 1H), 1.49-1.40 (m, 6H), 1.35 (s, 3H), 1.30 (m, 1H), 1.14 (m, 1H), 1.08 (s, 3H), 0.94 (d, J=7.0 Hz, 4H), 0.90 (d, J=6.4 Hz, 4H), 0.77 (t, J=12.7 Hz, 1H); MS: MS m/z 822.3 (M$^+$+1).

Preparation of Compound 6016

Compound 6016

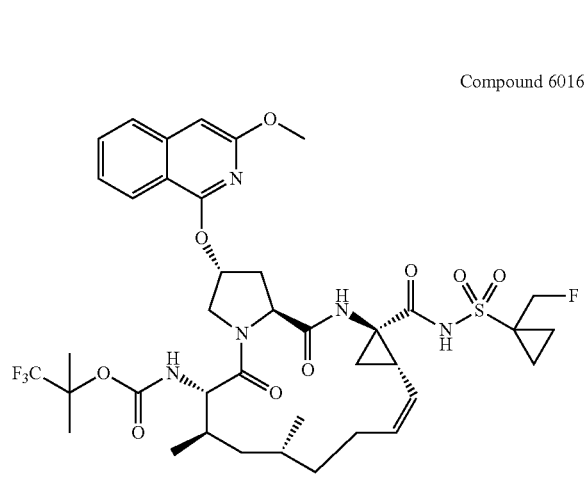 [SMILES: COc1cc2ccccc2c(O[C@@H]2C[C@H]3C(=O)N[C@]4(C(=O)NS(=O)(=O)C5(CF)CC5)C[C@H]4/C=C\CC[C@@H](C)C[C@@H](C)[C@H](NC(=O)OC(C)(C)C(F)(F)F)C(=O)N3C2)n1]

Compound 6016 was prepared using the intermediates described herein and by following the general procedure described for the synthesis of Compound 3117:

Compound 6016: 1,1,1-trifluoro-2-methylpropan-2-yl ((2R,6S,7R,9R,13aS,14aR,16aS,Z)-14a-(((1-(fluoromethyl)cyclopropyl)sulfonyl)carbamoyl)-2-((3-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.28 (br.s, 1H), 9.05 (br. s., 1H), 8.01 (d, J=8.2 Hz, 1H), 7.85 (d, J=7.9 Hz, 1H), 7.76 (d, J=8.5 Hz, 1H), 7.64 (t, J=7.6 Hz, 1H), 7.32 (t, J=7.6 Hz, 1H), 6.72 (s, 1H), 5.80 (br. s., 1H), 5.52 (m, 1H), 5.01 (t, J=9.8 Hz, 1H), 4.87-4.76 (m, 1H), 4.59-4.49 (m, 3H), 3.98-3.90 (m, 4H), 3.72 (m, 1H), 2.70-2.62 (m, 2H), 2.39-2.26 (m, 2H), 1.94-1.81 (m, 2H), 1.70 (d, J=6.1 Hz, 1H), 1.54 (m, 4H), 1.48-1.33 (m, 6H), 1.31-1.20 (m, 2H), 1.11 (s, 3H), 0.97-0.87 (m, 6H), 0.76 (t, J=12.5 Hz, 1H); MS: MS m/z 840.4 (M$^+$+1).

Preparation of Compound 6017 and Compound 6018

Compound 6017

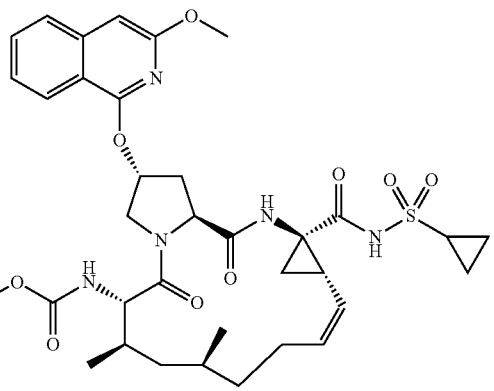

Compound 6018

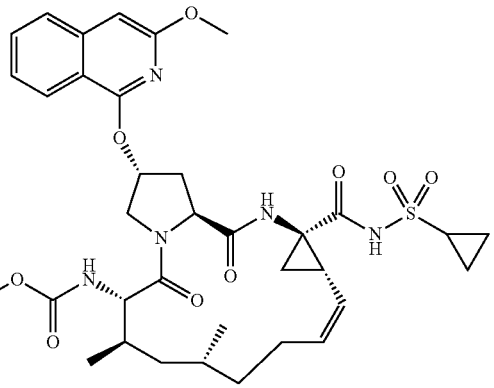

Compounds 6017 and 6018 were prepared using the intermediates described herein and by following the general procedure described for the synthesis of Compound 3117:

Compound 6017: 1,1,1-trifluoro-2-methylpropan-2-yl ((2R,6S,7R,9S,13aS,14aR,16aS,Z)-14a-((cyclopropylsulfonyl)carbamoyl)-2-((3-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 808.3 (M$^+$+1).

Compound 6018: 1,1,1-trifluoro-2-methylpropan-2-yl ((2R,6S,7R,9R,13aS,14aR,16aS,Z)-14a-((cyclopropylsulfonyl)carbamoyl)-2-((3-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate $^1$H NMR (500 MHz, DMSO-$d_6$) δ 11.20 (br.s, 1H), 9.01 (br. s., 1H), 8.01 (d, J=8.5 Hz, 1H), 7.85 (d, J=7.6 Hz, 1H), 7.75 (d, J=8.2 Hz, 1H), 7.63 (t, J=7.6 Hz, 1H), 7.32 (t, J=7.6 Hz, 1H), 6.72 (s, 1H), 5.80 (br. s., 1H), 5.53 (m, 1H), 5.06 (t, J=9.3 Hz, 1H), 4.58 (d, J=11.3 Hz, 1H), 4.54-4.42 (m, 1H), 3.93 (s, 3H), 3.92 (m, 1H), 3.72 (dd, J=10.7, 7.9 Hz, 1H), 2.97-2.89 (m, 1H), 2.68 (d, J=8.2 Hz, 2H), 2.40-2.27 (m, 2H), 1.97-1.80 (m, 2H), 1.71 (m, 1H), 1.61 (m, 2H), 1.56 (m, 1H), 1.43 (m, 1H), 1.37 (s, 3H), 1.19-0.97 (m, 8H), 0.96-0.87 (m, 6H), 0.75 (t, J=12.4 Hz, 1H); MS: MS m/z 808.3 (M$^+$+1).

Preparation of Compound 6019 and Compound 6020

Compound 6019

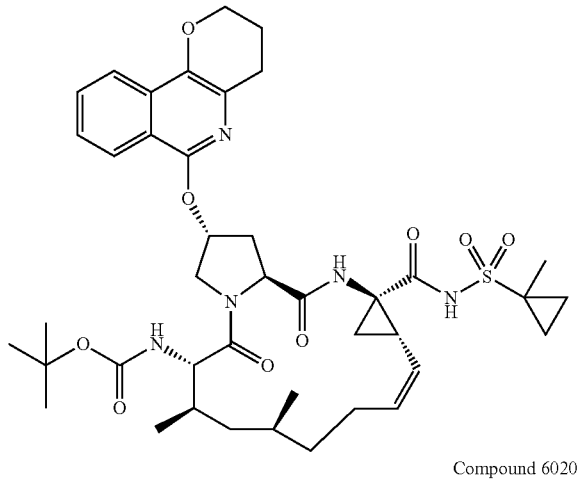

Compound 6020

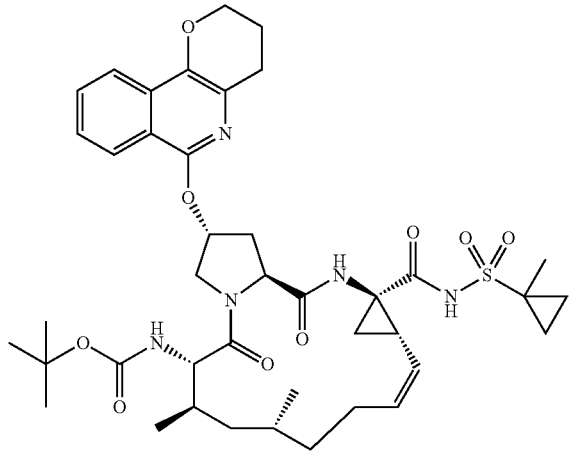

Compounds 6019 and 6020 were prepared using the intermediates described herein and by following the general procedure described for the synthesis of Compound 3117:

Compound 6019: tert-butyl ((2R,6S,7R,9S,13aS,14aR,16aS,Z)-2-((3,4-dihydro-2H-pyrano[3,2-c]isoquinolin-6-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 794.5 (M$^+$+1).

Compound 6020: tert-butyl ((2R,6S,7R,9R,13aS,14aR,16aS,Z)-2-((3,4-dihydro-2H-pyrano[3,2-c]isoquinolin-6-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate $^1$H NMR (500 MHz, METHANOL-$d_4$) δ 8.10 (d, J=8.5 Hz, 1H), 7.97 (d, J=8.5 Hz, 1H), 7.65 (t, J=7.6 Hz, 1H), 7.44 (t, J=7.6 Hz, 1H), 5.83 (br. s., 1H), 5.55 (td, J=10.1, 5.8 Hz, 1H), 5.14-5.00 (m, 1H), 4.69 (d, J=11.6 Hz, 1H), 4.60 (dd, J=9.9, 7.2 Hz, 1H), 4.35-4.24 (m, 2H), 4.03 (dd, J=11.6, 3.4 Hz, 1H), 3.90 (d, J=10.7 Hz, 1H), 2.97-2.86 (m, 2H), 2.77-2.66 (m, 2H), 2.40 (m, 2H), 2.19-2.13 (m, 2H), 1.94 (m, 1H), 1.89-1.69 (m, 3H), 1.65-1.59 (m, 1H), 1.57-1.36 (m, 6H), 1.28-1.19 (m, 1H), 1.16 (s, 9H), 1.06 (m, 1H), 0.99 (t, J=6.9 Hz, 6H), 0.90-0.78 (m, 3H); MS: MS m/z 794.5 (M$^+$+1).

Preparation of Compound 6021 and Compound 6022

Compound 6021

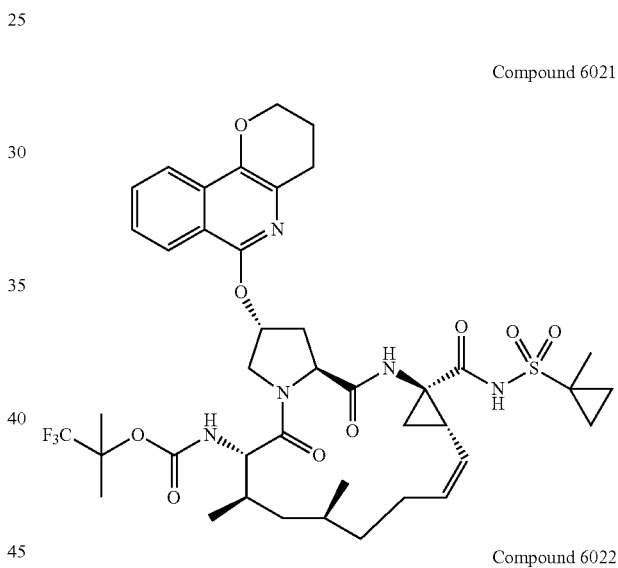

Compound 6022

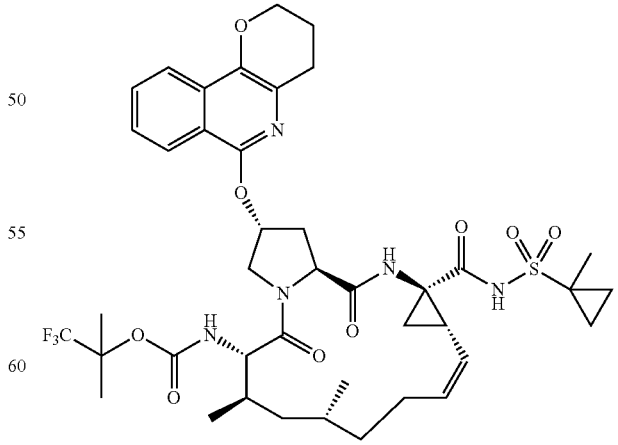

Compounds 6021 and 6022 were prepared using the intermediates described herein and by following the general procedure described for the synthesis of Compound 3117:

Compound 6021: 1,1,1-trifluoro-2-methylpropan-2-yl ((2R,6S,7R,9S,13aS,14aR,16aS,Z)-2-((3,4-dihydro-2H-pyrano[3,2-c]isoquinolin-6-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 848.5 (M$^+$+1).

Compound 6022: 1,1,1-trifluoro-2-methylpropan-2-yl ((2R,6S,7R,9R,13aS,14aR,16aS,Z)-2-((3,4-dihydro-2H-pyrano[3,2-c]isoquinolin-6-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.03 (br. s., 1H), 9.10 (br. s., 1H), 8.05 (d, J=8.2 Hz, 1H), 7.95 (d, J=8.5 Hz, 1H), 7.84 (d, J=7.9 Hz, 1H), 7.74 (t, J=7.6 Hz, 1H), 7.52 (t, J=7.6 Hz, 1H), 5.74 (br. s., 1H), 5.53 (m, 1H), 4.98 (m, 1H), 4.59-4.41 (m, 2H), 4.27 (t, J=4.6 Hz, 2H), 3.97-3.87 (m, 1H), 3.74 (dd, J=10.7, 8.2 Hz, 1H), 2.88 (t, J=6.4 Hz, 2H), 2.75-2.67 (m, 1H), 2.63 (dd, J=13.1, 6.7 Hz, 1H), 2.40-2.21 (m, 2H), 2.16-2.05 (m, 2H), 1.95-1.79 (m, 2H), 1.75-1.67 (m, 1H), 1.61 (m, 1H), 1.51-1.25 (m, 12H), 1.16 (s, 3H), 0.92 (m, 8H), 0.76 (t, J=12.7 Hz, 1H); MS: MS m/z 848.5 (M$^+$+1).

Preparation of Compound 6023 and Compound 6024

Compounds 6023 and 6024 were prepared using the intermediates described herein and by following the general procedure described for the synthesis of Compound 3117:

Compound 6023: tert-butyl ((2R,6S,7R,9S,13aS,14aR,16aS,Z)-2-((3,4-dihydro-2H-pyrano[3,2-c]isoquinolin-6-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 808.6 (M$^+$+1).

Compound 6024: tert-butyl ((2R,6S,7R,9R,13aS,14aR,16aS,Z)-2-((3,4-dihydro-2H-pyrano[3,2-c]isoquinolin-6-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, METHANOL-d$_4$) δ 8.08 (d, J=8.0 Hz, 1H), 7.97 (d, J=8.3 Hz, 1H), 7.70-7.59 (m, 1H), 7.51-7.37 (m, 1H), 5.84 (br. s., 1H), 5.53 (td, J=9.9, 6.0 Hz, 1H), 5.04 (br. s., 1H), 4.73 (d, J=11.3 Hz, 1H), 4.59 (dd, J=10.0, 7.3 Hz, 1H), 4.36-4.23 (m, 2H), 4.13 (d, J=11.3 Hz, 1H), 4.03 (dd, J=11.5, 3.5 Hz, 1H), 3.03-2.84 (m, 2H), 2.79-2.61 (m, 2H), 2.40 (ddd, J=13.8, 9.9, 4.1 Hz, 2H), 2.22-2.12 (m, 2H), 2.01-1.87 (m, 2H), 1.73 (dd, J=8.3, 5.5 Hz, 1H), 1.67-0.93 (m, 25H), 0.89-0.79 (m, 5H); MS: MS m/z 808.6 (M$^+$+1).

Preparation of Compound 6025 and Compound 6026

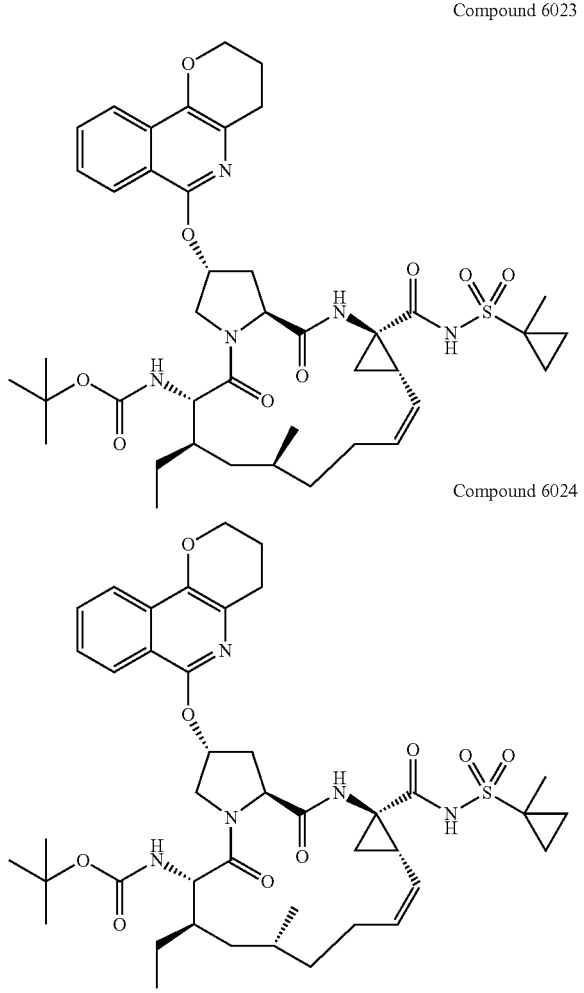

Compound 6023

Compound 6024

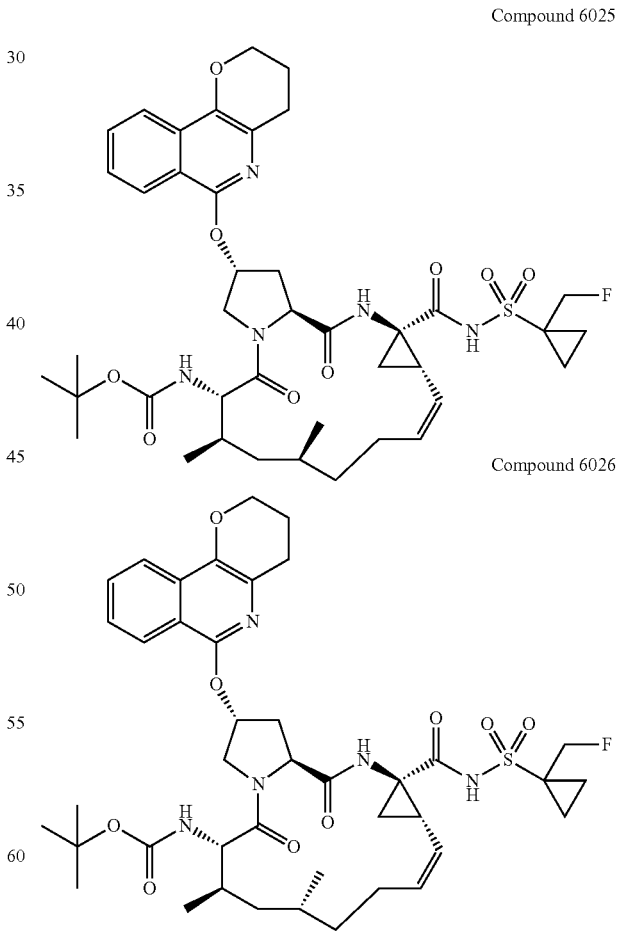

Compound 6025

Compound 6026

Compounds 6023 and 6024 were prepared using the intermediates described herein and by following the general procedure described for the synthesis of Compound 3117:

Compound 6023: tert-butyl ((2R,6S,7R,9S,13aS,14aR,16aS,Z)-2-((3,4-dihydro-2H-pyrano[3,2-c]isoquinolin-6-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 812.2 (M$^+$+1).

Compound 6024: tert-butyl ((2R,6S,7R,9R,13aS,14aR,16aS,Z)-2-((3,4-dihydro-2H-pyrano[3,2-c]isoquinolin-6-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.26 (s, 1H), 8.98 (s, 1H), 8.08 (d, J=8.2 Hz, 1H), 7.94 (d, J=8.2 Hz, 1H), 7.73 (t, J=7.3 Hz, 1H), 7.49 (t, J=7.6 Hz, 1H), 7.21 (d, J=7.9 Hz, 1H), 5.72 (br. s., 1H), 5.51 (d, J=5.5 Hz, 1H), 5.00 (t, J=10.1 Hz, 1H), 4.85 (d, J=11.0 Hz, 1H), 4.75 (d, J=11.3 Hz, 1H), 4.63-4.36 (m, 3H), 4.32-4.23 (m, 2H), 3.99-3.86 (m, 1H), 3.79-3.65 (m, 1H), 2.88 (t, J=6.1 Hz, 2H), 2.74-2.58 (m, 2H), 2.41-2.21 (m, 2H), 2.15-2.04 (m, 2H), 1.98-1.64 (m, 3H), 1.53 (m, 2H), 1.47-1.31 (m, 2H), 1.31-1.00 (m, 13H), 0.97-0.83 (m, 6H), 0.74 (t, J=12.7 Hz, 1H); MS: MS m/z 812.2 (M$^+$+1).

Preparation of Compound 6027 and Compound 6028

Compounds 6027 and 6028 were prepared using the intermediates described herein and by following the general procedure described for the synthesis of Compound 3117:

Compound 6027: 1,1,1-trifluoro-2-methylpropan-2-yl ((2R,6S,7R,9S,13aS,14aR,16aS,Z)-2-((3,4-dihydro-2H-pyrano[3,2-c]isoquinolin-6-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 862.5 (M$^+$+1).

Compound 6028: 1,1,1-trifluoro-2-methylpropan-2-yl ((2R,6S,7R,9R,13aS,14aR,16aS,Z)-2-((3,4-dihydro-2H-pyrano[3,2-c]isoquinolin-6-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.02 (s, 1H), 9.09 (s, 1H), 8.03 (d, J=8.5 Hz, 1H), 7.95 (d, J=8.2 Hz, 1H), 7.90 (d, J=8.9 Hz, 1H), 7.74 (t, J=7.6 Hz, 1H), 7.52 (t, J=7.0 Hz, 1H), 5.76 (br. s., 1H), 5.54 (s, 1H), 4.98 (m, 1H), 4.59-4.45 (m, 2H), 4.27 (m, 2H), 4.00-3.86 (m, 2H), 2.88 (t, J=6.4 Hz, 2H), 2.76-2.59 (m, 2H), 2.41-2.25 (m, 3H), 2.11 (br. s., 2H), 2.02-1.90 (m, 2H), 1.61 (br. s., 1H), 1.55-1.37 (m, 12H), 1.30 (m, 1H), 1.16 (s, 3H), 1.03 (d, J=14.3 Hz, 1H), 0.97-0.86 (m, 6H), 0.75 (t, J=7.5 Hz, 3H) MS: MS m/z 862.5 (M$^+$+1).

Preparation of Compound 6029 and Compound 6030

Compound 6027

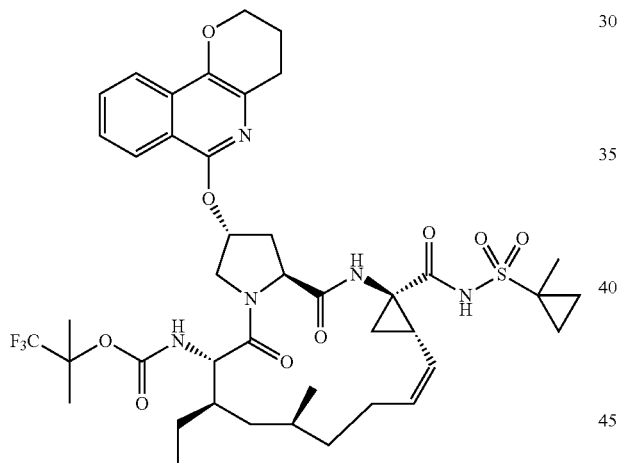

Compound 6028

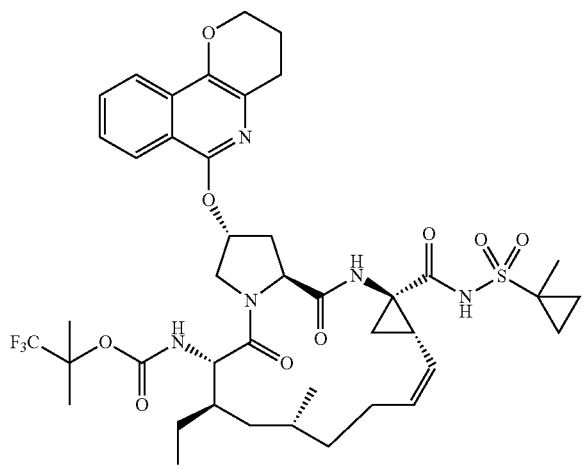

Compound 6029

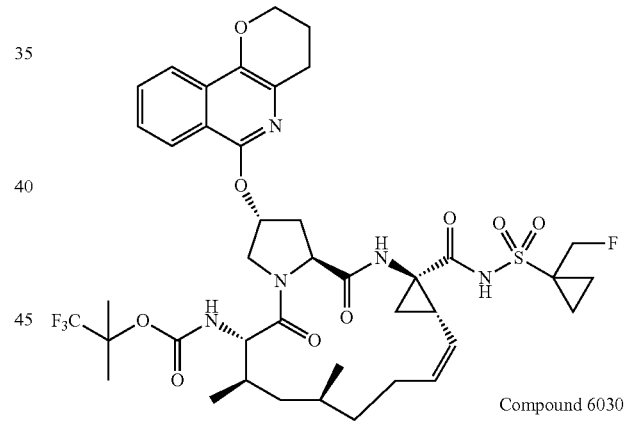

Compound 6030

Compounds 6029 and 6030 were prepared using the intermediates described herein and by following the general procedure described for the synthesis of Compound 3117:

Compound 6029: 1,1,1-trifluoro-2-methylpropan-2-yl ((2R,6S,7R,9S,13aS,14aR,16aS,Z)-2-((3,4-dihydro-2H-pyrano[3,2-c]isoquinolin-6-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 866.5 (M$^+$+1).

Compound 6030: 1,1,1-trifluoro-2-methylpropan-2-yl ((2R,6S,7R,9R,13aS,14aR,16aS,Z)-2-((3,4-dihydro-2H-pyrano[3,2-c]isoquinolin-6-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.26 (s, 1H), 9.02 (s, 1H), 8.06 (d, J=8.2 Hz, 1H), 7.95 (d, J=8.2 Hz, 1H), 7.85 (d, J=7.9 Hz, 1H), 7.74 (t, J=7.6 Hz, 1H), 7.52 (t, J=7.5 Hz, 1H), 5.74 (br. s., 1H), 5.57-5.42 (m, 1H), 5.06-5.00 (m, 1H), 4.90-4.58 (m, 1H), 4.55-4.44 (m, 2H), 4.27 (t, J=4.9 Hz, 2H), 3.92 (m, 1H), 3.80-3.72 (m, 2H), 2.95-2.84 (m, 2H), 2.72-2.56 (m, 2H), 2.38-2.23 (m, 2H), 2.16-2.04 (m, 2H), 1.94-1.81 (m, 3H), 1.74-1.67 (m, 1H), 1.60-1.48 (m, 4H), 1.43-1.10 (m, 11H), 0.98-0.87 (m, 5H), 0.81-0.71 (m, 1H); MS: MS m/z 866.5 (M$^+$+1).

Preparation of Compound 6031 and Compound 6032

Compounds 6031 and 6032 were prepared using the intermediates described herein and by following the general procedure described for the synthesis of Compound 3117:

Compound 6031: 3,3-difluoro-2-methylbutan-2-yl ((2R,6S,7R,9S,13aS,14aR,16aS,Z)-2-((3,4-dihydro-2H-pyrano[3,2-c]isoquinolin-6-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 862.6 (M$^+$+1).

Compound 6032: 3,3-difluoro-2-methylbutan-2-yl ((2R,6S,7R,9R,13aS,14aR,16aS,Z)-2-((3,4-dihydro-2H-pyrano[3,2-c]isoquinolin-6-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.26 (s, 1H), 8.99 (s, 1H), 8.06 (d, J=8.5 Hz, 1H), 7.95 (d, J=8.2 Hz, 1H), 7.74 (t, J=7.5 Hz, 1H), 7.64 (d, J=8.2 Hz, 1H), 7.51 (t, J=7.6 Hz, 1H), 5.74 (br. s., 1H), 5.52 (d, J=5.8 Hz, 1H), 5.01 (t, J=9.6 Hz, 1H), 4.89-4.56 (m, 1H), 4.54-4.42 (m, 2H), 4.32-4.20 (m, 2H), 3.99-3.88 (m, 1H), 3.80-3.73 (m, 1H), 2.95-2.84 (m, 2H), 2.77-2.57 (m, 2H), 2.41-2.23 (m, 2H), 2.14-2.05 (m, 2H), 1.96-1.49 (m, 10H), 1.46-1.38 (m, 2H), 1.34 (s, 3H), 1.30-1.15 (m, 4H), 1.12 (s, 3H), 0.93 (dd, J=18.2, 6.6 Hz, 6H), 0.76 (t, J=12.1 Hz, 1H); MS: MS m/z 862.6 (M$^+$+1).

Preparation of Compound 6033 and Compound 6034

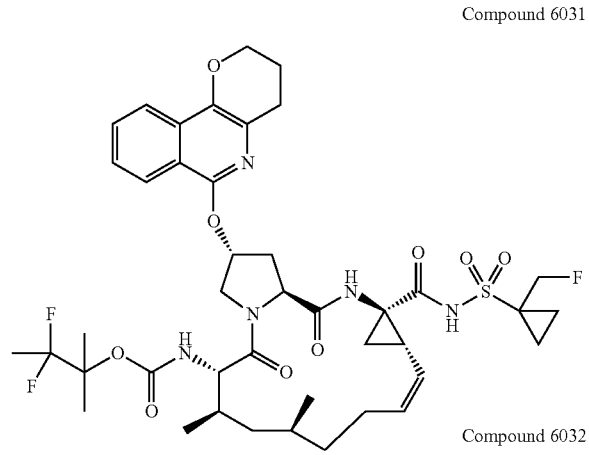

Compound 6031

Compound 6032

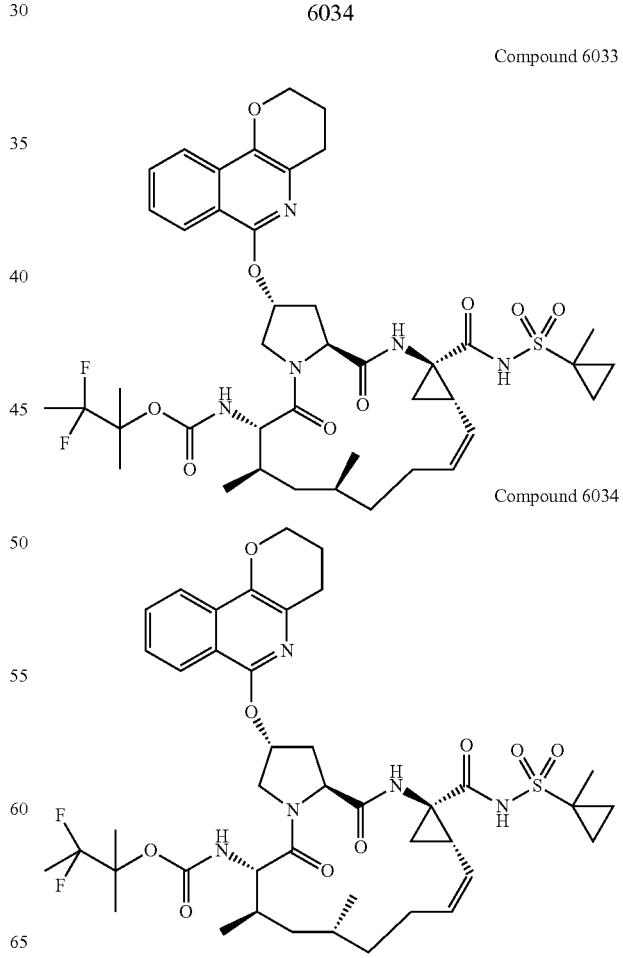

Compound 6033

Compound 6034

Compounds 6033 and 6034 were prepared using the intermediates described herein and by following the general procedure described for the synthesis of Compound 3117:

Compound 6033: 3,3-difluoro-2-methylbutan-2-yl ((2R,6S,7R,9S,13aS,14aR,16aS,Z)-2-((3,4-dihydro-2H-pyrano[3,2-c]isoquinolin-6-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 844.6 (M$^+$+1).

Compound 6034: 3,3-difluoro-2-methylbutan-2-yl ((2R,6S,7R,9R,13aS,14aR,16aS,Z)-2-((3,4-dihydro-2H-pyrano[3,2-c]isoquinolin-6-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.03 (br. s., 1H), 9.08 (br. s., 1H), 8.06 (d, J=8.5 Hz, 1H), 7.95 (d, J=8.2 Hz, 1H), 7.74 (t, J=7.5 Hz, 1H), 7.63 (d, J=8.5 Hz, 1H), 7.51 (t, J=7.6 Hz, 1H), 5.74 (br. s., 1H), 5.52 (br. s., 1H), 4.98 (br. s., 1H), 4.57-4.41 (m, 2H), 4.27 (t, J=4.9 Hz, 2H), 3.99-3.86 (m, 1H), 3.81-3.69 (m, 1H), 2.91-2.84 (m, 2H), 2.76-2.59 (m, 2H), 2.41-2.24 (m, 2H), 2.16-2.08 (m, 2H), 1.97-1.21 (m, 18H), 1.16 (br. s., 1H), 1.09 (s, 3H), 0.92 (dd, J=16.2, 6.7 Hz, 8H), 0.82-0.72 (m, 1H) MS: MS m/z 844.6 (M$^+$+1).

Preparation of Compound 6035 and Compound 6036

Compounds 6035 and 6036 were prepared using the intermediates described herein and by following the general procedure described for the synthesis of Compound 3117:

Compound 6035: 3,3-difluoro-2-methylbutan-2-yl ((2R,6S,7R,9S,13aS,14aR,16aS,Z)-14a-((cyclopropylsulfonyl)carbamoyl)-2-((3-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 804.5 (M$^+$+1).

Compound 6036: 3,3-difluoro-2-methylbutan-2-yl ((2R,6S,7R,9R,13aS,14aR,16aS,Z)-14a-((cyclopropylsulfonyl)carbamoyl)-2-((3-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.20 (s, 1H), 8.98 (s, 1H), 8.01 (d, J=8.2 Hz, 1H), 7.75 (d, J=8.5 Hz, 1H), 7.64 (t, J=7.3 Hz, 2H), 7.31 (t, J=7.6 Hz, 1H), 6.72 (s, 1H), 5.80 (br. s., 1H), 5.58-5.44 (m, 1H), 5.06 (t, J=9.9 Hz, 1H), 4.58 (d, J=12.5 Hz, 1H), 4.51-4.44 (m, 1H), 4.11 (d, J=5.2 Hz, 1H), 3.95 (br. s., 1H), 3.82-3.70 (m, 1H), 3.18 (d, J=5.2 Hz, 1H), 2.97-2.86 (m, 1H), 2.76-2.63 (m, 2H), 2.40-2.27 (m, 2H), 1.98-1.66 (m, 4H), 1.65-1.51 (m, 4H), 1.50-1.35 (m, 2H), 1.28 (s, 3H), 1.20-1.07 (m, 5H), 1.06-0.99 (m, 4H), 0.93 (dd, J=19.5, 6.7 Hz, 6H), 0.76 (t, J=12.5 Hz, 1H); MS: MS m/z 804.5 (M$^+$+1).

Preparation of Compound 6037 and Compound 6038

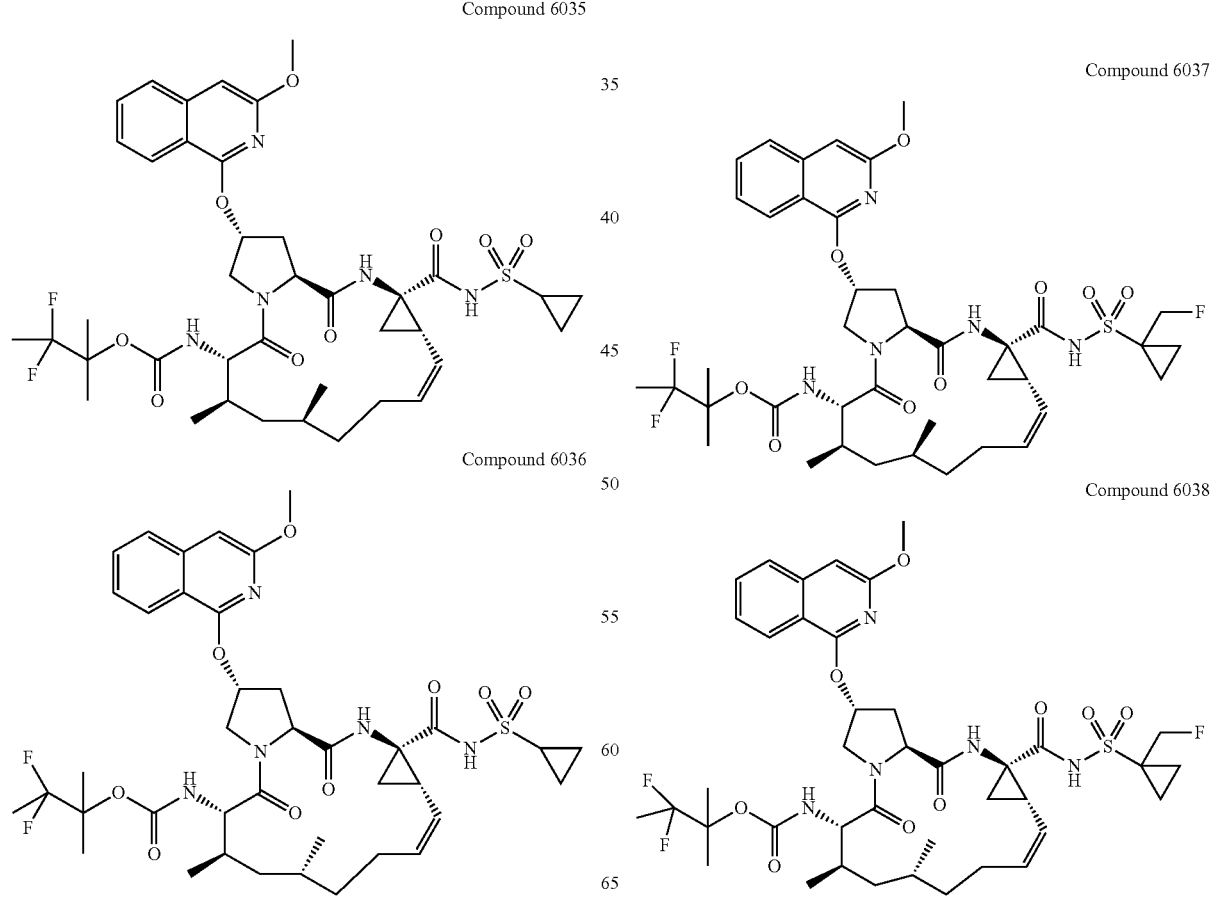

Compound 6035

Compound 6036

Compound 6037

Compound 6038

Compounds 6037 and 6038 were prepared using the intermediates described herein and by following the general procedure described for the synthesis of Compound 3117:

Compound 6037: 3,3-difluoro-2-methylbutan-2-yl ((2R,6S,7R,9S,13aS,14aR,16aS,Z)-14a-(((1-(fluoromethyl)cyclopropyl)sulfonyl)carbamoyl)-2-((3-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 836.5 (M$^+$+1).

Compound 6038: 3,3-difluoro-2-methylbutan-2-yl ((2R,6S,7R,9R,13aS,14aR,16aS,Z)-14a-(((1-(fluoromethyl)cyclopropyl)sulfonyl)carbamoyl)-2-((3-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.28 (s, 1H), 9.03 (s, 1H), 8.02 (d, J=8.2 Hz, 1H), 7.75 (d, J=8.2 Hz, 1H), 7.67-7.60 (m, 2H), 7.31 (t, J=7.6 Hz, 1H), 6.72 (s, 1H), 5.81 (br. s., 1H), 5.59-5.44 (m, 1H), 5.01 (t, J=10.1 Hz, 1H), 4.91-4.72 (m, 1H), 4.65-4.55 (m, 1H), 4.49 (t, J=10.1 Hz, 1H), 4.02-3.84 (m, 4H), 3.79-3.68 (m, 2H), 2.74-2.63 (m, 2H), 2.42-2.28 (m, 2H), 1.97-1.76 (m, 2H), 1.69 m, 2H), 1.64-1.50 (m, 6H), 1.49-1.34 (m, 2H), 1.31-1.12 (m, 6H), 1.04 (s, 3H), 0.92 (dd, J=18.5, 6.6 Hz, 6H), 0.77 (t, J=12.2 Hz, 1H); MS: MS m/z 836.5 (M$^+$+1).

Preparation of Intermediates and Compounds for Formula 1

Section 2

Preparation of 4-(2,2-difluoroethoxy)-1-fluoroisoquinoline

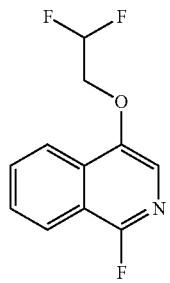

Scheme:

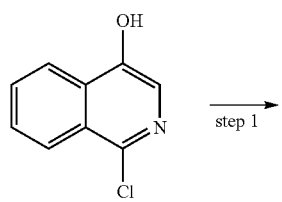

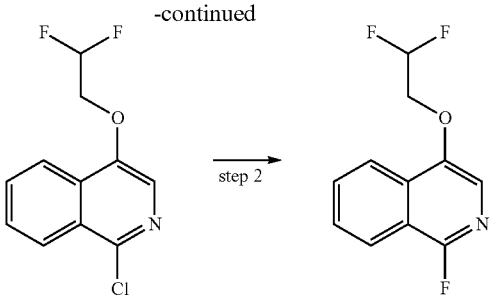

Step 1:
Potassium carbonate (0.462 g, 3.34 mmol) was added to a solution of 1-chloroisoquinolin-4-ol (0.5 g, 2.78 mmol) and 2-bromo-1,1-difluoroethane (0.807 g, 5.57 mmol) in dry DMF (10 mL) and heated to 50° C. for overnight. Water (20 mL) and EtOAc (50 mL) were added. The organic layer was washed with water 2 more times and then brine, dried over MgSO$_4$, filtered and evaporated to give the final product 1-chloro-4-(2,2-difluoroethoxy)isoquinoline (624 mg, 92% yield) as a light yellow solid. LCMS confirms product. No purification necessary. MS: MS m/z 244.1 (M$^+$+1).

Step 2:
To a solution of 1-chloro-4-(2,2-difluoroethoxy)isoquinoline (630 mg, 2.59 mmol) in DMSO (10 mL) was added CsF (786 mg, 5.17 mmol) and heated to 140° C. for 2 hrs. LC/MS showed the desired product. The reaction was diluted with Ethylactetate and washed with water, and brine. The organic phase was collected, dried over sodium sulfate, and concentrated under vacuum to give the crude product which was purified by silica gel chromatography using a gradient of 5-50% EtOAc/Hexanes. The product fractions were collected and the solvent removed under vacuum to givet the desired product 4-(2,2-difluoroethoxy)-1-fluoroisoquinoline (310 mg, 52.8% yield). MS: MS m/z 228.1 (M$^+$+1).

Preparation of 1-fluoro-4-(2-methoxyethoxyl)isoquinoline

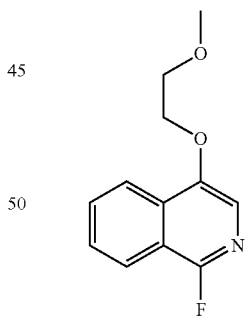

Scheme:

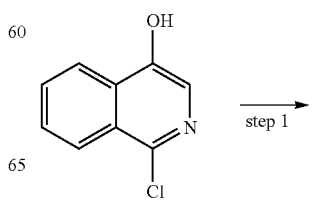

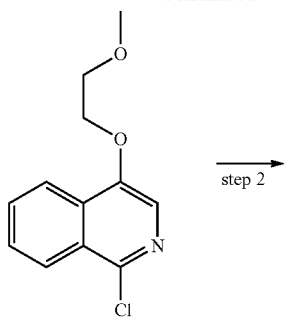 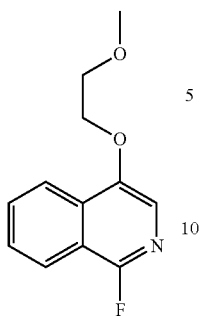 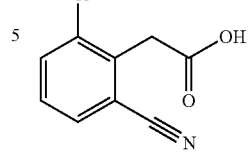 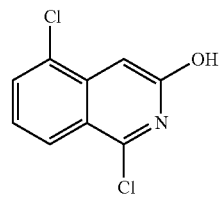

Step 1:

1-chloroisoquinolin-4-ol (0.5 g, 2.78 mmol), 1-bromo-2-methoxyethane (0.318 mL, 3.34 mmol), and potassium carbonate (0.539 g, 3.90 mmol) were added to a solution of DMF (10 mL) and heated to 45° C. for 1 hr. Ater 45 min, the temp was raised to 55° C. for 45 min. One half of an equivalent of 1-bromo-2-methoxyethane (0.318 mL, 3.34 mmol) was then added and then stirred at 40° C. for overnight. The reaction was diluted with water and extracted with EtOAc. The organic layer was washed with brine, collected, dried over MgSO4, filtered and evaporated to give the crude product. Crude material purified via silica gel chromatography (10-60% EtOAc:Hex) to give the desired product 1-chloro-4-(2-methoxyethoxyl)isoquinoline (368 mg, 1.548 mmol, 55.6% yield) as an orange solid. $^1$H NMR (400 MHz, CHLOROFORM-d) δ 8.33-8.24 (m, 2H), 7.83 (s, 1H), 7.81-7.68 (m, 2H), 4.40-4.32 (m, 2H), 3.95-3.84 (m, 2H), 3.52 (s, 3H). MS: MS m/z 238.15 (M$^+$+1).

Step 2:

To a solution of 1-chloro-4-(2-methoxyethoxyl)isoquinoline (368 mg, 1.548 mmol) in DMSO (7 mL) was added CsF (470 mg, 3.10 mmol) and heated to 140° C. for 2 hrs. LC/MS showed the desired product. The reaction was diluted with Ethylactetate and washed with water, and brine. The organic phase was collected, dried over sodium sulfate, and concentrated under vacuum to give the crude product which was purified by silica gel chromatography using a gradient of 5-25% EtOAc/Hexanes. The product fractions were collected and the solvent removed under vacuum to givet the desired product 1-fluoro-4-(2-methoxyethoxyl)isoquinoline (241 mg, 70.4% yield) as a white solid. MS: MS m/z 222.15 (M$^+$+1).

Preparation of 1,5-dichloroisoquinolin-3-ol

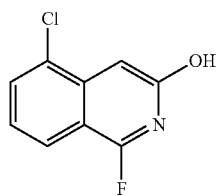 [SMILES: Oc1cc2c(Cl)cccc2c(F)n1]

Step 1:

2-(2-chloro-6-cyanophenyl)acetic acid (10.5 g, 53.7 mmol) and SOCl$_2$ (20 mL, 274 mmol) were stirred in dichloromethane (25 mL) at RT. The suspension became a solution over 4 h. The reaction was stirred overnight. The volatile organics were removed under vacuum and the residue was taken up in DCM and filtered. The filtrate was concentrated and then dissolved in 4 N HCl dioxane (30 mL) and transferred to a sealed vessel and heated to 60° C. for 3 h. The reaction was cooled and the solid was collected, washed with dioxane, and dried under vacuum to give the product 1,5-dichloroisoquinolin-3-ol (8 g, 69.6% yield) as a solid $^1$H NMR (400 MHz, DMSO-d$_6$) δ 11.66 (s, 1H), 8.11 (dt, J=8.6, 1.0 Hz, 1H), 7.90 (dd, J=7.6, 1.0 Hz, 1H), 7.46 (dd, J=8.6, 7.6 Hz, 1H), 7.11 (d, J=1.0 Hz, 1H). MS: MS m/z 214.08 (M$^+$+1).

Preparation of 5-chloro-1-fluoro-3-propoxyisoquinoline

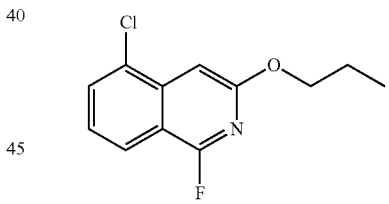

Scheme:

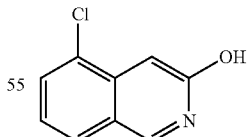

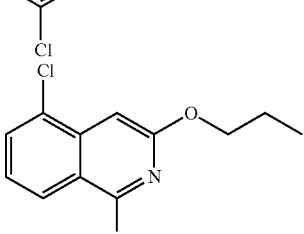

379

-continued

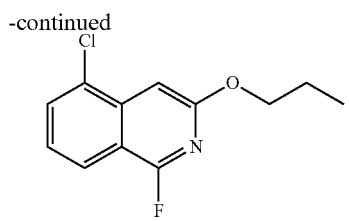

380

-continued

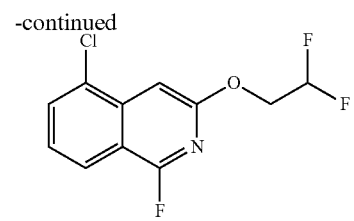

Step 1:

Potassium carbonate (646 mg, 4.67 mmol) was added to a solution of 1,5-dichloroisoquinolin-3-ol (500 mg, 2.336 mmol) and 1-bromopropane (0.234 mL, 2.57 mmol) and heated to 50° C. for 3 hrs. After 3 hours the reaction was diluted with water and extracted with EtOAc (2×). The organic layer was washed with water followed by brine, dried over MgSO$_4$, filtered and evaporated to give the crude product 1,5-dichloro-3-propoxyisoquinoline (550 mg, 92% yield), which was used as is in the next step. MS: MS m/z 256.1 (M$^+$+1).

Step 2:

To a solution of 1,5-dichloro-3-propoxyisoquinoline (565 mg, 2.206 mmol) in DMSO (5 mL) was added CsF (369 mg, 2.427 mmol) and heated to 140° C. for 2 hrs. LC/MS showed the desired product. The reaction was diluted with Ethylactetate and washed with water, and brine. The organic phase was collected, dried over MgSO$_4$, and concentrated under vacuum to give the crude product as a reddish brown solid. Crude material purified via silica gel chromatography (90 g column; 0-40% EtOAc:Hex) to get the product 5-chloro-1-fluoro-3-propoxyisoquinoline (440 mg, 83% yield) as a yellow solid. MS: MS m/z 240.05 (M$^+$+1).

Preparation of 5-chloro-3-(2,2-difluoroethoxy)-1-fluoroisoquinoline

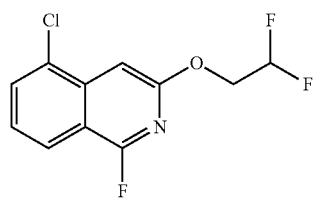 [SMILES: Fc1nc(OCC(F)F)cc2c(Cl)cccc12]

Step 1:

Potassium carbonate (646 mg, 4.67 mmol) was added to a solution of 1,5-dichloroisoquinolin-3-ol (500 mg, 2.336 mmol) and 2-bromo-1,1-difluoroethane (677 mg, 4.67 mmol) and heated to 50° C. for 18 hrs. The reaction was diluted with water and extracted with EtOAc. The organic layer was washed with water (2×) followed by brine. The organic layer was collected, dried over MgSO$_4$, filtered and evaporated to give the crude product 1,5-dichloro-3-(2,2-difluoroethoxy)isoquinoline (590 mg, 90% yield) which was used as is in the next step. MS: MS m/z 278.1 (M$^+$+1).

Step 2:

To a solution of 1,5-dichloro-3-(2,2-difluoroethoxy)isoquinoline (581 mg, 2.089 mmol) in DMSO (5 mL) was added CsF (349 mg, 2.298 mmol) and heated to 140° C. for 2 hrs. LC/MS showed the desired product. The reaction was diluted with ethyl acetate and washed with water, and brine. The organic phase was collected, dried over MgSO$_4$, and concentrated under vacuum to give the crude product as a reddish brown solid. Crude material purified via silica gel chromatography (90 g column; 0-40% EtOAc:Hex) to get the product 5-chloro-3-(2,2-difluoroethoxy)-1-fluoroisoquinoline (450 mg, 82% yield) as a yellow solid. MS: MS m/z 262.1 (M$^+$+1).

Preparation of 5-chloro-1-fluoro-3-isopropoxyisoquinoline

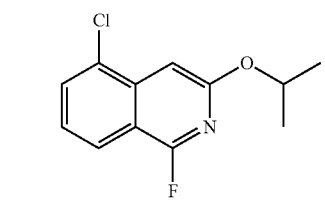 [SMILES: CC(C)Oc1cc2c(Cl)cccc2c(F)n1]

Scheme:

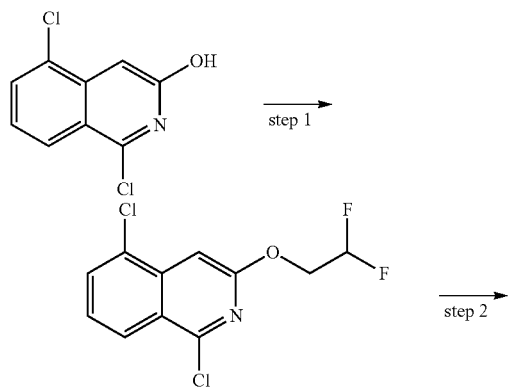

Scheme:

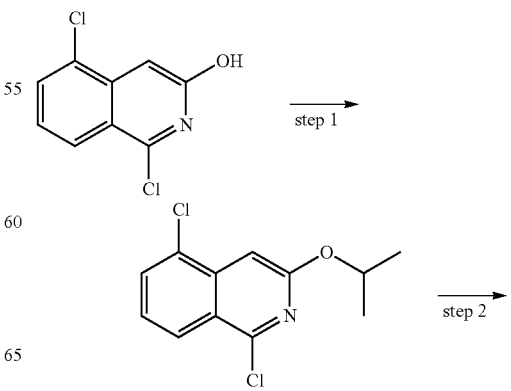

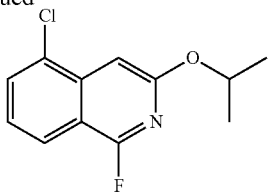

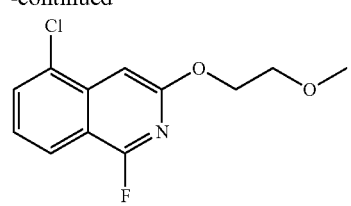

Step 1:

Sodium hydride (103 mg, 2.57 mmol) was added to a solution of 1,5-dichloroisoquinolin-3-ol (500 mg, 2.336 mmol) and 2-bromopropane (575 mg, 4.67 mmol) and stirred at rt for 3 hrs. The reaction was diluted with water and extracted with EtOAc. The organic layer was washed with water (2×) followed by brine. The organic layer was collected, dried over MgSO$_4$, filtered and evaporated to give the crude product 1,5-dichloro-3-isopropoxyisoquinoline (598 mg, 100% yield) which was used as is in next step. MS: MS m/z 256.1 (M$^+$+1).

Step 2:

To a solution of 1,5-dichloro-3-isopropoxyisoquinoline (598 mg, 2.335 mmol) in DMSO (5 mL) was added CsF (390 mg, 2.57 mmol) and heated to 140° C. for 2 hrs. LC/MS showed the desired product. The reaction was diluted with ethyl acetate and washed with water, and brine. The organic phase was collected, dried over MgSO$_4$, and concentrated under vacuum to give the crude product as a reddish brown solid. Crude material purified via silica gel chromatography (90 g column; 0-40% EtOAc:Hex) to get the product 5-chloro-1-fluoro-3-isopropoxyisoquinoline (520 mg, 93% yield) as a yellow solid. MS: MS m/z 240.15 (M$^+$+1).

Preparation of 5-chloro-1-fluoro-3-(2-methoxyethoxyl)isoquinoline

Step 1:

Potassium carbonate (646 mg, 4.67 mmol) was added to a solution of 1,5-dichloroisoquinolin-3-ol (500 mg, 2.336 mmol) and 1-bromo-2-methoxyethane (357 mg, 2.57 mmol) and heated to 50° C. for 3 hrs. After 3 hrs the reaction was diluted with water and extracted with EtOAc (2×). The organic layer was washed with water followed by brine, dried over MgSO4, filtered and evaporated to give the crude product 1,5-dichloro-3-(2-methoxyethoxyl)isoquinoline (550 mg, 87% yield), which was used as is in the next step. MS: MS m/z 272.1 (M$^+$+1).

Step 2:

To a solution of 1,5-dichloro-3-(2-methoxyethoxyl)isoquinoline (578 mg, 2.124 mmol) in DMSO (5 mL) was added CsF (323 mg, 2.124 mmol) and heated to 140° C. for 2 hrs. LC/MS showed the desired product. The reaction was diluted with ethyl acetate and washed with water, and brine. The organic phase was collected, dried over MgSO$_4$, and concentrated under vacuum to give the crude product as a reddish brown solid. Crude product purified via biotage (90 g column, 5-50% EtAOc:Hex) to give the product 5-chloro-1-fluoro-3-(2-methoxyethoxyl)isoquinoline (250 mg, 46% yield) as a light yellow solid. MS: MS m/z 256.15 (M$^+$+1).

Preparation of 4-(2,2-difluoroethoxy)-1-fluoro-6-methoxyisoquinoline

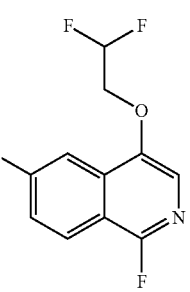

Scheme:

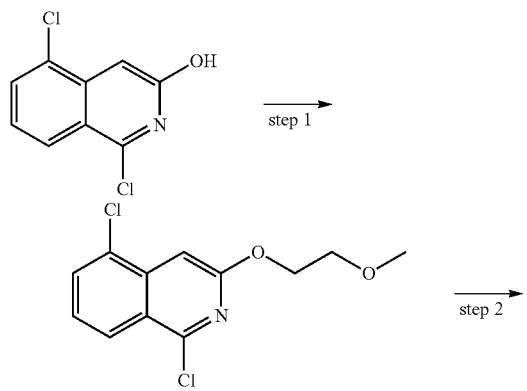

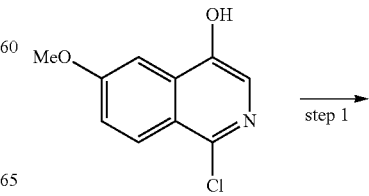

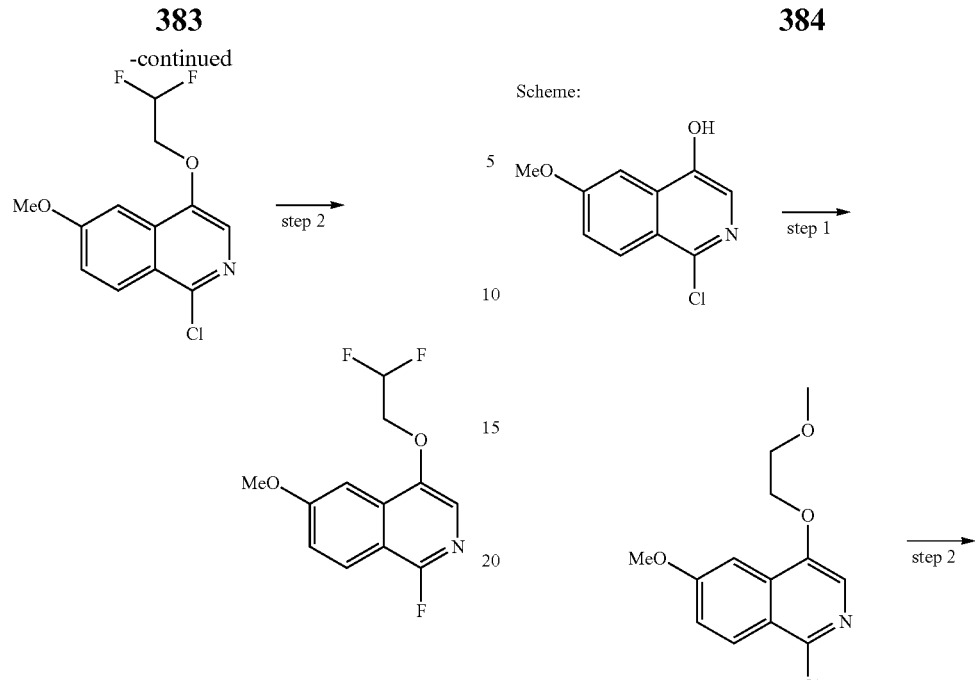

Scheme:

Step 1:

Potassium carbonate (659 mg, 4.77 mmol) was added to a solution of 1-chloro-6-methoxyisoquinolin-4-ol (500 mg, 2.385 mmol) and 2-bromo-1,1-difluoroethane (346 mg, 2.385 mmol) and stirred for 3 hrs at 50° C. After 3 hrs, the reaction was diluted with water and extracted with EtOAc. The organic layer was washed with water (2×) followed by brine. The organic layer was collected, dried over MgSO4, filtered and evaporated to give the crude product 1-chloro-4-(2,2-difluoroethoxy)-6-methoxyisoquinoline (538 mg, 82%) as an orange solid. Crude material used as is in next step. MS: MS m/z 274.1 (M$^+$+1).

Step 2:

To a solution of 1-chloro-4-(2,2-difluoroethoxy)-6-methoxyisoquinoline (538 mg, 1.966 mmol) in DMSO (5 mL) was added CsF (597 mg, 3.93 mmol) and heated to 140° C. for 2 hrs. LC/MS showed the desired product. The reaction was diluted with ethyl actetate and washed with water, and brine. The organic phase was collected, dried over MgSO$_4$, and concentrated under vacuum to give the crude product as a reddish brown solid. The crude material was purified via silica gel chromatography (5-50% EtOAc: Hex) to give the product 4-(2,2-difluoroethoxy)-1-fluoro-6-methoxyisoquinoline (237 mg, 0.921 mmol, 46.9% yield) as a light yellow solid. MS: MS m/z 258.2 (M$^+$+1).

Preparation of 1-fluoro-6-methoxy-4-(2-methoxyethoxyl)isoquinoline

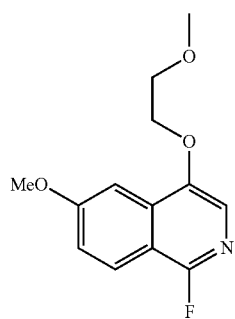 [SMILES: COCCOc1cnc(F)c2ccc(OC)cc12]

Step 1:

Potassium carbonate (659 mg, 4.77 mmol) was added to a solution of 1-chloro-6-methoxyisoquinolin-4-ol (500 mg, 2.385 mmol) and 1-bromo-2-methoxyethane (663 mg, 4.77 mmol) and stirred for 3 hrs at 50° C. After 3 hrs, the reaction was diluted with water and extracted with EtOAc. The organic layer was washed with water (2×) followed by brine. The organic layer was collected, dried over MgSO4, filtered and evaporated to give the crude product 1-chloro-6-methoxy-4-(2-methoxyethoxyl)isoquinoline (560 mg, 88% yield) as an orange solid. Crude material used as is in next step. MS: MS m/z 268.15 (M$^+$+1).

Step 2:

To a solution of 1-chloro-6-methoxy-4-(2-methoxyethoxyl)isoquinoline (560 mg, 2.092 mmol) in DMSO (5 mL) was added CsF (636 mg, 4.18 mmol) and heated to 140° C. for 2 hrs. LC/MS showed the desired product. The reaction was diluted with Ethylactetate and washed with water, and brine. The organic phase was collected, dried over MgSO$_4$, and concentrated under vacuum to give the crude product as a reddish brown solid. The crude material was purified via silica gel chromatography (5-50% EtOAc: Hex) to give the product 1-fluoro-6-methoxy-4-(2-methoxyethoxyl)isoquinoline (168 mg, 0.669 mmol, 32.0% yield) as a light yellow solid. MS: MS m/z 252.2 (M$^+$+1).

Preparation of 4-chloro-2-isopropylphthalazin-1(2H)-one

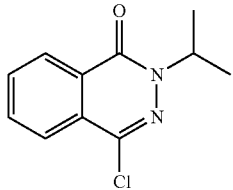

Scheme:

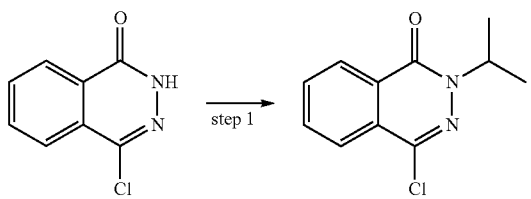

Step 1:

Potassium carbonate (459 mg, 3.32 mmol) was added to a solution of 4-chlorophthalazin-1(2H)-one (300 mg, 1.661 mmol) and 2-bromopropane (409 mg, 3.32 mmol) and heated to 50° C. for 3 hrs. After 3 hrs the reaction was diluted with water and extracted with EtOAc (2×). The organic layer was washed with water followed by brine, dried over MgSO4, filtered and evaporated to give the crude product 4-chloro-2-isopropylphthalazin-1(2H)-one (380 mg, 103% yield), which was used as is in the next step. MS: MS m/z 223.15 (M$^+$+1).

Preparation of 4-chloro-2-(2-methoxyethyl)phthalazin-1(2H)-one

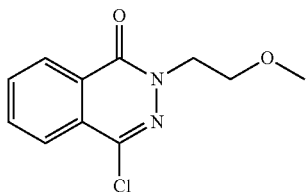

Scheme:

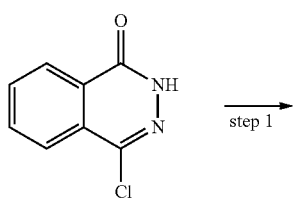

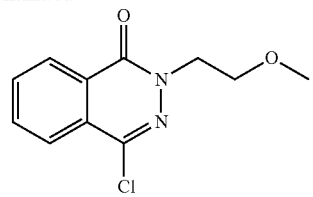 [SMILES: COCCn1nc(Cl)c2ccccc2c1=O]

Step 1:

Potassium carbonate (459 mg, 3.32 mmol) was added to a solution of 4-chlorophthalazin-1(2H)-one (300 mg, 1.661 mmol) and 1-bromo-2-methoxyethane (462 mg, 3.32 mmol) and heated to 50° C. for 3 hrs. After 3 hrs the reaction was diluted with water and extracted with EtOAc (2×). The organic layer was washed with water followed by brine, dried over MgSO4, filtered and evaporated to give the crude product. The crude material was purified via silica gel chromatography (90 g column, 5-45% EtOAc:Hex) to give the desired product 4-chloro-2-(2-methoxyethyl)phthalazin-1(2H)-one (280 mg, 70.6% yield) as a yellow solid. MS: MS m/z 223.15 (M$^+$+1).

Preparation of 1-chloro-N-ethyl-6-methoxy-N-methylisoquinolin-3-amine

Scheme:

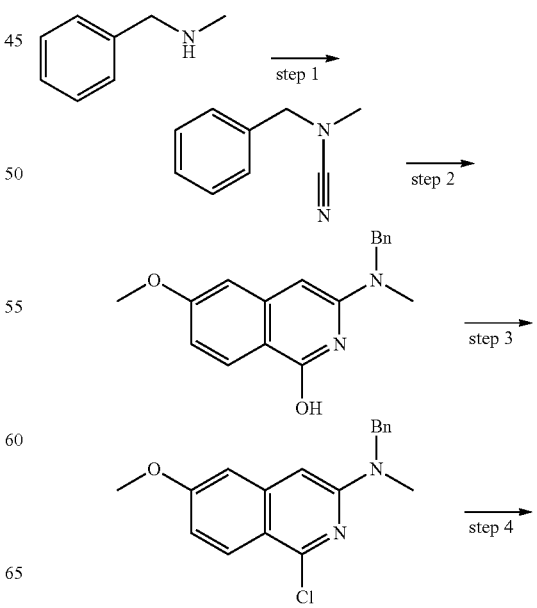

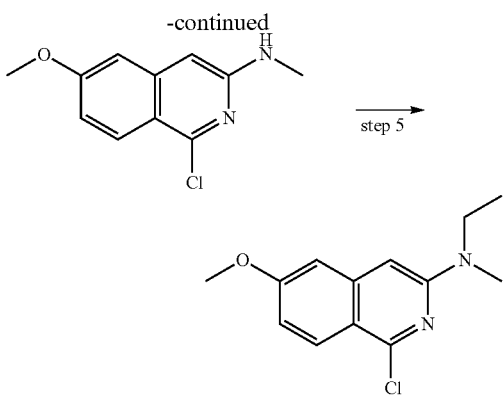

Step 1:

To a solution of N-methyl-1-phenylmethanamine (5.31 mL, 41.3 mmol) and Hunig's Base (7.93 mL, 45.4 mmol) in THF (110 mL) at 0° C. was added cyanic bromide (4.81 g, 45.4 mmol) in one pot. The reaction was stirred at 0° C. for 2 hr before allowing to warm up to RT for 16 hrs.

The reaction was concentrated under vacuum, and the residue was suspended in ethyl acetate. The resulting mixture was filtered, and the filtrate was washed with water (×2) and brine, dried over anhyd. sodium sulfate, filtered, and concentrated to afford N-benzyl-N-methylcyanamide (5.8 g, 39.7 mmol, 96% yield) as a light yellow thin oil. All aqueous workup solutions and any equipment using cyanic bromide were soaked in bleach and then washed with water. All bleach material put in cubitainer and properly labelled for disposal. MS: MS m/z 147.1 (M$^+$+1). $^1$H NMR (500 MHz, CHLOROFORM-d) δ 7.44-7.34 (m, 5H), 4.18 (s, 2H), 2.80 (s, 3H).

Step 2:

To a solution of N,N-diethyl-4-methoxy-2-methylbenzamide (2 g, 9.04 mmol) in THF (50 mL) was added tert-butyllithium (7.97 mL, 13.56 mmol) dropwise at −78° C. After stirring for 0.5 h, N-benzyl-N-methylcyanamide (1.453 g, 9.94 mmol) was added, then warmed to rt, and stirred for 16 h. The reaction mixture was quenched with water (1 mL) and partially evaporated to half to one third of original volume, neutralized with 1 N HCl. The solution was separated with EtOAc. Upon adding to reparatory funnel a solid mass precipitated out and was filtered off and washed with water then dried under high vacuum for overnight. The light yellow solid was the expected product 3-(benzyl(methyl)amino)-6-methoxyisoquinolin-1-ol (1.8 g, 6.12 mmol, 67.7% yield). MS: MS m/z 295.3 (M$^+$+1).

Step 3:

A solution of 3-(benzyl(methyl)amino)-6-methoxyisoquinolin-1-ol (1.8 g, 6.12 mmol) in POCl$_3$ (10 mL) was refluxed for 4 h. After concentration, the residue was taken into a mixture of 100 mL of DCM and 50 mL of water, cooled to 0° C., neutralized with 3 N NaOH, dried over MgSO$_4$, and concentrated to give N-benzyl-1-chloro-6-methoxy-N-methylisoquinolin-3-amine (1.44 g, 4.60 mmol, 75% yield) as a yellow solid. MS: MS m/z 313.15 (M$^+$+1).

Step 4:

Triflic acid (4.09 mL, 46.0 mmol) was added to a solution of N-benzyl-1-chloro-6-methoxy-N-methylisoquinolin-3-amine (1.44 g, 4.60 mmol) in DCM (20 mL) at RT and stirred for 1 hr at RT before reverse adding to a solution of sat. sodium bicarbonate. The organic layer was diluted with DCM and separated. The organic layer was dried over MgSO4, filtered and evaporated. The crude material was purified via silica gel chromatography (90 g column, 0-30% EtOAc:Hex) to give the expected product 1-chloro-6-methoxy-N-methylisoquinolin-3-amine (610 mg, 2.74 mmol, 59.5% yield) as an orange solid. MS: MS m/z 223.15 (M$^+$+1).

Step 5:

Hunig's base (0.235 mL, 1.347 mmol) was added to a solution of 1-chloro-6-methoxy-N-methylisoquinolin-3-amine (150 mg, 0.674 mmol) and acetaldehyde (0.042 mL, 0.741 mmol) in MeOH (5 mL) and stirred for 30 min. Acetic Acid (1 mL) and Cyanoborohydride, polymer supported (2 mmol/gram) (50 mg, 0.674 mmol) were then added and the reaction stirred at r.t. for 2 hrs. Reaction filtered through nylon frit filter and evaporated on rotovap to give the crude product with no purification. The material was taken up in EtOAc and washed with sat. sodium bicarbonate. The organic layer was collected, dried over MgSO4, filtered and evaporated to give the expected product 1-chloro-N-ethyl-6-methoxy-N-methylisoquinolin-3-amine (140 mg, 83% yield) as a dark orange solid. MS: MS m/z 251.15 (M$^+$+1).

Preparation of
1-chloro-6-methoxy-3-(trifluoromethyl)isoquinoline

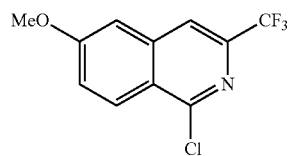 [SMILES: COc1ccc2c(Cl)nc(C(F)(F)F)cc2c1]

Scheme:

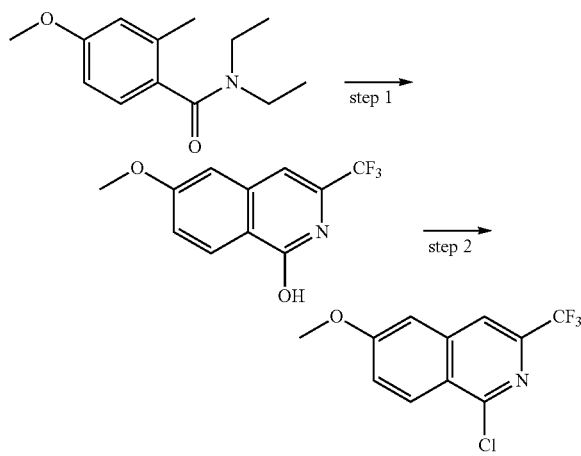

Step 1:

To a solution of N,N-diethyl-4-methoxy-2-methylbenzamide (1 g, 4.52 mmol) in THF (40 mL) was added tert-butyllithium (3.99 mL, 6.78 mmol) dropwise at −78° C. After stirring for 0.5 h, 2,2,2-trifluoroacetonitrile (0.472 g, 4.97 mmol) was bubbled through the solution via syringe for 1 minute, then warmed to rt, and stirred for 16 h. The reaction mixture was quenched with water (1 mL) and partially evaporated to half to one third of original volume, neutralized with 1 N HCl. The solution was separated with EtOAc. The organics were collected, washed with brine, dried over MgSO$_4$, filtered and evaporated to give crude material as a dark yellow solid. The crude material was purified via silica gel chromatography (90 g column, 10-50% EtOAc:Hex) to give the product 6-methoxy-3-(trifluoromethyl)isoquinolin-1-ol (271 mg, 1.114 mmol, 24.66% yield) as a light yellow solid. MS: MS m/z 244.19 (M++1).

Step 2:

A solution of 6-methoxy-3-(trifluoromethyl)isoquinolin-1-ol (271 mg, 1.114 mmol) in POCl3 (3 mL) was refluxed for 4 h. After concentration, the residue was taken into a mixture of 100 mL of DCM and 50 mL of water, cooled to 0° C., neutralized with 3 N NaOH, dried over MgSO4, concentrated and purified via silica gel chromatography (5-20% EtOAc:Hex) to give the pure product 1-chloro-6-methoxy-3-(trifluoromethyl)isoquinoline (250 mg, 0.956 mmol, 86% yield) as an orange solid. MS: MS m/z 262.1 (M++1).

Preparation of
1-chloro-6-methoxy-4-(trifluoromethyl)isoquinoline

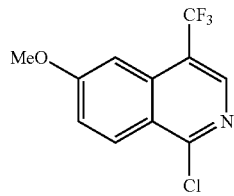 [SMILES: COc1ccc2c(Cl)ncc(C(F)(F)F)c2c1]

Scheme:

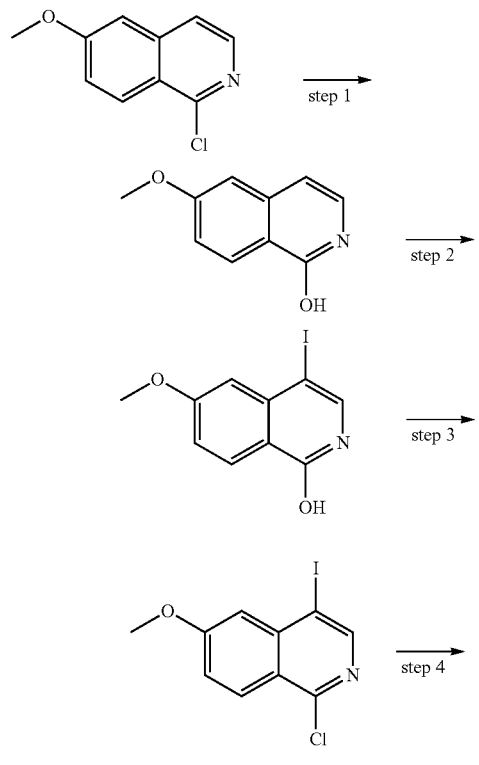

-continued

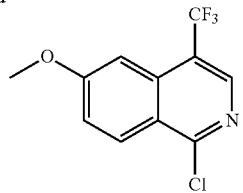

Step 1:

1-chloro-6-methoxyisoquinoline (5 g, 25.8 mmol) was added to a solution of HCl (21.52 ml, 129 mmol) and heated to 120° C. and monitored by LCMS. The reaction was stirred at this temp for over the weekend (3 days). Reaction was cooled and material precipitated. The slurry was diluted with DCM and water and separated in a reparatory funnel. The organic layer was washed with water (2×) followed by brine, dried over MgSO$_4$, filtered and evaporated to give the crude material. The crude material was purified via silica gel chromatography (240 g column, 0-15% MeOH:DCM) to give the expected product 6-methoxyisoquinolin-1-ol (2.38 g, 13.59 mmol, 52.6% yield) as a white solid. MS: MS m/z 176.09 (M++1).

Step 2:

To a solution of NIS (3.31 g, 14.73 mmol) in CH$_3$CN (25 mL) was added 6-methoxyisoquinolin-1-ol (2.58 g, 14.73 mmol). The resulting suspension was slowly warmed to reflux and maintained refluxing for 2 h. After concentration, the residue was taken into water. The solid was collected through filter paper washing with hot water to give a crude product 4-iodo-6-methoxyisoquinolin-1-ol (3.87 g, 87% yield) which was used in the next step with out further purification. MS: MS m/z 302 (M++1). $^1$H NMR (400 MHz, CHLOROFORM-d) δ 16.12 (br. s., 1H), 12.86 (d, J=9.0 Hz, 1H), 12.34 (d, J=5.8 Hz, 1H), 11.89 (dd, J=8.8, 2.5 Hz, 1H), 11.76 (d, J=2.3 Hz, 1H), 8.70-8.62 (m, 3H).

Step 3:

A solution of 4-iodo-6-methoxyisoquinolin-1-ol (2 g, 6.64 mmol) in POCl3 (10 mL) was refluxed for 4 h. After concentration, the residue was taken into a mixture of 100 mL of DCM and 50 mL of water, cooled to 0° C., neutralized with 3 N NaOH, dried over MgSO4, concentrated and purified via silica gel chromatography (5-20% EtOAc:Hex) to give the pure product 1-chloro-4-iodo-6-methoxyisoquinoline (1.3 g, 4.07 mmol, 61.2% yield) as an orange solid. $^1$H NMR (400 MHz, DMSO-d$_6$) δ 8.69 (s, 1H), 8.22 (d, J=9.3 Hz, 1H), 7.54 (dd, J=9.3, 2.5 Hz, 1H), 7.33 (d, J=2.5 Hz, 1H), 4.03 (s, 3H). MS: MS m/z 320 (M++1).

Step 4:

Copper(I) Iodide (298 mg, 1.565 mmol) and potassium fluoride (182 mg, 3.13 mmol) were weighed out in a flask and heated with a heat gun under vacuum until the solid turned a pale yellow green. After cooling to RT dry THF (3 mL), and dry DMF (3 mL) and trimethyl(trifluoromethyl)silane (0.463 mL, 3.13 mmol) were added at RT and then heated to 60° C. for 6 hrs. LCMS shows small product peak. Reaction heated for overnight. Reaction was then cooled and quenched with water added and separated with EtOAc. The organic layer was washed with brine, dried over MgSO$_4$, filtered and evaporated to give the crude product 1-chloro-6-methoxy-4-(trifluoromethyl)isoquinoline (175 mg, 0.669 mmol, 85% yield) which was used as is in following step. $^1$H NMR (400 MHz, CHLOROFORM-d) δ 8.59-8.53 (m, 1H), 8.37 (d, J=9.3 Hz, 1H), 7.45-7.34 (m, 2H), 4.02 (s, 3H). MS: MS m/z 262.1 (M++1).

Preparation of 1-fluoro-3,6-dimethoxyisoquinoline

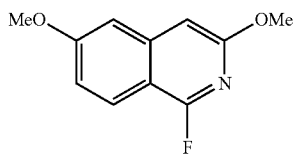 [SMILES: COc1ccc2c(F)nc(OC)cc2c1]

Scheme:

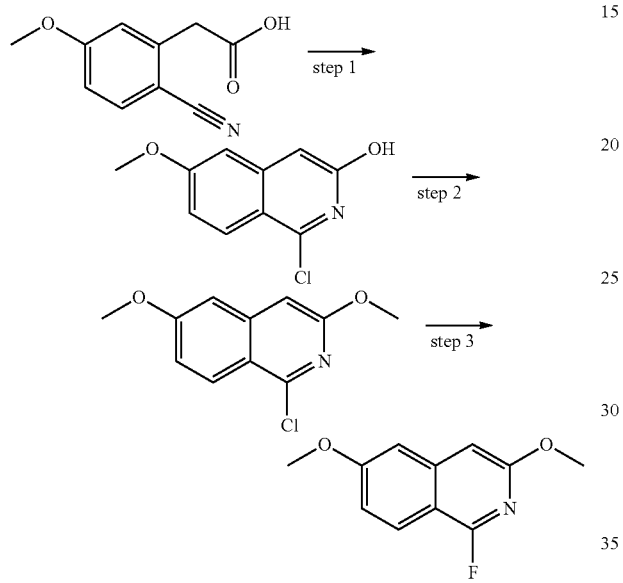

Step 1:

2-(2-cyano-5-methoxyphenyl)acetic acid (3.8 g, 19.88 mmol), and SOCl$_2$ (20 mL, 274 mmol) were stirred in dichloromethane (25 mL) at RT. The suspension became a solution over 8 h. The reaction was stirred overnight. The volatile organics were removed under vacuum and the residue was taken up in DCM and filtered. The filtrate was concentrated and then dissolved in 4 N HCl dioxane (30 mL) and transferred to a sealed vessel and heated to 60° C. for 3 h. The reaction was cooled and the solid was collected, washed with dioxane, and dried under vacuum to give the product 1-chloro-6-methoxyisoquinolin-3-ol (3.3 g, 70% yield). $^1$H NMR (400 MHz, CHLOROFORM-d) δ 8.10 (d, J=9.6 Hz, 1H), 7.12 (dd, J=9.3, 2.5 Hz, 1H), 6.95 (s, 2H), 3.98 (s, 3H).

Step 2:

To a mixture of 1-chloro-6-methoxyisoquinolin-3-ol (3.3 g, 15.74 mmol) in DMF (30 mL) was added potassium carbonate (2.61 g, 18.89 mmol) and iodomethane (1.969 mL, 31.5 mmol). It was then stirred at rt overnight. LC/MS showed 2 peaks with the desired mass and also starting material. An additional 1 equ. of MeI, and 1 equ of K$_2$CO$_3$ was added and the reaction warmed to 40° C. for 2 h. LC/MS showed all starting material had been consumed. The reaction was diluted with EtOAc and water. The organic layer was washed with water, brine, dried over sodium sulfate, and concentrated under vacuum. The crude material was purified by silica gel column using 20% EtOAc/Hexanes. The product fractions were collected and the solvent removed under vacuum to give the desired product 1-chloro-3,6-dimethoxyisoquinoline (2.47 g, 70% yield) as a white solid. MS: MS m/z 223.93 (M$^+$+1). $^1$H NMR (400 MHz, CHLOROFORM-d) δ 8.10 (d, J=9.3 Hz, 1H), 7.08 (dd, J=9.3, 2.5 Hz, 1H), 6.93 (d, J=2.5 Hz, 1H), 6.85 (s, 1H), 4.07-3.99 (m, 3H), 3.95 (s, 3H).

Step 3:

To a solution of 1-chloro-3,6-dimethoxyisoquinoline (300 mg, 1.341 mmol) in DMSO (5 mL) was added CsF (408 mg, 2.68 mmol) and heated to 140° C. for 2 hrs. LC/MS showed the desired product. The reaction was diluted with Ethylactetate and washed with water, and brine. The organic phase was collected, dried over MgSO$_4$, and concentrated under vacuum to give the crude product 1-fluoro-3,6-dimethoxyisoquinoline (250 mg, 90% yield) as a reddish brown solid. $^1$H NMR (400 MHz, CHLOROFORM-d) δ 7.93 (d, J=9.0 Hz, 1H), 7.03 (dd, J=9.3, 2.3 Hz, 1H), 6.95 (t, J=1.9 Hz, 1H), 6.75 (s, 1H), 4.01-3.96 (m, 3H), 3.96-3.90 (m, 3H). MS: MS m/z 208.07 (M$^+$+1).

Preparation of ethyl 2-(0-chloroisoquinolin-6-yl)oxy)acetate

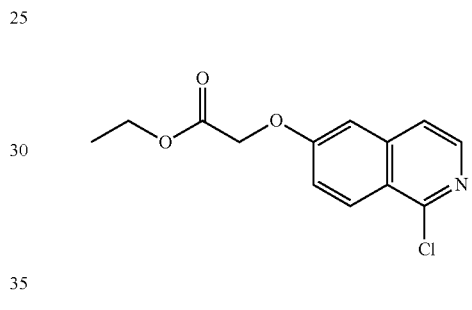

Scheme:

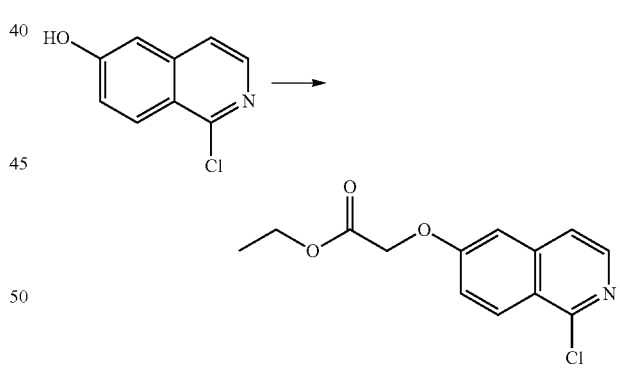

To a dry 40 mL vial equipped with a stir bar was added 1-chloroisoquinolin-6-ol (200 mg, 1.11 mmol) and potassium carbonate (231 mg, 1.67 mmol). To the vial was added dry ethyl acetate (6 mL) followed by ethyl 2-bromoacetate (0.148 mL, 1.34 mmol). The vial was sealed and then heated at 60° C. for 2 h. The mixture was cooled to room temperature, diluted with acetone, and then filtered. The filtrated was concentrated and the resulting solid residue was subjected to SiO2 chromatography (hexanes:EtOAc 85:15 to 70:30) to afford ethyl 2-((1-chloroisoquinolin-6-yl)oxy)acetate as a colorless, crystalline solid (296 mg, 66%). $^1$H NMR (400 MHz, CHLOROFORM-d) δ 8.29 (d, J=9.3 Hz, 1H), 8.22 (d, J=5.8 Hz, 1H), 7.49 (d, J=5.8 Hz, 1H), 7.40 (dd, J=9.3, 2.8

Hz, 1H), 7.04 (d, J=2.5 Hz, 1H), 4.79 (s, 2H), 4.32 (q, J=7.3 Hz, 2H), 1.33 (t, J=7.2 Hz, 3H); MS: MS m/z 266.15 (M⁺+1).

Preparation of oxetan-3-yl pyridin-2-yl carbonate

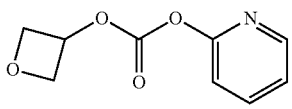 [SMILES: O=C(Oc1ccccn1)OC1COC1]

Scheme:

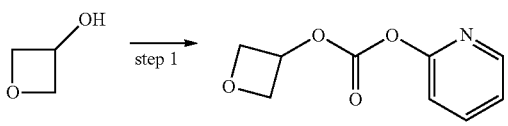

Step 1:

To a suspension of sodium hydride, 60% in mineral oil (0.594 g, 14.85 mmol) in THF (50 mL) was added oxetan-3-ol (1 g, 13.50 mmol) at 0° C. After stirring 30 min, the solution was transferred to a solution of di(pyridin-2-yl) carbonate (2.92 g, 13.50 mmol) in THF (50 mL) through a cannula. The formed slurry was stirred at 0° C. for 30 min. The slurry was warmed to rt and stirred for 2 h. The reaction was diluted with EtOAc, washed with brine, dried over MgSO₄, filtered, concentrated to give a residue that was purified by Biotage eluting with 20-50% EtOAc in hexanes to afford the desired product oxetan-3-yl pyridin-2-yl carbonate (452 mg, 17.16% yield) as an oil. 500 mg sm recovered. ¹H NMR (400 MHz, CHLOROFORM-d) δ 8.42 (dd, J=4.6, 1.6 Hz, 1H), 7.89-7.77 (m, 1H), 7.33-7.27 (m, 1H), 7.14 (d, J=8.3 Hz, 1H), 5.62-5.52 (m, 1H), 4.96-4.91 (m, 2H), 4.83-4.78 (m, 2H).

Preparation of 3-methyloxetan-3-yl pyridin-2-yl carbonate

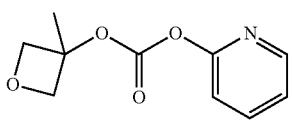

Scheme:

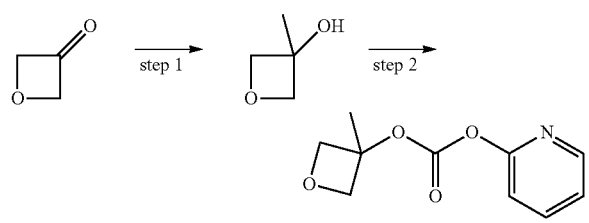

Methylmagnesium bromide (12.72 mL, 38.2 mmol) was added dropwise via syringe to a solution of oxetan-3-one (2.5 g, 34.7 mmol) in Diethyl ether (110 mL) at 0° C. and stirred at this temp for 1 hr before warming up to RT. The reaction was quenched with sat. ammonium chloride and extracted with ether. The organic layer was washed with brine, collected, dried over MgSO4, filtered and evaporated to give the crude product 3-methyloxetan-3-ol (1.5 g, 49.1% yield) as a clear oil. ¹H NMR (400 MHz, CHLOROFORM-d) δ 4.63 (d, J=6.5 Hz, 2H), 4.53-4.45 (m, 2H), 2.48 (br. s., 1H), 1.58 (s, 3H).

Step 2:

To a suspension of sodium hydride, 60% in mineral oil (0.817 g, 20.43 mmol) in THF (55 mL) was added 3-methyloxetan-3-ol (1.5 g, 17.03 mmol) at 0° C. After stirring 30 min, the solution was transferred to a solution of di(pyridin-2-yl) carbonate (3.68 g, 17.03 mmol) in THF (55 mL) through a cannula. The formed slurry was stirred at 0° C. for 30 min. The slurry was warmed to rt and stirred for 2 h. The reaction was diluted with EtOAc, washed with brine, dried over MgSO₄, filtered, concentrated to give a residue that was purified by Biotage (5-40% EtOAc:Hex) to afford the desired product 3-methyloxetan-3-ylpyridin-2-yl carbonate (1.00 g, 28.1% yield) as an oil. ¹H NMR (400 MHz, CHLOROFORM-d) δ 8.52-8.35 (m, 1H), 7.84 (ddd, J=8.1, 7.3, 2.1 Hz, 1H), 7.31-7.27 (m, 1H), 7.15 (dt, J=8.1, 0.8 Hz, 1H), 4.97-4.85 (m, 2H), 4.54 (d, J=8.0 Hz, 2H), 1.86 (s, 3H).

Preparation of pyridin-2-yl (3-(trifluoromethyl)oxetan-3-yl)carbonate

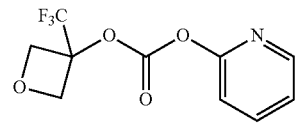 [SMILES: O=C(Oc1ccccn1)OC1(C(F)(F)F)COC1]

Scheme:

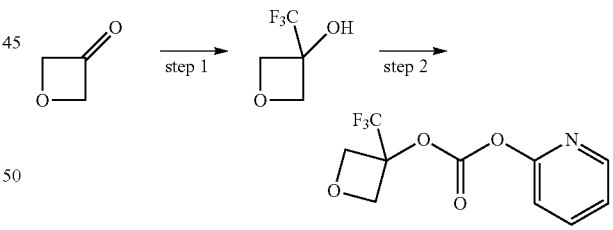

Step 1:

Tetrahydrofuran (110 mL) was added to a round bottom flask and placed under N₂. trimethyl(trifluoromethyl)silane (7.18 mL, 48.6 mmol) was then added and stirred under N₂ and then cooled to 0° C. oxetan-3-one (2.5 g, 34.7 mmol) was then added via syringe and stirred for 5 minutes at 0° C. to ensure complete mixing. TBAF (0.347 mL, 0.347 mmol) was added dropwise slowly via syringe and allowed to warm up to RT for 1 hr. The reaction was then cooled back down to 0° C. and added 30 mL of 1N HCl and stirred at RT for overnight. The reaction was then diluted with EtOAc and separated with water. The organic layer was washed with brine, dried over MgSO4, filtered and evaporated to give the product 3-(trifluoromethyl)oxetan-3-ol (2.00 g, 40.6% yield)

as an orange thin oil. ¹H NMR (400 MHz, CHLOROFORM-d) δ 4.82-4.74 (m, 2H), 4.70-4.60 (m, 2H), 3.23 (br. s., 1H).
Step 2:
To a suspension of sodium hydride, 60% in mineral oil (0.676 g, 16.89 mmol) in THF (55 mL) was added 3-(trifluoromethyl)oxetan-3-ol (2 g, 14.08 mmol) at 0° C. After stirring 30 min, the solution was transferred to a solution of di(pyridin-2-yl) carbonate (3.04 g, 14.08 mmol) in THF (55 mL) through a cannula. The formed slurry was stirred at 0° C. for 30 min. The slurry was warmed to rt and stirred for 2 h. The reaction was diluted with EtOAc, washed with brine, dried over MgSO₄, filtered, concentrated to give a residue that was purified by Biotage (90 g column, 5-40% EtOAc:Hex) to afford the desired product pyridin-2-yl(3-(trifluoromethyl)oxetan-3-yl)carbonate (1.00 g, 27% yield) as a clear oil. ¹H NMR (400 MHz, CHLOROFORM-d) δ 8.44 (ddd, J=5.0, 2.0, 0.8 Hz, 1H), 7.92-7.81 (m, 1H), 7.33 (ddd, J=7.3, 5.0, 1.0 Hz, 1H), 7.18 (dt, J=8.1, 0.8 Hz, 1H), 5.13-5.05 (m, 2H), 4.94-4.86 (m, 2H).

Preparation of 3-isopropyloxetan-3-yl pyridin-2-yl carbonate

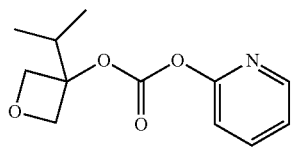 [SMILES: CC(C)C1(OC(=O)Oc2ccccn2)COC1]

Scheme:

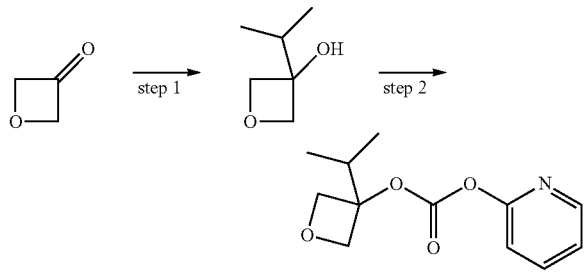

Step 1:
Isopropylmagnesium chloride (13.88 mL, 27.8 mmol) was added dropwise via syringe to a solution of oxetan-3-one (2, 27.8 mmol) in Diethyl ether (110 mL) at 0° C. and stirred at this temp for 1 hr before warming up to RT. The reaction was quenched with sat. ammonium chloride and extracted with ether. The organic layer was washed with brine, collected, dried over MgSO4, filtered and partially evaporated to give the crude product 3-isopropyloxetan-3-ol (2.00 g, 62% yield) as an oil. ¹H NMR (400 MHz, CHLOROFORM-d) δ 4.55 (d, J=7.0 Hz, 2H), 4.50 (d, J=7.0 Hz, 2H), 2.14-2.04 (m, 1H), 0.93 (s, 3H), 0.92 (s, 3H).
Step 2:
To a suspension of sodium hydride, 60% in mineral oil (331 mg, 8.26 mmol) in THF (25 mL) was added 3-isopropyloxetan-3-ol (800 mg, 6.89 mmol) at 0° C. After stirring 30 min, the solution was transferred to a solution of di(pyridin-2-yl) carbonate (1489 mg, 6.89 mmol) in THF (25 mL) through a cannula. The formed slurry was stirred at 0° C. for 30 min. The slurry was warmed to rt and stirred for 2 h. The reaction was diluted with EtOAc, washed with brine, dried over MgSO4, filtered, concentrated to give a residue that was purified by Biotage eluting with 20% EtOAc in hexanes to afford the desired product 3-isopropyloxetan-3-yl pyridin-2-yl carbonate (320 mg, 20.2% yield) as an oil. ¹H NMR (400 MHz, CHLOROFORM-d) δ 8.47-8.39 (m, 1H), 7.86-7.78 (m, 1H), 7.31-7.24 (m, 1H), 7.15 (d, J=8.0 Hz, 1H), 4.89 (d, J=8.5 Hz, 2H), 4.67 (d, J=8.5 Hz, 2H), 2.53 (dt, J=13.7, 7.0 Hz, 1H), 1.13 (s, 3H), 1.12 (s, 3H).

Preparation of 3-cyclopropyloxetan-3-yl pyridin-2-yl carbonate

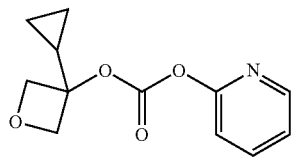 [SMILES: O=C(Oc1ccccn1)OC1(C2CC2)COC1]

Scheme:

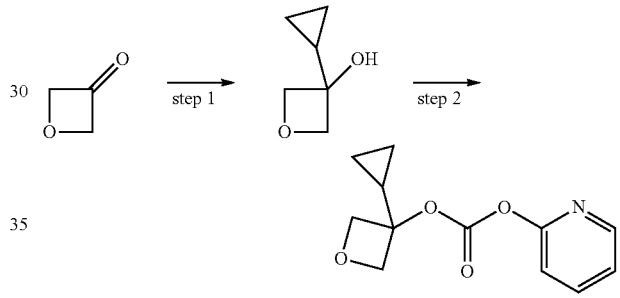

Step 1:
Cyclopropylmagnesium bromide (27.8 mL, 13.88 mmol) was added dropwise via syringe to a solution of oxetan-3-one (1 g, 13.88 mmol) in Diethyl ether (55 mL) at 0° C. and stirred at this temp for 1 hr before warming up to RT. The reaction was quenched with sat. ammonium chloride and extracted with ether. The organic layer was washed with brine, collected, dried over MgSO4, filtered and evaporated to give the crude product 3-cyclopropyloxetan-3-ol (1 g, 63.1% yield) as an oil. ¹H NMR (400 MHz, CHLOROFORM-d) δ 4.54 (d, J=7.3 Hz, 2H), 4.38 (d, J=7.3 Hz, 2H), 1.29-1.19 (m, 1H), 0.62-0.55 (m, 2H), 0.49-0.44 (m, 2H).
Step 2:
To a suspension of sodium hydride, 60% in mineral oil (315 mg, 7.88 mmol) in THF (20 mL) was added 3-cyclopropyloxetan-3-ol (750 mg, 6.57 mmol) at 0° C. After stirring 30 min, the solution was transferred to a solution of di(pyridin-2-yl) carbonate (1421 mg, 6.57 mmol) in THF (20 mL) through a cannula. The formed slurry was stirred at 0° C. for 30 min. The slurry was warmed to rt and stirred for 2 h. The reaction was diluted with EtOAc followed by brine. The organic layer was collected, dried over MgSO₄, filtered and evaporated to give the crude material. The crude material was purified via biotage (40 g column, 5-40% EtOAc: Hex) to give the expected product 3-cyclopropyloxetan-3-ylpyridin-2-yl carbonate (290 mg, 18.76% yield) as a clear thick oil. ¹H NMR (400 MHz, CHLOROFORM-d) δ 8.54-8.36 (m, 1H), 7.89-7.77 (m, 1H), 7.34-7.25 (m, 1H), 7.17 (d, J=8.3 Hz, 1H), 4.84 (d, J=8.5 Hz, 2H), 4.42 (d, J=8.3 Hz, 2H), 1.67-1.56 (m, 1H), 0.81-0.72 (m, 2H), 0.72-0.63 (m, 2H).

Preparation of 3-methyltetrahydrofuran-3-yl pyridin-2-yl carbonate

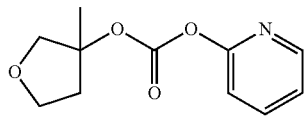 [SMILES: CC1(OC(=O)Oc2ccccn2)CCOC1]

Scheme:

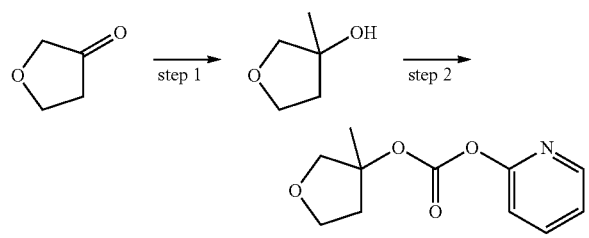

Step 1:

Methylmagnesium bromide (4.26 mL, 12.78 mmol) was added dropwise via syringe to a solution of dihydrofuran-3 (2H)-one (1 g, 11.62 mmol) in Diethyl ether (55 mL) at 0° C. and stirred at this temp for 1 hr before warming up to RT. The reaction was quenched with sat. ammonium chloride and extracted with ether. The organic layer was washed with brine, collected, dried over MgSO4, filtered and evaporated to give the crude product 3-methyltetrahydrofuran-3-ol (394 mg, 33.2% yield) as a clear oil. $^1$H NMR (400 MHz, CHLOROFORM-d) δ 4.05 (td, J=8.5, 7.4 Hz, 1H), 3.91 (td, J=8.5, 4.5 Hz, 1H), 3.71 (dd, J=9.2, 0.9 Hz, 1H), 3.53 (d, J=9.3 Hz, 1H), 2.00-1.95 (m, 2H), 1.43 (s, 3H).

Step 2:

To a suspension of sodium hydride, 60% in mineral oil (185 mg, 4.63 mmol) in THF (20 mL) was added 3-methyltetrahydrofuran-3-ol (394 mg, 3.86 mmol) at 0° C. After stirring 30 min, the solution was transferred to a solution of di(pyridin-2-yl)carbonate (834 mg, 3.86 mmol) in THF (20 mL) through a cannula. The formed slurry was stirred at 0° C. for 30 min. The slurry was warmed to rt and stirred for 2 h. The reaction was diluted with EtOAc, washed with brine, dried over MgSO4, filtered, concentrated to give a residue that was purified by Biotage (5-40% EtOAc:Hex) to afford the desired product 3-methyltetrahydrofuran-3-yl pyridin-2-yl carbonate (334 mg, 38.8% yield) as an oil. $^1$H NMR (400 MHz, CHLOROFORM-d) δ 8.48-8.29 (m, 1H), 7.91-7.73 (m, 1H), 7.29-7.25 (m, 1H), 7.16-7.12 (m, 1H), 4.23 (d, J=10.3 Hz, 1H), 4.02 (td, J=8.5, 7.2 Hz, 1H), 3.95 (td, J=8.4, 4.5 Hz, 1H), 3.76 (d, J=10.3 Hz, 1H), 2.58-2.47 (m, 1H), 2.11-2.02 (m, 1H), 1.76 (s, 3H).

Preparation of pyridin-2-yl (3-(trifluoromethyl)tetrahydrofuran-3-yl)carbonate

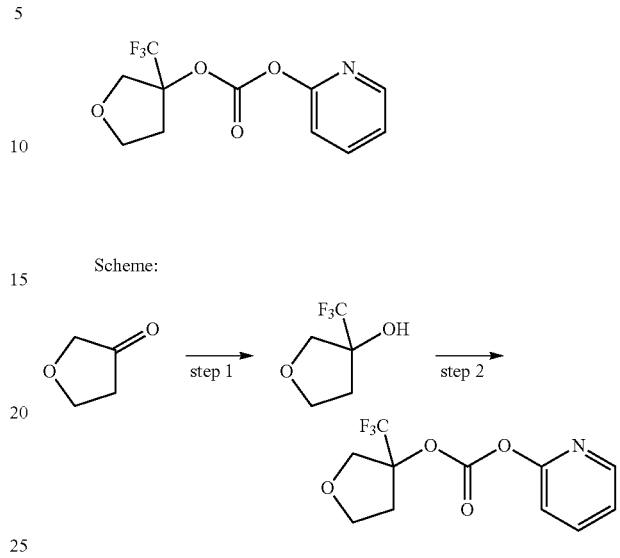

Step 1:

Tetrahydrofuran (55 mL) was added to a round bottom flask and placed under N$_2$. trimethyl(trifluoromethyl)silane (2.404 mL, 16.26 mmol) was then added and stirred under N$_2$ and then cooled to 0° C. Dihydrofuran-3(2H)-one (1 g, 11.62 mmol) was then added via syringe and stirred for 5 minutes at 0° C. to ensure complete mixing. TBAF (0.116 mL, 0.116 mmol) was added dropwise slowly via syringe and allowed to warm up to RT for 1 hr. The reaction was then cooled back down to 0° C. and added 30 mL of 1N HCl and stirred at RT for overnight. The reaction was then diluted with EtOAc and separated with water. The organic layer was washed with brine, dried over MgSO4, filtered and evaporated to give the product 3-(trifluoromethyl)tetrahydrofuran-3-ol (800 mg, 44.1% yield) as an orange thin oil. $^1$H NMR (400 MHz, CHLOROFORM-d) δ 4.05-3.92 (m, 3H), 3.80-3.75 (m, 1H), 2.31 (dt, J=13.3, 8.4 Hz, 1H), 2.08-2.03 (m, 1H).

Step 2:

To a suspension of sodium hydride, 60% in mineral oil (246 mg, 6.15 mmol) in THF (25 mL) was added 3-(trifluoromethyl)tetrahydrofuran-3-ol (800 mg, 5.12 mmol) at 0° C. After stirring 30 min, the solution was transferred to a solution of di(pyridin-2-yl)carbonate (1108 mg, 5.12 mmol) in THF (25 mL) through a cannula. The formed slurry was stirred at 0° C. for 30 min. The slurry was warmed to rt and stirred for 2 h. The reaction was diluted with EtOAc, washed with brine, dried over MgSO4, filtered, concentrated to give a residue that was purified by Biotage (5-40% EtOAc:Hex) to afford the desired product pyridin-2-yl (3-(trifluoromethyl)tetrahydrofuran-3-yl)carbonate (339 mg, 23.86% yield) as an oil. $^1$H NMR (400 MHz, CHLOROFORM-d) δ 8.47-8.33 (m, 1H), 7.88-7.82 (m, 1H), 7.30 (ddd, J=7.4, 4.9, 1.0 Hz, 1H), 7.16 (d, J=8.3 Hz, 1H), 4.40-4.21 (m, 2H), 4.11-3.91 (m, 2H), 2.71-2.61 (m, 1H), 2.58-2.46 (m, 1H).

399
Preparation of 4-methyltetrahydro-2H-pyran-4-yl pyridin-2-yl carbonate

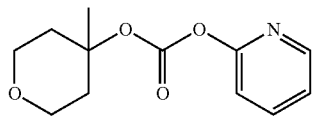 [SMILES: CC1(OC(=O)Oc2ccccn2)CCOCC1]

Scheme:

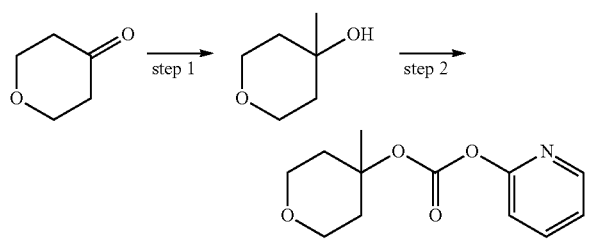

Step 1:

Methylmagnesium bromide (3.66 mL, 10.99 mmol) was added dropwise via syringe to a solution of dihydro-2H-pyran-4(3H)-one (1 g, 9.99 mmol) in Diethyl ether (50 mL) at 0° C. and stirred at this temp for 1 hr before warming up to RT. The reaction was quenched with sat. ammonium chloride and extracted with ether. The organic layer was washed with brine, collected, dried over MgSO$_4$, filtered and evaporated to give the crude product 4-methyltetrahydro-2H-pyran-4-ol (1 g, 86% yield) as an oil. $^1$H NMR (400 MHz, CHLOROFORM-d) δ 3.82-3.73 (m, 2H), 3.73-3.66 (m, 2H), 1.74-1.64 (m, 3H), 1.54 (ddt, J=13.7, 4.6, 2.1 Hz, 2H), 1.41 (br. s, 1H), 1.28 (s, 3H).

Step 2:

To a suspension of sodium hydride, 60% in mineral oil (207 mg, 5.17 mmol) in THF (20 mL) was added 4-methyltetrahydro-2H-pyran-4-ol (500 mg, 4.30 mmol) at 0° C. After stirring 30 min, the solution was transferred to a solution of di(pyridin-2-yl)carbonate (931 mg, 4.30 mmol) in THF (20 mL) through a cannula. The formed slurry was stirred at 0° C. for 30 min. The slurry was warmed to rt and stirred for 2 h. At room temperature, to the reaction mixture was added sat. aq. NH$_4$Cl (1 mL) upon which brief and significant effervescence was observed. The mixture was transferred to a 250 mL separatory funnel and was diluted with Et20 (50 mL). The solution was washed with water: brine (25 mL: 25 mL). The aq. phase was extracted with EtOAc (100 mL). The combined organics were dried over MgSO4; filtered; then concentrated in vacuo. The resulting residue was dissolved in acetone and then concentrated onto Celite in vacuo. The resulting powder was subjected to SiO2 purification on the Biotage system [90 g SiO$_2$ column, hexanes:EtOAc 90:10 to 60:40 over 8 CV] to get the product as a clear oil. $^1$H NMR (400 MHz, CHLOROFORM-d) δ 8.48-8.39 (m, 1H), 7.87-7.76 (m, 1H), 7.30-7.24 (m, 2H), 7.16-7.09 (m, 1H), 3.83-3.69 (m, 4H), 2.29-2.16 (m, 2H), 1.80 (ddd, J=14.3, 8.9, 5.9 Hz, 2H), 1.66 (s, 3H).

400
Preparation of pyridin-2-yl (4-(trifluoromethyl)tetrahydro-2H-pyran-4-yl)carbonate

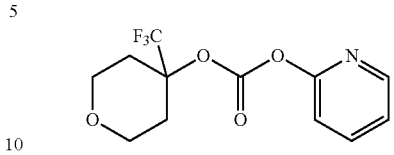

Scheme:

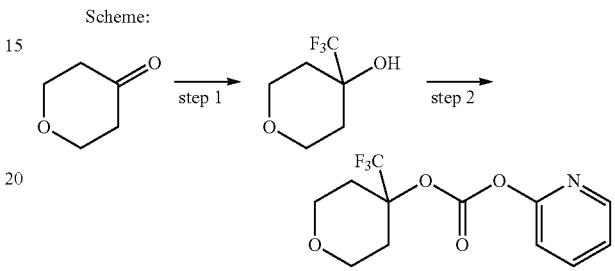

Step 1:

Tetrahydrofuran (110 mL) was added to a round bottom flask and placed under N$_2$. trimethyl(trifluoromethyl)silane (4.13 mL, 28.0 mmol) was then added and stirred under N$_2$ and then cooled to 0° C. Dihydro-2H-pyran-4(3H)-one (1.845 mL, 19.98 mmol) was then added via syringe and stirred for 5 minutes at 0° C. to ensure complete mixing. TBAF (0.200 mL, 0.200 mmol) was added dropwise slowly via syringe. The reaction was then allowed to warm up to RT for 30 min. The reaction was then cooled back down to 0° C. and added 1M HCl (50 mL) and then stirred at RT for overnight. The reaction was diluted with EtOAc and separated with brine. The organic layer was dried over MgSO4, filtered and evaporated to give the crude material which was crystallized from hexane to give the product 4-(trifluoromethyl)tetrahydro-2H-pyran-4-ol (1.45 g, 8.52 mmol, 42.7% yield) as white crystals. $^1$H NMR (400 MHz, CHLOROFORM-d) δ 3.96-3.84 (m, 2H), 3.76 (td, J=12.1, 2.1 Hz, 2H), 2.08-1.90 (m, 3H), 1.65-1.48 (m, 2H).

Step 2:

To a suspension of sodium hydride, 60% in mineral oil (226 mg, 5.64 mmol) in THF (20 mL) was added 4-(trifluoromethyl)tetrahydro-2H-pyran-4-ol (800 mg, 4.70 mmol) in 5 mL of THF via syringe at 0° C. After stirring 30 min, the solution was transferred to a solution of di(pyridin-2-yl)carbonate (1017 mg, 4.70 mmol) in THF (20 mL) through a cannula. The formed slurry was stirred at 0° C. for 30 min. The slurry was warmed to rt and stirred for 2 h. After 2 hr the reaction was diluted with EtOAc and washed with brine. The organic layer was dried over MgSO4, filtered and evaporated to give the crude material. The crude material was purified via biotage (90 g column, 5-40% EtOAc:Hex) to give pyridin-2-yl (4-(trifluoromethyl)tetrahydro-2H-pyran-4-yl)carbonate (500 mg, 1.717 mmol, 36.5% yield) as a white solid. $^1$H NMR (400 MHz, CHLOROFORM-d) δ 8.47-8.36 (m, 1H), 7.90-7.77 (m, 1H), 7.37-7.25 (m, 1H), 7.23-7.06 (m, 1H), 3.98 (dd, J=11.7, 4.4 Hz, 2H), 3.85-3.68 (m, 2H), 2.53 (dd, J=14.2, 2.1 Hz, 2H), 2.11-2.00 (m, 2H).

401
Preparation of 3-methyltetrahydro-2H-pyran-3-yl pyridin-2-yl carbonate

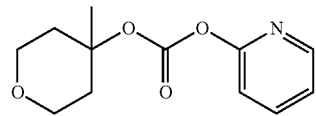 [SMILES: CC1(OC(=O)Oc2ccccn2)CCOCC1]

Scheme:

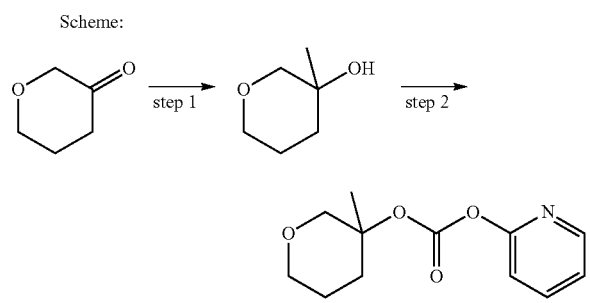

Step 1:

Methylmaganesium bromide (1.831 mL, 5.49 mmol) was added dropwise via syringe to a solution of dihydro-2H-pyran-3(4H)-one (500 mg, 4.99 mmol) in Diethyl ether (50 mL) at −20° C. and stirred at this temp for 1 hr before warming up to RT. The reaction was quenched with sat. ammonium chloride and extracted with ether. The organic layer was washed with brine, collected, dried over MgSO4, filtered and partially evaporated to give the crude product 3-methyltetrahydro-2H-pyran-3-ol (480 mg, 83% yield) as an oil. $^1$H NMR (400 MHz, CHLOROFORM-d) δ 3.90-3.81 (m, 1H), 3.55-3.50 (m, 1H), 3.40 (td, J=11.3, 2.8 Hz, 1H), 3.31 (d, J=11.3 Hz, 1H), 2.16 (br. s., 1H), 1.94-1.81 (m, 1H), 1.78-1.69 (m, 1H), 1.59-1.47 (m, 2H), 1.18-1.11 (m, 3H).

Step 2:

To a suspension of sodium hydride, 60% in mineral oil (207 mg, 5.17 mmol) in THF (20 mL) was added 3-methyltetrahydro-2H-pyran-3-ol (500 mg, 4.30 mmol) at 0° C. After stirring 30 min, the solution was transferred to a solution of di(pyridin-2-yl)carbonate (931 mg, 4.30 mmol) in THF (20 mL) through a cannula. The formed slurry was stirred at 0° C. for 30 min. The slurry was warmed to rt and stirred for 2 h. The reaction was diluted with EtOAc followed by brine. The organic layer was collected, dried over MgSO4, filtered and evaporated to give the crude material. the crude material was purified via biotage (40 g column, 5-40% EtOAc:Hex) to give the expected product 3-methyltetrahydro-2H-pyran-3-ylpyridin-2-yl carbonate (173 mg, 17.94% yield) as a clear thick oil. $^1$H NMR (400 MHz, CHLOROFORM-d) δ 8.50-8.30 (m, 1H), 7.89-7.74 (m, 1H), 7.27-7.22 (m, 1H), 7.14 (d, J=8.3 Hz, 1H), 4.22-4.05 (m, 1H), 3.88-3.74 (m, 1H), 3.60-3.49 (m, 1H), 3.44 (d, J=12.0 Hz, 1H), 2.38-2.20 (m, 1H), 2.03-1.88 (m, 1H), 1.84-1.72 (m, 1H), 1.63-1.57 (m, 1H), 1.56 (s, 3H).

402
Preparation of pyridin-2-yl (3-(trifluoromethyl)tetrahydro-2H-pyran-3-yl)carbonate

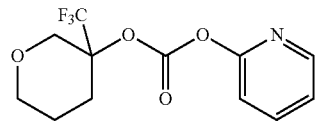 [SMILES: O=C(Oc1ccccn1)OC1(C(F)(F)F)CCCOC1]

Scheme:

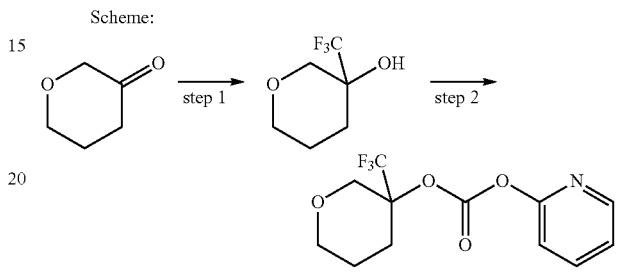

Step 1:

Tetrahydrofuran (50 mL) was added to a round bottom flask and placed under N$_2$. trimethyl(trifluoromethyl)silane (1.033 mL, 6.99 mmol) was then added and stirred under N$_2$ and then cooled to 0° C. Dihydro-2H-pyran-3(4H)-one (500 mg, 4.99 mmol) was then added via syringe and stirred for 5 minutes at 0° C. to ensure complete mixing. TBAF (0.050 mL, 0.050 mmol) was added dropwise slowly via syringe. The reaction was then allowed to warm up to RT for 30 min. The reaction was then cooled back down to 0° C. and added 1M HCl (50 mL) and then stirred at RT for overnight. The reaction was diluted with water and EtOAc. The organic layer was washed with brine, dried over MgSO4, filtered and evaporated to give the crude product 3-(trifluoromethyl)tetrahydro-2H-pyran-3-ol (400 mg, 47.1% yield) as an oil. $^1$H NMR (400 MHz, CHLOROFORM-d) δ 4.01-3.93 (m, 1H), 3.82 (dd, J=11.8, 2.5 Hz, 1H), 3.60 (d, J=12.0 Hz, 1H), 3.41 (td, J=11.8, 2.5 Hz, 1H), 2.10-2.08 (m, 2H), 1.97-1.90 (m, 1H), 1.82 (dd, J=12.9, 4.4 Hz, 1H), 1.65-1.55 (m, 1H).

Step 2:

To a suspension of sodium hydride, 60% in mineral oil (141 mg, 3.53 mmol) in THF (20 mL) was added 3-(trifluoromethyl)tetrahydro-2H-pyran-3-ol (500 mg, 2.94 mmol) at 0° C. After stirring 30 min, the solution was transferred to a solution of di(pyridin-2-yl)carbonate (635 mg, 2.94 mmol) in THF (20 mL) through a cannula. The formed slurry was stirred at 0° C. for 30 min. The slurry was warmed to rt and stirred for 2 h. The reaction was diluted with EtOAc followed by brine. The organic layer was collected, dried over MgSO4, filtered and evaporated to give the crude material. The crude material was purified via biotage (40 g column, 5-40% EtOAc:Hex) to give the expected product pyridin-2-yl (3-(trifluoromethyl)tetrahydro-2H-pyran-3-yl)carbonate (195 mg, 22.78% yield) as a clear thick oil. $^1$H NMR (400 MHz, CHLOROFORM-d) δ 8.43 (dd, J=4.9, 1.4 Hz, 1H), 7.88-7.75 (m, 1H), 7.32-7.24 (m, 1H), 7.19 (d, J=8.3 Hz, 1H), 4.70 (dd, J=12.4, 2.6 Hz, 1H), 4.02-3.92 (m, 1H), 3.67 (d, J=12.3 Hz, 1H), 3.60-3.42 (m, 1H), 2.68-2.53 (m, 1H), 2.08-1.92 (m, 2H), 1.77-1.62 (m, 1H).

Preparation of 3,3-difluoro-2-methylbutan-2-yl pyridin-2-yl carbonate

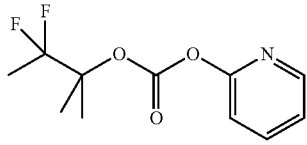 [SMILES: CC(F)(F)C(C)(C)OC(=O)Oc1ccccn1]

Scheme:

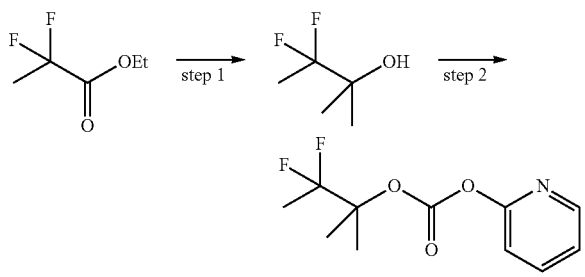

Step 1:
Methylmagnesium bromide (24.91 mL, 74.7 mmol) was added dropwise via syringe to a solution of ethyl 2,2-difluoropropanoate (3.44 g, 24.91 mmol) in Diethyl ether (50 mL) at −20° C. and stirred at this temp for 1 hr before warming up to RT. The reaction was quenched with sat. ammonium chloride and extracted with ether. The organic layer was washed with brine, collected, dried over $MgSO_4$, filtered and partially evaporated to give the crude product 3,3-difluoro-2-methylbutan-2-ol (1.84 g, 59.5% yield) as an oil. $^1H$ NMR (500 MHz, CHLOROFORM-d) δ 1.68-1.58 (m, 3H), 1.31 (t, J=1.2 Hz, 6H).

Step 2:
To a suspension of sodium hydride, 60% in mineral oil (0.652 g, 16.31 mmol) in THF (25 mL) was added 3,3-difluoro-2-methylbutan-2-ol (1.84 g, 14.82 mmol) at 0° C. After stirring 30 min, the solution was transferred to a solution of di(pyridin-2-yl)carbonate (3.20 g, 14.82 mmol) in THF (25 mL) through a cannula. The formed slurry was stirred at 0° C. for 30 min. The slurry was warmed to rt and stirred for 2 h. The reaction was diluted with EtOAc, washed with brine, dried over MgSO4, filtered, concentrated to give a residue that was purified by Biotage eluting with 10-50% EtOAc in hexanes to afford the desired product 3,3-difluoro-2-methylbutan-2-yl pyridin-2-yl carbonate (500 mg, 13.76%) as an oil that later crystallized to a white solid upon standing. $^1H$ NMR (500 MHz, CHLOROFORM-d) δ 8.43 (ddd, J=4.9, 2.0, 0.7 Hz, 1H), 7.95-7.75 (m, 1H), 7.31-7.24 (m, 1H), 7.15 (dt, J=8.2, 0.8 Hz, 1H), 1.72 (s, 6H), 1.77-1.66 (m, 3H).

Preparation of pyridin-2-yl (4,4,4-trifluoro-2-methylbutan-2-yl)carbonate

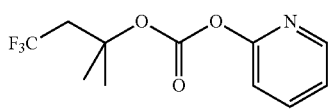

Scheme:

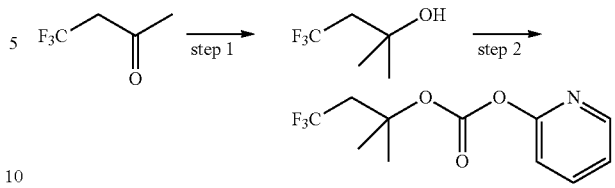

Step 1:
Methylmaganesium bromide (1.454 mL, 4.36 mmol) was added dropwise via syringe to a solution of 4,4,4-trifluorobutan-2-one (500 mg, 3.97 mmol) in Diethyl ether (25 mL) at 0° C. and stirred at this temp for 1 hr before warming up to RT. The reaction was quenched with sat. ammonium chloride and extracted with ether. The organic layer was washed with brine, collected, dried over MgSO4, filtered and partially evaporated to give the crude product 4,4,4-trifluoro-2-methylbutan-2-ol (500 mg, 89% yield) as an oil. $^1H$ NMR (400 MHz, CHLOROFORM-d) δ 2.34 (q, J=11.5 Hz, 2H), 1.88 (br. s, 1H), 1.37 (d, J=0.8 Hz, 6H).

Step 2:
To a suspension of sodium hydride, 60% in mineral oil (169 mg, 4.22 mmol) in THF (20 mL) was added 4,4,4-trifluoro-2-methylbutan-2-ol (500 mg, 3.52 mmol) at 0° C. After stirring 30 min, the solution was transferred to a solution of di(pyridin-2-yl)carbonate (761 mg, 3.52 mmol) in THF (20 mL) through a cannula. The formed slurry was stirred at 0° C. for 30 min. The slurry was warmed to rt and stirred for 2 h. The reaction was diluted with EtOAc followed by brine. The organic layer was collected, dried over MgSO4, filtered and evaporated to give the crude material. The crude material was purified via biotage (40 g column, 5-40% EtOAc:Hex) to give the expected product pyridin-2-yl (4,4,4-trifluoro-2-methylbutan-2-yl) carbonate (150 mg, 16.2% yield) as a clear thick oil. $^1H$ NMR (400 MHz, CHLOROFORM-d) δ 8.43 (dd, J=4.9, 1.4 Hz, 1H), 7.91-7.76 (m, 1H), 7.30-7.24 (m, 1H), 7.11 (d, J=8.3 Hz, 1H), 2.83 (q, J=11.0 Hz, 2H), 1.75-1.61 (m, 6H).

Preparation of 1-methoxy-2-methylpropan-2-yl pyridin-2-yl carbonate

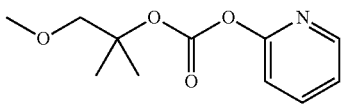 [SMILES: COCC(C)(C)OC(=O)Oc1ccccn1]

Scheme:

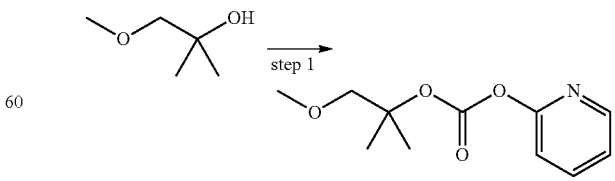

Step 1:
To a 40 mL vial equipped with a stir bar was added 1-methoxy-2-methylpropan-2-ol (361 mg, 3.47 mmol) and THF (15 mL). To the solution was added sodium hydride, 60% in mineral oil (167 mg, 4.16 mmol) upon which vigorous effervescence was observed. The mixture was placed under a stream of N2 until the effervescence decreased significantly (app. 5 mins). The vial was then capped with a septum-screw cap and the solution was stirred at room temperature for 30 minutes. To the slightly turbid mixture was added 1-methoxy-2-methylpropan-2-yl pyridin-2-yl carbonate (241 mg, 1.070 mmol, 30.8% yield) upon which minor and brief effervescence was observed. The solution was stirred at room temperature for 65 h, TLC found two well resolved spots. To the mixture was added a spatula tip of NH$_4$Cl, then the mixture was concentrated in vacuo. The residue was diluted with acetone and then concentrated onto Celite in vacuo. The resulting powder was subjected to SiO2 chromatography on the Biotage system as indicated (see attached. hexanes:EtOAc; 5% EtOAc to 50% EtOAc). This purification afforded the desired product 1-methoxy-2-methylpropan-2-ylpyridin-2-yl carbonate (241 mg, 30.8% yield) as a clear oil. $^1$H NMR (400 MHz, CHLOROFORM-d) δ 8.42 (ddd, J=5.0, 2.0, 0.8 Hz, 1H), 7.86-7.72 (m, 1H), 7.24 (ddd, J=7.4, 4.9, 0.8 Hz, 1H), 7.12 (dt, J=8.1, 0.8 Hz, 1H), 3.57 (s, 2H), 3.44 (s, 3H), 1.68-1.48 (m, 6H).

Compounds 1001 and 1002 were prepared using the intermediates described herein and by following the general procedure described for the synthesis of Compound 3117.

Compound 1001: tert-butyl ((2R,6S,7R,9S,13aS,14aR,16aS,Z)-14a-((cyclopropylsulfonyl)carbamoyl)-2-((3-isopropyl-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 783.5 (M$^+$+1).

Compound 1002: tert-butyl ((2R,6S,7R,9R,13aS,14aR,16aS,Z)-14a-((cyclopropylsulfonyl)carbamoyl)-2-((3-isopropyl-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 9.01 (br. s., 1H), 8.25 (d, J=5.2 Hz, 1H), 7.88 (d, J=5.5 Hz, 4H), 7.14 (br. s., 1H), 5.55 (br. s., 3H), 5.23-5.18 (m, 1H), 5.01 (br. s., 1H), 4.74 (br. s., 1H), 4.48 (br. s., 1H), 3.91-3.86 (m, 1H), 3.68 (t, J=8.9 Hz, 1H), 2.64 (br. s., 1H), 2.60 (br. s., 1H), 2.29 (d, J=10.7 Hz, 2H), 1.91 (br. s., 1H), 1.80 (br. s., 1H), 1.61 (br. s., 2H), 1.53 (br. s., 1H), 1.42 (br. s., 2H), 1.37-1.32 (m, 6H), 1.24 (br. s., 1H), 1.15 (br. s., 2H), 1.06 (d, J=11.9 Hz, 2H), 1.01 (s, 9H), 0.92 (d, J=6.7 Hz, 3H), 0.86 (d, J=6.4 Hz, 3H), 0.70 (br. s., 1H). MS: MS m/z 783.5 (M$^+$+1).

Preparation of 1001 and 1002

Preparation of Compound 1003 and 1004

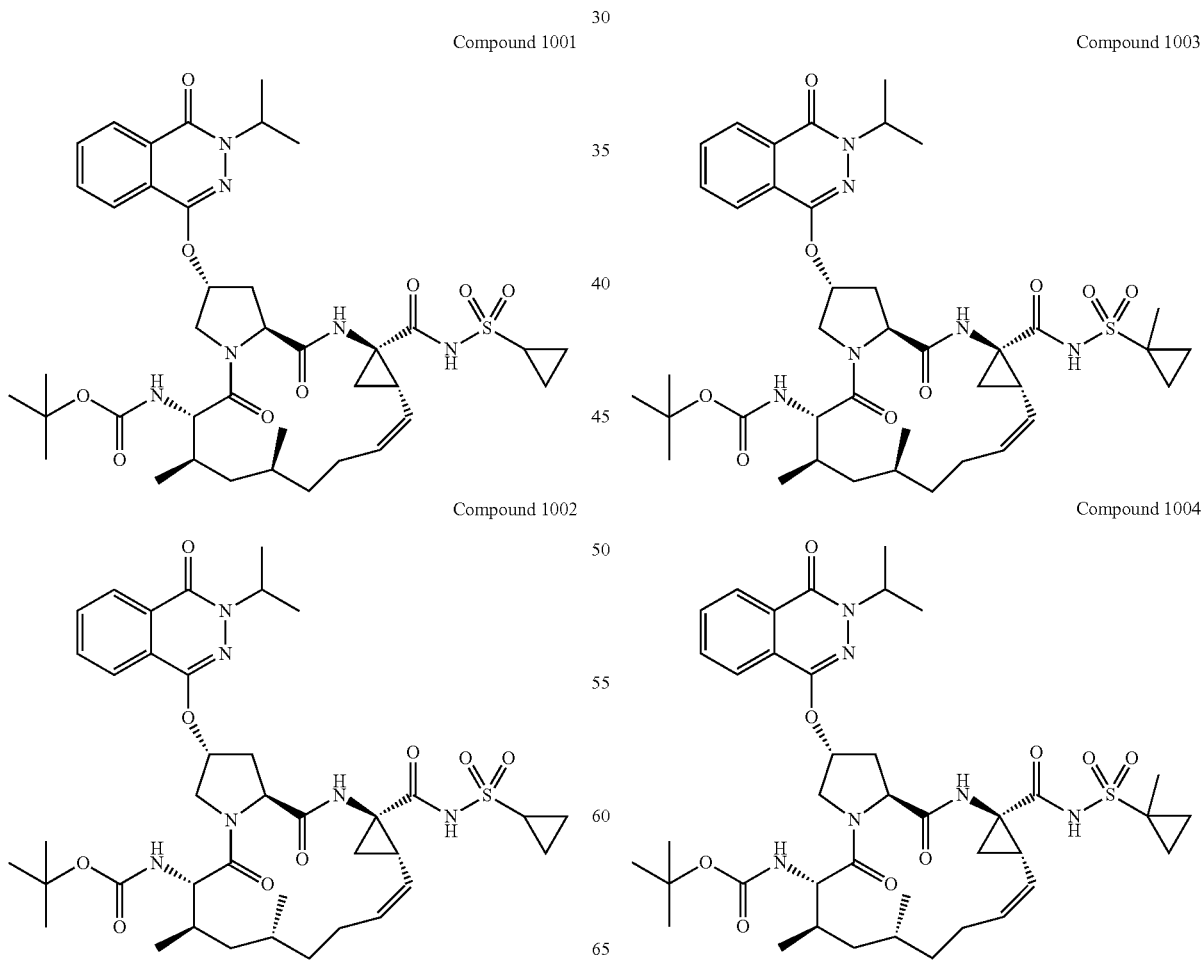

Compound 1001

Compound 1002

Compound 1003

Compound 1004

Compounds 1003 and 1004 were prepared using the intermediates described herein and by following the general procedure described for the synthesis of Compound 3117.

Compound 1003: tert-butyl ((2R,6S,7R,9S,13aS,14aR,16aS,Z)-2-((3-isopropyl-4-oxo-3,4-dihydrophthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 797.5 (M$^+$+1).

Compound 1004: tert-butyl ((2R,6S,7R,9R,13aS,14aR,16aS,Z)-2-((3-isopropyl-4-oxo-3,4-dihydrophthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 8.23 (d, J=5.5 Hz, 1H), 7.92-7.84 (m, 4H), 7.09 (d, J=7.0 Hz, 1H), 5.55 (br. s., 2H), 5.22-5.16 (m, 1H), 4.94 (br. s., 1H), 4.73 (br. s., 1H), 4.49 (br. s., 1H), 3.91-3.87 (m, 1H), 3.67 (t, J=9.5 Hz, 1H), 2.60 (br. s., 2H), 2.28 (br. s., 2H), 1.90 (s, 1H), 1.80 (br. s., 1H), 1.62 (br. s., 2H), 1.49 (br. s., 1H), 1.39 (br. s., 3H), 1.33 (t, J=5.8 Hz, 8H), 1.24 (d, J=16.2 Hz, 2H), 1.17-1.01 (m, 4H), 0.98 (s, 9H), 0.91 (d, J=6.7 Hz, 3H), 0.85 (d, J=6.1 Hz, 3H), 0.70 (br. s., 1H). MS: MS m/z 797 (M$^+$+1).

Compounds 1005 and 1006 were prepared using the intermediates described herein and by following the general procedure described for the synthesis of Compound 3117.

Compound 1005: tert-butyl ((2R,6S,7R,9S,13aS,14aR,16aS,Z)-2-((3-(2-methoxyethyl)-4-oxo-3,4-dihydrophthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 813.5 (M$^+$+1).

Compound 1006: tert-butyl ((2R,6S,7R,9R,13aS,14aR,16aS,Z)-2-((3-(2-methoxyethyl)-4-oxo-3,4-dihydrophthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 9.15 (br. s., 1H), 8.24 (d, J=6.7 Hz, 1H), 7.96-7.85 (m, 4H), 7.15 (br. s., 1H), 5.53 (br. s., 2H), 4.95 (br. s., 1H), 4.70 (br. s., 1H), 4.47 (br. s., 1H), 4.27-4.16 (m, 2H), 3.91-3.85 (m, 1H), 3.78-3.66 (m, 4H), 3.43 (d, J=5.8 Hz, 3H), 2.64 (br. s., 2H), 2.35-2.24 (m, 2H), 1.90 (d, J=15.0 Hz, 1H), 1.79 (br. s., 1H), 1.67 (br. s., 1H), 1.61 (br. s., 1H), 1.50 (br. s., 2H), 1.39 (br. s., 3H), 1.26 (br. s., 2H), 1.14 (s, 2H), 1.07 (s, 9H), 0.92 (d, J=6.7 Hz, 3H), 0.88 (d, J=6.1 Hz, 3H), 0.72 (br. s., 1H). MS: MS m/z 813.5 (M$^+$+1).

Preparation of Compound 1005 and 1006

Preparation of Compound 1007 and 1008

Compound 1005

Compound 1007

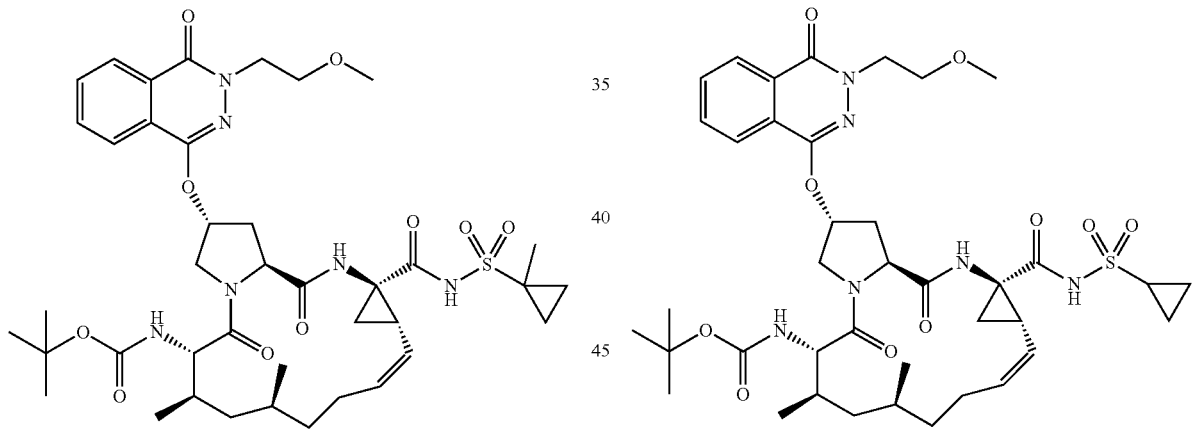

Compound 1006

Compound 1008

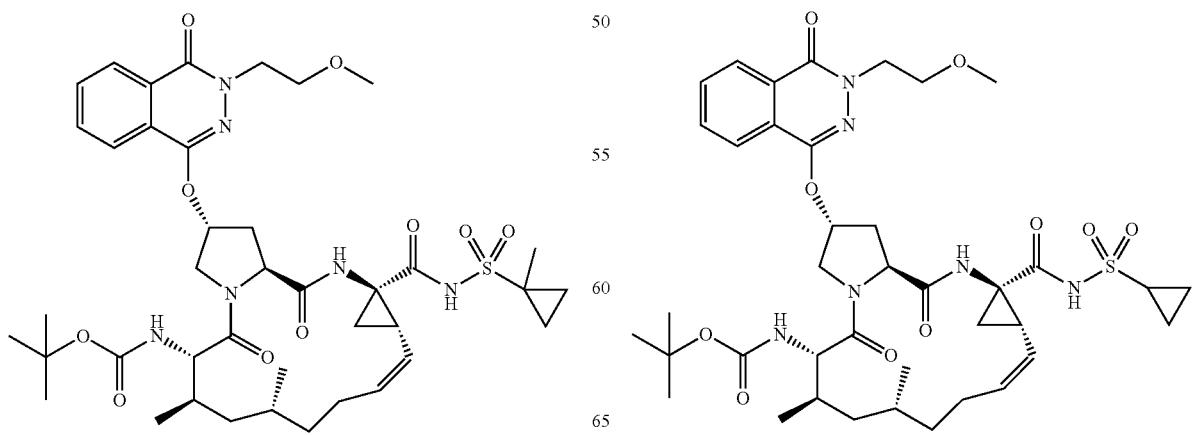

Compounds 1007 and 1008 were prepared using the intermediates described herein and by following the general procedure described for the synthesis of Compound 3117.

Compound 1007: tert-butyl ((2R,6S,7R,9S,13aS,14aR,16aS,Z)-14a-((cyclopropylsulfonyl)carbamoyl)-2-((3-(2-methoxyethyl)-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 799.5 (M$^+$+1).

Compound 1008: tert-butyl ((2R,6S,7R,9R,13aS,14aR,16aS,Z)-14a-((cyclopropylsulfonyl)carbamoyl)-2-((3-(2-methoxyethyl)-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 9.02 (br. s., 1H), 8.24 (d, J=6.1 Hz, 1H), 7.89 (d, J=9.2 Hz, 3H), 7.14 (br. s., 1H), 5.52 (br. s., 2H), 5.03 (br. s., 1H), 4.69 (d, J=9.8 Hz, 1H), 4.44 (br. s., 1H), 4.21 (br. s., 2H), 3.85 (d, J=11.3 Hz, 1H), 3.78-3.65 (m, 3H), 3.26 (d, J=3.7 Hz, 3H), 2.89 (br. s., 1H), 2.62 (br. s., 2H), 2.27 (d, J=10.1 Hz, 2H), 1.88 (br. s., 1H), 1.79 (br. s., 1H), 1.67 (br. s., 1H), 1.59 (br. s., 1H), 1.52 (br. s., 1H), 1.41 (br. s., 1H), 1.35 (br. s., 2H), 1.23 (br. s., 1H), 1.13 (br. s., 2H), 1.08-1.05 (m, 9H), 1.01-0.96 (m, 1H), 0.94-0.90 (m, 3H), 0.88-0.85 (m, 3H), 0.72 (d, J=12.2 Hz, 1H). MS: MS m/z 799.5 (M$^+$+1).

Preparation of Compound 1009 and 1010

Compounds 1009 and 1010 were prepared using the intermediates described herein and by following the general procedure described for the synthesis of Compound 3117.

Compound 1009: 1,1,1-trifluoro-2-methylpropan-2-yl ((2R,6S,7R,9S,13aS,14aR,16aS,Z)-14a-((cyclopropylsulfonyl)carbamoyl)-2-((3-isopropyl-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 837.5 (M$^+$+1).

Compound 1010: 1,1,1-trifluoro-2-methylpropan-2-yl ((2R,6S,7R,9R,13aS,14aR,16aS,Z)-14a-((cyclopropylsulfonyl)carbamoyl)-2-((3-isopropyl-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.22 (br. s., 1H), 9.04 (br. s., 1H), 8.30-8.25 (m, 1H), 7.97-7.86 (m, 3H), 7.83 (d, J=7.9 Hz, 1H), 5.57 (br. s., 1H), 5.52 (br. s., 1H), 5.23 (quin, J=6.6 Hz, 1H), 5.06 (br. s., 1H), 4.68 (d, J=11.0 Hz, 1H), 4.51 (t, J=8.1 Hz, 1H), 3.93-3.85 (m, 1H), 3.68 (dd, J=10.7, 8.2 Hz, 1H), 2.90 (s, 1H), 2.70-2.58 (m, 2H), 2.38-2.22 (m, 2H), 1.96-1.88 (m, 1H), 1.88-1.80 (m, 1H), 1.69 (br. s., 1H), 1.61 (br. s., 1H), 1.53 (d, J=19.8 Hz, 1H), 1.43 (br. s., 1H), 1.38-1.32 (m, 10H), 1.32-1.20 (m, 1H), 1.14 (br. s., 3H), 1.02-0.97 (m, 1H), 0.93 (s, 1H), 0.91 (s, 3H), 0.88 (d, J=6.4 Hz, 3H), 0.74 (t, J=12.1 Hz, 1H). MS: MS m/z 837.5 (M$^+$+1).

Preparation of compound 1011 and 1012

Compound 1009

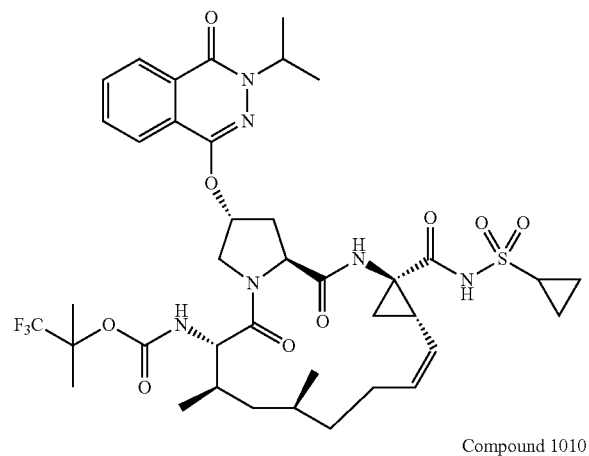

Compound 1011

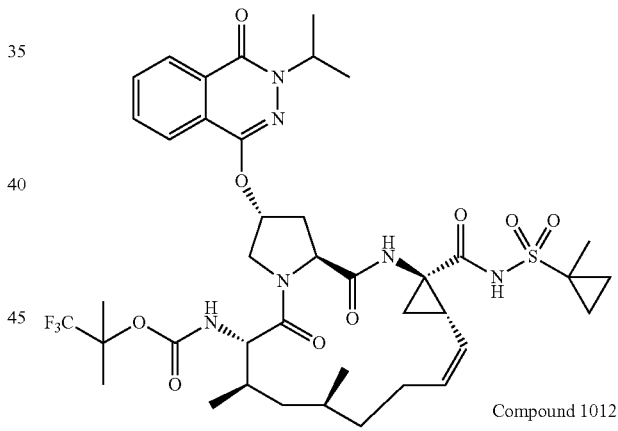

Compound 1010

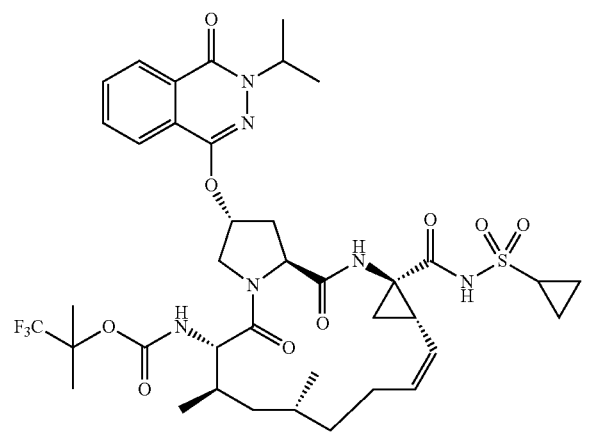

Compound 1012

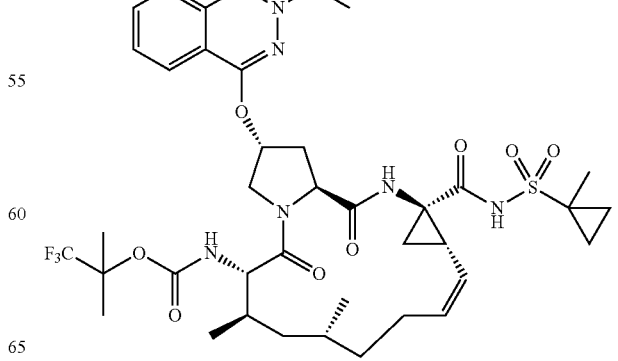

Compounds 1011 and 1012 were prepared using the intermediates described herein and by following the general procedure described for the synthesis of Compound 3117.

Compound 1011: 1,1,1-trifluoro-2-methylpropan-2-yl ((2R,6S,7R,9S,13aS,14aR,16aS,Z)-2-((3-isopropyl-4-oxo-3,4-dihydrophthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 851.5 (M$^+$+1).

Compound 1012: 1,1,1-trifluoro-2-methylpropan-2-yl ((2R,6S,7R,9R,13aS,14aR,16aS,Z)-2-((3-isopropyl-4-oxo-3,4-dihydrophthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.07 (br. s., 1H), 9.18 (br. s., 1H), 8.30-8.26 (m, 1H), 7.92-7.88 (m, 4H), 7.84 (d, J=7.3 Hz, 1H), 5.59-5.50 (m, 2H), 5.23 (quin, J=6.6 Hz, 1H), 4.97 (br. s., 1H), 4.69 (br. s., 1H), 4.54 (br. s., 1H), 3.94-3.89 (m, 2H), 3.68 (dd, J=10.7, 8.2 Hz, 1H), 2.65 (br. s., 2H), 2.36-2.27 (m, 2H), 1.92 (s, 1H), 1.85 (d, J=7.6 Hz, 1H), 1.64 (br. s., 2H), 1.52 (br. s., 1H), 1.49-1.44 (m, 1H), 1.41 (br. s., 3H), 1.37-1.32 (m, 12H), 1.30-1.23 (m, 1H), 1.15 (br. s., 1H), 0.93 (d, J=7.0 Hz, 3H), 0.92-0.90 (m, 2H), 0.88 (br. s., 3H), 0.76 (br. s., 1H). MS: MS m/z 851.5 (M$^+$+1).

Compounds 1013 and 1014 were prepared using the intermediates described herein and by following the general procedure described for the synthesis of Compound 3117.

Compound 1013: 1,1,1-trifluoro-2-methylpropan-2-yl ((2R,6S,7R,9S,13aS,14aR,16aS,Z)-2-((3-(2-methoxyethyl)-4-oxo-3,4-dihydrophthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 813.5 (M$^+$+1).

Compound 1014: 1,1,1-trifluoro-2-methylpropan-2-yl ((2R,6S,7R,9R,13aS,14aR,16aS,Z)-2-((3-(2-methoxyethyl)-4-oxo-3,4-dihydrophthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.04 (br. s., 1H), 9.18 (br. s., 1H), 8.29-8.25 (m, 1H), 7.94-7.88 (m, 3H), 7.85 (d, J=7.6 Hz, 1H), 5.54 (br. s., 2H), 4.98 (br. s., 1H), 4.67 (d, J=12.2 Hz, 1H), 4.51 (t, J=8.1 Hz, 1H), 4.29-4.19 (m, 2H), 3.88 (dd, J=11.6, 3.1 Hz, 1H), 3.74 (td, J=5.6, 1.8 Hz, 2H), 3.72-3.65 (m, 1H), 3.27 (s, 3H), 2.65 (br. s., 2H), 2.39-2.26 (m, 2H), 1.93-1.79 (m, 2H), 1.69 (br. s., 1H), 1.62 (br. s., 1H), 1.53 (br. s., 2H), 1.49-1.45 (m, 1H), 1.41 (s, 3H), 1.35 (br. s., 1H), 1.33 (s, 3H), 1.29 (br. s., 3H), 1.16 (br. s., 1H), 1.00 (s, 3H), 0.93 (d, J=6.7 Hz, 3H), 0.90 (d, J=6.4 Hz, 3H), 0.76 (t, J=12.2 Hz, 1H). MS: MS m/z 813.5 (M$^+$+1).

Preparation of Compound 1013 and 1014

Compound 1013

Preparation of Compound 1015 and 1016

Compound 1015

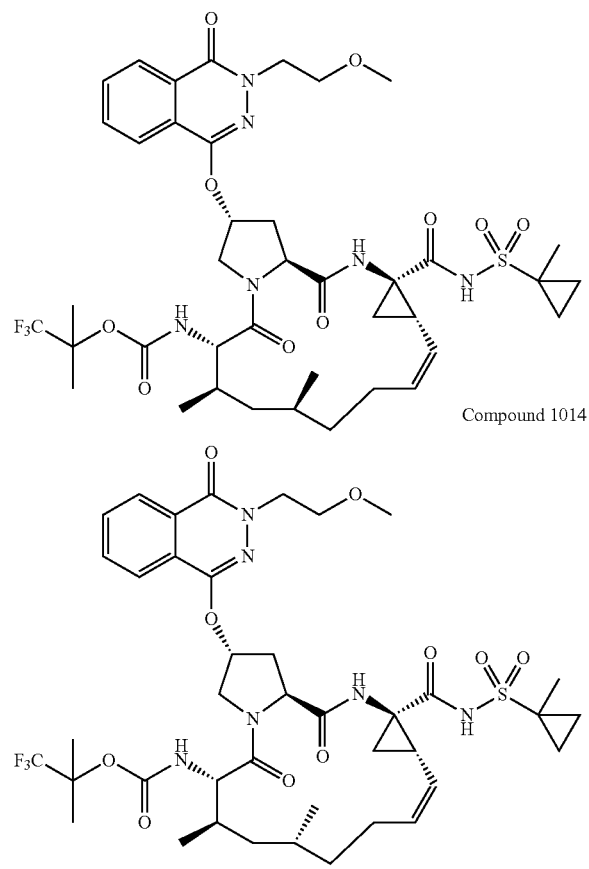

Compound 1014

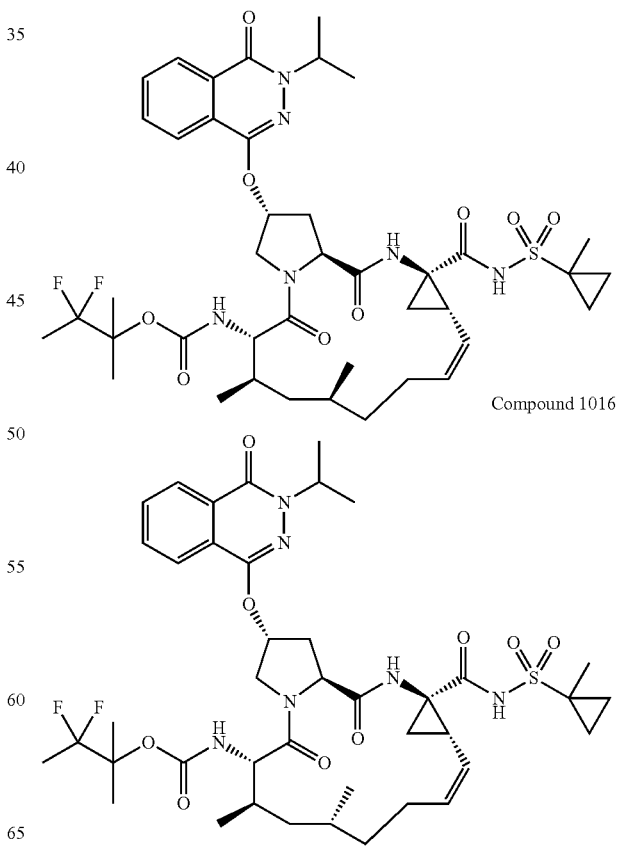

Compound 1016

Compounds 1015 and 1016 were prepared using the intermediates described herein and by following the general procedure described for the synthesis of Compound 3117.

Compound 1015: 3,3-difluoro-2-methylbutan-2-yl ((2R, 6S,7R,9S,13aS,14aR,16aS,Z)-2-((3-isopropyl-4-oxo-3,4-dihydrophthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 847.47 (M$^+$+1).

Compound 1016: 3,3-difluoro-2-methylbutan-2-yl ((2R, 6S,7R,9R,13aS,14aR,16aS,Z)-2-((3-isopropyl-4-oxo-3,4-dihydrophthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.08 (br. s., 1H), 9.16 (br. s., 1H), 8.27 (dd, J=6.3, 3.2 Hz, 1H), 7.93-7.86 (m, 3H), 7.61 (d, J=8.2 Hz, 1H), 5.60-5.50 (m, 2H), 5.23 (quin, J=6.6 Hz, 1H), 4.97 (br. s., 1H), 4.72 (d, J=11.9 Hz, 1H), 4.54 (t, J=8.2 Hz, 1H), 3.95-3.91 (m, 1H), 3.69 (dd, J=10.7, 8.5 Hz, 1H), 2.75-2.68 (m, 1H), 2.68-2.61 (m, 1H), 2.38-2.28 (m, 2H), 1.96-1.88 (m, 1H), 1.83 (d, J=6.4 Hz, 1H), 1.65 (br. s., 2H), 1.59-1.48 (m, J=19.7, 19.7 Hz, 4H), 1.47-1.44 (m, 2H), 1.42 (s, 3H), 1.39-1.38 (m, 1H), 1.35 (d, J=6.4 Hz, 6H), 1.29 (d, J=9.8 Hz, 1H), 1.23 (s, 3H), 1.14 (d, J=11.9 Hz, 1H), 0.94 (d, J=7.0 Hz, 3H), 0.89 (d, J=6.4 Hz, 3H), 0.79 (br. s., 3H), 0.78-0.72 (m, 1H). MS: MS m/z 847.47 (M$^+$+1).

Preparation of Compound 1017 and 1018

Compound 1017: 3,3-difluoro-2-methylbutan-2-yl ((2R, 6S,7R,9S,13aS,14aR,16aS,Z)-14a-((cyclopropylsulfonyl)carbamoyl)-2-((3-isopropyl-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 833.46 (M$^+$+1).

Compound 1018: 3,3-difluoro-2-methylbutan-2-yl ((2R, 6S,7R,9R,13aS,14aR,16aS,Z)-14a-((cyclopropylsulfonyl)carbamoyl)-2-((3-isopropyl-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.23 (br. s., 1H), 9.03 (br. s., 1H), 8.29-8.26 (m, 1H), 7.92-7.87 (m, 3H), 7.61 (d, J=7.9 Hz, 1H), 5.57 (br. s., 2H), 5.23 (quin, J=6.6 Hz, 1H), 5.08-5.01 (m, 1H), 4.70 (d, J=11.9 Hz, 1H), 4.54-4.48 (m, 1H), 3.92-3.88 (m, 1H), 3.69 (dd, J=10.5, 8.4 Hz, 1H), 2.92 (d, J=10.1 Hz, 1H), 2.70 (d, J=7.6 Hz, 1H), 2.64 (d, J=13.4 Hz, 1H), 2.38-2.25 (m, 2H), 1.92 (s, 1H), 1.87-1.79 (m, 1H), 1.67 (d, J=9.5 Hz, 1H), 1.63 (br. s., 1H), 1.53 (t, J=19.5 Hz, 4H), 1.45 (br. s., 1H), 1.42-1.39 (m, 1H), 1.35 (d, J=6.4 Hz, 6H), 1.23 (s, 3H), 1.16 (br. s., 3H), 1.02 (br. s., 2H), 0.94 (d, J=7.0 Hz, 3H), 0.89 (d, J=6.4 Hz, 3H), 0.81 (s, 3H), 0.75 (t, J=13.1 Hz, 1H). MS: MS m/z 833.46 (M$^+$+1).

Preparation of Compounds 1019 and 1020

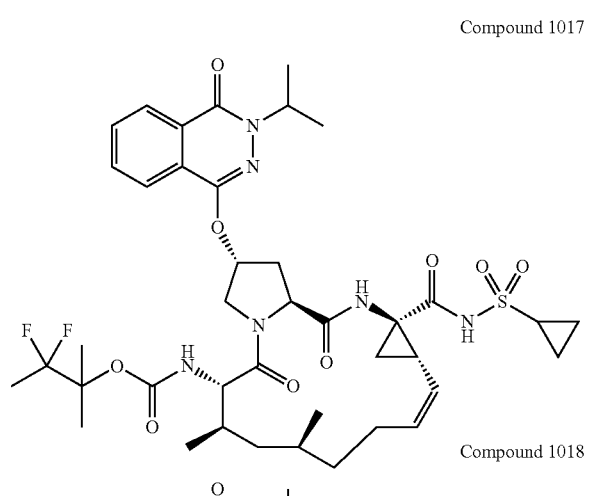

Compound 1017

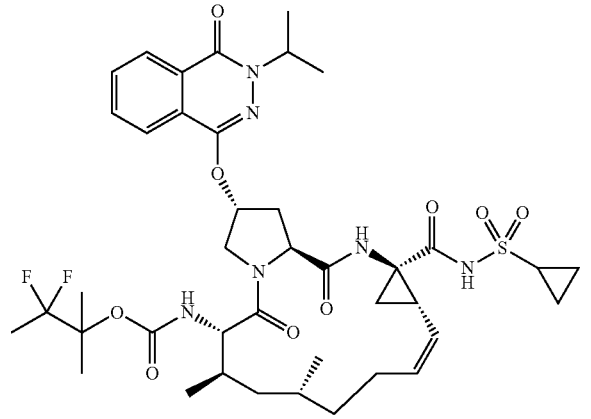

Compound 1018

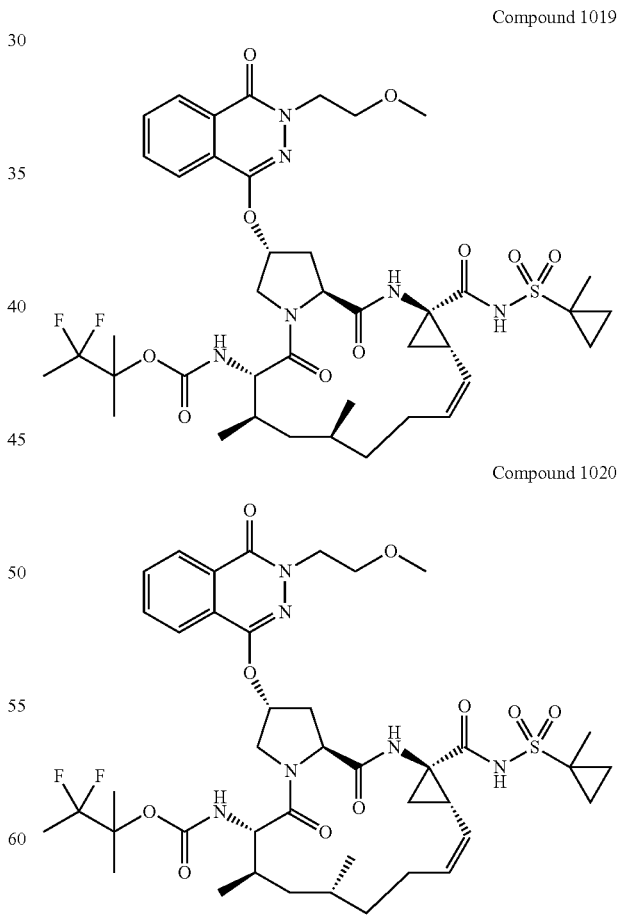

Compound 1019

Compound 1020

Compounds 1017 and 1018 were prepared using the intermediates described herein and by following the general procedure described for the synthesis of Compound 3117.

Compounds 1019 and 1020 were prepared using the intermediates described herein and by following the general procedure described for the synthesis of Compound 3117.

Compound 1019: 3,3-difluoro-2-methylbutan-2-yl ((2R,6S,7R,9S,13aS,14aR,16aS,Z)-2-((3-(2-methoxyethyl)-4-oxo-3,4-dihydrophthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 863.51 (M⁺+1).

Compound 1020: 3,3-difluoro-2-methylbutan-2-yl ((2R,6S,7R,9R,13aS,14aR,16aS,Z)-2-((3-(2-methoxyethyl)-4-oxo-3,4-dihydrophthalazin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.05 (br. s., 1H), 9.16 (br. s., 1H), 8.29-8.25 (m, 1H), 7.94-7.89 (m, 4H), 7.62 (d, J=7.0 Hz, 1H), 5.54 (br. s., 2H), 4.98 (br. s., 1H), 4.66 (br. s., 1H), 4.50 (br. s., 1H), 4.24 (t, J=5.3 Hz, 2H), 3.89 (d, J=8.5 Hz, 1H), 3.78-3.68 (m, 4H), 3.28 (s, 3H), 2.65 (br. s., 2H), 2.37-2.27 (m, 2H), 1.89 (br. s., 1H), 1.82 (d, J=5.8 Hz, 1H), 1.69 (br. s., 1H), 1.57 (t, J=19.7 Hz, 5H), 1.41 (br. s., 3H), 1.25 (s, 3H), 1.16 (br. s., 2H), 0.91 (d, J=14.6 Hz, 7H), 0.95-0.89 (m, J=15.3 Hz, 5H), 0.76 (br. s., 1H). MS: MS m/z 863.51 (M⁺+1).

Preparation of Compounds 1021 and 1022

Compounds 1021 and 1022 were prepared using the intermediates described herein and by following the general procedure described for the synthesis of Compound 3117.

Compound 1021: 1,1,1-trifluoro-2-methylpropan-2-yl ((2R,6S,7R,9S,13aS,14aR,16aS,Z)-14a-((cyclopropylsulfonyl)carbamoyl)-2-((3-(2-methoxyethyl)-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 853.5 (M⁺+1).

Compound 1022: 1,1,1-trifluoro-2-methylpropan-2-yl ((2R,6S,7R,9R,13aS,14aR,16aS,Z)-14a-((cyclopropylsulfonyl)carbamoyl)-2-((3-(2-methoxyethyl)-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.20 (br. s., 1H), 9.04 (br. s., 1H), 8.29-8.25 (m, 1H), 7.94-7.88 (m, 4H), 7.82 (br. s., 1H), 5.53 (br. s., 2H), 5.07 (br. s., 1H), 4.64 (br. s., 1H), 4.48 (br. s., 1H), 4.29-4.18 (m, 2H), 3.86 (d, J=8.5 Hz, 1H), 3.76-3.72 (m, 2H), 3.71-3.65 (m, 2H), 3.27 (s, 3H), 2.63 (d, J=16.8 Hz, 2H), 2.35-2.23 (m, 2H), 1.89 (br. s., 1H), 1.83 (br. s., 1H), 1.73 (br. s., 1H), 1.59 (br. s., 1H), 1.52 (br. s., 1H), 1.40 (br. s., 1H), 1.35 (br. s., 1H), 1.33 (s, 3H), 1.25 (s, 1H), 1.16 (br. s., 1H), 1.07 (br. s., 2H), 1.01 (s, 3H), 0.93 (d, J=6.7 Hz, 3H), 0.89 (d, J=6.1 Hz, 3H), 0.73 (br. s., 1H). MS: MS m/z 853.5 (M⁺+1).

Preparation of Compounds 1023 and 1024

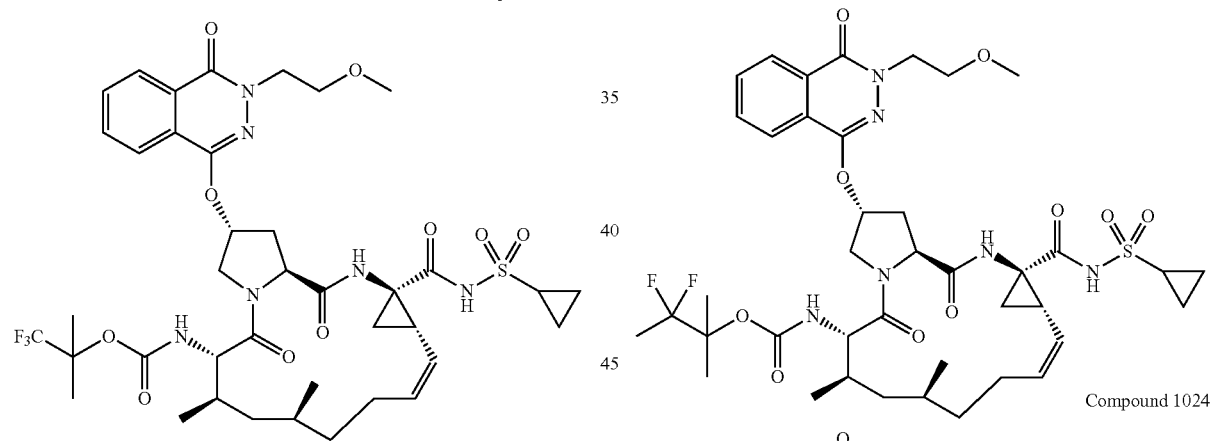

Compounds 1023 and 1024 were prepared using the intermediates described herein and by following the general procedure described for the synthesis of Compound 3117.

Compound 1023: 3,3-difluoro-2-methylbutan-2-yl ((2R,6S,7R,9S,13aS,14aR,16aS,Z)-14a-((cyclopropylsulfonyl)carbamoyl)-2-((3-(2-methoxyethyl)-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 849.6 (M⁺+1).

Compound 1024: 3,3-difluoro-2-methylbutan-2-yl ((2R,6S,7R,9R,13aS,14aR,16aS,Z)-14a-((cyclopropylsulfonyl)carbamoyl)-2-((3-(2-methoxyethyl)-4-oxo-3,4-dihydrophthalazin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.20 (br. s., 1H), 9.03 (br. s., 1H), 8.29-8.25 (m, 1H), 7.95-7.89 (m, 3H), 7.61 (d, J=7.9 Hz, 1H), 5.54 (br. s., 2H), 5.05 (br. s., 1H), 4.66 (d, J=10.4 Hz, 1H), 4.48 (br. s., 1H), 4.27-4.19 (m, 2H), 3.87 (dd, J=11.4, 3.2 Hz, 1H), 3.79-3.68 (m, 3H), 3.28 (s, 3H), 2.91 (br. s., 1H), 2.65 (br. s., 2H), 2.36-2.25 (m, 2H), 1.95-1.86 (m, 1H), 1.82 (d, J=6.1 Hz, 1H), 1.70 (br. s., 1H), 1.57 (t, J=19.7 Hz, 5H), 1.44 (br. s., 1H), 1.37 (br. s., 1H), 1.28-1.22 (m, 4H), 1.14 (br. s., 3H), 0.96-0.89 (m, 10H), 0.76 (d, J=10.1 Hz, 1H). MS: MS m/z 849.6 (M⁺+1).

Preparation of Compounds 1025 and 1026

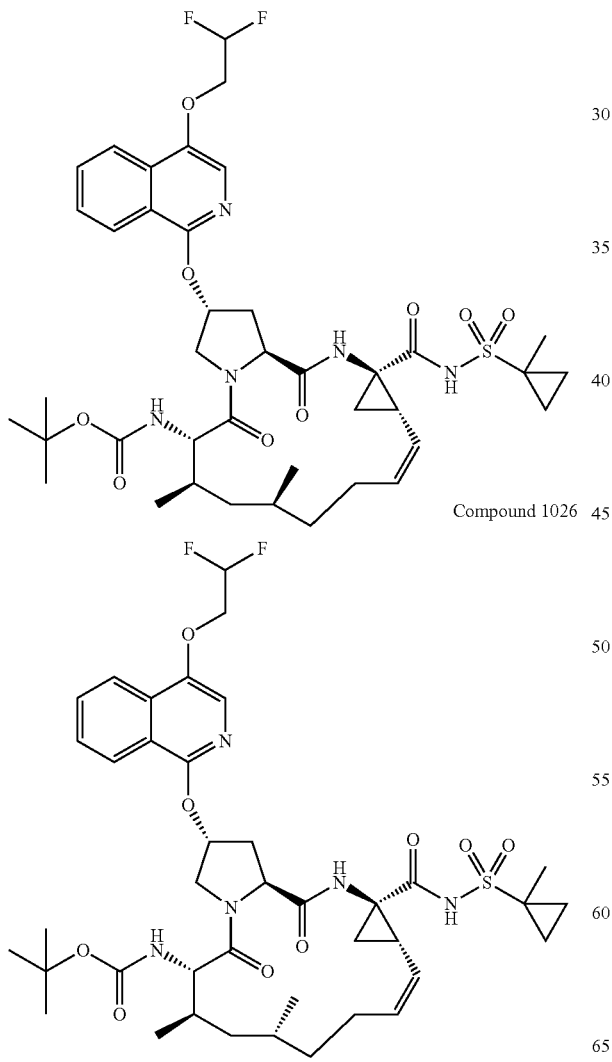

Compound 1025

Compound 1026

Compounds 1025 and 1026 were prepared using the intermediates described herein and by following the general procedure described for the synthesis of Compound 3117.

Compound 1025: tert-butyl ((2R,6S,7R,9S,13aS,14aR,16aS,Z)-2-((4-(2,2-difluoroethoxy)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 818.8 (M⁺+1).

Compound 1026: tert-butyl ((2R,6S,7R,9R,13aS,14aR,16aS,Z)-2-((4-(2,2-difluoroethoxy)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.06 (br. s., 1H), 9.11 (br. s., 1H), 8.16-8.04 (m, 2H), 7.88-7.81 (m, 1H), 7.79-7.72 (m, 1H), 7.62 (t, J=7.6 Hz, 1H), 7.17 (d, J=7.3 Hz, 1H), 6.67-6.39 (m, 1H), 5.78 (br. s., 1H), 5.52 (br. s., 1H), 4.97 (br. s., 1H), 4.62 (d, J=11.0 Hz, 1H), 4.50 (tdd, J=14.5, 6.2, 3.4 Hz, 3H), 3.94-3.89 (m, 1H), 3.78-3.68 (m, 1H), 2.91 (s, 1H), 2.75 (s, 1H), 2.71 (br. s., 1H), 2.61 (br. s., 1H), 2.35-2.26 (m, 2H), 1.94-1.86 (m, 1H), 1.82 (d, J=5.8 Hz, 1H), 1.70 (br. s., 1H), 1.61 (br. s., 1H), 1.50 (br. s., 1H), 1.44-1.36 (m, 4H), 1.27-1.22 (m, 1H), 1.14-1.06 (m, 9H), 1.04 (br. s., 1H), 0.93 (d, J=6.7 Hz, 3H), 0.88 (d, J=6.4 Hz, 3H), 0.73 (t, J=12.2 Hz, 1H). MS: MS m/z 818.8 (M⁺+1).

Preparation of Compound 1027

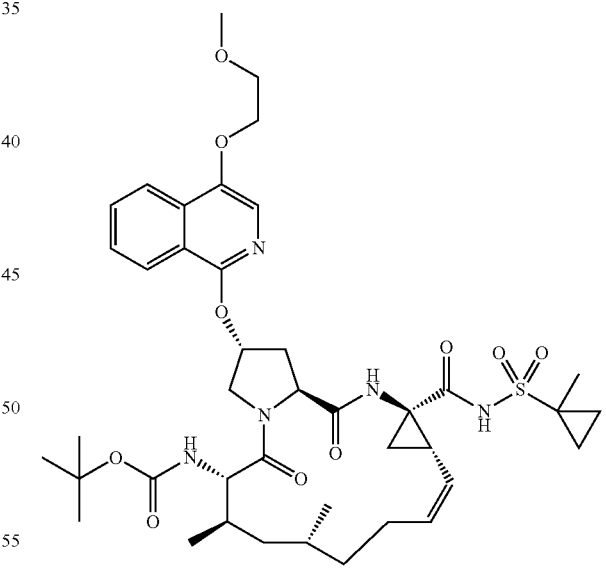

Compound 1027

Compound 1027 was prepared using the intermediates described herein and by following the general procedure described for the synthesis of Compound 3117.

Compound 1027: tert-butyl ((2R,6S,7R,9R,13aS,14aR,16aS,Z)-2-((4-(2-methoxyethoxyl)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.05 (br. s., 1H), 9.10 (br. s., 1H), 8.13-

8.05 (m, 2H), 7.80 (t, J=7.6 Hz, 1H), 7.68 (s, 1H), 7.60 (t, J=7.6 Hz, 1H), 7.17 (d, J=7.9 Hz, 1H), 5.77 (br. s., 1H), 5.52 (br. s., 1H), 4.97 (br. s., 1H), 4.60 (d, J=11.0 Hz, 1H), 4.51-4.45 (m, 1H), 4.28 (dd, J=5.3, 3.2 Hz, 2H), 3.94-3.89 (m, 1H), 3.81-3.76 (m, 2H), 3.72 (dd, J=10.7, 8.5 Hz, 1H), 3.18 (d, J=5.2 Hz, 1H), 2.91 (s, 1H), 2.75 (s, 1H), 2.74-2.66 (m, J=6.7 Hz, 1H), 2.66-2.56 (m, 1H), 2.39-2.23 (m, 2H), 1.95-1.86 (m, 1H), 1.86-1.76 (m, J=6.1 Hz, 1H), 1.70 (dd, J=12.4, 6.3 Hz, 1H), 1.61 (br. s., 1H), 1.51 (br. s., 1H), 1.48-1.43 (m, 2H), 1.41 (s, 3H), 1.39-1.32 (m, 1H), 1.32-1.14 (m, 3H), 1.12 (s, 9H), 1.09-0.96 (m, 1H), 0.93 (d, J=6.7 Hz, 3H), 0.89 (d, J=6.4 Hz, 3H), 0.74 (t, J=12.2 Hz, 1H). MS: MS m/z 812.8 (M$^+$+1).

Preparation of Compound 1028

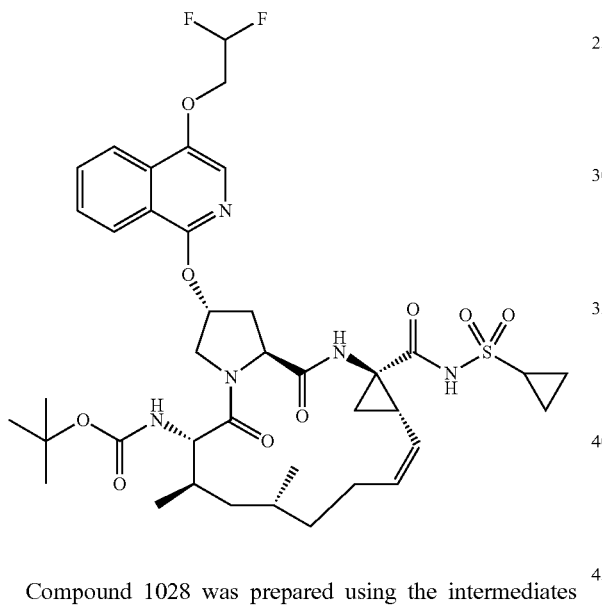

Compound 1028

Compound 1028 was prepared using the intermediates described herein and by following the general procedure described for the synthesis of Compound 3117.

Compound 1028: tert-butyl ((2R,6S,7R,9R,13aS,14aR,16aS,Z)-14a-((cyclopropylsulfonyl)carbamoyl)-2-((4-(2,2-difluoroethoxy)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.20 (br. s., 1H), 8.97 (br. s., 1H), 8.16-8.04 (m, 2H), 7.88-7.81 (m, 1H), 7.77 (s, 1H), 7.62 (t, J=7.6 Hz, 1H), 7.16 (d, J=7.9 Hz, 1H), 6.67-6.38 (m, 1H), 5.77 (br. s., 1H), 5.51 (br. s., 1H), 5.05 (br. s., 1H), 4.61 (d, J=10.1 Hz, 1H), 4.56-4.41 (m, 3H), 3.94-3.87 (m, 1H), 3.79-3.68 (m, 1H), 2.91 (s, 2H), 2.75 (s, 1H), 2.61 (br. s., 2H), 2.35-2.25 (m, 2H), 1.95-1.86 (m, 1H), 1.81 (d, J=5.5 Hz, 1H), 1.72 (br. s., 1H), 1.59 (br. s., 1H), 1.53 (br. s., 1H), 1.42 (br. s., 1H), 1.40-1.31 (m, 1H), 1.25 (br. s., 1H), 1.14-1.09 (m, 9H), 1.05 (br. s., 1H), 0.99 (br. s., 1H), 0.94 (d, J=7.0 Hz, 3H), 0.88 (d, J=6.1 Hz, 3H), 0.72 (t, J=12.8 Hz, 1H). MS: MS m/z 804.8 (M$^+$+1).

Preparation of Compounds 1029 and 1030

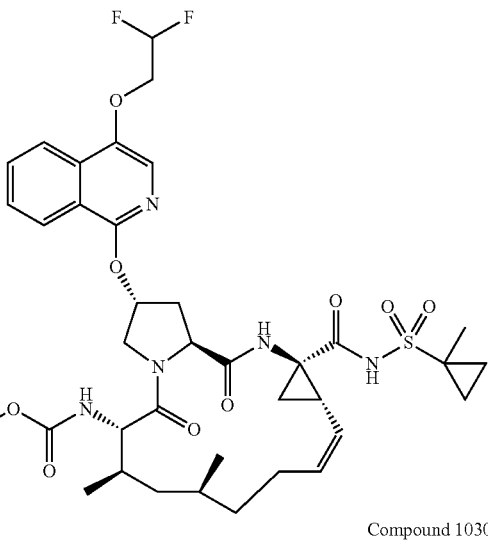

Compound 1029

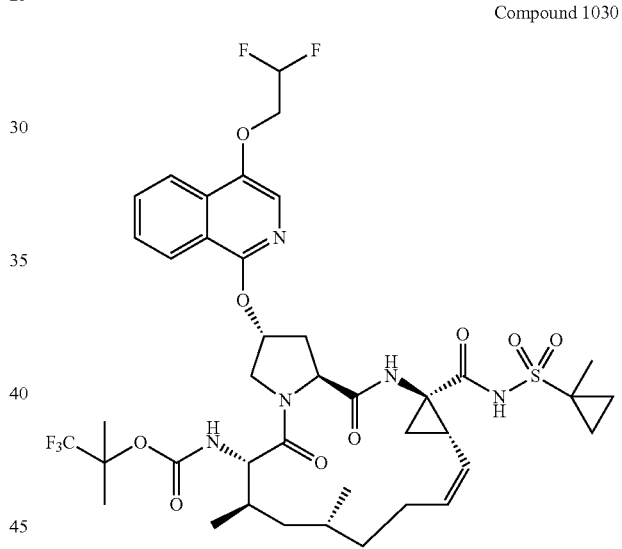

Compound 1030

Compounds 1029 and 1030 were prepared using the intermediates described herein and by following the general procedure described for the synthesis of Compound 3117.

Compound 1029: 1,1,1-trifluoro-2-methylpropan-2-yl ((2R,6S,7R,9S,13aS,14aR,16aS,Z)-2-((4-(2,2-difluoroethoxy)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 872.7 (M$^+$+1).

Compound 1030: 1,1,1-trifluoro-2-methylpropan-2-yl ((2R,6S,7R,9R,13aS,14aR,16aS,Z)-2-((4-(2,2-difluoroethoxy)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.06 (br. s., 1H), 9.14 (br. s., 1H), 8.13-8.05 (m, 2H), 7.86-7.79 (m, 2H), 7.79-7.75 (m, 1H), 7.66 (t, J=7.5 Hz, 1H), 6.69-6.38 (m, 1H), 5.79 (br. s., 1H), 5.52 (br. s., 1H), 4.99 (br. s., 1H), 4.60-4.43 (m, 4H), 3.95-3.88 (m, 1H), 3.69 (dd, J=10.7, 8.2 Hz, 1H), 2.91 (s, 2H), 2.75 (s, 2H), 2.65 (br. s., 1H), 2.61 (br. s., 1H), 2.39-2.28 (m, 2H), 1.94-1.87 (m, 1H), 1.84 (d, J=6.7 Hz, 1H), 1.71 (br. s., 1H), 1.64-1.57 (m, 1H), 1.50 (br. s., 1H), 1.41 (br. s., 4H), 1.32 (s, 3H), 1.26 (d, J=13.7 Hz, 1H), 1.18 (d, J=11.6 Hz, 1H), 1.01 (s, 3H), 0.93 (d, J=6.7 Hz, 3H), 0.89 (d, J=6.4 Hz, 3H), 0.79-0.70 (m, 1H). MS: MS m/z 872.7 (M$^+$+1).

Preparation of Compounds 1031 and 1032

Compound 1031

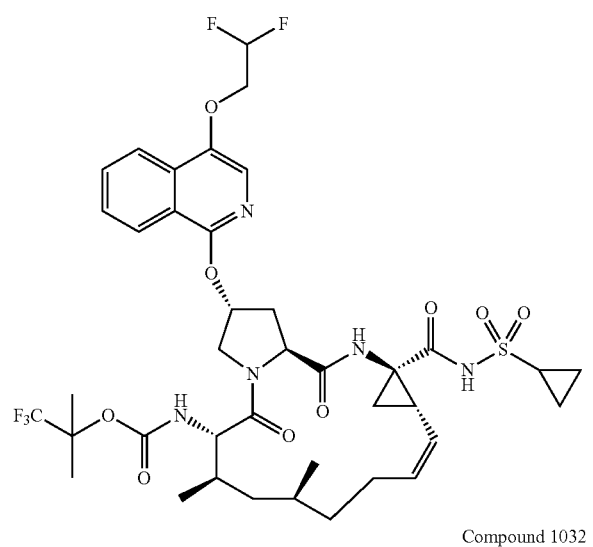

Compound 1032

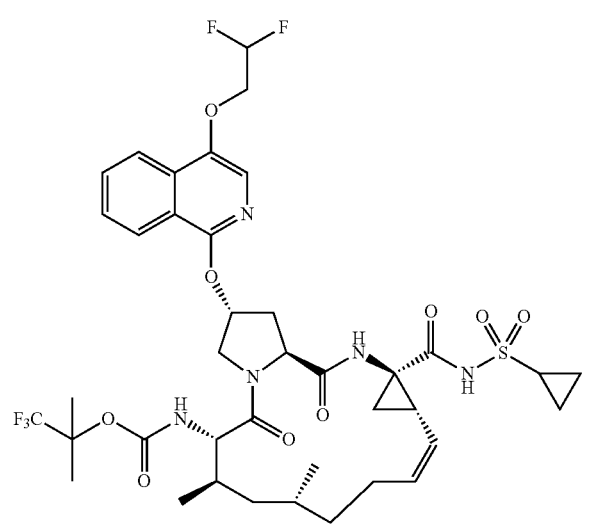

Compounds 1031 and 1032 were prepared using the intermediates described herein and by following the general procedure described for the synthesis of Compound 3117.

Compound 1031: 1,1,1-trifluoro-2-methylpropan-2-yl ((2R,6S,7R,9S,13aS,14aR,16aS,Z)-14a-((cyclopropylsulfonyl)carbamoyl)-2-((4-(2,2-difluoroethoxy)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 858.7 (M$^+$+1).

Compound 1032: 1,1,1-trifluoro-2-methylpropan-2-yl ((2R,6S,7R,9R,13aS,14aR,16aS,Z)-14a-((cyclopropylsulfonyl)carbamoyl)-2-((4-(2,2-difluoroethoxy)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.20 (br. s., 1H), 9.02 (br. s., 1H), 8.13-8.05 (m, 2H), 7.87-7.79 (m, 2H), 7.78 (s, 1H), 7.65 (t, J=7.6 Hz, 1H), 6.70-6.37 (m, 1H), 5.77 (br. s., 1H), 5.52 (br. s., 1H), 5.06 (br. s., 1H), 4.60-4.42 (m, 4H), 3.92-3.87 (m, 1H), 3.69 (dd, J=10.7, 7.9 Hz, 1H), 2.95-2.91 (m, 1H), 2.65 (d, J=1.8 Hz, 1H), 2.61 (br. s., 1H), 2.36-2.27 (m, 2H), 1.94-1.80 (m, 2H), 1.72 (br. s., 1H), 1.60 (br. s., 1H), 1.51 (br. s., 1H), 1.42 (br. s., 2H), 1.33 (s, 3H), 1.26-1.18 (m, 1H), 1.12 (br. s., 2H), 1.04 (s, 3H), 1.00 (br. s., 2H), 0.94 (d, J=6.7 Hz, 3H), 0.89 (d, J=6.4 Hz, 3H), 0.73 (br. s., 1H). MS: MS m/z 858.7 (M$^+$+1).

Preparation of Compound 1033

Compound 1033

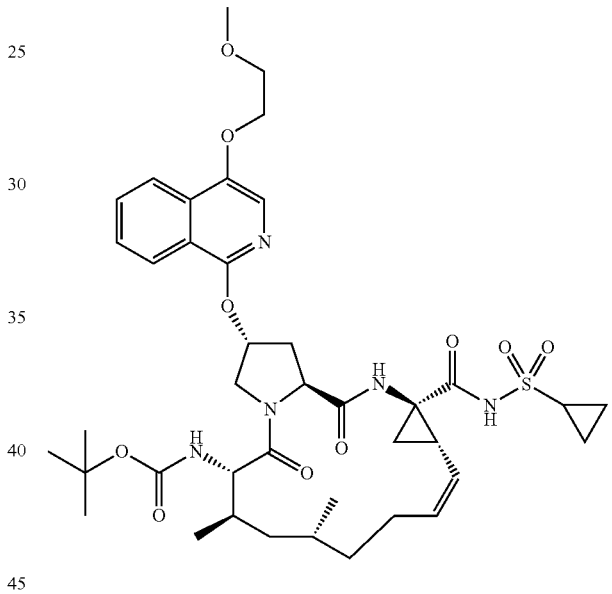

Compound 1033 was prepared using the intermediates described herein and by following the general procedure described for the synthesis of Compound 3117.

Compound 1033: tert-butyl ((2R,6S,7R,9R,13aS,14aR,16aS,Z)-14a-((cyclopropylsulfonyl)carbamoyl)-2-((4-(2-methoxyethoxy)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.19 (br. s., 1H), 8.97 (br. s., 1H), 8.14-8.05 (m, 2H), 7.80 (t, J=7.6 Hz, 1H), 7.68 (s, 1H), 7.60 (t, J=7.6 Hz, 1H), 7.17 (br. s., 1H), 5.75 (br. s., 1H), 5.52 (br. s., 1H), 5.05 (br. s., 1H), 4.59 (br. s., 1H), 4.43 (br. s., 1H), 4.28 (dd, J=5.5, 3.1 Hz, 2H), 3.92-3.87 (m, 1H), 3.82-3.77 (m, 2H), 3.73 (t, J=9.6 Hz, 1H), 3.38 (s, 3H), 2.72-2.59 (m, 2H), 2.34-2.25 (m, 2H), 1.95-1.85 (m, 1H), 1.81 (br. s., 1H), 1.71 (br. s., 1H), 1.59 (br. s., 1H), 1.54 (br. s., 2H), 1.42 (br. s., 1H), 1.36 (br. s., 1H), 1.25 (d, J=6.1 Hz, 2H), 1.14 (s, 9H), 1.05 (br. s., 1H), 1.01 (br. s., 1H), 0.93 (d, J=6.7 Hz, 3H), 0.88 (d, J=6.1 Hz, 3H), 0.72 (br. s., 1H). MS: MS m/z 798.65 (M$^+$+1).

Preparation of Compound 1034

Compound 1034

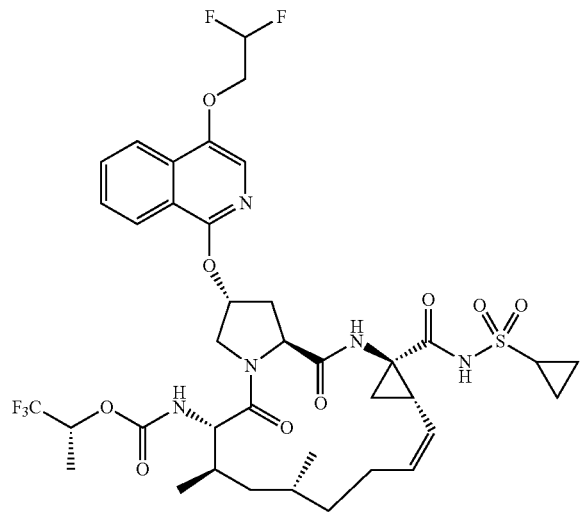

Compound 1034 was prepared using the intermediates described herein and by following the general procedure described for the synthesis of Compound 3117.

Compound 1034: (R)-1,1,1-trifluoropropan-2-yl ((2R,6S,7R,9R,13aS,14aR,16aS,Z)-14a-((cyclopropylsulfonyl)carbamoyl)-2-((4-(2,2-difluoroethoxy)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.18 (s, 1H), 8.98 (br. s., 1H), 8.07 (dd, J=8.2, 4.3 Hz, 2H), 7.87-7.81 (m, 1H), 7.77 (s, 1H), 7.60 (t, J=7.5 Hz, 1H), 6.68-6.37 (m, 1H), 5.79 (br. s., 1H), 5.53 (d, J=5.5 Hz, 1H), 5.06 (t, J=9.5 Hz, 1H), 4.71-4.65 (m, 1H), 4.56-4.43 (m, 4H), 3.95-3.90 (m, 1H), 3.77 (dd, J=10.7, 8.2 Hz, 1H), 2.95-2.88 (m, 1H), 2.70-2.59 (m, 2H), 2.39-2.27 (m, 2H), 1.96-1.82 (m, 2H), 1.71 (br. s., 1H), 1.63-1.52 (m, 2H), 1.44 (br. s., 1H), 1.41-1.31 (m, 1H), 1.19 (d, J=6.7 Hz, 3H), 1.12 (d, J=6.7 Hz, 3H), 0.99 (br. s., 3H), 0.94 (d, J=6.7 Hz, 3H), 0.90 (d, J=6.4 Hz, 3H), 0.76 (t, J=12.4 Hz, 1H). MS: MS m/z 798.65 (M$^+$+1).

Preparation of Compounds 1035 and 1036

Compound 1035

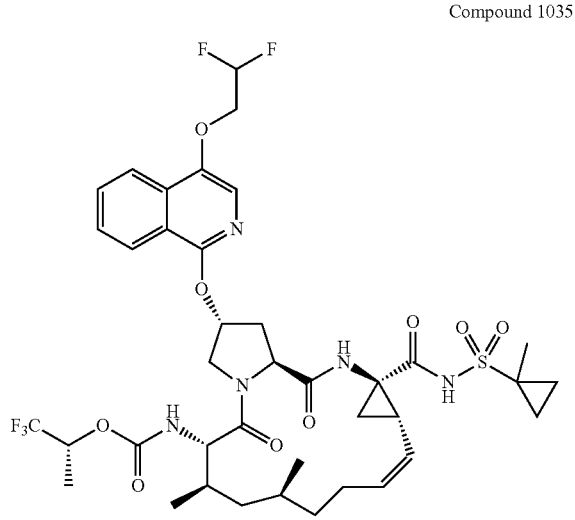

Compound 1036

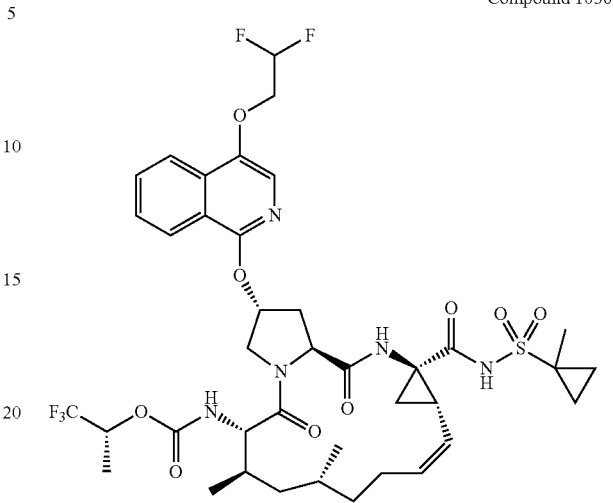

Compounds 1035 and 1036 were prepared using the intermediates described herein and by following the general procedure described for the synthesis of Compound 3117.

Compound 1035: (R)-1,1,1-trifluoropropan-2-yl ((2R,6S,7R,9S,13aS,14aR,16aS,Z)-2-((4-(2,2-difluoroethoxy)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 798.65 (M$^+$+1).

Compound 1036: (R)-1,1,1-trifluoropropan-2-yl ((2R,6S,7R,9R,13aS,14aR,16aS,Z)-2-((4-(2,2-difluoroethoxy)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.04 (br. s., 1H), 9.11 (br. s., 1H), 8.11-8.04 (m, 3H), 7.83 (t, J=8.2 Hz, 1H), 7.77 (s, 1H), 7.60 (t, J=7.6 Hz, 1H), 6.69-6.39 (m, 1H), 5.80 (br. s., 1H), 5.52 (br. s., 1H), 4.99 (br. s., 1H), 4.65 (br. s., 1H), 4.51 (td, J=14.5, 3.4 Hz, 4H), 3.95 (dd, J=11.3, 3.4 Hz, 1H), 3.77 (dd, J=10.5, 8.1 Hz, 1H), 2.63 (d, J=19.8 Hz, 2H), 2.31 (t, J=9.8 Hz, 2H), 1.95-1.90 (m, 1H), 1.90-1.79 (m, 1H), 1.70 (br. s., 1H), 1.60 (br. s., 1H), 1.51 (br. s., 1H), 1.48-1.31 (m, 6H), 1.28 (br. s., 1H), 1.19 (s, 3H), 1.14-1.09 (m, 1H), 0.93 (d, J=6.7 Hz, 3H), 0.90 (d, J=6.4 Hz, 3H), 0.88-0.82 (m, 2H), 0.76 (br. s., 1H). MS: MS m/z 798.65 (M$^+$+1).

Preparation of Compounds 1037 and 1038

Compound 1037

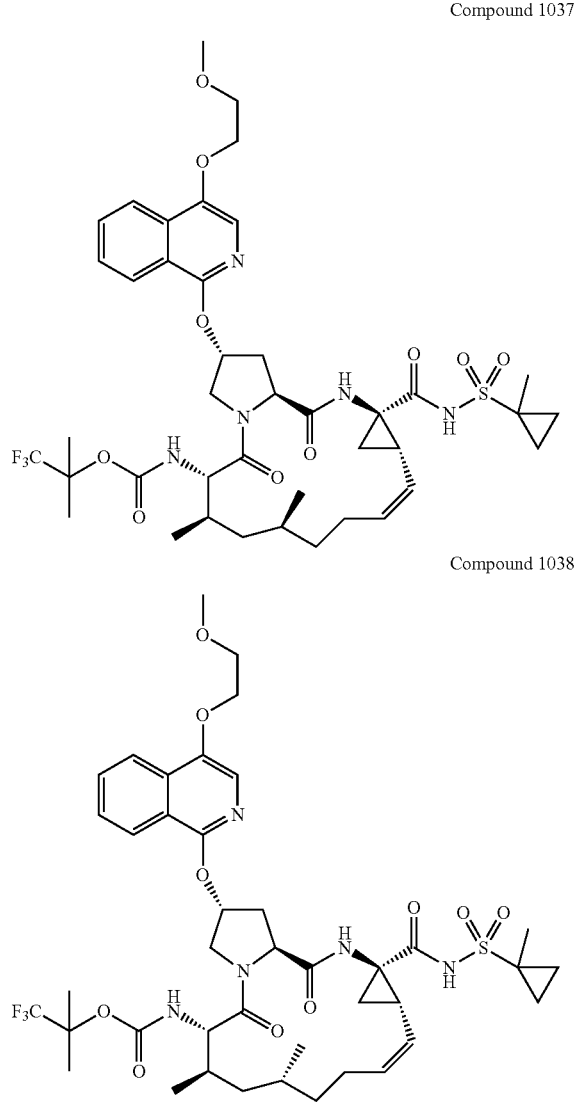

Compound 1038

Compounds 1037 and 1038 were prepared using the intermediates described herein and by following the general procedure described for the synthesis of Compound 3117.

Compound 1037: 1,1,1-trifluoro-2-methylpropan-2-yl ((2R,6S,7R,9S,13aS,14aR,16aS,Z)-2-((4-(2-methoxyethoxyl)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 866.66 (M⁺+1).

Compound 1038: 1,1,1-trifluoro-2-methylpropan-2-yl ((2R,6S,7R,9R,13aS,14aR,16aS,Z)-2-((4-(2-methoxyethoxyl)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.06 (br. s., 1H), 9.14 (s, 1H), 8.09 (t, J=9.0 Hz, 2H), 7.83-7.77 (m, 2H), 7.69 (s, 1H), 7.63 (t, J=7.6 Hz, 1H), 5.76 (br. s., 1H), 5.47 (br. s., 1H), 4.99 (s, 1H), 4.50 (br. s., 2H), 4.28 (d, J=3.1 Hz, 2H), 3.93-3.89 (m, 1H), 3.81-3.78 (m, 2H), 3.73-3.68 (m, 1H), 2.31 (t, J=9.9 Hz, 2H), 1.84 (br. s., 2H), 1.75 (br. s., 1H), 1.50 (br. s., 1H), 1.44-1.30 (m, 12H), 1.25 (br. s., 2H), 1.20 (br. s., 3H), 1.05 (s, 3H), 0.93 (d, J=6.7 Hz, 3H), 0.88 (d, J=6.1 Hz, 3H), 0.72 (br. s., 1H). MS: MS m/z 866.66 (M⁺+1).

Preparation of Compound 1039

Compound 1039

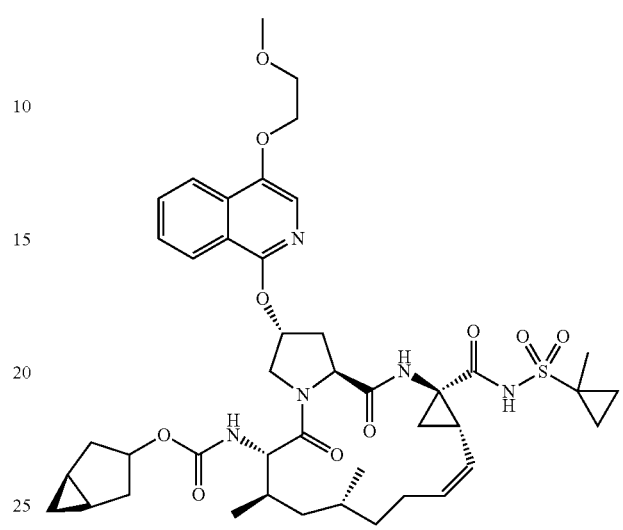

Compound 1039 was prepared using the intermediates described herein and by following the general procedure described for the synthesis of Compound 3117.

Compound 1039: (1S,5S)-bicyclo[3.1.0]hexan-3-yl ((2R,6S,7R,9R,13aS,14aR,16aS,Z)-2-((4-(2-methoxyethoxyl)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
1H NMR (500 MHz, DMSO-d6) Shift 8.09 (t, J=9.2 Hz, 2H), 7.82 (t, J=7.6 Hz, 1H), 7.70-7.63 (m, 2H), 7.35 (d, J=8.2 Hz, 1H), 5.76 (br. s., 1H), 5.40 (br. s., 1H), 4.61 (t, J=6.6 Hz, 1H), 4.42 (br. s., 2H), 4.31-4.26 (m, 2H), 3.96-3.91 (m, 1H), 3.82-3.73 (m, 3H), 2.35-2.20 (m, 2H), 1.97-1.86 (m, 3H), 1.86-1.69 (m, 3H), 1.56 (d, J=14.3 Hz, 1H), 1.47 (br. s., 1H), 1.41-1.22 (m, 8H), 1.22-1.14 (m, 2H), 1.14-1.06 (m, 2H), 1.05-0.95 (m, 1H), 0.92 (d, J=6.7 Hz, 3H), 0.86 (d, J=6.4 Hz, 3H), 0.67 (br. s., 1H), 0.60-0.41 (m, 1H), 0.37-0.28 (m, 2H). MS: MS m/z 836.71 (M⁺+1).

Preparation of Compound 1040

Compound 1040

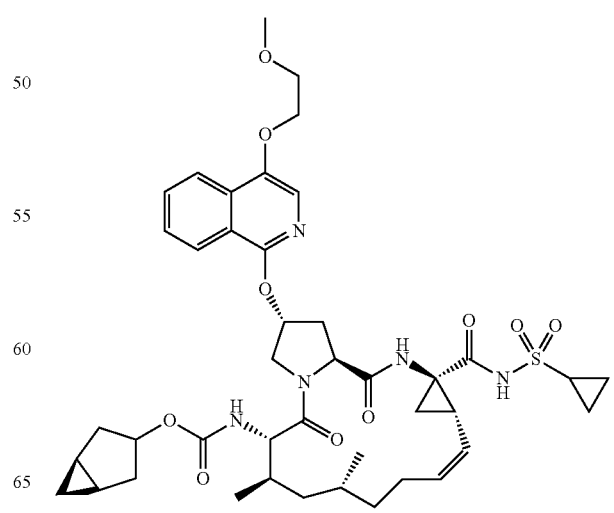

Compound 1040 was prepared using the intermediates described herein and by following the general procedure described for the synthesis of Compound 3117.

Compound 1040: (1S,5S)-bicyclo[3.1.0]hexan-3-yl ((2R,6S,7R,9R,13aS,14aR,16aS,Z)-14a-((cyclopropylsulfonyl)carbamoyl)-2-((4-(2-methoxyethoxyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.21 (br. s., 1H), 8.09 (t, J=8.5 Hz, 2H), 7.82 (t, J=7.6 Hz, 1H), 7.71-7.62 (m, 2H), 7.36 (br. s., 1H), 5.76 (br. s., 1H), 5.45 (br. s., 1H), 4.62 (t, J=6.7 Hz, 1H), 4.42 (br. s., 2H), 4.31-4.26 (m, 2H), 3.94-3.90 (m, 1H), 3.81-3.73 (m, 3H), 2.35-2.18 (m, 3H), 1.99-1.87 (m, 3H), 1.87-1.66 (m, 4H), 1.66-1.46 (m, 3H), 1.41 (br. s., 2H), 1.32 (d, J=14.3 Hz, 3H), 1.28-1.15 (m, 3H), 1.11 (t, J=11.6 Hz, 2H), 0.93 (d, J=6.4 Hz, 3H), 0.86 (d, J=6.4 Hz, 3H), 0.69 (br. s., 3H), 0.38-0.29 (m, 2H). MS: MS m/z 822.74 (M⁺+1).

Preparation of Compound 1041

Compound 1041

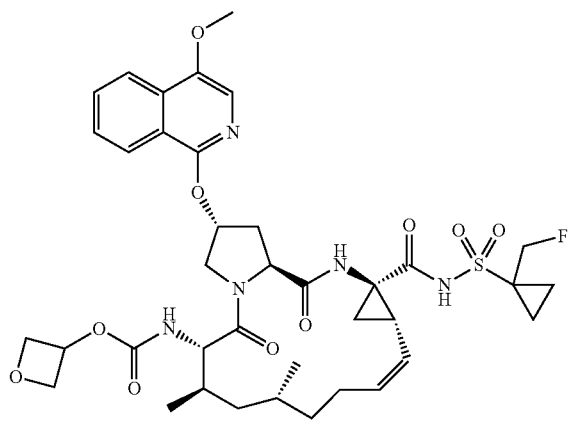

Compound 1041 was prepared using the intermediates described herein and by following the general procedure described for the synthesis of Compound 3117.

Compound 1041: oxetan-3-yl ((2R,6S,7R,9R,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.27 (s, 1H), 9.02 (s, 1H), 8.08 (t, J=7.8 Hz, 2H), 7.87-7.79 (m, 2H), 7.72-7.64 (m, 2H), 5.78 (br. s., 1H), 5.55-5.48 (m, 1H), 5.01 (t, J=9.9 Hz, 1H), 4.86 (d, J=11.6 Hz, 2H), 4.59 (d, J=11.6 Hz, 1H), 4.55-4.43 (m, 3H), 4.38 (t, J=6.9 Hz, 1H), 4.32-4.26 (m, 1H), 4.13-4.06 (m, 1H), 3.99 (s, 3H), 3.96-3.87 (m, 2H), 3.76-3.70 (m, 1H), 2.71-2.58 (m, 2H), 2.39-2.23 (m, 2H), 1.96-1.80 (m, 2H), 1.68 (dd, J=12.5, 7.0 Hz, 1H), 1.53 (br. s., 4H), 1.44 (br. s., 1H), 1.42-1.32 (m, 1H), 1.32-1.18 (m, 1H), 1.14 (d, J=12.5 Hz, 1H), 0.94 (d, J=6.7 Hz, 3H), 0.90 (d, J=6.1 Hz, 3H), 0.75 (t, J=12.4 Hz, 1H). MS: MS m/z 786.5 (M⁺+1).

Preparation of Compounds 1042 and 1043

Compound 1042

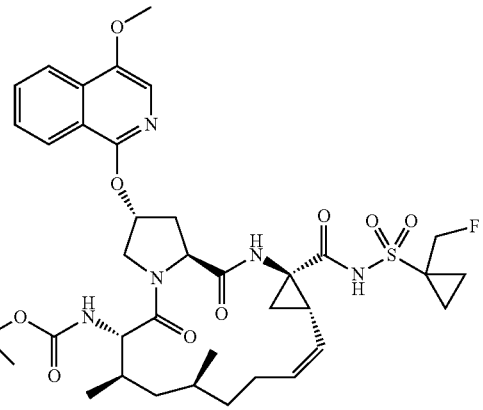

Compound 1043

Compounds 1042 and 1043 were prepared using the intermediates described herein and by following the general procedure described for the synthesis of Compound 3117.

Compound 1042: 3,3-difluoro-2-methylbutan-2-yl ((2R,6S,7R,9S,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 786.5 (M⁺+1).

Compound 1043: 3,3-difluoro-2-methylbutan-2-yl ((2R,6S,7R,9R,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.29 (s, 1H), 9.04 (s, 1H), 8.07 (d, J=8.2 Hz, 1H), 8.10 (d, J=8.5 Hz, 1H), 7.80 (t, J=7.6 Hz, 1H), 7.66 (s, 1H), 7.65-7.59 (m, 2H), 5.77 (br. s., 1H), 5.55-5.49 (m, 1H), 5.00 (t, J=10.1 Hz, 1H), 4.91-4.66 (m, J=11.6 Hz, 1H), 4.57 (dd, J=16.6, 11.7 Hz, 1H), 4.53-4.45 (m, 2H), 3.98 (s, 3H), 3.96-3.89 (m, 1H), 3.75-3.70 (m, 1H), 2.72-2.59 (m, 2H), 2.39-2.27 (m, 2H), 1.94-1.78 (m, 2H), 1.70 (dd, J=12.1, 6.9 Hz, 1H), 1.64-1.49 (m, 7H), 1.43 (br. s., 1H), 1.41-1.29 (m, 1H), 1.27 (s, 3H), 1.24-1.19 (m, 1H), 1.15 (d, J=12.2 Hz, 1H), 1.01 (s, 3H), 0.94 (d, J=6.7 Hz, 3H), 0.90 (d, J=6.4 Hz, 3H), 0.76 (t, J=12.7 Hz, 1H). MS: MS m/z 786.5 (M$^+$+1).

Preparation of Compound 1044

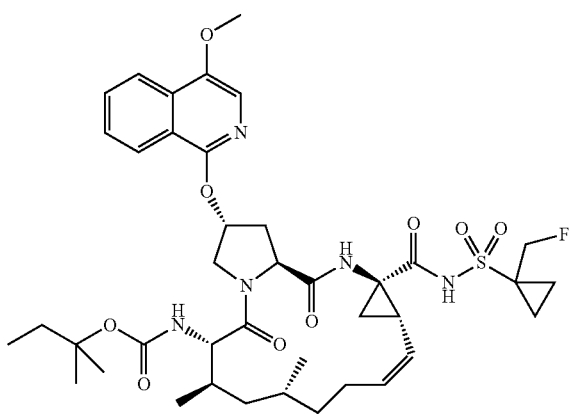

Compound 1044

Compound 1044 was prepared using the intermediates described herein and by following the general procedure described for the synthesis of Compound 3117.

Compound 1044: tert-pentyl ((2R,6S,7R,9R,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.29 (s, 1H), 9.03 (br. s., 1H), 8.12-8.05 (m, 2H), 7.79 (t, J=7.5 Hz, 1H), 7.66 (s, 1H), 7.60 (t, J=7.6 Hz, 1H), 7.19 (d, J=7.9 Hz, 1H), 5.76 (br. s., 1H), 5.51 (br. s., 1H), 4.98 (t, J=9.3 Hz, 1H), 4.90-4.69 (m, 1H), 4.59 (d, J=11.0 Hz, 1H), 4.52-4.42 (m, 1H), 3.98 (s, 3H), 3.95-3.88 (m, 1H), 3.76-3.71 (m, 1H), 2.71-2.63 (m, 1H), 2.60 (br. s., 1H), 2.35-2.24 (m, 2H), 1.93-1.87 (m, 1H), 1.83 (d, J=6.4 Hz, 1H), 1.69 (br. s., 1H), 1.58-1.36 (m, 6H), 1.34 (br. s., 1H), 1.24 (d, J=13.1 Hz, 3H), 1.14 (d, J=11.0 Hz, 1H), 1.07 (s, 3H), 1.10 (s, 3H), 0.94 (d, J=6.7 Hz, 3H), 0.88 (d, J=6.4 Hz, 3H), 0.81-0.70 (m, 2H), 0.68 (t, J=7.5 Hz, 3H). MS: MS m/z 800.5 (M$^+$+1).

Preparation of Compound 1045

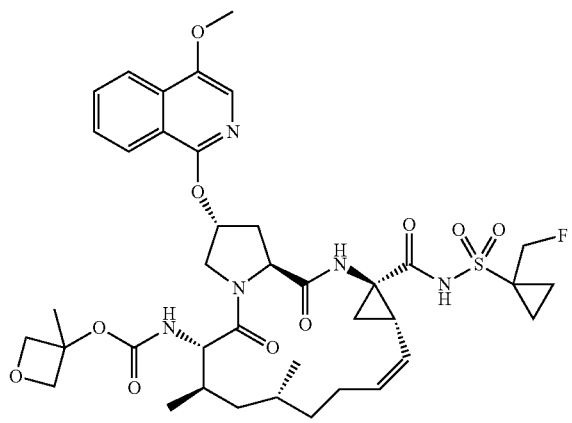

Compound 1045

Compound 1045 was prepared using the intermediates described herein and by following the general procedure described for the synthesis of Compound 3117.

Compound 1045: 3-methyloxetan-3-yl ((2R,6S,7R,9R,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, METHANOL-d4) Shift 8.17-8.10 (m, 2H), 7.78-7.71 (m, 1H), 7.64-7.53 (m, 2H), 5.79 (br. s., 1H), 5.53 (td, J=10.2, 5.8 Hz, 1H), 5.16 (br. s., 1H), 4.87-4.74 (m, 1H), 4.72-4.52 (m, 3H), 4.49 (d, J=7.0 Hz, 1H), 4.28 (d, J=7.0 Hz, 1H), 4.11 (d, J=7.0 Hz, 1H), 4.02 (s, 3H), 4.01-3.95 (m, 2H), 3.84 (d, J=10.7 Hz, 1H), 2.72 (dd, J=13.7, 7.0 Hz, 1H), 2.62 (q, J=9.0 Hz, 1H), 2.49-2.35 (m, 2H), 1.95-1.77 (m, 3H), 1.69 (dd, J=8.4, 5.3 Hz, 1H), 1.62 (td, J=10.2, 4.6 Hz, 2H), 1.54 (dd, J=9.5, 5.2 Hz, 1H), 1.50-1.38 (m, 2H), 1.32-1.23 (m, 1H), 1.22 (s, 3H), 1.21-1.08 (m, 2H), 1.01 (d, J=7.0 Hz, 3H), 0.99 (d, J=6.4 Hz, 3H), 0.89-0.78 (m, 1H). MS: MS m/z 800.4 (M$^+$+1).

Preparation of Compound 1046

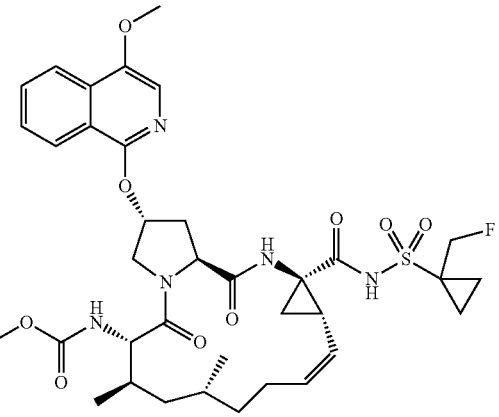

Compound 1046

Compound 1046 was prepared using the intermediates described herein and by following the general procedure described for the synthesis of Compound 3117.

Compound 1046: 3-(trifluoromethyl)oxetan-3-yl ((2R,6S,7R,9R,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.28 (s, 1H), 9.05 (s, 1H), 8.09-8.01 (m, 3H), 7.81 (t, J=7.5 Hz, 1H), 7.65 (s, 1H), 7.64-7.59 (m, 1H), 5.74 (br. s., 1H), 5.56-5.49 (m, 1H), 5.00 (t, J=9.9 Hz, 1H), 4.89-4.74 (m, J=11.6 Hz, 1H), 4.59 (d, J=11.3 Hz, 1H), 4.48 (ddd, J=17.2, 10.8, 6.7 Hz, 2H), 3.97 (s, 3H), 3.96-3.91 (m, 1H), 3.82-3.76 (m, 1H), 3.72 (d, J=7.9 Hz, 1H), 3.41 (t, J=10.4 Hz, 2H), 3.24-3.17 (m, 1H), 2.71-2.60 (m, 2H), 2.39-2.26 (m, 2H), 2.05 (d, J=12.2 Hz, 1H), 1.96-1.81 (m, 3H), 1.75-1.62 (m, 2H), 1.58-1.48 (m, 5H), 1.44 (br. s., 1H), 1.42-1.32 (m, 1H), 1.32-1.19 (m, 2H), 1.15 (d, J=11.9 Hz, 1H), 0.95 (d, J=7.0 Hz, 3H), 0.92 (d, J=6.4 Hz, 3H), 0.77 (t, J=12.4 Hz, 1H). MS: MS m/z 854.3 (M$^+$+1).

Preparation of Compounds 1047 and 1048

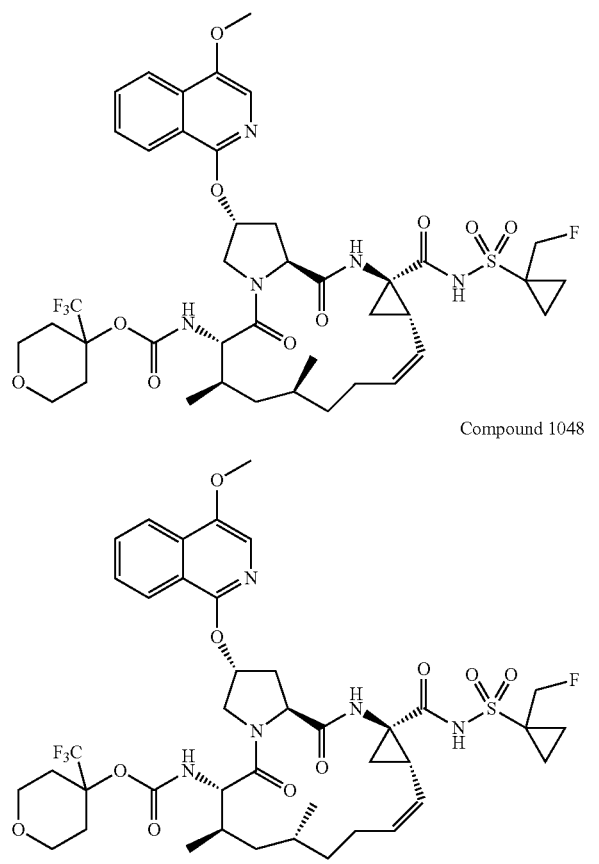

Compound 1047

Compound 1048

Compounds 1047 and 1048 were prepared using the intermediates described herein and by following the general procedure described for the synthesis of Compound 3117.

Compound 1047: 4-(trifluoromethyl)tetrahydro-2H-pyran-4-yl ((2R,6S,7R,9S,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 882.4 (M$^+$+1).

Compound 1048: 4-(trifluoromethyl)tetrahydro-2H-pyran-4-yl ((2R,6S,7R,9R,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.28 (s, 1H), 9.05 (s, 1H), 8.09-8.01 (m, 3H), 7.81 (t, J=7.5 Hz, 1H), 7.65 (s, 1H), 7.64-7.59 (m, 1H), 5.74 (br. s., 1H), 5.56-5.49 (m, 1H), 5.00 (t, J=9.9 Hz, 1H), 4.89-4.74 (m, J=11.6 Hz, 1H), 4.59 (d, J=11.3 Hz, 1H), 4.48 (ddd, J=17.2, 10.8, 6.7 Hz, 2H), 3.97 (s, 3H), 3.96-3.91 (m, 1H), 3.82-3.76 (m, 1H), 3.72 (d, J=7.9 Hz, 1H), 3.41 (t, J=10.4 Hz, 2H), 3.24-3.17 (m, 1H), 2.71-2.60 (m, 2H), 2.39-2.26 (m, 2H), 2.05 (d, J=12.2 Hz, 1H), 1.96-1.81 (m, 3H), 1.75-1.62 (m, 2H), 1.58-1.48 (m, 5H), 1.44 (br. s., 1H), 1.42-1.32 (m, 1H), 1.32-1.19 (m, 2H), 1.15 (d, J=11.9 Hz, 1H), 0.95 (d, J=7.0 Hz, 3H), 0.92 (d, J=6.4 Hz, 3H), 0.77 (t, J=12.4 Hz, 1H). MS: MS m/z 882.4 (M$^+$+1).

Preparation of Compounds 1049 and 1050

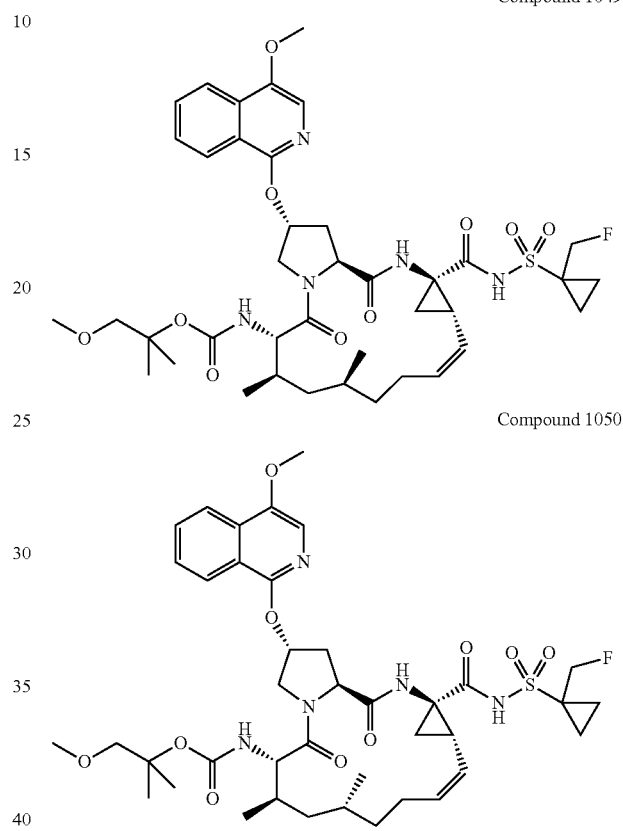

Compound 1049

Compound 1050

Compounds 1049 and 1050 were prepared using the intermediates described herein and by following the general procedure described for the synthesis of Compound 3117.

Compound 1049: 1-methoxy-2-methylpropan-2-yl ((2R,6S,7R,9S,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 816.7 (M$^+$+1).

Compound 1050: 1-methoxy-2-methylpropan-2-yl ((2R,6S,7R,9R,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.29 (s, 1H), 9.04 (br. s., 1H), 8.12 (d, J=8.2 Hz, 1H), 8.06 (d, J=8.2 Hz, 1H), 7.79 (t, J=7.5 Hz, 1H), 7.66 (s, 1H), 7.61 (t, J=7.6 Hz, 1H), 7.28 (d, J=7.9 Hz, 1H), 5.76 (br. s., 1H), 5.52 (d, J=6.4 Hz, 1H), 4.98 (t, J=9.5 Hz, 1H), 4.91-4.68 (m, 1H), 4.59 (d, J=11.0 Hz, 1H), 4.52-4.43 (m, 1H), 3.98 (s, 3H), 3.96-3.89 (m, 1H), 3.71 (dd, J=10.5, 8.4 Hz, 1H), 3.26-3.21 (m, 1H), 3.19-3.10 (m, 4H), 2.71-2.57 (m, 2H), 2.36-2.26 (m, 2H), 1.93-1.77 (m, 2H), 1.74-1.66 (m, 1H), 1.53 (br. s., 4H), 1.45-1.32 (m, 2H), 1.25

(d, J=12.8 Hz, 2H), 1.14 (d, J=13.1 Hz, 1H), 1.10-1.00 (m, 6H), 0.94 (d, J=6.7 Hz, 3H), 0.88 (d, J=6.1 Hz, 3H), 0.73 (t, J=12.7 Hz, 1H). MS: MS m/z 816.7 (M+ +1).

Preparation of Compounds 1051 and 1052

Preparation of Compounds 1053 and 1054

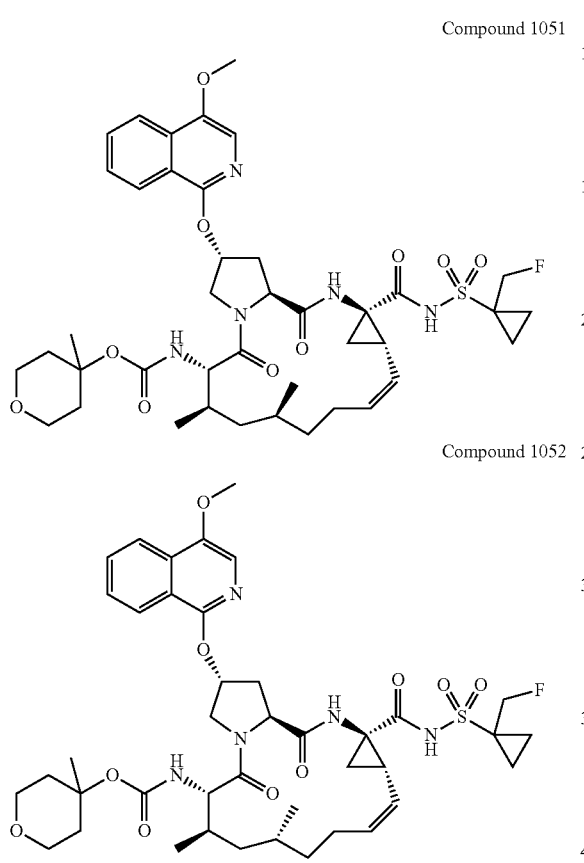

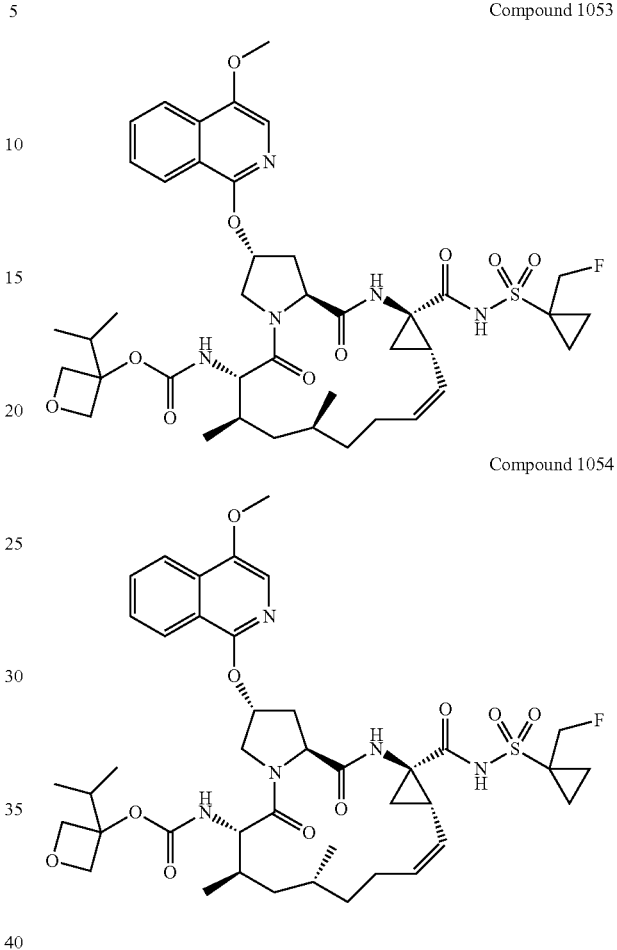

Compounds 1051 and 1052 were prepared using the intermediates described herein and by following the general procedure described for the synthesis of Compound 3117.

Compound 1051: 4-methyltetrahydro-2H-pyran-4-yl ((2R,6S,7R,9S,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 828.7 (M+ +1).

Compound 1052: 4-methyltetrahydro-2H-pyran-4-yl ((2R,6S,7R,9R,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 8.10-8.05 (m, 2H), 7.80 (t, J=7.6 Hz, 1H), 7.66 (s, 1H), 7.62 (t, J=7.8 Hz, 1H), 5.73 (br. s., 1H), 4.59 (br. s., 1H), 4.46 (br. s., 1H), 3.97 (s, 3H), 3.93-3.88 (m, 1H), 3.75-3.70 (m, 1H), 3.47 (d, J=3.7 Hz, 2H), 3.33-3.27 (m, 2H), 3.27-3.21 (m, 1H), 2.34-2.24 (m, 2H), 1.82 (br. s., 2H), 1.77 (d, J=14.0 Hz, 1H), 1.51 (d, J=15.3 Hz, 3H), 1.47-1.37 (m, 3H), 1.31-1.21 (m, 3H), 1.13 (s, 3H), 0.93 (d, J=6.7 Hz, 3H), 0.88 (d, J=5.8 Hz, 3H), 0.85 (br. s., 1H), 0.74 (br. s., 1H). MS: MS m/z 828.7 (M+ +1).

Compounds 1053 and 1054 were prepared using the intermediates described herein and by following the general procedure described for the synthesis of Compound 3117.

Compound 1053: 3-isopropyloxetan-3-yl ((2R,6S,7R,9S,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 828.8 (M+ +1).

Compound 1054: 3-isopropyloxetan-3-yl ((2R,6S,7R,9R,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.28 (s, 1H), 9.05 (br. s., 1H), 8.05 (d, J=8.5 Hz, 1H), 8.09 (d, J=8.2 Hz, 1H), 7.82 (t, J=7.6 Hz, 1H), 7.73-7.62 (m, 3H), 5.74 (br. s., 1H), 5.52 (d, J=6.1 Hz, 1H), 4.99 (t, J=9.8 Hz, 1H), 4.89-4.66 (m, 1H), 4.60 (d, J=11.0 Hz, 1H), 4.50 (d, J=11.3 Hz, 2H), 4.36 (d, J=7.3 Hz, 1H), 4.28 (d, J=7.3 Hz, 1H), 4.19-4.10 (m, 2H), 3.98 (s, 3H), 3.97-3.89 (m, 1H), 3.75 (dd, J=10.5, 8.7 Hz, 1H), 2.61 (d, J=6.1 Hz, 1H), 2.31 (ddd, J=13.7, 10.2, 4.1 Hz, 2H), 1.97-1.78 (m, 3H), 1.68 (d, J=5.8 Hz, 1H), 1.54 (br. s., 4H), 1.43 (br. s., 1H), 1.38 (br. s., 1H), 1.25 (d, J=12.5 Hz, 2H), 1.15 (br. s., 1H), 0.94 (d, J=6.7 Hz, 3H), 0.89 (d, J=6.4 Hz, 3H), 0.82 (d, J=16.8 Hz, 1H), 0.77 (d, J=7.0 Hz, 3H), 0.75-0.66 (m, 2H), 0.67-0.58 (m, 3H). MS: MS m/z 828.8 (M⁺+1).

Preparation of Compounds 1055 and 1056

Preparation of Compounds 1057 and 1058

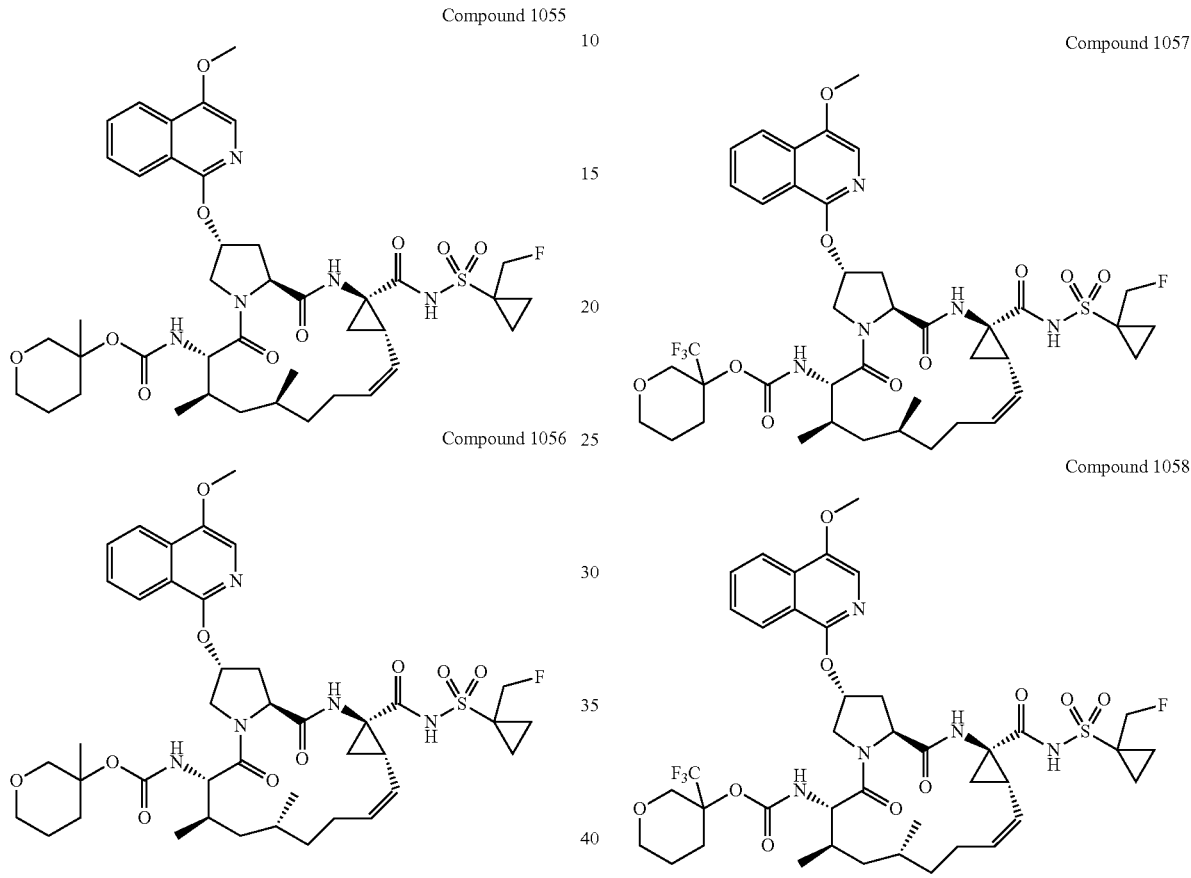

Compound 1055

Compound 1056

Compound 1057

Compound 1058

Compounds 1055 and 1056 were prepared using the intermediates described herein and by following the general procedure described for the synthesis of Compound 3117.

Compound 1055: 3-methyltetrahydro-2H-pyran-3-yl ((2R,6S,7R,9S,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 828.4 (M⁺+1).

Compound 1056: 3-methyltetrahydro-2H-pyran-3-yl ((2R,6S,7R,9R,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.28 (s, 1H), 9.01 (br. s., 1H), 8.12 (d, J=8.2 Hz, 1H), 8.10-8.04 (m, 1H), 7.80 (t, J=7.9 Hz, 1H), 7.65 (s, 1H), 7.60 (t, J=7.6 Hz, 1H), 7.37 (d, J=7.6 Hz, 1H), 5.74 (br. s., 1H), 5.51 (br. s., 1H), 5.00 (br. s., 1H), 4.91-4.72 (m, J=10.4 Hz, 1H), 4.65-4.56 (m, 1H), 4.52-4.41 (m, 1H), 3.97 (s, 3H), 3.93-3.88 (m, 1H), 3.75-3.70 (m, 1H), 3.64-3.54 (m, 2H), 3.40-3.36 (m, 1H), 3.19-3.12 (m, 1H), 2.71-2.59 (m, 1H), 2.35-2.25 (m, 2H), 1.88 (d, J=13.4 Hz, 2H), 1.68 (br. s., 1H), 1.63 (br. s., 1H), 1.58-1.48 (m, 4H), 1.45 (d, J=14.6 Hz, 2H), 1.36 (d, J=8.9 Hz, 2H), 1.24 (d, J=14.0 Hz, 2H), 1.17 (br. s., 2H), 1.05 (s, 3H), 0.94 (d, J=6.7 Hz, 3H), 0.91 (d, J=6.1 Hz, 3H), 0.84 (s, 1H), 0.74 (br. s., 1H). MS: MS m/z 828.4 (M⁺+1).

Compounds 1057 and 1058 were prepared using the intermediates described herein and by following the general procedure described for the synthesis of Compound 3117.

Compound 1057: 3-(trifluoromethyl)tetrahydro-2H-pyran-3-yl ((2R,6S,7R,9S,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 882.4 (M⁺+1).

Compound 1058: 3-(trifluoromethyl)tetrahydro-2H-pyran-3-yl ((2R,6S,7R,9R,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, METHANOL-d4) Shift 8.15 (d, J=8.2 Hz, 1H), 8.09 (d, J=8.2 Hz, 1H), 7.76-7.69 (m, 1H), 7.57-7.53 (m, 1H), 7.53 (s, 1H), 5.78 (t, J=3.4 Hz, 1H), 5.47 (td, J=10.1, 5.5 Hz, 1H), 5.20 (t, J=9.6 Hz, 1H), 4.85-4.71 (m, 1H), 4.65 (dd, J=11.0, 4.0 Hz, 2H), 4.62-4.53 (m, 2H), 4.13 (dd, J=11.9, 1.8 Hz, 1H), 4.05 (dd, J=11.4, 3.5 Hz, 1H), 4.01 (s, 3H), 3.94 (d, J=11.0 Hz, 1H), 3.64 (d, J=10.7 Hz, 1H), 3.48-3.43 (m, 1H), 3.43-3.33 (m, 1H), 2.73 (dd, J=14.0, 7.0 Hz, 1H), 2.59 (q, J=9.2 Hz, 1H), 2.47-2.25 (m, 3H), 1.93-1.83 (m, 2H), 1.83-1.76 (m, 1H), 1.76-1.68 (m, 2H), 1.66 (dd, J=8.5, 5.2 Hz, 1H), 1.63-1.55 (m, 2H), 1.55-1.48 (m, 2H), 1.43-1.36 (m, 1H), 1.36-1.26 (m, 2H), 1.23-1.16 (m, 1H), 1.16-1.07 (m, 2H), 1.01 (d, J=6.4 Hz, 3H), 0.98 (d, J=7.0 Hz, 3H), 0.84-0.78 (m, 1H). MS: MS m/z 882.4 (M$^+$+1).

Preparation of Compounds 1059 and 1060

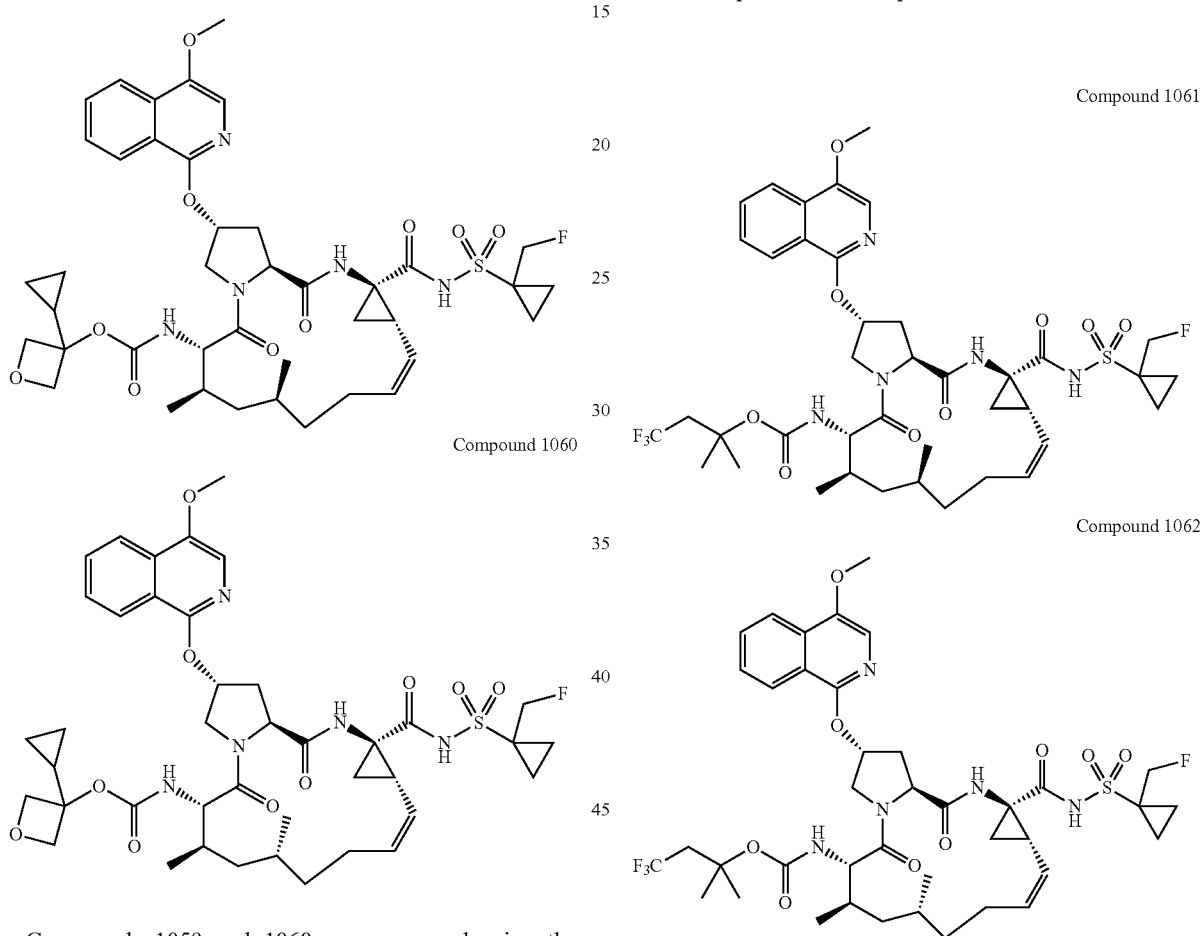

Compounds 1059 and 1060 were prepared using the intermediates described herein and by following the general procedure described for the synthesis of Compound 3117.

Compound 1059: 3-cyclopropyloxetan-3-yl((2R,6S,7R,9S,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 826.1 (M$^+$+1).

Compound 1060: 3-cyclopropyloxetan-3-yl ((2R,6S,7R,9R,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.29 (s, 1H), 9.06 (br. s., 1H), 8.07 (d, J=5.2 Hz, 1H), 8.06 (d, J=4.9 Hz, 1H), 7.80 (t, J=7.5 Hz, 1H), 7.71 (d, J=7.9 Hz, 1H), 7.65 (s, 1H), 7.62 (t, J=7.6 Hz, 1H), 5.74 (br. s., 1H), 5.52 (br. s., 1H), 5.02-4.97 (m, 1H), 4.90-4.73 (m, J=11.0 Hz, 1H), 4.62-4.47 (m, 3H), 4.34 (d, J=7.3 Hz, 1H), 4.07 (d, J=7.6 Hz, 1H), 4.02 (d, J=7.0 Hz, 1H), 3.98 (s, 3H), 3.95-3.91 (m, 1H), 3.77-3.72 (m, 2H), 2.73-2.63 (m, 1H), 2.61 (br. s., 1H), 2.35-2.26 (m, 2H), 1.91 (br. s., 1H), 1.84 (br. s., 1H), 1.70 (br. s., 1H), 1.53 (br. s., 4H), 1.43 (br. s., 1H), 1.38 (br. s., 1H), 1.31-1.20 (m, 2H), 1.16 (br. s., 1H), 1.01 (dt, J=13.4, 6.9 Hz, 1H), 0.94 (d, J=6.7 Hz, 3H), 0.90 (d, J=6.4 Hz, 3H), 0.79-0.70 (m, 1H), 0.34-0.28 (m, 2H), 0.24-0.15 (m, 2H). MS: MS m/z 826.1 (M$^+$+1).

Preparation of Compounds 1061 and 1062

Compounds 1061 and 1062 were prepared using the intermediates described herein and by following the general procedure described for the synthesis of Compound 3117.

Compound 1061: 4,4,4-trifluoro-2-methylbutan-2-yl ((2R,6S,7R,9S,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 854.4 (M$^+$+1).

Compound 1062: 4,4,4-trifluoro-2-methylbutan-2-yl ((2R,6S,7R,9R,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.

1H NMR (500 MHz, DMSO-d6) Shift 11.29 (br. s., 1H), 9.04 (br. s., 1H), 8.07 (d, J=5.2 Hz, 1H), 8.06 (d, J=5.8 Hz, 1H), 7.79 (t, J=8.1 Hz, 1H), 7.70-7.65 (m, 1H), 7.60 (t, J=7.6 Hz, 1H), 7.43 (d, J=6.4 Hz, 1H), 5.76 (br. s., 1H), 5.52 (br. s., 1H), 4.99 (br. s., 1H), 4.91-4.72 (m, J=9.2 Hz, 1H), 4.58 (br. s., 1H), 4.55-4.41 (m, 2H), 3.97 (s, 3H), 3.95-3.90 (m, 1H), 3.73 (dd, J=10.7, 8.5 Hz, 1H), 2.74-2.62 (m, 2H), 2.62-2.54 (m, 1H), 2.34-2.25 (m, 2H), 1.89 (br. s., 1H), 1.82 (br. s., 1H), 1.68 (br. s., 1H), 1.53 (br. s., 4H), 1.39 (d, J=16.5 Hz, 3H), 1.26 (br. s., 1H), 1.22 (s, 3H), 1.15 (br. s., 2H), 1.10-1.05 (m, 3H), 0.93 (d, J=7.0 Hz, 3H), 0.86 (d, J=6.4 Hz, 3H), 0.73 (br. s., 1H). MS: MS m/z 854.4 (M$^+$+1).

Preparation of Compound 1063 and 1064

Compound 1063

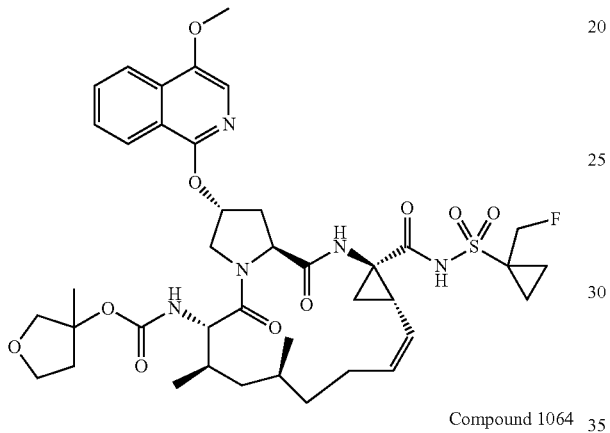

Compound 1064

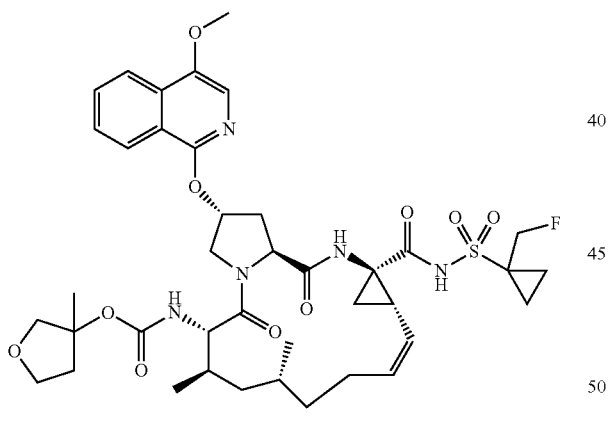

Compounds 1063 and 1064 were prepared using the intermediates described herein and by following the general procedure described for the synthesis of Compound 3117.

Compound 1063: 3-methyltetrahydrofuran-3-yl ((2R,6S,7R,9S,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 814.4 (M$^+$+1).

Compound 1064: 3-methyltetrahydrofuran-3-yl ((2R,6S,7R,9R,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (500 MHz, DMSO-d$_6$) δ 11.27 (br. s., 1H), 9.01 (br. s., 1H), 8.11 (d, J=8.2 Hz, 1H), 8.06 (d, J=8.2 Hz, 1H), 7.80 (t, J=7.8 Hz, 1H), 7.66 (s, 1H), 7.62 (t, J=7.6 Hz, 1H), 7.49 (br. s., 1H), 5.75 (br. s., 1H), 5.52 (br. s., 1H), 5.31 (br. s., 1H), 5.00 (br. s., 1H), 4.89-4.73 (m, 1H), 4.60 (br. s., 1H), 4.46 (br. s., 2H), 3.98 (s, 3H), 3.91 (d, J=10.7 Hz, 1H), 3.73 (dd, J=10.4, 8.5 Hz, 1H), 3.69-3.63 (m, 2H), 3.60 (d, J=9.5 Hz, 1H), 3.26 (d, J=10.1 Hz, 1H), 2.65 (d, J=1.8 Hz, 1H), 2.34-2.27 (m, 2H), 2.08 (dt, J=12.9, 6.2 Hz, 1H), 1.92 (s, 1H), 1.83 (br. s., 1H), 1.81-1.65 (m, 2H), 1.53 (br. s., 2H), 1.38 (br. s., 3H), 1.31-1.27 (m, 1H), 1.25 (s, 3H), 1.21-1.10 (m, 2H), 0.94 (d, J=6.1 Hz, 3H), 0.89 (br. s., 3H), 0.74 (br. s., 1H), 0.69-0.60 (m, 1H). MS: MS m/z 814.4 (M$^+$+1).

Preparation of Compounds 1065 and 1066

Compound 1065

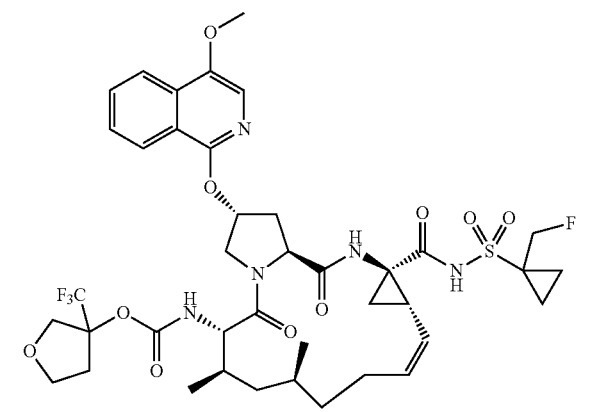

Compound 1066

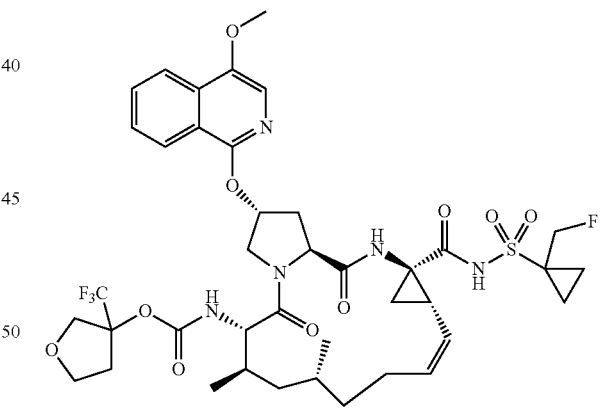

Compounds 1065 and 1066 were prepared using the intermediates described herein and by following the general procedure described for the synthesis of Compound 3117.

Compound 1065: 3-(trifluoromethyl)tetrahydrofuran-3-yl ((2R,6S,7R,9S,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 868.4 (M$^+$+1).

Compound 1066: 3-(trifluoromethyl)tetrahydrofuran-3-yl ((2R,6S,7R,9R,13aS,14aR,16aS,Z)-14a-(((1-(fluoromethyl)cyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.27 (br. s., 1H), 9.05 (br. s., 1H), 8.13-8.02 (m, 3H), 7.84-7.78 (m, 1H), 7.66 (d, J=2.1 Hz, 1H), 7.65-7.61 (m, 1H), 5.78 (d, J=15.9 Hz, 1H), 5.52 (br. s., 1H), 5.00 (br. s., 1H), 4.88-4.73 (m, J=11.3 Hz, 1H), 4.50 (d, J=9.5 Hz, 3H), 3.98 (d, J=2.4 Hz, 3H), 3.97-3.80 (m, 3H), 3.79-3.71 (m, 2H), 3.70-3.53 (m, 2H), 2.66 (d, J=9.8 Hz, 1H), 2.36-2.25 (m, 2H), 2.15-2.07 (m, 1H), 1.93-1.83 (m, 3H), 1.77 (br. s., 1H), 1.70 (br. s., 1H), 1.53 (br. s., 3H), 1.43 (br. s., 1H), 1.37 (br. s., 1H), 1.32-1.20 (m, 2H), 1.20-1.11 (m, 1H), 0.94 (d, J=5.2 Hz, 3H), 0.89 (dd, J=13.0, 6.3 Hz, 3H), 0.76 (br. s., 1H). MS: MS m/z 868.4 (M$^+$+1).

Preparation of Compounds 1067 and 1068

Compound 1067

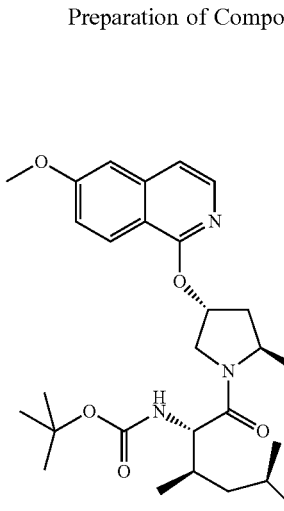

Compound 1068

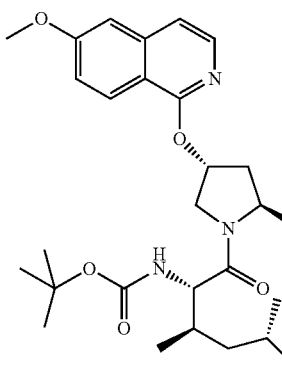

Compounds 1067 and 1068 were prepared using the intermediates described herein and by following the general procedure described for the synthesis of Compound 3117.

Compound 1067: tert-butyl ((2R,6S,7R,9S,13aS,14aR,16aS,Z)-14a-((cyclopropylsulfonyl)carbamoyl)-2-((6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 754.4 (M$^+$+1).

Compound 1068: tert-butyl ((2R,6S,7R,9R,13aS,14aR,16aS,Z)-14a-((cyclopropylsulfonyl)carbamoyl)-2-((6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, CHLOROFORM-d) δ ppm 0.72-0.83 (m, 2H) 0.88-0.94 (m, 1H) 0.99 (d, J=7.02 Hz, 6H) 1.05-1.13 (m, 2H) 1.15 (d, J=10.07 Hz, 2H) 1.20 (s, 9H) 1.35-1.40 (m, 2H) 1.40-1.48 (m, 2H) 1.48-1.51 (m, 1H) 1.64-1.72 (m, 1H) 1.72-1.86 (m, 1H) 1.92-1.99 (m, 2H) 2.21-2.36 (m, 1H) 2.44-2.56 (m, 1H) 2.66-2.78 (m, 1H) 2.86-2.97 (m, 1H) 3.92 (s, 3H) 3.99-4.09 (m, 1H) 4.38-4.46 (m, 1H) 4.71 (d, J=10.68 Hz, 1H) 4.93 (t, J=9.92 Hz, 1H) 5.51-5.65 (m, 1H) 5.87-6.00 (m, 1H) 7.01 (s, 1H) 7.05 (d, J=8.55 Hz, 1H) 7.16 (d, J=5.19 Hz, 1H) 7.93 (d, J=5.80 Hz, 1H) 8.03 (d, J=8.85 Hz, 1H) 10.42 (s, 1H). MS: MS m/z 754.4 (M$^+$+1).

Preparation of Compounds 1069 and 1070

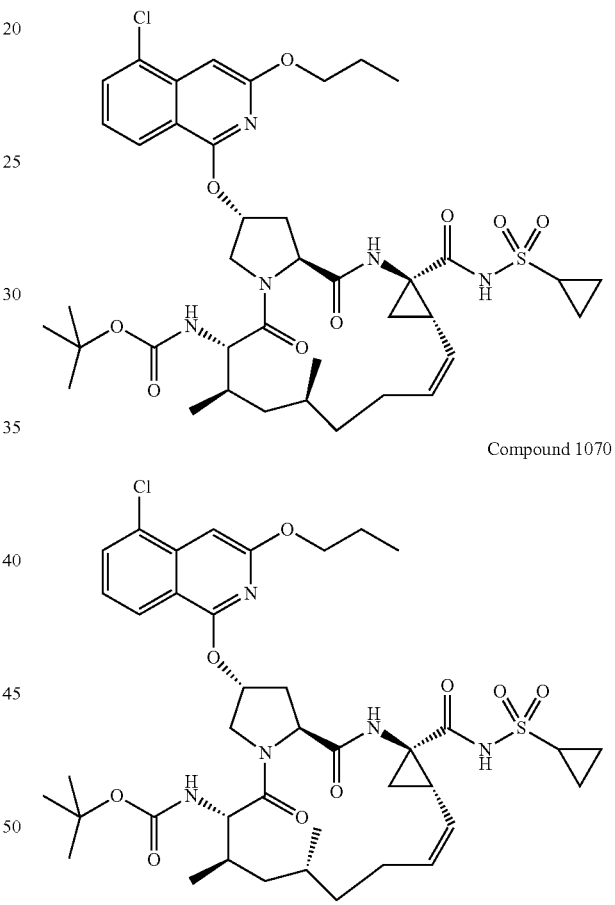

Compounds 1069 and 1070 were prepared using the intermediates described herein and by following the general procedure described for the synthesis of Compound 3117.

Compound 1069: tert-butyl ((2R,6S,7R,9S,13aS,14aR,16aS,Z)-2-((5-chloro-3-propoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 816.7 (M$^+$+1).

Compound 1070: tert-butyl ((2R,6S,7R,9R,13aS,14aR,16aS,Z)-2-((5-chloro-3-propoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.21 (br. s., 1H), 8.99 (br. s., 1H), 8.02 (d, J=8.2 Hz, 1H), 7.82 (d, J=7.3 Hz, 1H), 7.27 (t, J=7.8 Hz, 1H), 7.17 (br. s., 1H), 6.80-6.74 (m, 1H), 5.79 (br. s., 1H), 5.52 (br. s., 1H), 5.05 (br. s., 1H), 4.65 (br. s., 1H), 4.46 (br. s., 1H), 4.33-4.22 (m, 2H), 3.94-3.89 (m, 1H), 3.72-3.66 (m, 1H), 2.65 (br. s., 2H), 2.39-2.23 (m, 2H), 1.91 (d, J=9.5 Hz, 1H), 1.86-1.78 (m, 3H), 1.71 (br. s., 1H), 1.59 (br. s., 2H), 1.42 (br. s., 1H), 1.36 (br. s., 1H), 1.22 (br. s., 3H), 1.09 (s, 9H), 1.03 (t, J=7.5 Hz, 4H), 0.99-0.96 (m, 1H), 0.93 (d, J=6.7 Hz, 3H), 0.88 (d, J=6.1 Hz, 3H), 0.71 (br. s., 1H). MS: MS m/z 816.7 (M$^+$+1).

Preparation of Compounds 1071 and 1072

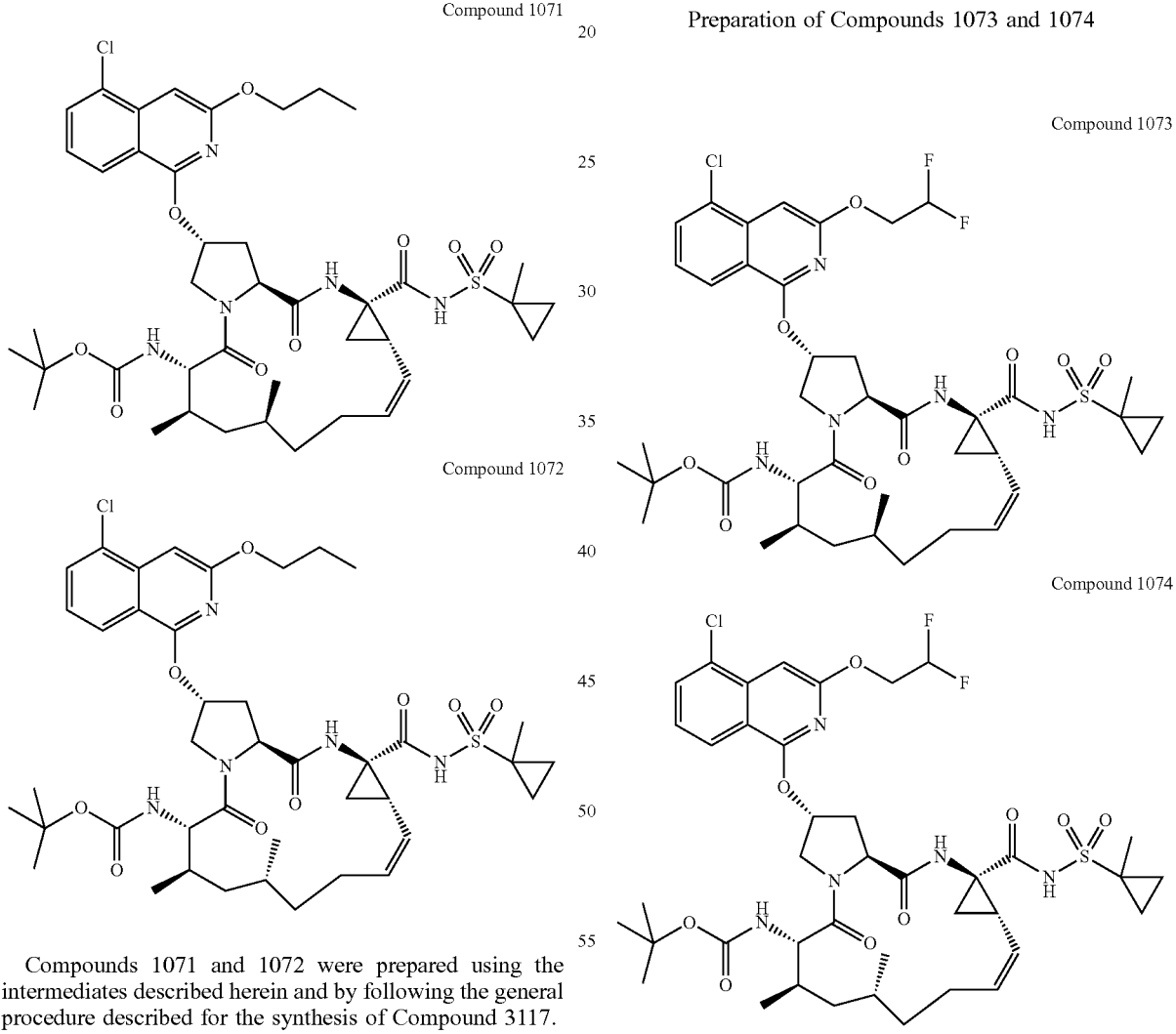

Compound 1071

Compound 1072

Compounds 1071 and 1072 were prepared using the intermediates described herein and by following the general procedure described for the synthesis of Compound 3117.

Compound 1071: tert-butyl ((2R,6S,7R,9S,13aS,14aR,16aS,Z)-2-((5-chloro-3-propoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 830.7 (M$^+$+1).

Compound 1072: tert-butyl ((2R,6S,7R,9R,13aS,14aR,16aS,Z)-2-((5-chloro-3-propoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.06 (s, 1H), 9.12 (br. s., 1H), 8.02 (d, J=8.2 Hz, 1H), 7.88-7.80 (m, 1H), 7.27 (t, J=7.9 Hz, 1H), 7.19 (d, J=7.9 Hz, 1H), 6.77-6.73 (m, 1H), 5.81 (br. s., 1H), 5.54 (d, J=6.1 Hz, 1H), 4.97 (t, J=9.8 Hz, 1H), 4.68 (d, J=11.0 Hz, 1H), 4.54-4.45 (m, 1H), 4.32-4.23 (m, 2H), 3.96-3.91 (m, 1H), 3.68 (dd, J=10.4, 8.2 Hz, 1H), 2.75-2.62 (m, 2H), 2.40-2.28 (m, 2H), 1.96-1.86 (m, 1H), 1.82 (dq, J=14.2, 7.0 Hz, 3H), 1.74-1.66 (m, 1H), 1.62 (br. s., 1H), 1.53 (d, J=9.2 Hz, 1H), 1.46 (d, J=10.7 Hz, 2H), 1.43-1.39 (m, 2H), 1.36 (br. s., 1H), 1.29 (d, J=9.8 Hz, 1H), 1.13 (d, J=11.9 Hz, 1H), 1.08 (s, 9H), 1.06-1.01 (m, 4H), 0.93 (d, J=7.0 Hz, 3H), 0.91-0.86 (m, J=6.4 Hz, 5H), 0.74 (t, J=12.2 Hz, 1H). MS: MS m/z 830.7 (M$^+$+1).

Preparation of Compounds 1073 and 1074

Compound 1073

Compound 1074

Compounds 1073 and 1074 were prepared using the intermediates described herein and by following the general procedure described for the synthesis of Compound 3117.

Compound 1073: tert-butyl ((2R,6S,7R,9S,13aS,14aR,16aS,Z)-2-((5-chloro-3-(2,2-difluoroethoxy)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15, 16,16a-hexadecahydrocyclopropa[e]pyrrolo[1,2-a][1,4]diazacyclopentadecin-6-yl)carbamate. MS: MS m/z 852.8 (M⁺+1).

Compound 1074: tert-butyl ((2R,6S,7R,9R,13aS,14aR,16aS,Z)-2-((5-chloro-3-(2,2-difluoroethoxy)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.07 (br. s., 1H), 9.14 (br. s., 1H), 8.10-8.03 (m, 1H), 7.86 (d, J=7.3 Hz, 1H), 7.33 (t, J=7.9 Hz, 1H), 7.19 (br. s., 1H), 6.88 (s, 1H), 6.64-6.31 (m, 1H), 5.84 (br. s., 1H), 5.52 (br. s., 1H), 4.97 (br. s., 1H), 4.69 (td, J=14.9, 3.5 Hz, 3H), 4.50 (br. s., 1H), 3.93 (dd, J=11.7, 2.9 Hz, 1H), 3.72-3.66 (m, 1H), 2.65 (br. s., 2H), 2.39-2.25 (m, 2H), 1.91 (d, J=14.0 Hz, 1H), 1.81 (br. s., 1H), 1.71 (br. s., 1H), 1.61 (br. s., 1H), 1.40 (br. s., 4H), 1.25 (br. s., 3H), 1.19 (br. s., 2H), 1.07 (s, 9H), 1.05 (br. s., 2H), 0.93 (d, J=6.7 Hz, 3H), 0.88 (d, J=6.4 Hz, 3H), 0.73 (br. s., 1H). MS: MS m/z 852.8 (M⁺+1).

Preparation of Compounds 1075 and 1076 yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 836.6 (M⁺−1).

Compound 1076: tert-butyl ((2R,6S,7R,9R,13aS,14aR,16aS,Z)-2-((5-chloro-3-(2,2-difluoroethoxy)isoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.22 (br. s., 1H), 9.02 (br. s., 1H), 8.05 (d, J=8.5 Hz, 1H), 7.86 (d, J=7.6 Hz, 1H), 7.33 (t, J=7.9 Hz, 1H), 7.19 (d, J=6.4 Hz, 1H), 6.88 (s, 1H), 6.65-6.34 (m, 1H), 5.83 (br. s., 1H), 5.53 (br. s., 1H), 5.04 (br. s., 1H), 4.75-4.64 (m, 3H), 4.49 (br. s., 1H), 3.94-3.89 (m, 1H), 3.72-3.66 (m, 1H), 2.68 (br. s., 2H), 2.39-2.24 (m, 2H), 1.92 (d, J=4.9 Hz, 1H), 1.81 (d, J=6.1 Hz, 1H), 1.70 (br. s., 1H), 1.61 (br. s., 1H), 1.56 (br. s., 1H), 1.43 (br. s., 1H), 1.37 (br. s., 1H), 1.19 (br. s., 1H), 1.13 (br. s., 2H), 1.07 (s, 9H), 1.01 (br. s., 3H), 0.94 (d, J=6.7 Hz, 3H), 0.88 (d, J=6.4 Hz, 3H), 0.74 (d, J=12.8 Hz, 1H). MS: MS m/z 836.6 (M⁺−1).

Preparation of Compounds 1077 and 1078

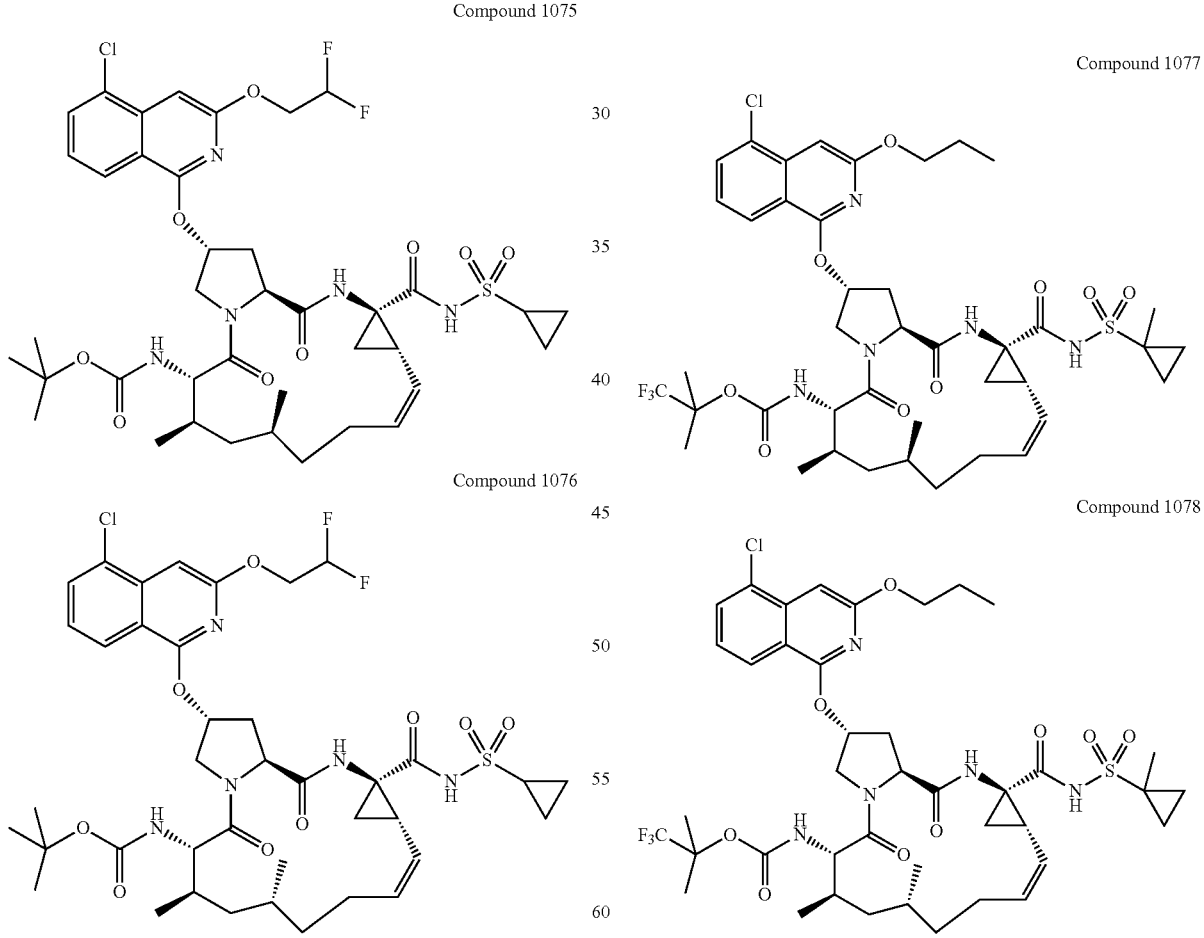

Compound 1075

Compound 1076

Compound 1077

Compound 1078

Compounds 1075 and 1076 were prepared using the intermediates described herein and by following the general procedure described for the synthesis of Compound 3117.

Compound 1075: tert-butyl ((2R,6S,7R,9R,13aS,14aR,16aS,Z)-2-((5-chloro-3-(2,2-difluoroethoxy)isoquinolin-1-

Compounds 1077 and 1078 were prepared using the intermediates described herein and by following the general procedure described for the synthesis of Compound 3117.

Compound 1077: 1,1,1-trifluoro-2-methylpropan-2-yl ((2R,6S,7R,9S,13aS,14aR,16aS,Z)-2-((5-chloro-3-propoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 884.66 (M$^+$+1).

Compound 1078: 1,1,1-trifluoro-2-methylpropan-2-yl ((2R,6S,7R,9R,13aS,14aR,16aS,Z)-2-((5-chloro-3-propoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.05 (br. s., 1H), 9.15 (br. s., 1H), 8.00 (d, J=8.2 Hz, 1H), 7.83 (d, J=7.3 Hz, 2H), 7.31 (t, J=7.9 Hz, 1H), 6.77 (s, 1H), 5.81 (br. s., 1H), 5.53 (br. s., 1H), 4.98 (br. s., 1H), 4.61 (d, J=11.3 Hz, 1H), 4.54 (br. s., 1H), 4.32-4.23 (m, 2H), 3.97-3.91 (m, 1H), 3.67 (dd, J=10.8, 8.1 Hz, 1H), 2.73-2.68 (m, 1H), 2.66 (br. s., 1H), 2.39-2.26 (m, 2H), 1.94-1.77 (m, 4H), 1.70 (br. s., 1H), 1.62 (br. s., 1H), 1.52 (d, J=16.2 Hz, 1H), 1.49-1.38 (m, 5H), 1.35 (br. s., 1H), 1.31 (s, 3H), 1.29-1.23 (m, 1H), 1.17 (d, J=8.5 Hz, 1H), 1.03 (t, J=7.3 Hz, 3H), 1.00 (s, 3H), 0.93 (d, J=7.0 Hz, 4H), 0.89 (d, J=6.1 Hz, 3H), 0.75 (t, J=12.4 Hz, 1H). MS: MS m/z 884.66 (M$^+$+1).

Preparation of Compounds 1079 and 1080

Compound 1079: (R)-1,1,1-trifluoropropan-2-yl ((2R,6S,7R,9S,13aS,14aR,16aS,Z)-2-((5-chloro-3-propoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 870.62 (M$^+$+1).

Compound 1080: (R)-1,1,1-trifluoropropan-2-yl ((2R,6S,7R,9R,13aS,14aR,16aS,Z)-2-((5-chloro-3-propoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.04 (br. s., 1H), 9.10 (br. s., 1H), 8.08 (d, J=7.6 Hz, 1H), 7.97 (d, J=8.2 Hz, 1H), 7.87-7.81 (m, 1H), 7.25 (t, J=7.9 Hz, 1H), 6.80-6.76 (m, 1H), 5.83 (br. s., 1H), 5.51 (br. s., 1H), 5.01 (br. s., 1H), 4.57 (d, J=6.1 Hz, 2H), 4.52-4.44 (m, 1H), 4.27 (t, J=6.7 Hz, 2H), 3.96 (dd, J=11.4, 3.2 Hz, 1H), 3.76 (dd, J=10.4, 8.2 Hz, 1H), 2.65 (br. s., 2H), 2.40-2.24 (m, 2H), 1.93-1.78 (m, 5H), 1.70 (br. s., 1H), 1.59 (br. s., 1H), 1.50 (br. s., 1H), 1.40 (br. s., 4H), 1.37 (d, J=6.4 Hz, 2H), 1.26 (br. s., 1H), 1.17 (d, J=6.7 Hz, 3H), 1.15-1.10 (m, 1H), 1.03 (t, J=7.3 Hz, 3H), 0.93 (d, J=6.7 Hz, 3H), 0.90 (d, J=6.4 Hz, 4H), 0.75 (d, J=6.7 Hz, 1H). MS: MS m/z 870.62 (M$^+$+1).

Preparation of Compounds 1081 and 1082

Compound 1079

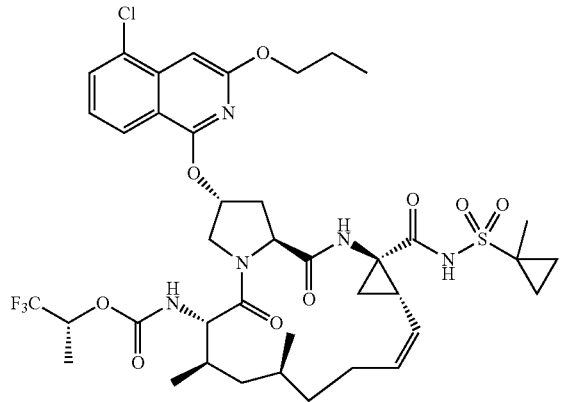

Compound 1080

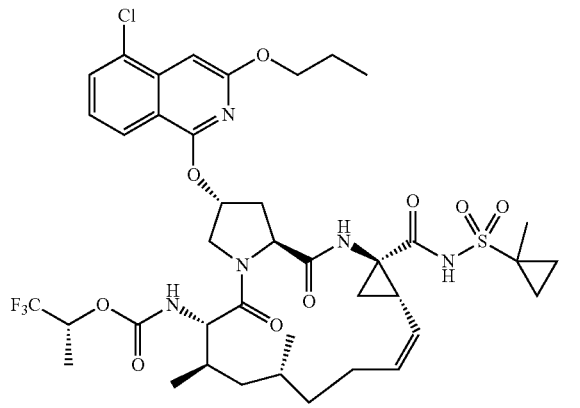

Compound 1081

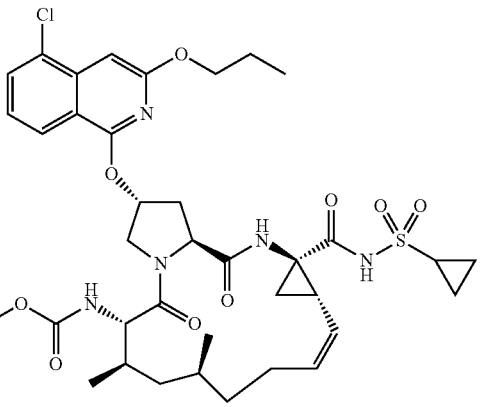

Compound 1082

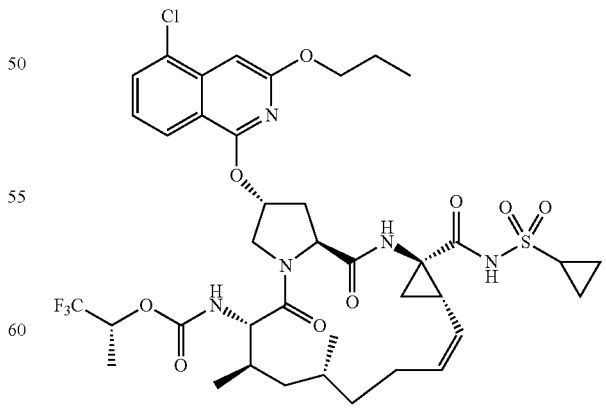

Compounds 1079 and 1080 were prepared using the intermediates described herein and by following the general procedure described for the synthesis of Compound 3117.

Compounds 1081 and 1082 were prepared using the intermediates described herein and by following the general procedure described for the synthesis of Compound 3117.

Compound 1081: (R)-1,1,1-trifluoropropan-2-yl ((2R,6S,7R,9S,13aS,14aR,16aS,Z)-2-((5-chloro-3-propoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 856.7 (M$^+$+1).

Compound 1082: (R)-1,1,1-trifluoropropan-2-yl ((2R,6S,7R,9R,13aS,14aR,16aS,Z)-2-((5-chloro-3-propoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.18 (s, 1H), 8.98 (br. s., 1H), 8.08 (d, J=7.9 Hz, 1H), 8.00-7.95 (m, 1H), 7.86-7.81 (m, 1H), 7.25 (t, J=7.8 Hz, 1H), 6.80-6.76 (m, 1H), 5.82 (br. s., 1H), 5.52 (br. s., 1H), 5.07 (t, J=9.0 Hz, 1H), 4.64-4.52 (m, 2H), 4.52-4.44 (m, 1H), 4.27 (t, J=6.6 Hz, 2H), 3.97-3.92 (m, 1H), 3.76 (dd, J=10.7, 7.9 Hz, 1H), 2.92 (br. s., 1H), 2.66 (d, J=6.4 Hz, 2H), 2.40-2.23 (m, 2H), 1.97-1.76 (m, 5H), 1.70 (br. s., 1H), 1.63-1.53 (m, 2H), 1.45 (br. s., 1H), 1.37 (br. s., 1H), 1.18 (d, J=6.7 Hz, 3H), 1.13 (br. s., 3H), 1.04 (t, J=7.5 Hz, 4H), 0.94 (d, J=7.0 Hz, 3H), 0.90 (d, J=6.4 Hz, 3H), 0.80-0.72 (m, 1H). MS: MS m/z 856.7 (M$^+$+1).

Preparation of Compounds 1083 and 1084

Compound 1083: 1,1,1-trifluoro-2-methylpropan-2-yl ((2R,6S,7R,9S,13aS,14aR,16aS,Z)-2-((5-chloro-3-propoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 870.67 (M$^+$+1).

Compound 1084: 1,1,1-trifluoro-2-methylpropan-2-yl ((2R,6S,7R,9R,13aS,14aR,16aS,Z)-2-((5-chloro-3-propoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.20 (br. s., 1H), 9.03 (br. s., 1H), 8.00 (d, J=8.5 Hz, 1H), 7.83 (d, J=7.6 Hz, 2H), 7.31 (t, J=7.9 Hz, 1H), 6.79-6.76 (m, 1H), 5.80 (br. s., 1H), 5.53 (br. s., 1H), 5.06 (br. s., 1H), 4.61 (d, J=11.6 Hz, 1H), 4.54-4.48 (m, 1H), 4.33-4.22 (m, 2H), 3.95-3.89 (m, 1H), 3.67 (dd, J=10.7, 7.9 Hz, 1H), 2.91 (d, J=8.2 Hz, 1H), 2.66 (br. s., 2H), 2.39-2.25 (m, 2H), 1.91 (d, J=12.2 Hz, 1H), 1.87-1.78 (m, 3H), 1.76-1.67 (m, 1H), 1.61 (br. s., 1H), 1.56 (br. s., 1H), 1.42 (br. s., 1H), 1.37 (br. s., 1H), 1.32 (s, 3H), 1.13 (br. s., 3H), 1.05-1.01 (m, 6H), 0.98 (br. s., 2H), 0.94 (d, J=6.7 Hz, 3H), 0.89 (d, J=6.4 Hz, 3H), 0.74 (t, J=12.1 Hz, 1H). MS: MS m/z 870.67 (M$^+$+1).

Preparation of Compounds 1085 and 1086

Compound 1083

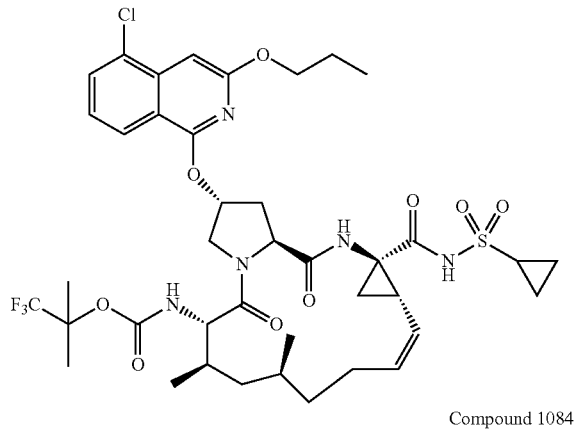

Compound 1085

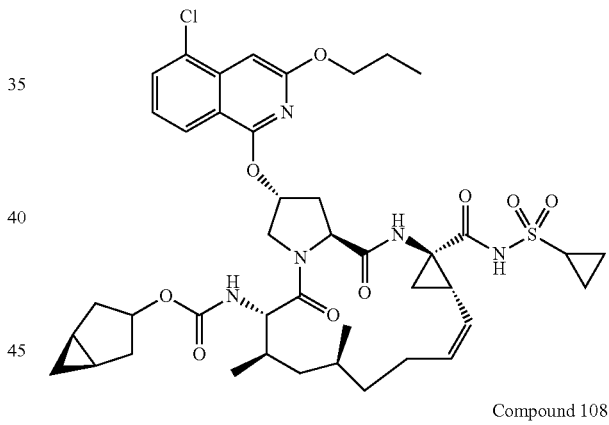

Compound 1084

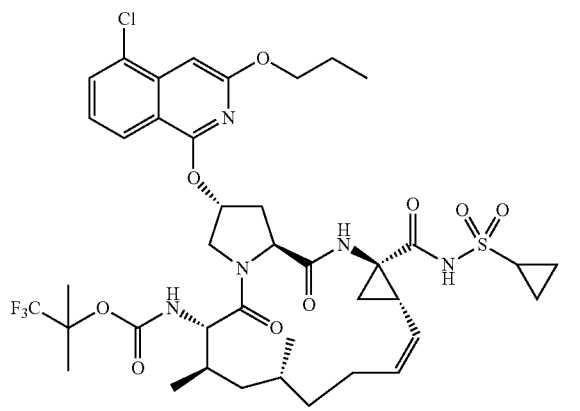

Compound 1086

Compounds 1083 and 1084 were prepared using the intermediates described herein and by following the general procedure described for the synthesis of Compound 3117.

Compounds 1085 and 1086 were prepared using the intermediates described herein and by following the general procedure described for the synthesis of Compound 3117.

Compound 1085: (1S,5S)-bicyclo[3.1.0]hexan-3-yl ((2R,6S,7R,9S,13aS,14aR,16aS,Z)-2-((5-chloro-3-propoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 840.8 (M$^+$+1).

Compound 1086: (1S,5S)-bicyclo[3.1.0]hexan-3-yl ((2R,6S,7R,9R,13aS,14aR,16aS,Z)-2-((5-chloro-3-propoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 8.01 (d, J=8.2 Hz, 1H), 7.84 (d, J=7.6 Hz, 1H), 7.39-7.29 (m, 2H), 6.77 (s, 1H), 5.80 (br. s., 1H), 5.41 (br. s., 1H), 4.54 (t, J=6.9 Hz, 1H), 4.48 (d, J=9.8 Hz, 1H), 4.42 (br. s., 1H), 4.28 (t, J=6.6 Hz, 2H), 3.97-3.91 (m, 1H), 3.77-3.71 (m, 1H), 2.56 (br. s., 2H), 2.39-2.30 (m, 2H), 2.21 (br. s., 2H), 1.97-1.87 (m, 2H), 1.82 (dq, J=14.1, 7.0 Hz, 4H), 1.78-1.70 (m, 2H), 1.54 (d, J=14.0 Hz, 2H), 1.50 (br. s., 1H), 1.38 (br. s., 2H), 1.30 (br. s., 2H), 1.24 (d, J=14.0 Hz, 2H), 1.21-1.13 (m, 2H), 1.13-1.07 (m, 2H), 1.04 (t, J=7.3 Hz, 4H), 0.92 (d, J=6.7 Hz, 3H), 0.85 (d, J=6.4 Hz, 3H), 0.67 (br. s., 1H), 0.35-0.28 (m, 2H). MS: MS m/z 840.8 (M$^+$+1).

Compound 1087: (1S,5S)-bicyclo[3.1.0]hexan-3-yl ((2R,6S,7R,9S,13aS,14aR,16aS,Z)-2-((5-chloro-3-propoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 854.72 (M$^+$+1).

Compound 1088: (1S,5S)-bicyclo[3.1.0]hexan-3-yl ((2R,6S,7R,9R,13aS,14aR,16aS,Z)-2-((5-chloro-3-propoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.06 (br. s., 1H), 9.08 (br. s., 1H), 8.01 (d, J=8.2 Hz, 1H), 7.85 (d, J=7.3 Hz, 1H), 7.43-7.37 (m, 1H), 7.34-7.29 (m, 1H), 6.77 (s, 1H), 5.83 (br. s., 1H), 5.51 (br. s., 1H), 4.58-4.45 (m, 3H), 4.27 (t, J=6.6 Hz, 2H), 3.98-3.93 (m, 1H), 3.75-3.70 (m, 1H), 2.65 (br. s., 1H), 2.39-2.24 (m, 2H), 1.97-1.88 (m, 2H), 1.82 (dq, J=14.2, 7.0 Hz, 3H), 1.78-1.69 (m, 1H), 1.63 (br. s., 2H), 1.55 (d, J=14.3 Hz, 1H), 1.52-1.43 (m, 3H), 1.40 (br. s., 4H), 1.37-1.27 (m, 3H), 1.24 (d, J=14.3 Hz, 2H), 1.21-1.16 (m, 1H), 1.16-1.06 (m, 2H), 1.04 (t, J=7.3 Hz, 3H), 0.92 (d, J=6.7 Hz, 3H), 0.90-0.88 (m, 1H), 0.86 (d, J=6.4 Hz, 3H), 0.73 (br. s., 1H), 0.35-0.29 (m, 2H). MS: MS m/z 854.72 (M$^+$+1).

Preparation of Compounds 1087 and 1088

Preparation of Compounds 1089 and 1090

Compound 1087

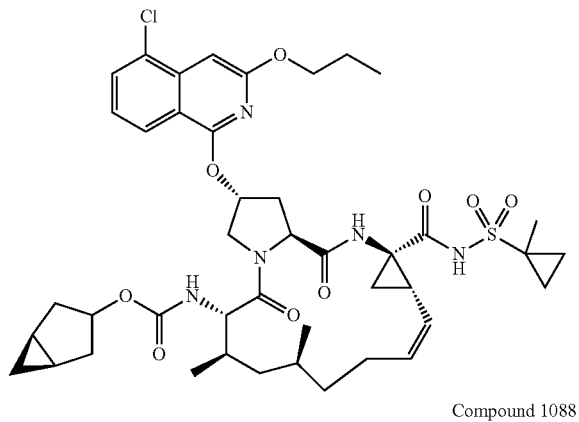

Compound 1089

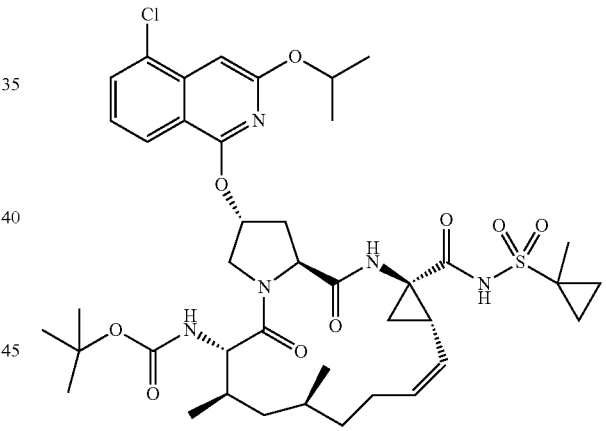

Compound 1088

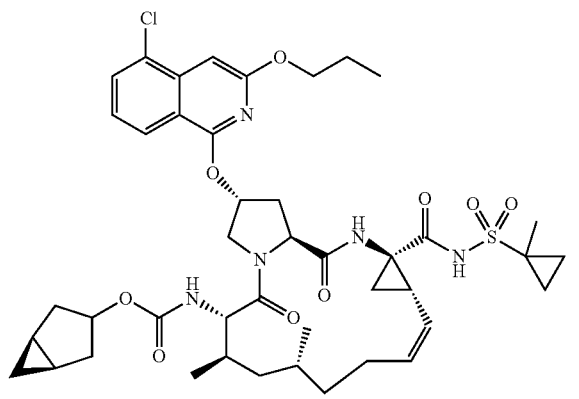

Compound 1090

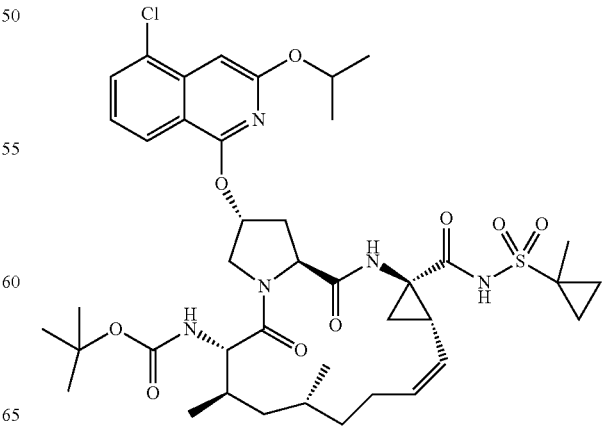

Compounds 1087 and 1088 were prepared using the intermediates described herein and by following the general procedure described for the synthesis of Compound 3117.

Compounds 1089 and 1090 were prepared using the intermediates described herein and by following the general procedure described for the synthesis of Compound 3117.

Compound 1089: tert-butyl ((2R,6S,7R,9S,13aS,14aR,16aS,Z)-2-((5-chloro-3-isopropoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 830.8 (M$^+$+1).

Compound 1090: tert-butyl ((2R,6S,7R,9R,13aS,14aR,16aS,Z)-2-((5-chloro-3-isopropoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.07 (br. s., 1H), 9.10 (br. s., 1H), 8.02 (d, J=8.2 Hz, 1H), 7.80 (d, J=7.0 Hz, 1H), 7.26 (t, J=7.9 Hz, 1H), 7.17 (br. s., 1H), 6.77-6.72 (m, 1H), 5.78 (br. s., 1H), 5.48 (br. s., 1H), 5.23 (dt, J=12.2, 6.1 Hz, 1H), 4.66 (br. s., 1H), 4.48 (br. s., 1H), 3.96-3.90 (m, 1H), 3.69 (dd, J=10.2, 8.7 Hz, 1H), 2.65 (br. s., 1H), 2.61 (br. s., 1H), 2.39-2.28 (m, 2H), 1.89 (br. s., 1H), 1.81 (d, J=5.2 Hz, 1H), 1.73 (br. s., 1H), 1.56 (br. s., 1H), 1.51 (br. s., 1H), 1.47-1.41 (m, 1H), 1.38 (dd, J=6.1, 2.4 Hz, 10H), 1.35-1.29 (m, 1H), 1.23 (d, J=17.7 Hz, 3H), 1.08 (s, 9H), 1.06-1.02 (m, 1H), 0.93 (d, J=6.7 Hz, 3H), 0.88 (d, J=6.4 Hz, 3H), 0.70 (br. s., 1H). MS: MS m/z 830.8 (M$^+$+1).

Preparation of Compounds 1091 and 1092

Compounds 1091 and 1092 were prepared using the intermediates described herein and by following the general procedure described for the synthesis of Compound 3117.

Compound 1091: tert-butyl ((2R,6S,7R,9S,13aS,14aR,16aS,Z)-2-((5-chloro-3-isopropoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 816.74 (M$^+$+1).

Compound 1092: tert-butyl ((2R,6S,7R,9R,13aS,14aR,16aS,Z)-2-((5-chloro-3-isopropoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.23 (br. s., 1H), 8.99 (br. s., 1H), 8.02 (d, J=8.2 Hz, 1H), 7.81 (d, J=7.3 Hz, 1H), 7.26 (t, J=7.9 Hz, 1H), 7.18 (br. s., 1H), 6.73 (s, 1H), 5.78 (br. s., 1H), 5.51 (br. s., 1H), 5.23 (dt, J=12.0, 6.1 Hz, 1H), 5.05 (br. s., 1H), 4.66 (br. s., 1H), 4.46 (br. s., 1H), 3.94-3.89 (m, 1H), 3.71-3.66 (m, 1H), 2.65 (br. s., 2H), 2.39-2.29 (m, 2H), 1.91 (br. s., 1H), 1.81 (d, J=5.5 Hz, 1H), 1.70 (br. s., 1H), 1.59 (br. s., 1H), 1.51 (d, J=6.1 Hz, 1H), 1.38 (d, J=6.1 Hz, 7H), 1.36-1.30 (m, 1H), 1.23 (d, J=18.9 Hz, 1H), 1.20-1.12 (m, 2H), 1.09 (s, 9H), 1.04 (br. s., 3H), 0.93 (d, J=6.7 Hz, 3H), 0.88 (d, J=6.4 Hz, 3H), 0.71 (br. s., 1H). MS: MS m/z 816.74 (M$^+$+1).

Preparation of Compounds 1093 and 1094

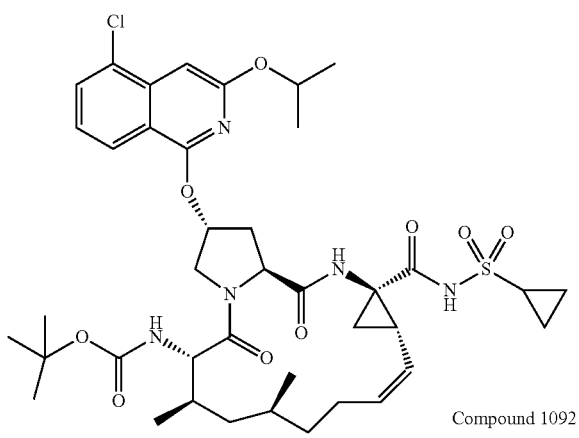

Compound 1091

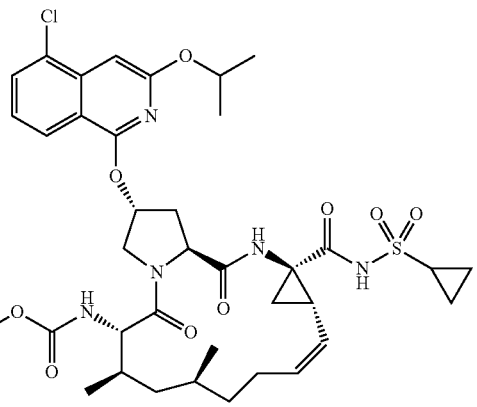

Compound 1093

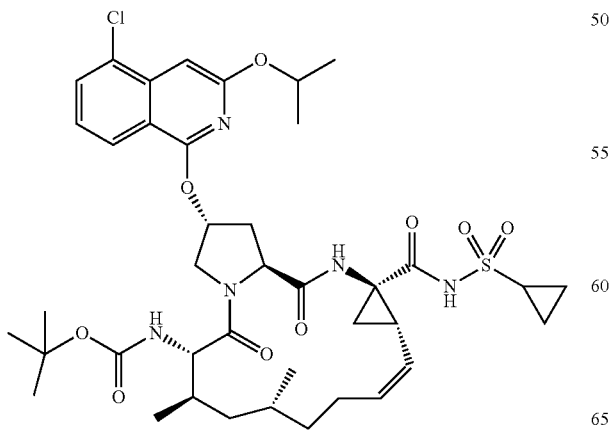

Compound 1092

Compound 1094

Compounds 1093 and 1094 were prepared using the intermediates described herein and by following the general procedure described for the synthesis of Compound 3117.

Compound 1093: 1,1,1-trifluoro-2-methylpropan-2-yl ((2R,6S,7R,9S,13aS,14aR,16aS,Z)-2-((5-chloro-3-isopropoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 870.46 (M$^+$+1).

Compound 1094: 1,1,1-trifluoro-2-methylpropan-2-yl ((2R,6S,7R,9R,13aS,14aR,16aS,Z)-2-((5-chloro-3-isopropoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.21 (br. s., 1H), 9.03 (br. s., 1H), 7.99 (d, J=8.2 Hz, 1H), 7.87-7.80 (m, 2H), 7.30 (t, J=7.9 Hz, 1H), 6.74 (s, 1H), 5.80 (br. s., 1H), 5.53 (br. s., 1H), 5.23 (dt, J=12.2, 6.1 Hz, 1H), 5.06 (br. s., 1H), 4.62 (d, J=11.3 Hz, 1H), 4.52 (t, J=8.4 Hz, 1H), 3.95-3.90 (m, 1H), 3.67 (dd, J=10.7, 7.9 Hz, 1H), 2.96-2.88 (m, 1H), 2.65 (br. s., 1H), 2.39-2.24 (m, 2H), 1.95-1.79 (m, 2H), 1.71 (br. s., 1H), 1.62 (br. s., 1H), 1.57 (br. s., 1H), 1.43 (br. s., 1H), 1.38 (dd, J=6.1, 2.4 Hz, 7H), 1.33 (s, 3H), 1.25 (br. s., 1H), 1.20 (br. s., 1H), 1.14 (br. s., 2H), 1.03 (br. s., 1H), 1.01 (s, 4H), 0.94 (d, J=7.0 Hz, 3H), 0.89 (d, J=6.4 Hz, 3H), 0.74 (t, J=12.1 Hz, 1H). MS: MS m/z 870.46 (M$^+$+1).

Preparation of Compounds 1095 and 1096

Compounds 1095 and 1096 were prepared using the intermediates described herein and by following the general procedure described for the synthesis of Compound 3117.

Compound 1095: 1,1,1-trifluoro-2-methylpropan-2-yl ((2R,6S,7R,9S,13aS,14aR,16aS,Z)-2-((5-chloro-3-(2,2-difluoroethoxy)isoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 892.43 (M$^+$+1).

Compound 1096: 1,1,1-trifluoro-2-methylpropan-2-yl ((2R,6S,7R,9R,13aS,14aR,16aS,Z)-2-((5-chloro-3-(2,2-difluoroethoxy)isoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.21 (br. s., 1H), 9.05 (br. s., 1H), 8.03 (d, J=8.2 Hz, 1H), 7.88 (d, J=7.6 Hz, 1H), 7.84 (d, J=7.6 Hz, 1H), 7.37 (t, J=7.9 Hz, 1H), 6.89 (s, 1H), 6.63-6.36 (m, 1H), 5.85 (br. s., 1H), 5.53 (br. s., 1H), 5.05 (br. s., 1H), 4.73-4.60 (m, 3H), 4.55-4.49 (m, 1H), 3.94-3.89 (m, 1H), 3.68 (dd, J=10.7, 7.9 Hz, 1H), 2.91 (d, J=8.9 Hz, 1H), 2.67 (br. s., 2H), 2.40-2.25 (m, 2H), 1.95-1.79 (m, 2H), 1.70 (br. s., 1H), 1.62 (br. s., 1H), 1.57 (br. s., 1H), 1.44 (br. s., 1H), 1.38 (d, J=13.4 Hz, 1H), 1.31 (s, 3H), 1.14 (br. s., 3H), 1.01 (s, 3H), 0.99-0.96 (m, 2H), 0.94 (d, J=7.0 Hz, 3H), 0.89 (d, J=6.4 Hz, 3H), 0.75 (t, J=12.1 Hz, 1H). MS: MS m/z 892.43 (M$^+$+1).

Preparation of Compounds 1097 and 1098

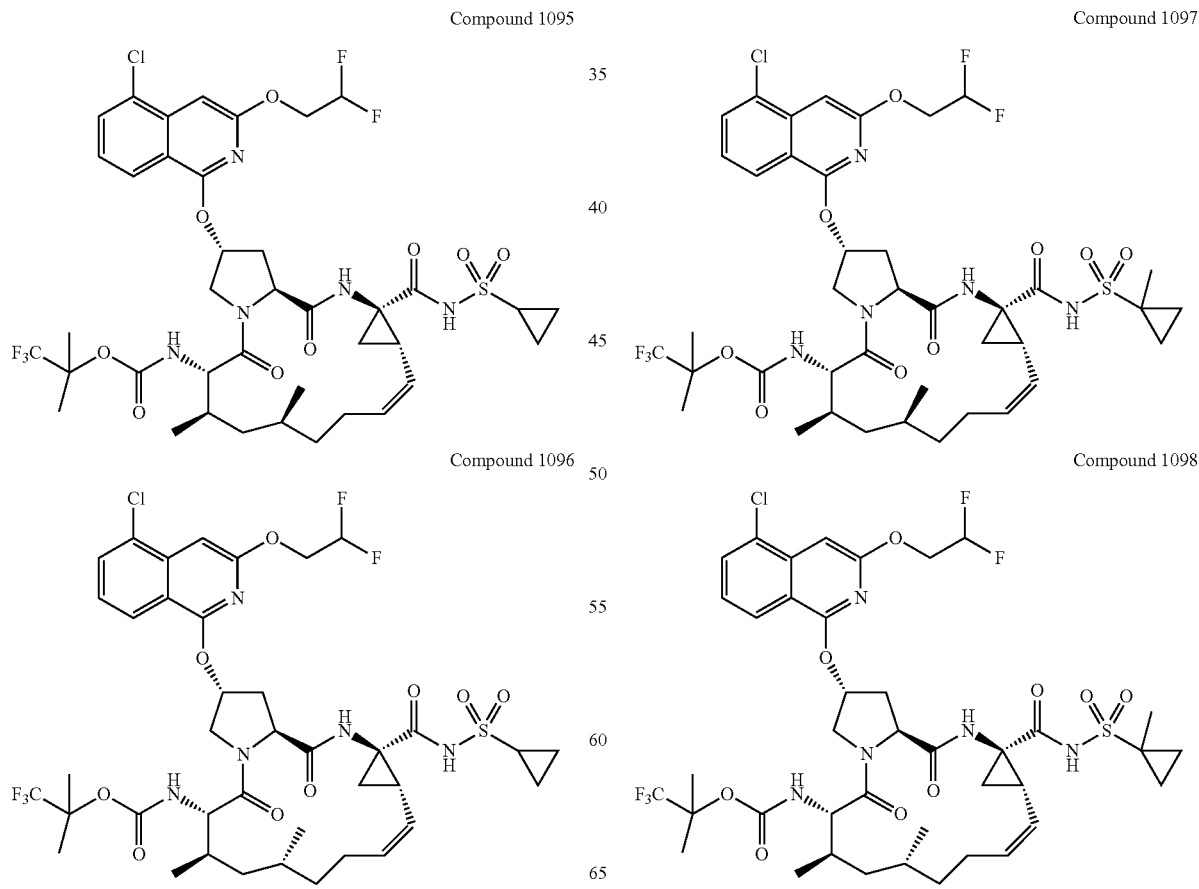

Compound 1095

Compound 1096

Compound 1097

Compound 1098

Compounds 1097 and 1098 were prepared using the intermediates described herein and by following the general procedure described for the synthesis of Compound 3117.

Compound 1097: 1,1,1-trifluoro-2-methylpropan-2-yl ((2R,6S,7R,9S,13aS,14aR,16aS,Z)-2-((5-chloro-3-(2,2-difluoroethoxy)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 904.5 (M$^+$−1).

Compound 1098: 1,1,1-trifluoro-2-methylpropan-2-yl ((2R,6S,7R,9R,13aS,14aR,16aS,Z)-2-((5-chloro-3-(2,2-difluoroethoxy)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.06 (br. s., 1H), 9.19 (br. s., 1H), 8.07-8.01 (m, 1H), 7.94-7.82 (m, 2H), 7.37 (t, J=7.9 Hz, 1H), 6.89 (s, 1H), 6.65-6.29 (m, 1H), 5.86 (br. s., 1H), 5.54 (d, J=6.1 Hz, 1H), 4.98 (d, J=8.9 Hz, 1H), 4.77-4.61 (m, 3H), 4.61-4.52 (m, 1H), 3.97-3.91 (m, 1H), 3.69 (dd, J=10.7, 7.9 Hz, 1H), 2.73-2.62 (m, 2H), 2.39-2.27 (m, 2H), 1.94-1.79 (m, 2H), 1.74-1.66 (m, 1H), 1.63 (br. s., 1H), 1.54 (br. s., 1H), 1.50 (br. s., 2H), 1.44-1.40 (m, 4H), 1.35 (d, J=12.8 Hz, 1H), 1.30 (s, 4H), 1.14 (d, J=13.4 Hz, 1H), 1.02-0.97 (m, 3H), 0.93 (d, J=7.0 Hz, 3H), 0.89 (d, J=6.1 Hz, 4H), 0.76 (t, J=12.2 Hz, 1H). MS: MS m/z 904.5 (M$^+$−1).

Preparation of Compounds 1099 and 1100

Compounds 1099 and 1100 were prepared using the intermediates described herein and by following the general procedure described for the synthesis of Compound 3117.

Compound 1099: (R)-1,1,1-trifluoropropan-2-yl ((2R,6S,7R,9S,13aS,14aR,16aS,Z)-2-((5-chloro-3-(2,2-difluoroethoxy)isoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 878.37 (M$^+$+1).

Compound 1100: (R)-1,1,1-trifluoropropan-2-yl ((2R,6S,7R,9R,13aS,14aR,16aS,Z)-2-((5-chloro-3-(2,2-difluoroethoxy)isoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.20 (s, 1H), 9.01 (br. s., 1H), 8.09 (d, J=7.9 Hz, 1H), 8.04-7.96 (m, 1H), 7.90-7.85 (m, 1H), 7.31 (t, J=7.9 Hz, 1H), 6.89 (s, 1H), 6.63-6.34 (m, 1H), 5.86 (br. s., 1H), 5.54 (d, J=6.4 Hz, 1H), 5.06 (t, J=9.6 Hz, 1H), 4.69 (tt, J=15.0, 3.7 Hz, 2H), 4.61 (d, J=11.9 Hz, 1H), 4.58-4.52 (m, 1H), 4.52-4.46 (m, 1H), 3.96-3.91 (m, 1H), 3.76 (dd, J=10.5, 8.1 Hz, 1H), 2.96-2.89 (m, 1H), 2.66 (d, J=8.9 Hz, 2H), 2.39-2.31 (m, 1H), 2.27 (d, J=11.0 Hz, 1H), 1.98-1.82 (m, 2H), 1.68 (br. s., 1H), 1.61 (br. s., 1H), 1.56 (br. s., 1H), 1.45 (br. s., 1H), 1.37 (br. s., 1H), 1.17 (d, J=6.7 Hz, 3H), 1.13 (br. s., 3H), 1.06-0.95 (m, 2H), 0.94 (d, J=6.7 Hz, 3H), 0.90 (d, J=6.4 Hz, 3H), 0.76 (t, J=12.1 Hz, 1H). MS: MS m/z 878.37 (M$^+$+1).

Preparation of Compounds 1101 and 1102

Compound 1099

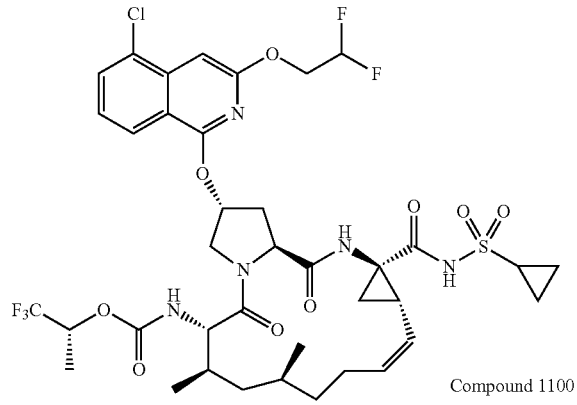

Compound 1100

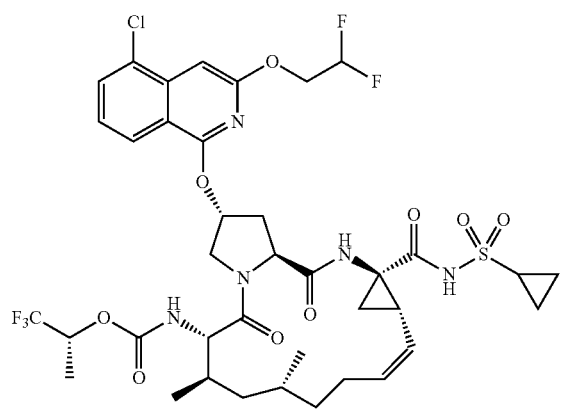

Compound 1101

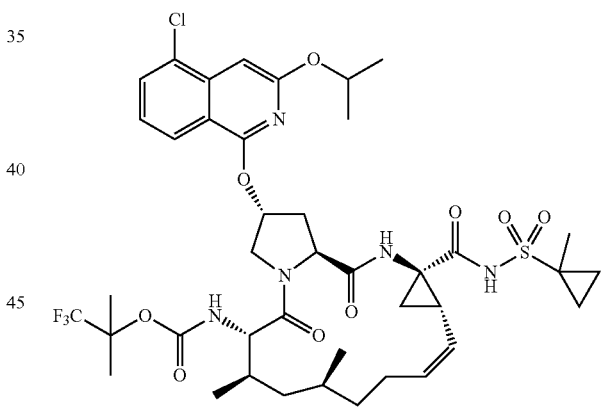

Compound 1102

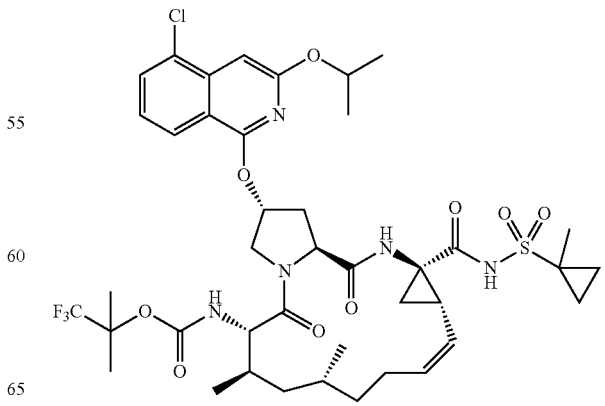

Compounds 1101 and 1102 were prepared using the intermediates described herein and by following the general procedure described for the synthesis of Compound 3117.

Compound 1101: 1,1,1-trifluoro-2-methylpropan-2-yl ((2R,6S,7R,9S,13aS,14aR,16aS,Z)-2-((5-chloro-3-isopropoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 884.5 (M$^+$+1).

Compound 1102: 1,1,1-trifluoro-2-methylpropan-2-yl ((2R,6S,7R,9R,13aS,14aR,16aS,Z)-2-((5-chloro-3-isopropoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.07 (br. s., 1H), 9.15 (br. s., 1H), 8.02-7.96 (m, 1H), 7.82 (d, J=7.0 Hz, 2H), 7.29 (t, J=7.9 Hz, 1H), 6.74 (s, 1H), 5.80 (br. s., 1H), 5.52 (br. s., 1H), 5.23 (dt, J=12.1, 5.9 Hz, 1H), 4.99 (br. s., 1H), 4.61 (br. s., 1H), 4.53 (br. s., 1H), 3.96-3.91 (m, 1H), 3.67 (dd, J=10.4, 7.9 Hz, 1H), 2.65 (br. s., 1H), 2.39-2.25 (m, 2H), 1.92 (s, 1H), 1.84 (br. s., 2H), 1.71 (br. s., 1H), 1.60 (br. s., 1H), 1.50 (br. s., 2H), 1.38 (d, J=6.1 Hz, 10H), 1.33 (br. s., 4H), 1.25 (br. s., 2H), 1.20 (br. s., 2H), 1.00 (br. s., 3H), 0.93 (d, J=6.7 Hz, 3H), 0.88 (d, J=6.4 Hz, 3H), 0.73 (br. s., 1H). MS: MS m/z 884.5 (M$^+$+1).

Preparation of Compounds 1103 and 1104

Compounds 1103 and 1104 were prepared using the intermediates described herein and by following the general procedure described for the synthesis of Compound 3117.

Compound 1103: 3,3-difluoro-2-methylbutan-2-yl ((2R,6S,7R,9S,13aS,14aR,16aS,Z)-2-((5-chloro-3-isopropoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 880.6 (M$^+$+1).

Compound 1104: 3,3-difluoro-2-methylbutan-2-yl ((2R,6S,7R,9R,13aS,14aR,16aS,Z)-2-((5-chloro-3-isopropoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.07 (br. s., 1H), 9.13 (br. s., 1H), 8.00 (d, J=8.2 Hz, 1H), 7.82 (d, J=7.3 Hz, 1H), 7.62 (d, J=7.6 Hz, 1H), 7.28 (t, J=7.8 Hz, 1H), 6.74 (s, 1H), 5.80 (br. s., 1H), 5.53 (br. s., 1H), 5.23 (dt, J=12.2, 6.1 Hz, 1H), 4.98 (br. s., 1H), 4.64 (d, J=10.7 Hz, 1H), 4.54 (br. s., 1H), 3.95 (dd, J=11.6, 3.1 Hz, 1H), 3.68 (dd, J=10.7, 8.2 Hz, 1H), 2.65 (br. s., 1H), 2.39-2.28 (m, 2H), 1.92 (d, J=8.9 Hz, 1H), 1.83 (d, J=6.4 Hz, 1H), 1.68 (br. s., 1H), 1.62 (br. s., 1H), 1.59 (s, 1H), 1.56 (s, 2H), 1.52 (s, 2H), 1.45 (d, J=7.3 Hz, 2H), 1.41 (br. s., 4H), 1.40-1.35 (m, 9H), 1.26 (d, J=14.0 Hz, 3H), 1.23 (s, 3H), 1.15 (d, J=6.7 Hz, 1H), 0.94 (d, J=6.7 Hz, 3H), 0.92-0.88 (m, 3H), 0.76 (t, J=11.7 Hz, 1H). MS: MS m/z 880.6 (M$^+$+1).

Preparation of Compounds 1105 and 1106

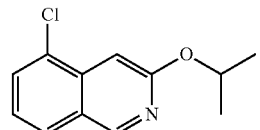

Compound 1103

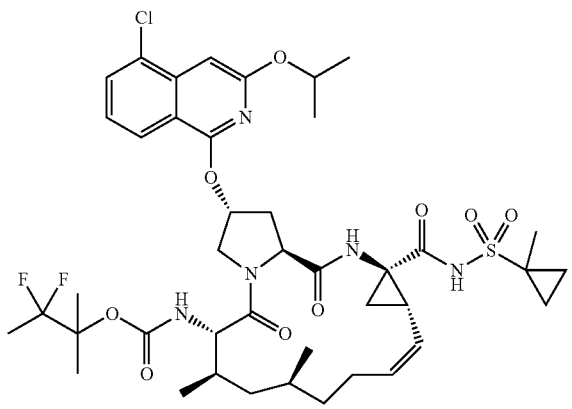

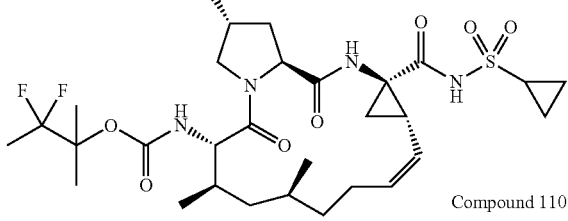

Compound 1105

Compound 1104

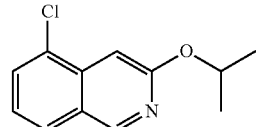

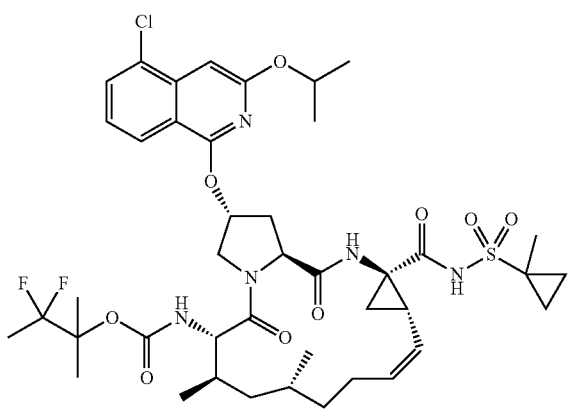

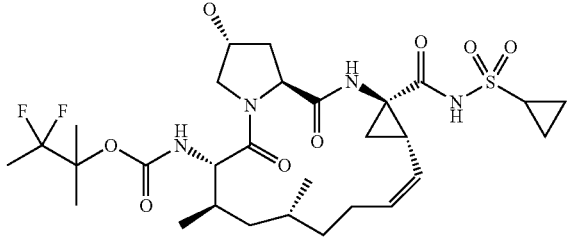

Compound 1106

Compounds 1105 and 1106 were prepared using the intermediates described herein and by following the general procedure described for the synthesis of Compound 3117.

Compound 1105: 3,3-difluoro-2-methylbutan-2-yl ((2R,6S,7R,9S,13aS,14aR,16aS,Z)-2-((5-chloro-3-isopropoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 866.6 (M$^+$+1).

Compound 1106: 3,3-difluoro-2-methylbutan-2-yl ((2R,6S,7R,9R,13aS,14aR,16aS,Z)-2-((5-chloro-3-isopropoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.22 (br. s., 1H), 9.01 (br. s., 1H), 8.02-7.96 (m, 1H), 7.82 (d, J=7.3 Hz, 1H), 7.61 (d, J=7.3 Hz, 1H), 7.28 (t, J=7.9 Hz, 1H), 6.74 (s, 1H), 5.79 (br. s., 1H), 5.52 (br. s., 1H), 5.23 (dt, J=12.1, 6.0 Hz, 1H), 5.06 (br. s., 1H), 4.63 (d, J=9.5 Hz, 1H), 4.50 (br. s., 1H), 3.95-3.90 (m, 1H), 3.68 (dd, J=10.7, 8.2 Hz, 1H), 2.65 (br. s., 2H), 2.40-2.22 (m, 2H), 1.96-1.87 (m, 1H), 1.82 (d, J=7.0 Hz, 1H), 1.71 (br. s., 1H), 1.56 (t, J=19.5 Hz, 4H), 1.49 (br. s., 1H), 1.43 (br. s., 1H), 1.38 (dd, J=6.1, 1.2 Hz, 7H), 1.24 (s, 3H), 1.13 (br. s., 3H), 1.07-0.96 (m, 2H), 0.96-0.91 (m, 6H), 0.89 (d, J=6.4 Hz, 4H), 0.74 (br. s., 1H). MS: MS m/z 866.6 (M$^+$+1).

Preparation of Compounds 1107 and 1108

Compound 1107: (R)-1,1,1-trifluoropropan-2-yl ((2R,6S,7R,9S,13aS,14aR,16aS,Z)-2-((5-chloro-3-(2,2-difluoroethoxy)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 892.5 (M$^+$+1).

Compound 1108: (R)-1,1,1-trifluoropropan-2-yl ((2R,6S,7R,9R,13aS,14aR,16aS,Z)-2-((5-chloro-3-(2,2-difluoroethoxy)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.06 (br. s., 1H), 9.13 (br. s., 1H), 8.09 (d, J=7.9 Hz, 1H), 8.03-7.98 (m, 1H), 7.90-7.85 (m, 1H), 7.31 (t, J=7.9 Hz, 1H), 6.89 (s, 1H), 6.65-6.27 (m, 1H), 5.87 (br. s., 1H), 5.53 (br. s., 1H), 4.98 (br. s., 1H), 4.73-4.64 (m, 2H), 4.64-4.58 (m, 1H), 4.53 (d, J=7.0 Hz, 2H), 3.96 (d, J=8.5 Hz, 1H), 3.76 (dd, J=10.7, 7.9 Hz, 1H), 2.67 (br. s., 2H), 2.39-2.27 (m, 2H), 1.92 (s, 1H), 1.87 (d, J=7.3 Hz, 1H), 1.67 (br. s., 1H), 1.62 (br. s., 1H), 1.52 (br. s., 1H), 1.48-1.43 (m, 2H), 1.41 (br. s., 3H), 1.34 (d, J=16.8 Hz, 3H), 1.28 (br. s., 1H), 1.25 (s, 1H), 1.16 (d, J=6.4 Hz, 3H), 0.93 (d, J=7.0 Hz, 3H), 0.91-0.89 (m, J=6.1 Hz, 3H), 0.79 (d, J=11.9 Hz, 1H). MS: MS m/z 892.5 (M$^+$+1).

Preparation of Compounds 1109 and 1110

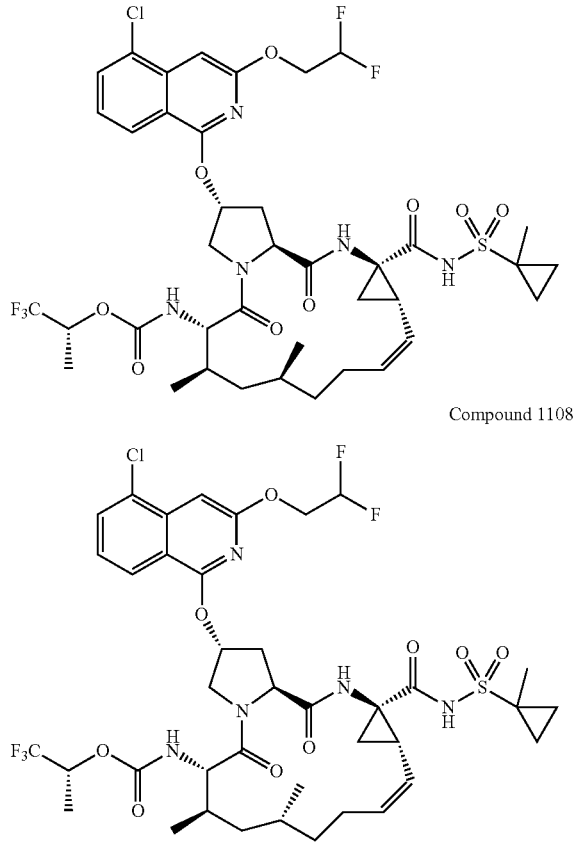

Compound 1107

Compound 1108

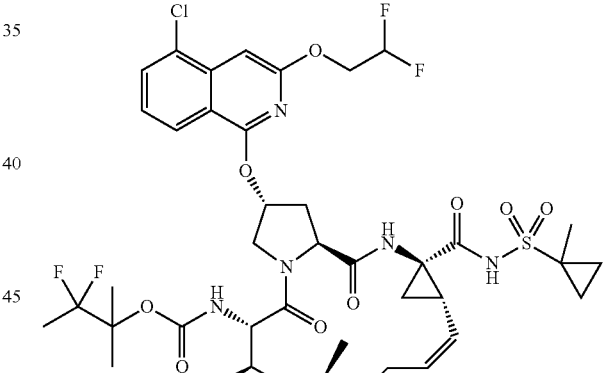

Compound 1109

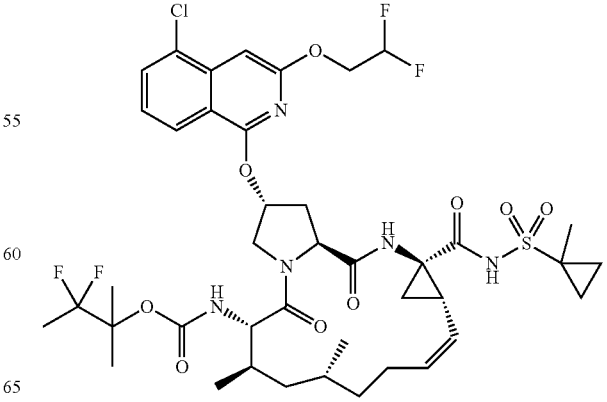

Compound 1110

Compounds 1107 and 1108 were prepared using the intermediates described herein and by following the general procedure described for the synthesis of Compound 3117.

Compounds 1109 and 1110 were prepared using the intermediates described herein and by following the general procedure described for the synthesis of Compound 3117.

Compound 1109: 3,3-difluoro-2-methylbutan-2-yl ((2R,6S,7R,9S,13aS,14aR,16aS,Z)-2-((5-chloro-3-(2,2-difluoroethoxy)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 903.4 ($M^+$+1).

Compound 1110: 3,3-difluoro-2-methylbutan-2-yl ((2R,6S,7R,9R,13aS,14aR,16aS,Z)-2-((5-chloro-3-(2,2-difluoroethoxy)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.06 (br. s., 1H), 9.12 (br. s., 1H), 8.08-8.02 (m, 1H), 7.92-7.85 (m, 1H), 7.60 (d, J=6.4 Hz, 1H), 7.35 (t, J=7.9 Hz, 1H), 6.93-6.87 (m, 1H), 6.49 (t, J=3.5 Hz, 1H), 5.84 (br. s., 1H), 5.47 (br. s., 1H), 4.69 (td, J=14.8, 2.7 Hz, 2H), 4.63 (d, J=10.1 Hz, 1H), 4.51 (br. s., 1H), 3.97-3.90 (m, 1H), 3.70 (dd, J=10.5, 8.4 Hz, 1H), 2.65 (br. s., 1H), 2.40-2.25 (m, 2H), 1.89 (br. s., 1H), 1.81 (d, J=6.4 Hz, 1H), 1.73 (br. s., 1H), 1.56 (t, J=19.5 Hz, 4H), 1.49 (br. s., 2H), 1.39 (br. s., 5H), 1.25 (br. s., 3H), 1.24-1.21 (m, 4H), 1.18-1.13 (m, 1H), 0.93 (d, J=6.7 Hz, 3H), 0.92-0.88 (m, 7H), 0.73 (br. s., 1H). MS: MS m/z 903.4 ($M^+$+1).

Preparation of Compounds 1111 and 1112

Compounds 1111 and 1112 were prepared using the intermediates described herein and by following the general procedure described for the synthesis of Compound 3117.

Compound 1111: 3,3-difluoro-2-methylbutan-2-yl ((2R,6S,7R,9S,13aS,14aR,16aS,Z)-2-((5-chloro-3-(2,2-difluoroethoxy)isoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 888.44 ($M^+$+1).

Compound 1112: 3,3-difluoro-2-methylbutan-2-yl ((2R,6S,7R,9R,13aS,14aR,16aS,Z)-2-((5-chloro-3-(2,2-difluoroethoxy)isoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.22 (br. s., 1H), 9.02 (br. s., 1H), 8.03 (d, J=8.2 Hz, 1H), 7.87 (d, J=7.3 Hz, 1H), 7.62 (d, J=7.9 Hz, 1H), 7.35 (t, J=7.9 Hz, 1H), 6.89 (s, 1H), 6.63-6.34 (m, 1H), 5.84 (br. s., 1H), 5.51 (br. s., 1H), 5.06 (br. s., 1H), 4.69 (td, J=15.0, 3.4 Hz, 2H), 4.63 (br. s., 1H), 4.49 (d, J=8.5 Hz, 1H), 3.95-3.90 (m, 1H), 3.69 (dd, J=10.4, 8.2 Hz, 1H), 2.67 (br. s., 1H), 2.40-2.24 (m, 2H), 1.95-1.87 (m, 1H), 1.81 (d, J=6.4 Hz, 1H), 1.71 (br. s., 1H), 1.65-1.52 (m, J=19.5, 19.5 Hz, 5H), 1.44 (br. s., 1H), 1.35 (d, J=7.3 Hz, 1H), 1.22 (s, 3H), 1.15 (br. s., 2H), 1.09 (br. s., 1H), 1.08-1.03 (m, 1H), 1.02-0.97 (m, 1H), 0.96-0.92 (m, J=6.7 Hz, 4H), 0.92-0.88 (m, 7H), 0.75 (d, J=11.0 Hz, 1H). MS: MS m/z 888.44 ($M^+$+1).

Preparation of Compounds 1113 and 1114

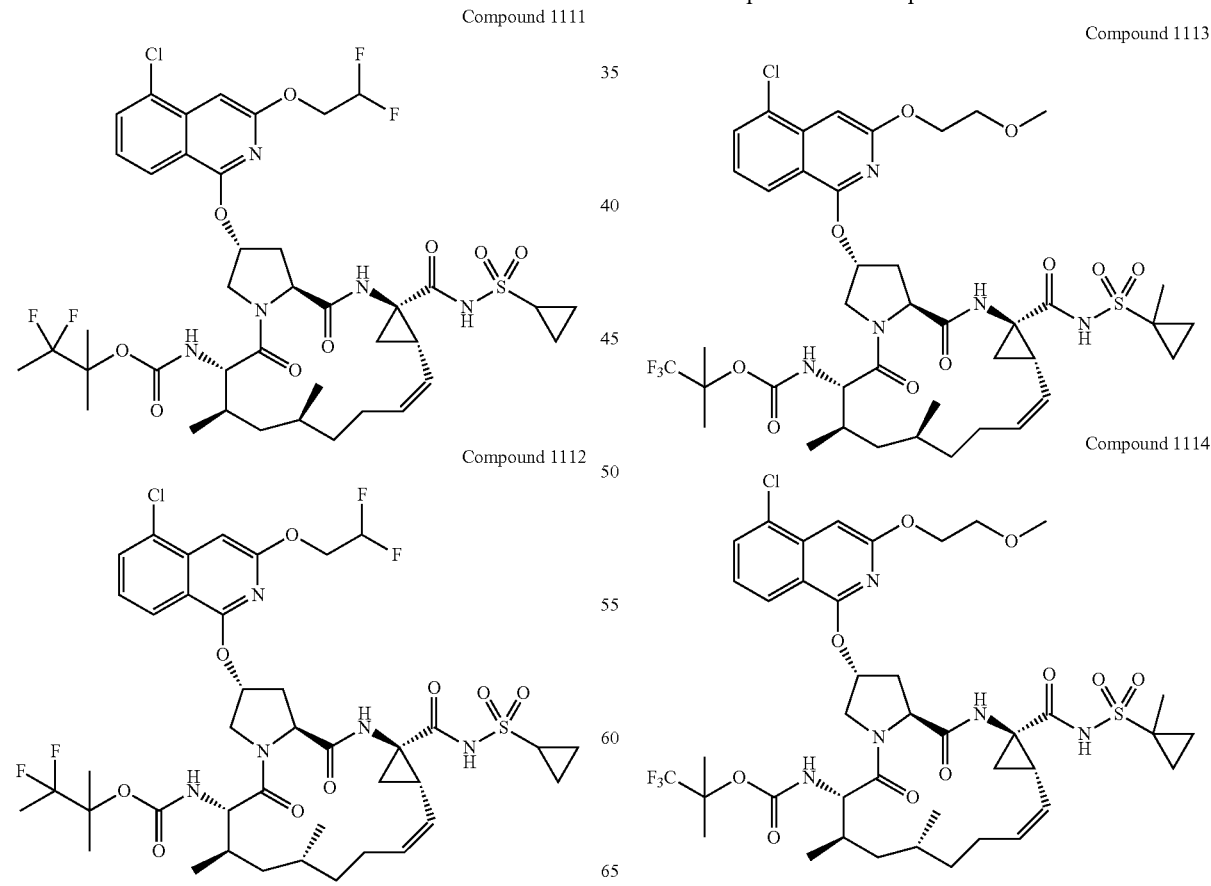

Compound 1111

Compound 1112

Compound 1113

Compound 1114

Compounds 1113 and 1114 were prepared using the intermediates described herein and by following the general procedure described for the synthesis of Compound 3117.

Compound 1113: 1,1,1-trifluoro-2-methylpropan-2-yl ((2R,6S,7R,9S,13aS,14aR,16aS,Z)-2-((5-chloro-3-(2-methoxyethoxyl)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 898.6 (M$^+$−1).

Compound 1114: 1,1,1-trifluoro-2-methylpropan-2-yl ((2R,6S,7R,9R,13aS,14aR,16aS,Z)-2-((5-chloro-3-(2-methoxyethoxyl)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.06 (br. s., 1H), 9.16 (br. s., 1H), 8.03-7.95 (m, 1H), 7.84 (d, J=7.3 Hz, 2H), 7.32 (t, J=7.9 Hz, 1H), 6.79 (s, 1H), 5.81 (br. s., 1H), 5.52 (br. s., 1H), 4.99 (br. s., 1H), 4.62 (d, J=10.7 Hz, 1H), 4.54 (br. s., 1H), 4.50-4.40 (m, 2H), 3.99-3.88 (m, 1H), 3.75 (t, J=4.6 Hz, 2H), 3.67 (dd, J=10.5, 8.1 Hz, 1H), 2.65 (br. s., 1H), 2.39-2.27 (m, 2H), 1.92-1.77 (m, 2H), 1.69 (br. s., 1H), 1.61 (br. s., 1H), 1.50 (br. s., 2H), 1.41 (br. s., 5H), 1.35 (br. s., 2H), 1.30 (s, 4H), 1.25 (br. s., 1H), 1.19 (d, J=18.0 Hz, 2H), 0.98 (s, 3H), 0.93 (d, J=6.7 Hz, 4H), 0.89 (d, J=6.4 Hz, 4H), 0.75 (br. s., 1H). MS: MS m/z 898.6 (M$^+$−1).

Preparation of Compounds 1115 and 1116

Compound 1115: 3,3-difluoro-2-methylbutan-2-yl ((2R,6S,7R,9S,13aS,14aR,16aS,Z)-2-((5-chloro-3-(2-methoxyethoxyl)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 897.5 (M$^+$+1).

Compound 1116: 3,3-difluoro-2-methylbutan-2-yl ((2R,6S,7R,9R,13aS,14aR,16aS,Z)-2-((5-chloro-3-(2-methoxyethoxyl)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.06 (br. s., 1H), 9.14 (br. s., 1H), 8.04-7.96 (m, 1H), 7.84 (d, J=7.3 Hz, 1H), 7.61 (d, J=7.9 Hz, 1H), 7.31 (t, J=7.9 Hz, 1H), 6.79 (s, 1H), 5.81 (br. s., 1H), 5.53 (br. s., 1H), 4.99 (br. s., 1H), 4.64 (d, J=11.6 Hz, 1H), 4.56-4.51 (m, 1H), 4.51-4.40 (m, 2H), 3.99-3.90 (m, 1H), 3.75 (t, J=4.7 Hz, 2H), 3.68 (dd, J=10.7, 8.2 Hz, 1H), 2.69 (br. s., 2H), 2.42-2.27 (m, 2H), 1.94-1.86 (m, 1H), 1.82 (d, J=6.1 Hz, 1H), 1.68 (br. s., 1H), 1.56 (t, J=19.7 Hz, 5H), 1.48-1.45 (m, 1H), 1.41 (br. s., 4H), 1.35 (d, J=11.3 Hz, 2H), 1.31-1.23 (m, 2H), 1.21 (s, 3H), 1.16 (br. s., 2H), 0.93 (d, J=7.0 Hz, 4H), 0.92-0.88 (m, 7H), 0.80-0.72 (m, 1H). MS: MS m/z 897.5 (M$^+$+1).

Preparation of Compounds 1117 and 1118

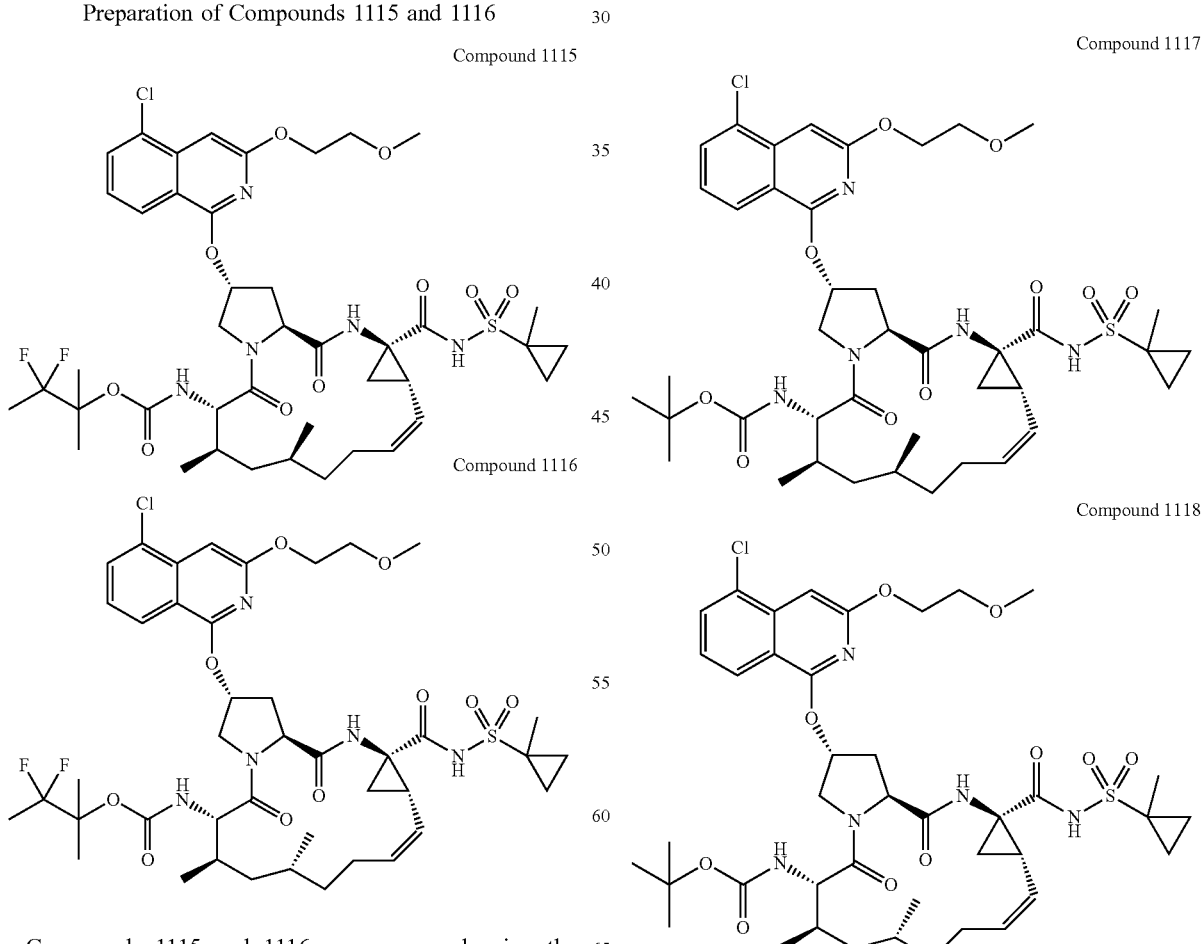

Compound 1115

Compound 1116

Compound 1117

Compound 1118

Compounds 1115 and 1116 were prepared using the intermediates described herein and by following the general procedure described for the synthesis of Compound 3117.

Compounds 1117 and 1118 were prepared using the intermediates described herein and by following the general procedure described for the synthesis of Compound 3117.

Compound 1117: tert-butyl ((2R,6S,7R,9S,13aS,14aR,16aS,Z)-2-((5-chloro-3-(2-methoxyethoxy)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 844.49 (M$^+$−1).

Compound 1118: tert-butyl ((2R,6S,7R,9R,13aS,14aR,16aS,Z)-2-((5-chloro-3-(2-methoxyethoxy)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.06 (br. s., 1H), 9.13 (br. s., 1H), 8.03 (d, J=8.5 Hz, 1H), 7.84-7.80 (m, 1H), 7.31-7.26 (m, 1H), 7.19 (d, J=7.6 Hz, 1H), 6.78 (s, 1H), 5.80 (br. s., 1H), 5.52 (br. s., 1H), 4.98 (br. s., 1H), 4.69 (d, J=11.0 Hz, 1H), 4.55-4.47 (m, 1H), 4.47-4.39 (m, 2H), 3.95-3.90 (m, 1H), 3.75 (t, J=4.7 Hz, 2H), 3.73-3.65 (m, 1H), 2.67 (d, J=17.1 Hz, 2H), 2.39-2.27 (m, 2H), 1.94-1.85 (m, 1H), 1.81 (d, J=6.7 Hz, 1H), 1.71 (s, 1H), 1.62 (br. s., 1H), 1.52 (br. s., 1H), 1.48-1.43 (m, 2H), 1.44-1.39 (m, 5H), 1.36 (br. s., 2H), 1.32-1.22 (m, 1H), 1.22-1.10 (m, 1H), 1.06 (s, 9H), 1.04 (br. s., 1H), 0.93 (d, J=7.0 Hz, 3H), 0.88 (d, J=6.4 Hz, 4H), 0.78-0.70 (m, 1H). MS: MS m/z 844.49 (M$^+$−1).

Preparation of Compounds 1119 and 1120

Compounds 1119 and 1120 were prepared using the intermediates described herein and by following the general procedure described for the synthesis of Compound 3117.

Compound 1119: 1,1,1-trifluoro-2-methylpropan-2-yl ((2R,6S,7R,9S,13aS,14aR,16aS,Z)-2-((3,6-dimethoxyisoquinolin-1-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 866.43 (M$^+$+1).

Compound 1120: 1,1,1-trifluoro-2-methylpropan-2-yl ((2R,6S,7R,9R,13aS,14aR,16aS,Z)-2-((3,6-dimethoxyisoquinolin-1-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.03 (br. s., 1H), 9.12 (br. s., 1H), 7.87 (d, J=8.9 Hz, 2H), 7.15 (d, J=2.4 Hz, 1H), 6.90 (dd, J=9.0, 2.3 Hz, 1H), 6.63 (s, 1H), 5.78 (br. s., 1H), 5.52 (br. s., 1H), 4.98 (br. s., 1H), 4.49 (br. s., 2H), 3.95 (dd, J=11.3, 3.7 Hz, 2H), 3.90 (s, 3H), 3.87 (s, 3H), 2.64 (d, J=14.3 Hz, 1H), 2.56 (br. s., 1H), 2.39-2.28 (m, 2H), 2.02-1.94 (m, 1H), 1.91-1.82 (m, 1H), 1.66-1.57 (m, 1H), 1.52 (br. s., 3H), 1.42 (s, 5H), 1.39 (br. s., 4H), 1.29 (br. s., 2H), 1.23 (d, J=14.3 Hz, 2H), 1.16 (s, 3H), 1.14-1.08 (m, 1H), 1.05-0.96 (m, 1H), 0.92 (d, J=6.1 Hz, 3H), 0.90-0.82 (m, 1H), 0.75 (t, J=7.5 Hz, 3H). MS: MS m/z 866.43 (M$^+$+1).

Preparation of Compounds 1121 and 1122

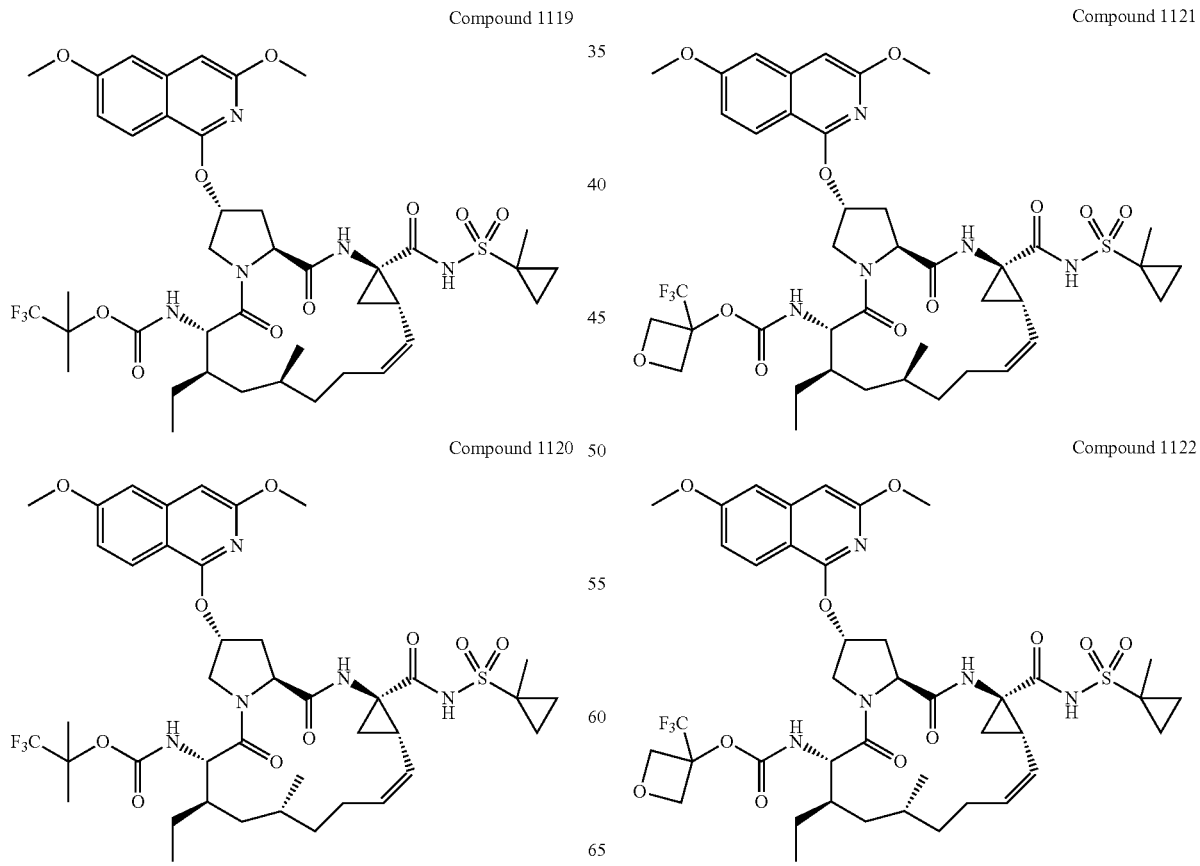

Compound 1119

Compound 1121

Compound 1120

Compound 1122

Compounds 1121 and 1122 were prepared using the intermediates described herein and by following the general procedure described for the synthesis of Compound 3117.

Compound 1121: 3-(trifluoromethyl)oxetan-3-yl ((2R,6S,7R,9S,13aS,14aR,16aS,Z)-2-((3,6-dimethoxyisoquinolin-1-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 880.39 (M$^+$+1).

Compound 1122: 3-(trifluoromethyl)oxetan-3-yl ((2R,6S,7R,9R,13aS,14aR,16aS,Z)-2-((3,6-dimethoxyisoquinolin-1-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.01 (s, 1H), 9.11 (s, 1H), 8.36 (d, J=8.2 Hz, 1H), 7.85 (d, J=9.2 Hz, 1H), 7.16 (d, J=2.1 Hz, 1H), 6.91 (dd, J=9.2, 2.1 Hz, 1H), 6.64 (s, 1H), 5.79 (br. s., 1H), 5.53 (d, J=6.1 Hz, 1H), 5.00 (t, J=10.2 Hz, 1H), 4.70 (d, J=8.5 Hz, 1H), 4.54 (d, J=8.2 Hz, 1H), 4.52-4.46 (m, 1H), 4.43 (s, 3H), 4.00-3.90 (m, 2H), 3.89 (s, 3H), 3.86 (s, 3H), 2.73-2.62 (m, 2H), 2.39-2.28 (m, 2H), 2.00 (br. s., 1H), 1.92 (s, 1H), 1.61 (d, J=6.7 Hz, 1H), 1.52 (br. s., 2H), 1.45 (br. s., 4H), 1.41 (s, 3H), 1.36 (br. s., 1H), 1.29 (d, J=9.8 Hz, 1H), 1.17 (br. s., 1H), 1.03 (t, J=11.3 Hz, 1H), 0.93 (d, J=5.5 Hz, 3H), 0.90 (br. s., 2H), 0.75 (t, J=7.5 Hz, 3H). MS: MS m/z 880.39 (M$^+$+1).

Compounds 1123 and 1124 were prepared using the intermediates described herein and by following the general procedure described for the synthesis of Compound 3117.

Compound 1123: 3,3-difluoro-2-methylbutan-2-yl ((2R,6S,7R,9S,13aS,14aR,16aS,Z)-2-((3,6-dimethoxyisoquinolin-1-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 862.5 (M$^+$+1).

Compound 1124: 3,3-difluoro-2-methylbutan-2-yl ((2R,6S,7R,9R,13aS,14aR,16aS,Z)-2-((3,6-dimethoxyisoquinolin-1-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.04 (s, 1H), 9.10 (s, 1H), 7.87 (d, J=8.9 Hz, 1H), 7.69 (d, J=8.5 Hz, 1H), 7.16 (d, J=2.1 Hz, 1H), 6.89 (dd, J=9.0, 2.3 Hz, 1H), 6.63 (s, 1H), 5.79 (br. s., 1H), 5.57-5.49 (m, 1H), 4.99 (t, J=9.9 Hz, 1H), 4.57-4.44 (m, 2H), 3.99-3.92 (m, 2H), 3.90 (s, 3H), 3.87 (s, 3H), 2.76-2.59 (m, 2H), 2.40-2.27 (m, 2H), 2.00-1.87 (m, 2H), 1.65-1.57 (m, 3H), 1.56-1.49 (m, 3H), 1.46 (br. s., 3H), 1.41 (s, 4H), 1.36 (br. s., 1H), 1.32 (s, 3H), 1.31-1.23 (m, 1H), 1.18 (br. s., 1H), 1.08 (s, 3H), 1.02 (t, J=11.7 Hz, 1H), 0.93 (d, J=6.1 Hz, 3H), 0.90 (br. s., 2H), 0.76 (t, J=7.5 Hz, 3H). MS: MS m/z 862.5 (M$^+$+1).

Preparation of Compound 1125

Preparation of Compounds 1123 and 1124

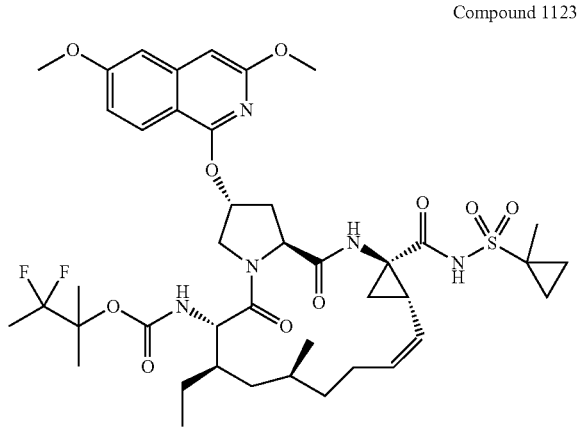

Compound 1123

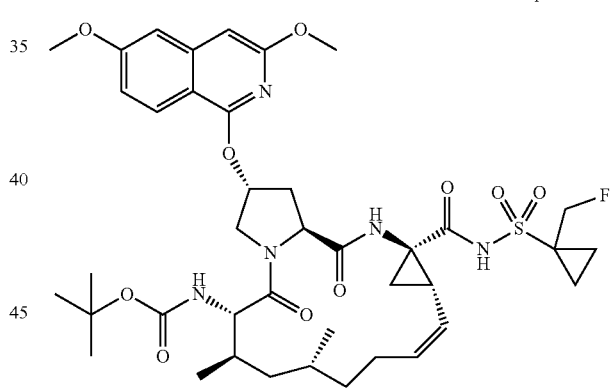

Compound 1125

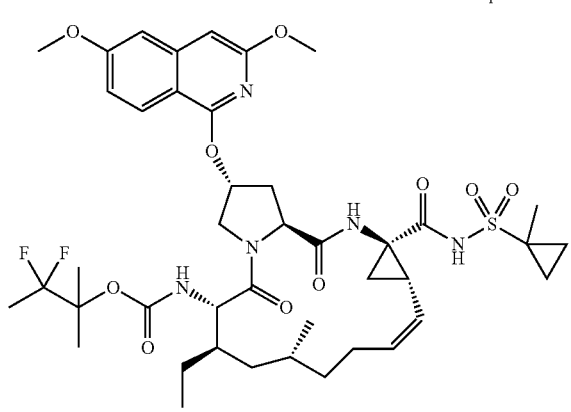

Compound 1124

Compound 1125 was prepared using the intermediates described herein and by following the general procedure described for the synthesis of Compound 3117.

Compound 1125: tert-butyl ((2R,6S,7R,9R,13aS,14aR,16aS,Z)-2-((3,6-dimethoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.27 (br. s., 1H), 9.01 (br. s., 1H), 7.92 (d, J=9.2 Hz, 1H), 7.21 (d, J=7.6 Hz, 1H), 7.14 (d, J=2.1 Hz, 1H), 6.86 (dd, J=9.0, 2.3 Hz, 1H), 6.66-6.61 (m, 1H), 5.76 (br. s., 1H), 5.51 (br. s., 1H), 5.00 (br. s., 1H), 4.90-4.71 (m, J=11.3 Hz, 1H), 4.58 (br. s., 2H), 4.50 (d, J=11.6 Hz, 1H), 4.44 (d, J=9.8 Hz, 1H), 3.95-3.91 (m, 1H), 3.90 (s, 3H), 3.87 (s, 3H), 3.77-3.72 (m, 1H), 2.71-2.58 (m, 2H), 2.35-2.26 (m, 2H), 1.91 (d, J=13.1 Hz, 1H), 1.83 (d, J=6.4 Hz, 1H), 1.70 (br. s., 1H), 1.53 (br. s., 2H), 1.38 (d, J=16.5 Hz, 3H), 1.25

(br. s., 1H), 1.20 (s, 9H), 1.16 (br. s., 1H), 1.08 (br. s., 1H), 0.94 (d, J=7.0 Hz, 3H), 0.89 (d, J=6.4 Hz, 3H), 0.74 (t, J=12.8 Hz, 1H). MS: MS m/z 816.5 (M$^+$+1).

Preparation of Compounds 1126 and 1127

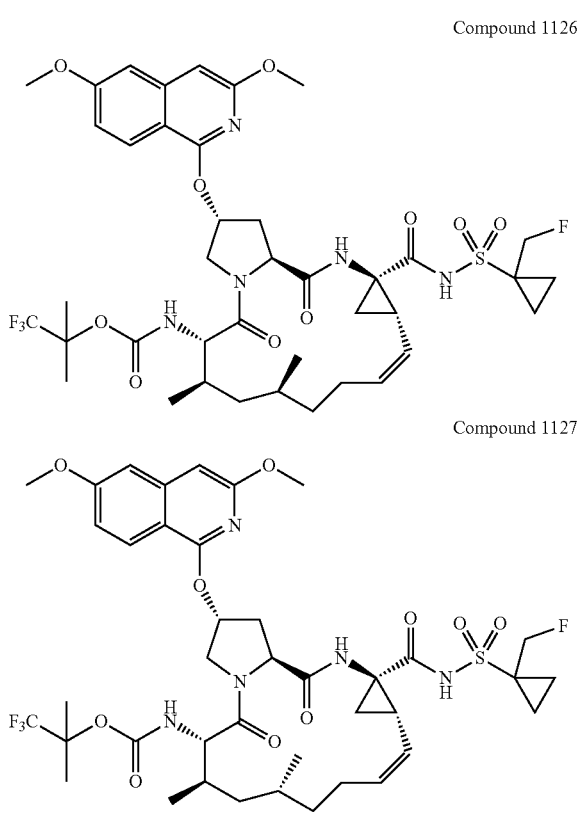

Compound 1126

Compound 1127

Compounds 1126 and 1127 were prepared using the intermediates described herein and by following the general procedure described for the synthesis of Compound 3117.

Compound 1126: 1,1,1-trifluoro-2-methylpropan-2-yl ((2R,6S,7R,9S,13aS,14aR,16aS,Z)-2-((3,6-dimethoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 870.4 (M$^+$+1).

Compound 1127: 1,1,1-trifluoro-2-methylpropan-2-yl ((2R,6S,7R,9R,13aS,14aR,16aS,Z)-2-((3,6-dimethoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.27 (s, 1H), 9.05 (s, 1H), 7.89 (d, J=9.2 Hz, 1H), 7.85 (d, J=7.6 Hz, 1H), 7.15 (d, J=2.1 Hz, 1H), 6.90 (dd, J=9.2, 2.4 Hz, 1H), 6.62 (s, 1H), 5.77 (br. s., 1H), 5.55-5.48 (m, 1H), 5.00 (t, J=9.9 Hz, 1H), 4.62-4.44 (m, 3H), 3.95-3.91 (m, 1H), 3.90 (s, 3H), 3.87 (s, 3H), 3.73 (dd, J=10.7, 7.9 Hz, 1H), 2.70-2.59 (m, 2H), 2.38-2.25 (m, 2H), 1.94-1.80 (m, 2H), 1.73-1.66 (m, 1H), 1.53 (br. s., 4H), 1.48-1.43 (m, 1H), 1.41 (s, 4H), 1.40-1.31 (m, 1H), 1.31-1.20 (m, 2H), 1.19 (s, 3H), 1.15 (d, J=12.2 Hz, 1H), 0.94 (d, J=7.0 Hz, 3H), 0.90 (d, J=6.4 Hz, 3H), 0.76 (t, J=12.1 Hz, 1H). MS: MS m/z 870.4 (M$^+$+1).

Preparation of Compound 1128

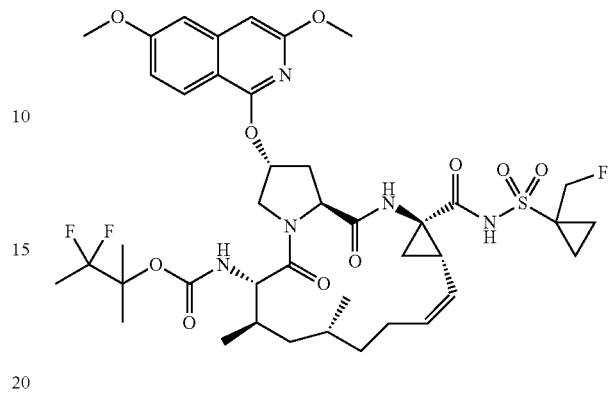

Compound 1128

Compound 1128 was prepared using the intermediates described herein and by following the general procedure described for the synthesis of Compound 3117.

Compound 1128: 3,3-difluoro-2-methylbutan-2-yl ((2R,6S,7R,9R,13aS,14aR,16aS,Z)-2-((3,6-dimethoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.27 (s, 1H), 9.02 (s, 1H), 7.89 (d, J=9.2 Hz, 1H), 7.64 (d, J=7.9 Hz, 1H), 7.15 (d, J=2.1 Hz, 1H), 6.89 (dd, J=9.2, 2.4 Hz, 1H), 6.63 (s, 1H), 5.78 (br. s., 1H), 5.55-5.48 (m, 1H), 5.01 (t, J=9.6 Hz, 1H), 4.88-4.73 (m, J=11.3 Hz, 1H), 4.63-4.43 (m, 3H), 3.96-3.91 (m, 1H), 3.90 (s, 3H), 3.87 (s, 3H), 3.77-3.71 (m, 1H), 2.72-2.60 (m, 2H), 2.39-2.27 (m, 2H), 1.96-1.87 (m, 1H), 1.87-1.79 (m, 1H), 1.73-1.65 (m, 1H), 1.65-1.55 (m, 4H), 1.55-1.50 (m, 3H), 1.49-1.33 (m, 2H), 1.32 (s, 3H), 1.31-1.20 (m, 2H), 1.15 (d, J=13.7 Hz, 1H), 1.11 (s, 3H), 0.94 (d, J=6.7 Hz, 3H), 0.91 (d, J=6.4 Hz, 3H), 0.76 (t, J=12.1 Hz, 1H). MS: MS m/z 866.5 (M$^+$+1).

Preparation of Compound 1129

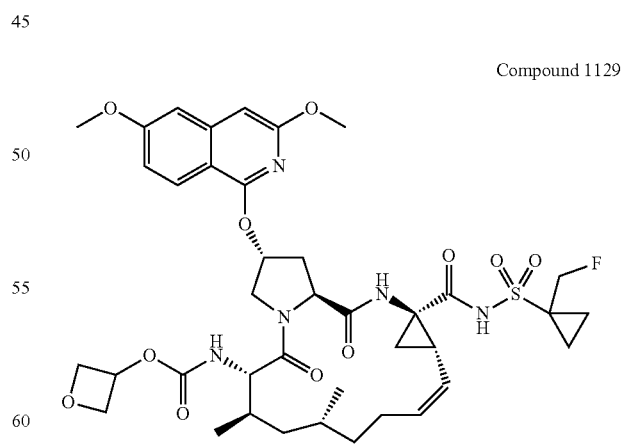

Compound 1129

Compound 1129 was prepared using the intermediates described herein and by following the general procedure described for the synthesis of Compound 3117.

Compound 1129: oxetan-3-yl ((2R,6S,7R,9R,13aS,14aR,16aS,Z)-2-((3,6-dimethoxyisoquinolin-1-yl)oxy)-14a-(((1-

(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.26 (br. s., 1H), 9.00 (br. s., 1H), 7.89-7.80 (m, 2H), 7.17 (d, J=2.1 Hz, 1H), 6.97 (dd, J=8.9, 2.1 Hz, 1H), 6.64 (s, 1H), 5.78 (br. s., 1H), 5.51 (br. s., 1H), 5.02 (br. s., 1H), 4.91-4.80 (m, 1H), 4.76 (d, J=9.5 Hz, 1H), 4.64-4.52 (m, 2H), 4.48-4.40 (m, 3H), 4.34-4.29 (m, 1H), 4.14 (dd, J=7.3, 5.5 Hz, 1H), 3.96-3.91 (m, 1H), 3.90 (s, 3H), 3.88 (s, 3H), 3.78-3.72 (m, 1H), 2.70-2.58 (m, 1H), 2.40-2.24 (m, 2H), 1.92 (br. s., 1H), 1.85 (br. s., 1H), 1.67 (br. s., 1H), 1.53 (br. s., 3H), 1.44 (br. s., 1H), 1.37 (br. s., 1H), 1.31-1.20 (m, 4H), 1.15 (br. s., 1H), 0.93 (d, J=6.7 Hz, 3H), 0.90 (d, J=6.1 Hz, 3H), 0.77 (d, J=11.3 Hz, 1H). MS: MS m/z 816.5 (M$^+$+1).

Preparation of Compounds 1130 and 1131

16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.05 (br. s., 1H), 9.09 (br. s., 1H), 7.92 (d, J=8.9 Hz, 1H), 7.21 (d, J=8.2 Hz, 1H), 7.14 (d, J=2.1 Hz, 1H), 6.86 (dd, J=9.0, 2.3 Hz, 1H), 6.61 (s, 1H), 5.77 (br. s., 1H), 5.52 (br. s., 1H), 4.98 (br. s., 1H), 4.58 (d, J=10.7 Hz, 1H), 4.49-4.43 (m, 1H), 3.96-3.91 (m, 1H), 3.90 (s, 3H), 3.87 (s, 3H), 3.74 (dd, J=10.4, 8.5 Hz, 1H), 2.76-2.67 (m, 1H), 2.67-2.58 (m, 1H), 2.39-2.26 (m, 2H), 1.95-1.87 (m, 1H), 1.87-1.78 (m, 1H), 1.74-1.65 (m, 1H), 1.61 (br. s., 1H), 1.51 (br. s., 1H), 1.41 (s, 4H), 1.39-1.22 (m, 3H), 1.19 (s, 9H), 1.15 (br. s., 2H), 1.07 (br. s., 1H), 0.93 (d, J=7.0 Hz, 3H), 0.89 (d, J=6.4 Hz, 3H), 0.74 (t, J=12.5 Hz, 1H). MS: MS m/z 798.4 (M$^+$+1).

Preparation of Compounds 1132 and 1133

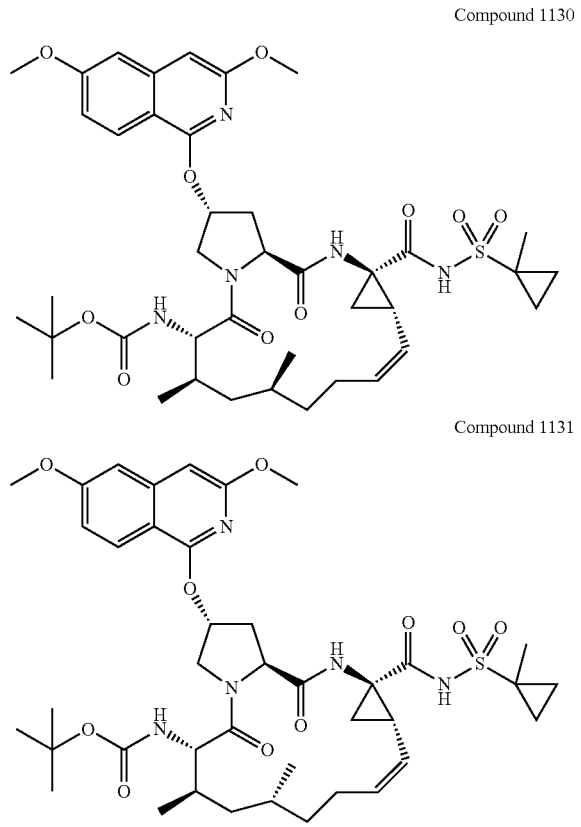

Compound 1130

Compound 1131

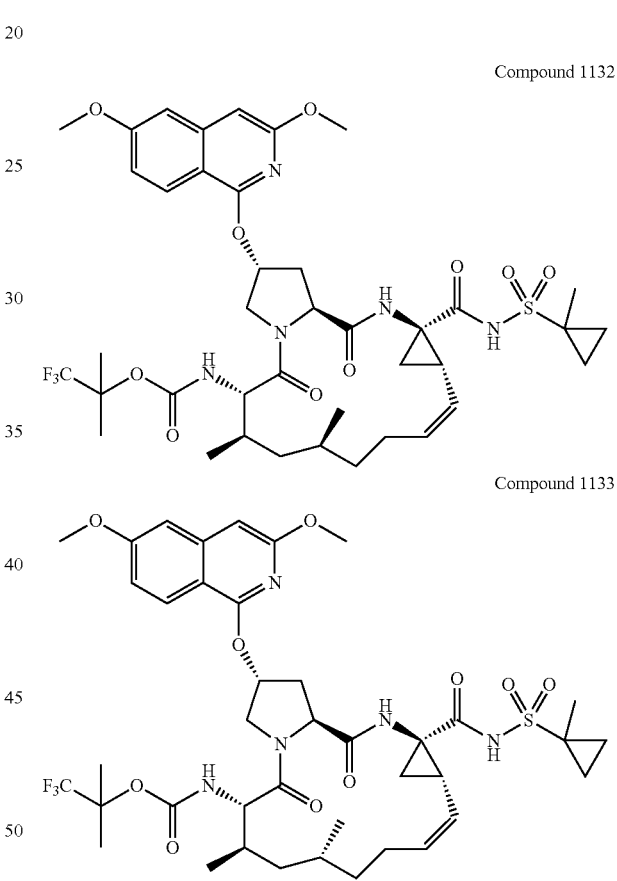

Compound 1132

Compound 1133

Compounds 1130 and 1131 were prepared using the intermediates described herein and by following the general procedure described for the synthesis of Compound 3117.

Compound 1130: tert-butyl ((2R,6S,7R,9S,13aS,14aR,16aS,Z)-2-((3,6-dimethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 798.4 (M$^+$+1).

Compound 1131: tert-butyl ((2R,6S,7R,9R,13aS,14aR,16aS,Z)-2-((3,6-dimethoxyisoquinolin-1-yl)oxy)-7,9-dimethyl-14a-(((1-methylcyclopropyl)sulfonyl)carbamoyl)-5, Compounds 1132 and 1133 were prepared using the intermediates described herein and by following the general procedure described for the synthesis of Compound 3117.

Compound 1132: 1,1,1-trifluoro-2-methylpropan-2-yl ((2R,6S,7R,9S,13aS,14aR,16aS,Z)-2-((3,6-dimethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 852.4 (M$^+$+1).

Compound 1133: 1,1,1-trifluoro-2-methylpropan-2-yl ((2R,6S,7R,9R,13aS,14aR,16aS,Z)-2-((3,6-dimethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11, 13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.04 (br. s., 1H), 9.13 (br. s., 1H), 7.91-7.82 (m, 2H), 7.15 (d, J=2.1 Hz, 1H), 6.90 (dd, J=9.2, 2.4 Hz, 1H), 6.64-6.61 (m, 1H), 5.78 (br. s., 1H), 5.53 (br. s., 1H), 4.98 (br. s., 1H), 4.57-4.47 (m, 2H), 3.96-3.91 (m, 1H), 3.90 (s, 3H), 3.87 (s, 3H), 3.73 (dd, J=10.7, 7.9 Hz, 1H), 2.73-2.60 (m, 2H), 2.39-2.28 (m, 2H), 1.94-1.81 (m, 2H), 1.69 (br. s., 1H), 1.61 (br. s., 1H), 1.52 (br. s., 1H), 1.49-1.43 (m, 2H), 1.40 (s, 6H), 1.36 (br. s., 1H), 1.29 (d, J=8.5 Hz, 3H), 1.16 (s, 3H), 1.14-1.06 (m, 1H), 0.93 (d, J=6.7 Hz, 3H), 0.90 (d, J=6.1 Hz, 3H), 0.76 (t, J=12.2 Hz, 1H). MS: MS m/z 852.4 (M$^+$+1).

Preparation of Compounds 1134 and 1135

1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, METHANOL-d4) Shift 7.81 (d, J=9.2 Hz, 1H), 6.84 (d, J=2.4 Hz, 1H), 6.60 (dd, J=9.0, 2.3 Hz, 1H), 6.16 (s, 1H), 5.83 (br. s., 1H), 5.57 (d, J=5.8 Hz, 1H), 4.87-4.71 (m, 1H), 4.62 (t, J=10.2 Hz, 2H), 4.57-4.51 (m, 2H), 4.09-4.05 (m, 1H), 3.96-3.90 (m, 1H), 3.86 (s, 3H), 3.73-3.65 (m, 2H), 3.06 (s, 3H), 2.75-2.68 (m, 1H), 2.63 (br. s., 1H), 2.45-2.35 (m, 2H), 1.96 (s, 1H), 1.89-1.77 (m, 3H), 1.68 (dd, J=8.2, 5.2 Hz, 2H), 1.62 (br. s., 2H), 1.57-1.41 (m, 3H), 1.26 (s, 9H), 1.23 (br. s., 1H), 1.20 (t, J=7.0 Hz, 3H), 1.12 (br. s., 3H), 1.01 (d, J=7.0 Hz, 3H), 0.99 (d, J=6.4 Hz, 3H), 0.82 (t, J=12.7 Hz, 1H). MS: MS m/z 843.46 (M$^+$+1).

Preparation of Compounds 1136 and 1137

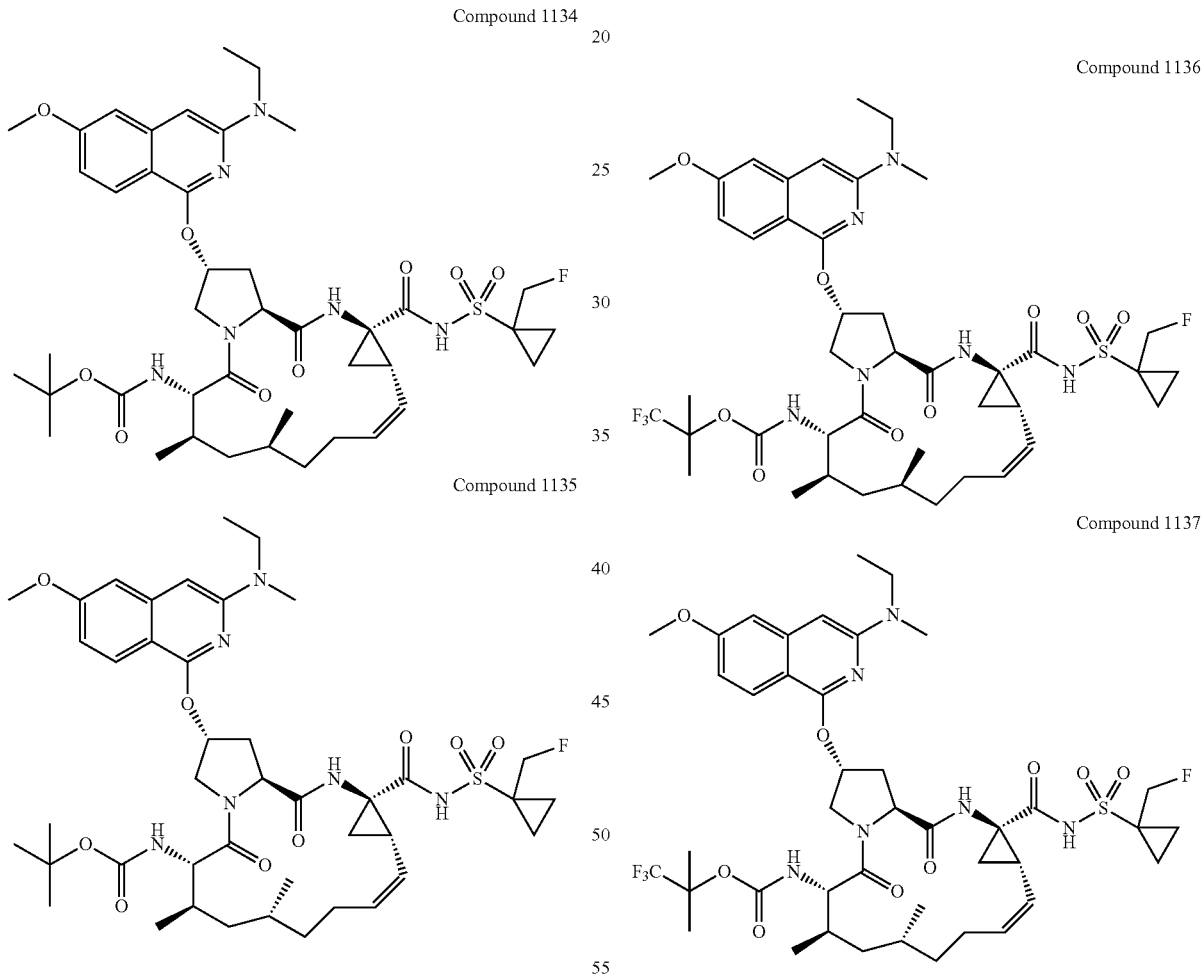

Compound 1134

Compound 1135

Compound 1136

Compound 1137

Compounds 1134 and 1135 were prepared using the intermediates described herein and by following the general procedure described for the synthesis of Compound 3117.

Compound 1134: tert-butyl ((2R,6S,7R,9S,13aS,14aR,16aS,Z)-2-((3-(ethyl(methyl)amino)-6-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 843.46 (M$^+$+1).

Compound 1135: tert-butyl ((2R,6S,7R,9R,13aS,14aR,16aS,Z)-2-((3-(ethyl(methyl)amino)-6-methoxyisoquinolin- Compounds 1136 and 1137 were prepared using the intermediates described herein and by following the general procedure described for the synthesis of Compound 3117.

Compound 1136: 1,1,1-trifluoro-2-methylpropan-2-yl ((2R,6S,7R,9S,13aS,14aR,16aS,Z)-2-((3-(ethyl(methyl)amino)-6-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 897.5 (M$^+$+1).

Compound 1137: 1,1,1-trifluoro-2-methylpropan-2-yl ((2R,6S,7R,9R,13aS,14aR,16aS,Z)-2-((3-(ethyl(methyl)amino)-6-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, METHANOL-d4) Shift 7.80 (d, J=9.2 Hz, 1H), 6.85 (d, J=2.4 Hz, 1H), 6.61 (dd, J=9.2, 2.4 Hz, 1H), 6.17 (s, 1H), 5.80 (br. s., 1H), 5.55 (td, J=10.1, 5.8 Hz, 1H), 5.21 (br. s., 1H), 4.86-4.72 (m, 1H), 4.70-4.60 (m, 2H), 4.60-4.54 (m, 2H), 4.03 (dd, J=11.3, 3.7 Hz, 1H), 3.88 (s, 1H), 3.86 (s, 3H), 3.77-3.64 (m, 2H), 3.06 (s, 3H), 2.72 (dd, J=13.7, 7.3 Hz, 1H), 2.59 (d, J=9.2 Hz, 1H), 2.46-2.32 (m, 2H), 2.01-1.94 (m, 1H), 1.92-1.83 (m, 1H), 1.79 (dd, J=13.3, 4.7 Hz, 1H), 1.68 (dd, J=8.2, 5.2 Hz, 1H), 1.66-1.56 (m, 2H), 1.53 (dd, J=9.5, 5.2 Hz, 1H), 1.46 (s, 5H), 1.42 (br. s., 1H), 1.31-1.22 (m, 1H), 1.20 (t, J=7.0 Hz, 3H), 1.15 (s, 4H), 1.11 (br. s., 2H), 1.01 (d, J=6.7 Hz, 3H), 0.98 (d, J=6.4 Hz, 3H), 0.84-0.76 (m, 1H). MS: MS m/z 897.5 (M$^+$+1).

Preparation of Compounds 1138 and 1139 cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 893.41 (M$^+$+1).

Compound 1139: 3,3-difluoro-2-methylbutan-2-yl ((2R,6S,7R,9R,13aS,14aR,16aS,Z)-2-((3-(ethyl(methyl)amino)-6-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, METHANOL-d4) Shift 7.80 (d, J=8.9 Hz, 1H), 6.85 (d, J=2.1 Hz, 1H), 6.60 (dd, J=9.2, 2.4 Hz, 1H), 6.17 (s, 1H), 5.82 (br. s., 1H), 5.56 (td, J=10.1, 6.1 Hz, 1H), 5.07 (br. s., 1H), 4.87-4.74 (m, 1H), 4.66-4.50 (m, 3H), 4.04 (dd, J=11.6, 3.7 Hz, 1H), 3.89 (d, J=10.7 Hz, 1H), 3.86 (s, 3H), 3.74-3.64 (m, 2H), 3.05 (s, 3H), 2.75-2.60 (m, 2H), 2.44-2.32 (m, 2H), 1.98-1.83 (m, 2H), 1.77 (dd, J=13.6, 5.6 Hz, 1H), 1.72-1.57 (m, 4H), 1.57-1.42 (m, 6H), 1.41-1.38 (m, 4H), 1.30 (s, 1H), 1.24 (br. s., 1H), 1.20 (t, J=7.0 Hz, 4H), 1.17-1.13 (m, 1H), 1.12 (s, 3H), 0.99 (dd, J=9.5, 6.7 Hz, 6H), 0.84-0.77 (m, 1H). MS: MS m/z 893.41 (M$^+$+1).

Preparation of Compounds 1140 and 1141

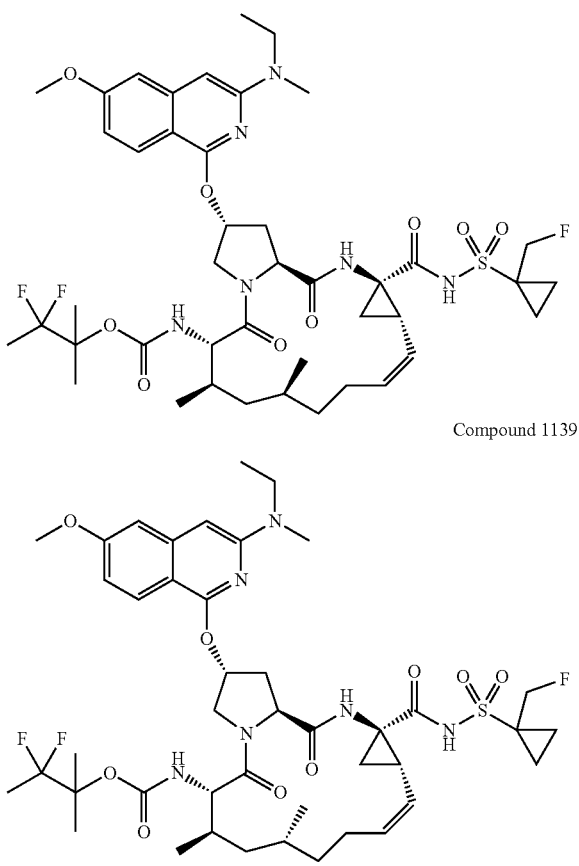

Compound 1138

Compound 1139

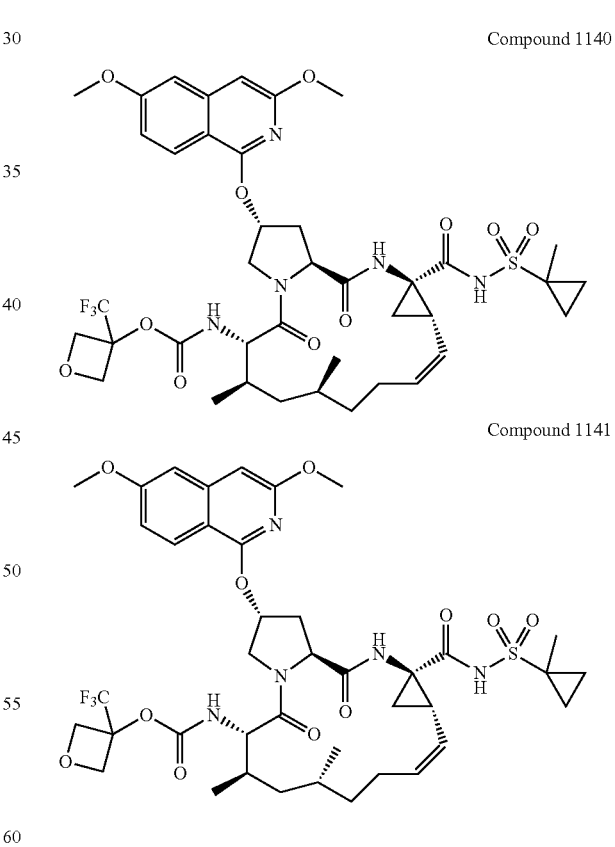

Compound 1140

Compound 1141

Compounds 1138 and 1139 were prepared using the intermediates described herein and by following the general procedure described for the synthesis of Compound 3117.

Compound 1138: 3,3-difluoro-2-methylbutan-2-yl ((2R,6S,7R,9S,13aS,14aR,16aS,Z)-2-((3-(ethyl(methyl)amino)-6-methoxyisoquinolin-1-yl)oxy)-14a-(((1-(fluoromethyl)

Compounds 1140 and 1141 were prepared using the intermediates described herein and by following the general procedure described for the synthesis of Compound 3117.

Compound 1140: 3-(trifluoromethyl)oxetan-3-yl ((2R,6S,7R,9S,13aS,14aR,16aS,Z)-2-((3,6-dimethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15, 16,16a-hexadecahydrocyclopropa[e]pyrrolo[1,2-a][1,4]diazacyclopentadecin-6-yl)carbamate. MS: MS m/z 866.4 (M$^+$+1).

Compound 1141: 3-(trifluoromethyl)oxetan-3-yl ((2R,6S,7R,9R,13aS,14aR,16aS,Z)-2-((3,6-dimethoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.01 (br. s., 1H), 9.10 (br. s., 1H), 8.29 (d, J=7.9 Hz, 1H), 7.85 (d, J=9.2 Hz, 1H), 7.16 (d, J=2.4 Hz, 1H), 6.90 (dd, J=9.0, 2.3 Hz, 1H), 6.63 (s, 1H), 5.78 (br. s., 1H), 5.52 (br. s., 1H), 5.00 (br. s., 1H), 4.72 (d, J=8.9 Hz, 1H), 4.53-4.36 (m, 5H), 3.96 (dd, J=11.4, 3.2 Hz, 1H), 3.89 (s, 3H), 3.86 (s, 3H), 3.80-3.74 (m, 1H), 2.64 (d, J=11.6 Hz, 1H), 2.39-2.26 (m, 2H), 1.93-1.84 (m, 2H), 1.71 (br. s., 1H), 1.59 (br. s., 1H), 1.51 (br. s., 1H), 1.47-1.42 (m, 2H), 1.40 (br. s., 3H), 1.37-1.31 (m, 2H), 1.26 (d, J=7.3 Hz, 1H), 1.17 (br. s., 1H), 0.93 (d, J=7.0 Hz, 4H), 0.91 (d, J=6.4 Hz, 3H), 0.88-0.82 (m, 1H), 0.77 (br. s., 1H). MS: MS m/z 866.4 (M$^+$+1).

Preparation of Compounds 1142 and 1143

Compound 1142: 3,3-difluoro-2-methylbutan-2-yl ((2R,6S,7R,9S,13aS,14aR,16aS,Z)-14a-(((1-(fluoromethyl)cyclopropyl)sulfonyl)carbamoyl)-2-((6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 836.44 (M$^+$+1).

Compound 1143: 3,3-difluoro-2-methylbutan-2-yl ((2R,6S,7R,9R,13aS,14aR,16aS,Z)-14a-(((1-(fluoromethyl)cyclopropyl)sulfonyl)carbamoyl)-2-((6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.28 (s, 1H), 9.03 (s, 1H), 8.02 (d, J=9.2 Hz, 1H), 7.97 (d, J=6.1 Hz, 1H), 7.63 (d, J=8.2 Hz, 1H), 7.35-7.30 (m, 2H), 7.14 (dd, J=9.2, 2.4 Hz, 1H), 5.82 (br. s., 1H), 5.55-5.48 (m, 1H), 5.00 (t, J=10.1 Hz, 1H), 4.88-4.72 (m, 1H), 4.63-4.42 (m, 3H), 3.96-3.91 (m, 2H), 3.90 (s, 3H), 3.73 (dd, J=10.5, 8.4 Hz, 1H), 2.72-2.59 (m, 2H), 2.36-2.27 (m, 2H), 1.95-1.86 (m, 1H), 1.86-1.78 (m, 1H), 1.70 (dd, J=13.1, 6.1 Hz, 1H), 1.64-1.55 (m, 4H), 1.53 (br. s., 2H), 1.44 (br. s., 1H), 1.41-1.32 (m, 1H), 1.30 (s, 3H), 1.29-1.20 (m, 2H), 1.15 (d, J=13.1 Hz, 1H), 1.07 (s, 3H), 0.94 (d, J=6.7 Hz, 3H), 0.90 (d, J=6.4 Hz, 3H), 0.76 (t, J=12.8 Hz, 1H). MS: MS m/z 836.44 (M$^+$+1).

Preparation of Compounds 1144 and 1145

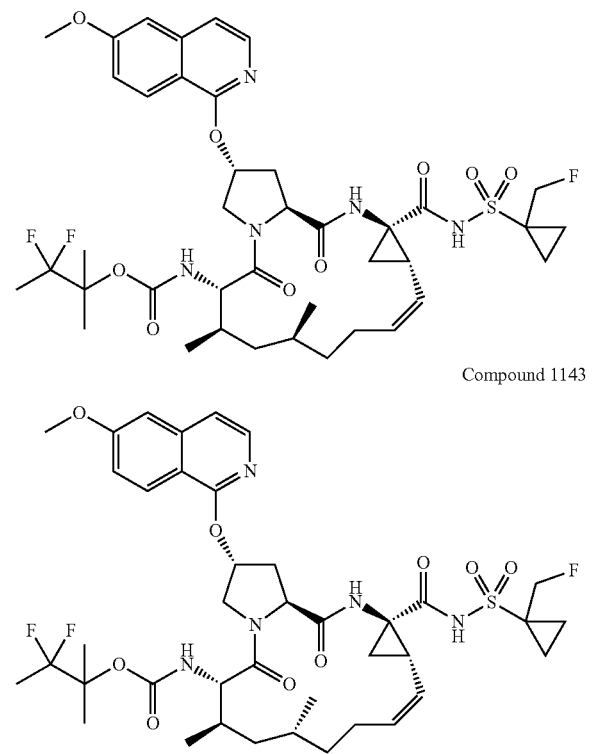

Compound 1142

Compound 1143

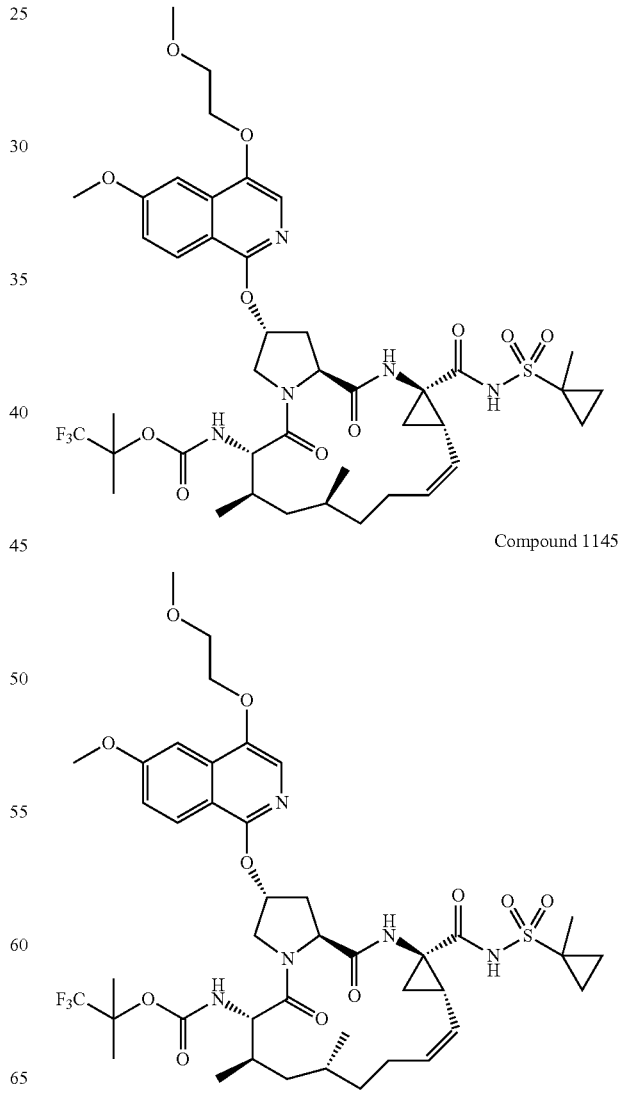

Compound 1144

Compound 1145

Compounds 1142 and 1143 were prepared using the intermediates described herein and by following the general procedure described for the synthesis of Compound 3117.

Compounds 1144 and 1145 were prepared using the intermediates described herein and by following the general procedure described for the synthesis of Compound 3117.

Compound 1144: 1,1,1-trifluoro-2-methylpropan-2-yl ((2R,6S,7R,9S,13aS,14aR,16aS,Z)-2-((6-methoxy-4-(2-methoxyethoxy)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 896.8 (M$^+$+1).

Compound 1145: 1,1,1-trifluoro-2-methylpropan-2-yl ((2R,6S,7R,9R,13aS,14aR,16aS,Z)-2-((6-methoxy-4-(2-methoxyethoxy)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.06 (br. s., 1H), 9.11 (br. s., 1H), 8.00 (d, J=9.2 Hz, 1H), 7.81 (d, J=7.6 Hz, 1H), 7.66 (s, 1H), 7.37 (d, J=2.4 Hz, 1H), 7.20 (dd, J=9.0, 2.6 Hz, 1H), 5.75 (br. s., 1H), 5.49 (br. s., 1H), 5.03 (br. s., 1H), 4.48 (br. s., 2H), 4.30-4.24 (m, 2H), 3.92 (s, 3H), 3.89 (d, J=3.7 Hz, 1H), 3.81-3.76 (m, 2H), 3.71 (dd, J=10.5, 8.1 Hz, 1H), 3.39 (s, 3H), 2.56 (br. s., 1H), 2.35-2.25 (m, 2H), 1.91-1.78 (m, 2H), 1.73 (br. s., 1H), 1.57 (br. s., 1H), 1.51 (br. s., 1H), 1.39 (br. s., 4H), 1.38 (s, 5H), 1.35-1.30 (m, 1H), 1.25 (br. s., 1H), 1.19 (d, J=14.3 Hz, 2H), 1.12 (s, 3H), 0.93 (d, J=7.0 Hz, 3H), 0.88 (d, J=6.4 Hz, 3H), 0.86-0.80 (m, 1H), 0.74 (d, J=11.3 Hz, 1H). MS: MS m/z 896.8 (M$^+$+1).

Preparation of Compounds 1146 and 1147

Compound 1146

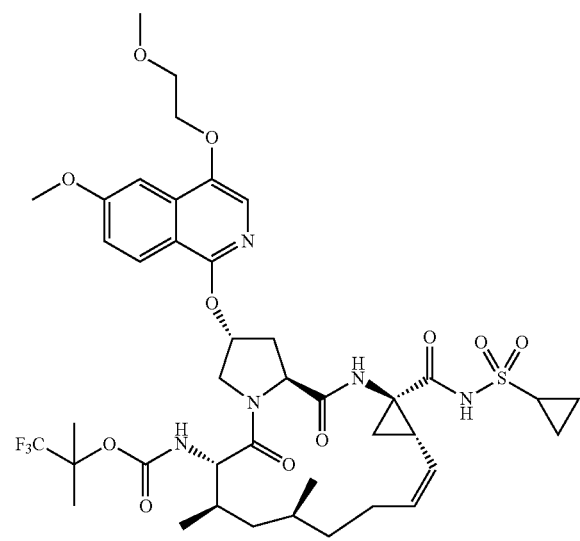

Compound 1147

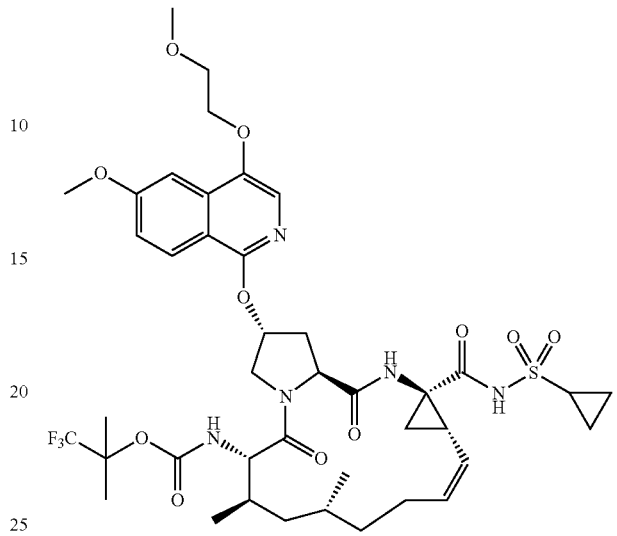

Compounds 1146 and 1147 were prepared using the intermediates described herein and by following the general procedure described for the synthesis of Compound 3117.

Compound 1146: 1,1,1-trifluoro-2-methylpropan-2-yl ((2R,6S,7R,9S,13aS,14aR,16aS,Z)-14a-((cyclopropylsulfonyl)carbamoyl)-2-((6-methoxy-4-(2-methoxyethoxy)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 882.8 (M$^+$+1).

Compound 1147: 1,1,1-trifluoro-2-methylpropan-2-yl ((2R,6S,7R,9R,13aS,14aR,16aS,Z)-14a-((cyclopropylsulfonyl)carbamoyl)-2-((6-methoxy-4-(2-methoxyethoxy)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
1H NMR (500 MHz, DMSO-d6) Shift 11.19 (br. s., 1H), 9.13-8.85 (m, 1H), 8.00 (d, J=9.2 Hz, 1H), 7.82 (d, J=7.9 Hz, 1H), 7.67-7.64 (m, 1H), 7.37 (d, J=2.4 Hz, 1H), 7.20 (dd, J=9.2, 2.4 Hz, 1H), 5.74 (br. s., 1H), 5.52 (br. s., 1H), 4.53-4.43 (m, 2H), 4.30-4.22 (m, 2H), 3.92 (s, 3H), 3.88 (dd, J=11.4, 3.5 Hz, 1H), 3.82-3.77 (m, 2H), 3.71 (dd, J=10.8, 8.1 Hz, 2H), 3.39 (s, 3H), 2.65 (br. s., 1H), 2.60 (br. s., 1H), 2.33-2.25 (m, 2H), 1.92-1.78 (m, 2H), 1.71 (br. s., 1H), 1.62-1.58 (m, 2H), 1.56 (br. s., 1H), 1.51 (br. s., 1H), 1.41 (br. s., 1H), 1.38 (s, 4H), 1.14 (s, 4H), 0.98 (br. s., 3H), 0.94 (d, J=7.0 Hz, 3H), 0.89 (d, J=6.4 Hz, 3H), 0.73 (t, J=12.4 Hz, 1H). MS: MS m/z 882.8 (M$^+$+1).

Preparation of Compounds 1148 and 1149

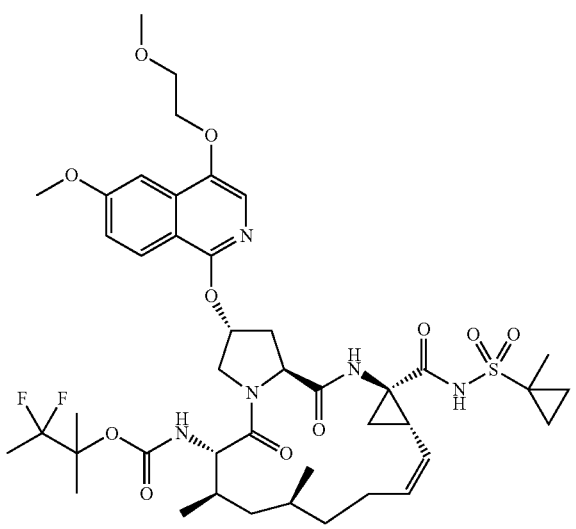

Compound 1148

Compound 1149

Compounds 1148 and 1149 were prepared using the intermediates described herein and by following the general procedure described for the synthesis of Compound 3117.

Compound 1148: 3,3-difluoro-2-methylbutan-2-yl ((2R,6S,7R,9S,13aS,14aR,16aS,Z)-2-((6-methoxy-4-(2-methoxyethoxyl)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 892.8 (M$^+$+1).

Compound 1149: 3,3-difluoro-2-methylbutan-2-yl ((2R,6S,7R,9R,13aS,14aR,16aS,Z)-2-((6-methoxy-4-(2-methoxyethoxyl)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 8.01 (d, J=8.9 Hz, 1H), 7.66 (s, 1H), 7.56 (d, J=7.9 Hz, 1H), 7.36 (d, J=2.4 Hz, 1H), 7.19 (dd, J=9.2, 2.4 Hz, 1H), 5.73 (br. s., 1H), 5.51-5.25 (m, 1H), 4.42 (br. s., 2H), 4.27 (d, J=3.1 Hz, 2H), 3.91 (s, 3H), 3.89 (br. s., 1H), 3.79 (t, J=4.4 Hz, 2H), 3.73 (t, J=9.6 Hz, 1H), 3.39 (s, 3H), 2.30 (t, J=9.8 Hz, 2H), 1.86 (d, J=13.1 Hz, 1H), 1.79 (br. s., 2H), 1.57 (t, J=19.7 Hz, 3H), 1.43 (br. s., 2H), 1.34 (br. s., 6H), 1.30 (s, 4H), 1.25 (br. s., 3H), 1.16 (br. s., 2H), 1.05 (s, 3H), 0.92 (d, J=6.7 Hz, 3H), 0.88 (d, J=6.4 Hz, 4H), 0.68 (br. s., 1H). MS: MS m/z 892.8 (M$^+$+1).

Preparation of Compounds 1150 and 1151

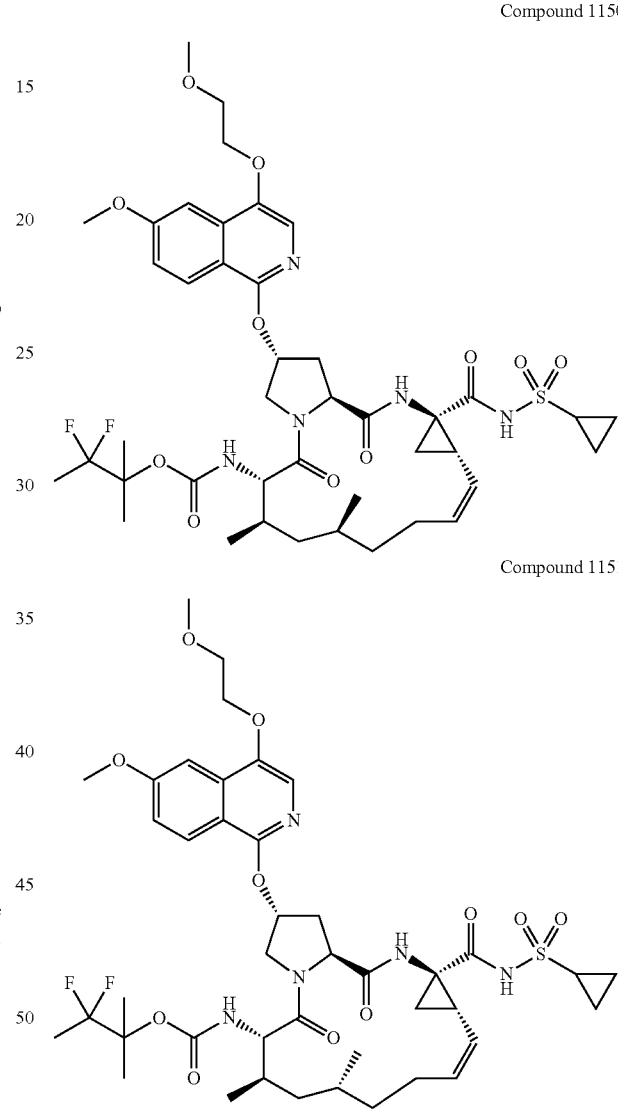

Compound 1150

Compound 1151

Compounds 1150 and 1151 were prepared using the intermediates described herein and by following the general procedure described for the synthesis of Compound 3117.

Compound 1150: 3,3-difluoro-2-methylbutan-2-yl ((2R,6S,7R,9S,13aS,14aR,16aS,Z)-14a-((cyclopropylsulfonyl)carbamoyl)-2-((6-methoxy-4-(2-methoxyethoxyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 878.56 (M$^+$+1).

Compound 1151: 3,3-difluoro-2-methylbutan-2-yl ((2R,6S,7R,9R,13aS,14aR,16aS,Z)-14a-((cyclopropylsulfonyl)

carbamoyl)-2-((6-methoxy-4-(2-methoxyethoxyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.65-10.88 (m, 1H), 9.17-8.67 (m, 1H), 8.00 (d, J=9.2 Hz, 1H), 7.66 (s, 1H), 7.57 (d, J=6.4 Hz, 1H), 7.36 (d, J=2.4 Hz, 1H), 7.19 (dd, J=9.0, 2.3 Hz, 1H), 5.73 (br. s., 1H), 5.39 (br. s., 1H), 4.41 (br. s., 2H), 4.27 (d, J=2.7 Hz, 2H), 3.91 (s, 3H), 3.88 (br. s., 2H), 3.81-3.77 (m, 2H), 3.73 (t, J=9.6 Hz, 1H), 3.39 (s, 3H), 2.33-2.24 (m, 2H), 1.89 (br. s., 1H), 1.80 (br. s., 2H), 1.73-1.63 (m, 1H), 1.58 (t, J=19.5 Hz, 4H), 1.48 (br. s., 1H), 1.43 (br. s., 1H), 1.38 (br. s., 2H), 1.30 (s, 3H), 1.25 (br. s., 2H), 1.16 (br. s., 1H), 1.06 (s, 3H), 1.01-0.96 (m, 1H), 0.93 (d, J=6.7 Hz, 3H), 0.89 (d, J=6.1 Hz, 3H), 0.85-0.74 (m, 2H), 0.69 (br. s., 1H). MS: MS m/z 878.56 (M$^+$+1).

Preparation of Compounds 1152 and 1153

Compounds 1152 and 1153 were prepared using the intermediates described herein and by following the general procedure described for the synthesis of Compound 3117.

Compound 1152: tert-butyl ((2R,6S,7R,9S,13aS,14aR,16aS,Z)-2-((6-methoxy-4-(2-methoxyethoxyl)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 842.6 (M$^+$+1).

Compound 1153: tert-butyl ((2R,6S,7R,9R,13aS,14aR,16aS,Z)-2-((6-methoxy-4-(2-methoxyethoxy)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.04 (br. s., 1H), 9.06 (s, 1H), 8.03 (d, J=9.2 Hz, 1H), 7.65 (s, 1H), 7.36 (d, J=2.1 Hz, 1H), 7.19-7.12 (m, 2H), 5.74 (br. s., 1H), 5.48 (br. s., 1H), 4.50 (br. s., 1H), 4.43 (br. s., 1H), 4.27 (br. s., 2H), 3.92 (s, 3H), 3.89 (br. s., 2H), 3.80-3.77 (m, 2H), 3.76-3.68 (m, 1H), 3.39 (s, 3H), 2.29 (d, J=9.8 Hz, 2H), 1.88 (br. s., 1H), 1.81 (br. s., 1H), 1.74 (br. s., 1H), 1.61-1.44 (m, 2H), 1.38 (br. s., 5H), 1.26 (d, J=14.6 Hz, 4H), 1.16 (s, 9H), 1.06 (br. s., 3H), 0.93 (d, J=6.7 Hz, 3H), 0.88 (d, J=6.4 Hz, 4H), 0.70 (br. s., 1H). MS: MS m/z 842.6 (M$^+$+1).

Preparation of Compounds 1154 and 1155

Compound 1152

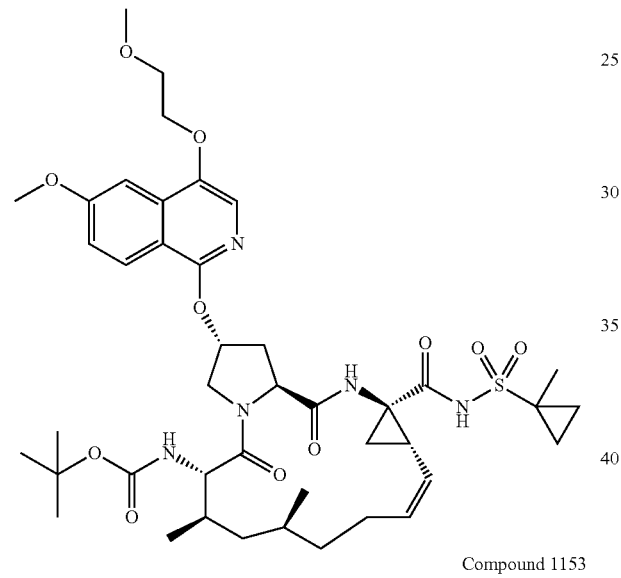

Compound 1153

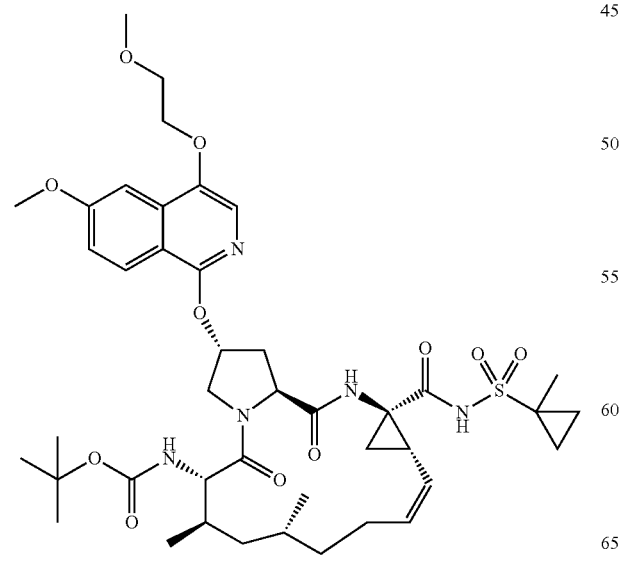

Compound 1154

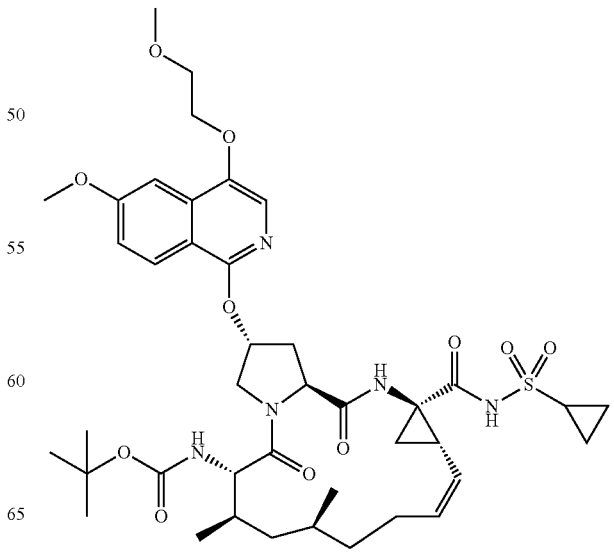

Compound 1155

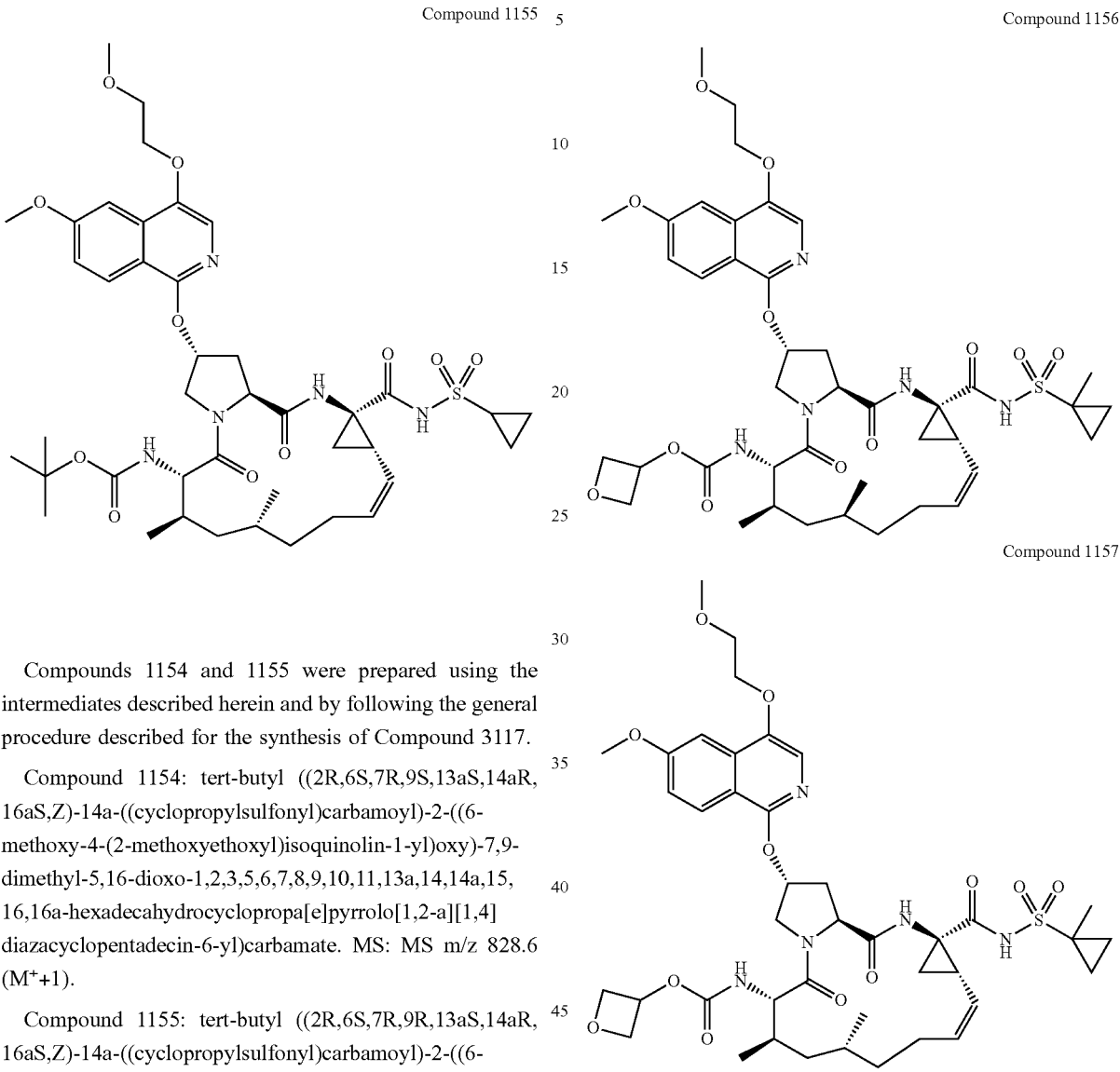

Compound 1156

Compound 1157

Compounds 1154 and 1155 were prepared using the intermediates described herein and by following the general procedure described for the synthesis of Compound 3117.

Compound 1154: tert-butyl ((2R,6S,7R,9S,13aS,14aR,16aS,Z)-14a-((cyclopropylsulfonyl)carbamoyl)-2-((6-methoxy-4-(2-methoxyethoxyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 828.6 (M$^+$+1).

Compound 1155: tert-butyl ((2R,6S,7R,9R,13aS,14aR,16aS,Z)-14a-((cyclopropylsulfonyl)carbamoyl)-2-((6-methoxy-4-(2-methoxyethoxyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.22 (s, 1H), 8.88 (d, J=18.6 Hz, 1H), 8.03 (d, J=9.2 Hz, 1H), 7.65 (s, 1H), 7.36 (d, J=2.1 Hz, 1H), 7.19-7.13 (m, 2H), 5.73 (br. s., 1H), 5.48 (br. s., 1H), 4.51 (br. s., 1H), 4.40 (br. s., 1H), 4.26 (d, J=4.9 Hz, 2H), 3.92 (s, 4H), 3.88 (d, J=7.6 Hz, 1H), 3.81-3.76 (m, 2H), 3.76-3.70 (m, 1H), 3.39 (s, 3H), 2.84 (br. s., 1H), 2.32-2.24 (m, 2H), 1.94-1.85 (m, 1H), 1.80 (br. s., 1H), 1.73 (br. s., 1H), 1.56 (br. s., 1H), 1.40 (br. s., 1H), 1.35 (br. s., 2H), 1.25 (br. s., 1H), 1.21-1.14 (m, 10H), 1.07 (br. s., 3H), 0.95-0.92 (m, J=6.7 Hz, 4H), 0.90-0.86 (m, J=6.1 Hz, 4H), 0.70 (br. s., 1H). MS: MS m/z 828.6 (M$^+$+1).

Preparation of Compounds 1156 and 1157

Compounds 1156 and 1157 were prepared using the intermediates described herein and by following the general procedure described for the synthesis of Compound 3117.

Compound 1156: oxetan-3-yl ((2R,6S,7R,9S,13aS,14aR,16aS,Z)-2-((6-methoxy-4-(2-methoxyethoxy)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 842.5 (M$^+$+1).

Compound 1157: oxetan-3-yl ((2R,6S,7R,9R,13aS,14aR,16aS,Z)-2-((6-methoxy-4-(2-methoxyethoxyl)isoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.04 (br. s., 1H), 9.10 (br. s., 1H), 7.98 (d, J=9.2 Hz, 1H), 7.82 (d, J=8.9 Hz, 1H), 7.64 (s, 1H), 7.39 (d, J=2.4 Hz, 1H), 7.28 (dd, J=9.2, 2.4 Hz, 1H), 5.76 (br. s., 1H), 5.52 (br. s., 1H), 4.99 (br. s., 1H), 4.81-4.78 (m, 1H), 4.54-4.45 (m, 2H), 4.38 (t, J=6.9 Hz, 2H), 4.31-4.26 (m, 3H), 4.10 (t, J=6.4 Hz, 1H), 3.93 (s, 3H), 3.93-3.88 (m, 2H), 3.81-3.78 (m, 2H), 3.76-3.69 (m, J=8.9 Hz, 1H), 3.40 (s, 3H), 2.75-2.66 (m, 1H), 2.59 (br. s., 1H), 2.29 (br. s., 2H), 1.92 (s, 1H), 1.84 (br. s., 1H), 1.67 (br. s., 1H), 1.60 (br. s., 1H), 1.55-1.47 (m, 1H), 1.40 (br. s., 4H), 1.37-1.32 (m, 1H), 1.26 (d, J=10.4 Hz, 2H), 1.14 (br. s., 1H), 0.93 (d, J=7.0 Hz, 3H), 0.89 (d, J=6.1 Hz, 4H), 0.74 (br. s., 1H). MS: MS m/z 842.5 ($M^+$+1).

Preparation of Compounds 1158 and 1159

Compound 1158

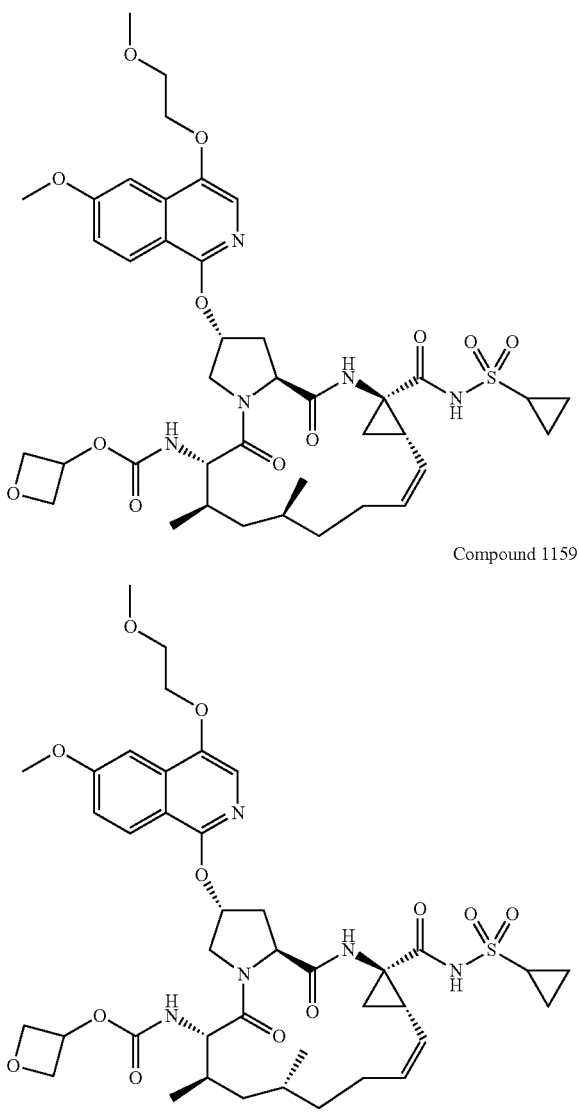

Compound 1159

Compounds 1158 and 1159 were prepared using the intermediates described herein and by following the general procedure described for the synthesis of Compound 3117.

Compound 1158: oxetan-3-yl ((2R,6S,7R,9S,13aS,14aR, 16aS,Z)-14a-((cyclopropylsulfonyl)carbamoyl)-2-((6-methoxy-4-(2-methoxyethoxyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 828.5 ($M^+$+1).

Compound 1159: oxetan-3-yl ((2R,6S,7R,9R,13aS,14aR, 16aS,Z)-14a-((cyclopropylsulfonyl)carbamoyl)-2-((6-methoxy-4-(2-methoxyethoxyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.18 (br. s., 1H), 8.97 (br. s., 1H), 7.98 (d, J=9.2 Hz, 1H), 7.82 (d, J=8.2 Hz, 1H), 7.64 (s, 1H), 7.38 (d, J=2.4 Hz, 1H), 7.28 (dd, J=9.0, 2.6 Hz, 1H), 5.75 (br. s., 1H), 5.52 (br. s., 1H), 5.06 (br. s., 1H), 4.82 (quin, J=5.8 Hz, 1H), 4.53 (t, J=6.7 Hz, 1H), 4.47-4.37 (m, 3H), 4.32-4.26 (m, 4H), 4.13-4.10 (m, 1H), 3.93 (s, 3H), 3.92-3.87 (m, 1H), 3.81-3.78 (m, 2H), 3.75-3.71 (m, 1H), 3.40 (s, 3H), 2.69 (br. s., 1H), 2.59 (br. s., 1H), 2.29 (t, J=9.6 Hz, 2H), 1.92 (s, 1H), 1.84 (br. s., 1H), 1.69 (br. s., 1H), 1.60 (br. s., 1H), 1.55 (br. s., 1H), 1.44 (br. s., 1H), 1.37 (br. s., 1H), 1.12 (br. s., 3H), 1.04-0.97 (m, 2H), 0.93 (d, J=6.7 Hz, 3H), 0.89 (d, J=6.1 Hz, 3H), 0.74 (br. s., 1H). MS: MS m/z 828.5 ($M^+$+1).

Preparation of Compounds 1160 and 1161

Compound 1160

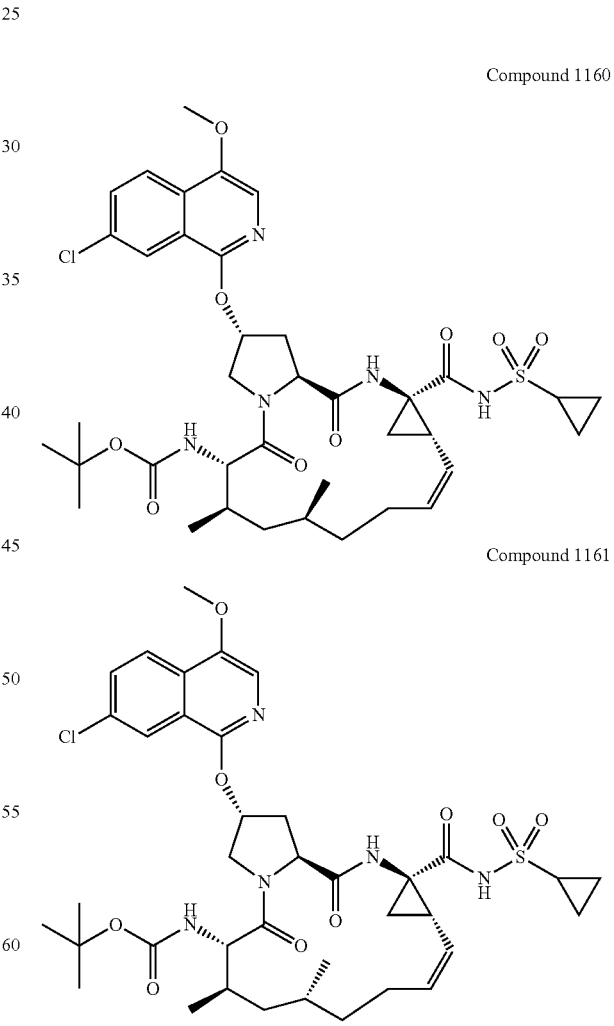

Compound 1161

Compounds 1160 and 1161 were prepared using the intermediates described herein and by following the general procedure described for the synthesis of Compound 3117.

Compound 1160: tert-butyl ((2R,6S,7R,9S,13aS,14aR,16aS,Z)-2-((7-chloro-4-methoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 788.4 (M$^+$+1).

Compound 1161: tert-butyl ((2R,6S,7R,9R,13aS,14aR,16aS,Z)-2-((7-chloro-4-methoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, CHLOROFORM-d) δ ppm 0.74-0.84 (m, 2H) 0.86 (d, J=6.41 Hz, 1H) 0.88-0.94 (m, 1H) 0.97 (t, J=5.95 Hz, 6H) 1.06-1.16 (m, 9H) 1.40-1.54 (m, 4H) 1.64-1.71 (m, 1H) 1.74-1.87 (m, 1H) 1.88-1.99 (m, 2H) 2.22-2.35 (m, 1H) 2.43-2.54 (m, 1H) 2.63-2.71 (m, 1H) 2.75 (q, J=8.65 Hz, 1H) 2.83-2.96 (m, 1H) 3.89 (t, J=9.92 Hz, 1H) 3.97-4.00 (m, 3H) 4.01 (d, J=3.66 Hz, 1H) 4.43-4.59 (m, 1H) 4.67 (d, J=10.99 Hz, 1H) 4.92 (t, J=9.31 Hz, 1H) 5.49-5.59 (m, 1H) 5.72-5.89 (m, 2H) 7.40-7.52 (m, 1H) 7.56-7.65 (m, 1H) 7.98 (d, J=1.83 Hz, 1H) 8.00-8.11 (m, 1H) 10.42-10.57 (m, 1H). MS: MS m/z 788.4 (M$^+$+1).

Preparation of Compound 1162 and 1163

Compounds 1162 and 1163 were prepared using the intermediates described herein and by following the general procedure described for the synthesis of Compound 3117.

Compound 1162: tert-butyl ((2R,6S,7R,9S,13aS,14aR,16aS,Z)-2-((3-chloro-6-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 820.4 (M$^+$+1).

Compound 1163: tert-butyl ((2R,6S,7R,9R,13aS,14aR,16aS,Z)-2-((3-chloro-6-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.26 (s, 1H), 8.99 (br. s., 1H), 8.03 (d, J=8.9 Hz, 1H), 7.46 (s, 1H), 7.32 (d, J=2.1 Hz, 1H), 7.20 (d, J=7.6 Hz, 1H), 7.12 (dd, J=9.2, 2.4 Hz, 1H), 5.75 (br. s., 1H), 5.51 (d, J=6.7 Hz, 1H), 5.02 (t, J=9.5 Hz, 1H), 4.76 (d, J=11.9 Hz, 1H), 4.65-4.55 (m, 1H), 4.55-4.36 (m, 2H), 3.94-3.87 (m, 4H), 3.70 (dd, J=10.4, 8.2 Hz, 1H), 2.71-2.59 (m, 2H), 2.39-2.25 (m, 2H), 1.91 (d, J=17.1 Hz, 1H), 1.80 (br. s., 1H), 1.69 (br. s., 1H), 1.53 (br. s., 3H), 1.47-1.31 (m, 2H), 1.31-1.19 (m, 3H), 1.15 (s, 9H), 1.08 (d, J=7.0 Hz, 1H), 0.94 (d, J=7.0 Hz, 3H), 0.89 (d, J=6.4 Hz, 3H), 0.74 (t, J=12.1 Hz, 1H). MS: MS m/z 820.4 (M$^+$+1).

Preparation of Compound 1164 and 1165

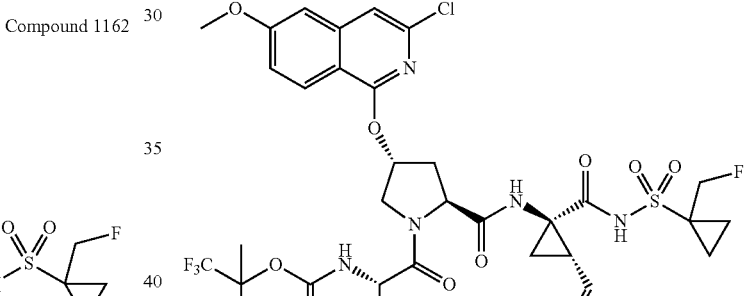

Compound 1162

Compound 1163

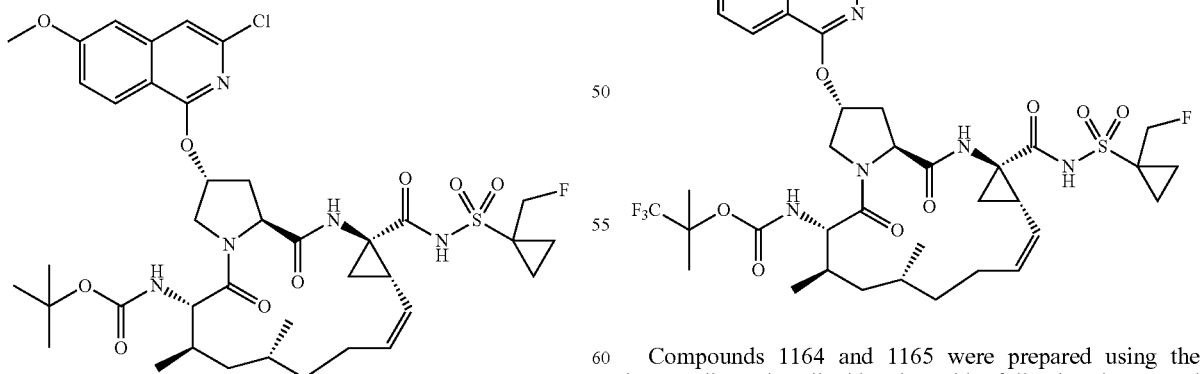

Compound 1164

Compound 1165

Compounds 1164 and 1165 were prepared using the intermediates described herein and by following the general procedure described for the synthesis of Compound 3117.

Compound 1164: 1,1,1-trifluoro-2-methylpropan-2-yl ((2R,6S,7R,9S,13aS,14aR,16aS,Z)-2-((3-chloro-6-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a- hexadecahydrocyclopropa[e]pyrrolo[1,2-a][1,4]diazacyclopentadecin-6-yl)carbamate. MS: MS m/z 874.4 (M$^+$+1).

Compound 1165: 1,1,1-trifluoro-2-methylpropan-2-yl ((2R,6S,7R,9R,13aS,14aR,16aS,Z)-2-((3-chloro-6-methoxyisoquinolin-1-yl)oxy)-14a-(((1-(fluoromethyl)cyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.26 (br. s., 1H), 9.03 (br. s., 1H), 8.19 (br. s., 1H), 8.00 (d, J=9.2 Hz, 1H), 7.47 (br. s., 1H), 7.33 (s, 1H), 7.17 (dd, J=9.2, 2.4 Hz, 1H), 5.75 (br. s., 1H), 5.52 (br. s., 1H), 5.03 (br. s., 1H), 4.68 (br. s., 1H), 4.57 (br. s., 1H), 4.47 (br. s., 2H), 3.93-3.87 (m, 4H), 3.69 (br. s., 1H), 3.19-3.13 (m, 1H), 2.65 (br. s., 1H), 2.32 (d, J=11.0 Hz, 2H), 1.84 (br. s., 2H), 1.71 (br. s., 1H), 1.54 (br. s., 2H), 1.37 (s, 3H), 1.27 (br. s., 6H), 1.18 (dd, J=14.8, 7.5 Hz, 2H), 1.11 (br. s., 3H), 0.93 (d, J=6.1 Hz, 3H), 0.89 (br. s., 3H), 0.74 (br. s., 1H). MS: MS m/z 874.4 (M$^+$+1).

Preparation of Compounds 1166 and 1167

Compound 1166

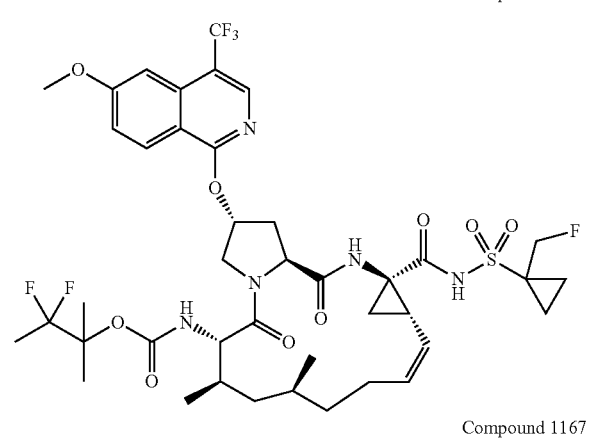

Compound 1167

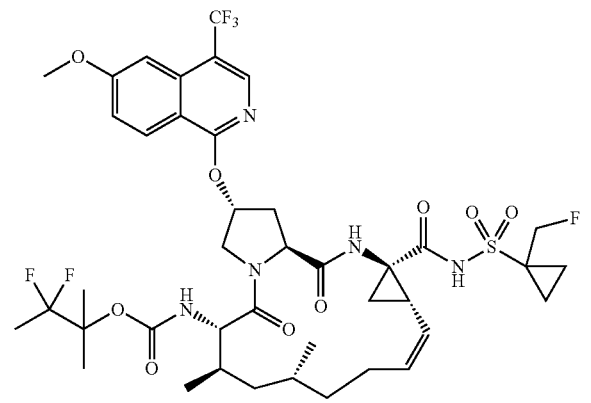

Compounds 1166 and 1167 were prepared using the intermediates described herein and by following the general procedure described for the synthesis of Compound 3117.

Compound 1166: 3,3-difluoro-2-methylbutan-2-yl ((2R,6S,7R,9S,13aS,14aR,16aS,Z)-14a-(((1-(fluoromethyl)cyclopropyl)sulfonyl)carbamoyl)-2-((6-methoxy-4-(trifluoromethyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 904.5 (M$^+$+1).

Compound 1167: 3,3-difluoro-2-methylbutan-2-yl ((2R,6S,7R,9R,13aS,14aR,16aS,Z)-14a-(((1-(fluoromethyl)cyclopropyl)sulfonyl)carbamoyl)-2-((6-methoxy-4-(trifluoromethyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.30 (s, 1H), 9.09 (s, 1H), 8.47 (s, 1H), 8.18 (d, J=9.2 Hz, 1H), 7.59 (d, J=8.2 Hz, 1H), 7.37 (dd, J=9.2, 2.1 Hz, 1H), 7.22 (s, 1H), 5.86 (br. s., 1H), 5.55-5.49 (m, 1H), 4.99 (t, J=10.1 Hz, 1H), 4.89-4.73 (m, 1H), 4.67 (d, J=13.1 Hz, 1H), 4.62-4.51 (m, 2H), 3.95 (s, 3H), 3.91 (br. s., 1H), 3.66-3.62 (m, 1H), 2.67 (d, J=9.5 Hz, 2H), 2.41-2.27 (m, 3H), 1.93-1.86 (m, 1H), 1.79 (br. s., 1H), 1.66 (br. s., 1H), 1.59-1.48 (m, 7H), 1.43 (br. s., 1H), 1.36 (d, J=14.3 Hz, 1H), 1.25 (d, J=13.4 Hz, 2H), 1.15 (s, 3H), 0.94 (d, J=7.0 Hz, 3H), 0.88 (d, J=6.1 Hz, 3H), 0.77 (s, 3H), 0.76-0.70 (m, 1H). MS: MS m/z 904.5 (M$^+$+1).

Preparation of Compounds 1168 and 1169

Compound 1168

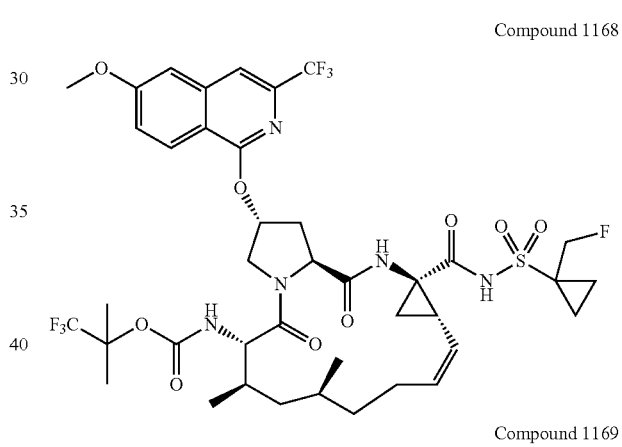

Compound 1169

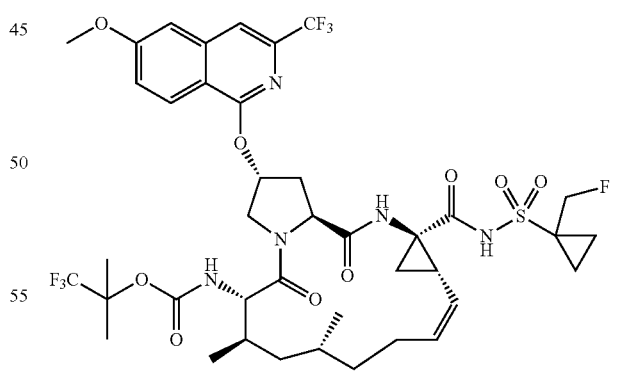

Compounds 1168 and 1169 were prepared using the intermediates described herein and by following the general procedure described for the synthesis of Compound 3117.

Compound 1168: 1,1,1-trifluoro-2-methylpropan-2-yl ((2R,6S,7R,9S,13aS,14aR,16aS,Z)-14a-(((1-(fluoromethyl)cyclopropyl)sulfonyl)carbamoyl)-2-((6-methoxy-3-(trifluoromethyl)isoquinolin-1-yl)oxy)-7,9-dimethyl-5,16-dioxo-1,2,3,5,6,7,8,9,10,11,13a,14,14a,15,16,16a- hexadecahydrocyclopropa[e]pyrrolo[1,2-a][1,4]diazacyclopentadecin-6-yl)carbamate. MS: MS m/z 908.45 (M++1).

Compound 1169: 1,1,1-trifluoro-2-methylpropan-2-yl ((2R,6S,7R,9R,13aS,14aR,16aS,Z)-14a-(((1-(fluoromethyl)cyclopropyl)sulfonyl)carbamoyl)-2-((6-methoxy-3-(trifluoromethyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.26 (s, 1H), 9.02 (s, 1H), 8.11 (d, J=9.2 Hz, 1H), 7.93 (s, 1H), 7.85 (d, J=7.9 Hz, 1H), 7.60 (d, J=2.1 Hz, 1H), 7.35 (dd, J=9.0, 2.3 Hz, 1H), 5.82 (br. s., 1H), 5.55-5.49 (m, 1H), 5.02 (t, J=10.1 Hz, 1H), 4.90-4.70 (m, 1H), 4.59 (t, J=11.9 Hz, 2H), 4.54-4.48 (m, 1H), 3.96-3.91 (m, 4H), 3.69 (dd, J=10.4, 7.9 Hz, 1H), 2.69-2.61 (m, 2H), 2.39-2.26 (m, 2H), 1.91 (d, J=15.0 Hz, 1H), 1.85 (d, J=6.1 Hz, 1H), 1.70 (dd, J=13.1, 7.0 Hz, 1H), 1.58-1.49 (m, 4H), 1.42 (br. s., 1H), 1.40-1.36 (m, 4H), 1.30-1.20 (m, 2H), 1.15 (d, J=12.5 Hz, 1H), 1.11 (s, 3H), 0.94 (d, J=6.7 Hz, 3H), 0.90 (d, J=6.4 Hz, 3H), 0.76 (t, J=12.8 Hz, 1H). MS: MS m/z 908.45 (M++1).

Preparation of Compounds 1170 and 1171 hexadecahydrocyclopropa[e]pyrrolo[1,2-a][1,4]diazacyclopentadecin-6-yl)carbamate. MS: MS m/z 904.5 (M++1).

Compound 1171: 3,3-difluoro-2-methylbutan-2-yl ((2R,6S,7R,9R,13aS,14aR,16aS,Z)-14a-(((1-(fluoromethyl)cyclopropyl)sulfonyl)carbamoyl)-2-((6-methoxy-3-(trifluoromethyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.27 (s, 1H), 9.00 (s, 1H), 8.11 (d, J=9.2 Hz, 1H), 7.93 (s, 1H), 7.63 (d, J=8.2 Hz, 1H), 7.60 (d, J=2.4 Hz, 1H), 7.33 (dd, J=9.3, 2.3 Hz, 1H), 5.82 (br. s., 1H), 5.54-5.49 (m, 1H), 5.02 (t, J=9.5 Hz, 1H), 4.90-4.71 (m, 1H), 4.59 (t, J=10.5 Hz, 2H), 4.52-4.47 (m, 1H), 3.95 (br. s., 1H), 3.94 (s, 3H), 3.72-3.68 (m, 1H), 3.18 (d, J=5.2 Hz, 1H), 2.71-2.61 (m, 2H), 2.39-2.27 (m, 2H), 1.93-1.87 (m, 1H), 1.82 (d, J=6.7 Hz, 1H), 1.72-1.66 (m, 1H), 1.62 (s, 1H), 1.58 (s, 1H), 1.56 (br. s., 1H), 1.54 (br. s., 3H), 1.44 (br. s., 1H), 1.37 (br. s., 1H), 1.28 (s, 3H), 1.23 (br. s., 2H), 1.21-1.13 (m, 1H), 1.01 (s, 3H), 0.94 (d, J=7.0 Hz, 3H), 0.90 (d, J=6.4 Hz, 3H), 0.77 (t, J=12.7 Hz, 1H). MS: MS m/z 904.5 (M++1).

Preparation of Compound 1172 and 1173

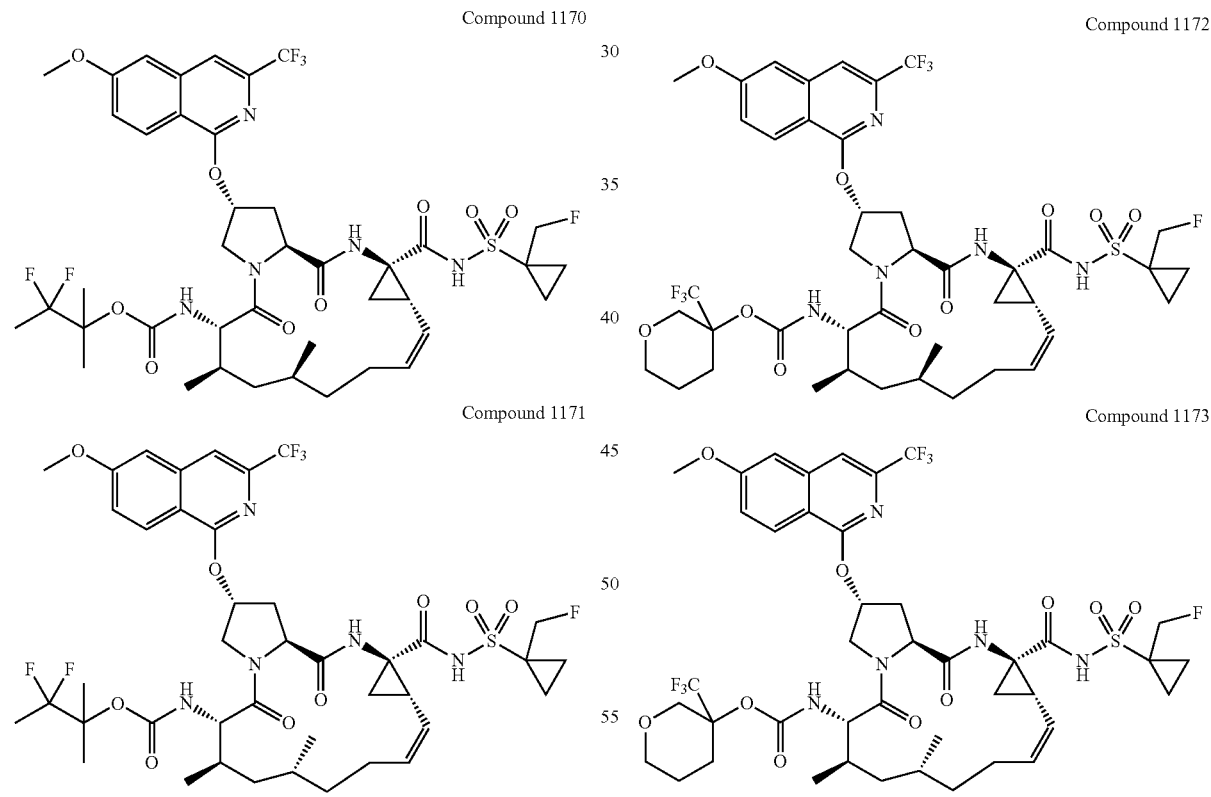

Compound 1170

Compound 1171

Compound 1172

Compound 1173

Compounds 1170 and 1171 were prepared using the intermediates described herein and by following the general procedure described for the synthesis of Compound 3117.

Compound 1170: 3,3-difluoro-2-methylbutan-2-yl ((2R,6S,7R,9S,13aS,14aR,16aS,Z)-14a-(((1-(fluoromethyl)cyclopropyl)sulfonyl)carbamoyl)-2-((6-methoxy-3-(trifluoromethyl)isoquinolin-1-yl)oxy)-7,9-dimethyl-5,16-dioxo-1,2,3,5,6,7,8,9,10,11,13a,14,14a,15,16,16a-

Compounds 1172 and 1173 were prepared using the intermediates described herein and by following the general procedure described for the synthesis of Compound 3117.

Compound 1172: 3-(trifluoromethyl)tetrahydro-2H-pyran-3-yl ((2R,6S,7R,9S,13aS,14aR,16aS,Z)-14a-(((1-(fluoromethyl)cyclopropyl)sulfonyl)carbamoyl)-2-((6-methoxy-3-(trifluoromethyl)isoquinolin-1-yl)oxy)-7,9-dimethyl-5,16-dioxo-1,2,3,5,6,7,8,9,10,11,13a,14,14a,15, 16,16a-hexadecahydrocyclopropa[e]pyrrolo[1,2-a][1,4]diazacyclopentadecin-6-yl)carbamate. MS: MS m/z 950.5 (M⁺+1).

Compound 1173: 3-(trifluoromethyl)tetrahydro-2H-pyran-3-yl ((2R,6S,7R,9R,13aS,14aR,16aS,Z)-14a-(((1-(fluoromethyl)cyclopropyl)sulfonyl)carbamoyl)-2-((6-methoxy-3-(trifluoromethyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. Diastereomer 1 HNMR: 1H NMR (500 MHz, DMSO-d6) Shift 11.26 (s, 1H), 9.01 (s, 1H), 8.08 (d, J=9.2 Hz, 1H), 7.97 (d, J=8.2 Hz, 1H), 7.93 (s, 1H), 7.60 (d, J=2.4 Hz, 1H), 7.29 (dd, J=9.2, 2.4 Hz, 1H), 5.82 (br. s., 1H), 5.55-5.49 (m, 1H), 5.02 (t, J=9.6 Hz, 1H), 4.86 (d, J=11.3 Hz, 1H), 4.64-4.38 (m, 3H), 4.15-4.10 (m, 1H), 3.97 (d, J=11.3 Hz, 1H), 3.94 (s, 3H), 3.77-3.72 (m, 1H), 3.56 (d, J=11.0 Hz, 1H), 3.49 (d, J=11.6 Hz, 1H), 3.40 (t, J=10.7 Hz, 1H), 2.70-2.60 (m, 2H), 2.38-2.27 (m, 2H), 2.14-2.08 (m, 1H), 1.90 (d, J=19.5 Hz, 2H), 1.77-1.68 (m, 2H), 1.58-1.50 (m, 5H), 1.43 (br. s., 1H), 1.41-1.29 (m, 2H), 1.29-1.20 (m, 2H), 1.20-1.10 (m, 1H), 0.94 (d, J=6.7 Hz, 3H), 0.91 (d, J=6.4 Hz, 3H), 0.77 (t, J=13.1 Hz, 1H). Diastereomer 2 HNMR: 1H NMR (500 MHz, DMSO-d6) Shift 11.25 (s, 1H), 8.97 (s, 1H), 8.10 (d, J=9.2 Hz, 1H), 7.95 (d, J=7.9 Hz, 1H), 7.93 (s, 1H), 7.59 (d, J=2.1 Hz, 1H), 7.29 (dd, J=8.9, 2.4 Hz, 1H), 5.80 (br. s., 1H), 5.52 (d, J=6.4 Hz, 1H), 5.03 (t, J=10.1 Hz, 1H), 4.76 (d, J=11.3 Hz, 1H), 4.61-4.42 (m, 3H), 4.10 (d, J=13.1 Hz, 1H), 3.96 (br. s., 1H), 3.94 (s, 3H), 3.79-3.74 (m, 1H), 3.59 (d, J=11.0 Hz, 1H), 3.49 (d, J=11.9 Hz, 1H), 3.44-3.39 (m, 1H), 2.71-2.60 (m, 2H), 2.39-2.26 (m, 2H), 2.16 (d, J=12.2 Hz, 1H), 1.96-1.83 (m, 2H), 1.83-1.76 (m, 1H), 1.75-1.63 (m, 2H), 1.53 (br. s., 3H), 1.44 (br. s., 2H), 1.36 (d, J=17.7 Hz, 1H), 1.24 (d, J=15.0 Hz, 2H), 1.21-1.09 (m, 2H), 0.94 (d, J=6.7 Hz, 3H), 0.92 (d, J=6.1 Hz, 3H), 0.77 (t, J=12.7 Hz, 1H). MS: MS m/z 950.5 (M⁺+1).

Preparation of Compounds 1174 and 1175

Compound 1175

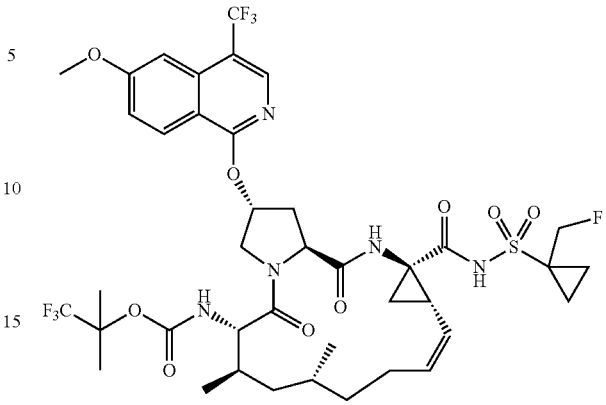

Compounds 1174 and 1175 were prepared using the intermediates described herein and by following the general procedure described for the synthesis of Compound 3117.

Compound 1174: 1,1,1-trifluoro-2-methylpropan-2-yl ((2R,6S,7R,9S,13aS,14aR,16aS,Z)-14a-(((1-(fluoromethyl)cyclopropyl)sulfonyl)carbamoyl)-2-((6-methoxy-4-(trifluoromethyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 908.45 (M⁺+1).

Compound 1175: 1,1,1-trifluoro-2-methylpropan-2-yl ((2R,6S,7R,9R,13aS,14aR,16aS,Z)-14a-(((1-(fluoromethyl)cyclopropyl)sulfonyl)carbamoyl)-2-((6-methoxy-4-(trifluoromethyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, METHANOL-d4)

Shift 8.36 (s, 1H), 8.24 (d, J=9.2 Hz, 1H), 7.30 (s, 1H), 7.26 (dd, J=9.2, 2.4 Hz, 1H), 5.91 (br. s., 1H), 5.57 (td, J=10.0, 5.6 Hz, 1H), 5.13 (br. s., 1H), 4.86-4.74 (m, 2H), 4.68-4.58 (m, 2H), 4.02 (dd, J=11.7, 3.2 Hz, 1H), 3.96 (s, 3H), 3.77 (d, J=10.7 Hz, 1H), 2.76 (dd, J=14.0, 7.0 Hz, 1H), 2.62 (q, J=8.9 Hz, 1H), 2.48 (ddd, J=14.1, 10.3, 4.0 Hz, 1H), 2.43-2.32 (m, 1H), 1.99-1.89 (m, 1H), 1.89-1.82 (m, 1H), 1.82-1.74 (m, 1H), 1.70 (dd, J=8.4, 5.3 Hz, 1H), 1.68-1.59 (m, 2H), 1.56 (dd, J=9.5, 5.2 Hz, 1H), 1.51-1.39 (m, 2H), 1.29 (s, 3H), 1.28-1.08 (m, 3H), 1.00 (d, J=7.0 Hz, 3H), 0.97 (d, J=6.4 Hz, 3H), 0.87 (s, 3H), 0.81 (t, J=11.4 Hz, 1H). MS: MS m/z 908.45 (M⁺+1).

Preparation of Compounds 1176 and 1177

Compound 1176

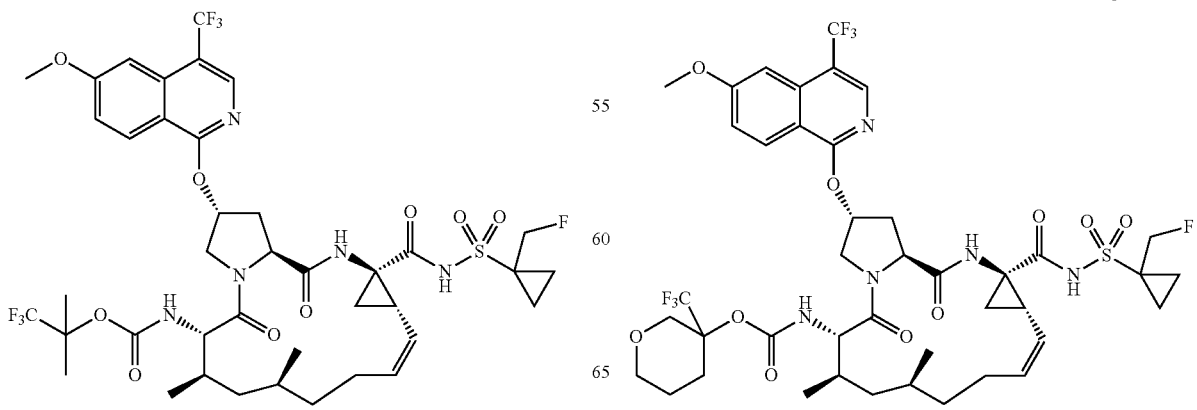

Compound 1177

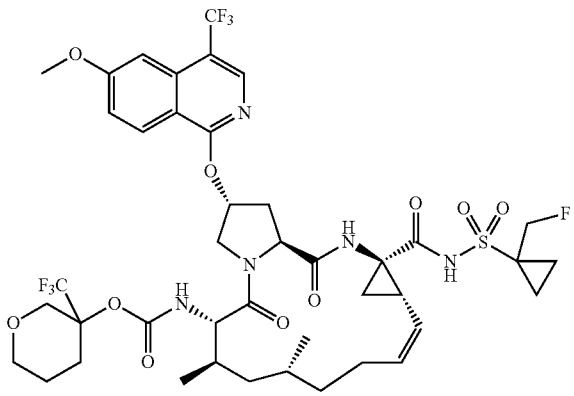

Compounds 1176 and 1177 were prepared using the intermediates described herein and by following the general procedure described for the synthesis of Compound 3117.

Compound 1176: 3-(trifluoromethyl)tetrahydro-2H-pyran-3-yl ((2R,6S,7R,9S,13aS,14aR,16aS,Z)-14a-(((1-(fluoromethyl)cyclopropyl)sulfonyl)carbamoyl)-2-((6-methoxy-4-(trifluoromethyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 950.5 (M$^+$+1).

Compound 1177: 3-(trifluoromethyl)tetrahydro-2H-pyran-3-yl ((2R,6S,7R,9R,13aS,14aR,16aS,Z)-14a-(((1-(fluoromethyl)cyclopropyl)sulfonyl)carbamoyl)-2-((6-methoxy-4-(trifluoromethyl)isoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. Diastereomer 1 HNMR: 1H NMR (500 MHz, METHANOL-d4) Shift 8.34 (s, 1H), 8.23 (d, J=9.2 Hz, 1H), 7.29 (s, 1H), 7.24 (dd, J=9.2, 2.1 Hz, 1H), 5.92 (br. s., 1H), 5.57 (td, J=10.1, 5.6 Hz, 1H), 5.10 (br. s., 1H), 4.79-4.75 (m, 2H), 4.65-4.57 (m, 2H), 4.54 (d, J=11.0 Hz, 1H), 4.16-4.10 (m, 1H), 4.04 (dd, J=11.6, 3.4 Hz, 1H), 3.96 (s, 3H), 3.83 (d, J=10.7 Hz, 1H), 3.63-3.56 (m, 1H), 3.42-3.33 (m, 2H), 2.75 (dd, J=14.0, 7.0 Hz, 1H), 2.65 (q, J=8.9 Hz, 1H), 2.47 (ddd, J=14.0, 10.2, 4.1 Hz, 1H), 2.44-2.34 (m, 1H), 2.06 (d, J=15.0 Hz, 1H), 1.99-1.85 (m, 2H), 1.81 (dd, J=13.3, 6.0 Hz, 1H), 1.72-1.67 (m, 1H), 1.67-1.60 (m, 3H), 1.59-1.51 (m, 2H), 1.50-1.41 (m, 2H), 1.33-1.27 (m, 1H), 1.27-1.18 (m, 2H), 1.18-1.12 (m, 1H), 1.01 (t, J=5.8 Hz, 6H), 0.83 (t, J=11.7 Hz, 1H). Diastereomer 2 HNMR: 1H NMR (500 MHz, METHANOL-d4) Shift 8.33 (s, 1H), 8.23 (d, J=9.2 Hz, 1H), 7.29 (s, 1H), 7.25 (dd, J=9.2, 2.4 Hz, 1H), 5.94-5.90 (m, 1H), 5.55 (td, J=10.1, 5.8 Hz, 1H), 5.03 (br. s., 1H), 4.80-4.70 (m, 2H), 4.64-4.58 (m, 2H), 4.52 (d, J=11.3 Hz, 1H), 4.05 (ddd, J=11.7, 5.6, 2.7 Hz, 2H), 3.96 (s, 3H), 3.87 (d, J=11.0 Hz, 1H), 3.61 (d, J=10.1 Hz, 1H), 3.39-3.33 (m, 1H), 2.75 (dd, J=13.9, 6.9 Hz, 1H), 2.67 (q, J=9.1 Hz, 1H), 2.45 (ddd, J=14.1, 10.3, 4.0 Hz, 1H), 2.42-2.34 (m, 1H), 2.21 (br. s., 1H), 1.93-1.82 (m, 2H), 1.82-1.74 (m, 1H), 1.74-1.67 (m, 3H), 1.67-1.60 (m, 2H), 1.54 (dd, J=9.5, 5.5 Hz, 1H), 1.49 (br. s., 1H), 1.45-1.35 (m, 2H), 1.25-1.14 (m, 3H), 1.00 (t, J=6.6 Hz, 6H), 0.83 (t, J=11.6 Hz, 1H). MS: MS m/z 950.5 (M$^+$+1).

Preparation of Compounds 1178 and 1179

Compound 1178

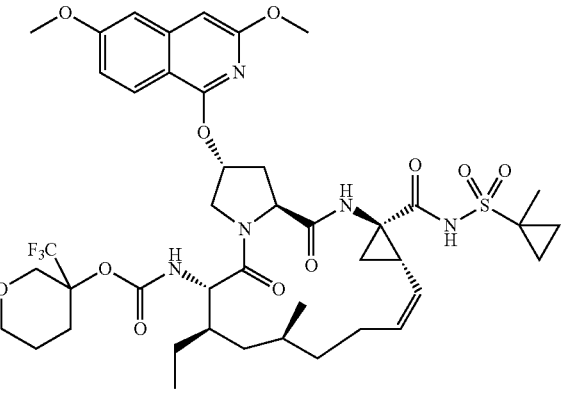

Compound 1179

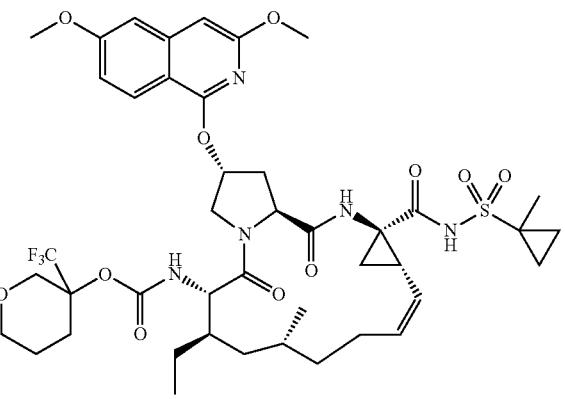

Compounds 1178 and 1179 were prepared using the intermediates described herein and by following the general procedure described for the synthesis of Compound 3117.

Compound 1178: 3-(trifluoromethyl)tetrahydro-2H-pyran-3-yl ((2R,6S,7R,9S,13aS,14aR,16aS,Z)-2-((3,6-dimethoxyisoquinolin-1-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 908.8 (M$^+$+1).

Compound 1179: 3-(trifluoromethyl)tetrahydro-2H-pyran-3-yl ((2R,6S,7R,9R,13aS,14aR,16aS,Z)-2-((3,6-dimethoxyisoquinolin-1-yl)oxy)-7-ethyl-9-methyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. Diastereomer 1: 1H NMR (500 MHz, METHANOL-d4) Shift 7.93 (d, J=8.9 Hz, 1H), 7.04-6.97 (m, 1H), 6.84 (dd, J=9.2, 2.1 Hz, 1H), 6.55 (s, 1H), 5.85 (br. s., 1H), 5.62-5.55 (m, 1H), 5.06 (br. s., 1H), 4.71 (d, J=11.3 Hz, 1H), 4.60 (dd, J=9.6, 7.2 Hz, 1H), 4.17-4.12 (m, 2H), 4.07 (dd, J=11.4, 3.5 Hz, 1H), 3.97 (s, 3H), 3.89 (s, 3H), 3.59 (d, J=11.3 Hz, 1H), 3.45 (d, J=11.9 Hz, 1H), 3.44-3.38 (m, 1H), 2.78-2.66 (m, 2H), 2.48-2.40 (m, 2H), 2.27 (d, J=14.0 Hz, 1H), 2.05-1.92 (m, 2H), 1.77-1.70 (m, 2H), 1.66-1.52 (m, 3H), 1.51 (s, 3H), 1.46 (br. s., 2H), 1.41 (dd, J=9.6, 5.3 Hz, 2H), 1.34-1.21 (m, 2H), 1.12 (t, J=13.1 Hz, 1H), 1.00 (d, J=7.0 Hz, 3H), 0.85 (t, J=7.3 Hz, 6H), 0.79 (d, J=8.2 Hz, 1H). Diastereomer 2: 1H NMR (500 MHz, METHANOL-d4) Shift 7.94 (d, J=9.2 Hz, 1H), 7.01 (d, J=2.4 Hz, 1H), 6.85 (dd, J=9.0, 2.3 Hz, 1H), 6.55 (s, 1H), 5.84 (br. s., 1H), 5.62-5.49 (m, 1H), 5.05 (br. s., 1H), 4.70 (d, J=11.6 Hz, 1H), 4.56 (dd, J=9.8, 7.3 Hz, 1H), 4.20-4.13 (m, 2H), 4.10-4.06 (m, 1H), 3.99-3.92 (m, 3H), 3.90 (s, 3H), 3.70-3.65 (m, 1H), 3.53 (d, J=11.9 Hz, 1H), 3.48-3.42 (m, 1H), 2.76 (dd, J=13.9, 7.2 Hz, 1H), 2.67 (br. s., 1H), 2.43 (ddd, J=13.9, 9.9, 4.3 Hz, 2H), 2.35 (d, J=13.7 Hz, 1H), 2.00 (t, J=11.4 Hz, 1H), 1.96-1.90 (m, 1H), 1.90-1.70 (m, 2H), 1.67-1.50 (m, 3H), 1.49 (s, 3H), 1.43-1.34 (m, 3H), 1.34-1.27 (m, 1H), 1.26-1.08 (m, 3H), 0.98 (d, J=7.0 Hz, 3H), 0.86 (t, J=7.5 Hz, 6H), 0.78 (d, J=7.9 Hz, 1H). MS: MS m/z 908.8 (M$^+$+1).

Preparation of Compound 1180

Compound 1180

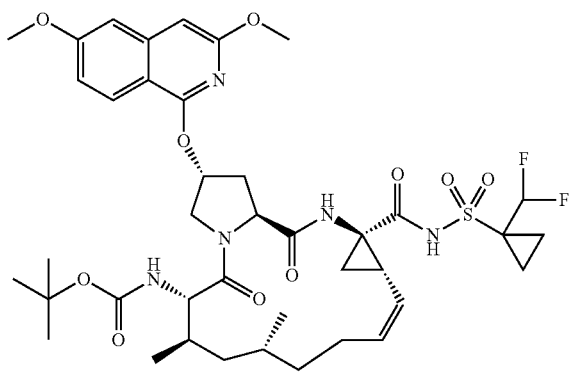

Compound 1180 was prepared using the intermediates described herein and by following the general procedure described for the synthesis of Compound 3117.

Compound 1180: tert-butyl ((2R,6S,7R,9R,13aS,14aR,16aS,Z)-14a-(((1-(difluoromethyl)cyclopropyl)sulfonyl)carbamoyl)-2-((3,6-dimethoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.53 (s, 1H), 9.00 (s, 1H), 7.92 (d, J=9.2 Hz, 1H), 7.21 (d, J=7.6 Hz, 1H), 7.14 (s, 1H), 6.86 (dd, J=9.2, 2.1 Hz, 1H), 6.63-6.61 (m, 1H), 6.60-6.33 (m, 1H), 5.76 (br. s., 1H), 5.51 (d, J=6.7 Hz, 1H), 5.03 (t, J=9.8 Hz, 1H), 4.58 (d, J=10.7 Hz, 1H), 4.45-4.40 (m, 1H), 3.95-3.91 (m, 2H), 3.90 (s, 3H), 3.87 (s, 3H), 3.76-3.71 (m, 1H), 2.73-2.60 (m, 2H), 2.34-2.25 (m, 2H), 1.92 (d, J=8.2 Hz, 1H), 1.82 (br. s., 1H), 1.69 (br. s., 1H), 1.56 (d, J=8.2 Hz, 4H), 1.43 (br. s., 1H), 1.37 (br. s., 3H), 1.21 (s, 9H), 1.16 (d, J=13.7 Hz, 1H), 1.09 (br. s., 1H), 0.93 (d, J=6.7 Hz, 3H), 0.89 (d, J=6.4 Hz, 3H), 0.74 (t, J=11.6 Hz, 1H). MS: MS m/z 834.6 (M$^+$+1).

Preparation of Compound 1181

Compound 1181

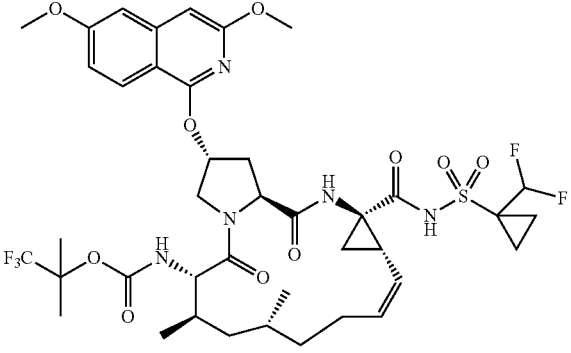

Compound 1181 was prepared using the intermediates described herein and by following the general procedure described for the synthesis of Compound 3117.

Compound 1181: 1,1,1-trifluoro-2-methylpropan-2-yl ((2R,6S,7R,9R,13aS,14aR,16aS,Z)-14a-(((1-(difluoromethyl)cyclopropyl)sulfonyl)carbamoyl)-2-((3,6-dimethoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.52 (s, 1H), 9.04 (s, 1H), 7.89 (d, J=9.2 Hz, 1H), 7.85 (d, J=7.6 Hz, 1H), 7.16 (d, J=1.8 Hz, 1H), 6.90 (dd, J=8.9, 2.1 Hz, 1H), 6.63 (s, 1H), 6.60-6.35 (m, 1H), 5.77 (br. s., 1H), 5.52 (d, J=6.7 Hz, 1H), 5.04 (t, J=9.9 Hz, 1H), 4.53 (d, J=11.6 Hz, 1H), 4.49-4.45 (m, 1H), 3.96-3.91 (m, 1H), 3.90 (s, 3H), 3.87 (s, 3H), 3.75-3.71 (m, 1H), 2.69-2.61 (m, 2H), 2.35-2.27 (m, 2H), 1.92 (s, 1H), 1.85 (d, J=5.8 Hz, 1H), 1.69 (br. s., 1H), 1.58 (d, J=5.2 Hz, 4H), 1.50-1.45 (m, 1H), 1.41 (s, 3H), 1.37 (br. s., 3H), 1.20 (s, 3H), 1.15 (br. s., 1H), 0.93 (d, J=7.0 Hz, 3H), 0.90 (d, J=6.4 Hz, 3H), 0.75 (t, J=12.8 Hz, 1H). MS: MS m/z 888.5 (M$^+$+1).

Preparation of Compound 1182

Compound 1182

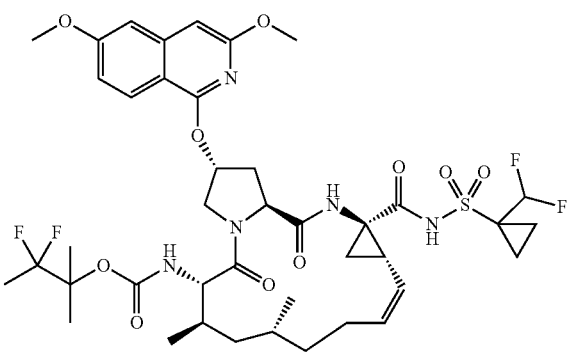

Compound 1182 was prepared using the intermediates described herein and by following the general procedure described for the synthesis of Compound 3117.

Compound 1182: 3,3-difluoro-2-methylbutan-2-yl ((2R,6S,7R,9R,13aS,14aR,16aS,Z)-14a-(((1-(difluoromethyl)cyclopropyl)sulfonyl)carbamoyl)-2-((3,6-dimethoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. 1H NMR (500 MHz, DMSO-d6) Shift 11.53 (s, 1H), 9.01 (s, 1H), 7.89 (d, J=9.2 Hz, 1H), 7.64 (d, J=8.2 Hz, 1H), 7.16 (d, J=2.1 Hz, 1H), 6.89 (dd, J=9.0, 2.3 Hz, 1H), 6.63 (s, 1H), 6.60-6.34 (m, 1H), 5.77 (br. s., 1H), 5.52 (d, J=6.1 Hz, 1H), 5.04 (t, J=10.1 Hz, 1H), 4.53 (d, J=11.0 Hz, 1H), 4.48-4.43 (m, 1H), 3.96-3.91 (m, 1H), 3.90 (s, 3H), 3.87 (s, 3H), 3.76-3.72 (m, 1H), 2.71 (d, J=9.2 Hz, 1H), 2.64 (d, J=11.0 Hz, 1H), 2.35-2.26 (m, 2H), 1.92 (d, J=8.2 Hz, 1H), 1.83 (d, J=6.1 Hz, 1H), 1.68 (br. s., 1H), 1.64 (s, 1H), 1.61-1.54 (m, 6H), 1.45 (br. s., 1H), 1.37 (br. s., 3H), 1.32 (s, 3H), 1.21-1.14 (m, 1H), 1.12 (s, 3H), 0.94 (d, J=6.7 Hz, 3H), 0.90 (d, J=6.4 Hz, 3H), 0.76 (t, J=12.2 Hz, 1H). MS: MS m/z 884.5 (M$^+$+1).

Preparation of Compound 2001 and Compound 2002

Compound 2001

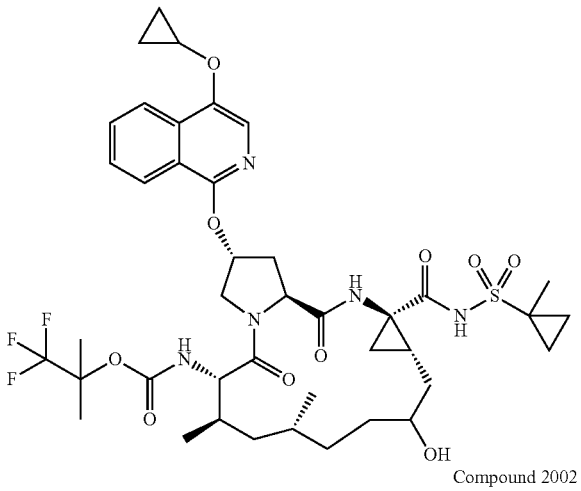

Compound 2002

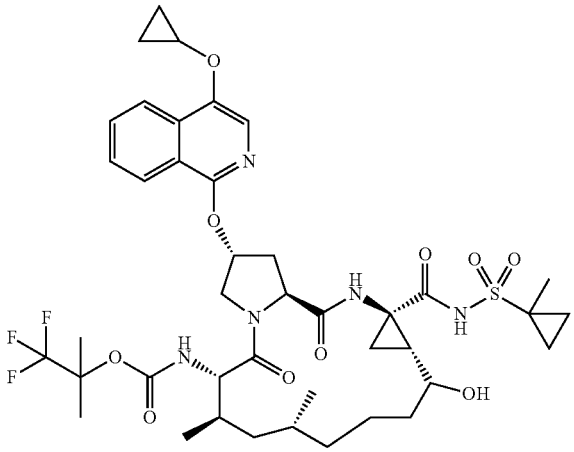

To a 2 dram vial equipped with a stir bar was added 1,1,1-trifluoro-2-methylpropan-2-yl ((2R,6S,7R,9R,13aS,14aR,16aS,Z)-2-((4-cyclopropoxyisoquinolin-1-yl)oxy)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate, Compound 4056 (200 mg, 0.236 mmol) and THF (0.8 mL). The solution was cooled to 0° C. To the stirred solution was added borane in THF (0.7 mL, 1.0 M). The solution was allowed to warm to room temperature with stirring for 1 h. The solution was cooled to 0° C. and to the solution was added potassium acetate (225 mg, 2.29 mmol). To the solution was added dropwise hydrogen peroxide (0.75 mL, 30% wt. aq.). The mixture was allowed to warm to room temperature with stirring for 17 h. The mixture was transferred to a 125 mL separatory funnel and was diluted with EtOAc (50 mL). The organic solution was washed with water:brine (15 mL:15 mL); dried over MgSO4; filtered; then concentrated in vacuo. The resulting residue was subjected to HPLC purification as follows: Column=Waters XBridge C18, 19×200 mm, 5-μm particles; Guard Column=Waters XBridge C18, 19×10 mm, 5-μm particles; Mobile Phase A=water with 20-mM ammonium acetate; Mobile Phase B=95:5 acetonitrile:water with 20-mM ammonium acetate; Gradient=55-95% B over 12 minutes, then a 5-minute hold at 100% B; Flow=20 mL/min. The appropriate fractions were combined and dried via centrifugal evaporation to afford Compound 2001 (30 mg, 15%). The appropriate fractions were combined and dried via centrifugal evaporation to afford Compound 2002 (13 mg, 6%); Compound 2001: 1,1,1-trifluoro-2-methylpropan-2-yl ((2R,6S,7R,9R,13aS,14aR,16aS)-2-((4-cyclopropoxyisoquinolin-1-yl)oxy)-12-hydroxy-7,9-dimethyl-14a-(((1-methylcyclopropyl)sulfonyl)carbamoyl)-5,16-dioxooctadecahydrocyclopropa[e]pyrrolo[1,2-a][1,4]diazacyclopentadecin-6-yl)carbamate. $^1$H NMR (400 MHz, MeOD) δ 8.14 (d, J=8.3 Hz, 1H), 8.01 (d, J=8.3 Hz, 1H), 7.87 (s, 1H), 7.70 (ddd, J=8.3, 7.0, 1.3 Hz, 1H), 7.54 (ddd, J=8.2, 7.1, 1.0 Hz, 1H), 5.83-5.78 (m, 1H), 4.74 (d, J=11.0 Hz, 1H), 4.60 (dd, J=10.2, 6.9 Hz, 1H), 4.02-3.95 (m, 2H), 3.81 (d, J=10.8 Hz, 1H), 3.66 (br. s., 1H), 2.74 (dd, J=13.7, 6.9 Hz, 1H), 2.39 (ddd, J=13.8, 10.2, 4.1 Hz, 1H), 2.02 (q, J=9.5 Hz, 1H), 1.90-1.78 (m, 1H), 1.76-1.65 (m, 3H), 1.63-1.51 (m, 6H), 1.51-1.48 (m, 1H), 1.47-1.42 (m, 2H), 1.41-1.34 (m, 2H), 1.33 (s, 3H), 1.20-1.09 (m, 1H), 1.00 (d, J=6.8 Hz, 3H), 0.95 (d, J=6.5 Hz, 3H), 0.93-0.86 (m, 7H), 0.84-0.80 (m, 2H), 0.80-0.73 (m, 1H); MS: MS m/z 866.4 (M$^+$+1).

Compound 2002: 1,1,1-trifluoro-2-methylpropan-2-yl ((2R,6S,7R,9R,13S,13aR,14aR,16aS)-2-((4-cyclopropoxyisoquinolin-1-yl)oxy)-13-hydroxy-7,9-dimethyl-14a-(((1-methylcyclopropyl)sulfonyl)carbamoyl)-5,16-dioxooctadecahydrocyclopropa[e]pyrrolo[1,2-a][1,4]diazacyclopentadecin-6-yl)carbamate. $^1$H NMR (400 MHz, MeOD) δ 8.16 (d, J=8.3 Hz, 1H), 8.03 (d, J=8.3 Hz, 1H), 7.90-7.86 (m, 1H), 7.72 (ddd, J=8.3, 7.1, 1.1 Hz, 1H), 7.55 (td, J=0.7, 1.0 Hz, 1H), 5.82 (br. s., 1H), 4.77 (d, J=11.3 Hz, 1H), 4.62 (dd, J=10.2, 6.9 Hz, 1H), 4.05-3.96 (m, 2H), 3.84-3.78 (m, 1H), 3.69 (d, J=6.0 Hz, 1H), 2.76 (dd, J=13.6, 7.0 Hz, 1H), 2.41 (ddd, J=13.7, 10.1, 4.0 Hz, 1H), 1.99-1.89 (m, 1H), 1.85-1.60 (m, 7H), 1.58 (s, 3H), 1.54-1.40 (m, 4H), 1.34 (s, 3H), 1.30-1.19 (m, 1H), 1.17-1.08 (m, 1H), 1.06 (d, J=6.8 Hz, 3H), 0.99 (d, J=6.5 Hz, 3H), 0.97-0.87 (m, 7H), 0.87-0.82 (m, 2H), 0.82-0.75 (m, 1H); MS: MS m/z 866.4 (M$^+$+1).

Preparation of Compound 2003

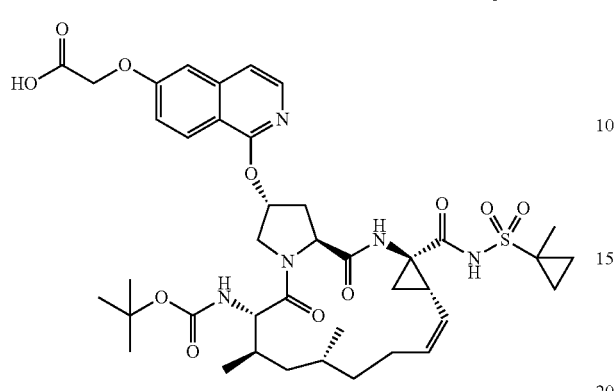

Compound 2003

Compound 2003 was prepared using the intermediates described herein and by following the general procedure described for the synthesis of Compound 3117.

Compound 2003: 2-((1-(((2R,6S,7R,9R,13aS,14aR,16aS, Z)-6-((tert-butoxycarbonyl)amino)-7,9-dimethyl-14a-(((1-methylcyclopropyl)sulfonyl)carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl)oxy)isoquinolin-6-yl)oxy)acetic acid. $^1$H NMR (500 MHz, DMSO-d$_6$) δ 9.05 (br. s., 1H), 8.05 (d, J=9.2 Hz, 1H), 7.93 (d, J=5.8 Hz, 1H), 7.27 (d, J=5.8 Hz, 1H), 7.23 (d, J=2.4 Hz, 1H), 7.18 (d, J=7.9 Hz, 1H), 7.13 (dd, J=9.2, 2.4 Hz, 1H), 5.80 (br. s., 1H), 5.55-5.47 (m, 1H), 4.97 (t, J=9.8 Hz, 1H), 4.78 (s, 2H), 4.59 (d, J=11.0 Hz, 1H), 4.46 (dd, J=10.4, 7.0 Hz, 1H), 3.93-3.87 (m, 1H), 3.74-3.68 (m, 1H), 2.72-2.62 (m, 1H), 2.59 (dd, J=13.4, 7.0 Hz, 1H), 2.38-2.23 (m, 3H), 1.93-1.77 (m, 2H), 1.68 (dd, J=12.7, 6.3 Hz, 1H), 1.58 (dd, J=8.1, 5.3 Hz, 1H), 1.49 (dd, J=9.3, 5.0 Hz, 1H), 1.45-1.23 (m, 8H), 1.14 (s, 9H), 0.92 (d, J=7.0 Hz, 3H), 0.89-0.85 (m, 4H), 0.72 (t, J=12.5 Hz, 1H); MS: MS m/z 812.4 (M$^+$+1).

Preparation of intermediates and Compounds of Formula 1

Section 3

Scheme: Preparation of (3R)-2-((tert-butoxycarbonyl)amino)-3,5-dimethylnon-8-enoic acid

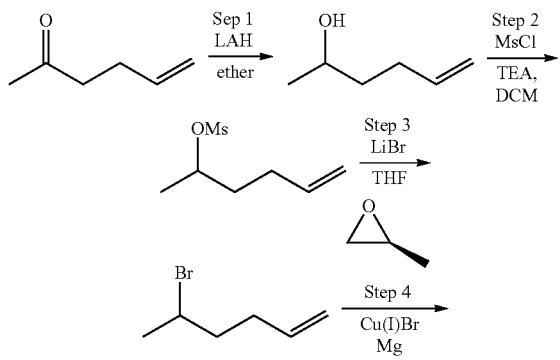

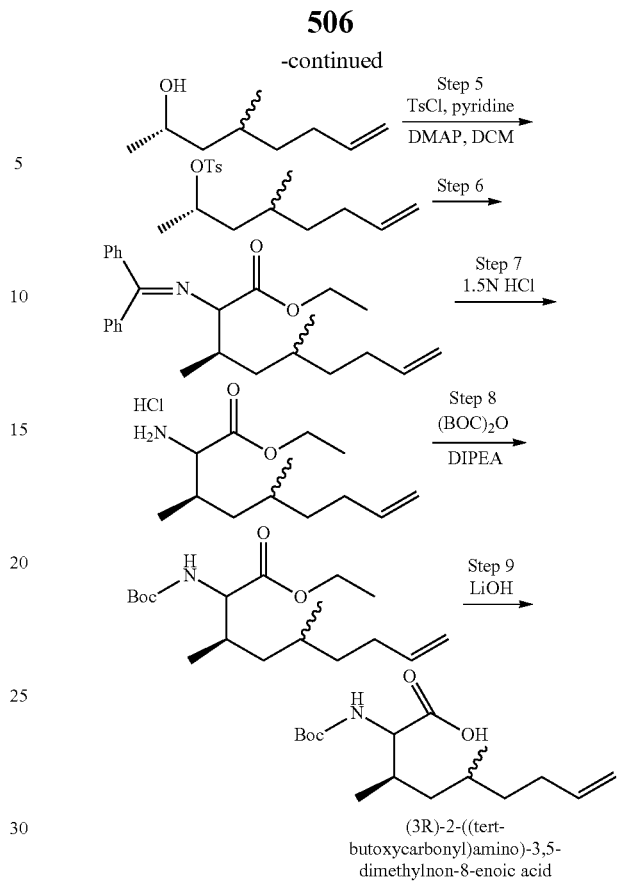

(3R)-2-((tert-butoxycarbonyl)amino)-3,5-dimethylnon-8-enoic acid

Step 1: Preparation of Hex-5-en-2-ol

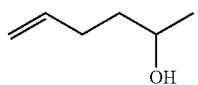

To a solution of lithium aluminum hydride in THF (LAH, 20.1 g, 106.12 mmol, 509 mL, 1M solution) was added a solution of Hex-5-en-2-one (50 g, 102.04 mmol) over a period of 30 min. at −20° C. under nitrogen. The reaction mass was allowed to warm to room temperature and stirred for 1 h. The solution was cooled to −20° C. and to it was added aqueous 10% NaOH solution (~100 mL). The organic layer was separated and the aqueous layer was extracted with ether. The combined organics were dried over anhydrous sodium sulfate and concentrated to get crude compound Hex-5-en-2-ol as colorless liquid (50 g, 98%). $^1$H NMR (400 MHz, CDCl$_3$): δ ppm 5.87-5.02 (m, 1H), 4.99-4.95 (m, 2H), 3.81-3.83 (m, 1H), 2.17-2.13 (m, 2H), 1.58-1.53 (m, 2H), 1.20-1.19 (d, J=8 Hz, 3H).

Step 2: Preparation of Hex-5-en-2-yl methanesulfonate

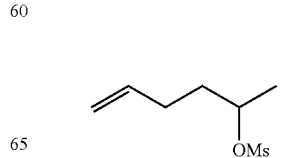

To a solution of Hex-5-en-2-ol (50 g crude, 500 mmole) in dichloromethane was added triethylamine (103 mL, 750 mmol) at room temperature. The reaction mass was cooled to 0° C. and to it was added a solution of methane sulfonyl chloride (50.4 mL, 650 mmol) in DCM over a period of 30 min. The reaction mass was allowed to come to room temperature and stirred for 2 h. The solution was washed with water, dried over anhydrous sodium sulfate, filtered and concentrated under reduced pressure to get crude compound Hex-5-en-2-yl methanesulfonate as light brown oily liquid (73 g, 82%). $^1$H NMR (400 MHz, CDCl$_3$): δ ppm 5.84-5.80 (m, 1H), 5.10-5.0 (m, 2H), 4.99-4.98 (m, 1H), 3.15 (s, 3H), 2.52-2.09 (m, 2H), 1.75-1.66 (m, 2H), 1.36-1.34 (d, J=6.4 Hz, 3H).

Step 3: Preparation of 5-bromohex-1-ene

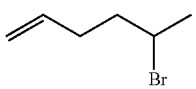

To a solution of Hex-5-en-2-yl methanesulfonate (20 g, 0.112 moles) in dry THF (200 mL) was added LiBr (14.6 g, 0.168 moles) portionwise at room temperature over a period of 15 min. The reaction mass was heated at 70° C. for 3 h. The reaction mass was cooled to room temperature and was diluted with water (200 mL). The aqueous solution was extracted with ether (100 mL×3). The combined organics were dried over anhydrous Na$_2$SO$_4$ and concentrated at room temperature. The crude compound was distilled under reduced pressure at 115° C. to afford 5-bromohex-1-ene as colorless liquid (14.5 g, 80%). $^1$H NMR (400 MHz, CDCl$_3$): δ ppm 5.80-5.74 (m, 1H), 5.08-4.98 (m, 2H), 4.14-4.09 (m, 1H), 2.28-2.17 (m, 2H), 1.94-1.81 (m, 2H), 1.71-1.70 (d, J=6.8 Hz, 3H); MS: GC-MS m/z 162.

Step 4: Preparation of (2S)-4-methyloct-7-en-2-ol

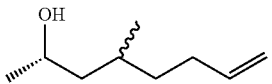

To magnesium turnings (7.44 g, 0.020 moles) in dry THF (100 mL) and was added a iodine (100 mg) at room temperature. To this reaction mass was added a solution of 5-bromohex-1-ene (50 g, 362 mmoles) in THF (200 mL). The reaction mass was heated with hot air gun to initiate the reaction. Upon completion of the reaction the solution was transferred by cannula to a solution of (S)-propylene oxide (14 g, 241 mmol) and copper bromide (3.45 g, 24 mmol) in THF (100 mL) at −78° C. The reaction mass was allowed to come to room temperature and was stirred overnight. The reaction mass was quenched with saturated aq. ammonium chloride solution and extracted with diethyl ether (200 mL×3). The combined organic layers were dried over anhydrous Na$_2$SO$_4$ and concentrated at room temperature to get crude compound. The crude compound was purified by column chromotography (Silica gel, 10% TBME in pet ether) to get (2S)-4-methyloct-7-en-2-ol (12.4 g, 30%) as an oil. $^1$H NMR (400 MHz, CDCl$_3$): δ ppm 5.84-5.77 (m, 1H), 5.02-4.92 (m, 2H), 4.05-3.85 (sb, 1H), 2.08-2.06 (m, 2H), 1.29-1.20 (m, 2H), 1.19-1.16 (m, 4H), 0.97-0.87 (m, 6H).

Step 5: Preparation of (2S)-4-methyloct-7-en-2-yl 4-methylbenzenesulfonate

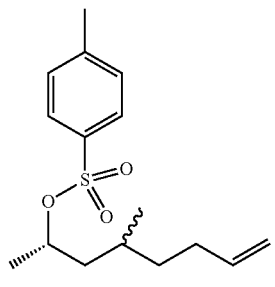 [SMILES: C=CCCC(C)C[C@H](C)OS(=O)(=O)c1ccc(C)cc1]

To a solution of (2S)-4-methyloct-7-en-2-ol (39 g, 0.274 moles) in pyridine (400 mL) was added 4-(dimethylamino)pyridine (DMAP, 1.67 g, 0.013 moles) and the solution was stirred for 10 min. P-toluenesulfonyl chloride (60 g, 0.315 moles) was added to the reaction mass at 0° C. The reaction mass was allowed to come to room temperature and stirred overnight. Pyridine was removed under reduced pressure and the residue was diluted with ethyl acetate (200 mL). The organic solution was washed with aqueous 1.5 N HCl solution, saturated aq. bicarbonate solution, brine solution, dried over anhydrous Na$_2$SO$_4$, filter, and concentrated under reduced pressure to get crude compound (2S)-4-methyloct-7-en-2-yl 4-methylbenzenesulfonate (54 g, 61%). The crude compound was taken to the next step without further purification.

Step 6: Preparation of (3R)-ethyl 2-((diphenylmethylene)amino)-3,5-dimethylnon-8-enoate

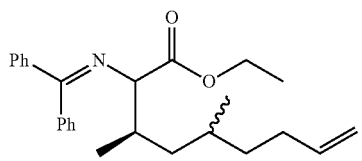 [SMILES: C=CCCC(C)C[C@@H](C)C(N=C(c1ccccc1)c1ccccc1)C(=O)OCC]

To a solution of (2S)-4-methyloct-7-en-2-yl 4-methylbenzenesulfonate (54 g, 0.182 moles) and N-(diphenylmethylene)glycinate ethyl ester (48.7 g, 0.182 moles) in toluene (500 mL) was added LiHMDS (36.5 g, 0.218 moles, 1 M solution in THF) at 0° C. The reaction mass was allowed to come to room temperature and was then heated at 110° C. for 2 h. The reaction mass was cooled to room temperature, quenched with water and extracted with ethyl acetate (200 mL×3). The combined organic layers were dried over anhydrous Na$_2$SO$_4$, filtered and concentrated under reduced pressure to get crude compound (3R)-ethyl 2-((diphenylmethylene)amino)-3,5-dimethylnon-8-enoate (75 g). The crude compound was taken to the next step without further purification.

Step 7: Preparation of (3R)-ethyl 2-amino-3,5-dimethylnon-8-enoate hydrochloride

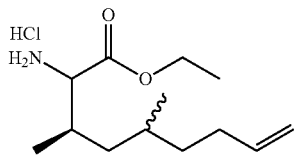 [SMILES: Cl ; C=CCCC(C)C[C@@H](C)C(N)C(=O)OCC]

To a solution of (3R)-ethyl 2-((diphenylmethylene)amino)-3,5-dimethylnon-8-enoate (20 g) in diethyl ether (20 mL) was added aqueous 1.5 N HCl solution (200 mL) and the reaction mass was stirred at room temperature overnight. The reaction mass was washed with diethyl ether (100 mL). The aqueous solution was basified using saturated sodium bicarbonate solution and was extracted with ethyl acetate (100 mL×3). The combined organic layers were dried over anhydrous $Na_2SO_4$, filtered, and concentrated under reduced pressure to get crude compound (3R)-ethyl 2-amino-3,5-dimethylnon-8-enoate hydrochloride (4 g, 30%). The crude compound was taken to the next step without further purification.

Step 8: Preparation of (3R)-ethyl 2-(tert-butoxycarbonylamino)-3,5-dimethylnon-8-enoate

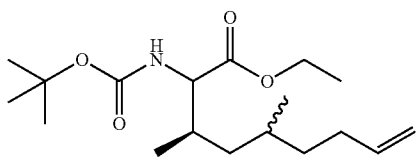 [SMILES: C=CCCC(C)C[C@@H](C)C(NC(=O)OC(C)(C)C)C(=O)OCC]

A solution of (3R)-ethyl 2-amino-3,5-dimethylnon-8-enoate hydrochloride (4 g, 0.017 moles) in DCM (40 mL) was added N,N-diisopropylethylamine (DIPEA, 3.4 g, 0.026 moles) followed by di-tert-butyl dicarbonate (4.6 g, 0.021 moles) at room temperature. The reaction mass was stirred at room temperature overnight. The reaction mass was diluted with DCM and washed with water. The organic layer was dried over anhydrous $Na_2SO_4$, filtered, and concentrated under reduced pressure to afford the crude compound. The crude compound was purified by column chromatography (Silica gel, 20% ethyl acetate in pet-ether) to get 4.7 g, (94%) of (3R)-ethyl 2-(tert-butoxycarbonylamino)-3,5-dimethylnon-8-enoate as an oil.

Step 9: Preparation of (3R)-2-(tert-butoxycarbonylamino)-3,5-dimethylnon-8-enoic acid

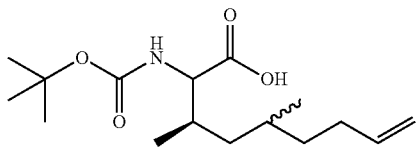 [SMILES: C=CCCC(C)C[C@@H](C)C(NC(=O)OC(C)(C)C)C(=O)O]

To a solution of (3R)-ethyl 2-(tert-butoxycarbonylamino)-3,5-dimethylnon-8-enoate (20 g, 0.061 moles) in THF/water (200 mL, 1:1) was added methanol (60 mL) followed by LiOH (7.7 g, 0.183 moles) at room temperature. The reaction mass was stirred at room temperature overnight. The solution was concentrated under reduced pressure and the residue was diluted with water (200 mL). The aqueous solution was acidified with aqueous 1.5 N HCl solution to pH~3 and extracted with ethyl acetate (100 mL×3). The combined organic layers were dried over anhydrous $Na_2SO_4$ and concentrated under reduce pressure to get crude compound. The crude compound was purified by column chromatography (Silica gel, 3% methanol in DCM) to get 12.4 g (68%) of (3R)-2-(tert-butoxycarbonylamino)-3,5-dimethylnon-8-enoic acid as gummy liquid. $^1$H NMR (400 MHz, DMSO-$d_6$): δ ppm 12.4 (sb, 1H), 6.92-6.85 (m, 1H), 5.81-5.75 (m, 1H), 5.04-4.93 (m, 2H), 4.12-3.91 (m, 1H), 2.18-1.98 (m, 4H), 1.5 (s, 9H), 1.35-1.02 (m, 3H), 0.98-0.85 (m, 6H).

Scheme

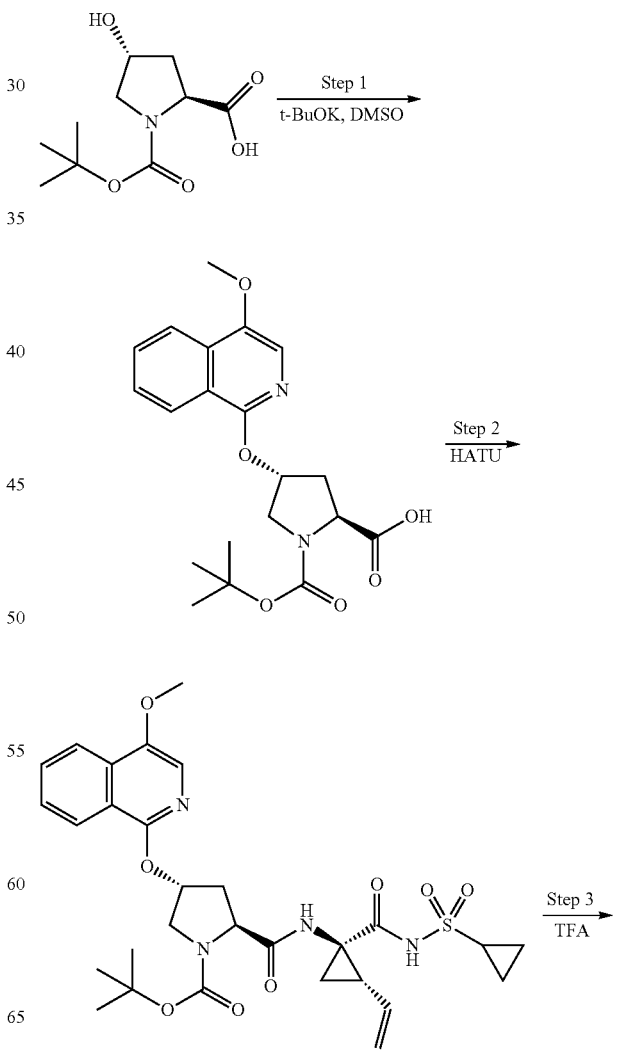

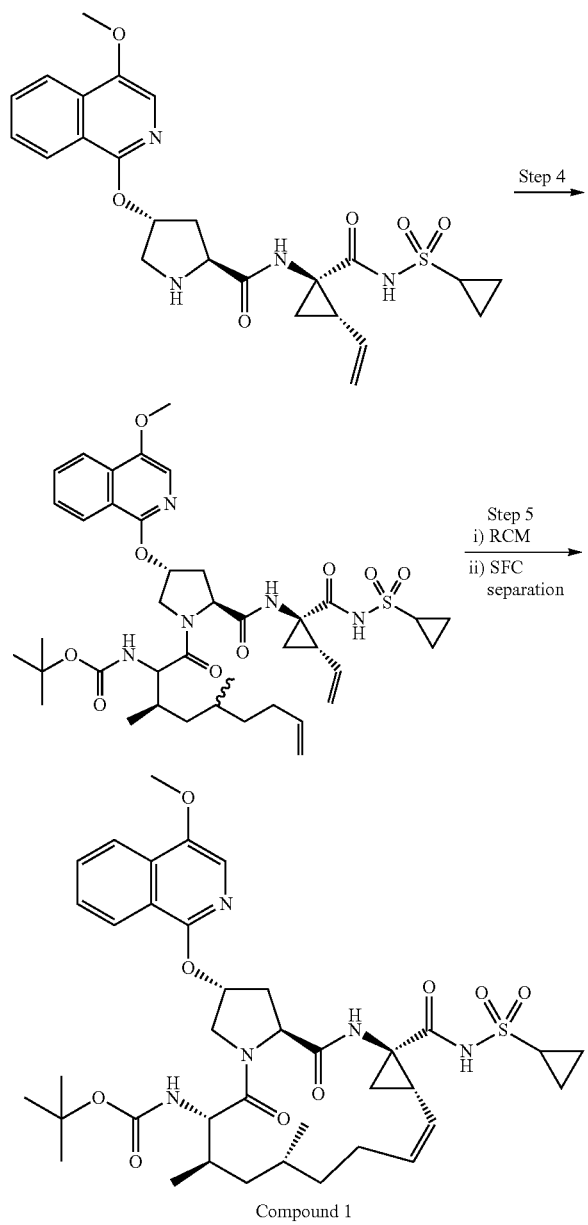

Compound 1

Compound 2

512

Step 1: Preparation of (2S,4R)-1-(tert-butoxycarbonyl)-4-((4-methoxyisoquinolin-1-yl)oxy)pyrrolidine-2-carboxylic acid

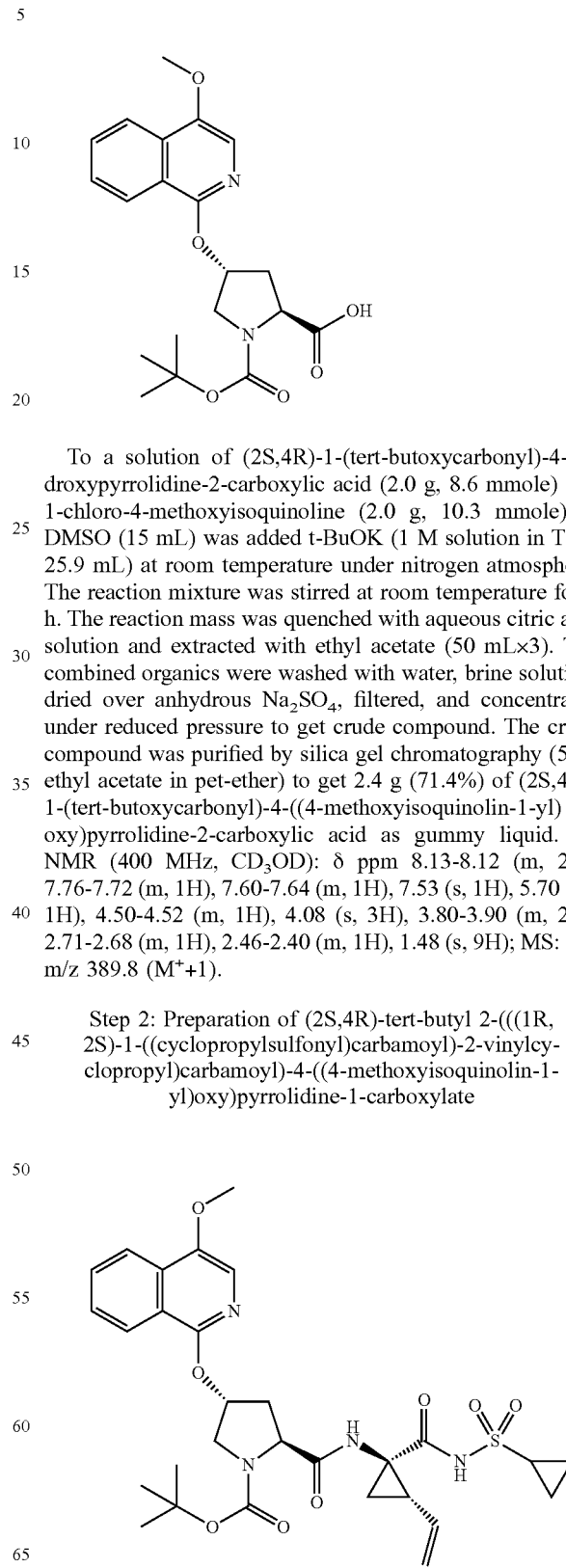

To a solution of (2S,4R)-1-(tert-butoxycarbonyl)-4-hydroxypyrrolidine-2-carboxylic acid (2.0 g, 8.6 mmole) and 1-chloro-4-methoxyisoquinoline (2.0 g, 10.3 mmole) in DMSO (15 mL) was added t-BuOK (1 M solution in THF, 25.9 mL) at room temperature under nitrogen atmosphere. The reaction mixture was stirred at room temperature for 2 h. The reaction mass was quenched with aqueous citric acid solution and extracted with ethyl acetate (50 mL×3). The combined organics were washed with water, brine solution, dried over anhydrous $Na_2SO_4$, filtered, and concentrated under reduced pressure to get crude compound. The crude compound was purified by silica gel chromatography (55% ethyl acetate in pet-ether) to get 2.4 g (71.4%) of (2S,4R)-1-(tert-butoxycarbonyl)-4-((4-methoxyisoquinolin-1-yl)oxy)pyrrolidine-2-carboxylic acid as gummy liquid. $^1$H NMR (400 MHz, $CD_3OD$): δ ppm 8.13-8.12 (m, 2H), 7.76-7.72 (m, 1H), 7.60-7.64 (m, 1H), 7.53 (s, 1H), 5.70 (sb, 1H), 4.50-4.52 (m, 1H), 4.08 (s, 3H), 3.80-3.90 (m, 2H), 2.71-2.68 (m, 1H), 2.46-2.40 (m, 1H), 1.48 (s, 9H); MS: MS m/z 389.8 ($M^+$+1).

Step 2: Preparation of (2S,4R)-tert-butyl 2-(((1R,2S)-1-((cyclopropylsulfonyl)carbamoyl)-2-vinylcyclopropyl)carbamoyl)-4-((4-methoxyisoquinolin-1-yl)oxy)pyrrolidine-1-carboxylate To a solution of (2S,4R)-1-(tert-butoxycarbonyl)-4-((4-methoxyisoquinolin-1-yl)oxy)pyrrolidine-2-carboxylic acid (1.1 g, 2.8 mmole) in dichloromethane (15 mL) was added HATU (1.07 g, 2.8 mmole) followed by DIPEA (2.4 mL, 14.1 mmole) at room temperature. The reaction mass was stirred at the same temperature for 10 min. (1R,2S)-1-amino-N-(cyclopropylsulfonyl)-2-vinylcyclopropanecarboxamide hydrochloride (prepared according to the procedure described in WO 03/099274) was added to the reaction mass and stirred at room temperature for 30 min. The reaction mass was diluted with dichloromethane and washed with water. The organic layer was dried over anhydrous $Na_2SO_4$, filtered, and concentrated under reduced pressure to get the crude compound. The crude compound was purified by silica gel chromatography (70% ethyl acetate in pet ether) to get 1.3 g (76.4%) of (2S,4R)-tert-butyl 2-(((1R,2S)-1-((cyclopropylsulfonyl)carbamoyl)-2-vinylcyclopropyl)carbamoyl)-4-((4-methoxyisoquinolin-1-yl)oxy)pyrrolidine-1-carboxylate as a white solid. MS: MS m/z 601.2 ($M^+$+1).

Step 3: Preparation of TFA salt of (2S,4R)—N-((1R,2S)-1-((cyclopropylsulfonyl)carbamoyl)-2-vinylcyclopropyl)-4-((4-methoxyisoquinolin-1-yl)oxy)pyrrolidine-2-carboxamide

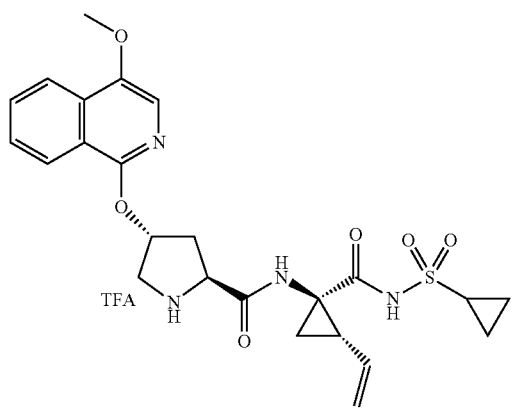 [SMILES: C=C[C@@H]1C[C@]1(NC(=O)[C@@H]1C[C@@H](Oc2ncc(OC)c3ccccc23)CN1)C(=O)NS(=O)(=O)C1CC1]

To a solution of (2S,4R)-tert-butyl 2-(((1R,2S)-1-((cyclopropylsulfonyl)carbamoyl)-2-vinylcyclopropyl)carbamoyl)-4-((4-methoxyisoquinolin-1-yl)oxy)pyrrolidine-1-carboxylate (1.3 g, 2.1 mmole) in DCM was added trifluoroacetic acid (TFA, 5 mL) at room temperature. The reaction mass was stirred at room temperature for 30 min. The solvent was evaporated under reduced pressure to get crude compound (2S,4R)—N-((1R,2S)-1-((cyclopropylsulfonyl)carbamoyl)-2-vinylcyclopropyl)-4-((4-methoxyisoquinolin-1-yl)oxy)pyrrolidine-2-carboxamide (1.05 g, 97.2%) as a TFA salt. The crude compound was taken to the next step without further purification. MS: MS m/z 501.3 ($M^+$+1).

Step 4: Preparation of tert-butyl ((3R)-1-((2S,4R)-2-(((1R,2S)-1-((cyclopropylsulfonyl)carbamoyl)-2-vinylcyclopropyl)carbamoyl)-4-((4-methoxyisoquinolin-1-yl)oxy)pyrrolidin-1-yl)-3,5-dimethyl-1-oxonon-8-en-2-yl)carbamate

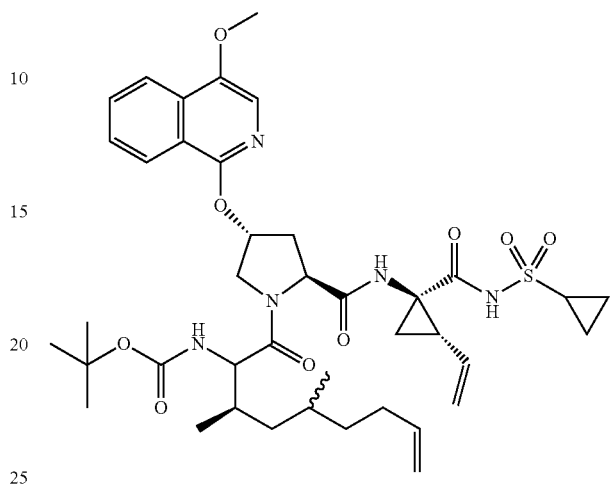

To a solution of (2S,4R)—N-((1R,2S)-1-((cyclopropylsulfonyl)carbamoyl)-2-vinylcyclopropyl)-4-((4-methoxyisoquinolin-1-yl)oxy)pyrrolidine-2-carboxamide (595 mg, 1.9 mmol) in dichloromethane (15 mL) was added HATU (755 mg, 1.9 mmol) followed by DIPEA (1.7 mL, 9.9 mmole) at room temperature. The reaction mass was stirred at the same temperature for 10 min. (3R)-2-(tert-butoxycarbonylamino)-3,5-dimethylnon-8-enoic acid (1.0 g, 1.9 mmole) was added to the reaction mass and the solution was stirred at room temperature for 30 min. The reaction mass was diluted with dichloromethane and washed with water. The organic layer was dried over anhydrous $Na_2SO_4$, filtered, and concentrated under reduced pressure to get the crude compound. The crude compound was purified by silica gel chromatography (70% ethyl acetate in pet ether) to get desired product tert-butyl ((3R)-1-((2S,4R)-2-(((1R,2S)-1-((cyclopropylsulfonyl)carbamoyl)-2-vinylcyclopropyl)carbamoyl)-4-((4-methoxyisoquinolin-1-yl)oxy)pyrrolidin-1-yl)-3,5-dimethyl-1-oxonon-8-en-2-yl)carbamate as a pale yellow solid. MS: MS m/z 782.1 ($M^+$+1).

Step 5: Preparation of Compound 1 & Compound 2

Compound 1

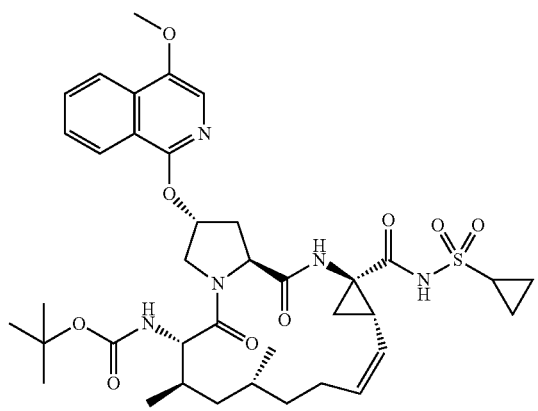

-continued

Compound 2

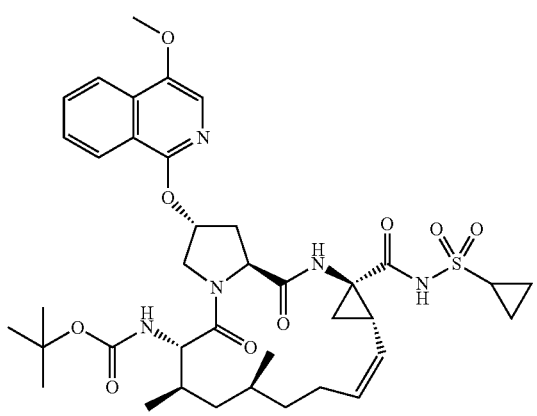

To a degassed solution of tert-butyl ((3R)-1-((2S,4R)-2-(((1R,2S)-1-((cyclopropylsulfonyl)carbamoyl)-2-vinylcyclopropyl)carbamoyl)-4-((4-methoxyisoquinolin-1-yl)oxy)pyrrolidin-1-yl)-3,5-dimethyl-1-oxonon-8-en-2-yl)carbamate (240 mg, 0.3 mmole) in dichloroethane (100 mL) was added (1,3-bis(2,4,6-trimethylphenyl)-2-imidazolidinylidene)dichloro(phenylmethylene)(tricyclohexylphosphine) ruthenium (Grubbs second generation catalyst, 24 mg, 10% w/w) at room temperature under nitrogen atmosphere. The reaction mass was heated at 95° C. overnight. The solvent was evaporated under reduced pressure to afford the desired compound as a diastereomeric mixture.

The diastereomers were separated by SFC purification to afford Compound 1 (18 mg, 8%) as a white solid and Compound 2 (8 mg, 3%) as a white solid.

Compound 1: tert-butyl ((2R,6S,7R,9R,13aS,14aR,16aS,Z)-14a-((cyclopropylsulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
$^1$H NMR (400 MHz, CD$_3$OD): δ ppm 8.18-8.16 (d, J=8.4 Hz, 1H), 8.11-8.09 (d, J=8.4 Hz, 1H), 7.74-7.70 (t, J=8 Hz, 1H), 7.56-7.53 (m, 2H), 5.83 (sb, 1H), 5.63-5.57 (m, 1H), 5.09-5.01 (m, 1H), 4.71-4.69 (m, 1H), 4.62-4.52 (m, 1H), 4.05-4.04 (m, 4H), 3.93-3.87 (m, 1H), 2.92 (m, 1H), 2.74-2.71 (m, 2H), 2.43-2.39 (m, 2H), 2.05-1.98 (m, 1H), 1.84-1.75 (m, 3H), 1.59-1.41 (m, 3H), 1.33-1.23 (m, 4H), 1.13-1.06 (m, 10H), 1.03-0.97 (m, 6H), 0.90-0.83 (m, 1H); MS: MS m/z 755.2 (M$^+$+1).

Compound 2: tert-butyl ((2R,6S,7R,9S,13aS,14aR,16aS,Z)-14a-((cyclopropylsulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate.
$^1$H NMR (400 MHz, CD$_3$OD): δ ppm 8.18-8.16 (d, J=8.4 Hz, 1H), 8.11-8.09 (d, J=8.4 Hz, 1H), 7.74-7.71 (t, J=7.2 Hz, 1H), 7.59-7.55 (m, 2H), 5.83 (sb, 1H), 5.63-5.67 (m, 1H), 5.21-5.19 (m, 1H), 4.67-4.48 (m, 2H), 4.02-4.18 (m, 2H), 4.01 (s, 3H), 3.08-3.03 (m, 1H), 2.89-2.88 (m, 1H), 2.73-2.68 (m, 1H), 2.50-2.34 (m, 4H), 2.05-1.95 (m, 2H), 1.76-1.65 (m, 2H), 1.47-1.36 (m, 5H), 1.33-1.24 (m, 6H), 1.20-1.08 (m, 7H), 1.03-0.97 (m, 4H), 0.97-0.92 (m, 1H); MS: MS m/z 806.2 (M$^+$−1). MS: MS m/z 755.3 (M$^+$+1).

Preparation of pyridin-2-yl (1,1,1-trifluoro-2-methylpropan-2-yl)carbonate

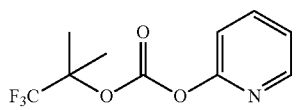 [SMILES: CC(C)(OC(=O)Oc1ccccn1)C(F)(F)F]

To a slurry of NaH (1.03 g, 25.8 mmol) in THF (70 mL) was added 1,1,1-trifluoro-2-methylpropan-2-ol (3 g, 23.42 mmol). The reaction was stirred at 0° C. for 20 min. A solution of dipyridin-2-yl carbonate (5.06 g, 23.42 mmol) in THF (30 mL) was then added to the mixture. The resulting solution was stirred at room temperature overnight. The residue was filtered washing with EtOAc (2×20 mL). The filtrated was transferred to a separatory funnel and was washed with water, dried over anhydrous Na$_2$SO$_4$, filtered and concentrated under reduced pressure. The resulting white solid, pyridin-2-yl (1,1,1-trifluoro-2-methylpropan-2-yl)carbonate (1.24 g, 21%), was used in subsequent steps without additional purification.

Scheme:

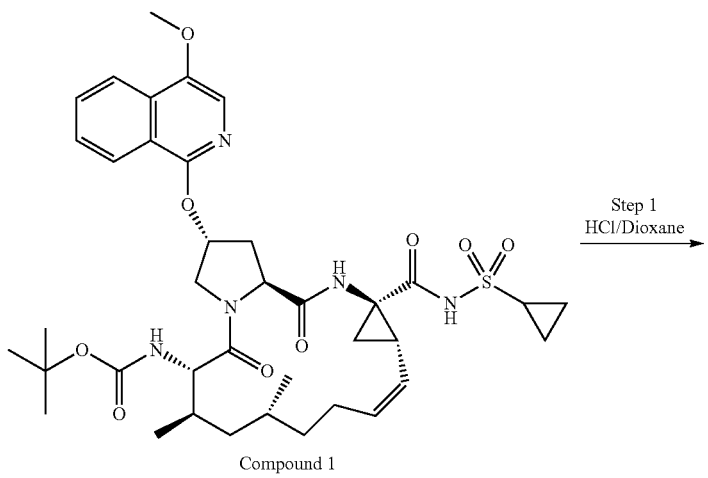

Compound 1

-continued

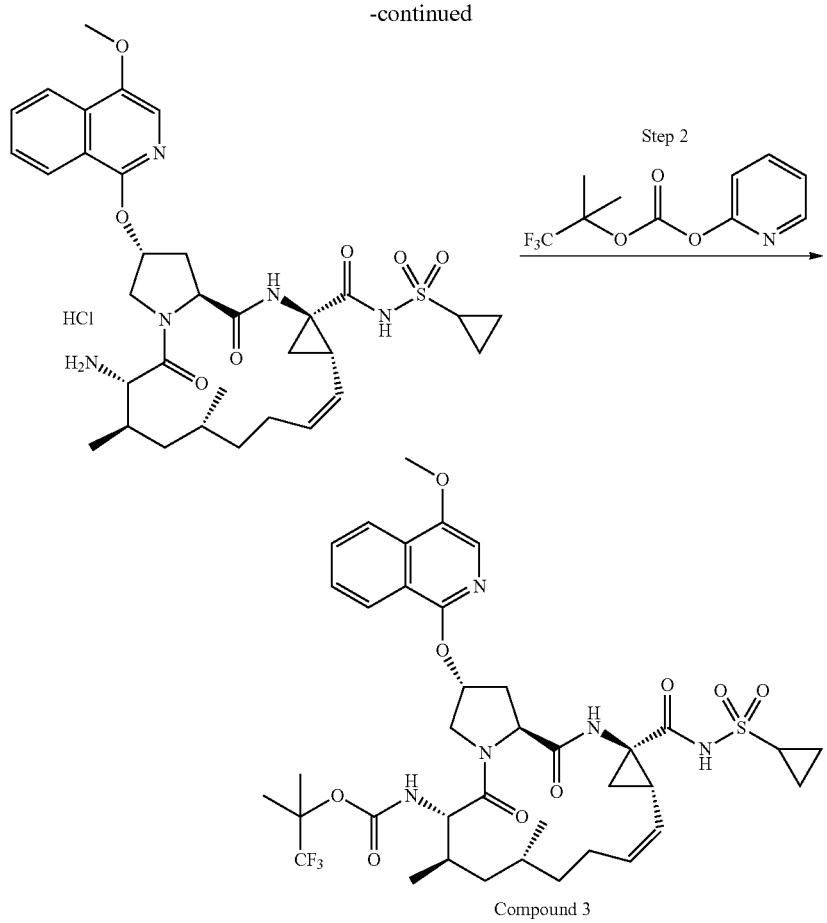

Compound 3

Step 1: Preparation of (2R,6S,7R,9R,13aS,14aR, 16aS,Z)-6-amino-N-(cyclopropylsulfonyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride

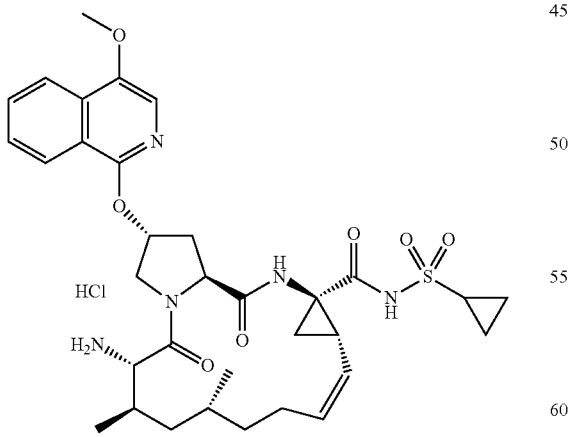

To a solution of HCl in Dioxane was added Compound 1 (300 mg, 0.39 mmol) and the solution was stirred at room temperature for 30 min. The solvent was concentrated under reduced pressure to afford (2R,6S,7R,9R,13aS,14aR,16aS, Z)-6-amino-N-(cyclopropylsulfonyl)-2-((4-methoxyisoqui-nolin-1-yl)oxy)-7,9-dimethyl-5,16-dioxo-1,2,3,5,6,7,8,9,10, 11,13a,14,14a,15,16,16a-hexadecahydrocyclopropa[e] pyrrolo[1,2-a][1,4]diazacyclopentadecine-14a-carboxamide hydrochloride (250 mg, 96%). The material was triturated with diethyl ether and used in step 2 without further purification. MS: MS m/z 655.2 (M$^+$+1).

Step 2: Preparation of Compound 3

Compound 3

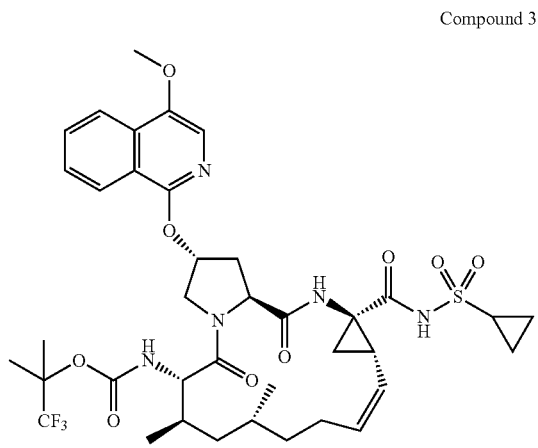 [SMILES: COc1cnc(O[C@@H]2C[C@H]3C(=O)N[C@]4(C(=O)NS(=O)(=O)C5CC5)C[C@H]4/C=C\CC[C@@H](C)C[C@@H](C)[C@H](NC(=O)OC(C)(C)C(F)(F)F)C(=O)N3C2)c2ccccc12]

To a solution of (2R,6S,7R,9R,13aS,14aR,16aS,Z)-6-amino-N-(cyclopropylsulfonyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride (250 mg, 0.36 mmol) in DCM (4 mL) was added DIPEA (0.3 mL, 1.8 mmole) followed by pyridin-2-yl (1,1,1-trifluoro-2-methylpropan-2-yl)carbonate (180 mg, 0.72 mmole) at room temperature. The reaction mixture was stirred at room temperature for 30 min. The reaction mass was diluted with DCM and washed with water. The organic layer was dried over anhydrous $Na_2SO_4$, filtered, and concentrated under reduced pressure. The resulting residue was purified by HPLC to afford compound 3 (51 mg, 17%) as a white solid.

Compound 3: 1,1,1-trifluoro-2-methylpropan-2-yl ((2R,6S,7R,9R,13aS,14aR,16aS,Z)-14a-((cyclopropylsulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, $CD_3OD$): δ ppm 8.17-8.15 (d, J=8.0 Hz, 1H), 8.13-8.11 (d, J=8.0 Hz, 1H), 7.75-7.71 (dt, J=6.8 & 1.2 Hz, 1H), 7.58-7.54 (m, 2H), 5.82 (m, 1H), 5.62-5.59 (m, 1H), 5.08 (m, 1H), 4.76-4.73 (m, 1H), 4.66-4.56 (m, 1H), 4.02 (s, 3H), 3.99-3.98 (m, 1H), 3.84-3.81 (m, 1H), 2.94-2.91 (m, 2H), 2.47-2.40 (m, 2H), 2.97-2.75 (m, 4H), 1.60-1.57 (m, 1H), 1.50-1.48 (m, 2H), 1.34-1.22 (m, 6H), 1.10-0.96 (m, 12H), 0.85-0.82 (m, 1H); $^{19}$F NMR: δ ppm −85.11 (3 F); MS: MS m/z 806.2 (M$^+$−1).

Preparation of Compound 4

Compound 4

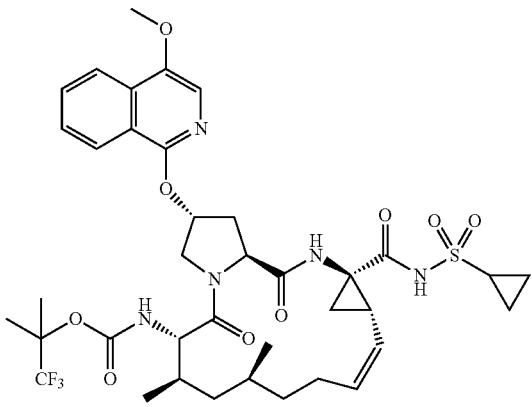

Compound 4 was prepared using the intermediates described herein and by following the general procedure described for the synthesis of Compound 3.

Compound 4: 1,1,1-trifluoro-2-methylpropan-2-yl ((2R,6S,7R,9S,13 aS,14aR,16aS,Z)-14a-((cyclopropylsulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 808.1 (M$^+$+1).

Preparation of Compounds 5 and 6

Compound 5

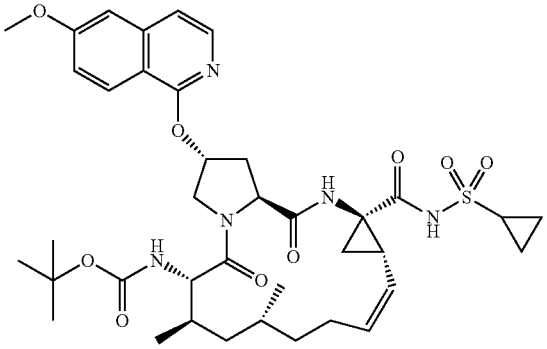

Compound 6

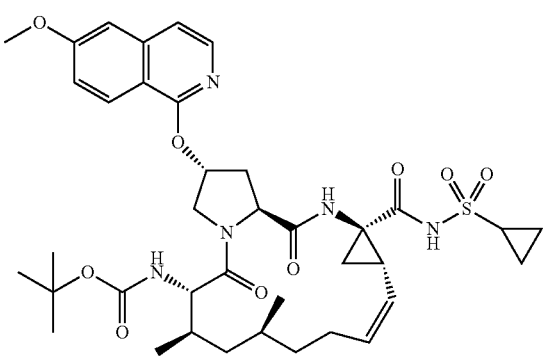

Compounds 5 and 6 were prepared using the intermediates described herein and by following the general procedure described for the synthesis of Compound 1.

Compound 5: tert-butyl ((2R,6S,7R,9R,13aS,14aR,16aS,Z)-14a-((cyclopropylsulfonyl)carbamoyl)-2-((6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, $CD_3OD$): δ ppm 8.13-8.11 (d, J=8.8 Hz, 1H), 7.92-7.91 (d, J=6.0 Hz, 1H), 7.27-7.26 (d, J=6.0 Hz, 1H), 7.20-7.21 (d, J=2.0 Hz, 1H), 7.13-7.11 (dd, J=8.8 Hz, 1H), 5.90 (m, 1H), 5.75-5.73 (m, 1H), 5.10-5.05 (m, 1H), 4.70-4.65 (m, 1H), 4.51-4.48 (m, 1H), 4.18-4.17 (m, 1H), 4.12-4.07 (m, 1H), 3.94 (s, 3H), 2.96-2.89 (m, 1H), 2.74-2.65-(m, 2H), 2.49-2-42 (m, 2H), 1.99-1.96 (m, 2H), 1.74-1.71 (m, 1H), 1.63-1.62 (m, 2H), 1.46-1.43 (m, 2H), 1.25 (m, 11H), 1.12-1.10 (m, 8H), 0.94-0.93 (m, 3H); MS: MS m/z 755.2 (M$^+$+1).

Compound 6: tert-butyl ((2R,6S,7R,9S,13aS,14aR,16aS,Z)-14a-((cyclopropylsulfonyl)carbamoyl)-2-((6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, $CD_3OD$): δ ppm 8.12-8.10 (d, J=8.8 Hz, 1H), 7.92-7.90 (d, J=6.0 Hz, 1H), 7.26-7.25 (d, J=6.0 Hz, 1H), 7.19-7.20 (d, J=2.4 Hz, 1H), 7.10-7.07 (dd, J=9.2 and 2.4 Hz, 1H), 6.67-6.65 (db, 1H), 5.87-5.89 (m, 1H), 5.64-5.58 (m, 1H), 5.07-5.02 (m, 1H), 4.73-4.70 (m, 1H), 4.62-4.58 (m, 1H), 4.04-4.01 (m, 1H), 3.93 (s, 3H), 3.90-2.85 (m, 1H), 2.95-2.91 (m, 1H), 2.76-2-71 (m, 2H), 2.45-1.40 (m, 2H), 1.99-1.95 (m, 1H), 1.83-1.75 (m, 3H), 1.60-

1.33 (m, 3H), 1.32-1.24 (m, 2H), 1.13 (s, 9H), 1.24-1.08 (m, 3H), 1.07-0.98 (m, 6H), 0.86-0.80 (m, 1H); MS: MS m/z 755.2 (M⁺+1).

Preparation of Compounds 7 and 8

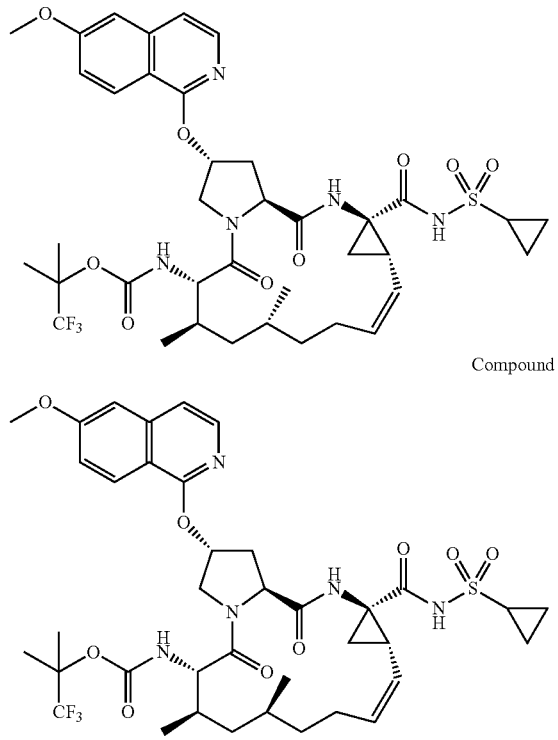

Compounds 7 and 8 were prepared using the intermediates described herein and by following the general procedure described for the synthesis of Compound 3.

Compound 7: 1,1,1-trifluoro-2-methylpropan-2-yl ((2R,6S,7R,9R,13aS,14aR,16aS,Z)-14a-((cyclopropylsulfonyl)carbamoyl)-2-((6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (400 MHz, CD₃OD): δ ppm 8.11-8.09 (d, J=9.2 Hz, 1H), 7.93-7.92 (d, J=6.0 Hz, 1H), 7.28-7.26 (d, J=5.6 Hz, 1H), 7.21-7.20 (d, J=2.4 Hz, 1H), 7.12-7.10 (dd, J=9.2 and 2.4 Hz, 1H), 5.87 (m, 1H), 5.63-5.62 (m, 1H), 5.10-5.05 (m, 1H), 4.75-4.72 (m, 1H), 4.67-4.62 (m, 1H), 4.03-3.99 (m, 1H), 3.94 (s, 3H), 2.84-2.82 (m, 1H), 2.96-2.92-(m, 1H), 2.77-2-71 (m, 2H), 2.47-1.40 (m, 2H), 1.98-1.76 (m, 4H), 1.61-1.51 (m, 1H), 1.49-1.38 (m, 2H), 1.35-1.31 (m, 5H), 1.25-1.22 (m, 1H), 1.14-1.0 (m, 12H), 0.98-0.83 (m, 1H); ¹⁹F NMR: −76.94 (3 F), −193.32 (1 F); MS: MS m/z 807.1 (M⁺-1).

Compound 8: 1,1,1-trifluoro-2-methylpropan-2-yl ((2R,6S,7R,9S,13aS,14aR,16aS,Z)-14a-((cyclopropylsulfonyl)carbamoyl)-2-((6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 807.3 (M⁺-1).

Preparation of Compounds 9 and 10

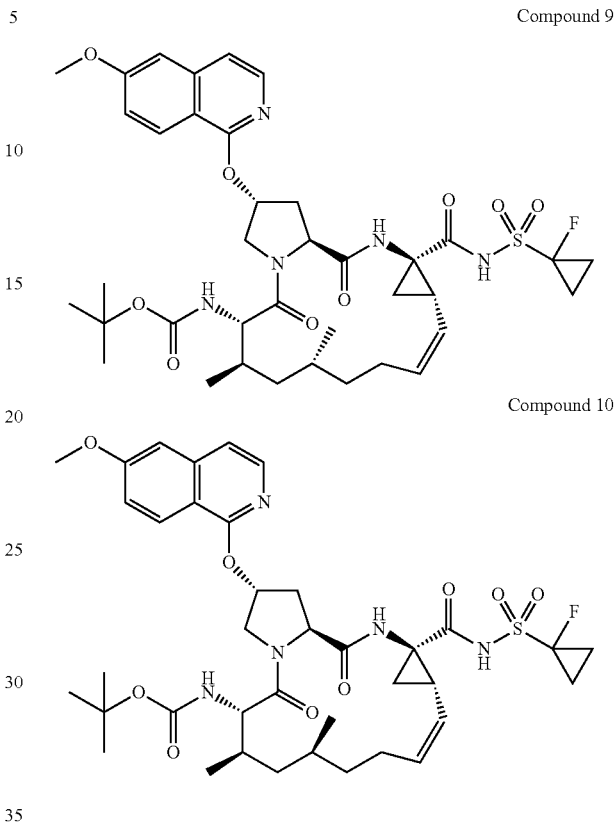

Compounds 9 and 10 were prepared using the intermediates described herein and by following the general procedure described for the synthesis of Compound 1.

Compound 9: tert-butyl ((2R,6S,7R,9R,13aS,14aR,16aS,Z)-14a-(((1-fluorocyclopropyl)sulfonyl)carbamoyl)-2-((6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (400 MHz, CD₃OD): δ ppm 9.027 (sb, 1H), 8.13-8.11 (d, J=8.8 Hz, 1H), 7.93-7.91 (d, J=6.0 Hz, 1H), 7.28-7.27 (d, J=5.6 Hz, 1H), 7.21-7.20 (d, J=2.4 Hz, 1H), 7.12-7.09 (dd, J=9.2 and 2.4 Hz, 1H), 5.89 (m, 1H), 5.65-5.58 (m, 1H), 5.02-4.97 (m, 1H), 4.74-4.71 (m, 1H), 4.64-4.60 (m, 1H), 4.07-4.03 (m, 1H), 3.94 (s, 3H), 3.89-3.87 (m, 1H), 2.78-2.73 (m, 2H), 2.48-2.38-(m, 2H), 2.02-1.96 (m, 1H), 1.88-1.73 (m, 4H), 1.69-1.59 (m, 2H), 1.58-1.56 (m, 5H), 1.29-1.23 (m, 1H), 1.17 (s, 9H), 1.03-0.99 (m, 6H), 0.87-0.81 (m, 1H); ¹⁹F NMR: δ ppm −193.21 (1 F); MS: MS m/z 770.2 (M⁺−1).

Compound 10: tert-butyl ((2R,6S,7R,9S,13aS,14aR,16aS,Z)-14a-(((1-fluorocyclopropyl)sulfonyl)carbamoyl)-2-((6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (400 MHz, CD₃OD): δ ppm 8.13-8.11 (d, J=9.2 Hz, 1H), 7.92-7.90 (d, J=6.0 Hz, 1H), 7.26-7.25 (dt, J=6 Hz, 1H), 7.20-7.19 (d, J=2 Hz, 1H), 7.12-1.10 (d, J=8 Hz, 1H), 5.89 (m, 1H), 5.72-5.70 (m, 1H), 5.04 (m, 1H), 4.69-4.66 (m, 1H), 4.51-4.48 (m, 1H), 4.18-4.09 (m, 2H), 3.94 (s, 3H), 2.78-2.63 (m, 2H), 2.49-2.44-(m, 2H), 2.0-1-95 (m, 2H), 1.75-1.64 (m, 4H), 1.49-1.40 (m, 4H), 1.33-1.17 (m, 11H), 1.25-1.11 (m, 5H), 0.98-0.91 (d, J=7 Hz, 3H); $^{19}$F NMR: δ ppm 193.32 (1 F); MS: MS m/z 773.2 (M$^+$+1).

Preparation of Compound 11

Compound 11

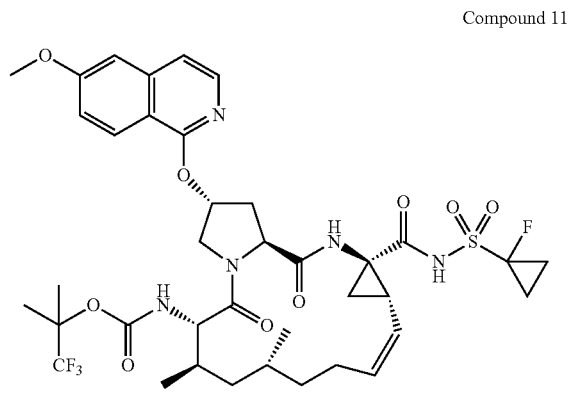 [SMILES: COc1ccc2c(O[C@@H]3C[C@H]4C(=O)N[C@]5(C(=O)NS(=O)(=O)C6(F)CC6)C[C@H]5/C=C\CC[C@@H](C)C[C@@H](C)[C@H](NC(=O)OC(C)(C)C(F)(F)F)C(=O)N4C3)nccc2c1]

Compound 11 was prepared using the intermediates described herein and by following the general procedure described for the synthesis of Compound 3.

Compound 11: 1,1,1-trifluoro-2-methylpropan-2-yl ((2R,6S,7R,9R,13aS,14aR,16aS,Z)-14a-(((1-fluorocyclopropyl)sulfonyl)carbamoyl)-2-(((6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.11-8.08 (d, J=9.2 Hz, 1H), 7.93-7.91 (d, J=6.0 Hz, 1H), 7.27-7.26 (dt, J=6 Hz, 1H), 7.21-7.20 (d, J=2.4 Hz, 1H), 7.12-0.7.09 (dd, J=9.2 and 2.4 Hz, 1H), 5.87 (m, 1H), 5.61-5.59 (m, 1H), 4.94 (m, 1H), 4.74-4.71 (m, 1H), 4.67-4.62 (m, 1H), 4.03-4.0 (m, 1H), 3.94 (s, 3H), 3.86-2.81 (m, 1H), 2.77-2.72-(m, 3H), 2.48-2-36 (m, 2H), 1.99-1.80 (m, 2H), 1.79-1.72 (m, 2H), 1.66-1.58 (m, 4H), 1.49 (sb, 3H), 1.46-1.22 (m, 2H), 1.02-0.97 (m, 9H), 0.86-0.79 (m, 1H); $^{19}$F NMR: δ ppm −85.08 (1 F), −193.20 (1 F); MS: MS m/z 826.2 (M$^+$+1).

Preparation of Compound 12

Compound 12

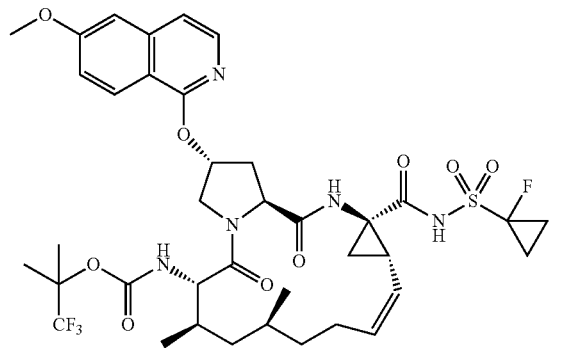

Compound 12 was prepared using the intermediates described herein and by following the general procedure described for the synthesis of Compound 3. 1,1,1-trifluoro-2-methylpropan-2-yl ((2R,6S,7R,9S,13aS,14aR,16aS,Z)-14a-(((1-fluorocyclopropyl)sulfonyl)carbamoyl)-2-((6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 826.2 (M$^+$+1).

Preparation of Compound 13

Compound 13

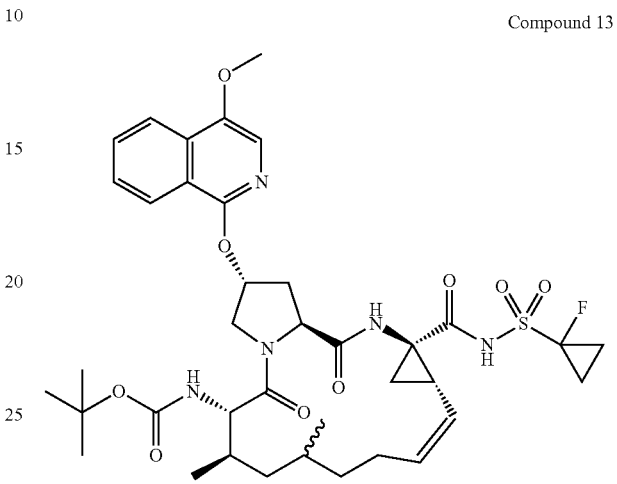

Compound 13 was prepared using the intermediates described herein and by following the general procedure described for the synthesis of Compound 1.

Compound 13: tert-butyl ((2R,6S,7R,13aS,14aR,16aS,Z)-14a-(((1-fluorocyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.20-8.12 (m, 2H), 7.79-7.70 (m, 1H), 7.64-7.52 (m, 2H), 5.90-5.80 (m, 1H), 5.65-5.55 (m, 1H), 5.10-4.95 (m, 1H), 4.75-4.55 (m, 1H), 4.39-4.16 (m, 1H), 4.05 (s, 3H), 4.01-3.95 (m, 1H), 2.82-2.70 (m, 2H), 2.49-2.37 (m, 2H), 2.10-1.95 (m, 2H), 1.87-1.70 (m, 4H), 1.67-1.55 (m, 2H), 1.50-1.40 (m, 5H), 1.37-1.25 (m, 1H), 1.20 (s, 9H), 1.10-0.90 (m, 6H), 0.85-0.70 (m, 1H); MS: MS m/z 773 (M$^+$+1).

Preparation of Compounds 14 and 15

Compound 14

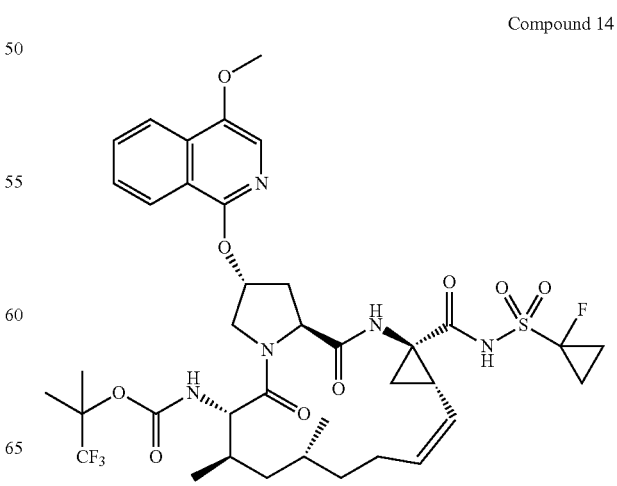

-continued

Compound 15

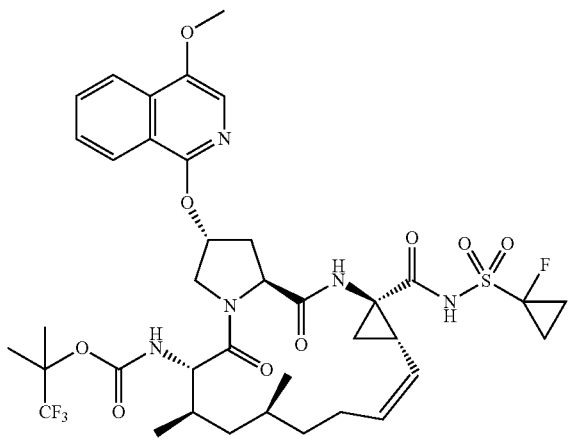

Compounds 14 and 15 were prepared using the intermediates described herein and by following the general procedure described for the synthesis of Compound 3.

Compound 14: 1,1,1-trifluoro-2-methylpropan-2-yl ((2R,6S,7R,9R,13aS,14aR,16aS,Z)-14a-(((1-fluorocyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 9.04 (sb, 1H), 8.18-8.15 (db, J=8.4 Hz, 1H), 8.13-8.11 (db, J=8.4 Hz, 1H), 7.76-7.71 (dt, J=6.8 and 1.2 Hz, 1H), 7.58-7.54 (m, 2H), 5.85 (sb, 1H), 5.63-5.59 (m, 1H), 5.01-5.96 (m, 1H), 4.77-4.74 (m, 1H), 4.68-4.63 (m, 1H), 4.03 (s, 3H), 4.01-3.99 (m, 1H), 3.84-3.81 (m, 1H), 2.77-2.73 (m, 2H), 2.47-2-40 (m, 2H), 1.98-1.80 (m, 2H), 1.79-1.73 (m, 3H), 1.67-1.57 (m, 3H), 1.54-1.43 (m, 4H), 1.34 (sb, 3H), 1.30-1.22 (m, 2H), 1.02-0.96 (m, 9H), 0.86-0.80 (m, 1H); $^{19}$F NMR: δ ppm −85.11 (3 F), −193.22 (1 F); MS: MS m/z 827.3 (M$^+$+1).

Compound 15: 1,1,1-trifluoro-2-methylpropan-2-yl ((2R,6S,7R,9S,13aS,14aR,16aS,Z)-14a-(((1-fluorocyclopropyl)sulfonyl)carbamoyl)-2-((4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.19-8.17 (d, J=8.0 Hz, 1H), 8.13-8.11 (d, J=8.4 Hz, 1H), 7.76-7.72 (dt, J=7.2 and 1.2 Hz, 1H), 7.59-7.55 (m, 2H), 5.85 (sb, 1H), 5.33-5.70 (m, 1H), 5.05-5.0 (m, 1H), 4.73-4.69 (m, 1H), 4.57-4.54 (m, 1H), 4.11-4.04 (m, 2H), 4.02 (s, 3H), 2.76-2.60 (m, 3H), 2.58-2.42 (m, 2H), 2.01-1.98 (m, 2H), 1.78-1-61 (m, 5H), 1.60-1.41 (m, 7H), 1.30-1.21 (m, 4H), 1.19-1.18 (m, 3H), 1.15-1.10 (m, 2H), 0-0.94-0.93 (m, 3H); $^{19}$F NMR: δ ppm −85.05 (3 F), −193.33 (1 F); MS: MS m/z 825.2 (M$^+$−1).

Preparation of 1-chloro-4-ethoxyisoquinoline

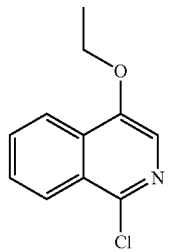

To a solution of 1-chloroisoquinolin-4-ol (1.0 g, 5.5 mmole) in acetonitrile (10 mL) was added K$_2$CO$_3$ (2.3 g, 16.7 mmole) followed by ethyl iodide (0.87 mL, 11.0 mmole) at room temperature. The reaction mixture was stirred at room temperature for overnight. Solvent was evaporated under reduced pressure and the residue was diluted with water and extracted with ethyl acetate. The organic layer was dried over anhydrous Na$_2$SO$_4$, filtered, and concentrated under reduced. The resulting residue was purified by silica gel chromatography to afford 1-chloro-4-ethoxyisoquinoline (700 mg, 62%) as an off-white solid. $^1$H NMR (400 MHz, CD$_3$OD): δ ppm 8.26-8.24 (m, 2H), 7.79 (s, 1H), 7.76-7.26 (m, 2H), 4.29-4.24 (q, J=6.8 Hz, 2H), 1.58-1.1.54 (t, J=6.8 Hz, 3H); MS: MS m/z 207.7 (M$^+$+1).

Scheme

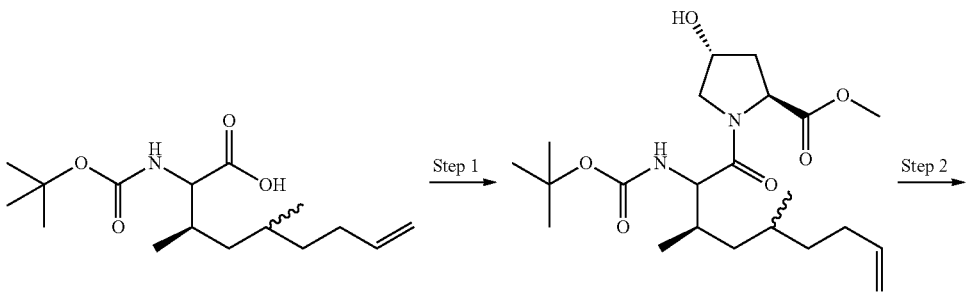

-continued
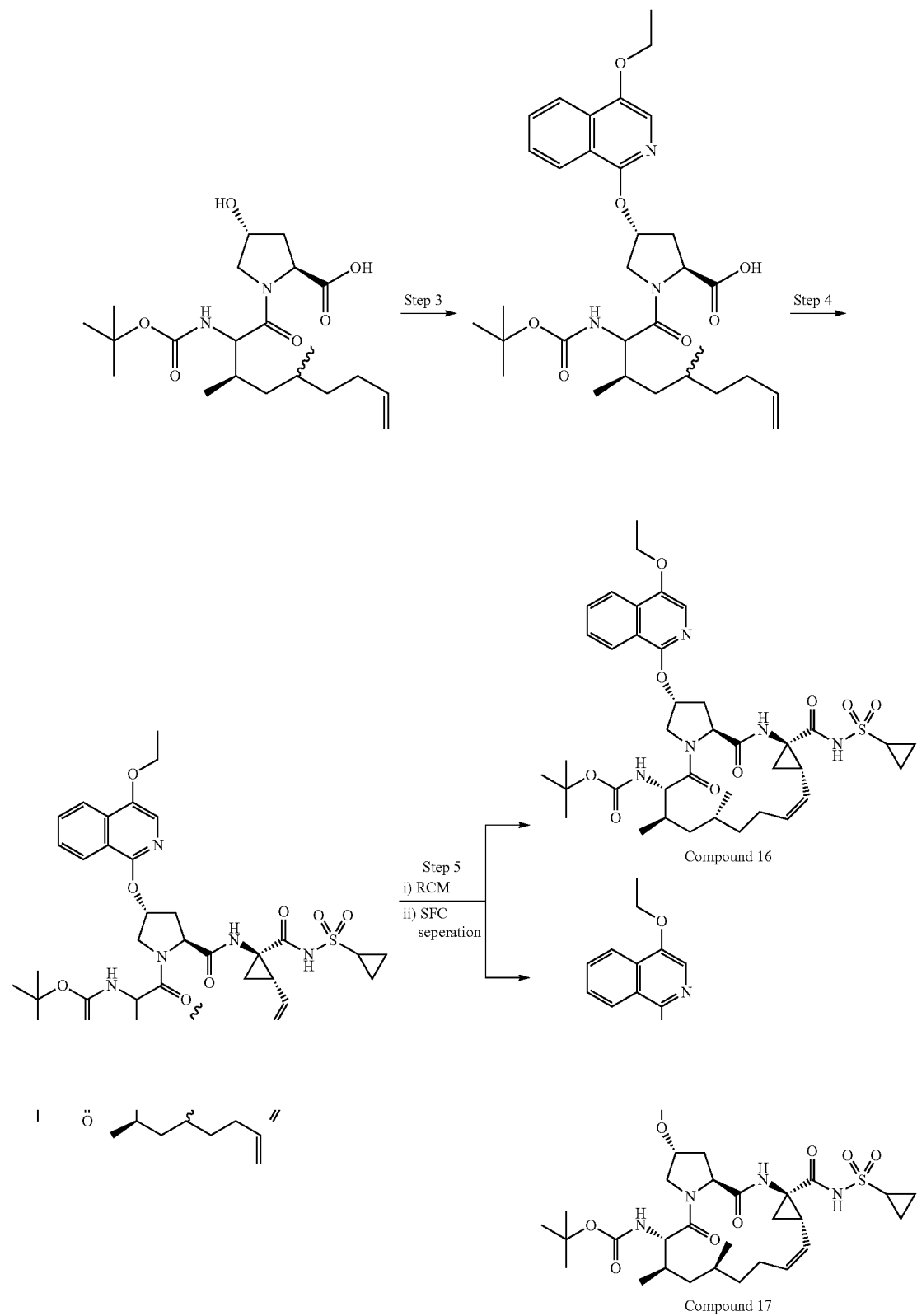

Step 1: Preparation of (2S,4R)-methyl 1-((3R)-2-((tert-butoxycarbonyl)amino)-3,5-dimethylnon-8-enoyl)-4-hydroxypyrrolidine-2-carboxylate

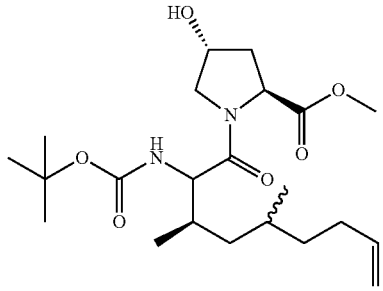 [SMILES: C=CCCC(C)C[C@@H](C)C(NC(=O)OC(C)(C)C)C(=O)N1C[C@H](O)C[C@H]1C(=O)OC]

To a solution of (3R)-2-((tert-butoxycarbonyl)amino)-3,5-dimethylnon-8-enoic acid (2 g, 6.6 mmole), synthesized using Scheme 1, in dichloromethane (20 mL) was added DIPEA (11.5 mL, 33.0 mmole), HATU (2.7 g, 7.2 mmole) followed by (2S,4R)-methyl 4-hydroxypyrrolidine-2-carboxylate (1.3 g, 7.2 mmole) at room temperature. The reaction mixture was stirred at room temperature for 2 h. The reaction mass was diluted with DCM and washed with water. The organic layer was dried over anhydrous $Na_2SO_4$ and concentrated under reduced pressure to get crude (2S,4R)-methyl 1-((3R)-2-((tert-butoxycarbonyl)amino)-3,5-dimethylnon-8-enoyl)-4-hydroxypyrrolidine-2-carboxylate. The crude product was taken to the next step without further purification (2.2 g, 80%). MS: MS m/z 427.2 ($M^+$+1).

Step 2: Preparation of (2S,4R)-1-((3R)-2-((tert-butoxycarbonyl)amino)-3,5-dimethylnon-8-enoyl)-4-hydroxypyrrolidine-2-carboxylic acid

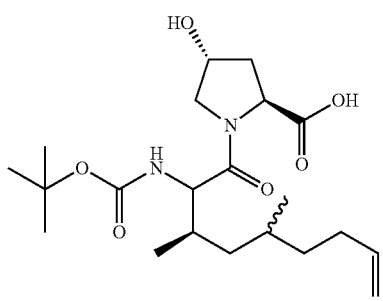 [SMILES: C=CCCC(C)C[C@@H](C)C(NC(=O)OC(C)(C)C)C(=O)N1C[C@H](O)C[C@H]1C(=O)O]

To a solution of (2S,4R)-methyl 1-((3R)-2-((tert-butoxycarbonyl)amino)-3,5-dimethylnon-8-enoyl)-4-hydroxypyrrolidine-2-carboxylate (2.2 g, 5.1 mmole) in THF/water (20 mL, 1:1) was added LiOH (650 mg, 15 mmole) followed by 5 mL of methanol at room temperature. The reaction mass was stirred at room temperature for overnight. The solvent was evaporated under reduced pressure and the residue was diluted with water and acidified with aqueous 1.5 N HCl solution. The aqueous solution was extracted with ethyl acetate (20 mL×3). The combined organic layer was dried over anhydrous $Na_2SO_4$ and concentrated under reduced pressure to get desired product (2S,4R)-1-((3R)-2-((tert-butoxycarbonyl)amino)-3,5-dimethylnon-8-enoyl)-4-hydroxypyrrolidine-2-carboxylic acid (1.8 g, 85%) as white solid. MS: MS m/z 411.2 ($M^+$−1).

Step 3: Preparation of (2S,4R)-1-((3R)-2-((tert-butoxycarbonyl)amino)-3,5-dimethylnon-8-enoyl)-4-((4-ethoxyisoquinolin-1-yl)oxy)pyrrolidine-2-carboxylic acid

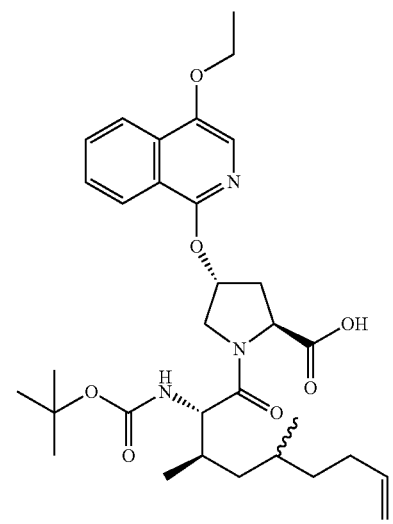 [SMILES: C=CCCC(C)C[C@@H](C)[C@H](NC(=O)OC(C)(C)C)C(=O)N1C[C@H](Oc2ncc(OCC)c3ccccc23)C[C@H]1C(=O)O]

To a solution of (2S,4R)-1-((3R)-2-((tert-butoxycarbonyl)amino)-3,5-dimethylnon-8-enoyl)-4-hydroxypyrrolidine-2-carboxylic acid (700 mg, 1.6 mmole) in DMSO was added 1-chloro-4-ethoxyisoquinoline (420 mg, 2.0 mmole), prepared above, followed by t-BuOK (1M sol. in THF, 8 mL, 8 mmole) at room temperature under nitrogen atmosphere. The reaction mass was stirred at room temperature for 4 h. The reaction mass was quenched with aqueous citric acid solution and extracted with ethyl acetate. The combined organic layer was dried over anhydrous $Na_2SO_4$ and concentrated under reduced pressure to get crude compound. The crude compound was purified by combiflash to get desired product (2S,4R)-1-((3R)-2-((tert-butoxycarbonyl)amino)-3,5-dimethylnon-8-enoyl)-4-((4-ethoxyisoquinolin-1-yl)oxy)pyrrolidine-2-carboxylic acid (600 mg, 64%) as off-white solid. MS: MS m/z 585.1 ($M^+$+1).

Step 4: Preparation of tert-butyl ((3R)-1-((2S,4R)-2-(((1R,2S)-1-((cyclopropylsulfonyl)carbamoyl)-2-vinylcyclopropyl)carbamoyl)-4-((4-ethoxyisoquinolin-1-yl)oxy)pyrrolidin-1-yl)-3,5-dimethyl-1-oxonon-8-en-2-yl)carbamate

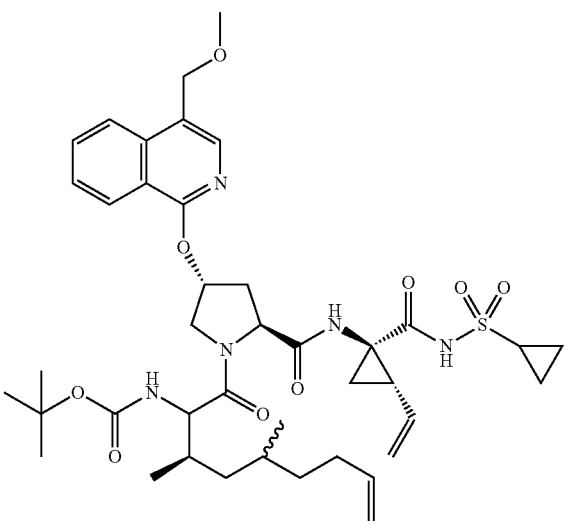 [SMILES: C=CCCC(C)C[C@@H](C)C(NC(=O)OC(C)(C)C)C(=O)N1C[C@H](Oc2ncc(COC)c3ccccc23)C[C@H]1C(=O)N[C@]1(C(=O)NS(=O)(=O)C2CC2)C[C@H]1C=C]

To a solution of (2S,4R)-1-((3R)-2-((tert-butoxycarbonyl)amino)-3,5-dimethylnon-8-enoyl)-4-((4-ethoxyisoquinolin-1-yl)oxy)pyrrolidine-2-carboxylic acid (600 mg, 1.0 mmole) in dichloromethane (10 mL) was added DIPEA (0.87 mL, 5 mmole), HATU (380 mg, 1.0 mmole) followed by (1R,2S)-1-amino-N-(cyclopropylsulfonyl)-2-vinylcyclopropanecarboxamide hydrochloride (prepared according to the procedure described in WO 03/099274) (457 mg, 1.1 mmole) at room temperature. The reaction mixture was stirred at room temperature for 2 h. The reaction mass was diluted with DCM and washed with water. The organic layer was dried over anhydrous $Na_2SO_4$ and concentrated under reduced pressure to get crude compound. The crude compound was purified by silica gel chromatography to get desired product tert-butyl ((3R)-1-((2S,4R)-2-(((1R,2S)-1-((cyclopropylsulfonyl)carbamoyl)-2-vinylcyclopropyl)carbamoyl)-4-((4-ethoxyisoquinolin-1-yl)oxy)pyrrolidin-1-yl)-3,5-dimethyl-1-oxonon-8-en-2-yl)carbamate (500 mg, 61%) as off-white solid. MS: MS m/z 797.2 ($M^+$+1).

Step 5: Preparation of Compounds 16 and 17

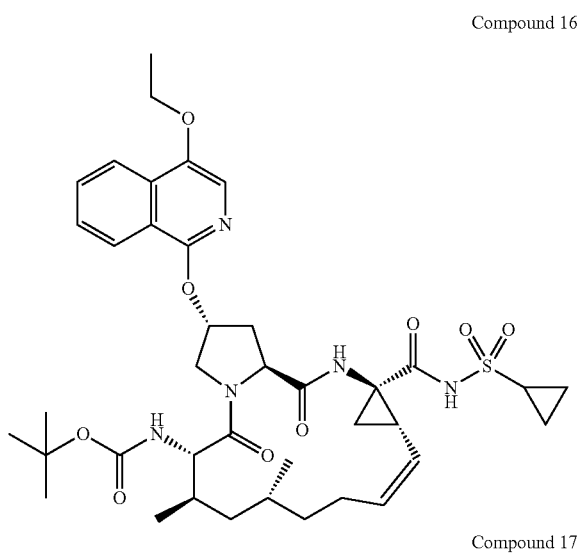

Compound 16

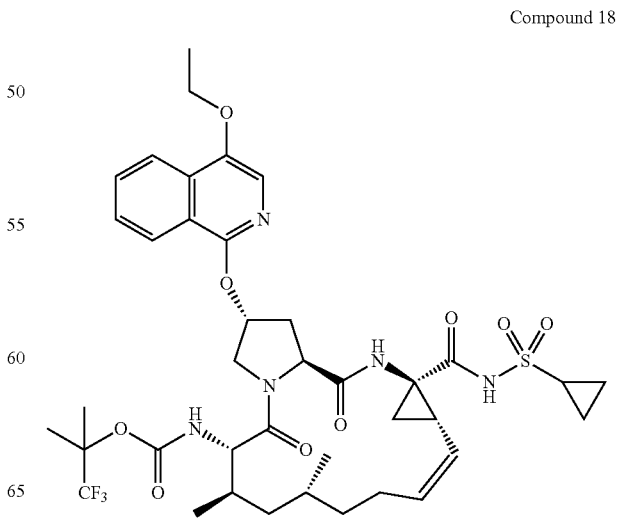

Compound 17

Compounds 16 and 17 were prepared using the intermediates described above and by following the general procedure described for the synthesis of Compound 1 and Compound 2, step 5.

Compound 16: tert-butyl ((2R,6S,7R,9R,13aS,14aR,16aS,Z)-14a-((cyclopropylsulfonyl)carbamoyl)-2-((4-ethoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, $CD_3OD$): δ ppm 8.17-8.15 (d, J=8.4 Hz, 1H), 8.13-8.11 (d, J=8 Hz, 1H), 7.74-7.70 (t, J=7.2 Hz, 1H), 7.56-7.52 (m, 2H), 5.83 (m, 1H), 5.65-5.59 (m, 1H), 5.06-5.01 (m, 1H), 4.73-4.70 (m, 1H), 4.63-4.56 (m, 2H), 4.25-4.20 (q, J=6.8 Hz, 2H), 4.04-4.01 (m, 1H), 3.90-3.86 (m, 1H), 2.94-2.92 (m, 1H), 2.76-2.71 (m, 2H), 2.44-2.38 (m, 2H), 1.98-1.95 (m, 1H), 1.96-1.76 (m, 3H), 1.60-1.46 (m, 6H), 1.35-1.30 (m, 3H), 1.18-1.10 (m, 11H), 1.09-0.98 (m, 6H), 0.86-0.80 (m, 1H); MS: MS m/z 769.1 ($M^+$+1).

Compound 17: tert-butyl ((2R,6S,7R,9S,13aS,14aR,16aS,Z)-14a-((cyclopropylsulfonyl)carbamoyl)-2-((4-ethoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, $CD_3OD$): δ ppm 8.19-8.17 (d, J=8 Hz, 1H), 8.15-8.13 (d, J=8.4 Hz, 1H), 7.75-7.72 (t, J=8 Hz, 1H), 7.59-7.55 (m, 2H), 5.85 (m, 1H), 5.75-5.73 (m, 1H), 5.08 (m, 1H), 4.70-4.66 (m, 1H), 4.52-4.49 (m, 1H), 4.26-4.21 (q, J=6.8 Hz, 2H), 4.17-4.16 (m, 1H), 4.10-4.07 (m, 1H), 2.96-2.90 (m, 1H), 2.74-2.65 (m, 2H), 2.48-2.42 (m, 2H), 1.99-1.96 (m, 2H), 1.75-1.71 (m, 1H), 1.61 (m, 2H), 1.56-1.52 (t, J=6.8 Hz, 3H), 1.46-1.40 (m, 2H), 1.31-1.27 (m, 11H), 1.13-1.0 (m, 8H), 0.95-0.93 (m, 3H); MS: MS m/z 769.1 ($M^+$+1).

Preparation of Compounds 18 and 19

Compound 18

Preparation of Compounds 20 and 21

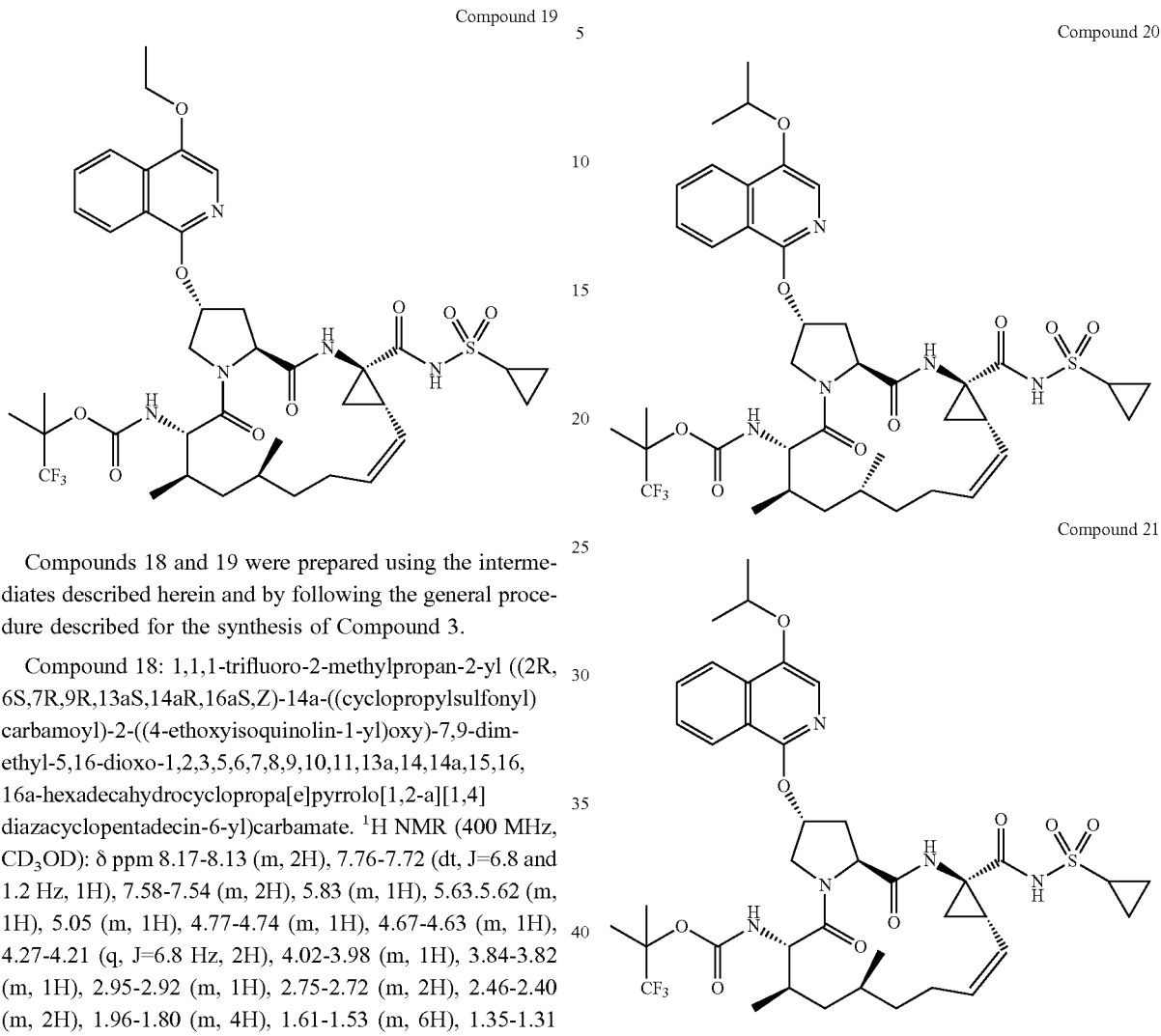

Compound 19

Compound 20

Compound 21

Compounds 18 and 19 were prepared using the intermediates described herein and by following the general procedure described for the synthesis of Compound 3.

Compound 18: 1,1,1-trifluoro-2-methylpropan-2-yl ((2R, 6S,7R,9R,13aS,14aR,16aS,Z)-14a-((cyclopropylsulfonyl)carbamoyl)-2-((4-ethoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.17-8.13 (m, 2H), 7.76-7.72 (dt, J=6.8 and 1.2 Hz, 1H), 7.58-7.54 (m, 2H), 5.83 (m, 1H), 5.63.5.62 (m, 1H), 5.05 (m, 1H), 4.77-4.74 (m, 1H), 4.67-4.63 (m, 1H), 4.27-4.21 (q, J=6.8 Hz, 2H), 4.02-3.98 (m, 1H), 3.84-3.82 (m, 1H), 2.95-2.92 (m, 1H), 2.75-2.72 (m, 2H), 2.46-2.40 (m, 2H), 1.96-1.80 (m, 4H), 1.61-1.53 (m, 6H), 1.35-1.31 (m, 5H), 1.27-1.14 (m, 4H), 1.09-1.0.98 (m, 9H), 0.96-0.90 (m, 1H); $^{19}$F NMR: δ ppm −85.11 (3 F); MS: MS m/z 822.2 (M$^+$+1).

Compound 19: 1,1,1-trifluoro-2-methylpropan-2-yl ((2R, 6S,7R,9S,13aS,14aR,16aS,Z)-14a-((cyclopropylsulfonyl)carbamoyl)-2-((4-ethoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.18-8.16 (d, J=8 Hz, 1H), 8.14-8.12 (d, J=8.8 Hz, 1H), 7.75-7.71 (dt, J=6.8 and 1.2 Hz, 1H), 7.58-7.55 (m, 2H), 5.83 (m, 1H), 5.75-5.73 (m, 1H), 5.08 (m, 1H), 4.72-4.65 (m, 1H), 4.56-4.53 (m, 2H), 4.26-4.20 (q, J=7.2 Hz, 2H), 4.12-4.11 (m, 2H), 2.92-2.90 (m, 1H), 2.74-2.66 (m, 2H), 2.49-2.46 (m, 2H), 2.03-2.01 (m, 2H), 1.75-1.73 (m, 3H), 1.65-1.54 (t, J=7.2 Hz, 3H), 1.48-1.38 (m, 5H), 1.30-1.23 (m, 6H), 1.14-1.01 (m, 9H), 0.94-0.87 (m, 1H); $^{19}$F NMR: δ ppm −85.04 (3 F); MS: MS m/z 822.2 (M$^+$+1).

Compounds 20 and 21 were prepared using the intermediates described herein and by following the general procedure described for the synthesis of Compound 3.

Compound 20: 1,1,1-trifluoro-2-methylpropan-2-yl ((2R, 6S,7R,9R,13aS,14aR,16aS,Z)-14a-((cyclopropylsulfonyl)carbamoyl)-2-((4-isopropoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 9.0 (sb, 1H), 8.16-8.14 (d, J=8.4, 1H), 8.12-8.10 (d, J=8.4, 1H), 7.74-7.70 (dt, J=7.2 and 1.2 Hz, 1H), 7.61 (s, 1H), 7.57-7.53 (m, 1H), 5.82 (m, 1H), 5.64.5.59 (m, 1H), 5.06-5.01 (m, 1H), 4.94-4.90 (m, 1H), 4.80-4.71 (m, 2H), 4.69-4.63 (m, 1H), 4.02-3.98 (m, 1H), 3.83-3.81 (m, 1H), 2.95-2.91 (m, 1H), 2.77-2.71 (m, 2H), 2.46-2.40 (m, 2H), 1.81-1.76 (m, 4H), 1.60-1.57 (m, 1H), 1.51-1.44 (m, 8H), 1.33-1.30 (m, 5H), 1.16-0.98 (m, 9H), 0.97 (m, 3H), 0.91-0.83 (m, 1H); $^{19}$F NMR: δ ppm −85.13 (3 F); MS: MS m/z 836.2 (M$^+$+1).

Compound 21: 1,1,1-trifluoro-2-methylpropan-2-yl ((2R, 6S,7R,9S,13aS,14aR,16aS,Z)-14a-((cyclopropylsulfonyl)carbamoyl)-2-((4-isopropoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (400 MHz, CD₃OD): δ ppm 9.03 (sb, 1H), 8.18-8.16 (d, J=8.4, 1H), 8.12-8.10 (d, J=8.4, 1H), 7.75-7.70 (dt, J=7.2 and 1.2 Hz, 1H), 7.60 (s, 1H), 7.58-7.54 (m, 1H), 5.84 (m, 1H), 5.73.5.71 (m, 1H), 5.10-5.05 (m, 1H), 4.75-4.70 (m, 2H), 4.69-4.56 (m, 1H), 4.10-4.03 (m, 2H), 2.98-2.90 (m, 1H), 2.78-2.61 (m, 2H), 2.50-2.45 (m, 2H), 2.01-1.99 (m, 2H), 1.74-1.58 (m, 3H), 1.49-1.42 (m, 11H), 1.35-1.21 (m, 4H), 1.15-1.02 (m, 9H), 0.95-0.93 (m, 3H); ¹⁹F NMR: δ ppm −85.05 (3 F); MS: MS m/z 836.3 (M⁺+1).

Preparation of Compounds 22 and 23

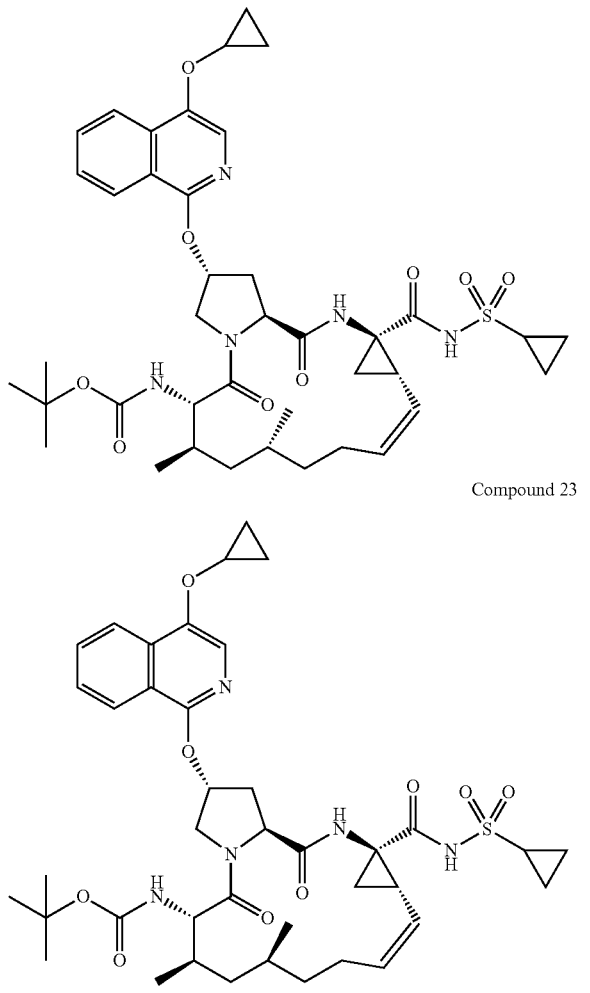

Compound 22

Compound 23

Compounds 22 and 23 were prepared using the intermediates described herein and by following the general procedure described for the synthesis of Compound 1.

Compound 22: tert-butyl ((2R,6S,7R,9R,13aS,14aR,16aS,Z)-2-((4-cyclopropoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (400 MHz, CD₃OD): δ ppm 8.17-8.15 (d, J=8.0 Hz, 1H), 8.02-8.00 (d, J=8.4 Hz, 1H), 7.87 (s, 1H), 7.72-7.68 (t, J=7.2 Hz, 1H), 7.56-7.52 (t, J=8 Hz, 1H), 6.62-6.60 (db, 1H), 5.84-5 (m, 1H), 5.65-5.59 (m, 1H), 5.06-5.01 (m, 1H), 4.75-4.72 (m, 1H), 4.64-4.56 (m, 1H), 4.05-3.97 (m, 2H), 3.97-3.3.90 (m, 1H), 2.95-2.91 (m, 1H), 2.77-2-72 (m, 2H), 2.43-2.40 (m, 2H), 2.02-1.98 (m, 1H), 1.83-1.76 (m, 3H), 1.60-1.56 (m, 1H), 1.51-1.48 (m, 2H), 1.34-1.30 (m, 2H), 1.25-1.21 (m, 1H), 1.18-1.06 (m, 10H), 1.05-0.97 (m, 8H), 0.91-0.81 (m, 4H); MS: MS m/z 781.2 (M⁺+1).

Compound 23: tert-butyl ((2R,6S,7R,9S,13aS,14aR,16aS,Z)-2-((4-cyclopropoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 781.2 (M⁺+1).

Preparation of Compounds 24 and 25

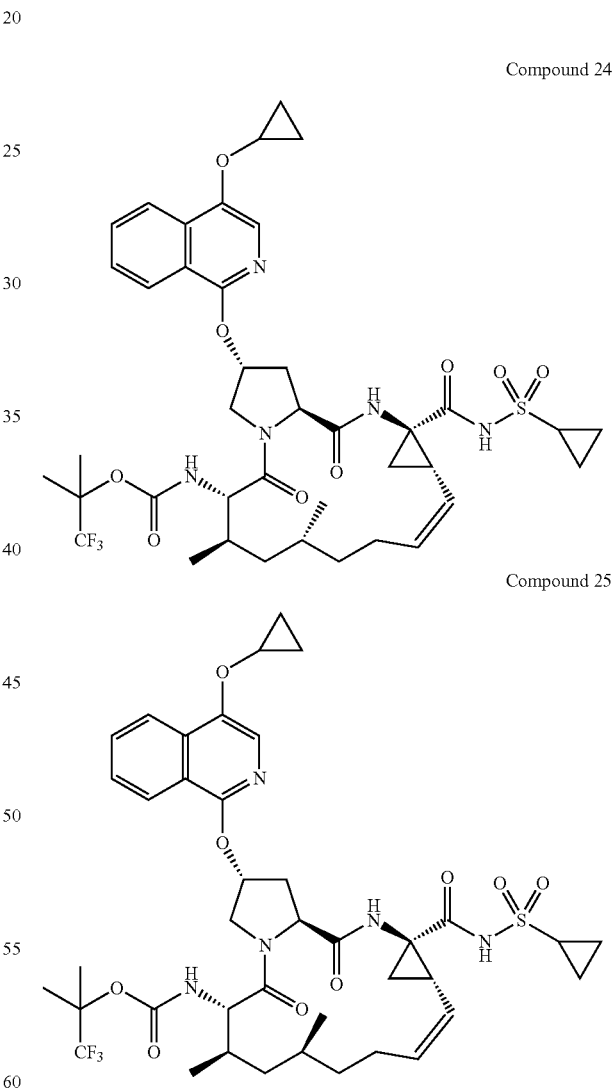

Compound 24

Compound 25

Compounds 24 and 25 were prepared using the intermediates described herein and by following the general procedure described for the synthesis of Compound 3.

Compound 24: 1,1,1-trifluoro-2-methylpropan-2-yl ((2R,6S,7R,9R,13aS,14aR,16aS,Z)-2-((4-cyclopropoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.17-8.15 (d, J=8.4 Hz, 1H), 8.04-8.02 (d, J=8.4 Hz, 1H), 7.88 (s, 1H), 7.73-7.69 (dt, J=7.1 and 1.2 Hz, 1H), 7.57-7.53 (dt, J=8 and 1.2 Hz, 1H), 7.27-7.25 (db, 1H), 5.84-5.83 (m, 1H), 5.66-5.59 (m, 1H), 5.06-5.01 (m, 1H), 4.78-4.75 (m, 1H), 4.67-4.63 (m, 1H), 4.02-3.97 (m, 2H), 3.85-3.80 (m, 1H), 2.94-2.91 (m, 1H), 2.76-2-71 (m, 2H), 2.44-2.40 (m, 2H), 1.90-1.81 (m, 4H), 1.67-1.57 (m, 2H), 1.52-1.49 (m, 1H), 1.49-1.37 (m, 4H), 1.14-1.10 (m, 3H), 1.08-0.97 (m, 7H), 0.91-0.80 (m, 8H); $^{19}$F NMR: δ ppm −85.11 (3 F); MS: MS m/z 832.2 (M$^+$−1).

Compound 25: 1,1,1-trifluoro-2-methylpropan-2-yl ((2R,6S,7R,9S,13aS,14aR,16aS,Z)-2-((4-cyclopropoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.18-8.16 (d, J=8.0 Hz, 1H), 8.03-8.01 (d, J=8.4 Hz, 1H), 7.88 (s, 1H), 7.73-7.69 (dt, J=7.2 and 1.2 Hz, 1H), 7.58-7.54 (dt, J=8 and 1.2 Hz, 1H), 7.21-7.19 (db, 1H), 5.84 (m, 1H), 5.73-5.71 (m, 1H), 5.10-5.06 (m, 1H), 4.72-4.68 (m, 1H), 4.58-4.55 (m, 1H), 413-3.98 (m, 3H), 2.93-2.91 (m, 1H), 2.73-2-70 (m, 2H), 2.52-2.45 (m, 2H), 2.02-1.95 (m, 2H), 1.72-1.63 (m, 4H), 1.49-1.43 (m, 4H), 1.34-1.22 (m, 3H), 1.12-1.02 (m, 9H), 0.95-0.83 (m, 8H); $^{19}$F NMR: δ ppm −85.04 (3 F); MS: MS m/z 832.3 (M$^+$−1).

Preparation of Compound 26

Compound 26

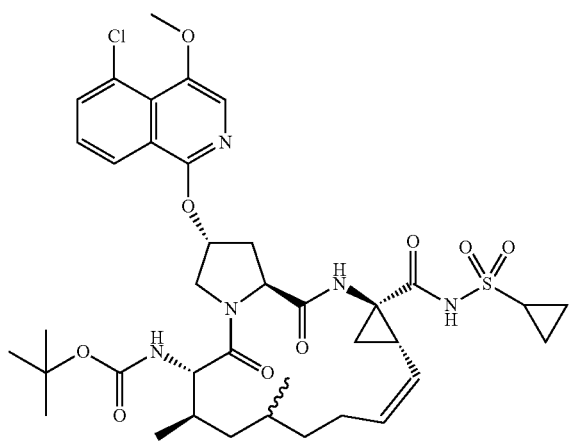

Compound 26 was prepared using the intermediates described herein and by following the general procedure described for the synthesis of Compound 1.

Compound 26: tert-butyl ((2R,6S,7R,13aS,14aR,16aS,Z)-2-((5-chloro-4-methoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. MS: MS m/z 789.2 (M$^+$+1).

Preparation of Compounds 27 and 28

Compound 27

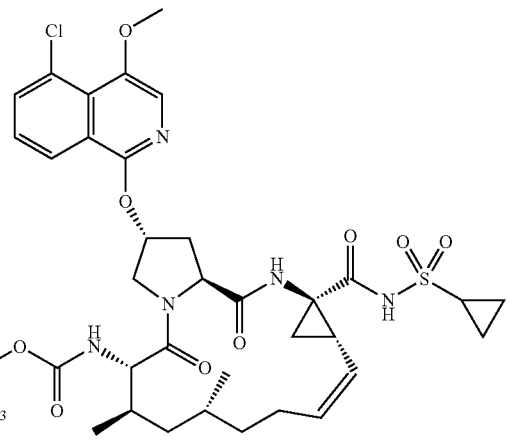

Compound 28

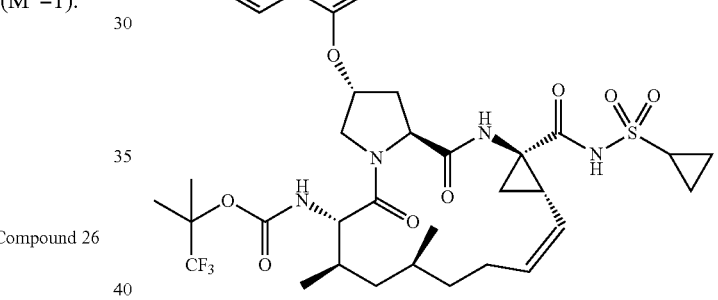

Compounds 27 and 28 were prepared using the intermediates described herein and by following the general procedure described for the synthesis of Compound 3.

Compound 27: 1,1,1-trifluoro-2-methylpropan-2-yl ((2R,6S,7R,9R,13aS,14aR,16aS,Z)-2-((5-chloro-4-methoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 9.0 (sb, 1H), 8.18-8.16 (dd, J=8.0 and 1.2 Hz, 1H), 7.78-7.76 (dd, J=7.6 and 1.2 Hz, 1H), 7.71 (s, 1H), 7.49-7.45 (tb, J=8.0 Hz, 1H), 5.83-5.82 (m, 1H), 5.65.5.59 (m, 1H), 5.06-5.01 (m, 1H), 4.78-4.75 (m, 1H), 4.67-4.65 (m, 1H), 4.0-3.96 (m, 4H), 3.79-3.77 (m, 1H), 2.97-2.91 (m, 1H), 2.75-2.70 (m, 2H), 2.46-2.39 (m, 2H), 2.01-1.92 (m, 1H), 1.82-1.76 (m, 3H), 1.60-1.57 (m, 1H), 1.50-1.49 (m, 2H), 1.35-1.30 (m, 4H), 1.26-1.21 (m, 2H), 1.16-1.07 (m, 3H), 1.07-0.98 (m, 9H), 0.85-0.82 (m, 1H); $^{19}$F NMR: δ ppm −85.10 (3 F); MS: MS m/z 841.2 (M$^+$−1).

Compound 28: 1,1,1-trifluoro-2-methylpropan-2-yl ((2R,6S,7R,9S,13aS,14aR,16aS,Z)-2-((5-chloro-4-methoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.20-8.18 (dd, J=8.4 and 1.2 Hz, 1H), 7.79-7.76 (dd, J=7.6 and 1.2 Hz, 1H), 7.70 (s, 1H), 7.49-7.45 (tb, J=8.0 Hz, 1H), 7.22-7.20 (sb, 1H), 5.84-5.82 (m, 1H), 5.73.5.71 (m, 1H), 5.10-5.05 (m, 1H), 4.72-4.68 (m, 1H), 4.58-4.55 (m, 1H), 4.09-4.01 (m, 2H), 3.96 (s, 3H), 2.93-2.91 (m, 1H), 2.75-2.68 (m, 2H), 2.51-2.45 (m, 2H), 1.99-1.95 (m, 2H), 1.74-1.70 (m, 2H), 1.62-1.59 (m, 2H), 1.49-1.43 (m, 4H), 1.35-1.30 (m, 4H), 1.18-1.05 (m, 9H), 0.94-0. (m, 3H); $^{19}$F NMR: δ ppm −85.04 (3 F); MS: MS m/z 841.2 (M$^+$−1).

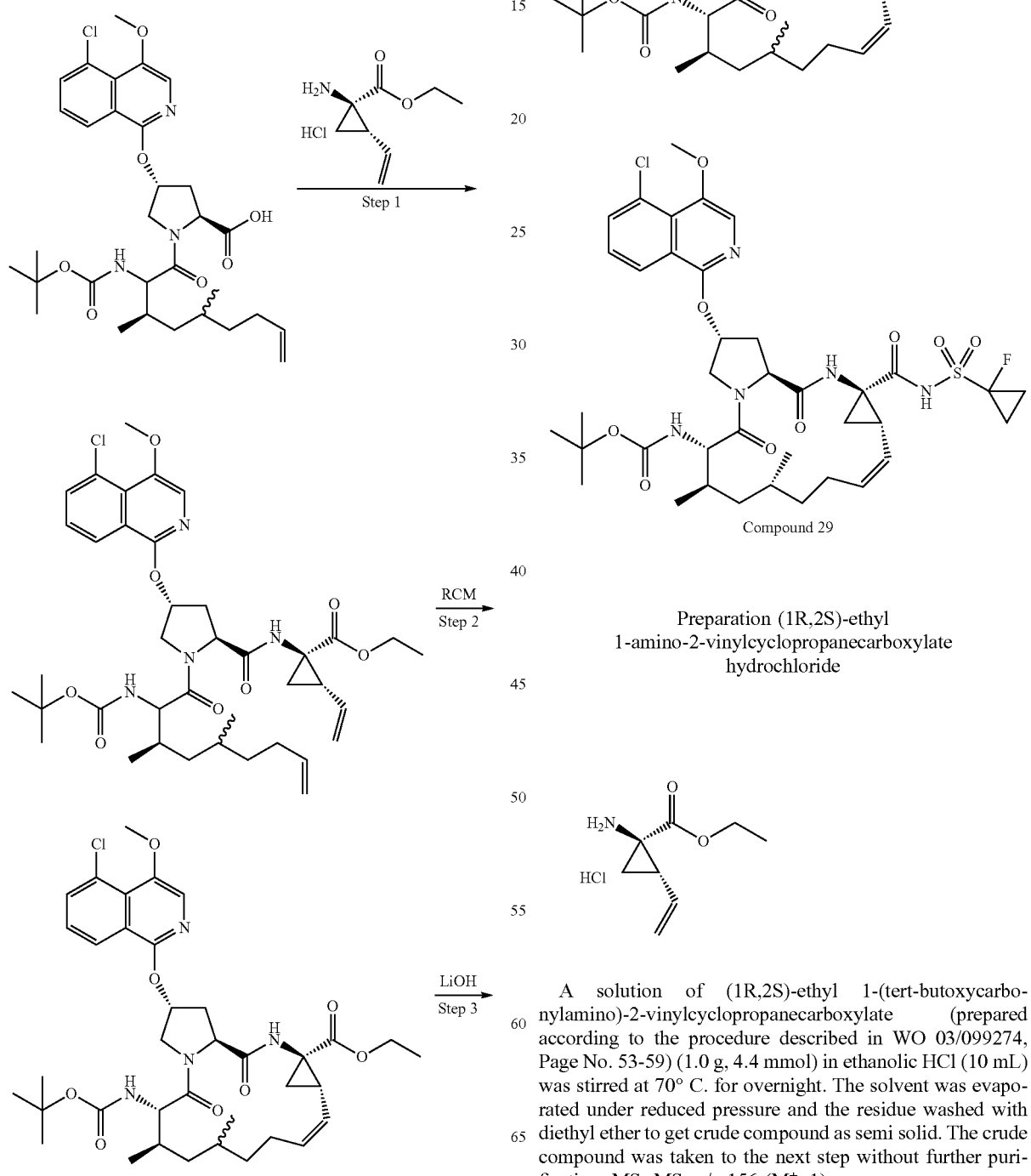

Compound 29

Preparation (1R,2S)-ethyl 1-amino-2-vinylcyclopropanecarboxylate hydrochloride

A solution of (1R,2S)-ethyl 1-(tert-butoxycarbonylamino)-2-vinylcyclopropanecarboxylate (prepared according to the procedure described in WO 03/099274, Page No. 53-59) (1.0 g, 4.4 mmol) in ethanolic HCl (10 mL) was stirred at 70° C. for overnight. The solvent was evaporated under reduced pressure and the residue washed with diethyl ether to get crude compound as semi solid. The crude compound was taken to the next step without further purification. MS: MS m/z 156 (M$^+$+1).

Step 1: Preparation of (1R,2S)-ethyl 1-((2S,4R)-1-((3R)-2-((tert-butoxycarbonyl)amino)-3,5-dimethyl-non-8-enoyl)-4-((5-chloro-4-methoxyisoquinolin-1-yl)oxy)pyrrolidine-2-carboxamido)-2-vinylcyclopropanecarboxylate

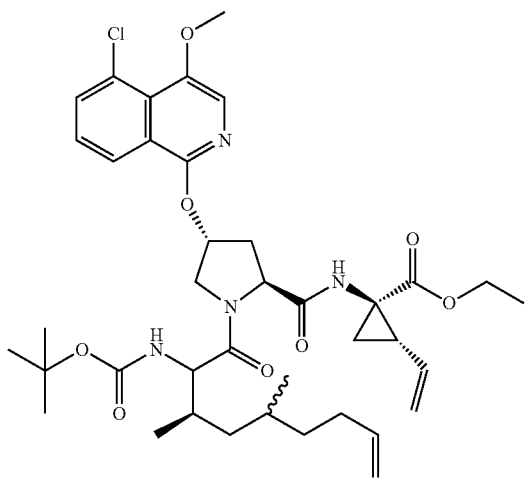 [SMILES: C=CCCC(C)C[C@@H](C)C(NC(=O)OC(C)(C)C)C(=O)N1C[C@H](Oc2ncc(OC)c3c(Cl)cccc23)C[C@H]1C(=O)N[C@]1(C(=O)OCC)C[C@H]1C=C]

A procedure was followed analogous to that described for tert-butyl ((3R)-1-((2S,4R)-2-(((1R,2S)-1-((cyclopropylsulfonyl)carbamoyl)-2-vinylcyclopropyl)carbamoyl)-4-((4-methoxyisoquinolin-1-yl)oxy)pyrrolidin-1-yl)-3,5-dimethyl-1-oxonon-8-en-2-yl)carbamate to afford (1R,2S)-ethyl 1-((2S,4R)-1-((3R)-2-((tert-butoxycarbonyl)amino)-3,5-dimethylnon-8-enoyl)-4-((5-chloro-4-methoxyisoquinolin-1-yl)oxy)pyrrolidine-2-carboxamido)-2-vinylcyclopropanecarboxylate. MS: MS m/z 742.3 (M$^+$+1).

Step 2: Preparation of (2R,6S,7R,13aS,14aR,16aS,Z)-ethyl 6-((tert-butoxycarbonyl)amino)-2-((5-chloro-4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate

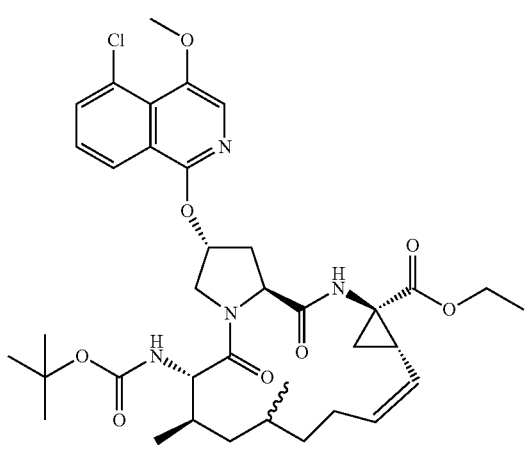 [SMILES: CCOC(=O)[C@@]12C[C@H]1/C=C\CCC(C)C[C@@H](C)[C@H](NC(=O)OC(C)(C)C)C(=O)N1C[C@H](Oc3ncc(OC)c4c(Cl)cccc34)C[C@H]1C(=O)N2]

The general procedure as described for Compound 1 and 2 was followed with the modification that the diastereomer products were not separated. MS: MS m/z 714 (M$^+$+1).

Step 3: Preparation of (2R,6S,7R,13aS,14aR,16aS,Z)-6-((tert-butoxycarbonyl)amino)-2-((5-chloro-4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid

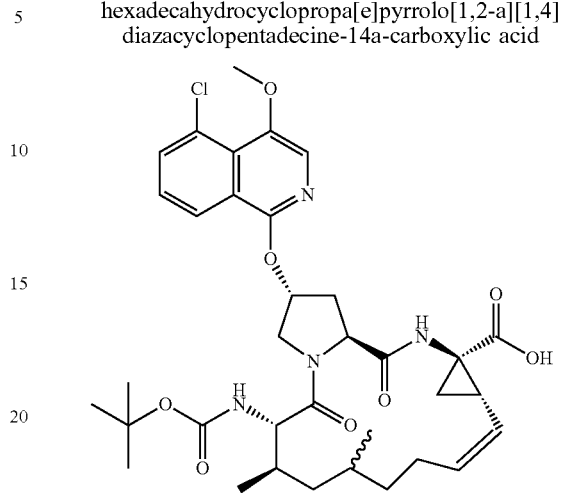

To a solution of (2R,6S,7R,13aS,14aR,16aS,Z)-ethyl 6-((tert-butoxycarbonyl)amino)-2-((5-chloro-4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (400 mg, 0.56 mmol) in THF/water (1:1) was added LiOH (235 mg, 5.61 mmol) followed by 5 mL of methanol at room temperature. The reaction mixture was stirred at room temperature for overnight. The solvent was removed under reduced pressure and the residue was diluted with water and acidified by aqueous 1.5 N HCl solutions. The aqueous solution was extracted with ethyl acetate. The combined organic layer was washed with water, dried over anhydrous Na$_2$SO$_4$ and concentrated to get desired product (2R,6S,7R,13aS,14aR,16aS,Z)-6-((tert-butoxycarbonyl)amino)-2-((5-chloro-4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid as diastereomeric mixture (310 mg, 81%). MS: MS m/z 686.3 (M$^+$+1).

Step 4: Preparation of Compound 29

Compound 29

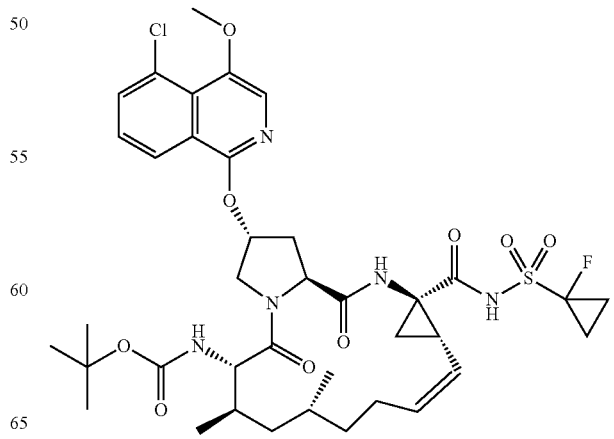

To a solution of (2R,6S,7R,13aS,14aR,16aS,Z)-6-((tert-butoxycarbonyl)amino)-2-((5-chloro-4-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid (300 mg, 0.43 mmol) in DMF (20 mL) was added 1,1'-carbonyldiimidazole (CDI, 92 mg, 0.57 mmol) at room temperature. The reaction mass was heated at 50° C. for 2 h. To this hot solution was added 1-fluorocyclopropane-1-sulfonamide TFA (166 mg, 0.65 mmol) followed by DBU (135 mg, 0.87 mmol). The resulting solution was stirred at 50° C. for overnight. The reaction mass was diluted with water and extracted with ethyl acetate. The combined organic layer was washed with water, dried over anhydrous Na$_2$SO$_4$ and concentrated under reduced pressure to get desired product as diastereomeric mixture. The diastereomeric mixture was separated by HPLC to get desired product Compound 29 (110 mg, 33%). tert-butyl ((2R,6S,7R,9R,13aS,14aR,16aS,Z)-2-((5-chloro-4-methoxyisoquinolin-1-yl)oxy)-14a-(((1-fluorocyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate MS: MS m/z 808.2 (M$^+$+1).

Preparation of Compound 30

Compound 30

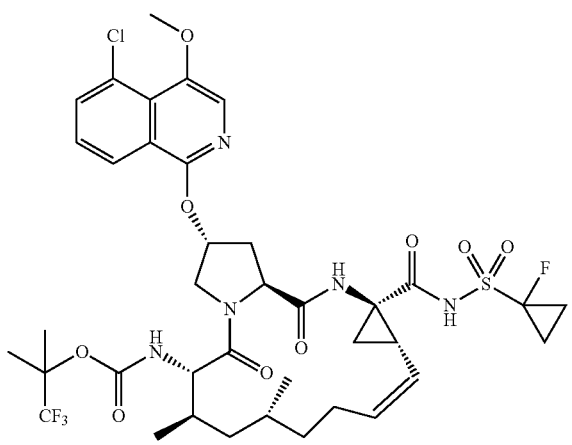

Compound 30 was prepared using the intermediates described herein and by following the general procedure described for the synthesis of Compound 3.

Compound 30: 1,1,1-trifluoro-2-methylpropan-2-yl ((2R,6S,7R,9R,13aS,14aR,16aS,Z)-2-((5-chloro-4-methoxyisoquinolin-1-yl)oxy)-14a-(((1-fluorocyclopropyl)sulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.18-8.18 (dd, J=8.2 Hz & 1.2, 1H), 7.78-7.76 (dd, J=7.6 & 1.2 Hz, 1H), 716 (sb, 1H), 7.49-7.45 (t, J=8 Hz, 1H), 7.27-7.25 (db, 1H), 5.83 (m, 1H), 5.60-5.58 (m, 1H), 4.77-4.74 (m, 1H), 4.64-4.56 (m, 1H), 4.01-4.0 (m, 1H), 4.98 (s, 3H), 3.81-3.77 (m, 1H), 2.77-2.72 (m, 2H), 2.45-2-39 (m, 2H), 1.99-1.59 (m, 7H), 1.55-1.39 (m, 5H), 1.38-1.20 (m, 6H), 1.04-0.91 (m, 7H), 0.87-0.76 (m, 1H); $^{19}$F NMR: δ ppm −85.10 (3 F), 193.21 (1 F); MS: MS m/z 860.9 (M$^+$+1).

Preparation of Compound 31

Compound 31

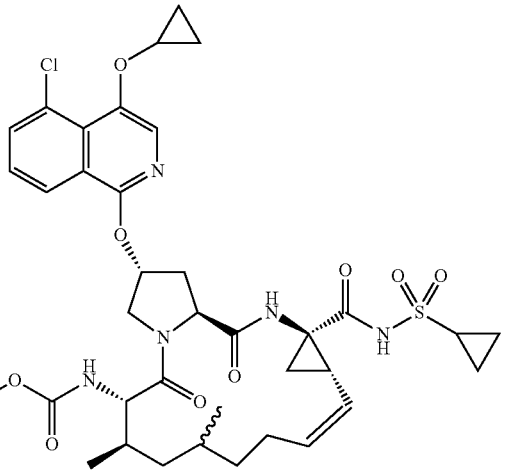

Compound 31 was prepared using the intermediates described herein and by following the general procedure described for the synthesis of Compound 1.

Compound 31: tert-butyl ((2R,6S,7R,13aS,14aR,16aS,Z)-2-((5-chloro-4-cyclopropoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.15-8.13 (d, J=8.4 Hz, 1H), 7.96 (s, 1H), 7.71-7.67 (m, 1H), 7.44-7.39 (m, 1H), 5.80 (m, 1H), 5.62-5.55 (m, 1H), 5.05-5.01 (m, 1H), 4.74-4.71 (m, 1H), 4.64-4.50 (m, 1H), 4.11-3.79 (m, 3H), 2.91-2.88 (m, 1H), 2.72-2.65 (m, 2H), 2.43-2-37 (m, 2H), 1.95-1.82 (m, 2H), 1.81-1.70 (m, 2H), 1.69-1.35 (m, 4H), 1.34-1.20 (m, 4H), 1.19-1.13 (m, 4H), 1.12-1.03 (m, 9H), 1.12-0.92 (m, 5H), 0.92-0.8 (m, 4H); MS: MS m/z 815.3 (M$^+$+1).

Preparation of Compound 32

Compound 32

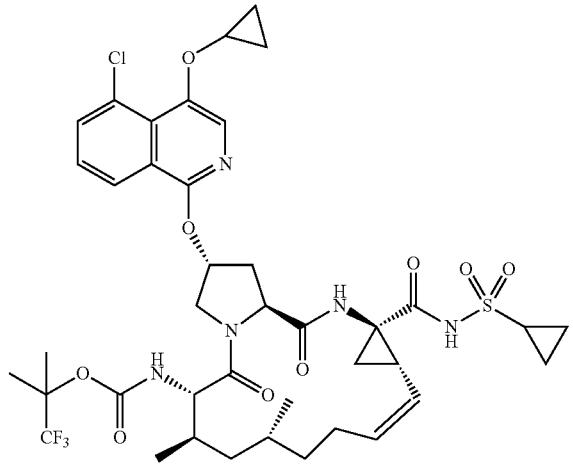

Compound 32 was prepared using the intermediates described herein and by following the general procedure described for the synthesis of Compound 3.

Compound 32: 1,1,1-trifluoro-2-methylpropan-2-yl ((2R,6S,7R,9R,13aS,14aR,16aS,Z)-2-((5-chloro-4-cyclopropoxyisoquinolin-1-yl)oxy)-14a-((cyclopropylsulfonyl)carbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.17-8.15 (dd, J=8.4 Hz & 1.2, 1H), 8.0 (sb, 1H), 7.76-7.74 (dd, J=7.6 & 1.2 Hz, 1H), 7.47-7.43 (t, J=8 Hz, 1H), 5.88 (m, 1H), 5.64-5.60 (m, 1H), 5.08-5.03 (m, 1H), 4.81-4.76 (m, 1H), 4.67-4.56 (m, 1H), 4.0-3.94 (m, 2H), 3.80-3.77 (m, 1H), 2.94-2.72 (m, 1H), 2.78-2-66 (m, 2H), 2.48-2.32 (m, 2H), 2.05-1.90 (m, 1H), 1.89-1.77 (m, 3H), 1.63-1.55 (m, 1H), 1.53-1.42 (m, 2H), 1.38-1.22 (m, 6H), 1.20-1.06 (m, 3H), 1.02-0.96 (m, 6H), 0.94-0.90 (3H), 0.9-0.8 (6H); $^{19}$F NMR: δ ppm -85.10 (3 F); MS: MS m/z 866.0 (M$^+$-2).

Preparation of tert-butyl (1-(hydroxymethyl)cyclopropyl)sulfonylcarbamate

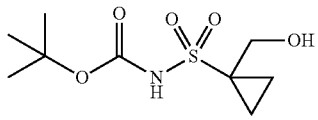 [SMILES: CC(C)(C)OC(=O)NS(=O)(=O)C1(CO)CC1]

To a solution of tert-butyl cyclopropylsulfonylcarbamate (30 g, 136 mmol) in 750 mL of THF was added dropwise butyllithium (1.6 M in hexane, 212 mL, 339 mmol) over 30 min at -78° C. and the resulting mixture was stirred at -78° C. for 1 h. Formaldehyde gas was generated from paraformaldehyde (by heating at 180° C.) and was purged in to the above reaction mass for 30 min at -30° C. The reaction was stirred at the same temperature for 1 h, then allowed to warm to room temperature. The reaction was quenched with aqueous ammonium chloride solution and diluted with water. The resulting mass was washed with ethyl acetate and the aqueous layer was acidified to pH~2 and extracted with ethyl acetate. The combined organics were dried over sodium sulfate and evaporated under reduced pressure to get desired compound (27 g, 79%) as white solid. $^1$H NMR (400 MHz, DMSO-d$_6$): δ ppm 10.90 (sb, 1H), 4.95 (sb, 1H), 3.75 (s, 2H), 1.42 (s, 9H), 1.27 (m, 2H), 1.08 (m, 2H).

Preparation of tert-butyl 1-fluoromethylcyclopropylsulfonylcarbamate

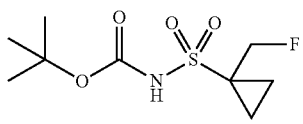

A solution of tert-butyl 1-hydroxymethylcyclopropylsulfonylcarbamate (26 g, 103 mmol) in DCM (300 mL) was cooled to -78° C. To this solution was added DAST (41 mL, 310 mmol) and the reaction mass was stirred at the same temperature for 30 min. The reaction mass was quenched with aqueous 1N NaOH solutions. The organic layer was separated and the aqueous layer was acidified to pH~2 by using 1.5 N HCl solutions. The aqueous solution was extracted with DCM (50 mL×4). The combined organic layer was dried over anhydrous sodium sulphate and evaporated to get desired compound (19 g, 72%) as gummy mass. $^1$H NMR (400 MHz, DMSO-d$_6$): δ ppm 11.25 (sb, 1H), 4.75 (s, 1H), 4.63 (s, 1H), 1.44 (s, 9H), 1.28 (m, 2H), 1.07 (m, 2H). $^{19}$F NMR: -211.7 (1F).

Preparation of 1-fluoromethylcyclopropane-1-sulfonamide

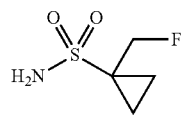

To a solution of tert-butyl 1-fluoromethyl cyclopropylsulfonylcarbamate (19 g, 75 mmol) in dichlomethane (200 mL) was added TFA (50 mL) at room temperature. The reaction mass was stirred at room temperature for 1 h. The solvent was evaporated under reduced pressure and the residue was diluted with hexane. The precipitated solid was filtered and washed with hexane to get pure compound (11 g, 96%) as off-white solid. $^1$H NMR (400 MHz, DMSO-d$_6$): δ ppm 6.98 (sb, 2H), 4.75 (s, 1H), 4.63 (s, 1H), 1.28 (m, 2H), 1.08 (m, 2H). $^{19}$F NMR: -211.74 (1F).

Preparation of tert-butyl (1R,2S)-1-(1-(fluoromethyl)cyclopropylsulfonylcarbamoyl)-2-vinylcyclopropylcarbamate

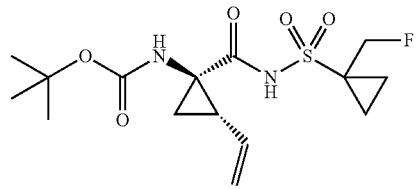 [SMILES: C=C[C@@H]1C[C@]1(NC(=O)OC(C)(C)C)C(=O)NS(=O)(=O)C1(CF)CC1]

To a solution of (1R,2S)-1-(tert-butoxycarbonylamino)-2-vinylcyclopropanecarboxylic acid (7.5 g, 33 mmol) in DMF (50 mL) was added CDI (10.69 g, 66 mmol) and the reaction mass was heated at 55° C. for 4 h. To this reaction mass was added 1-fluoromethylcyclopropane-1-sulfonamide (6.5 g, 42.9 mmol) followed by DBU (6 mL, 42.9 mmol). The reaction mixture was stirred at 55° C. for 18 h. The solvent was evaporated under reduced pressure and the residue was diluted with water and acidified to pH~2 by using 1.5 N HCl solution. The precipitated solid was filtered and washed with water to get desired compound (11.5 g, 96%) as off-white solid. MS: MS m/z 361.4 (M$^+$-1).

547

Preparation of (1R,2S)-1-amino-N-(1-(fluoromethyl)cyclopropylsulfonyl)-2-vinylcyclopropanecarboxamide hydrochloride

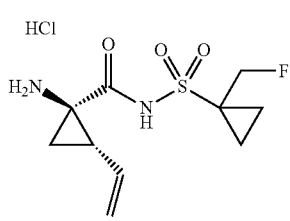 [SMILES: Cl ; C=C[C@@H]1C[C@]1(N)C(=O)NS(=O)(=O)C1(CF)CC1]

A solution of tert-butyl (1R,2S)-1-(1-(fluoromethyl)cyclopropylsulfonylcarbamoyl)-2-vinylcyclopropylcarbamate (11.5 g, 31.7 mmol) in 4 N HCl in dioxane (100 mL) was stirred at room temperature for 1 h. The solvent was evaporated under reduced pressure and the residue was washed with diethyl ether to get crude compound (6 g, 72%). The crude compound was taken to the next step without further purification. MS: MS m/z 263.14 (M$^+$+1)

548

Preparation of 4-chloro-2-(4-isopropoxyphenyl)-7-methoxyquinoline

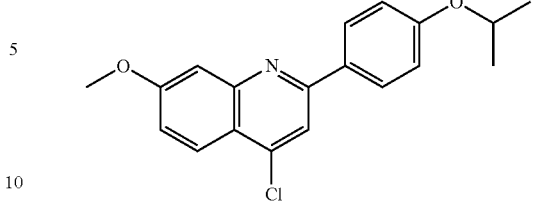

To a degassed solution of 2,4-dichloro-7-methoxyquinoline (1 g, 4.3 mmol) in dioxane/water (8:2) was added 4-isopropoxyphenylboronic acid (870 mg, 4.82 mmol) followed by potassium carbonate (1.2 g, 8.7 mmol) and Pd(PPh$_3$)$_4$ (253 mg, 0.22 mmol) at room temperature under nitrogen atmosphere. The reaction mass was heated at 90° C. for 18 h. The solvent was removed under reduced pressure and the residue was diluted with water and extracted with ethyl acetate. The combined organic layer was dried over anhydrous sodium sulphate and evaporated under reduced pressure to get crude compound. The crude compound was purified by silica gel chromatography to afford 4-chloro-2-(4-isopropoxyphenyl)-7-methoxyquinoline (1.2 g, 85%) as off white solid. MS: MS m/z 328.7 (M$^+$+1).

Scheme

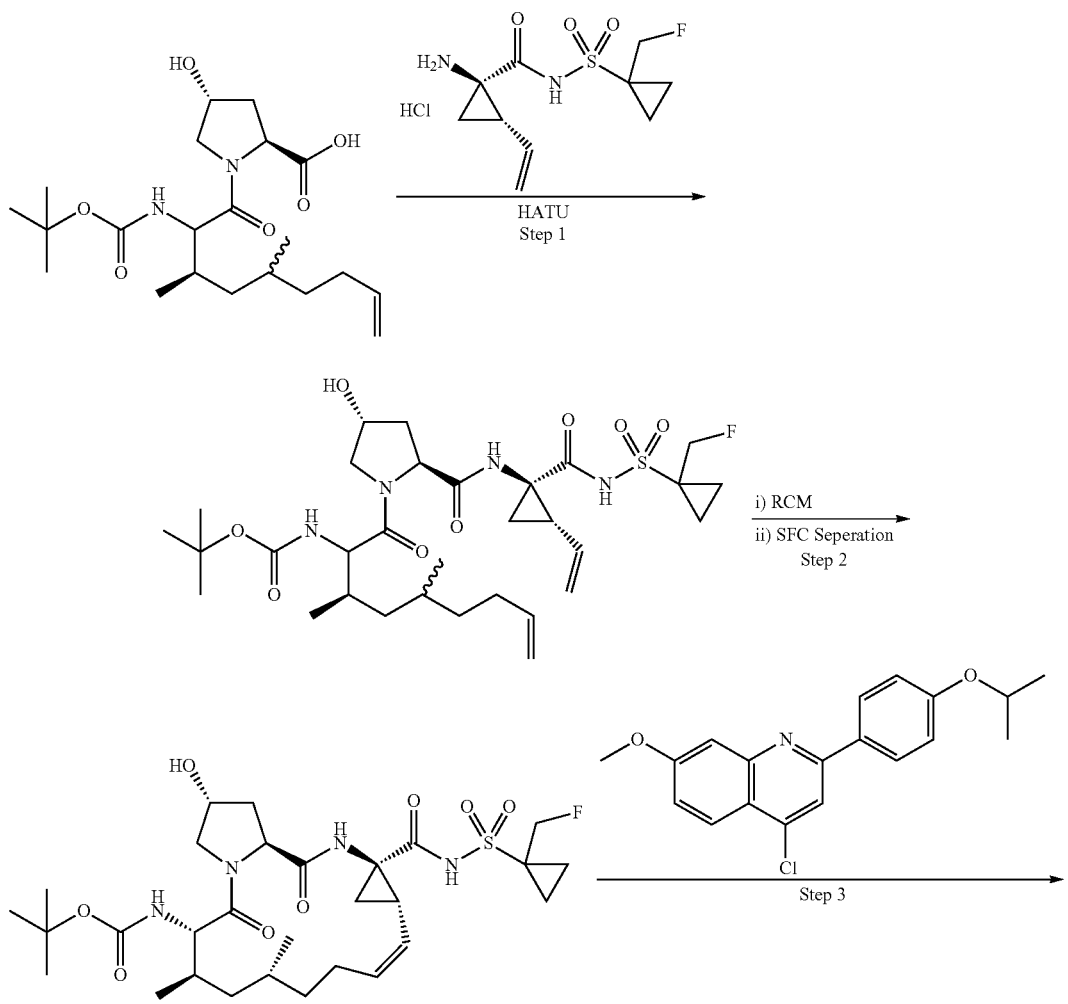

-continued
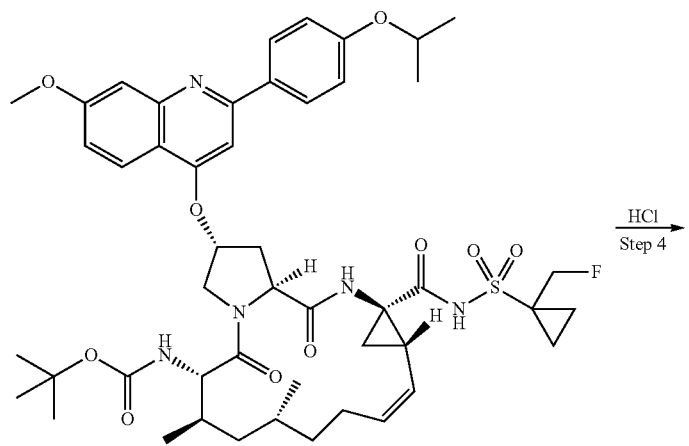
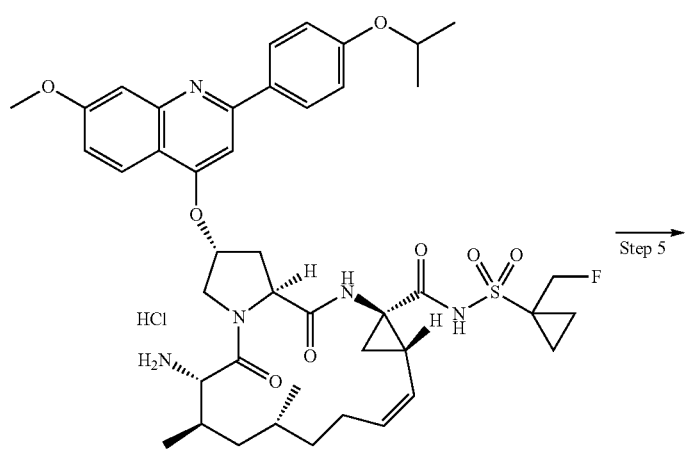
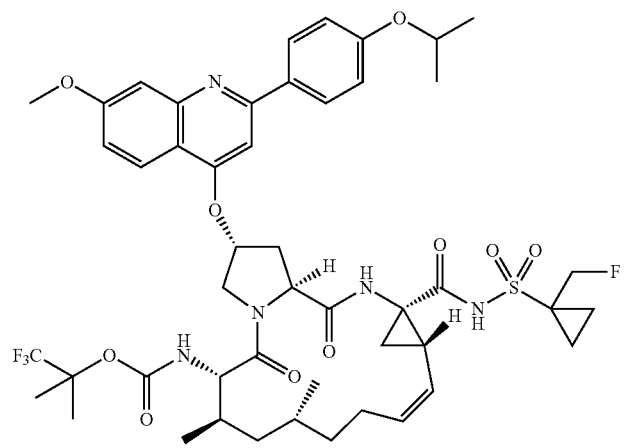
Compound 4148

Step 1: Preparation of tert-butyl (2S,3R)-1-((2S, 4R)-2-((1R,2S)-1-(1-(fluoromethyl)cyclopropylsulfonylcarbamoyl)-2-vinylcyclopropylcarbamoyl)-4-hydroxypyrrolidin-1-yl)-3,5-dimethyl-1-oxonon-8-en-2-ylcarbamate

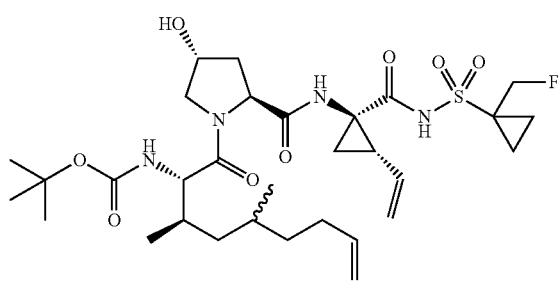 [SMILES: C=CCCC(C)C[C@@H](C)[C@H](NC(=O)OC(C)(C)C)C(=O)N1C[C@H](O)C[C@H]1C(=O)N[C@]1(C(=O)NS(=O)(=O)C2(CF)CC2)C[C@H]1C=C]

To a solution of (2S,4R)-1-((2S,3R)-2-(tert-butoxycarbonylamino)-3,5-dimethylnon-8-enoyl)-4-hydroxypyrrolidine-2-carboxylic acid (5.7 g, 13.82 mmol) in dichloromethane (60 mL) was added HATU (5.78 g, 15.2 mmole) followed by DIPEA (7.13 mL, 41.4 mmoles) at room temperature. The reaction mass was stirred at the same temperature for 10 min. (1R,2S)-1-amino-N-(1-(fluoromethyl)cyclopropylsulfonyl)-2-vinylcyclopropanecarboxamide hydrochloride (4.34 g, 16.58 mmole) was added to the reaction mass and stirred at room temperature for 6 h. The reaction mass was diluted with dichloromethane and washed with water. The organic layer was dried over anhydrous Na₂SO₄ and evaporated under reduced pressure to get the crude compound. The crude compound was purified by silica gel chromatography (5% methanol in chloroform) to get 6.6 g (73%) of desired product as white solid. MS: MS m/z 658.3 (M⁺+1).

Step 2: Preparation of tert-butyl ((2R,6S,7R,13aS,14aR,16aS,Z)-14a-(((1-(fluoromethyl)cyclopropyl)sulfonyl)carbamoyl)-2-hydroxy-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate

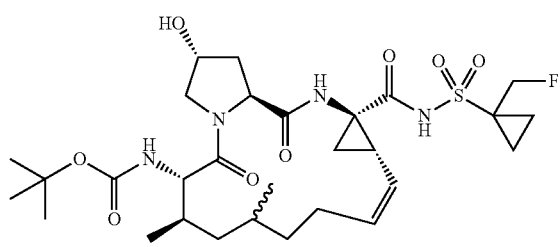 [SMILES: CC1CC/C=C\[C@@H]2C[C@@]2(C(=O)NS(=O)(=O)C2(CF)CC2)NC(=O)[C@@H]2C[C@@H](O)CN2C(=O)[C@@H](NC(=O)OC(C)(C)C)[C@H](C)C1]

To a degassed solution of tert-butyl (2S,3R)-1-((2S,4R)-2-((1R,2S)-1-(1-(fluoromethyl)cyclopropylsulfonylcarbamoyl)-2-vinylcyclopropylcarbamoyl)-4-hydroxypyrrolidin-1-yl)-3,5-dimethyl-1-oxonon-8-en-2-ylcarbamate (2.8 g, 4.26 mmole) in dichloroethane (200 mL) was added Grubbs II generation catalyst (280 mg) at room temperature under nitrogen atmosphere. The reaction mass was heated at 95° C. overnight. The solvent was evaporated under reduced pressure and the resulting residue was purified by silica gel chromatography (5% methanol in chloroform) to get desired compound tert-butyl (2R,6S,7R,13aS,14aR,16aS,Z)-14a-(1-(fluoromethyl)cyclopropylsulfonylcarbamoyl)-2-hydroxy-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (1.87 g, 70%) as pale yellow crystalline solid. MS: MS m/z 629.3 (M⁺+1).

Step 3: Preparation of tert-butyl (2R,6S,7R,13aS,14aR,16aS,Z)-14a-(1-(fluoromethyl)cyclopropylsulfonylcarbamoyl)-2-(2-(4-isopropoxyphenyl)-7-methoxyquinolin-4-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate

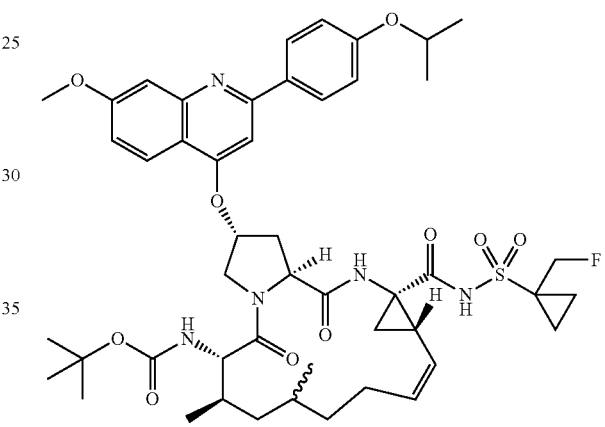

To a solution of tert-butyl ((2R,6S,7R,13aS,14aR,16aS,Z)-14a-(((1-(fluoromethyl)cyclopropyl)sulfonyl)carbamoyl)-2-hydroxy-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (150 mg, 0.238 mmole) and 4-chloro-2-(4-isopropoxyphenyl)-7-methoxyquinoline (93 mg, 0.284 mmole) in DMSO (8 mL) was added t-BuOK (133 mg, 1.19 mmol, 1 M solution in THF, 1.2 mL) at room temperature under nitrogen atmosphere. The reaction mixture was stirred at room temperature for 2 h. The reaction mass was quenched with aqueous citric acid solution and extracted with ethyl acetate (10 mL×2). The combined organic layer was washed with water, brine solution, dried over anhydrous Na₂SO₄ and evaporated under reduced pressure to get crude compound. The crude compound was purified by HPLC to get 130 mg (60%) of desired compound tert-butyl (2R,6S,7R,13aS,14aR,16aS,Z)-14a-(1-(fluoromethyl)cyclopropylsulfonylcarbamoyl)-2-(2-(4-isopropoxyphenyl)-7-methoxyquinolin-4-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate as white solid. MS: MS m/z 921.5 (M⁺+1).

Step 4: Preparation of (2R,6S,7R,9R,13aS,14aR, 16aS,Z)-6-amino-N-(1-(fluoromethyl)cyclopropyl-sulfonyl)-2-(2-(4-isopropoxyphenyl)-7-methoxyquinolin-4-yloxy)-7,9-dimethyl-5,16-dioxo-1,2,3,5,6,7, 8,9,10,11,13a,14,14a,15,16,16a-hexadecahydrocyclopropa[e]pyrrolo[1,2-a][1,4] diazacyclopentadecine-14a-carboxamide hydrochloride

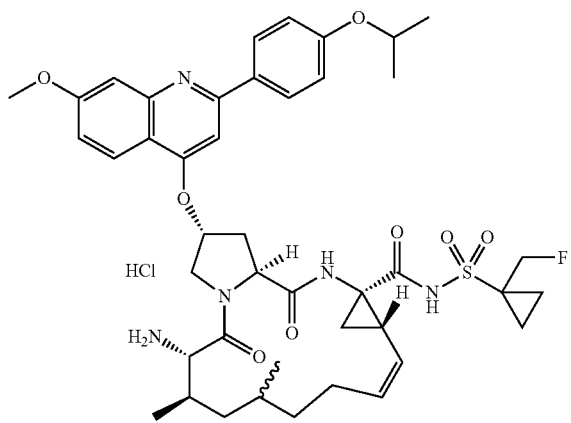 [SMILES: COc1ccc2c(O[C@@H]3C[C@H]4C(=O)N[C@]5(C(=O)NS(=O)(=O)C6(CF)CC6)C[C@H]5/C=C\CCC(C)C[C@@H](C)[C@H](N)C(=O)N4C3)cc(-c3ccc(OC(C)C)cc3)nc2c1 ; Cl]

A solution of tert-butyl (2R,6S,7R,13aS,14aR,16aS,Z)-14a-(1-(fluoromethyl)cyclopropylsulfonylcarbamoyl)-2-(2-(4-isopropoxyphenyl)-7-methoxyquinolin-4-yloxy)-7,9-dimethyl-5,16-dioxo-1,2,3,5,6,7,8,9,10,11,13a,14,14a,15,16, 16a-hexadecahydrocyclopropa[e]pyrrolo[1,2-a][1,4] diazacyclopentadecin-6-ylcarbamate (130 mg, 0.14 mmole) was added to a solution of HCl in dioxane (4N, 5 mL) and the solution was stirred at room temperature for 30 min. The solvent was evaporated under reduced pressure to get crude compound. The crude compound was washed with diethyl ether to afford (2R,6S,7R,9R,13aS,14aR,16aS,Z)-6-amino-N-(1-(fluoromethyl)cyclopropylsulfonyl)-2-(2-(4-isopropoxyphenyl)-7-methoxyquinolin-4-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4] diazacyclopentadecine-14a-carboxamide hydrochloride (100 mg, 90%) as off-white solid. MS: MS m/z 821.3 (M$^+$+1).

Step 5: Preparation of Compound 4148

Compound 4148

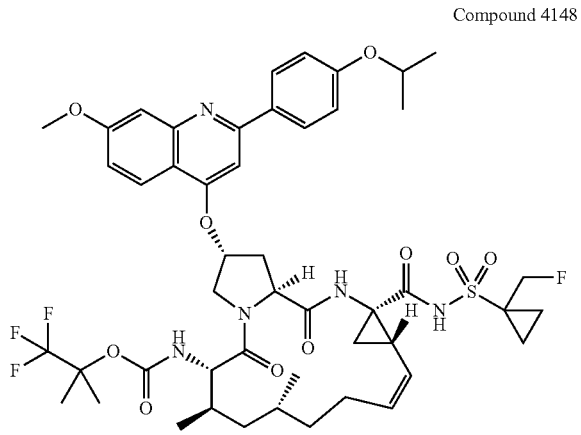 [SMILES: COc1ccc2c(O[C@@H]3C[C@H]4C(=O)N[C@]5(C(=O)NS(=O)(=O)C6(CF)CC6)C[C@H]5/C=C\CC[C@@H](C)C[C@@H](C)[C@H](NC(=O)OC(C)(C)C(F)(F)F)C(=O)N4C3)cc(-c3ccc(OC(C)C)cc3)nc2c1]

To a solution of 2R,6S,7R,9R,13aS,14aR,16aS,Z)-6-amino-N-(1-(fluoromethyl)cyclopropylsulfonyl)-2-(2-(4-isopropoxyphenyl)-7-methoxyquinolin-4-yloxy)-7,9-dimethyl-5,16-dioxo-1,2,3,5,6,7,8,9,10,11,13a,14,14a,15,16, 16a-hexadecahydrocyclopropa[e]pyrrolo[1,2-a][1,4] diazacyclopentadecine-14a-carboxamide hydrochloride (100 mg, 0.16 mmol) in DCM (4 mL) was added DIPEA (0.06 mL, 0.48 mmole) followed by pyridin-2-yl (1,1,1-trifluoro-2-methylpropan-2-yl)carbonate (32.12 mg, 0.16 mmole) at room temperature. The reaction mixture was stirred at room temperature for 30 min. The reaction mass was diluted with DCM and washed with water. The organic layer was dried over anhydrous Na$_2$SO$_4$, filtered, and evaporated under reduced pressure to get crude compound. The crude compound was purified by HPLC to get Compound 4148 (30 mg, 26%) as a white solid.

Compound 4148: 1,1,1-trifluoro-2-methylpropan-2-yl ((2R,6S,7R,9R,13aS,14aR,16aS,Z)-14a-(((1-(fluoromethyl) cyclopropyl)sulfonyl)carbamoyl)-2-((2-(4-isopropoxyphenyl)-7-methoxyquinolin-4-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4] diazacyclopentadecin-6-yl)carbamate. $^1$H NMR (400 MHz, CD$_3$OD): δ ppm 8.08-8.06 (d, J=9.2 Hz, 1H), 8.03-8.01 (d, J=8.8 Hz, 2H), 7.40-7.39 (m, 1H), 7.24 (s, 1H), 7.10-7.08 (d, J=8.8, Hz, 2H), 7.06 (m, 1H), 5.62 (m, 2H), 4.92-4.84 (m, 1H), 4.77-4.73 (m, 2H), 4.64-4.62 (m, 4H), 4.10 (m, 1H), 3.97 (s, 3H), 3.89-3.86 (m, 1H), 2.85-2.79 (m, 1H), 2.78-2.68 (m, 1H), 2.55-2.2.35 (m, 2H), 2.05-1.74 (m, 6H), 1.73-1.69 (m, 3H), 1.59-1.56 (m, 9H), 1.48-1.38 (m, 4H), 1.27-1.19 (m, 9H), 1.03-0.98 (m, 1H); MS: MS m/z 974.4 (M$^+$+1).

Scheme:

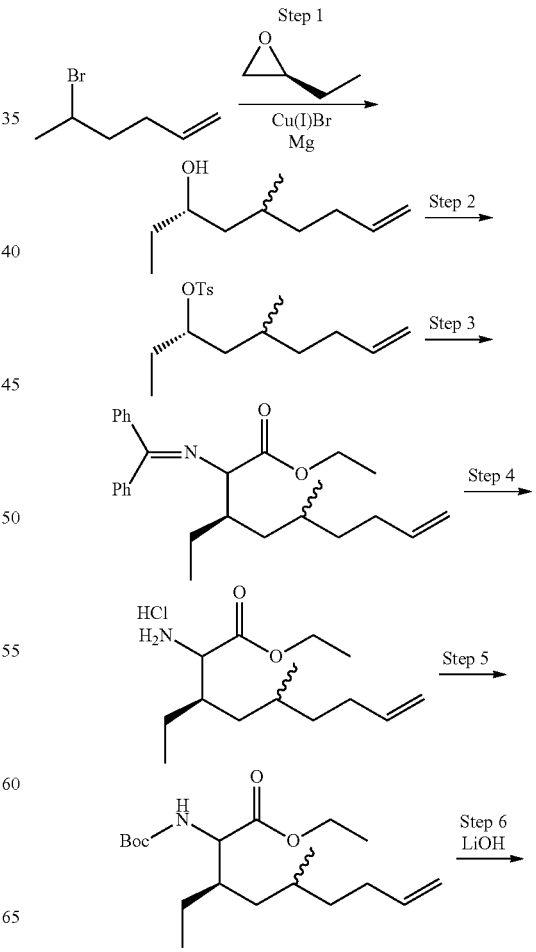

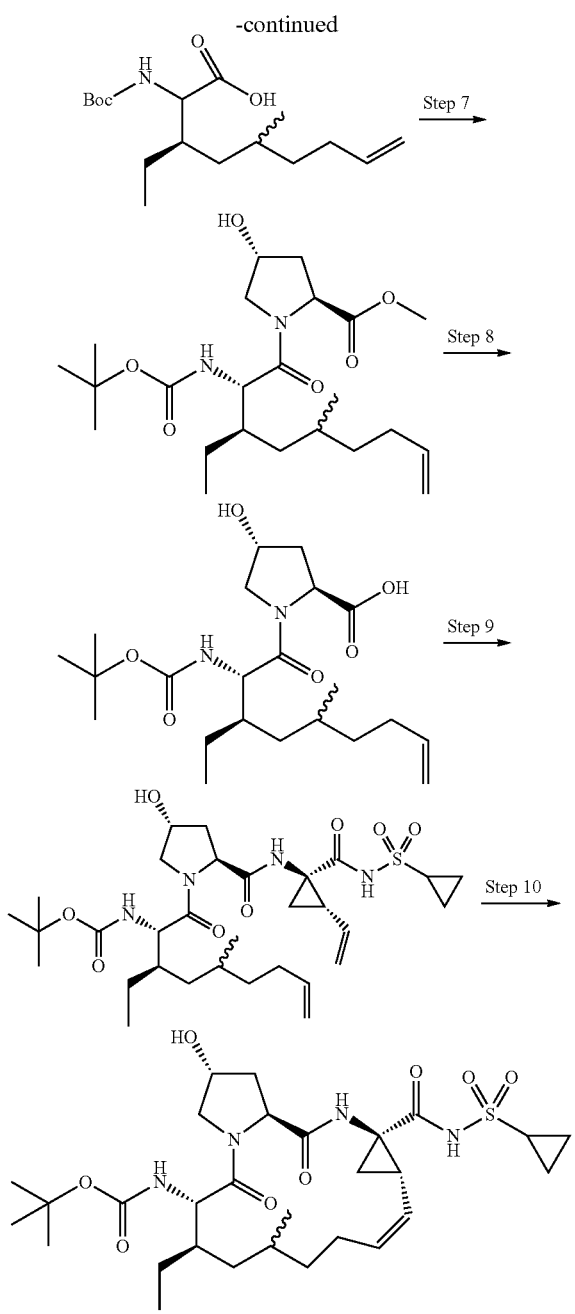

Step 1: Preparation of (S)-5-methylnon-8-en-3-ol

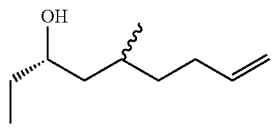

Magnesium turnings (3.03 g, 125 mmole) were taken in dry THF (100 mL) and was added a pinch of iodine (100 mg) at room temperature. To this reaction mass was added a solution of 5-bromohex-1-ene (20.37 g, 125 mmole) in THF (200 mL). The reaction mass was heated with hot air gun to initiate the reaction. This reagent was cannulated to a solution of (S)-2-ethyloxirane (6.05 g, 83 mmol) and copper bromide (1.19 g, 8.32 mmol) in THF (100 mL) at −78° C. The reaction mass was allowed to come to room temperature and stirred for overnight. The reaction mass was quenched with saturated aqueous ammonium chloride solution and extracted with diethyl ether (200 mL×3). The combined organic layers were dried over anhydrous $Na_2SO_4$ and evaporated at room temperature to get crude compound. The crude compound was purified by column chromotography (Silica gel, 10% TBME in pet ether) to get (S)-5-methylnon-8-en-3-ol (9.5 g, 73.1%) as an oily liquid. $^1$H NMR (400 MHz, $CDCl_3$): δ ppm 0.87-0.97 (m, 6H), 1.22-1.32 (m, 4H), 1.52-1.72 (m, 2H), 1.90-2.29 (m, 2H), 3.38-3.45 (m, 2H), 4.16-4.19 (m, 1H), 4.91-5.02 (m, 2H), 5.75-5.82 (m, 1H),

Step 2: Preparation of (S)-5-methylnon-8-en-3-yl 4-methylbenzenesulfonate

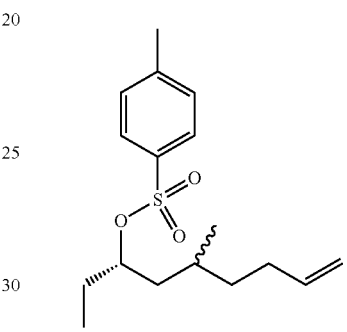

To a solution of (S)-5-methylnon-8-en-3-ol (9.5 g, 60.8 mmole) in DCM (100 mL) was added pyridine (20 mL) followed by DMAP (0.74 g, 6.08 mmole) and the solution was stirred for 10 min. p-Toluenesulfonyl chloride (17.39 g, 91 mmole) was added to the reaction mass at 0° C. The reaction mass was allowed to come to room temperature and stirred for overnight. Solvent was removed under reduced pressure and the residue was diluted with ethyl acetate (100 mL). The organic solution was washed with aqueous 1.5 N HCl solution, saturated bicarbonate solution, brine solution, dried over anhydrous $Na_2SO_4$ and evaporated under reduced pressure to get crude compound (15 g, 79%). The crude compound was taken to the next step without further purification. MS: MS m/z 328.4 ($M^+$+18).

Step 3: Preparation of (3R)-ethyl 2-(diphenylmethyleneamino)-3-ethyl-5-methylnon-8-enoate

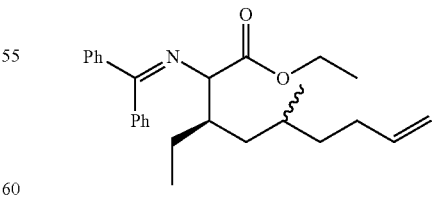

To a solution of (S)-5-methylnon-8-en-3-yl 4-methylbenzenesulfonate (15 g, 48.3 mmole) and N-(diphenylmethylene)glycinate ethyl ester (15.5 g, 58.0 mmole) in toluene (150 mL) was added LiHMDS (72.5 mL, 72.5 mmole, 1 M solution in THF) at 0° C. The reaction mass was allowed to come to room temperature heated at 110° C. for 2 h. The reaction mass was cooled to room temperature, quenched with water and extracted with ethyl acetate (100 mL×3). The combined organic layers were dried over anhydrous Na₂SO₄ and evaporated under reduced pressure to get crude compound (7.0 g, 35.7%). The crude compound was taken to the next step without further purification. MS: MS m/z 406.4 (M⁺+1).

Step 4: Preparation of (3R)-ethyl 2-amino-3-ethyl-5-methylnon-8-enoate hydrochloride

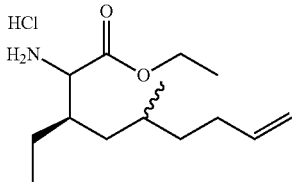 [SMILES: Cl ; C=CCCC(C)C[C@@H](CC)C(N)C(=O)OCC]

A solution of (3R)-ethyl 2-(diphenylmethyleneamino)-3-ethyl-5-methylnon-8-enoate (7 g, 17.26 mmole) in diethyl ether (20 mL) was added aqueous 1.5 N HCl solutions (100 mL) and the reaction mass was stirred at room temperature for overnight. The reaction mass was washed with diethyl ether (100 mL). The aqueous solution was basified using saturated sodium bicarbonate solution and extracted with ethyl acetate (100 mL×3). The combined organic layers were dried over anhydrous Na₂SO₄ and evaporated under reduced pressure to get crude compound (2.6 g, 62.4%). The crude compound was taken to the next step without further purification. MS: MS m/z 242.4 (M⁺+1).

Step 5: Preparation of (3R)-ethyl 2-(tert-butoxycarbonylamino)-3-ethyl-5-methylnon-8-enoate

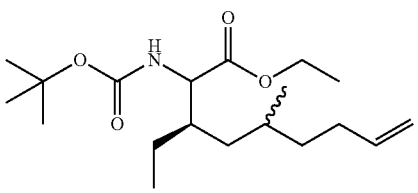 [SMILES: C=CCCC(C)C[C@@H](CC)C(NC(=O)OC(C)(C)C)C(=O)OCC]

A solution of (3R)-ethyl 2-amino-3-ethyl-5-methylnon-8-enoate hydrochloride (2.99 g, 10.77 mmole) in DCM (20 mL) was added DIPEA (1.08 mL, 10.77 mmole) followed by (BOC)₂O (2.39 mL, 10.77 mmole) at room temperature. The reaction mass was stirred at room temperature for overnight. The reaction mass was diluted with DCM and washed with water. The organic layer was dried over anhydrous Na₂SO₄ and evaporated under reduced pressure to get crude compound. The crude compound was purified by column chromotography (Silica gel, 20% ethyl acetate in pet-ether) to get 2.3 g, (62.5%) of (3R)-ethyl 2-(tert-butoxycarbonylamino)-3,5-dimethylnon-8-enoate as an oily liquid. MS: MS m/z 342.4 (M⁺+1).

Step 6: Preparation of (3R)-2-(tert-butoxycarbonylamino)-3-ethyl-5-methylnon-8-enoic acid

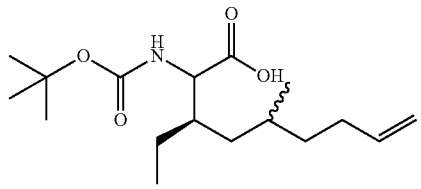 [SMILES: C=CCCC(C)C[C@@H](CC)C(NC(=O)OC(C)(C)C)C(=O)O]

To a solution of (3R)-ethyl 2-(tert-butoxycarbonylamino)-3-ethyl-5-methylnon-8-enoate (2.3 g, 6.74 mmole) in THF/water (50 mL, 1:1) was added methanol (10 mL) followed by LiOH (0.84 g, 20.21 mmole) at room temperature. The reaction mass was stirred at room temperature for overnight. Solvent was evaporated under reduced pressure and the residue was diluted with water (10 mL). The aqueous solution was acidified with aqueous 1.5 N HCl solutions to pH~3 and extracted with ethyl acetate (100 mL×3). The combined organic layers were dried over anhydrous Na₂SO₄ and evaporated under reduce pressure to get crude compound. The crude compound was purified by column chromotography (Silica gel, 2% methanol in DCM) to get 1.5 g (71%) of Intermediate 9 as an off-white solid. ¹H NMR (400 MHz, DMSO-d₆): δ ppm 1.27-1.09 (m, 8H), 1.02-1.35 (m, 3H), 1.39 (s, 11H), 1.91-1.97 (m, 1H), 1.99-2.02 (m, 2H), 4.03-4.12 (m, 1H), 4.90-5.03 (m, 2H), 5.74-5.84 (m, 1H), 6.80-6.83 (m, 1H), 12.47 (sb, 1H).

Step 7: Preparation of (2S,4R)-methyl 1-((2S,3R)-2-(tert-butoxycarbonylamino)-3-ethyl-5-methylnon-8-enoyl)-4-hydroxypyrrolidine-2-carboxylate

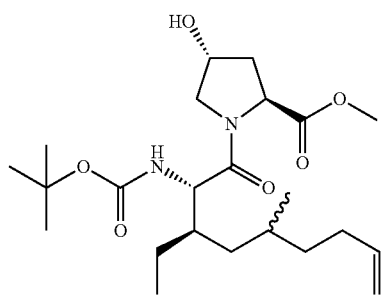 [SMILES: C=CCCC(C)C[C@@H](CC)[C@H](NC(=O)OC(C)(C)C)C(=O)N1C[C@H](O)C[C@H]1C(=O)OC]

To a solution of (3R)-2-(tert-butoxycarbonylamino)-3-ethyl-5-methylnon-8-enoic acid (2 g, 6.38 mmole) in dichloromethane (20 mL) was added DIPEA (1.93 mL, 19.19 mmole), HATU (2.42 g, 6.38 mmole) followed by (2S,4R)-methyl 4-hydroxypyrrolidine-2-carboxylate (1.15 g, 6.38 mmole) at room temperature. The reaction mixture was stirred at room temperature for 2 h. The reaction mass was diluted with DCM and washed with water. The organic layer was dried over anhydrous Na₂SO₄ and concentrated under reduced pressure to get crude compound. The crude compound was taken to the next step without further purification (1.5 g, 53.4%). MS: MS m/z 441.6 (M⁺+1)

Step 8: Preparation of (2S,4R)-1-((2S,3R)-2-(tert-butoxycarbonylamino)-3-ethyl-5-methylnon-8-enoyl)-4-hydroxypyrrolidine-2-carboxylic acid

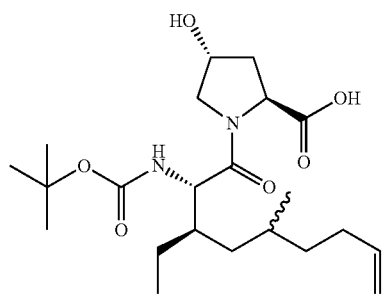 [SMILES: C=CCCC(C)C[C@@H](CC)[C@H](NC(=O)OC(C)(C)C)C(=O)N1C[C@H](O)C[C@H]1C(=O)O]

To a solution of (2S,4R)-methyl 1-((2S,3R)-2-(tert-butoxycarbonylamino)-3-ethyl-5-methylnon-8-enoyl)-4-hydroxypyrrolidine-2-carboxylate (1.5 g, 3.40 mmole) in THF/water (16 mL, 1:1) was added LiOH (286 mg, 6.80 mmole) followed by 3 mL of methanol at room temperature. The reaction mass was stirred at room temperature for overnight. The solvent was evaporated under reduced pressure and the residue was diluted with water and acidified with aqueous 1.5 N HCl solutions. The aqueous solution was extracted with ethyl acetate (20 mL×3). The combined organic layer was dried over anhydrous Na$_2$SO$_4$ and concentrated under reduced pressure to get desired product (1.3 g, 90%) as white solid. $^1$H NMR (400 MHz, DMSO-d$_6$): δ ppm 0.81-0.93 (m, 6H), 1.12-1.29 (m, 5H), 1.30-1.50 (m, 11H), 1.71-1.80 (m, 2H), 1.91-2.51 (m, 4H), 3.57-3.59 (m, 1H), 4.27-4.35 (m, 3H), 4.92-4.97 (m, 2H), 5.01-5.15 (m, 1H), 5.74-5.79 (m, 1H), 6.30-6.80 (m, 1H), 12.50 (sb, 1H). MS: MS m/z 427.6 (M$^+$+1).

Step 9: Preparation of tert-butyl (2S,3R)-1-((2S,4R)-2-((1R,2S)-1-(cyclopropylsulfonylcarbamoyl)-2-vinylcyclopropylcarbamoyl)-4-hydroxypyrrolidin-1-yl)-3-ethyl-5-methyl-1-oxonon-8-en-2-ylcarbamate

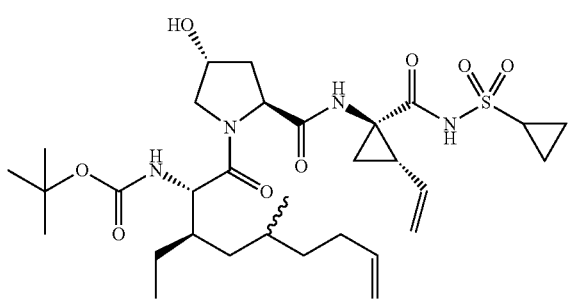 [SMILES: C=CCCC(C)C[C@@H](CC)[C@H](NC(=O)OC(C)(C)C)C(=O)N1C[C@H](O)C[C@H]1C(=O)N[C@]1(C(=O)NS(=O)(=O)C2CC2)C[C@H]1C=C]

To a solution of (2S,4R)-1-((2S,3R)-2-(tert-butoxycarbonylamino)-3-ethyl-5-methylnon-8-enoyl)-4-hydroxypyrrolidine-2-carboxylic acid (1.3 g, 3.05 mmole) in dichloromethane (50 mL) was added HATU (1.15 g, 3.05 mmole) followed by DIPEA (1.6 mL, 9.13 mmole) at room temperature. The reaction mass was stirred at the same temperature for 10 min. (1R,2S)-1-amino-N-(cyclopropylsulfonyl)-2-vinylcyclopropanecarboxamide (1.22 g, 3.05 mmole) was added to the reaction mass and was stirred at room temperature for 1 h. The reaction mass was diluted with dichloromethane and washed with water. The organic layer was dried over anhydrous Na$_2$SO$_4$ and evaporated under reduced pressure to get the crude compound. The crude compound was purified by Silica gel chromatography (6% methanol in chloroform) to get 1.7 g (87%) of desired product as a white solid. MS: MS m/z 639.55 (M$^+$+1).

Step 10: Preparation of tert-butyl (2R,6S,7R,13aS,14aR,16aS,Z)-14a-(cyclopropylsulfonylcarbamoyl)-7-ethyl-2-hydroxy-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate

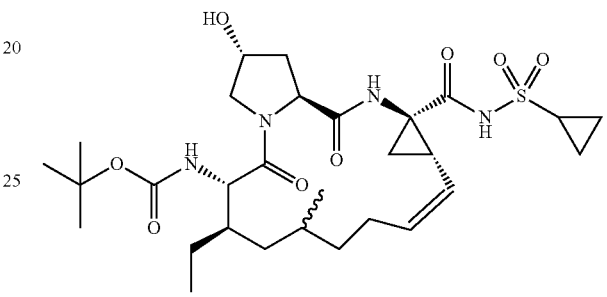

To a degassed solution of tert-butyl (2S,3R)-1-((2S,4R)-2-((1R,2S)-1-(cyclopropylsulfonylcarbamoyl)-2-vinylcyclopropylcarbamoyl)-4-hydroxypyrrolidin-1-yl)-3-ethyl-5-methyl-1-oxonon-8-en-2-ylcarbamate (1.7 g, 2.66 mmole) in dichloroethane (100 mL) was added Grubbs II generation catalyst (266 mg, 10% w/w) at room temperature under nitrogen atmosphere. The reaction mass was heated at 95° C. for overnight. The solvent was evaporated under reduced pressure and the residue was purified by silica gel chromatography (5% methanol in chloroform) to get the desired compound (770 mg, 47.4%) as pale yellow crystalline solid. MS: MS m/z 609.20 (M$^+$−1).

Preparation of 1-Fluoro-4-methoxyisoquinoline

Synthesis of 1-fluoro-4-methoxyisoquinoline

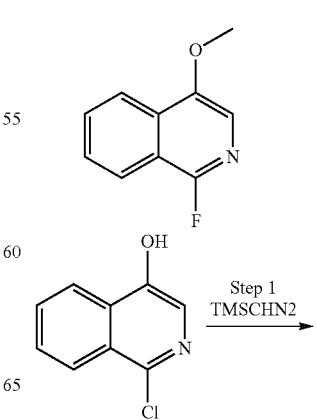

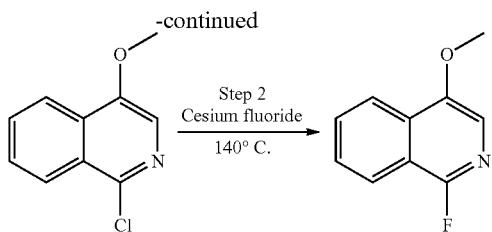

Step 1: Preparation of 1-chloro-4-methoxyisoquinoline

To a solution of 1-chloroisoquinolin-4-ol (5.0 g, 27.8 mmol) in acetonitrile (50 mL) was added TMS-diazomethane (12.73 g, 111.2 mmol) at 0° C. The reaction mixture was allowed to come to room temperature and stirred for 2 h. Solvent was evaporated under reduced pressure to get crude compound. The crude compound was purified by silica gel chromatography to get 1-chloro-4-methoxyisoquinoline (2.5 g, 46.4%) as off-white solid. $^1$H NMR (400 MHz, CD$_3$OD): δ ppm 8.29-8.17 (m, 2H), 7.97 (s, 1H), 7.91-7.82 (m, 2H), 4.05 (s, 3H); MS: MS m/z 194.7 (M$^+$+1).

Step 2: Preparation of 1-Fluoro-4-methoxyisoquinoline

To a solution of 1-chloro-4-methoxyisoquinolin (2.5 g, 12.91 mmol) in DMSO was added cesium fluoride (4.01 g, 25.82 mmol) at room temperature. The reaction vessel (Pressure tube) was sealed and heated at 145° C. for 18 h. The reaction mass was diluted with water and extracted with ethyl acetate. The organic layer was dried over anhydrous Na$_2$SO$_4$ and evaporated under reduced pressure to get crude compound. The crude compound was purified by silica gel chromatography to get desired compound (700 mg, 62%) as a white solid. $^1$H NMR (400 MHz, CD$_3$OD): δ ppm 8.10 (m, 1H), 8.08 (m, 1H), 7.78-7.75 (m, 1H), 7.69-7.65 (m, 1H), 7.49 (m, 1H), 4.04 (s, 3H); $^{19}$F NMR: δ ppm −78.66 (1 F); MS: MS m/z 178.1 (M$^+$+1).

Preparation of 1-fluoro-4-ethoxyisoquinoline

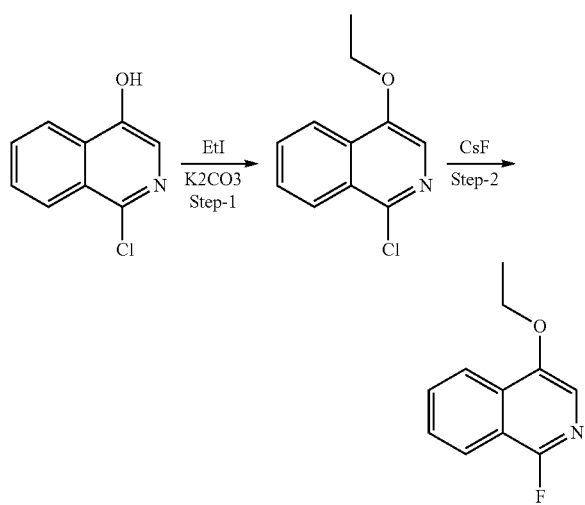

Step 1: Preparation of 1-chloro-4-ethoxyisoquinoline

To a solution of 1-chloroisoquinolin-4-ol (1.0 g, 5.5 mmol) in acetonitrile (10 mL) was added K$_2$CO$_3$ (2.3 g, 16.7 mmol) followed by ethyl iodide (0.87 ml, 11.0 mmol) at room temperature. The reaction mixture was stirred at room temperature for overnight. The solvent was evaporated under reduced pressure and the residue was diluted with water and extracted with ethyl acetate. The combined organic layer was dried over anhydrous Na$_2$SO$_4$ and evaporated under reduced pressure to get crude compound. The crude compound was purified by silica gel chromatography to get 1-chloro-4-ethoxyisoquinoline (0.7 g, 62%) as off-white solid. $^1$H NMR (400 MHz, CD$_3$OD): δ ppm 8.26-8.24 (m, 2H), 7.79 (s, 1H), 7.76-7.26 (m, 2H), 4.29-4.24 (q, J=6.8 Hz, 2H), 1.58-1.54 (t, J=6.8 Hz, 3H); MS: MS m/z 207.7 (M$^+$+1).

Step 2: Preparation of 1-Fluoro-4-ethoxyisoquinoline

To a solution of 1-chloro-4-ethoxyisoquinolin (4.8 g, 23.12 mmol) in DMSO was added cesium fluoride (6.9 g, 46.24 mmol) at room temperature. The reaction vessel (Pressure tube) was sealed and heated at 145° C. for 18 h. The reaction mass was diluted with water and extracted with ethyl acetate. The organic layer was dried over anhydrous Na$_2$SO$_4$ and evaporated under reduced pressure to get crude compound. The crude compound was purified by silica gel chromatography to get desired compound (2.6 g, 58.8%) as white solid. MS: MS m/z 192.3 (M$^+$+1).

Scheme: Preparation of 1-fluoro-4-cyclopropoxyisoquinoline

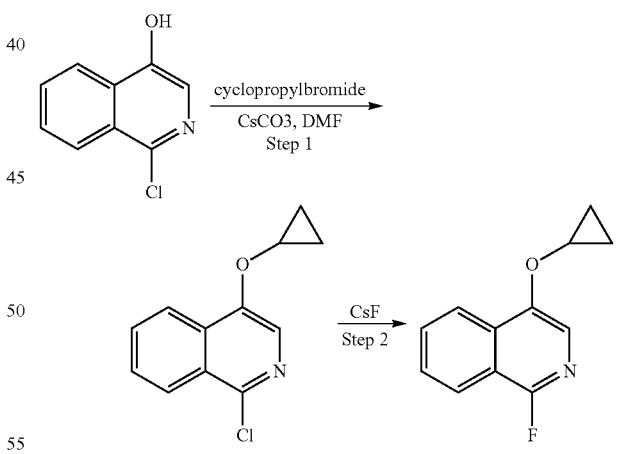

Step 1: Preparation of 1-chloro-4-cyclopropoxyisoquinoline

To a solution of 1-chloroisoquinolin-4-ol (1.0 g, 55.7 mmol) in DMF (20 m) was added Cs$_2$CO$_3$ (2.72 g, 8.35 mmol) followed by cyclopropylbromide (6.74 g, 55.7 mmol) at room temperature. The reaction vessel (Pressure tube) was sealed and heated at 145° C. for 18 h. The reaction mass was diluted with water and extracted with ethyl acetate. The combined organic layer was dried over anhydrous Na$_2$SO$_4$ and evaporated under reduced pressure to get crude compound. The crude compound was purified by silica gel chromatography to get desired compound (0.4 g, 32.7%) as a yellow solid. $^1$H NMR (400 MHz, CDCl$_3$): δ ppm 8.22-8.24 (m, 2H), 8.14 (s, 1H), 8.14-8.12 (m, 1H), 7.74-7.67 (m, 2H), 4.00-3.95 (m, 1H), 0.92-0.90 (m, 4H); MS: MS m/z 220.0 (M$^+$+1).

Step 2: Preparation of
1-Fluoro-4-cyclopropoxyisoquinoline

To a solution of 1-chloro-4-cyclopropoxyisoquinolin (2.3 g, 10.47 mmol) in DMSO (20 ml) was added cesium fluoride (6.36 g, 41.9 mmol) at room temperature. The reaction vessel (Pressure tube) was sealed and heated at 145° C. for 18 h. The reaction mass was diluted with water and extracted with ethyl acetate. The organic layer was dried over anhydrous Na$_2$SO$_4$ and evaporated under reduced pressure to get crude compound. The crude compound was purified by silica gel chromatography to get desired compound (0.8 g, 37.6%) as a white solid. $^1$H NMR (400 MHz, CDCl$_3$): δ ppm 8.09-8.07 (m, 2H), 7.83 (s, 1H), 7.76-7.71 (m, 1H), 7.67-7.63 (m, 1H), 3.96-3.94 (m, 1H), 0.90-0.89 (m, 4H); $^{19}$F NMR: δ ppm −78.58 (1 F); MS: MS m/z 204.2 (M$^+$+1).

Scheme: Preparation of
1-Chloro-4-methylisoquinoline

Synthesis of 1-Chloro-4-methylisoquinoline

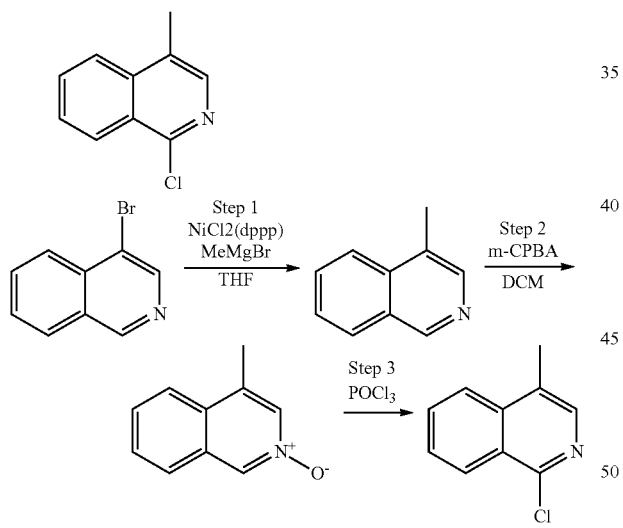

Step 1: Preparation of 4-methylisoquinoline

To a solution of 4-bromoisoquinoline (1 g, 4.81 mmol) in THF (20 ml) was added [1,3-Bis(diphenylphosphino)propane]nickel(II)chloride (0.026 g, 0.048 mmol) followed by methyl magnesium bromide in diethyl ether (1.923 ml, 5.77 mmol) at room temperature. The reaction mass was stirred at the same temperature for 18 h. The reaction mixture was acidified with 1N HCl and extracted with ethyl acetate. The organic layer was dried over anhydrous sodium sulfate, filtered and evaporated under reduced pressure to get crude compound. The crude compound was purified by silica gel chromatography (5% ethyl acetate in pet ether) to get desired compound (0.6 g, 78%) as an oil. $^1$H NMR (400 MHz, DMSO-d6): δ ppm 9.15 (s, 1H), 8.37 (s, 1H), 8.13-8.11 (d, J=8 Hz 1H), 8.05-8.03 (d, J=8 Hz, 1H), 7.83 (t, J=8 Hz, 1H), 7.71 (t, J=8 Hz, 1H) 2.59 (s, 3H); GC-MS: MS m/z 143 (M$^+$).

Step 2: Preparation of 4-methylisoquinoline 2-oxide

To a solution of 4-methylisoquinoline (0.6 g, 4.19 mmol) in DCM (20 ml) was added m-CPBA (2.169 g, 12.57 mmol) at room temperature. The reaction mass was stirred at the same temperature for 18 h. The reaction mass was diluted with DCM and extracted with water. The combined organic layer was dried over anhydrous Na$_2$SO$_4$ and evaporated under reduced pressure to get desired compound (0.65 g, 88%) as a semi solid. The crude compound was taken further without purification.

Step 3: Preparation of
1-chloro-4-methylisoquinoline

A solution of 4-methylisoquinoline 2-oxide (0.65 g, 4.08 mmol) in POCl$_3$ (6 ml) was refluxed for 18 h. The solvent was evaporated under reduced pressure and the residue was diluted with cold water. The aqueous solution was basified with solid sodium carbonate and extracted with ethyl acetate. The organic layer was dried over anhydrous sodium sulfate, filtered and evaporated under reduced pressure to get crude compound. The crude compound was purified by silica gel chromatography (10% ethyl acetate in pet ether) to get desired compound (0.17 g, 18.75%) as oil. $^1$H NMR (400 MHz, DMSO-d6): δ ppm 8.14-8.12 (d, J=8 Hz, 1H), 7.97 (s, 1H), 7.95-7.93 (d, J=8 Hz, 1H), 7.86 (t, J=4 Hz, 1H), 7.84 (t, J=8 Hz, 1H), 2.59 (s, 3H); MS: MS m/z 178.2 (M$^+$+1).

Scheme: Preparation of
1-Chloro-4-cyclopropylisoquinoline

Synthesis of 1-Chloro-4-cyclopropylisoquinoline

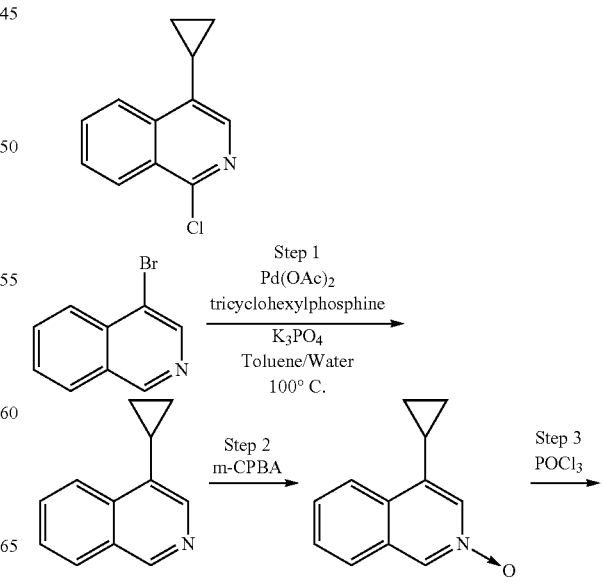

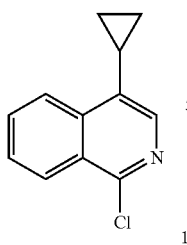

Step 1: Preparation of 4-cyclopropylisoquinoline

To a solution of 4-bromoisoquinoline (0.5 g, 2.403 mmol) and cyclopropylboronic acid (0.248 g, 2.88 mmol) in Toluene/water (11 ml, 10:1) was added phosphoric acid, potassium salt (1.02 g, 4.81 mmol) followed by addition of tricyclohexylphosphine (0.067 g, 0.240 mmol) and palladium(II) acetate (0.027 g, 0.120 mmol). The reaction mass was heated 100° C. and stirred for overnight. The reaction mass was diluted with water and extracted with ethyl acetate. The organic layer was dried over anhydrous $Na_2SO_4$ and evaporated under reduced pressure to get crude compound. The crude compound was purified by silica gel chromatography (10% ethyl acetate in pet ether) to get desired compound (0.4 g, 93%) as an oil.

$^1$H NMR (400 MHz, $CDCl_3$): δ ppm 9.12 (s, 1H), 8.34-8.32 (d, J=8 Hz, 1H), 8.31 (s, 1H), 7.98-7.96 (d, J=8 Hz, 1H), 7.76 (t, J=4 Hz, 1H), 7.62 (t, J=4 Hz, 1H), 2.23 (s, 1H), 1.11 (t, J=4 Hz, 2H), 0.82 (t, J=8 Hz, 2H).

Step 2: Preparation of 4-cyclopropylisoquinoline-2-oxide

To a solution of 4-cyclopropylisoquinoline (0.4 g, 2.364 mmol) in DCM (10 ml) was added m-CPBA (1.224 g, 7.09 mmol) at room temperature. The reaction mass was stirred at the same temperature for 18 h. The reaction mass was diluted with DCM and washed with water and aqueous sodium bicarbonate solution. The combined organic layer was dried over anhydrous $Na_2SO_4$ and evaporated under reduced pressure to get desired compound (0.35 g, 80%) as solid. The crude compound was taken further without purification.

Step 3: Preparation of 1-chloro-4-cyclopropylisoquinoline

A solution of 4-cyclopropylisoquinoline-2-oxide (0.3 g, 1.620 mmol) in $POCl_3$ (15 ml) was refluxed for overnight. The solvent was evaporated under reduced pressure and the residue was diluted with cold water. The aqueous solution was basified by solid sodium carbonate and extracted with ethyl acetate. The organic layer was dried over anhydrous sodium sulfate, filtered and evaporated under reduced pressure to get crude compound. The crude compound was purified by silica gel chromatography (10% ethyl acetate in pet ether) to get the desired compound (0.02 g, 5.76%) as oil.
$^1$H NMR (400 MHz, $CDCl_3$): δ ppm 8.37-8.35 (d, J=8 Hz, 2H), 8.08 (s, 1H), 7.81 (t, J=8 Hz, 1H), 7.70 (t, J=4 Hz, 1H), 2.18 (m, 1H), 1.11 (1, J=4 Hz, 2H), 0.80 (t, J=8 Hz, 2H); MS: MS m/z 204.28 ($M^+$+1).

Scheme: Preparation of 1-chloro-7-fluoro-4-methoxyisoquinoline

Synthesis of 1-Chloro-7-fluoro-4-methoxyisoquinoline

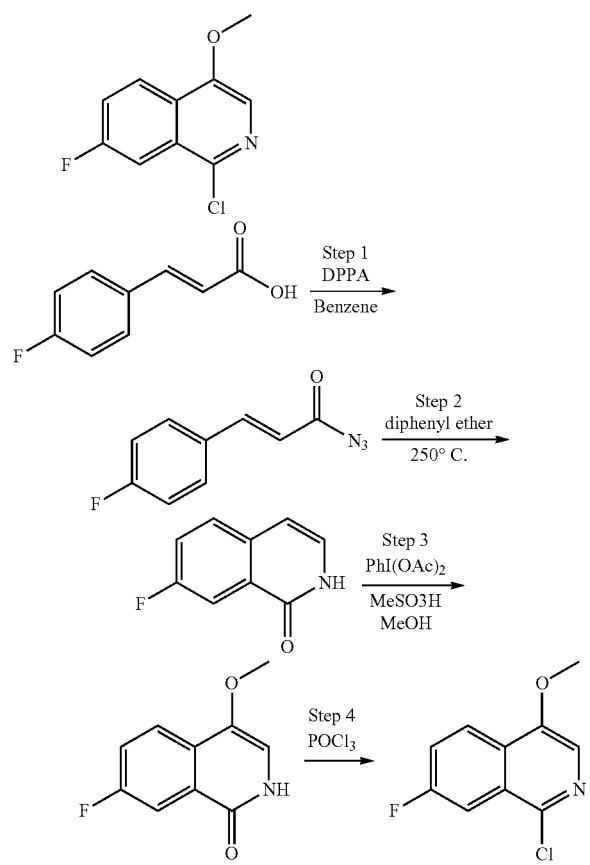

Step 1: Preparation of (E)-3-(4-fluorophenyl) acryloyl azide

To a solution of (E)-3-(4-fluorophenyl) acrylic acid (25 g, 150 mmol) in benzene (120 mL) was added triethylamine (30.5 g, 301 mmol) followed by DPPA (41.4 g, 150 mmol) at room temperature. The reaction mass was stirred at the same temperature for 18 h. The solvent was evaporated under reduced pressure and the residue was diluted with water and extracted with dichloromethane. The organic layer was dried over anhydrous sodium sulfate, filtered and evaporated to get crude compound. The crude compound was purified by conventional column chromatography (Silica gel, 60-120 mesh) using 10% ethyl acetate in pet ether as mobile phase to get the desired compound as a white solid (26 g, 90%). $^1$H NMR (400 MHz, $CDCl_3$): δ ppm 7.73-7.69 (d, J=16 Hz, 1H), 7.55-7.51 (m, 2H), 7.11-7.07 (m, 2H), 6.36-6.32 (d, J=16 Hz, 1H).

Step 2: Preparation of 7-fluoroisoquinolin-1(2H)-one

To a hot (125° C.) diphenyl ether (25 ml) was added (E)-3-(4-fluorophenyl) acryloyl azide (5 g, 26.2 mmol)

portion wise. The reaction was heated at 250° C. for 4 h. The reaction mass was cooled to room temperature and diluted with pet ether. The precipitated solid was filtered washed with pet ether to get crude compound (2.45 g, 57%). The crude compound was taken to the next step without further purification. ¹H NMR (400 MHz, CD₃OD): δ ppm 7.96-7.93 (m, 1H), 7.76-7.72 (m, 1H), 7.56-7.51 (m, 1H), 7.18-7.16 (m, 1H), 6.72-6.70 (m, 1H); MS: MS m/z 164.1 (M⁺+1).

Step 3: Preparation of 7-fluoro-4-methoxyisoquinolin-1(2H)-one

To a solution of 7-fluoroisoquinolin-1(2H)-one (11 g, 67.4 mmol) in methanol was added iodozobenzenediacetate (21.7 g, 67.4 mmol) followed by methane sulphonic acid (7.78 g, 81 mmol) at room temperature. The reaction mass was heated at reflux for 3 h. The solvent was evaporated and the residue was diluted with cold water. The precipitated solid was filtered and washed with water to get crude compound (11 g, 84%) as light red color solid. ¹H NMR (400 MHz, CD₃OD): δ ppm 8.06-8.04 (m, 1H), 7.96-7.93 (m, 1H), 7.62-7.54 (m, 2H), 6.74 (s, 1H), 3.89 (s, 3H); MS: MS m/z 194.1 (M⁺+1).

Step 4: Preparation of 1-chloro-7-fluoro-4-methoxyisoquinoline

A solution of 7-fluoro-4-methoxyisoquinolin-1(2H)-one (11 g, 56.9 mmol) in POCl₃ (100 ml) was refluxed for 18 h. The solvent was evaporated under reduced pressure and the residue was diluted with cold water. The aqueous solution was basified by solid sodium carbonate and extracted with ethyl acetate. The combine organic layer was dried over anhydrous sodium sulfate, filtered and evaporated under reduced pressure to get crude compound. The crude compound was purified by silica gel chromatography (20% ethyl acetate in pet ether) to get desired compound (2.9 g, 24%) as off-white solid. ¹H NMR (400 MHz, CDCl₃): δ ppm 8.36-8.32 (m, 1H), 7.93-7.90 (m, 1H), 7.88 (s, 1H), 7.70-7.65 (m, 1H), 4.11 (s, 3H); MS: MS m/z 212.1 (M⁺+1).

Scheme: Preparation of 7-difluoro-4-methoxyisoquinoline

Synthesis of 1,7-Difluoro-4-methoxyisoquinoline

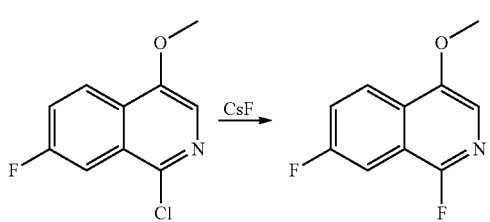

To a solution of 1-chloro-7-fluoro-4-methoxyisoquinoline (3.7 g, 17.48 mmol) in DMSO was added cesium fluoride (10.26 g, 69.9 mmol) at room temperature. The reaction vessel (Pressure tube) was sealed and heated at 145° C. for 18 h. The reaction mass was diluted with water and extracted with ethyl acetate. The combined organic layer was dried over anhydrous Na₂SO₄ and evaporated under reduced pressure to get crude compound. The crude compound was purified by silica gel chromatography to get desired compound (1.7 g, 49%) as white solid. ¹H NMR (400 MHz, CD₃OD): δ ppm 8.20-8.18 (m, 1H), 7.69-7.66 (m, 1H), 7.54-7.47 (m, 1H), 7.46 (s, 1H), 4.04 (s, 3H); ¹⁹F NMR: δ ppm 109.65 (1F), −78.53 (1F); MS: MS m/z 196.1 (M⁺+1).

Scheme: Preparation of 1,7-diflouro-4cyclopropoxyisoquinoline

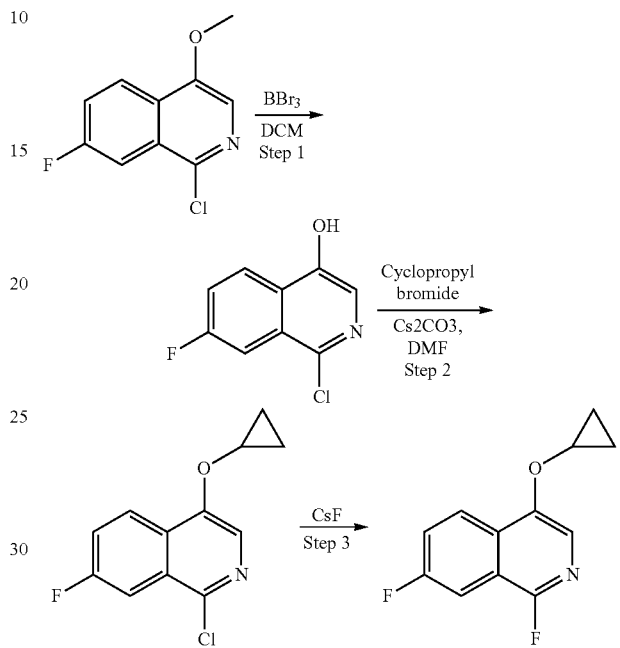

Scheme: Preparation of 1,7-diflouro-4cyclopropoxyisoquinoline

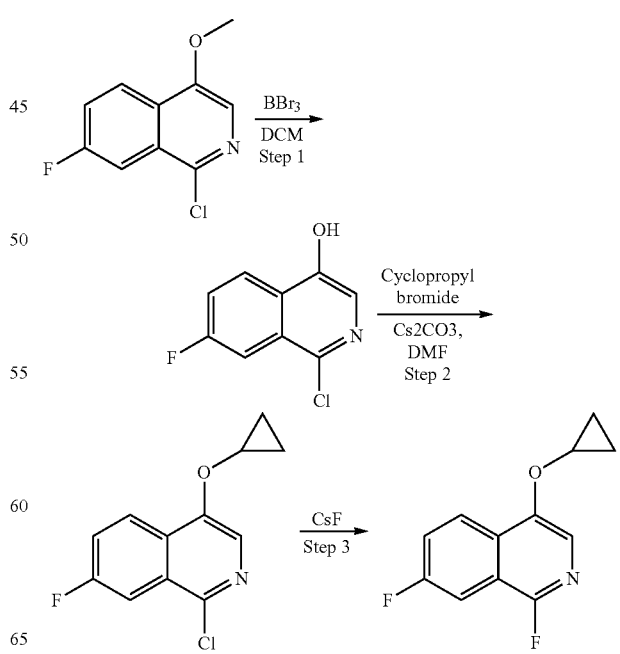

Step 1: Preparation of 1-chloro-7-flouro-4-hydroxyisoquinoline

A solution of 1-chloro-7-flouro-4-methoxyisoquinoline (0.75 g, 3.54 mmol) in DCM (10 ml) was added BBr₃ (6.22 g, 24.81 mmol) at 0° C. drop wise. The reaction mass was refluxed for 5 h. The residue was cooled and quenched with methanol. The solvent was evaporated under reduced pressure and the residue was diluted with cold water. The precipitated solid was filtered, washed with water to get crude compound (0.65 g, 93%) as a pale yellow solid. $^1$H NMR (400 MHz, CD₃OD): δ ppm 8.36-8.33 (m, 1H), 7.89-7.86 (d, J=12 Hz, 1H), 7.76 (s, 1H), 7.64 (t, J=10 Hz, 1H); MS: MS m/z 198.0 (M$^+$+1).

Step 2: Preparation of 1-chloro-7-flouro-4-cyclopropoxyisoquinoline

To a solution of 1-chloro-7-flouroisoquinolin-4-ol (1 g, 5.06 mmol) in DMF (5 mL) was added Cs₂CO₃ (4.95 g, 15.18 mmol) followed by cyclopropyl bromide (1.2 mL, 15.18 mmol) at room temperature. The reaction vessel (Pressure tube) was sealed and heated at 145° C. for 18 h. The reaction mass was diluted with water and extracted with ethyl acetate. The organic layer was dried over anhydrous Na₂SO₄ and evaporated under reduced pressure to get crude compound. The crude compound was purified by silica gel chromatography to get desired compound (0.24 g, 20%) as a yellow solid.

Step 3: Preparation of 1,7-difluoro-4-cyclopropoxyisoquinoline

To a solution of 1-chloro-7-flouro-4-cyclopropoxyisoquinolin (0.24 g, 1.01 mmol) in DMSO (2 ml) was added cesium fluoride (0.38 g 2.52 mmol) at room temperature. The reaction vessel (Pressure tube) was sealed and heated at 145° C. for 18 h. The reaction mass was diluted with water and extracted with ethyl acetate. The combined organic layer was dried over anhydrous Na₂SO₄ and evaporated under reduced pressure to get crude compound. The crude compound was purified by silica gel chromatography to get desired compound (0.15 g 67%) as a white solid.

Scheme: Preparation of 1-Fluoro-4-ethoxy-7-fluoroisoquinoline

Synthesis of 1-Fluoro-4-ethoxy-7-fluoroisoquinoline

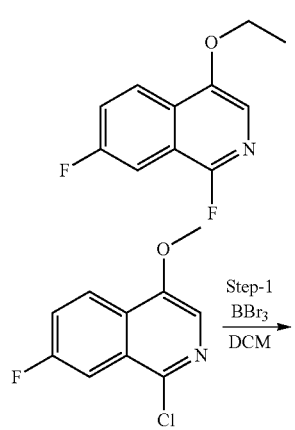

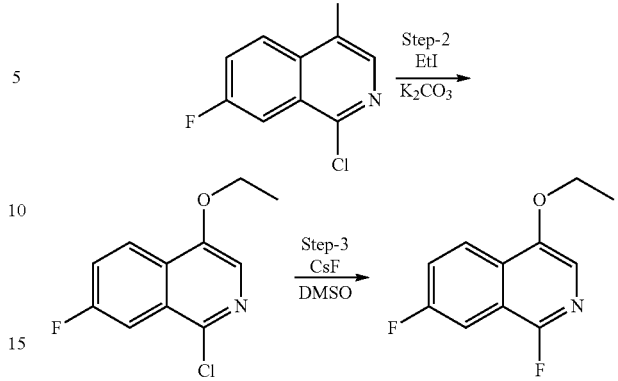

Step 1: Preparation of 1-chloro-7-flouro-4-hydroxyisoquinoline

A solution of 1-chloro-7-flouro-4-methoxyisoquinoline (0.75 g, 3.54 mmol) in DCM (10 ml) was added BBr₃ (6.22 g, 24.81 mmol) at 0° C. drop wise. The reaction mass was refluxed for 5 h. The residue was cooled and quenched with methanol. The solvent was evaporated under reduced pressure and the residue was diluted with cold water. The precipitated solid was filtered, washed with water to get crude compound (0.65 g, 93%) as pale yellow solid. $^1$H NMR (400 MHz, CD₃OD): δ ppm 8.36-8.33 (m, 1H), 7.89-7.86 (d, J=12 Hz, 1H), 7.76 (s, 1H), 7.64 (t, J=10 Hz, 1H); MS: MS m/z 198.0 (M$^+$+1).

Step 2: Preparation of 1-chloro-7-flouro-4-ethoxyisoquinoline

To a solution of 1-chloro-7-flouroisoquinolin-4-ol (0.5 g, 2.53 mmol) in acetonitrile (10 ml) was added K₂CO₃ (700 mg, 5.06 mmol) followed by ethyl iodide (475 mg, 3.04 mmol) at room temperature. The reaction mixture was stirred at room temperature for overnight. The solvent was evaporated under reduced pressure and the residue was diluted with water and extracted with ethyl acetate. The combined organic layer was dried over anhydrous Na₂SO₄ and evaporated under reduced pressure to get crude compound. The crude compound was purified by silica gel chromatography to get 1-chloro-7-flouro-4-ethoxyisoquinoline (400 mg 70%) as off-white solid.

Step 3: Preparation of 1,7-difluoro-4-ethoxyisoquinoline

To a solution of 1-chloro-4-ethoxyisoquinolin (0.2 g, 0.88 mmol) in DMSO (2 mL) was added cesium fluoride (0.37 g, 2.21 mmol) at room temperature. The reaction vessel (Pressure tube) was sealed and heated at 145° C. for 18 h. The reaction mass was diluted with water and extracted with ethyl acetate. The organic layer was dried over anhydrous Na₂SO₄ and evaporated under reduced pressure to get crude compound. The crude compound was purified by silica gel chromatography to get desired compound (120 mg, 65%) as white solid. MS: MS m/z (M$^+$+1).

Scheme: Preparation of 1-chloro-7-flouro-4-cyclopropylmethoxyisoquinoline

Synthesis of 1-Chloro-4-(cyclopropylmethoxy)-7-fluoroisoquinoline

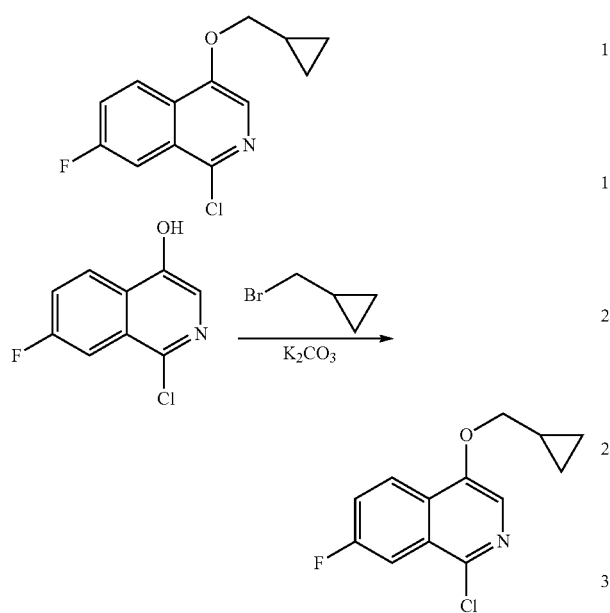

To a solution of 1-chloro-7-flouro-4-hydroxyisoquinoline (1.0 g, 5.06 mmol) in acetonitrile (10 ml) was added $K_2CO_3$ (2 g, 15.18 mmol) followed by cyclopropylmethylbromide (1.36 g, 10.12 mmol) at room temperature. The reaction mixture was heated to 50° C. for 2 hr. Solvent was evaporated under reduced pressure and the residue was diluted with water and extracted with ethyl acetate. The combined organic layer was dried over anhydrous $Na_2SO_4$ and evaporated under reduced pressure to get crude compound. The crude compound was purified by silica gel chromatography to get 1-chloro-4-ethoxyisoquinoline (0.7 g, 55%) as pale yellow solid. $^1$H NMR (400 MHz, $CDCl_3$): δ ppm 8.38-8.34 (q, J=8 Hz, 1H), 7.89-7.86 (d, J=12 Hz, 1H), 7.81 (s, 1H), 7.65 (t, J=10 Hz, 1H), 4.11-4.09 (d, J=8 Hz, 2H), 1.43-1.37 (m, 1H), 0.72-0.67 (m, 2H), 0.46-0.39 (m, 2H); MS: MS m/z 252.0 ($M^+$+1).

Preparation of 1,7-difluoro-4-cyclopropylmethoxyisoquinoline

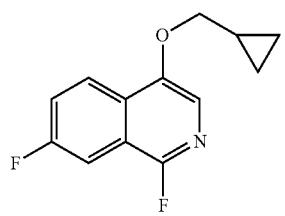 [SMILES: Fc1ccc2c(OCC3CC3)cnc(F)c2c1]

To a solution of 1-Chloro-4-(cyclopropylmethoxy)-7-fluoroisoquinoline (0.7 g, 2.78 mmol) in DMSO (5 mL) was added cesium fluoride (1.0 g, 6.95 mmol) at room temperature. The reaction vessel (Pressure tube) was sealed and heated at 145° C. for 18 h. The reaction mass was diluted with water and extracted with ethyl acetate. The organic layer was dried over anhydrous $Na_2SO_4$ and evaporated under reduced pressure to get crude compound. The crude compound was purified by silica gel chromatography to get desired compound (0.43 g, 65%) as white solid. $^1$H NMR (400 MHz, $CD_3OD$): δ ppm 8.35-8.33 (m, 1H), 7.77-7.74 (d, J=12 Hz, 1H) 7.73 (t, J=8 Hz, 1H), 7.52-7.51 (d, J=4 Hz, 1H), 4.10-4.08 (d, J=8 Hz, 2H), 1.42-1.40 (m, 1H), 0.74-0.69 (m, 2H), 0.49-0.46 (m, 2H); MS: MS m/z 237.0 ($M^+$+1).

Scheme: Preparation of 1,7-difluoro-6-methoxyisoquinoline

Synthesis of 1,7-difluoro-6-methoxyisoquinoline

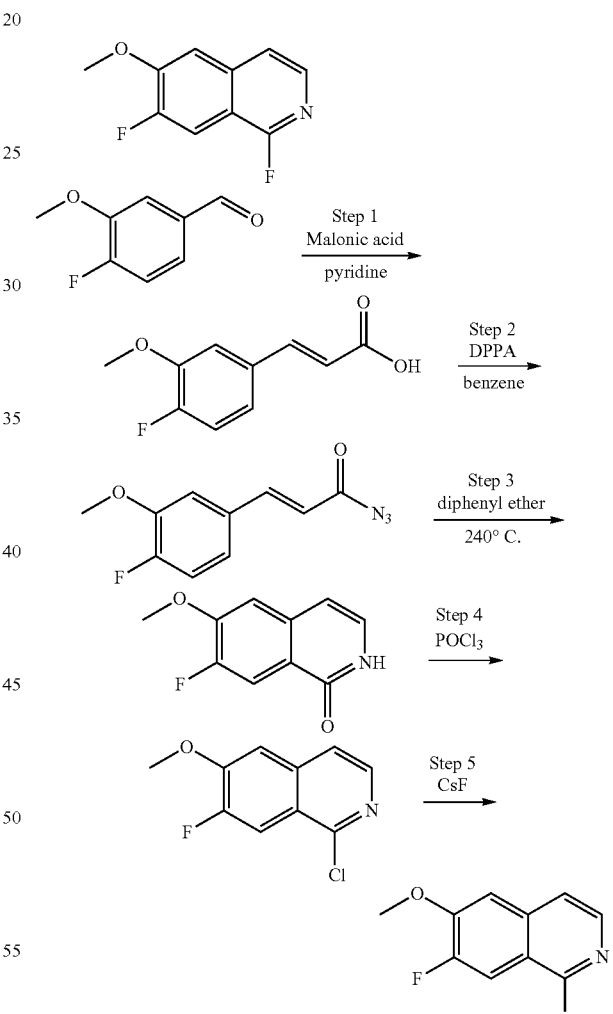

Step 1: Preparation of (E)-3-(4-fluoro-3-methoxyphenyl) acrylic acid

To a solution of 4-fluoro-3-methoxybenzaldehyde (30 g, 195 mmol) in pyridine (134 ml) and Piperidine (4.12 ml) was added malonic acid (30.4 g, 292 mmol) at room temperature. The reaction mass was refluxed for 18 h. The solvent was evaporated under reduced pressure and the residue was acidified with 1.5N HCl solution. The precipitated solid was filtered washed with pet ether to get crude compound (37 g, 97%) as white solid. The crude compound was taken to the next step without further purification. $^1$H NMR (400 MHz, CDCl$_3$): δ ppm 12.37 (s, 1H), 7.59-7.55 (d, J=16 Hz, 1H), 7.53 (s, 1H), 7.26-7.22 (m, 2H), 6.59-6.55 (d, J=16 Hz, 1H), 3.89 (s, 3H); MS: MS m/z 195.0 (M$^+$−1).

Step 2: Preparation of (E)-3-(4-fluoro-3-methoxyphenyl) acryloyl azide

To a solution of (E)-3-(4-fluoro-3-methoxyphenyl) acrylic acid (5 g, 25.5 mmol) in benzene (30 ml) was added triethylamine (5.16 g, 51 mmol) followed by DPPA (7.01 g, 25.5 mmol) at room temperature. The reaction mass was stirred at the same temperature for 18 h. The solvent was evaporated under reduced pressure and the residue was diluted with water and extracted with dichloromethane. The organic layer was dried over anhydrous sodium sulfate, filtered and evaporated to get crude compound. The crude compound was purified by conventional column chromatography (Silica gel, 60-120 mesh) using 10% ethyl acetate in pet ether as mobile phase to get the desire compound as white solid (4 g, 71%). $^1$H NMR (400 MHz, CDCl$_3$): δ ppm 7.70-7.66 (d, J=16 Hz, 1H), 7.12-7.07 (m, 3H), 6.35-6.31 (d, J=16 Hz, 1H), 3.92 (s, 3H).

Step 3: Preparation of 7-fluoro-6-methoxyisoquinolin-1(2H)-one

To a hot (125° C.) diphenyl ether (20 ml) was added (E)-3-(4-fluoro-3-methoxyphenyl) acryloyl azide (4 g, 18.08 mmol) portion wise. The reaction was heated at 250° C. for 4 h. The reaction mass was cooled to room temperature and diluted with pet ether. The precipitated solid was filtered washed with pet ether to get crude compound (3.1 g, 89%). The crude compound was taken to the next step without further purification. MS: MS m/z 194.1 (M$^+$+1).

Step 4: Preparation of 1-chloro-7-fluoro-6-methoxyisoquinoline

A solution of 7-fluoro-6-methoxyisoquinolin-1(2H)-one (3.1 g, 16.05 mmol) in POCl$_3$ (25 ml) was refluxed for 18 h. The solvent was evaporated under reduced pressure and the residue was diluted with cold water. The aqueous solution was basified by solid sodium carbonate and extracted with ethyl acetate. The organic layer was dried over anhydrous sodium sulfate, filtered and evaporated under reduced pressure to get crude compound. The crude compound was purified by silica gel chromatography (20% ethyl acetate in pet ether) to get desired compound (1.9 g, 55%) as off-white solid. $^1$H NMR (400 MHz, CDCl$_3$): δ ppm 8.22-8.20 (d, J=8 Hz, 1H), 7.97-7.94 (m, 1H), 7.49-7.48 (m, 1H), 7.18-7.16 (d, J=8 Hz, 1H), 4.04 (s, 3H); MS: MS m/z 211.7 (M$^+$+1).

Step 5: Preparation of 1,7-difluoro-6-methoxyisoquinoline

To a solution of 1-chloro-7-fluoro-6-methoxyisoquinoline (1.5 g, 7.09 mmol) in DMSO was added cesium fluoride (2.15 g, 14.18 mmol) at room temperature. The reaction vessel (Pressure tube) was sealed and heated at 145° C. for 18 h. The reaction mass was diluted with water and extracted with ethyl acetate. The combined organic layer was dried over anhydrous Na$_2$SO$_4$ and evaporated under reduced pressure to get crude compound. The crude compound was purified by silica gel chromatography to get desired compound (950 mg, 68%) as white solid. $^1$H NMR (400 MHz, CDCl$_3$): δ ppm 8.0-7.98 (m, 1H), 7.77-7.74 (d, J=12 Hz, 1H), 7.42-7.40 (m, 1H), 7.21-7.19 (m, 1H), 4.04 (s, 3H); $^{19}$F NMR: δ ppm −129.05 (1 F), −71.98 (1F); MS: MS m/z 196.1

Scheme: Preparation of 1-Chloro-4-ethoxy-6-methoxyisoquinoline

Synthesis of 1-Chloro-4-ethoxy-6-methoxyisoquinoline

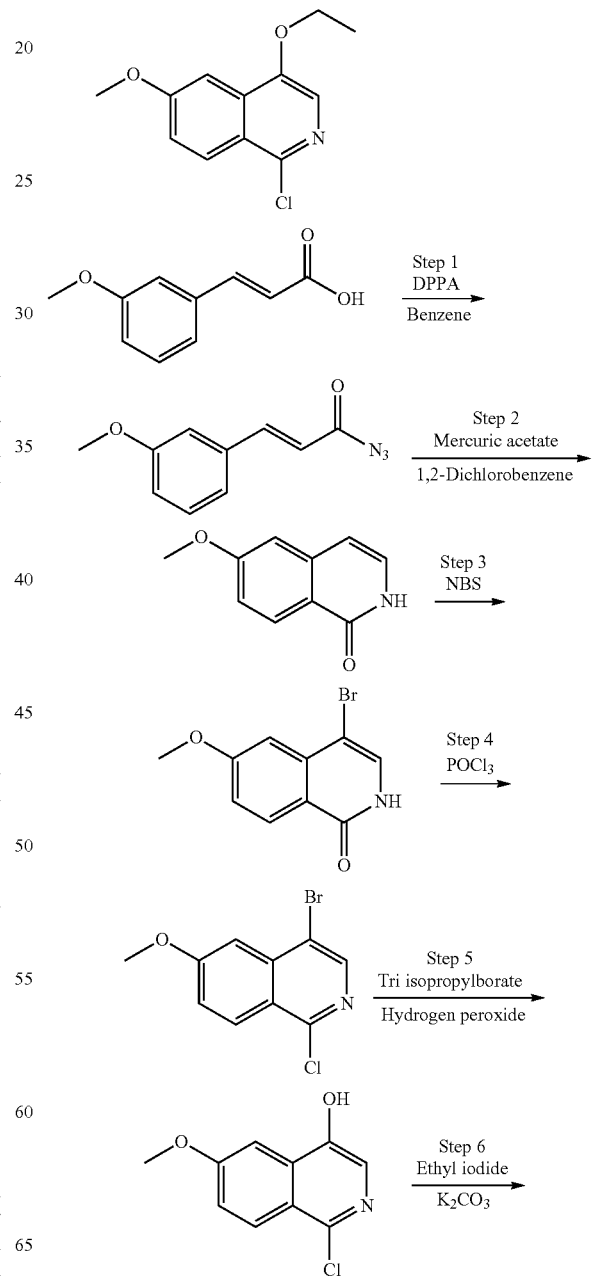

-continued

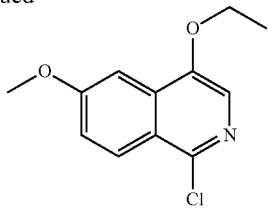

Step 1: Preparation of (E)-3-(3-methoxyphenyl)acryloyl azide

To a solution of (E)-3-(3-methoxyphenyl)acrylic acid (15 g, 84 mmol) in benzene (100 ml) was added triethylamine (11.73 ml, 84 mmol) followed by DPPA (23.17 g, 84 mmol) at room temperature. The reaction mass was stirred at the same temperature for 18 h. The solvent was evaporated under reduced pressure and the residue was diluted with water and extracted with dichloromethane. The organic layer was dried over anhydrous sodium sulfate, filtered and evaporated to get crude compound. The crude compound was purified by conventional column chromatography (Silica gel, 60-120 mesh) using 10% ethyl acetate in pet ether as mobile phase to get the desire compound as white solid (15 g, 88%). $^1$H NMR (400 MHz, CDCl$_3$): δ ppm 7.75-7.70 (d, J=20 Hz, 1H), 7.36-6.97 (m, 4H), 6.45-6.40 (d, J=20 Hz, 1H), 3.85 (s, 3H).

Step 2: Preparation of 6-methoxyisoquinolin-1(2H)-one

To a solution of (E)-3-(3-methoxyphenyl)acryloylazide (2.0 g, 9.84 mmol) in 1,2-dichlorobenzene (10 ml) was added mercuric acetate (0.031 g, 0.098 mmol). The reaction was heated at 120° C. and stirred for 5 minutes at this temperature and then it was heated to 180° C. for 1 h. The reaction mass was cooled to room temperature and diluted with pet ether. The precipitated solid was filtered washed with pet ether to get crude compound (1.2 g, 69.6%). The crude compound was taken to the next step without further purification. $^1$H NMR (400 MHz, DMSO-d6): δ ppm 11.03 (s, 1H), 8.08-8.06 (d, J=8 Hz, 1H), 7.14-7.03 (m, 3H), 6.48-6.46 (d, J=8 Hz, 1H), 3.87 (s, 3H); MS: MS m/z 176.1 (M$^+$+1).

Step 3: Preparation of 4-bromo-6-methoxyisoquinolin-1(2H)-one

To a solution of 6-methoxyisoquinolin-1(2H)-one (2.5 g, 14.27 mmol) in acetonitrile (10 ml) was added NBS (2.54 g, 14.27 mmol) at room temperature under argon atmosphere. The reaction mass was stirred at the same temperature for 2 hr. The precipitated solid was filtered to get crude compound (2 g, 55.2%). The crude compound was taken to the next step without further purification. $^1$H NMR (400 MHz, DMSO-d6): δ ppm 11.41 (s, 1H), 8.17-8.15 (d, J=8 Hz, 1H), 7.53 (s, 1H), 7.19-7.11 (m, 2H), 3.93 (s, 3H); MS: MS m/z 256.06 (M$^+$+2).

Step 4: Preparation of 4-bromo-1-chloro-6-methoxyisoquinoline

A solution of 4-bromo-6-methoxyisoquinolin-1(2H)-one (1.5 g, 5.90 mmol) in POCl$_3$ (15 ml) was refluxed for overnight. The solvent was evaporated under reduced pressure and the residue was diluted with cold water. The aqueous solution was basified by solid sodium carbonate and extracted with ethyl acetate. The combine organic layer was dried over anhydrous sodium sulfate, filtered and evaporated under reduced pressure to get crude compound. The crude compound was purified by silica gel chromatography (10% ethyl acetate in pet ether) to get desired compound (1.1 g, 65%) as white solid. $^1$H NMR (400 MHz, DMSO-d6): δ ppm 8.53 (s, 1H), 8.27-8.24 (d, J=12 Hz, 1H), 7.56-7.53 (d, J=12 Hz, 1H), 7.41 (s, 1H), 4.02 (s, 3H); MS: MS m/z 273.99 (M$^+$+1).

Step 5: Preparation of 1-chloro-6-methoxyisoquinolin-4-ol

To a solution of 4-bromo-1-chloro-6-methoxyisoquinoline (0.25 g, 0.917 mmol) in THF (30 ml) was added n-Butyl Lithium (1.147 ml, 1.835 mmol) at −78° C. under nitrogen. The reaction mixture was stirred for 30 minutes and Triisopropyl borate (0.426 ml, 1.835 mmol) was added and stirred for another 30 minutes. To this Hydrogen Peroxide (0.273 ml, 8.90 mmol) (30% solution 1.5M) was added followed by the addition of sodium hydroxide (0.917 ml, 0.917 mmol). The resulting mixture was stirred for additional 1 h at room temperature. The reaction mixture was cooled to −40° C. and added sodium sulfite solution in water (1.156 g, 9.17 mmol). The resulting slurry was neutralized with 6N HCl solution and extracted with ethyl acetate. The combine organic layer was dried over anhydrous sodium sulfate, filtered and evaporated under reduced pressure to get crude compound. The crude compound was purified by silica gel chromatography (20% ethyl acetate in pet ether) to get desired compound (0.13 g, 67.6%) as solid. MS: MS m/z 210.06 (M$^+$+1).

Step 6: Preparation of 1-chloro-4-ethoxy-6-methoxyisoquinoline

To a solution of 1-chloro-6-methoxyisoquinolin-4-ol (0.05 g, 0.239 mmol) in acetonitrile (5 ml) was added potassium carbonate (0.099 g, 0.716 mmol) followed by iodoethane (0.039 ml, 0.477 mmol) at room temperature. The reaction mass was stirred at the same temperature for 18 h. The solvent was evaporated under reduced pressure and the residue was diluted with water and extracted with dichloromethane. The organic layer was dried over anhydrous sodium sulfate, filtered and evaporated to get crude compound. The crude compound was purified by silica gel chromatography (10% ethyl acetate in pet ether) to get desired compound (0.015 g, 25.1%) as solid. $^1$H NMR (400 MHz, DMSO-d6): δ ppm 8.14-8.12 (d, J=8 Hz, 1H), 7.90 (s, 1H), 7.46-7.42 (m, 2H), 4.34-4.27 (q, J=8 Hz, 2H), 3.95 (s, 3H), 1.48 (t, J=10 Hz, 3H).

Scheme: Preparation of 1,4-dichloro-6-methoxyisoquinoline

Synthesis of 1,4-Dichloro-6-methoxyisoquinoline

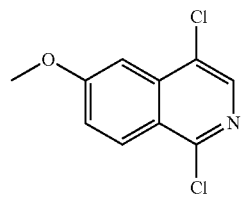

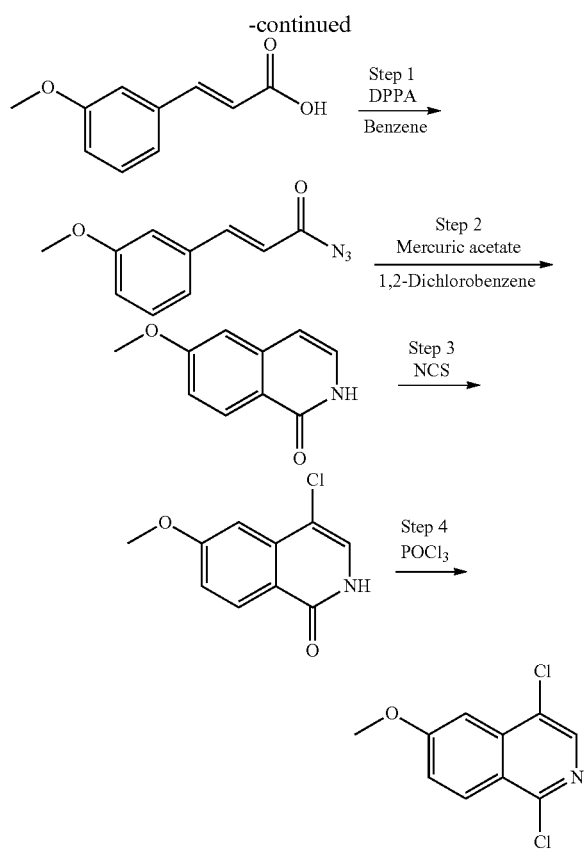

Step 1: Preparation of (E)-3-(3-methoxyphenyl)acryloyl azide

To a solution of (E)-3-(3-methoxyphenyl)acrylic acid (15 g, 84 mmol) in benzene (100 ml) was added triethylamine (11.73 ml, 84 mmol) followed by DPPA (23.17 g, 84 mmol) at room temperature. The reaction mass was stirred at the same temperature for 18 h. The solvent was evaporated under reduced pressure and the residue was diluted with water followed by extraction with dichloromethane. The organic layer was dried over anhydrous sodium sulfate, filtered and evaporated to get crude compound. The crude compound was purified by conventional column chromatography (Silica gel, 60-120 mesh) using 10% ethyl acetate in pet ether as mobile phase to get the desire compound as white solid (15 g, 88%). $^1$H NMR (400 MHz, CDCl$_3$): δ ppm 7.75-7.70 (d, J=20 Hz, 1H), 7.36-6.97 (m, 4H), 6.45-6.40 (d, J=20 Hz, 1H), 3.85 (s, 3H).

Step 2: Preparation of 6-methoxyisoquinolin-1(2H)-one

To a solution of (E)-3-(3-methoxyphenyl) acryloylazide (2.0 g, 9.84 mmol) in 1,2-dichlorobenzene (10 ml) was added mercuric acetate (0.031 g, 0.098 mmol). The reaction was heated at 120° C. and stirred for 5 minutes at this temperature and then it was heated to 180° C. for 1 h. The reaction mass was cooled to room temperature and diluted with pet ether. The precipitated solid was filtered and washed with pet ether to get crude compound (1.2 g, 69.6%). The crude compound was taken to the next step without further purification. $^1$H NMR (400 MHz, DMSO-d6): δ ppm 11.03 (s, 1H), 8.08-8.06 (d, J=8 Hz, 1H), 7.14-7.03 (m, 3H), 6.48-6.46 (d, J=8 Hz, 1H), 3.87 (s, 3H); MS: MS m/z 176.1 (M$^+$+1).

Step 3: Preparation of 4-chloro-6-methoxyisoquinolin-1(2H)-one

To a solution of 6-methoxyisoquinolin-1(2H)-one (2.5 g, 14.27 mmol) in acetonitrile (10 ml) was added NCS (2.54 g, 14.27 mmol) at 80° C. for overnight. The reaction mass was cooled to room temperature and the precipitated solid was filtered to get crude compound (2 g, 55.2%). The crude compound was taken to the next step without further purification. $^1$H NMR (400 MHz, DMSO-d6): δ ppm 11.41 (s, 1H), 8.17-8.15 (d, J=8 Hz, 1H), 7.53 (s, 1H), 7.19-7.11 (m, 2H), 3.93 (s, 3H); MS: MS m/z 210.02 (M$^+$+1).

Step 4: Preparation of 1,4-dichloro-6-methoxyisoquinoline

A solution of 4-chloro-6-methoxyisoquinolin-1(2H)-one (1.5 g, 5.90 mmol) in POCl$_3$ (15 ml) was refluxed for overnight. The solvent was evaporated under reduced pressure and the residue was diluted with cold water. The aqueous solution was basified by solid sodium carbonate and extracted with ethyl acetate. The combine organic layer was dried over anhydrous sodium sulfate, filtered and evaporated under reduced pressure to get crude compound. The crude compound was purified by silica gel chromatography (10% ethyl acetate in pet ether) to get desired compound (1.1 g, 65.0%) as white solid. $^1$H NMR (400 MHz, DMSO-d6): δ ppm 8.53 (s, 1H), 8.27-8.24 (d, J=12 Hz, 1H), 7.56-7.53 (d, J=12 Hz, 1H), 7.41 (s, 1H), 4.02 (s, 3H); MS: MS m/z 230.03 (M$^+$+2).

Scheme: Preparation of 4-(1-Chloro-6-methoxy isoquinoline-4-yl) morpholine & 4-(1-Chloro-6-methoxy isoquinoline-4-yl)-2,6-dimethyl morpholine

Synthesis of 4-(1-Chloro-6-methoxy isoquinoline-4-yl) morpholine

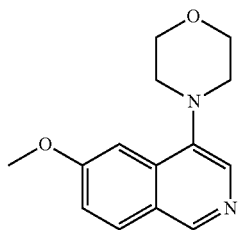

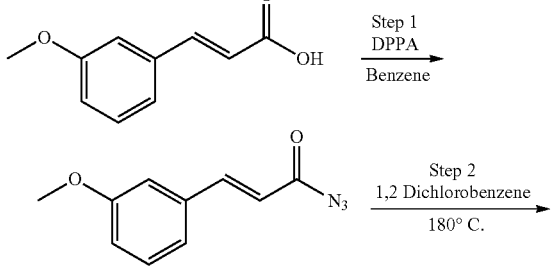

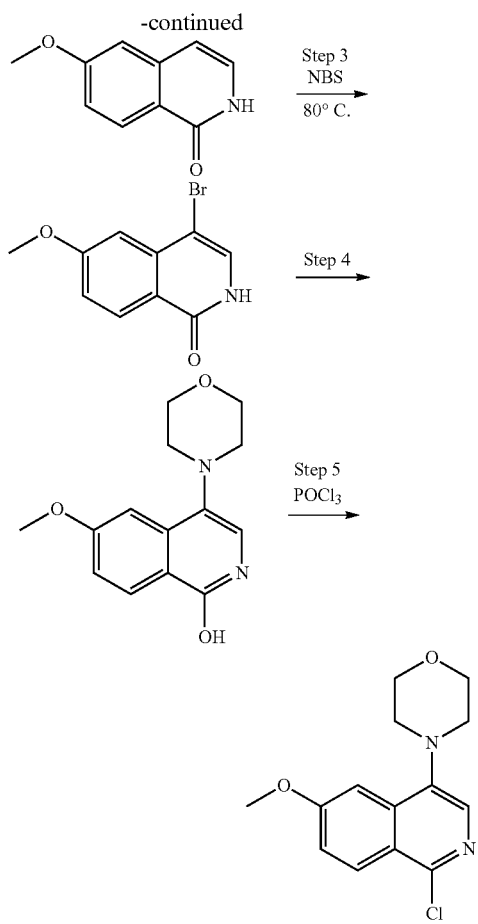

Step 1: Preparation of (E)-3-(3-methoxyphenyl)acryloyl azide

To a solution of (E)-3-(3-methoxyphenyl)acrylic acid (15 g, 84 mmol) in benzene (100 ml) was added triethylamine (11.73 ml, 84 mmol) followed by DPPA (23.17 g, 84 mmol) at room temperature. The reaction mass was stirred at the same temperature for 18 h. The solvent was evaporated under reduced pressure and the residue was diluted with water and extracted with dichloromethane. The organic layer was dried over anhydrous sodium sulfate, filtered and evaporated to get crude compound. The crude compound was purified by conventional column chromatography (Silica gel, 60-120 mesh) using 10% ethyl acetate in pet ether as mobile phase to get the desire compound as a white solid (15 g, 88%). $^1$H NMR (400 MHz, CDCl$_3$): δ ppm 7.75-7.70 (d, J=20 Hz, 1H), 7.36-6.97 (m, 4H), 6.45-6.40 (d, J=20 Hz, 1H), 3.85 (s, 3H).

Step 2: Preparation of 6-methoxyisoquinolin-1(2H)-one

To a solution of (E)-3-(3-methoxyphenyl)acryloyl azide (2.0 g, 9.84 mmol) in 1,2-dichlorobenzene (10 ml) was added mercuric acetate (0.031 g, 0.098 mmol). The reaction was heated at 120° C. and stirred for 5 minutes at this temperature and then it was heated to 180° C. for 1 h. The reaction mass was cooled to room temperature and diluted with pet ether. The precipitated solid was filtered washed with pet ether to get crude compound (1.2 g, 69.6%). The crude compound was taken to the next step without further purification. $^1$H NMR (400 MHz, DMSO-d6): δ ppm 11.03 (s, 1H), 8.08-8.06 (d, J=8 Hz, 1H), 7.14-7.03 (m, 3H), 6.48-6.46 (d, J=8 Hz, 1H), 3.87 (s, 3H); MS: MS m/z 176.1 (M$^+$+1).

Step 3: Preparation of 4-bromo-6-methoxyisoquinolin-1(2H)-one

To a solution of 6-methoxyisoquinolin-1(2H)-one (2.5 g, 14.27 mmol) in acetonitrile (10 ml) was added NBS (2.54 g, 14.27 mmol) at room temperature under argon atmosphere. The reaction mass was stirred at the same temperature for 2 h. The precipitated solid was filtered to get crude compound (2 g, 55.2%). The crude compound was taken to the next step without further purification. $^1$H NMR (400 MHz, DMSO-d6): δ ppm 11.41 (s, 1H), 8.17-8.15 (d, J=8 Hz, 1H), 7.53 (s, 1H), 7.19-7.11 (m, 2H), 3.93 (s, 3H); MS: MS m/z 256.06 (M$^+$+2).

Step 4: Preparation of 6-methoxy-4-morpholinoisoquinolin-1-ol

To a solution of 4-bromo-6-methoxyisoquinolin-1(2H)-one (0.5 g, 1.968 mmol) and morpholine (0.429 g, 4.92 mmol) in ethylene glycol (2.5 ml) was added DIPEA (1.031 ml, 5.90 mmol). The reaction was irradiated in a microwave at 145° C. for 1.5 h. The reaction mixture was adsorbed on silica was purified by silica gel chromatography (30% ethyl acetate in pet ether) to get desired compound (0.29 g, 53.8%) as solid. $^1$H NMR (400 MHz, CDCl$_3$): δ ppm 10.98 (s, 1H), 8.11 (s, 1H), 7.24-7.11 (m, 3H), 3.88 (s, 3H), 3.56-3.55 (m, 4H), 2.52-2.51 (m, 4H); MS: MS m/z 261 (M$^+$+1).

Step 5: Preparation of 4-(1-chloro-6-methoxyisoquinolin-4-yl) morpholine

A solution of 6-methoxy-4-morpholinoisoquinolin-1-ol (0.33 g, 1.268 mmol) in POCl$_3$ (5 ml) was refluxed for overnight. The solvent was evaporated under reduced pressure and the residue was diluted with cold water. The aqueous solution was basified by solid sodium carbonate and extracted with ethyl acetate. The combine organic layer was dried over anhydrous sodium sulfate, filtered and evaporated under reduced pressure to get crude compound. The crude compound was purified by silica gel chromatography (10% ethyl acetate in pet ether) to get desired compound (0.065 g, 18%) as oil. $^1$H NMR (400 MHz, DMSO-d6): δ ppm 8.18-8.16 (d, J=8 Hz 1H), 7.94 (s, 1H), 7.45-7.40 (m, 2H), 3.98 (s, 3H), 3.88-3.86 (m, 4H), 3.09-3.07 (m, 4H); MS: MS m/z 279.1 (M$^+$+1).

Scheme: Preparation of 4-(1-Chloro-6-methoxy isoquinoline-4-yl)-2,6-dimethyl morpholine Synthesis of 4-(1-Chloro-6-methoxy isoquinoline-4-yl)-2,6-dimethyl morpholine

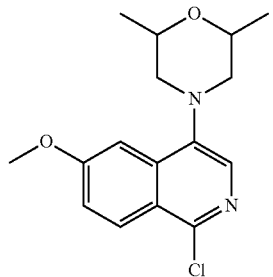

-continued

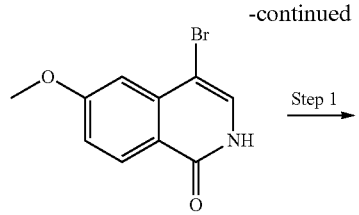

Step 1 →

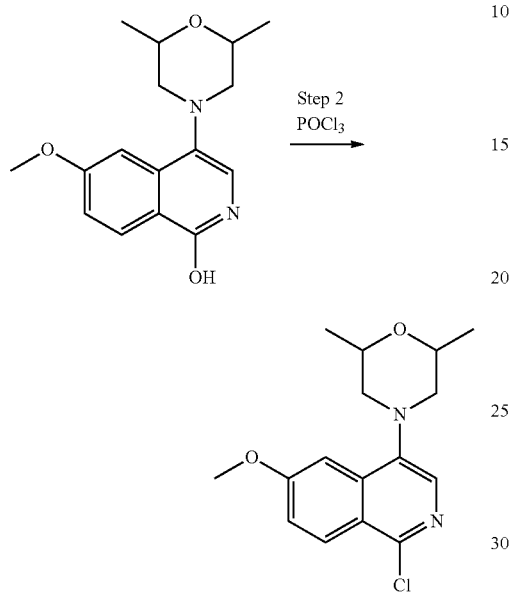

Step 1: Preparation of 4-(2,6-dimethylmorpholino)-6-methoxyisoquinolin-1(2H)-one To a solution of 4-bromo-6-methoxyisoquinolin-1(2H)-one (0.2 g, 0.787 mmol) and (2S,6R)-2,6-dimethylmorpholine (0.181 g, 1.574 mmol) in ethylene glycol (2.5 ml) was added DIPEA (0.412 ml, 2.361 mmol). The reaction was irradiated in microwave at 145° C. for 1.5 h. The reaction mixture was adsorbed on silica was purified by silica gel chromatography (30% ethyl acetate in pet ether) to get desired compound (0.11 g, 48.5%) as solid. MS: MS m/z 289.18 (M$^+$+1).

Step 2: Preparation of 4-(1-chloro-6-methoxyisoquinolin-4-yl)-2,6-dimethylmorpholine A solution of 4-((2S,6R)-2,6-dimethylmorpholino)-6-methoxyisoquinolin-1(2H)-one (0.15 g, 0.520 mmol) in POCl$_3$ (5 ml) was refluxed for overnight. The solvent was evaporated under reduced pressure and the residue was diluted with cold water. The aqueous solution was basified by solid sodium carbonate and extracted with ethyl acetate. The organic layer was dried over anhydrous sodium sulfate, filtered and evaporated under reduced pressure to get crude compound. The crude compound was purified by silica gel chromatography (10% ethyl acetate in pet ether) to get the desired compound (0.085 g, 49%) as oil. MS: MS m/z 307.17 (M$^+$+1).

Scheme: Preparation of 1-Chloro-4-(4-(2,2-difluoro-ethyl)piperazin-1-yl)isopropoxyphenyl)-6-methoxy-isoquinoline & 1-Chloro-6-methoxy-4-(4-methyl-piperazin-1-yl)isoquinoline Synthesis of 1-Chloro-4-(4-(2,2-difluoroethyl)piper-azin-1-yl)isopropoxyphenyl)-6-methoxyisoquinoline

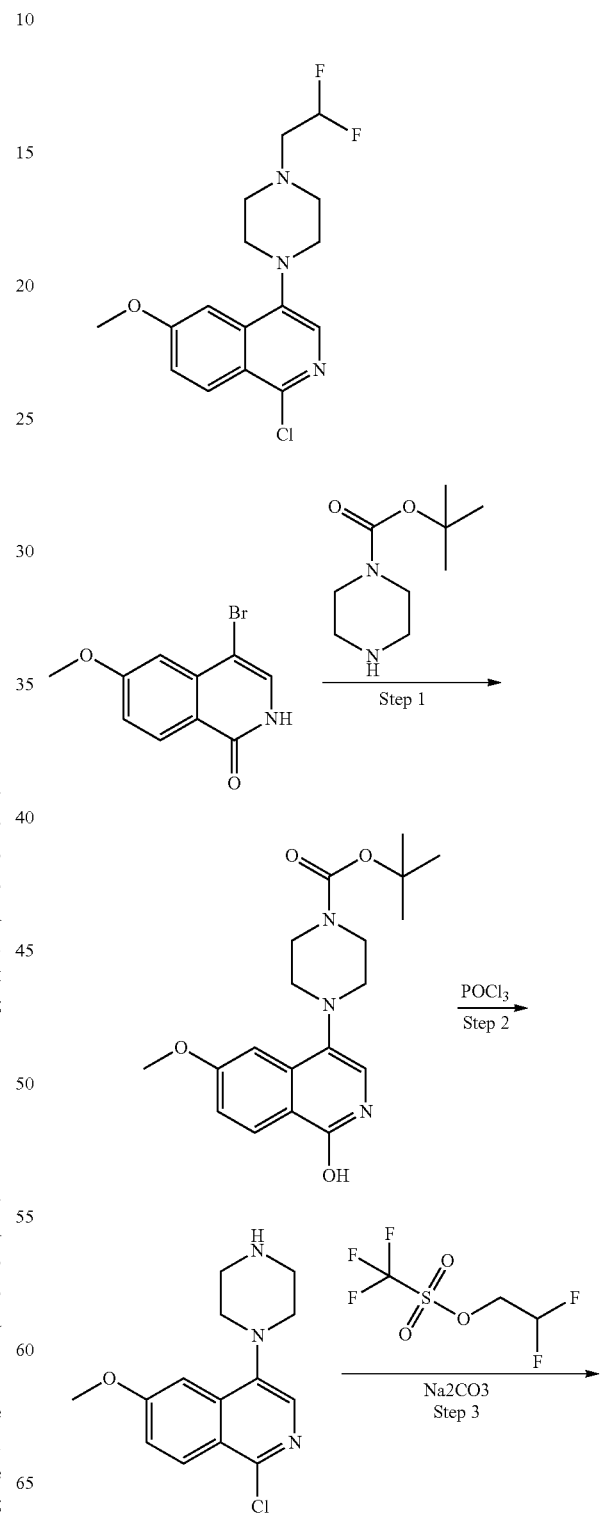

583
-continued

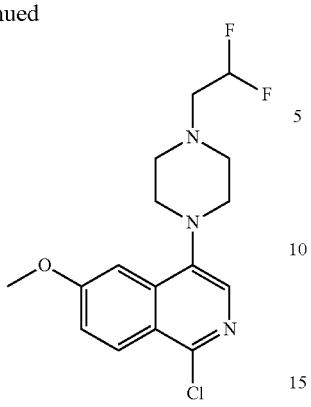

Step 1: Preparation of tert-butyl 4-(1-hydroxy-6-methoxyisoquinolin-4-yl)piperazine-1-carboxylate To a solution of 4-bromo-6-methoxyisoquinolin-1(2H)-one (0.5 g, 1.968 mmol) and tert-butyl piperizine-1-carboxylate (0.916 g, 4.92 mmol) in ethylene glycol (5 ml) was added DIPEA (1.0.31 ml, 5.90 mmol) and heated to 145° C. for overnight in sealed tube. The reaction mixture was diluted with water and extracted with ethyl acetate. Combined organic layer was dried over anhydrous sodium sulfate, filtered and evaporated to get crude compound (0.3 g, 29.4%). The crude compound was taken for the next step without further purification. MS: MS m/z 260.20 ($M^+$+1).

Step 2: Preparation of 1-chloro-6-methoxy-4-(piperazin-1-yl)isoquinoline

A solution of tert-butyl 4-(1-hydroxy-6-methoxyisoquinolin-4-yl)piperazine-1-carboxylate (0.3 g, 1.157 mmol) in $POCl_3$ (5 ml) was refluxed for overnight. The solvent was evaporated under reduced pressure and the residue was diluted with cold water. The aqueous solution was basified by solid sodium carbonate and extracted with ethyl acetate. The organic layer was dried over anhydrous sodium sulfate, filtered and evaporated under reduced pressure to get crude compound. The crude compound was purified by silica gel chromatography (10% ethyl acetate in pet ether) to get desired compound (0.2 g, 37.3%) as a gummy compound MS: MS m/z 278.56 ($M^+$+1).

Step 3: Preparation of 1-chloro-4-(4-(2,2-difluoroethyl)piperazin-1-yl)-6-methoxyisoquinoline To a solution of 1-chloro-6-methoxy-4-(piperazin-1-yl) isoquinoline (0.2 g, 0.720 mmol) in DMF (5 ml) was added 2,2-Difluoroethyl trifluoromethanesulfonate (0.154 g, 0.720 mmol) followed by sodium carbonate (0.114 g, 1.080 mmol). The reaction mass was stirred until judged complete. The reaction mixture was diluted with water and extracted with ethyl acetate. The organic layer was dried over anhydrous sodium sulfate, filtered and evaporated to get crude compound. The crude compound was purified by silica gel chromatography (10% ethyl acetate in pet ether) to get desired compound (0.04 g, 15.93%) as semi solid. $^1$H NMR (400 MHz, DMSO-d6): δ ppm 8.18-8.15 (d, J=12 Hz, 1H), 7.93 (s, 1H), 7.45-7.42 (d, J=12 Hz, 1H), 7.37 (s, 1H), 6.36-5.76 (tf, 1H), 3.97 (s, 3H), 3.10 (m, 4H), 2.84 (m, 4H); $^{19}$F NMR: δ ppm −118.59 (1 F); MS: MS m/z 342.19 ($M^+$+1).

584

Scheme: Preparation of 1-Chloro-6-methoxy-4-(4-methylpiperazin-1-yl)isoquinoline Synthesis of 1-Chloro-6-methoxy-4-(4-methylpiperazin-1-yl)isoquinoline

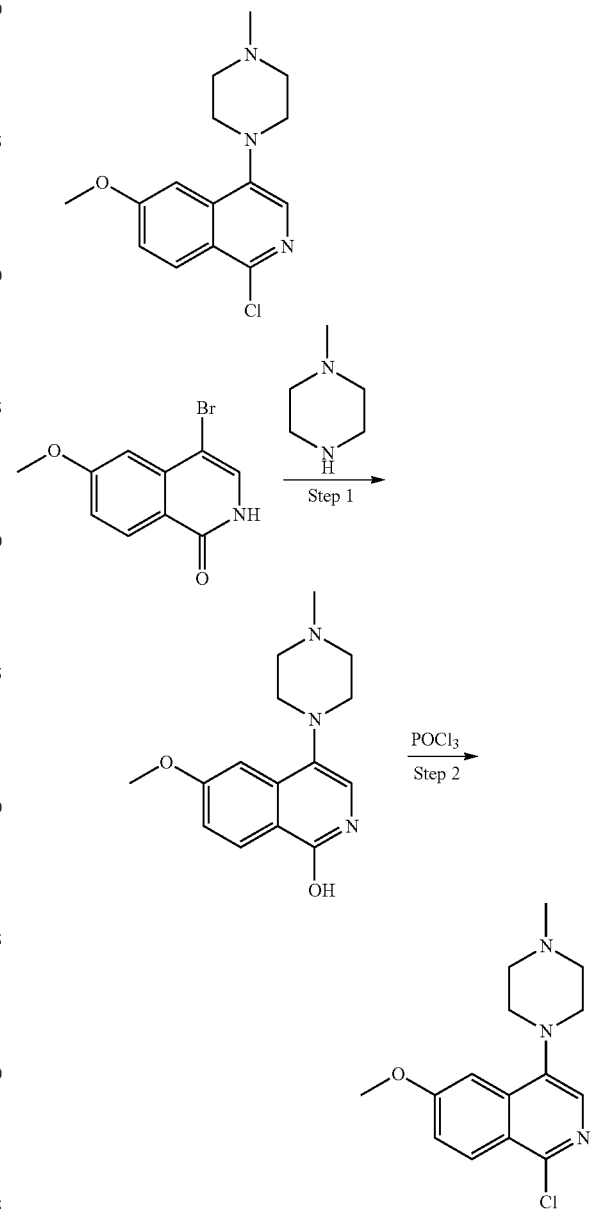

Step 1: Preparation of 6-methoxy-4-(4-methylpiperazin-1-yl) isoquinolin-1(2H)-one To a solution of 4-bromo-6-methoxyisoquinolin-1(2H)-one (0.25 g, 0.984 mmol) and 1-methylpiperazine (0.197 g, 1.968 mmol) in ethylene glycol (2 ml) was added DIPEA (0.516 ml, 2.95 mmol). The reaction was irradiated in microwave at 140° C. for 1 h. The reaction mixture was adsorbed on silica was purified by silica gel chromatography (30% ethyl acetate in pet ether) to get the desired compound (0.16 g, 53.5%) as solid. MS: MS m/z 274.18 (M$^+$+1).

Step 2: Preparation of 1-chloro-6-methoxy-4-(4-methylpiperazin-1-yl)isoquinoline A solution of 6-methoxy-4-(4-methylpiperazin-1-yl)isoquinolin-1(2H)-one (0.16 g, 0.585 mmol) in POCl$_3$ (5 ml) was refluxed for overnight. The solvent was evaporated under reduced pressure and the residue was diluted with cold water. The aqueous solution was basified by solid sodium carbonate and extracted with ethyl acetate. The organic layer was dried over anhydrous sodium sulfate, filtered and evaporated under reduced pressure to get crude compound. The crude compound was purified by silica gel chromatography (10% MeOH in CHCl$_3$) to get desired compound (0.05 g, 27.8%) as solid. $^1$H NMR (400 MHz, DMSO-d6): δ ppm 8.18-8.15 (d, J=12 Hz, 1H), 7.92 (s, 1H), 7.45-7.42 (d, J=12 Hz, 1H), 7.36 (s, 1H), 3.97 (s, 3H), 3.09 (m, 4H), 2.52 (m, 4H), 2.31 (s, 3H); MS: MS m/z 292.15 (M$^+$+1).

Scheme: Preparation of 3-(4-(tert-butyl)phenyl)-1-chloro-6-methoxyisoquinoline

Synthesis of 3-(4-(tert-butyl)phenyl)-1-chloro-6-methoxyisoquinoline

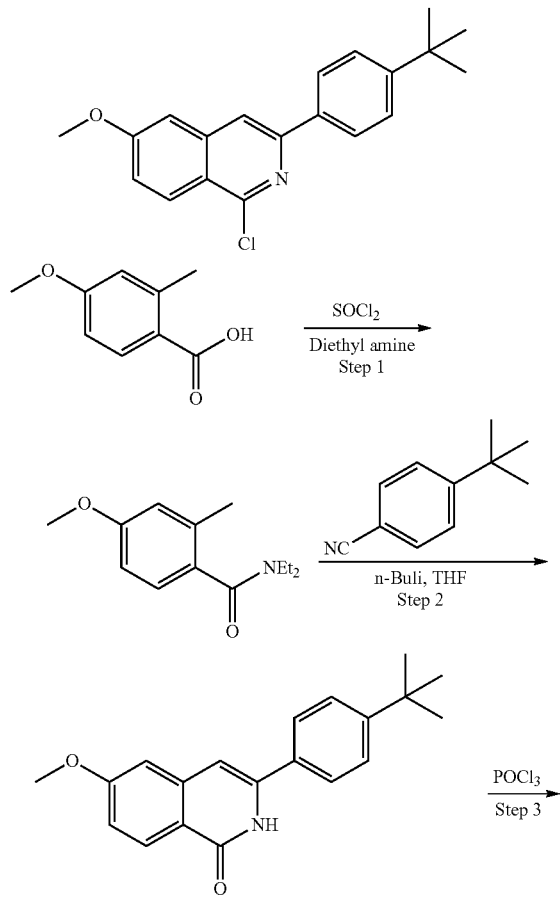

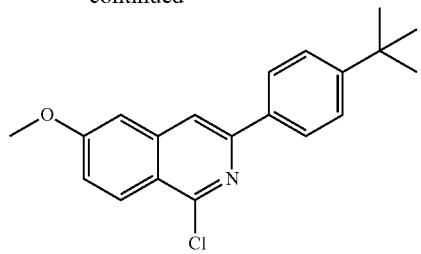

Step 1: Preparation of N,N-diethyl-4-methoxy-2-methylbenzamide 4-methoxy-2-methylbenzoic acid (3.0 g, 18.05 mmol) was taken in thionyl chloride (20 ml) and refluxed for 1 h at 80° C. The reaction mixture was evaporated under reduced pressure. Under nitrogen the crude was quenched with diethyl amine (1.870 ml, 18.05 mmol) slowly under cooling conditions. The reaction mixture was dissolved in water and extracted with ethyl acetate. The organic layer was dried over anhydrous sodium sulfate, filtered and evaporated under reduced pressure to get crude compound. The crude compound was purified by silica gel chromatography (20% ethyl acetate in pet ether) to get desired compound (2.3 g, 54.7%) as oil. $^1$H NMR (400 MHz, DMSO-d6): δ ppm 7.06-7.04 (d, J=8 Hz, 1H), 6.79 (s, 1H), 6.78-6.76 (d, J=8 Hz, 1H), 3.75 (s, 3H), 3.43 (br, s, 2H), 3.06-3.05 (m, 2H), 2.16 (s, 3H), 1.14 (d, J=8 Hz, 3H), 0.95 (d, J=8 Hz, 3H).

Step 2: Preparation of 3-(4-(tert-butyl)phenyl)-6-methoxyisoquinolin-1(2H)-one

To a stirred solution of N,N-diethyl-4-methoxy-2-methylbenzamide (1 g, 4.52 mmol) in THF (10 ml) was added n-BuLi (2.82 ml, 4.52 mmol, in hexane) at −78° C. and stirred for 1 h. Then to this 4-(tert-butyl)benzonitrile (0.72 g, 4.52 mmol) was added at same temperature and allowed to warm to room temperature and continued the stirring for another 1 h at room temperature. The reaction mixture was quenched with saturated NH$_4$Cl solution and extracted with EtOac (2*100 ml). The organic phase was washed with brine, dried on Na$_2$SO$_4$, and evaporated under reduced pressure to get crude compound. The crude compound was purified by silica gel chromatography (20% ethyl acetate in pet ether) to get desired compound (0.72 g, 46.7%) as a solid. $^1$H NMR (400 MHz, DMSO-d6): δ ppm 11.26 (s, 1H), 8.11-8.09 (d, J=8 Hz, 1H), 7.73-7.71 (d, J=8 Hz, 2H), 7.52-7.50 (d, J=8 Hz, 2H), 7.06 (s, 1H), 7.05-7.03 (d, J=8 Hz, 1H), 6.82 (s, 1H), 3.89 (s, 3H), 1.32 (s, 9H); MS: MS m/z 308.2 (M$^+$+1).

Step 3: Preparation of 3-(4-(tert-butyl)phenyl)-1-chloro-6-methoxyisoquinoline

A solution of 3-(4-(tert-butyl)phenyl)-6-methoxyisoquinolin-1(2H)-one (0.7 g, 2.277 mmol) in POCl$_3$ (7 ml) was refluxed for overnight. The solvent was evaporated under reduced pressure and the residue was diluted with cold water. The aqueous solution was basified by solid sodium carbonate and extracted with ethyl acetate. The organic layer was dried over anhydrous sodium sulfate, filtered and evaporated under reduced pressure to get crude compound. The crude compound was purified by silica gel chromatography (10% ethyl acetate in pet ether) to get desired compound (0.21 g, 28.0%) as solid. $^1$H NMR (400 MHz, DMSO-d6): δ ppm 8.34 (s, 1H), 8.18-8.16 (d, J=8 Hz, 1H), 8.08-8.06 (d, J=8 Hz, 2H), 7.57-7.55 (d, J=8 Hz, 2H), 7.41 (s, 1H), 7.40-7.38 (d, J=8 Hz, 1H), 3.97 (s, 3H), 1.34 (s, 9H); MS: MS m/z 362.2 (M$^+$+1).

Scheme: Preparation of 1-chloro-3-(4-isopropoxy-phenyl)-6-methoxyisoquinoline

Synthesis of 1-Chloro-3-(4-isopropoxyphenyl)-6-methoxyisoquinoline

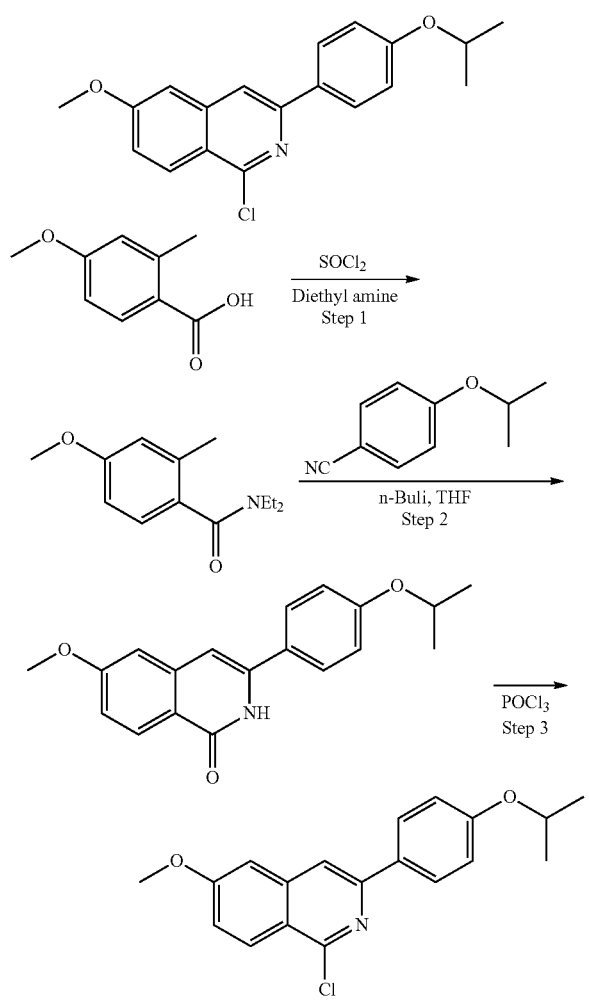

Step 1: Preparation of N,N-diethyl-4-methoxy-2-methylbenzamide 4-methoxy-2-methylbenzoic acid (3.0 g, 18.05 mmol) was taken in thionyl chloride (20 ml) and refluxed for 1 h at 80° C. The reaction mixture was evaporated under reduced pressure. Under nitrogen the crude was quenched with diethyl amine (1.870 ml, 18.05 mmol) slowly under cooling condition. The reaction mixture was dissolved in water and extracted with ethyl acetate. The organic layer was dried over anhydrous sodium sulfate, filtered and evaporated under reduced pressure to get crude compound. The crude compound was purified by silica gel chromatography (20% ethyl acetate in pet ether) to get desired compound (2.3 g, 54.7%) as an oil. $^1$H NMR (400 MHz, DMSO-d6): δ ppm 7.06-7.04 (d, J=8 Hz, 1H), 6.79 (s, 1H), 6.78-6.76 (d, J=8 Hz, 1H), 3.75 (s, 3H), 3.43 (br, s, 2H), 3.06-3.05 (m, 2H), 2.16 (s, 3H), 1.14 (d, J=8 Hz, 3H), 0.95 (d, J=8 Hz, 3H).

Step 2: Preparation of 3-(4-isopropoxyphenyl)-6-methoxyisoquinolin-1(2H)-one

To a stirred solution of N,N-diethyl-4-methoxy-2-methylbenzamide (3.5 g, 15.82 mmol) in THF (35 ml) was added n-BuLi (2.82 ml, 4.52 mmol, in hexane) at −78° C. and stirred for 1 h. 4-isopropoxy benzonitrile (2.55 g, 15.82 mmol) was added at same temperature and allowed to warm to room temperature and continued the stirring for another 1 h at room temperature. The reaction mixture was quenched with saturated aqueous NH$_4$Cl solution and extracted with EtOAc (2*100 ml). The organic phase was washed with brine then dried on Na$_2$SO$_4$ and evaporated under reduced pressure to get crude compound. The crude compound was purified by silica gel chromatography (20% ethyl acetate in pet ether) to get desired compound (3.5 g, 71.5%) as white solid. $^1$H NMR (400 MHz, DMSO-d6): δ ppm 11.21 (s, 1H), 8.09-8.07 (d, J=8 Hz, 1H), 7.71-7.69 (d, J=8 Hz, 2H), 7.14 (d, J=8 Hz, 1H), 7.03-7.01 (d, J=8 Hz, 3H), 6.76 (s, 1H), 4.71 (m, 1H), 3.88 (s, 3H), 1.30 (m, 6H); MS: MS m/z 310.7 (M$^+$+1).

Step 3: Preparation of 1-chloro-3-(4-isopropoxyphenyl)-6-methoxyisoquinoline

A solution of 3-(4-isopropoxyphenyl)-6-methoxyisoquinolin-1(2H)-one (3.5 g, 11.31 mmol) in POCl$_3$ (11 ml) was refluxed for overnight. The solvent was evaporated under reduced pressure and the residue was diluted with cold water. The aqueous solution was basified by solid sodium carbonate and extracted with ethyl acetate. The organic layer was dried over anhydrous sodium sulfate, filtered and evaporated under reduced pressure to get crude compound. The crude compound was purified by silica gel chromatography (10% ethyl acetate in pet ether) to get desired compound (2.5 g, 67.4%) as pale yellow solid. $^1$H NMR (400 MHz, CDCl$_3$): δ ppm 8.06-8.04 (d, J=8 Hz, 1H), 8.03-8.01 (d, J=8 Hz, 2H), 7.81 (s, 1H), 7.22-7.20 (d, J=8 Hz, 1H), 7.00 (s, 1H), 6.99-6.97 (d, J=8 Hz, 1H), 4.63 (m, 1H), 3.96 (s, 3H), 1.38 (m, 6H).

Scheme: Preparation of 4-(1-Chloro-7-fluoro-6-methoxy isoquinoline-4-yl) morpholine Synthesis of 4-(1-Chloro-7-fluoro-6-methoxy isoquinoline-4-yl) morpholine

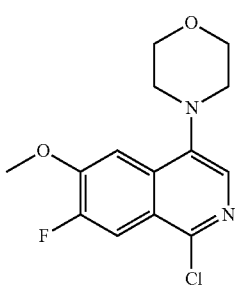 [SMILES: COc1cc2c(N3CCOCC3)cnc(Cl)c2cc1F]

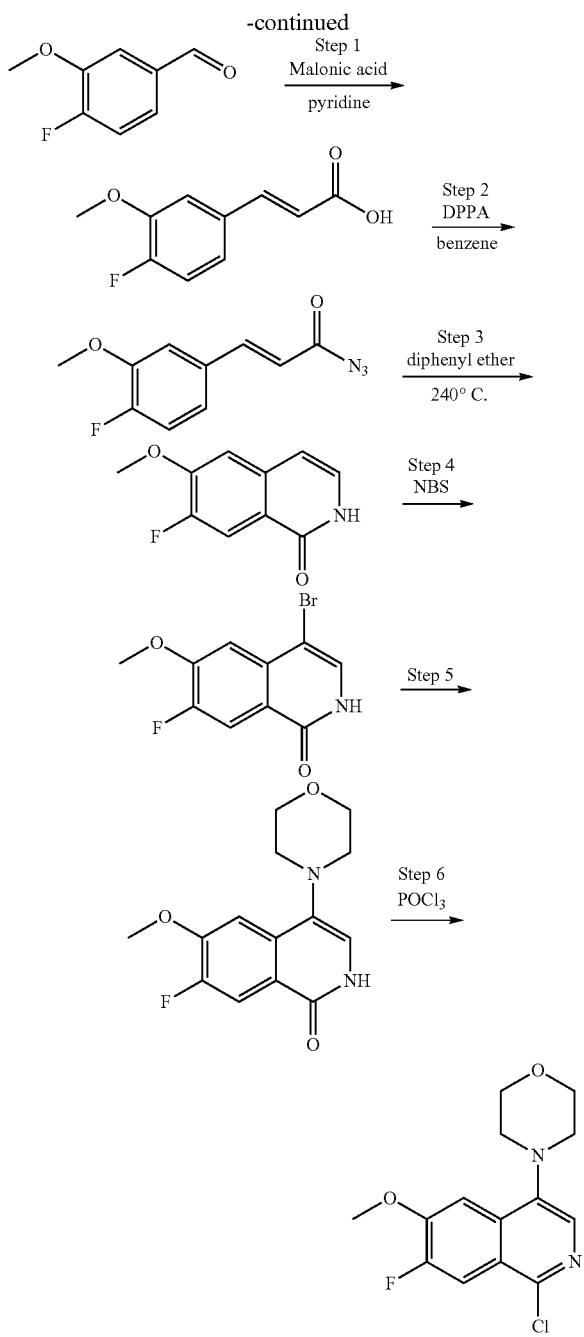

Step 1: Preparation of (E)-3-(4-fluoro-3-methoxyphenyl) acrylic acid

To a solution of 4-fluoro-3-methoxybenzaldehyde (30 g, 195 mmol) in pyridine (134 ml) and piperidine (4.12 ml) was added malonic acid (30.4 g, 292 mmol) at room temperature. The reaction mass was refluxed for 18 h. The solvent was evaporated under reduced pressure and the residue was acidified with 1.5N HCl solution. The precipitated solid was filtered washed with pet ether to get crude compound (37 g, 97%) as white solid. The crude compound was taken to the next step without further purification. $^1$H NMR (400 MHz, CDCl$_3$): δ ppm 12.37 (s, 1H), 7.59-7.55 (d, J=16 Hz, 1H), 7.53 (s, 1H), 7.26-7.22 (m, 2H), 6.59-6.55 (d, J=16 Hz, 1H), 3.89 (s, 3H); MS: MS m/z 195.0 (M$^+$−1).

Step 2: Preparation of (E)-3-(4-fluoro-3-methoxyphenyl) acryloyl azide

To a solution of (E)-3-(4-fluoro-3-methoxyphenyl)acrylic acid (25 g, 127 mmol) in benzene (250 ml) was added triethylamine (35.5 ml, 255 mmol) followed by DPPA (35.1 g, 127 mmol) at room temperature. The reaction mass was stirred at the same temperature for 18 h. The solvent was evaporated under reduced pressure and the residue was diluted with water and extracted with dichloromethane. The organic layer was dried over anhydrous sodium sulfate, filtered and evaporated to get crude compound. The crude compound was purified by conventional column chromatography (Silica gel, 60-120 mesh) using 10% ethyl acetate in pet ether as mobile phase to get the desire compound as white solid (15 g, 88%). $^1$H NMR (400 MHz, CDCl$_3$): δ ppm 7.70-7.66 (d, J=16 Hz, 1H), 7.12-7.07 (m, 3H), 6.35-6.31 (d, J=16 Hz, 1H), 3.92 (s, 3H).

Step 3: Preparation of 7-fluoro-6-methoxyisoquinolin-1(2H)-one

To a hot (125° C.) diphenyl ether (20 ml) was added (E)-3-(4-fluoro-3-methoxyphenyl)acryloyl azide (4 g, 18.08 mmol) portion wise. The reaction was heated at 250° C. for 4 h. The reaction mass was cooled to room temperature and diluted with pet ether. The precipitated solid was filtered washed with pet ether to get crude compound (3.1 g, 89%). The crude compound was taken to the next step without further purification. MS: MS m/z 194.1 (M$^+$+1).

Step 4: Preparation of 4-bromo-7-fluoro-6-methoxyisoquinolin-1(2H)-one

To a solution of 7-fluoro-6-methoxyisoquinolin-1(2H)-one (1.5 g, 7.7 mmol) in acetonitrile (3 ml) was added NBS (1.382 g, 7.7 mmol) at room temperature under argon atmosphere. The reaction mass was stirred at the same temperature for 2 h. The reaction mass was cooled to room temperature and precipitated solid was filtered to get crude compound (1.25 g, 59.2%). The crude compound was taken to the next step without further purification. $^1$H NMR (400 MHz, DMSO-d6): δ ppm 11.59 (s, 1H), 7.93-7.91 (d, J=8 Hz, 1H), 7.56 (s, 1H), 7.29-7.27 (d, J=8 Hz, 1H), 4.03 (s, 3H); MS: MS m/z 272.03 (M$^+$+2).

Step 5: Preparation of 7-fluoro-6-methoxy-4-morpholinoisoquinolin-1(2H)-one

To a solution of 4-bromo-7-fluoro-6-methoxyisoquinolin-1(2H)-one (0.5 g, 1.838 mmol) and morpholine (0.4 g, 4.59 mmol) in ethylene glycol (2.5 ml) was added DIPEA (1.031 ml, 5.90 mmol). The reaction was irradiated in microwave at 145° C. for 1.5 h. The reaction was cooled to ambient temperature and diluted with water. The aqueous layer was extracted with EtOAc. The organic layer was washed with 1N HCl, followed by washing with brine. The organic layer was dried over anhydrous sodium sulfate, filtered and evaporated under reduced pressure to get the crude compound. The crude compound (0.25 g, 31.8%) was taken to the next step without further purification. MS: MS m/z 279.22 (M$^+$+1).

Step 6: Preparation of 4-(1-chloro-7-fluoro-6-methoxyisoquinolin-4-yl)morpholine A solution of 7-fluoro-6-methoxy-4-morpholinoisoquinolin-1(2H)-one (0.25 g, 0.898 mmol) in POCl$_3$ (5 ml) was refluxed for overnight. The solvent was evaporated under reduced pressure and the residue was diluted with cold water. The aqueous solution was basified by solid sodium carbonate and extracted with ethyl acetate. The organic layer was dried over anhydrous sodium sulfate, filtered and evaporated under reduced pressure to get crude compound. The crude compound was purified by silica gel chromatography (30% ethyl acetate in pet ether) to get desired compound (0.13 g, 46.8%) as solid. $^1$H NMR (400 MHz, DMSO-d6): δ ppm 7.98-7.95 (m, 2H), 7.56-7.54 (d, J=8 Hz, 1H), 7.45-7.40 (m, 2H), 4.08 (s, 3H), 3.89-3.86 (m, 4H), 3.11-3.09 (m, 4H); MS: MS m/z 297.07 (M$^+$+1).

Scheme: Preparation of
4-(1,7-difluoro-6-methoxyisoquinolin-4-yl)morpholine

Synthesis of 4-(1,7-difluoro-6-methoxyisoquinolin-4-yl)morpholine

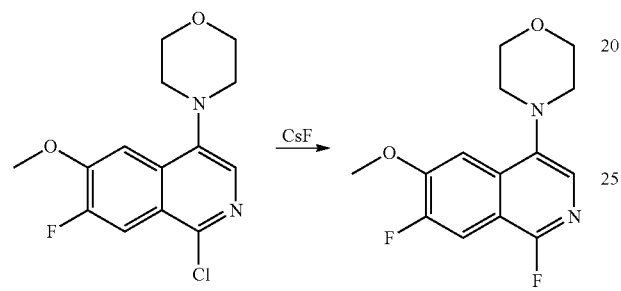

To a solution of 4-(1-chloro-7-fluoro-6-methoxyisoquinolin-4-yl)morpholine (0.12 g, 0.404 mmol) in DMSO (2 ml) was added cesium fluoride (0.245 g, 1.618 mmol) at room temperature. The reaction vessel (Pressure tube) was sealed and heated at 145° C. for 18 h. The reaction mass was diluted with water and extracted with ethyl acetate. The organic layer was dried over anhydrous Na$_2$SO$_4$ and evaporated under reduced pressure to get crude compound. The crude compound was purified by silica gel chromatography to get the desired compound (0.06 g, 51.9%) as a white solid. $^1$H NMR (400 MHz, DMSO-d6): δ ppm 7.94-7.91 (d, J=12 Hz, 1H), 7.73 (s, 1H), 7.56-7.53 (d, J=12 Hz, 1H), 4.07 (s, 3H), 3.88-3.86 (m, 4H), 3.08-3.06 (m, 4H); $^{19}$F NMR: δ ppm −130.03 (1F), −76.45 (1F); MS: MS m/z 281.10 (M$^+$+1).

Scheme: Preparation of
2-chloro-6-methoxy-3-methylquinoxaline and
3-chloro-6-methoxy-2-methylquinoxaline Preparation of
2-chloro-6-methoxy-3-methylquinoxaline and
3-chloro-6-methoxy-2-methylquinoxaline

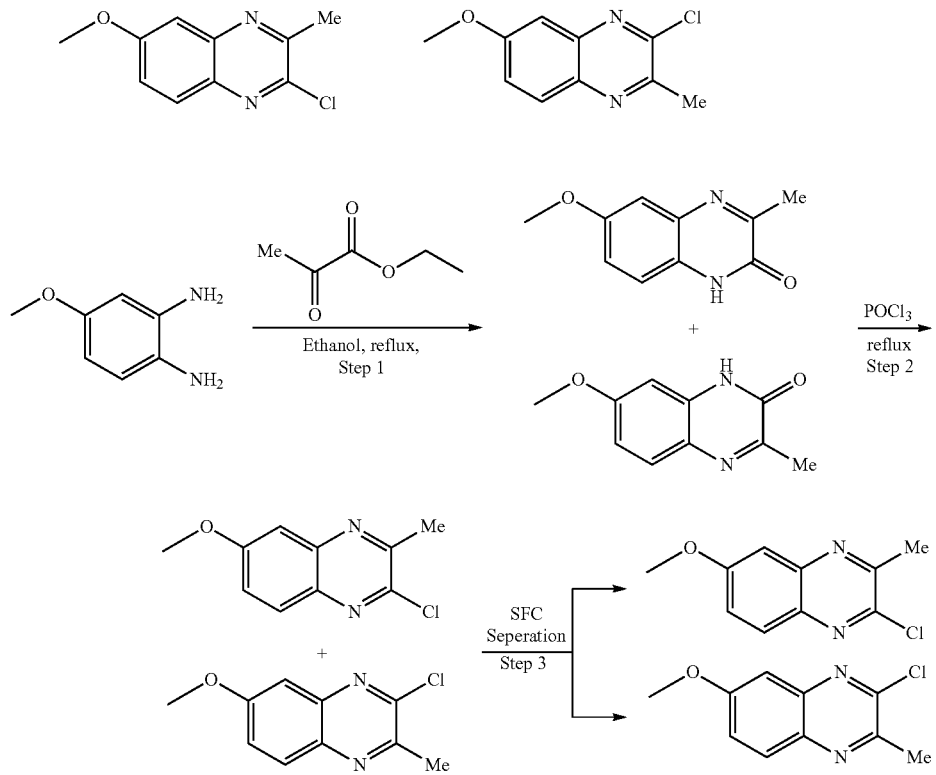

Step 1: Preparation of 6-methoxy-3-methylquinoxalin-2(1H)-one and 7-methoxy-3-methylquinoxalin-2(1H)-one To a solution of 4-methoxybenzene-1,2-diamine (1 g, 7.24 mmol) in ethanol (10 ml) was added ethyl 2-oxopropanoate (0.84 g, 7.24 mmol)). The reaction mass was heated at reflux for overnight. The solvent was evaporated under reduced pressure and the residue was diluted with ethyl acetate and then evaporated to dryness to get the crude compound. The crude compound was washed with pet ether to get the product (1.20 g, 6.31 mmol, 87% yield) as a mixture of regioisomers (black solid). This crude compound was taken to the next step without separation of isomers. $^1$H NMR (400 MHz, DMSO-d6): δ ppm 12.20 (br, s, 2H), 7.61-7.59 (d, J=8 Hz, 1H), 7.22-7.20 (d, J=8 Hz, 2H), 7.19 (s, 1H), 7.14-7.12 (d, J=8 Hz, 1H), 6.88-6.86 (d, J=8 Hz, 1H), 6.74-6.72 (d, J=8 Hz, 1H), 3.81 (s, 6H), 2.50 (m, 3H), 2.37 (m, 3H); MS: MS m/z 191.10 (M$^+$+1).

Step 2: Preparation of 2-chloro-6-methoxy-3-methylquinoxaline and 3-chloro-6-methoxy-2-methylquinoxaline A solution of 6-methoxy-3-methylquinoxalin-2(1H)-one & 7-methoxy-3-methylquinoxalin-2(1H)-one (1.2 g, 6.31 mmol) in POCl$_3$ (10 ml) was refluxed for 3 h. The solvent was evaporated under reduced pressure and the residue was diluted with cold water. The aqueous solution was basified by solid sodium carbonate and extracted with ethyl acetate. The organic layer was dried over anhydrous sodium sulfate, filtered and evaporated under reduced pressure to get crude compound. The crude compound was purified by silica gel chromatography (20% ethyl acetate in pet ether) to get regioisomers as a mixture. The mixture of regioisomers were separated by SFC purification to afford 2-chloro-6-methoxy-3-methylquinoxaline (0.51 g, 38.7%) and 3-chloro-6-methoxy-2-methylquinoxaline (required isomer) (0.48 g, 36.5%) as off white solids.

2-chloro-6-methoxy-3-methylquinoxaline: $^1$H NMR (400 MHz, DMSO-d6): δ ppm 7.92-7.90 (d, J=8 Hz, 1H), 7.49-7.44 (m, 2H), 3.95 (s, 3H), 3.31 (s, 3H); MS: MS m/z 209.14 (M$^+$+1).

3-chloro-6-methoxy-2-methylquinoxaline: $^1$H NMR (400 MHz, DMSO-d6): δ ppm 7.97-7.95 (d, J=8 Hz, 1H), 7.51-49 (d, J=8 Hz, 1H), 7.40 (s, 1H), 3.94 (s, 3H), 2.72 (s, 3H); MS: MS m/z 209.14 (M$^+$+1).

Scheme: Preparation of 2-chloro-6-methoxy-3-(trifluoromethyl)quinoxaline and 3-chloro-6-methoxy-2-(trifluoromethyl)quinoxaline Synthesis of 2-chloro-6-methoxy-3-(trifluoromethyl)quinoxaline & 3-chloro-6-methoxy-2-(trifluoromethyl)quinoxaline

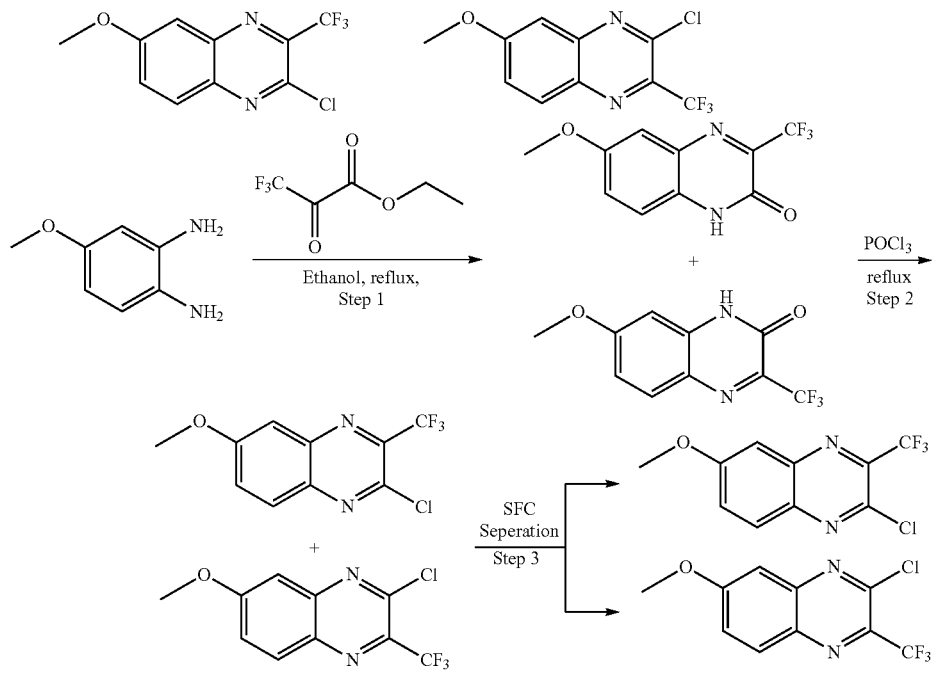

Step 1: Preparation of 6-methoxy-3-(trifluoromethyl)quinoxalin-2(1H)-one and 7-methoxy-3-(trifluoromethyl)quinoxalin-2(1H)-one To a solution of 4-methoxybenzene-1,2-diamine (1 g, 7.24 mmol) in ethanol (10 ml) was added ethyl 3,3,3-trifluoro-2-oxopropanoate (1.23 g, 7.24 mmol)). The reaction mass was heated at reflux for overnight. The solvent was evaporated under reduced pressure and the residue was diluted with ethyl acetate and then evaporated to dryness to get the crude compound. The crude compound was washed with pet ether to get the product (1.55 g, 88% yield) as a mixture of regioisomers (black solid). This crude compound was taken to the next step without separation of isomers. $^1$H NMR (400 MHz, DMSO-d6): δ ppm 12.92 (br, s, 2H), 7.84-7.81 (d, J=12 Hz, 1H), 7.44-7.33 (m, 4H), 7.82 (s, 1H), 3.87 (s, 6H), MS: MS m/z 245.15 (M$^+$+1).

Step 2: Preparation of 2-chloro-6-methoxy-3-(trifluoromethyl)quinoxaline and 3-chloro-6-methoxy-2-(trifluoromethyl)quinoxaline A solution of 6-methoxy-3-(trifluoromethyl)quinoxalin-2 (1H)-one & 7-methoxy-3-(trifluoromethyl)quinoxalin-2 (1H)-one (0.90 g, 3.69 mmol) in POCl$_3$ (10 ml) was refluxed for 3 h. The solvent was evaporated under reduced pressure and the residue was diluted with cold water. The aqueous solution was basified by solid sodium carbonate and extracted with ethyl acetate. The combine organic layer was dried over anhydrous sodium sulfate, filtered and evaporated under reduced pressure to get crude compound. The crude compound was purified by silica gel chromatography (20% ethyl acetate in pet ether) to get regioisomers as mixture. The mixture of regioisomers were separated by SFC purification to afford 2-chloro-6-methoxy-3-methylquinoxaline (0.51 g, 38.7%) and 3-chloro-6-methoxy-2-methylquinoxaline (required isomer) (0.48 g, 36.5%) as off white solids. The mixture of regioisomers were separated by SFC purification to afford 2-chloro-6-methoxy-3-methylquinoxaline (required isomer) (0.31 g, 32%) and 3-chloro-6-methoxy-2-methylquinoxaline (0.15 g, 15.5%) as off white solids. 2-chloro-6-methoxy-3-(trifluoromethyl)quinoxaline: $^1$H NMR (400 MHz, DMSO-d6): δ ppm 8.10-8.07 (d, J=12 Hz, 1H), 7.75-7.44 (m, 2H), 3.95 (s, 3H); $^{19}$F NMR: δ ppm −65.36 (1F) MS: MS m/z 263.10 (M$^+$+1).

3-chloro-6-methoxy-2-(trifluoromethyl)quinoxaline: $^1$H NMR (400 MHz, DMSO-d6): δ ppm 8.11-8.08 (d, J=12 Hz, 1H), 7.78-7.75 (d, J=12 Hz, 1H), 7.68 (s, 1H), 4.00 (s, 3H); $^{19}$F NMR: δ ppm −65.36 (1F) MS: MS m/z 263.09 (M$^+$+1).

Scheme: Preparation of 1,5-dichloro-4-methoxyisoquinoline

Synthesis of 1,5-Dichloro-4-methoxyisoquinoline

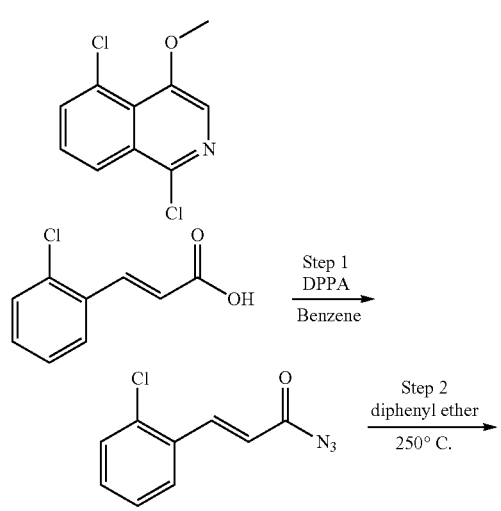

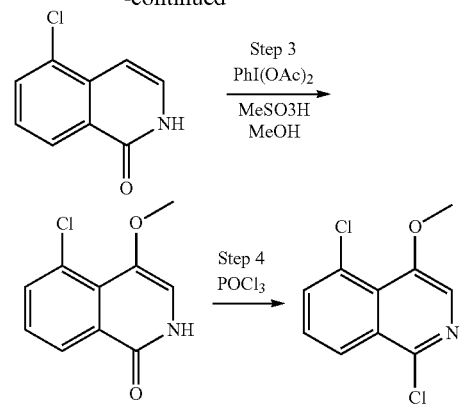

Step 1: Preparation of (E)-3-(2-chlorophenyl) acryloyl azide

To a solution of (E)-3-(2-chlorophenyl) acrylic acid (13 g, 71.2 mmol) in benzene (100 ml) was added triethylamine (14.4 g, 141 mmol) followed by DPPA (19.5 g, 71.2 mmol) at room temperature. The reaction mass was stirred at the same temperature for 18 h. The solvent was evaporated under reduced pressure and the residue was diluted with water and extracted with dichloromethane. The organic layer was dried over anhydrous sodium sulfate, filtered and evaporated to get crude compound. The crude compound was purified by conventional column chromatography (Silica gel, 60-120 mesh) using 10% ethyl acetate in pet ether as mobile phase to get the desire compound as pale yellow solid (14 g, 95%). $^1$H NMR (400 MHz, CDCl$_3$): δ ppm 8.19-8.15 (d, J=16 Hz, 1H), 7.63-7.61 (d, J=8 Hz, 1H), 7.44-7.42 (m, 1H), 7.36-7.26 (m, 2H), 6.44-6.40 (d, J=16 Hz, 1H).

Step 2: Preparation of 5-choroisoquinolin-1(2H)-one

To a hot (125° C.) diphenyl ether (10 ml) was added (E)-3-(2-chlorophenyl) acryloyl azide (2 g, 9.63 mmol) portion wise. The reaction was heated at 250° C. for 2 h. The reaction mass was cooled to room temperature and diluted with pet ether. The precipitated solid was filtered washed with pet ether to get crude compound (1.1 g, 63.6%) as yellow solid. The crude compound was taken to the next step without further purification. $^1$H NMR (400 MHz, CD$_3$OD): δ ppm 8.29-8.27 (d, J=8 Hz, 1H), 7.84-7.82 (d, J=8 Hz, 1H), 7.49 (t, J=8 Hz, 1H), 7.32-7.30 (d, J=8 Hz, 1H), 6.98-6.96 (d, J=8 Hz, 1H); MS: MS m/z 180.7 (M$^+$+1).

Step 3: Preparation of 5-chloro-4-methoxyisoquinolin-1-(2H)-one

To a solution of 5-choroisoquinolin-1(2H)-one (3.8 g, 21.2 mmol) in methanol (70 ml) was added iodosobenzene-diacetate (7.5 g, 23.4 mmol) followed by methane sulphonic acid (2.45 g, 25.5 mmol) at room temperature. The reaction mass was heated at reflux for 3 h. The solvent was evaporated and the residue was diluted with cold water. The precipitated solid was filtered, washed with water to get crude compound (3.9 g, 88%) as a light red colored solid. $^1$H NMR (400 MHz, CDCl$_3$): δ ppm 8.06-8.03 (d, J=12 Hz, 1H), 7.60-7.57 (d, J=12 Hz, 1H), 7.42 (d, J=8 Hz, 1H), 7.01-6.99 (br s, 1H), 3.51 (s, 3H); MS: MS m/z 209.1 (M⁺+1).

Step 4: Preparation of 1,5-dichloro-4-methoxyisoquinoline

A solution of 5-chloro-4-methoxyisoquinolin-1-(2H)-one (6.4 g, 30.5 mmol) in POCl₃ (45 ml) was refluxed for 18 h. The solvent was evaporated under reduced pressure and the residue was diluted with cold water. The precipitated solid was filtered, washed with water to get crude compound (4 g, 57.4%) as a light brown colored solid. ¹H NMR (400 MHz, CDCl₃): δ ppm 8.28-8.25 (d, J=12 Hz, 1H), 7.87 (s, 1H), 7.79-7.76 (d, J=12 Hz, 1H), 7.58-7.54 (m, 1H), 4.03 (s, 3H); MS: MS m/z 228.0 (M⁺+1).

Scheme: Preparation of 1,5-dichloro-4-ethoxyisoquinoline

Synthesis of 1,5-Dichloro-4-ethoxyisoquinoline

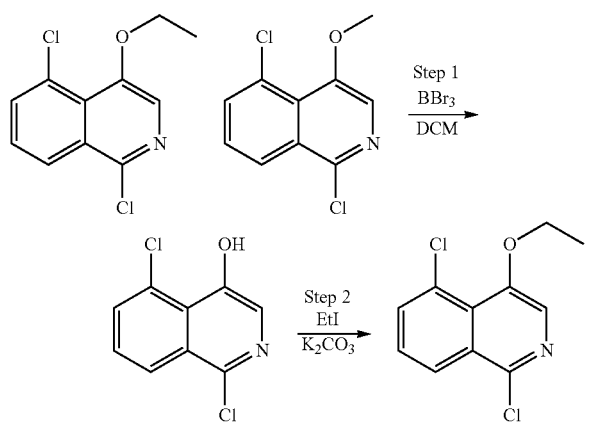

Step 1: Preparation of 1,5-dichloro-4-hydroxyisoquinoline

A solution of 1,5-dichloro-4-methoxyisoquinoline (1.2 g, 5.26 mmol) in DCM (15 ml) was added BBr₃ (9.23 g, 34.8 mmol) at 0° C. drop wise. The reaction mass was refluxed for 5 h. The residue was cooled and quenched with methanol. The solvent was evaporated under reduced pressure and the residue was diluted with cold water. The precipitated solid was filtered, washed with water to get crude compound (0.7 g, 62.2%) as light brown color solid. ¹H NMR (400 MHz, CD₃OD): δ ppm 8.28-8.25 (d, J=12 Hz, 1H), 7.85-7.82 (m, 2H), 7.68-7.64 (m, 1H); MS: MS m/z 214.0 (M⁺+1).

Step 2: Preparation of 1,5-dichloro-4-ethoxyisoquinoline

To a solution of 1,5-dichloroisoquinolin-4-ol (0.5 g, 2.33 mmol) in acetonitrile (15 ml) was added K₂CO₃ (0.96 g, 7.01 mmol) followed by ethyl iodide (0.72 g, 4.67 mmol) at room temperature. The reaction mixture was stirred at room temperature for overnight. The solvent was evaporated under reduced pressure and the residue was diluted with water and extracted with ethyl acetate. The combined organic layer was dried over anhydrous Na₂SO₄ and evaporated under reduced pressure to get crude compound. The crude compound was purified by silica gel chromatography to get 1,5-dichloro-4-ethoxyisoquinoline (0.3 g, 53%) as pale yellow solid. ¹H NMR (400 MHz, CDCl₃): δ ppm 8.26-8.24 (d, J=8 Hz, 1H), 7.86 (s, 1H), 7.78-7.76 (d, J=8 Hz, 1H), 7.55 (t, J=8 Hz, 1H), 4.26-4.21 (m, 2H), 1.57 (t, J=7 Hz, 3H); MS: MS m/z 242.6 (M⁺+1).

Scheme: Preparation of 1,5-dichloro-4-isopropoxyisoquinoline

Synthesis of 1,5-Dichloro-4-isopropoxyisoquinoline

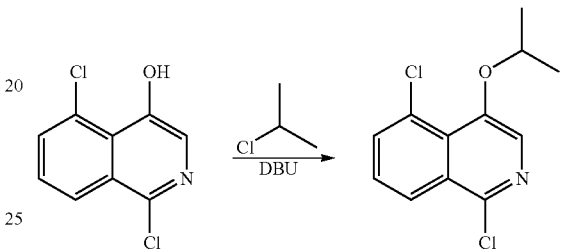

To a solution of 1,5-dichloroisoquinoline-4-ol (0.5 g, 2.33 mmol) in DBU (1.06 g, 7.01 mmol) was added isopropyl chloride (0.27 g, 3.5 mmol) at room temperature. The reaction vessel (Pressure tube) was sealed and heated at 120° C. for 6 h. The reaction mass was quenched with 1.5 N HCl solution and extracted with ethyl acetate. The combined organic layer was dried over anhydrous Na₂SO₄ and evaporated under reduced pressure to get crude compound. The crude compound was purified by silica gel chromatography to get desired compound (0.3 g, 50.1%) as pale yellow solid. ¹H NMR (400 MHz, DMSO): δ ppm 8.26-8.23 (d, J=12 Hz, 1H), 8.11 (s, 1H), 7.96-7.94 (d, J=8 Hz, 1H), 7.76 (t, J=8 Hz, 1H), 4.93-4.90 (m, 1H), 1.42-1.40 (d, J=8 Hz, 6H); MS: MS m/z 256.7 (M⁺+1).

Scheme: Preparation of 1,5-dichloro-4-cyclopropoxyisoquinoline

Synthesis of 1,5-Dichloro-4-cyclopropoxyisoquinoline

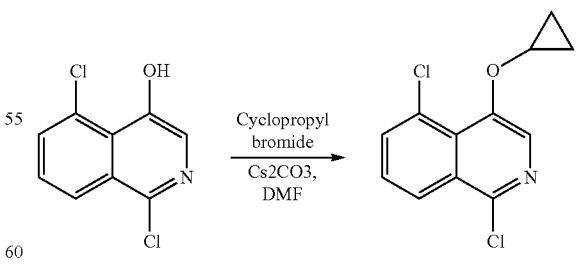

To a solution of 1,5-dichloroisoquinolin-4-ol (0.5 g, 2.33 mmol) in DBU (1.7 ml, 11.68 mmol) was added cyclopropylbromide (0.93 ml, 11.68 mmol) at room temperature. The reaction vessel (Pressure tube) was sealed and heated at 120° C. for 18 h. The reaction mass was diluted with water and extracted with ethyl acetate. The combined organic layer was dried over anhydrous Na$_2$SO$_4$ and evaporated under reduced pressure to get crude compound. The crude compound was purified by silica gel chromatography to get desired compound (0.01 g, 2.1%) as yellow solid. $^1$H NMR (400 MHz, CDCl$_3$): δ ppm 8.27-8.24 (m, 2H), 7.76-7.74 (d, J=8 Hz, 1H), 7.54 (t, J=8 Hz, 1H), 3.96-3.94 (m, 1H), 0.95-0.90 (m, 4H).

Scheme: Synthesis of 3-Fluoro-6-methoxyisoquinoline

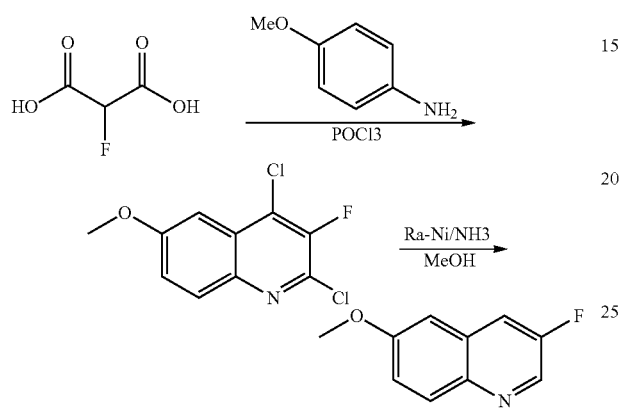

Step: 1 Synthesis of 2,4-dichloro-3-fluoro-6-methoxyquinoline 2-fluoromalonic acid (0.67 g, 5.49 mmol) was combined with POCl$_3$ (4.5 ml, 48.3 mmol) and heated to 80° C. to dissolve all of the solids. Once the solids were dissolved, the reaction was cooled to 60° C.; 4-methoxyaniline (0.676 g, 5.49 mmol) was added portion wise carefully. Once the addition was complete, the reaction mixture was slowly heated and refluxed at 100-105° C. for 2 h. The volatiles were removed under vacuum and the resulting residue was cooled to 0-10° C.; ice was carefully added into the reaction mixture, stirred vigorously to get the solid. NH$_4$OH is slowly added until the pH 9.5, stirred the resulting yellow suspension for another 10 min. Filtered the solids, washed with water dried the yellow solids to afford 2,4-dichloro-3-fluoro-6-methoxyquinoline (0.95 g, 3.86 mmol, 70.3% yield). $^1$H NMR (400 MHz, CDCl$_3$): δ ppm 7.93 (d, J=9.1 Hz, 1H), 7.40-7.34 (dd, J=9.0 Hz, J=2.9 Hz, 1H), 7.26-7.25 (d, J=2.9 Hz 1H), 3.98 (s, 3H), MS: MS m/z 247.0 (M$^+$+1).

Step 2: Synthesis of 3-Fluoro-6-methoxy quinoline

To a suspension of 2,4-dichloro-3-fluoro-6-methoxyquinoline (0.9 g, 3.66 mmol) in ammonia in methanol (10 mL, 462 mmol) was added carefully the slurry of Raney Nickel (5 g, 3.66 mmol) in Methanol (10 mL). The resulting reaction mixture was hydrogenated at 150 psi pressure, stirred at room temperature for 24 h. Filtered the catalyst, washed with methanol, evaporated the filtrate under reduced pressure to afford crude mass, purified by silica gel chromatography eluting with 10%-50% ethyl acetate in pet-ether to afford 3-Fluoro-6-methoxy quinoline (0.27 g, 41%) as pink solid. $^1$H NMR (400 MHz, CDCl$_3$): δ ppm 8.65 (d, J=2.9 Hz, 1H), 8.01-7.98 (d, J=9 Hz, 1H) 7.67-7.64 (dd, J=9 Hz, J=2.9 Hz 1H), 7.33-7.30 (dd, J=9.0 Hz, J=2.9 Hz, 1H), 7.03 (d, J=2.9 Hz 1H), 3.93 (s, 3H).

Synthesis of 4-chloro-2-(3-fluoro-4-isopropoxyphenyl)-7-methoxyquinoline

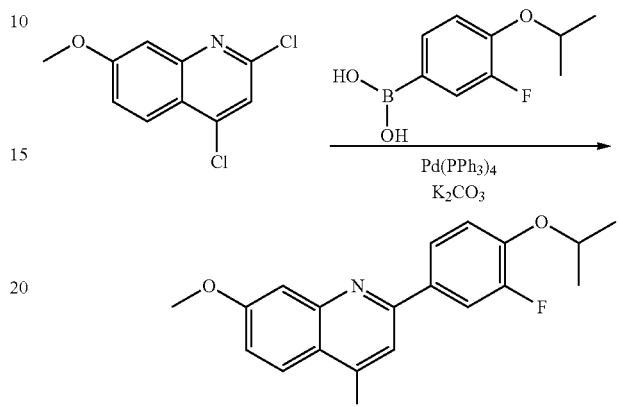

Step 1: Preparation of 4-chloro-2-(3-fluoro-4-isopropoxyphenyl)-7-methoxyisoquinoline To a solution of 2,4-dichloro-7-methoxyisoquinolin (0.25 g, 1.1 mmol), 3-Fluoro-4-isopropoxyphenylboronic acid (0.21 g, 1.1 mmol) in 1,4-Dioxane (5 ml) and water (1 ml) was added K$_2$CO$_3$ (0.3 g, 2.2 mmol). The reaction mass was degasified for 20 min. Pd (Ph$_3$P)$_4$ (0.06 g, 0.05 mmol) was added to the above reaction mass and degasified again for 5 min at room temperature. The reaction vessel (Pressure tube) was sealed and heated at 90° C. for 18 h. The reaction mass was evaporated under reduced pressure. The residue was diluted with water and extracted with ethyl acetate. The organic layer was dried over anhydrous Na$_2$SO$_4$ and evaporated under reduced pressure to get crude compound. The crude compound was purified by silica gel chromatography to get desired compound (0.2 g, 54%) as white solid. $^1$H NMR (400 MHz, CHLOROFORM-d): δ ppm 8.08 (d, J=9.26 Hz, 1H) 7.93 (dd, J=12.51, 2.25 Hz, 1H) 7.80 (dt, J=8.50, 1.00 Hz, 1H) 7.74 (s, 1H) 7.45 (d, J=2.50 Hz, 1H) 7.09 (t, J=8.50 Hz, 1H), 3.99 (s, 3H), 3.95 (m, 1H), 1.41 (d, J=6.25 Hz, 6H).

Scheme: Synthesis of 1-chloro-6-methoxy-4-(1H-pyrazol-1-yl)isoquinoline

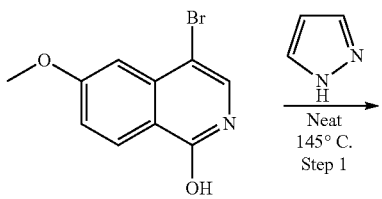

602

Synthesis of 1-chloro-6-methoxy-4-(4-(methylsulfonyl) piperazin-1-yl) isoquinoline

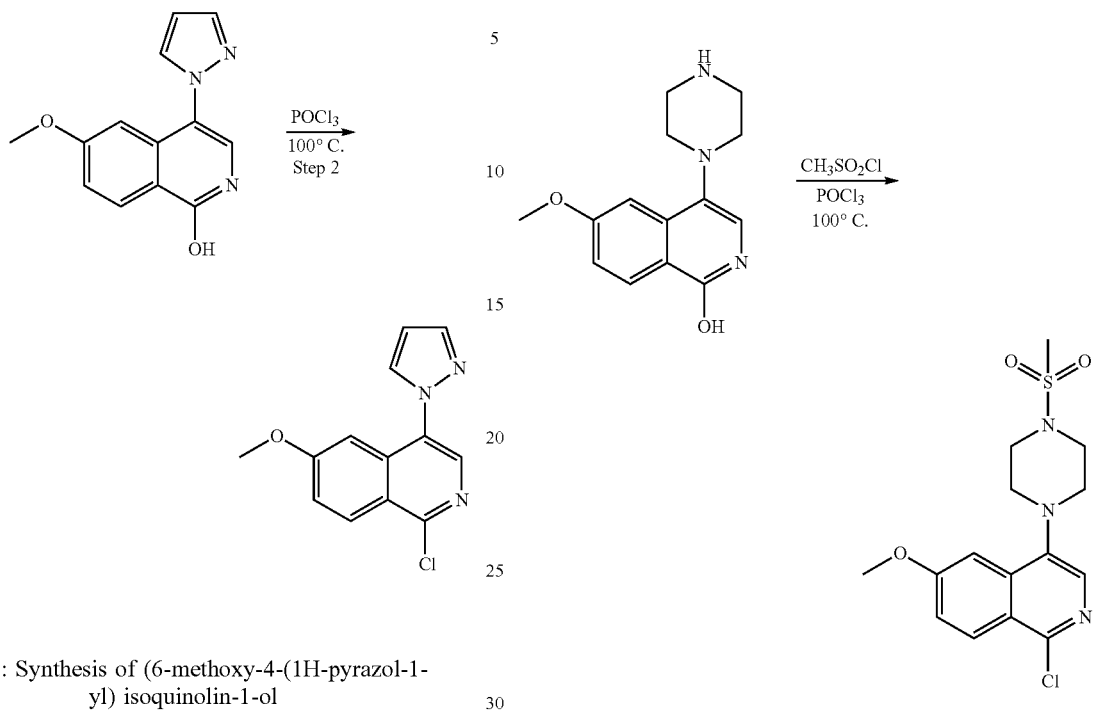

6-methoxy-4-(piperazin-1-yl)isoquinolin-1-ol (0.15 g, 0.578 mmol) was taken in methane sulfonyl chloride (0.090 mL, 1.157 mmol) and added phosphorous oxychloride (5 mL) and stirred for 1 h at 110° C. The volatiles were evaporated and the crude was poured into ice. This solution PH was adjusted to 9.0 and extracted with ethyl acetate and washed with brine solution. The organic layer was dried over anhydrous sodium sulfate, filtered and concentrated. The crude sample was purified by silica gel chromatography using 45% ethyl acetate in pet ether to get 1-chloro-6-methoxy-4-(4-(methylsulfonyl)piperazin-1-yl)isoquinoline (0.041 g, 0.114 mmol, 19.72% yield) as solid. $^1$H NMR (300 MHz, DMSO-$d_6$): ppm 8.18 (d, J=9.16 Hz, 1H) 7.98 (s, 1H) 7.42-7.50 (m, 1H) 7.38 (s, 1H), 3.99 (s, 3H), 3.41 (br. s., 4H) 3.19 (br. s., 4H) 3.00 (s, 3H). MS: MS m/z 346.20 (M$^+$+1).

Synthesis of 1-chloro-6-methoxy-N,N-dimethylisoquinolin-4-amine

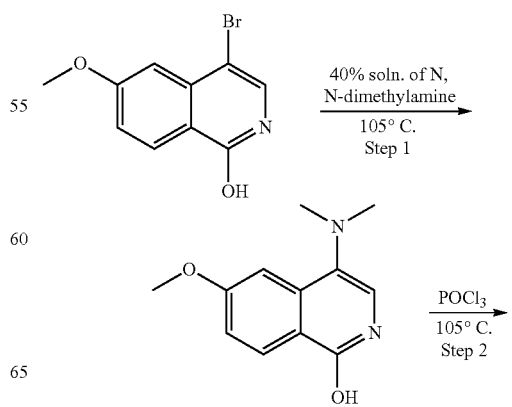

601

-continued

<br/>

Step 1: Synthesis of (6-methoxy-4-(1H-pyrazol-1-yl) isoquinolin-1-ol 1H-pyrazole (0.201 g, 2.95 mmol) was taken in sealed tube vessel and heated to 80° C. To the melted compound 4-bromo-6-methoxyisoquinolin-1-ol (0.25 g, 0.984 mmol) was added and heating was raised to 150° C. and stirred for overnight. The reaction mixture was cooled to RT. The resulting solid (6-methoxy-4-(1H-pyrazol-1-yl) isoquinolin-1-ol (0.25 g, 0.114 mmol) 11.59% yield) was taken to the next step without further purification. MS: MS m/z 242.10 (M$^+$+1).

Step 2: Synthesis of 1-chloro-6-methoxy-4-(1H-pyrazol-1-yl) isoquinoline 6-methoxy-4-(1H-pyrazol-1-yl) isoquinolin-1(2H)-one (0.25 g, 1.036 mmol) was taken in phosphorous oxychloride (5 mL) and stirred for 1 h at 100° C. The volatiles were evaporated and the crude was poured into ice. The pH was adjusted to 9.0, extracted with ethyl acetate and washed with brine solution. The organic layer was dried over anhydrous sodium sulfate, filtered, concentrated under reduced pressure. The crude product was purified by silica gel chromatography using 10% Ethyl acetate in Pet-ether to get 1-chloro-6-methoxy-4-(1H-pyrazol-1-yl) isoquinoline (0.019 g, 0.062 mmol, 6.00% yield) as solid. $^1$H NMR (400 MHz, DMSO-$d_6$) δ ppm 8.77-8.84 (m, 2H) 8.74-8.84 (m, 1H) 8.52-8.58 (m, 2H) 8.52-8.57 (m, 1H) 8.28-8.34 (m, 1H) 8.27-8.34 (m, 2H) 7.90-7.96 (m, 1H) 7.77-7.83 (m, 1H) 7.46-7.52 (m, 1H) 7.32-7.38 (m, 1H) 6.58-6.66 (m, 1H) 3.96 (s, 3H). MS: MS m/z 260.10 (M$^+$+1).

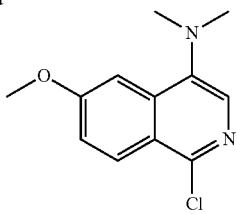

Step 1: Synthesis of 4-(Dimethylamine)-6-methoxyisoquinolin-1-ol

A solution of 4-bromo-6-methoxyisoquinolin-1(2H)-one (1 g, 3.94 mmol) in dimethylamine (5 ml, 39.5 mmol) was heated to 105° C. for 48 h. After cooling, the reaction mixture was concentrated under reduced pressure to get 4-(Dimethylamino)-6-methoxyisoquinolin-1(2H)-one (0.8 g, 4.58 mmol, 85% yield). MS: MS m/z 219.20 (M$^+$+1).

Step 2: Synthesis of 1-chloro-6-methoxy-N,N-dimethylisoquinolin-4-amine

To 4-(Dimethylamino)-6-methoxyisoquinolin-1(2H)-one (0.5 g, 2.291 mmol) was added POCl$_3$ (3 ml, 32.2 mmol) at room temperature. Then the reaction mixture was heated to 100° C. for 1 h.

The reaction mixture was concentrated under reduced pressure; the resultant residue was suspended in 10% sodium bicarbonate solution and extracted with ethyl acetate. The organic layer was washed with brine solution, dried over anhydrous sodium sulfate, filtered, concentrated to afford the crude product. The crude was purified by silica gel chromatography eluting with 20% ethyl acetate in pet-ether to afford 1-chloro-6-methoxy-N,N-dimethylisoquinolin-4-amine (0.32 g, 1.352 mmol, 59.0% yield). $^1$H NMR (400 MHz, CHLOROFORM-d): ppm 8.20 (d, J=9.29 Hz, 1H) 7.88 (s, 1H) 7.42 (d, J=2.51 Hz, 1H) 7.28 (d, J=2.51 Hz, 1H) 3.99 (s, 3H) 2.90 (s, 6H) MS: MS m/z 237.20 (M$^+$+1).

Synthesis of 1,5-Dichloro-4-(difluoromethoxy)isoquinoline

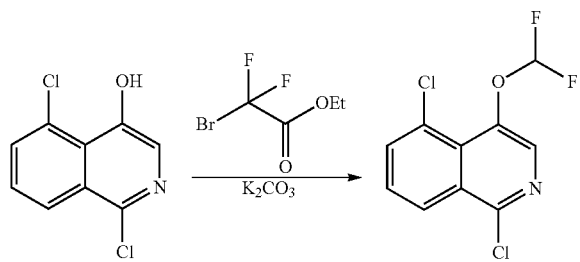

To a stirred solution of 1,5-dichloroisoquinolin-4-ol (0.3 g, 1.402 mmol) in DMF (10 mL) was added potassium carbonate (0.291 g, 2.102 mmol) followed by ethyl bromodifluoro acetate (0.216 mL, 1.682 mmol) under nitrogen at rt and was stirred for 30 min at the same temperature. Then temperature was raised to 120° C. and refluxed for 2 h. The reaction mixture was cooled to RT and poured into water, extracted with ethyl acetate. The combined organic layer was dried over anhydrous sodium sulfate, filtered and concentrated under reduced pressure to afford crude product, purified by silica gel chromatography using 5% ethyl acetate in pet-ether to get pure 1,5-dichloro-4-(difluoromethoxy)isoquinoline (0.05 g, 0.182 mmol, 12.97% yield) as pale yellow solid. $^1$H NMR (300 MHz, DMSO-d$_6$): ppm 8.40-8.38 (d, J=8.0, 1H), 8.37 (s, 1H), 8.14-8.12 (d, J=8.0, 1H), 7.90-7.88 (t, J=8.0, 1H), 7.55-7.18 (t, 1H) MS: MS m/z 265.20 (M$^+$+1).

Synthesis of 1,7-Difluoro-4,6-dimethoxyisoquinoline

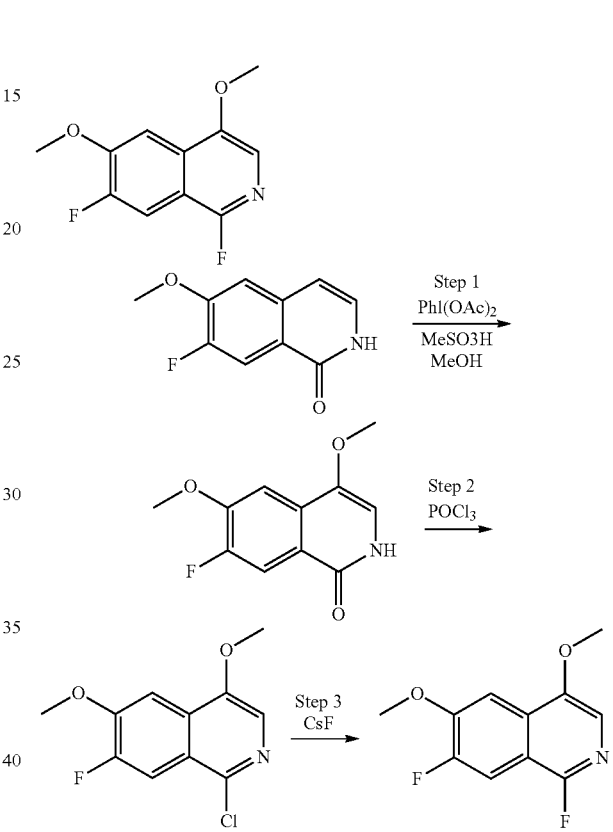

Step 1: Preparation of 7-fluoro-4,6-dimethoxyisoquinolin-1(2H)-one

To a solution of 7-fluoro-6-methoxyisoquinolin-1(2H)-one (6.3 g, 32.6 mmol) in methanol (70 ml) was added iodozobenzenediacetate (10.5 g, 32.6 mmol) followed by methane sulphonic acid (3.76 g, 39.1 mmol) at room temperature. The reaction mass was heated at reflux for 3 h. The solvent was evaporated and the residue was diluted with cold water. The precipitated solid was filtered, washed with water to get crude compound (6.6 g, 91%) as a light red colored solid. MS: MS m/z 224.0 (M$^+$+1).

Step 2: Preparation of 1-chloro-7-fluoro-4,6-dimethoxyisoquinoline

A solution of 7-fluoro-4,6-dimethoxyisoquinolin-1(2H)-one (7.6 g, 34.1 mmol) in POCl$_3$ (50 ml) was refluxed for 18 h. The solvent was evaporated under reduced pressure and the residue was diluted with cold water. The aqueous solution was basified by solid sodium carbonate and extracted with ethyl acetate. The organic layer was dried over anhydrous sodium sulfate, filtered and evaporated under reduced pressure to get crude compound. The crude compound was purified by silica gel chromatography (20% ethyl acetate in pet ether) to get desired compound (2 g, 24.3%) as pale yellow solid. $^1$H NMR (400 MHz, CDCl$_3$): δ ppm 7.88-7.85 (d, J=12 Hz, 1H), 7.75 (s, 1H), 7.54-7.52 (d, J=8 Hz, 1H), 4.05 (s, 3H); MS: MS m/z 242.0 (M$^+$+1).

Step 3: Preparation of 1,7-difluoro-4,6-dimethoxyisoquinoline

To a solution of 1-chloro-7-fluoro-4,6-dimethoxyisoquinoline (2 g, 8.28 mmol) in DMSO (5 ml) was added cesium fluoride (2.51 g, 16.55 mmol) at room temperature. The reaction vessel (Pressure tube) was sealed and heated at 145° C. for 18 h. The reaction mass was diluted with water and extracted with ethyl acetate. The combined organic layer was dried over anhydrous Na$_2$SO$_4$ and evaporated under reduced pressure to get crude compound. The crude compound was purified by silica gel chromatography to get desired compound (475 mg, 25.5%) as white solid. $^1$H NMR (400 MHz, CDCl$_3$): δ ppm 7.69-7.67 (d, J=8 Hz, 1H), 7.53-7.51 (d, J=8 Hz, 1H), 7.45-7.44 (m, 1H), 4.05 (s, 3H), 4.03 (s, 3H); $^{19}$F NMR: δ ppm −129.58 (1 F), −79.2 (1F); MS: MS m/z 226.0 (M$^+$+1).

Scheme: Preparation of 1-fluoro-4,6-dimethoxyisoquinoline

Synthesis of 1-Fluoro-4,6-dimethoxyisoquinoline

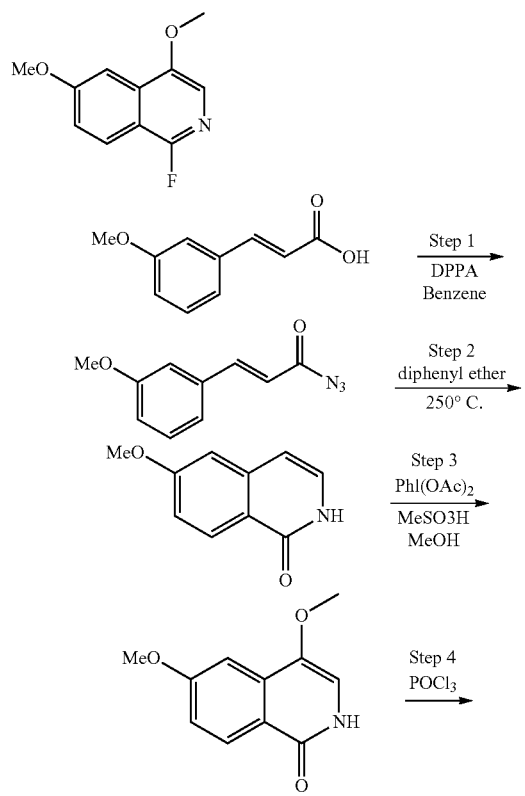

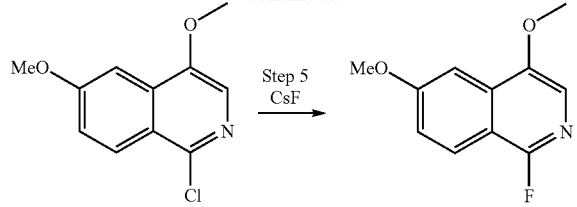

Step 1: Preparation of (E)-3-(3-methoxyphenyl) acrylic azide

To a solution of (E)-3-(3-methoxyphenyl) acrylic acid (20 g, 112 mmol) in benzene (200 ml) was added triethylamine (22.72 g, 224 mmol) followed by DPPA (30.9 g, 112 mmol) at room temperature. The reaction mass was stirred at the same temperature for 18 h. The solvent was evaporated under reduced pressure and the residue was diluted with water and extracted with dichloromethane. Combined organic layer was dried over anhydrous sodium sulfate, filtered and evaporated to get crude compound. The crude compound was purified by conventional column chromatography (Silica gel, 60-120 mesh) using 10% ethyl acetate in pet ether as mobile phase to get the desire compound as white solid (18 g, 79%). $^1$H NMR (400 MHz, CDCl$_3$): δ ppm 7.73-7.69 (d, J=16 Hz, 1H), 7.33-7.29 (t, J=8 Hz, 1H), 7.26 (s, 1H), 7.14-7.12 (d, J=8 Hz, 1H), 7.05 (s, 1H) 6.98-6.96 (d, J=4 Hz, 1H), 6.43-6.39 (d, J=16 Hz, 1H), 3.86 (s, 3H);

Step 2: Preparation of-6-methoxyisoquinolin-1(2H)-one

To a solution of (E)-3-(3-methoxyphenyl) acryloyl azide (7 g, 34.4 mmol) in 1,2-dichlorobenzene (70 ml) was added mercuric acetate (0.11 g, 0.34 mmol). The reaction was heated at 150° C. for 10 min and the temperature was raised to 180° C. for 1 h. The reaction mass was cooled to room temperature and diluted with pet ether. The precipitated solid was filtered washed with pet ether to get crude compound (3.5 g, 58%) as yellow solid. The crude compound was taken to the next step without further purification. $^1$H NMR (400 MHz, DMSO): δ ppm 8.09-8.06 (d, J=12 Hz, 1H), 7.14-7.11 (m, 2H), 7.05-7.03 (d, J=8 Hz, 1H), 6.48-6.46 (d, J=4 Hz, 1H), 3.86 (s, 3H); MS: MS m/z 176.0 (M$^+$+1).

Step 3: Preparation of 4,6-dimethoxyisoquinolin-1(2H)-one

To a solution of 7-fluoro-6-methoxyisoquinolin-1(2H)-one (7 g, 40.0 mmol) in methanol (70 ml) was added iodozobenzenediacetate (14.16 g, 40.0 mmol) followed by methane sulphonic acid (11.52 g, 120 mmol) at room temperature. The reaction mass was heated at reflux for 3 h. The solvent was evaporated and the residue was diluted with cold water. The precipitated solid was filtered, washed with water to get crude compound (4 g, 48.8%) as a light red colored solid. $^1$H NMR (400 MHz, DMSO): δ ppm 8.11-8.09 (d, J=8 Hz, 1H), 7.19 (s, 1H), 7.13-7.11 (d, J=8 Hz, 1H), 6.72-6.71 (d, J=12 Hz, 1H), 3.89 (s, 3H), 3.79 (s, 3H); MS: MS m/z 206.1 (M$^+$+1).

Step 4: Preparation of 1-chloro-4,6-dimethoxyisoquinoline

A solution of 4,6-dimethoxyisoquinolin-1(2H)-one (4 g, 19.49 mmol) in POCl$_3$ (40 mL) was refluxed for 18 h. The solvent was evaporated under reduced pressure and the residue was diluted with cold water. The aqueous solution was basified by solid sodium carbonate and extracted with ethyl acetate. The organic layer was dried over anhydrous sodium sulfate, filtered and evaporated under reduced pressure to get crude compound. The crude compound was purified by silica gel chromatography (20% ethyl acetate in pet ether) to get desired compound (1.2 g, 27.5%) as pale yellow solid. $^1$H NMR (400 MHz, CDCl$_3$): δ ppm 8.16-8.13 (d, J=12 Hz, 1H), 7.74 (s, 1H), 7.44-7.43 (d, J=4 Hz, 1H), 7.30-7.27 (d, J=12 Hz, 1H), 7.26 (s, 1H), 4.05 (s, 3H), 3.97 (s, 3H); MS: MS m/z 224.2 (M$^+$+1).

Step 5: Preparation of 1-fluoro-4,6-dimethoxyisoquinoline

To a solution of 1-chloro-4,6-dimethoxyisoquinoline (1.5 g, 6.71 mmol) in DMSO (15 ml) was added cesium fluoride (4 g, 26.8 mmol) at room temperature. The reaction vessel (Pressure tube) was sealed and heated at 145° C. for 18 h. The reaction mass was diluted with water and extracted with ethyl acetate. The combined organic layer was dried over anhydrous Na$_2$SO$_4$ and evaporated under reduced pressure to get crude compound. The crude compound was purified by silica gel chromatography to get desired compound (280 mg, 20.15%) as white solid. $^1$H NMR (400 MHz, CDCl$_3$): δ ppm 7.99-7.97 (d, J=8 Hz, 1H), 7.44-7.39 (m, 2H), 7.27-7.11 (m, 1H), 4.03 (s, 3H), 3.97 (s, 3H); $^{19}$F NMR: δ ppm −79.32 (1F); MS: MS m/z 208.0 (M$^+$+1).

Scheme: Preparation of 2,4-dichloro-5-methoxyquinoline & 2,4-dichloro-7-methoxyquinoline Synthesis of 2,4-Dichloro-5-methoxy quinoline & 2,4-Dichloro-7-methoxy quinoline

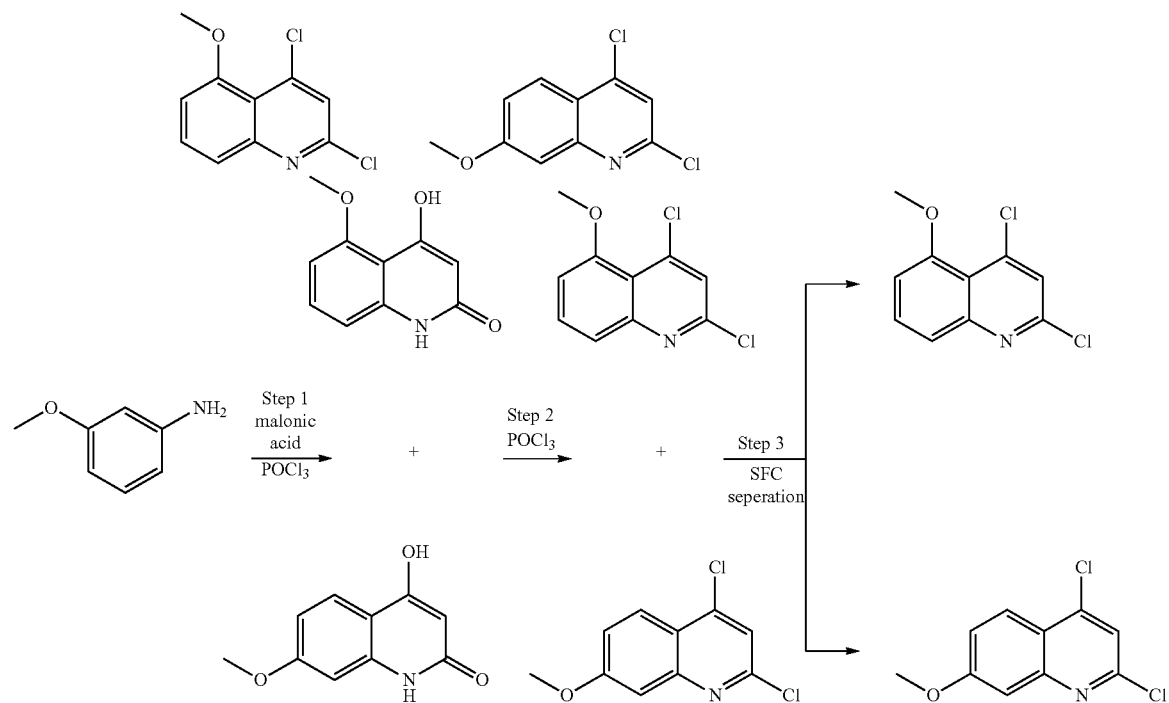

Step 1: Preparation of 4-hydroxy-5-methoxyquinoline-2(1H)-one & 4-hydroxy-7-methoxyquinoline-2(1H)-one POCl$_3$ (4.16 ml, 44.7 mmol) was added to the mixture of 3-methoxy aniline (5.0 g, 40.6 mmol) and malonic acid (4.22 g, 40.6 mmol). The reaction mass was heated to 105° C. for 1 h. The reaction mass was diluted with water (20 ml) and stirred for 30 min. The precipitated solid was filtered and washed with water. 2N NaOH solution (30 ml) was added to the solid and stirred for 18 hr. The remaining solid was filtered off and ethanol (5 ml) was added to the filtrate was acidified to PH 2 using conc. HCl. The precipitated solid was filtered and washed with water. The solid was dried under reduced pressure to get desired regio isomer in the ratio 50:50 (3 g, 38.6%) as white solid. $^1$H NMR (400 MHz, DMSO): δ ppm 11.27-11.07 (m, 3H), 10.01 (s, 1H), 7.68- 7.65 (d, J=12 Hz, 1H), 7.41 (t, J=12 Hz, 1H) 6.91-6.88 (d, J=12 Hz, 1H), 6.76-6.72 (m, 3H), 5.62-5.60 (d, J=8 Hz, 2H), 3.92 (s, 3H), 3.72 (s, 3H).

Step 2: Preparation of 2,4-dichloro-5-methoxyquinoline & 2,4-dichloro-7-methoxyquinoline A solution of 4-hydroxy-5-methoxyquinoline-2(1H)-one & 4-hydroxy-7-methoxyquinoline-2(1H)-one (3 g, 15.70 mmol) in POCl$_3$ (3.66 ml, 39.2 mmol) was refluxed for 3 h. The solvent was evaporated under reduced pressure and the residue was diluted with cold water. The aqueous solution was basified by solid sodium carbonate and extracted with ethyl acetate. The organic layer was dried over anhydrous sodium sulfate, filtered and evaporated under reduced pressure to get crude compound. The crude compound was purified by silica gel chromatography (20% ethyl acetate in pet ether) to afford mixture of regioisomers. This mixture of regioisomers was separated by SFC purification to afford 2,4-dichloro-5-methoxyquinoline (0.7 g, 39%) and 2,4-dichloro-7-methoxyquinoline (required isomer) (1.3 g, 72.6%) as white solid. 2,4-dichloro-7-methoxyquinoline: $^1$H NMR (400 MHz, CDCl$_3$): δ ppm 8.07-8.04 (d, J=12 Hz, 1H), 7.35-7.34 (m, 2H), 7.28-7.26 (m, 1H), 3.94 (s, 3H); 2,4-dichloro-5-methoxyquinoline: $^1$H NMR (400 MHz, CDCl$_3$): δ ppm 7.66-7.60 (m, 2H), 7.40 (m, 1H), 7.25 (s, 1H), 6.95-6.93 (d, J=8 Hz, 1H), 3.97 (s, 3H).

Scheme 17: Preparation of 4-Chloro-7-methoxy-2-(pyrrolidin-1-yl) quinoline

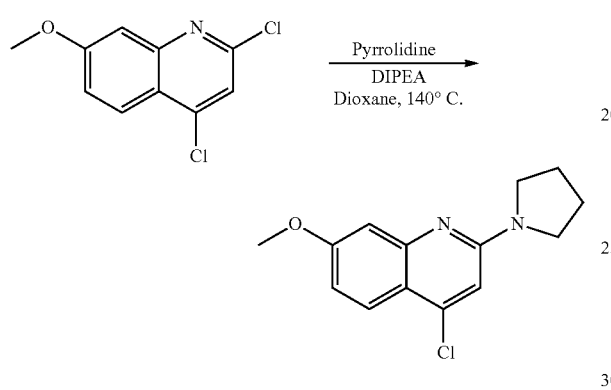

To a solution of 2,4-dichloro-7-methoxyquinoline (0.1 g, 0.43 mmol) in 1,4-Dioxane (10 ml) was added pyrrolidine (0.3 g, 0.43 mmol) followed by DIPEA (0.11 g, 0.87 mmol) at room temperature. The reaction mass was heated at 140° C. for 18 h. The reaction mass was diluted with water and extracted with ethyl acetate. The combined organic layer was dried over anhydrous Na$_2$SO$_4$ and evaporated under reduced pressure to get crude compound. The crude compound was purified by silica gel chromatography to get desired compound (50 mg, 43.4%) as white solid. $^1$H NMR (400 MHz, CDCl$_3$): δ ppm 7.86-7.83 (d, J=12 Hz, 1H), 7.06 (s, 1H), 6.88-6.85 (d, J=12 Hz, 1H), 6.67 (s, 1H), 3.91 (s, 3H), 3.58 (t, J=8 Hz, 4H), 2.03 (t, J=6 Hz, 1H); MS: MS m/z 263.1 (M$^+$+1).

Scheme 18: Preparation of 4-(4-Chloro-7-methoxy quinoline-2-yl) morpholine

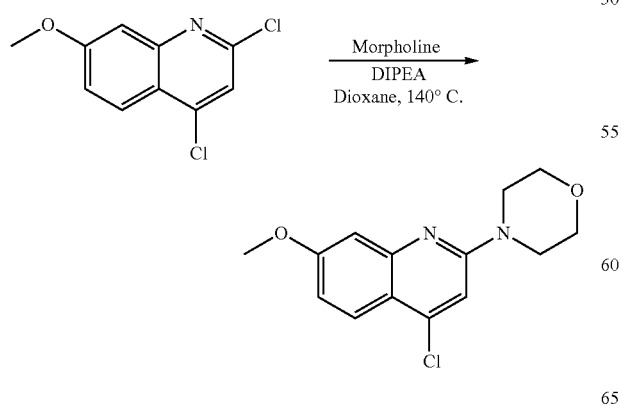

To a solution of 2,4-dichloro-7-methoxyquinoline (1 g, 4.38 mmol) in 1,4-dioxane (15 ml) was added morpholine (1.9 g, 4.38 mmol) followed by DIPEA (1.7 g, 13.15 mmol) at room temperature. The reaction mass was heated at 140° C. for 18 h. The reaction mass was diluted with water and extracted with ethyl acetate. The combined organic layer was dried over anhydrous Na$_2$SO$_4$ and evaporated under reduced pressure to get crude compound. The crude compound was purified by silica gel chromatography to get desired compound (0.6 g, 49.1%) as white solid. $^1$H NMR (400 MHz, CDCl$_3$): δ ppm 7.89-7.86 (d, J=12 Hz, 1H), 7.07 (s, 1H), 6.97-6.94 (d, J=12 Hz, 1H), 6.89 (s, 1H), 3.91 (s, 3H), 3.85-3.82 (m, 4H), 3.69-3.66 (m, 4H); MS: MS m/z 279.1 (M$^+$+1).

Scheme: Preparation of 1,7-difluoro-4-cyclopropoxyisoquinoline

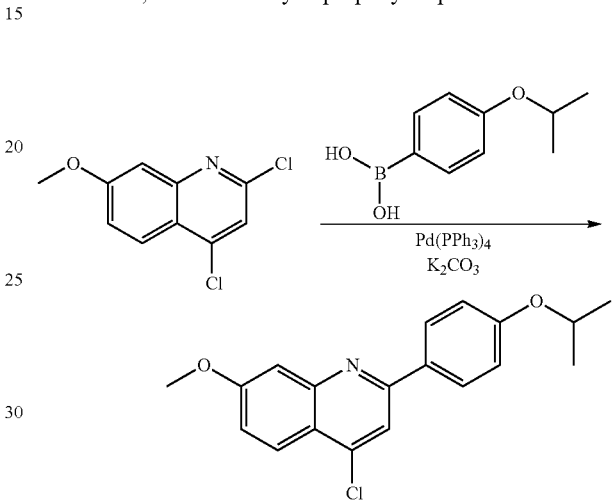

Step 1: Preparation of 4-chloro-2-(4-isopropoxyphenyl)-7-methoxyisoquinoline

To a solution of 2,4-dichloro-7-methoxyisoquinolin (0.7 g, 3.07 mmol), 4-isopropoxyphenylboronic acid (0.60 g, 3.38 mmol) in 1,4-Dioxane (15 ml) and water (10 ml) was added K$_2$CO$_3$ (0.84 g, 6.14 mmol). The reaction mass was degasified for 20 min. Pd (Ph$_3$P)$_4$ (0.17 g, 0.15 mmol) was added to the above reaction mass and degasified again for 5 min at room temperature. The reaction vessel (Pressure tube) was sealed and heated at 90° C. for 18 h. The reaction mass was evaporated under reduced pressure. The residue was diluted with water and extracted with ethyl acetate. The combined organic layer was dried over anhydrous Na$_2$SO$_4$ and evaporated under reduced pressure to get crude compound. The crude compound was purified by silica gel chromatography to get desired compound (0.85 g, 84%) as white solid. $^1$H NMR (400 MHz, CDCl$_3$): δ ppm 8.25-8.22 (d, J=8 Hz, 1H), 8.13 (s, 1H), 8.07-8.05 (d, J=8 Hz, 1H), 7.48-7.47 (d, J=4 Hz, 1H), 7.34-7.32 (d, J=8 Hz, 1H), 7.07-7.05 (m, 2H), 4.77-4.71 (m, 1H), 4.15 (s, 3H), 1.32-1.31 (d, J=4 Hz, 6H); MS: MS m/z 328.20 (M$^+$+1).

Scheme: Preparation 4-Chloro-7-methoxy-2-(1H-pyrazol-1-yl) quinoline

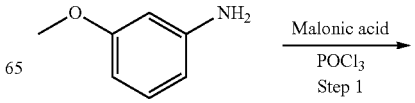

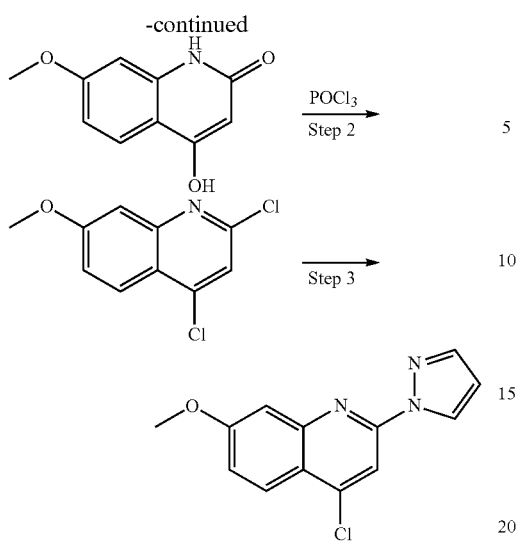

Step 1: Preparation of 4-hydroxy-5-methoxyquinoline-2(1H)-one & 4-hydroxy-7-methoxyquinoline-2(1H)-one POCl$_3$ (4.16 ml, 44.7 mmol) was added to the mixture of 3-methoxy aniline (5.0 g, 40.6 mmol) and malonic acid (4.22 g, 40.6 mmol). The reaction mass was heated to 105° C. for 1 h. The reaction mass was diluted with water (20 ml) and stirred for 30 min. The precipitated solid was filtered and washed with water. 2N NaOH solution (30 ml) was added to the solid and stirred for 18 hr. The remaining solid was filtered off and ethanol (5 ml) was added to the filtrate was acidified to PH 2 using conc. HCl. The precipitated solid was filtered and washed with water. The solid was dried under reduced pressure to get desired regio isomer in the ratio 50:50 (3 g, 38.6%) as white solid. $^1$H NMR (400 MHz, DMSO): δ ppm 11.27-11.07 (m, 3H), 10.01 (s, 1H), 7.68-7.65 (d, J=12 Hz, 1H), 7.41 (t, J=12 Hz, 1H) 6.91-6.88 (d, J=12 Hz, 1H), 6.76-6.72 (m, 3H), 5.62-5.60 (d, J=8 Hz, 2H), 3.92 (s, 3H), 3.72 (s, 3H).

Step 2: Preparation of 2,4-dichloro-5-methoxyquinoline & 2,4-dichloro-7-methoxyquinoline A solution of 4-hydroxy-5-methoxyquinoline-2(1H)-one & 4-hydroxy-7-methoxyquinoline-2(1H)-one (3 g, 15.70 mmol) in POCl$_3$ (3.66 m, 39.2 mmol) was refluxed for 3 h. The solvent was evaporated under reduced pressure and the residue was diluted with cold water. The aqueous solution was basified by solid sodium carbonate and extracted with ethyl acetate. The organic layer was dried over anhydrous sodium sulfate, filtered and evaporated under reduced pressure to get crude compound. The crude compound was purified by silica gel chromatography (20% ethyl acetate in pet ether) to get regio isomers as mixture was separated by SFC purification to get desired compound 2,4-dichloro-5-methoxyquinoline (0.7 g, 39%) and 2,4-dichloro-7-methoxyquinoline (required isomer) (1.3 g, 72.6%) as white solid. 2,4-dichloro-7-methoxyquinoline: $^1$H NMR (400 MHz, CDCl$_3$): δ ppm 8.07-8.04 (d, J=12 Hz, 1H), 7.35-7.34 (m, 2H), 7.28-7.26 (m, 1H), 3.94 (s, 3H); 2,4-dichloro-5-methoxyquinoline: $^1$H NMR (400 MHz, CDCl$_3$): δ ppm 7.66-7.60 (m, 2H), 7.40 (m, 1H), 7.25 (s, 1H), 6.95-6.93 (d, J=8 Hz, 1H), 3.97 (s, 3H).

Step 3: Preparation of 4-Chloro-7-methoxy-2-(1H-pyrazol-1-yl) quinoline

Solid pyrazole (3.2 g, 47.36 mmol) was heated to 80° C. Then 2,4-Dichloro-7-methoxyquinoline (3.6 g, 15.78 mmol) was added. The reaction mass was heated to 115° C. for 3 hr. The reaction mass was cooled to RT and was purified by silica gel chromatography (20% ethyl acetate in pet ether) to get desired compound (2.3 g, 56%) as white solid.
$^1$H NMR (400 MHz, CDCl$_3$): δ ppm 8.77 (d, J=2.8 Hz, 1H), 8.18 (s, 1H), 8.10 (d, J=9.2 Hz, 1H), 7.79 (s, 1H), 7.38 (d, J=2.8 Hz, 1H), 7.23 (dd, J=2.0, 8.8 Hz, 1H), 6.53-6.52 (m, 1H), 3.98 (s, 3H); MS: MS m/z 260.0 (M$^+$+1).

Scheme: Preparation 4-chloro-7-methoxyquinazoline

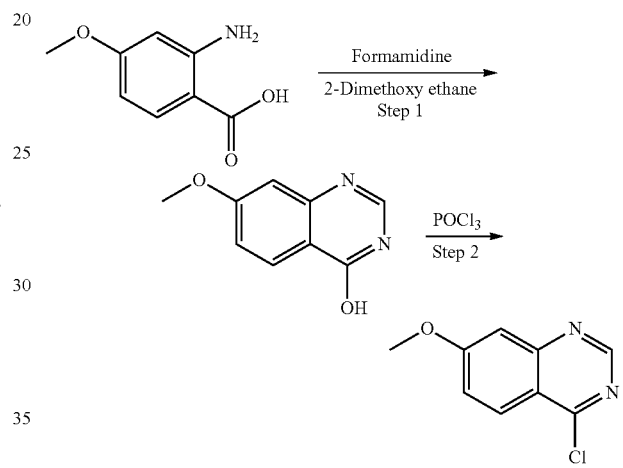

Step 1: Preparation of 7-methoxyquinazolin-4-ol

To a solution of 2-amino-4-methoxy benzoic acid (8.6 g, 51.4 mmol) in 2-dimethoxy ethane (100 ml) was added formamidine (10.71 g, 103 mmol). The reaction mass was heated to 125° C. 18 h. The reaction mass was diluted with cold water. The precipitated solid was filtered, washed with water to get crude compound (6.92 g, 74.8%) as pale yellow solid. $^1$H NMR (400 MHz, DMSO): δ ppm 12.10 (br, s, 1H), 8.06 (s, 1H), 8.03-8.01 (d, J=8 Hz, 1H), 7.11-7.09 (m, 2H), 3.89 (s, 3H);

Step 2: Preparation of 4-chloro-7-methoxyquinazoline

A solution of 4,6-dimethoxyisoquinolin-1(2H)-one (1 g, 5.68 mmol) in POCl$_3$ (25 ml) was refluxed for 18 h. The solvent was evaporated under reduced pressure and the residue was diluted with cold water. The aqueous solution was basified by solid sodium carbonate and extracted with ethyl acetate. The combine organic layer was dried over anhydrous sodium sulfate, filtered and evaporated under reduced pressure to get crude compound. The crude compound was purified by silica gel chromatography (20% ethyl acetate in pet ether) to get desired compound (0.87 g, 72.5%) as pale yellow solid. $^1$H NMR (400 MHz, DMSO): δ ppm 8.52 (br, s, 1H), 8.07-8.05 (d, J=8 Hz, 1H), 7.20-7.17 (m, 2H), 3.91 (s, 3H); MS: MS m/z 195.0 (M$^+$+1).

Scheme 22: Preparation of 2-chloro-6-methoxyquinoxaline and 3-chloro-6-methoxyquinoxaline Synthesis of 2-chloro-6-methoxyquinoxaline & 2-chloro-7-methoxyquinoxaline

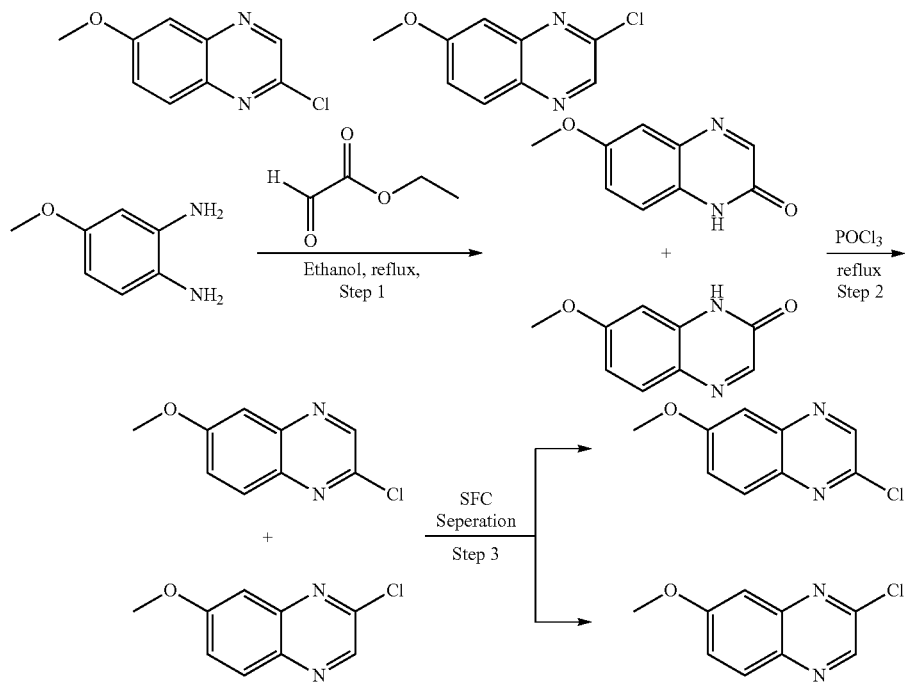

Step 1: Preparation of 6-methoxyquinoxalin-2(1H)-one and 7-methoxyquinoxalin-2(1H)-one To a solution of 4-methoxybenzene-1,2-diamine (5 g, 36.2 mmol) in ethanol (50 ml) was added ethyl 2-oxoacetate (4.06 g, 39.8 mmol)). The reaction mass was heated at reflux for overnight. The solvent was evaporated under reduced pressure and the residue was diluted with ethyl acetate and then evaporated to dryness to get the crude compound. The crude compound was washed with pet ether to get crude compound (5.1 g, 80% yield) as a mixture of regioisomers (black solid). This crude compound was taken to the next step without separation of isomers. $^1$H NMR (400 MHz, DMSO-d6): δ ppm 8.17 (s, 1H), 7.98 (s, 1H), 7.70-7.68 (d, J=8 Hz, 1H), 7.31-7.30 (d, J=4 Hz, 1H), 7.27-7.20 (m, 2H), 6.93-6.90 (m, 1H), 6.77-6.76 (d, J=4 Hz, 1H), 3.84 (s, 3H), 3.83 (s, 3H); MS: MS m/z 177.0 (M$^+$+1).

Step 2: Preparation of 2-chloro-6-methoxyquinoxaline and 3-chloro-6-methoxyquinoxaline A solution of 6-methoxyquinoxalin-2(1H)-one & 7-methoxyquinoxalin-2(1H)-one (3 g, 18.28 mmol) in POCl$_3$ (20 ml) was refluxed for 3 h. The solvent was evaporated under reduced pressure and the residue was diluted with cold water. The aqueous solution was basified by solid sodium carbonate and extracted with ethyl acetate. The combine organic layer was dried over anhydrous sodium sulfate, filtered and evaporated under reduced pressure to get crude compound. The crude compound was purified by silica gel chromatography (20% ethyl acetate in pet ether) to afford mixture of regioisomers (3.7 g). 2 g of the above mixture was separated by SFC purification to afford 2-chloro-7-methoxyquinoxaline (0.7 g, 34.7%) and 2-chloro-7-methoxyquinoxaline (0.9 g, 44.6%) as off white solid.

2-chloro-6-methoxyquinoxaline: $^1$H NMR (400 MHz, DMSO-d6): δ ppm $^1$H NMR (400 MHz, CDCl$_3$): δ ppm 8.71 (s, 1H), 7.91-7.89 (d, J=8 Hz, 1H), 7.46-7.38 (m, 2H), 3.97 (s, 3H); MS: MS m/z 194.9 (M$^+$+1).

2-chloro-7-methoxyquinoxaline: $^1$H NMR (400 MHz, CDCl$_3$): δ ppm 8.63 (s, 1H), 7.99-7.96 (d, J=12 Hz, 1H), 7.43-7.40 (d, J=12 Hz, 1H), 7.30 (s, 1H), 3.96 (s, 3H); MS: MS m/z 194.9 (M$^+$+1).

Scheme: Preparation of 2-chloro-6 fluoroquinoxaline and 3-chloro-6-fluoroquinoxaline Synthesis of 2-chloro-6-fluoroquinoxaline & 2-chloro-7-fluoroquinoxaline

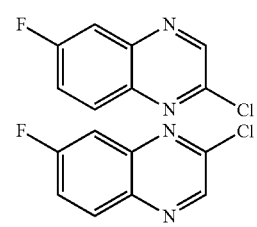

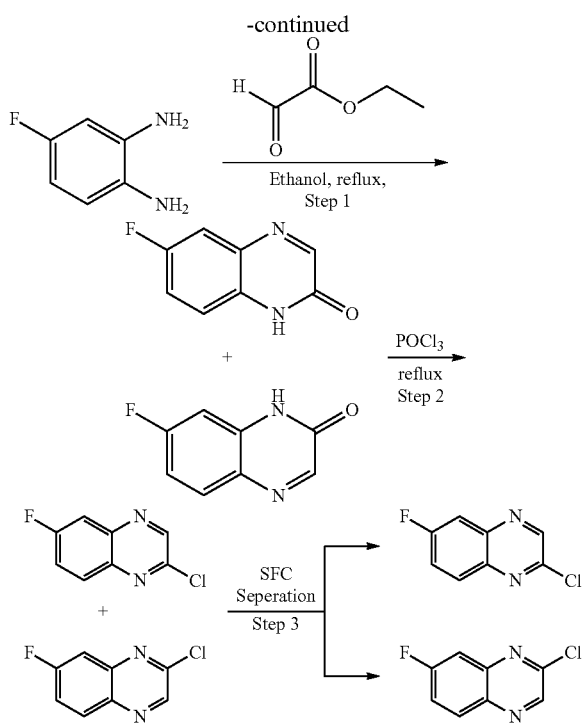

Step 1: Preparation of 6-flouroquinoxalin-2(1H)-one and 7-flouroquinoxalin-2(1H)-one To a solution of 4-flourobenzene-1,2-diamine (5 g, 39.6 mmol) in ethanol (20 ml) was added ethyl 2-oxoacetate (4.45 g, 43.6 mmol)). The reaction mass was heated at reflux for overnight. The solvent was evaporated under reduced pressure and the residue was diluted with ethyl acetate and then evaporated to dryness to get the crude compound. The crude compound was washed with pet ether to get crude compound (4.6 g, 70% yield) as a mixture of regioisomers (black solid). This crude compound was taken to the next step without separation of isomers. MS: MS m/z 162.8 ($M^+-1$).

Step 2: Preparation of 2-chloro-6-methoxyquinoxaline and 3-chloro-6-methoxyquinoxaline A solution of 6-flouroquinoxalin-2(1H)-one & 7-flouro-quinoxalin-2(1H)-one (3 g, 18.28 mmol) in POCl$_3$ (20 ml) was refluxed for 3 h. The solvent was evaporated under reduced pressure and the residue was diluted with cold water. The aqueous solution was basified by solid sodium carbonate and extracted with ethyl acetate. The combine organic layer was dried over anhydrous sodium sulfate, filtered and evaporated under reduced pressure to get crude compound. The crude compound was purified by silica gel chromatography (20% ethyl acetate in pet ether) to afford regioisomers as a mixture. The above mixture was separated by SFC purification to afford 2-chloro-6-fluoroquinoxaline (0.75 g, 44%) and 2-chloro-7-fluoroquinoxaline (0.65 g, 38%) as white solid.

2-chloro-6-fluoroquinoxaline: $^1$H NMR (400 MHz, DMSO-d6): δ ppm 8.75 (s, 1H), 8.14-8.11 (d, J=12 Hz, 1H), 7.67-7.64 (d, J=12 Hz, 1H), 7.59-7.54 (m, 1H); $^{19}$F NMR: δ ppm −107.15 (1 F).

2-chloro-7-fluoroquinoxaline: $^1$H NMR (400 MHz, DMSO-d6): δ ppm 8.79 (s, 1H), 8.05-8.02 (d, J=12 Hz, 1H), 7.77-7.74 (d, J=12 Hz, 1H), 7.62-7.56 (m, 1H); $^{19}$F NMR: δ ppm −107.15 (1 F).

Scheme: Preparation of 3-methoxy-6 fluoroquinoxaline

Synthesis of 7-fluoro-2-methoxyquinoxaline

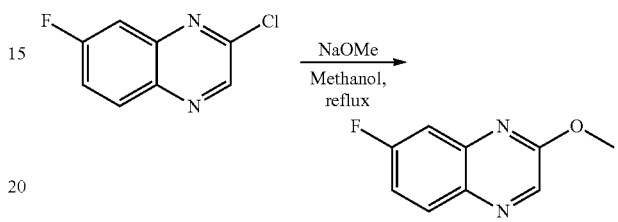

To a solution of 2-chloro-7-fluoroquinoxaline (0.1 g, 0.54 mmol) in methanol (15 ml) was added sodium methoxide (0.29 g, 0.54 mmol) at room temperature under nitrogen atmosphere. The reaction mass was heated at reflux for 3 h. The solvent was evaporated under reduced pressure and the residue was diluted with DCM and washed with water. The organic layer was dried over anhydrous sodium sulfate, filtered and evaporated to get crude compound 7-fluoro-2-methoxyquinoxaline (0.09 g, 88% yield) as white solid. $^1$H NMR (400 MHz, CDCl$_3$): δ ppm 8.41 (s, 1H), 8.01-7.98 (d, J=12 Hz, 1H), 7.49-7.46 (d, J=12 Hz, 2H), 7.34-7.3 (m, 1H), 4.09-4 (s, 3H); $^{19}$F NMR: δ ppm −108.99 (1 F).

Scheme 39: Preparation of 1-methylcyclopropane-1-sulfonamide

Synthesis of 1-Methylcyclopropane-1-sulfonamide

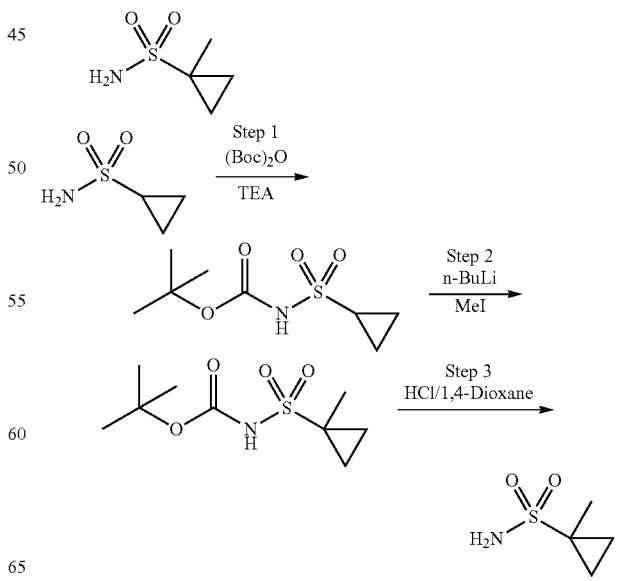

Step 1: Preparation of tert-butyl cyclopropylsulfonylcarbamate

To a solution of cyclopropanesulfonamide (100 g, 82.6 mmol) in DCM (800 ml) was added triethylamine (234 ml, 165 mmol) followed by DMAP (10.28 g, 82.6 mmol) at 0° C. under nitrogen. To this reaction mixture Boc anhydride (247 ml, 107 mmol) in DCM (400 ml) was added slowly. The resulting mixture was stirred for 4 h at room temperature. The reaction mixture was diluted with water and extracted with ethyl acetate. The combine organic layer was washed with 1.5 N HCl solution and 10% $NaHCO_3$ and dried over anhydrous sodium sulfate, filtered and evaporated under reduced pressure to get crude compound (143 g, 65.0%) as solid. The crude compound was directly taken for the next step. $^1$H NMR (400 MHz, DMSO-d6): δ ppm 11.08 (s, 1H), 2.90 (m, 1H), 1.48 (s, 9H), 1.06 (m, 4H).

Step 2: Preparation of tert-butyl(1-methylcyclopropyl) sulfonylcarbamate

A solution of tert-butyl cyclopropylsulfonylcarbamate (4.3 g, 20 mmol) was dissolved in dry THF (100 ml) and cooled to −78° C. To this solution was added n-BuLi (17.6 ml, 44 mmol, 2.5 M in hexane) slowly. The reaction mixture was allowed to warm to room temperature over a period of 1.5 h. This mixture was then cooled to −78° C., and a solution of n-BuLi (20 mmol, 8 ml, 2.5M in hexane) was added, stirred for 1 h and a neat solution of methyl iodide (5.68 g, 40 mmol) was added. The reaction mixture was allowed to warm to room temperature for overnight, quenched with aqueous saturated $NH_4Cl$ (100 ml) at room temperature. It was extracted with EtOAc (100 ml). The combined organic layer was washed with brine dried on $Na_2SO_4$, filtered and evaporated under reduced pressure to give a yellow oil which was crystallized from hexane to afford the product as a slightly yellow solid. (3.1 g, 81%). $^1$H NMR (400 MHz, DMSO-d6): δ ppm 10.97 (s, 1H), 1.44 (s, 12H), 1.35-1.33 (m, 2H), 0.93-0.91 (m, 2H).

Step 3: Preparation of 1-methylcyclopropane-1-sulfonamide

A solution of N-ter-butyl-(1-methyl)cyclopropyl-sulfonamide (1.91 g, 10 mmol) was dissolved in 4M HCl in dioxane (30 ml) and the reaction mixture stirred at rt for 16 h. The solvent was removed in vacuo to give a yellow oil which was crystallized from EtOAc/hexane (1:4, 40 ml) to yield 1-methyl-cyclopropylsulfonamide, as a white solid (1.25 g, 96%). $^1$H NMR (400 MHz, $CDCl_3$): δ ppm 6.73 (s, 2H), 1.43 (s, 3H), 1.14-1.12 (m, 2H), 0.75-0.73 (m, 2H).

Scheme 40: Preparation 1-(Fluoro methyl)cyclopropane-1-sulfonamide 1-(Fluoromethyl)cyclopropane-1-sulfonamide

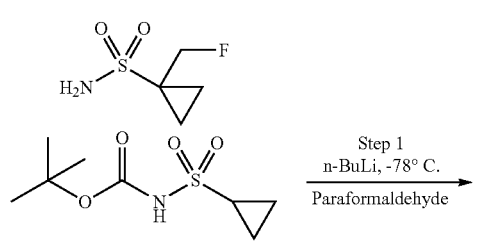

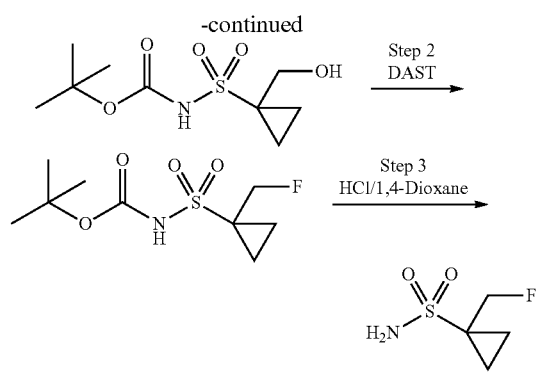

Step 1: Preparation of tert-butyl 1-(hydroxymethyl)cyclopropylsulfonylcarbamate To a solution of tert-butyl cyclopropylsulfonylcarbamate (30 g, 136 mmol) in 750 mL of THF was added dropwise butyllithium (1.6 M in hexane, 212 mL, 339 mmol) over 30 min at −78° C. and the resulting mixture was stirred at −78° C. for 1 h. Formaldehyde gas was generated from paraformaldehyde (by heating at 180° C.) and was purged into the above reaction mass for 30 min at −30° C. The reaction was stirred at the same temperature for 1 h, then allowed to warm to room temperature. The reaction was quenched with aqueous ammonium chloride solution and diluted with water. The resulting mass was washed with ethyl acetate and the aqueous layer was acidified to pH~2 and extracted with ethyl acetate. The combined organics were dried over sodium sulfate, filtered and evaporated under reduced pressure to get desired compound (27 g, 79%) as white solid. $^1$H NMR (400 MHz, DMSO-$d_6$): δ ppm 10.90 (sb, 1H), 4.95 (sb, 1H), 3.75 (s, 2H), 1.42 (s, 9H), 1.27 (m, 2H), 1.08 (m, 2H).

Step 2: Preparation of tert-butyl (1-(fluoromethyl)cyclopropyl)sulfonylcarbamate To a solution of tert-butyl(1-hydroxymethyl)cyclopropyl) sulfonylcarbamate (10 g, 39.98 mmol) in DCM (150 ml) at −78° C. was added DAST (25.7 g, 159 mmol) drop wise. The reaction mass was stirred for 2 hr. The reaction mass was quenched with 1N NaOH solution (200 ml), separated the DCM layer. The DCM layer was washed with NaOH solution (400 ml), combined aqueous layer was acidified with 1.5N HCl solution (600 ml) and extracted with DCM. The combine organic layer was dried over anhydrous sodium sulfate, filtered and evaporated under reduced pressure to get desired compound (9.8 g, 97%) as a light brown solid. $^1$H NMR (400 MHz, $CDCl_3$): δ ppm 6.97 (br, s, 1H), 4.74-4.62 (d, J=48 Hz, 2H), 1.83-1.80 (m, 2H), 1.56-1.44 (m, 9H), 1.20-1.11 (m, 2H).

Step 3: Preparation of 1-(fluoromethyl)cyclopropane-1-sulfonamide

To a solution of tert-butyl (1-(fluoromethyl)cyclopropyl) sulfonylcarbamate (19.8 g, 38.7 mmol) in DCM (100 ml) was added TFA (30 ml, 387 mmol) drop wise at room temperature. The reaction mass was stirred for 2 hr. The reaction mass was evaporated under reduced pressure to get desired compound (6 g, 100%) as off white solid. $^1$H NMR (400 MHz, $CDCl_3$): δ ppm 4.78-4.66 (d, J=48 Hz, 2H), 2.61 (br, s, 1H), 1.59-1.56 (m, 2H), 1.13-1.10 (m, 2H).

Scheme 41: Preparation 1-Fluoro cyclopropane-1-sulfonamide 1-fluorocyclopropane-1-sulfonamide

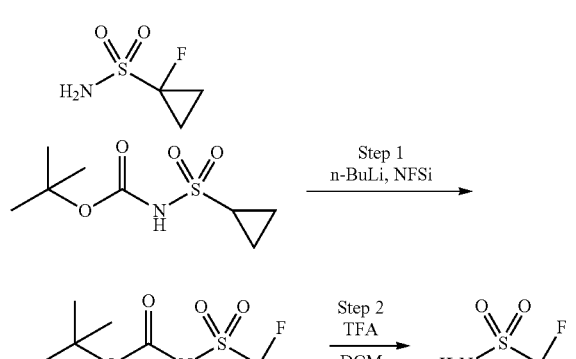

Step 1: Preparation of tert-butyl(1-fluorocyclopropyl)sulfonylcarbamate

A solution of tert-butyl cyclopropyl sulfonyl carbamate (25 g, 113 mmol) in THF (750 mL) was added n-BuLi (156 mL, 249 mmol, 1.6 M in hexane) at −78° C. The reaction mixture was stirred for 1 h at −78° C., and NFSi (42.8 g, 136 mmol) in THF (250 ml) was added drop wise. The reaction mass was stirred at 0° C. for 2 h, then allowed to warm to room temperature and stirred for overnight. The reaction mass was diluted with Ethyl acetate, quenched with saturated aqueous NH$_4$Cl (700 mL) at room temperature and separated the Ethyl acetate layer. The combined organic layer was evaporated under reduced pressure. To the residue ether (500 ml) was added, washed with 1M NaOH solution (600 ml). Then aqueous layer was acidified to PH 2 using 1.5 N HCl solution (700 ml) and extracted with DCM. The organic layer was dried over anhydrous sodium sulfate, filtered and evaporated under reduced pressure to get crude compound. The crude compound was purified by silica gel chromatography (10% ethyl acetate in pet ether) to get desired (5.7 g, 21%) as pale yellow solid. $^1$H NMR (400 MHz, CDCl$_3$): δ ppm 7.14 (s, br, 1H), 1.80-1.76 (m, 2H), 1.56-1.49 (m, 11H).

Step 2: Preparation of 1-fluorocyclopropane-1-sulfonamide

To a solution of tert-butyl(1-fluorocyclopropyl)sulfonyl-carbamate (11.1 g, 46.4 mmol) in DCM (110 ml) was added TFA (52.9 g, 464 mmol) drop wise at room temperature. The reaction mass was stirred for 2 hr. The reaction mass was evaporated under reduced pressure to get desired compound (5.93 g, 92%) as a light red solid. $^1$H NMR (400 MHz, DMSO): δ ppm 7.51 (br, s, 2H), 1.52-1.45 (m, 2H), 1.45-1.37 (m, 2H).

Scheme 42: Preparation 1-chloro cyclopropane-1-sulfonamide 1-chlorocyclopropane-1-sulfonamide

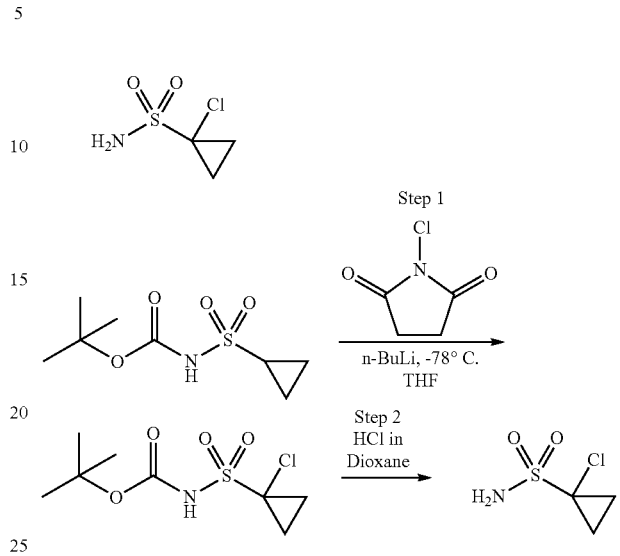

Step 1: Preparation of tert-butyl(1-chlorocyclopropyl) sulfonylcarbamate

A solution of tert-butyl cyclopropyl sulfonyl carbamate (2 g, 9.04 mmol) in THF (20 ml) was added n-BuLi (12.7 ml, 20.34 mmol, 1.6 M in hexane) at −78° C. The reaction mixture was stirred for 1 h at −78° C. and N-chlorosuccinamide (1.69 g, 12.65 mmol) in THF (20 ml) was added drop wise. The reaction mass was stirred at −78° C. for 3 h. The reaction mass was diluted with ice water, acidified to P$^H$ 4 using 1.5 N HCl solution and extracted with DCM. The organic layer was dried over anhydrous sodium sulfate, filtered and evaporated under reduced pressure to get crude compound. The crude compound was purified by silica gel chromatography (60% ethyl acetate in pet ether) to get desired (1 g, 43.3%) as white solid. $^1$H NMR (400 MHz, CDCl$_3$): δ ppm 7.09 (br, s, 1H), 2.07-2.03 (m, 2H), 1.53-1.49 (m, 11H); MS: MS m/z 254.05 (M$^+$−1).

Step 2: Preparation of 1-chlorocyclopropane-1-sulfonamide

To tert-butyl (1-chlorocyclopropyl) sulfonylcarbamate (3.2 g, 12.51 mmol) was added HCl in 1,4-Dioxane (40 ml, 4 M solution) at room temperature. The reaction mass was stirred for 2 hr. The reaction mass was evaporated under reduced pressure to get desired compound (1.8 g, 92%) as white solid. $^1$H NMR (400 MHz, DMSO): δ ppm 7.43 (br, s, 2H), 1.62-1.58 (m, 2H), 1.45-1.41 (m, 2H).

Scheme 43: Preparation 1-chloro cyclopropane-1-sulfonamide 1-(methoxymethyl)cyclopropane-1-sulfonamide

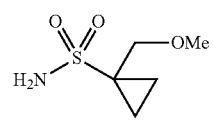

621

-continued

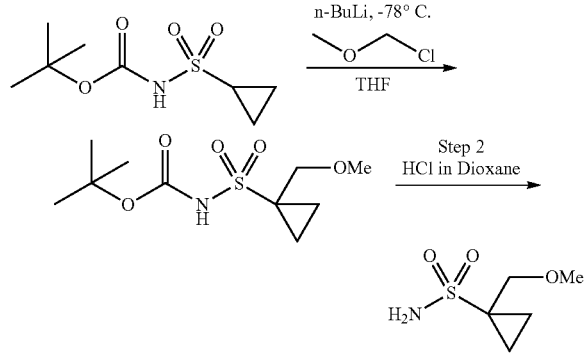

Step 1: Preparation of tert-butyl (1-(methoxymethyl)cyclopropyl)sulfonylcarbamate A solution of tert-butyl cyclopropyl sulfonyl carbamate (2 g, 9.04 mmol) in THF (60 ml) was added n-BuLi (12.77 ml, 20.43 mmol, 1.6 M in hexane) at −78° C. The reaction mixture was stirred for 1 h at −78° C. and Chloromethyl methyl ether (0.84 g, 10.48 mmol) was added drop wise. The reaction mass was allowed to warm to room temperature and stirred for overnight. The reaction mass was diluted with ice water, acidified to $P^H$ 3 using 1.5 N HCl solution and extracted with DCM. The organic layer was dried over anhydrous sodium sulfate, filtered and evaporated under reduced pressure to get crude compound (2.2 g, 92%) as white solid. $^1$H NMR (400 MHz, CDCl$_3$): δ ppm 7.35 (br, s, 1H), 3.70 (s, 2H), 3.35 (s, 3H), 1.53-1.44 (m, 11H), 1.06-1.03 (m, 2H).

Step 2: Preparation of 1-(methoxymethyl)cyclopropane-1-sulfonamide

To tert-butyl (1-(methoxymethyl)cyclopropyl)sulfonylcarbamate (2.2 g, 8.29 mmol) was added HCl in 1,4-Dioxane (20 ml, 4M solution) at room temperature. The reaction mass was stirred for 2 hr. The reaction mass was evaporated under reduced pressure to get desired compound (1.2 g, 88%) as white solid. $^1$H NMR (400 MHz, DMSO): δ ppm 6.68 (br, s, 2H), 3.62 (s, 2H), 3.27 (s, 3H), 1.22-1.09 (m, 2H), 0.96-0.91 (m, 2H).

Scheme 44: Preparation 1-(difluoromethyl)cyclopropane-1-sulfonamide

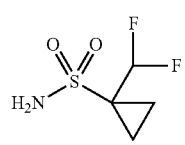

1-(difluoromethyl)cyclopropane-1-sulfonamide

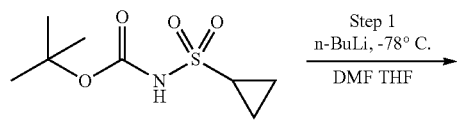

622

-continued

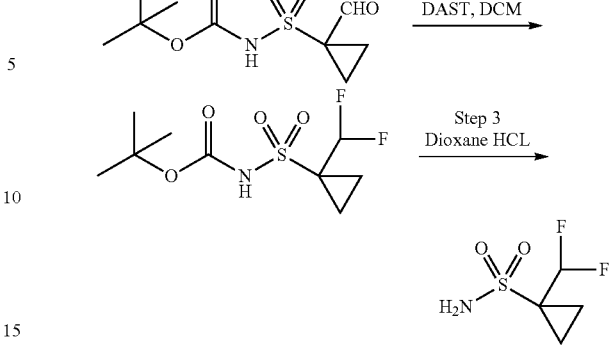

Step 1: Preparation of tert-butyl (1-formylcyclopropyl) sulfonylcarbamate

A solution of tert-butyl cyclopropyl sulfonyl carbamate (10 g, 45.2 mmol) in THF (150 ml) was added n-BuLi (70.6 ml, 113 mmol, 1.6 M in hexane) at −78° C. The reaction mixture was stirred for 1 h at −78° C., and DMF (6.6 g, 90 mmol) was added drop wise. The reaction mass was stirred at −78° C. for 1 h. The reaction mass was diluted water (100 ml) and extracted with Ethyl acetate. Then aqueous layer was acidified to $P^H$ 2 using 1.5 N HCl solution and extracted with DCM. The combine organic layer was dried over anhydrous sodium sulfate, filtered and evaporated under reduced pressure to get desired compound (10 g, 89%) as white solid. $^1$H NMR (400 MHz, DMSO): δ ppm 11.70 (br, s, 1H), 9.95 (s, 1H), 1.80-1.70 (m, 4H), 1.42 (m, 9H); MS: MS m/z 248.08 (M$^+$−1).

Step 2: Preparation of tert-butyl (1-(difluoromethyl)cyclopropyl)sulfonylcarbamate To a solution of tert-butyl (1-formylcyclopropyl) sulfonylcarbamate (1 g, 4.01 mmol) in DCM (10 ml) at −78° C. was added DAST (1.94 g, 12.03 mmol) drop wise. The reaction mass was stirred for 4 hr at room temperature. The reaction mass was quenched with 1N NaOH solution (20 ml), separated the DCM layer. The DCM layer was washed with NaOH solution (40 ml), combined aqueous layer was acidified with 1.5N HCl solution (60 ml) and extracted with DCM. The combine organic layer was dried over anhydrous sodium sulfate, filtered and evaporated under reduced pressure to get desired compound (0.4 g, 36.8%) as light brown solid. $^1$H NMR (400 MHz, CDCl$_3$): δ ppm 7.25 (br, s, 1H), 6.43 (t, J=56 Hz, 1H), 1.77 (m, 2H), 1.51 (m, 9H), 1.42-1.41 (m, 2H); $^{19}$F NMR: δ ppm −120.81(2F).

Step 3: Preparation of 1-(difluoromethyl)cyclopropane-1-sulfonamide

To tert-butyl (1-(fluoromethyl)cyclopropyl) sulfonylcarbamate (1.60 g, 5.90 mmol) was added HCl in 1,4-Dioxane (10 ml, 4M solution) drop wise at room temperature. The reaction mass was stirred for 2 hr. The reaction mass was evaporated under reduced pressure to get desired compound (0.97 g, 96%) as off white solid. $^1$H NMR (400 MHz, DMSO): δ ppm 7.26 (br, s, 2H), 6.49 (t, J=136 Hz, 1H), 1.33-1.19 (m, 4H); $^{19}$F NMR: δ ppm −118.52 (2F).

Scheme 45: Preparation 1-ethyl cyclopropane-1-sulfonamide 1-ethylcyclopropane-1-sulfonamide

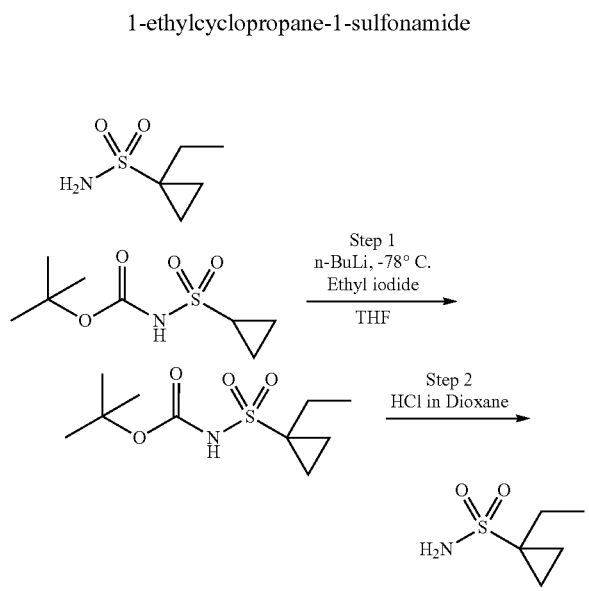

Step 1: Preparation of tert-butyl (1-ethyl cyclopropyl) sulfonylcarbamate

A solution of tert-butyl cyclopropyl sulfonyl carbamate (10 g, 63.6 mmol) in THF (100 ml) was added n-BuLi (59.6 ml, 95 mmol, 1.6 M in hexane) at −78° C. The reaction mixture was stirred for 1 h at −78° C. and ethyl iodide (49.6 g, 318 mmol) was added drop wise. The reaction mass was allowed to warm to room temperature and stirred for overnight. The reaction mass was quenched with aqueous NH$_4$Cl solution and extracted with DCM. The combine organic layer was washed with brine solution, dried over anhydrous sodium sulfate, filtered and evaporated under reduced pressure to get crude compound (4.8 g, 40.7%) as pale yellow solid. $^1$H NMR (400 MHz, DMSO): δ ppm 1.80-1.77 (m, 2H), 1.49-1.36 (m, 12H), 0.95 (t, J=8 Hz, 3H), 0.89-0.88 (m, 2H).

Step 2: Preparation of 1-ethyl cyclopropane-1-sulfonamide

To tert-butyl (1-ethyl cyclopropyl) sulfonylcarbamate (4.8 g, 19.25 mmol) was added HCl in 1,4-Dioxane (20 ml, 4M solution) at room temperature. The reaction mass was stirred for 3 hr. The reaction mass was evaporated under reduced pressure to get desired compound (2.5 g, 87%) as brown semi solid. $^1$H NMR (400 MHz, DMSO): δ ppm 6.70 (br, s, 2H), 1.85-1.81 (m, 2H), 1.10-1.08 (m, 2H), 0.95 (t, J=8 Hz, 3H), 0.89-0.87 (m, 2H).

Scheme 46: Preparation 1-cyno cyclopropane-1-sulfonamide 1-cyanocyclopropane-1-sulfonamide

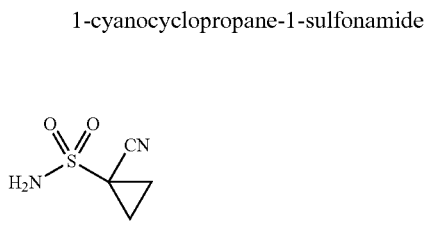

-continued

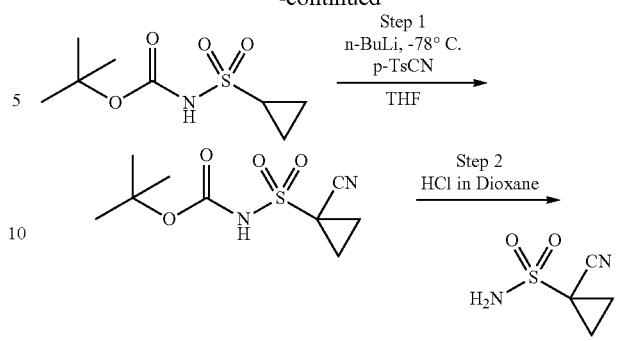

Step 1: Preparation of tert-butyl (1-cyano cyclopropyl) sulfonylcarbamate

A solution of tert-butyl cyclopropyl sulfonyl carbamate (1 g, 4.52 mmol) in THF (10 ml) was added n-BuLi (6.38 ml, 10.21 mmol, 1.6 M in hexane) at −78° C. The reaction mixture was stirred for 1 h at −78° C. and p-TsCN (0.98 g, 5.42 mmol) was added drop wise. The reaction mass was allowed to warm to room temperature and stirred for overnight. The reaction mass was quenched with aqueous NH$_4$Cl solution and extracted with ethyl acetate. The combine organic layer was washed with brine solution, dried over anhydrous sodium sulfate, filtered and evaporated under reduced pressure to get crude compound (0.5 g, 44.9%) as semi solid. $^1$H NMR (400 MHz, DMSO): δ ppm 1.89-1.76 (m, 2H), 1.51-1.45 (m, 12H).

Step 2: Preparation of 1-cyano cyclopropane-1-sulfonamide

To tert-butyl (1-ethyl cyclopropyl) sulfonylcarbamate (0.5 g, 2.03 mmol) was added HCl in 1,4-Dioxane (5 ml, 4M solution) at room temperature. The reaction mass was stirred for 3 hr. The reaction mass was evaporated under reduced pressure to get desired compound (0.1 g, 33.7%) as off white solid. $^1$H NMR (400 MHz, DMSO): δ ppm 7.78 (br, s, 2H), 1.79-1.76 (m, 2H), 1.59-1.56 (m, 2H).

Preparation of Compound 4001 tert-butyl tert-butyl (2R,6S,7R,9R,13aS,14aR,16aS, Z)-14a-(cyclopropylsulfonylcarbamoyl)-7-ethyl-2-(7-fluoro-4-methoxyisoquinolin-1-yloxy)-9-methyl-5,16-dioxo-1,2,3,5,6,7,8,9,10,11,13a,14,14a,15,16, 16a-hexadecahydrocyclopropa[e]pyrrolo[1,2-a][1,4]diazacyclopentadecin-6-ylcarbamate Compound 4001

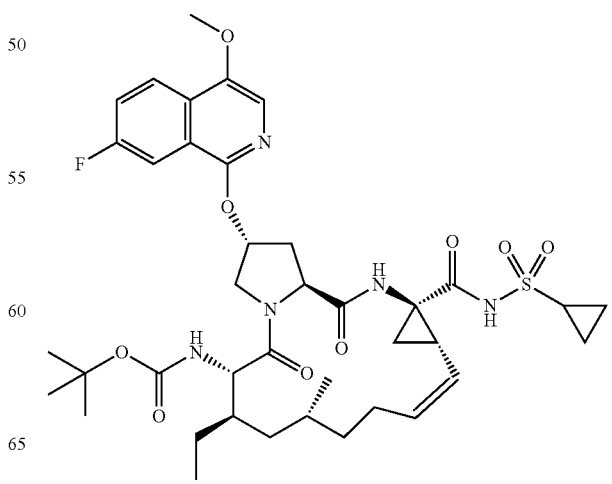

To a solution of tert-butyl (2R,6S,7R,13aS,14aR,16aS,Z)-14a-(cyclopropylsulfonylcarbamoyl)-7-ethyl-2-hydroxy-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (300 mg, 0.49 mmole) and 1,7-difluoro-4-methoxyisoquinoline (95.9 mg, 0.49 mmole) in DMSO (5 mL) was added t-BuOK (274 mg, 2.45 mmol, 1M solution in THF, 2.74 mL) at room temperature under nitrogen atmosphere. The reaction mixture was stirred at room temperature for 2 h. The reaction mass was quenched with aqueous citric acid solution and extracted with ethyl acetate (50 mL×3). The combined organic layers were washed with water, brine solution, dried over anhydrous $Na_2SO_4$ and evaporated under reduced pressure to get crude compound. The crude compound was purified by prep-HPLC to get 138 mg (36%) of desired compound as white solid. $^1$H NMR (400 MHz, $CD_3OD$): δ ppm 0.84 (d, J=14.81 Hz, 3H), 1.03 (s, 4H) 1.06-1.15 (m, 9H), 1.19-1.36 (m, 3H), 1.40-1.63 (m, 6H), 1.78 (dd, J=8.16, 5.65 Hz, 1H), 1.90-2.05 (m, 2H), 2.37-2.48 (m, 2H), 2.68-2.78 (m, 2H), 2.91-2.96 (m, 1H), 3.98-4.04 (m, 3H), 4.11 (s, 1H), 4.62 (dd, J=10.29, 7.03 Hz, 1, H), 4.77 (s, 1, H), 5.06 (br. s., 1H), 5.57-5.67 (m, 1H), 5.85 (br. s., 1H), 6.60 (d, J=9.03 Hz, 1H), 7.49-7.58 (m, 2H), 7.73 (dd, J=9.54, 2.51 Hz, 1H), 8.17 (dd, J=9.16, 5.40 Hz, 1H); MS: MS m/z 787.4 ($M^+$+1).

Preparation of (2R,6S,7R,9R,13aS,14aR,16aS,Z)-6-amino-N-(cyclopropylsulfonyl)-7-ethyl-2-(7-fluoro-4-methoxyisoquinolin-1-yloxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride

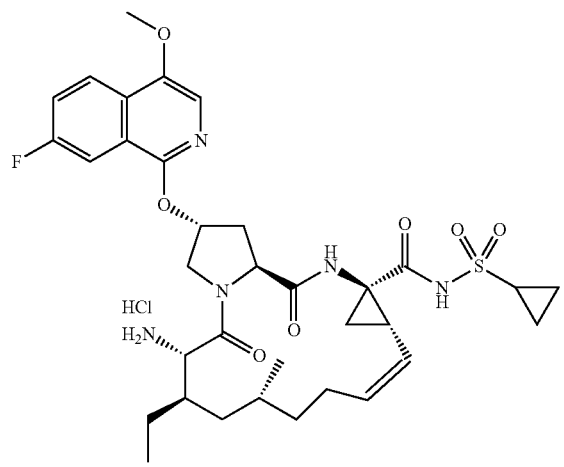 [SMILES: CC[C@@H]1C[C@H](C)CC/C=C\[C@@H]2C[C@@]2(C(=O)NS(=O)(=O)C2CC2)NC(=O)[C@@H]2C[C@@H](Oc3ncc(OC)c4ccc(F)cc34)CN2C(=O)[C@H]1N ; Cl]

A solution of Compound 4001 (100 mg, 0.10 mmole) in 4M HCl in dioxane was stirred at room temperature for 30 min. The solvent was evaporated under reduced pressure to get crude compound (69 mg, 96%). The crude compound was washed with diethyl ether and taken to the next step without further purification. MS: MS m/z 686.7 ($M^+$+1).

Preparation of Compound 4002

1,1,1-trifluoro-2-methylpropan-2-yl (2R,6S,7R,9R,13aS,14aR,16aS,Z)-14a-(cyclopropylsulfonylcarbamoyl)-7-ethyl-2-(7-fluoro-4-methoxyisoquinolin-1-yloxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate Compound 4002

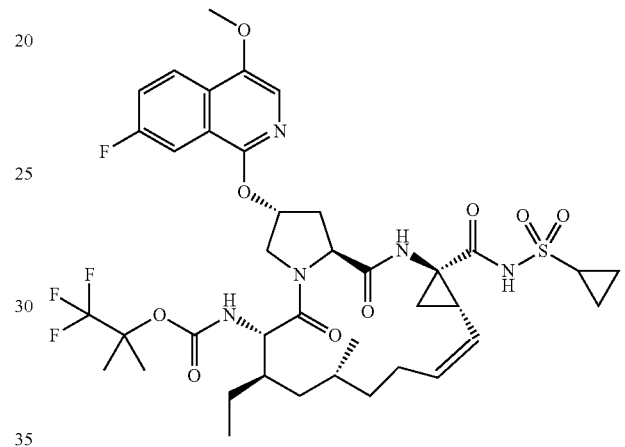

To a solution of (2R,6S,7R,9R,13aS,14aR,16aS,Z)-6-amino-N-(cyclopropylsulfonyl)-7-ethyl-2-(7-fluoro-4-methoxyisoquinolin-1-yloxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride (95 mg, 0.13 mmol) in DCM (4 mL) was added DIPEA (0.07 mL, 0.39 mmole) followed by carbonic acid pyridin-2-yl ester 2,2,2-trifluoro-1,1-dimethyl-ethyl ester (32.37 mg, 0.13 mmole) at room temperature. The reaction mixture was stirred at room temperature for 30 min. The reaction mass was diluted with DCM and washed with water. The organic layer was dried over anhydrous $Na_2SO_4$ and evaporated under reduced pressure to get crude compound. The crude compound was purified by prep-HPLC to get compound 4002 (18.5 mg, 17%) as white solid. $^1$H NMR (400 MHz, $CD_3OD$): δ ppm 0.80-0.90 (m, 3H), 0.97-1.06 (m, 4H), 1.09-1.18 (m, 10H), 1.22-1.39 (m, 3H), 1.49-1.65 (m, 6H), 1.78 (dd, J=8.28, 5.52 Hz, 1H), 1.97 (d, J=10.54 Hz, 2H), 2.38-2.49 (m, 2H), 2.66-2.79 (m, 2H), 2.88-2.97 (m, 1H), 3.98-4.07 (m, 5H), 4.61-4.68 (m, 1H), 4.77 (s, 1H), 5.08 (br. s., 1H), 5.63 (td, J=10.04, 5.77 Hz, 1H), 5.85 (br. s., 1H), 7.52-7.61 (m, 2H), 7.75 (dd, J=9.54, 2.51 Hz, 1H), 8.19 (dd, J=9.16, 5.40 Hz, 1H); MS: MS m/z 841.4 ($M^+$+1).

Preparation of Compound 4003 tert-butyl (2R,6S,7R,9R,13aS,14aR,16aS,Z)-14a-(cyclopropylsulfonylcarbamoyl)-7-ethyl-2-(7-fluoro-6-methoxyisoquinolin-1-yloxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate Compound 4003

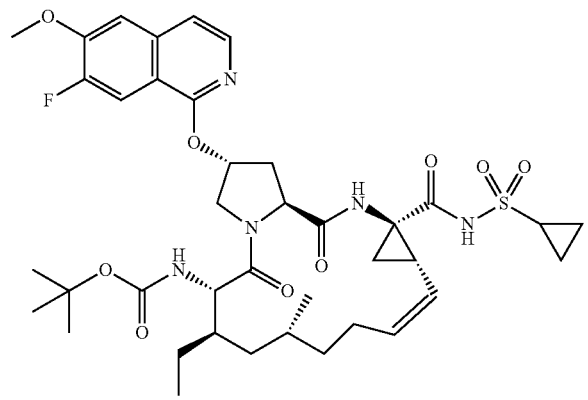

Compound 4003 was prepared using the intermediates described herein and by following the general procedure described for the synthesis of Compound 4001. $^1$H NMR (400 MHz, CD$_3$OD): δ ppm 0.85 (d, J=15.06 Hz, 3H), 1.02 (m, 7H), 1.06-1.19 (m, 7H), 1.29 (t, J=9.16 Hz, 3H), 1.42-1.63 (m, 6H), 1.77 (dd, J=8.28, 5.27 Hz, 1H), 1.96 (s, 3H), 2.37-2.49 (m, 2H), 2.66-2.78 (m, 2H), 2.92 (br. s., 1H), 4.01 (br. s., 5H), 4.09 (d, J=11.04 Hz, 1H), 4.58-4.65 (m, 1H), 4.75 (d, J=11.29 Hz, 1H), 5.15 (br. s., 1H), 5.56-5.65 (m, 1H), 5.90 (br. s., 1H), 7.26-7.33 (m, 1H), 7.40 (s, 1H), 7.78 (s, 1H), 7.92-7.93 (m, 1H); MS: MS m/z 786.4 (M$^+$+1).

Preparation of (2R,6S,7R,9R,13aS,14aR,16aS,Z)-6-amino-N-(cyclopropylsulfonyl)-7-ethyl-2-(7-fluoro-6-methoxyisoquinolin-1-yloxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride

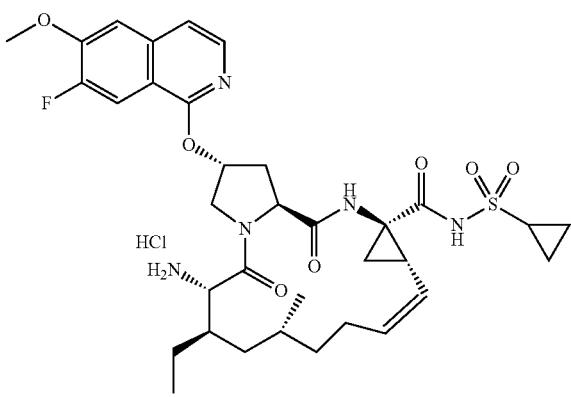 [SMILES: CC[C@@H]1C[C@H](C)CC/C=C\[C@@H]2C[C@@]2(C(=O)NS(=O)(=O)C2CC2)NC(=O)[C@@H]2C[C@@H](Oc3nccc4cc(OC)c(F)cc34)CN2C(=O)[C@H]1N ; Cl]

A solution of Compound 4003 (100 mg, 0.10 mmole) in 4M HCl in dioxane was stirred at room temperature for 30 min. The solvent was evaporated under reduced pressure to get crude compound (70.6 mg, 98%). The crude compound was washed with diethyl ether and taken to the next step without further purification. MS: MS m/z 687.2 (M$^+$+1).

Preparation of Compound 4004

1,1,1-trifluoro-2-methylpropan-2-yl (2R,6S,7R,9R,13aS,14aR,16aS,Z)-14a-(cyclopropylsulfonylcarbamoyl)-7-ethyl-2-(7-fluoro-6-methoxyisoquinolin-1-yloxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate Compound 4004

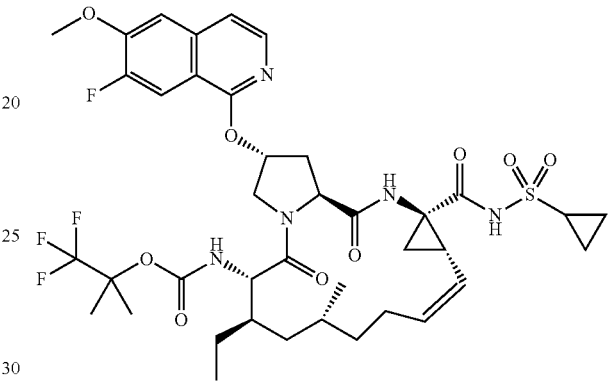

Compound 4004 was prepared using the intermediates described herein and by following the general procedure described for the synthesis of Compound 3. $^1$H NMR (400 MHz, CD$_3$OD): δ ppm 0.83 (t, J=7.40 Hz, 3H), 0.99-1.05 (m, 4H), 1.08-1.17 (m, 6H), 1.30-1.42 (m, 5H), 1.52-1.64 (m, 5H), 1.78 (dd, J=8.41, 5.65 Hz, 1H), 1.98 (t, J=10.67 Hz, 2H), 2.43 (ddd, J=13.74, 10.23, 3.89 Hz, 2H), 2.68-2.79 (m, 2H), 2.90-2.98 (m, 1H), 3.98-4.08 (m, 5H), 4.64 (dd, J=10.04, 7.03 Hz, 1H), 4.73 (d, J=10.54 Hz, 1H), 5.04 (t, J=10.04 Hz, 1H), 5.63 (td, J=10.23, 5.90 Hz, 1H), 5.85-5.93 (m, 1H), 7.31 (d, J=5.77 Hz, 1H), 7.40 (d, J=8.28 Hz, 1H), 7.77 (d, J=11.54 Hz, 1H), 7.93-7.98 (m, 1H), 7.95 (d, J=6.02 Hz, 1H); MS: MS m/z 841.2 (M$^+$+1).

Preparation of Compound 4005 tert-butyl (2R,6S,7R,9R,13aS,14aR,16aS,Z)-14a-(cyclopropylsulfonylcarbamoyl)-7-ethyl-2-(6-methoxyisoquinolin-1-yloxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate Compound 4005

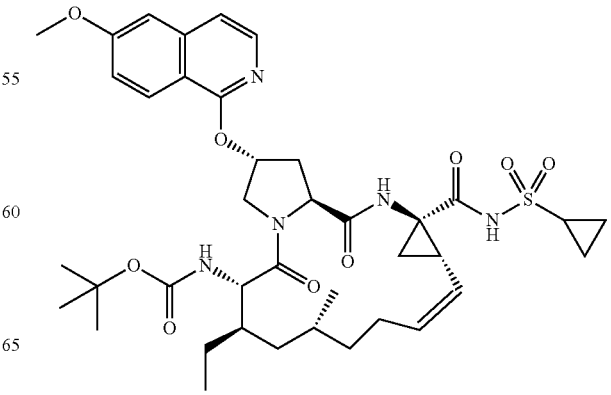

Compound 4005 was prepared using the intermediates described herein and by following the general procedure described for the synthesis of Compound 1. ¹H NMR (400 MHz, CD₃OD): δ ppm 0.79-0.92 (m, 4H), 1.03 (m, 4H), 1.16 (s, 9H) 1.28-1.37 (m, 2H), 1.44-1.67 (m, 6H), 1.78 (d, J=5.52 Hz, 1H), 1.85-2.02 (m, 2H), 2.43 (t, J=10.16 Hz, 2H), 2.68-2.79 (m, 2H), 2.87-2.99 (m, 1H), 3.94 (s, 3H), 4.01-4.17 (m, 2H), 4.51-4.63 (m, 1H), 4.75 (d, J=11.04 Hz, 1H), 5.08 (br. s., 1H), 5.56-5.67 (m, 1H), 5.89 (br. s., 1H), 7.09 (dd, J=9.03, 2.26 Hz, 1H), 7.19 (d, J=2.26 Hz, 1H), 7.26 (d, J=5.77 Hz, 1H), 7.93 (s, 1H), 8.10 (d, J=9.29 Hz, 1H); MS: MS m/z 768.4 (M⁺+1).

Preparation of (2R,6S,7R,9R,13aS,14aR,16aS,Z)-6-amino-N-(cyclopropylsulfonyl)-7-ethyl-2-(6-methoxyisoquinolin-1-yloxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride

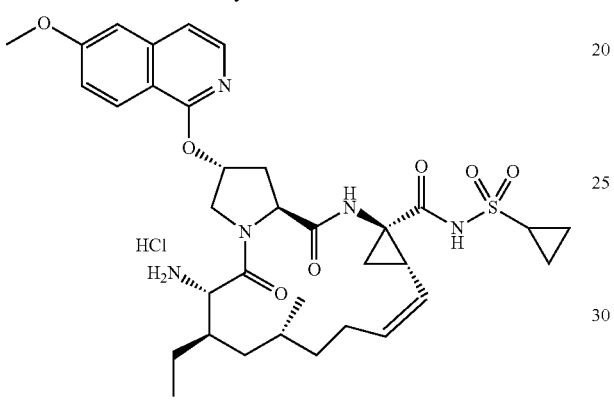

A solution of Compound 4005 (100 mg, 0.13 mmole) in 4M HCl in dioxane was stirred at room temperature for 30 min. The solvent was evaporated under reduced pressure to get crude compound (89 mg, 97%). The crude compound was washed with diethyl ether and taken to the next step without further purification. MS: MS m/z 669.1 (M⁺+1).

Preparation of Compound 4006

1,1,1-trifluoro-2-methylpropan-2-yl (2R,6S,7R,9R,13aS,14aR,16aS,Z)-14a-(cyclopropylsulfonylcarbamoyl)-7-ethyl-2-(6-methoxyisoquinolin-1-yloxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate Compound 4006

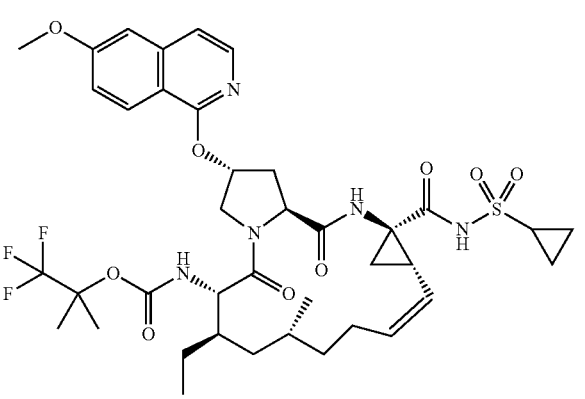

Compound 4006 was prepared using the intermediates described herein and by following the general procedure described for the synthesis of Compound 3. ¹H NMR (400 MHz, CD₃OD): δ ppm 0.83 (d, J=15.06 Hz, 3H), 0.94-1.18 (m, 11H), 1.28-1.41 (m, 5H), 1.43-1.64 (m, 7H), 1.75-1.81 (m, 1H), 1.92-2.05 (m, 2H), 2.36-2.50 (m, 2H), 2.66-2.78 (m, 2H), 2.88-2.98 (m, 1H), 3.95 (s, 3H), 3.99-4.09 (m, 2H), 4.65 (dd, J=10.29, 7.03 Hz, 1H), 4.72-4.80 (m, 1H), 5.04 (t, J=9.79 Hz, 1H), 5.63 (td, J=10.16, 6.02 Hz, 1H), 5.88 (d, J=6.27 Hz, 1H), 7.12 (dd, J=9.03, 2.51 Hz, 1H), 7.22 (d, J=2.51 Hz, 1H), 7.28 (d, J=6.02 Hz, 1H), 7.90-7.96 (m, 1H), 8.09 (d, J=9.04 Hz, 1H), 9.00 (s, 1H); MS: MS m/z 822.2 (M⁺+1).

Preparation of Compound 4007 tert-butyl (2R,6S,7R,9R,13aS,14aR,16aS,Z)-14a-(cyclopropylsulfonylcarbamoyl)-7-ethyl-2-(4-methoxyisoquinolin-1-yloxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate Compound 4007

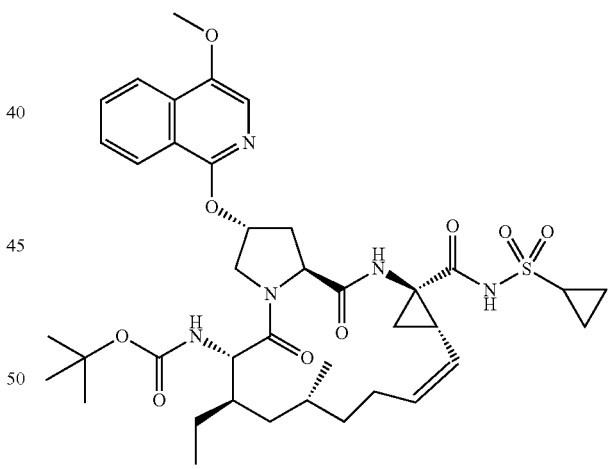

Compound 4007 was prepared using the intermediates described herein and by following the general procedure described for the synthesis of Compound 1. ¹H NMR (400 MHz, CD₃OD): δ ppm 0.82-0.86 (m, 4H), 1.01-1.12 (m, 7H), 1.16 (s, 9H), 1.27-1.34 (m, 7H), 1.51-1.58 (m, 1H), 1.60-1.95 (m, 2H), 2.42-2.43 (m, 2H), 2.71-2.75 (m, 2H), 2.93 (m, 1H), 4.02-4.04 (m, 4H), 4.11 (m, 1H), 4.61-4.62 (m, 1H), 4.75-4.84 (m, 1H), 5.04 (m, 1H), 5.84 (m, 1H), 6.58-6.61 (m, 1H), 7.55-7.57 (m, 2H), 7.72 (m, 1H), 8.09-8.14 (m, 2H); MS: MS m/z 768.5 (M⁺+1).

Preparation of (2R,6S,7R,9R,13aS,14aR,16aS,Z)-6-amino-N-(cyclopropylsulfonyl)-7-ethyl-2-(4-methoxyisoquinolin-1-yloxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride

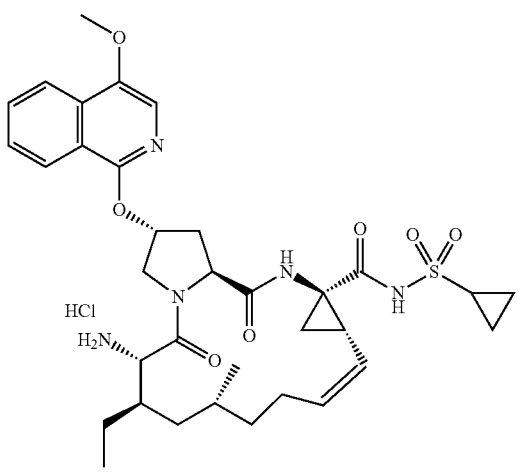 [SMILES: CC[C@@H]1C[C@H](C)CC/C=C\[C@@H]2C[C@@]2(C(=O)NS(=O)(=O)C2CC2)NC(=O)[C@@H]2C[C@@H](Oc3ncc(OC)c4ccccc34)CN2C(=O)[C@H]1N ; Cl]

A solution of Compound 4007 (100 mg, 0.13 mmole) in 4M HCl in dioxane was stirred at room temperature for 30 min. The solvent was evaporated under reduced pressure to get crude compound (70 mg, 99%). The crude compound was washed with diethyl ether and taken to the next step without further purification. MS: MS m/z 668.6 (M$^+$+1).

Preparation of Compound 4008

1,1,1-trifluoro-2-methylpropan-2-yl (2R,6S,7R,9R,13aS,14aR,16aS,Z)-14a-(cyclopropylsulfonylcarbamoyl)-7-ethyl-2-(4-methoxyisoquinolin-1-yloxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate Compound 4008

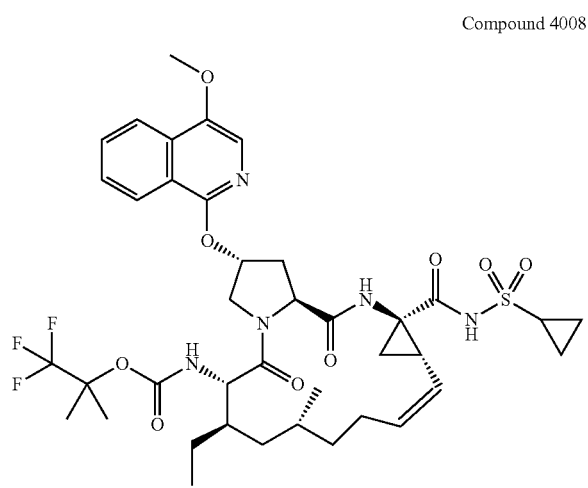 [SMILES: CC[C@@H]1C[C@H](C)CC/C=C\[C@@H]2C[C@@]2(C(=O)NS(=O)(=O)C2CC2)NC(=O)[C@@H]2C[C@@H](Oc3ncc(OC)c4ccccc34)CN2C(=O)[C@H]1NC(=O)OC(C)(C)C(F)(F)F]

Compound 4008 was prepared using the intermediates described herein and by following the general procedure described for the synthesis of Compound 3. $^1$H NMR (400 MHz, CD$_3$OD): δ ppm 0.80 (d, J=15.06 Hz, 3H), 0.89 (s, 3H), 0.97-1.16 (m, 8H), 1.25-1.36 (m, 6H), 1.41-1.61 (m, 7H), 1.76 (dd, J=8.28, 5.52 Hz, 1H), 1.90-2.02 (m, 2H), 2.41 (ddd, J=13.87, 10.10, 3.89 Hz, 2H), 2.66-2.77 (m, 2H), 2.87-2.96 (m, 1H), 3.93-4.04 (m, 5H), 4.63 (dd, J=10.16, 6.90 Hz, 1H), 4.96-5.07 (m, 1H), 5.60 (td, J=9.98, 6.15 Hz, 1H), 5.82 (br. s., 1H), 7.52-7.58 (m, 2H), 7.72 (ddd, J=8.28, 7.03, 1.25 Hz, 1H), 8.12 (dd, J=12.17, 8.41 Hz, 2H); $^{19}$F NMR: δ ppm −85.11 (3 F); MS: MS m/z 822.52 (M$^+$+1).

Preparation of Compound 4009 tert-butyl (2R,6S,7R,9R,13aS,14aR,16aS,Z)-14a-(cyclopropylsulfonylcarbamoyl)-2-(4-ethoxyisoquinolin-1-yloxy)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate Compound 4009

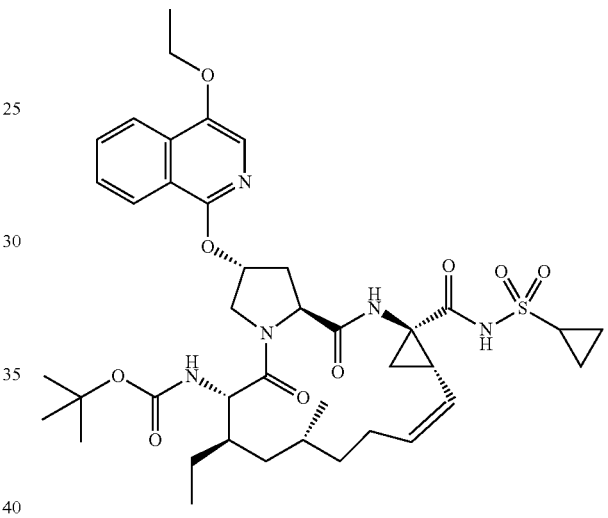

Compound 4009 was prepared using the intermediates described herein and by following the general procedure described for the synthesis of Compound 1. MS: MS m/z 783.3 (M$^+$+1).

Preparation of Compound 4013

Compound 4013

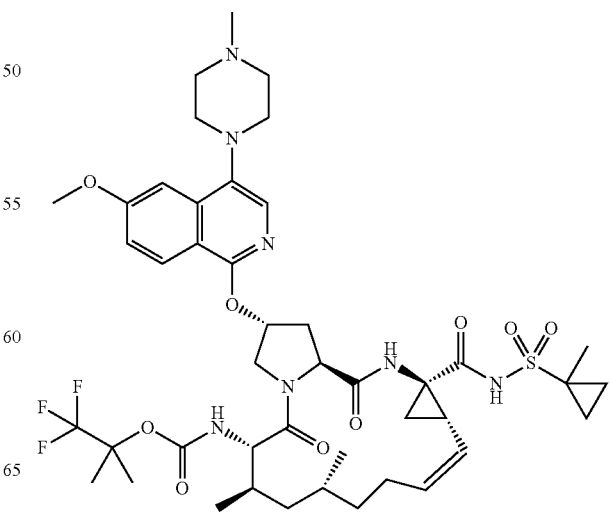

Compound 4013 was prepared using the intermediates described herein and by following the general procedure described for the synthesis of Compound 3.

Compound 4013: 1,1,1-trifluoro-2-methylpropan-2-yl (2R,6S,7R,9R,13aS,14aR,16aS,Z)-2-(6-methoxy-4-(4-methylpiperazin-1-yl)isoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 9.05 (s, 1H) 8.11-8.17 (m, 1H) 7.79 (s, 1H) 7.41 (d, J=2.51 Hz, 1H) 7.35 (d, J=8.03 Hz, 1H) 7.18 (dd, J=9.03, 2.51 Hz, 1H) 5.87 (br. s., 1H) 5.63 (td, J=10.48, 5.40 Hz, 1H) 5.00 (t, J=9.91 Hz, 1H) 4.61-4.75 (m, 2H) 3.97-4.06 (m, 4H) 3.78-3.84 (m, 1H) 3.65-3.72 (m, 2H) 3.45-3.57 (m, 4H) 3.19-3.28 (m, 2H) 3.06 (s, 3H) 2.68-2.76 (m, 2H) 2.44 (ddd, J=13.80, 10.04, 4.27 Hz, 2H) 1.77 (dd, J=8.28, 5.52 Hz, 1H) 1.64-1.70 (m, 1H) 1.57 (dd, J=9.41, 5.65 Hz, 1H) 1.39-1.53 (m, 6H) 1.20-1.37 (m, 6H) 0.96-1.05 (m, 9H) 0.79-0.94 (m, 4H); MS: MS m/z 920.9 (M$^+$+1).

Scheme:

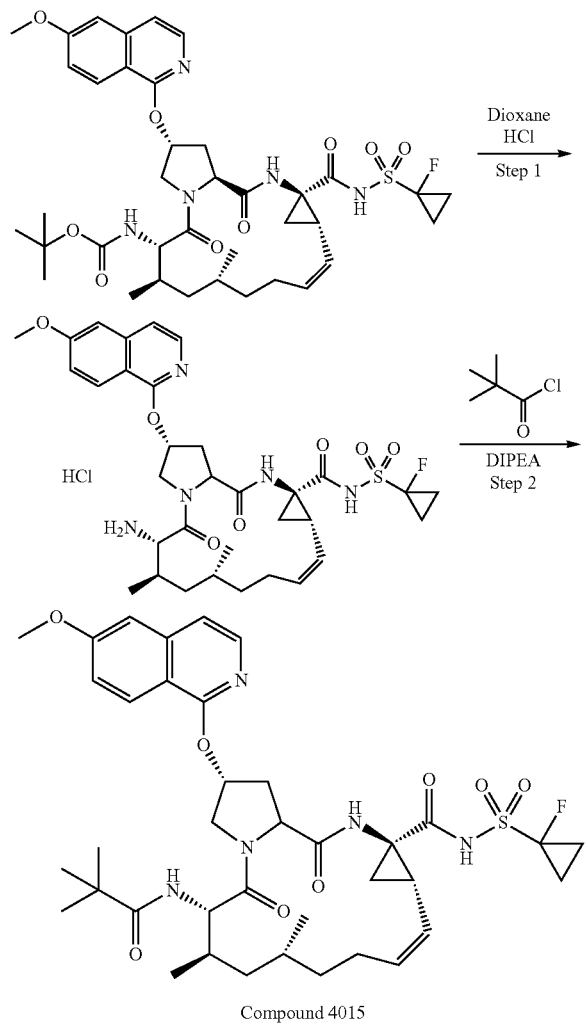

Compound 4015

Step 1: Preparation of (2R,6S,7R,9R,13aS,14aR,16aS,Z)-6-amino-N-(1-fluorocyclopropylsulfonyl)-2-(6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride A solution of tert-butyl ((2R,6S,7R,9R,13aS,14aR,16aS,Z)-14a-(((1-fluorocyclopropyl)sulfonyl)carbamoyl)-2-((6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (30 mg, 0.039 mmol) in 4M HCl in dioxane (5 ml 4M solution) was stirred at room temperature for 2 h. The solvent was evaporated under reduced pressure to get crude compound (23 mg, 90%) as brown solid. The crude compound was washed with diethyl ether and taken to the next step without further purification. MS: MS m/z 772.8.0 (M$^+$−36).

Step 2: Preparation of Compound 4015

To a solution of (2R,6S,7R,9R,13aS,14aR,16aS,Z)-6-amino-N-(1-fluorocyclopropylsulfonyl)-2-(6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride (23 mg, 0.034 mmol) in DCM was added pivaloyl chloride (4 mg, 0.034 mmol) followed by DIPEA (15 mg, 0.12 mmol) at room temperature. The reaction mass was stirred at room temperature for 30 min. The reaction mass was diluted with DCM and washed with water. The organic layer was dried over anhydrous sodium sulfate, filtered and evaporated to get crude compound. The crude compound was purified by prep-HPLC to get 10 mg (40%) of Compound 4015 as a white solid. $^1$H NMR (400 MHz, CD$_3$OD): δ ppm 8.97 (s, 1H) 8.05 (d, J=9.29 Hz, 1H) 7.89 (d, J=5.77 Hz, 1H) 7.25 (d, J=6.02 Hz, 1H) 7.17-7.20 (m, 1H) 7.07 (dd, J=9.03, 2.26 Hz, 1H) 5.86-5.90 (m, 1H) 5.57-5.64 (m, 1H) 4.98 (t, J=10.04 Hz, 1H) 4.53-4.63 (m, 2H) 4.27 (dd, J=10.67, 8.66 Hz, 1H) 4.05 (dd, J=11.54, 3.76 Hz, 1H) 3.92 (s, 3H) 2.73 (t, J=8.16 Hz, 2H) 2.35-2.46 (m, 2H) 1.94-2.06 (m, 2H) 1.69-1.82 (m, 3H) 1.44-1.66 (m, 6H) 1.19-1.38 (m, 3H) 0.96-1.02 (m, 11H) 0.93 (d, J=6.53 Hz, 3H) 0.80-0.88 (m, 1H); MS: MS m/z 756.0 (M$^+$+1).

Preparation of Compound 4016

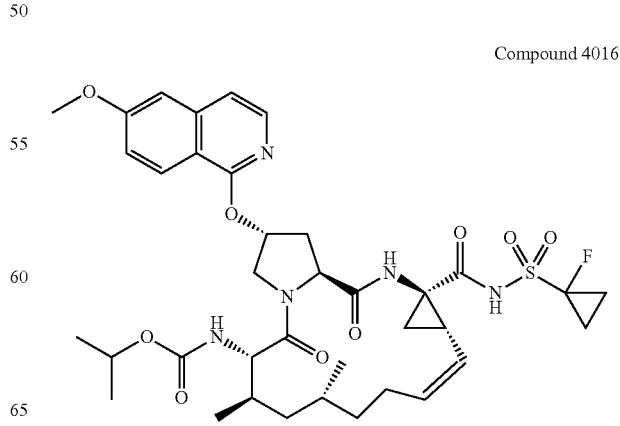

Compound 4016

Compound 4016 was prepared using the intermediates described herein and by following the general procedure described for the synthesis of Compound 3.

Compound 4016: isopropyl (2R,6S,7R,9R,13aS,14aR,16aS,Z)-14a-(1-fluorocyclopropylsulfonylcarbamoyl)-2-(6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 9.02 (s, 1H) 8.12 (d, J=9.03 Hz, 1H) 7.92 (d, J=6.02 Hz, 1H) 7.29 (d, J=6.02 Hz, 1H) 7.22 (d, J=2.26 Hz, 1H) 7.12 (d, J=9.03 Hz, 1H) 5.91 (br. s., 1H) 5.57-5.65 (m, 1H) 4.94-5.02 (m, 1H) 4.70 (d, J=11.04 Hz, 1H) 4.62 (dd, J=9.79, 7.03 Hz, 1H) 4.30-4.38 (m, 1H) 4.05 (dd, J=11.29, 3.51 Hz, 1H) 3.90-3.96 (m, 4H) 2.69-2.79 (m, 2H) 2.33-2.49 (m, 2H) 1.99 (br. s., 1H) 1.89 (d, J=5.52 Hz, 1H) 1.72-1.83 (m, 3H) 1.56-1.70 (m, 2H) 1.45-1.54 (m, 4H) 1.20-1.33 (m, 2H) 1.08 (d, J=6.27 Hz, 3H) 1.00 (dd, J=11.29, 6.53 Hz, 6H) 0.92 (d, J=6.27 Hz, 3H) 0.81-0.88 (m, 1H); MS: MS m/z 758.9 (M$^+$+1).

Preparation of Compound 4017

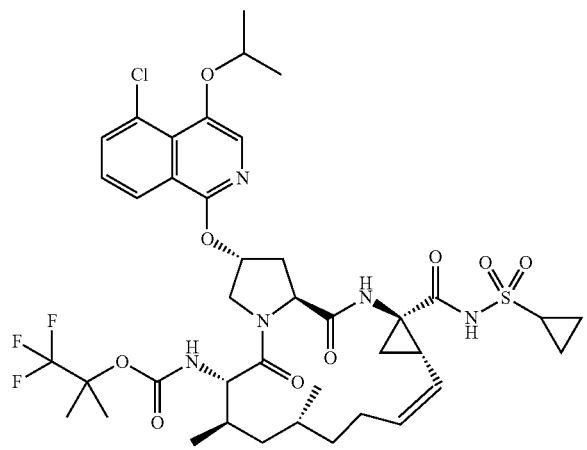

Compound 4017

Compound 4017 was prepared using the intermediates described herein and by following the general procedure described for the synthesis of Compound 3.

Compound 4017: 1,1,1-trifluoro-2-methylpropan-2-yl (2R,6S,7R,9R,13aS,14aR,16aS,Z)-2-(5-chloro-4-isopropoxyisoquinolin-1-yloxy)-14a-(cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.17 (dd, J=8.28, 1.00 Hz, 1H) 7.72-7.77 (m, 2H) 7.45 (t, J=7.91 Hz, 1H) 5.83 (br. s., 1H) 5.59-5.66 (m, 1H) 5.04 (t, J=9.91 Hz, 1H) 4.77 (d, J=11.80 Hz, 1H) 4.64-4.70 (m, 2H) 3.98 (dd, J=11.54, 3.26 Hz, 1H) 3.76-3.82 (m, 1H) 2.90-2.97 (m, 1H) 2.68-2.78 (m, 2H) 2.43 (ddd, J=13.87, 10.23, 4.02 Hz, 2H) 2.00 (br. s., 1H) 1.75-1.90 (m, 3H) 1.59 (dd, J=9.54, 5.52 Hz, 1H) 1.50 (d, J=7.03 Hz, 2H) 1.44 (dd, J=6.02, 2.76 Hz, 7H) 1.31-1.36 (m, 4H) 1.21-1.28 (m, 1H) 1.05-1.19 (m, 3H) 1.02 (d, J=7.03 Hz, 3H) 0.98 (d, J=6.27 Hz, 3H) 0.92 (s, 3H) 0.78-0.86 (m, 3H); MS: MS m/z 870.8 (M$^+$+1).

Preparation of Compound 4018

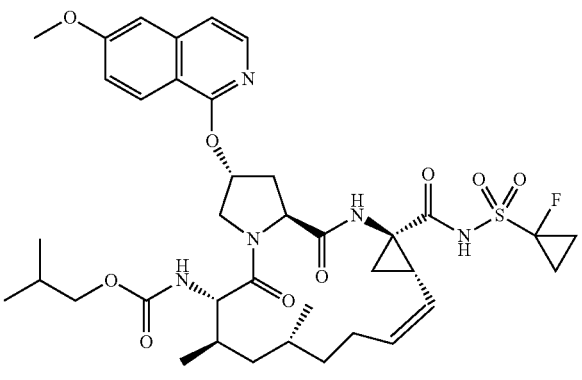

Compound 4018

Compound 4018 was prepared using the intermediates described herein and by following the general procedure described for the synthesis of Compound 3.

Compound 4018: isobutyl (2R,6S,7R,9R,13aS,14aR,16aS,Z)-14a-(1-fluorocyclopropylsulfonylcarbamoyl)-2-(6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 9.02 (s, 1H) 8.10 (d, J=9.29 Hz, 1H) 7.92 (d, J=5.77 Hz, 1H) 7.28 (d, J=6.02 Hz, 1H) 7.21 (d, J=2.26 Hz, 1H) 7.11 (dd, J=9.16, 2.38 Hz, 1H) 5.91 (br. s., 1H) 5.61 (td, J=10.16, 6.02 Hz, 1H) 5.00 (t, J=9.91 Hz, 1H) 4.59-4.72 (m, 2H) 4.04 (dd, J=11.42, 3.39 Hz, 1H) 3.88-3.96 (m, 4H) 3.43-3.49 (m, 1H) 2.71-2.79 (m, 2H) 2.36-2.48 (m, 2H) 1.91 (d, J=5.77 Hz, 3H) 1.72-1.81 (m, 3H) 1.58-1.68 (m, 3H) 1.46-1.55 (m, 3H) 1.21-1.31 (m, 2H) 1.00 (dd, J=10.79, 6.78 Hz, 6H) 0.81-0.88 (m, 1H) 0.78 (dd, J=6.78, 1.76 Hz, 6H); MS: MS m/z 772.4 (M$^+$+1).

Preparation of Compound 4019

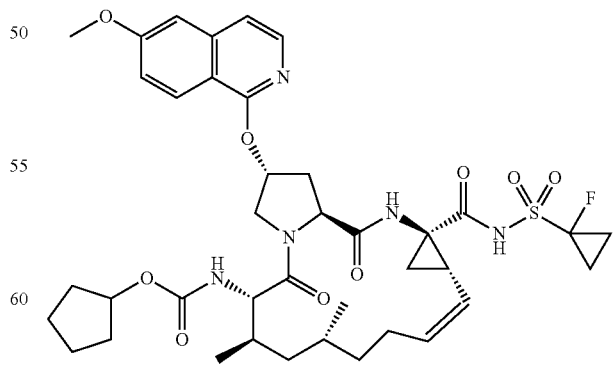

Compound 4019

Compound 4019 was prepared using the intermediates described herein and by following the general procedure described for the synthesis of Compound 3.

Compound 4019: cyclopentyl (2R,6S,7R,9R,13aS,14aR,16aS,Z)-14a-(1-fluorocyclopropylsulfonylcarbamoyl)-2-(6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

¹H NMR (400 MHz, CD₃OD): δ ppm 9.02 (s, 1H) 8.12 (d, J=9.03 Hz, 1H) 7.92 (d, J=6.02 Hz, 1H) 7.29 (d, J=6.02 Hz, 1H) 7.22 (d, J=2.26 Hz, 1H) 7.13 (dd, J=9.03, 2.51 Hz, 1H) 5.91 (br. s., 1H) 5.61 (td, J=10.04, 6.02 Hz, 1H) 4.99 (t, J=9.91 Hz, 1H) 4.60-4.73 (m, 2H) 4.50 (br. s., 1H) 4.04 (dd, J=11.54, 3.26 Hz, 1H) 3.89-3.97 (m, 4H) 2.71-2.79 (m, 2H) 2.33-2.48 (m, 2H) 1.84-2.05 (m, 2H) 1.72-1.81 (m, 3H) 1.57-1.70 (m, 4H) 1.40-1.55 (m, 9H) 1.20-1.34 (m, 3H) 0.99 (dd, J=14.18, 6.65 Hz, 6H) 0.79-0.87 (m, 1H); MS: MS m/z 784.4 (M⁺+1).

Preparation of Compound 4020

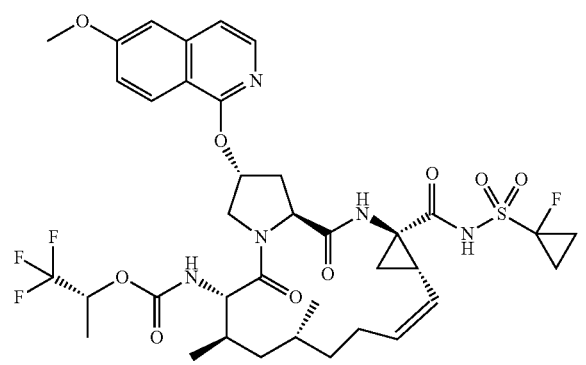

Compound 4020

Compound 4020 was prepared using the intermediates described herein and by following the general procedure described for the synthesis of Compound 3.

Compound 4020: (R)-1,1,1-trifluoropropan-2-yl (2R,6S,7R,9R,13aS,14aR,16aS,Z)-14a-(1-fluorocyclopropylsulfonylcarbamoyl)-2-(6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

¹H NMR (400 MHz, CD₃OD): δ ppm 9.01 (s, 1H) 8.09 (s, 1H) 7.89-7.93 (m, 1H) 7.28 (d, J=5.77 Hz, 1H) 7.21 (d, J=2.51 Hz, 1H) 7.08 (dd, J=9.16, 2.38 Hz, 1H) 5.89 (br. s., 1H) 5.61 (td, J=9.85, 6.15 Hz, 1H) 4.96-5.03 (m, 1H) 4.77 (s, 1H) 4.63 (dd, J=10.04, 7.28 Hz, 1H) 4.52 (dt, J=13.43, 6.84 Hz, 1H) 4.02 (dd, J=11.42, 3.39 Hz, 1H) 3.92-3.96 (m, 3H) 3.85-3.90 (m, 1H) 2.69-2.79 (m, 2H) 2.33-2.48 (m, 2H) 1.89-2.05 (m, 2H) 1.70-1.83 (m, 3H) 1.57-1.69 (m, 2H) 1.41-1.56 (m, 4H) 1.30-1.37 (m, 2H) 1.18-1.27 (m, 4H) 1.01 (dd, J=8.28, 6.78 Hz, 6H) 0.81-0.88 (m, 1H); MS: MS m/z 810.2 (M⁺−1).

Preparation of Compound 4022

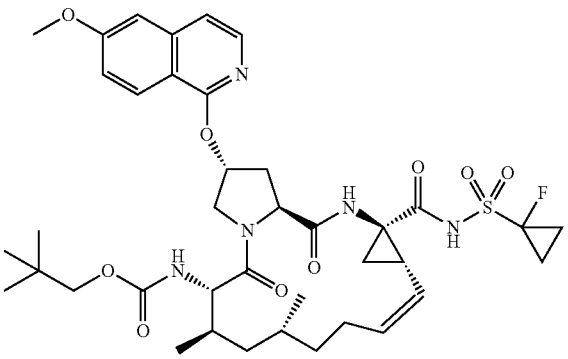

Compound 4022

Compound 4022 was prepared using the intermediates described herein and by following the general procedure described for the synthesis of Compound 3.

Compound 4022: neopentyl (2R,6S,7R,9R,13aS,14aR,16aS,Z)-14a-(1-fluorocyclopropylsulfonylcarbamoyl)-2-(6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

¹H NMR (400 MHz, CD₃OD): δ ppm 9.05 (s, 1H) 8.12 (d, J=9.29 Hz, 1H) 7.93 (d, J=6.02 Hz, 1H) 7.30 (d, J=6.02 Hz, 1H) 7.23 (d, J=2.51 Hz, 1H) 7.12 (dd, J=9.16, 2.38 Hz, 1H) 5.91 (br. s., 1H) 5.58-5.66 (m, 1H) 5.01 (t, J=9.91 Hz, 1H) 4.74 (d, J=11.29 Hz, 1H) 4.63 (dd, J=10.29, 7.28 Hz, 1H) 4.04 (dd, J=11.67, 3.64 Hz, 1H) 3.95 (s, 3H) 3.93 (s, 1H) 3.21 (d, J=10.29 Hz, 1H) 2.72-2.79 (m, 2H) 2.39-2.47 (m, 1H) 1.88-2.04 (m, 2H) 1.74-1.81 (m, 3H) 1.60-1.69 (m, 3H) 1.48-1.55 (m, 3H) 1.26 (br. s., 2H) 1.01 (d, J=3.26 Hz, 6H) 0.85 (s, 1H) 0.79 (s, 9H) 0.70 (br. s., 1H); MS: MS m/z 786.2 (M⁺+1).

Preparation of Compound 4024

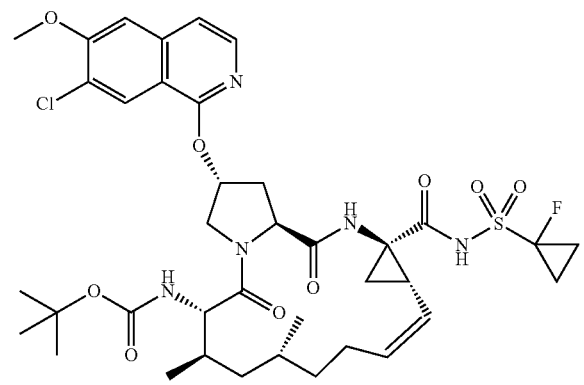

Compound 4024

Compound 4024 was prepared using the intermediates described herein and by following the general procedure described for the synthesis of Compound 1.

Compound 2024: tert-butyl (2R,6S,7R,9R,13aS,14aR,16aS,Z)-2-(7-chloro-6-methoxyisoquinolin-1-yloxy)-14a-

(1-fluorocyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

¹H NMR (400 MHz, CD₃OD): δ ppm 8.12 (s, 1H) 7.96 (d, J=6.02 Hz, 1H) 7.35 (s, 1H) 7.29 (d, J=6.02 Hz, 1H) 6.60 (d, J=8.53 Hz, 1H) 5.92 (br. s., 1H) 5.55-5.61 (m, 1H) 4.68 (s, 2H) 4.02-4.06 (m, 4H) 3.83 (d, J=10.29 Hz, 1H) 2.69-2.75 (m, 1H) 2.35-2.51 (m, 2H) 2.01 (s, 2H) 1.79-1.89 (m, 2H) 1.73-1.76 (m, 1H) 1.60 (dd, J=9.66, 5.40 Hz, 2H) 1.40-1.52 (m, 3H) 1.23-1.32 (m, 2H) 1.15 (br. s., 1H) 1.08 (s, 9H) 1.00 (dd, J=14.05, 6.78 Hz, 6H) 0.81 (t, J=12.17 Hz, 1H); MS: MS m/z 804.2 (M⁺−1).

Preparation of Compound 4025

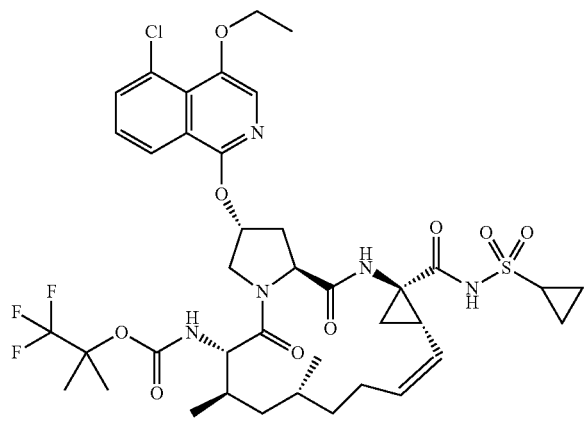

Compound 4025

Compound 4025 was prepared using the intermediates described herein and by following the general procedure described for the synthesis of Compound 3.

Compound 2025: 1,1,1-trifluoro-2-methylpropan-2-yl (2R,6S,7R,9R,13aS,14aR,16aS,Z)-2-(5-chloro-4-ethoxyisoquinolin-1-yloxy)-14a-(cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. ¹H NMR (400 MHz, CD₃OD): δ ppm 8.18 (dd, J=8.41, 1.13 Hz, 1H) 7.78 (dd, J=7.65, 1.13 Hz, 1H) 7.71 (s, 1H) 7.47 (t, J=8.03 Hz, 1H) 5.83 (br. s., 1H) 5.59-5.66 (m, 1H) 5.06 (t, J=9.41 Hz, 1H) 4.78 (d, J=11.80 Hz, 1H) 4.65 (dd, J=10.54, 7.03 Hz, 1H) 4.18 (q, J=6.86 Hz, 2H) 3.98 (dd, J=11.42, 3.14 Hz, 1H) 3.72-3.81 (m, 2H) 3.26 (d, J=7.28 Hz, 1H) 2.91-2.98 (m, 1H) 2.68-2.78 (m, 2H) 2.40-2.47 (m, 2H) 1.91-2.02 (m, 1H) 1.76-1.88 (m, 3H) 1.60 (d, J=4.02 Hz, 1H) 1.51-1.55 (m, 3H) 1.44-1.50 (m, 1H) 1.40 (d, J=5.52 Hz, 3H) 1.35 (s, 2H) 1.24 (d, J=9.03 Hz, 1H) 1.14-1.18 (m, 1H) 0.98-1.04 (m, 6H) 0.94 (s, 3H) 0.83 (t, J=11.92 Hz, 1H); MS: MS m/z 855.4 (M⁺−1).

Preparation of Compound 4026

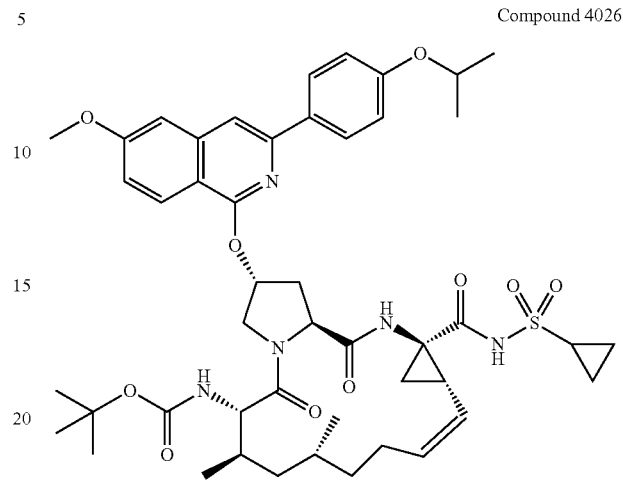 [SMILES: COc1ccc2c(O[C@@H]3C[C@H]4C(=O)N[C@]5(C(=O)NS(=O)(=O)C6CC6)C[C@H]5/C=C\CC[C@@H](C)C[C@@H](C)[C@H](NC(=O)OC(C)(C)C(F)(F)F)C(=O)N4C3)nc(-c3ccc(OC(C)C)cc3)cc2c1]

Compound 4026

Compound 4026 was prepared using the intermediates described herein and by following the general procedure described for the synthesis of Compound 1.

Compound 4026: tert-butyl (2R,6S,7R,9R,13aS,14aR,16aS,Z)-14a-(cyclopropylsulfonylcarbamoyl)-2-((3-(4-isopropoxyphenyl)-6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

¹H NMR (400 MHz, CD₃OD): δ ppm 8.05-8.13 (m, 3H) 7.68 (s, 1H) 7.23 (s, 1H) 7.02 (d, J=8.78 Hz, 3H) 6.08 (br. s., 1H) 5.59-5.66 (m, 1H) 5.05 (t, J=10.16 Hz, 1H) 4.55-4.74 (m, 3H) 4.15 (d, J=8.53 Hz, 1H) 3.95 (s, 3H) 2.94 (br. s., 1H) 2.72-2.85 (m, 2H) 2.41-2.54 (m, 2H) 2.00 (br. s., 1H) 1.76-1.92 (m, 4H) 1.60 (d, J=9.54 Hz, 1H) 1.44-1.55 (m, 3H) 1.37 (s, 4H) 1.31 (br. s., 3H) 1.23 (s, 6H) 1.08-1.17 (m, 2H) 1.02 (dd, J=16.19, 6.40 Hz, 9H) 0.83-0.93 (m, 2H); MS: MS m/z 886.9 (M⁺−1).

Preparation of Compound 4027

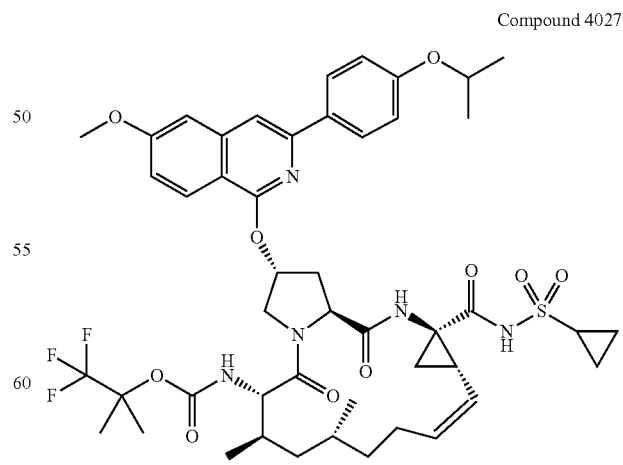

Compound 4027

Compound 4027 was prepared using the intermediates described herein and by following the general procedure described for the synthesis of Compound 3.

Compound 4027: 1,1,1-trifluoro-2-methylpropan-2-yl (2R,6S,7R,9R,13aS,14aR,16aS,Z)-14a-(cyclopropylsulfonylcarbamoyl)-2-((3-(4-isopropoxyphenyl)-6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. ¹H NMR (400 MHz, CD₃OD): δ ppm 8.05-8.13 (m, 3H) 7.69 (s, 1H) 7.22-7.32 (m, 1H) 6.99-7.06 (m, 3H) 6.07 (br. s., 1H) 5.64 (td, J=10.04, 5.52 Hz, 1H) 5.03-5.09 (m, 1H) 4.78 (d, J=11.04 Hz, 1H) 4.64-4.74 (m, 2H) 4.12 (dd, J=11.54, 3.51 Hz, 1H) 3.96 (s, 3H) 3.87-3.92 (m, 1H) 2.91-2.98 (m, 1H) 2.70-2.84 (m, 2H) 2.38-2.53 (m, 2H) 1.77-2.03 (m, 4H) 1.58-1.62 (m, 1H) 1.45-1.55 (m, 2H) 1.41-1.43 (m, 3H) 1.37 (s, 4H) 1.30-1.35 (m, 2H) 1.26 (dd, J=8.91, 4.64 Hz, 1H) 1.13 (s, 3H) 1.04 (d, J=7.03 Hz, 3H) 1.00 (s, 6H) 0.83-0.89 (m, 2H); MS: MS m/z 940.2 (M⁺−1).

Preparation of Compound 4028

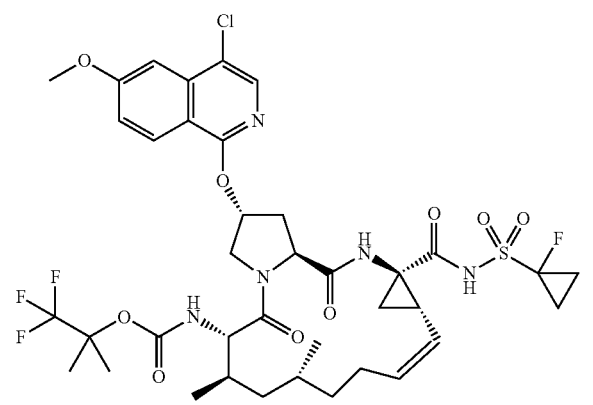

Compound 4028

Compound 4028 was prepared using the intermediates described herein and by following the general procedure described for the synthesis of Compound 3.

Compound 4028: 1,1,1-trifluoro-2-methylpropan-2-yl (2R,6S,7R,9R,13aS,14aR,16aS,Z)-2-(4-chloro-6-methoxyisoquinolin-1-yloxy)-14a-(1-fluorocyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. ¹H NMR (400 MHz, CD₃OD): δ ppm 8.12-8.18 (m, 1H) 8.02-8.06 (m, 1H) 7.40-7.43 (m, 1H) 7.20-7.24 (m, 1H) 5.83-5.87 (m, 1H) 5.56-5.63 (m, 1H) 4.72-4.78 (m, 1H) 4.62-4.67 (m, 1H) 4.00 (s, 4H) 3.78-3.83 (m, 1H) 2.71-2.77 (m, 1H) 2.35-2.49 (m, 2H) 1.94-2.02 (m, 1H) 1.71-1.89 (m, 4H) 1.56-1.67 (m, 3H) 1.40-1.51 (m, 4H) 1.33-1.36 (m, 3H) 1.30-1.32 (m, 1H) 1.20-1.27 (m, 1H) 1.06-1.16 (m, 1H) 0.95-1.03 (m, 6H) 0.89-0.92 (m, 1H) 0.78-0.86 (m, 2H); MS: MS m/z 858.2 (M⁺−1).

Preparation of Compound 4029

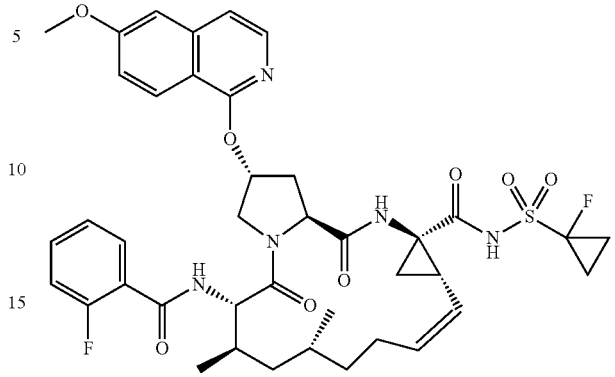

Compound 4029

To a solution (2R,6S,7R,9R,13aS,14aR,16aS,Z)-6-amino-N-(1-fluorocyclopropylsulfonyl)-2-(6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride (30 mg, 0.044 mmol) in DCM (10 ml) was added 2-fluorobenzoic acid (6.2 mg, 0.044 mmol) followed by HATU (15 mg, 0.05 mmol) and DIPEA (13 mg, 0.1 mmol) at room temperature. The reaction mixture was stirred at room temperature for 30 min. The reaction mass was diluted with water and extracted with DCM and washed with brine solution. The combine organic layer was dried over anhydrous Na₂SO₄ and evaporated under reduced pressure to get crude compound. The crude compound was purified by prep-HPLC to get desired compound (14 mg, 40%) as a white solid. ¹H NMR (400 MHz, CD₃OD): δ ppm 9.05 (s, 1H) 8.21-8.28 (m, 1H) 8.09 (d, J=9.04 Hz, 1H) 7.93 (d, J=5.77 Hz, 1H) 7.46-7.54 (m, 1H) 7.11-7.29 (m, 4H) 7.01-7.07 (m, 1H) 5.91-5.97 (m, 1H) 5.63 (d, J=6.02 Hz, 1H) 4.99-5.06 (m, 1H) 4.80 (d, J=12.55 Hz, 1H) 4.64 (dd, J=9.91, 6.90 Hz, 1H) 4.43-4.50 (m, 1H) 4.13 (dd, J=11.42, 3.64 Hz, 1H) 3.94 (s, 3H) 2.71-2.83 (m, 3H) 2.38-2.50 (m, 2H) 1.97-2.12 (m, 2H) 1.83-1.91 (m, 1H) 1.72-1.80 (m, 2H) 1.43-1.70 (m, 5H) 1.22-1.41 (m, 3H) 1.06 (dd, J=10.16, 6.65 Hz, 3H) 0.90-0.96 (m, 1H); MS: MS m/z 794.2 (M⁺+1).

Preparation of Compound 4030

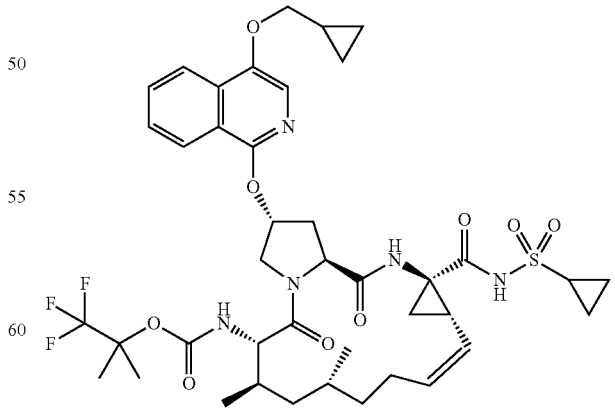

Compound 4030

Compound 4030 was prepared using the intermediates described herein and by following the general procedure described for the synthesis of Compound 3.

Compound 4030: 1,1,1-trifluoro-2-methylpropan-2-yl (2R,6S,7R,9R,13aS,14aR,16aS,Z)-2-(4-(cyclopropylmethoxy)isoquinolin-1-yloxy)-14a-(cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.17 (dd, J=8.28, 4.52 Hz, 2H) 7.75 (td, J=7.72, 1.13 Hz, 1H) 7.54-7.59 (m, 2H) 5.83 (br. s., 1H) 5.59-5.67 (m, 1H) 5.04 (t, J=9.91 Hz, 1H) 4.76 (d, J=11.54 Hz, 1H) 4.64-4.68 (m, 1H) 3.98-4.05 (m, 3H) 3.80-3.85 (m, 1H) 2.90-2.97 (m, 1H) 2.69-2.77 (m, 2H) 2.43 (ddd, J=13.80, 10.04, 4.02 Hz, 2H) 1.76-2.03 (m, 4H) 1.60 (dd, J=9.54, 5.52 Hz, 1H) 1.44-1.55 (m, 2H) 1.30-1.43 (m, 6H) 1.06-1.26 (m, 3H) 0.95-1.04 (m, 9H) 0.83 (t, J=11.80 Hz, 1H) 0.67-0.72 (m, 2H) 0.43-0.47 (m, 2H); MS: MS m/z 846.7 (M$^+$−1).

Preparation of Compound 4031

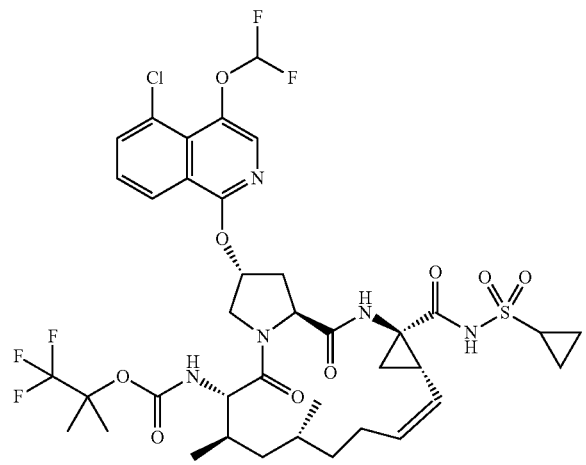

Compound 4031

Compound 4031 was prepared using the intermediates described herein and by following the general procedure described for the synthesis of Compound 3.

Compound 4031: 1,1,1-trifluoro-2-methylpropan-2-yl (2R,6S,7R,9R,13aS,14aR,16aS,Z)-2-(5-chloro-4-(difluoromethoxy)isoquinolin-1-yloxy)-14a-(cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.26 (dd, J=8.41, 1.13 Hz, 1H) 8.01 (s, 1H) 7.89 (dd, J=7.53, 1.00 Hz, 1H) 7.56 (t, J=7.91 Hz, 1H) 6.84 (s, 1H) 5.88-5.92 (m, 1H) 5.63 (td, J=10.48, 5.65 Hz, 1H) 5.04 (t, J=9.91 Hz, 1H) 4.67 (dd, J=10.29, 7.03 Hz, 1H) 4.57 (br. s., 1H) 4.01 (dd, J=11.54, 3.26 Hz, 1H) 3.78 (dd, J=10.79, 7.78 Hz, 1H) 2.91-2.97 (m, 1H) 2.68-2.79 (m, 2H) 2.39-2.49 (m, 2H) 1.75-1.90 (m, 3H) 1.60 (dd, J=9.54, 5.52 Hz, 1H) 1.42-1.54 (m, 2H) 1.30-1.36 (m, 6H) 1.06-1.28 (m, 3H) 1.00 (dd, J=15.18, 6.65 Hz, 6H) 0.93 (s, 3H) 0.79-0.86 (m, 1H); MS: MS m/z 876.2 (M$^+$−1).

Preparation of Compound 4032

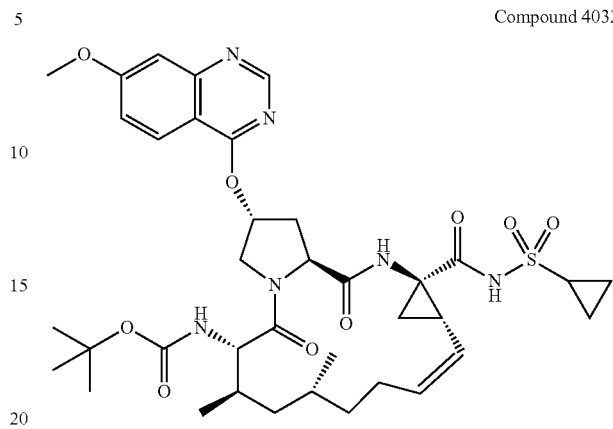

Compound 4032

Compound 4032 was prepared using the intermediates described herein and by following the general procedure described for the synthesis of Compound 1.

Compound 4032: tert-butyl (2R,6S,7R,9R,13aS,14aR,16aS,Z)-14a-(cyclopropylsulfonylcarbamoyl)-2-(7-methoxyquinazolin-4-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 9.02 (s, 1H) 8.86 (s, 1H) 8.15 (d, J=10.04 Hz, 1H) 7.24-7.31 (m, 2H) 6.04 (br. s., 1H) 5.64 (td, J=10.16, 5.52 Hz, 1H) 5.05 (t, J=10.04 Hz, 1H) 4.65 (dd, J=10.04, 7.28 Hz, 1H) 4.07 (dd, J=11.80, 3.26 Hz, 1H) 4.01 (s, 3H) 3.79 (d, J=10.79 Hz, 1H) 2.90-3.00 (m, 1H) 2.67-2.83 (m, 2H) 2.39-2.55 (m, 2H) 1.92-2.02 (m, 1H) 1.76-1.88 (m, 3H) 1.57-1.63 (m, 2H) 1.43-1.54 (m, 2H) 1.28-1.39 (m, 2H) 1.12-1.27 (m, 3H) 1.06-1.10 (m, 9H) 1.01 (dd, J=13.43, 6.65 Hz, 6H) 0.84 (t, J=12.92 Hz, 1H); MS: MS m/z 756.4 (M$^+$+1).

Preparation of Compound 4033

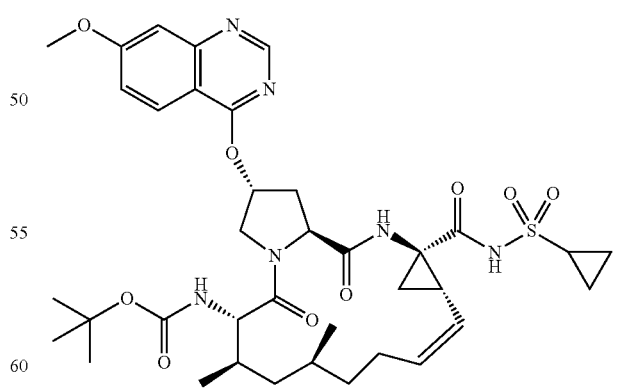

Compound 4033

Compound 4033 was prepared using the intermediates described herein and by following the general procedure described for the synthesis of Compound 1.

Compound 4033: tert-butyl (2R,6S,7R,9S,13aS,14aR,16aS,Z)-14a-(cyclopropylsulfonylcarbamoyl)-2-(7- methoxyquinazolin-4-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.72 (s, 1H) 8.11 (d, J=9.04 Hz, 1H) 7.18-7.29 (m, 2H) 6.01 (br. s., 1H) 5.73 (d, J=7.78 Hz, 1H) 5.02-5.16 (m, 1H) 4.60-4.73 (m, 2H) 4.10 (d, J=7.03 Hz, 2H) 3.98 (s, 3H) 2.87-2.97 (m, 1H) 2.75 (dd, J=13.93, 7.40 Hz, 1H) 2.49 (d, J=9.54 Hz, 2H) 1.98 (br. s., 2H) 1.73 (dd, J=8.03, 5.52 Hz, 1H) 1.63 (br. s., 2H) 1.46 (d, J=6.53 Hz, 2H) 1.21-1.35 (m, 4H) 1.18 (s, 9H) 1.07-1.14 (m, 5H) 1.02 (br. s., 1H) 0.94 (d, J=6.78 Hz, 3H); MS: MS m/z 756.4 (M$^+$+1).

Preparation of Compound 4034

Compound 4034

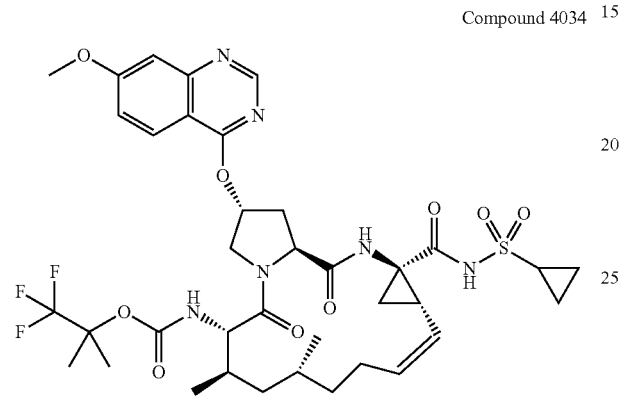

Compound 4034 was prepared using the intermediates described herein and by following the general procedure described for the synthesis of Compound 3.

Compound 4034: 1,1,1-trifluoro-2-methylpropan-2-yl (2R,6S,7R,9R,13aS,14aR,16aS,Z)-14a-(cyclopropylsulfonylcarbamoyl)-2-(7-methoxyquinazolin-4-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 9.02 (s, 1H) 8.78 (s, 1H) 8.10 (d, J=9.03 Hz, 1H) 7.14-7.30 (m, 2H) 5.97-6.01 (m, 1H) 5.63 (td, J=10.16, 5.52 Hz, 1H) 5.05 (t, J=10.04 Hz, 1H) 4.67 (dd, J=10.16, 7.15 Hz, 1H) 4.02-4.07 (m, 1H) 4.00 (s, 3H) 3.73-3.80 (m, 1H) 2.89-2.99 (m, 1H) 2.65-2.82 (m, 2H) 2.37-2.53 (m, 2H) 1.73-2.03 (m, 5H) 1.61 (dd, J=9.54, 5.52 Hz, 1H) 1.42-1.54 (m, 2H) 1.28-1.33 (m, 4H) 1.05-1.25 (m, 4H) 0.96-1.03 (m, 9H) 0.79-0.88 (m, 1H); MS: MS m/z 807.2 (M$^+$−1).

Preparation of Compound 4036

Compound 4036

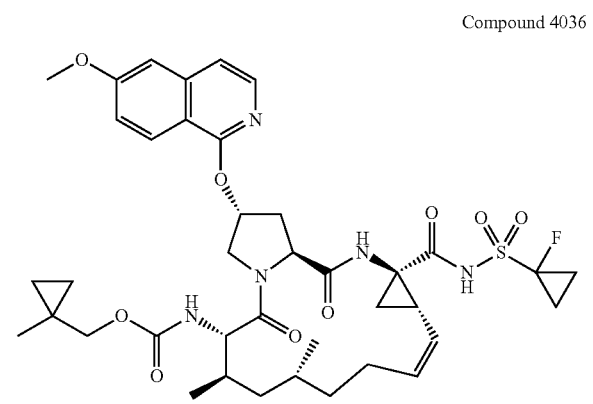 [SMILES: COc1ccc2c(O[C@@H]3C[C@H]4C(=O)N[C@]5(C(=O)NS(=O)(=O)C6(F)CC6)C[C@H]5/C=C\CC[C@@H](C)C[C@@H](C)[C@H](NC(=O)OCC5(C)CC5)C(=O)N4C3)nccc2c1]

Compound 4036 was prepared using the intermediates described herein and by following the general procedure described for the synthesis of Compound 3.

Compound 4036: (1-methylcyclopropyl)methyl (2R,6S,7R,9R,13aS,14aR,16aS,Z)-14a-(1-fluorocyclopropylsulfonylcarbamoyl)-2-(6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.10 (d, J=9.03 Hz, 1H) 7.92 (d, J=5.77 Hz, 1H) 7.27 (d, J=5.77 Hz, 1H) 7.21 (d, J=2.26 Hz, 1H) 7.11 (dd, J=9.03, 2.51 Hz, 1H) 7.03 (d, J=8.28 Hz, 1H) 5.91 (br. s., 1H) 5.62 (td, J=10.10, 5.90 Hz, 1H) 5.01 (t, J=9.91 Hz, 1H) 4.58-4.73 (m, 2H) 4.04 (dd, J=11.54, 3.51 Hz, 1H) 3.89-3.97 (m, 5H) 3.47 (s, 1H) 2.71-2.80 (m, 2H) 2.33-2.51 (m, 2H) 1.86-2.07 (m, 2H) 1.72-1.83 (m, 3H) 1.58-1.69 (m, 3H) 1.45-1.56 (m, 4H) 1.20-1.33 (m, 2H) 0.96-1.06 (m, 7H) 0.81-0.89 (m, 1H) 0.15-0.35 (m, 4H); MS: MS m/z 784.4 (M$^+$+1).

Preparation of Compound 4037

Compound 4037

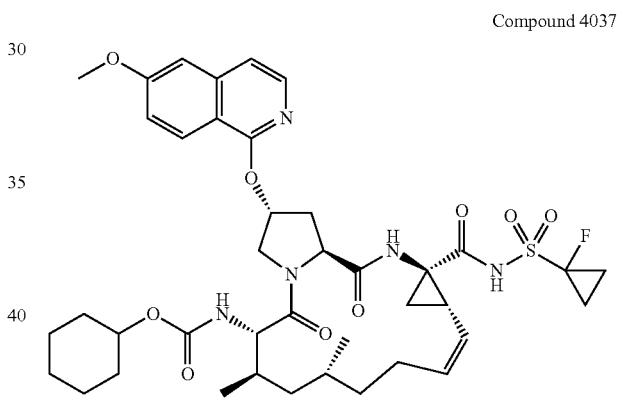

Compound 4037 was prepared using the intermediates described herein and by following the general procedure described for the synthesis of Compound 3.

Compound 4037: cyclohexyl (2R,6S,7R,9R,13aS,14aR,16aS,Z)-14a-(1-fluorocyclopropylsulfonylcarbamoyl)-2-(6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 9.03 (s, 1H) 8.10 (d, J=9.29 Hz, 1H) 7.92 (d, J=6.02 Hz, 1H) 7.29 (d, J=6.02 Hz, 1H) 7.23 (d, J=2.51 Hz, 1H) 7.12 (dd, J=9.16, 2.38 Hz, 1H) 5.90 (br. s., 1H) 5.61 (td, J=10.04, 5.77 Hz, 1H) 5.00 (t, J=9.79 Hz, 1H) 4.73 (d, J=11.54 Hz, 1H) 4.63 (dd, J=10.04, 7.53 Hz, 1H) 4.04 (dd, J=11.17, 3.39 Hz, 2H) 3.95 (s, 3H) 3.91 (d, J=10.79 Hz, 2H) 2.69-2.79 (m, 2H) 2.33-2.49 (m, 2H) 2.00 (br. s., 1H) 1.89 (d, J=5.52 Hz, 1H) 1.71-1.81 (m, 3H) 1.62-1.69 (m, 3H) 1.54-1.62 (m, 3H) 1.45-1.54 (m, 4H) 1.41 (m, 1H) 1.05-1.31 (m, 6H) 1.00 (dd, J=12.92, 6.65 Hz, 6H) 0.76-0.89 (m, 1H); MS: MS m/z 798.4 (M$^+$+1).

Preparation of Compound 4038

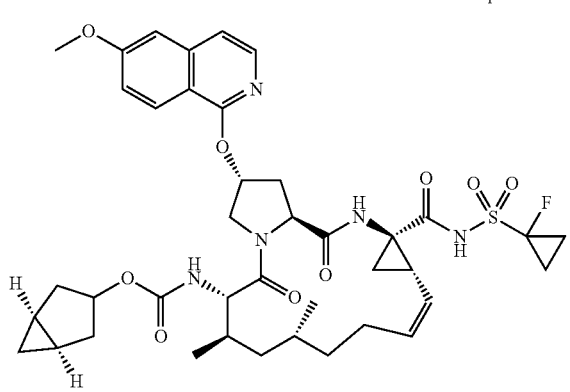

Compound 4038

Compound 4038 was prepared using the intermediates described herein and by following the general procedure described for the synthesis of Compound 3.

Compound 4038: (1R,5S)-bicyclo[3.1.0]hexan-3-yl (2R,6S,7R,9R,13aS,14aR,16aS,Z)-14a-(1-fluorocyclopropylsulfonylcarbamoyl)-2-(6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 9.02 (s, 1H) 8.11 (d, J=9.03 Hz, 1H) 7.92 (d, J=6.02 Hz, 1H) 7.31 (d, J=6.02 Hz, 1H) 7.24 (d, J=2.51 Hz, 1H) 7.16 (dd, J=9.16, 2.38 Hz, 1H) 5.91 (br. s., 1H) 5.62 (td, J=10.04, 6.02 Hz, 1H) 4.95-5.04 (m, 1H) 4.52-4.72 (m, 3H) 4.04 (dd, J=11.54, 3.26 Hz, 1H) 3.96 (s, 3H) 3.90 (d, J=11.04 Hz, 1H) 2.69-2.79 (m, 2H) 2.32-2.49 (m, 2H) 1.94-2.05 (m, 2H) 1.86-1.92 (m, 1H) 1.76 (td, J=8.78, 5.52 Hz, 4H) 1.56-1.71 (m, 3H) 1.45-1.55 (m, 3H) 1.41-1.45 (m, 1H) 1.29-1.39 (m, 2H) 1.19-1.27 (m, 1H) 1.14 (d, J=3.26 Hz, 1H) 0.99 (dd, J=17.32, 6.78 Hz, 6H) 0.77-0.87 (m, 1H) 0.27-0.41 (m, 2H); MS: MS m/z 794.2 (M$^+$−1).

Preparation of Compound 4039

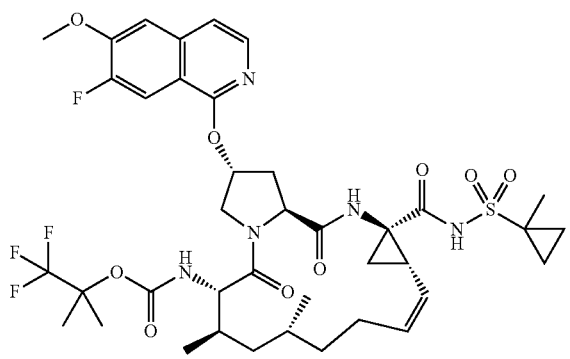

Compound 4039

Compound 4039 was prepared using the intermediates described herein and by following the general procedure described for the synthesis of Compound 3.

Compound 4039: 1,1,1-trifluoro-2-methylpropan-2-yl (2R,6S,7R,9R,13aS,14aR,16aS,Z)-2-(7-fluoro-6-methoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 9.04 (s, 1H) 7.96 (s, 1H) 7.80 (d, J=11.54 Hz, 1H) 7.41 (d, J=8.28 Hz, 1H) 7.31 (d, J=5.77 Hz, 1H) 5.90 (t, J=3.26 Hz, 1H) 5.63 (td, J=10.48, 5.90 Hz, 1H) 5.01 (t, J=10.04 Hz, 1H) 4.64-4.74 (m, 2H) 4.03 (s, 4H) 3.83 (d, J=10.79 Hz, 1H) 2.66-2.79 (m, 2H) 2.39-2.51 (m, 2H) 1.74-2.02 (m, 4H) 1.62-1.70 (m, 1H) 1.58 (dd, J=9.54, 5.52 Hz, 1H) 1.38-1.53 (m, 9H) 1.25-1.30 (m, 1H) 1.13 (s, 3H) 1.01 (t, J=6.27 Hz, 6H) 0.85-0.93 (m, 3H); MS: MS m/z 838.2 (M$^+$−1).

Preparation of Compound 4040

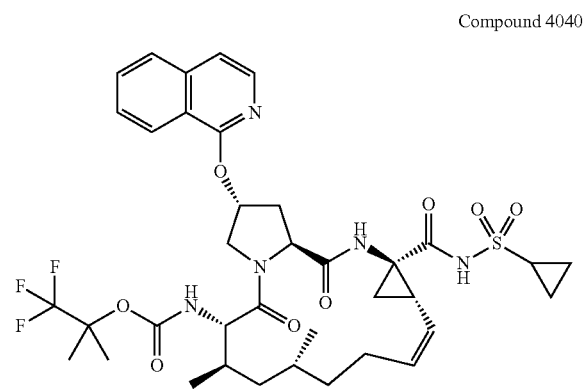 [SMILES: C[C@@H]1CC/C=C\[C@@H]2C[C@@]2(C(=O)NS(=O)(=O)C2CC2)NC(=O)[C@@H]2C[C@@H](Oc3nccc4ccccc34)CN2C(=O)[C@@H](NC(=O)OC(C)(C)C(F)(F)F)[C@H](C)C1]

Compound 4040

Compound 4040 was prepared using the intermediates described herein and by following the general procedure described for the synthesis of Compound 3.

Compound 4040: 1,1,1-trifluoro-2-methylpropan-2-yl (2R,6S,7R,9R,13aS,14aR,16aS,Z)-14a-(cyclopropylsulfonylcarbamoyl)-2-(isoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 11.18 (br. s., 1H) 9.00 (br. s., 1H) 8.13 (d, J=8.28 Hz, 1H) 8.04 (d, J=5.77 Hz, 1H) 7.91 (d, J=8.03 Hz, 1H) 7.73-7.83 (m, 1H) 7.58 (t, J=7.53 Hz, 1H) 7.41 (d, J=5.77 Hz, 1H) 5.84 (br. s., 1H) 5.48-5.59 (m, 1H) 5.05 (t, J=9.91 Hz, 1H) 4.49-4.60 (m, 2H) 3.91 (dd, J=11.42, 3.39 Hz, 1H) 3.71 (dd, J=10.79, 8.03 Hz, 1H) 2.88-2.96 (m, 1H) 2.62-2.73 (m, 2H) 2.27-2.36 (m, 2H) 1.79-1.94 (m, 2H) 1.66-1.73 (m, 1H) 1.53-1.62 (m, 2H) 1.43 (d, J=7.53 Hz, 1H) 1.37 (br. s., 2H) 1.33 (s, 3H) 1.13 (dd, J=11.80, 7.28 Hz, 3H) 1.04 (s, 3H) 0.89-0.99 (m, 6H) 0.71-0.78 (m, 1H); MS: MS m/z 778.2 (M$^+$+1).

Preparation of Compound 4041

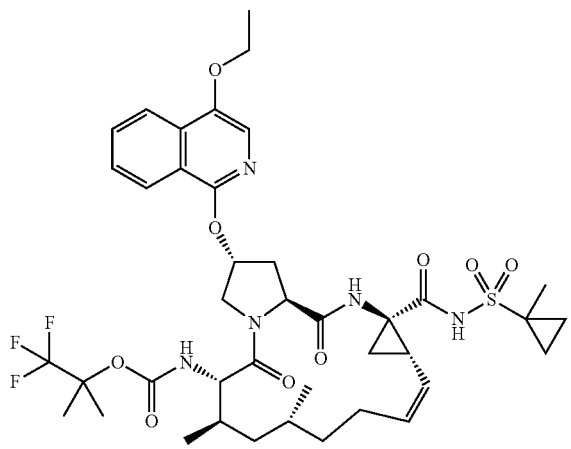

Compound 4041

Compound 4041 was prepared using the intermediates described herein and by following the general procedure described for the synthesis of Compound 3.

Compound 4041: 1,1,1-trifluoro-2-methylpropan-2-yl (2R,6S,7R,9R,13aS,14aR,16aS,Z)-2-(4-ethoxyisoquinolin-1-yloxy)-7,9-dimethyl-14a-(1-methylcyclopropylsulfonyl-carbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.15 (t, J=7.91 Hz, 2H) 7.73 (t, J=7.65 Hz, 1H) 7.52-7.59 (m, 2H) 5.83 (br. s., 1H) 5.58-5.66 (m, 1H) 4.98 (br. s., 1H) 4.76 (d, J=12.55 Hz, 2H) 4.66 (dd, J=10.04, 7.03 Hz, 1H) 4.57 (s, 1H) 4.21-4.26 (m, 2H) 4.02 (dd, J=11.54, 3.26 Hz, 1H) 3.83 (d, J=10.79 Hz, 1H) 2.70-2.78 (m, 2H) 2.43 (ddd, J=13.74, 9.85, 4.27 Hz, 2H) 1.97 (br. s., 3H) 1.73-1.83 (m, 2H) 1.66 (d, J=11.04 Hz, 1H) 1.51-1.59 (m, 7H) 1.37-1.51 (m, 4H) 1.30-1.36 (m, 3H) 1.24 (d, J=12.80 Hz, 1H) 0.93-1.04 (m, 6H) 0.79-0.91 (m, 2H); MS: MS m/z 836.4 (M$^+$+1).

Preparation of Compound 4042

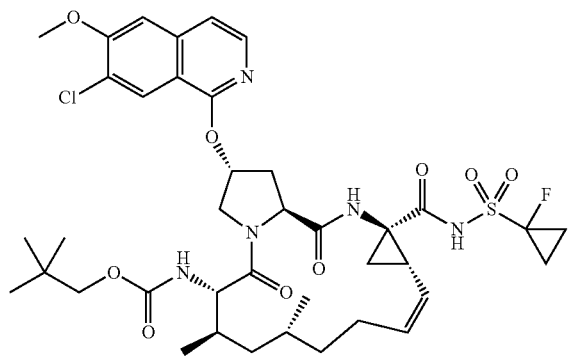

Compound 4042

Compound 4042 was prepared using the intermediates described herein and by following the general procedure described for the synthesis of Compound 3.

Compound 4042: neopentyl (2R,6S,7R,9R,13aS,14aR,16aS,Z)-2-(7-chloro-6-methoxyisoquinolin-1-yloxy)-14a-(1-fluorocyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.16 (s, 1H) 7.96 (d, J=6.02 Hz, 1H) 7.36 (s, 1H) 7.31 (d, J=5.77 Hz, 1H) 5.93 (br. s., 1H) 5.61 (br. s., 1H) 4.74 (d, J=11.04 Hz, 2H) 4.57-4.67 (m, 2H) 4.00-4.05 (m, 4H) 3.88 (d, J=10.79 Hz, 1H) 3.39 (br. s., 1H) 3.22 (d, J=10.54 Hz, 1H) 2.70-2.79 (m, 2H) 2.36-2.49 (m, 2H) 2.01 (br. s., 1H) 1.90 (br. s., 1H) 1.71-1.83 (m, 3H) 1.62 (br. s., 2H) 1.49 (d, J=12.80 Hz, 4H) 1.01 (t, J=6.65 Hz, 6H) 0.82-0.95 (m, 2H) 0.78 (s, 9H); MS: MS m/z 818.2 (M$^+$-1).

Preparation of Compound 4043

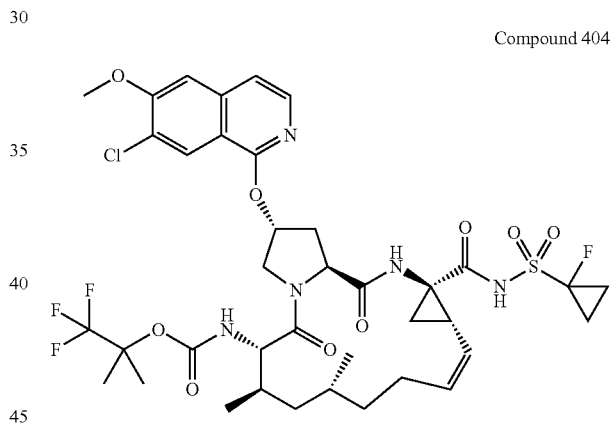

Compound 4043

Compound 4043 was prepared using the intermediates described herein and by following the general procedure described for the synthesis of Compound 3.

Compound 4043: 1,1,1-trifluoro-2-methylpropan-2-yl (2R,6S,7R,9R,13aS,14aR,16aS,Z)-2-(7-chloro-6-methoxy-isoquinolin-1-yloxy)-14a-(1-fluorocyclopropylsulfonylcar-bamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.13 (s, 1H) 7.98 (s, 1H) 7.37 (s, 1H) 7.31 (s, 1H) 5.93 (br. s., 1H) 5.61 (d, J=5.77 Hz, 1H) 5.01 (br. s., 1H) 4.68-4.76 (m, 2H) 3.97-4.05 (m, 4H) 3.76-3.81 (m, 1H) 3.28 (br. s., 1H) 2.71-2.78 (m, 2H) 2.35-2.50 (m, 2H) 2.00 (d, J=12.55 Hz, 1H) 1.83-1.92 (m, 1H) 1.72-1.82 (m, 3H) 1.57-1.70 (m, 3H) 1.40-1.56 (m, 4H) 1.28-1.32 (m, 2H) 1.23 (br. s., 1H) 0.97-1.03 (m, 9H) 0.79-0.87 (m, 1H); MS: MS m/z 860.2 (M$^+$+1).

Preparation of Compound 4044

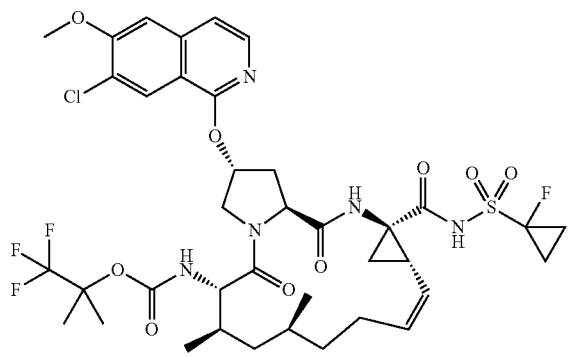

Compound 4044

Compound 4044 was prepared using the intermediates described herein and by following the general procedure described for the synthesis of Compound 3.

Compound 4044: 1,1,1-trifluoro-2-methylpropan-2-yl (2R,6S,7R,9S,13aS,14aR,16aS,Z)-2-(7-chloro-6-methoxy-isoquinolin-1-yloxy)-14a-(1-fluorocyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.15 (s, 1H) 7.97 (d, J=5.77 Hz, 1H) 7.36 (s, 1H) 7.31 (d, J=5.77 Hz, 1H) 5.93 (br. s., 1H) 5.70 (br. s., 1H) 5.05 (br. s., 1H) 4.72-4.79 (m, 1H) 4.55 (d, J=11.54 Hz, 1H) 4.09 (br. s., 1H) 4.04 (s, 3H) 2.72 (br. s., 1H) 2.51 (br. s., 1H) 2.01 (br. s., 2H) 1.59-1.76 (m, 5H) 1.42-1.55 (m, 6H) 1.40 (s, 3H) 1.29-1.34 (m, 2H) 1.24 (br. s., 2H) 1.18 (s, 3H) 1.13-1.16 (m, 1H) 1.10 (d, J=6.78 Hz, 3H) 0.97-1.04 (m, 1H) 0.94 (d, J=6.78 Hz, 3H); MS: MS m/z 858.2 (M$^+$−1).

Preparation of Compound 4045

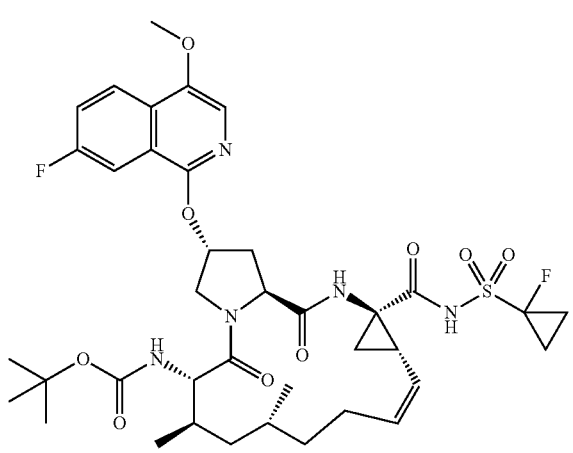

Compound 4045

Compound 4012 was prepared using the intermediates described herein and by following the general procedure described for the synthesis of Compound 1.

Compound 4045: tert-butyl (2R,6S,7R,9R,13aS,14aR,16aS,Z)-2-(7-fluoro-4-methoxyisoquinolin-1-yloxy)-14a-(1-fluorocyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.17 (dd, J=9.03, 5.27 Hz, 1H) 7.75 (dd, J=9.54, 2.51 Hz, 1H) 7.50-7.58 (m, 2H) 6.62 (d, J=7.78 Hz, 1H) 5.84 (br. s., 1H) 5.54-5.63 (m, 1H) 5.14 (br. s., 1H) 4.71 (d, J=11.29 Hz, 1H) 4.57-4.65 (m, 1H) 4.01-4.06 (m, 4H) 3.82-3.89 (m, 1H) 2.74 (dd, J=14.05, 7.03 Hz, 1H) 2.32-2.49 (m, 2H) 2.01 (s, 1H) 1.78-1.91 (m, 2H) 1.69-1.77 (m, 2H) 1.57-1.68 (m, 2H) 1.39-1.55 (m, 3H) 1.20-1.36 (m, 2H) 1.12 (s, 9H) 1.00 (dd, J=11.67, 6.65 Hz, 6H) 0.82 (t, J=11.54 Hz, 1H); MS: MS m/z 790.4 (M$^+$+1).

Preparation of Compound 4046

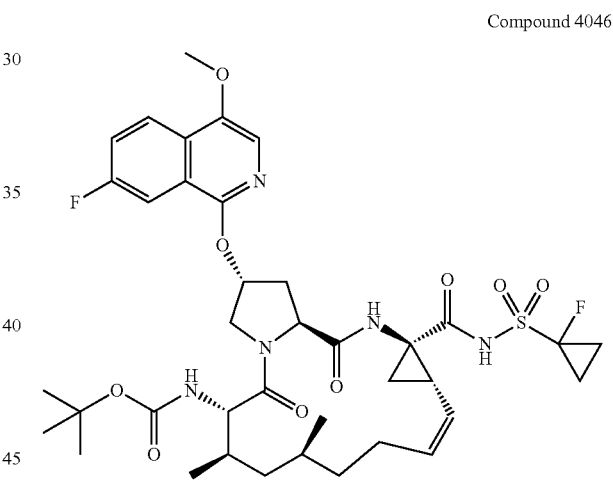

Compound 4046

Compound 4046 was prepared using the intermediates described herein and by following the general procedure described for the synthesis of Compound 1.

Compound 4046: tert-butyl (2R,6S,7R,9S,13aS,14aR,16aS,Z)-2-(7-fluoro-4-methoxyisoquinolin-1-yloxy)-14a-(1-fluorocyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.17 (dd, J=9.16, 5.40 Hz, 1H) 7.73-7.78 (m, 1H) 7.50-7.58 (m, 2H) 5.86 (br. s., 1H) 5.72 (d, J=9.54 Hz, 1H) 5.07 (br. s., 1H) 4.65-4.74 (m, 1H) 4.52 (d, J=11.54 Hz, 1H) 4.06-4.17 (m, 2H) 4.03 (s, 3H) 2.72 (dd, J=13.93, 7.15 Hz, 1H) 2.56-2.67 (m, 1H) 2.41-2.55 (m, 2H) 1.91-2.04 (m, 2H) 1.71 (dd, J=8.16, 5.65 Hz, 2H) 1.65 (dd, J=10.79, 5.77 Hz, 3H) 1.39-1.54 (m, 3H) 1.29 (d, J=17.82 Hz, 3H) 1.21 (s, 9H) 1.10 (d, J=6.78 Hz, 3H) 0.93 (d, J=6.78 Hz, 3H); MS: MS m/z 790.4 (M$^+$+1).

Preparation of Compound 4047

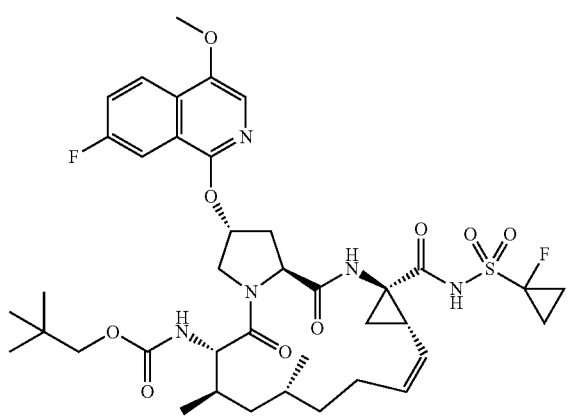

Compound 4047

Compound 4047 was prepared using the intermediates described herein and by following the general procedure described for the synthesis of Compound 3.

Compound 4047: neopentyl (2R,6S,7R,9R,13aS,14aR,16aS,Z)-2-(7-fluoro-4-methoxyisoquinolin-1-yloxy)-14a-(1-fluorocyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.18 (dd, J=9.16, 5.14 Hz, 1H) 7.82 (dd, J=9.66, 2.38 Hz, 1H) 7.50-7.58 (m, 1H) 7.07 (d, J=7.78 Hz, 1H) 5.84 (br. s., 1H) 5.61 (d, J=5.27 Hz, 1H) 4.73 (d, J=11.80 Hz, 2H) 4.56-4.63 (m, 1H) 4.04 (s, 3H) 4.01 (br. s., 1H) 3.92 (d, J=10.54 Hz, 1H) 3.44-3.48 (m, 1H) 2.70-2.79 (m, 2H) 2.36-2.48 (m, 2H) 2.01 (s, 1H) 1.85-1.96 (m, 1H) 1.70-1.85 (m, 3H) 1.57-1.69 (m, 2H) 1.49 (d, J=16.81 Hz, 3H) 1.19-1.38 (m, 1H) 0.98-1.06 (m, 6H) 0.84-0.93 (m, 2H) 0.81 (s, 9H) 0.72 (br. s., 1H); MS: MS m/z 804.4 (M$^+$+1).

Preparation of Compound 4048

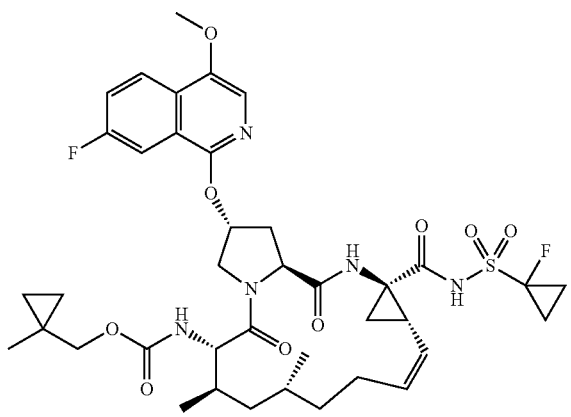

Compound 4048

Compound 4048 was prepared using the intermediates described herein and by following the general procedure described for the synthesis of Compound 3.

Compound 4048: (1-methylcyclopropyl)methyl (2R,6S,7R,9R,13aS,14aR,16aS,Z)-2-(7-fluoro-4-methoxyisoquinolin-1-yloxy)-14a-(1-fluorocyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.37 (dd, J=9.04, 5.52 Hz, 1H) 7.00 (dd, J=9.54, 2.51 Hz, 1H) 6.69-6.77 (m, 2H) 6.25 (d, J=8.53 Hz, 1H) 5.03 (br. s., 1H) 4.76-4.85 (m, 1H) 4.21 (br. s., 1H) 3.91 (d, J=11.04 Hz, 1H) 3.80 (dd, J=9.91, 7.40 Hz, 1H) 3.18-3.24 (m, 4H) 3.11 (dd, J=10.54, 8.53 Hz, 1H) 2.71-2.75 (m, 1H) 2.60-2.64 (m, 1H) 1.87-1.99 (m, 2H) 1.54-1.67 (m, 2H) 1.05-1.24 (m, 2H) 0.90-1.03 (m, 2H) 0.77-0.88 (m, 2H) 0.60-0.75 (m, 3H) 0.42-0.58 (m, 2H) 0.17-0.24 (m, 9H) 0.00-0.08 (m, 1H) −0.63--0.45 (m, 4H); MS: MS m/z 800.2 (M$^+$−1).

Preparation of Compound 4049

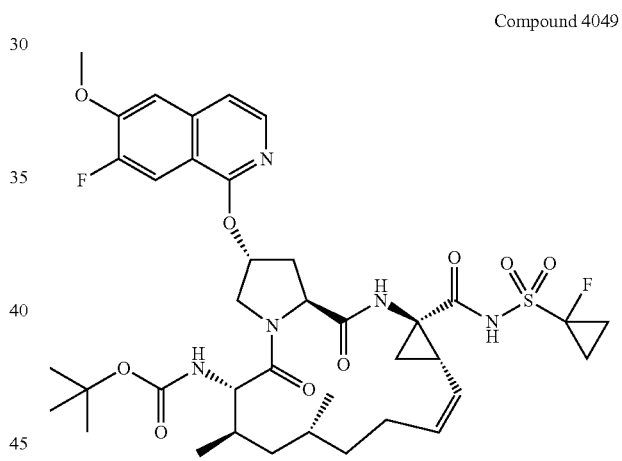

Compound 4049

Compound 4049 was prepared using the intermediates described herein and by following the general procedure described for the synthesis of Compound 1.

Compound 4049: tert-butyl (2R,6S,7R,9R,13aS,14aR,16aS,Z)-2-(7-fluoro-6-methoxyisoquinolin-1-yloxy)-14a-(1-fluorocyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 7.94 (d, J=6.02 Hz, 1H) 7.79 (s, 1H) 7.39 (d, J=8.28 Hz, 1H) 7.30 (d, J=6.02 Hz, 1H) 5.91 (br. s., 1H) 5.57-5.65 (m, 1H) 5.01 (br. s., 1H) 4.71 (d, J=11.04 Hz, 1H) 4.63 (dd, J=10.04, 7.03 Hz, 1H) 4.00-4.06 (m, 4H) 3.86 (d, J=10.79 Hz, 1H) 2.70-2.80 (m, 2H) 2.36-2.49 (m, 2H) 1.93-2.06 (m, 1H) 1.71-1.91 (m, 3H) 1.58-1.69 (m, 2H) 1.44-1.57 (m, 4H) 1.22-1.34 (m, 2H) 1.16 (s, 9H) 1.01 (dd, J=8.78, 6.78 Hz, 6H) 0.80-0.87 (m, 1H); MS: MS m/z 790.2 (M$^+$+1).

Preparation of Compound 4050

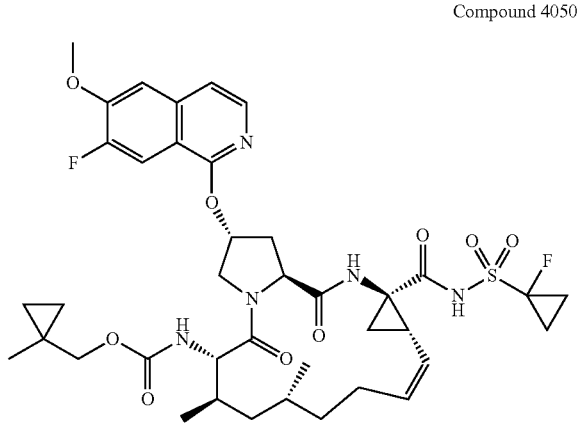 [SMILES: COc1cc2ccnc(O[C@@H]3C[C@H]4C(=O)N[C@]5(C(=O)NS(=O)(=O)C6(F)CC6)C[C@H]5/C=C\CC[C@@H](C)C[C@@H](C)[C@H](NC(=O)OCC5(C)CC5)C(=O)N4C3)c2cc1F]

Compound 4050

Compound 4050 was prepared using the intermediates described herein and by following the general procedure described for the synthesis of Compound 3.

Compound 4050: (1-methylcyclopropyl)methyl (2R,6S,7R,9R,13aS,14aR,16aS,Z)-2-(7-fluoro-6-methoxyisoquinolin-1-yloxy)-14a-(1-fluorocyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 9.03 (s, 1H) 7.94 (d, J=6.02 Hz, 1H) 7.86 (d, J=11.54 Hz, 1H) 7.40 (d, J=8.28 Hz, 1H) 7.31 (d, J=5.77 Hz, 1H) 5.89 (br. s., 1H) 5.56-5.67 (m, 1H) 4.97-5.05 (m, 1H) 4.74 (d, J=11.29 Hz, 1H) 4.57-4.64 (m, 1H) 4.00-4.06 (m, 4H) 3.91 (d, J=10.79 Hz, 1H) 3.56 (s, 1H) 3.45 (d, J=11.04 Hz, 1H) 2.69-2.81 (m, 2H) 2.33-2.48 (m, 2H) 1.86-2.04 (m, 2H) 1.71-1.85 (m, 3H) 1.56-1.70 (m, 2H) 1.40-1.55 (m, 3H) 1.18-1.40 (m, 2H) 0.97-1.05 (m, 9H) 0.86 (t, J=11.92 Hz, 1H) 0.18-0.37 (m, 4H); MS: MS m/z 802.2 (M$^+$+1).

Preparation of Compound 4051

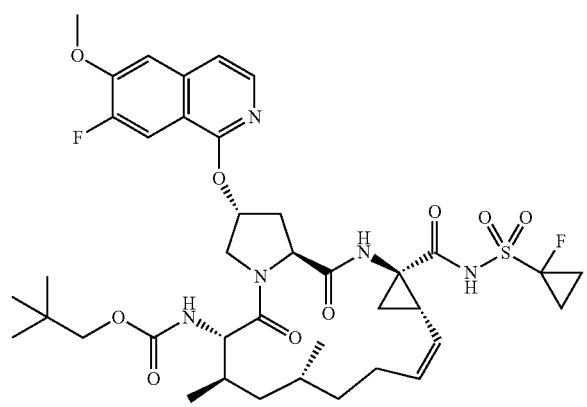

Compound 4051

Compound 4051 was prepared using the intermediates described herein and by following the general procedure described for the synthesis of Compound 1.

Compound 4051: neopentyl (2R,6S,7R,9R,13aS,14aR,16aS,Z)-2-(7-fluoro-6-methoxyisoquinolin-1-yloxy)-14a-(1-fluorocyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 7.94 (d, J=6.02 Hz, 1H) 7.87 (s, 1H) 7.39 (d, J=8.28 Hz, 1H) 7.30 (d, J=6.02 Hz, 1H) 5.88 (br. s., 1H) 5.58 (d, J=6.02 Hz, 1H) 4.73 (d, J=12.05 Hz, 1H) 4.54-4.64 (m, 1H) 4.00-4.05 (m, 4H) 3.89-3.96 (m, 1H) 3.45-3.49 (m, 1H) 3.37 (s, 1H) 2.76 (dd, J=13.55, 6.78 Hz, 1H) 2.64 (br. s., 1H) 2.34-2.52 (m, 2H) 1.86-2.04 (m, 2H) 1.77-1.85 (m, 1H) 1.73 (dd, J=7.78, 5.52 Hz, 2H) 1.55-1.67 (m, 2H) 1.44 (d, J=14.31 Hz, 3H) 1.22-1.36 (m, 2H) 0.98-1.05 (m, 6H) 0.87 (br. s., 1H) 0.83 (s, 9H) 0.73 (br. s., 1H); MS: MS m/z 802.2 (M$^+$−1).

Preparation of Compound 4052

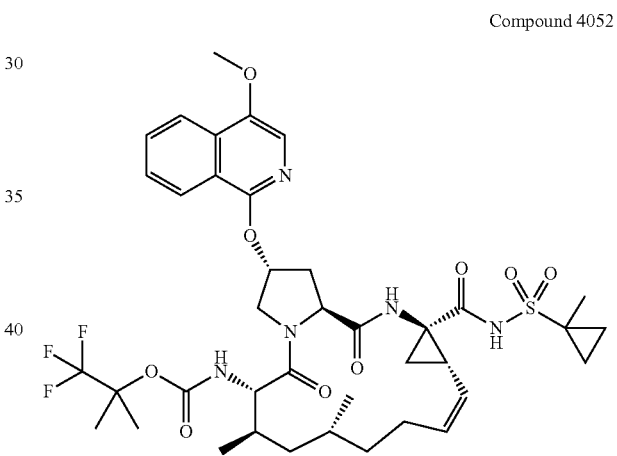

Compound 4052

Compound 4052 was prepared using the intermediates described herein and by following the general procedure described for the synthesis of Compound 3.

Compound 4052: 1,1,1-trifluoro-2-methylpropan-2-yl (2R,6S,7R,9R,13aS,14aR,16aS,Z)-2-(4-methoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.14 (dd, J=17.07, 8.28 Hz, 2H) 7.74 (t, J=7.28 Hz, 1H) 7.52-7.60 (m, 2H) 5.84 (br. s., 1H) 5.57-5.67 (m, 1H) 5.01 (t, J=9.66 Hz, 1H) 4.76 (d, J=11.54 Hz, 1H) 4.66 (dd, J=10.29, 7.03 Hz, 1H) 3.99-4.05 (m, 4H) 3.82 (s, 1H) 2.69-2.79 (m, 2H) 2.39-2.49 (m, 2H) 1.98 (br. s., 1H) 1.88 (d, J=5.77 Hz, 1H) 1.72-1.82 (m, 2H) 1.62-1.69 (m, 1H) 1.57 (dd, J=9.54, 5.52 Hz, 1H) 1.53 (s, 3H) 1.39-1.51 (m, 3H) 1.35 (s, 3H) 1.21-1.31 (m, 1H) 0.94-1.04 (m, 9H) 0.79-0.93 (m, 3H); MS: MS m/z 820.2 (M$^+$−1).

Preparation of Compound 4053

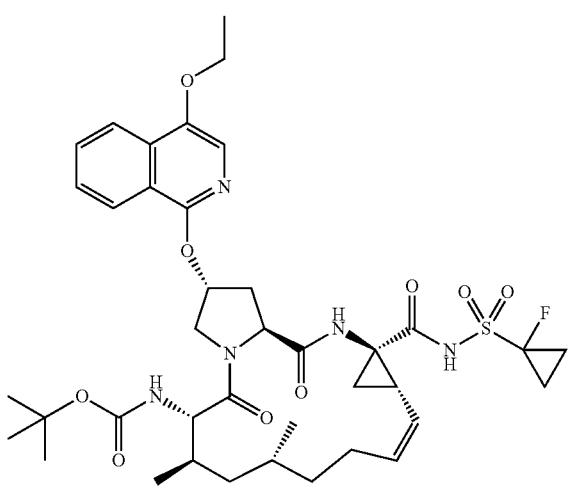

Compound 4053

Compound 4053 was prepared using the intermediates described herein and by following the general procedure described for the synthesis of Compound 1.

Compound 4053: tert-butyl (2R,6S,7R,9R,13aS,14aR,16aS,Z)-2-(4-ethoxyisoquinolin-1-yloxy)-14a-(1-fluorocyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 9.03 (s, 1H) 8.15 (dd, J=15.69, 8.41 Hz, 2H) 7.72 (t, J=7.28 Hz, 1H) 7.50-7.58 (m, 2H) 5.84 (br. s., 1H) 5.61 (td, J=10.16, 6.02 Hz, 1H) 4.99 (t, J=9.91 Hz, 1H) 4.73 (d, J=11.04 Hz, 1H) 4.62 (dd, J=10.16, 7.15 Hz, 1H) 4.23 (q, J=6.86 Hz, 2H) 4.04 (dd, J=11.42, 3.39 Hz, 1H) 3.88 (d, J=10.79 Hz, 1H) 2.71-2.79 (m, 2H) 2.34-2.48 (m, 2H) 1.93-2.03 (m, 1H) 1.72-1.91 (m, 4H) 1.57-1.70 (m, 2H) 1.51-1.56 (m, 4H) 1.39-1.50 (m, 3H) 1.22-1.32 (m, 1H) 1.13 (s, 9H) 1.00 (dd, J=11.92, 6.65 Hz, 6H) 0.78-0.86 (m, 1H); MS: MS m/z 784.2 (M$^+$−1).

Preparation of Compound 4054

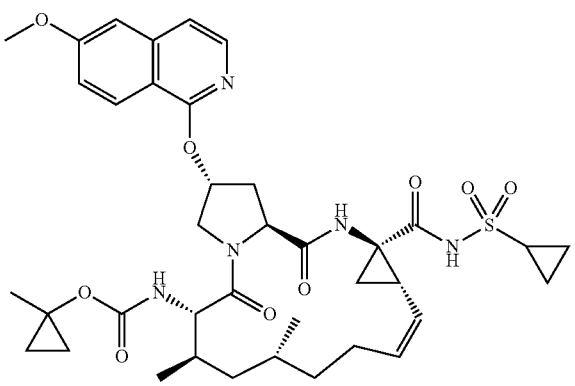

Compound 4054

Compound 4054 was prepared using the intermediates described herein and by following the general procedure described for the synthesis of Compound 3.

Compound 4054: 1-methylcyclopropyl (2R,6S,7R,9R,13aS,14aR,16aS,Z)-14a-(cyclopropylsulfonylcarbamoyl)-2-(6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.95-9.00 (m, 1H) 8.09-8.18 (m, 1H) 7.93-8.01 (m, 1H) 7.34-7.39 (m, 1H) 7.27-7.33 (m, 1H) 5.93-6.01 (m, 1H) 5.59-5.75 (m, 1H) 5.06-5.13 (m, 1H) 4.57-4.71 (m, 2H) 4.00-4.10 (m, 4H) 3.90-3.96 (m, 1H) 2.87-2.98 (m, 1H) 2.68-2.76 (m, 1H) 2.56-2.66 (m, 2H) 2.45-2.54 (m, 1H) 1.92-2.03 (m, 1H) 1.79-1.90 (m, 1H) 1.72-1.78 (m, 1H) 1.53-1.70 (m, 3H) 1.27-1.47 (m, 5H) 1.00-1.18 (m, 8H) 0.89-0.98 (m, 3H) 0.58-0.66 (m, 1H) 0.44-0.51 (m, 1H) 0.36-0.42 (m, 1H) 0.27-0.32 (m, 1H); MS: MS m/z 753.2 (M$^+$+1).

Preparation of Compound 4055

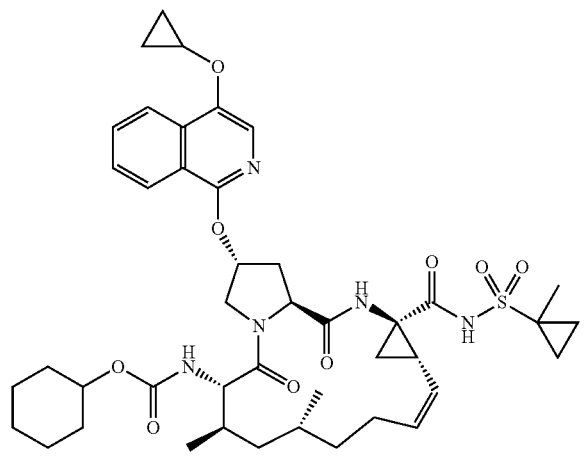

Compound 4055

Compound 4055 was prepared using the intermediates described herein and by following the general procedure described for the synthesis of Compound 3.

Compound 4055: cyclohexyl (2R,6S,7R,9R,13aS,14aR,16aS,Z)-2-(4-cyclopropoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.15 (d, J=8.03 Hz, 1H) 8.04 (d, J=8.53 Hz, 1H) 7.89 (s, 1H) 7.72 (t, J=7.78 Hz, 1H) 7.53-7.58 (m, 1H) 6.89 (d, J=8.28 Hz, 1H) 5.87 (br. s., 1H) 5.59-5.67 (m, 1H) 5.02 (t, J=10.04 Hz, 1H) 4.73 (d, J=12.05 Hz, 1H) 4.65 (dd, J=9.91, 7.40 Hz, 1H) 4.01 (d, J=3.26 Hz, 3H) 3.91 (br. s., 1H) 3.07 (q, J=7.78 Hz, 1H) 2.71-2.79 (m, 2H) 2.40-2.48 (m, 1H) 2.00 (br. s., 1H) 1.89 (br. s., 1H) 1.77 (dd, J=8.28, 5.77 Hz, 2H) 1.63-1.71 (m, 3H) 1.56-1.60 (m, 1H) 1.53 (s, 3H) 1.49 (d, J=4.02 Hz, 1H) 1.43-1.46 (m, 1H) 1.38-1.43 (m, 2H) 1.30-1.34 (m, 4H) 1.23 (d, J=8.53 Hz, 2H) 1.13 (br. s., 2H) 1.00 (dd, J=14.93, 6.65 Hz, 6H) 0.89-0.94 (m, 4H) 0.86 (d, J=2.76 Hz, 3H); MS: MS m/z 821.4 (M$^+$+1).

Preparation of Compound 4056

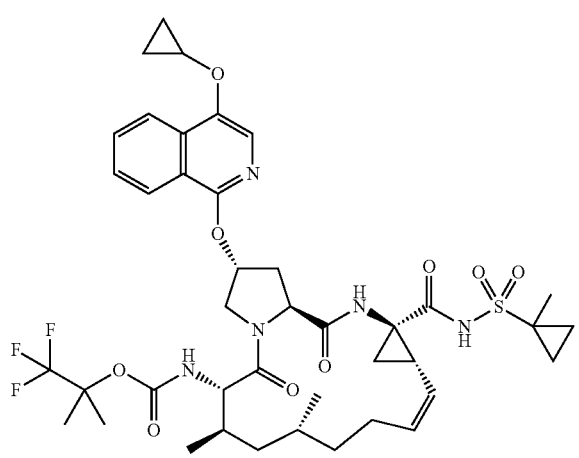

Compound 4056

Compound 4056 was prepared using the intermediates described herein and by following the general procedure described for the synthesis of Compound 3.

Compound 4056: 1,1,1-trifluoro-2-methylpropan-2-yl (2R,6S,7R,9R,13aS,14aR,16aS,Z)-2-(4-cyclopropoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.16 (d, J=8.28 Hz, 1H) 8.03 (d, J=8.28 Hz, 1H) 7.89 (s, 1H) 7.72 (td, J=7.65, 1.25 Hz, 1H) 7.53-7.58 (m, 1H) 7.28 (d, J=8.03 Hz, 1H) 5.84 (br. s., 1H) 5.59-5.66 (m, 1H) 5.01 (t, J=9.91 Hz, 1H) 4.78 (d, J=12.05 Hz, 1H) 4.67 (dd, J=10.29, 7.03 Hz, 1H) 3.97-4.05 (m, 2H) 3.80-3.86 (m, 1H) 2.70-2.78 (m, 2H) 2.40-2.48 (m, 2H) 1.98 (br. s., 1H) 1.83-1.92 (m, 1H) 1.77 (dd, J=8.28, 5.52 Hz, 2H) 1.66 (dd, J=9.66, 4.64 Hz, 1H) 1.54-1.59 (m, 1H) 1.53 (s, 3H) 1.41-1.49 (m, 2H) 1.34 (s, 3H) 1.31 (br. s., 1H) 1.21-1.29 (m, 1H) 1.00 (dd, J=12.05, 6.78 Hz, 6H) 0.88-0.93 (m, 7H) 0.79-0.88 (m, 3H); MS: MS m/z 847.2 (M$^+$−1).

Preparation of Compound 4057

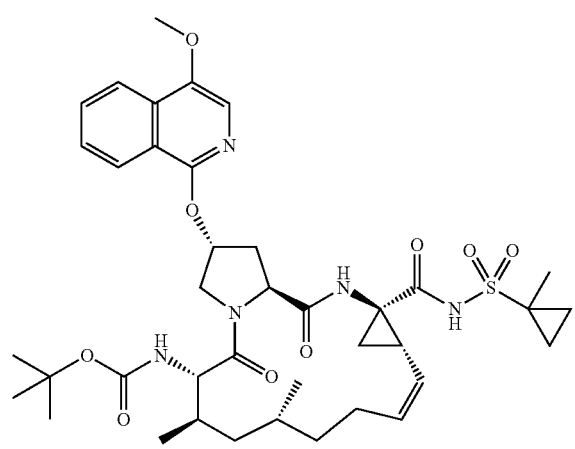

Compound 4057

Compound 4057 was prepared using the intermediates described herein and by following the general procedure described for the synthesis of Compound 1.

Compound 4057: tert-butyl (2R,6S,7R,9R,13aS,14aR,16aS,Z)-2-(4-methoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 9.04 (s, 1H) 8.08-8.20 (m, 2H) 7.73 (t, J=8.03 Hz, 1H) 7.52-7.60 (m, 2H) 5.85 (br. s., 1H) 5.63 (td, J=10.16, 6.02 Hz, 1H) 5.01 (t, J=10.04 Hz, 1H) 4.73 (d, J=11.04 Hz, 1H) 4.63 (dd, J=9.91, 6.90 Hz, 1H) 4.00-4.09 (m, 4H) 3.89 (d, J=11.04 Hz, 1H) 2.70-2.80 (m, 2H) 2.38-2.49 (m, 2H) 1.92-2.03 (m, 1H) 1.74-1.91 (m, 3H) 1.61-1.70 (m, 1H) 1.40-1.59 (m, 6H) 1.20-1.38 (m, 2H) 1.14 (s, 9H) 1.01 (dd, J=10.67, 6.65 Hz, 6H) 0.79-0.94 (m, 3H); MS: MS m/z 768.4 (M$^+$+1).

Preparation of Compound 4058

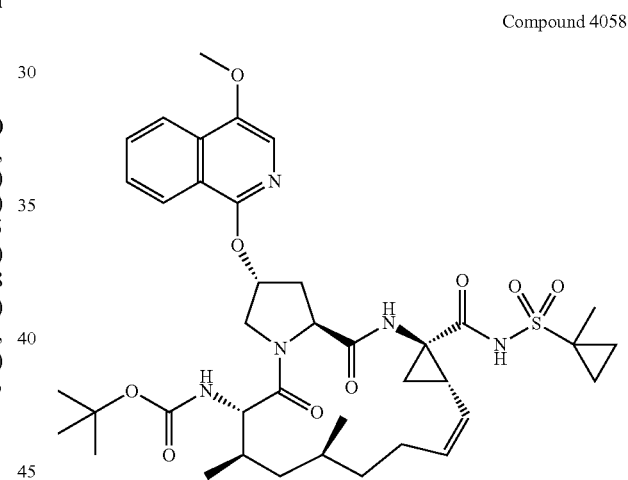

Compound 4058

Compound 4058 was prepared using the intermediates described herein and by following the general procedure described for the synthesis of Compound 1.

Compound 4058: tert-butyl (2R,6S,7R,9S,13aS,14aR,16aS,Z)-2-(4-methoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 9.09 (s, 1H) 8.19 (d, J=8.53 Hz, 1H) 8.12 (d, J=8.28 Hz, 1H) 7.74 (t, J=7.53 Hz, 1H) 7.53-7.62 (m, 2H) 5.87 (br. s., 1H) 5.75 (q, J=8.53 Hz, 1H) 5.01-5.08 (m, 1H) 4.70 (t, J=8.53 Hz, 1H) 4.51 (d, J=11.54 Hz, 1H) 4.18 (d, J=6.78 Hz, 1H) 4.10 (d, J=8.28 Hz, 1H) 4.03 (s, 3H) 2.62-2.78 (m, 2H) 2.49 (dq, J=17.38, 8.93 Hz, 2H) 1.89-2.06 (m, 2H) 1.72 (dd, J=8.03, 5.52 Hz, 1H) 1.54-1.67 (m, 3H) 1.52 (s, 3H) 1.37-1.49 (m, 3H) 1.16-1.34 (m, 10H) 1.11 (d, J=6.53 Hz, 4H) 0.86-0.96 (m, 5H); MS: MS m/z 766.2 (M$^+$−1).

Preparation of Compound 4059

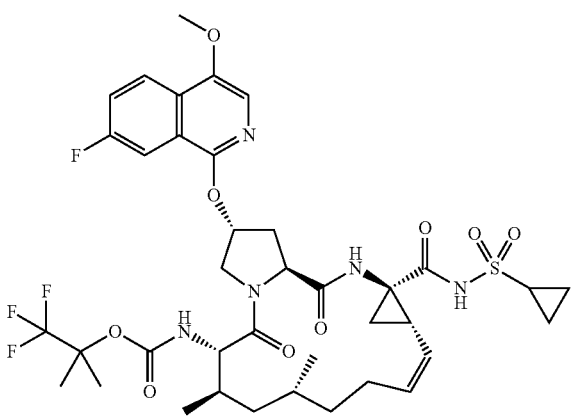

Compound 4059

Compound 4059 was prepared using the intermediates described herein and by following the general procedure described for the synthesis of Compound 3.

Compound 4059: 1,1,1-trifluoro-2-methylpropan-2-yl (2R,6S,7R,9R,13aS,14aR,16aS,Z)-14a-(cyclopropylsulfonylcarbamoyl)-2-(7-fluoro-4-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.19 (dd, J=9.03, 5.52 Hz, 1H) 7.74-7.79 (m, 1H) 7.58 (s, 1H) 7.51-7.56 (m, 1H) 7.30 (d, J=7.78 Hz, 1H) 5.84 (br. s., 1H) 5.63 (td, J=10.10, 5.90 Hz, 1H) 5.02-5.09 (m, 1H) 4.74 (d, J=11.54 Hz, 1H) 4.65 (dd, J=10.16, 6.90 Hz, 1H) 3.97-4.05 (m, 4H) 3.77-3.85 (m, 1H) 2.89-2.98 (m, 1H) 2.67-2.78 (m, 2H) 2.43 (ddd, J=13.87, 10.10, 4.14 Hz, 2H) 1.97 (t, J=12.67 Hz, 1H) 1.81-1.92 (m, 2H) 1.79 (dd, J=8.41, 5.65 Hz, 1H) 1.60 (dd, J=9.41, 5.65 Hz, 1H) 1.42-1.55 (m, 2H) 1.36 (s, 2H) 1.28-1.34 (m, 2H) 1.24 (d, J=13.30 Hz, 1H) 1.07-1.20 (m, 2H) 0.98-1.07 (m, 9H) 0.84 (t, J=12.05 Hz, 1H); MS: MS m/z 824.2 (M$^+$–1).

Preparation of Compound 4060

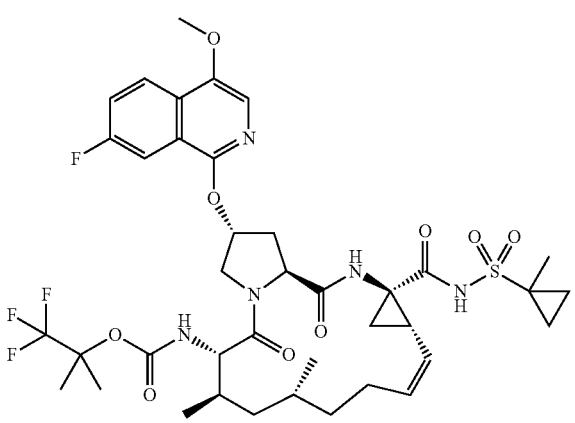

Compound 4060

Compound 4060 was prepared using the intermediates described herein and by following the general procedure described for the synthesis of Compound 3.

Compound 4060: 1,1,1-trifluoro-2-methylpropan-2-yl (2R,6S,7R,9R,13aS,14aR,16aS,Z)-2-(7-fluoro-4-methoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.19 (dd, J=9.29, 5.27 Hz, 1H) 7.77 (dd, J=9.54, 2.51 Hz, 1H) 7.58 (s, 1H) 7.52-7.56 (m, 1H) 5.85 (br. s., 1H) 5.62 (d, J=5.02 Hz, 1H) 5.04 (br. s., 1H) 4.74 (d, J=12.55 Hz, 1H) 4.66 (dd, J=10.04, 6.78 Hz, 1H) 3.98-4.05 (m, 4H) 3.82 (d, J=10.79 Hz, 1H) 2.70-2.79 (m, 2H) 2.39-2.48 (m, 2H) 1.97 (d, J=4.52 Hz, 1H) 1.88 (d, J=6.27 Hz, 1H) 1.73-1.86 (m, 2H) 1.65 (br. s., 1H) 1.58 (dd, J=9.54, 5.52 Hz, 1H) 1.53 (s, 3H) 1.39-1.51 (m, 2H) 1.37 (s, 3H) 1.18-1.32 (m, 2H) 1.06 (s, 3H) 0.98-1.04 (m, 6H) 0.77-0.95 (m, 3H); MS: MS m/z 838.2 (M$^+$–1).

Preparation of Compound 4061

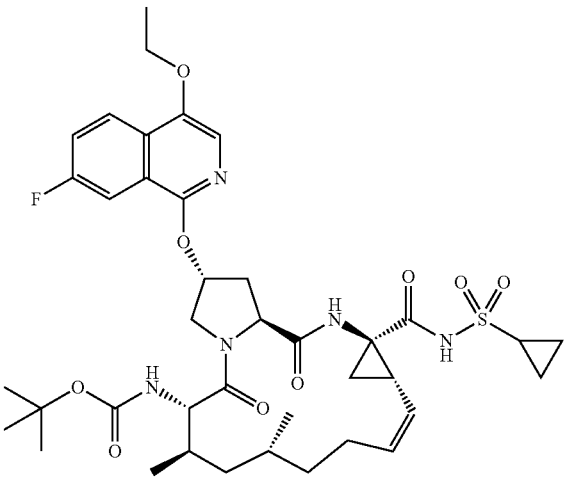

Compound 4061

Compound 4061 was prepared using the intermediates described herein and by following the general procedure described for the synthesis of Compound 1.

Compound 4061: tert-butyl (2R,6S,7R,9R,13aS,14aR,16aS,Z)-14a-(cyclopropylsulfonylcarbamoyl)-2-(4-ethoxy-7-fluoroisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.20 (dd, J=9.16, 5.40 Hz, 1H) 7.93 (s, 1H) 7.74 (dd, J=9.54, 2.51 Hz, 1H) 7.48-7.59 (m, 2H) 5.84 (br. s., 1H) 5.63 (d, J=4.77 Hz, 1H) 4.99-5.12 (m, 1H) 4.73 (d, J=11.54 Hz, 1H) 4.59-4.66 (m, 1H) 4.24 (q, J=6.94 Hz, 2H) 3.96-4.06 (m, 1H) 3.85 (d, J=10.29 Hz, 1H) 2.94 (br. s., 1H) 2.72 (d, J=7.78 Hz, 2H) 2.44 (d, J=9.54 Hz, 2H) 1.98 (br. s., 1H) 1.74-1.89 (m, 2H) 1.60 (dd, J=9.29, 5.02 Hz, 1H) 1.41-1.56 (m, 5H) 1.29-1.38 (m, 1H) 1.26 (br. s., 1H) 1.05-1.16 (m, 12H) 0.97-1.04 (m, 6H) 0.77-0.88 (m, 1H); MS: MS m/z 786.4 (M$^+$+1).

Preparation of Compound 4062

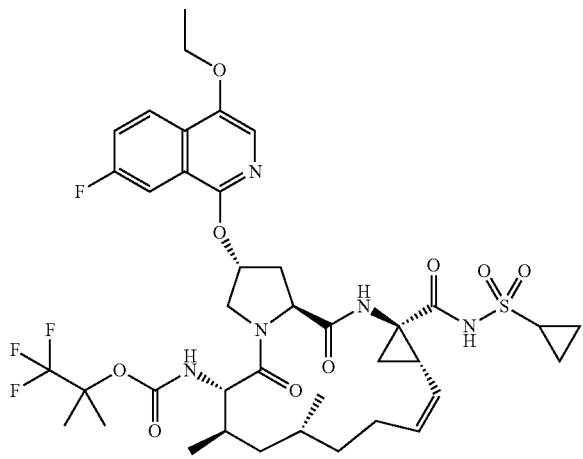

Compound 4062

Compound 4062 was prepared using the intermediates described herein and by following the general procedure described for the synthesis of Compound 3.

Compound 4062: 1,1,1-trifluoro-2-methylpropan-2-yl (2R,6S,7R,9R,13aS,14aR,16aS,Z)-14a-(cyclopropylsulfonylcarbamoyl)-2-(4-ethoxy-7-fluoroisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.21 (dd, J=9.29, 5.27 Hz, 1H) 7.93 (s, 1H) 7.76 (dd, J=9.54, 2.51 Hz, 1H) 7.52-7.59 (m, 2H) 5.81-5.86 (m, 1H) 5.63 (td, J=10.10, 5.65 Hz, 1H) 5.00-5.10 (m, 1H) 4.74 (d, J=11.80 Hz, 1H) 4.61-4.67 (m, 1H) 4.21-4.28 (m, 2H) 3.99 (dd, J=11.42, 3.39 Hz, 1H) 3.81 (d, J=10.79 Hz, 1H) 2.91-2.98 (m, 1H) 2.69-2.79 (m, 2H) 2.43 (ddd, J=13.87, 10.10, 4.14 Hz, 2H) 1.97 (d, J=4.27 Hz, 1H) 1.83-1.92 (m, 2H) 1.76-1.82 (m, 2H) 1.60 (dd, J=9.41, 5.40 Hz, 1H) 1.54 (t, J=6.90 Hz, 3H) 1.44-1.51 (m, 2H) 1.36 (s, 3H) 1.17-1.33 (m, 2H) 1.07-1.17 (m, 2H) 0.98-1.06 (m, 9H) 0.84 (t, J=11.80 Hz, 1H); MS: MS m/z 840.2 (M$^+$+1).

Preparation of Compound 4063

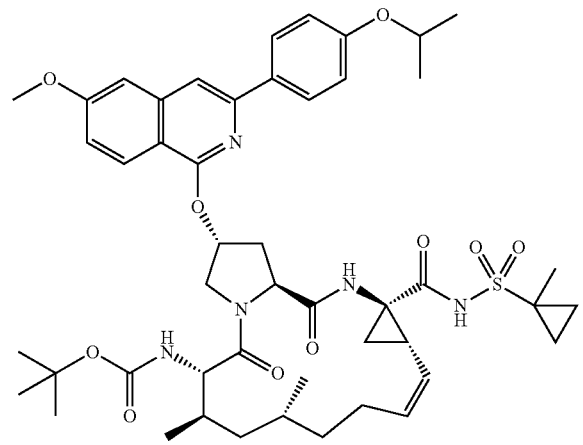

Compound 4063

Compound 4063 was prepared using the intermediates described herein and by following the general procedure described for the synthesis of Compound 1.

Compound 4063: tert-butyl (2R,6S,7R,9R,13aS,14aR,16aS,Z)-2-((3-(4-isopropoxyphenyl)-6-methoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.02-8.14 (m, 3H) 7.62-7.72 (m, 1H) 7.23 (br. s., 1H) 6.99-7.08 (m, 3H) 6.09 (br. s., 1H) 5.45-5.81 (m, 1H) 4.96-5.08 (m, 1H) 4.59-4.78 (m, 3H) 4.08-4.23 (m, 1H) 3.90-3.99 (m, 4H) 2.66-2.86 (m, 2H) 2.39-2.59 (m, 2H) 1.93-2.05 (m, 1H) 1.55-1.90 (m, 5H) 1.52 (d, J=5.77 Hz, 4H) 1.40-1.48 (m, 2H) 1.34-1.39 (m, 7H) 1.26-1.32 (m, 4H) 1.18-1.24 (m, 5H) 1.12 (d, J=6.02 Hz, 2H) 0.97-1.06 (m, 4H) 0.81-0.96 (m, 3H); MS: MS m/z 902.8 (M$^+$+1).

Preparation of Compound 4064

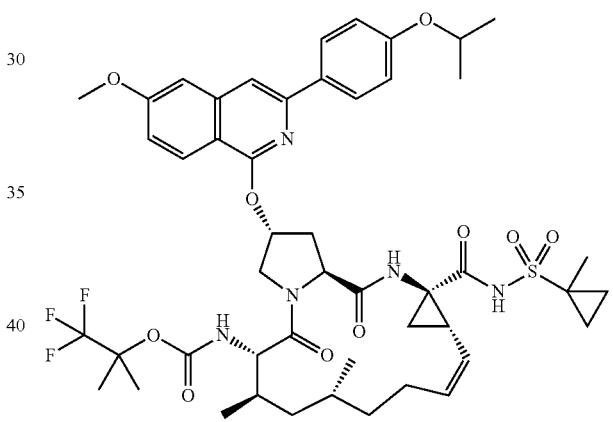

Compound 4064

Compound 4064 was prepared using the intermediates described herein and by following the general procedure described for the synthesis of Compound 3.

Compound 4064: 1,1,1-trifluoro-2-methylpropan-2-yl (2R,6S,7R,9R,13aS,14aR,16aS,Z)-2-((3-(4-isopropoxyphenyl)-6-methoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.05-8.16 (m, 3H) 7.70 (s, 1H) 7.25 (d, J=2.51 Hz, 1H) 6.99-7.10 (m, 3H) 6.08 (br. s., 1H) 5.64 (td, J=10.35, 5.40 Hz, 1H) 5.02 (t, J=9.91 Hz, 1H) 4.80 (d, J=12.05 Hz, 1H) 4.60-4.75 (m, 2H) 4.14 (dd, J=11.42, 3.64 Hz, 1H) 3.96 (s, 3H) 3.84-3.92 (m, 1H) 2.71-2.86 (m, 2H) 2.39-2.59 (m, 2H) 1.78 (dd, J=8.41, 5.65 Hz, 3H) 1.67 (d, J=11.04 Hz, 1H) 1.57-1.61 (m, 1H) 1.53 (s, 3H) 1.43-1.50 (m, 2H) 1.34-1.41 (m, 10H) 1.31 (s, 2H) 1.11 (s, 3H) 1.01 (dd, J=14.56, 6.78 Hz, 6H) 0.80-0.94 (m, 3H); MS: MS m/z 956.9 (M$^+$+1).

Preparation of Compound 4065

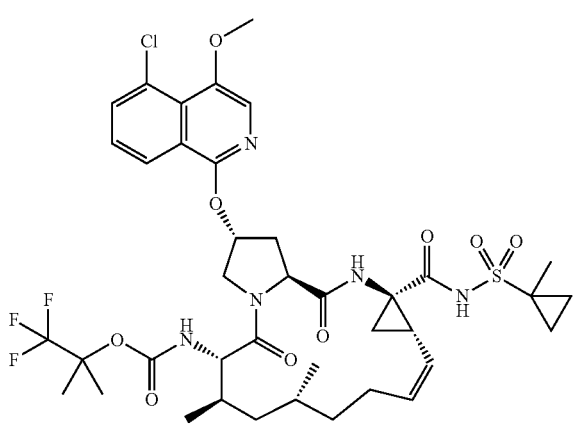

Compound 4065

Compound 4065 was prepared using the intermediates described herein and by following the general procedure described for the synthesis of Compound 3.

Compound 4065: 1,1,1-trifluoro-2-methylpropan-2-yl (2R,6S,7R,9R,13aS,14aR,16aS,Z)-2-(5-chloro-4-methoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.18 (dd, J=8.41, 1.13 Hz, 1H) 7.78 (dd, J=7.65, 1.13 Hz, 1H) 7.72 (s, 1H) 7.48 (t, J=7.91 Hz, 1H) 5.83-5.86 (m, 1H) 5.57-5.68 (m, 1H) 5.01 (t, J=10.16 Hz, 1H) 4.78 (d, J=12.05 Hz, 1H) 4.67 (dd, J=10.29, 7.03 Hz, 1H) 4.01 (dd, J=11.67, 3.39 Hz, 1H) 3.98 (s, 3H) 3.74-3.84 (m, 1H) 3.38 (dt, J=3.26, 1.63 Hz, 1H) 3.28 (dt, J=3.33, 1.73 Hz, 1H) 2.68-2.80 (m, 2H) 2.45 (ddd, J=13.68, 10.16, 4.02 Hz, 2H) 1.81-2.03 (m, 3H) 1.78 (dd, J=8.41, 5.65 Hz, 1H) 1.64-1.71 (m, 1H) 1.58 (dd, J=9.54, 5.52 Hz, 1H) 1.53 (s, 2H) 1.41-1.51 (m, 2H) 1.36 (s, 3H) 1.21-1.32 (m, 1H) 1.00 (dd, J=12.30, 6.78 Hz, 6H) 0.96 (s, 3H) 0.79-0.93 (m, 3H); MS: MS m/z 857.1 (M$^+$+1).

Preparation of Compound 4066

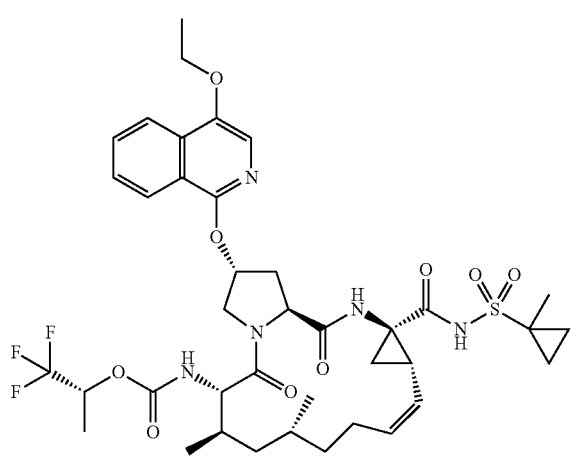

Compound 4066

Compound 4066 was prepared using the intermediates described herein and by following the general procedure described for the synthesis of Compound 3.

Compound 4066: (R)-1,1,1-trifluoropropan-2-yl (2R,6S,7R,9R,13aS,14aR,16aS,Z)-2-(4-ethoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.14 (d, J=9.04 Hz, 2H) 7.70-7.76 (m, 1H) 7.55 (s, 1H) 7.50-7.54 (m, 1H) 5.86 (br. s., 1H) 5.58-5.67 (m, 1H) 5.02 (t, J=9.79 Hz, 1H) 4.74 (d, J=11.04 Hz, 1H) 4.64 (dd, J=10.16, 7.15 Hz, 1H) 4.50 (quin, J=6.78 Hz, 1H) 4.25 (q, J=7.03 Hz, 2H) 4.03 (dd, J=11.29, 3.26 Hz, 1H) 3.89 (d, J=10.79 Hz, 1H) 2.69-2.79 (m, 2H) 2.43 (ddd, J=13.68, 9.91, 4.02 Hz, 2H) 1.92 (d, J=7.53 Hz, 2H) 1.72-1.85 (m, 2H) 1.66 (d, J=11.04 Hz, 1H) 1.49-1.60 (m, 9H) 1.40-1.49 (m, 1H) 1.22-1.32 (m, 1H) 1.20 (d, J=6.78 Hz, 3H) 0.97-1.05 (m, 6H) 0.82-0.95 (m, 3H); MS: MS m/z 820.4 (M$^+$−1).

Preparation of Compound 4067

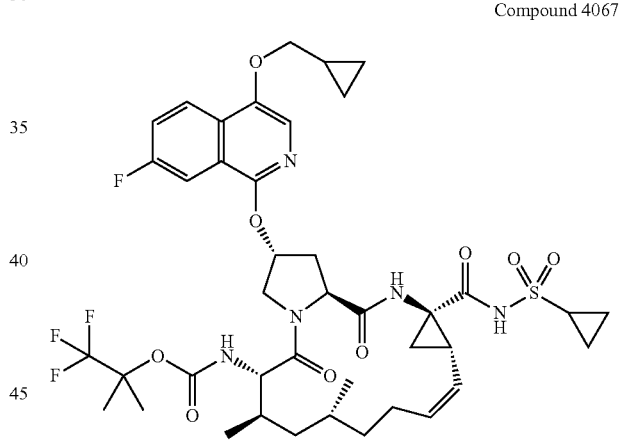

Compound 4067

Compound 4067 was prepared using the intermediates described herein and by following the general procedure described for the synthesis of Compound 3.

Compound 4067: 1,1,1-trifluoro-2-methylpropan-2-yl (2R,6S,7R,9R,13aS,14aR,16aS,Z)-2-(4-(cyclopropylmethoxy)-7-fluoroisoquinolin-1-yloxy)-14a-(cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.24 (dd, J=9.16, 5.40 Hz, 1H) 7.76 (dd, J=9.41, 2.38 Hz, 1H) 7.48-7.61 (m, 2H) 5.82 (br. s., 1H) 5.61 (br. s., 1H) 4.73 (d, J=12.30 Hz, 1H) 4.61-4.67 (m, 1H) 3.94-4.06 (m, 3H) 3.81 (d, J=11.04 Hz, 1H) 2.90 (br. s., 1H) 2.65-2.80 (m, 2H) 2.44 (br. s., 2H) 1.70-2.03 (m, 4H) 1.45-1.66 (m, 3H) 1.21-1.44 (m, 9H) 0.97-1.11 (m, 9H) 0.78-0.94 (m, 2H) 0.64-0.74 (m, 2H) 0.39-0.49 (m, 2H); MS: MS m/z 866.2 (M$^+$+1).

Preparation of Compound 4068

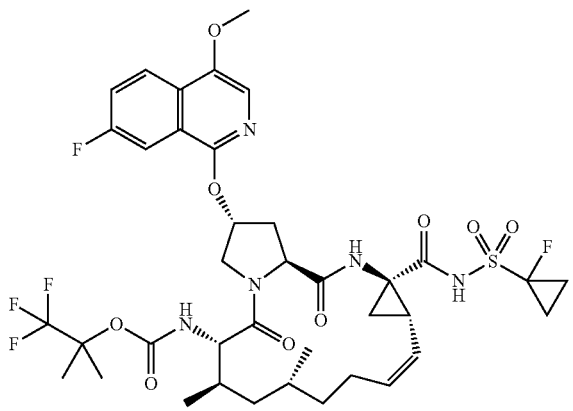

Compound 4068

Compound 4068 was prepared using the intermediates described herein and by following the general procedure described for the synthesis of Compound 3.

Compound 4068: 1,1,1-trifluoro-2-methylpropan-2-yl (2R,6S,7R,9R,13aS,14aR,16aS,Z)-2-(7-fluoro-4-methoxy-isoquinolin-1-yloxy)-14a-(1-fluorocyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.17 (dd, J=9.13, 5.38 Hz, 1H) 7.90 (s, 1H) 7.74 (dd, J=9.51, 2.50 Hz, 1H) 7.50-7.57 (m, 2H) 5.83 (s, 1H) 5.53-5.64 (m, 1H) 4.98 (t, J=10.01 Hz, 1H) 4.73 (s, 1H) 4.64 (dd, J=10.38, 6.88 Hz, 1H) 3.97-4.02 (m, 4H) 3.79 (d, J=10.76 Hz, 1H) 2.68-2.77 (m, 2H) 2.34-2.46 (m, 2H) 1.80-2.00 (m, 2H) 1.70-1.79 (m, 2H) 1.56-1.68 (m, 3H) 1.41-1.53 (m, 3H) 1.34 (s, 2H) 1.29 (s, 2H) 1.18-1.25 (m, 1H) 0.95-1.05 (m, 6H) 0.77-0.92 (m, 3H); MS: MS m/z 844.2 (M$^+$+1).

Preparation of Compound 4069

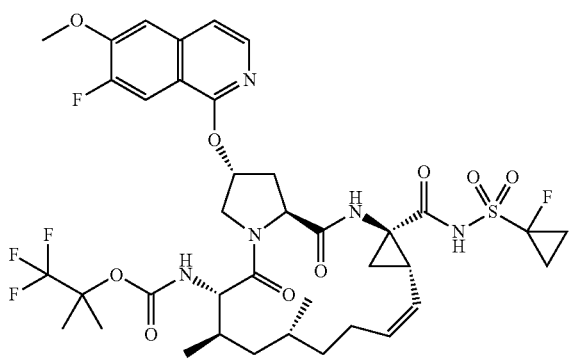

Compound 4069

Compound 4069 was prepared using the intermediates described herein and by following the general procedure described for the synthesis of Compound 3.

Compound 4069: 1,1,1-trifluoro-2-methylpropan-2-yl (2R,6S,7R,9R,13aS,14aR,16aS,Z)-2-(7-fluoro-6-methoxy-isoquinolin-1-yloxy)-14a-(1-fluorocyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 9.04 (s, 1H) 7.95 (d, J=5.77 Hz, 1H) 7.79 (d, J=11.80 Hz, 1H) 7.41 (d, J=8.28 Hz, 1H) 7.31 (d, J=6.02 Hz, 1H) 5.90 (s, 1H) 5.62 (d, J=6.02 Hz, 1H) 5.01 (t, J=9.79 Hz, 1H) 4.73 (d, J=11.29 Hz, 1H) 4.66 (dd, J=10.16, 6.90 Hz, 1H) 3.99-4.06 (m, 4H) 3.83 (dd, J=10.92, 8.16 Hz, 1H) 2.71-2.79 (m, 2H) 2.37-2.50 (m, 2H) 1.72-1.83 (m, 2H) 1.56-1.70 (m, 3H) 1.44-1.55 (m, 3H) 1.39 (s, 2H) 1.30-1.35 (m, 3H) 1.13 (s, 3H) 1.01 (t, J=7.15 Hz, 6H) 0.82-0.93 (m, 2H); MS: MS m/z 844.6 (M$^+$+1).

Preparation of Compound 4070

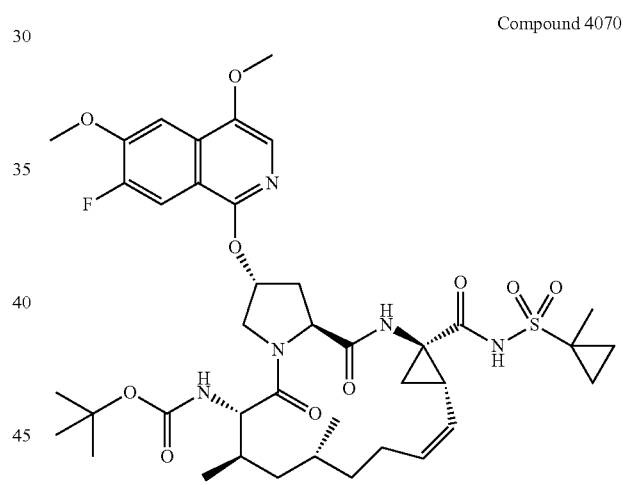

Compound 4070

Compound 4070 was prepared using the intermediates described herein and by following the general procedure described for the synthesis of Compound 1.

Compound 4070: tert-butyl (2R,6S,7R,9R,13aS,14aR,16aS,Z)-2-(7-fluoro-4,6-dimethoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.22 (s, 1H) 6.92 (d, J=11.54 Hz, 1H) 6.70-6.79 (m, 2H) 5.02 (br. s., 1H) 4.82 (d, J=5.52 Hz, 1H) 4.20 (t, J=10.04 Hz, 1H) 3.75-3.91 (m, 2H) 3.22 (d, J=1.51 Hz, 7H) 3.02-3.07 (m, 1H) 1.89-1.97 (m, 2H) 1.56-1.68 (m, 2H) 1.17 (br. s., 1H) 0.89-1.09 (m, 3H) 0.74-0.87 (m, 2H) 0.72 (s, 3H) 0.58-0.67 (m, 2H) 0.35 (s, 9H) 0.20 (dd, J=9.03, 6.78 Hz, 6H) −0.01-0.13 (m, 4H); MS: MS m/z 816.2 (M$^+$+1).

Preparation of Compound 4071

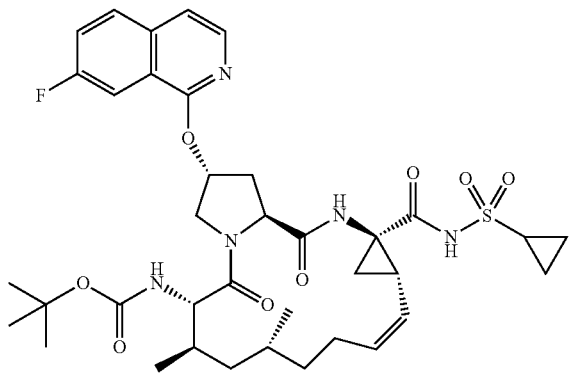

Compound 4071

Compound 4071 was prepared using the intermediates described herein and by following the general procedure described for the synthesis of Compound 1.

Compound 4071: tert-butyl (2R,6S,7R,9R,13aS,14aR,16aS,Z)-14a-(cyclopropylsulfonylcarbamoyl)-2-(7-fluoroisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.00 (d, J=5.77 Hz, 1H) 7.88-7.93 (m, 1H) 7.81 (dd, J=9.54, 2.76 Hz, 1H) 7.56 (d, J=2.76 Hz, 1H) 7.36-7.39 (m, 1H) 5.94 (br. s., 1H) 5.62 (d, J=5.77 Hz, 1H) 4.76 (d, J=11.04 Hz, 1H) 4.61-4.67 (m, 1H) 4.04 (dd, J=11.67, 3.39 Hz, 1H) 3.85 (d, J=10.79 Hz, 1H) 2.94 (br. s., 1H) 2.72-2.79 (m, 2H) 2.40-2.50 (m, 2H) 1.97-2.03 (m, 1H) 1.76-1.89 (m, 3H) 1.60 (dd, J=9.41, 5.40 Hz, 1H) 1.43-1.54 (m, 3H) 1.20-1.38 (m, 4H) 1.08-1.13 (m, 9H) 1.01 (dd, J=13.30, 6.78 Hz, 6H) 0.89-0.96 (m, 1H) 0.81 (s, 1H); MS: MS m/z 742.4 (M$^+$+1).

Preparation of Compound 4072

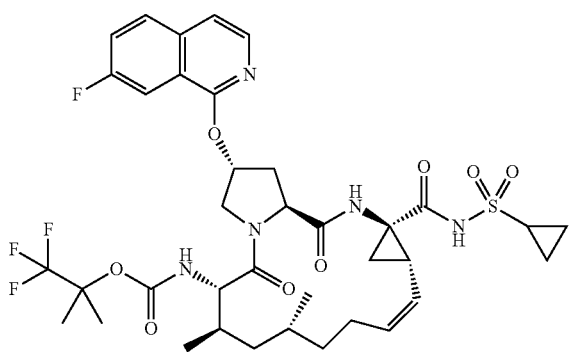

Compound 4072

Compound 4072 was prepared using the intermediates described herein and by following the general procedure described for the synthesis of Compound 3.

Compound 4072: 1,1,1-trifluoro-2-methylpropan-2-yl (2R,6S,7R,9R,13aS,14aR,16aS,Z)-14a-(cyclopropylsulfonylcarbamoyl)-2-(7-fluoroisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.01 (d, J=5.77 Hz, 1H) 7.92 (dd, J=9.03, 5.27 Hz, 1H) 7.83 (dd, J=9.29, 2.76 Hz, 1H) 7.56 (td, J=8.85, 2.64 Hz, 1H) 7.39 (d, J=5.52 Hz, 1H) 5.92 (br. s., 1H) 5.62 (d, J=5.52 Hz, 1H) 5.09 (br. s., 1H) 4.77 (d, J=10.29 Hz, 1H) 4.61-4.70 (m, 1H) 4.02 (dd, J=11.67, 3.39 Hz, 1H) 3.81 (d, J=10.79 Hz, 1H) 2.94 (br. s., 1H) 2.68-2.81 (m, 2H) 2.37-2.50 (m, 2H) 1.74-2.00 (m, 4H) 1.60 (dd, J=9.54, 5.27 Hz, 1H) 1.44-1.53 (m, 2H) 1.30-1.36 (m, 5H) 1.10 (dt, J=9.72, 4.80 Hz, 2H) 0.99-1.06 (m, 10H) 0.80-0.89 (m, 1H); MS: MS m/z 796.2 (M$^+$+1).

Preparation of Compound 4073

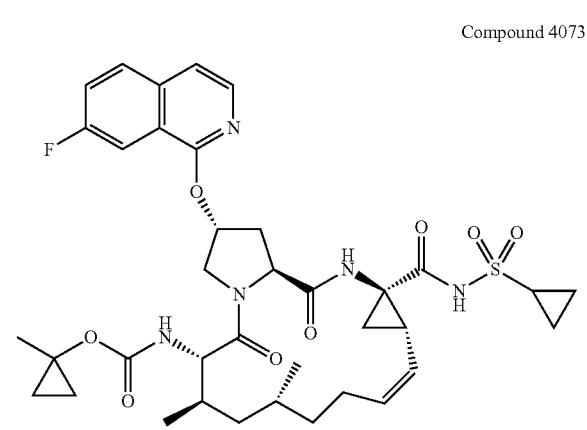 [SMILES: C[C@@H]1CC/C=C\[C@@H]2C[C@@]2(C(=O)NS(=O)(=O)C2CC2)NC(=O)[C@@H]2C[C@@H](Oc3nccc4ccc(F)cc34)CN2C(=O)[C@@H](NC(=O)OC2(C)CC2)[C@H](C)C1]

Compound 4073

Compound 4073 was prepared using the intermediates described herein and by following the general procedure described for the synthesis of Compound 3.

Compound 4073: 1-methylcyclopropyl (2R,6S,7R,9R,13aS,14aR,16aS,Z)-14a-(cyclopropylsulfonylcarbamoyl)-2-(7-fluoroisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.01 (d, J=5.77 Hz, 1H) 7.92 (dd, J=9.03, 5.27 Hz, 1H) 7.84 (dd, J=9.54, 2.51 Hz, 1H) 7.55 (td, J=8.85, 2.64 Hz, 1H) 7.39 (d, J=5.77 Hz, 1H) 5.97 (br. s., 1H) 5.61 (br. s., 1H) 5.07 (br. s., 1H) 4.69 (d, J=12.30 Hz, 1H) 4.57-4.64 (m, 1H) 4.09 (dd, J=11.42, 3.64 Hz, 1H) 3.92 (d, J=10.79 Hz, 1H) 2.94 (br. s., 1H) 2.76 (dd, J=14.18, 7.40 Hz, 2H) 2.40-2.51 (m, 2H) 1.74-2.03 (m, 5H) 1.59 (dd, J=9.41, 5.14 Hz, 1H) 1.49 (br. s., 2H) 1.31 (br. s., 2H) 1.20 (s, 3H) 1.09 (dd, J=9.91, 4.89 Hz, 2H) 1.02 (dd, J=14.93, 6.65 Hz, 7H) 0.86 (t, J=11.92 Hz, 1H) 0.63-0.70 (m, 1H) 0.54 (dt, J=11.23, 5.55 Hz, 1H) 0.40-0.47 (m, 1H) 0.31-0.39 (m, 1H); MS: MS m/z 738.2 (M$^+$+1).

Preparation of Compound 4074

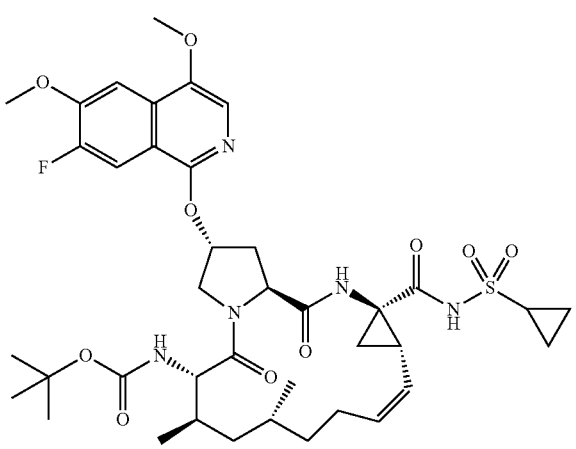

Compound 4074

Compound 4074 was prepared using the intermediates described herein and by following the general procedure described for the synthesis of Compound 1.

Compound 4074: tert-butyl (2R,6S,7R,9R,13aS,14aR,16aS,Z)-14a-(cyclopropylsulfonylcarbamoyl)-2-(7-fluoro-4,6-dimethoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 7.73 (d, J=11.54 Hz, 1H) 7.49-7.58 (m, 2H) 6.63 (d, J=7.53 Hz, 1H) 5.81 (br. s., 1H) 5.62 (d, J=4.77 Hz, 1H) 5.06 (br. s., 1H) 4.56-4.70 (m, 2H) 3.98-4.05 (m, 7H) 3.81-3.90 (m, 1H) 3.07 (q, J=7.28 Hz, 1H) 2.92 (br. s., 1H) 2.65-2.78 (m, 2H) 2.42 (br. s., 2H) 1.98 (br. s., 1H) 1.73-1.88 (m, 2H) 1.59 (dd, J=9.29, 5.27 Hz, 1H) 1.49 (br. s., 1H) 1.28-1.36 (m, 3H) 1.20-1.27 (m, 1H) 1.16 (s, 9H) 1.11 (br. s., 1H) 1.01 (dd, J=13.05, 6.78 Hz, 6H) 0.73-0.89 (m, 1H); MS: MS m/z 802.8 (M$^+$+1).

Preparation of Compound 4075

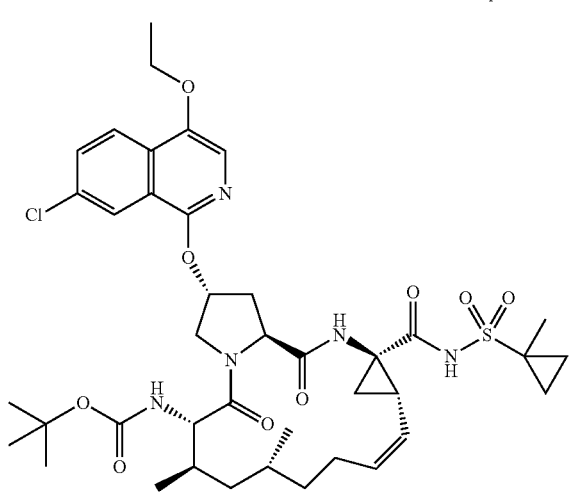

Compound 4075

Compound 4075 was prepared using the intermediates described herein and by following the general procedure described for the synthesis of Compound 1.

Compound 4075: tert-butyl (2R,6S,7R,9R,13aS,14aR,16aS,Z)-2-(7-chloro-4-ethoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.13 (d, J=9.03 Hz, 1H) 8.07 (d, J=2.01 Hz, 1H) 7.70 (dd, J=8.91, 2.13 Hz, 1H) 7.60 (s, 1H) 6.66 (d, J=8.53 Hz, 1H) 5.87 (br. s., 1H) 5.63 (td, J=10.23, 5.65 Hz, 1H) 5.02 (t, J=10.04 Hz, 1H) 4.60-4.76 (m, 2H) 4.24 (q, J=6.86 Hz, 2H) 4.03 (dd, J=11.54, 3.26 Hz, 1H) 3.79-3.86 (m, 1H) 2.69-2.80 (m, 2H) 2.44 (ddd, J=13.74, 9.98, 4.39 Hz, 2H) 1.98 (br. s., 1H) 1.75-1.89 (m, 3H) 1.64-1.71 (m, 1H) 1.55-1.62 (m, 2H) 1.51-1.54 (m, 6H) 1.40-1.49 (m, 3H) 1.13-1.33 (m, 3H) 1.05 (s, 9H) 0.96-1.02 (m, 6H) 0.80-0.91 (m, 2H); MS: MS m/z 816.2 (M$^+$+1).

Preparation of Compound 4076

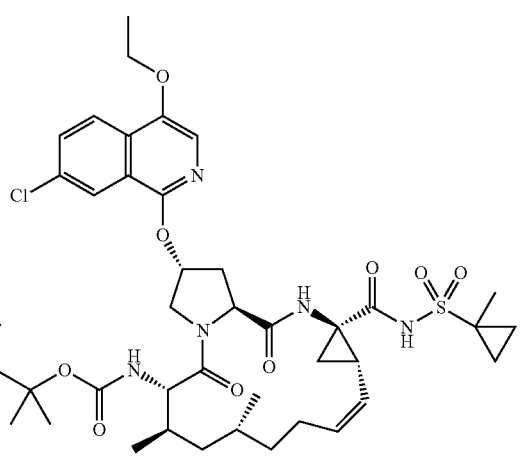

Compound 4076

Compound 4076 was prepared using the intermediates described herein and by following the general procedure described for the synthesis of Compound 3.

Compound 4076: 1,1,1-trifluoro-2-methylpropan-2-yl (2R,6S,7R,9R,13aS,14aR,16aS,Z)-2-(7-chloro-4-ethoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.15 (d, J=9.03 Hz, 1H) 8.08 (d, J=2.01 Hz, 1H) 7.72 (dd, J=8.91, 2.13 Hz, 1H) 7.61 (s, 1H) 5.86 (br. s., 1H) 5.62 (d, J=5.52 Hz, 1H) 5.01 (d, J=12.05 Hz, 1H) 4.66-4.78 (m, 2H) 4.25 (q, J=7.03 Hz, 2H) 4.00 (dd, J=11.54, 3.26 Hz, 1H) 3.77 (d, J=10.79 Hz, 1H) 2.74 (dd, J=13.05, 6.78 Hz, 2H) 2.38-2.51 (m, 2H) 1.91-2.02 (m, 1H) 1.75-1.90 (m, 3H) 1.57-1.72 (m, 2H) 1.51-1.57 (m, 7H) 1.39-1.49 (m, 3H) 1.31 (s, 1H) 1.21-1.28 (m, 3H) 1.00 (dd, J=12.92, 6.65 Hz, 6H) 0.94 (s, 3H) 0.78-0.90 (m, 2H); MS: MS m/z 870.2 (M$^+$+1).

Preparation of Compound 4077

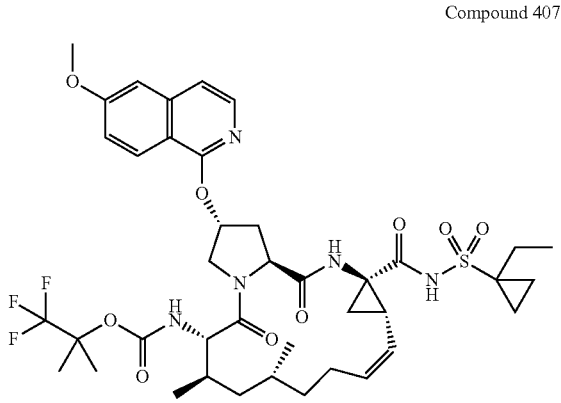

Compound 4077

Compound 4077 was prepared using the intermediates described herein and by following the general procedure described for the synthesis of Compound 3.

Compound 4077: 1,1,1-trifluoro-2-methylpropan-2-yl (2R,6S,7R,9R,13aS,14aR,16aS,Z)-14a-(1-ethylcyclopropylsulfonylcarbamoyl)-2-(6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 9.06 (s, 1H) 8.12 (d, J=9.04 Hz, 1H) 7.82-8.00 (m, 1H) 7.30 (d, J=6.27 Hz, 1H) 7.23 (d, J=2.26 Hz, 1H) 7.13 (dd, J=9.03, 2.51 Hz, 1H) 5.89 (br. s., 1H) 5.50-5.71 (m, 1H) 4.99 (t, J=9.91 Hz, 1H) 4.76 (d, J=11.04 Hz, 1H) 4 4.05 (dd, J=11.54, 3.51 Hz, 1H) 3.95 (s, 3H) 3.84 (d, J=10.79 Hz, 1H) 2.66-2.80 (m, 2H) 2.34-2.52 (m, 2H) 2.01-2.12 (m, 1H) 1.86-2.00 (m, 2H) 1.73-1.85 (m, 3H) 1.60-1.71 (m, 1H) 1.56 (dd, J=9.41, 5.65 Hz, 1H) 1.43-1.52 (m, 2H) 1.35-1.43 (m, 4H) 1.19-1.34 (m, 2H) 0.96-1.06 (m, 12H) 0.76-0.95 (m, 3H); MS: MS m/z 836.4 (M$^+$+1).

Preparation of Compound 4078

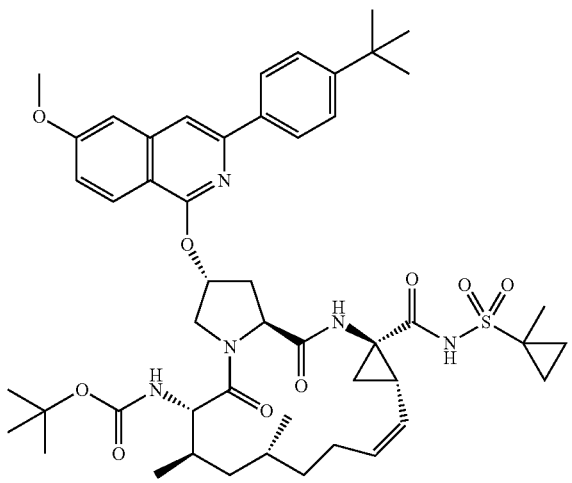

Compound 4078

Compound 4078 was prepared using the intermediates described herein and by following the general procedure described for the synthesis of Compound 1.

Compound 4078: tert-butyl (2R,6S,7R,9R,13aS,14aR,16aS,Z)-2-((3-(4-tert-butylphenyl)-6-methoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.06-8.13 (m, 3H) 7.76 (s, 1H) 7.55 (d, J=8.53 Hz, 2H) 7.27 (d, J=2.26 Hz, 1H) 7.06 (d, J=9.29 Hz, 1H) 6.11 (br. s., 1H) 5.58-5.67 (m, 1H) 5.04 (br. s., 1H) 4.59-4.74 (m, 2H) 4.19 (d, J=8.28 Hz, 1H) 3.90-3.99 (m, 4H) 2.71-2.87 (m, 3H) 2.42-2.57 (m, 2H) 1.97 (s, 1H) 1.74-1.92 (m, 3H) 1.66 (d, J=8.78 Hz, 1H) 1.44-1.60 (m, 6H) 1.41 (s, 9H) 1.27-1.37 (m, 2H) 1.22 (s, 9H) 1.02 (dd, J=13.43, 6.65 Hz, 6H) 0.84-0.94 (m, 2H); MS: MS m/z 900.9 (M$^+$+1).

Preparation of Compound 4079

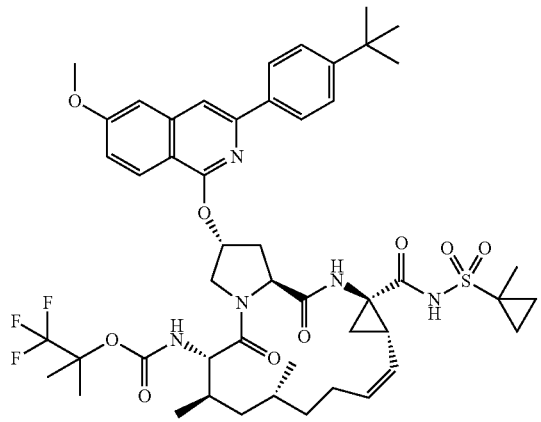

Compound 4079

Compound 4079 was prepared using the intermediates described herein and by following the general procedure described for the synthesis of Compound 3.

Compound 4079: 1,1,1-trifluoro-2-methylpropan-2-yl (2R,6S,7R,9R,13aS,14aR,16aS,Z)-2-((3-(4-tert-butylphenyl)-6-methoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.07-8.13 (m, 3H) 7.77 (s, 1H) 7.55 (d, J=8.53 Hz, 2H) 7.25-7.31 (m, 1H) 7.07 (dd, J=9.03, 2.26 Hz, 1H) 6.09 (br. s., 1H) 5.64 (td, J=10.10, 5.90 Hz, 1H) 5.02 (t, J=9.91 Hz, 1H) 4.78 (s, 1H) 4.69 (dd, J=9.91, 7.15 Hz, 1H) 4.16 (dd, J=11.29, 3.51 Hz, 1H) 3.97 (s, 3H) 3.90 (dd, J=10.67, 8.41 Hz, 1H) 2.71-2.86 (m, 2H) 2.41-2.56 (m, 2H) 1.95-2.06 (m, 1H) 1.74-1.93 (m, 3H) 1.64-1.70 (m, 1H) 1.58 (dd, J=9.66, 5.65 Hz, 1H) 1.54 (s, 3H) 1.43-1.51 (m, 3H) 1.41 (s, 11H) 1.21-1.36 (m, 2H) 1.11 (s, 3H) 1.01 (dd, J=15.69, 6.65 Hz, 6H) 0.85-0.92 (m, 3H); MS: MS m/z 952.9 (M$^+$−1).

Preparation of Compound 4080

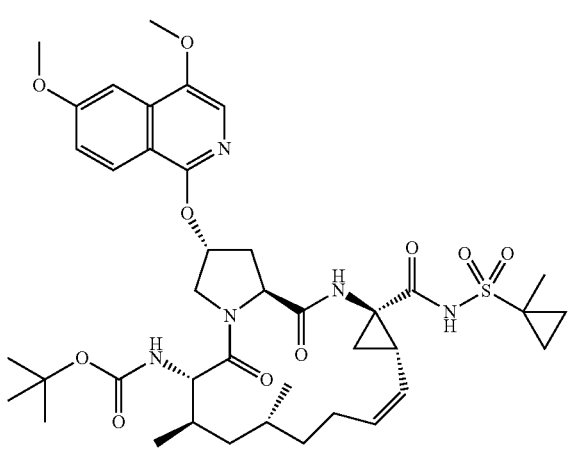

Compound 4080

Compound 4080 was prepared using the intermediates described herein and by following the general procedure described for the synthesis of Compound 1.

Compound 4080: tert-butyl (2R,6S,7R,9R,13aS,14aR,16aS,Z)-2-(4,6-dimethoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.04 (d, J=9.03 Hz, 1H) 7.49 (s, 1H) 7.39 (d, J=2.26 Hz, 1H) 7.09 (dd, J=9.16, 2.38 Hz, 1H) 5.79 (br. s., 1H) 5.60 (td, J=10.10, 5.90 Hz, 1H) 4.98 (t, J=9.91 Hz, 1H) 4.52-4.68 (m, 2H) 3.96-4.03 (m, 4H) 3.92 (s, 3H) 3.85 (d, J=10.79 Hz, 1H) 2.66-2.76 (m, 2H) 2.32-2.46 (m, 2H) 1.95 (t, J=13.30 Hz, 1H) 1.73 (dd, J=8.28, 5.77 Hz, 3H) 1.63 (d, J=10.54 Hz, 1H) 1.38-1.56 (m, 6H) 1.28 (s, 2H) 1.14 (s, 9H) 0.98 (dd, J=9.91, 6.65 Hz, 6H) 0.81-0.88 (m, 3H); MS: MS m/z 798.5 (M$^+$+1).

Preparation of Compound 4081

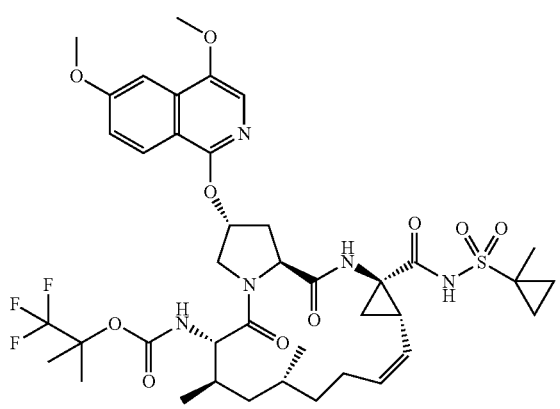

Compound 4081

Compound 4081 was prepared using the intermediates described herein and by following the general procedure described for the synthesis of Compound 3.

Compound 4081: 1,1,1-trifluoro-2-methylpropan-2-yl (2R,6S,7R,9R,13aS,14aR,16aS,Z)-2-(4,6-dimethoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.04 (d, J=9.03 Hz, 1H) 7.49 (s, 1H) 7.39 (d, J=2.26 Hz, 1H) 7.09 (dd, J=9.16, 2.38 Hz, 1H) 5.79 (br. s., 1H) 5.60 (td, J=10.10, 5.90 Hz, 1H) 4.98 (t, J=9.91 Hz, 1H) 4.52-4.69 (m, 2H) 3.97-4.03 (m, 4H) 3.82-3.93 (m, 4H) 2.64-2.76 (m, 2H) 2.33-2.46 (m, 2H) 1.95 (t, J=13.30 Hz, 1H) 1.70-1.88 (m, 3H) 1.60-1.68 (m, 1H) 1.52-1.56 (m, 1H) 1.49 (s, 3H) 1.36-1.45 (m, 2H) 1.20-1.31 (m, 2H) 1.08-1.16 (m, 10H) 0.98 (dd, J=9.91, 6.65 Hz, 6H) 0.79-0.89 (m, 3H); MS: MS m/z 852.6 (M$^+$+1).

Preparation of Compound 4082

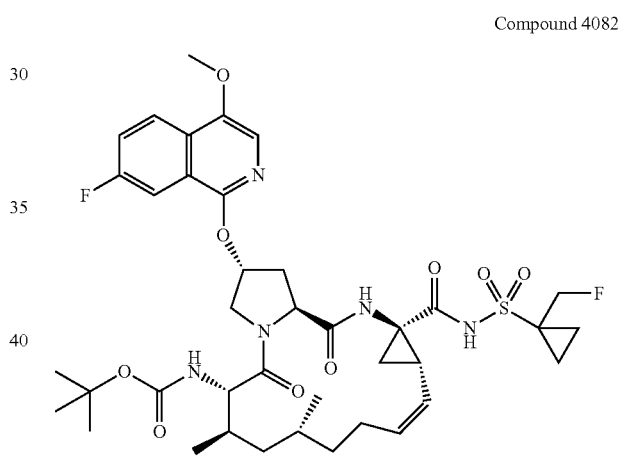

Compound 4082

Compound 4082 was prepared using the intermediates described herein and by following the general procedure described for the synthesis of Compound 1.

Compound 4082: tert-butyl (2R,6S,7R,9R,13aS,14aR,16aS,Z)-2-(7-fluoro-4-methoxyisoquinolin-1-yloxy)-14a-(1-(fluoromethyl)cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.17 (dd, J=9.16, 5.40 Hz, 1H) 7.74 (dd, J=9.54, 2.51 Hz, 1H) 7.55-7.57 (m, 1H) 7.49-7.54 (m, 1H) 5.84 (br. s., 1H) 5.62 (td, J=10.23, 5.65 Hz, 1H) 5.00 (t, J=10.16 Hz, 1H) 4.71 (d, J=11.80 Hz, 1H) 4.59-4.66 (m, 2H) 4.50 (s, 1H) 3.99-4.06 (m, 4H) 3.85 (d, J=10.79 Hz, 1H) 2.68-2.76 (m, 2H) 2.40-2.49 (m, 2H) 1.91-2.02 (m, 1H) 1.77-1.89 (m, 2H) 1.62-1.74 (m, 3H) 1.57 (dd, J=9.54, 5.52 Hz, 1H) 1.43-1.53 (m, 2H) 1.17-1.35 (m, 3H) 1.12 (s, 9H) 1.01 (dd, J=14.05, 6.78 Hz, 6H) 0.80-0.92 (m, 1H); MS: MS m/z 804.4 (M$^+$+1).

Preparation of Compound 4083

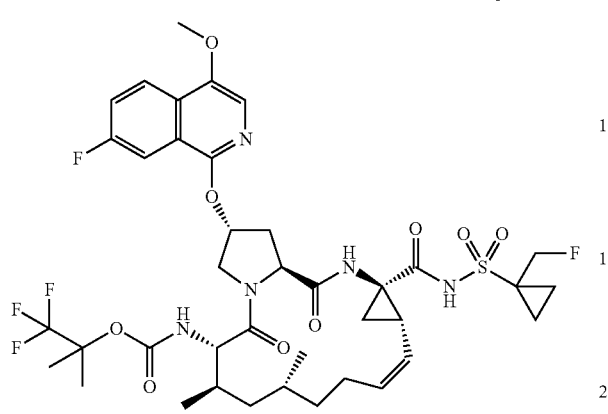

Compound 4083

Compound 4083 was prepared using the intermediates described herein and by following the general procedure described for the synthesis of Compound 3.

Compound 4083: 1,1,1-trifluoro-2-methylpropan-2-yl (2R,6S,7R,9R,13aS,14aR,16aS,Z)-2-(7-fluoro-4-methoxy-isoquinolin-1-yloxy)-14a-(1-(fluoromethyl)cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.19 (dd, J=9.03, 5.27 Hz, 1H) 7.76 (dd, J=9.54, 2.51 Hz, 1H) 7.47-7.59 (m, 2H) 5.83 (br. s., 1H) 5.59 (br. s., 1H) 4.68-4.76 (m, 1H) 4.55-4.66 (m, 2H) 3.98-4.05 (m, 4H) 3.82 (d, J=11.04 Hz, 1H) 2.73 (dd, J=14.05, 6.78 Hz, 1H) 2.34-2.50 (m, 2H) 2.06 (s, 2H) 1.97 (t, J=14.05 Hz, 1H) 1.78-1.90 (m, 2H) 1.61-1.75 (m, 2H) 1.57 (dd, J=9.41, 5.40 Hz, 1H) 1.48 (br. s., 3H) 1.37 (s, 3H) 1.31 (s, 2H) 1.12-1.28 (m, 3H) 0.97-1.07 (m, 9H) 0.79-0.95 (m, 1H); MS: MS m/z 859.2 (M$^+$+1).

Preparation of Compound 4084

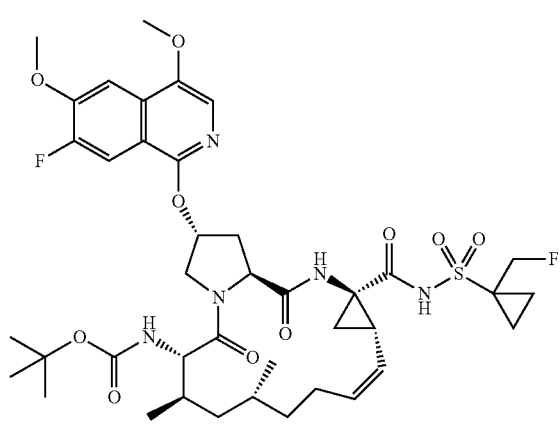

Compound 4084

Compound 4084 was prepared using the intermediates described herein and by following the general procedure described for the synthesis of Compound 1.

Compound 4084: tert-butyl (2R,6S,7R,9R,13aS,14aR,16aS,Z)-2-(7-fluoro-4,6-dimethoxyisoquinolin-1-yloxy)-14a-(1-(fluoromethyl)cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.73 (d, J=11.54 Hz, 1H) 7.51-7.58 (m, 2H) 5.82 (br. s., 1H) 5.62 (td, J=10.23, 5.90 Hz, 1H) 4.96-5.05 (m, 1H) 4.79 (d, J=11.29 Hz, 1H) 4.48-4.70 (m, 3H) 3.97-4.06 (m, 7H) 3.81-3.90 (m, 1H) 2.64-2.76 (m, 2H) 2.42 (ddd, J=13.99, 10.10, 4.52 Hz, 2H) 1.97 (t, J=12.80 Hz, 1H) 1.76-1.90 (m, 2H) 1.62-1.75 (m, 2H) 1.55-1.61 (m, 1H) 1.45-1.53 (m, 1H) 1.39 (dt, J=6.96, 3.67 Hz, 1H) 1.30-1.35 (m, 1H) 1.20-1.29 (m, 3H) 1.16 (s, 9H) 1.01 (dd, J=13.05, 6.53 Hz, 6H) 0.84 (t, J=12.30 Hz, 1H); MS: MS m/z 834.4 (M$^+$+1).

Preparation of Compound 4085

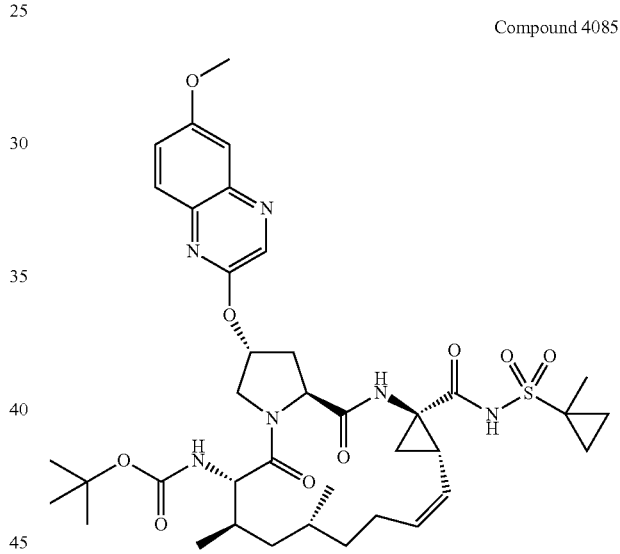

Compound 4085

Compound 4085 was prepared using the intermediates described herein and by following the general procedure described for the synthesis of Compound 1.

Compound 4085: tert-butyl (2R,6S,7R,9R,13aS,14aR,16aS,Z)-2-(6-methoxyquinoxalin-2-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.39 (s, 1H) 7.83 (d, J=9.03 Hz, 1H) 7.39 (d, J=2.51 Hz, 2H) 6.65 (d, J=8.78 Hz, 1H) 5.89 (br. s., 1H) 5.63 (td, J=10.23, 5.65 Hz, 1H) 5.02 (t, J=9.66 Hz, 1H) 4.69 (d, J=11.80 Hz, 1H) 4.61 (dd, J=10.04, 7.28 Hz, 1H) 4.08 (dd, J=11.92, 3.39 Hz, 1H) 3.96 (s, 3H) 3.80-3.87 (m, 1H) 2.66-2.76 (m, 2H) 2.39-2.52 (m, 2H) 1.99 (br. s., 1H) 1.86 (d, J=6.53 Hz, 1H) 1.78 (dd, J=8.28, 5.52 Hz, 2H) 1.63-1.70 (m, 1H) 1.59 (dd, J=9.41, 5.65 Hz, 1H) 1.53 (s, 3H) 1.40-1.50 (m, 3H) 1.31 (s, 2H) 1.21-1.28 (m, 1H) 1.16 (s, 9H) 0.95-1.04 (m, 6H) 0.77-0.91 (m, 1H); MS: MS m/z 768.1 (M$^+$−1).

Preparation of Compound 4086

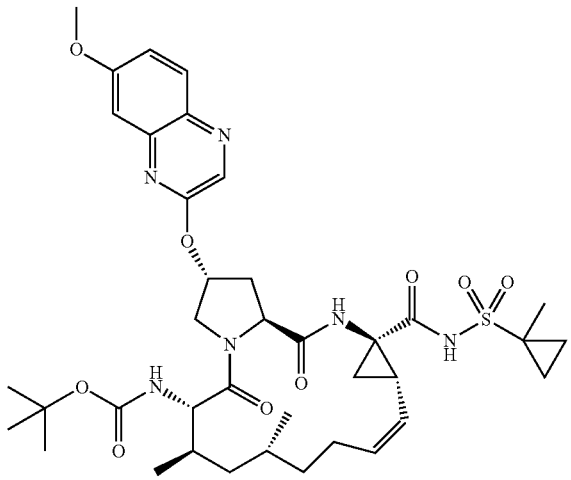

Compound 4086

Compound 4086 was prepared using the intermediates described herein and by following the general procedure described for the synthesis of Compound 1.

Compound 4086: tert-butyl (2R,6S,7R,9R,13aS,14aR,16aS,Z)-2-(7-methoxyquinoxalin-2-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.26 (s, 1H) 7.86 (d, J=9.03 Hz, 1H) 7.33 (d, J=2.76 Hz, 1H) 7.27 (dd, J=9.03, 2.76 Hz, 1H) 6.70 (d, J=8.78 Hz, 1H) 5.92 (br. s., 1H) 5.64 (s, 1H) 4.97-5.06 (m, 1H) 4.72 (d, J=11.04 Hz, 1H) 4.59-4.65 (m, 1H) 4.10 (d, J=11.54 Hz, 1H) 3.99 (s, 3H) 3.81-3.87 (m, 1H) 2.70 (d, J=7.03 Hz, 2H) 2.49 (s, 2H) 1.99 (br. s., 1H) 1.87 (br. s., 1H) 1.74-1.82 (m, 2H) 1.67 (d, J=12.05 Hz, 1H) 1.59 (dd, J=9.66, 5.65 Hz, 1H) 1.53 (s, 3H) 1.48 (br. s., 1H) 1.38-1.46 (m, 2H) 1.31 (s, 2H) 1.22 (br. s., 1H) 1.15 (s, 9H) 0.99 (dd, J=19.83, 6.53 Hz, 6H) 0.90 (br. s., 1H); MS: MS m/z 769.4 (M$^+$+1).

Preparation of Compound 4087

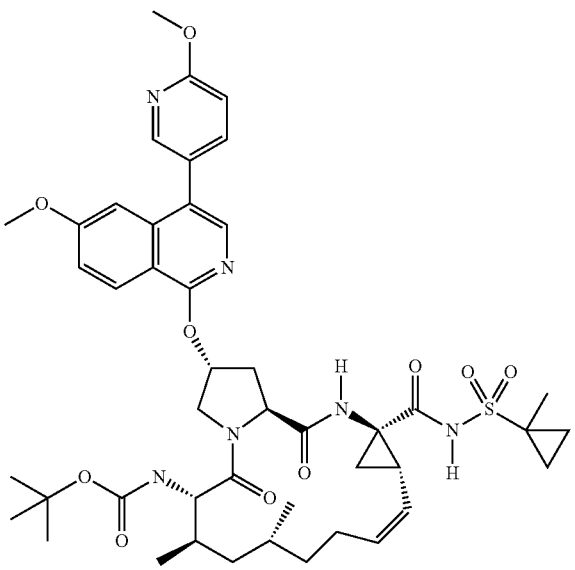

Compound 4087

Compound 4087 was prepared using the intermediates described herein and by following the general procedure described for the synthesis of Compound 1.

Compound 4087: tert-butyl (2R,6S,7R,9R,13aS,14aR,16aS,Z)-2-(6-methoxy-4-(6-methoxypyridin-3-yl)isoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 9.07 (s, 1H) 8.22-8.26 (m, 2H) 7.84-7.90 (m, 2H) 7.18 (dd, J=9.16, 2.38 Hz, 1H) 7.01-7.06 (m, 2H) 5.94 (br. s., 1H) 5.63 (d, J=5.27 Hz, 1H) 5.02 (t, J=10.04 Hz, 1H) 4.78-4.84 (m, 1H) 4.67 (dd, J=10.04, 7.03 Hz, 1H) 4.03 (s, 4H) 3.81-3.90 (m, 4H) 2.71-2.83 (m, 2H) 2.47 (ddd, J=13.80, 10.04 Hz, 2H) 1.93-2.06 (m, 1H) 1.75-1.92 (m, 3H) 1.63-1.72 (m, 1H) 1.52-1.61 (m, 5H) 1.38-1.50 (m, 3H) 1.31 (s, 2H) 1.13 (s, 9H) 1.01 (dd, J=8.66, 6.90 Hz, 5H) 0.79-0.94 (m, 2H); MS: MS m/z 875.5 (M$^+$+1).

Preparation of Compound 4088

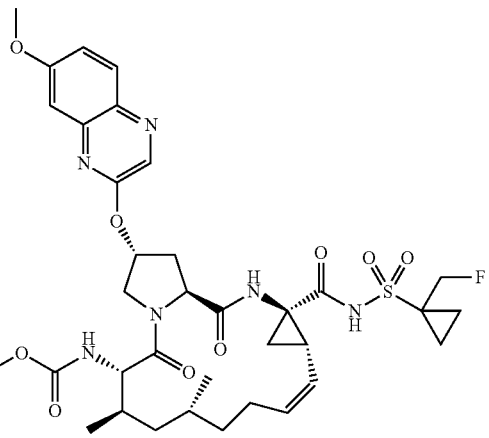

Compound 4088

Compound 4088 was prepared using the intermediates described herein and by following the general procedure described for the synthesis of Compound 3.

Compound 4088: 1,1,1-trifluoro-2-methylpropan-2-yl (2R,6S,7R,9R,13aS,14aR,16aS,Z)-14a-(1-(fluoromethyl)cyclopropylsulfonylcarbamoyl)-2-(7-methoxyquinoxalin-2-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 9.08 (s, 1H) 8.27 (s, 1H) 7.85-7.93 (m, 1H) 7.25-7.35 (m, 2H) 5.90 (br. s., 1H) 5.63 (d, J=5.77 Hz, 1H) 4.72-4.81 (m, 2H) 4.59-4.66 (m, 2H) 4.09 (d, J=3.51 Hz, 1H) 3.99 (s, 3H) 3.81 (d, J=11.04 Hz, 1H) 2.64-2.74 (m, 2H) 2.34-2.53 (m, 2H) 1.93-2.04 (m, 1H) 1.82-1.92 (m, 1H) 1.64-1.82 (m, 4H) 1.59 (dd, J=9.54, 5.77 Hz, 1H) 1.41-1.54 (m, 2H) 1.16-1.33 (m, 11H) 0.95-1.07 (m, 4H) 0.77-0.93 (m, 2H); MS: MS m/z 841.2 (M$^+$+1).

Preparation of Compound 4089

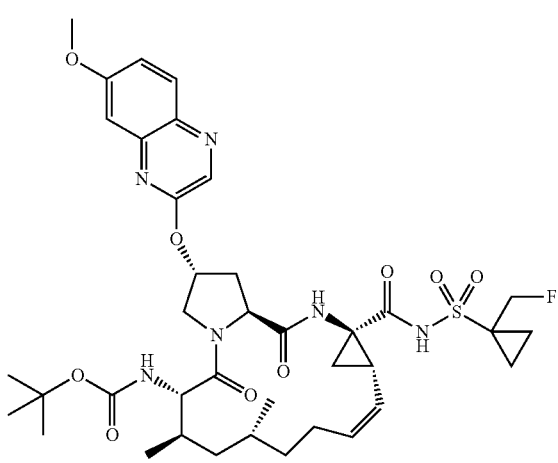

Compound 4089

Compound 4089 was prepared using the intermediates described herein and by following the general procedure described for the synthesis of Compound 1.

Compound 4089: tert-butyl (2R,6S,7R,9R,13aS,14aR,16aS,Z)-14a-(1-(fluoromethyl)cyclopropylsulfonylcarbamoyl)-2-(7-methoxyquinoxalin-2-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.
$^1$H NMR (400 MHz, CD$_3$OD): δ ppm 9.07 (s, 1H) 8.25 (s, 1H) 7.83-7.93 (m, 1H) 7.24-7.34 (m, 2H) 5.92 (br. s., 1H) 5.63 (td, J=10.42, 5.77 Hz, 1H) 5.01 (t, J=10.04 Hz, 1H) 4.65-4.74 (m, 1H) 4.55-4.64 (m, 1H) 4.10 (dd, J=11.80, 3.76 Hz, 1H) 3.99 (s, 3H) 3.84 (d, J=10.79 Hz, 1H) 2.64-2.74 (m, 2H) 2.34-2.54 (m, 2H) 1.93-2.04 (m, 1H) 1.78-1.91 (m, 2H) 1.63-1.78 (m, 4H) 1.59 (dd, J=9.54, 5.52 Hz, 1H) 1.42-1.55 (m, 2H) 1.19-1.39 (m, 5H) 1.15 (s, 10H) 0.94-1.07 (m, 3H) 0.78-0.93 (m, 2H); MS: MS m/z 787.2 (M$^+$+1).

Preparation of Compound 4090

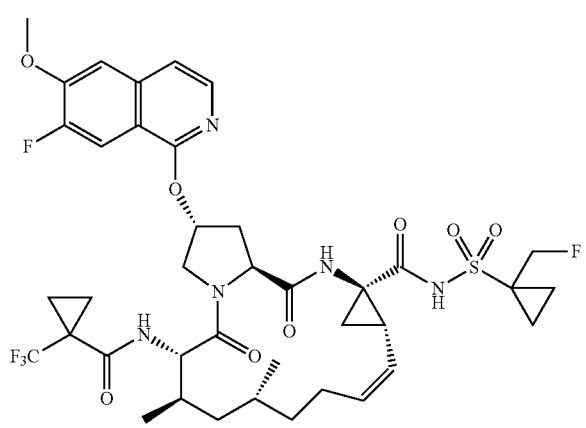

Compound 4090

Compound 4090 was prepared using the intermediates described herein and by following the general procedure described for the synthesis of Compound 4029.

Compound 4090: (2R,6S,7R,9R,13aS,14aR,16aS,Z)-2-(7-fluoro-6-methoxyisoquinolin-1-yloxy)-N-(1-(fluoromethyl)cyclopropylsulfonyl)-7,9-dimethyl-5,16-dioxo-6-(1-(trifluoromethyl)cyclopropanecarboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (400 MHz, CD$_3$OD): δ ppm 8.99 (s, 1H) 7.94 (d, J=6.02 Hz, 1H) 7.77 (d, J=11.80 Hz, 1H) 7.58 (d, J=7.78 Hz, 1H) 7.41 (d, J=8.03 Hz, 1H) 7.31 (d, J=5.52 Hz, 1H) 5.90 (br. s., 1H) 5.63 (d, J=5.52 Hz, 1H) 5.02 (t, J=9.91 Hz, 1H) 4.77-4.82 (m, 2H) 4.48-4.66 (m, 3H) 4.25 (dd, J=10.92, 8.41 Hz, 1H) 4.02-4.09 (m, 4H) 2.71 (d, J=9.03 Hz, 2H) 2.39-2.49 (m, 2H) 2.01 (d, J=4.77 Hz, 2H) 1.81-1.89 (m, 1H) 1.64-1.75 (m, 3H) 1.46-1.61 (m, 3H) 1.17-1.35 (m, 4H) 1.08-1.16 (m, 3H) 1.02 (dd, J=16.06, 6.78 Hz, 4H) 0.83-0.98 (m, 1H); MS: MS m/z 840.2 (M$^+$+1).

Preparation of Compound 4091

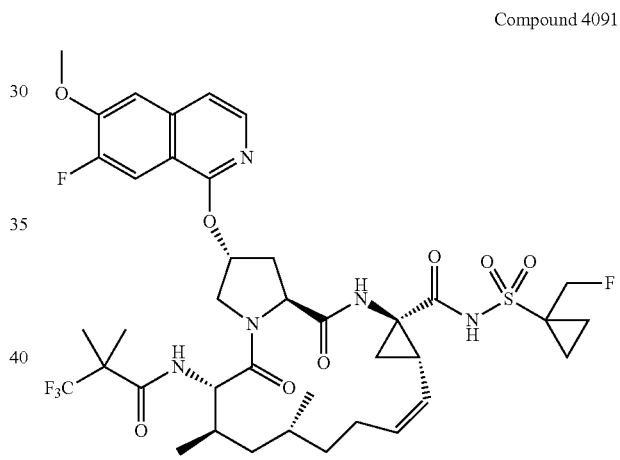

Compound 4091

Compound 4091 was prepared using the intermediates described herein and by following the general procedure described for the synthesis of Compound 4029.

Compound 4091: (2R,6S,7R,9R,13aS,14aR,16aS,Z)-2-(7-fluoro-6-methoxyisoquinolin-1-yloxy)-N-(1-(fluoromethyl)cyclopropylsulfonyl)-7,9-dimethyl-5,16-dioxo-6-(3,3,3-trifluoro-2,2-dimethylpropanamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (400 MHz, CD$_3$OD): δ ppm 8.98 (s, 1H) 7.94 (d, J=6.02 Hz, 1H) 7.78 (d, J=11.80 Hz, 1H) 7.60 (s, 1H) 7.40 (d, J=8.28 Hz, 1H) 7.31 (d, J=5.77 Hz, 1H) 5.91 (s, 1H) 5.64 (d, J=5.52 Hz, 1H) 5.02 (t, J=10.16 Hz, 1H) 4.77-4.82 (m, 2H) 4.49-4.70 (m, 4H) 4.27 (dd, J=10.79, 8.28 Hz, 1H) 4.00-4.10 (m, 5H) 3.43 (s, 1H) 3.28 (dt, J=3.26, 1.63 Hz, 1H) 2.73 (d, J=9.54 Hz, 3H) 2.38-2.50 (m, 3H) 1.94-2.14 (m, 2H) 1.81-1.90 (m, 1H) 1.64-1.76 (m, 4H) 1.49-1.60 (m, 2H) 1.17-1.34 (m, 5H) 0.96-1.08 (m, 2H) 0.88 (d, J=11.04 Hz, 1H); MS: MS m/z 842.2 (M$^+$+1).

Preparation of Compound 4092

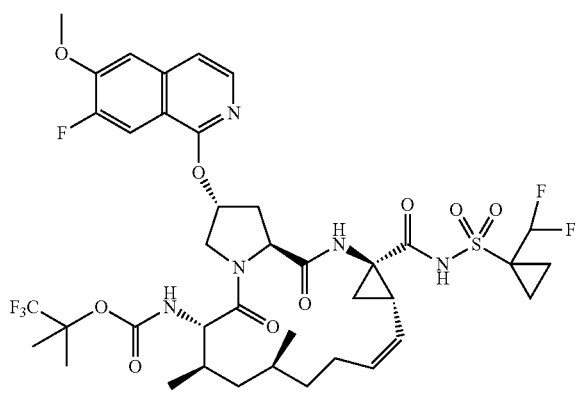

Compound 4092

Compound 4092 was prepared using the intermediates described herein and by following the general procedure described for the synthesis of Compound 3.

Compound 4092: 1,1,1-trifluoro-2-methylpropan-2-yl (2R,6S,7R,9S,13aS,14aR,16aS,Z)-14a-(1-(difluoromethyl)cyclopropylsulfonylcarbamoyl)-2-(7-fluoro-6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 7.94 (d, J=5.77 Hz, 1H) 7.83 (d, J=11.54 Hz, 1H) 7.39 (d, J=8.28 Hz, 1H) 7.30 (d, J=5.77 Hz, 1H) 7.25 (d, J=7.28 Hz, 1H) 6.53 (s, 1H) 5.89 (br. s., 1H) 5.70 (br. s., 1H) 5.03-5.20 (m, 1H) 4.81 (s, 1H) 4.66-4.73 (m, 1H) 4.52 (d, J=11.80 Hz, 1H) 4.06-4.22 (m, 2H) 4.00-4.05 (m, 3H) 3.66 (br. s., 1H) 3.28 (br. s., 1H) 2.63-2.78 (m, 1H) 2.48 (br. s., 1H) 2.01 (s, 2H) 1.54-1.76 (m, 5H) 1.43-1.53 (m, 5H) 1.21-1.42 (m, 9H) 1.12 (d, J=6.78 Hz, 1H) 1.03 (d, J=7.28 Hz, 1H) 0.93 (d, J=7.03 Hz, 3H); MS: MS m/z 875.0 (M$^+$−1).

Preparation of Compound 4093

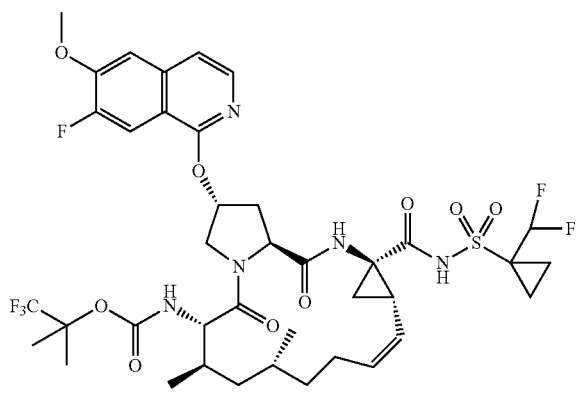

Compound 4093

Compound 4093 was prepared using the intermediates described herein and by following the general procedure described for the synthesis of Compound 3.

Compound 4093: 1,1,1-trifluoro-2-methylpropan-2-yl (2R,6S,7R,9R,13aS,14aR,16aS,Z)-14a-(1-(difluoromethyl)cyclopropylsulfonylcarbamoyl)-2-(7-fluoro-6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 7.95 (d, J=5.77 Hz, 1H) 7.79 (d, J=11.80 Hz, 1H) 7.40 (d, J=8.28 Hz, 1H) 7.30 (d, J=6.02 Hz, 2H) 6.55 (s, 1H) 5.89 (br. s., 1H) 5.61 (d, J=6.27 Hz, 1H) 5.07 (br. s., 1H) 4.58-4.74 (m, 2H) 3.97-4.07 (m, 4H) 3.79-3.87 (m, 1H) 3.29 (d, J=1.51 Hz, 1H) 2.63-2.79 (m, 2H) 2.34-2.52 (m, 2H) 1.91-2.04 (m, 1H) 1.78-1.90 (m, 2H) 1.74 (dd, J=8.41, 5.65 Hz, 2H) 1.60 (dd, J=9.54, 5.52 Hz, 2H) 1.49 (d, J=13.30 Hz, 2H) 1.22-1.42 (m, 6H) 1.13 (s, 3H) 1.01 (dd, J=9.29, 6.78 Hz, 5H) 0.77-0.95 (m, 3H); MS: MS m/z 874.9 (M$^+$−1).

Preparation of Compound 4094

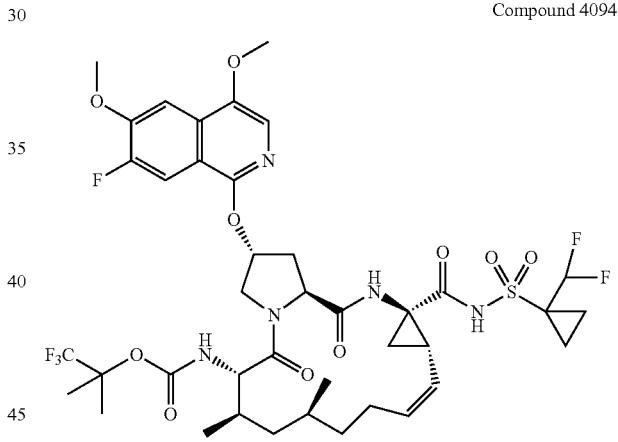

Compound 4094

Compound 4094 was prepared using the intermediates described herein and by following the general procedure described for the synthesis of Compound 3.

Compound 4094: 1,1,1-trifluoro-2-methylpropan-2-yl (2R,6S,7R,9S,13aS,14aR,16aS,Z)-14a-(1-(difluoromethyl)cyclopropylsulfonylcarbamoyl)-2-(7-fluoro-4,6-dimethoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 7.78 (d, J=11.80 Hz, 1H) 7.51-7.60 (m, 2H) 5.81 (br. s., 1H) 5.69 (br. s., 1H) 5.04-5.21 (m, 1H) 4.65-4.71 (m, 1H) 4.48 (d, J=11.04 Hz, 1H) 4.14 (d, J=6.53 Hz, 1H) 4.00-4.10 (m, 8H) 2.63-2.73 (m, 2H) 2.45 (br. s., 2H) 2.01 (s, 2H) 1.70 (d, J=7.28 Hz, 2H) 1.49 (s, 2H) 1.29-1.40 (m, 10H) 1.18-1.28 (m, 4H) 1.12 (d, J=6.78 Hz, 3H) 0.93 (d, J=6.78 Hz, 3H); MS: MS m/z 905.0 (M$^+$−1).

Preparation of Compound 4095

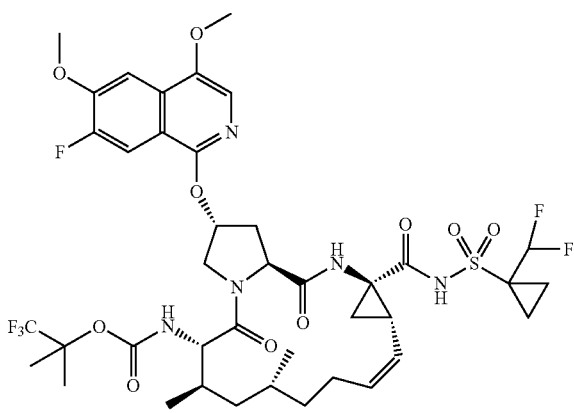

Compound 4095

Compound 4095 was prepared using the intermediates described herein and by following the general procedure described for the synthesis of Compound 3.

Compound 4095: 1,1,1-trifluoro-2-methylpropan-2-yl (2R,6S,7R,9R,13aS,14aR,16aS,Z)-14a-(1-(difluoromethyl)cyclopropylsulfonylcarbamoyl)-2-(7-fluoro-4,6-dimethoxy-isoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.75 (d, J=11.54 Hz, 1H) 7.53-7.60 (m, 2H) 5.81 (br. s., 1H) 5.56-5.66 (m, 1H) 5.00-5.19 (m, 1H) 4.57-4.71 (m, 2H) 3.96-4.07 (m, 7H) 3.82 (d, J=10.79 Hz, 1H) 3.28 (br. s., 1H) 2.72 (dd, J=12.92, 7.40 Hz, 2H) 2.35-2.48 (m, 2H) 2.01 (s, 1H) 1.77-1.91 (m, 2H) 1.73 (dd, J=8.28, 5.52 Hz, 2H) 1.60 (d, J=9.29 Hz, 2H) 1.49 (d, J=11.54 Hz, 2H) 1.30-1.44 (m, 7H) 1.26 (d, J=9.54 Hz, 2H) 1.14 (s, 3H) 1.01 (dd, J=10.67, 6.65 Hz, 4H) 0.77-0.95 (m, 1H); MS: MS m/z 906.6 (M$^+$+1).

Preparation of Compound 4086

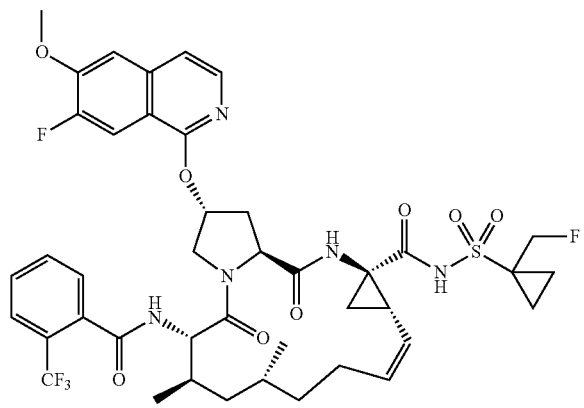

Compound 4096

Compound 4096 was prepared using the intermediates described herein and by following the general procedure described for the synthesis of Compound 4029.

Compound 4096: (2R,6S,7R,9R,13aS,14aR,16aS,Z)-2-(7-fluoro-6-methoxyisoquinolin-1-yloxy)-N-(1-(fluoromethyl)cyclopropylsulfonyl)-7,9-dimethyl-5,16-dioxo-6-(2-(trifluoromethyl)benzamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (400 MHz, CD$_3$OD): δ ppm 9.02 (s, 1H) 8.78 (d, J=9.03 Hz, 1H) 7.92 (d, J=5.77 Hz, 2H) 7.82 (d, J=11.54 Hz, 1H) 7.68 (dd, J=5.52, 3.76 Hz, 1H) 7.55-7.62 (m, 2H) 7.25-7.36 (m, 3H) 5.99 (br. s., 1H) 5.59-5.67 (m, 1H) 5.00 (t, J=10.04 Hz, 1H) 4.61-4.73 (m, 3H) 4.44-4.55 (m, 2H) 4.19 (dd, J=11.42, 3.64 Hz, 1H) 4.01 (s, 3H) 3.29 (dd, J=3.26, 1.51 Hz, 1H) 2.68-2.80 (m, 3H) 2.47 (ddd, J=14.05, 10.04, 4.27 Hz, 2H) 1.95-2.15 (m, 2H) 1.90 (dd, J=13.93, 5.65 Hz, 1H) 1.63-1.77 (m, 3H) 1.47-1.62 (m, 2H) 1.16-1.36 (m, 3H) 1.07 (dd, J=9.54, 6.53 Hz, 4H) 0.94 (t, J=12.30 Hz, 1H); MS: MS m/z 876.4 (M$^+$+1).

Preparation of Compound 4097

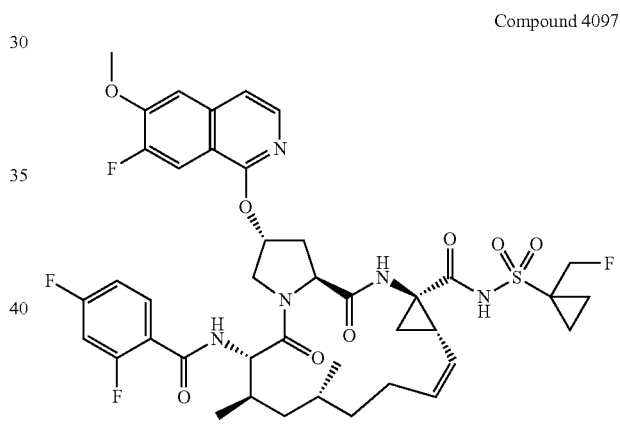

Compound 4097

Compound 4097 was prepared using the intermediates described herein and by following the general procedure described for the synthesis of Compound 4029.

Compound 4097: (2R,6S,7R,9R,13aS,14aR,16aS,Z)-6-(2,4-difluorobenzamido)-2-(7-fluoro-6-methoxyisoquinolin-1-yloxy)-N-(1-(fluoromethyl)cyclopropylsulfonyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (400 MHz, CD$_3$OD): δ ppm 8.13-8.19 (m, 1H) 7.94 (d, J=6.02 Hz, 1H) 7.81 (d, J=11.54 Hz, 1H) 7.41 (q, J=8.03 Hz, 1H) 5.94 (br. s., 1H) 5.62 (td, J=9.98, 6.15 Hz, 1H) 5.01 (t, J=10.04 Hz, 1H) 4.79 (dd, J=11.42, 6.90 Hz, 2H) 4.59-4.66 (m, 2H) 4.38-4.44 (m, 1H) 4.10 (dd, J=11.54, 3.26 Hz, 1H) 4.03 (s, 4H) 3.28 (dt, J=3.26, 1.63 Hz, 1H) 2.65-2.80 (m, 3H) 2.46 (ddd, J=13.80, 10.04, 4.02 Hz, 3H) 1.96-2.13 (m, 2H) 1.82-1.90 (m, 1H) 1.64-1.75 (m, 3H) 1.46-1.60 (m, 3H) 1.17-1.34 (m, 3H) 1.06 (dd, J=6.40, 5.40 Hz, 6H) 0.93 (s, 1H); MS: MS m/z 842.2 (M$^+$−1).

Preparation of Compound 4099

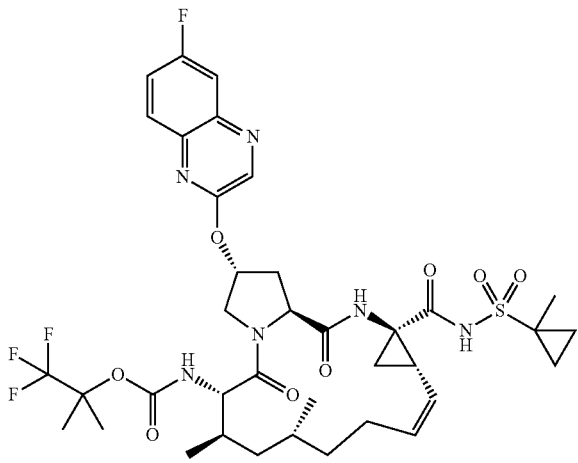

Compound 4099

Compound 4099 was prepared using the intermediates described herein and by following the general procedure described for the synthesis of Compound 3.

Compound 4099: 1,1,1-trifluoro-2-methylpropan-2-yl (2R,6S,7R,9R,13aS,14aR,16aS,Z)-2-(6-fluoroquinoxalin-2-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.97 (dd, J=9.03, 5.52 Hz, 1H) 7.92 (s, 1H) 7.57-7.72 (m, 1H) 7.34 (d, J=8.28 Hz, 1H) 5.89 (br. s., 1H) 5.63 (d, J=5.52 Hz, 1H) 5.02 (t, J=9.91 Hz, 1H) 4.73-4.81 (m, 2H) 4.63 (dd, J=9.79, 7.28 Hz, 1H) 4.07 (dd, J=11.92, 3.39 Hz, 1H) 3.79 (dd, J=10.67, 8.16 Hz, 1H) 3.25-3.29 (m, 2H) 2.66-2.77 (m, 2H) 2.35-2.53 (m, 2H) 1.98 (br. s., 1H) 1.88 (d, J=5.77 Hz, 1H) 1.78 (dd, J=8.28, 5.77 Hz, 2H) 1.63-1.72 (m, 1H) 1.59 (dd, J=8.78, 6.53 Hz, 1H) 1.39-1.55 (m, 7H) 1.17-1.36 (m, 8H) 0.94-1.05 (m, 3H) 0.79-0.93 (m, 1H); MS: MS m/z 811.4 (M$^+$+1).

Preparation of Compound 4100

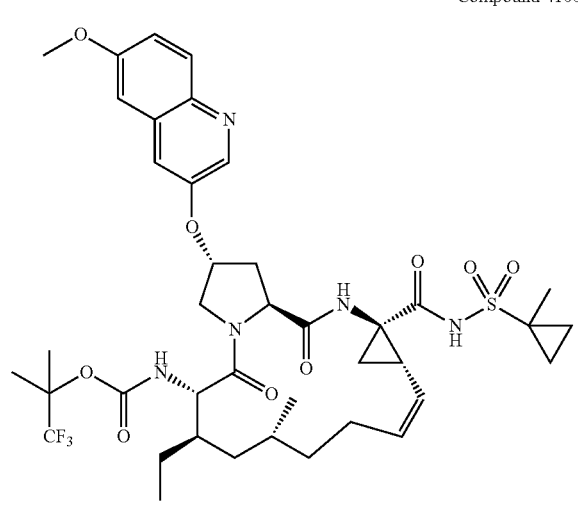

Compound 4100

Compound 4100 was prepared using the intermediates described herein and by following the general procedure described for the synthesis of Compound 3.

Compound 4100: 1,1,1-trifluoro-2-methylpropan-2-yl (2R,6S,7R,9R,13aS,14aR,16aS,Z)-7-ethyl-2-(6-methoxyquinolin-3-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.37 (d, J=2.76 Hz, 1H) 7.84 (d, J=9.03 Hz, 1H) 7.75 (d, J=2.76 Hz, 1H) 7.23-7.31 (m, 2H) 5.62 (br. s., 1H) 5.39 (br. s., 1H) 5.02 (br. s., 1H) 4.71 (d, J=12.30 Hz, 1H) 4.57-4.63 (m, 1H) 4.02-4.12 (m, 2H) 3.97 (s, 3H) 2.70 (d, J=6.27 Hz, 2H) 2.44 (d, J=10.29 Hz, 2H) 1.95-2.07 (m, 2H) 1.76 (d, J=7.53 Hz, 1H) 1.50-1.62 (m, 8H) 1.43 (d, J=10.79 Hz, 2H) 1.30-1.38 (m, 5H) 1.13 (s, 3H) 1.01 (d, J=6.53 Hz, 3H) 0.88-0.95 (m, 3H) 0.82 (t, J=7.53 Hz, 3H) MS: MS m/z 836.93 (M$^+$+1).

Preparation of Compound 4101

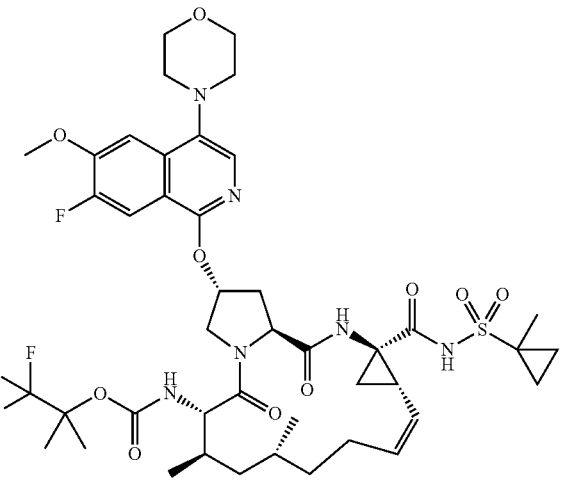

Compound 4101

Compound 4101 was prepared using the intermediates described herein and by following the general procedure described for the synthesis of Compound 3.

Compound 4101: 1,1,1-trifluoro-2-methylpropan-2-yl (2R,6S,7R,9R,13aS,14aR,16aS,Z)-2-(7-fluoro-6-methoxy-4-morpholinoisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 9.04 (s, 1H) 7.71-7.82 (m, 2H) 7.60 (d, J=8.53 Hz, 1H) 5.83-5.88 (m, 1H) 5.63 (d, J=5.77 Hz, 1H) 5.01 (t, J=10.04 Hz, 1H) 4.61-4.73 (m, 2H) 4.01-4.09 (m, 4H) 3.91-4.01 (m, 4H) 3.82 (d, J=10.79 Hz, 1H) 3.03-3.13 (m, 4H) 2.67-2.79 (m, 2H) 2.36-2.49 (m, 2H) 1.87-2.02 (m, 2H) 1.71-1.86 (m, 2H) 1.61-1.70 (m, 1H) 1.48-1.61 (m, 5H) 1.35-1.47 (m, 5H) 1.19-1.34 (m, 2H) 1.13 (s, 3H) 1.01 (t, J=6.40 Hz, 6H) 0.79-0.95 (m, 3H); MS: MS m/z 926.4 (M$^+$+1).

Preparation of Compound 4102

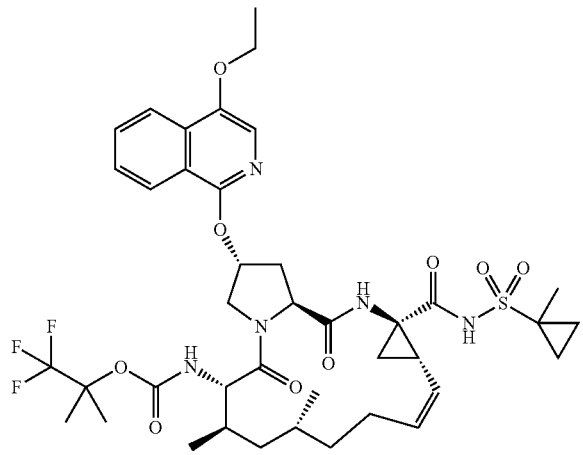

Compound 4102

Compound 4102 was prepared using the intermediates described herein and by following the general procedure described for the synthesis of Compound 3.

Compound 4102: 1,1,1-trifluoro-2-methylpropan-2-yl (2R,6S,7R,9R,13aS,14aR,16aS,Z)-2-(4-ethoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.09 (dd, J=17.19, 8.16 Hz, 2H) 7.75-7.83 (m, 2H) 7.59-7.66 (m, 1H) 5.84 (br. s., 1H) 5.72 (br. s., 1H) 5.00 (br. s., 1H) 4.38 (t, J=8.53 Hz, 1H) 4.21 (d, J=7.28 Hz, 2H) 4.13 (br. s., 1H) 3.90-3.98 (m, 1H) 2.43-2.48 (m, 1H) 1.92 (br. s., 1H) 1.57 (br. s., 2H) 1.39-1.54 (m, 10H) 1.34 (br. s., 5H) 1.25 (br. s., 4H) 1.02-1.11 (m, 4H) 0.82-0.96 (m, 10H) 0.76 (d, J=9.29 Hz, 1H); MS: MS m/z 838.6 (M$^+$+1).

Preparation of Compound 4103

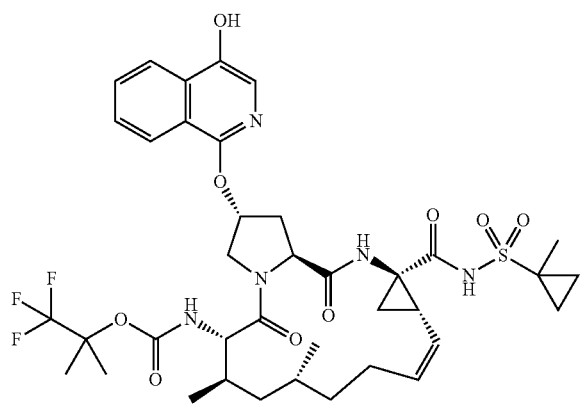

Compound 4103

Compound 4103 was prepared using the intermediates described herein and by following the general procedure described for the synthesis of Compound 3.

Compound 4103: 1,1,1-trifluoro-2-methylpropan-2-yl (2R,6S,7R,9R,13aS,14aR,16aS,Z)-2-(4-hydroxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 11.04 (s, 1H) 9.76 (s, 1H) 9.13 (s, 1H) 8.06 (d, J=9.29 Hz, 2H) 7.71-7.85 (m, 2H) 7.58 (d, J=8.03 Hz, 1H) 7.55 (s, 1H) 5.71-5.78 (m, 1H) 5.74 (br. s., 1H) 5.49-5.58 (m, 1H) 5.48-5.58 (m, 1H) 4.96 (t, J=10.04 Hz, 1H) 4.47-4.56 (m, 2H) 3.86-3.93 (m, 1H) 3.71 (dd, J=10.54, 8.28 Hz, 1H) 2.56-2.75 (m, 2H) 2.23-2.40 (m, 2H) 1.76-1.95 (m, 2H) 1.60-1.75 (m, 2H) 1.39-1.58 (m, 6H) 1.22-1.38 (m, 5H) 1.04-1.21 (m, 4H) 0.91 (dd, J=17.44, 6.90 Hz, 6H) 0.75 (t, J=12.17 Hz, 1H); MS: MS m/z 808.5 (M$^+$+1).

Preparation of Compound 4104

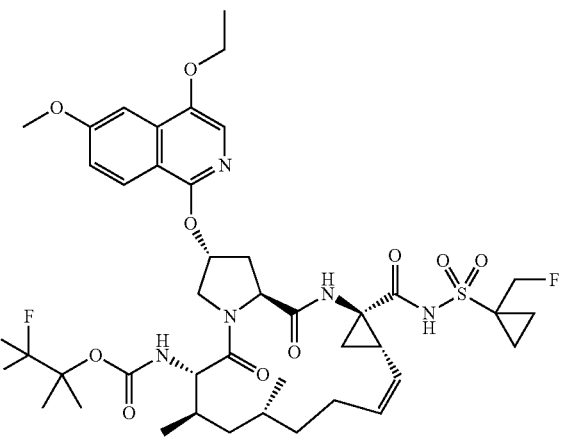

Compound 4104

Compound 4104 was prepared using the intermediates described herein and by following the general procedure described for the synthesis of Compound 3.

Compound 4104: 1,1,1-trifluoro-2-methylpropan-2-yl (2R,6S,7R,9R,13aS,14aR,16aS,Z)-2-(4-ethoxy-6-methoxyisoquinolin-1-yloxy)-14a-(1-(fluoromethyl)cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 9.03 (s, 1H) 8.07 (d, J=9.03 Hz, 1H) 7.52 (s, 1H) 7.45 (d, J=2.51 Hz, 1H) 7.14 (dd, J=9.29, 2.51 Hz, 1H) 5.80 (br. s., 1H) 5.62 (td, J=10.35, 5.90 Hz, 1H) 4.95-5.04 (m, 1H) 4.76-4.82 (m, 1H) 4.71 (d, J=11.54 Hz, 1H) 4.59-4.67 (m, 2H) 4.24 (q, J=6.86 Hz, 2H) 4.01 (dd, J=11.54, 3.51 Hz, 1H) 3.96 (s, 3H) 3.81-3.88 (m, 1H) 3.28 (dt, J=3.39, 1.57 Hz, 1H) 2.67-2.75 (m, 2H) 2.37-2.48 (m, 2H) 1.86-2.03 (m, 2H) 1.77-1.85 (m, 1H) 1.64-1.76 (m, 3H) 1.44-1.63 (m, 5H) 1.35-1.43 (m, 3H) 1.17-1.34 (m, 3H) 0.96-1.07 (m, 9H) 0.83 (t, J=11.67 Hz, 1H); MS: MS m/z 884.5 (M$^+$+1).

Preparation of Compound 4105

Compound 4105

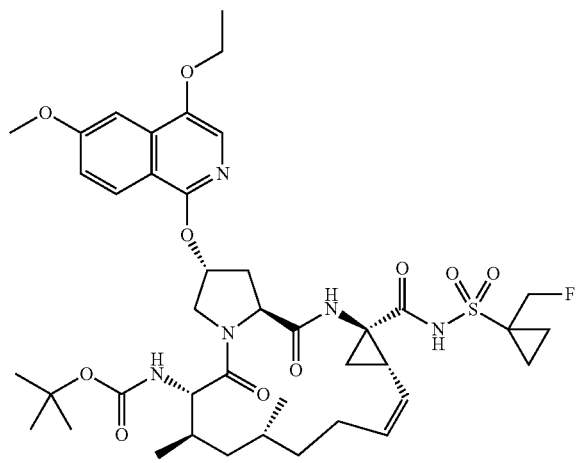

Compound 4105 was prepared using the intermediates described herein and by following the general procedure described for the synthesis of Compound 1.

Compound 4105: tert-butyl (2R,6S,7R,9R,13aS,14aR,16aS,Z)-2-(4-ethoxy-6-methoxyisoquinolin-1-yloxy)-14a-(1-(fluoromethyl)cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.07 (d, J=9.29 Hz, 1H) 7.51 (s, 1H) 7.43 (d, J=2.51 Hz, 1H) 7.13 (dd, J=9.03, 2.51 Hz, 1H) 5.81 (br. s., 1H) 5.58-5.66 (m, 1H) 5.00 (t, J=9.91 Hz, 1H) 4.79 (d, J=11.29 Hz, 1H) 4.64-4.71 (m, 1H) 4.56-4.63 (m, 1H) 4.52 (d, J=11.04 Hz, 1H) 4.23 (q, J=7.03 Hz, 2H) 4.03 (dd, J=11.54, 3.51 Hz, 1H) 3.96 (s, 3H) 3.85-3.92 (m, 1H) 3.29 (d, J=1.76 Hz, 1H) 2.67-2.76 (m, 2H) 2.37-2.48 (m, 2H) 1.97 (br. s., 1H) 1.77-1.92 (m, 2H) 1.62-1.76 (m, 3H) 1.47-1.60 (m, 6H) 1.30-1.46 (m, 1H) 1.11-1.29 (m, 9H) 1.01 (dd, J=13.93, 6.65 Hz, 6H) 0.84 (t, J=11.54 Hz, 3H); MS: MS m/z 830.2 (M$^+$+1).

Preparation of Compound 4106

Compound 4106

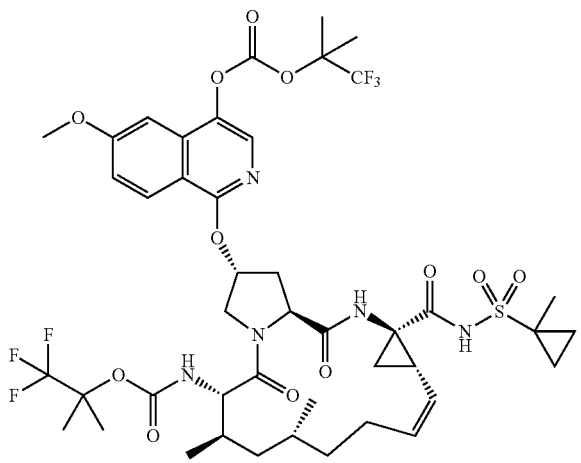

Compound 4106 was prepared using the intermediates described herein and by following the general procedure described for the synthesis of Compound 3.

Compound 4106: 1,1,1-trifluoro-2-methylpropan-2-yl (2R,6S,7R,9R,13aS,14aR,16aS,Z)-2-(6-methoxy-4-((1,1,1-trifluoro-2-methylpropan-2-yloxy)carbonyloxy)isoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.16 (d, J=9.03 Hz, 1H) 7.94 (s, 1H) 7.30 (d, J=7.78 Hz, 1H) 7.21 (dd, J=9.16, 2.38 Hz, 1H) 7.05 (d, J=2.51 Hz, 1H) 5.91 (br. s., 1H) 5.63 (d, J=6.02 Hz, 1H) 5.02 (t, J=10.16 Hz, 1H) 4.76-4.82 (m, 3H) 4.64-4.70 (m, 1H) 4.03 (d, J=7.78 Hz, 1H) 3.96 (s, 4H) 3.80-3.87 (m, 1H) 3.28 (br. s., 2H) 2.69-2.81 (m, 3H) 2.40-2.50 (m, 2H) 1.98 (br. s., 1H) 1.86-1.93 (m, 1H) 1.76-1.86 (m, 5H) 1.67 (d, J=9.29 Hz, 1H) 1.50-1.61 (m, 4H) 1.40-1.49 (m, 3H) 1.29-1.40 (m, 3H) 1.26 (br. s., 1H) 0.96-1.06 (m, 6H) 0.86-0.95 (m, 2H) 0.79-0.86 (m, 1H); MS: MS m/z 992.6 (M$^+$+1).

Preparation of Compound 4107

Compound 4107

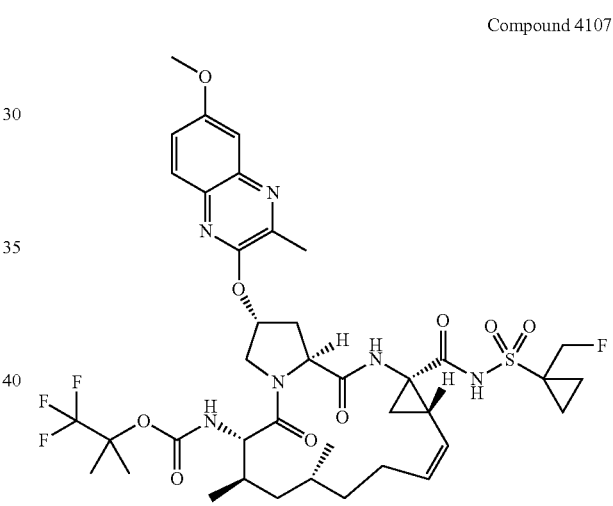

Compound 4107 was prepared using the intermediates described herein and by following the general procedure described for the synthesis of Compound 3.

Compound 107: 1,1,1-trifluoro-2-methylpropan-2-yl (2R,6S,7R,9R,13aS,14aR,16aS,Z)-14a-(1-(fluoromethyl)cyclopropylsulfonylcarbamoyl)-2-(6-methoxy-3-methylquinoxalin-2-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 7.78 (d, J=9.03 Hz, 1H) 7.31-7.37 (m, 2H) 5.88 (br. s., 1H) 5.63 (td, J=10.10, 5.90 Hz, 1H) 5.01 (t, J=9.79 Hz, 1H) 4.89-4.94 (m, 2H) 4.77-4.82 (m, 1H) 4.71 (s, 1H) 4.60-4.68 (m, 1H) 4.04 (dd, J=11.67, 3.39 Hz, 1H) 3.95 (s, 3H) 3.74-3.80 (m, 1H) 3.37-3.44 (m, 2H) 3.28 (dt, J=3.26, 1.63 Hz, 1H) 2.70 (q, J=9.20 Hz, 2H) 2.57 (s, 3H) 2.39-2.52 (m, 2H) 1.96 (br. s., 1H) 1.81 (dd, J=13.30, 5.52 Hz, 1H) 1.64-1.76 (m, 3H) 1.59 (dd, J=9.54, 5.52 Hz, 2H) 1.48 (br. s., 2H) 1.16-1.34 (m, 9H) 1.00 (dd, J=19.32, 6.78 Hz, 5H) 0.79-0.88 (m, 1H); MS: MS m/z 855.5 (M$^+$+1).

Preparation of Compound 4108

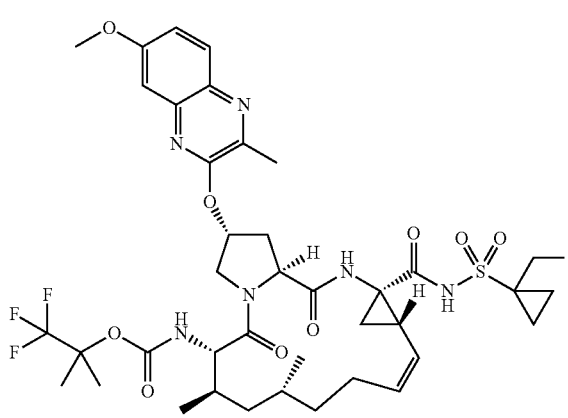

Compound 4108

Compound 4108 was prepared using the intermediates described herein and by following the general procedure described for the synthesis of Compound 3.

Compound 4108: 1,1,1-trifluoro-2-methylpropan-2-yl (2R,6S,7R,9R,13aS,14aR,16aS,Z)-14a-(1-(fluoromethyl)cyclopropylsulfonylcarbamoyl)-2-(7-methoxy-3-methylquinoxalin-2-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 9.08 (s, 1H) 7.79 (d, J=8.53 Hz, 1H) 7.21-7.33 (m, 2H) 5.91 (br. s., 1H) 5.63 (d, J=5.02 Hz, 1H) 5.01 (t, J=10.04 Hz, 1H) 4.92 (d, J=11.04 Hz, 1H) 4.77 (dd, J=18.57, 11.29 Hz, 2H) 4.64 (d, J=10.29 Hz, 2H) 4.52 (d, J=11.29 Hz, 1H) 4.06 (d, J=12.05 Hz, 1H) 3.97 (s, 4H) 3.77 (d, J=10.54 Hz, 1H) 2.64-2.77 (m, 2H) 2.35-2.58 (m, 7H) 1.96 (br. s., 1H) 1.77-1.90 (m, 1H) 1.63-1.76 (m, 2H) 1.59 (d, J=8.03 Hz, 2H) 1.49 (br. s., 2H) 1.16-1.42 (m, 9H) 1.01 (dd, J=18.70, 6.15 Hz, 3H) 0.84 (t, J=12.80 Hz, 1H); MS: MS m/z 855.5 (M$^+$+1).

Preparation of Compound 4109

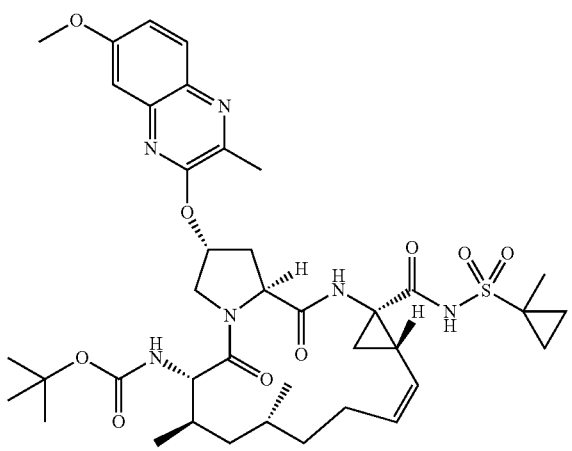

Compound 4109

Compound 4109 was prepared using the intermediates described herein and by following the general procedure described for the synthesis of Compound 1.

Compound 4109: tert-butyl (2R,6S,7R,9R,13aS,14aR,16aS,Z)-2-(7-methoxy-3-methylquinoxalin-2-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.78 (d, J=9.03 Hz, 1H) 7.30 (d, J=2.51 Hz, 1H) 7.23 (dd, J=9.29, 2.76 Hz, 1H) 6.66 (d, J=7.28 Hz, 1H) 5.94 (br. s., 1H) 5.59-5.67 (m, 1H) 5.02 (t, J=10.04 Hz, 1H) 4.90-4.97 (m, 2H) 4.70-4.81 (m, 2H) 4.60-4.67 (m, 1H) 4.08 (d, J=8.28 Hz, 1H) 3.97 (s, 4H) 3.77-3.85 (m, 1H) 3.29 (dd, J=3.26, 1.51 Hz, 2H) 2.67-2.78 (m, 2H) 2.41-2.58 (m, 5H) 1.98 (br. s., 1H) 1.75-1.90 (m, 3H) 1.64-1.74 (m, 1H) 1.58 (dd, J=9.54, 5.77 Hz, 1H) 1.41-1.56 (m, 4H) 1.21-1.38 (m, 3H) 1.08-1.21 (m, 7H) 1.00 (dd, J=14.43, 6.65 Hz, 2H) 0.80-0.92 (m, 1H); MS: MS m/z 783.5 (M$^+$+1).

Preparation of Compound 4110

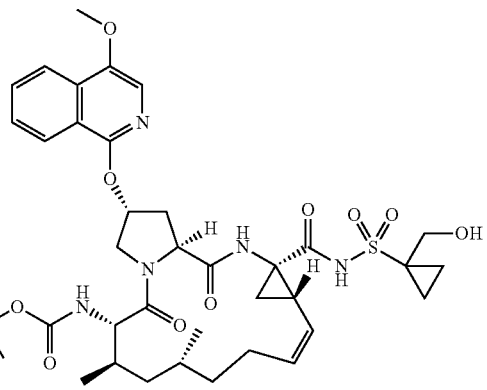

Compound 4110

Compound 4110 was prepared using the intermediates described herein and by following the general procedure described for the synthesis of Compound 3.

Compound 4110: 1,1,1-trifluoro-2-methylpropan-2-yl (2R,6S,7R,9R,13aS,14aR,16aS,Z)-14a-(1-(hydroxymethyl)cyclopropylsulfonylcarbamoyl)-2-(4-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.11-8.20 (m, 2H) 7.72-7.77 (m, 1H) 7.55-7.60 (m, 2H) 5.83 (br. s., 1H) 5.58 (td, J=10.35, 5.14 Hz, 1H) 5.36-5.43 (m, 1H) 4.71 (d, J=11.54 Hz, 1H) 4.52-4.63 (m, 2H) 4.39 (d, J=12.30 Hz, 1H) 3.98-4.05 (m, 2H) 3.84 (d, J=10.79 Hz, 1H) 3.28 (br. s., 1H) 2.70 (dd, J=13.80, 7.28 Hz, 1H) 2.60 (q, J=9.37 Hz, 1H) 2.35-2.53 (m, 2H) 1.82-1.97 (m, 3H) 1.66-1.74 (m, 2H) 1.35-1.46 (m, 9H) 1.15-1.34 (m, 4H) 1.05-1.14 (m, 1H) 0.94-1.05 (m, 7H) 0.73-0.83 (m, 3H); MS: MS m/z 838.2 (M$^+$+1).

Preparation of Compound 4111

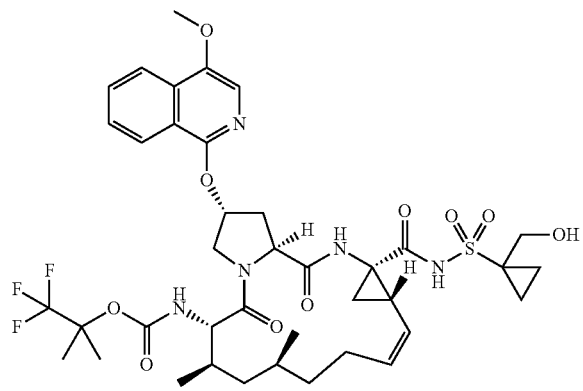

Compound 4111

Compound 4111 was prepared using the intermediates described herein and by following the general procedure described for the synthesis of Compound 3.

Compound 4111: 1,1,1-trifluoro-2-methylpropan-2-yl (2R,6S,7R,9S,13aS,14aR,16aS,Z)-14a-(1-(hydroxymethyl)cyclopropylsulfonylcarbamoyl)-2-(4-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.10-8.22 (m, 2H) 7.75 (t, J=7.65 Hz, 1H) 7.55-7.62 (m, 2H) 5.83 (br. s., 1H) 5.65-5.74 (m, 1H) 5.36 (t, J=9.54 Hz, 1H) 4.73 (t, J=8.16 Hz, 1H) 4.48-4.56 (m, 2H) 4.36-4.43 (m, 1H) 4.07-4.18 (m, 2H) 4.03 (s, 3H) 2.63-2.72 (m, 1H) 2.49-2.58 (m, 2H) 2.39 (q, J=9.03 Hz, 1H) 1.89-2.09 (m, 3H) 1.55-1.73 (m, 3H) 1.36-1.49 (m, 7H) 1.15-1.33 (m, 7H) 0.97-1.14 (m, 5H) 0.90 (d, J=6.78 Hz, 3H); MS: MS m/z 838.2 (M$^+$+1).

Preparation of Compound 4112

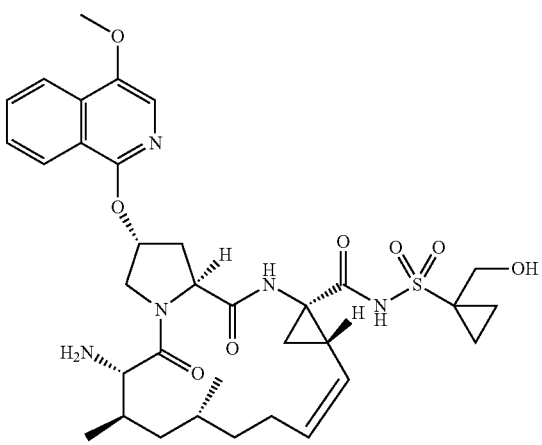

Compound 4112

Compound 4112 was prepared using the intermediates described herein and by following the general procedure described for the synthesis of Compound 3.

Compound 4112: (2R,6S,7R,9R,13aS,14aR,16aS,Z)-6-amino-N-(1-(hydroxymethyl)cyclopropylsulfonyl)-2-(4-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (400 MHz, CD$_3$OD): δ ppm 8.10-8.26 (m, 2H) 7.77 (ddd, J=8.28, 7.03, 1.25 Hz, 1H) 7.57-7.67 (m, 2H) 5.88 (d, J=2.26 Hz, 1H) 5.58 (td, J=10.60, 4.89 Hz, 1H) 5.38 (t, J=10.29 Hz, 1H) 4.52-4.64 (m, 2H) 4.35 (d, J=12.30 Hz, 1H) 4.10-4.21 (m, 2H) 4.03 (s, 3H) 3.36-3.43 (m, 1H) 2.41-2.71 (m, 4H) 1.77-2.03 (m, 5H) 1.71 (ddd, J=17.00, 9.22, 5.14 Hz, 3H) 1.36-1.51 (m, 3H) 1.14-1.34 (m, 3H) 0.98-1.12 (m, 7H) 0.79-0.91 (m, 1H); MS: MS m/z 684.5 (M$^+$+1).

Preparation of Compound 4113

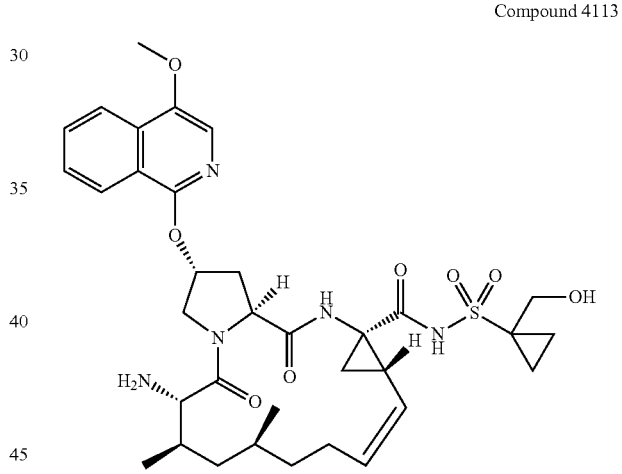

Compound 4113

Compound 4113 was prepared using the intermediates described herein and by following the general procedure described for the synthesis of Compound 3.

Compound 4113: (2R,6S,7R,9S,13aS,14aR,16aS,Z)-6-amino-N-(1-(hydroxymethyl)cyclopropylsulfonyl)-2-(4-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (400 MHz, CD$_3$OD): δ ppm 8.15 (t, J=7.78 Hz, 2H) 7.92 (s, 1H) 7.74-7.79 (m, 1H) 7.59-7.65 (m, 2H) 5.88 (br. s., 1H) 5.75-5.83 (m, 1H) 5.32 (t, J=9.66 Hz, 1H) 4.74-4.81 (m, 1H) 4.49-4.55 (m, 1H) 4.37-4.43 (m, 1H) 4.11-4.23 (m, 2H) 3.97-4.05 (m, 4H) 3.29 (d, J=1.51 Hz, 1H) 2.65-2.79 (m, 2H) 2.49-2.58 (m, 1H) 2.28 (q, J=8.45 Hz, 1H) 1.87-1.99 (m, 4H) 1.59-1.73 (m, 3H) 1.34-1.46 (m, 4H) 1.25-1.33 (m, 4H) 1.14-1.24 (m, 2H) 1.01-1.13 (m, 2H) 0.87-1.00 (m, 3H); MS: MS m/z 684.5 (M$^+$+1).

Preparation of Compound 4114

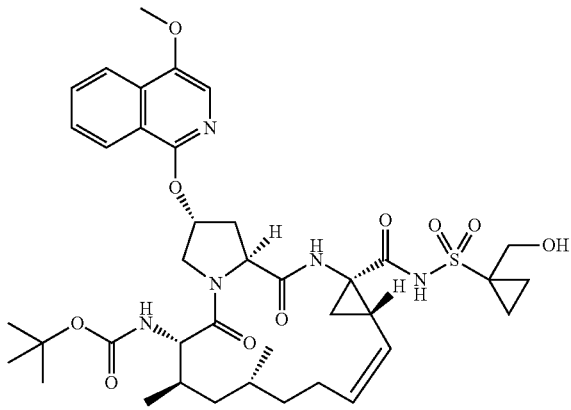

Compound 4114

Compound 4114 was prepared using the intermediates described herein and by following the general procedure described for the synthesis of Compound 1.

Compound 4114: tert-butyl (2R,6S,7R,9R,13aS,14aR,16aS,Z)-14a-(1-(hydroxymethyl)cyclopropylsulfonylcarbamoyl)-2-(4-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.09-8.21 (m, 2H) 7.73 (t, J=7.65 Hz, 1H) 7.53-7.60 (m, 2H) 5.84 (br. s., 1H) 5.58 (td, J=10.29, 5.02 Hz, 1H) 5.39 (t, J=10.16 Hz, 1H) 4.67 (d, J=11.04 Hz, 1H) 4.50-4.61 (m, 2H) 4.38 (d, J=12.55 Hz, 1H) 4.00-4.08 (m, 5H) 3.90 (d, J=10.79 Hz, 1H) 3.79-3.93 (m, 2H) 3.06 (q, J=7.28 Hz, 1H) 2.57-2.74 (m, 2H) 2.35-2.53 (m, 2H) 1.78-2.00 (m, 3H) 1.69 (dd, J=9.03, 2.51 Hz, 2H) 1.37-1.51 (m, 4H) 1.22-1.36 (m, 3H) 1.06-1.21 (m, 9H) 0.94-1.05 (m, 5H) 0.74-0.84 (m, 1H); MS: MS m/z 784.5 (M$^+$+1).

Preparation of Compound 4115

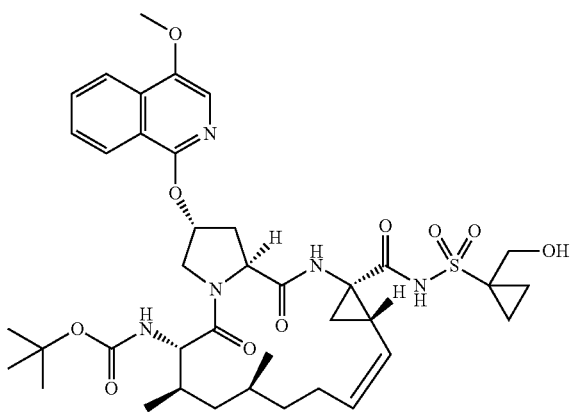

Compound 4115

Compound 4115 was prepared using the intermediates described herein and by following the general procedure described for the synthesis of Compound 1.

Compound 4115: tert-butyl (2R,6S,7R,9S,13aS,14aR,16aS,Z)-14a-(1-(hydroxymethyl)cyclopropylsulfonylcarbamoyl)-2-(4-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.09-8.19 (m, 2H) 7.73 (t, J=7.53 Hz, 1H) 7.51-7.59 (m, 2H) 5.83 (br. s., 1H) 5.59 (s, 1H) 4.89-4.98 (m, 2H) 4.56-4.73 (m, 2H) 3.99-4.07 (m, 4H) 3.81-3.93 (m, 2H) 3.29 (d, J=1.76 Hz, 2H) 2.72 (s, 1H) 2.36-2.54 (m, 2H) 1.97 (br. s., 1H) 1.85 (br. s., 2H) 1.71 (br. s., 1H) 1.47 (br. s., 5H) 1.20-1.36 (m, 3H) 1.08-1.18 (m, 9H) 1.01 (dd, J=13.93, 6.65 Hz, 7H) 0.93 (s, 1H) 0.76-0.86 (m, 1H); MS: MS m/z 784.5 (M$^+$−1).

Preparation of Compound 4116

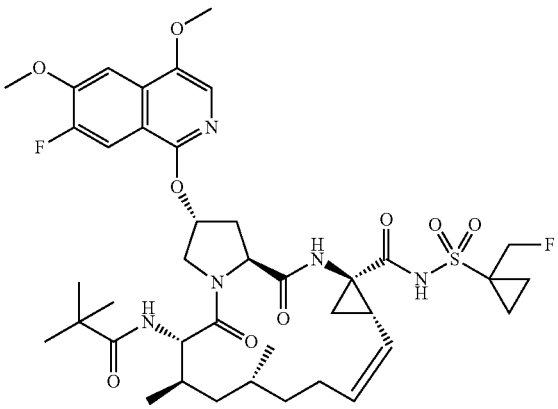

Compound 4116

Compound 4116 was prepared using the intermediates described herein and by following the general procedure described for the synthesis of Compound 4015.

Compound 4116: (2R,6S,7R,9R,13aS,14aR,16aS,Z)-2-(7-fluoro-4,6-dimethoxyisoquinolin-1-yloxy)-N-(1-(fluoromethyl)cyclopropylsulfonyl)-7,9-dimethyl-5,16-dioxo-6-pivalamido-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (400 MHz, CD$_3$OD): δ ppm 8.98 (s, 1H) 7.72 (d, J=11.54 Hz, 1H) 7.52-7.59 (m, 2H) 7.22 (d, J=9.54 Hz, 1H) 5.84 (br. s., 1H) 5.60-5.68 (m, 1H) 5.01 (t, J=9.91 Hz, 1H) 4.89-4.95 (m, 2H) 4.76-4.82 (m, 2H) 4.49-4.67 (m, 3H) 4.27 (dd, J=11.04, 8.78 Hz, 1H) 4.01-4.08 (m, 7H) 3.25-3.30 (m, 2H) 2.67-2.78 (m, 2H) 2.37-2.47 (m, 2H) 2.02 (br. s., 2H) 1.79-1.88 (m, 1H) 1.65-1.76 (m, 3H) 1.45-1.62 (m, 3H) 1.16-1.34 (m, 4H) 0.94-1.07 (m, 9H) 0.83-0.91 (m, 2H); MS: MS m/z 818.4 (M$^+$+1).

Preparation of Compound 4117

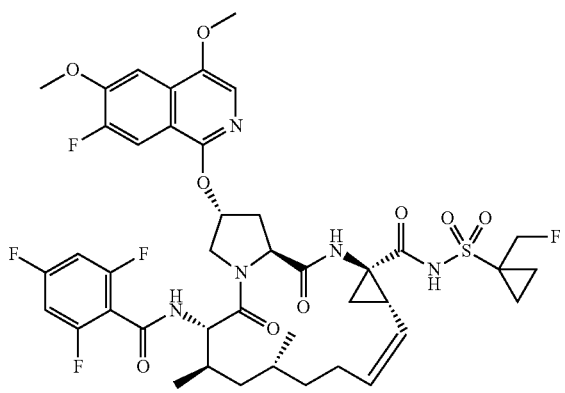

Compound 4117

Compound 4117 was prepared using the intermediates described herein and by following the general procedure described for the synthesis of Compound 4029.

Compound 4117: (2R,6S,7R,9R,13aS,14aR,16aS,Z)-2-(7-fluoro-4,6-dimethoxyisoquinolin-1-yloxy)-N-(1-(fluoromethyl)cyclopropylsulfonyl)-7,9-dimethyl-5,16-dioxo-6-(2,4,6-trifluorobenzamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (400 MHz, CD$_3$OD): δ ppm 8.97-9.04 (m, 2H) 7.75 (d, J=11.80 Hz, 1H) 7.50-7.55 (m, 2H) 6.87 (dd, J=9.03, 7.53 Hz, 2H) 5.87 (br. s., 1H) 5.63 (td, J=10.16, 6.02 Hz, 1H) 4.95-5.04 (m, 2H) 4.64-4.73 (m, 2H) 4.42-4.63 (m, 4H) 4.13 (dd, J=11.54, 3.76 Hz, 1H) 4.01 (s, 6H) 2.69-2.79 (m, 2H) 2.37-2.47 (m, 2H) 1.97-2.12 (m, 2H) 1.82-1.90 (m, 1H) 1.64-1.74 (m, 3H) 1.45-1.60 (m, 4H) 1.18-1.33 (m, 4H) 1.07 (t, J=6.53 Hz, 6H) 0.87-0.96 (m, 1H); MS: MS m/z 893.2 (M$^+$+1).

Preparation of Compound 4118

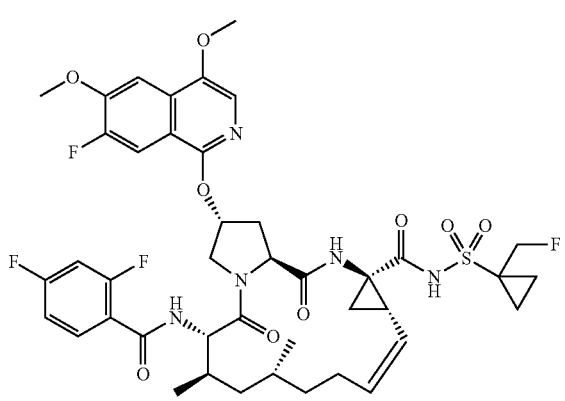

Compound 4118

Compound 4118 was prepared using the intermediates described herein and by following the general procedure described for the synthesis of Compound 4029.

Compound 4118: (2R,6S,7R,9R,13aS,14aR,16aS,Z)-6-(2,4-difluorobenzamido)-2-(7-fluoro-4,6-dimethoxyisoquinolin-1-yloxy)-N-(1-(fluoromethyl)cyclopropylsulfonyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (400 MHz, CD$_3$OD): δ ppm 9.02 (s, 1H) 8.13 (br. s., 1H) 7.92 (s, 1H) 7.74 (d, J=11.80 Hz, 1H) 7.49-7.55 (m, 1H) 7.33-7.41 (m, 1H) 6.90-7.02 (m, 2H) 5.85 (s, 1H) 5.63 (d, J=6.02 Hz, 1H) 5.02 (t, J=10.29 Hz, 1H) 4.72 (d, J=11.29 Hz, 1H) 4.59-4.68 (m, 2H) 4.38-4.45 (m, 1H) 4.00-4.10 (m, 8H) 3.25-3.30 (m, 1H) 2.67-2.78 (m, 3H) 2.39-2.48 (m, 2H) 2.05 (d, J=13.30 Hz, 2H) 1.86 (s, 1H) 1.67-1.75 (m, 3H) 1.48-1.61 (m, 3H) 1.15-1.34 (m, 4H) 1.05 (d, J=6.53 Hz, 3H) 0.92 (t, J=11.04 Hz, 1H); MS: MS m/z 872.2 (M$^+$-1).

Preparation of Compound 4119

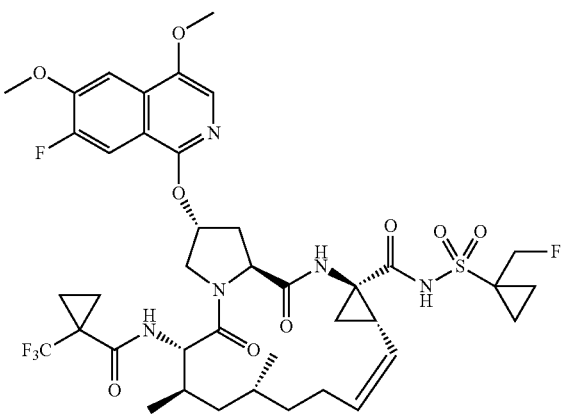

Compound 4119

Compound 4119 was prepared using the intermediates described herein and by following the general procedure described for the synthesis of Compound 4029.

Compound 4119: (2R,6S,7R,9R,13aS,14aR,16aS,Z)-2-(7-fluoro-4,6-dimethoxyisoquinolin-1-yloxy)-N-(1-(fluoromethyl)cyclopropylsulfonyl)-7,9-dimethyl-5,16-dioxo-6-(1-(trifluoromethyl)cyclopropanecarboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide.

$^1$H NMR (400 MHz, CD$_3$OD): δ ppm 8.99 (s, 1H) 7.92 (s, 1H) 7.72 (d, J=11.54 Hz, 1H) 7.55-7.61 (m, 2H) 7.53 (s, 1H) 5.83 (br. s., 1H) 5.63 (d, J=5.27 Hz, 1H) 5.01 (t, J=9.79 Hz, 1H) 4.77-4.82 (m, 1H) 4.48-4.65 (m, 3H) 4.24 (dd, J=11.04, 8.28 Hz, 1H) 4.00-4.07 (m, 7H) 3.28 (dt, J=3.26, 1.63 Hz, 2H) 2.66-2.75 (m, 2H) 2.37-2.47 (m, 2H) 2.03 (d, J=9.29 Hz, 2H) 1.82 (s, 1H) 1.65-1.76 (m, 3H) 1.49-1.60 (m, 3H) 1.19-1.36 (m, 4H) 1.09-1.16 (m, 3H) 1.02 (dd, J=18.57, 6.78 Hz, 3H) 0.86-0.95 (m, 2H); MS: MS m/z 870.4 (M$^+$+1).

Preparation of Compound 4120

Compound 4120

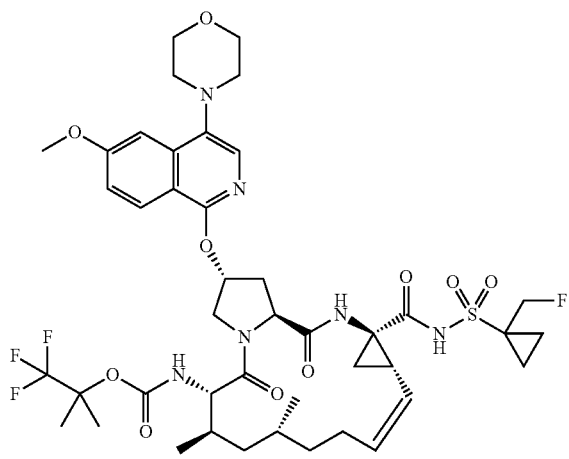

Compound 4120 was prepared using the intermediates described herein and by following the general procedure described for the synthesis of Compound 3.

Compound 4120: 1,1,1-trifluoro-2-methylpropan-2-yl (2R,6S,7R,9R,13aS,14aR,16aS,Z)-14a-(1-(fluoromethyl)cyclopropylsulfonylcarbamoyl)-2-(6-methoxy-4-morpholinoisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.12 (d, J=9.03 Hz, 1H) 7.71 (s, 1H) 7.46 (d, J=2.51 Hz, 1H) 7.14 (dd, J=9.29, 2.51 Hz, 1H) 5.84 (br. s., 1H) 5.57-5.66 (m, 1H) 5.02 (br. s., 1H) 4.50-4.75 (m, 6H) 3.94-4.05 (m, 8H) 3.83 (d, J=10.79 Hz, 1H) 3.28 (br. s., 1H) 3.06-3.17 (m, 4H) 2.66-2.77 (m, 2H) 2.44 (ddd, J=13.80, 9.79, 4.27 Hz, 3H) 1.78-2.03 (m, 3H) 1.63-1.76 (m, 2H) 1.57 (dd, J=9.41, 5.40 Hz, 1H) 1.49 (d, J=7.03 Hz, 2H) 1.14-1.41 (m, 6H) 0.96-1.07 (m, 7H) 0.84 (t, J=12.42 Hz, 1H); MS: MS m/z 923.5 (M$^+$−1).

Preparation of Compound 4121

Compound 4121

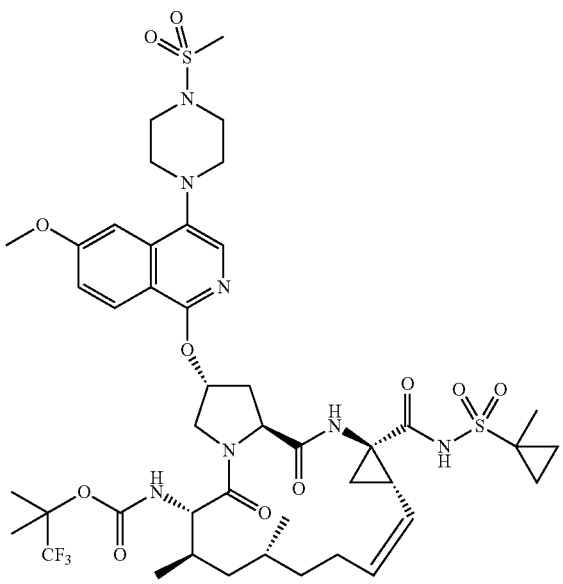

Compound 4121 was prepared using the intermediates described herein and by following the general procedure described for the synthesis of Compound 1.

Compound 4121: tert-butyl (2R,6S,7R,9R,13aS,14aR,16aS,Z)-2-(6-methoxy-4-(4-(methylsulfonyl)piperazin-1-yl)isoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.13 (d, J=9.03 Hz, 1H) 7.92 (s, 1H) 7.74 (s, 1H) 7.43 (d, J=2.51 Hz, 1H) 7.13 (dd, J=9.03, 2.51 Hz, 1H) 5.82-5.88 (m, 1H) 5.58-5.67 (m, 1H) 5.01 (t, J=10.04 Hz, 2H) 4.72 (d, J=11.80 Hz, 1H) 4.62 (d, J=3.01 Hz, 1H) 4.04 (d, J=7.53 Hz, 1H) 3.98 (s, 3H) 3.87 (d, J=10.79 Hz, 1H) 2.98 (s, 3H) 2.75 (d, J=8.78 Hz, 3H) 2.39-2.47 (m, 2H) 1.95-2.05 (m, 1H) 1.74-1.89 (m, 3H) 1.63-1.70 (m, 1H) 1.55-1.59 (m, 1H) 1.53 (s, 3H) 1.40-1.49 (m, 3H) 1.25-1.32 (m, 2H) 1.15 (s, 10H) 0.99-1.04 (m, 8H) 0.83-0.92 (m, 5H). MS: MS m/z 931.14 (M$^+$+1).

Preparation of Compound 4122

Compound 4122

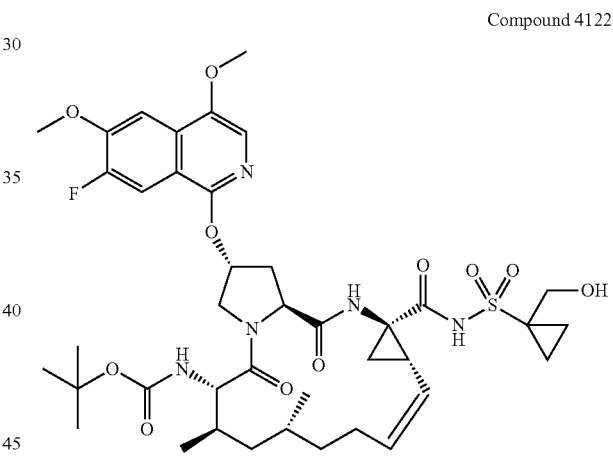

Compound 4122 was prepared using the intermediates described herein and by following the general procedure described for the synthesis of Compound 1.

Compound 4122: tert-butyl (2R,6S,7R,9R,13aS,14aR,16aS,Z)-2-(7-fluoro-4,6-dimethoxyisoquinolin-1-yloxy)-14a-(1-(hydroxymethyl)cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.72 (d, J=11.54 Hz, 1H) 7.51-7.58 (m, 2H) 6.66 (d, J=8.28 Hz, 1H) 5.81 (br. s., 1H) 5.61 (br. s., 1H) 5.08 (br. s., 1H) 4.55-4.71 (m, 2H) 3.93-4.06 (m, 8H) 3.78-3.89 (m, 2H) 2.63-2.76 (m, 2H) 2.34-2.49 (m, 2H) 1.97 (br. s., 1H) 1.76-1.90 (m, 2H) 1.72 (dd, J=8.03, 5.52 Hz, 1H) 1.54-1.63 (m, 2H) 1.49 (d, J=12.30 Hz, 3H) 1.39 (s, 1H) 1.23-1.36 (m, 3H) 1.07-1.21 (m, 9H) 1.01 (dd, J=13.43, 6.65 Hz, 7H) 0.82 (t, J=12.67 Hz, 1H); MS: MS m/z 833.2 (M$^+$+1).

Preparation of Compound 4123

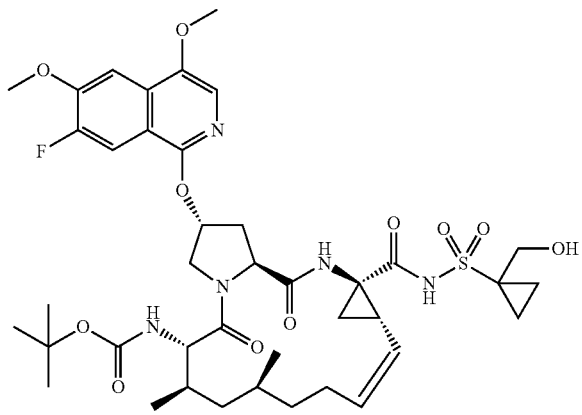

Compound 4123

Compound 4123 was prepared using the intermediates described herein and by following the general procedure described for the synthesis of Compound 1.

Compound 4123: tert-butyl (2R,6S,7R,9S,13aS,14aR,16aS,Z)-2-(7-fluoro-4,6-dimethoxyisoquinolin-1-yloxy)-14a-(1-(hydroxymethyl)cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.72 (d, J=11.80 Hz, 1H) 7.47-7.56 (m, 2H) 5.79 (br. s., 1H) 5.70 (d, J=7.28 Hz, 1H) 5.07 (br. s., 1H) 4.65 (d, J=7.28 Hz, 1H) 4.43 (d, J=11.04 Hz, 1H) 4.12 (d, J=6.27 Hz, 1H) 3.95-4.03 (m, 7H) 3.77 (d, J=12.55 Hz, 1H) 2.64 (d, J=5.02 Hz, 2H) 2.44 (br. s., 1H) 1.92-2.04 (m, 2H) 1.55-1.68 (m, 4H) 1.43 (br. s., 3H) 1.26-1.35 (m, 6H) 1.22 (br. s., 9H) 1.08 (d, J=6.02 Hz, 5H) 0.90 (d, J=6.53 Hz, 3H); MS: MS m/z 833.2 (M$^+$+1).

Preparation of Compound 4124

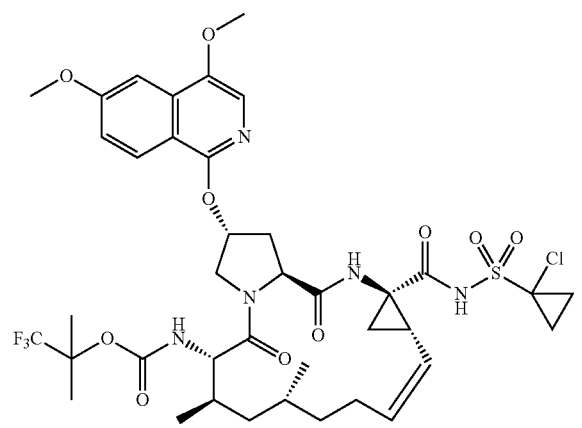

Compound 4124

Compound 4124 was prepared using the intermediates described herein and by following the general procedure described for the synthesis of Compound 3.

Compound 4124: 1,1,1-trifluoro-2-methylpropan-2-yl (2R,6S,7R,9R,13aS,14aR,16aS,Z)-14a-(1-chlorocyclopropylsulfonylcarbamoyl)-2-(4,6-dimethoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.07 (d, J=9.03 Hz, 1H) 7.53 (s, 1H) 7.43 (d, J=2.51 Hz, 1H) 7.14 (dd, J=9.03, 2.51 Hz, 1H) 5.80 (br. s., 1H) 5.60 (br. s., 1H) 4.54-4.74 (m, 3H) 3.99-4.07 (m, 4H) 3.95 (s, 3H) 3.81-3.88 (m, 1H) 3.28 (br. s., 1H) 2.66-2.78 (m, 2H) 2.44 (d, J=9.03 Hz, 2H) 1.88-2.04 (m, 3H) 1.70-1.87 (m, 3H) 1.59 (d, J=10.29 Hz, 2H) 1.45 (br. s., 5H) 1.39 (s, 3H) 1.31 (s, 1H) 0.96-1.06 (m, 7H) 0.78-0.87 (m, 1H); MS: MS m/z 872.4 (M$^+$+1).

Preparation of Compound 4125

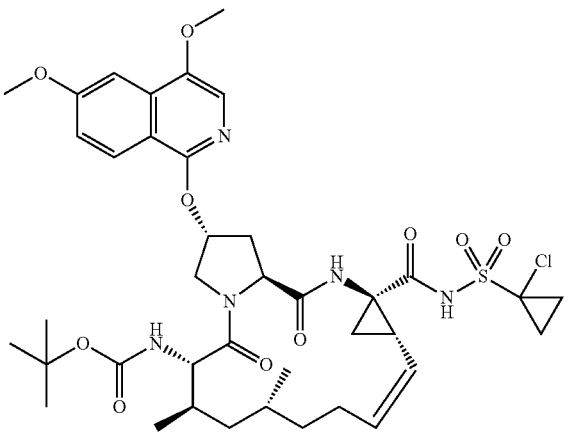

Compound 4125

Compound 4125 was prepared using the intermediates described herein and by following the general procedure described for the synthesis of Compound 1.

Compound 4125: tert-butyl (2R,6S,7R,9R,13aS,14aR,16aS,Z)-14a-(1-chlorocyclopropylsulfonylcarbamoyl)-2-(4,6-dimethoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.07 (d, J=9.29 Hz, 1H) 7.51 (s, 1H) 7.42 (s, 1H) 7.12 (d, J=11.29 Hz, 1H) 6.66 (d, J=9.03 Hz, 1H) 5.81 (br. s., 1H) 5.61 (s, 1H) 5.00 (br. s., 1H) 4.57-4.73 (m, 2H) 3.99-4.07 (m, 4H) 3.85-3.98 (m, 4H) 3.24-3.29 (m, 1H) 2.75 (d, J=7.28 Hz, 2H) 2.43 (d, J=9.29 Hz, 2H) 1.89-2.08 (m, 3H) 1.71-1.88 (m, 3H) 1.43-1.62 (m, 5H) 1.23-1.35 (m, 3H) 1.09-1.21 (m, 7H) 1.00 (dd, J=10.29, 6.53 Hz, 6H) 0.85 (d, J=13.30 Hz, 1H); MS: MS m/z 818.4 (M$^+$+1).

Preparation of Compound 4126

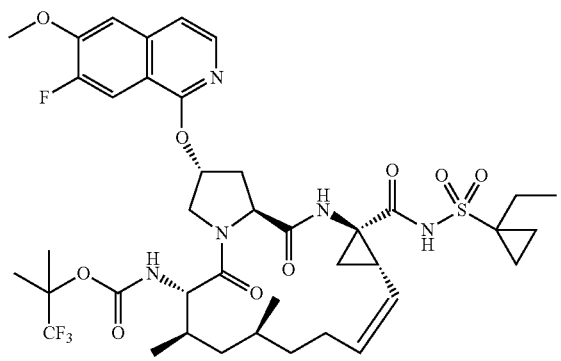

Compound 4126

Compound 4126 was prepared using the intermediates described herein and by following the general procedure described for the synthesis of Compound 3.

Compound 4126: 1,1,1-trifluoro-2-methylpropan-2-yl (2R,6S,7R,9S,13aS,14aR,16aS,Z)-14a-(1-ethylcyclopropylsulfonylcarbamoyl)-2-(7-fluoro-6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.95 (d, J=5.77 Hz, 1H) 7.79 (d, J=11.54 Hz, 1H) 7.27-7.43 (m, 2H) 5.90 (br. s., 1H) 5.61 (td, J=10.16, 5.52 Hz, 1H) 4.98 (t, J=10.16 Hz, 1H) 4.60-4.75 (m, 2H) 3.98-4.06 (m, 4H) 3.82 (d, J=10.79 Hz, 1H) 2.69-2.79 (m, 2H) 2.44 (ddd, J=13.93, 10.04, 4.14 Hz, 2H) 2.06 (dd, J=14.81, 7.53 Hz, 1H) 1.87-2.00 (m, 2H) 1.71-1.86 (m, 3H) 1.43-1.67 (m, 5H) 1.33-1.42 (m, 4H) 1.18-1.33 (m, 2H) 1.13 (s, 3H) 0.88-1.07 (m, 9H) 0.80-0.87 (m, 1H); MS: MS m/z 855.2 (M$^+$+1).

Preparation of Compound 4127

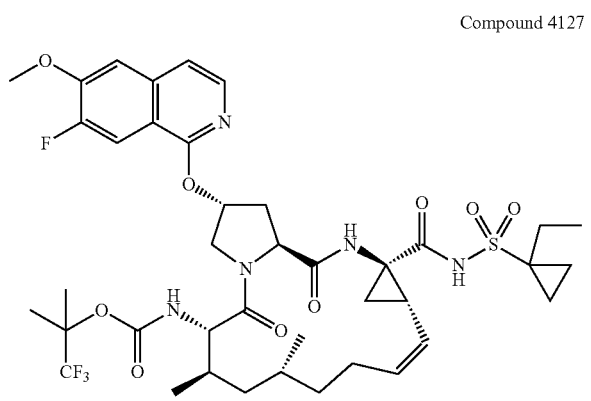 [SMILES: CCC1(S(=O)(=O)NC(=O)[C@@]23C[C@H]2/C=C\CC[C@@H](C)C[C@@H](C)[C@H](NC(=O)OC(C)(C)C(F)(F)F)C(=O)N2C[C@H](Oc4nccc5cc(OC)c(F)cc45)C[C@H]2C(=O)N3)CC1]

Compound 4127

Compound 4127 was prepared using the intermediates described herein and by following the general procedure described for the synthesis of Compound 3.

Compound 4127: 1,1,1-trifluoro-2-methylpropan-2-yl (2R,6S,7R,9R,13aS,14aR,16aS,Z)-14a-(1-ethylcyclopropylsulfonylcarbamoyl)-2-(7-fluoro-6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 9.10 (s, 1H) 7.94 (d, J=6.02 Hz, 1H) 7.83 (d, J=11.54 Hz, 1H) 7.39 (d, J=8.28 Hz, 1H) 7.30 (d, J=5.77 Hz, 1H) 5.90 (br. s., 1H) 5.68-5.77 (m, 1H) 5.02 (t, J=9.54 Hz, 1H) 4.71 (dd, J=10.04, 7.03 Hz, 1H) 4.52 (d, J=11.80 Hz, 1H) 4.13 (d, J=6.27 Hz, 1H) 4.00-4.09 (m, 4H) 2.58-2.77 (m, 2H) 2.40-2.52 (m, 2H) 1.91-2.07 (m, 3H) 1.76-1.89 (m, 1H) 1.70 (dd, J=8.03, 5.52 Hz, 1H) 1.54-1.64 (m, 3H) 1.36-1.51 (m, 6H) 1.18-1.33 (m, 6H) 1.12 (d, J=6.78 Hz, 3H) 0.88-1.05 (m, 7H); MS: MS m/z 855.2 (M$^+$+1).

Preparation of Compound 4128

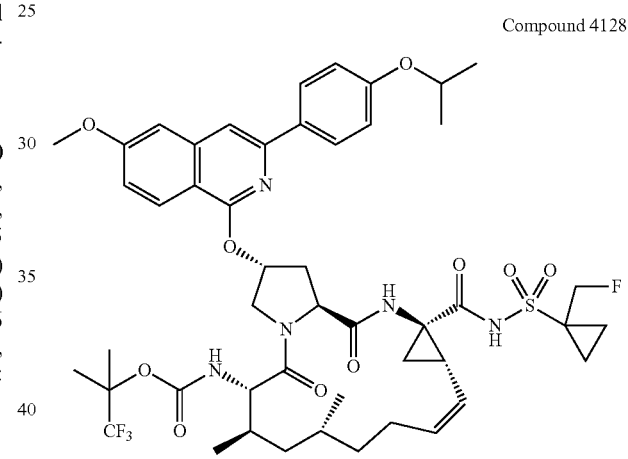

Compound 4128

Compound 4128 was prepared using the intermediates described herein and by following the general procedure described for the synthesis of Compound 3.

Compound 4128: 1,1,1-trifluoro-2-methylpropan-2-yl (2R,6S,7R,9R,13aS,14aR,16aS,Z)-14a-(1-(fluoromethyl)cyclopropylsulfonylcarbamoyl)-2-((3-(4-isopropoxyphenyl)-6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 9.03 (s, 1H) 8.03-8.14 (m, 3H) 7.69 (s, 1H) 7.24 (d, J=2.51 Hz, 1H) 7.00-7.06 (m, 3H) 6.07 (br. s., 1H) 5.63 (td, J=10.29, 5.77 Hz, 1H) 5.01 (t, J=9.91 Hz, 1H) 4.60-4.81 (m, 4H) 4.13 (dd, J=11.42, 3.64 Hz, 1H) 3.95 (s, 3H) 3.89 (d, J=10.79 Hz, 1H) 2.67-2.84 (m, 2H) 2.36-2.56 (m, 2H) 1.77-2.05 (m, 3H) 1.62-1.76 (m, 3H) 1.44-1.61 (m, 4H) 1.33-1.43 (m, 8H) 1.16-1.31 (m, 4H) 1.11 (s, 3H) 1.01 (dd, J=18.95, 6.65 Hz, 6H) 0.86 (t, J=11.80 Hz, 1H); MS: MS m/z 975.2 (M$^+$+1).

Preparation of Compound 4129

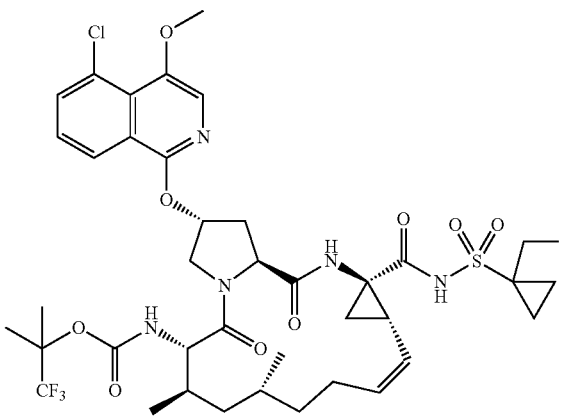

Compound 4129

Compound 4129 was prepared using the intermediates described herein and by following the general procedure described for the synthesis of Compound 3.

Compound 4129: 1,1,1-trifluoro-2-methylpropan-2-yl (2R,6S,7R,9R,13aS,14aR,16aS,Z)-2-(5-chloro-4-methoxy-isoquinolin-1-yloxy)-14a-(1-(fluoromethyl)cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. ¹H NMR (400 MHz, CD₃OD): δ ppm 8.16-8.20 (m, 1H) 7.76-7.81 (m, 1H) 7.72 (s, 1H) 7.48 (t, J=7.91 Hz, 1H) 7.28 (d, J=8.03 Hz, 1H) 5.84 (br. s., 1H) 5.62 (d, J=5.52 Hz, 1H) 5.00 (t, J=9.41 Hz, 1H) 4.60-4.69 (m, 2H) 3.95-4.04 (m, 4H) 3.80 (dd, J=10.79, 7.78 Hz, 1H) 2.61-2.78 (m, 3H) 2.36-2.50 (m, 2H) 2.13-2.22 (m, 1H) 1.91-2.02 (m, 1H) 1.76-1.90 (m, 2H) 1.62-1.76 (m, 3H) 1.58 (dd, J=9.41, 5.40 Hz, 1H) 1.48 (br. s., 2H) 1.30-1.40 (m, 3H) 1.15-1.29 (m, 5H) 0.93-1.05 (m, 7H) 0.79-0.87 (m, 1H); MS: MS m/z 872.4 (M⁺−1).

Preparation of Compound 4130

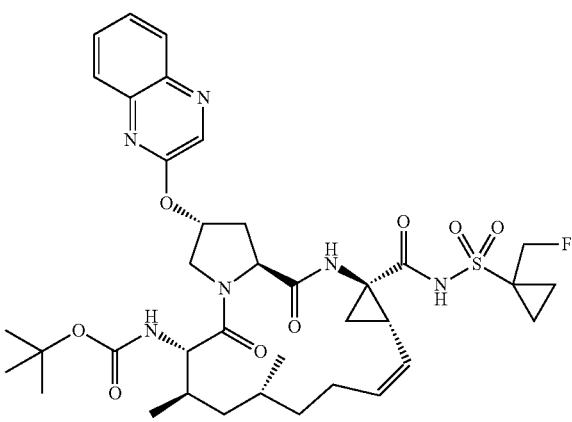

Compound 4130

Compound 4130 was prepared using the intermediates described herein and by following the general procedure described for the synthesis of Compound 1.

Compound 4130: tert-butyl (2R,6S,7R,9R,13aS,14aR,16aS,Z)-14a-(1-(fluoromethyl)cyclopropylsulfonylcarbamoyl)-7,9-dimethyl-5,16-dioxo-2-(quinoxalin-2-yloxy)-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

¹H NMR (400 MHz, CD₃OD): δ ppm 8.44 (s, 1H) 8.00 (d, J=8.03 Hz, 1H) 7.90-7.95 (m, 1H) 7.77 (t, J=7.03 Hz, 1H) 7.62-7.68 (m, 1H) 5.92 (br. s., 1H) 5.59 (br. s., 1H) 4.93-5.04 (m, 2H) 4.55-4.64 (m, 2H) 4.05-4.13 (m, 1H) 3.82 (d, J=10.54 Hz, 1H) 2.66-2.73 (m, 2H) 2.50 (br. s., 1H) 2.37 (br. s., 1H) 1.98 (br. s., 1H) 1.82 (br. s., 2H) 1.72 (dd, J=8.41, 5.40 Hz, 2H) 1.58 (br. s., 2H) 1.47 (br. s., 3H) 1.25-1.34 (m, 5H) 1.13 (s, 9H) 0.93-1.05 (m, 7H) 0.77-0.86 (m, 1H); MS: MS m/z 757.2 (M⁺+1).

Preparation of Compound 4131

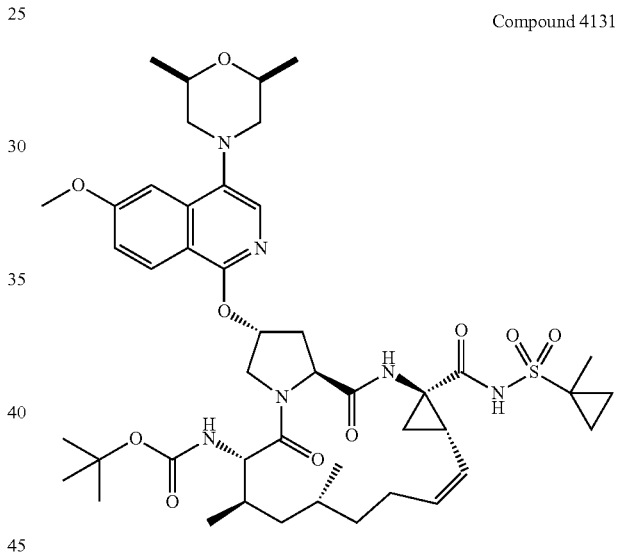

Compound 4131

Compound 4131 was prepared using the intermediates described herein and by following the general procedure described for the synthesis of Compound 1.

Compound 4131: tert-butyl (2R,6S,7R,9R,13aS,14aR,16aS,Z)-2-(4-((2S,6R)-2,6-dimethylmorpholino)-6-methoxyisoquinolin-1-yloxy)-7,9-dimethyl-14a-(1-methyl-cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. ¹H NMR (400 MHz, CD₃OD): δ ppm 8.12 (d, J=9.03 Hz, 1H) 7.67 (s, 1H) 7.42 (d, J=2.51 Hz, 1H) 7.12 (dd, J=9.03, 2.26 Hz, 1H) 6.63 (d, J=8.78 Hz, 1H) 5.84 (br. s., 1H) 5.58-5.66 (m, 1H) 5.00 (t, J=9.79 Hz, 1H) 4.68-4.75 (m, 1H) 4.60 (dd, J=16.31, 9.03 Hz, 1H) 3.98-4.06 (m, 3H) 3.82-3.97 (m, 4H) 3.16 (d, J=11.29 Hz, 3H) 2.68-2.78 (m, 2H) 2.50-2.65 (m, 2H) 2.37-2.48 (m, 2H) 1.92-2.03 (m, 1H) 1.73-1.90 (m, 3H) 1.66 (d, J=10.04 Hz, 1H) 1.49-1.59 (m, 5H) 1.38-1.48 (m, 3H) 1.28-1.37 (m, 3H) 1.19-1.28 (m, 5H) 1.14 (s, 7H) 1.00 (dd, J=9.79, 6.78 Hz, 5H) 0.79-0.93 (m, 2H); MS: MS m/z 882.6 (M⁺+1).

Preparation of Compound 4132

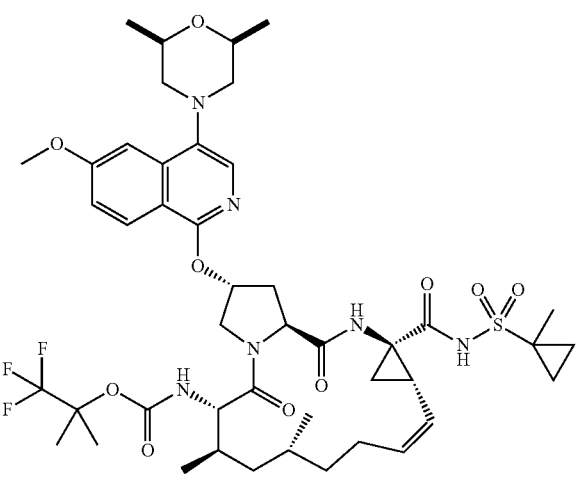

Compound 4132

Compound 4132 was prepared using the intermediates described herein and by following the general procedure described for the synthesis of Compound 3.

Compound 4132: 1,1,1-trifluoro-2-methylpropan-2-yl (2R,6S,7R,9R,13aS,14aR,16aS,Z)-2-(4-((2S,6R)-2,6-dimethylmorpholino)-6-methoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 9.08 (s, 1H) 8.13 (d, J=9.29 Hz, 1H) 7.65-7.70 (m, 1H) 7.44 (d, J=2.51 Hz, 1H) 7.15 (dd, J=9.29, 2.51 Hz, 1H) 5.84 (br. s., 1H) 5.62 (dt, J=10.29, 5.14 Hz, 1H) 4.97-5.06 (m, 2H) 4.61-4.77 (m, 2H) 3.99-4.07 (m, 3H) 3.93-3.99 (m, 3H) 3.82 (d, J=10.79 Hz, 1H) 3.12-3.22 (m, 2H) 2.70-2.79 (m, 2H) 2.53-2.66 (m, 2H) 2.44 (ddd, J=13.68, 9.91, 4.27 Hz, 2H) 1.86-2.03 (m, 2H) 1.73-1.84 (m, 2H) 1.63-1.73 (m, 1H) 1.57 (dd, J=9.54, 5.52 Hz, 1H) 1.41-1.54 (m, 5H) 1.30-1.39 (m, 4H) 1.17-1.29 (m, 7H) 0.96-1.09 (m, 9H) 0.79-0.94 (m, 2H); MS: MS m/z 935.8 (M$^+$+1).

Preparation of Compound 4133

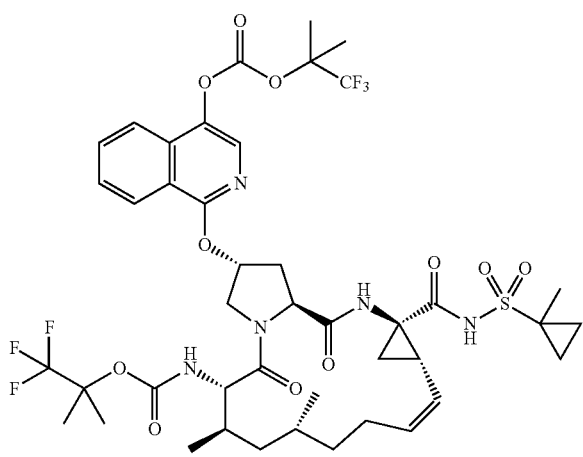

Compound 4133

Compound 4133 was prepared using the intermediates described herein and by following the general procedure described for the synthesis of Compound 3.

Compound 4133: 1,1,1-trifluoro-2-methylpropan-2-yl (2R,6S,7R,9R,13aS,14aR,16aS,Z)-7,9-dimethyl-14a-(1-methylcyclopropylsulfonylcarbamoyl)-5,16-dioxo-2-(4-((1,1,1-trifluoro-2-methylpropan-2-yloxy)carbonyloxy)isoquinolin-1-yloxy)-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.27 (d, J=8.53 Hz, 1H) 7.99 (s, 1H) 7.79-7.87 (m, 2H) 7.64 (t, J=7.53 Hz, 1H) 5.93 (br. s., 1H) 5.62 (d, J=4.52 Hz, 1H) 5.05 (br. s., 1H) 4.68 (dd, J=10.16, 7.15 Hz, 1H) 4.04 (dd, J=11.54, 3.01 Hz, 1H) 3.82 (d, J=10.79 Hz, 1H) 2.79 (dd, J=13.30, 7.28 Hz, 1H) 2.40-2.52 (m, 2H) 1.94-2.03 (m, 2H) 1.79-1.85 (m, 7H) 1.74-1.78 (m, 1H) 1.57 (dd, J=9.54, 5.52 Hz, 1H) 1.52 (s, 3H) 1.39-1.46 (m, 2H) 1.29-1.35 (m, 5H) 1.22-1.28 (m, 2H) 1.00 (dd, J=10.16, 6.65 Hz, 6H) 0.91 (s, 5H) 0.80-0.89 (m, 3H); MS: MS m/z 962.6 (M$^+$+1).

Preparation of Compound 4134

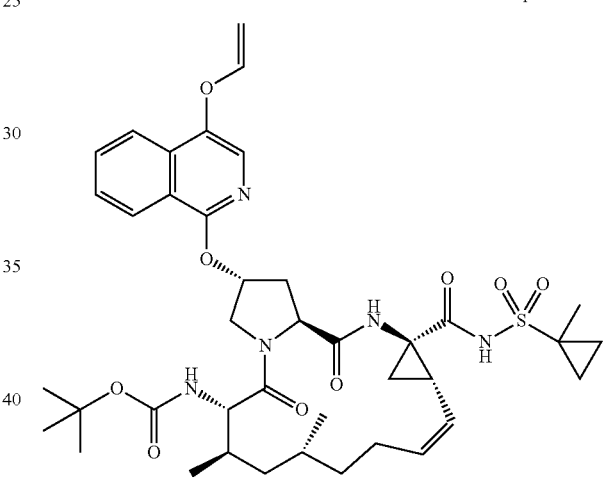

Compound 4134

Compound 4134 was prepared using the intermediates described herein and by following the general procedure described for the synthesis of Compound 1.

Compound 4134: tert-butyl (2R,6S,7R,9R,13aS,14aR,16aS,Z)-7,9-dimethyl-14a-(1-methylcyclopropylsulfonylcarbamoyl)-5,16-dioxo-2-(4-(vinyloxy)isoquinolin-1-yloxy)-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.22 (d, J=8.28 Hz, 1H) 8.03 (d, J=8.53 Hz, 1H) 7.77 (t, J=7.53 Hz, 1H) 7.72 (s, 1H) 7.56-7.62 (m, 1H) 6.86 (dd, J=13.68, 6.15 Hz, 1H) 6.63 (d, J=8.53 Hz, 1H) 5.89 (br. s., 1H) 5.63 (td, J=10.29, 5.52 Hz, 1H) 5.01 (t, J=10.04 Hz, 1H) 4.71-4.80 (m, 2H) 4.64 (dd, J=10.04, 7.03 Hz, 1H) 4.48 (dd, J=6.02, 1.51 Hz, 1H) 4.05 (dd, J=11.42, 3.39 Hz, 1H) 3.84-3.91 (m, 1H) 2.70-2.81 (m, 2H) 2.38-2.50 (m, 2H) 1.98 (t, J=12.92 Hz, 1H) 1.73-1.91 (m, 3H) 1.62-1.70 (m, 1H) 1.57 (dd, J=9.41, 5.65 Hz, 1H) 1.39-1.54 (m, 6H) 1.18-1.36 (m, 3H) 1.11 (s, 9H) 1.00 (dd, J=10.67, 6.65 Hz, 4H) 0.79-0.94 (m, 3H); MS: MS m/z 780.4 (M$^+$+1).

Preparation of Compound 4135

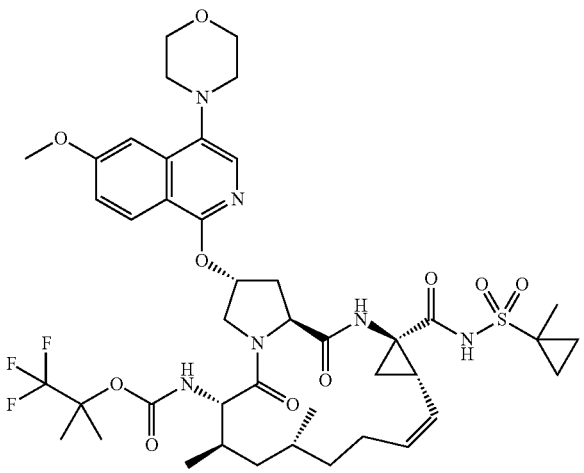

Compound 4135

Compound 4135 was prepared using the intermediates described herein and by following the general procedure described for the synthesis of Compound 3.

Compound 4135: 1,1,1-trifluoro-2-methylpropan-2-yl (2R,6S,7R,9R,13aS,14aR,16aS,Z)-2-(6-methoxy-4-morpholinoisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 9.06 (s, 1H) 8.13 (d, J=9.03 Hz, 1H) 7.71 (s, 1H) 7.47 (d, J=2.26 Hz, 1H) 7.15 (dd, J=9.03, 2.51 Hz, 1H) 5.85 (br. s., 1H) 5.60-5.68 (m, 1H) 5.01 (t, J=10.04 Hz, 1H) 4.74 (d, J=11.54 Hz, 1H) 4.65 (dd, J=10.29, 7.03 Hz, 1H) 4.03 (dd, J=11.42, 3.39 Hz, 1H) 3.93-3.99 (m, 7H) 3.83 (d, J=10.79 Hz, 1H) 3.29 (dd, J=3.26, 1.51 Hz, 1H) 3.06-3.13 (m, 4H) 2.69-2.79 (m, 2H) 2.44 (ddd, J=13.87, 9.98, 4.27 Hz, 2H) 1.86-2.04 (m, 2H) 1.75-1.85 (m, 2H) 1.63-1.70 (m, 1H) 1.55-1.61 (m, 1H) 1.40-1.55 (m, 6H) 1.30-1.37 (m, 4H) 1.24 (d, J=13.55 Hz, 1H) 0.96-1.05 (m, 7H) 0.80-0.92 (m, 3H); MS: MS m/z 905.4 (M$^+$−1).

Preparation of Compound 4136

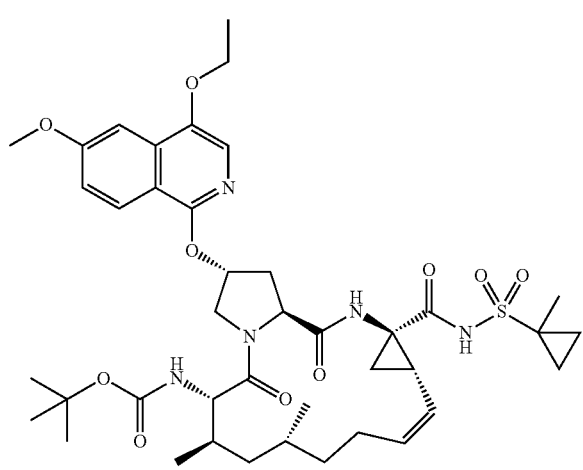

Compound 4136

Compound 4136 was prepared using the intermediates described herein and by following the general procedure described for the synthesis of Compound 1.

Compound 4136: tert-butyl (2R,6S,7R,9R,13aS,14aR,16aS,Z)-2-(4-ethoxy-6-methoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.07 (d, J=9.03 Hz, 1H) 7.50 (s, 1H) 7.43 (d, J=2.26 Hz, 1H) 7.12 (dd, J=9.16, 2.38 Hz, 1H) 6.62 (d, J=8.53 Hz, 1H) 5.81 (br. s., 1H) 5.62 (dt, J=10.04, 5.02 Hz, 1H) 5.00 (t, J=10.04 Hz, 1H) 4.68 (d, J=11.29 Hz, 1H) 4.60 (dd, J=9.79, 7.53 Hz, 1H) 4.23 (q, J=7.03 Hz, 2H) 4.03 (dd, J=11.42, 3.39 Hz, 1H) 3.95 (s, 3H) 3.85-3.92 (m, 1H) 2.68-2.80 (m, 2H) 2.36-2.49 (m, 2H) 1.98 (br. s., 1H) 1.84 (dd, J=14.93, 5.65 Hz, 2H) 1.73-1.80 (m, 2H) 1.62-1.69 (m, 1H) 1.50-1.59 (m, 7H) 1.40-1.48 (m, 2H) 1.23-1.33 (m, 3H) 1.17 (s, 7H) 0.97-1.04 (m, 5H) 0.86-0.93 (m, 3H) 0.79-0.85 (m, 1H); MS: MS m/z 812.4 (M$^+$+1).

Preparation of Compound 4137

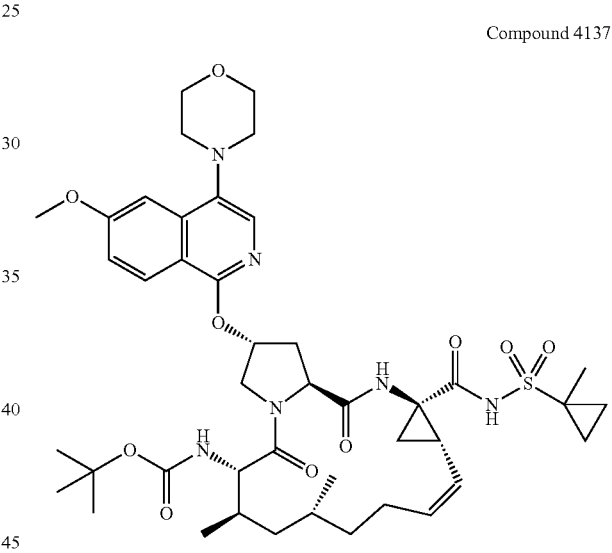

Compound 4137

Compound 4137 was prepared using the intermediates described herein and by following the general procedure described for the synthesis of Compound 1.

Compound 4137: tert-butyl (2R,6S,7R,9R,13aS,14aR,16aS,Z)-2-(6-methoxy-4-morpholinoisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.12 (d, J=9.29 Hz, 1H) 7.70 (s, 1H) 7.45 (d, J=2.51 Hz, 1H) 7.12 (dd, J=9.03, 2.26 Hz, 1H) 6.63 (d, J=8.28 Hz, 1H) 5.84 (br. s., 1H) 5.62 (td, J=10.16, 5.77 Hz, 1H) 5.00 (t, J=10.04 Hz, 1H) 4.69-4.76 (m, 1H) 4.61 (dd, J=9.79, 7.28 Hz, 1H) 4.04 (dd, J=11.42, 3.14 Hz, 1H) 3.93-3.99 (m, 7H) 3.84-3.91 (m, 1H) 3.35 (br. s., 2H) 3.06-3.12 (m, 4H) 2.68-2.79 (m, 2H) 2.38-2.51 (m, 2H) 1.93-2.07 (m, 1H) 1.74-1.91 (m, 3H) 1.62-1.72 (m, 1H) 1.56 (dd, J=9.41, 5.65 Hz, 1H) 1.46-1.53 (m, 2H) 1.39-1.45 (m, 2H) 1.21-1.38 (m, 2H) 1.14 (s, 9H) 1.00 (dd, J=9.91, 6.65 Hz, 4H) 0.86-0.95 (m, 3H) 0.80-0.86 (m, 1H); MS: MS m/z 853.4 (M$^+$+1).

Preparation of Compound 4138

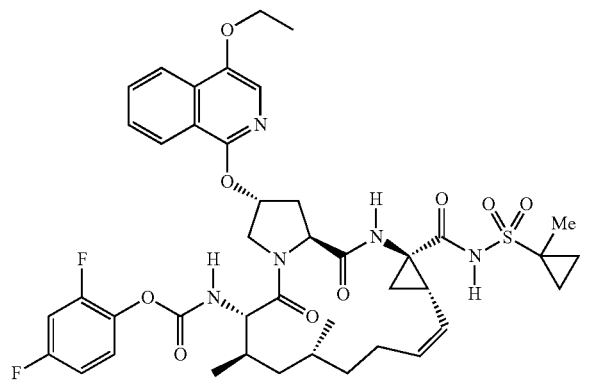

Compound 4138

Compound 4138 was prepared using the intermediates described herein and by following the general procedure described for the synthesis of Compound 3.

Compound 4138: 2,4-difluorophenyl (2R,6S,7R,9R,13aS,14aR,16aS,Z)-2-(4-ethoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.12 (t, J=9.29 Hz, 2H) 7.74 (t, J=7.65 Hz, 2H) 7.46-7.54 (m, 2H) 6.76-6.95 (m, 2H) 5.81 (br. s., 1H) 5.59-5.72 (m, 1H) 5.04 (br. s., 1H) 4.50-4.70 (m, 2H) 3.96-4.24 (m, 4H) 3.25-3.31 (m, 2H) 2.67-2.82 (m, 2H) 2.36-2.57 (m, 2H) 1.91-2.12 (m, 2H) 1.73-1.88 (m, 2H) 1.62-1.73 (m, 1H) 1.53 (s, 8H) 1.20-1.37 (m, 1H) 1.01-1.17 (m, 6H) 0.82-0.96 (m, 3H); MS: MS m/z 838.2 (M$^+$+1).

Preparation of Compound 4139

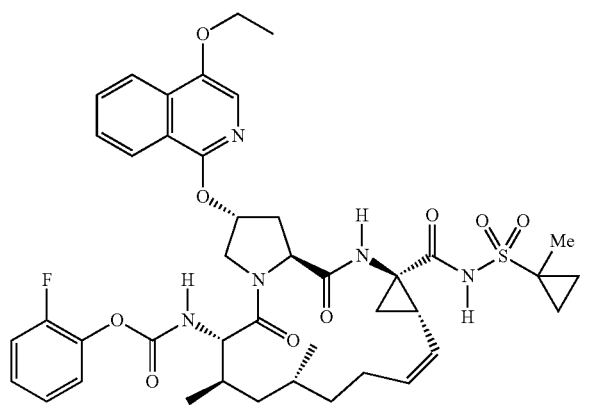

Compound 4139

Compound 4139 was prepared using the intermediates described herein and by following the general procedure described for the synthesis of Compound 3.

Compound 4139: 2-fluorophenyl (2R,6S,7R,9R,13aS,14aR,16aS,Z)-2-(4-ethoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.09-8.15 (m, 2H) 7.42-7.51 (m, 2H) 7.17-7.27 (m, 2H) 7.03-7.11 (m, 2H) 6.86 (td, J=8.03, 1.51 Hz, 1H) 5.83 (br. s., 1H) 5.59-5.70 (m, 1H) 4.98-5.08 (m, 1H) 4.85 (s, 1H) 4.60-4.66 (m, 2H) 4.01-4.23 (m, 5H) 3.28 (br. s., 1H) 2.72-2.84 (m, 2H) 2.39-2.55 (m, 2H) 2.03 (dd, J=11.80, 5.77 Hz, 2H) 1.82-1.91 (m, 1H) 1.77 (dd, J=8.28, 5.77 Hz, 1H) 1.64-1.70 (m, 1H) 1.50-1.61 (m, 9H) 1.41-1.46 (m, 1H) 1.25-1.32 (m, 2H) 1.10 (d, J=6.53 Hz, 2H) 1.05 (d, J=6.78 Hz, 2H) 0.87-0.95 (m, 2H); MS: MS m/z 820.4 (M$^+$+1).

Preparation of Compound 4140

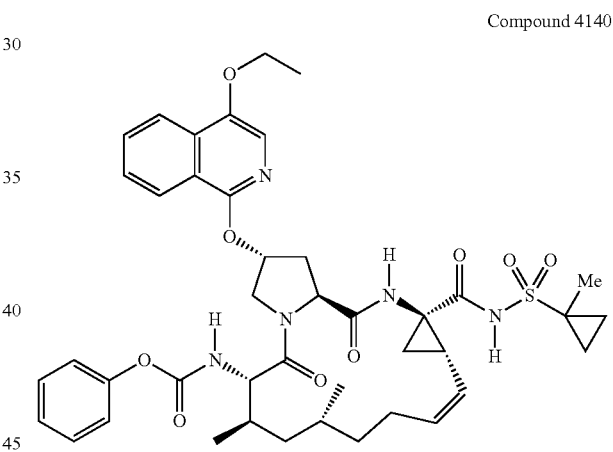

Compound 4140

Compound 440 was prepared using the intermediates described herein and by following the general procedure described for the synthesis of Compound 3.

Compound 4140: phenyl (2R,6S,7R,9R,13aS,14aR,16aS,Z)-2-(4-ethoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.10-8.16 (m, 2H) 7.68-7.79 (m, 2H) 7.50 (s, 1H) 7.39-7.46 (m, 1H) 7.12-7.27 (m, 3H) 6.73-6.79 (m, 2H) 5.84 (br. s., 1H) 5.64 (td, J=10.04, 5.77 Hz, 1H) 5.02 (t, J=10.04 Hz, 1H) 4.60-4.68 (m, 2H) 4.14-4.24 (m, 2H) 4.00-4.11 (m, 2H) 2.72-2.82 (m, 2H) 2.39-2.53 (m, 2H) 1.96-2.08 (m, 2H) 1.75-1.90 (m, 2H) 1.63-1.71 (m, 1H) 1.48-1.60 (m, 9H) 1.40-1.47 (m, 1H) 1.22-1.35 (m, 2H) 1.06 (dd, J=19.32, 6.78 Hz, 5H) 0.84-0.94 (m, 3H); MS: MS m/z 802.5 (M$^+$+1).

Preparation of Compound 4141

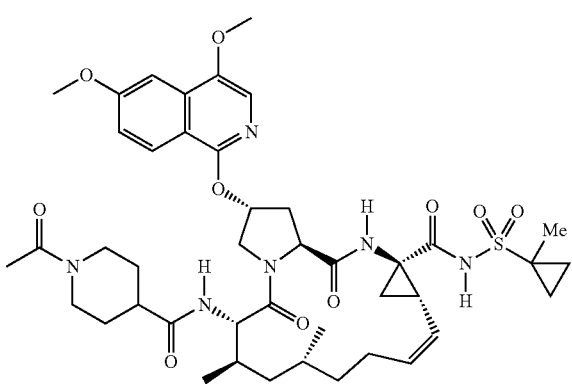

Compound 4141

Compound 4141 was prepared using the intermediates described herein and by following the general procedure described for the synthesis of Compound 4029.

Compound 4141: (2R,6S,7R,9R,13aS,14aR,16aS,Z)-6-(1-acetylpiperidine-4-carboxamido)-2-(4,6-dimethoxyisoquinolin-1-yloxy)-7,9-dimethyl-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (400 MHz, CD$_3$OD): δ ppm 9.04 (s, 1H) 7.96-8.07 (m, 2H) 7.52 (d, J=7.78 Hz, 1H) 7.45 (d, J=2.51 Hz, 1H) 7.17 (ddd, J=11.73, 9.10, 2.51 Hz, 1H) 5.83 (d, J=2.76 Hz, 1H) 5.64 (td, J=10.04, 5.77 Hz, 1H) 5.02 (t, J=10.04 Hz, 1H) 4.55-4.66 (m, 2H) 4.18-4.32 (m, 2H) 3.94-4.08 (m, 7H) 3.75 (d, J=13.55 Hz, 1H) 3.02 (t, J=11.17 Hz, 1H) 2.86-2.95 (m, 1H) 2.68-2.82 (m, 2H) 2.49-2.66 (m, 1H) 2.36-2.47 (m, 2H) 2.28 (br. s., 1H) 1.94-2.10 (m, 5H) 1.75-1.84 (m, 2H) 1.63-1.71 (m, 1H) 1.46-1.62 (m, 7H) 1.31-1.45 (m, 2H) 1.11-1.29 (m, 2H) 0.92-1.07 (m, 7H) 0.79-0.91 (m, 2H); MS: MS m/z 849.2 (M$^+$−1).

Preparation of Compound 4142

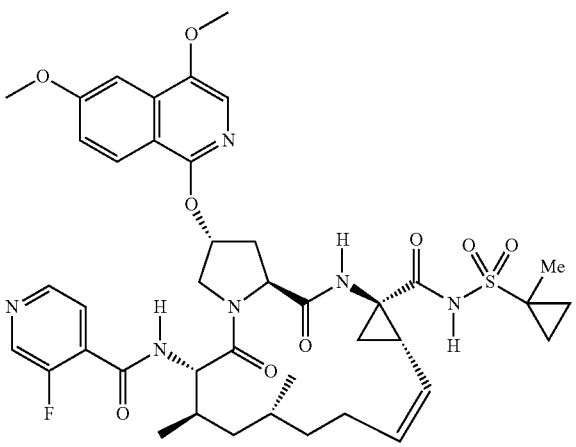

Compound 4142

Compound 4142 was prepared using the intermediates described herein and by following the general procedure described for the synthesis of Compound 4029.

Compound 4142: (2R,6S,7R,9R,13aS,14aR,16aS,Z)-2-(4,6-dimethoxyisoquinolin-1-yloxy)-6-(3-fluoroisonicotinamido)-7,9-dimethyl-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (400 MHz, CD$_3$OD): δ ppm 9.07 (s, 1H) 8.50 (d, J=1.76 Hz, 1H) 8.34 (d, J=4.52 Hz, 1H) 8.08 (d, J=9.29 Hz, 1H) 7.50 (s, 1H) 7.39 (d, J=2.51 Hz, 1H) 7.16 (dd, J=9.29, 2.01 Hz, 1H) 7.05 (t, J=5.52 Hz, 1H) 5.87 (br. s., 1H) 5.64 (td, J=10.16, 6.27 Hz, 1H) 5.03 (t, J=9.91 Hz, 1H) 4.73-4.82 (m, 2H) 4.68 (dd, J=10.04, 7.03 Hz, 1H) 4.35-4.42 (m, 1H) 4.11 (dd, J=11.67, 3.39 Hz, 1H) 4.04 (s, 4H) 3.95 (s, 4H) 3.29 (dd, J=3.26, 1.51 Hz, 1H) 2.72-2.85 (m, 3H) 2.48 (ddd, J=13.93, 10.04, 3.89 Hz, 3H) 1.97-2.16 (m, 2H) 1.86 (dd, J=13.18, 5.90 Hz, 1H) 1.78 (dd, J=8.41, 5.65 Hz, 1H) 1.63-1.72 (m, 1H) 1.50-1.62 (m, 3H) 1.23-1.49 (m, 3H) 1.00-1.08 (m, 3H) 0.86-0.96 (m, 2H); MS: MS m/z 821.4 (M$^+$+1).

Preparation of Compound 4143

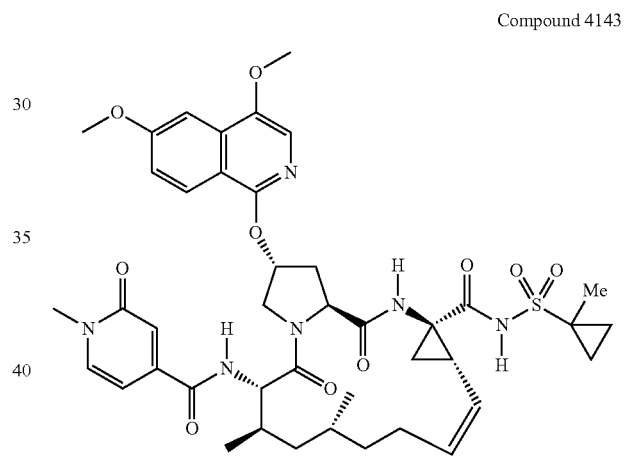

Compound 4143

Compound 4143 was prepared using the intermediates described herein and by following the general procedure described for the synthesis of Compound 4029.

Compound 4143: (2R,6S,7R,9R,13aS,14aR,16aS,Z)-2-(4,6-dimethoxyisoquinolin-1-yloxy)-7,9-dimethyl-6-(1-methyl-2-oxo-1,2-dihydropyridine-4-carboxamido)-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (400 MHz, CD$_3$OD): δ ppm 9.06 (s, 1H) 8.65 (d, J=8.28 Hz, 1H) 8.02 (d, J=9.29 Hz, 1H) 7.59 (d, J=6.78 Hz, 1H) 7.49 (s, 1H) 7.42 (d, J=2.51 Hz, 1H) 7.12 (dd, J=9.03, 2.51 Hz, 1H) 6.61 (d, J=1.51 Hz, 1H) 6.25 (dd, J=6.90, 1.88 Hz, 1H) 5.85 (br. s., 1H) 5.63 (td, J=9.91, 6.27 Hz, 1H) 5.02 (t, J=10.04 Hz, 1H) 4.76 (d, J=11.29 Hz, 1H) 4.64 (dd, J=9.79, 7.28 Hz, 1H) 4.29-4.36 (m, 1H) 4.02-4.09 (m, 4H) 3.96 (s, 3H) 3.57 (s, 3H) 2.71-2.81 (m, 2H) 2.46 (ddd, J=13.87, 9.98, 4.02 Hz, 2H) 1.97-2.18 (m, 2H) 1.75-1.88 (m, 2H) 1.63-1.72 (m, 1H) 1.49-1.60 (m, 6H) 1.21-1.47 (m, 3H) 1.01 (dd, J=14.43, 6.65 Hz, 4H) 0.84-0.94 (m, 3H); MS: MS m/z 833.5 (M$^+$+1).

Preparation of Compound 4144

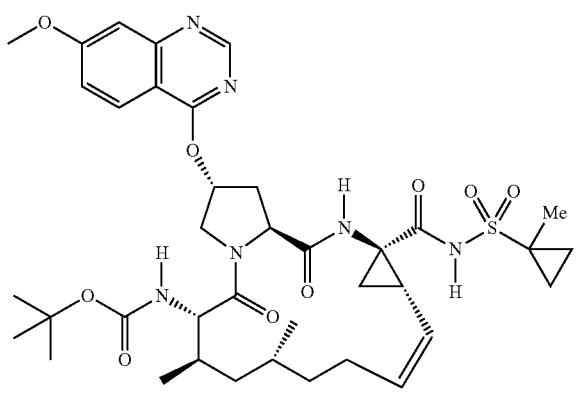

Compound 4144

Compound 4144 was prepared using the intermediates described herein and by following the general procedure described for the synthesis of Compound 1.

Compound 4144: tert-butyl (2R,6S,7R,9R,13aS,14aR,16aS,Z)-2-(7-methoxyquinazolin-4-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.73 (s, 1H) 8.09 (d, J=9.03 Hz, 1H) 7.17-7.28 (m, 2H) 6.00 (br. s., 1H) 5.63 (td, J=10.23, 5.90 Hz, 1H) 5.01 (t, J=10.16 Hz, 1H) 4.65 (dd, J=9.91, 7.15 Hz, 1H) 4.06 (dd, J=11.92, 3.39 Hz, 1H) 3.98 (s, 3H) 3.81 (d, J=10.79 Hz, 1H) 2.70-2.86 (m, 3H) 2.38-2.53 (m, 2H) 1.98 (br. s., 1H) 1.75-1.87 (m, 3H) 1.55-1.70 (m, 2H) 1.40-1.54 (m, 6H) 1.19-1.35 (m, 3H) 1.08 (s, 7H) 1.00 (dd, J=9.41, 6.65 Hz, 6H) 0.80-0.95 (m, 3H); MS: MS m/z 769.4 (M$^+$+1).

Preparation of Compound 4145

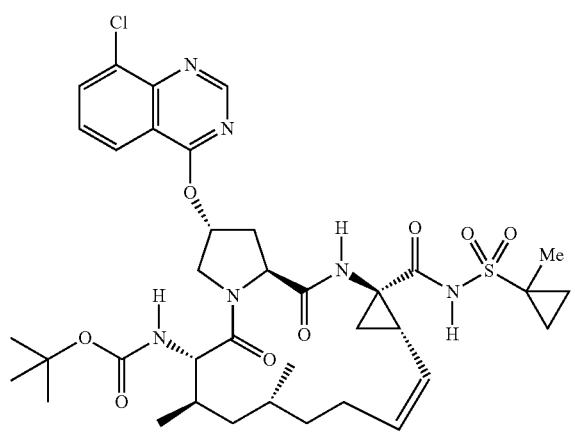

Compound 4145

Compound 4145 was prepared using the intermediates described herein and by following the general procedure described for the synthesis of Compound 1.

Compound 4145: tert-butyl (2R,6S,7R,9R,13aS,14aR,16aS,Z)-2-(8-chloroquinazolin-4-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.89 (s, 1H) 8.17 (dd, J=8.28, 1.25 Hz, 1H) 8.05 (dd, J=7.65, 1.13 Hz, 1H) 7.58 (t, J=7.91 Hz, 1H) 6.64 (d, J=7.78 Hz, 1H) 6.01 (br. s., 1H) 5.59-5.67 (m, 1H) 5.02 (t, J=10.04 Hz, 1H) 4.93 (d, J=10.54 Hz, 1H) 4.67 (dd, J=10.16, 7.15 Hz, 1H) 4.06 (dd, J=12.05, 3.01 Hz, 1H) 3.77 (dd, J=10.42, 8.16 Hz, 1H) 3.27 (dt, J=3.33, 1.73 Hz, 1H) 2.82 (dd, J=14.56, 6.78 Hz, 1H) 2.68-2.77 (m, 1H) 2.36-2.57 (m, 2H) 1.91-2.03 (m, 1H) 1.74-1.85 (m, 3H) 1.67 (d, J=11.04 Hz, 1H) 1.58 (dd, J=9.29, 5.52 Hz, 1H) 1.40-1.54 (m, 6H) 1.31 (s, 3H) 1.09-1.27 (m, 2H) 0.96-1.05 (m, 10H) 0.89 (t, J=9.54 Hz, 3H) 0.79-0.85 (m, 1H); MS: MS m/z 773.3 (M$^+$+1).

Preparation of Compound 4146

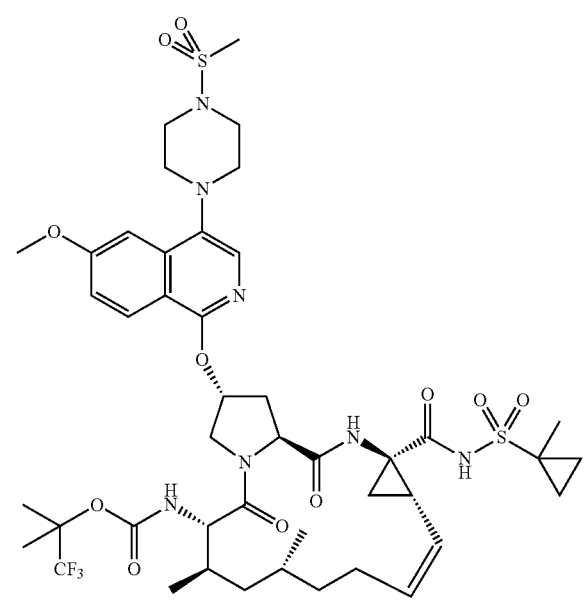

Compound 4146

Compound 4146 was prepared using the intermediates described herein and by following the general procedure described for the synthesis of Compound 3.

Compound 4146: 1,1,1-trifluoro-2-methylpropan-2-yl (2R,6S,7R,9R,13aS,14aR,16aS,Z)-2-(6-methoxy-4-(4-(methylsulfonyl)piperazin-1-yl)isoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 9.05 (s, 1H) 8.13 (d, J=9.04 Hz, 1H) 7.75 (s, 1H) 7.44 (d, J=2.26 Hz, 1H) 7.15 (dd, J=9.03, 2.51 Hz, 1H) 5.85 (br. s., 1H) 5.63 (td, J=9.91, 5.77 Hz, 1H) 5.01 (t, J=10.04 Hz, 2H) 4.73 (d, J=11.29 Hz, 1H) 4.65 (dd, J=10.16, 7.15 Hz, 1H) 3.96-4.05 (m, 6H) 3.83 (d, J=10.79 Hz, 1H) 2.98 (s, 3H) 2.67-2.78 (m, 2H) 2.38-2.52 (m, 2H) 1.75-2.04 (m, 4H) 1.64-1.71 (m, 1H) 1.41-1.60 (m, 8H) 1.37 (s, 5H) 1.20-1.31 (m, 3H) 0.98-1.04 (m, 8H) 0.82-0.94 (m, 5H). MS: MS m/z 985.11 (M$^+$+1).

Preparation of Compound 4147

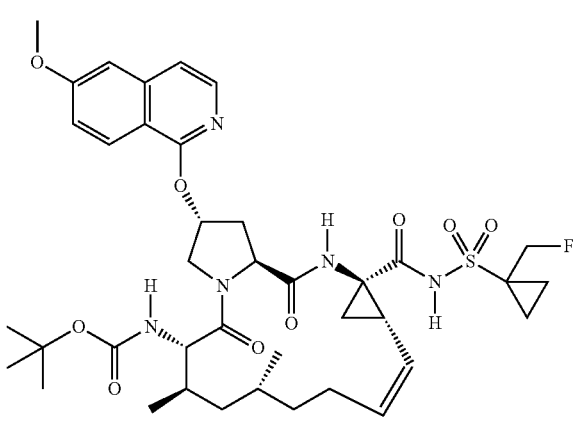

Compound 4147

Compound 4147 was prepared using the intermediates described herein and by following the general procedure described for the synthesis of Compound 1.

Compound 4147: tert-butyl (2R,6S,7R,9R,13aS,14aR,16aS,Z)-14a-(1-(fluoromethyl)cyclopropylsulfonylcarbamoyl)-2-(6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.12 (d, J=9.03 Hz, 1H) 7.90-7.94 (m, 1H) 7.26 (d, J=5.77 Hz, 1H) 7.20 (d, J=2.51 Hz, 1H) 7.10 (dd, J=9.29, 2.51 Hz, 1H) 6.64 (d, J=8.28 Hz, 1H) 5.89 (br. s., 1H) 5.62 (d, J=5.77 Hz, 1H) 4.96-5.05 (m, 1H) 4.79 (d, J=12.80 Hz, 1H) 4.71 (d, J=11.29 Hz, 1H) 4.48-4.67 (m, 2H) 4.06 (dd, J=11.67, 3.39 Hz, 1H) 3.86-3.98 (m, 5H) 3.29 (d, J=1.76 Hz, 1H) 2.68-2.77 (m, 2H) 2.39-2.50 (m, 2H) 1.97 (br. s., 1H) 1.78-1.91 (m, 2H) 1.72 (dd, J=8.53, 5.52 Hz, 3H) 1.57 (dd, J=9.41, 5.65 Hz, 1H) 1.43-1.53 (m, 2H) 1.23-1.33 (m, 3H) 1.18 (s, 5H) 1.13 (br. s., 1H) 1.02 (dd, J=12.05, 6.78 Hz, 7H) 0.85 (t, J=11.80 Hz, 1H); MS: MS m/z 786.5 (M$^+$+1).

Preparation of Compound 4149

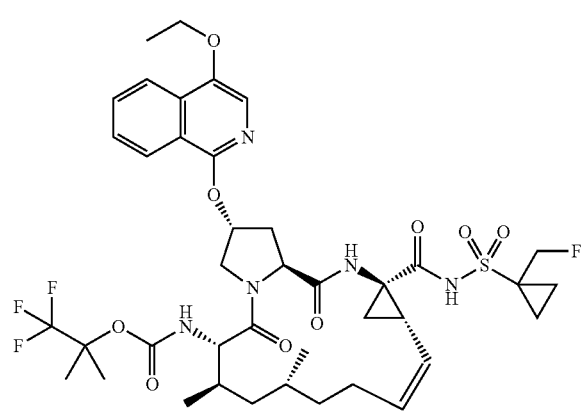

Compound 4149

Compound 4149 was prepared using the intermediates described herein and by following the general procedure described for the synthesis of Compound 3.

Compound 4149: 1,1,1-trifluoro-2-methylpropan-2-yl (2R,6S,7R,9R,13aS,14aR,16aS,Z)-2-(4-ethoxyisoquinolin-1-yloxy)-14a-(1-(fluoromethyl)cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.17 (dd, J=16.56, 8.28 Hz, 2H) 7.75 (td, J=7.65, 1.25 Hz, 1H) 7.55-7.61 (m, 2H) 5.84 (br. s., 1H) 5.71 (d, J=10.04 Hz, 1H) 5.07 (br. s., 1H) 4.60-4.83 (m, 2H) 4.49-4.59 (m, 1H) 4.24 (q, J=6.94 Hz, 2H) 4.01-4.15 (m, 2H) 2.67-2.78 (m, 1H) 2.61 (br. s., 1H) 2.47 (ddd, J=13.80, 9.66, 4.14 Hz, 2H) 1.92-2.07 (m, 2H) 1.59-1.74 (m, 5H) 1.55 (t, J=7.03 Hz, 4H) 1.35-1.50 (m, 5H) 1.21-1.33 (m, 3H) 1.13-1.20 (m, 4H) 1.10 (d, J=6.78 Hz, 3H) 0.97-1.05 (m, 1H) 0.94 (d, J=7.03 Hz, 3H); MS: MS m/z 854.4 (M$^+$+1).

Preparation of Compound 4150

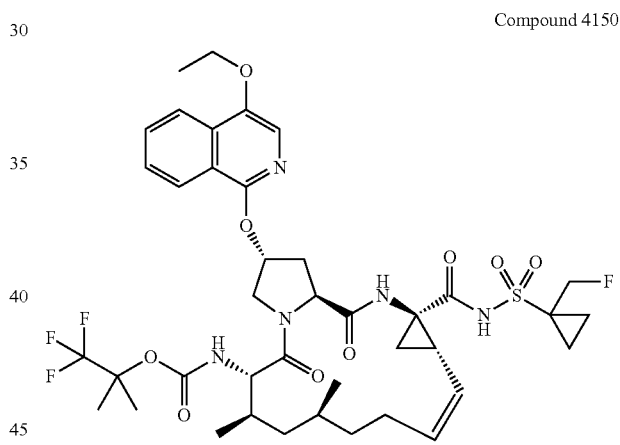

Compound 4150

Compound 4150 was prepared using the intermediates described herein and by following the general procedure described for the synthesis of Compound 3.

Compound 4150: 1,1,1-trifluoro-2-methylpropan-2-yl (2R,6S,7R,9S,13aS,14aR,16aS,Z)-2-(4-ethoxyisoquinolin-1-yloxy)-14a-(1-(fluoromethyl)cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.15 (t, J=7.28 Hz, 2H) 7.74 (ddd, J=8.28, 7.15, 0.88 Hz, 1H) 7.52-7.60 (m, 2H) 5.80-5.85 (m, 1H) 5.61 (td, J=10.23, 5.90 Hz, 1H) 5.03 (br. s., 1H) 4.78 (t, J=12.17 Hz, 2H) 4.60-4.69 (m, 2H) 4.52 (d, J=11.29 Hz, 1H) 4.24 (q, J=6.86 Hz, 2H) 4.02 (dd, J=11.54, 3.26 Hz, 1H) 3.83 (d, J=10.79 Hz, 1H) 2.65-2.79 (m, 2H) 2.37-2.50 (m, 2H) 1.77-2.03 (m, 3H) 1.62-1.75 (m, 3H) 1.41-1.61 (m, 7H) 1.14-1.40 (m, 7H) 0.94-1.07 (m, 7H) 0.83 (t, J=11.80 Hz, 1H); MS: MS m/z 854.4 (M$^+$+1).

Preparation of Compound 4151

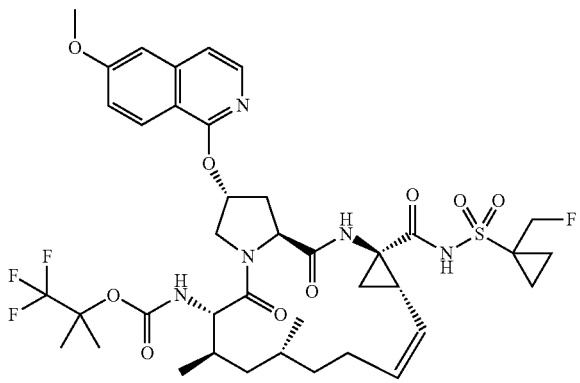

Compound 4151

Compound 4151 was prepared using the intermediates described herein and by following the general procedure described for the synthesis of Compound 3.

Compound 4151: 1,1,1-trifluoro-2-methylpropan-2-yl (2R,6S,7R,9R,13aS,14aR,16aS,Z)-14a-(1-(fluoromethyl)cyclopropylsulfonylcarbamoyl)-2-(6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.10 (d, J=9.03 Hz, 1H) 7.93 (d, J=6.02 Hz, 1H) 7.26-7.35 (m, 2H) 7.22 (d, J=2.26 Hz, 1H) 7.11 (dd, J=9.03, 2.51 Hz, 1H) 5.88 (t, J=3.26 Hz, 1H) 5.62 (d, J=5.52 Hz, 1H) 5.00 (t, J=10.04 Hz, 1H) 4.72-4.83 (m, 2H) 4.61-4.68 (m, 2H) 4.51 (d, J=11.04 Hz, 1H) 4.03 (dd, J=11.54, 3.51 Hz, 1H) 3.95 (s, 3H) 3.84 (dd, J=10.67, 8.16 Hz, 1H) 2.66-2.78 (m, 2H) 2.35-2.51 (m, 2H) 1.76-2.02 (m, 3H) 1.63-1.75 (m, 3H) 1.58 (dd, J=9.54, 5.52 Hz, 1H) 1.43-1.53 (m, 2H) 1.38 (s, 3H) 1.15-1.34 (m, 4H) 0.95-1.08 (m, 9H) 0.81-0.88 (m, 1H); MS: MS m/z 839.4 (M$^+$−1).

Preparation of Compound 4152

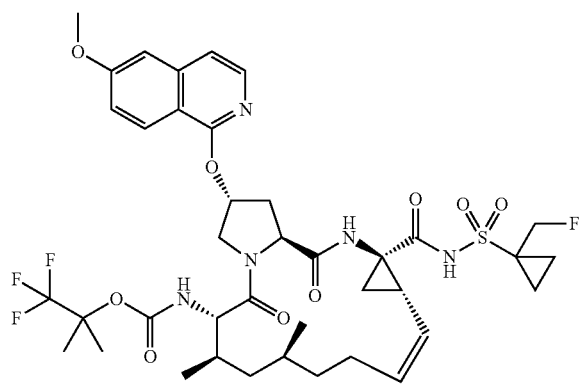

Compound 4152

Compound 4152 was prepared using the intermediates described herein and by following the general procedure described for the synthesis of Compound 3.

Compound 4152: 1,1,1-trifluoro-2-methylpropan-2-yl (2R,6S,7R,9S,13aS,14aR,16aS,Z)-14a-(1-(fluoromethyl)cyclopropylsulfonylcarbamoyl)-2-(6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.13 (d, J=9.03 Hz, 1H) 7.93 (d, J=5.77 Hz, 1H) 7.20-7.30 (m, 3H) 7.12 (dd, J=9.29, 2.51 Hz, 1H) 5.89 (br. s., 1H) 5.69-5.77 (m, 1H) 5.04 (t, J=9.54 Hz, 1H) 4.92-4.98 (m, 1H) 4.76-4.85 (m, 1H) 4.60-4.75 (m, 2H) 4.47-4.59 (m, 2H) 4.03-4.17 (m, 2H) 3.95 (s, 3H) 2.57-2.76 (m, 2H) 2.42-2.52 (m, 2H) 1.90-2.07 (m, 2H) 1.54-1.74 (m, 4H) 1.38-1.51 (m, 5H) 1.15-1.37 (m, 7H) 1.11 (d, J=6.78 Hz, 4H) 0.88-0.97 (m, 1H); MS: MS m/z 839.4 (M$^+$−1).

Preparation of Compound 4153

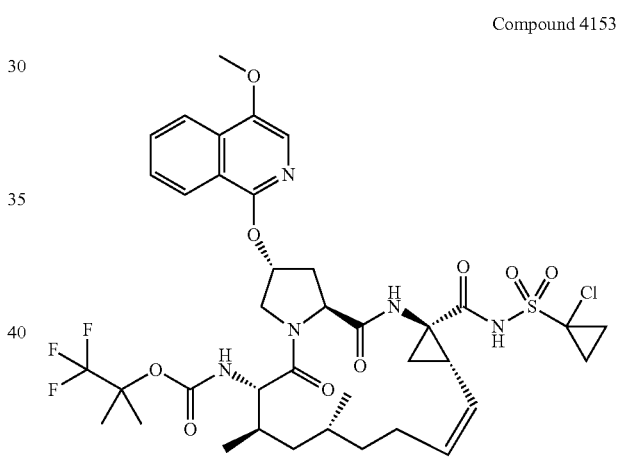

Compound 4153

Compound 44153 was prepared using the intermediates described herein and by following the general procedure described for the synthesis of Compound 3.

Compound 4153: 1,1,1-trifluoro-2-methylpropan-2-yl (2R,6S,7R,9R,13aS,14aR,16aS,Z)-14a-(1-chlorocyclopropylsulfonylcarbamoyl)-2-(4-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.15 (dd, J=17.57, 8.28 Hz, 2H) 7.74 (td, J=7.65, 1.25 Hz, 1H) 7.55-7.60 (m, 2H) 5.84 (br. s., 1H) 5.62 (d, J=5.77 Hz, 1H) 4.94-5.08 (m, 1H) 4.73-4.81 (m, 1H) 4.67 (dd, J=10.29, 7.03 Hz, 1H) 3.99-4.07 (m, 4H) 3.80-3.88 (m, 1H) 3.29 (d, J=1.76 Hz, 1H) 2.75 (dd, J=13.93, 6.90 Hz, 2H) 2.45 (ddd, J=13.87, 9.98, 4.27 Hz, 2H) 1.85-2.08 (m, 4H) 1.72-1.85 (m, 3H) 1.60 (dd, J=9.54, 5.52 Hz, 1H) 1.41-1.54 (m, 3H) 1.22-1.40 (m, 5H) 1.06-1.20 (m, 1H) 0.94-1.04 (m, 7H) 0.79-0.93 (m, 1H); MS: MS m/z 842.7 (M$^+$+1).

Preparation of Compound 4154

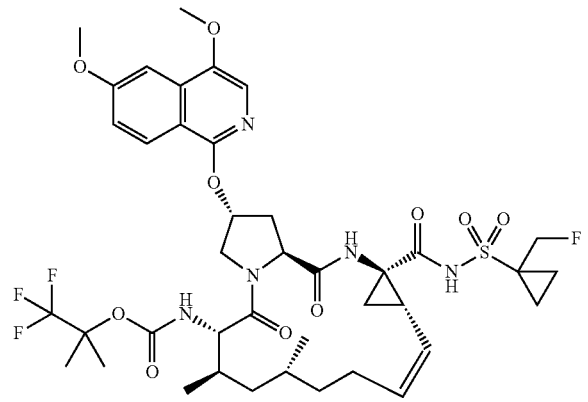

Compound 4154

Compound 4154 was prepared using the intermediates described herein and by following the general procedure described for the synthesis of Compound 3.

Compound 4154: 1,1,1-trifluoro-2-methylpropan-2-yl (2R,6S,7R,9R,13aS,14aR,16aS,Z)-2-(4,6-dimethoxyisoquinolin-1-yloxy)-14a-(1-(fluoromethyl)cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.07 (d, J=9.29 Hz, 1H) 7.53 (s, 1H) 7.44 (d, J=2.51 Hz, 1H) 7.14 (dd, J=9.03, 2.51 Hz, 1H) 5.81 (br. s., 1H) 5.57-5.68 (m, 1H) 4.95-5.05 (m, 2H) 4.77-4.84 (m, 2H) 4.71 (d, J=11.29 Hz, 1H) 4.59-4.66 (m, 2H) 3.98-4.08 (m, 4H) 3.95 (s, 3H) 3.84 (d, J=10.79 Hz, 1H) 3.28 (dt, J=3.33, 1.73 Hz, 1H) 2.64-2.77 (m, 2H) 2.43 (ddd, J=13.87, 10.23, 4.27 Hz, 2H) 1.76-2.03 (m, 2H) 1.62-1.76 (m, 2H) 1.58 (dd, J=9.54, 5.52 Hz, 1H) 1.50 (d, J=8.78 Hz, 1H) 1.36-1.43 (m, 3H) 1.09-1.35 (m, 5H) 0.94-1.06 (m, 7H) 0.84 (t, J=11.54 Hz, 1H); MS: MS m/z 868.7 (M$^+$−1).

Preparation of Compound 4155

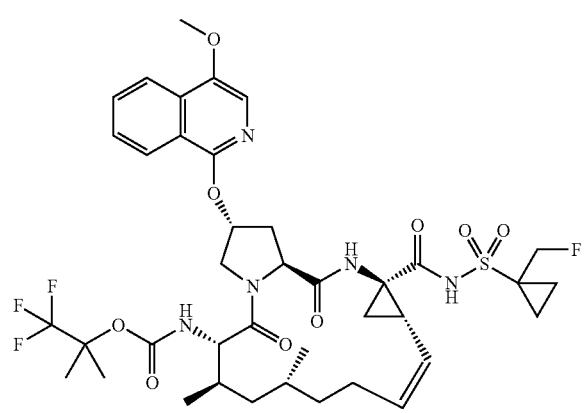

Compound 4155

Compound 4155 was prepared using the intermediates described herein and by following the general procedure described for the synthesis of Compound 3.

Compound 4155: 1,1,1-trifluoro-2-methylpropan-2-yl (2R,6S,7R,9R,13aS,14aR,16aS,Z)-14a-(1-(fluoromethyl)cyclopropylsulfonylcarbamoyl)-2-(4-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 7.74 (t, J=7.65 Hz, 1H) 7.54-7.60 (m, 2H) 7.28 (d, J=8.03 Hz, 1H) 5.84 (br. s., 1H) 5.63 (d, J=6.02 Hz, 1H) 5.00 (t, J=10.04 Hz, 2H) 4.73-4.82 (m, 2H) 4.62-4.68 (m, 2H) 4.01-4.06 (m, 4H) 3.81-3.87 (m, 1H) 3.27-3.30 (m, 1H) 2.68-2.78 (m, 3H) 2.37-2.49 (m, 2H) 1.97 (br. s., 1H) 1.78-1.84 (m, 1H) 1.69-1.75 (m, 2H) 1.58 (dd, J=9.66, 5.65 Hz, 2H) 1.43-1.54 (m, 2H) 1.36 (s, 4H) 1.16-1.33 (m, 3H) 1.03 (d, J=7.03 Hz, 1H) 0.95-1.01 (m, 7H) 0.80-0.88 (m, 1H); MS: MS m/z 838.6 (M$^+$−1).

Preparation of Compound 4156

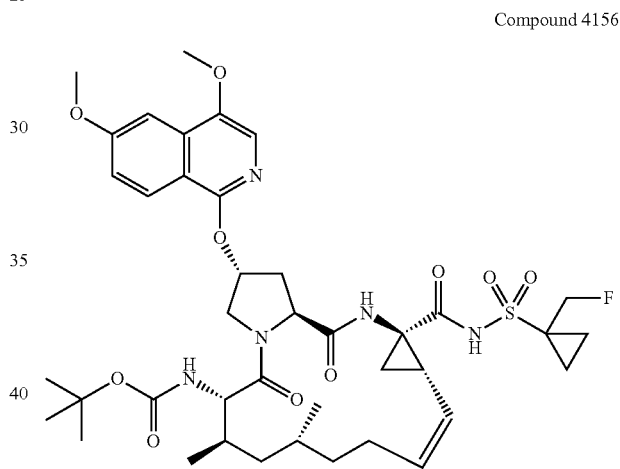

Compound 4156

Compound 4156 was prepared using the intermediates described herein and by following the general procedure described for the synthesis of Compound 1.

Compound 4156: tert-butyl (2R,6S,7R,9R,13aS,14aR,16aS,Z)-2-(4,6-dimethoxyisoquinolin-1-yloxy)-14a-(1-(fluoromethyl)cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.07 (d, J=9.03 Hz, 1H) 7.51 (s, 1H) 7.42 (d, J=2.51 Hz, 1H) 7.12 (dd, J=9.29, 2.51 Hz, 1H) 5.81 (br. s., 1H) 5.61 (dt, J=10.35, 5.24 Hz, 1H) 4.96-5.05 (m, 1H) 4.76-4.84 (m, 1H) 4.63-4.72 (m, 1H) 4.55-4.63 (m, 1H) 4.51 (d, J=11.29 Hz, 1H) 3.99-4.06 (m, 4H) 3.85-3.96 (m, 4H) 3.36-3.40 (m, 1H) 3.28 (d, J=1.51 Hz, 1H) 2.67-2.76 (m, 2H) 2.36-2.48 (m, 2H) 1.97 (br. s., 1H) 1.76-1.90 (m, 2H) 1.62-1.75 (m, 3H) 1.56 (dd, J=9.41, 5.65 Hz, 1H) 1.42-1.53 (m, 2H) 1.20-1.35 (m, 4H) 1.07-1.19 (m, 9H) 1.01 (dd, J=14.18, 6.65 Hz, 3H) 0.84 (t, J=11.54 Hz, 1H); MS: MS m/z 816.4 (M$^+$+1).

Preparation of Compound 4157

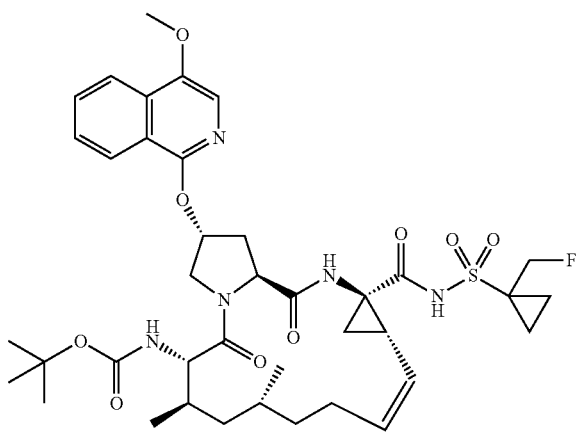

Compound 4157

Compound 4157 was prepared using the intermediates described herein and by following the general procedure described for the synthesis of Compound 1.

Compound 4157: tert-butyl (2R,6S,7R,9R,13aS,14aR,16aS,Z)-14a-(1-(fluoromethyl)cyclopropylsulfonylcarbamoyl)-2-(4-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.05-8.17 (m, 2H) 7.70 (t, J=7.53 Hz, 1H) 7.50-7.56 (m, 2H) 6.59 (d, J=8.28 Hz, 1H) 5.82 (br. s., 1H) 5.59 (td, J=10.10, 5.65 Hz, 1H) 4.91-5.01 (m, 1H) 4.86-4.91 (m, 1H) 4.73-4.79 (m, 1H) 4.69 (d, J=11.29 Hz, 1H) 4.54-4.63 (m, 2H) 4.49 (d, J=11.29 Hz, 1H) 3.97-4.05 (m, 4H) 3.83-3.90 (m, 1H) 3.25 (br. s., 1H) 2.64-2.74 (m, 2H) 2.35-2.45 (m, 2H) 1.89-2.01 (m, 1H) 1.74-1.87 (m, 2H) 1.60-1.72 (m, 2H) 1.40-1.57 (m, 3H) 1.15-1.30 (m, 2H) 1.11 (s, 9H) 0.98 (dd, J=14.93, 6.65 Hz, 4H) 0.77-0.85 (m, 1H); MS: MS m/z 786.7 (M$^+$+1).

Preparation of Compound 4158

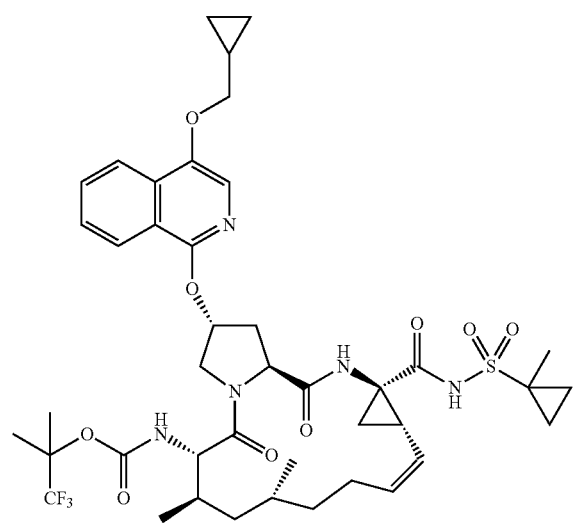

Compound 4158

Compound 4158 was prepared using the intermediates described herein and by following the general procedure described for the synthesis of Compound 3.

Compound 4158: 1,1,1-trifluoro-2-methylpropan-2-yl (2R,6S,7R,9R,13aS,14aR,16aS,Z)-2-(4-(cyclopropylmethoxy)isoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.17 (dd, J=8.41, 4.39 Hz, 2H) 7.72-7.79 (m, 1H) 7.54-7.60 (m, 2H) 7.29 (d, J=8.28 Hz, 1H) 5.84 (br. s., 1H) 5.62 (dt, J=10.42, 5.08 Hz, 1H) 5.01 (t, J=9.79 Hz, 1H) 4.74-4.82 (m, 2H) 4.67 (dd, J=10.16, 7.15 Hz, 1H) 3.99-4.06 (m, 3H) 3.80-3.87 (m, 1H) 3.29 (d, J=1.76 Hz, 2H) 2.70-2.79 (m, 2H) 2.44 (ddd, J=13.80, 10.04, 4.27 Hz, 2H) 1.96 (d, J=13.55 Hz, 1H) 1.81-1.91 (m, 1H) 1.77 (dd, J=8.16, 5.65 Hz, 2H) 1.66 (dd, J=9.54, 4.52 Hz, 1H) 1.57 (dd, J=9.54, 5.52 Hz, 1H) 1.38-1.54 (m, 3H) 1.17-1.38 (m, 5H) 0.94-1.05 (m, 9H) 0.86-0.93 (m, 2H) 0.79-0.85 (m, 1H) 0.67-0.73 (m, 2H) 0.43-0.49 (m, 2H); MS: MS m/z 861.0 (M$^+$−1).

Preparation of Compound 4159

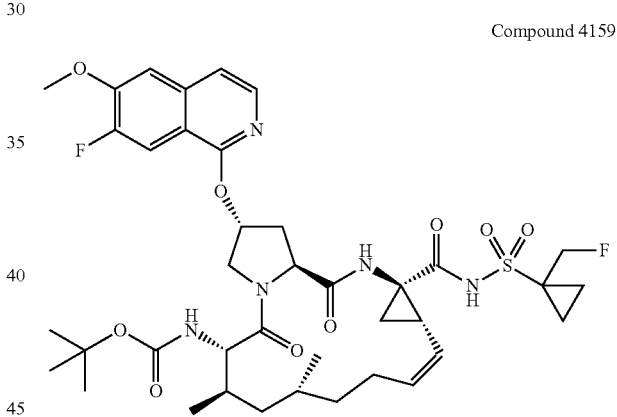

Compound 4159

Compound 4159 was prepared using the intermediates described herein and by following the general procedure described for the synthesis of Compound 1.

Compound 4159: tert-butyl (2R,6S,7R,9R,13aS,14aR,16aS,Z)-2-(7-fluoro-6-methoxyisoquinolin-1-yloxy)-14a-(1-(fluoromethyl)cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 7.91-7.98 (m, 1H) 7.78 (d, J=11.29 Hz, 1H) 7.28-7.42 (m, 2H) 6.67 (d, J=8.78 Hz, 1H) 5.90 (br. s., 1H) 5.63 (br. s., 1H) 4.68-4.83 (m, 2H) 4.48-4.66 (m, 2H) 3.98-4.10 (m, 4H) 3.81-3.97 (m, 1H) 2.72 (d, J=7.53 Hz, 2H) 2.38-2.50 (m, 2H) 1.99 (d, J=16.31 Hz, 1H) 1.85 (br. s., 2H) 1.65-1.76 (m, 3H) 1.58 (dd, J=9.66, 5.65 Hz, 1H) 1.50 (d, J=7.03 Hz, 2H) 1.31 (s, 3H) 1.17 (s, 9H) 1.02 (dd, J=11.54, 6.53 Hz, 7H) 0.79-0.89 (m, 1H); MS: MS m/z 802.4 (M$^+$−1).

Preparation of Compound 4160

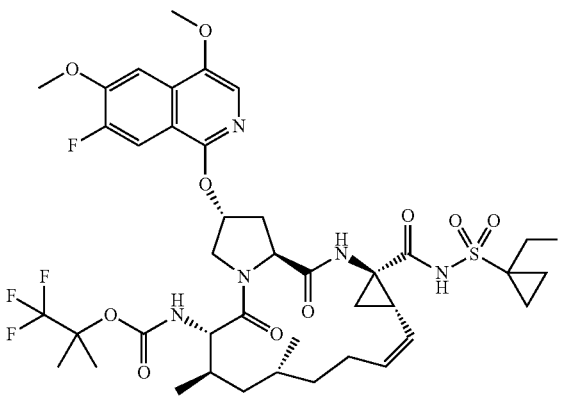

Compound 4160

Compound 4160 was prepared using the intermediates described herein and by following the general procedure described for the synthesis of Compound 3.

Compound 4160: 1,1,1-trifluoro-2-methylpropan-2-yl (2R,6S,7R,9R,13aS,14aR,16aS,Z)-2-(7-fluoro-4,6-dimethoxyisoquinolin-1-yloxy)-14a-(1-(fluoromethyl)cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.75 (d, J=11.54 Hz, 1H) 7.53-7.60 (m, 2H) 7.30 (d, J=7.78 Hz, 1H) 5.82 (br. s., 1H) 5.62 (dt, J=10.16, 4.96 Hz, 1H) 5.00 (t, J=10.16 Hz, 1H) 4.89-4.94 (m, 2H) 4.76-4.82 (m, 2H) 4.60-4.71 (m, 3H) 3.97-4.05 (m, 7H) 3.83 (dd, J=10.79, 8.03 Hz, 1H) 3.28 (dt, J=3.26, 1.63 Hz, 2H) 2.67-2.75 (m, 2H) 2.36-2.48 (m, 2H) 1.79-2.02 (m, 2H) 1.64-1.75 (m, 2H) 1.58 (dd, J=9.29, 5.52 Hz, 1H) 1.50 (d, J=6.27 Hz, 2H) 1.41 (s, 2H) 1.18-1.33 (m, 3H) 1.14 (s, 2H) 1.02 (dd, J=11.29, 6.78 Hz, 5H) 0.84 (t, J=12.30 Hz, 1H); MS: MS m/z 888.2 (M$^+$+1).

Preparation of Compound 4161

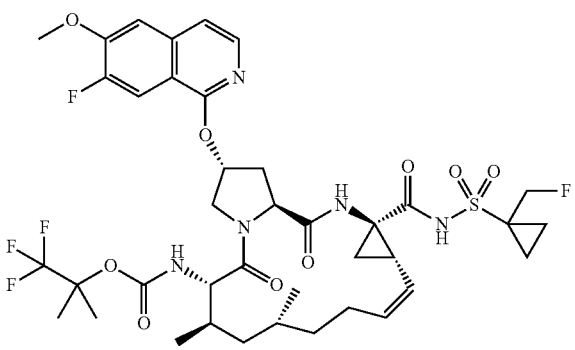

Compound 4161

Compound 4161 was prepared using the intermediates described herein and by following the general procedure described for the synthesis of Compound 3.

Compound 161: 1,1,1-trifluoro-2-methylpropan-2-yl (2R,6S,7R,9R,13aS,14aR,16aS,Z)-2-(7-fluoro-6-methoxyisoquinolin-1-yloxy)-14a-(1-(fluoromethyl)cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.95 (d, J=5.77 Hz, 1H) 7.79 (d, J=11.29 Hz, 1H) 7.40 (d, J=8.28 Hz, 1H) 7.31 (d, J=6.02 Hz, 2H) 5.89 (s, 1H) 5.63 (d, J=5.27 Hz, 1H) 4.96-5.06 (m, 1H) 4.61-4.76 (m, 3H) 4.51 (d, J=11.54 Hz, 1H) 4.00-4.07 (m, 4H) 3.78-3.87 (m, 1H) 3.25-3.30 (m, 2H) 2.64-2.78 (m, 3H) 2.46 (d, J=10.54 Hz, 2H) 1.65-1.77 (m, 3H) 1.58 (dd, J=10.04, 5.52 Hz, 1H) 1.49 (s, 2H) 1.40 (s, 3H) 1.17-1.35 (m, 4H) 1.14 (s, 3H) 1.02 (dd, J=10.04, 6.78 Hz, 5H) 0.82-0.92 (m, 1H); MS: MS m/z 858.2 (M$^+$+1).

Preparation of Compound 4162

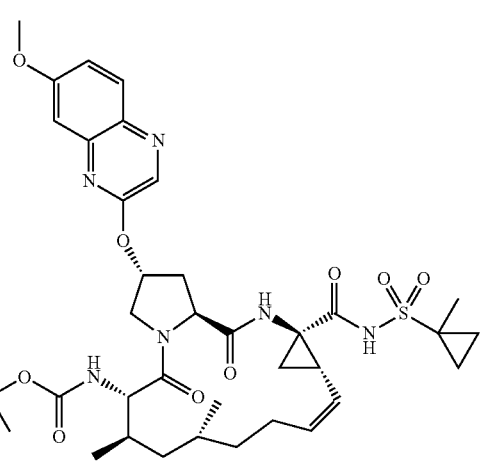

Compound 4162

Compound 4162 was prepared using the intermediates described herein and by following the general procedure described for the synthesis of Compound 3.

Compound 4162: 1,1,1-trifluoro-2-methylpropan-2-yl (2R,6S,7R,9R,13aS,14aR,16aS,Z)-2-(7-methoxyquinoxalin-2-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.27 (s, 1H) 7.87 (d, J=9.29 Hz, 1H) 7.26-7.40 (m, 3H) 5.90 (br. s., 1H) 5.63 (d, J=6.02 Hz, 1H) 4.98-5.07 (m, 1H) 4.76 (d, J=12.05 Hz, 1H) 4.63 (dd, J=9.54, 7.28 Hz, 1H) 4.08 (dd, J=11.54, 3.51 Hz, 1H) 3.95-4.02 (m, 3H) 3.81 (dd, J=10.54, 8.28 Hz, 1H) 3.28 (dt, J=3.33, 1.73 Hz, 1H) 2.65-2.76 (m, 3H) 2.39-2.53 (m, 2H) 1.85-2.04 (m, 2H) 1.78 (dd, J=8.16, 5.65 Hz, 2H) 1.64-1.71 (m, 1H) 1.59 (dd, J=9.41, 5.65 Hz, 1H) 1.38-1.55 (m, 3H) 1.23-1.34 (m, 9H) 0.99 (dd, J=19.32, 6.53 Hz, 5H) 0.79-0.93 (m, 3H); MS: MS m/823.4 (M$^+$+1).

Preparation of Compound 4163

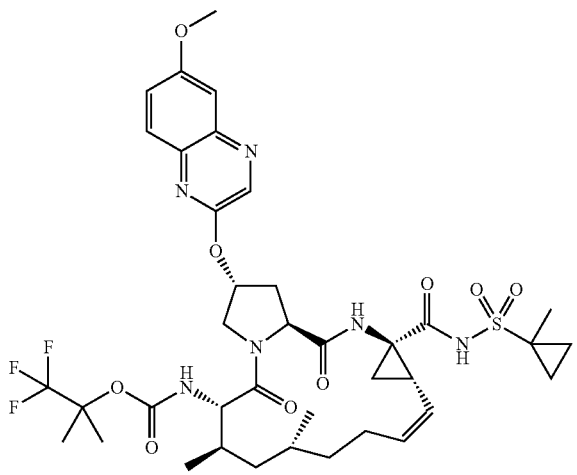

Compound 4163

Compound 4163 was prepared using the intermediates described herein and by following the general procedure described for the synthesis of Compound 3.

Compound 4163: 1,1,1-trifluoro-2-methylpropan-2-yl (2R,6S,7R,9R,13aS,14aR,16aS,Z)-2-(6-methoxyquinoxalin-2-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.41 (s, 1H) 7.83 (d, J=9.29 Hz, 1H) 7.33-7.46 (m, 2H) 5.87 (br. s., 1H) 5.63 (td, J=10.35, 5.90 Hz, 1H) 4.98-5.06 (m, 1H) 4.74 (d, J=11.54 Hz, 1H) 4.63 (dd, J=9.91, 7.15 Hz, 1H) 4.06 (dd, J=11.92, 3.39 Hz, 1H) 3.93-3.98 (m, 3H) 3.80 (d, J=11.04 Hz, 1H) 3.27-3.30 (m, 1H) 2.67-2.76 (m, 2H) 2.39-2.52 (m, 2H) 1.84-2.05 (m, 2H) 1.78 (dd, J=8.41, 5.65 Hz, 2H) 1.64-1.72 (m, 1H) 1.59 (dd, J=9.54, 5.52 Hz, 1H) 1.40-1.55 (m, 6H) 1.22-1.33 (m, 6H) 0.94-1.05 (m, 6H) 0.79-0.93 (m, 3H); MS: MS m/z 823.4 (M$^+$+1).

Preparation of Compound 4164

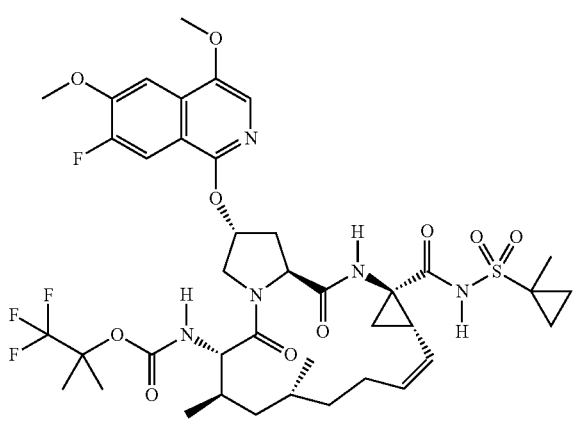

Compound 4164

Compound 4164 was prepared using the intermediates described herein and by following the general procedure described for the synthesis of Compound 3.

Compound 4164: 1,1,1-trifluoro-2-methylpropan-2-yl (2R,6S,7R,9R,13aS,14aR,16aS,Z)-2-(7-fluoro-4,6-dimethoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.74 (d, J=11.54 Hz, 1H) 7.52-7.60 (m, 2H) 5.82 (br. s., 1H) 5.62 (dt, J=10.29, 5.14 Hz, 1H) 5.01 (t, J=9.91 Hz, 1H) 4.59-4.72 (m, 2H) 3.96-4.06 (m, 7H) 3.82 (d, J=10.79 Hz, 1H) 2.69-2.78 (m, 2H) 2.36-2.50 (m, 2H) 1.73-2.03 (m, 5H) 1.62-1.69 (m, 1H) 1.57 (dd, J=9.54, 5.52 Hz, 2H) 1.46-1.53 (m, 3H) 1.36-1.45 (m, 5H) 1.31 (s, 2H) 1.17-1.28 (m, 2H) 1.13 (s, 2H) 1.01 (t, J=6.90 Hz, 4H) 0.80-0.94 (m, 3H); MS: MS m/z 869.5 (M$^+$+1).

Preparation of Compound 4165

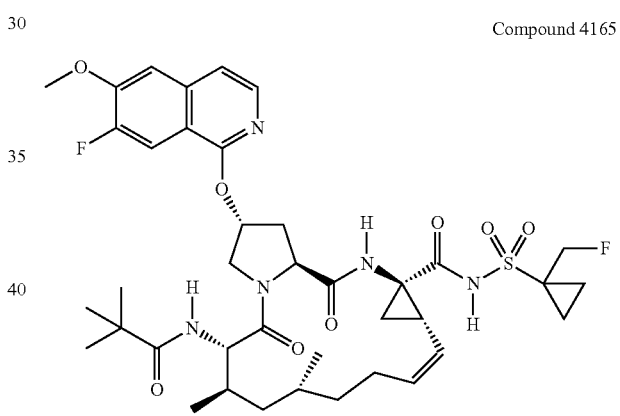

Compound 4165

Compound 4165 was prepared using the intermediates described herein and by following the general procedure described for the synthesis of Compound 4015.

Compound 4165: (2R,6S,7R,9R,13aS,14aR,16aS,Z)-2-(7-fluoro-6-methoxyisoquinolin-1-yloxy)-N-(1-(fluoromethyl)cyclopropylsulfonyl)-7,9-dimethyl-5,16-dioxo-6-pivalamido-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (400 MHz, CD$_3$OD): δ ppm 8.99 (s, 1H) 7.94 (d, J=6.02 Hz, 1H) 7.78 (d, J=11.54 Hz, 1H) 7.40 (d, J=8.28 Hz, 1H) 7.32 (d, J=5.77 Hz, 1H) 5.91 (br. s., 1H) 5.58-5.68 (m, 1H) 4.98-5.06 (m, 1H) 4.76-4.82 (m, 1H) 4.48-4.69 (m, 3H) 4.21-4.29 (m, 1H) 4.01-4.10 (m, 4H) 2.67-2.78 (m, 2H) 2.44 (ddd, J=13.93, 10.04, 4.14 Hz, 2H) 1.95-2.10 (m, 2H) 1.83 (dd, J=13.93, 5.90 Hz, 1H) 1.62-1.75 (m, 3H) 1.46-1.60 (m, 3H) 1.14-1.33 (m, 4H) 1.00-1.07 (m, 10H) 0.97 (d, J=6.27 Hz, 3H) 0.83-0.93 (m, 2H); MS: MS m/z 789.3 (M$^+$+1).

Preparation of Compound 4166

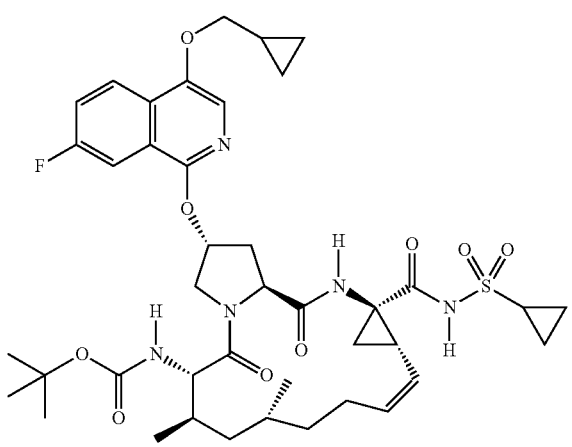

Compound 4166

Compound 4166 was prepared using the intermediates described herein and by following the general procedure described for the synthesis of Compound 1.

Compound 4166: tert-butyl (2R,6S,7R,9R,13aS,14aR,16aS,Z)-2-(4-(cyclopropylmethoxy)-7-fluoroisoquinolin-1-yloxy)-14a-(cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.22 (dd, J=9.03, 5.27 Hz, 1H) 7.74 (dd, J=9.54, 2.51 Hz, 1H) 7.53 (s, 2H) 5.83 (br. s., 1H) 5.62 (d, J=6.02 Hz, 1H) 5.06 (br. s., 1H) 4.71 (d, J=11.29 Hz, 1H) 4.55-4.66 (m, 2H) 3.97-4.05 (m, 3H) 3.81-3.88 (m, 1H) 2.88-2.98 (m, 1H) 2.72 (dd, J=14.43, 6.40 Hz, 2H) 2.34-2.48 (m, 2H) 1.97 (d, J=13.05 Hz, 1H) 1.74-1.90 (m, 3H) 1.59 (dd, J=9.54, 5.52 Hz, 1H) 1.44-1.55 (m, 2H) 1.19-1.43 (m, 4H) 1.06-1.18 (m, 9H) 1.00 (dd, J=14.93, 6.65 Hz, 5H) 0.83 (t, J=11.42 Hz, 1H) 0.66-0.72 (m, 1H) 0.44 (q, J=4.43 Hz, 2H); MS: MS m/z 812.4 (M$^+$+1).

Preparation of Compound 4167

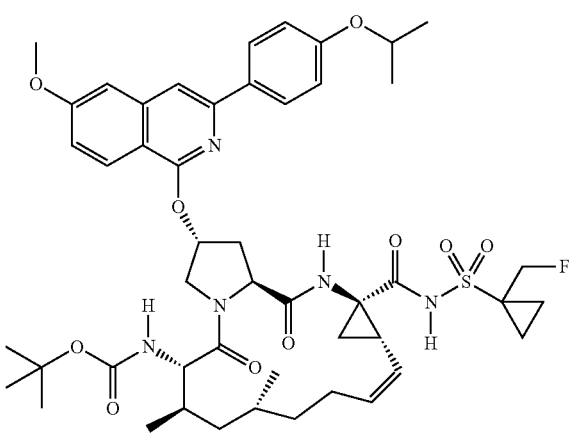

Compound 4167

Compound 4167 was prepared using the intermediates described herein and by following the general procedure described for the synthesis of Compound 1.

Compound 4167: tert-butyl (2R,6S,7R,9R,13aS,14aR,16aS,Z)-14a-(1-(fluoromethyl)cyclopropylsulfonylcarbamoyl)-2-((3-(4-isopropoxyphenyl)-6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.99 (s, 1H) 8.05-8.14 (m, 4H) 7.68 (s, 1H) 7.23 (d, J=2.01 Hz, 1H) 7.02 (d, J=8.78 Hz, 3H) 6.09 (br. s., 1H) 5.59-5.67 (m, 1H) 5.01 (t, J=10.04 Hz, 2H) 4.74-4.81 (m, 1H) 4.58-4.73 (m, 3H) 4.16 (dd, J=11.17, 3.64 Hz, 1H) 3.90-3.99 (m, 4H) 2.67-2.86 (m, 2H) 2.38-2.56 (m, 2H) 1.93-2.06 (m, 1H) 1.79-1.92 (m, 2H) 1.44-1.76 (m, 5H) 1.37 (d, J=6.02 Hz, 4H) 1.26-1.34 (m, 3H) 1.18-1.24 (m, 9H) 1.02 (dd, J=16.31, 6.78 Hz, 5H) 0.82-0.94 (m, 2H); MS: MS m/z 920.5 (M$^+$+1).

Preparation of Compound 4168

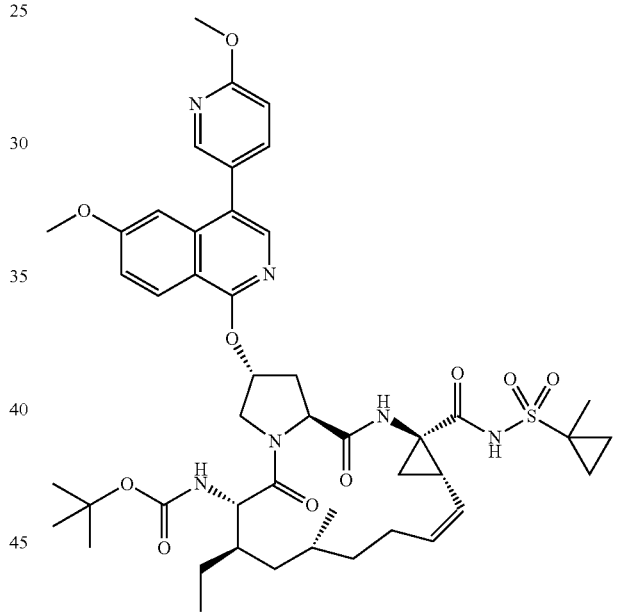

Compound 4168 was prepared using the intermediates described herein and by following the general procedure described for the synthesis of Compound 1.

Compound 4168: tert-butyl (2R,6S,7R,9R,13aS,14aR,16aS,Z)-7-ethyl-2-(6-methoxy-4-(6-methoxypyridin-3-yl)isoquinolin-1-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.20-8.24 (m, 2H) 7.88 (s, 1H) 7.83 (dd, J=8.41, 2.38 Hz, 1H) 7.17 (d, J=9.29 Hz, 1H) 6.97-7.04 (m, 2H) 5.93 (br. s., 1H) 5.61 (br. s., 1H) 4.66 (br. s., 1H) 4.00-4.14 (m, 5H) 3.81-3.85 (m, 3H) 2.74 (br. s., 2H) 2.38-2.55 (m, 2H) 1.97 (br. s., 3H) 1.78 (d, J=7.28 Hz, 1H) 1.52-1.65 (m, 9H) 1.29-1.36 (m, 4H) 1.13 (s, 10H) 1.01 (d, J=6.53 Hz, 3H) 0.82-0.93 (m, 5H). MS: MS m/z 890.07 (M$^+$+1).

Preparation of Compound 4169

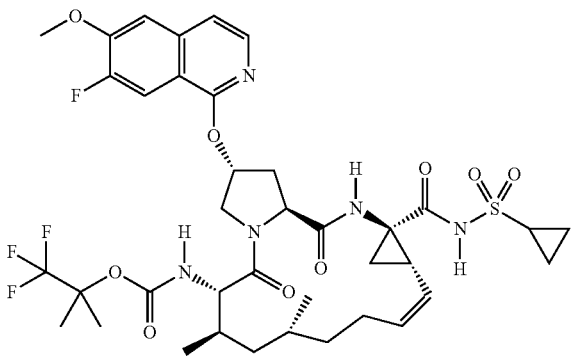

Compound 4169

Compound 4169 was prepared using the intermediates described herein and by following the general procedure described for the synthesis of Compound 3.

Compound 4169: 1,1,1-trifluoro-2-methylpropan-2-yl (2R,6S,7R,9R,13aS,14aR,16aS,Z)-14a-(cyclopropylsulfonylcarbamoyl)-2-(7-fluoro-6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.19 (dd, J=9.03, 5.52 Hz, 1H) 7.76 (dd, J=9.41, 2.64 Hz, 1H) 7.52-7.60 (m, 2H) 7.30 (d, J=7.78 Hz, 1H) 5.84 (br. s., 1H) 5.63 (td, J=10.10, 5.90 Hz, 1H) 5.01-5.10 (m, 1H) 4.74 (d, J=11.54 Hz, 1H) 4.56-4.69 (m, 1H) 3.96-4.07 (m, 4H) 3.79-3.87 (m, 1H) 2.90-2.99 (m, 1H) 2.68-2.79 (m, 2H) 2.43 (ddd, J=13.87, 10.10, 4.14 Hz, 2H) 1.75-2.04 (m, 4H) 1.60 (dd, J=9.41, 5.65 Hz, 1H) 1.43-1.56 (m, 2H) 1.19-1.42 (m, 7H) 1.08-1.18 (m, 2H) 0.97-1.07 (m, 9H) 0.84 (t, J=12.05 Hz, 1H); MS: MS m/z 826.4 (M$^+$+1).

Scheme:

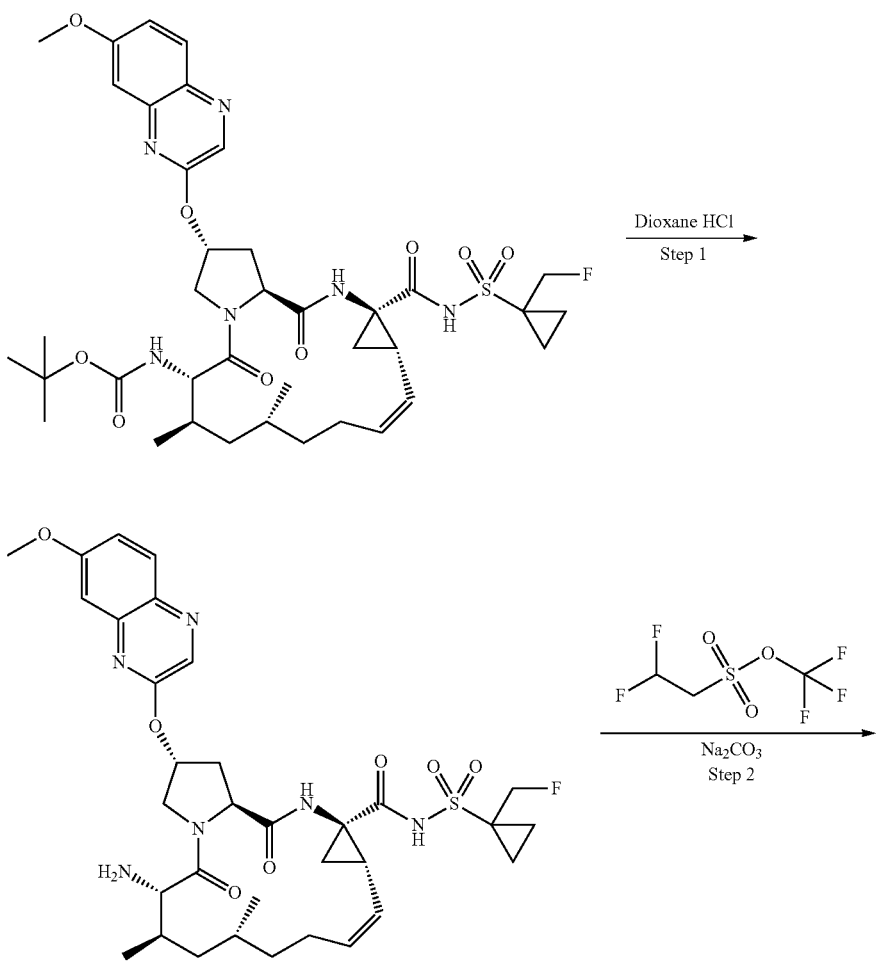

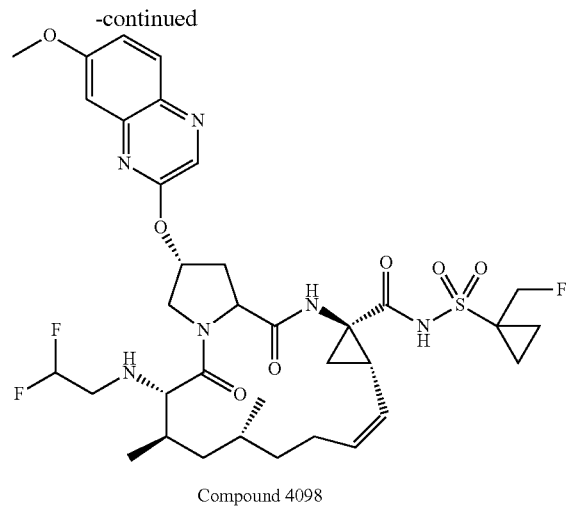

Compound 4098

Step 1: Preparation of (2R,6S,7R,9R,13aS,14aR,16aS,Z)-6-amino-N-(1-(fluoromethyl)cyclopropyl-sulfonyl)-2-(7-methoxyquinoxalin-2-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride A solution of tert-butyl ((2R,6S,7R,9R,13aS,14aR,16aS,Z)-14a-(((1-(fluoromethyl)cyclopropyl)sulfonyl)carbamoyl)-2-((7-methoxyquinoxalin-2-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (120 mg, 0.15 mmol) in 4M HCl in dioxane (10 ml 4 M solution) was stirred at room temperature for 2 h. The solvent was evaporated under reduced pressure to get crude compound (100 mg, 95%) as brown solid. The crude compound was washed with diethyl ether and taken to the next step without further purification. $^1$H NMR (400 MHz, CD$_3$OD): δ ppm 9.19 (s, 1H) 8.26-8.34 (m, 2H) 7.90 (d, J=8.78 Hz, 2H) 7.26-7.34 (m, 3H) 6.02 (br. s., 1H) 5.58-5.67 (m, 1H) 5.04 (t, J=9.54 Hz, 1H) 4.59-4.71 (m, 2H) 4.33-4.53 (m, 1H) 4.12-4.26 (m, 2H) 3.98 (s, 3H) 3.73-3.81 (m, 2H) 3.66-3.71 (m, 2H) 2.77-2.97 (m, 2H) 2.42-2.75 (m, 3H) 1.91-2.11 (m, 2H) 1.67-1.78 (m, 2H) 1.44-1.62 (m, 2H) 1.21-1.42 (m, 5H) 1.01-1.15 (m, 5H) 0.92 (br. s., 1H): MS: MS m/z 687.4 (M$^+$–36).

Step 2: Preparation of Compound 4170

To a solution of (2R,6S,7R,9R,13aS,14aR,16aS,Z)-6-amino-N-((1-(fluoromethyl)cyclopropyl)sulfonyl)-2-((7-methoxyquinoxalin-2-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide (100 mg, 0.14 mmol) in DMF (1 ml) was added trifluoromethyl 2,2-difluoroethanesulfonate (31.2 mg, 0.14 mmol) followed by sodium carbonate (23.15 mg, 0.21 mmol) at room temperature. The reaction mixture was stirred at room temperature for 30 min. The reaction mass was diluted with water and extracted with ethyl acetate and washed with brine solution. The combine organic layer was dried over anhydrous Na$_2$SO$_4$ and evaporated under reduced pressure to get crude compound. The crude compound was purified by prep-HPLC to get desired compound (15 mg, 13.5%) as white solid. $^1$H NMR (400 MHz, CD$_3$OD): δ ppm 9.14 (s, 1H) 8.28 (s, 1H) 7.86-7.93 (m, 1H) 7.25-7.34 (m, 2H) 5.92-6.07 (m, 1H) 5.64 (td, J=10.42, 5.52 Hz, 1H) 5.04 (t, J=10.04 Hz, 1H) 4.60-4.71 (m, 2H) 4.51 (d, J=11.29 Hz, 1H) 4.21-4.27 (m, 1H) 4.11-4.17 (m, 1H) 3.98 (s, 3H) 3.04-3.12 (m, 1H) 2.55-2.74 (m, 3H) 2.38-2.49 (m, 1H) 1.85-1.99 (m, 3H) 1.64-1.78 (m, 3H) 1.43-1.62 (m, 4H) 1.19-1.36 (m, 4H) 1.14 (d, J=6.53 Hz, 3H) 1.05 (d, J=6.78 Hz, 3H) 0.89-0.97 (m, 2H); MS: MS m/z 751.2 (M$^+$+1).

Preparation of Compound 4171

Compound 4170

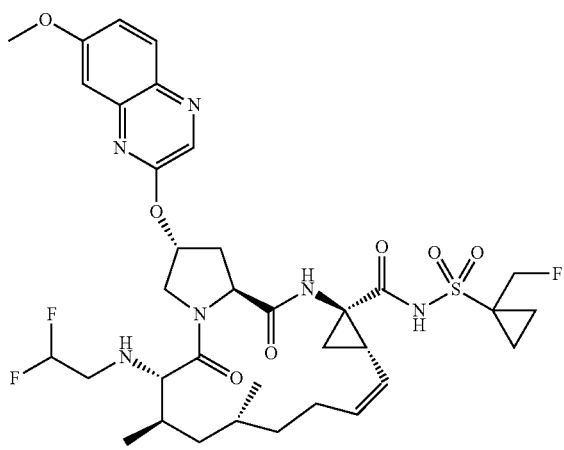

Compound 4171

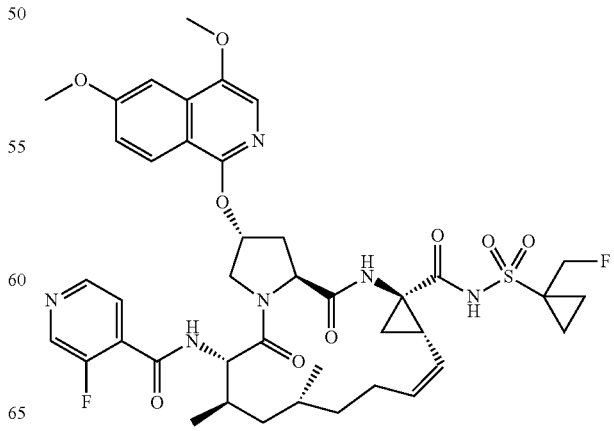

Compound 4171 was prepared using the intermediates described herein and by following the general procedure described for the synthesis of Compound 4029.

Compound 4171: (2R,6S,7R,9R,13aS,14aR,16aS,Z)-2-(4,6-dimethoxyisoquinolin-1-yloxy)-6-(3-fluoroisonicotinamido)-N-(1-(fluoromethyl)cyclopropylsulfonyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. $^1$H NMR (400 MHz, CD$_3$OD): δ ppm 9.05 (s, 1H) 8.50 (s, 1H) 8.34 (d, J=4.27 Hz, 1H) 8.08 (d, J=9.03 Hz, 1H) 7.51 (s, 1H) 7.37-7.40 (m, 1H) 7.15 (d, J=11.54 Hz, 1H) 7.05 (t, J=5.40 Hz, 1H) 5.87 (br. s., 1H) 5.60-5.69 (m, 1H) 4.99-5.05 (m, 1H) 4.74-4.79 (m, 1H) 4.63-4.69 (m, 2H) 4.39 (d, J=11.29 Hz, 1H) 4.08-4.13 (m, 1H) 4.03 (s, 3H) 3.95 (s, 3H) 2.71-2.81 (m, 2H) 2.43-2.53 (m, 2H) 1.99-2.13 (m, 2H) 1.81-1.89 (m, 1H) 1.66-1.77 (m, 3H) 1.50-1.61 (m, 3H) 1.19-1.33 (m, 4H) 1.05 (dd, J=6.65, 2.64 Hz, 8H) 0.92 (t, J=12.17 Hz, 1H). MS: MS m/z 840.2 (M$^+$+1).

Preparation of Compound 4172

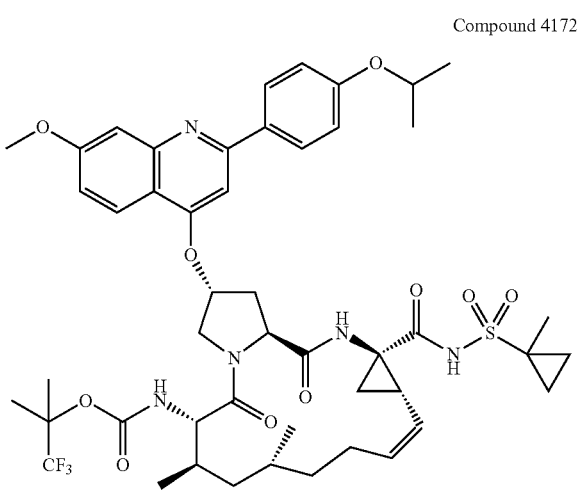 [SMILES: COc1ccc2c(O[C@@H]3C[C@H]4C(=O)N[C@]5(C(=O)NS(=O)(=O)C6(C)CC6)C[C@H]5/C=C\CC[C@@H](C)C[C@@H](C)[C@H](NC(=O)OC(C)(C)C(F)(F)F)C(=O)N4C3)cc(-c3ccc(OC(C)C)cc3)nc2c1]

Compound 4172

Compound 4172 was prepared using the intermediates described herein and by following the general procedure described for the synthesis of Compound 3.

Compound 4172: 1,1,1-trifluoro-2-methylpropan-2-yl (2R,6S,7R,9R,13aS,14aR,16aS,Z)-2-(2-(4-isopropoxyphenyl)-7-methoxyquinolin-4-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.95 (d, J=6.27 Hz, 2H) 7.79 (d, J=11.80 Hz, 2H) 7.40 (d, J=8.03 Hz, 2H) 7.30 (d, J=5.52 Hz, 2H) 5.89 (br. s., 2H) 4.03 (s, 6H) 3.79-3.86 (m, 1H) 2.70 (br. s., 3H) 2.43 (s, 3H) 2.00 (s, 3H) 1.85 (br. s., 4H) 1.71-1.80 (m, 2H) 1.60 (s, 2H) 1.48 (br. s., 4H) 1.40 (s, 3H) 1.28-1.34 (m, 6H) 1.13 (s, 3H) 1.01 (t, J=6.27 Hz, 6H) 0.92 (s, 1H).

MS: MS m/z 956 (M$^+$+1).

Preparation of Compound 4173

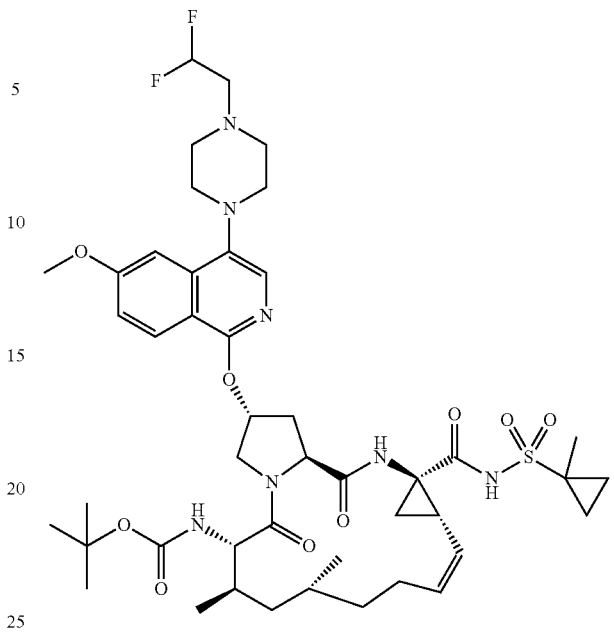

Compound 4173 was prepared using the intermediates described herein and by following the general procedure described for the synthesis of Compound 1.

Compound 4173: tert-butyl (2R,6S,7R,9R,13aS,14aR,16aS,Z)-2-(4-(4-(2,2-difluoroethyl)piperazin-1-yl)-6-methoxyisoquinolin-1-yloxy)-7,9-dimethyl-14a-(1-ethylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.12 (d, J=9.03 Hz, 1H) 7.69 (s, 1H) 7.41 (d, J=2.51 Hz, 1H) 7.12 (dd, J=9.16, 2.38 Hz, 1H) 5.84 (br. s., 1H) 5.61 (br. s., 1H) 4.71 (d, J=11.29 Hz, 1H) 4.57-4.64 (m, 1H) 4.04 (dd, J=11.42, 3.39 Hz, 1H) 3.95-3.98 (m, 4H) 3.88 (d, J=11.04 Hz, 1H) 3.13 (m, 2H) 2.91 (td, J=15.25, 4.39 Hz, 6H) 2.72 (dd, J=12.80, 6.78 Hz, 2H) 2.44 (d, J=9.79 Hz, 2H) 1.99 (s, 1H) 1.74-1.88 (m, 5H) 1.40-1.59 (m, 9H) 1.21-1.34 (m, 6H) 1.15 (s, 8H) 1.01 (dd, J=9.54, 6.78 Hz, 9H) 0.80-0.92 (m, 4H). MS: MS m/z 916.4 (M$^+$+1).

Preparation of Compound 4174

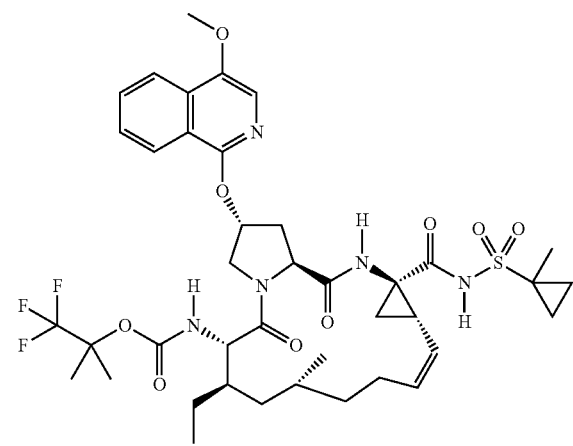

Compound 4174

Compound 4174 was prepared using the intermediates described herein and by following the general procedure described for the synthesis of Compound 3.

Compound 4174: 1,1,1-trifluoro-2-methylpropan-2-yl (2R,6S,7R,9R,13aS,14aR,16aS,Z)-7-ethyl-2-(4-methoxy-isoquinolin-1-yloxy)-9-methyl-14a-(1-methylcyclopropyl-sulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.14 (dd, J=12.30, 8.28 Hz, 2H) 7.74 (td, J=7.65, 1.25 Hz, 1H) 7.55-7.61 (m, 2H) 5.85 (br. s., 1H) 5.57-5.67 (m, 1H) 5.06 (br. s., 1H) 4.75-4.82 (m, 2H) 4.67 (dd, J=10.16, 7.15 Hz, 1H) 4.00-4.10 (m, 5H) 3.26-3.30 (m, 1H) 2.66-2.79 (m, 2H) 2.37-2.50 (m, 2H) 1.92-2.06 (m, 3H) 1.77 (dd, J=8.28, 5.52 Hz, 1H) 1.54-1.70 (m, 5H) 1.53 (s, 4H) 1.40-1.48 (m, 2H) 1.36 (s, 2H) 1.25-1.33 (m, 2H) 1.08-1.18 (m, 1H) 1.02 (d, J=6.78 Hz, 2H) 0.93 (s, 2H) 0.88 (br. s., 2H) 0.84 (t, J=7.53 Hz, 3H); MS: MS m/z 836.6 (M$^+$+1).

Preparation of Compound 4175

Compound 4175

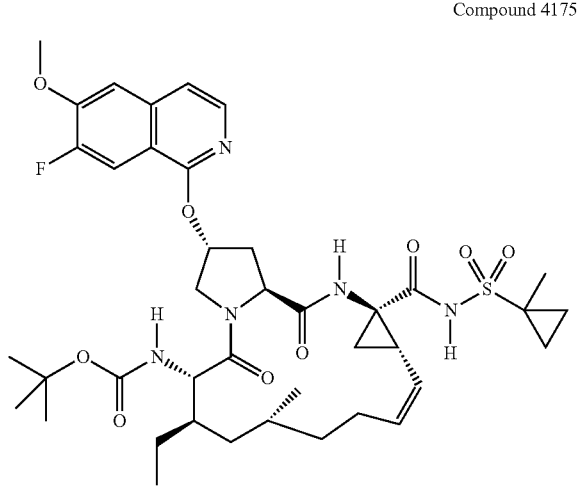 [SMILES: CC[C@@H]1C[C@H](C)CC/C=C\[C@@H]2C[C@@]2(C(=O)NS(=O)(=O)C2(C)CC2)NC(=O)[C@@H]2C[C@@H](Oc3nccc4cc(OC)c(F)cc34)CN2C(=O)[C@H]1NC(=O)OC(C)(C)C]

Compound 4175 was prepared using the intermediates described herein and by following the general procedure described for the synthesis of Compound 1.

Compound 4175: tert-butyl (2R,6S,7R,9R,13aS,14aR,16aS,Z)-7-ethyl-2-(7-fluoro-6-methoxyisoquinolin-1-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.95 (d, J=5.77 Hz, 1H) 7.77 (d, J=11.54 Hz, 1H) 7.26-7.42 (m, 2H) 6.62 (br. s., 1H) 5.91 (br. s., 1H) 5.62 (br. s., 1H) 5.01 (br. s., 1H) 4.75 (d, J=12.30 Hz, 1H) 4.63 (br. s., 1H) 3.97-4.14 (m, 5H) 3.28 (dt, J=3.33, 1.73 Hz, 4H) 2.65-2.80 (m, 2H) 2.45 (br. s., 2H) 1.98 (d, J=13.05 Hz, 2H) 1.76 (br. s., 1H) 1.48-1.69 (m, 6H) 1.43 (d, J=9.79 Hz, 2H) 1.23-1.37 (m, 1H) 1.07-1.21 (m, 9H) 1.02 (d, J=6.78 Hz, 3H) 0.80-0.96 (m, 4H); MS: MS m/z 800.7 (M$^+$+1).

Preparation of Compound 4176

Compound 4176

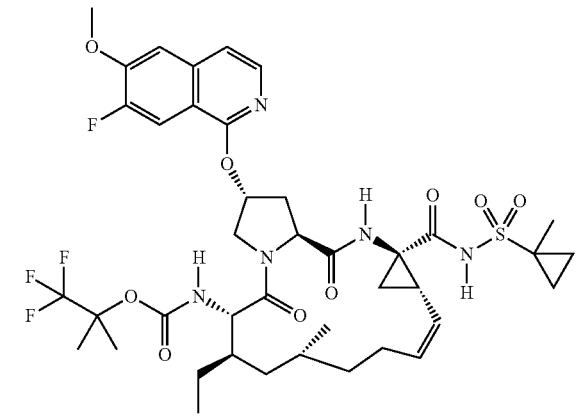

Compound 4176 was prepared using the intermediates described herein and by following the general procedure described for the synthesis of Compound 3.

Compound 4176: 1,1,1-trifluoro-2-methylpropan-2-yl (2R,6S,7R,9R,13aS,14aR,16aS,Z)-7-ethyl-2-(7-fluoro-6-methoxyisoquinolin-1-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.91-7.98 (m, 2H) 7.78 (d, J=11.54 Hz, 1H) 7.41 (d, J=8.28 Hz, 1H) 7.30-7.34 (m, 1H) 5.91 (br. s., 1H) 5.58-5.67 (m, 1H) 5.03 (t, J=10.04 Hz, 1H) 4.77-4.80 (m, 2H) 4.74 (d, J=11.54 Hz, 2H) 4.66 (dd, J=10.16, 7.15 Hz, 1H) 4.00-4.10 (m, 6H) 3.49-3.56 (m, 1H) 3.22-3.29 (m, 5H) 2.39-2.49 (m, 2H) 1.99 (br. s., 2H) 1.77 (dd, J=8.28, 5.77 Hz, 1H) 1.54-1.69 (m, 3H) 1.53 (s, 3H) 1.38-1.47 (m, 3H) 1.20-1.34 (m, 2H) 1.07-1.19 (m, 2H) 1.02 (d, J=6.78 Hz, 3H) 0.87-0.94 (m, 3H) 0.84 (t, J=7.53 Hz, 3H); MS: MS m/z 854.6 (M$^+$+1).

Preparation of Compound 4177

Compound 4177

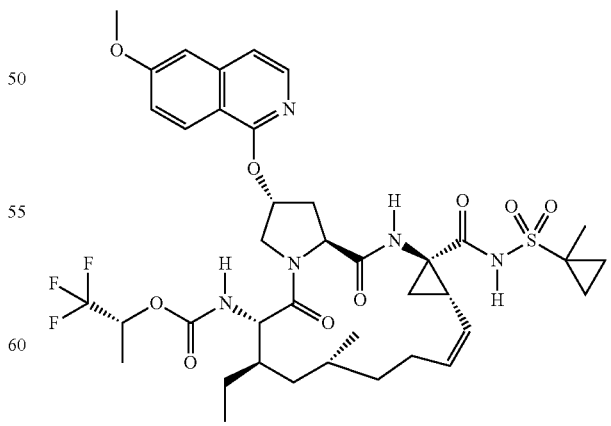

Compound 4177 was prepared using the intermediates described herein and by following the general procedure described for the synthesis of Compound 3.

741

Compound 4177: (R)-1,1,1-trifluoropropan-2-yl (2R,6S,7R,9R,13aS,14aR,16aS,Z)-7-ethyl-2-(6-methoxyisoquinolin-1-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.06 (d, J=9.03 Hz, 1H) 7.92 (d, J=5.77 Hz, 1H) 7.18-7.31 (m, 2H) 7.08 (dd, J=9.16, 2.38 Hz, 1H) 5.90 (br. s., 1H) 5.63 (d, J=6.02 Hz, 1H) 4.97-5.10 (m, 1H) 4.73-4.82 (m, 2H) 4.63 (dd, J=10.04, 7.28 Hz, 1H) 4.45-4.58 (m, 1H) 3.98-4.16 (m, 2H) 3.89-3.96 (m, 3H) 3.29 (d, J=1.76 Hz, 1H) 2.67-2.81 (m, 2H) 2.38-2.51 (m, 2H) 1.94-2.09 (m, 2H) 1.76 (dd, J=8.41, 5.65 Hz, 1H) 1.55-1.70 (m, 5H) 1.39-1.53 (m, 5H) 1.24-1.38 (m, 2H) 1.10-1.23 (m, 3H) 1.02 (d, J=6.78 Hz, 3H) 0.87-0.95 (m, 3H) 0.84 (t, J=7.53 Hz, 3H); MS: MS m/z 822.6 (M$^+$+1).

Preparation of Compound 4178

Compound 4178

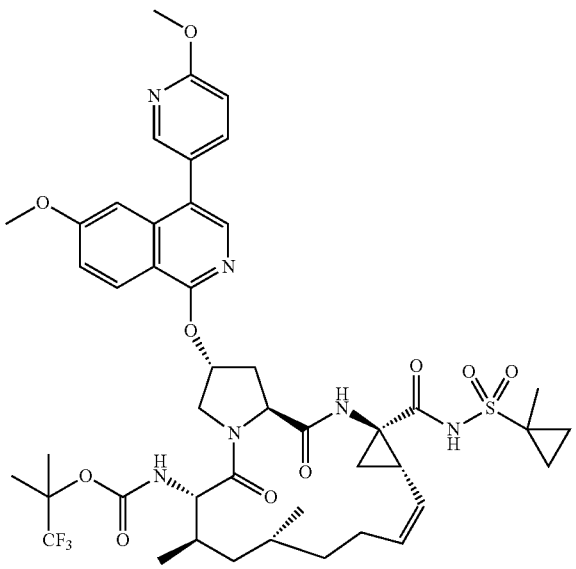

Compound 4178 was prepared using the intermediates described herein and by following the general procedure described for the synthesis of Compound 3.

Compound 4178: 1,1,1-trifluoro-2-methylpropan-2-yl (2R,6S,7R,9R,13aS,14aR,16aS,Z)-2-(6-methoxy-4-(6-methoxypyridin-3-yl)isoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.20-8.24 (m, 2H) 7.89 (s, 1H) 7.83 (dd, J=8.53, 2.51 Hz, 1H) 7.19 (dd, J=9.16, 2.38 Hz, 1H) 6.98-7.05 (m, 2H) 5.93 (br. s., 1H) 5.62 (br. s., 1H) 4.96-5.08 (m, 1H) 4.82 (d, J=12.05 Hz, 1H) 4.70 (dd, J=10.04, 7.03 Hz, 1H) 4.00-4.08 (m, 4H) 3.80-3.87 (m, 4H) 2.79 (dd, J=13.80, 7.28 Hz, 2H) 2.40-2.53 (m, 2H) 1.75-2.03 (m, 3H) 1.51-1.61 (m, 5H) 1.36-1.50 (m, 6H) 1.20-1.32 (m, 2H) 1.01 (t, J=7.91 Hz, 9H) 0.80-0.94 (m, 3H). MS: MS m/z 929.4 (M$^+$+1).

742

Preparation of Compound 4179

Compound 4179

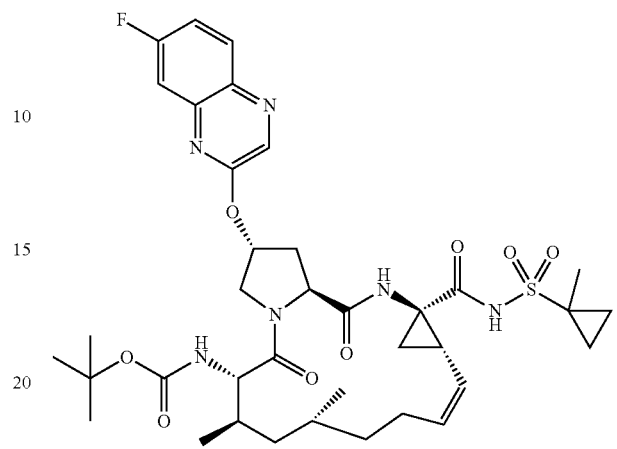

Compound 4179 was prepared using the intermediates described herein and by following the general procedure described for the synthesis of Compound 1.

Compound 4179: tert-butyl (2R,6S,7R,9R,13aS,14aR,16aS,Z)-2-(7-fluoroquinoxalin-2-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.41 (s, 1H) 8.02 (dd, J=9.16, 5.90 Hz, 1H) 7.58 (dd, J=9.66, 2.89 Hz, 1H) 7.46 (td, J=8.66, 2.76 Hz, 1H) 5.88 (br. s., 1H) 5.53 (br. s., 1H) 4.70 (d, J=11.54 Hz, 1H) 4.56 (t, J=8.41 Hz, 1H) 4.09 (dd, J=11.80, 3.51 Hz, 1H) 3.83 (d, J=10.79 Hz, 1H) 3.00 (q, J=7.28 Hz, 3H) 2.91 (d, J=7.03 Hz, 2H) 2.70 (dd, J=13.93, 7.40 Hz, 1H) 2.45-2.57 (m, 1H) 2.37 (br. s., 1H) 1.95-2.05 (m, 1H) 1.69-1.89 (m, 3H) 1.38-1.57 (m, 6H) 1.29 (t, J=7.28 Hz, 4H) 1.21 (t, J=7.28 Hz, 1H) 1.13 (s, 6H) 0.94-1.02 (m, 5H) 0.72-0.84 (m, 2H). MS: MS m/z 757.4 (M$^+$+1).

Preparation of Compound 4180

Compound 4180

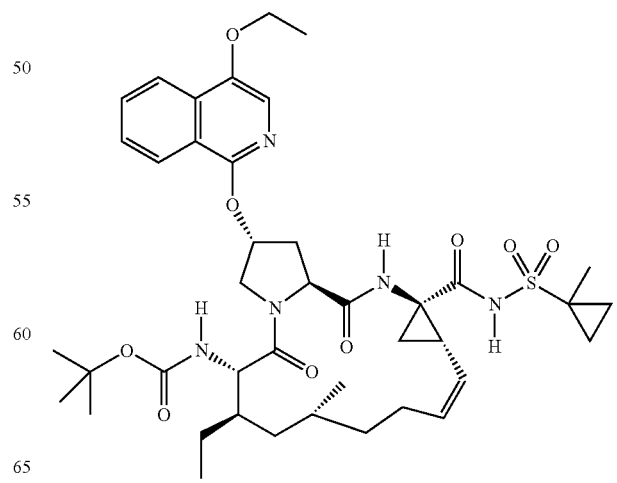

Compound 4180 was prepared using the intermediates described herein and by following the general procedure described for the synthesis of Compound 1.

Compound 4180: tert-butyl (2R,6S,7R,9R,13aS,14aR,16aS,Z)-2-(4-ethoxyisoquinolin-1-yloxy)-7-ethyl-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.10-8.19 (m, 2H) 7.73 (t, J=7.28 Hz, 1H) 7.51-7.60 (m, 2H) 6.62 (d, J=8.78 Hz, 1H) 5.85 (br. s., 1H) 5.63 (td, J=10.04, 5.77 Hz, 1H) 5.01 (t, J=9.79 Hz, 1H) 4.78 (d, J=11.80 Hz, 1H) 4.63 (dd, J=9.91, 7.15 Hz, 1H) 4.24 (q, J=7.03 Hz, 2H) 4.01-4.17 (m, 2H) 3.28 (br. s., 2H) 2.68-2.81 (m, 2H) 2.43 (ddd, J=13.87, 10.10, 4.14 Hz, 2H) 1.91-2.05 (m, 2H) 1.77 (dd, J=8.28, 5.77 Hz, 1H) 1.63-1.71 (m, 1H) 1.48-1.62 (m, 9H) 1.42 (s, 2H) 1.31 (s, 2H) 1.13 (s, 9H) 1.02 (d, J=6.78 Hz, 3H) 0.90 (d, J=2.51 Hz, 3H) 0.82-0.87 (m, 3H); MS: MS m/z 796.7 (M$^+$+1).

Preparation of Compound 4181

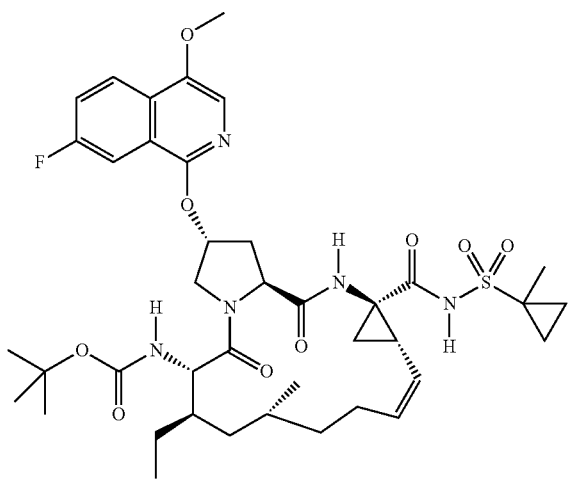

Compound 4181

Compound 4181 was prepared using the intermediates described herein and by following the general procedure described for the synthesis of Compound 1.

Compound 4181: tert-butyl (2R,6S,7R,9R,13aS,14aR,16aS,Z)-7-ethyl-2-(7-fluoro-4-methoxyisoquinolin-1-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.18 (dd, J=9.16, 5.40 Hz, 1H) 7.74 (dd, J=9.54, 2.51 Hz, 1H) 7.50-7.60 (m, 2H) 6.62 (d, J=8.78 Hz, 1H) 5.86 (br. s., 1H) 5.57-5.68 (m, 1H) 5.02 (br. s., 1H) 4.77 (d, J=11.80 Hz, 2H) 4.64 (dd, J=10.04, 7.28 Hz, 1H) 4.00-4.13 (m, 4H) 3.38 (br. s., 2H) 3.22-3.26 (m, 3H) 2.73 (t, J=7.91 Hz, 2H) 2.45 (d, J=9.79 Hz, 1H) 1.97 (d, J=11.80 Hz, 2H) 1.77 (dd, J=8.28, 5.77 Hz, 1H) 1.66 (d, J=10.54 Hz, 1H) 1.47-1.62 (m, 5H) 1.39-1.47 (m, 2H) 1.22-1.34 (m, 2H) 1.06-1.19 (m, 9H) 1.02 (d, J=6.78 Hz, 3H) 0.90 (br. s., 1H) 0.85 (t, J=7.40 Hz, 3H); MS: MS m/z 800.7 (M$^+$+1).

Preparation of Compound 4182

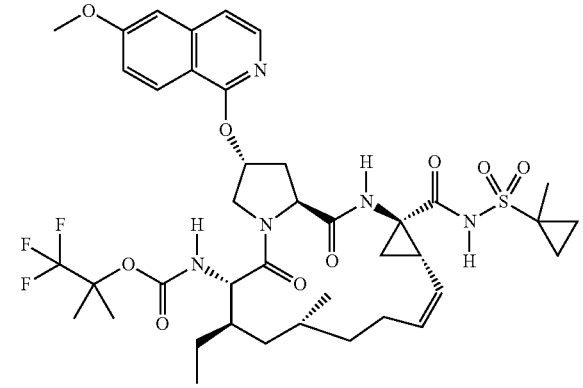

Compound 4182

Compound 4182 was prepared using the intermediates described herein and by following the general procedure described for the synthesis of Compound 3.

Compound 4182: 1,1,1-trifluoro-2-methylpropan-2-yl (2R,6S,7R,9R,13aS,14aR,16aS,Z)-7-ethyl-2-(6-methoxyisoquinolin-1-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.09 (d, J=9.29 Hz, 1H) 7.94 (d, J=6.02 Hz, 1H) 7.26-7.32 (m, 2H) 7.22 (d, J=2.51 Hz, 1H) 7.12 (dd, J=9.16, 2.38 Hz, 1H) 5.90 (br. s., 1H) 5.63 (td, J=10.10, 6.15 Hz, 1H) 5.02 (t, J=9.91 Hz, 1H) 4.91 (s, 1H) 4.77-4.81 (m, 2H) 4.76 (br. s., 1H) 4.67 (dd, J=10.16, 7.15 Hz, 1H) 4.01-4.11 (m, 2H) 3.95 (s, 3H) 3.29 (dd, J=3.26, 1.51 Hz, 2H) 2.70-2.79 (m, 2H) 2.40-2.49 (m, 2H) 1.99 (t, J=11.54 Hz, 2H) 1.77 (dd, J=8.41, 5.65 Hz, 1H) 1.66 (dd, J=9.54, 4.52 Hz, 1H) 1.58 (dd, J=9.41, 5.65 Hz, 2H) 1.53 (s, 2H) 1.41-1.47 (m, 2H) 1.39 (s, 2H) 1.23-1.34 (m, 2H) 1.14 (s, 1H) 0.97-1.04 (m, 5H) 0.88-0.92 (m, 2H) 0.84 (t, J=7.40 Hz, 3H); MS: MS m/z 836.6 (M$^+$+1).

Preparation of Compound 4183

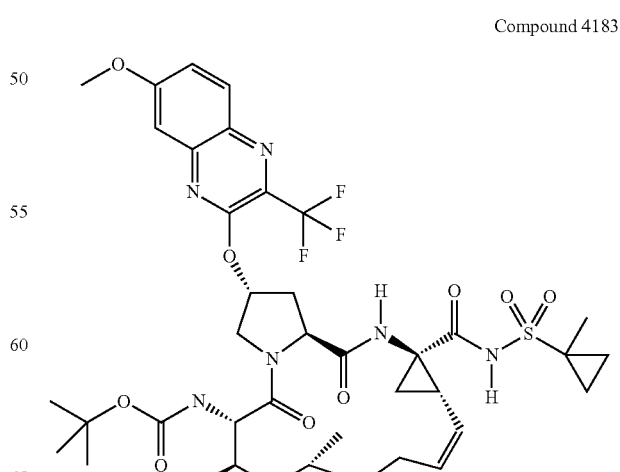

Compound 4183

Compound 4183 was prepared using the intermediates described herein and by following the general procedure described for the synthesis of Compound 1.

Compound 4183: tert-butyl (2R,6S,7R,9R,13aS,14aR,16aS,Z)-2-(7-methoxy-3-(trifluoromethyl)quinoxalin-2-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.97 (d, J=10.04 Hz, 1H) 7.34-7.40 (m, 2H) 5.98 (br. s., 1H) 5.59 (br. s., 1H) 4.81 (br. s., 1H) 4.59-4.65 (m, 1H) 4.02-4.09 (m, 4H) 3.78 (d, J=10.79 Hz, 1H) 2.68 (br. s., 2H) 2.42-2.54 (m, 2H) 1.98 (s, 3H) 1.75-1.87 (m, 3H) 1.51-1.60 (m, 5H) 1.44 (d, J=16.06 Hz, 3H) 1.22-1.36 (m, 3H) 1.07-1.10 (m, 8H) 0.95-1.03 (m, 6H) 0.79-0.88 (m, 1H). MS: MS m/z 837.5 (M$^+$+1).

Preparation of Compound 4184

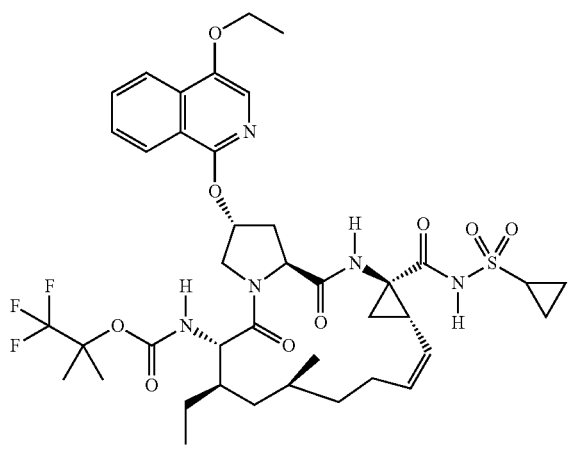

Compound 4184

Compound 4184 was prepared using the intermediates described herein and by following the general procedure described for the synthesis of Compound 3.

Compound 4184: 1,1,1-trifluoro-2-methylpropan-2-yl (2R,6S,7R,9S,13aS,14aR,16aS,Z)-14a-(cyclopropylsulfonylcarbamoyl)-2-(4-ethoxyisoquinolin-1-yloxy)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.16 (dd, J=12.67, 8.16 Hz, 2H) 7.72-7.77 (m, 1H) 7.55-7.60 (m, 2H) 5.84 (br. s., 1H) 5.73 (d, J=9.29 Hz, 1H) 5.08 (br. s., 1H) 4.81 (br. s., 2H) 4.68-4.74 (m, 1H) 4.60 (d, J=11.04 Hz, 1H) 4.30 (d, J=6.78 Hz, 1H) 4.25 (q, J=7.03 Hz, 2H) 4.01-4.09 (m, 1H) 3.29 (d, J=1.76 Hz, 4H) 2.93 (br. s., 1H) 2.73 (dd, J=12.55, 7.28 Hz, 1H) 2.48 (d, J=9.79 Hz, 2H) 2.03 (br. s., 1H) 1.91 (br. s., 1H) 1.70-1.77 (m, 1H) 1.63 (br. s., 2H) 1.55 (t, J=6.90 Hz, 4H) 1.46-1.51 (m, 1H) 1.44 (s, 4H) 1.30-1.40 (m, 5H) 1.12 (s, 3H) 0.97-1.01 (m, 2H) 0.92-0.97 (m, 3H); MS: MS m/z 836.5 (M$^+$+1).

Preparation of Compound 4185

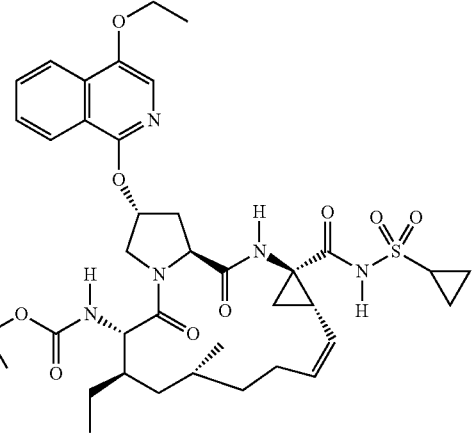

Compound 4185

Compound 4185 was prepared using the intermediates described herein and by following the general procedure described for the synthesis of Compound 3.

Compound 4185: 1,1,1-trifluoro-2-methylpropan-2-yl (2R,6S,7R,9R,13aS,14aR,16aS,Z)-14a-(cyclopropylsulfonylcarbamoyl)-2-(4-ethoxyisoquinolin-1-yloxy)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.15 (d, J=9.29 Hz, 2H) 7.74 (t, J=7.15 Hz, 1H) 7.54-7.60 (m, 2H) 5.84 (br. s., 1H) 5.63 (d, J=6.02 Hz, 1H) 5.05 (br. s., 1H) 4.76-4.81 (m, 4H) 4.63-4.70 (m, 1H) 4.25 (q, J=7.03 Hz, 2H) 3.98-4.10 (m, 2H) 3.24-3.28 (m, 2H) 2.94 (br. s., 1H) 2.70-2.79 (m, 2H) 2.38-2.48 (m, 1H) 1.97 (d, J=10.29 Hz, 2H) 1.74-1.82 (m, 1H) 1.50-1.63 (m, 6H) 1.47 (br. s., 1H) 1.30-1.39 (m, 4H) 1.28 (br. s., 1H) 1.06-1.19 (m, 3H) 1.03 (d, J=6.53 Hz, 4H) 0.93 (s, 2H) 0.83 (t, J=7.40 Hz, 3H); MS: MS m/z 836.5 (M$^+$+1).

Preparation of Compound 4186

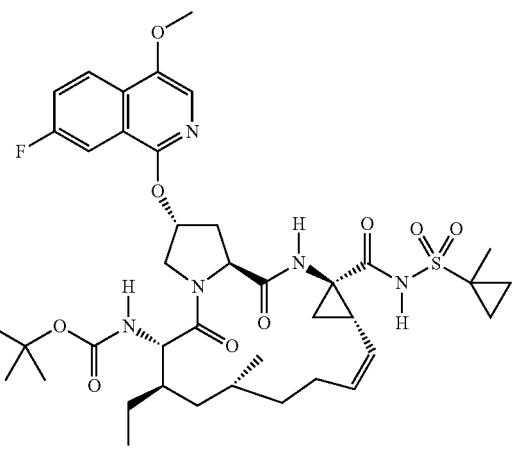

Compound 4186

Compound 4186 was prepared using the intermediates described herein and by following the general procedure described for the synthesis of Compound 3.

Compound 4186: 1,1,1-trifluoro-2-methylpropan-2-yl (2R,6S,7R,9R,13aS,14aR,16aS,Z)-7-ethyl-2-(7-fluoro-4-methoxyisoquinolin-1-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.19 (dd, J=9.16, 5.40 Hz, 1H) 7.75 (dd, J=9.54, 2.51 Hz, 1H) 7.52-7.60 (m, 2H) 5.85 (br. s., 1H) 5.63 (d, J=5.02 Hz, 1H) 5.01 (d, J=12.05 Hz, 1H) 4.77 (d, J=12.05 Hz, 1H) 4.61-4.69 (m, 1H) 3.99-4.08 (m, 5H) 3.23-3.27 (m, 2H) 2.72-2.79 (m, 2H) 2.40-2.49 (m, 2H) 1.93-2.04 (m, 2H) 1.77 (dd, J=8.41, 5.65 Hz, 1H) 1.64 (br. s., 1H) 1.55-1.63 (m, 4H) 1.53 (s, 4H) 1.43 (dd, J=9.91, 4.89 Hz, 2H) 1.37 (s, 3H) 1.20-1.34 (m, 3H) 1.14 (t, J=13.05 Hz, 1H) 0.99-1.05 (m, 5H) 0.89 (br. s., 2H) 0.84 (t, J=7.53 Hz, 3H); MS: MS m/z 854.5 (M$^+$+1).

Preparation of Compound 4187

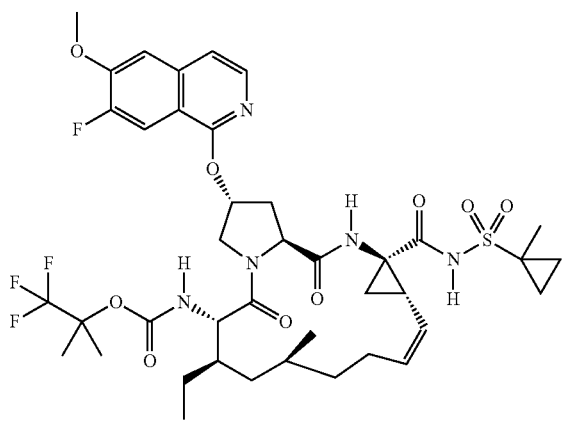

Compound 4187

Compound 4187 was prepared using the intermediates described herein and by following the general procedure described for the synthesis of Compound 3.

Compound 4187: 1,1,1-trifluoro-2-methylpropan-2-yl (2R,6S,7R,9S,13aS,14aR,16aS,Z)-7-ethyl-2-(7-fluoro-6-methoxyisoquinolin-1-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.95 (d, J=5.77 Hz, 1H) 7.83 (d, J=11.80 Hz, 1H) 7.40 (d, J=8.28 Hz, 1H) 7.31 (d, J=5.77 Hz, 1H) 7.25-7.29 (m, 1H) 5.91 (br. s., 1H) 5.75 (d, J=10.04 Hz, 1H) 5.04 (br. s., 1H) 4.72 (dd, J=9.79, 7.28 Hz, 1H) 4.56 (d, J=11.54 Hz, 1H) 4.31 (d, J=5.27 Hz, 1H) 4.01-4.07 (m, 4H) 2.73 (dd, J=14.43, 7.15 Hz, 1H) 2.61 (d, J=9.29 Hz, 1H) 2.40-2.52 (m, 2H) 1.95-2.07 (m, 1H) 1.88 (br. s., 1H) 1.71 (dd, J=8.16, 5.65 Hz, 1H) 1.56-1.67 (m, 4H) 1.52 (s, 3H) 1.48 (s, 3H) 1.39-1.46 (m, 3H) 1.30-1.37 (m, 1H) 1.28 (s, 3H) 1.10 (s, 1H) 0.97-1.05 (m, 2H) 0.93 (d, J=6.78 Hz, 3H) 0.82-0.91 (m, 3H); MS: MS m/z 854.4 (M$^+$+1).

Preparation of Compound 4188

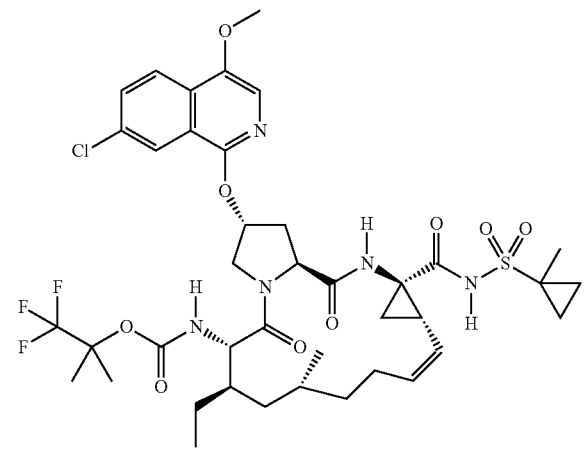

Compound 4188

Compound 4188 was prepared using the intermediates described herein and by following the general procedure described for the synthesis of Compound 3.

Compound 4188: 1,1,1-trifluoro-2-methylpropan-2-yl (2R,6S,7R,9R,13aS,14aR,16aS,Z)-2-(7-chloro-4-methoxyisoquinolin-1-yloxy)-7-ethyl-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.06-8.15 (m, 2H) 7.72 (dd, J=8.91, 2.13 Hz, 1H) 7.64 (s, 1H) 7.30 (d, J=8.78 Hz, 1H) 5.88 (s, 1H) 5.63 (d, J=5.52 Hz, 1H) 5.02 (t, J=9.29 Hz, 1H) 4.67-4.80 (m, 2H) 3.98-4.06 (m, 5H) 3.38-3.42 (m, 1H) 2.70-2.79 (m, 2H) 2.45 (t, J=9.66 Hz, 2H) 1.98 (br. s., 2H) 1.74-1.81 (m, 1H) 1.67 (d, J=11.54 Hz, 1H) 1.51-1.63 (m, 8H) 1.39-1.47 (m, 2H) 1.27-1.33 (m, 3H) 1.07-1.23 (m, 1H) 1.02 (d, J=6.78 Hz, 3H) 0.87-0.94 (m, 5H) 0.83 (t, J=7.28 Hz, 3H); MS: MS m/z 870.2 (M$^+$+1).

Preparation of Compound 4189

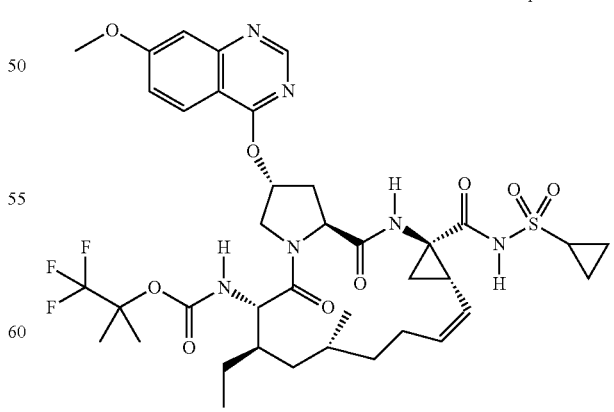

Compound 4189

Compound 4189 was prepared using the intermediates described herein and by following the general procedure described for the synthesis of Compound 3.

Compound 4189: 1,1,1-trifluoro-2-methylpropan-2-yl (2R,6S,7R,9R,13aS,14aR,16aS,Z)-14a-(cyclopropylsulfonylcarbamoyl)-7-ethyl-2-(7-methoxyquinazolin-4-yloxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. ¹H NMR (400 MHz, CD₃OD): δ ppm 8.75 (br. s., 1H) 8.07 (d, J=5.77 Hz, 1H) 7.26 (d, J=17.07 Hz, 2H) 6.00 (br. s., 1H) 5.63 (br. s., 1H) 5.06 (br. s., 1H) 4.56-4.73 (m, 1H) 3.96-4.10 (m, 5H) 3.24-3.30 (m, 1H) 3.16 (br. s., 1H) 2.94 (br. s., 1H) 2.66-2.84 (m, 2H) 2.34-2.55 (m, 2H) 1.99 (br. s., 2H) 1.80 (br. s., 1H) 1.57 (d, J=17.82 Hz, 5H) 1.33 (br. s., 7H) 0.97-1.19 (m, 7H) 0.94 (br. s., 3H) 0.82 (br. s., 3H); MS: MS m/z 821.5 (M⁺−1).

Preparation of Compound 4190

Compound 4190

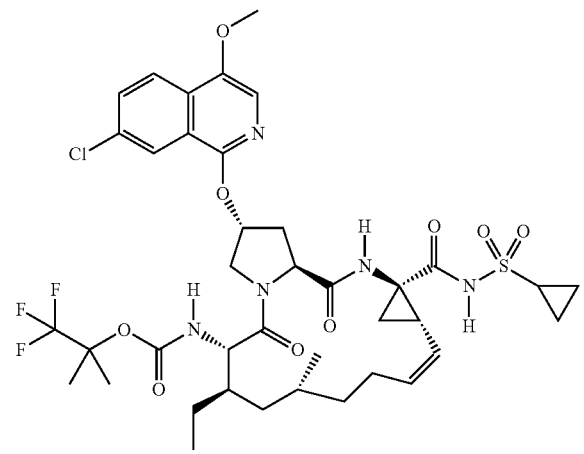

Compound 4190 was prepared using the intermediates described herein and by following the general procedure described for the synthesis of Compound 3.

Compound 4190: 1,1,1-trifluoro-2-methylpropan-2-yl (2R,6S,7R,9R,13aS,14aR,16aS,Z)-2-(7-chloro-4-methoxyisoquinolin-1-yloxy)-14a-(cyclopropylsulfonylcarbamoyl)-7-ethyl-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. ¹H NMR (400 MHz, CD₃OD): δ ppm 8.06-8.16 (m, 2H) 7.72 (dd, J=8.78, 2.26 Hz, 1H) 7.64 (s, 1H) 7.29 (d, J=8.53 Hz, 1H) 5.88 (br. s., 1H) 5.58-5.67 (m, 1H) 5.05 (t, J=10.04 Hz, 1H) 4.74-4.82 (m, 1H) 4.70 (dd, J=10.54, 7.28 Hz, 1H) 3.97-4.06 (m, 5H) 3.29 (dd, J=3.39, 1.63 Hz, 1H) 2.95 (br. s., 1H) 2.69-2.78 (m, 2H) 2.39-2.50 (m, 2H) 1.93-2.05 (m, 2H) 1.79 (dd, J=8.53, 5.52 Hz, 1H) 1.46-1.64 (m, 7H) 1.30-1.46 (m, 4H) 1.21-1.30 (m, 3H) 1.06-1.18 (m, 2H) 1.03 (d, J=6.78 Hz, 3H) 0.92 (s, 3H) 0.83 (t, J=7.40 Hz, 2H); MS: MS m/z 857.5 (M⁺+1).

Preparation of Compound 4191

Compound 4191

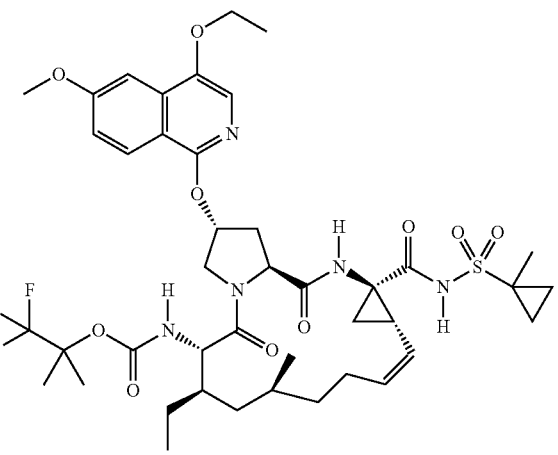

Compound 4191 was prepared using the intermediates described herein and by following the general procedure described for the synthesis of Compound 3.

Compound 4191: 1,1,1-trifluoro-2-methylpropan-2-yl (2R,6S,7R,9S,13aS,14aR,16aS,Z)-2-(4-ethoxy-6-methoxyisoquinolin-1-yloxy)-7-ethyl-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. ¹H NMR (400 MHz, CD₃OD): δ ppm 8.08 (d, J=9.29 Hz, 1H) 7.52 (s, 1H) 7.45 (d, J=2.26 Hz, 1H) 7.15 (dd, J=9.03, 2.51 Hz, 1H) 5.82 (br. s., 1H) 5.74 (d, J=9.03 Hz, 1H) 5.05 (br. s., 1H) 4.67-4.74 (m, 1H) 4.55 (d, J=11.54 Hz, 1H) 4.31 (d, J=6.78 Hz, 1H) 4.24 (q, J=6.86 Hz, 2H) 4.04 (d, J=11.04 Hz, 1H) 3.96 (s, 3H) 2.71 (dd, J=13.30, 7.28 Hz, 1H) 2.60 (br. s., 1H) 2.40-2.52 (m, 2H) 1.96-2.09 (m, 1H) 1.89 (br. s., 1H) 1.69-1.75 (m, 1H) 1.60 (d, J=8.53 Hz, 5H) 1.53-1.58 (m, 5H) 1.52 (s, 3H) 1.38-1.48 (m, 5H) 1.30-1.36 (m, 3H) 1.20 (s, 3H) 0.99 (t, J=7.40 Hz, 3H) 0.93 (d, J=6.78 Hz, 3H) 0.89 (br. s., 2H); MS: MS m/z 880.4 (M⁺+1).

Preparation of Compound 4192

Compound 4192

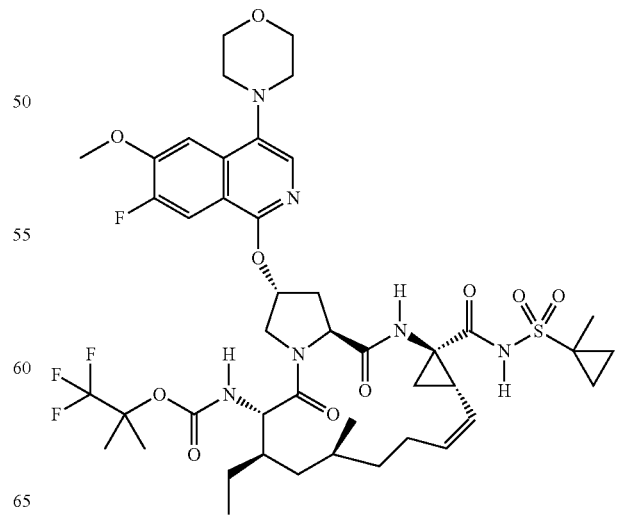

Compound 4192 was prepared using the intermediates described herein and by following the general procedure described for the synthesis of Compound 3.

Compound 4192: 1,1,1-trifluoro-2-methylpropan-2-yl (2R,6S,7R,9S,13aS,14aR,16aS,Z)-7-ethyl-2-(7-fluoro-6-methoxy-4-morpholinoisoquinolin-1-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.82 (d, J=11.54 Hz, 1H) 7.74 (s, 1H) 7.60 (d, J=8.28 Hz, 1H) 5.86 (br. s., 1H) 5.70-5.79 (m, 1H) 5.05 (br. s., 1H) 4.71 (dd, J=9.79, 7.28 Hz, 2H) 4.54 (d, J=11.54 Hz, 1H) 4.31 (d, J=6.27 Hz, 1H) 4.01-4.09 (m, 5H) 3.93-3.99 (m, 5H) 3.06-3.12 (m, 4H) 2.71 (dd, J=13.30, 7.53 Hz, 1H) 2.59 (br. s., 1H) 2.40-2.50 (m, 2H) 2.00 (t, J=7.53 Hz, 1H) 1.87 (br. s., 1H) 1.72 (dd, J=8.03, 5.52 Hz, 1H) 1.56-1.68 (m, 4H) 1.49-1.54 (m, 4H) 1.40-1.49 (m, 3H) 1.30-1.39 (m, 3H) 1.27 (s, 3H) 1.00 (t, J=7.40 Hz, 3H) 0.93 (d, J=6.78 Hz, 3H) 0.89 (br. s., 2H); MS: MS m/z 939.4 (M$^+$+1).

Preparation of Compound 4193

Compound 4193

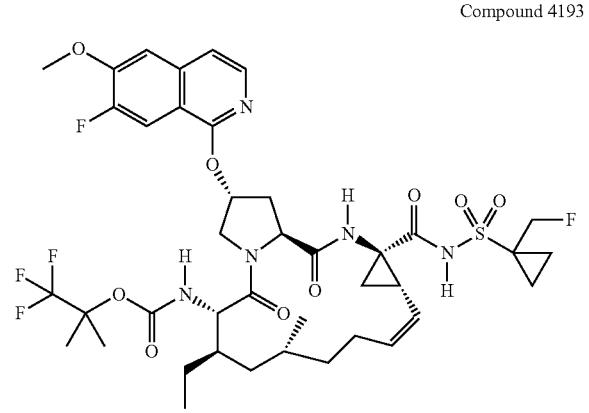 [SMILES: CC[C@@H]1C[C@H](C)CC/C=C\[C@@H]2C[C@@]2(C(=O)NS(=O)(=O)C2(CF)CC2)NC(=O)[C@@H]2C[C@@H](Oc3nccc4cc(OC)c(F)cc34)CN2C(=O)[C@H]1NC(=O)OC(C)(C)C(F)(F)F]

Compound 4193 was prepared using the intermediates described herein and by following the general procedure described for the synthesis of Compound 3.

Compound 4193: 1,1,1-trifluoro-2-methylpropan-2-yl (2R,6S,7R,9R,13aS,14aR,16aS,Z)-7-ethyl-2-(7-fluoro-6-methoxyisoquinolin-1-yloxy)-14a-(1-(fluoromethyl)cyclopropylsulfonylcarbamoyl)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.96 (d, J=5.77 Hz, 1H) 7.78 (d, J=11.80 Hz, 1H) 7.40 (d, J=8.28 Hz, 1H) 7.31 (d, J=6.02 Hz, 1H) 5.89 (br. s., 1H) 5.61 (s, 1H) 4.73 (d, J=12.55 Hz, 2H) 4.64 (br. s., 2H) 3.99-4.09 (m, 6H) 2.72 (br. s., 2H) 2.44 (d, J=11.80 Hz, 2H) 1.97 (br. s., 2H) 1.72 (br. s., 1H) 1.59 (br. s., 5H) 1.49 (br. s., 2H) 1.38-1.44 (m, 3H) 1.25-1.35 (m, 6H) 1.11 (s, 3H) 1.02 (d, J=6.78 Hz, 2H) 0.92 (s, 1H) 0.84 (t, J=7.53 Hz, 3H); MS: MS m/z 872.4 (M$^+$+1).

Preparation of Compound 4194

Compound 4194

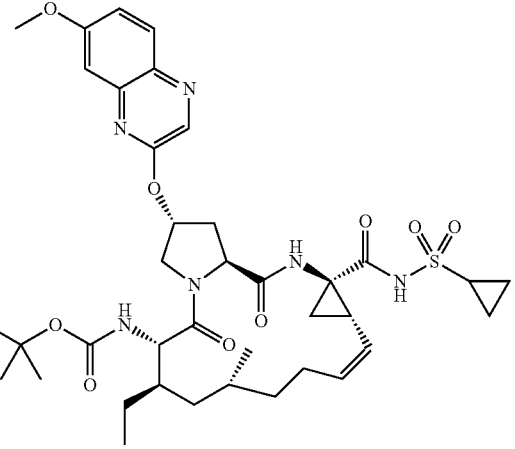

Compound 4194 was prepared using the intermediates described herein and by following the general procedure described for the synthesis of Compound 3.

Compound 4194: 1,1,1-trifluoro-2-methylpropan-2-yl (2R,6S,7R,9R,13aS,14aR,16aS,Z)-14a-(cyclopropylsulfonylcarbamoyl)-7-ethyl-2-(7-methoxyquinoxalin-2-yloxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 9.06 (s, 1H) 8.27 (s, 1H) 7.87 (d, J=9.03 Hz, 1H) 7.32-7.38 (m, 1H) 7.29 (dd, J=9.03, 2.76 Hz, 1H) 5.91 (br. s., 1H) 5.59-5.69 (m, 1H) 5.05 (t, J=9.91 Hz, 1H) 4.74 (d, J=12.30 Hz, 1H) 4.61 (d, J=2.01 Hz, 1H) 4.03-4.10 (m, 2H) 3.99 (s, 3H) 3.38 (br. s., 1H) 2.91-2.99 (m, 1H) 2.66-2.75 (m, 2H) 2.35-2.53 (m, 2H) 1.92-2.06 (m, 2H) 1.80 (dd, J=8.41, 5.65 Hz, 1H) 1.43-1.65 (m, 7H) 1.30-1.39 (m, 4H) 1.20-1.26 (m, 4H) 1.05-1.20 (m, 4H) 1.03 (d, J=6.53 Hz, 3H) 0.82 (t, J=7.53 Hz, 3H); MS: MS m/z 823.5 (M$^+$+1).

Preparation of Compound 4195

Compound 4195

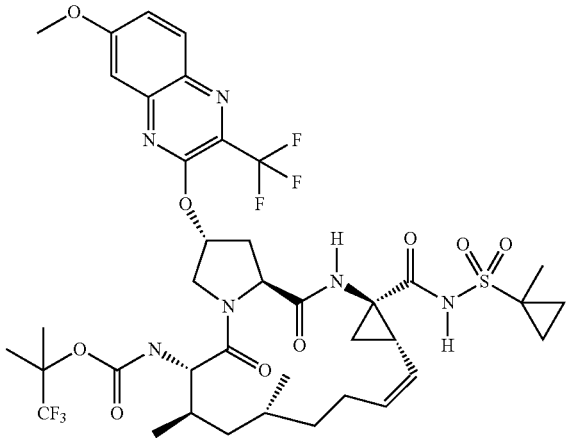

Compound 4195 was prepared using the intermediates described herein and by following the general procedure described for the synthesis of Compound 3.

Compound 4195: 1,1,1-trifluoro-2-methylpropan-2-yl (2R,6S,7R,9R,13aS,14aR,16aS,Z)-2-(7-methoxy-3-(trifluoromethyl)quinoxalin-2-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.98 (br. s., 1H) 5.62 (br. s., 1H) 4.98-5.06 (m, 1H) 4.82 (d, J=6.02 Hz, 1H) 4.65 (dd, J=10.16, 7.15 Hz, 1H) 4.02-4.08 (m, 4H) 3.74 (d, J=10.79 Hz, 1H) 2.68-2.77 (m, 2H) 2.40-2.54 (m, 2H) 1.74-2.02 (m, 4H) 1.66 (br. s., 1H) 1.59 (dd, J=9.41, 5.90 Hz, 1H) 1.53 (s, 3H) 1.40-1.50 (m, 3H) 1.34 (t, J=7.28 Hz, 9H) 1.21 (s, 3H) 0.99 (dd, J=19.83, 6.53 Hz, 6H) 0.80-0.91 (m, 1H). MS: MS m/z 891.5 (M$^+$+1).

Preparation of Compound 4196

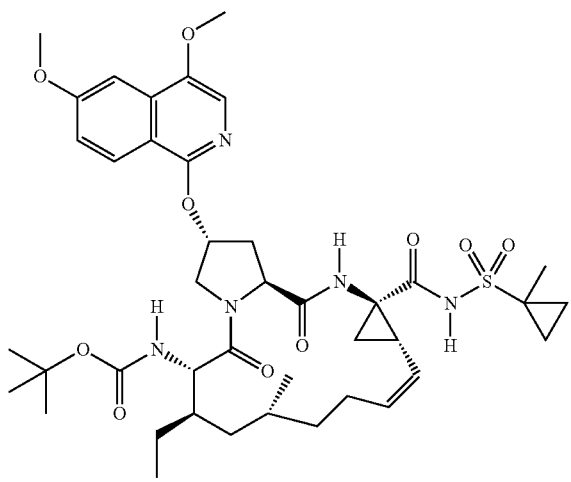

Compound 4196

Compound 4196 was prepared using the intermediates described herein and by following the general procedure described for the synthesis of Compound 1.

Compound 4196: tert-butyl (2R,6S,7R,9R,13aS,14aR,16aS,Z)-2-(4,6-dimethoxyisoquinolin-1-yloxy)-7-ethyl-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.06 (d, J=9.03 Hz, 1H) 7.52 (s, 1H) 7.42 (d, J=2.51 Hz, 1H) 7.12 (dd, J=9.03, 2.26 Hz, 1H) 6.61 (d, J=9.54 Hz, 1H) 5.82 (br. s., 1H) 5.62 (d, J=6.27 Hz, 1H) 5.02 (d, J=10.04 Hz, 1H) 4.73 (d, J=11.04 Hz, 1H) 4.55-4.65 (m, 1H) 4.07-4.17 (m, 1H) 3.99-4.07 (m, 4H) 3.94 (s, 3H) 3.24-3.31 (m, 2H) 2.74 (d, J=8.03 Hz, 2H) 2.43 (d, J=9.29 Hz, 2H) 1.95 (br. s., 2H) 1.77 (br. s., 1H) 1.49-1.69 (m, 6H) 1.39-1.47 (m, 2H) 1.31 (s, 2H) 1.15 (s, 9H) 1.08 (br. s., 2H) 1.01 (d, J=6.78 Hz, 2H) 0.89 (br. s., 3H) 0.85 (t, J=7.28 Hz, 3H); MS: MS m/z 810.4 (M$^+$−1).

Preparation of Compound 4197

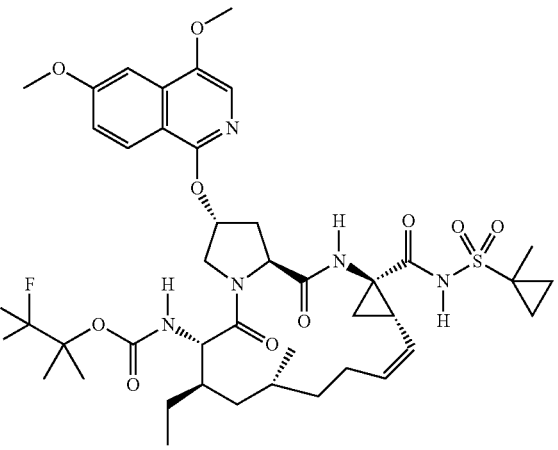

Compound 4197

Compound 4197 was prepared using the intermediates described herein and by following the general procedure described for the synthesis of Compound 3.

Compound 4197: 1,1,1-trifluoro-2-methylpropan-2-yl (2R,6S,7R,9R,13aS,14aR,16aS,Z)-2-(4,6-dimethoxyisoquinolin-1-yloxy)-7-ethyl-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.05 (d, J=9.03 Hz, 1H) 7.54 (s, 1H) 7.43 (d, J=2.51 Hz, 1H) 7.28 (d, J=8.78 Hz, 1H) 7.14 (dd, J=9.03, 2.51 Hz, 1H) 5.82 (br. s., 1H) 5.58-5.67 (m, 1H) 5.01 (t, J=10.29 Hz, 1H) 4.74 (d, J=10.54 Hz, 1H) 4.64 (dd, J=10.04, 7.03 Hz, 1H) 3.98-4.13 (m, 5H) 3.90-3.97 (m, 3H) 2.67-2.79 (m, 2H) 2.42 (ddd, J=13.93, 10.16, 4.27 Hz, 2H) 1.97 (d, J=12.55 Hz, 2H) 1.77 (dd, J=8.28, 5.52 Hz, 1H) 1.66 (d, J=9.29 Hz, 1H) 1.50-1.62 (m, 6H) 1.36-1.49 (m, 3H) 1.31 (s, 2H) 1.07-1.28 (m, 3H) 0.98-1.04 (m, 6H) 0.87-0.95 (m, 3H) 0.83 (t, J=7.53 Hz, 3H); MS: MS m/z 864.4 (M$^+$−1).

Preparation of Compound 4198

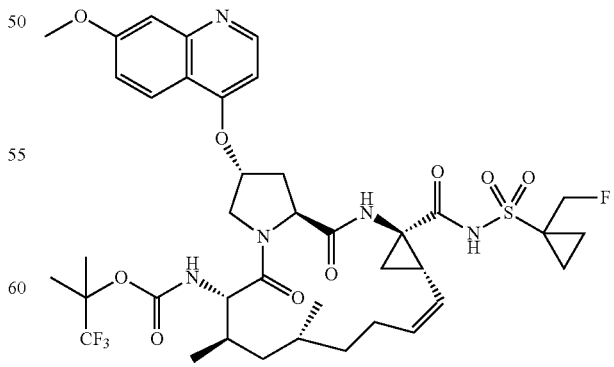

Compound 4198

Compound 4198 was prepared using the intermediates described herein and by following the general procedure described for the synthesis of Compound 3.

Compound 4198: 1,1,1-trifluoro-2-methylpropan-2-yl (2R,6S,7R,9R,13aS,14aR,16aS,Z)-14a-(1-(fluoromethyl)cyclopropylsulfonylcarbamoyl)-2-(7-methoxyquinolin-4-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.65 (d, J=5.52 Hz, 1H) 8.11 (d, J=9.03 Hz, 1H) 7.32 (d, J=2.51 Hz, 1H) 7.14 (dd, J=9.29, 2.51 Hz, 1H) 6.97 (d, J=5.52 Hz, 1H) 5.56-5.65 (m, 1H) 5.52 (br. s., 1H) 5.09 (br. s., 1H) 4.78 (d, J=11.29 Hz, 2H) 4.62 (dd, J=10.16, 6.90 Hz, 2H) 4.06 (dd, J=11.54, 3.01 Hz, 1H) 3.94-3.97 (m, 3H) 3.84 (d, J=10.79 Hz, 1H) 2.64-2.81 (m, 2H) 2.33-2.56 (m, 2H) 1.78-2.02 (m, 3H) 1.42-1.75 (m, 7H) 1.38 (s, 3H) 1.16-1.32 (m, 3H) 0.97-1.04 (m, 8H) 0.84 (t, J=11.54 Hz, 1H). MS: MS m/z 840.4 (M$^+$+1).

Preparation of Compound 4199

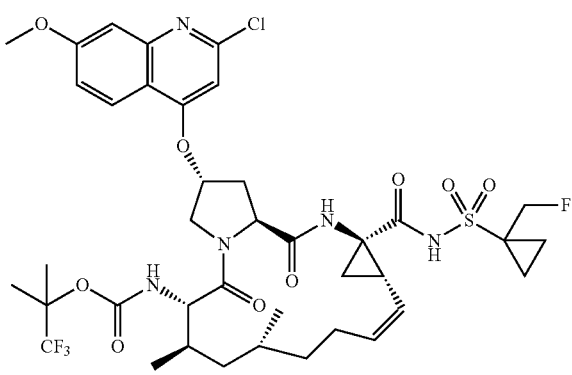

Compound 4199

Compound 4199 was prepared using the intermediates described herein and by following the general procedure described for the synthesis of Compound 3.

Compound 4199: 1,1,1-trifluoro-2-methylpropan-2-yl (2R,6S,7R,9R,13aS,14aR,16aS,Z)-2-(2-chloro-7-methoxyquinolin-4-yloxy)-14a-(1-(fluoromethyl)cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.06 (d, J=9.29 Hz, 1H) 7.24 (d, J=2.26 Hz, 1H) 7.14 (dd, J=9.29, 2.51 Hz, 1H) 7.02 (s, 1H) 5.60 (br. s., 1H) 5.51 (br. s., 1H) 4.77-4.81 (m, 2H) 4.57-4.64 (m, 2H) 4.03 (dd, J=11.80, 3.01 Hz, 1H) 3.96 (s, 3H) 3.83 (d, J=10.79 Hz, 1H) 3.23 (d, J=7.28 Hz, 2H) 2.67-2.80 (m, 2H) 2.34-2.54 (m, 3H) 1.93-2.03 (m, 1H) 1.72 (dd, J=8.53, 5.52 Hz, 3H) 1.46-1.58 (m, 2H) 1.38 (s, 3H) 1.33 (t, J=7.28 Hz, 4H) 0.99-1.04 (m, 9H) 0.80-0.88 (m, 1H). MS: MS m/z 874.4 (M$^+$+1).

Preparation of Compound 4200

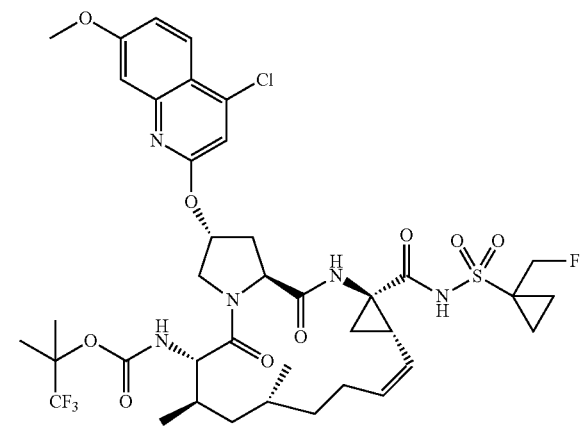

Compound 4200

Compound 4200 was prepared using the intermediates described herein and by following the general procedure described for the synthesis of Compound 3.

Compound 4200: 1,1,1-trifluoro-2-methylpropan-2-yl (2R,6S,7R,9R,13aS,14aR,16aS,Z)-2-(4-chloro-7-methoxyquinolin-2-yloxy)-14a-(1-(fluoromethyl)cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.01 (d, J=9.04 Hz, 1H) 7.33 (d, J=2.26 Hz, 1H) 7.17 (dd, J=9.16, 2.38 Hz, 1H) 6.91 (s, 1H) 5.89 (br. s., 1H) 5.60 (br. s., 1H) 4.78 (d, J=11.04 Hz, 1H) 4.68 (d, J=11.29 Hz, 1H) 4.52-4.60 (m, 2H) 4.06 (dd, J=11.54, 3.26 Hz, 1H) 3.97 (s, 3H) 3.83 (d, J=10.79 Hz, 1H) 2.64 (dd, J=13.43, 7.15 Hz, 2H) 2.36-2.51 (m, 2H) 1.85-2.05 (m, 2H) 1.65-1.81 (m, 4H) 1.42-1.62 (m, 4H) 1.31-1.36 (m, 6H) 1.26 (s, 3H) 0.95-1.04 (m, 6H) 0.78-0.85 (m, 1H). MS: MS m/z 875.34 (M$^+$+1).

Preparation of Compound 4201

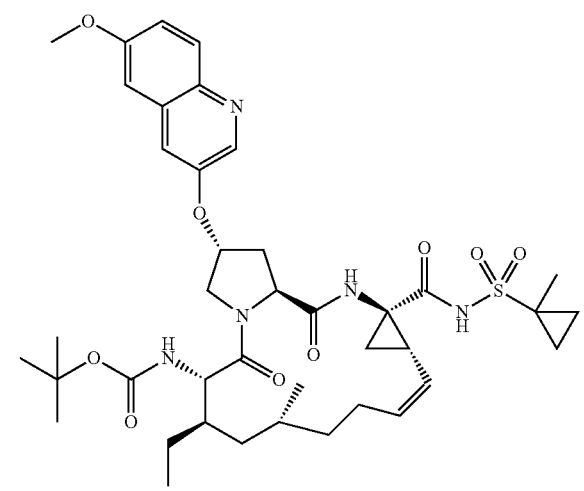

Compound 4201

Compound 4201 was prepared using the intermediates described herein and by following the general procedure described for the synthesis of Compound 1.

Compound 4201: tert-butyl (2R,6S,7R,9R,13aS,14aR,16aS,Z)-7-ethyl-2-(6-methoxyquinolin-3-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. MS: MS m/z 782.9 (M$^+$+1).

Preparation of Compound 4202

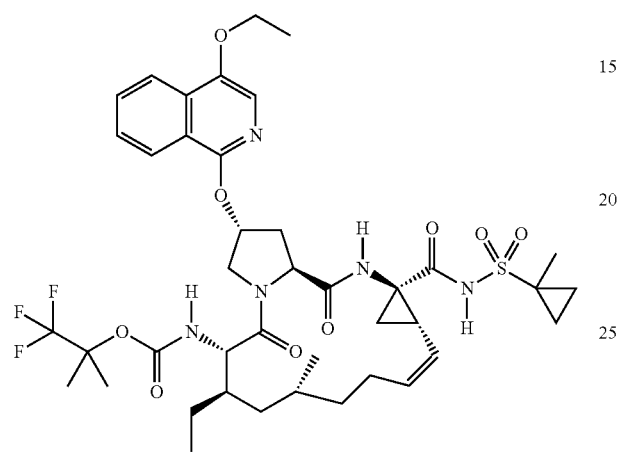

Compound 4202

Compound 4202 was prepared using the intermediates described herein and by following the general procedure described for the synthesis of Compound 3.

Compound 4202: 1,1,1-trifluoro-2-methylpropan-2-yl (2R,6S,7R,9R,13aS,14aR,16aS,Z)-2-(4-ethoxyisoquinolin-1-yloxy)-7-ethyl-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.15 (dd, J=8.91, 2.38 Hz, 2H) 7.70-7.76 (m, 1H) 7.53-7.60 (m, 2H) 5.84 (br. s., 1H) 5.57-5.67 (m, 1H) 5.01 (t, J=10.04 Hz, 1H) 4.78 (d, J=11.54 Hz, 1H) 4.66 (dd, J=10.29, 7.03 Hz, 1H) 4.25 (q, J=7.03 Hz, 2H) 3.98-4.09 (m, 2H) 2.67-2.79 (m, 2H) 2.38-2.49 (m, 2H) 1.93-2.05 (m, 2H) 1.72-1.79 (m, 1H) 1.65 (br. s., 1H) 1.50-1.61 (m, 11H) 1.41 (br. s., 2H) 1.36 (s, 3H) 1.31 (s, 2H) 1.14 (d, J=11.80 Hz, 1H) 1.01 (d, J=6.78 Hz, 3H) 0.92 (s, 3H) 0.89 (br. s., 2H) 0.83 (t, J=7.40 Hz, 3H); MS: MS m/z 850.6 (M$^+$+1).

Preparation of Compound 4203

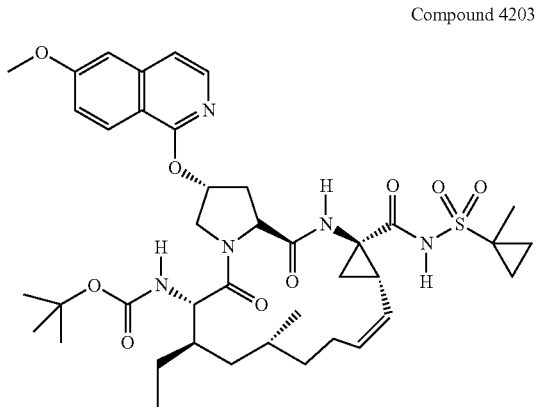

Compound 4203

Compound 4203 was prepared using the intermediates described herein and by following the general procedure described for the synthesis of Compound 1.

Compound 4203: tert-butyl (2R,6S,7R,9R,13aS,14aR,16aS,Z)-7-ethyl-2-(6-methoxyisoquinolin-1-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 9.02 (s, 1H) 8.10 (d, J=9.03 Hz, 1H) 7.92 (d, J=6.02 Hz, 1H) 7.26 (d, J=6.02 Hz, 1H) 7.20 (d, J=2.26 Hz, 1H) 7.09 (dd, J=8.91, 2.38 Hz, 1H) 5.90 (br. s., 1H) 5.62 (td, J=10.04, 6.02 Hz, 1H) 5.01 (t, J=9.91 Hz, 1H) 4.76 (d, J=11.04 Hz, 1H) 4.62 (dd, J=9.91, 7.40 Hz, 1H) 4.11 (d, J=11.29 Hz, 1H) 4.05 (dd, J=11.17, 3.39 Hz, 1H) 3.94 (s, 3H) 2.68-2.80 (m, 2H) 2.36-2.49 (m, 2H) 1.89-2.05 (m, 2H) 1.76 (dd, J=8.16, 5.65 Hz, 1H) 1.56-1.69 (m, 4H) 1.52 (s, 4H) 1.43 (dd, J=9.79, 4.52 Hz, 2H) 1.22-1.36 (m, 3H) 1.13-1.19 (m, 9H) 1.09 (d, J=11.04 Hz, 1H) 1.01 (d, J=6.78 Hz, 3H) 0.82-0.93 (m, 5H); MS: MS m/z 782.2 (M$^+$+1).

Preparation of Compound 4204

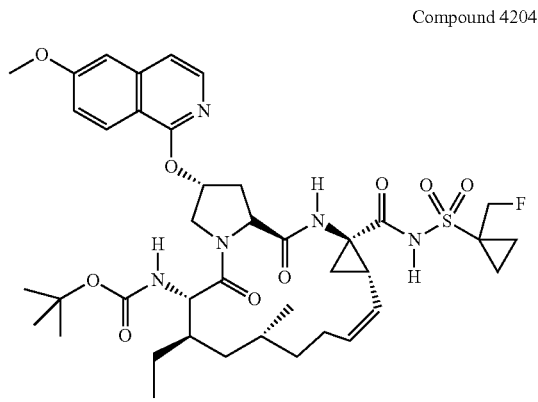

Compound 4204

Compound 4204 was prepared using the intermediates described herein and by following the general procedure described for the synthesis of Compound 1.

Compound 4204: tert-butyl (2R,6S,7R,9R,13aS,14aR,16aS,Z)-7-ethyl-14a-(1-(fluoromethyl)cyclopropylsulfonylcarbamoyl)-2-(6-methoxyisoquinolin-1-yloxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.10 (d, J=9.03 Hz, 1H) 7.92 (d, J=6.02 Hz, 1H) 7.26 (d, J=5.77 Hz, 1H) 7.20 (d, J=2.26 Hz, 1H) 7.09 (dd, J=9.29, 2.26 Hz, 1H) 6.61 (d, J=10.04 Hz, 1H) 5.89 (br. s., 1H) 5.62 (d, J=5.52 Hz, 1H) 5.01 (br. s., 1H) 4.77 (t, J=12.17 Hz, 1H) 4.47-4.66 (m, 2H) 4.02-4.14 (m, 2H) 3.94 (s, 3H) 2.64-2.76 (m, 2H) 2.43 (d, J=10.29 Hz, 2H) 1.95 (br. s., 2H) 1.52-1.76 (m, 7H) 1.39-1.51 (m, 2H) 1.31 (s, 4H) 1.17 (s, 7H) 1.13 (br. s., 2H) 1.02 (d, J=6.78 Hz, 3H) 0.85 (t, J=7.28 Hz, 3H); MS: MS m/z 799.9 (M$^+$−1).

Preparation of Compound 4205

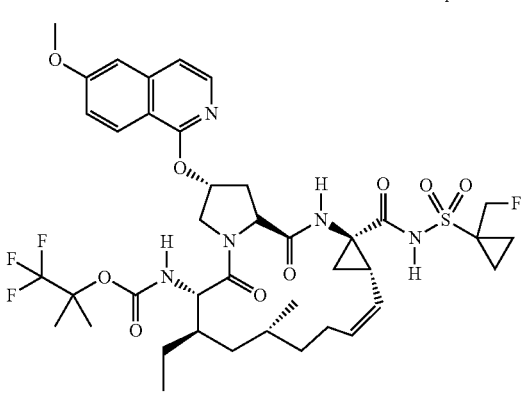

Compound 4205

Compound 4205 was prepared using the intermediates described herein and by following the general procedure described for the synthesis of Compound 3.

Compound 4205: 1,1,1-trifluoro-2-methylpropan-2-yl (2R,6S,7R,9R,13aS,14aR,16aS,Z)-7-ethyl-14a-(1-(fluoromethyl)cyclopropylsulfonylcarbamoyl)-2-(6-methoxyisoquinolin-1-yloxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.06 (d, J=9.03 Hz, 1H) 7.91 (d, J=6.02 Hz, 1H) 7.24 (d, J=6.02 Hz, 1H) 7.18 (d, J=2.51 Hz, 1H) 7.08 (dd, J=9.29, 2.51 Hz, 1H) 5.86 (br. s., 1H) 5.59 (td, J=10.16, 6.02 Hz, 1H) 4.97 (t, J=10.16 Hz, 1H) 4.71-4.77 (m, 1H) 4.59-4.63 (m, 1H) 3.96-4.08 (m, 2H) 3.91 (s, 3H) 2.68 (dt, J=18.07, 9.03 Hz, 2H) 2.35-2.46 (m, 2H) 1.88-2.01 (m, 2H) 1.61-1.72 (m, 3H) 1.54 (dd, J=9.79, 5.77 Hz, 4H) 1.47 (br. s., 2H) 1.36 (s, 3H) 1.07-1.29 (m, 5H) 0.96-1.01 (m, 6H) 0.80 (t, J=7.40 Hz, 3H); MS: MS m/z 855.6 (M$^+$+1).

Preparation of Compound 4206

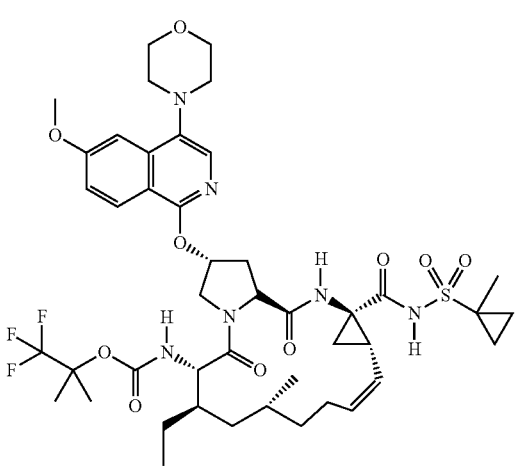

Compound 4206

Compound 4206 was prepared using the intermediates described herein and by following the general procedure described for the synthesis of Compound 3.

Compound 4206: 1,1,1-trifluoro-2-methylpropan-2-yl (2R,6S,7R,9R,13aS,14aR,16aS,Z)-7-ethyl-2-(6-methoxy-4-morpholinoisoquinolin-1-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.10 (d, J=9.03 Hz, 1H) 7.72 (s, 1H) 7.46 (d, J=2.51 Hz, 1H) 7.14 (dd, J=9.03, 2.51 Hz, 1H) 5.84 (br. s., 1H) 5.61 (br. s., 1H) 5.01 (br. s., 1H) 4.75 (d, J=11.54 Hz, 2H) 4.61-4.68 (m, 1H) 3.99-4.08 (m, 2H) 3.94-3.98 (m, 8H) 3.05-3.12 (m, 4H) 2.73 (dd, J=13.80, 6.78 Hz, 2H) 2.38-2.48 (m, 2H) 1.91-2.03 (m, 2H) 1.77 (dd, J=8.41, 5.40 Hz, 1H) 1.55-1.63 (m, 4H) 1.50-1.53 (m, 4H) 1.39-1.47 (m, 2H) 1.37 (s, 3H) 1.31 (s, 3H) 1.13 (d, J=13.05 Hz, 1H) 0.97-1.03 (m, 6H) 0.87-0.94 (m, 2H) 0.83 (t, J=7.40 Hz, 3H); MS: MS m/z 919.9 (M$^+$−1).

Preparation of Compound 4207

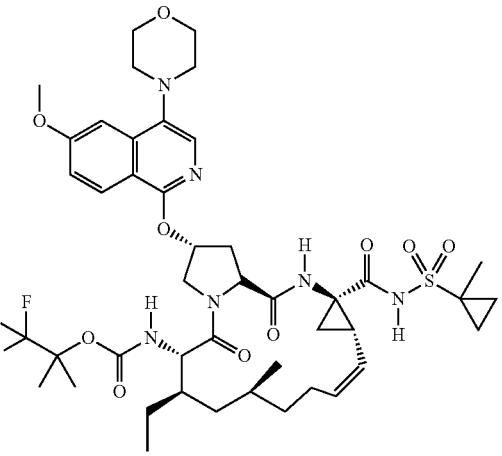

Compound 4207

Compound 4207 was prepared using the intermediates described herein and by following the general procedure described for the synthesis of Compound 3.

Compound 4207: 1,1,1-trifluoro-2-methylpropan-2-yl (2R,6S,7R,9S,13aS,14aR,16aS,Z)-7-ethyl-2-(6-methoxy-4-morpholinoisoquinolin-1-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.13 (d, J=9.29 Hz, 1H) 7.71 (s, 1H) 7.46 (d, J=2.51 Hz, 1H) 7.14 (dd, J=9.16, 2.38 Hz, 1H) 5.85 (br. s., 1H) 5.72 (br. s., 1H) 5.05 (br. s., 1H) 4.70 (t, J=8.53 Hz, 1H) 4.51-4.58 (m, 1H) 4.31 (br. s., 1H) 4.07 (br. s., 1H) 3.93-3.99 (m, 7H) 3.66 (d, J=2.26 Hz, 1H) 3.06-3.11 (m, 4H) 2.66-2.74 (m, 1H) 2.46 (br. s., 2H) 2.21 (t, J=7.53 Hz, 1H) 1.94-2.08 (m, 2H) 1.85-1.93 (m, 5H) 1.72 (br. s., 1H) 1.60 (d, J=7.28 Hz, 3H) 1.48-1.53 (m, 5H) 1.45 (s, 4H) 1.28-1.37 (m, 8H) 1.18 (s, 3H) 0.98 (t, J=7.28 Hz, 3H) 0.92 (d, J=6.78 Hz, 3H); MS: MS m/z 919.9 (M$^+$−1).

Example 4208

Preparation of Compound 4208

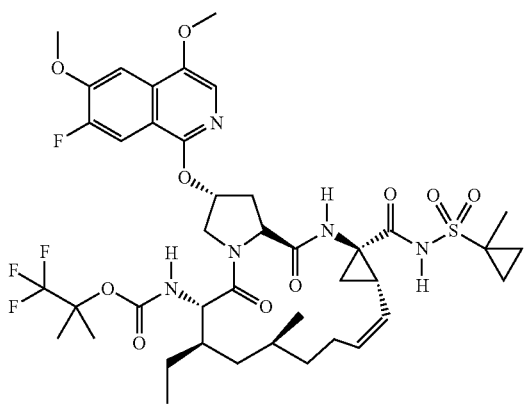

Compound 4208

Compound 4208 was prepared using the intermediates described herein and by following the general procedure described for the synthesis of Compound 3.

Compound 4208: 1,1,1-trifluoro-2-methylpropan-2-yl (2R,6S,7R,9S,13aS,14aR,16aS,Z)-7-ethyl-2-(7-fluoro-4,6-dimethoxyisoquinolin-1-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.78 (d, J=11.54 Hz, 1H) 7.51-7.60 (m, 2H) 5.82 (br. s., 1H) 5.72 (d, J=8.28 Hz, 1H) 5.13 (br. s., 1H) 4.66-4.72 (m, 1H) 4.52 (d, J=11.04 Hz, 1H) 4.33 (d, J=6.27 Hz, 1H) 3.99-4.09 (m, 8H) 2.71 (dd, J=13.30, 7.28 Hz, 1H) 2.54 (br. s., 1H) 2.38-2.49 (m, 2H) 1.94-2.06 (m, 2H) 1.82-1.91 (m, 1H) 1.69-1.76 (m, 1H) 1.60 (br. s., 5H) 1.50 (d, J=9.03 Hz, 6H) 1.43 (d, J=11.04 Hz, 2H) 1.33 (d, J=13.05 Hz, 3H) 1.27 (s, 2H) 1.01 (t, J=7.40 Hz, 2H) 0.93 (d, J=6.78 Hz, 3H) 0.85 (br. s., 2H); MS: MS m/z 882.4 (M$^+$−1).

Preparation of Compound 4209

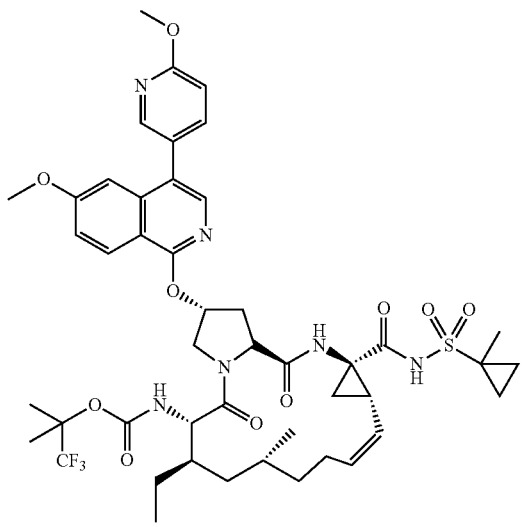

Compound 4209

Compound 4209 was prepared using the intermediates described herein and by following the general procedure described for the synthesis of Compound 3.

Compound 4209: 1,1,1-trifluoro-2-methylpropan-2-yl (2R,6S,7R,9R,13aS,14aR,16aS,Z)-7-ethyl-2-(6-methoxy-4-(6-methoxypyridin-3-yl)isoquinolin-1-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.19-8.25 (m, 2H) 7.90 (s, 1H) 7.83 (dd, J=8.53, 2.51 Hz, 1H) 7.19 (dd, J=9.29, 2.51 Hz, 1H) 6.97-7.06 (m, 2H) 5.94 (br. s., 1H) 5.53-5.69 (m, 1H) 4.67-4.74 (m, 1H) 4.00-4.11 (m, 5H) 3.79-3.85 (m, 3H) 2.77 (d, J=8.28 Hz, 2H) 2.40-2.55 (m, 2H) 1.93-2.07 (m, 2H) 1.78 (dd, J=8.53, 5.52 Hz, 1H) 1.51-1.62 (m, 8H) 1.39 (s, 3H) 1.26-1.34 (m, 4H) 1.06-1.19 (m, 2H) 0.97-1.04 (m, 6H) 0.79-0.92 (m, 6H). MS: MS m/z 944.04 (M$^+$+1).

Preparation of Compound 4210

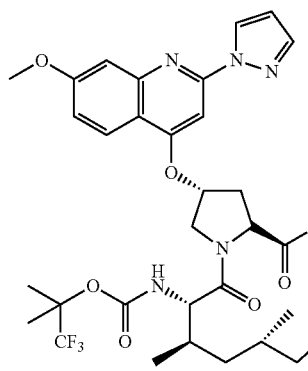

Compound 4210

Compound 4210 was prepared using the intermediates described herein and by following the general procedure described for the synthesis of Compound 3.

Compound 4210: 1,1,1-trifluoro-2-methylpropan-2-yl (2R,6S,7R,9R,13aS,14aR,16aS,Z)-2-(7-methoxy-2-(1H-pyrazol-1-yl)quinolin-4-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 9.08 (s, 1H) 8.82 (d, J=2.26 Hz, 1H) 8.09 (d, J=9.29 Hz, 1H) 7.89 (d, J=1.26 Hz, 1H) 7.57 (s, 1H) 7.38 (d, J=2.26 Hz, 1H) 7.10 (dd, J=9.16, 2.38 Hz, 1H) 6.62-6.67 (m, 1H) 5.59-5.68 (m, 2H) 5.03 (t, J=9.91 Hz, 1H) 4.66 (dd, J=10.16, 7.15 Hz, 1H) 4.11 (dd, J=11.67, 2.89 Hz, 1H) 3.98 (s, 3H) 3.85 (d, J=10.79 Hz, 1H) 2.85 (dd, J=14.05, 7.03 Hz, 1H) 2.65-2.76 (m, 1H) 2.40-2.59 (m, 2H) 1.76-2.03 (m, 4H) 1.64-1.70 (m, 1H) 1.51-1.60 (m, 5H) 1.41-1.48 (m, 2H) 1.36 (s, 3H) 1.09 (s, 3H) 1.01 (dd, J=9.29, 6.78 Hz, 6H) 0.83-0.94 (m, 3H). MS: MS m/z 888.96 (M$^+$+1).

Preparation of Compound 4211

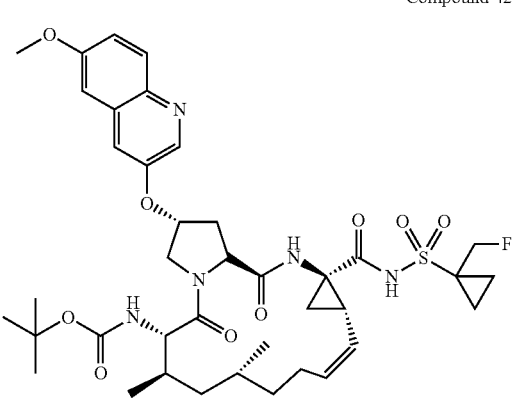

Compound 4211

Compound 4211 was prepared using the intermediates described herein and by following the general procedure described for the synthesis of Compound 1.

Compound 4211: tert-butyl (2R,6S,7R,9R,13aS,14aR,16aS,Z)-14a-(1-(fluoromethyl)cyclopropylsulfonylcarbamoyl)-2-(6-methoxyquinolin-3-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.36 (d, J=2.76 Hz, 1H) 7.85 (s, 1H) 7.74 (s, 1H) 7.24-7.31 (m, 2H) 5.60 (br. s., 1H) 5.37 (br. s., 1H) 4.51-4.64 (m, 3H) 4.05 (d, J=10.54 Hz, 1H) 3.96 (s, 3H) 3.90 (d, J=11.04 Hz, 1H) 2.67 (d, J=8.53 Hz, 2H) 2.33-2.54 (m, 3H) 1.99 (br. s., 2H) 1.86 (br. s., 3H) 1.72 (dd, J=8.16, 5.40 Hz, 3H) 1.41-1.60 (m, 6H) 1.21-1.36 (m, 6H) 1.15 (s, 15H) 0.96-1.06 (m, 8H). MS: MS m/z 887.4 (M$^+$+1).

Preparation of Compound 4212

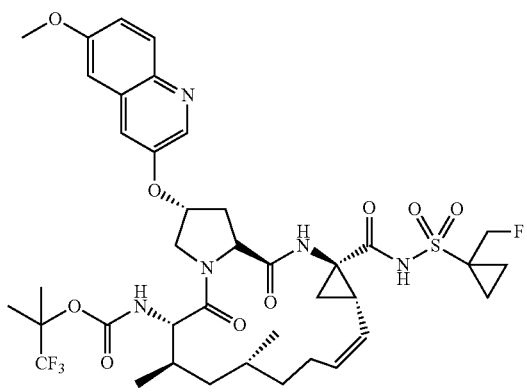

Compound 4212

Compound 4212 was prepared using the intermediates described herein and by following the general procedure described for the synthesis of Compound 3.

Compound 4212: 1,1,1-trifluoro-2-methylpropan-2-yl (2R,6S,7R,9R,13aS,14aR,16aS,Z)-14a-(1-(fluoromethyl)cyclopropylsulfonylcarbamoyl)-2-(6-methoxyquinolin-3-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.49 (d, J=2.51 Hz, 1H) 7.86-7.97 (m, 3H) 7.86-7.97 (m, 3H) 7.32-7.39 (m, 3H) 5.58-5.68 (m, 1H) 5.43 (br. s., 1H) 5.01 (t, J=9.79 Hz, 1H) 4.49-4.71 (m, 3H) 4.02-4.08 (m, 1H) 3.99 (s, 3H) 3.85 (d, J=10.79 Hz, 1H) 2.65-2.77 (m, 2H) 2.36-2.54 (m, 2H) 1.86-2.03 (m, 3H) 1.65-1.83 (m, 4H) 1.42-1.62 (m, 6H) 1.16-1.36 (m, 10H) 0.94-1.07 (m, 6H). MS: MS m/z 840.89 (M$^+$+1).

Preparation of Compound 4213

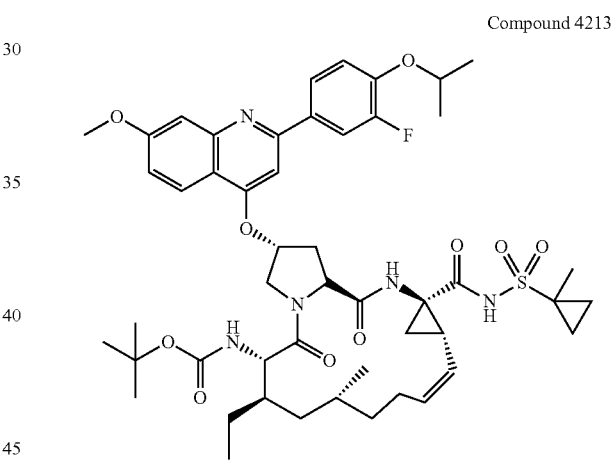

Compound 4213

Compound 4213 was prepared using the intermediates described herein and by following the general procedure described for the synthesis of Compound 1.

Compound 4213: tert-butyl (2R,6S,7R,9R,13aS,14aR,16aS,Z)-7-ethyl-2-(2-(3-fluoro-4-isopropoxyphenyl)-7-methoxyquinolin-4-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.07 (d, J=9.29 Hz, 1H) 7.84-7.95 (m, 2H) 7.39 (d, J=2.26 Hz, 1H) 7.25-7.31 (m, 2H) 7.08 (d, J=9.03 Hz, 1H) 6.73 (d, J=8.78 Hz, 1H) 5.63 (br. s., 2H) 5.03 (br. s., 1H) 4.75 (dt, J=12.11, 6.12 Hz, 1H) 4.56-4.68 (m, 1H) 4.06-4.17 (m, 2H) 3.97 (s, 3H) 2.80 (dd, J=13.30, 7.03 Hz, 2H) 2.38-2.57 (m, 2H) 1.98 (br. s., 2H) 1.73-1.83 (m, 1H) 1.50-1.67 (m, 10H) 1.42 (s, 9H) 1.31 (br. s., 2H) 1.17 (s, 10H) 1.00-1.08 (m, 4H) 0.87 (d, J=7.53 Hz, 4H). MS: MS m/z 935.13 (M$^+$+1).

Preparation of Compound 4214

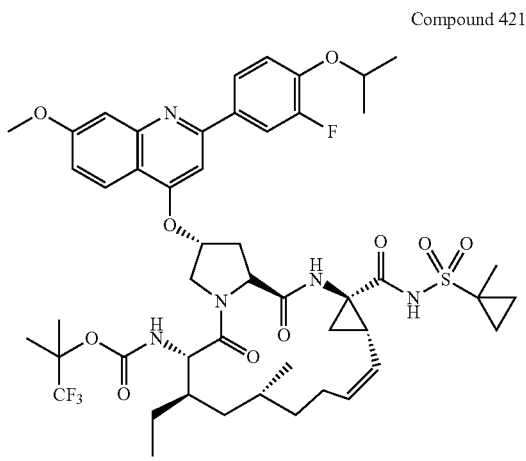

Compound 4214

Compound 4214 was prepared using the intermediates described herein and by following the general procedure described for the synthesis of Compound 3.

Compound 4214: 1,1,1-trifluoro-2-methylpropan-2-yl (2R,6S,7R,9R,13aS,14aR,16aS,Z)-7-ethyl-2-(2-(3-fluoro-4-isopropoxyphenyl)-7-methoxyquinolin-4-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.06 (d, J=9.29 Hz, 1H) 7.86-7.95 (m, 2H) 7.40 (d, J=2.26 Hz, 2H) 7.24-7.32 (m, 2H) 7.10 (dd, J=9.16, 2.38 Hz, 1H) 5.64 (br. s., 2H) 5.03 (br. s., 1H) 4.71-4.78 (m, 1H) 4.66 (d, J=17.07 Hz, 1H) 4.11 (d, J=11.29 Hz, 2H) 3.98 (s, 3H) 3.66-3.80 (m, 2H) 2.70-2.86 (m, 2H) 2.39-2.57 (m, 2H) 2.01 (br. s., 2H) 1.78 (dd, J=8.28, 5.77 Hz, 1H) 1.49-1.64 (m, 9H) 1.38-1.47 (m, 11H) 1.31 (s, 2H) 1.16 (d, J=11.54 Hz, 1H) 1.03 (br. s., 4H) 0.84-0.93 (m, 4H). MS: MS m/z 989.09 (M$^+$+1).

Preparation of Compound 4215

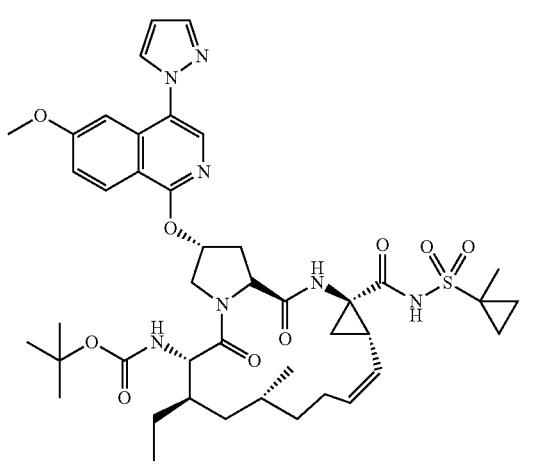

Compound 4215

Compound 4215 was prepared using the intermediates described herein and by following the general procedure described for the synthesis of Compound 1.

Compound 4215: tert-butyl (2R,6S,7R,9R,13aS,14aR,16aS,Z)-7-ethyl-2-(6-methoxy-4-(1H-pyrazol-1-yl)isoquinolin-1-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 9.05 (s, 1H) 8.70 (d, J=2.51 Hz, 1H) 8.09 (d, J=9.03 Hz, 1H) 7.79 (s, 1H) 7.72 (s, 1H) 7.23-7.31 (m, 1H) 7.27 (d, J=2.26 Hz, 1H) 7.02-7.09 (m, 1H) 7.02-7.10 (m, 1H) 6.55-6.60 (m, 1H) 6.05 (br. s., 1H) 5.63 (br. s., 1H) 4.97-5.07 (m, 1H) 4.64 (dd, J=9.66, 7.15 Hz, 1H) 4.08-4.18 (m, 2H) 3.96 (s, 3H) 2.70-2.86 (m, 2H) 2.41-2.58 (m, 2H) 1.92-2.04 (m, 2H) 1.77 (dd, J=8.28, 5.52 Hz, 1H) 1.49-1.69 (m, 10H) 1.39-1.48 (m, 2H) 0.95-1.07 (m, 7H) 0.95-1.06 (m, 5H) 0.78-0.92 (m, 8H). MS: MS m/z 849.02 (M$^+$+1).

Preparation of Compound 4216

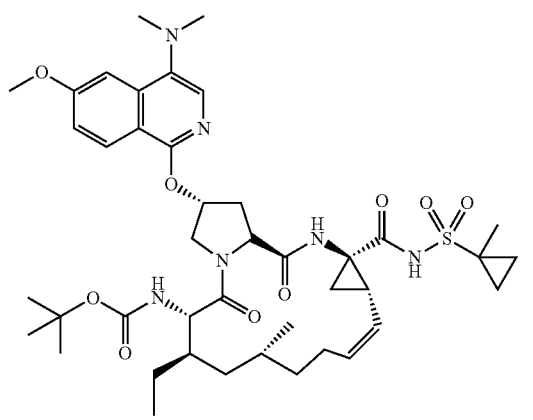

Compound 4216

Compound 4216 was prepared using the intermediates described herein and by following the general procedure described for the synthesis of Compound 1.

Compound 4216: tert-butyl (2R,6S,7R,9R,13aS,14aR,16aS,Z)-2-(4-(dimethylamino)-6-methoxyisoquinolin-1-yloxy)-7-ethyl-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.10 (d, J=9.03 Hz, 1H) 7.70 (s, 1H) 7.44 (d, J=2.51 Hz, 1H) 7.41-7.47 (m, 1H) 7.11 (dd, J=8.91, 2.38 Hz, 1H) 6.63 (d, J=8.78 Hz, 1H) 5.84 (br. s., 1H) 5.62 (d, J=5.27 Hz, 1H) 5.01 (t, J=9.79 Hz, 1H) 4.58-4.66 (m, 1H) 4.01-4.16 (m, 2H) 3.97 (s, 3H) 2.87 (s, 6H) 2.68-2.79 (m, 2H) 2.36-2.48 (m, 2H) 1.97 (d, J=11.80 Hz, 2H) 1.77 (dd, J=8.03, 5.77 Hz, 1H) 1.51-1.69 (m, 10H) 1.39-1.46 (m, 2H) 1.22-1.35 (m, 3H) 1.16 (br. s., 9H) 0.96-1.05 (m, 2H) 0.81-0.94 (m, 6H). MS: MS m/z 826.03 (M$^+$+1).

Preparation of Compound 4219

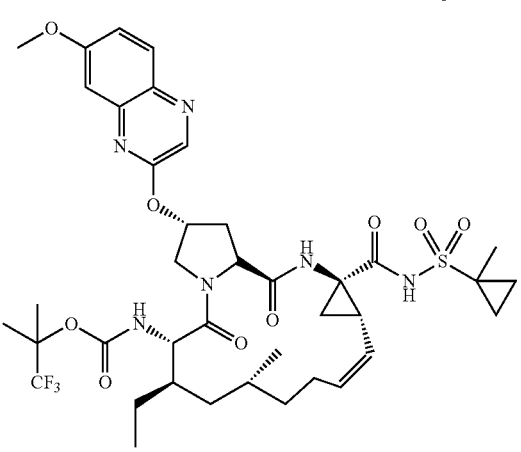

Compound 4219

Compound 4219 was prepared using the intermediates described herein and by following the general procedure described for the synthesis of Compound 3.

Compound 4219: 1,1,1-trifluoro-2-methylpropan-2-yl (2R,6S,7R,9R,13aS,14aR,16aS,Z)-7-ethyl-2-(7-methoxy-quinoxalin-2-yloxy)-9-methyl-14a-(1-methylcyclopropyl-sulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.26 (s, 1H) 7.87 (d, J=9.04 Hz, 1H) 7.26-7.37 (m, 2H) 5.92 (br. s., 1H) 5.58-5.68 (m, 1H) 5.02 (t, J=10.16 Hz, 2H) 4.74 (d, J=11.29 Hz, 1H) 4.58-4.66 (m, 1H) 3.97-4.12 (m, 5H) 3.70-3.79 (m, 1H) 2.66-2.74 (m, 2H) 2.37-2.54 (m, 2H) 1.97 (d, J=11.80 Hz, 2H) 1.78 (dd, J=8.41, 5.65 Hz, 1H) 1.49-1.61 (m, 9H) 1.29-1.40 (m, 13H) 1.01 (d, J=6.53 Hz, 4H) 0.87-0.94 (m, 5H). MS: MS m/z 837.2 (M$^+$+1).

Preparation of Compound 4220

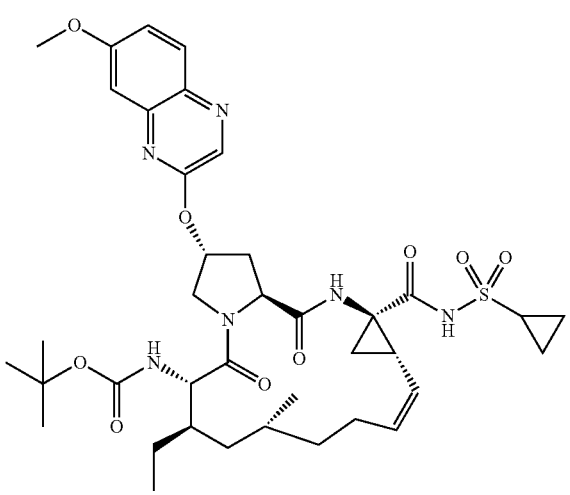

Compound 4220

Compound 4220 was prepared using the intermediates described herein and by following the general procedure described for the synthesis of Compound 1.

Compound 4220: tert-butyl (2R,6S,7R,9R,13aS,14aR,16aS,Z)-14a-(1-(fluoromethyl)cyclopropylsulfonylcarbamoyl)-2-(6-methoxy-3-methylquinoxalin-2-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.24 (s, 1H) 7.85 (d, J=9.29 Hz, 2H) 7.82-7.88 (m, 1H) 7.24-7.35 (m, 3H) 7.24-7.34 (m, 3H) 5.92 (br. s., 1H) 5.61 (d, J=5.77 Hz, 1H) 5.15 (br. s., 1H) 4.71 (d, J=12.30 Hz, 1H) 4.54-4.63 (m, 2H) 4.03-4.11 (m, 3H) 3.94-4.00 (m, 3H) 2.90 (br. s., 1H) 2.66 (d, J=7.78 Hz, 2H) 2.35-2.56 (m, 2H) 1.89-2.05 (m, 3H) 1.78 (dd, J=8.28, 5.52 Hz, 1H) 1.40-1.62 (m, 6H) 1.25-1.35 (m, 3H) 1.09-1.19 (m, 11H) 1.02 (d, J=6.78 Hz, 4H) 0.82 (t, J=7.28 Hz, 2H). MS: MS m/z 769.52 (M$^+$+1).

Preparation of Compound 4221

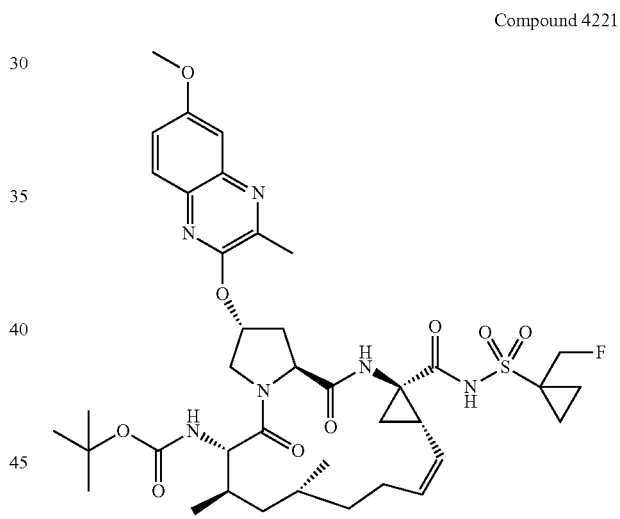

Compound 4221

Compound 4221 was prepared using the intermediates described herein and by following the general procedure described for the synthesis of Compound 1.

Compound 4221: tert-butyl (2R,6S,7R,9R,13aS,14aR,16aS,Z)-14a-(1-(fluoromethyl)cyclopropylsulfonylcarbamoyl)-2-(6-methoxy-3-methylquinoxalin-2-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.77 (d, J=9.04 Hz, 1H) 7.27-7.36 (m, 2H) 5.89 (br. s., 1H) 5.56-5.66 (m, 1H) 5.00 (t, J=10.16 Hz, 1H) 4.59-4.72 (m, 3H) 4.05 (dd, J=11.80, 3.26 Hz, 1H) 3.94 (s, 3H) 3.77-3.82 (m, 1H) 2.69 (dd, J=13.30, 7.53 Hz, 2H) 2.56 (s, 3H) 2.36-2.51 (m, 2H) 1.92-2.01 (m, 1H) 1.85 (br. s., 2H) 1.70-1.75 (m, 2H) 1.63-1.68 (m, 1H) 1.55-1.60 (m, 1H) 1.44-1.53 (m, 3H) 1.22-1.32 (m, 3H) 1.18 (s, 9H) 1.00 (dd, J=19.45, 6.65 Hz, 6H) 0.80-0.87 (m, 1H). MS: MS m/z 801.5 (M$^+$+1).

Preparation of Compound 4222

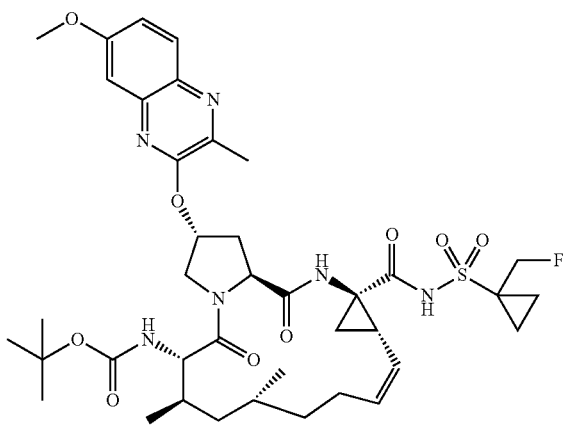

Compound 4222

Compound 4222 was prepared using the intermediates described herein and by following the general procedure described for the synthesis of Compound 1.

Compound 4222: tert-butyl (2R,6S,7R,9R,13aS,14aR,16aS,Z)-14a-(1-(fluoromethyl)cyclopropylsulfonylcarbamoyl)-2-(7-methoxy-3-methylquinoxalin-2-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 7.77 (d, J=9.04 Hz, 1H) 7.27-7.36 (m, 2H) 5.89 (br. s., 1H) 5.56-5.66 (m, 1H) 5.00 (t, J=10.16 Hz, 1H) 4.59-4.72 (m, 3H) 4.05 (dd, J=11.80, 3.26 Hz, 1H) 3.94 (s, 3H) 3.77-3.82 (m, 1H) 2.69 (dd, J=13.30, 7.53 Hz, 2H) 2.56 (s, 3H) 2.36-2.51 (m, 2H) 1.92-2.01 (m, 1H) 1.85 (br. s., 2H) 1.70-1.75 (m, 2H) 1.63-1.68 (m, 1H) 1.55-1.60 (m, 1H) 1.44-1.53 (m, 3H) 1.22-1.32 (m, 3H) 1.18 (s, 9H) 1.00 (dd, J=19.45, 6.65 Hz, 6H) 0.80-0.87 (m, 1H). MS: MS m/z 801.4 (M$^+$+1).

Preparation of Compound 4223

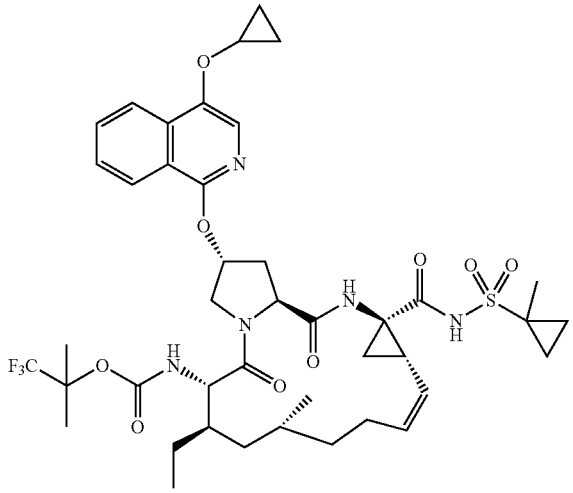

Compound 4223

Compound 4223 was prepared using the intermediates described herein and by following the general procedure described for the synthesis of Compound 3.

Compound 4223: 1,1,1-trifluoro-2-methylpropan-2-yl (2R,6S,7R,9R,13aS,14aR,16aS,Z)-2-(4-cyclopropoxyisoquinolin-1-yloxy)-7-ethyl-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.16 (d, J=8.28 Hz, 1H) 8.04 (d, J=8.53 Hz, 1H) 7.89-7.92 (m, 1H) 7.72 (td, J=7.65, 1.00 Hz, 1H) 7.53-7.59 (m, 1H) 7.29 (d, J=8.78 Hz, 1H) 5.86 (br. s., 1H) 5.63 (td, J=10.10, 5.65 Hz, 1H) 5.01 (t, J=10.16 Hz, 1H) 4.82 (d, J=7.78 Hz, 1H) 4.68 (dd, J=10.16, 7.15 Hz, 1H) 3.97-4.12 (m, 3H) 2.69-2.80 (m, 2H) 2.38-2.49 (m, 2H) 1.93-2.05 (m, 2H) 1.78 (dd, J=8.41, 5.65 Hz, 1H) 1.64-1.70 (m, 1H) 1.55-1.62 (m, 4H) 1.48-1.54 (m, 5H) 1.40-1.47 (m, 2H) 1.36 (s, 3H) 1.22-1.32 (m, 1H) 1.14 (t, J=12.17 Hz, 1H) 1.02 (d, J=6.78 Hz, 3H) 0.89-0.93 (m, 6H) 0.81-0.87 (m, 5H). MS: MS m/z 860.4 (M$^+$−1).

Preparation of Compound 4224

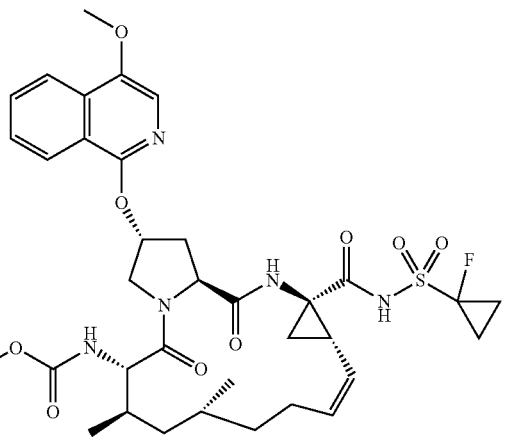

Compound 4224

Compound 4224 was prepared using the intermediates described herein and by following the general procedure described for the synthesis of Compound 1.

Compound 4224: 1,1,1-trifluoro-2-methylpropan-2-yl (2R,6S,7R,9R,13aS,14aR,16aS,Z)-2-(4-ethoxy-6-methoxyisoquinolin-1-yloxy)-7-ethyl-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.77 (d, J=9.03 Hz, 2H) 7.29 (d, J=2.51 Hz, 2H) 7.22 (dd, J=9.03, 2.76 Hz, 2H) 5.92 (br. s., 1H) 5.62 (d, J=6.02 Hz, 1H) 5.01 (br. s., 1H) 4.72 (d, J=11.29 Hz, 1H) 4.55-4.65 (m, 1H) 4.07 (dd, J=11.67, 3.39 Hz, 1H) 3.96 (s, 3H) 3.77-3.85 (m, 1H) 2.66-2.74 (m, 2H) 2.50-2.57 (m, 4H) 1.93-2.03 (m, 1H) 1.78-1.85 (m, 2H) 1.73 (dd, J=8.53, 5.52 Hz, 2H) 1.58 (dd, J=9.29, 5.52 Hz, 1H) 1.49 (d, J=8.53 Hz, 2H) 1.22-1.32 (m, 3H) 1.13-1.20 (m, 9H) 1.00 (dd, J=18.70, 6.65 Hz, 6H). MS: MS m/z 772.9 (M$^+$+1).

Preparation of Compound 4225

Compound 4225

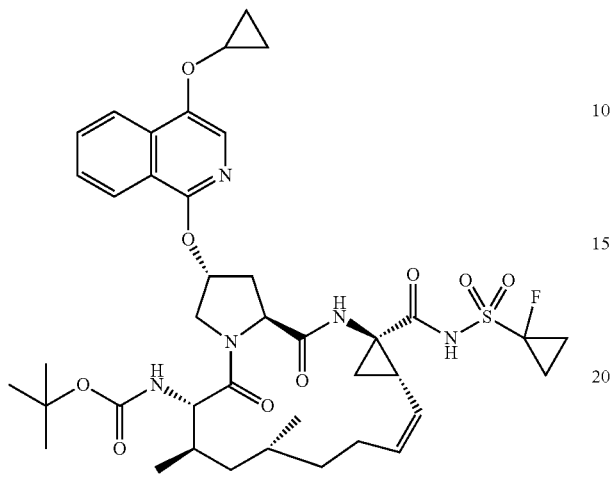

Compound 4225 was prepared using the intermediates described herein and by following the general procedure described for the synthesis of Compound 1.

Compound 4225: tert-butyl (2R,6S,7R,9R,13aS,14aR,16aS,Z)-2-(4-cyclopropoxyisoquinolin-1-yloxy)-14a-(1-fluorocyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

$^1$H NMR (400 MHz, CD$_3$OD): δ ppm 8.16 (d, J=8.28 Hz, 1H) 7.99-8.03 (m, 1H) 7.87 (s, 1H) 7.70 (t, J=7.65 Hz, 1H) 7.51-7.56 (m, 1H) 5.82 (br. s., 1H) 5.54 (br. s., 1H) 4.70 (br. s., 1H) 4.57 (br. s., 1H) 4.05 (dd, J=11.67, 3.14 Hz, 1H) 3.98 (tt, J=5.99, 2.92 Hz, 1H) 3.90 (d, J=10.79 Hz, 1H) 3.06 (q, J=7.28 Hz, 2H) 2.72 (d, J=7.03 Hz, 2H) 2.33-2.52 (m, 3H) 1.98 (br. s., 1H) 1.83 (br. s., 3H) 1.72 (br. s., 1H) 1.58 (br. s., 1H) 1.45 (d, J=6.78 Hz, 3H) 1.32 (t, J=7.28 Hz, 3H) 1.11 (s, 8H) 0.97-1.02 (m, 4H) 0.87-0.92 (m, 3H) 0.81-0.86 (m, 3H). MS: MS m/z 798.7 (M$^+$+1).

Preparation of Compound 4226

Compound 4226

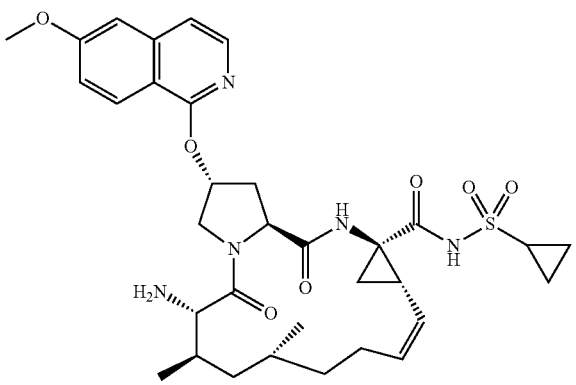

Compound 4226 was prepared using the intermediates described herein and by following the general procedure described for the synthesis of Compound 3.

Compound 4226: (2R,6S,7R,9R,13aS,14aR,16aS,Z)-6-amino-N-(cyclopropylsulfonyl)-2-((6-methoxyisoquinolin-1-yl)oxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. MS: MS m/z 654.3 (M$^+$−36).

Preparation of Compound 4227

Compound 4227

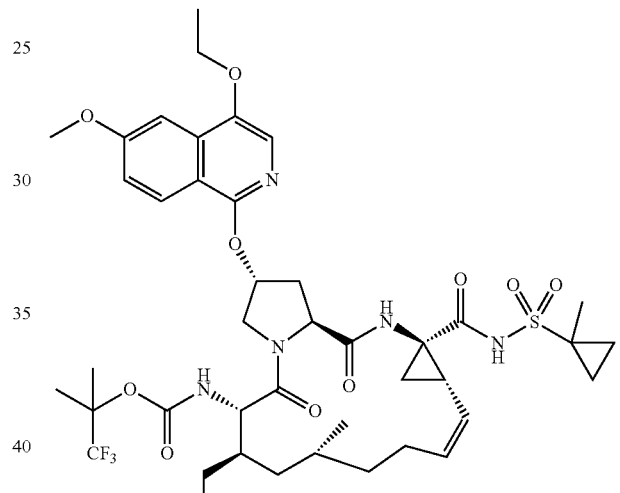

Compound 4227 was prepared using the intermediates described herein and by following the general procedure described for the synthesis of Compound 3.

Compound 4227: 1,1,1-trifluoro-2-methylpropan-2-yl (2R,6S,7R,9R,13aS,14aR,16aS,Z)-2-(4-ethoxy-6-methoxy-isoquinolin-1-yloxy)-7-ethyl-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.05 (d, J=9.03 Hz, 1H) 7.53 (s, 1H) 7.45 (d, J=2.51 Hz, 1H) 7.15 (dd, J=9.16, 2.64 Hz, 1H) 5.82 (br. s., 1H) 5.63 (d, J=5.77 Hz, 1H) 5.01 (t, J=9.66 Hz, 2H) 4.74 (d, J=11.29 Hz, 1H) 4.65 (dd, J=10.04, 7.03 Hz, 1H) 4.25 (q, J=6.86 Hz, 2H) 3.99-4.11 (m, 2H) 3.96 (s, 3H) 2.74 (d, J=9.79 Hz, 2H) 2.44 (d, J=10.04 Hz, 2H) 1.94-2.04 (m, 2H) 1.77 (dd, J=8.41, 5.65 Hz, 1H) 1.51-1.60 (m, 10H) 1.37-1.44 (m, 5H) 1.31 (s, 3H) 1.09-1.19 (m, 1H) 0.98-1.04 (m, 6H) 0.85-0.93 (m, 4H). MS: MS m/z 880.4 (M$^+$+1).

Preparation of Compound 4228

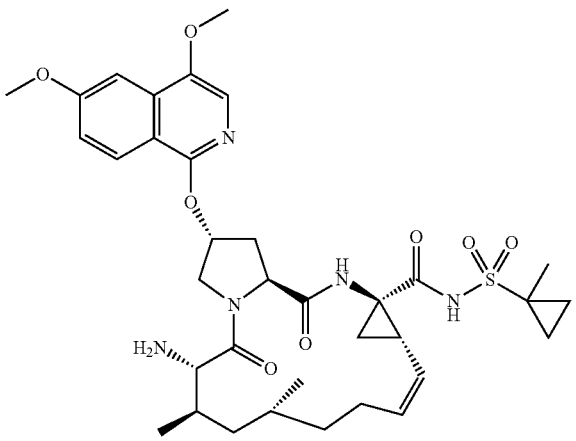

Compound 4228

Compound 4228 was prepared using the intermediates described herein and by following the general procedure described for the synthesis of Compound 3.

Compound 4228: (2R,6S,7R,9R,13aS,14aR,16aS,Z)-6-amino-2-(4,6-dimethoxyisoquinolin-1-yloxy)-7,9-dimethyl-N-(1-methylcyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide: $^1$H NMR (400 MHz, CD$_3$OD): δ ppm 8.10 (d, J=9.29 Hz, 1H) 7.53 (s, 1H) 7.46 (d, J=2.26 Hz, 1H) 7.23 (dd, J=9.16, 2.13 Hz, 1H) 5.90 (br. s., 1H) 5.60-5.69 (m, 1H) 5.04 (t, J=10.04 Hz, 1H) 4.69-4.74 (m, 1H) 4.22-4.28 (m, 1H) 4.11-4.17 (m, 1H) 4.03 (s, 3H) 3.96 (s, 3H) 3.79 (d, J=10.29 Hz, 1H) 2.67-2.79 (m, 2H) 2.49-2.59 (m, 2H) 2.04 (dd, J=13.30, 7.78 Hz, 2H) 1.92 (br. s., 1H) 1.78-1.84 (m, 1H) 1.66 (d, J=10.04 Hz, 1H) 1.55-1.59 (m, 2H) 1.53 (s, 3H) 1.32-1.50 (m, 4H) 1.13 (d, J=6.27 Hz, 3H) 1.06 (d, J=7.03 Hz, 3H) 0.97-1.02 (m, 1H) 0.90 (s, 2H) MS: MS m/z 696.2 (M$^+$−1).

Preparation of Compound 4229

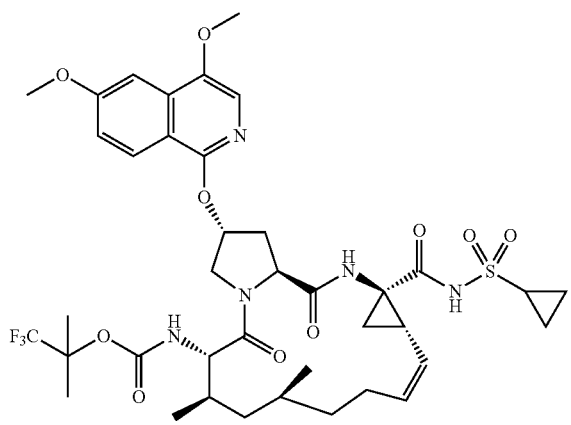

Compound 4229

Compound 4229 was prepared using the intermediates described herein and by following the general procedure described for the synthesis of Compound 3.

Compound 4229: 1,1,1-trifluoro-2-methylpropan-2-yl (2R,6S,7R,9S,13aS,14aR,16aS,Z)-14a-(cyclopropylsulfonylcarbamoyl)-2-(4,6-dimethoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate: $^1$H NMR (400 MHz, CD$_3$OD): δ ppm 8.07 (d, J=9.29 Hz, 1H) 7.53 (s, 1H) 7.44 (d, J=2.51 Hz, 1H) 7.14 (dd, J=9.03, 2.51 Hz, 1H) 5.81 (br. s., 1H) 5.58-5.67 (m, 1H) 5.05 (br. s., 1H) 4.56-4.73 (m, 3H) 4.03 (s, 3H) 3.95 (s, 3H) 3.83 (d, J=10.79 Hz, 1H) 2.93 (td, J=8.34, 4.14 Hz, 1H) 2.73 (dd, J=13.18, 6.15 Hz, 2H) 2.37-2.47 (m, 2H) 1.92-2.06 (m, 1H) 1.74-1.92 (m, 3H) 1.59 (dd, J=9.54, 5.52 Hz, 1H) 1.50 (d, J=7.03 Hz, 2H) 1.39 (s, 3H) 1.21-1.33 (m, 3H) 1.10 (dd, J=9.79, 5.27 Hz, 2H) 1.02-1.05 (m, 7H) 0.99 (d, J=6.53 Hz, 3H) 0.83 (t, J=13.68 Hz, 1H). MS: MS m/z 836.2 (M$^+$−1).

Preparation of Compound 4230

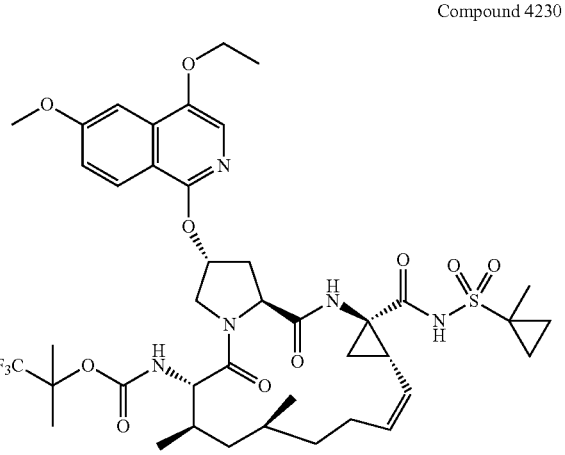

Compound 4230

Compound 4230 was prepared using the intermediates described herein and by following the general procedure described for the synthesis of Compound 3.

Compound 4230: 1,1,1-trifluoro-2-methylpropan-2-yl (2R,6S,7R,9S,13aS,14aR,16aS,Z)-2-(4-ethoxy-6-methoxyisoquinolin-1-yloxy)-7,9-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate: $^1$H NMR (400 MHz, CD$_3$OD): δ ppm 9.06 (s, 1H) 8.07 (d, J=9.03 Hz, 1H) 7.52 (s, 1H) 7.45 (d, J=2.26 Hz, 1H) 7.15 (dd, J=9.03, 2.51 Hz, 1H) 5.81 (br. s., 1H) 5.63 (td, J=10.48, 5.40 Hz, 1H) 5.01 (t, J=9.79 Hz, 1H) 4.63-4.74 (m, 2H) 4.24 (q, J=7.03 Hz, 2H) 3.99-4.06 (m, 1H) 3.96 (s, 3H) 3.84 (d, J=10.54 Hz, 1H) 2.67-2.77 (m, 2H) 2.35-2.48 (m, 2H) 1.74-2.01 (m, 4H) 1.63-1.70 (m, 1H) 1.51-1.59 (m, 8H) 1.42-1.49 (m, 2H) 1.39 (s, 3H) 1.20-1.32 (m, 1H) 0.98-1.05 (m, 9H) 0.81-0.92 (m, 3H). MS: MS m/z 864.4 (M$^+$−1).

Preparation of Compound 4231

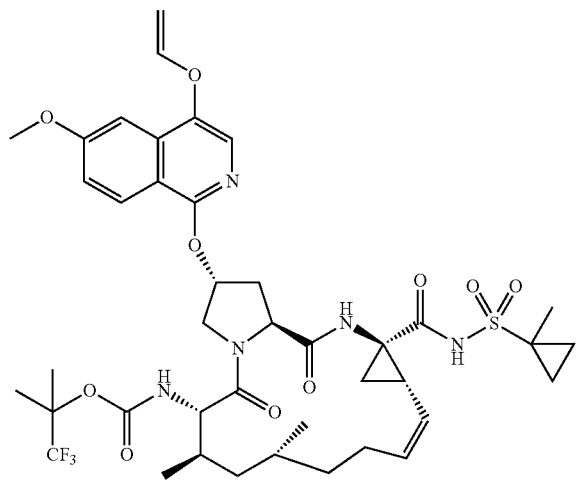

Compound 4231

Compound 4231 was prepared using the intermediates described herein and by following the general procedure described for the synthesis of Compound 3.

Compound 4231: (2R,6S,7R,9R,13aS,14aR,16aS,Z)-6-amino-N-(cyclopropylsulfonyl)-2-(6-methoxyisoquinolin-1-yloxy)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide. MS: MS m/z 864.95 (M$^+$+1).

Preparation of Compound 4232

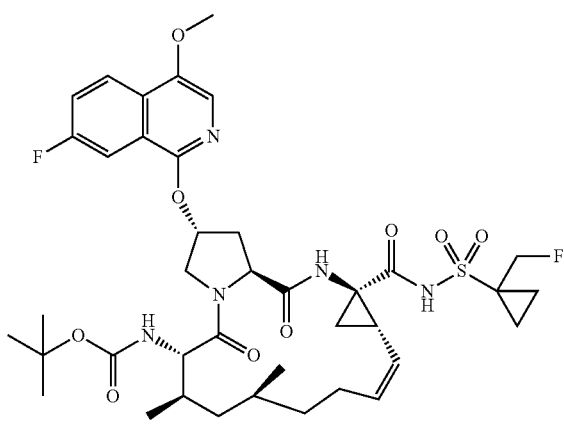

Compound 4232

Compound 4232 was prepared using the intermediates described herein and by following the general procedure described for the synthesis of Compound 1.

Compound 4232: 1 tert-butyl (2R,6S,7R,9S,13aS,14aR,16aS,Z)-2-(7-fluoro-4-methoxyisoquinolin-1-yloxy)-14a-(1-(fluoromethyl)cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate: $^1$H NMR (400 MHz, CD$_3$OD): δ ppm 8.17 (dd, J=9.16, 5.14 Hz, 1H) 7.77 (d, J=7.53 Hz, 1H) 7.51-7.57 (m, 2H) 5.84 (br. s., 1H) 5.60-5.72 (m, 1H) 4.62-4.72 (m, 2H) 4.50 (d, J=11.80 Hz, 1H) 4.17 (d, J=7.53 Hz, 1H) 4.03 (s, 3H) 2.66-2.73 (m, 1H) 2.49 (br. s., 2H) 1.99 (br. s., 2H) 1.62 (br. s., 5H) 1.36-1.50 (m, 5H) 1.28-1.33 (m, 2H) 1.22 (s, 9H) 1.11 (d, J=6.78 Hz, 7H) 0.93 (br. s., 3H). MS: MS m/z 803.4 (M$^+$−1).

Preparation of Compound 4234

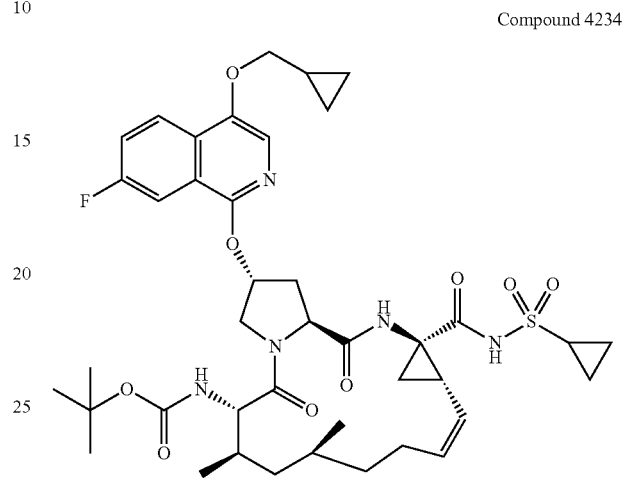

Compound 4234

Compound 4234 was prepared using the intermediates described herein and by following the general procedure described for the synthesis of Compound 1.

Compound 4234: tert-butyl (2R,6S,7R,9S,13aS,14aR,16aS,Z)-2-(4-(cyclopropylmethoxy)-7-fluoroisoquinolin-1-yloxy)-14a-(cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate: $^1$H NMR (400 MHz, CD$_3$OD): δ ppm 8.23 (dd, J=8.91, 5.40 Hz, 1H) 7.76 (dd, J=9.54, 2.26 Hz, 1H) 7.52-7.58 (m, 2H) 5.83 (br. s., 1H) 5.69 (d, J=8.78 Hz, 1H) 5.20 (br. s., 1H) 4.59-4.70 (m, 1H) 4.51 (d, J=11.04 Hz, 1H) 4.15 (d, J=6.78 Hz, 2H) 4.03 (d, J=6.78 Hz, 2H) 3.24 (s, 1H) 2.90 (d, J=4.77 Hz, 1H) 2.71 (dd, J=13.80, 7.78 Hz, 2H) 2.41-2.53 (m, 2H) 1.98 (d, J=4.52 Hz, 3H) 1.70-1.78 (m, 2H) 1.65 (br. s., 1H) 1.29-1.45 (m, 7H) 1.21 (s, 9H) 1.09 (d, J=6.78 Hz, 3H) 0.93 (d, J=7.03 Hz, 3H) 0.66-0.73 (m, 2H) 0.43-0.48 (m, 2H); MS: MS m/z 812.4 (M$^+$+1).

Preparation of Compound 4235

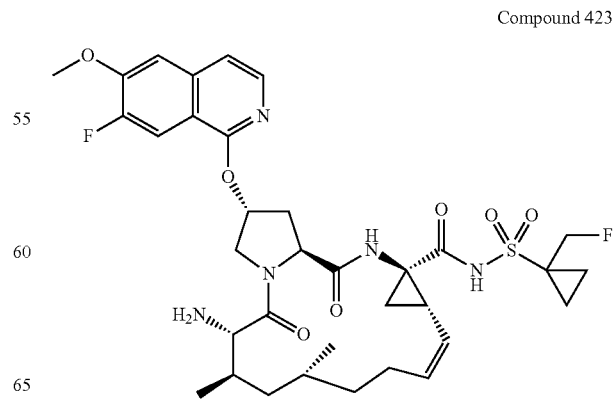

Compound 4235

Compound 4235 was prepared using the intermediates described herein and by following the general procedure described for the synthesis of Compound 3.

Compound 4235: (2R,6S,7R,9R,13aS,14aR,16aS,Z)-6-amino-2-(7-fluoro-6-methoxyisoquinolin-1-yloxy)-N-(1-(fluoromethyl)cyclopropylsulfonyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide: $^1$H NMR (400 MHz, CD$_3$OD): δ ppm 9.16 (s, 1H) 7.95 (d, J=5.77 Hz, 1H) 7.86 (d, J=11.54 Hz, 1H) 7.44 (d, J=8.03 Hz, 1H) 7.35 (d, J=6.02 Hz, 1H) 5.97 (br. s., 1H) 5.63 (td, J=10.29, 5.52 Hz, 1H) 5.03 (t, J=10.16 Hz, 1H) 4.78-4.82 (m, 1H) 4.71 (dd, J=9.41, 7.40 Hz, 1H) 4.47-4.63 (m, 1H) 4.24-4.29 (m, 1H) 4.13-4.17 (m, 1H) 4.04 (s, 3H) 3.79 (d, J=10.29 Hz, 1H) 3.66-3.71 (m, 3H) 3.46-3.54 (m, 2H) 2.45-2.79 (m, 2H) 1.98-2.13 (m, 2H) 1.85-1.94 (m, 1H) 1.65-1.77 (m, 3H) 1.53-1.61 (m, 2H) 1.30-1.48 (m, 2H) 1.20 (t, J=7.03 Hz, 3H) 1.13 (d, J=6.53 Hz, 3H) 1.06 (d, J=6.78 Hz, 3H) 0.96-1.02 (m, 1H). MS: MS m/z 704.8 (M$^+$+1).

Preparation of Compound 4236

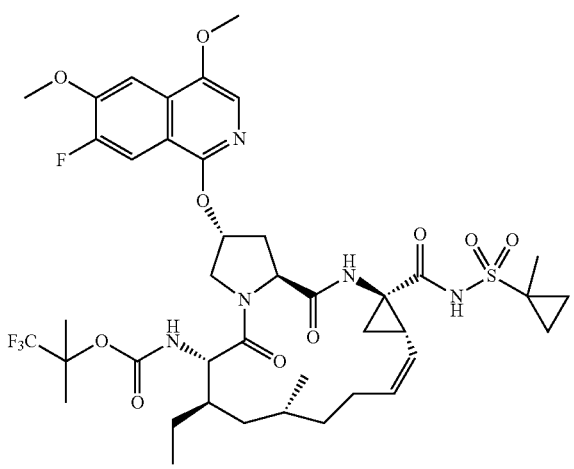

Compound 4236

Compound 4236 was prepared using the intermediates described herein and by following the general procedure described for the synthesis of Compound 3.

Compound 4236: 1,1,1-trifluoro-2-methylpropan-2-yl (2R,6S,7R,9R,13aS,14aR,16aS,Z)-7-ethyl-2-(7-fluoro-4,6-dimethoxyisoquinolin-1-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate: $^1$H NMR (400 MHz, CD$_3$OD): δ ppm 7.73 (d, J=11.54 Hz, 1H) 7.53-7.60 (m, 2H) 5.82 (br. s., 1H) 5.62 (td, J=10.10, 6.40 Hz, 1H) 5.01 (t, J=9.91 Hz, 1H) 4.57-4.75 (m, 3H) 3.98-4.08 (m, 8H) 2.67-2.77 (m, 2H) 2.37-2.47 (m, 2H) 1.92-2.04 (m, 2H) 1.73-1.79 (m, 1H) 1.54-1.69 (m, 6H) 1.52 (s, 3H) 1.44 (d, J=3.76 Hz, 2H) 1.40 (s, 3H) 1.21-1.34 (m, 1H) 1.12-1.17 (m, 1H) 1.09 (s, 3H) 1.01 (d, J=6.78 Hz, 3H) 0.87-0.93 (m, 2H) 0.81-0.85 (m, 3H). MS: MS m/z 884.5 (M$^+$+1).

Preparation of Compound 4237

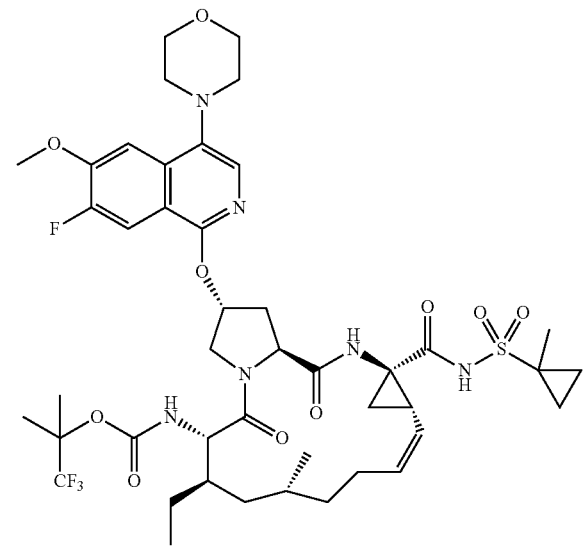

Compound 4237

Compound 4237 were prepared using the intermediates described herein and by following the general procedure described for the synthesis of Compound 3.

Compound 4237: 1,1,1-trifluoro-2-methylpropan-2-yl (2R,6S,7R,9R,13aS,14aR,16aS,Z)-7-ethyl-2-(7-methoxyquinoxalin-2-yloxy)-9-methyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.74-7.81 (m, 2H) 7.60 (d, J=8.28 Hz, 1H) 5.86 (br. s., 1H) 5.62 (d, J=5.27 Hz, 1H) 5.04 (br. s., 1H) 4.73 (d, J=11.54 Hz, 1H) 4.64 (dd, J=10.16, 7.15 Hz, 1H) 4.02-4.09 (m, 5H) 3.94-4.00 (m, 5H) 3.06-3.12 (m, 4H) 2.68-2.78 (m, 2H) 2.44 (ddd, J=13.80, 10.04, 4.02 Hz, 2H) 1.94-2.04 (m, 3H) 1.77 (dd, J=8.41, 5.65 Hz, 1H) 1.57-1.68 (m, 4H) 1.53 (s, 4H) 1.38-1.45 (m, 4H) 1.08-1.18 (m, 4H) 1.02 (d, J=6.78 Hz, 3H) 0.81-0.92 (m, 6H). MS: MS m/z 939.4 (M$^+$+1).

Preparation of Compound 4238

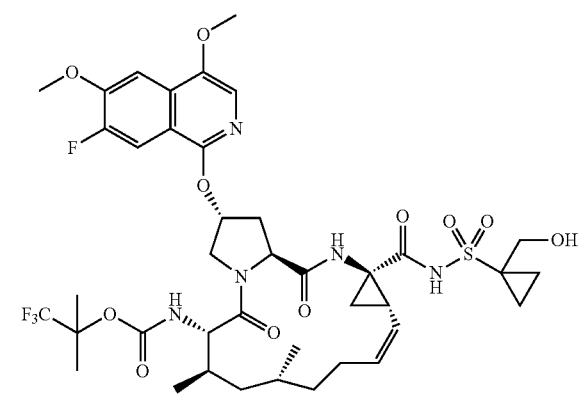

Compound 4238

Compound 4238 was prepared using the intermediates described herein and by following the general procedure described for the synthesis of Compound 3.

Compound 4238: 1,1,1-trifluoro-2-methylpropan-2-yl (2R,6S,7R,9R,13aS,14aR,16aS,Z)-2-(7-fluoro-4,6-dimethoxyisoquinolin-1-yloxy)-14a-(1-(hydroxymethyl)cyclopropylsulfonylcarbamoyl)-7,9-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate: $^1$H NMR (400 MHz, CD$_3$OD): δ ppm 8.78 (s, 1H) 7.76 (d, J=11.54 Hz, 1H) 7.53-7.61 (m, 2H) 5.80 (br. s., 1H) 5.58 (td, J=10.35, 5.14 Hz, 1H) 5.34-5.43 (m, 1H) 4.52-4.66 (m, 3H) 4.38 (d, J=12.30 Hz, 1H) 4.04 (d, J=0.75 Hz, 6H) 3.99 (dd, J=11.29, 3.51 Hz, 1H) 3.83 (d, J=11.04 Hz, 1H) 2.57-2.72 (m, 2H) 2.37-2.50 (m, 2H) 1.80-1.92 (m, 3H) 1.66-1.74 (m, 2H) 1.39-1.45 (m, 5H) 1.31 (s, 2H) 1.19-1.28 (m, 2H) 1.16 (s, 3H) 1.08 (dd, J=9.29, 2.01 Hz, 1H) 0.98-1.04 (m, 6H) 0.92 (br. s., 1H) 0.78 (t, J=11.67 Hz, 1H). MS: MS m/z 886.96 (M$^+$+1).

Preparation of Compound 4239

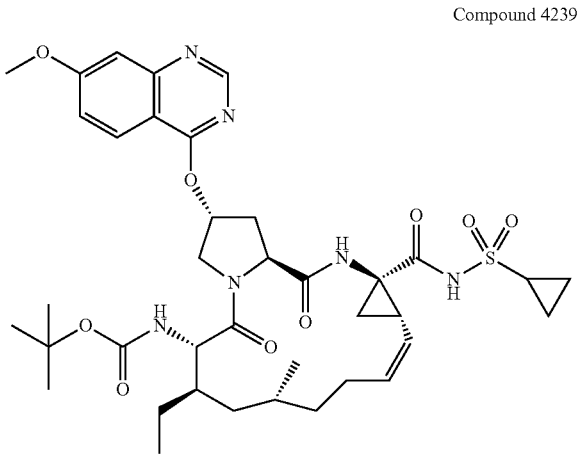 [SMILES: CC[C@@H]1C[C@H](C)CC/C=C\[C@@H]2C[C@@]2(C(=O)NS(=O)(=O)C2CC2)NC(=O)[C@@H]2C[C@@H](Oc3ncnc4cc(OC)ccc34)CN2C(=O)[C@H]1NC(=O)OC(C)(C)C]

Compound 4239

Compound 4239 was prepared using the intermediates described herein and by following the general procedure described for the synthesis of Compound 1.

Compound 4239: tert-butyl ((2R,6S,7R,9R,13aS,14aR,16aS,Z)-14a-((cyclopropylsulfonyl)carbamoyl)-7-ethyl-2-((7-methoxyquinazolin-4-yl)oxy)-9-methyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. $^1$H NMR (400 MHz, CD$_3$OD): δ ppm 8.73 (s, 1H) 8.08 (d, J=9.29 Hz, 1H) 7.26 (d, J=2.26 Hz, 1H) 7.20 (dd, J=9.03, 2.51 Hz, 1H) 6.63 (d, J=8.28 Hz, 1H) 6.00 (br. s., 1H) 5.63 (td, J=10.16, 6.53 Hz, 1H) 5.05 (t, J=10.04 Hz, 1H) 4.64 (dd, J=10.04, 7.28 Hz, 1H) 4.01-4.08 (m, 2H) 3.98 (s, 3H) 2.89-2.97 (m, 1H) 2.68-2.81 (m, 2H) 2.35-2.53 (m, 2H) 1.90-2.03 (m, 2H) 1.79 (dd, J=8.28, 5.77 Hz, 1H) 1.44-1.63 (m, 7H) 1.24-1.38 (m, 3H) 1.06-1.17 (m, 12H) 1.02 (d, J=6.53 Hz, 3H) 0.83 (t, J=7.40 Hz, 3H). MS: MS m/z 769.92 (M$^+$+1).

Biological Studies

HCV NS3/4A protease complex enzyme assays and cell-based HCV replicon assays were utilized in the present disclosure, and were prepared, conducted and validated as follows:

Generation of Recombinant HCV NS3/4A Protease Complex

HCV NS3 protease complexes, derived from the BMS strain, H77 strain or J4L6S strain, were generated, as described below. These purified recombinant proteins were generated for use in a homogeneous assay (see below) to provide an indication of how effective compounds of the present disclosure would be in inhibiting HCV NS3 proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, *J. Clin. Microbiol.*, 31(6), 1493-1503 (1993)). The amino acid sequence of the nonstructural region, NS2-5B, was shown to be >97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in Genbank (AAB67036, see Yanagi, M., Purcell, R. H., Emerson, S. U. and Bukh, *J. Proc. Natl. Acad. Sci. U.S.A.* 94(16), 8738-8743 (1997); AF054247, see Yanagi, M., St Claire, M., Shapiro, M., Emerson, S. U., Purcell, R. H. and Bukh, J., *Virology* 244 (1), 161-172. (1998)).

The H77 and J4L6S strains were used for production of recombinant NS3/4A protease complexes. DNA encoding the recombinant HCV NS3/4A protease complex (amino acids 1027 to 1711) for these strains was manipulated as described by P. Gallinari et al. (see Gallinari P, Paolini C, Brennan D, Nardi C, Steinkuhler C, De Francesco R. *Biochemistry.* 38(17):5620-32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia. coli* strain BL21 (DE3) (Invitrogen) following the protocol described by P. Gallinari et al. (see Gallinari P, Brennan D, Nardi C, Brunetti M, Tomei L, Steinkuhler C, De Francesco R., *J Virol.* 72(8):6758-69 (1998)) with modifications. Briefly, the NS3/4A protease complex expression was induced with 0.5 millimolar (mM) Isopropyl β-D-1-thiogalactopyranoside (IPTG) for 22 hours (h) at 20° C. A typical fermentation (1 Liter (L)) yielded approximately 10 grams (g) of wet cell paste. The cells were resuspended in lysis buffer (10 mL/g) consisting of 25 mM N-(2-Hydroxyethyl)Piperazine-N'-(2-Ethane Sulfonic acid)

(HEPES), pH 7.5, 20% glycerol, 500 mM Sodium Chloride (NaCl), 0.5% Triton X-100, 1 microgram/milliliter ("µg/mL") lysozyme, 5 mM Magnesium Chloride (MgCl$_2$), 1 µg/ml DnaseI, 5 mM β-Mercaptoethanol (βME), Protease inhibitor-Ethylenediamine Tetraacetic acid (EDTA) free (Roche), homogenized and incubated for 20 minutes (min) at 4° C. The homogenate was sonicated and clarified by ultra-centrifugation at 235000 g for 1 hour (h) at 4° C. Imidazole was added to the supernatant to a final concentration of 15 mM and the pH adjusted to 8.0. The crude protein extract was loaded on a Nickel-Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-5200 pre-equilibrated with buffer D (25 mM HEPES, pH 7.5, 20% glycerol, 300 mM NaCl, 0.2% Triton X-100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77 and J4L6S strains, were judged to be greater than 90% by SDS-PAGE and mass spectrometry analyses. The enzyme was stored at −80° C., thawed on ice and diluted prior to use in assay buffer.

FRET Peptide Assay to Monitor HCV NS3/4A Proteolytic Activity

The purpose of this in vitro assay was to measure the inhibition of HCV NS3 protease complexes, derived from the BMS strain, H77 strain or J4L6S strain, as described above, by compounds of the present disclosure. This assay provides an indication of how effective compounds of the present disclosure would be in inhibiting HCV NS3 proteolytic activity.

In order to monitor HCV NS3/4A protease activity, an NS3/4A peptide substrate was used. The substrate was RET S1 (Resonance Energy Transfer Depsipeptide Substrate; AnaSpec, Inc. cat #22991)(FRET peptide), described by Taliani et al. in *Anal. Biochem.* 240(2):60-67 (1996). The sequence of this peptide is loosely based on the NS4A/NS4B natural cleavage site for the HCV NS3 protease except there is an ester linkage rather than an amide bond at the cleavage site. The peptide also contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The peptide substrate was incubated with one of the three recombinant NS3/4A protease complexes, in the absence or presence of a compound of the present disclosure. The inhibitory effects of a compound were determined by monitoring the formation of fluorescent reaction product in real time using a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad.

Assay buffer: 50 mM HEPES, pH 7.5; 0.15 M NaCl; 0.1% Triton; 15% Glycerol; 10 mM βME. Substrate: 2 µM final concentration (from a 2 mM stock solution in DMSO stored at −20° C.). HCV NS3/4A protease type 1a (1b), 2-3 nM final concentration (from a 5 µM stock solution in 25 mM HEPES, pH 7.5, 20% glycerol, 300 mM NaCl, 0.2% Triton-X100, 10 mM βME). For compounds with potencies approaching the assay limit, the assay was made more sensitive by adding 50 µg/ml Bovine Serum Albumin (Sigma) to the assay buffer and reducing the end protease concentration to 300 pM.

The assay was performed in a 96-well polystyrene black plate from Falcon. Each well contained 25 µl NS3/4A protease complex in assay buffer, 50 µl of a compound of the present disclosure in 10% DMSO/assay buffer and 25 µl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 min.

The percent inhibition was calculated with the following equation:

$$100-[(\delta F_{inh}/\delta F_{con})\times 100]$$

where δF is the change in fluorescence over the linear range of the curve. A non-linear curve fit was applied to the inhibition-concentration data, and the 50% effective concentration (IC$_{50}$) was calculated by the use of Excel XLfit software using the equation, $y=A+4B-A)/(1+((C/x)^D)))$.

Compounds of the present disclosure, which were tested against more than one type of NS3/4A complex, were found to have similar inhibitory properties though the compounds uniformly demonstrated greater potency against the 1b strains as compared to the 1a strains.

Generation of HCV Replicon

An HCV replicon whole cell system was established as described by Lohmann V, Korner F, Koch J, Herian U, Theilmann L, Bartenschlager R., *Science* 285(5424):110-3 (1999) and modified to introduce a luciferase reporter, as first described by Krieger et al (Krieger N, Lohmann V, and Bartenschlager R, *J. Virol.* 75(10):4614-4624 (2001)). CDNA encoding a humanized form of the Renilla luciferase gene and a linker sequence fused directly to the 3'-end of the luciferase gene were introduced into the replicon construct using an Asc1 restriction site located in core, directly upstream of the neomycin marker gene. The adaptive mutation at position 1179 (serine to isoleucine) was also introduced (Blight K J, Kolykhalov, A A, Rice, C M, *Science* 290(5498):1972-1974). A stable cell line constitutively expressing this HCV replicon construct was generated by first linearizing plasmid DNAs with ScaI. RNA transcripts were synthesized in vitro using the T7 MegaScript transcription kit (Ambion, Austin, Tex.) according to manufacturer's directions. In vitro transcripts of the cDNA were transfected into the human hepatoma cell line, HUH-7. Selection for cells constitutively expressing the HCV replicon was achieved in the presence of the selectable marker, neomycin (G418). Resulting cell lines were characterized for positive and negative strand RNA production and protein production over time.

A stable HCV replicon luciferase reporter cell line representing the genotype 1a H77 strain (Yanagi M, Purcell R H, Emerson S U, et al. Transcripts from a single full-length cDNA clone of hepatitis C virus are infectious when directly transfected into the liver of a chimpanzee. Proc Natl Acad Sci USA 1997; 94(16):8738-8743) was generated as described previously for the genotype 1b (Con1) replicon luciferase cell line. The replicon construct was modified by introducing mutations were introduced into the genes encoding the NS3 helicase domain (proline replaced by leucine at position 1496) and NS5A (serine to isoleucine at position 2204) to improve replication in cell culture.

HCV Replicon Luciferase Reporter Assay

HCV replicon luciferase assays were developed to monitor the inhibitory effects of compounds described in the disclosure on HCV genotypes 1a and 1b viral replication. HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/mL G418 (Gibco-BRL). Compounds were serially diluted 3 folds in DMSO for a twenty-point titration and subsequently transferred to sterile 384-well tissue-culture treated plates (Corning cat #3571). The plates were then seeded with 50 μL of cells at a density of $3.0 \times 10^3$ cells/well in DMEM containing 4% FCS (final DMSO concentration at 0.5%). After 3 days incubation at 37° C., cells were analyzed for Renilla Luciferase activity using the EnduRen as substrate (Promega cat #E6485). The EnduRen substrate was diluted in DMEM and then added to the plates to a final concentration of 7.5 μM. The plates were incubated for 2 hrs at 37° C. and then read immediately for 30 seconds with Viewlux Imager (PerkinElmer) using a luminescence program. To assess cytotoxicity of compounds, $CC_{50}$ values were generated by multiplexing the EnduRen-containing plates with Cell Titer-Blue (Promega, cat # G8082). Cell-Titer Blue (3 μL) was added to each well and incubated for 8 hrs at 37° C. The fluorescence signal from each well was read, with an excitation wavelength at 525/10 nm and an emission wavelength of 598/10 nm, using the Viewlux Imager.

The $EC_{50}$ values for compounds were calculated by using a four-parameter logistic equation:

$$y = A + ((B-A)/(1+((C/x)^D)))$$, where A and B denotes minimal and maximal % inhibition, respectively, C is the $EC_{50}$, D is the hill slope and x represents compound concentration.

Table 2 shows the EC50 values of representative compounds of the present disclosure. Ranges are as follows: A=0.10 nM-0.50 nM; B=0.51 nM-1.00 nM; C=1.01 nM-5.00 nM; D=5.01 nM-35.00 nM.

TABLE 2

| Patent Compound Number | LE_1a (EC50, nM) | LE_1b (EC50, nM) | LE_1a (EC50, range) | LE_1b (EC50, range) |
| --- | --- | --- | --- | --- |
| 3 |  |  | A | A |
| 5 |  |  |  |  |
| 6 |  |  |  |  |
| 7 |  |  | A | A |
| 9 |  |  | A | A |
| 10 | 3.08 | 0.80 | A | A |
| 11 |  |  | A | A |
| 14 |  |  | A | A |
| 15 |  |  | A | A |
| 16 |  |  | A | A |
| 18 |  |  | A | A |
| 20 |  |  | A | A |
| 22 | 0.43 | 0.40 | A | A |
| 24 |  |  | A | A |
| 25 |  |  | B | B |
| 27 |  |  | A | A |
| 28 |  |  | A | A |
| 30 |  |  | A | A |
| 32 |  |  | A | A |
| 1001 | 1000.00 | 449.10 | C | C |
| 1002 |  |  | C | B |
| 1003 |  |  | C | C |
| 1004 | 109.70 | 48.77 | C | B |
| 1005 |  |  | C | C |
| 1006 |  |  | B | B |
| 1007 | 1000.00 | 438.40 | C | C |
| 1008 |  |  | B | B |
| 1009 |  |  | C | C |
| 1010 |  |  | B | B |
| 1011 | 1000.00 | 362.30 | C | C |
| 1012 |  |  | B | B |
| 1013 |  |  | C | C |
| 1014 |  |  | B | B |
| 1015 |  |  | C | C |
| 1016 |  |  | B | B |
| 1017 |  |  | C | C |
| 1018 |  |  | B | B |
| 1019 | 1000.00 | 506.00 | C | C |
| 1020 |  |  | B | B |
| 1021 |  |  | C | C |
| 1022 |  |  | B | B |
| 1023 |  |  |  | C |
| 1024 |  |  | B | B |
| 1025 |  |  | B | A |
| 1026 |  |  | A | A |
| 1027 |  |  | A | A |
| 1028 |  |  | A | A |
| 1029 |  |  | B | B |
| 1030 |  |  | A | A |
| 1031 |  |  | B | B |
| 1032 |  |  | A | A |
| 1033 |  |  | A | A |
| 1034 |  |  | A | A |
| 1035 |  |  | B | B |
| 1036 |  |  | A | A |
| 1037 |  |  | B | B |
| 1038 |  |  | A | A |
| 1039 |  |  | A | A |
| 1040 |  |  | A | A |
| 1041 |  |  | B | A |
| 1042 |  |  |  |  |
| 1043 |  |  | A | A |
| 1044 |  |  | A | A |
| 1045 |  |  | A | A |
| 1046 |  |  | A | A |
| 1047 |  |  | B | B |
| 1048 |  |  | A | A |
| 1049 |  |  | B | B |
| 1050 |  |  | A | A |
| 1051 |  |  | B | B |
| 1052 |  |  | B | A |
| 1053 |  |  | B | B |
| 1054 |  |  | A | A |
| 1055 |  |  | A | A |
| 1056 |  |  | A | A |
| 1057 |  |  | A | A |
| 1058 |  |  | A | A |
| 1059 |  |  | B | B |
| 1060 |  |  | A | A |
| 1061 |  |  | B | B |
| 1062 |  |  | A | A |

TABLE 2-continued

| Patent Compound Number | LE_1a (EC50, nM) | LE_1b (EC50, nM) | LE_1a (EC50, range) | LE_1b (EC50, range) |
|---|---|---|---|---|
| 1063 | | | B | A |
| 1064 | | | A | A |
| 1065 | | | B | A |
| 1066 | | | A | A |
| 1067 | | | A | A |
| 1068 | | | A | A |
| 1069 | | | A | A |
| 1070 | | | A | A |
| 1071 | | | A | A |
| 1072 | | | A | A |
| 1073 | | | A | A |
| 1074 | | | A | A |
| 1075 | | | A | A |
| 1076 | | | A | A |
| 1077 | | | B | A |
| 1078 | | | A | A |
| 1079 | | | B | A |
| 1080 | | | A | A |
| 1081 | | | B | A |
| 1082 | | | A | A |
| 1083 | | | B | A |
| 1084 | | | A | A |
| 1085 | | | A | A |
| 1086 | | | A | A |
| 1087 | | | B | A |
| 1088 | | | A | A |
| 1089 | | | B | A |
| 1090 | | | A | A |
| 1091 | | | B | A |
| 1092 | | | A | A |
| 1093 | | | B | A |
| 1094 | | | A | A |
| 1095 | | | B | A |
| 1096 | | | A | A |
| 1097 | | | B | A |
| 1098 | | | A | A |
| 1099 | | | A | A |
| 1100 | | | A | A |
| 1101 | | | B | B |
| 1102 | | | A | A |
| 1103 | | | B | A |
| 1104 | | | A | A |
| 1105 | | | A | A |
| 1106 | | | A | A |
| 1107 | | | B | A |
| 1108 | | | A | A |
| 1109 | | | | |
| 1110 | | | A | A |
| 1111 | | | A | A |
| 1112 | | | A | A |
| 1113 | | | A | A |
| 1114 | | | A | A |
| 1115 | | | A | A |
| 1116 | | | A | A |
| 1117 | | | A | A |
| 1118 | | | A | A |
| 1119 | | | A | A |
| 1120 | | | A | A |
| 1121 | | | A | A |
| 1122 | | | A | A |
| 1123 | | | A | A |
| 1124 | | | A | A |
| 1125 | | | A | A |
| 1126 | | | B | A |
| 1127 | | | A | A |
| 1128 | | | A | A |
| 1129 | | | A | A |
| 1130 | | | A | A |
| 1131 | | | A | A |
| 1132 | | | A | A |
| 1133 | | | A | A |
| 1134 | | | C | C |
| 1135 | | | B | A |
| 1136 | | | C | C |
| 1137 | | | B | A |
| 1138 | | | C | C |
| 1139 | | | B | B |
| 1140 | | | A | A |
| 1141 | | | A | A |
| 1142 | | | | A |
| 1143 | | | B | A |
| 1144 | | | A | A |
| 1145 | | | A | A |
| 1146 | | | A | A |
| 1147 | | | A | A |
| 1148 | | | A | A |
| 1149 | | | A | A |
| 1150 | | | A | A |
| 1151 | | | A | A |
| 1152 | | | A | A |
| 1153 | | | A | A |
| 1154 | | | A | A |
| 1155 | | | A | A |
| 1156 | | | B | B |
| 1157 | | | B | B |
| 1158 | | | B | B |
| 1159 | | | B | B |
| 1160 | | | B | A |
| 1161 | | | A | A |
| 1162 | | | B | B |
| 1163 | | | A | A |
| 1164 | | | B | B |
| 1165 | | | A | A |
| 1166 | | | B | B |
| 1167 | | | A | A |
| 1168 | | | B | B |
| 1169 | | | A | A |
| 1170 | | | B | B |
| 1171 | | | A | A |
| 1172 | | | C | B |
| 1173 | | | A | A |
| 1173 | | | B | A |
| 1174 | | | B | B |
| 1175 | | | A | A |
| 1176 | | | B | B |
| 1177 | | | A | A |
| 1177 | | | A | A |
| 1178 | | | A | A |
| 1179 | | | | |
| 1179 | | | | |
| 1180 | | | A | A |
| 1181 | | | A | A |
| 1182 | | | A | A |
| 2001 | | | B | B |
| 2002 | | | B | B |
| 2003 | 329.70 | 157.80 | C | C |
| 3001 | | | A | A |
| 3002 | | | A | A |
| 3003 | | | A | A |
| 3004 | | | A | A |
| 3005 | | | B | B |
| 3006 | | | A | A |
| 3007 | | | A | A |
| 3008 | | | A | A |
| 3009 | | | B | B |
| 3010 | | | A | A |
| 3011 | | | B | A |
| 3012 | | | A | A |
| 3013 | | | B | B |
| 3014 | | | B | B |
| 3015 | | | A | A |
| 3016 | | | A | A |
| 3017 | | | A | A |
| 3018 | | | B | B |
| 3019 | | | B | A |
| 3020 | | | B | A |
| 3021 | | | A | A |
| 3022 | | | A | A |
| 3023 | | | B | B |
| 3024 | | | A | A |
| 3025 | | | B | B |
| 3026 | | | A | A |

TABLE 2-continued

| Patent Compound Number | LE_1a (EC50, nM) | LE_1b (EC50, nM) | LE_1a (EC50, range) | LE_1b (EC50, range) |
|---|---|---|---|---|
| 3027 | | | B | B |
| 3028 | | | A | A |
| 3029 | | | B | B |
| 3030 | | | A | A |
| 3031 | | | B | B |
| 3032 | | | A | A |
| 3033 | | | B | B |
| 3034 | | | A | A |
| 3035 | | | B | A |
| 3036 | | | A | A |
| 3037 | | | B | A |
| 3038 | | | | |
| 3039 | | | A | A |
| 3040 | | | A | A |
| 3041 | | | A | A |
| 3042 | | | A | A |
| 3043 | | | A | A |
| 3044 | | | A | A |
| 3045 | | | A | A |
| 3046 | | | A | A |
| 3047 | | | B | A |
| 3048 | | | A | A |
| 3049 | | | A | A |
| 3050 | | | A | A |
| 3051 | | | B | A |
| 3052 | | | A | A |
| 3053 | | | A | A |
| 3054 | | | A | A |
| 3055 | | | B | A |
| 3056 | | | A | A |
| 3057 | | | A | A |
| 3058 | | | A | A |
| 3059 | | | B | A |
| 3060 | | | A | A |
| 3061 | | | B | A |
| 3062 | | | A | A |
| 3063 | | | B | A |
| 3064 | | | A | A |
| 3065 | | | B | A |
| 3066 | | | A | A |
| 3067 | | | B | A |
| 3068 | | | A | A |
| 3069 | | | B | A |
| 3070 | | | A | A |
| 3071 | | | B | A |
| 3072 | | | A | A |
| 3073 | | | B | A |
| 3074 | | | A | A |
| 3075 | | | B | A |
| 3076 | | | A | A |
| 3077 | | | B | A |
| 3078 | | | A | A |
| 3079 | | | B | A |
| 3080 | | | A | A |
| 3081 | | | B | A |
| 3082 | | | A | A |
| 3083 | | | A | A |
| 3084 | | | B | A |
| 3085 | | | A | A |
| 3086 | | | A | A |
| 3087 | | | A | A |
| 3088 | | | A | A |
| 3089 | | | A | A |
| 3090 | | | B | A |
| 3091 | | | A | A |
| 3092 | | | A | A |
| 3093 | | | A | A |
| 3094 | | | B | A |
| 3095 | | | A | A |
| 3096 | | | B | A |
| 3097 | | | A | A |
| 3098 | | | A | A |
| 3099 | | | A | A |
| 3100 | | | A | A |
| 3101 | | | A | A |
| 3102 | | | B | A |
| 3103 | | | A | A |
| 3104 | | | B | B |
| 3105 | | | A | A |
| 3106 | | | B | B |
| 3107 | | | A | A |
| 3108 | | | B | B |
| 3109 | | | B | B |
| 3110 | | | B | B |
| 3111 | | | A | B |
| 3112 | | | B | B |
| 3113 | | | A | B |
| 3114 | | | B | B |
| 3115 | | | B | B |
| 3116 | | | B | A |
| 3117 | | | A | A |
| 3118 | | | B | B |
| 3119 | | | A | A |
| 3120 | | | B | B |
| 3121 | | | B | A |
| 3122 | | | B | B |
| 3123 | | | B | B |
| 3124 | | | B | B |
| 3125 | | | B | A |
| 3126 | | | B | B |
| 3127 | | | B | A |
| 3128 | | | B | A |
| 3129 | | | | |
| 3130 | | | A | A |
| 3131 | | | | |
| 3132 | | | A | A |
| 3133 | | | | |
| 3134 | | | A | A |
| 3135 | | | A | A |
| 3136 | | | A | A |
| 3137 | | | A | A |
| 3138 | | | A | A |
| 3139 | | | A | A |
| 3140 | | | A | A |
| 3141 | | | A | A |
| 3142 | | | A | A |
| 3143 | | | A | A |
| 3144 | | | A | A |
| 3145 | | | B | B |
| 3146 | | | A | A |
| 3147 | | | B | A |
| 3148 | | | A | A |
| 3149 | | | B | A |
| 3150 | | | A | A |
| 3151 | | | B | A |
| 3152 | | | A | A |
| 3153 | | | B | B |
| 3154 | | | A | A |
| 3155 | | | B | B |
| 3156 | | | A | A |
| 3157 | | | B | A |
| 3158 | | | A | A |
| 3159 | | | B | A |
| 3160 | | | A | A |
| 3161 | | | B | A |
| 3162 | | | A | A |
| 3163 | | | B | B |
| 3164 | | | A | A |
| 3165 | | | B | B |
| 3166 | | | A | A |
| 3167 | | | B | A |
| 3168 | | | A | A |
| 3169 | | | B | A |
| 3170 | | | A | A |
| 3171 | | | B | A |
| 3172 | 1.04 | 1.18 | A | A |
| 3173 | | | B | B |
| 3174 | | | A | A |
| 3175 | | | B | B |
| 3176 | | | A | A |
| 3177 | | | B | A |
| 3178 | 3.16 | 0.61 | A | A |

TABLE 2-continued

| Patent Compound Number | LE_1a (EC50, nM) | LE_1b (EC50, nM) | LE_1a (EC50, range) | LE_1b (EC50, range) |
|---|---|---|---|---|
| 3179 | | | B | B |
| 3180 | | | A | A |
| 3181 | | | B | A |
| 3182 | | | A | A |
| 3183 | | | B | A |
| 3184 | 2.78 | 1.26 | A | A |
| 3185 | | | B | B |
| 3186 | | | A | A |
| 3187 | | | A | A |
| 3188 | | | A | A |
| 3189 | | | B | A |
| 3190 | | | A | A |
| 3191 | | | B | A |
| 3192 | | | A | A |
| 4001 | | | A | A |
| 4002 | | | A | A |
| 4003 | | | A | A |
| 4004 | | | A | A |
| 4005 | | | A | A |
| 4006 | | | A | A |
| 4007 | | | A | A |
| 4008 | | | A | A |
| 4013 | | | A | A |
| 4015 | | | A | A |
| 4016 | | | A | A |
| 4017 | | | A | A |
| 4018 | | | A | A |
| 4019 | | | A | A |
| 4020 | | | A | A |
| 4022 | | | A | A |
| 4024 | | | A | A |
| 4025 | | | A | A |
| 4026 | | | A | A |
| 4027 | | | A | A |
| 4028 | | | A | A |
| 4029 | | | A | A |
| 4030 | | | A | A |
| 4031 | | | A | A |
| 4032 | | | A | A |
| 4033 | | | A | A |
| 4034 | | | A | A |
| 4036 | | | A | A |
| 4037 | | | A | A |
| 4038 | | | A | A |
| 4039 | | | A | A |
| 4040 | | | A | A |
| 4041 | | | A | A |
| 4042 | | | A | A |
| 4043 | | | A | A |
| 4044 | | | B | A |
| 4045 | | | A | A |
| 4046 | | | B | B |
| 4047 | | | A | A |
| 4048 | | | A | A |
| 4049 | | | A | A |
| 4050 | | | A | A |
| 4051 | | | A | A |
| 4052 | | | A | A |
| 4053 | | | A | A |
| 4054 | | | A | A |
| 4055 | | | A | A |
| 4056 | | | A | A |
| 4057 | | | A | A |
| 4058 | | | A | A |
| 4059 | | | A | A |
| 4060 | | | A | A |
| 4061 | | | A | A |
| 4062 | | | A | A |
| 4063 | | | A | A |
| 4064 | | | A | A |
| 4065 | | | A | A |
| 4066 | | | A | A |
| 4067 | | | B | A |
| 4068 | | | A | A |
| 4069 | | | A | A |
| 4070 | | | A | A |
| 4071 | | | A | A |
| 4072 | | | A | A |
| 4073 | | | A | A |
| 4074 | | | A | A |
| 4075 | | | A | A |
| 4076 | | | A | A |
| 4077 | | | A | A |
| 4078 | | | B | B |
| 4079 | | | B | B |
| 4080 | | | A | A |
| 4081 | | | A | A |
| 4082 | | | A | A |
| 4083 | | | A | A |
| 4084 | | | A | A |
| 4085 | | | B | A |
| 4086 | | | A | A |
| 4087 | | | A | A |
| 4088 | | | A | A |
| 4089 | | | B | A |
| 4090 | | | A | A |
| 4091 | | | A | A |
| 4092 | | | | |
| 4093 | | | A | A |
| 4094 | | | | |
| 4095 | | | A | A |
| 4096 | | | A | A |
| 4097 | | | A | A |
| 4099 | | | A | A |
| 4100 | | | A | A |
| 4101 | | | A | A |
| 4102 | | | A | A |
| 4103 | | | B | B |
| 4104 | | | A | A |
| 4105 | | | A | A |
| 4106 | | | B | B |
| 4107 | | | A | A |
| 4108 | | | A | A |
| 4109 | | | A | A |
| 4110 | | | B | B |
| 4111 | | | C | B |
| 4112 | | | C | C |
| 4113 | | | C | C |
| 4114 | | | B | B |
| 4115 | | | A | A |
| 4116 | | | A | A |
| 4117 | | | A | A |
| 4118 | | | A | A |
| 4119 | | | A | A |
| 4120 | | | A | A |
| 4121 | | | A | A |
| 4122 | | | A | A |
| 4123 | | | B | B |
| 4124 | | | A | A |
| 4125 | | | A | A |
| 4126 | | | A | A |
| 4127 | | | B | A |
| 4128 | | | A | A |
| 4129 | | | A | A |
| 4130 | | | B | B |
| 4131 | | | A | A |
| 4132 | | | A | A |
| 4133 | | | B | A |
| 4134 | | | A | A |
| 4135 | | | A | A |
| 4136 | | | A | A |
| 4137 | | | A | A |
| 4138 | | | B | B |
| 4139 | | | B | B |
| 4140 | | | A | A |
| 4141 | | | B | B |
| 4142 | | | A | A |
| 4143 | | | B | B |
| 4144 | | | A | A |
| 4145 | | | A | A |
| 4146 | | | | |
| 4147 | | | A | A |

TABLE 2-continued

| Patent Compound Number | LE_1a (EC50, nM) | LE_1b (EC50, nM) | LE_1a (EC50, range) | LE_1b (EC50, range) |
|---|---|---|---|---|
| 4148 | | | A | A |
| 4149 | | | A | A |
| 4150 | | | | |
| 4151 | | | A | A |
| 4152 | | | | |
| 4153 | | | A | A |
| 4154 | | | A | A |
| 4155 | | | A | A |
| 4156 | | | A | A |
| 4157 | | | A | A |
| 4158 | | | A | A |
| 4159 | | | A | A |
| 4160 | | | A | A |
| 4161 | | | A | A |
| 4162 | | | A | A |
| 4163 | 9.80 | 1.89 | B | A |
| 4164 | | | A | A |
| 4165 | | | A | A |
| 4166 | | | A | A |
| 4167 | | | A | A |
| 4168 | | | | |
| 4169 | | | A | A |
| 4170 | | | C | B |
| 4171 | | | A | A |
| 4172 | | | A | A |
| 4173 | | | A | A |
| 4174 | | | A | A |
| 4175 | | | A | A |
| 4176 | | | A | A |
| 4177 | | | A | A |
| 4178 | | | A | A |
| 4179 | | | A | A |
| 4180 | | | A | A |
| 4181 | | | A | A |
| 4182 | | | A | A |
| 4183 | | | A | A |
| 4184 | | | | |
| 4185 | | | A | A |
| 4186 | | | A | A |
| 4187 | | | | |
| 4188 | | | A | A |
| 4189 | | | A | A |
| 4190 | | | A | A |
| 4191 | | | | |
| 4192 | | | | |
| 4193 | | | A | A |
| 4194 | | | A | A |
| 4195 | | | A | A |
| 4196 | | | A | A |
| 4197 | | | A | A |
| 4198 | | | B | A |
| 4199 | | | A | A |
| 4200 | | | B | A |
| 4201 | | | A | A |
| 4202 | | | A | A |
| 4203 | | | A | A |
| 4204 | | | A | A |
| 4205 | | | A | A |
| 4206 | | | A | A |
| 4207 | | | A | A |
| 4208 | | | B | A |
| 4209 | | | | |
| 4210 | | | | |
| 4211 | | | | |
| 4212 | | | | |
| 4213 | | | | |
| 4214 | | | | |
| 4215 | | | | |
| 4216 | | | | |
| 4219 | | | A | A |
| 4220 | | | A | A |
| 4221 | | | A | A |
| 4222 | | | A | A |
| 4223 | | | A | A |
| 4224 | | | A | A |
| 4225 | | | A | A |
| 4226 | | | | |
| 4227 | | | A | A |
| 4228 | | | A | A |
| 4229 | | | A | A |
| 4230 | | | A | A |
| 4231 | | | A | A |
| 4232 | | | | |
| 4234 | | | | |
| 4235 | | | B | B |
| 4236 | | | A | A |
| 4237 | | | A | A |
| 4238 | | | B | B |
| 4239 | | | A | A |
| 5001 | | | A | A |
| 5002 | | | A | A |
| 5003 | 5.46 | 1.96 | B | A |
| 5004 | | | A | A |
| 5005 | | | A | A |
| 5006 | | | A | A |
| 5007 | | | A | A |
| 5008 | | | A | A |
| 5009 | | | A | A |
| 5010 | | | A | A |
| 5011 | 41.15 | 14.17 | B | B |
| 5012 | | | A | A |
| 5013 | | | A | A |
| 5014 | | | A | A |
| 5015 | | | B | A |
| 5016 | | | A | A |
| 5017 | | | B | A |
| 5018 | | | A | A |
| 5019 | 7.27 | 3.65 | B | A |
| 5020 | | | A | A |
| 5021 | | | B | A |
| 5022 | | | A | A |
| 5023 | 16.02 | 24.64 | B | B |
| 5024 | | | A | A |
| 5025 | | | B | A |
| 5026 | | | A | A |
| 5027 | | | A | A |
| 5028 | 6.28 | 2.96 | B | A |
| 5029 | | | A | A |
| 5030 | | | B | B |
| 5031 | | | A | A |
| 5032 | | | B | B |
| 5033 | | | A | A |
| 5034 | | | B | B |
| 5035 | | | A | A |
| 5036 | | | B | B |
| 5037 | | | A | A |
| 5038 | | | B | B |
| 5039 | | | A | A |
| 5040 | | | C | C |
| 5041 | | | A | B |
| 5042 | | | B | B |
| 5043 | | | A | A |
| 5044 | | | B | B |
| 5045 | | | A | A |
| 5046 | | | B | A |
| 5047 | | | A | A |
| 5048 | | | B | B |
| 5049 | | | A | A |
| 5050 | | | B | B |
| 5051 | | | A | A |
| 5052 | 330.40 | 76.16 | C | B |
| 5053 | | | B | A |
| 5054 | | | C | C |
| 5055 | | | B | A |
| 5056 | 255.80 | 61.03 | C | B |
| 5057 | | | A | A |
| 5058 | | | C | C |
| 5059 | | | B | B |
| 5060 | 1000.00 | 950.10 | C | C |
| 5061 | | | B | B |
| 5062 | 1000.00 | 1000.00 | C | C |
| 5063 | 1000.00 | 478.70 | C | C |

TABLE 2-continued

| Patent Compound Number | LE_1a (EC50, nM) | LE_1b (EC50, nM) | LE_1a (EC50, range) | LE_1b (EC50, range) |
|---|---|---|---|---|
| 5064 | | | C | B |
| 5065 | | | B | A |
| 5066 | | | C | C |
| 5067 | | | B | B |
| 5068 | | | C | C |
| 5069 | 14.95 | 7.21 | B | B |
| 5070 | | | B | A |
| 5071 | 1000.00 | 1000.00 | C | C |
| 5072 | | | C | B |
| 5073 | | | C | C |
| 5074 | | | B | B |
| 5075 | 1000.00 | 1000.00 | C | C |
| 5076 | | | C | C |
| 5077 | | | B | B |
| 5078 | 28.89 | 8.73 | B | B |
| 5079 | | | A | A |
| 5080 | | | C | B |
| 5081 | | | B | A |
| 5082 | 198.00 | 45.51 | C | B |
| 5083 | | | A | A |
| 5084 | 520.20 | 131.00 | C | C |
| 5085 | | | B | B |
| 5086 | 411.40 | 155.00 | C | C |
| 5087 | | | A | A |
| 5088 | 102.80 | 20.30 | C | B |
| 5089 | | | A | A |
| 5090 | 521.50 | 87.44 | C | B |
| 5091 | | | | |
| 5092 | | | C | B |
| 5093 | | | B | A |
| 5094 | | | C | C |
| 5095 | | | B | B |
| 5096 | | | C | B |
| 5097 | | | A | A |
| 5098 | | | C | C |
| 5099 | | | A | A |
| 5100 | | | A | A |
| 5101 | | | A | A |
| 5102 | | | A | A |
| 5103 | | | A | A |
| 5104 | | | A | A |
| 5105 | | | A | A |
| 5106 | | | A | A |
| 5107 | | | A | A |
| 5108 | | | A | A |
| 5109 | | | A | A |
| 5110 | | | B | A |
| 5111 | | | A | A |
| 5112 | | | B | B |
| 5113 | | | A | A |
| 5114 | | | | |
| 5115 | | | A | A |
| 5116 | | | C | B |
| 5117 | | | A | A |
| 5118 | | | B | B |
| 5119 | | | A | A |
| 5120 | | | A | A |
| 5121 | | | | |
| 5122 | | | A | A |
| 5123 | | | | |
| 5124 | | | A | A |
| 5125 | | | | |
| 5126 | | | A | A |
| 5127 | | | A | A |
| 5128 | | | A | A |
| 5129 | | | B | A |
| 5130 | | | A | A |
| 5131 | | | A | A |
| 5132 | | | A | A |
| 5133 | | | B | A |
| 5134 | | | A | A |
| 5135 | | | B | A |
| 5136 | | | A | A |
| 5137 | | | A | A |
| 5138 | | | A | A |
| 5139 | | | B | A |
| 5140 | | | A | A |
| 5141 | | | B | A |
| 5142 | | | A | A |
| 5143 | | | B | A |
| 5144 | | | B | A |
| 5145 | | | B | A |
| 5146 | | | A | A |
| 5147 | | | B | B |
| 5148 | | | A | A |
| 5149 | | | B | A |
| 5150 | | | A | A |
| 5151 | | | A | A |
| 5152 | | | B | B |
| 5153 | | | A | A |
| 5154 | | | B | B |
| 5155 | | | A | A |
| 5156 | | | B | B |
| 5157 | | | A | A |
| 5158 | | | B | A |
| 5159 | | | A | A |
| 5160 | | | B | A |
| 5161 | | | A | A |
| 5162 | | | B | A |
| 5163 | | | A | A |
| 5164 | | | B | B |
| 5165 | | | A | A |
| 5166 | | | B | B |
| 5167 | | | A | A |
| 5168 | | | A | A |
| 5169 | | | A | A |
| 5170 | | | B | A |
| 5171 | | | A | A |
| 5172 | | | B | A |
| 5173 | | | A | A |
| 5174 | | | A | A |
| 5175 | | | A | A |
| 5176 | | | B | A |
| 5177 | | | A | A |
| 5178 | | | B | A |
| 5179 | | | A | A |
| 5180 | | | A | A |
| 5181 | | | A | A |
| 5182 | | | A | A |
| 5183 | | | A | A |
| 5184 | | | | |
| 5185 | | | A | A |
| 5186 | | | A | A |
| 5187 | | | | |
| 5188 | | | A | A |
| 5189 | | | A | A |
| 5190 | | | | |
| 5191 | | | A | A |
| 5192 | | | A | A |
| 5193 | | | A | A |
| 5194 | | | A | A |
| 5195 | | | A | A |
| 5196 | | | A | A |
| 5197 | | | A | A |
| 5198 | | | B | A |
| 5199 | | | A | A |
| 5200 | | | A | A |
| 5201 | | | A | A |
| 5202 | | | A | A |
| 5203 | | | A | A |
| 5204 | | | A | A |
| 5205 | | | A | A |
| 5206 | | | A | A |
| 5207 | | | A | A |
| 5208 | | | A | A |
| 5209 | | | A | A |
| 5210 | | | A | A |
| 5211 | | | A | A |
| 5212 | | | A | A |
| 5213 | | | A | A |
| 5214 | | | B | A |
| 5215 | | | A | A |

TABLE 2-continued

| Patent Compound Number | LE_1a (EC50, nM) | LE_1b (EC50, nM) | LE_1a (EC50, range) | LE_1b (EC50, range) |
|---|---|---|---|---|
| 5216 | | | B | A |
| 5217 | | | A | A |
| 5218 | | | A | A |
| 5219 | | | A | A |
| 5220 | | | A | A |
| 5221 | | | A | A |
| 5222 | | | B | A |
| 5223 | | | A | A |
| 5224 | | | B | B |
| 5225 | | | A | A |
| 5226 | | | B | B |
| 5227 | | | A | A |
| 5228 | | | B | A |
| 5229 | | | A | A |
| 5230 | | | B | A |
| 5231 | | | A | A |
| 5232 | | | | |
| 5233 | | | A | A |
| 5234 | | | | |
| 5235 | | | A | A |
| 5236 | | | A | A |
| 5237 | | | A | A |
| 5238 | | | | |
| 5239 | | | A | A |
| 5240 | | | | |
| 5241 | | | A | A |
| 5242 | | | | |
| 5243 | | | A | A |
| 5244 | | | B | B |
| 5245 | | | A | A |
| 5246 | | | B | B |
| 5247 | | | A | A |
| 5248 | | | B | A |
| 5249 | | | A | A |
| 5250 | 22.64 | 5.50 | B | B |
| 5251 | | | A | A |
| 5251 | | | | |
| 5252 | 15.08 | 4.04 | B | A |
| 5253 | | | A | A |
| 5254 | | | B | A |
| 5255 | | | A | A |
| 5256 | 20.87 | 12.95 | B | B |
| 5257 | | | A | A |
| 5258 | | | B | A |
| 5259 | | | A | A |
| 5260 | | | A | A |
| 5261 | 14.26 | 2.18 | B | A |
| 5262 | | | A | A |
| 5263 | | | B | A |
| 5264 | | | A | A |
| 5265 | | | B | A |
| 5266 | | | A | A |
| 5267 | | | B | B |
| 5268 | | | A | A |
| 5269 | | | B | B |
| 5270 | | | A | A |
| 5271 | | | B | B |
| 5272 | | | A | A |
| 5273 | | | B | B |
| 5274 | | | A | A |
| 5275 | | | A | A |
| 5276 | | | A | A |
| 5277 | | | A | A |
| 5278 | | | A | A |
| 5279 | | | B | B |
| 5280 | | | A | A |
| 5281 | | | A | A |
| 5282 | | | A | A |
| 5283 | 4.82 | 3.12 | A | A |
| 5284 | | | A | A |
| 5285 | | | B | A |
| 5286 | | | A | A |
| 5287 | | | A | A |
| 5288 | | | A | A |
| 5289 | | | B | A |
| 5290 | 1.25 | 0.64 | A | A |
| 5291 | | | A | A |
| 5292 | | | A | A |
| 5293 | | | B | A |
| 5294 | | | A | A |
| 5295 | | | B | A |
| 5296 | | | A | A |
| 5297 | 7.06 | 3.16 | B | A |
| 5298 | | | A | A |
| 5299 | | | A | A |
| 5300 | | | A | A |
| 5301 | | | B | A |
| 5302 | | | A | A |
| 5303 | | | B | A |
| 5304 | | | A | A |
| 5305 | | | B | B |
| 5306 | 2.97 | 2.45 | A | A |
| 5307 | | | B | A |
| 5308 | | | A | A |
| 5309 | | | B | A |
| 5310 | | | A | A |
| 5311 | | | A | A |
| 5312 | | | A | A |
| 5313 | | | A | A |
| 5314 | 1.59 | 1.06 | A | A |
| 5315 | | | B | B |
| 5316 | | | A | A |
| 5317 | | | B | B |
| 5318 | | | A | A |
| 5319 | 33.59 | 14.25 | B | B |
| 5320 | | | A | A |
| 5321 | | | A | A |
| 5322 | | | A | A |
| 5323 | | | A | A |
| 5324 | | | A | A |
| 5325 | | | | |
| 5326 | | | A | A |
| 5327 | | | | |
| 5328 | | | A | A |
| 5329 | | | | |
| 5330 | | | A | A |
| 5331 | 12.82 | 3.94 | B | A |
| 5332 | | | A | A |
| 5333 | | | B | B |
| 5334 | | | A | A |
| 5335 | 6.50 | 2.03 | B | A |
| 5336 | | | A | A |
| 5337 | | | B | A |
| 5338 | | | A | A |
| 5339 | | | B | A |
| 5340 | | | A | A |
| 5341 | | | A | A |
| 5342 | | | A | A |
| 5343 | | | | |
| 5344 | | | A | A |
| 5345 | | | B | A |
| 5346 | | | A | A |
| 5347 | | | | |
| 5348 | | | A | A |
| 5349 | | | B | A |
| 5350 | 2.12 | 1.48 | A | A |
| 5352 | | | A | A |
| 5353 | | | B | A |
| 5354 | | | A | A |
| 6001 | | | A | A |
| 6002 | | | B | A |
| 6003 | 1.33 | 0.22 | A | A |
| 6004 | | | B | A |
| 6005 | 1.29 | 0.28 | A | A |
| 6006 | | | | |
| 6007 | | | A | A |
| 6008 | | | A | A |
| 6009 | 1.12 | 0.30 | A | A |
| 6010 | | | | |
| 6011 | | | A | A |
| 6012 | | | | |
| 6013 | | | A | A |

TABLE 2-continued

| Patent Compound Number | LE_1a (EC50, nM) | LE_1b (EC50, nM) | LE_1a (EC50, range) | LE_1b (EC50, range) |
| --- | --- | --- | --- | --- |
| 6014 | | | | |
| 6015 | 1.19 | 0.24 | A | A |
| 6016 | | | A | A |
| 6017 | | | A | A |
| 6018 | | | A | A |
| 6019 | | | | |
| 6020 | | | A | A |
| 6021 | | | | |
| 6022 | | | A | A |
| 6023 | | | B | B |
| 6024 | | | A | A |
| 6025 | | | | |
| 6026 | 1.13 | 0.70 | A | A |
| 6027 | | | | |
| 6028 | | | A | A |
| 6029 | | | B | B |
| 6030 | 1.43 | 0.81 | A | A |
| 6031 | | | B | B |
| 6032 | | | A | A |
| 6033 | 10.71 | 4.38 | B | A |
| 6034 | | | A | A |
| 6035 | | | | |
| 6036 | 0.53 | 0.38 | A | A |
| 6037 | | | | |
| 6038 | | | A | A |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

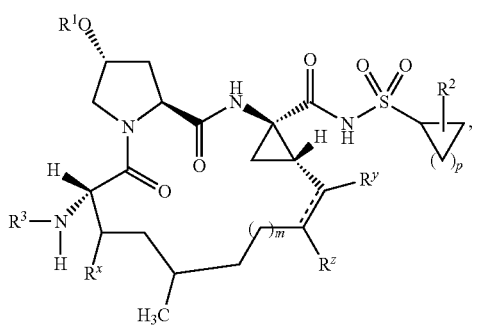

or a pharmaceutically acceptable salt thereof, wherein
p is 1 or 2;
---- is a single or double bond;
$R^1$ is selected from

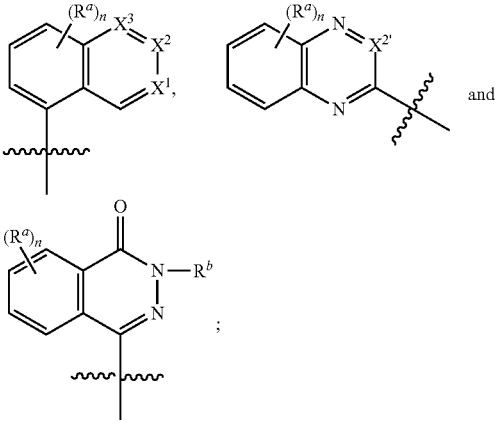

wherein "⌇" denotes the point of attachment to the parent molecular moiety;
m is 0, 1, or 2;
n is 0, 1, 2, 3, 4, 5, or 6;
$X^1$ is selected from N, CH, and $CR^a$; wherein when $X^1$ is N then one of $X^2$ and $X^3$ is selected from N, CH, and $CR^a$ and the other is selected from CH and $CR^a$; and wherein when $X^1$ is selected from CH and $CR^a$, then $X^2$ is selected from CH and $CR^a$ and $X^3$ is N;
$X^{2'}$ is selected from CH and $CR^a$;
each $R^a$ is independently selected from alkenyloxy, alkoxy, alkoxyalkoxy, alkyl, benzodioxanyl, carboxamido, carboxy, carboxyalkoxy, cyano, cycloalkylalkoxy, cycloalkyloxy, deuteroalkoxy, dialkylamino, halo, haloalkyl, haloalkoxy, haloalkoxycarbonyl, hydroxy, morpholinyl, phenyl, piperazinyl, pyrazolyl, and pyridinyl, pyrrolidinyl, wherein the morpholinyl, the phenyl, the piperazinyl, the pyridinyl, and the pyrrolidinyl are optionally substituted with one or two groups independently selected from alkoxy, alkyl, alkylsulfonyl, halo, haloalkoxy, haloalkyl, and morpholinyl; and wherein two adjacent $R^a$ groups, together with the carbon atoms to which they are attached, can optionally form a ring selected from dioxanyl, dioxolanyl, morpholinyl, pyranyl, and phenyl, wherein the ring is optionally substituted with one or two groups independently selected from alkyl and halo; provided that no more than one additional ring is formed;
$R^b$ is selected from alkoxyalkyl and alkyl;
$R^x$ is selected from methyl and ethyl;
$R^y$ and $R^z$ are independently selected from hydrogen and hydroxy; provided that when ---- is a double bond, $R^y$ and $R^z$ are each hydrogen;
$R^2$ is selected from hydrogen, alkyl, halo, haloalkoxy, haloalkyl, and hydroxyalkyl; and
$R^3$ is selected from hydrogen, alkoxyalkoxycarbonyl, alkoxycarbonyl, alkylaminocarbonyl, alkylcarbonyl, cycloalkylalkoxycarbonyl, cycloalkylcarbonyl, cycloalkyloxycarbonyl, deuteroalkoxycarbonyl, deuterohaloalkoxycarbonyl, dialkylaminocarbonyl, dialkylaminocarbonylcarbonyl, haloalkoxycarbonyl, haloalkylaminocarbonyl, haloalkylcarbonyl, heterocyclylcarbonyl, heterocyclyloxycarbonyl, phenylcarbonyl, and phenyloxycarbonyl, wherein the cycloalkyl part of the cycloalkylalkoxycarbonyl, the cycloalkylcarbonyl, and the cycloalkyloxycarbonyl, the heterocyclyl part of the heterocyclylcarbonyl and the heterocyclyloxycarbonyl, and the phenyl part of the phenylcarbonyl and the phenyloxycarbonyl, is optionally substituted with one, two, or three groups independently selected from alkyl, alkylamino, alkylcarbonyl, cycloalkyl, dialkylamino, halo, haloalkoxy, and haloalkyl; wherein the heterocycle and the heterocyclyl part of the heterocyclylcarbonyl and the heterocyclyloxycarbonyl is a four-, five-, or six-membered ring containing one heteroatom selected from oxygen and nitrogen and optionally an oxo group.

2. A compound of claim 1, or a pharmaceutically acceptable salt thereof, wherein m is 1.

3. A compound of claim 1, or a pharmaceutically acceptable salt thereof, wherein - - - - - is a double bond.

4. A compound of claim 3, or a pharmaceutically acceptable salt thereof, wherein $R^x$ is methyl.

5. A compound of formula (II)

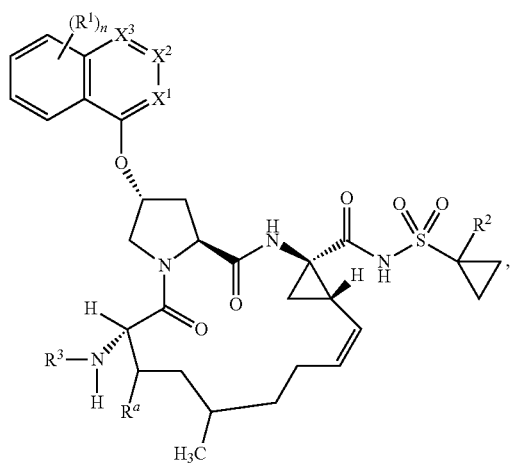

(II)

or a pharmaceutically acceptable salt thereof, wherein
n is 0, 1, 2, 3, 4, 5, or 6;
$X^1$ is selected from N, CH, and $CR^a$; wherein when $X^1$ is N then one of $X^2$ and $X^3$ is selected from N, CH, and $CR^a$ and the other is selected from CH and $CR^a$; and wherein when $X^1$ is selected from CH and $CR^a$, then $X^2$ is selected from CH and $CR^a$ and $X^3$ is N;
$R^a$ is selected from methyl and ethyl;
each $R^1$ is independently selected from alkoxy, alkyl, carboxamido, carboxy, cyano, cycloalkyloxy, dialkylamino, halo, haloalkyl, haloalkoxy, phenyl, and pyridinyl, wherein the phenyl and the pyridinyl are optionally substituted with one or two groups independently selected from alkoxy, alkyl, halo, haloalkoxy, and haloalkyl;

$R^2$ is selected from hydrogen, alkyl, halo, and haloalkyl; and
$R^3$ is selected from alkoxycarbonyl, alkylcarbonyl, haloalkoxycarbonyl, haloalkylcarbonyl, and phenylcarbonyl, wherein the phenyl is optionally substituted with one or two groups independently selected from alkyl and halo.

6. A compound of formula (III)

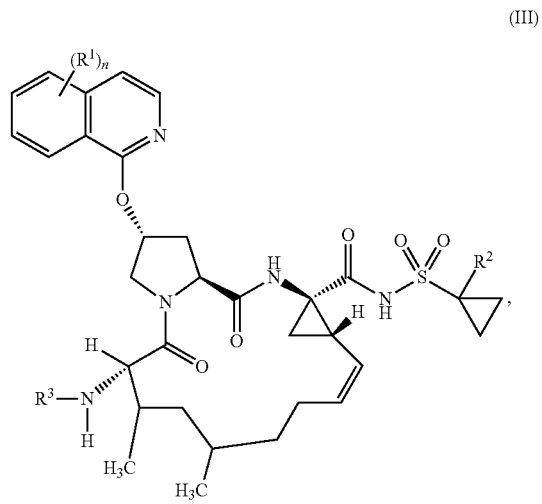

(III)

or a pharmaceutically acceptable salt thereof, wherein
n is 0, 1, 2, 3, 4, 5, or 6;
each $R^1$ is independently selected from alkoxy, alkyl, carboxamido, carboxy, cyano, cycloalkyloxy, dialkylamino, halo, haloalkyl, haloalkoxy, and phenyl, wherein the phenyl is optionally substituted with one or two groups independently selected from alkoxy, alkyl, halo, haloalkoxy, and haloalkyl;
$R^2$ is selected from hydrogen, alkyl, halo, and haloalkyl; and
$R^3$ is selected from alkoxycarbonyl, alkylcarbonyl, haloalkoxycarbonyl, haloalkylcarbonyl, and phenylcarbonyl, wherein the phenyl is optionally substituted with one or two groups independently selected from alkyl and halo;

or a pharmaceutically acceptable salt thereof.

7. A composition comprising a compound of claim 1, or a pharmaceutically acceptable salt thereof, and a pharmaceutically acceptable carrier.

8. A method of treating an HCV infection in a patient, comprising administering to the patient a therapeutically effective amount of a compound of claim 1, or a pharmaceutically acceptable salt thereof.

* * * * *

UNITED STATES PATENT AND TRADEMARK OFFICE
CERTIFICATE OF CORRECTION

PATENT NO. : 9,527,885 B2  
APPLICATION NO. : 14/592313  
DATED : December 27, 2016  
INVENTOR(S) : Hiebert et al.

Page 1 of 1

It is certified that error appears in the above-identified patent and that said Letters Patent is hereby corrected as shown below:

In the Claims

Claim 1, Column 798, Lines 4-11:

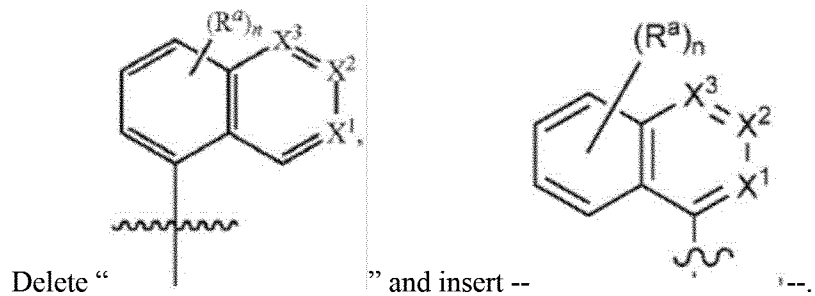

Claim 1, Column 798, Line 53:
Delete "-----" and insert --  --.

Claim 3, Column 799, Line 14:
Delete "-----" and insert -- ﹏﹏﹏ --.

Signed and Sealed this  
Twentieth Day of November, 2018

Andrei Iancu  
*Director of the United States Patent and Trademark Office*